(12) United States Patent
Fukushima et al.

(10) Patent No.: US 8,188,277 B2
(45) Date of Patent: May 29, 2012

(54) AROMATIC COMPOUNDS FOR SUPPRESSING THE GENERATION OF COLLAGEN

(75) Inventors: Tae Fukushima, Tokushima (JP); Shuji Matsumura, Tokushima (JP); Noriaki Takemura, Tokushima (JP); Hideaki Satou, Tokushima (JP); Nobuaki Ito, Tokushima (JP); Takuya Shitsuta, Otsu (JP); Hironori Tsutsui, Tokushima (JP); Michinori Tanaka, Otsu (JP); Keizo Kan, Tokushima (JP); Hitoshi Nagao, Tokushima (JP); Kenji Watanabe, Tokushima (JP); Kuninori Tai, Tokushima (JP); Takashi Nakagawa, Otsu (JP); Hideki Takasu, Otsu (JP); Makoto Sakamoto, Otsu (JP); Keisuke Miyajima, Otsu (JP); Satoshi Yamada, Otsu (JP); Yutaka Kojima, Otsu (JP); Koichi Yasumura, Otsu (JP); Naoto Ohi, Otsu (JP); Mitsuhiro Okuno, Otsu (JP); Kazuhisa Sugiyama, Otsu (JP); Kunihiko Kiyono, Otsu (JP); Takashi Suzuki, Otsu (JP); Seiji Akamatsu, Otsu (JP); Takeshi Kodama, Otsu (JP); Yasuo Yanagihara, Otsu (JP); Takumi Sumida, Otsu (JP)

(73) Assignee: Otsuka Pharmaceutical Co., Ltd., Tokyo (JP)

(*) Notice: Subject to any disclaimer, the term of this patent is extended or adjusted under 35 U.S.C. 154(b) by 825 days.

(21) Appl. No.: 11/659,689

(22) PCT Filed: Aug. 3, 2005

(86) PCT No.: PCT/JP2005/014611
§ 371 (c)(1),
(2), (4) Date: Feb. 6, 2007

(87) PCT Pub. No.: WO2006/014012
PCT Pub. Date: Feb. 9, 2006

(65) Prior Publication Data
US 2007/0270422 A1 Nov. 22, 2007

(30) Foreign Application Priority Data

Aug. 6, 2004 (JP) ................................ 2004-230092
Mar. 25, 2005 (JP) ................................ 2005-090149

(51) Int. Cl.
C07D 241/36 (2006.01)
C07D 413/12 (2006.01)
C07D 403/12 (2006.01)
C07D 221/02 (2006.01)
C07D 401/12 (2006.01)
C07D 213/62 (2006.01)
A61K 31/535 (2006.01)
A61K 31/497 (2006.01)
A61K 31/445 (2006.01)

(52) U.S. Cl. ........ 544/344; 544/343; 544/359; 544/361; 544/364; 544/386; 544/391; 544/111; 546/16; 546/208; 546/244; 546/269.7; 546/297; 514/235.5; 514/231.2; 514/252.13; 514/253.01; 514/278; 514/318; 514/326; 514/340; 514/354; 514/616

(58) Field of Classification Search ............... 514/235.5, 514/231.2, 252.13, 253.01, 278, 318, 326, 514/327, 340, 354, 616, 617; 544/111, 343, 544/344, 359, 361, 364, 386, 391; 546/16, 546/208, 244, 269.7, 272.4, 297
See application file for complete search history.

(56) References Cited

U.S. PATENT DOCUMENTS
3,715,375 A 2/1973 Shen et al.
(Continued)

FOREIGN PATENT DOCUMENTS
DE 2146450 3/1972
(Continued)

OTHER PUBLICATIONS

Barnstein et al., "STAT5 Expression Is Required for IgE-Mediated Mast Cell Function", The Journal of Immunology, vol. 177, pp. 3421-3426, (2006).
(Continued)

*Primary Examiner* — James O Wilson
*Assistant Examiner* — Ebenezer O Sackey
(74) *Attorney, Agent, or Firm* — Finnegan, Henderson, Farabow, Garrett & Dunner, L.L.P.

(57) ABSTRACT

The present invention provides a novel compound, which has an excellent effect of suppressing the generation of collagen and less side effects, with being excellent in terms of safety. The compound of the present invention is represented by the following general formula (1):

$$R^1 \underset{X_1}{\overset{R^2}{\bigcirc}} Y - A \quad (1)$$

[wherein $X_1$ represents a nitrogen atom or a group —CH=; $R^1$ represents a group —Z—$R^6$, wherein Z represents a group —CO—, a group —CH(OH)—, or the like, and $R^6$ represents a 5- to 15-membered monocyclic, dicyclic, or tricyclic, saturated or unsaturated heterocyclic group having 1 to 4 nitrogen atoms, oxygen atoms, or sulfur atoms; $R^2$ represents a hydrogen atom, a halogen atom or a lower alkylene group; Y represents a group —O—, a group —CO—, a group —CH(OH)—, a lower alkylene group, or the like; and A represents a group $$-\bigcirc\underset{R^4}{\overset{(R^3)_p}{\bigcirc}}$$

or the like, wherein $R^3$ represents a hydrogen atom, a lower alkoxy group, or the like, p represents 1 or 2, and $R^4$ represents an imidazolyl lower alkyl group or the like.

14 Claims, No Drawings

U.S. PATENT DOCUMENTS

| | | | |
|---|---|---|---|
| 4,153,775 | A | 5/1979 | Winkelmann et al. |
| 4,211,699 | A | 7/1980 | Winkelmann et al. |
| 4,482,721 | A | 11/1984 | Wegner et al. |
| 5,210,169 | A | 5/1993 | Mühlebach et al. |
| 5,401,772 | A | 3/1995 | Yokoyama et al. |
| 6,511,995 | B1 | 1/2003 | Edamatsu et al. |
| 2002/0065296 | A1 | 5/2002 | Dumas et al. |
| 2010/0004438 | A1 | 1/2010 | Matsuyama et al. |
| 2010/0210661 | A1 | 8/2010 | Sekiguchi et al. |
| 2010/0261720 | A1 | 10/2010 | Sumida et al. |

FOREIGN PATENT DOCUMENTS

| | | | |
|---|---|---|---|
| DE | 27 07 659 | A1 | 8/1978 |
| DE | 27 07 660 | A1 | 8/1978 |
| EP | 0 500 495 | A2 | 8/1992 |
| EP | 0 580 550 | A1 | 1/1994 |
| EP | 1 101 755 | A1 | 5/2001 |
| EP | 1 211 235 | A2 | 6/2002 |
| EP | 1 256 341 | A1 | 11/2002 |
| EP | 1 604 981 | A1 | 12/2005 |
| FR | 2 289 489 | | 5/1976 |
| GB | 1 353 520 | | 5/1974 |
| GB | 1 494 117 | | 12/1977 |
| GB | 2 374 009 | A | 10/2002 |
| JP | 2001-89412 | | 4/2001 |
| JP | 2001-89450 | | 4/2001 |
| JP | 2002-507601 | | 3/2002 |
| JP | 2004-35475 | | 2/2004 |
| WO | WO-95/01326 | | 1/1995 |
| WO | WO-96/40620 | | 12/1996 |
| WO | WO-99/24404 | | 5/1999 |
| WO | WO-99/40073 | | 8/1999 |
| WO | WO-99/40083 | | 8/1999 |
| WO | WO-99/48871 | | 9/1999 |
| WO | WO-00/00470 | | 1/2000 |
| WO | WO-02/32408 | A2 | 4/2000 |
| WO | WO-00/42012 | | 7/2000 |
| WO | WO-00/46203 | | 8/2000 |
| WO | WO-00/58279 | | 10/2000 |
| WO | WO-01/02359 | A1 | 11/2001 |
| WO | WO-01/98256 | A1 | 12/2001 |
| WO | WO-02/16358 | A2 | 2/2002 |
| WO | WO-02/26191 | A2 | 4/2002 |
| WO | WO-02/053150 | A1 | 7/2002 |
| WO | WO-02/102787 | A2 | 12/2002 |
| WO | WO-03/018586 | A1 | 3/2003 |
| WO | WO-03/035602 | A1 | 5/2003 |
| WO | WO-03/035627 | A1 | 5/2003 |
| WO | WO-03/070728 | A2 | 8/2003 |
| WO | WO-03/076406 | A1 | 9/2003 |
| WO | WO-2004/080966 | A1 | 9/2004 |
| WO | WO-2005/007621 | A2 | 1/2005 |
| WO | WO-2005/009940 | A1 | 2/2005 |
| WO | WO-2006/014012 | A2 | 2/2006 |
| WO | WO 01/90101 | A1 | 11/2011 |

OTHER PUBLICATIONS

Gao et al., "Disruption of Neural Signal Transducer and Activator of Transcription 3 Causes Obesity, Diabetes, Infertility, and Thermal Dysregulation", PNAS, vol. 101, No. 13, pp. 4661-4666, (2004).

George et al., "Metabolic Activation Stimulates Acid Secretion and Expression of Matrix Degrading Proteases in Human Osteoblasts", Annals of the Rheumatic Diseases, vol. 63, No. 1, pp. 67-70, (2004).

Maggio et al., "Interleukin-6 in Aging and Chronic Disease: A Magnificent Pathway", The Journal of Gerontology, vol. 61A, No. 6, pp. 575-584, (2006).

Sano et al., "STAT3 Links Activated Keratinocytes and Immunocytes Required for Development of Psoriasis in a Novel Transgenic Mouse Model"; Nature Medicine, vol. 11, No. 1, pp. 43-49, (2005).

Yoshida et al., "Activation of STAT3 by the Hepatitis C Virus Core Protein Leads to Cellular Transformation", The Journal of Experimental Medicine, vol. 196, No. 5, pp. 641-653, (2002).

Balcells et al.; "Synthesis of Phenoxyphenyl Pyridine and Pyrazine Carboxamides. Activity Against *Cydia pomonella* (L.) Eggs"; J. Agric Food Chem., vol. 48, No. 1, pp. 83-87, (2000).

Mühlebach; "Pyrazoles—A Novel Class of Blocking Agents for Isocyanates"; Journal of Polymer Science, vol. 32, No. 4, pp. 735-765, (1994).

Bethegnies et al.; "Substituted Phenylthiophenylamines With Antiinflammatory Activity"; IL Farmaco, vol. 44, Nos. 7-8, pp. 683-694, (1989).

Anagnostou et al.; "Synthesis of Blocked MDI Adducts, Their DSC Evaluation and Effect of Pigmentation"; Journal of Coating Technology, vol. 53, No. 673, pp. 35-45, (1981).

Molina, Vered et al., "Intravenous Immunoglobulin and Fibrosis," Clinical Reviews in Allergy & Immunology, vol. 29, No. 3, pp. 321-326 (2005).

Korean Office Action for Korean Patent Application No. 10-2009-7006358 dated Apr. 1, 2011.

European Office Action in Counterpart EP Application No. 05 780 290.2-1521 dated Sep. 15, 2011.

Abad-Zapatero, C. et al., "Ligand Efficiency Indices For an Effective Mapping of Chemico-Biological Space: The Concept of an Atlas-Like Representation," Drug Discovery Today, 1-8 (2010).

Bastian, B.C., "Genetic Progression From Melanocyte to Malignant Melanoma," The Progression to Malignancy 197, 201 (V.J. Hearing et al., eds. (2006).

Cannistra, S. et al., "Ovarian Cancer, Fallopian Tube Carcinoma, and Peritoneal Carcinoma," 2 Cancer Principles & Practice of Oncology 1568 (V.T. DeVita, Jr. et al. eds., $8^{th}$ ed.) (2008).

Collins, I. et al., "Design and Development of Signal Transduction Inhibitors for Cancer Treatment: Experience and Challenges With Kinase Targets," Current Signal Transduction Therapy, 1, 13-14 (2006).

De Arruda MD, F.F. et al.,"Intensity-Modulated Radiation Therapy For the Treatment of Oropharyngeal Carcinoma: The Memorial Sloan-Kettering Cancer Center Experience," Int. J. Radiation Oncology Biol. Phys., 64(2), 363-373 (2006).

Druker, B.J., "Chronic Myelogenous Leukemia," 2 Cancer Principles & Practice of Oncology 2121 (V.T. DeVita, Jr. et al. eds., $7^{th}$ ed. (2005).

Faderi, S. et al., "Myelodysplastic Syndromes," 2 Cancer Principles & Practice of Oncology 2133 (V.T. DeVita, Jr. et al. eds., $7^{th}$ ed. (2005).

Gao, H. et al., "Stat3 and Suppressor of Cytokine Signaling 3: Potential Targets in Lung Inflammatory Responses," Expert Opin. Ther. Targets 11:869-880 (2007).

Hann, B. et al., "Building 'Validated' Mouse Models of Human Cancer," Current Opinion in Cell Biology, 13, 778-784 (2001).

Hawley, A.T. et al., "Etiology of Cancer: Cancer Susceptibility Syndromes," 2 Cancer Principles & Practice of Oncology, 157-166, 157 (V.T. DeVita, Jr. et al. eds., $8^{th}$ ed., 2008).

Kamb, A., "What's Wrong With Our Cancer Models?," Nature Reviews Drug Discovery 2, 161-165 (2005).

Kumar, P. et al., "Pulmonary Fibrosis and Lung Cancer: Risk and Benefit Analysis of Pulmonary Resection," The Journal of Thoracic and Cardiovascular Surgery, 125(6) 1321-1327, 1322 (2003).

Levinthal, MD., G.N. et a., "Liver Disease and Diabetes Mellitus," Clinical Diabetes 17(2) (1999).

Libutti, S.K. et al., "Colon Cancer," 1 Cancer Principles & Practice of Oncology 1232, 1243 (V.T. DeVita, Jr. et al eds., $8^{th}$ ed.) (2008).

Montori, V. et al., "Waking Up From the DREAM of Preventing Diabetes With Drugs," BMJ 334:882-884 (2007).

Nishizawa, R. et al., Machine Translation of WO2004/080966 (Sep. 23, 2004).

O'Brien, S. et al., "Chronic Lymphoid Leukemias," 2 Cancer Principles & Practice of Oncology 2133 (V.T. DeVita, Jr. et al. eds, $7^{th}$ ed. (2005).

Odunsi, K et al., "Molecular Biology of Gynecologic Cancers," 2 Cancer Principles & Practice of Oncology 1487, 1492 (V.T. DeVita, Jr. et al. eds., $8^{th}$ ed) (2008).

Office Action for copending U.S. Appl. No. 12/095,930 dated Aug. 17, 2011.

Office Action for copending U.S. Appl. No. 12/311,500 dated Oct. 5, 2011.

Olive, K.P. et al., "The Use of Targeted Mouse Models for Preclinical Testing of Novel Cancer Therapeutics," Clinical Cancer Research 12, 5277-5287 (2006).

Pusztai, L. et al., "Histopathologic and Molecular Markers of Prognosis and Response to Therapy," Breast Cancer 324, 326-328 (Kelly K. Hunt et al., ed., $2^{nd}$ ed.) (2008).

Rustgi, A.K., "Molecular Biology of the Esophagus and Stomach," 1 Cancer Principles & Practice of Oncology, 989-993, 991 (V.T DeVita, Jr. et al. eds, 8$^{th}$ ed.) (2008).

Scheinberg, D.A. et al., "Management of Acute Leukemias," 2 Cancer Principles & Practice of Oncology 2088, 2092 (V.T. DeVita, Jr. et al. eds., 7$^{th}$ ed.) (2005).

Sharpless, N.E. et al., "The Mighty Mouse: Genetically Engineered Mouse Models in Cancer Drug Development," Nature Reviews Drug Discovery 5, 741-754 (2006).

Smith, N.F. et al., "The Application of Cassette Dosing For Pharmacokinetic Screening in Small-Molecule Cancer Drug Discovery," Molecular Cancer Therapeutics, 6, 428-440, 428 (2007).

Song, Y. et al., "Cancer: A Conceptual Framework," 1 Cancer Principles & Practice of Oncology 1, 5-6 (V.T. Devita, Jr. et al. eds., 8$^{th}$ ed., 2008).

Traynor, A.M., "Systemic Treatment of Advanced Non-Small Cell Lung Cancer," Drugs of Today, 40(8), 697-710, 698 (2004).

Belikov, V.G., "Pharmaceutical Chemistry," Highest School, Moscow, pp. 43-47 (1993).

Final Office Action in U.S. Appl. No. 12/311,500 dated Oct. 5, 2011.

Kholodov, L.E. et al., "Clinic Pharmacokinetics," Manual, Medicine, Moscow, pp. 83-98, 134-138, 160, 378-380, (1985).

Mosby Medical Encyclopedia, Revised Edition, p. 320 (1996).

Restriction Requirement in U.S. Appl. No. 12/095,930 mailed May 26, 2011.

Restriction Requirement in U.S. Appl. No. 12/311,500 dated Dec. 9, 2010.

Russian Office Action for Russian Application No. 2009116653 dated Oct. 21, 2011.

Sergeev, Professor, "Short Course of Molecular Pharmacology," Moscow Medical Institute, Moscow, p. 10, (1975).

ically, it is said that the disease known as fibrosis includes 130 types or more of diseases, if rare diseases are

AROMATIC COMPOUNDS FOR SUPPRESSING THE GENERATION OF COLLAGEN

TECHNICAL FIELD

The present invention relates to an aromatic compound.

BACKGROUND ART

Currently, it is said that the disease known as fibrosis includes 130 types or more of diseases, if rare diseases are also included therein. Representative examples of such fibrosis include lung fibrosis, hepatic fibrosis, and glomerulosclerosis.

In general, lung fibrosis refers to a group of diseases associated with loss of lung functions due to a lesion regarding the reconstruction of an alveolar region, which is caused by the phenomenon whereby the alveolar structure is destroyed by an inflammatory reaction, and as a result, growth of fibroblasts and an excessive increase in extracellular matrix mainly composed of collagen take place, so that the lung becomes hardened.

Moreover, hepatic fibrosis refers to a pathologic condition associated with fibrosis of the liver, which is caused by the phenomenon whereby hepatic cells are necrotized by various types of hepatopathy such as chronic viral hepatitis or alcoholic hepatitis, and thereafter, extracellular matrix increases to replenish the necrotized portion, resulting in such fibrosis of the liver. This pathologic condition finally leads to hepatic cirrhosis, in which the entire hepatic fibers shrink and become hardened.

In order to suppress the aforementioned hepatic fibrosis, drugs such as Penicillamine or Lufironil have been used. Penicillamine has been known as a drug for treating Wilkinson's disease that is developed as a result of accumulation of copper in the liver due to abnormality of copper metabolism. Lufironil has been studied for its use as a proline hydroxylase inhibitor.

However, taking into consideration their side effects and effectiveness, the aforementioned drugs do not sufficiently function as drugs for preventing fibrosis of the liver. Thus, as a matter of fact, neither therapeutic agents nor methods for treating fibrosis, which are effective for fibrosis, including hepatic fibrosis as a representative example, have been established to date. A method of specifically inhibiting a process of developing fibrosis has become a focus of attention in the research field.

As stated above, it has been known that an excessive increase in extracellular matrix mainly composed of collagen takes place during a process of development of fibrosis in the lung tissues or hepatic tissues. Moreover, it has also been known that such an increase in extracellular matrix in hepatic cells takes place mainly in sinusoidal wall Disse's space, and that Ito cells that are mesenchymal cells in the liver are main sources for production of such extracellular matrix.

Accordingly, in order to suppress fibrosis occurring in the liver, the lung, or other organs, it is important to suppress an excessive increase in extracellular matrix (namely, collagen).

JP-A-2002-507601 and JP-A-2001-89450 disclose that a certain type of pyridine derivative has an effect of suppressing the generation of collagen and thus is effective for fibrosis. JP-A-2001-89412 discloses that a certain type of benzene derivative has an effect of suppressing the production of collagen and thus is effective for fibrosis.

However, the effect of suppressing the generation of collagen of the compounds described in JP-A-2002-507601, JP-A-2001-89450, and JP-A-2001-89412 are insufficient, or these compounds have serious side effects. Accordingly, it has strongly been desired that a compound, which has a superior effect of suppressing the production of collagen, less side effects, and excellent safety, will be developed.

DISCLOSURE OF THE INVENTION

It is an object of the present invention to provide a novel compound, which has a superior effect of suppressing the generation of collagen, for example, a pharmaceutical composition being useful for preventing and treating fibrosis such as lung fibrosis, hepatic fibrosis, glomerulosclerosis and the like, with less side effects, and excellent safety.

As a result of intensive studies directed towards achieving the aforementioned object, the present inventors have found that an aromatic compound represented by the following general formula (1) and a salt thereof have a superior effect of suppressing the generation of collagen, less side effects, and excellent safety. The present invention has been completed based on these findings.

The present invention provides an aromatic compound represented by the general formula (1) or a salt thereof:

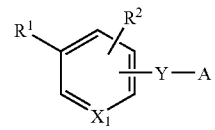
(1)

[wherein $X_1$ represents a nitrogen atom or a group —CH=,
$R^1$ represents a group —Z—$R^6$,
Z represents a group —N($R^8$)—B—, a group —B—N($R^8$)—, a group —$B_0$—O—, a group

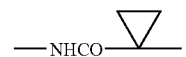

a group —CO—, a group —CH(OH)—, a group

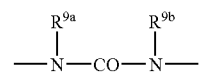

a group —N=CH—, a group

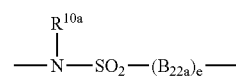

a lower alkenylene group, a group —NHCO—$B_1$—, a group —NHCO—$B_2$—(W)u-, a group —$B_0$—O—$B_{19a}$, a group

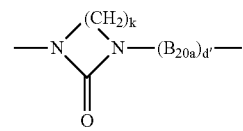

a group

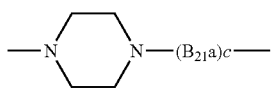

a group

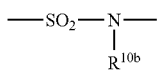

a group —S—, a lower alkynylene group, a lower alkylene group, a group

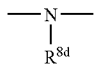

or a group CO—NH—B$_{18}$a-,
wherein R$^8$ represents a hydrogen atom, a lower alkyl group that may have a lower alkoxy group as a substituent, a lower alkanoyl group, a phenyl lower alkyl group, or a lower alkylsulfonyl group,
B represents a group —CO— or a lower alkylene group,
B$_0$ represents a lower alkylene group,
each of R$^{9a}$ and R$^{9b}$, which are identical or different, represents a hydrogen atom or a lower alkyl group
R$^{10a}$ represents a hydrogen atom or a lower alkyl group,
B$_{22a}$ represents a lower alkylene group or a lower alkenylene group,
e represents 0 or 1,
B$_1$ represents a lower alkenylene group that may have a phenyl group as a substituent,
B$_2$ represents a lower alkylene group that may be substituted by a group selected from the group consisting of a lower alkoxy group and a phenyl group,
W represents an oxygen atom, a group —NH—, or a sulfur atom,
u represents 0 or 1,
B$_{18a}$ represents a lower alkylene group,
B$_{19a}$ represents a lower alkylene group,
B$_{20a}$ represents a lower alkylene group,
B$_{21a}$ represents a lower alkylene group,
R$^{8d}$ represents a hydrogen atom or a lower alkyl group,
k represents 2 or 3,
c represents 0 or 1,
d' represents 0 or 1,
R$^{10b}$ represents a hydrogen atom or a lower alkyl group,
R$^6$ represents a 5- to 15-membered monocyclic, dicyclic, or tricyclic saturated or unsaturated heterocyclic group having 1 to 4 nitrogen atoms, oxygen atoms, or sulfur atoms (wherein, the heterocyclic ring may be substituted by 1 to 3 groups selected from the group consisting of an oxo group; an optionally halogenated lower alkoxy group; an optionally halogenated lower alkyl group; a halogen atom; a lower alkylsulfonyl group; a phenyl group that may be substituted, on the phenyl ring, by an optionally halogenated lower alkyl group; a lower alkylthio group; a pyrrolyl group; a benzoyl group; a lower alkanoyl group; a lower alkoxycarbonyl group; and an amino group that may have a group selected from the group consisting of a lower alkyl group and a lower alkanoyl group as a substituent), an adamantyl group, a naphthyl group (wherein, the naphthalene ring may be substituted by 1 to 3 groups selected from the group consisting of a lower alkyl group, a halogen atom, and an amino group that may have a group selected from the group consisting of a lower alkyl group and a lower alkanoyl group as a substituent), an alkyl group that may have a lower alkoxy group as a substituent, a cycloalkyl group that may be substituted, on the cycloalkyl ring, by a group selected from the group consisting of an amino-substituted lower alkyl group that may have a lower alkyl group on the amino group and a lower alkyl group that may have a halogen atom as a substituent, a lower alkenyl group that may have a halogen atom as a substituent, a lower alkanoyl group, a benzoyl group that may be substituted, on the phenyl ring, by 1 to 3 groups selected from the group consisting of a lower alkyl group that may have a halogen atom as a substituent and a halogen atom, a group

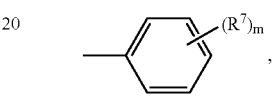

a halogen atom-substituted lower alkyl group, or a cycloalkyl lower alkyl group,
R$^7$ represents a hydrogen atom, a phenyl group, a carboxy group, a hydroxyl group, a halogen atom, a lower alkyl group that may have a halogen atom as a substituent, a phenoxy group, a lower alkoxy group that may have a halogen atom as a substituent, a lower alkylenedioxy group, an amino group that may have, as a substituent, a group selected from the group consisting of a lower alkyl group, a lower alkanoyl group, a benzoyl group, and a cycloalkyl group, a cyano group, a lower alkanoyl group that may have a halogen atom as a substituent, a lower alkylsulfonyl group, an aminosulfonyl group, a lower alkoxycarbonyl group, a lower alkanoyloxy group, a 5- or 6-membered saturated or unsaturated heterocyclic group having 1 to 4 nitrogen atoms, oxygen atoms, or sulfur atoms (wherein the heterocyclic ring may be substituted, by an oxo group), or a lower alkoxycarbonyl lower alkyl group,
m represents an integer between 1 and 5, wherein when m represents 2 to 5, two to five R$^7$s may be identical or different,
R$^2$ represents a hydrogen atom, a halogen atom, or a lower alkyl group,
Y represents a group —O—, a group —N(R$^5$)—, a group —CO—, a group —CH(OH)—, a lower alkylene group, a group —S(O)n-, or a group —C(=N—OH)—,
R$^5$ represents a hydrogen atom, a lower alkyl group, a lower alkanoyl group, a benzoyl group, a phenyl lower alkyl group, or a cycloalkyl group,
n represents 0, 1, or 2,
A represents a group

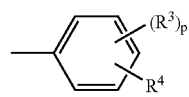

or a group

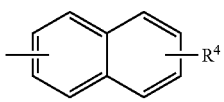

p represents 1 or 2,
$R^3$ represents a hydrogen atom, a lower alkoxy group, a halogen atom, a lower alkyl group that may have a halogen atom as a substituent, a lower alkoxycarbonyl group, a carboxy group, a group —$CONR^{11}R^{12}$, or a cyano group,
wherein each of $R^{11}$ and $R^{12}$, which are identical or different, represents a hydrogen atom, a lower alkyl group, a cycloalkyl group, or a phenyl group, or $R^{11}$ and $R^{12}$, together with the nitrogen atom to which they bind, may bind to each other, directly or via a nitrogen atom, oxygen atom, or sulfur atom to form a 5- to 7-membered saturated heterocyclic ring,
$R^4$ represents an imidazolyl lower alkyl group, a 1,2,4-triazolyl lower alkyl group, a 1,2,3-triazolyl lower alkyl group, a 1,2,5-triazolyl lower alkyl group, a pyrazolyl lower alkyl group, a pyrimidinyl lower alkyl group that may have an oxo group as a substituent on the pyrimidine ring, a 3,5-dioxoisoxazolidin-4-ylidene lower alkyl group, a 1,2,4-oxadiazolyl lower alkyl group that may have a lower alkyl group as a substituent on the 1,2,4-oxadiazole ring, a thiazolidinyl lower alkyl group that may have an oxo group as a substituent on the thiazolidine ring, a group

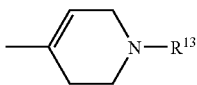

a group

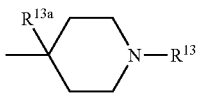

or a group -$(T)_1$-$N(R^{14})R^{15}$,
$R^{13}$ represents a hydrogen atom, a lower alkyl group that may have a halogen atom as a substituent, a lower alkanoyl group that may have a halogen atom as a substituent, a lower alkoxycarbonyl group, a phenyl lower alkyl group that may have a lower alkylenedioxy group as a substituent on the phenyl ring, an imidazolyl lower alkyl group, a lower alkoxycarbonyl lower alkyl group, a carboxy lower alkyl group, a benzoyl group, a morpholino-substituted lower alkanoyl group, a piperazinyl carbonyl lower alkyl group that may be substituted, on the piperazine ring, by a phenyl lower alkyl group that may have a lower alkylenedioxy group as a substituent on the phenyl ring, a piperazinyl lower alkanoyl group that may be substituted, on the piperazine ring, by a phenyl lower alkyl group that may have a lower alkylenedioxy group as a substituent on the phenyl ring, a morpholinocarbonyl-substituted lower alkyl group, or an imidazolyl lower alkanoyl group,
$R^{13a}$ represents a hydrogen atom or a hydroxyl group,
T represents a lower alkylene group, a group —$N(R^{17})$—$B_3$—CO—, a group —$B_{19}$—$N(R^{18})$—CO—, a group —$B_4$—CO—, a group -Q-$B_5$—CO—, a group —$B_6$—$N(R^{19})$—$B_7$—CO—, a group —CO—$B_8$—, a group —CH(OH)—$B_9$—, a group —CO—$B_{10}$—CO—, a group —CH(OH)—$B_{11}$—CO—, a group —CO—, a group —$SO_2$—, or a group —$B_{23a}$—CO—CO—,
wherein $R^{17}$ represents a hydrogen atom, a lower alkyl group, a cycloalkyl group, a cycloalkylcarbonyl group, a lower alkanoyl group that may have a halogen atom as a substituent, a lower alkenyl group, an amino-substituted lower alkanoyl group that may have a lower alkyl group as a substituent, or a lower alkylsulfonyl group,
$B_3$ represents a lower alkylene group,
$B_{19}$ represents a lower alkylene group,
$R^{18}$ represents a hydrogen atom or a lower alkyl group,
$B_4$ represents a lower alkenylene group or a lower alkylene group that may have a hydroxyl group as a substituent,
Q represents an oxygen atom or a group —S(O)n- (wherein n has the same meanings as described above),
$B_5$ represents a lower alkylene group,
$B_6$ represents a lower alkylene group,
$R^{19}$ represents a hydrogen atom or a lower alkanoyl group,
$B_7$ represents a lower alkylene group,
$B_8$ represents a lower alkylene group,
$B_9$ represents a lower alkylene group,
$B_{10}$ represents a lower alkylene group,
$B_{11}$ represents a lower alkylene group,
$B_{23a}$ represents a lower alkylene group,
l represents 0 or 1,
$R^{14}$ represents a hydrogen atom or an alkyl group that may have a hydroxyl group as a substituent,
$R^{15}$ represents (2) a hydroxyl group-substituted alkyl group, (3) a cycloalkyl group that may have a group selected from the group consisting of a hydroxyl group and a lower alkyl group as a substituent, (4) a phenoxy lower alkyl group, (5) a phenyl group that may be substituted, on the phenyl ring, by 1 to 3 groups selected from the group consisting of a lower alkyl group; a lower alkoxy group that may have a halogen atom as a substituent; a halogen atom; an amino lower alkoxy group that may have a lower alkyl group as a substituent; a hydroxyl group-substituted lower alkyl group; a phenyl lower alkyl group; a lower alkynyl group; an amino group that may have a lower alkylsulfonyl group as a substituent; a lower alkylthio group; a cycloalkyl group; a phenylthio group; an adamantyl group; an anilino group that may have a halogen atom as a substituent on the phenyl ring; a lower alkoxycarbonyl group; a piperazinyl group that may have a lower alkyl group as a substituent on the piperazine ring; a pyrrolidinyl group that may have an oxo group as a substituent on the pyrrolidine ring; a lower alkanoylamino group; a cyano group; and a phenoxy group, (6) a phenoxy group, (7) a phenyl lower alkyl group that may be substituted, on the phenyl ring, by 1 to 3 groups selected from the group consisting of a halogen atom, a lower alkoxy group that may have a halogen atom as a substituent, and a lower alkyl group, (8) a phenyl lower alkyl group that has a lower alkylenedioxy group as a substituent on the phenyl ring, (10) a lower alkoxycarbonyl-substituted lower alkyl group, (11) a carboxy-substituted lower alkyl group, (12) an amino group that may have a lower alkanoyl group as a substituent, (13) a 1,2,3,4-tetrahydroquinolyl group that may have 1 to 3 groups selected from the group consisting of an oxo group, a lower alkoxy group, and a lower alkylenedioxy group as a substituent(s) on the tetrahydroquinoline ring, (14) a cycloalkyl lower alkyl group, (15) a piperazinyl lower alkanoyl group that may be substituted, on the piperazine ring, by a phenyl lower alkyl group that may have a lower alkylenedioxy group as a substituent on the phenyl ring, (16) a pyridyl Lower alkyl group, (17) an amino group-substituted lower alkyl group that may have a group selected from the group consisting of a lower alkyl group and a lower alkanoyl group as a substituent, (18) a lower alkoxy lower alkyl group, (19) an imidazolyl group, (20) an imidazolyl lower alkyl group, (21) a 1,2,3,4-tetrahydroisoquinolylcarbonyl-substituted lower alkyl group, (22) a piperidinylcarbonyl group that may have a group selected from the group consisting of a lower alkoxycarbonyl group, a phenyl lower alkyl group, and a furyl lower alkyl group as a substituent on the piperidine ring, (23) a thiazolidinyl lower alkanoyl group that may have an oxo group as a substituent on the thiazolidine ring, (24) a piperidinyl group that may be substituted, on the piperidine ring, by a group selected from the group consisting of a lower alkoxycarbonyl group, a phenyl lower alkyl group, a lower alkyl group, a benzoyl group, and a furyl lower alkyl group, (25) a carbonyl lower alkyl group substituted by a group

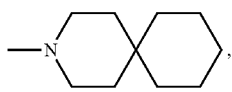

, (26) a carbonyl lower alkyl group substituted by a group

(27) a group —CO—$B_{20}$—N($R^{36}$)$R^{37}$, (26a) a pyrrolidinyl lower alkyl group, (27a) a morpholino lower alkyl group, (28a) a phenyl lower alkenyl group, (29a) an anilinocarbonyl lower alkyl group that may have a lower alkyl group as a substituent on the phenyl ring, (30a) an indolyl group, (31a) a piperazinyl lower alkyl group that may have, as a substituent on the piperazine ring, a group selected from the group consisting of a lower alkyl group and a phenyl lower alkyl group that may have a lower alkylenedioxy group as a substituent on the phenyl ring, (32a) an amidino lower alkyl group that may have a lower alkyl group as a substituent, (33a) a fluorenyl group, (34a) a carbazolyl group that may have a lower alkyl group as a substituent on the carbazole ring, (35a) an amidino group that may have a lower alkyl group as a substituent, (36a) a piperazinyl-substituted oxalyl group that may have 1 to 3 groups selected from the group consisting of a phenyl lower alkyl group (that may have 1 to 3 groups selected from the group consisting of a lower alkylenedioxy group and a lower alkoxy group as a substituent(s) on the phenyl ring) and a pyridyl lower alkyl group as a substituent(s) on the piperazine ring, or (37a) a cyano-substituted lower alkyl group, $R^{34}$ represents an oxo group or a phenyl group, d represents an integer between 0 and 3, $B_{20}$ represents a lower alkylene group, $R^{36}$ and $R^{37}$, together with the nitrogen atom to which they bind, may bind to each other, directly or via a nitrogen atom, oxygen atom, or sulfur atom to form a 5- to 7-membered saturated heterocyclic group, wherein the heterocyclic group may be substituted by 1 to 3 phenyl lower alkyl groups that may have a lower alkylenedioxy group as a substituent on the phenyl ring, $R^{14}$ and $R^{15}$, together with the nitrogen atom to which they bind, may bind to each other, directly or via a nitrogen atom, oxygen atom, or sulfur atom to form a 5- to 10-membered saturated or unsaturated heterocyclic ring; or a group

wherein the heterocyclic ring may be substituted by 1 to 3 groups selected from the group consisting of (28) a phenyl-substituted lower alkyl group, which has 1 to 2 phenyl groups and which may have a pyridyl group on the lower alkyl group, wherein the phenyl ring may be substituted by 1 to 3 groups selected from the group consisting of a lower alkanoyl group, an amino group that may have a lower alkanoyl group as a substituent, a lower alkoxycarbonyl group, a cyano group, a nitro group, a phenyl group, a halogen atom, a lower alkyl group that may have a halogen atom as a substituent, a lower alkoxy group that may have a halogen atom as a substituent, a phenyl lower alkoxy group, a hydroxyl group, and a lower alkylenedioxy group, (29) a carbamoyl group, (30) a pyridyl lower alkyl group that may have, as a substituent(s) on the pyridine ring, 1 to 3 groups selected from the group consisting of a hydroxyl group and a lower alkyl group that may have a hydroxyl group as a substituent, (31) a pyrrolyl lower alkyl group that may have 1 to 3 lower alkyl groups as a substituent(s) on the pyrrole ring, (32) a benzoxazolyl lower alkyl group, (33) a benzothiazolyl lower alkyl group, (34) a furyl lower alkyl group, (35) a benzoyl group that may be substituted, on the phenyl ring, by 1 to 3 groups selected from the group consisting of a cyano group, an amino group that may have a lower alkylsulfonyl group as a substituent, a halogen atom, a lower alkoxy group, a lower alkyl group that may have a halogen atom as a substituent, a thiazolidinyl lower alkyl group that may have an oxo group as a substituent on the thiazolidine ring, a thiazolidinylidene lower alkyl group that may have an oxo group as a substituent on the thiazolidine ring, and a lower alkylenedioxy group, (36) a pyrimidinyl group, (37) a pyrazinyl group, (38) a pyridyl group, (39) a lower alkoxycarbonyl group, (40) a thiazolidinyl lower alkanoyl group that may be substituted, on the thiazolidine ring, by a group selected from the group consisting of an oxo group and a group

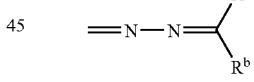

(wherein each of $R^a$ and $R^b$ represents a lower alkyl group), (41) a lower alkyl group that may have a group selected from the group consisting of a hydroxyl group and a halogen atom as a substituent, (42) a lower alkanoyl group that may have a halogen atom as a substituent, (43) a phenyl group that may be substituted, on the phenyl ring, by 1 to 3 groups selected from the group consisting of a carbamoyl group that may have a group selected from the group consisting of a lower alkoxy lower alkyl group and a lower alkyl group, a lower alkoxycarbonyl group, a carboxy group, a cyano group, a phenyl group, a halogen atom, a lower alkyl group that may have a halogen atom as a substituent, a lower alkoxy group that may have a halogen atom as a substituent, a benzoyl group that may have a halogen atom as a substituent on the phenyl ring, a phenyl lower alkyl group that may have a halogen atom as a substituent on the phenyl ring, and a hydroxyl group, (44) a phenyl group that may have a lower alkylenedioxy group as a substituent on the phenyl ring, (45) a naphthyl lower alkyl group, (46) a phenoxy group that may be substituted, on the phenyl ring, by 1 to 3 groups selected from the group consisting of a cyano group, a lower alkyl group that may have a halogen atom as a substituent, and a lower alkoxy group that may have a halogen atom as a substituent, (47) a phenoxy lower alkyl group, (48) a phenyl lower alkoxy group that may be substituted, on the phenyl ring, by 1 to 3 groups selected from the group consisting of a halogen atom, a lower alkyl group that may have a halogen atom as a substituent, and a lower alkoxy group that may have a halogen atom as a substituent, (49) a group —($B_{12}$CO)t-N($R^{20}$)$R^{21}$, (50) a group —(CO)o-$B_{13}$—N($R^{22}$)$R^{23}$, (51) a 1,2,3,4-tetrahydronaphthyl-substituted lower alkyl group that may be substituted, on the 1,2,3,4-tetrahydronaphthalene ring, by 1 to 5 lower alkyl groups as a substituent(s), (52) a cycloalkyl group that may have a hydroxyl group as a substituent, (53) a piperidinyl group that may be substituted, on the piperidine ring, by 1 to 3 lower alkyl groups as a substituent(s), (54) a quinolyl lower alkyl group, (55) a 1,2,3,4-tetrazolyl lower alkyl group that may have a group selected from the group consisting of a lower alkyl group and a phenyl lower alkyl group as a substituent on the tetrazole ring, (56) a thiazolyl lower alkyl group that may have a phenyl group as a substituent on the thiazole ring, (57) a benzoyl lower alkyl group that may have 1 to 3 groups selected from the group consisting of a lower alkoxy group and a halogen atom as a substituent(s) on the phenyl ring, (58) a piperidinyl lower alkyl group that may have a lower alkyl group as a substituent on the piperidine ring, (59) an imidazolyl group that may have 1 to 3 phenyl groups as a substituent(s) on the imidazole ring, (60) a benzimidazolyl group that may have 1 to 3 lower alkyl groups as a substituent(s) on the benzimidazole ring, (61) a pyridyl lower alkoxy group, (62) a 1,2,3,4-tetrahydroquinolyl lower alkyl group that may have an oxo group as a substituent on the tetrahydroquinoline ring, (63) a 1,3,4-oxadiazolyl lower alkyl group that may have an oxo group as a substituent on the 1,3,4-oxadiazole ring, (64) a cycloalkyl lower alkyl group, (65) a tetrahydropyranyl group, (66) a thienyl lower alkyl group, (67) a pyrimidinylcarbonyl group that may have an oxo group as a substituent on the pyrimidine ring, (68) a hydroxyl group, (69) a carboxy group, (70) a lower alkoxy lower alkyl group, (71) a lower alkoxy lower alkoxy group, (72) a benzoyloxy group, (73) a lower alkoxycarbonyl lower alkoxy group, (74) a carboxy lower alkoxy group, (75) a phenoxy lower alkanoyl group, (76) a 1,2,3,4-tetrahydroquinolylcarbonyl group that may have an oxo group as a substituent on the tetrahydroquinoline ring, (77) a phenylsulfonyl group, (78) an imidazolyl lower alkanoyl group, (79) an imidazolyl lower alkyl group, (80) a pyridylcarbonyl group, (81) an imidazolylcarbonyl group, (82) a lower alkoxycarbonyl lower alkyl group, (83) a carboxy lower alkyl group, (84) a group —(O—$B_{15}$)s-CO—N($R^{26}$)$R^{27}$, (85) a group —N($R^{28}$)—CO—$B_{16}$—N($R^{29}$)$R^{30}$, (86) a group —N($R^{31}$)—$B_{17}$—CO—N($R^{32}$)$R^{33}$ (87) a benzoxazolyl group, (88a) a benzothienyl group, (89a) an oxo group, and (90a) a 1,2,3,4-tetrahydroquinolyl group that may have an oxo group as a substituent on the tetrahydroquinoline ring, $B_{12}$ represents a lower alkylene group, t represents 0 or 1, each of $R^{20}$ and $R^{21}$, which are identical or different, represents a hydrogen atom; a cycloalkyl group; an amino group that may have a lower alkoxycarbonyl group as a substituent; a benzoyl group that may have 1 to 3 lower alkoxy groups as a substituent(s) on the phenyl ring; a lower alkyl group; a lower alkyl group having 1 to 2 phenyl groups that may be substituted, on the phenyl ring, by 1 to 3 groups selected from the group consisting of a lower alkoxycarbonyl group, a cyano group, a nitro group, a phenyl group, a halogen atom, a lower alkyl group that may have a halogen atom as a substituent, a lower alkoxy group that may have a halogen atom as a substituent, and a lower alkylthio group; a phenyl group that may be substituted, on the phenyl ring, by 1 to 3 groups selected from the group consisting of a lower alkoxy group that may have a halogen atom as a substituent and a lower alkyl group that may have a halogen atom as a substituent; a lower alkoxycarbonyl group; a cycloalkyl lower alkyl group; a pyrrolidinyl lower alkyl group that may have 1 to 3 lower alkyl groups that may have a hydroxyl group as a substituent on the pyrrolidine ring; an amino-substituted lower alkyl group that may have a group selected from the group consisting of a phenyl group and a lower alkyl group as a substituent; a 1,2,3,4-tetrahydronaphthyl-substituted lower alkyl group that may have 1 to 5 lower alkyl groups as a substituent(s) on the 1,2,3,4-tetrahydronaphthalene ring; a naphthyl lower alkyl group; a pyridyl lower alkyl group; a quinolyl lower alkyl group; a 1,2,3,4-tetrazolyl lower alkyl group that may have 1 to 3 groups selected from the group consisting of a lower alkyl group and a phenyl lower alkyl group as a substituent(s) on the tetrazole ring; a 1,2,4-triazolyl lower alkyl group; a tetrahydrofuryl lower alkyl group that may have a hydroxyl group as a substituent on the lower alkyl group; a phenoxy lower alkyl group that may have 1 to 3 groups selected from the group consisting of a lower alkyl group and a nitro group as a substituent(s) on the phenyl ring; a phenyl lower alkanoyl group; a lower alkanoyl group that may have a halogen atom as a substituent; an imidazolyl lower alkanoyl group; a lower alkoxycarbonyl lower alkyl group; a pyridyl group; or a carboxy lower alkyl group, or $R^{20}$ and $R^{21}$, together with the nitrogen atom to which they bind, may bind to each other, directly or via a nitrogen atom, oxygen atom, or sulfur atom to form a 5- to 7-membered saturated heterocyclic ring, wherein the heterocyclic ring may be substituted by 1 to 3 groups selected from the group consisting of a lower alkyl group, a phenyl group that may have 1 to 3 groups selected from the group consisting of a halogen atom and a lower alkyl group that may have a halogen atom as a substituent(s) on the phenyl ring, and a phenyl lower alkyl group that may have a lower alkylenedioxy group as a substituent on the phenyl ring, o represents 0 or 1, $B_{13}$ represents a lower alkylene group, each of $R^{22}$ and $R^{23}$, which are identical or different, represents a hydrogen atom, a lower alkyl group, a benzoyl group that may have 1 to 3 lower alkoxy groups as a substituent(s) on the phenyl ring, a phenoxy lower alkyl group that may have a lower alkyl group as a substituent on the phenyl ring, a phenyl lower alkyl group, or a phenyl group, or $R^{22}$ and $R^{23}$, together with the nitrogen atom to which they bind, may bind to each other, directly or via a nitrogen atom, oxygen atom, or sulfur atom to form a 5- to 7-membered saturated heterocyclic ring, wherein the heterocyclic ring may be substituted by 1 to 3 groups selected from the group consisting of a lower alkyl group and a phenyl lower alkyl group that may have a lower alkylenedioxy group as a substituent on the phenyl ring, $B_{15}$ represents a lower alkylene group, s represents 0 or 1, each of $R^{26}$ and $R^{27}$, which are identical or different, represents a hydrogen atom, a lower alkyl group, a phenyl lower alkyl group, or an imidazolyl lower alkyl group, or $R^{26}$ and $R^{27}$, together with the nitrogen atom to which they bind, may bind to each other, directly or via a nitrogen atom, oxygen atom, or sulfur atom to form a 5- to 7-membered saturated heterocyclic ring, wherein the heterocyclic ring may be substituted by 1 to 3 phenyl lower alkyl groups that may have a lower alkylenedioxy group as a substituent on the phenyl ring, as a substituent(s), $R^{28}$ represents a hydrogen atom or a lower alkyl group, $B_{16}$ represents a lower alkylene group, $R^{29}$ and $R^{30}$, together with the nitrogen atom to which they bind, may bind to each other, directly or via a nitrogen atom, oxygen atom, or sulfur atom to form a 5- to 7-membered saturated heterocyclic group, wherein the heterocyclic ring may be substituted by 1 to 3 groups selected from the group consisting of a lower alkyl group, a phenyl group, and a phenyl lower alkyl group that may have a lower alkylenedioxy group as a substituent on the phenyl ring, $R^{31}$ represents a hydrogen atom or a lower alkyl group, $B_{17}$ represents a lower alkylene group, $R^{32}$ and $R^{33}$, together with the nitrogen atom to which they bind, may bind to each other, directly or via a nitrogen atom, oxygen atom, or sulfur atom to form a 5- to 7-membered saturated heterocyclic group, wherein the heterocyclic ring may be substituted by 1 to 3 groups selected from the group consisting of a lower alkyl group, a phenyl group, and a phenyl lower alkyl group that may have a lower alkylenedioxy group as a substituent on the phenyl ring, provided that the above described aromatic compound or a salt thereof satisfy the following requirements (i) to (v):

(i) when $X_1$ represents a group —CH=, then $R^3$ represents a hydrogen atom;

(ii) when $X_1$ represents a group —CH=, l represents 1, T represents —CO—, and $R^{14}$ represents a hydrogen atom or an alkyl group that may have a hydroxyl group as a substituent, then $R^{15}$ represents the group (24) described above;

(iii) when $X_1$ represents a group —CH=, 8 represents 1, and T represents —N($R^{17}$)—$B_3$—CO—, then $R^{14}$ and $R^{15}$, together with the nitrogen atom to which they bind, may bind to each other, directly or via a nitrogen atom, oxygen atom, or sulfur atom to form a 5- to 10-membered saturated or unsaturated heterocyclic ring, wherein the heterocyclic ring is substituted by 1 to 3 groups of (28) described above;

(iv) when $X_1$ represents a nitrogen atom, and l represents 0, or when $X_1$ represents a nitrogen atom, l represents 1, and T represents —CO— or —SO$_2$, then $R^{15}$ is not the group being any one of (5), (7), (19), and (20) described above; and (v) when $R^6$ represents a cycloalkyl group wherein the cycloalkyl ring may be substituted by a group selected from the group consisting of an amino-substituted lower alkyl group that may have a lower alkyl group and a lower alkyl group that may have a halogen atom as a substituent, then $R^{14}$ represents a group -(T)$_l$-N($R^{14}$)$R^{15}$ (wherein T and l have the same meanings as described above, and $R^{14}$ and $R^{15}$, together with the nitrogen atom to which they bind, may bind to each other, directly or via a nitrogen atom, oxygen atom, or sulfur atom to form a 5- to 10-membered saturated heterocyclic ring; or $R^{14}$ and $R^{15}$ form a group)].

The above aromatic compound represented by the general formula (1) or a salt thereof includes the following aromatic compounds or salts thereof represented by the general formulas (1-1) to (1-7):

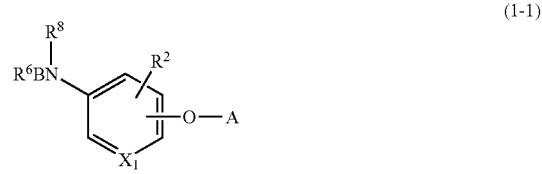
(1-1)

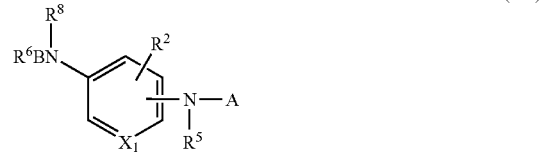
(1-2)

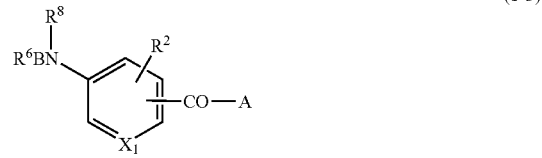
(1-3)

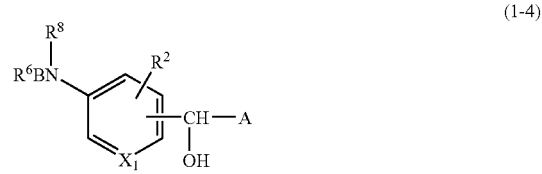
(1-4)

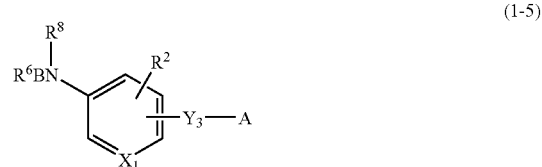
(1-5)

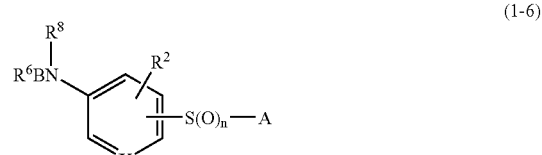
(1-6)

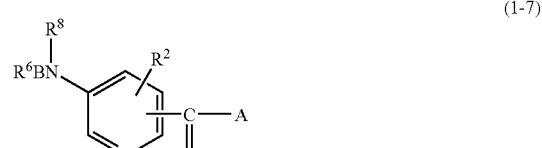
(1-7)

[wherein, in said general formulas (1-1) to (1-7), $R^6$, B, $R^8$, $R^2$, $R^5$, n, $X_1$, and A have the same meanings as described above, and $Y_3$ represents a lower alkylene group].

The above aromatic compound represented by the general formula (1) or a salt thereof includes the following aromatic compounds or salts thereof represented by the general formulas (1-8) to (1-14):

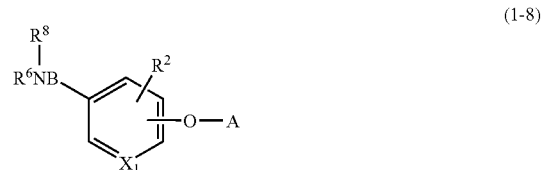
(1-8)

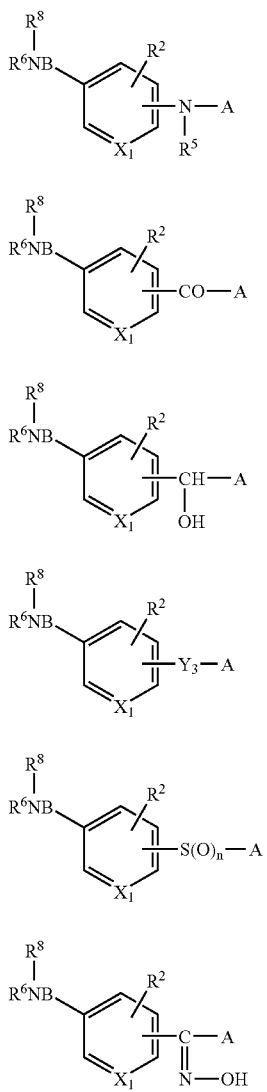

(1-9)
(1-10)
(1-11)
(1-12)
(1-13)
(1-14)

[wherein, in said general formulas (1-8) to (1-14), $R^6$, B, $R^8$, $R^2$, $R^5$, n, $X_1$, A and $Y_3$ have the same meanings as described above].

The above aromatic compound represented by the general formula (1) or a salt thereof includes the following aromatic compounds or salts thereof represented by the general formulas (1-15) to (1-21):

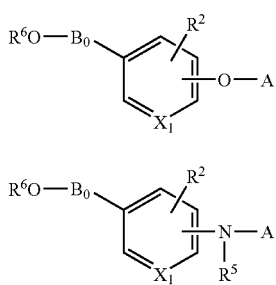

(1-15)
(1-16)

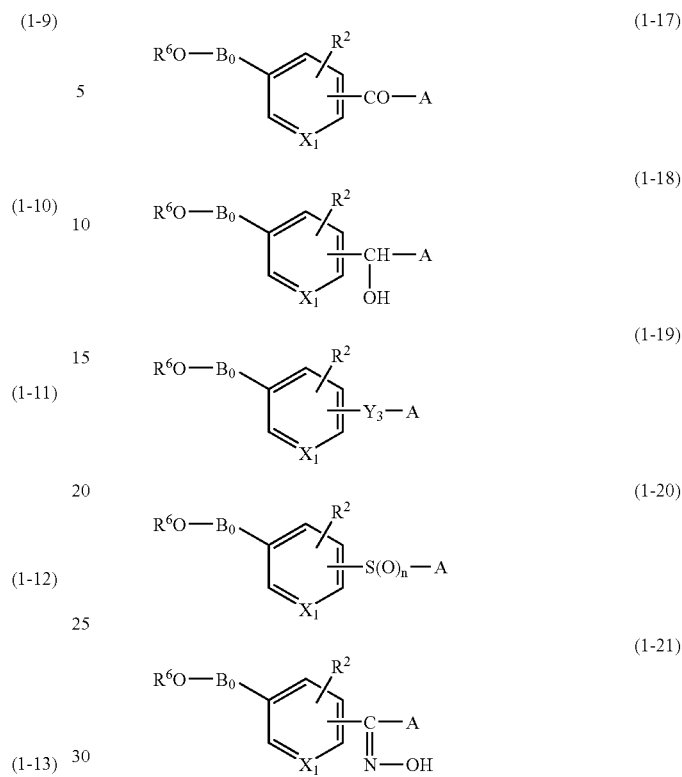

(1-17)
(1-18)
(1-19)
(1-20)
(1-21)

[wherein, in said general formulas (1-15) to (1-21), $R^6$, $B_0$, $R^2$, $R^5$, n, $X_1$, A and $Y_3$ have the same meanings as described above].

The above aromatic compound represented by the general formula (1) or a salt thereof includes the following aromatic compounds or salts thereof represented by the general formulas (1-22) to (1-28):

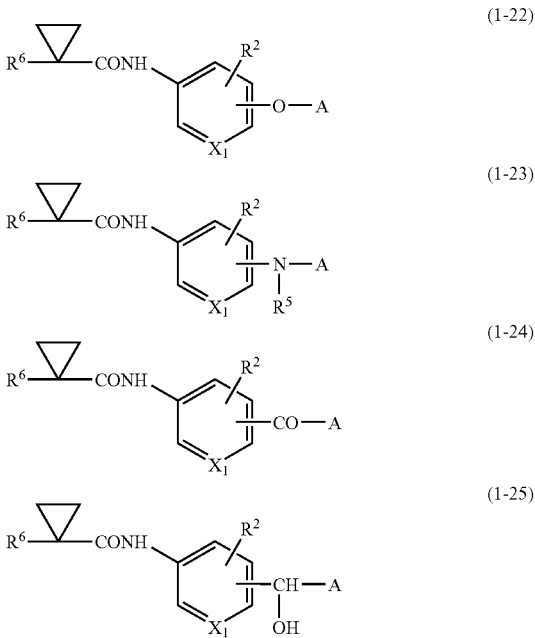

(1-22)
(1-23)
(1-24)
(1-25)

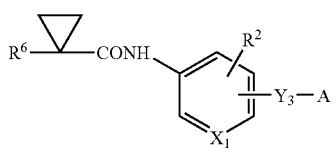 (1-26)

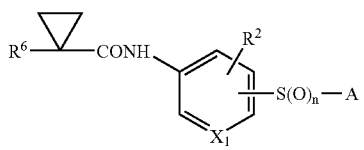 (1-27)

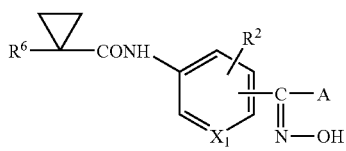 (1-28)

[wherein, in said general formulas (1-22) to (1-28), $R^6$, $R^2$, $R^5$, n, $X_1$, A and $Y_3$ have the same meanings as described above].

The above aromatic compound represented by the general formula (1) or a salt thereof includes the following aromatic compounds or salts thereof represented by the general formulas (1-29) to (1-35):

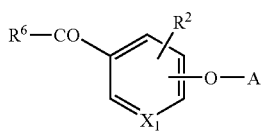 (1-29)

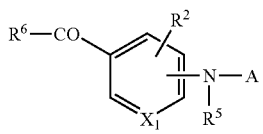 (1-30)

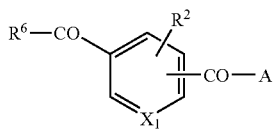 (1-31)

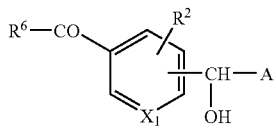 (1-32)

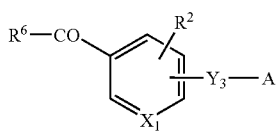 (1-33)

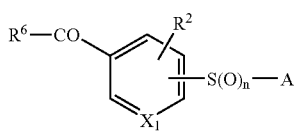 (1-34)

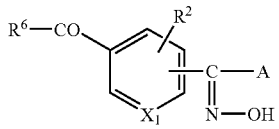 (1-35)

[wherein, in said general formulas (1-29) to (1-35), $R^6$, $R^2$, $R^5$, n, $X_1$, A and $Y_3$ have the same meanings as described above].

The above aromatic compound represented by the general formula (1) or a salt thereof includes the following aromatic compounds or salts thereof represented by the general formulas (1-36) to (1-42):

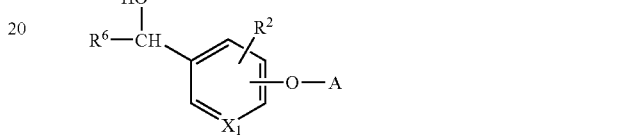 (1-36)

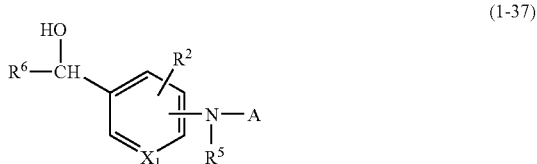 (1-37)

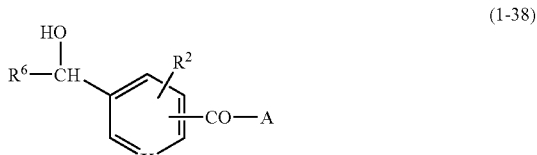 (1-38)

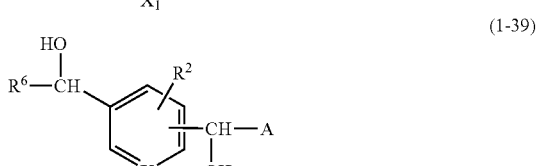 (1-39)

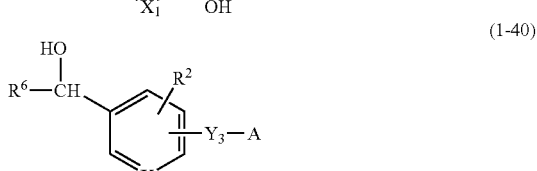 (1-40)

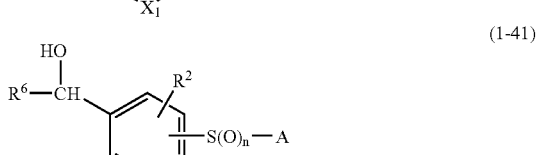 (1-41)

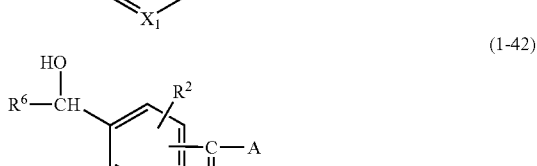 (1-42)

[wherein, in said general formulas (1-36) to (1-42), $R^6$, $R^2$, $R^5$, n, $X_1$, A and $Y_3$ have the same meanings as described above].

The above aromatic compound represented by the general formula (1) or a salt thereof includes the following aromatic compounds or salts thereof represented by the general formulas (1-43) to (1-49):

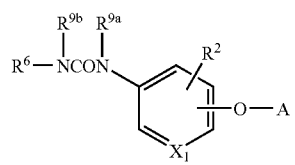
(1-43)

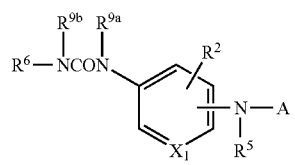
(1-44)

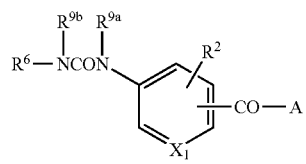
(1-45)

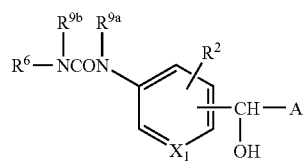
(1-46)

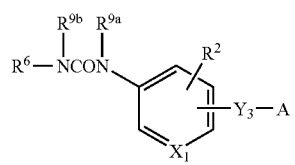
(1-47)

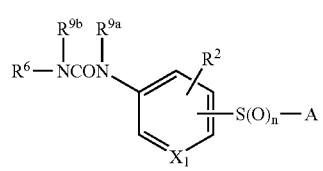
(1-48)

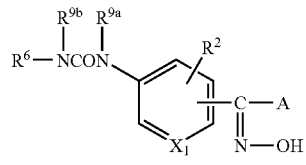
(1-49)

[wherein, in said general formulas (1-43) to (1-49), $R^6$, $R^2$, $R^5$, n, $X_1$, A, $R^{9a}$, $R^{9b}$ and $Y_3$ have the same meanings as described above].

The above aromatic compound represented by the general formula (1) or a salt thereof includes the following aromatic compounds or salts thereof represented by the general formulas (1-50) to (1-56):

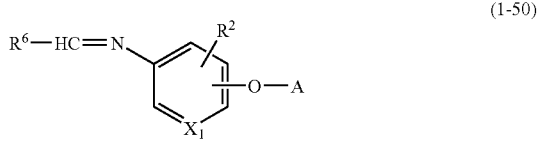
(1-50)

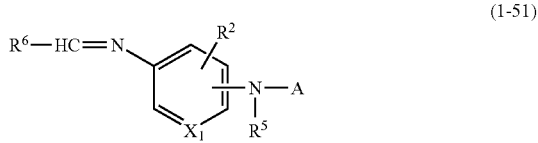
(1-51)

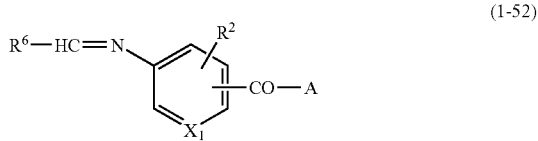
(1-52)

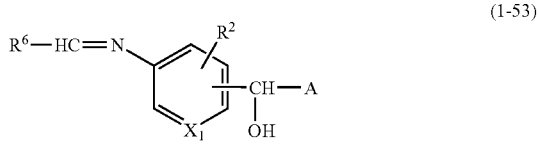
(1-53)

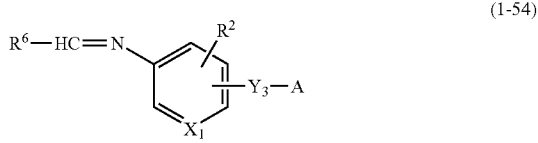
(1-54)

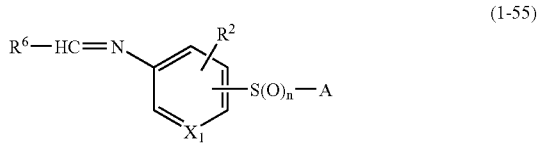
(1-55)

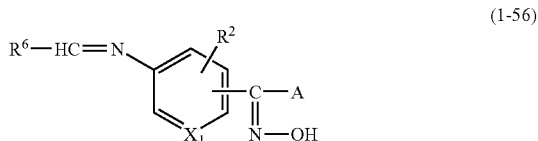
(1-56)

[wherein, in said general formulas (1-50) to (1-56), $R^6$, $R^2$, $R^5$, n, $X_1$, A and $Y_3$ have the same meanings as described above].

The above aromatic compound represented by the general formula (1) or a salt thereof includes the following aromatic compounds or salts thereof represented by the general formulas (1-57) to (1-63):

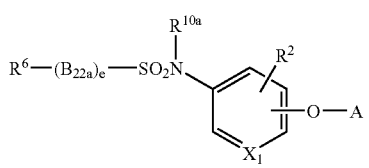
(1-57)

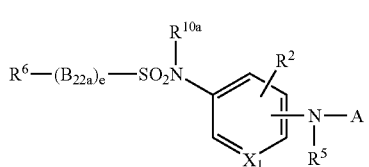
(1-58)

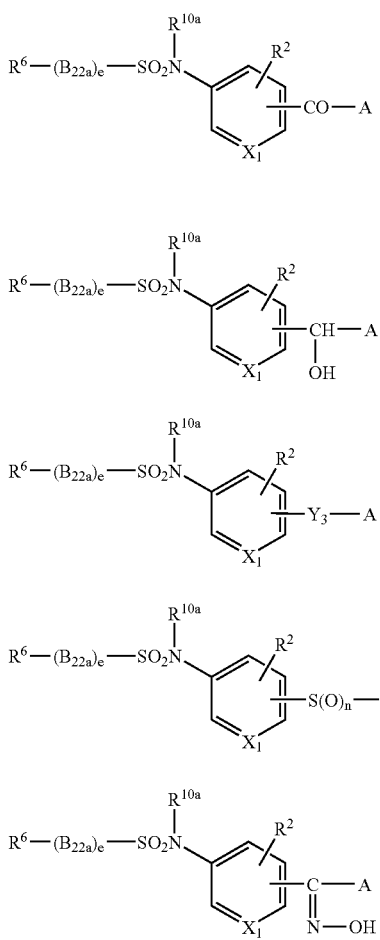

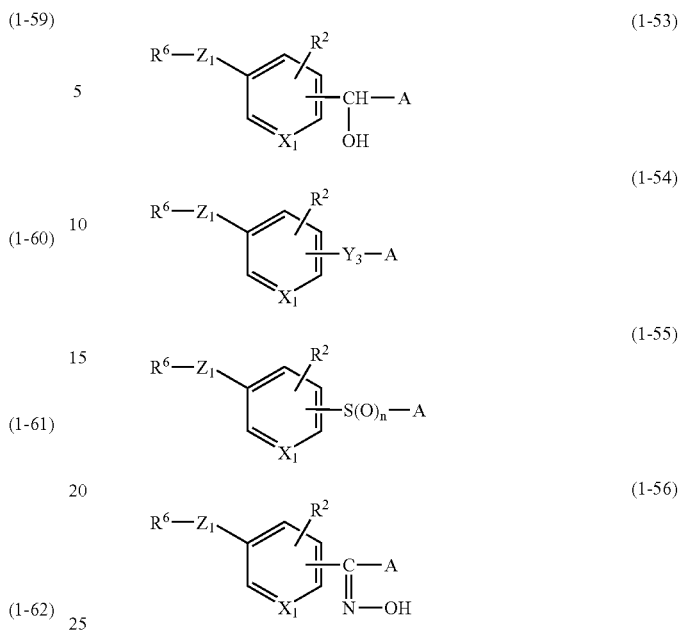

[wherein, in said general formulas (1-64) to (1-70), $R^6$, $R^2$, $R^5$, n, $X_1$, A and $Y_3$ have the same meanings as described above, and $Z_1$ represents a lower alkenylene group].

The above aromatic compound represented by the general formula (1) or a salt thereof includes the following aromatic compounds represented by the general formulas (1-71) to (1-77) or salts thereof:

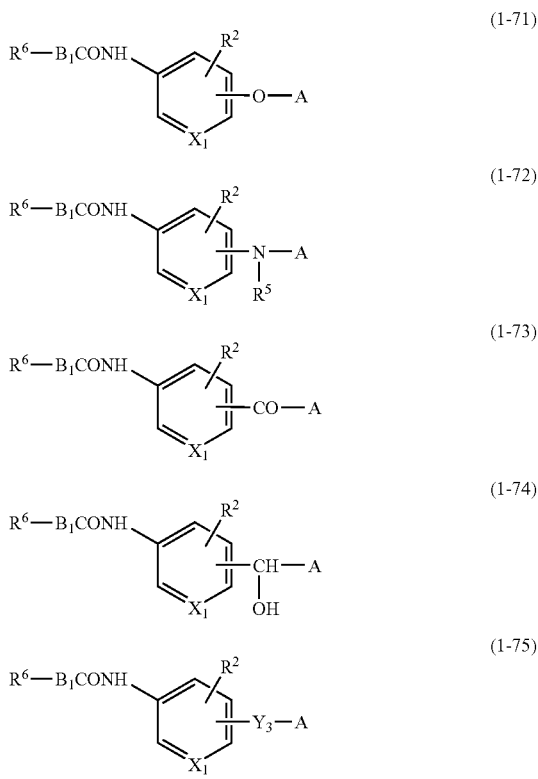

[wherein, in said general formulas (1-57) to (1-63), $R^6$, $R^2$, $R^5$, n, $X_1$, A, $R^{10a}$, $B_{22a}$, e and $Y_3$ have the same meanings as described above].

The above aromatic compound represented by the general formula (1) or a salt thereof includes the following aromatic compounds represented by the general formulas (1-64) to (1-70) or salts thereof:

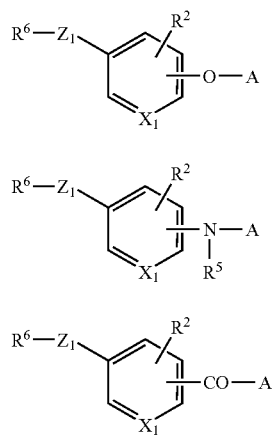

-continued

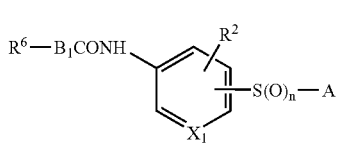
(1-76)

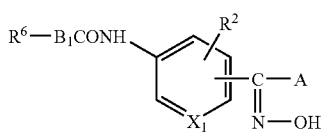
(1-77)

[wherein, in said general formulas (1-71) to (1-77), $R^6$, $R^{25}$, $B_1$, $R^5$, n, $X_1$, A and $Y_3$ have the same meanings as described above].

The above aromatic compound represented by the general formula (1) or a salt thereof includes the following aromatic compounds represented by the general formulas (1-78) to (1-84) or salts thereof:

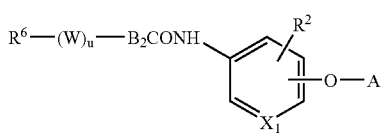
(1-78)

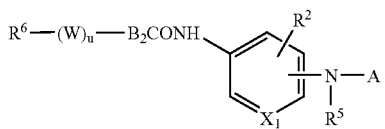
(1-79)

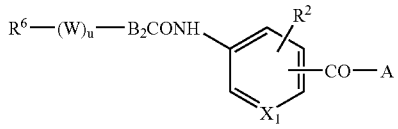
(1-80)

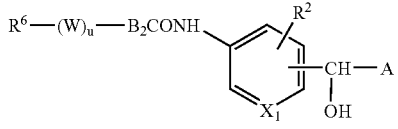
(1-81)

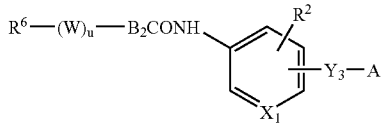
(1-82)

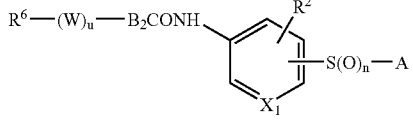
(1-83)

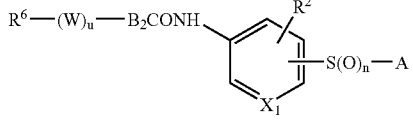
(1-84)

[wherein, in said general formulas (1-78) to (1-84), $R^6$, W, u, $B_2$, $R^2$, $R^5$, n, $X_1$, A and $Y_3$ have the same meanings as described above].

The above aromatic compound represented by the general formula (1) or a salt thereof includes the following aromatic compounds represented by the general formulas (1-85) to (1-91) or salts thereof:

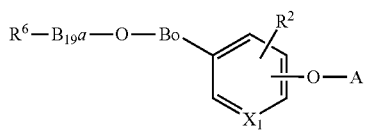
(1-85)

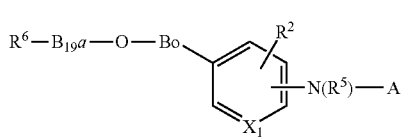
(1-86)

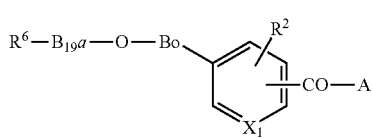
(1-87)

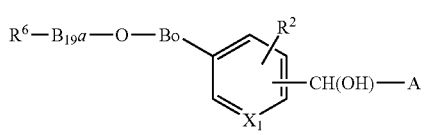
(1-88)

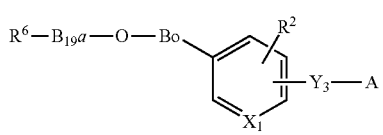
(1-89)

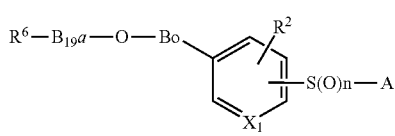
(1-90)

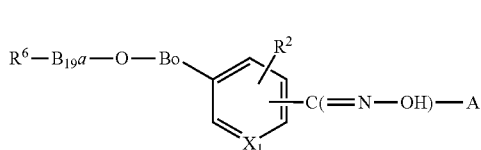
(1-91)

[wherein, in said general formulas (1-85) to (1-91), $R^5$, $R^6$, $B_{19a}$, $B_0$, $R^2$, $X_1$, n, A and $Y_3$ have the same meanings as described above].

The above aromatic compound represented by the general formula (1) or a salt thereof includes the following aromatic compounds represented by the general formulas (1-92) to (1-98) or salts thereof:

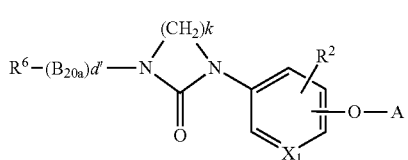
(1-92)

-continued (1-93)
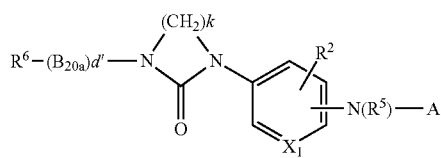

(1-94)
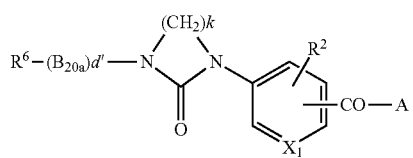

(1-95)
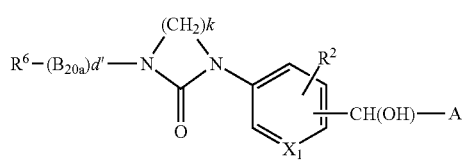

(1-96)
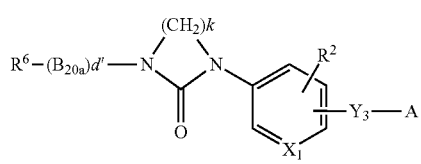

(1-97)
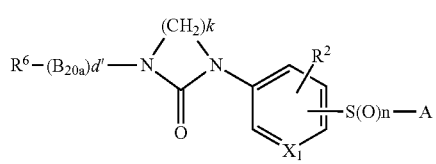

(1-98)
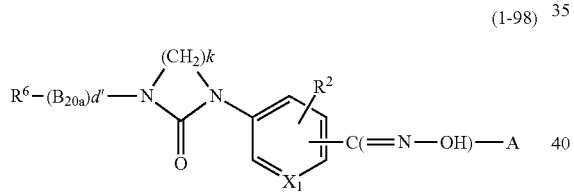

[wherein, in said general formulas (1-92) to (1-98), $R^5$, $R^6$, $B_{20a}$, $R^2$, $X_1$, A, n, d', k and $Y_3$ have the same meanings as described above].

The above aromatic compound represented by the general formula (1) or a salt thereof includes the following aromatic compounds represented by the general formulas (1-99) to (1-105) or salts thereof:

(1-99)
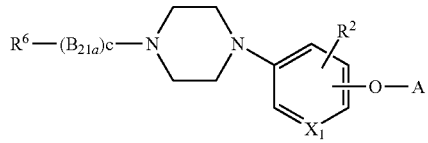

(1-100)
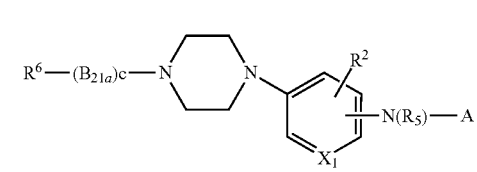

(1-101)
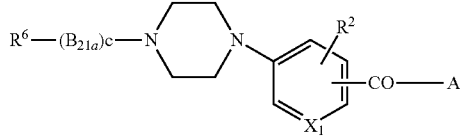

(1-102)
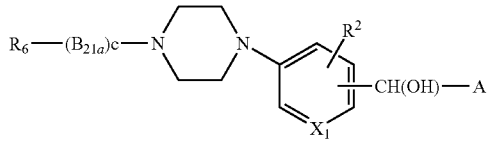

(1-103)
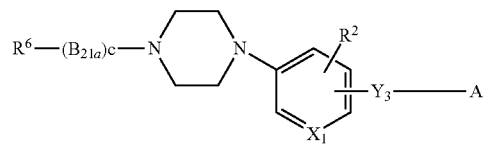

(1-104)
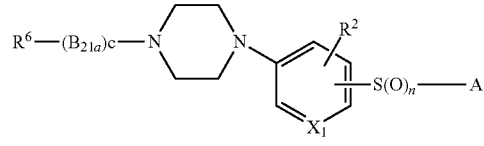

(1-105)
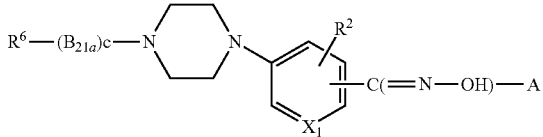

[wherein, in said general formulas (1-99) to (1-105), $R^6$, $R^5$, $B_{21a}$, $R^2$, $X_1$, A, n, c and $Y_3$ have the same meanings as described above].

The above aromatic compound represented by the general formula (1) or a salt thereof includes the following aromatic compounds represented by the general formulas (1-106) to (1-112) or salts thereof:

(1-106)
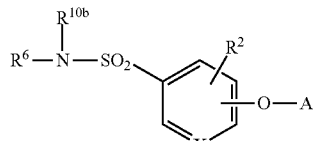

(1-107)
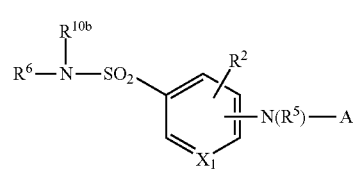

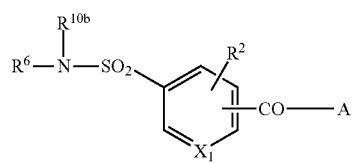 (1-108)

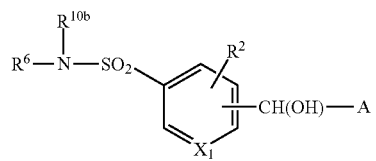 (1-109)

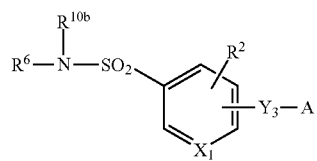 (1-110)

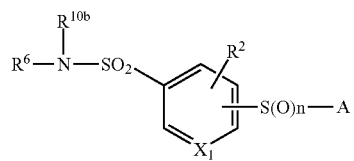 (1-111)

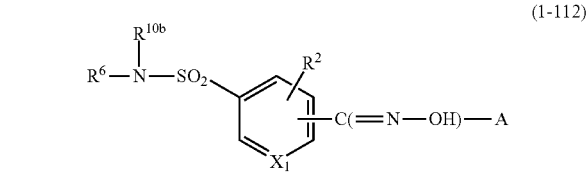 (1-112)

[wherein, in said general formulas (1-106) to (1-112), $R^5$, n, $R^5$, $R^6$, $X_1$, $R^2$, A and $Y_3$ have the same meanings as described above].

The above aromatic compound represented by the general formula (1) or a salt thereof includes the following aromatic compounds represented by the general formulas (1-113) to (1-119) or salts thereof:

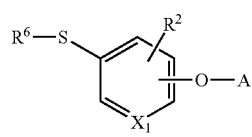 (1-113)

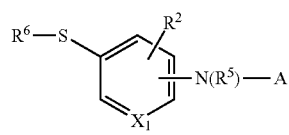 (1-114)

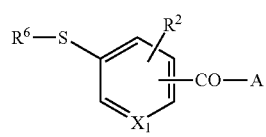 (1-115)

 (1-116)

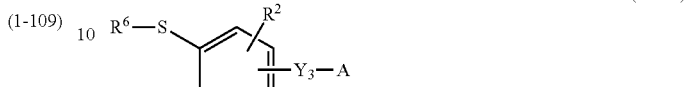 (1-117)

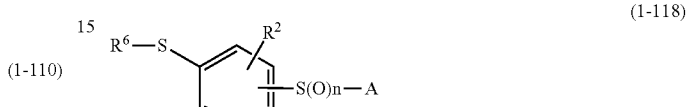 (1-118)

 (1-119)

[wherein, in said general formulas (1-113) to (1-119), $R^6$, $R^2$, $X_1$, $R^5$, n, A and $Y_3$ have the same meanings as described above].

The above aromatic compound represented by the general formula (1) or a salt thereof includes the following aromatic compounds represented by the general formulas (1-120) to (1-126) or salts thereof:

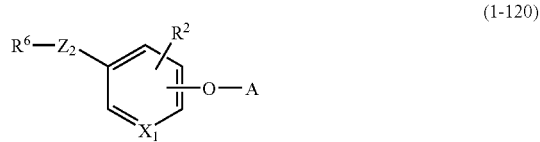 (1-120)

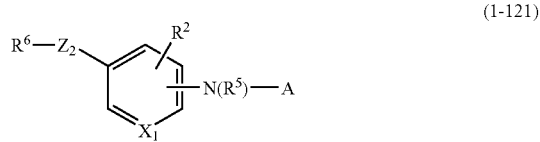 (1-121)

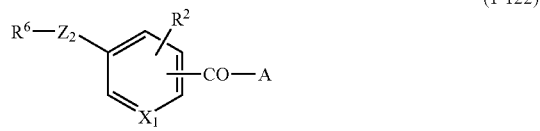 (1-122)

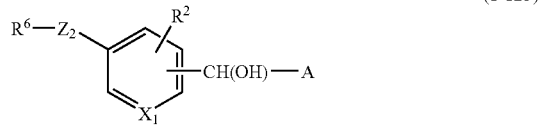 (1-123)

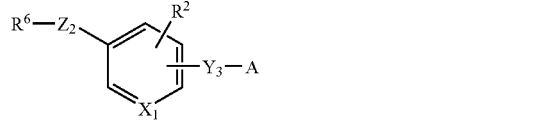 (1-124)

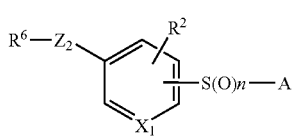
(1-125)

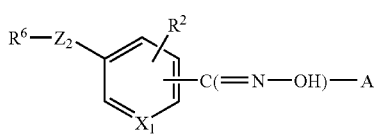
(1-126)

[wherein, in said general formulas (1-120) to (1-126), $R^6$, $R^2$, $X_1$, A, $R^5$, n and $Y_3$ have the same meanings as described above, and $Z_2$ represents a lower alkynylene group].

The above aromatic compound represented by the general formula (1) or a salt thereof includes the following aromatic compounds represented by the general formulas (1-127) to (1-133) or salts thereof:

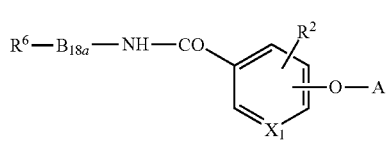
(1-127)

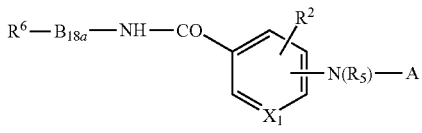
(1-128)

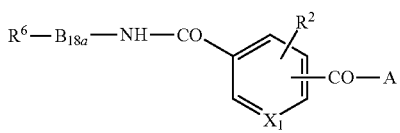
(1-129)

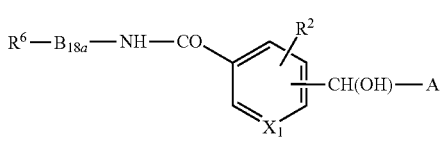
(1-130)

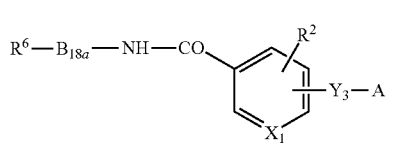
(1-131)

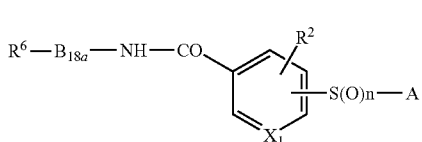
(1-132)

(1-133)

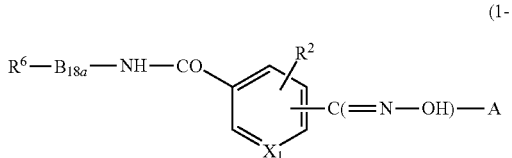

[wherein, in said general formulas (1-127) to (1-133), $R^6$, $B_{18a}$, $R^2$, $X_1$, A, $R^5$, n and $Y_3$ have the same meanings as described above].

The above aromatic compound represented by the general formula (1) or a salt thereof includes the following aromatic compounds represented by the general formulas (1-134) to (1-140) or salts thereof:

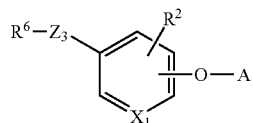
(1-134)

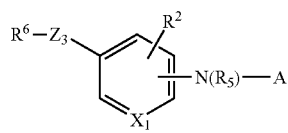
(1-135)

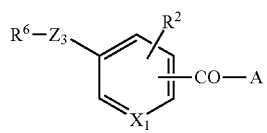
(1-136)

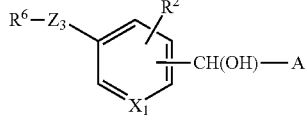
(1-137)

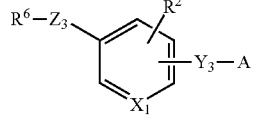
(1-138)

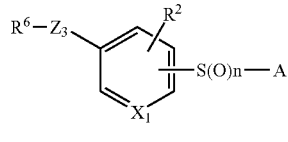
(1-139)

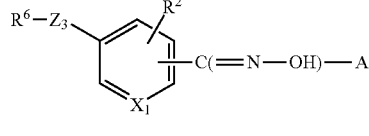
(1-140)

[wherein, in said general formulas (1-134) to (1-140), $R^6$, $R^2$, $X_1$, A, $R^5$, and n have the same meanings as described in claim 1, $Y_3$ has the same meanings as described in claim 2, and $Z_3$ represents a lower alkylene group or a group $$-\underset{R^{8d}}{\underset{|}{N}}-$$

($R^{8d}$ is the same meanings as described above)].

The present invention provides the above-mentioned aromatic compound or salt thereof wherein Y is a group —O—.

The present invention provides the above-mentioned aromatic compound or salt thereof wherein Y is a group —N($R^5$)— ($R^5$ has the same meanings as described above).

The present invention provides the above-mentioned aromatic compound or salt thereof wherein Y is a group —CO—, a group —CH(OH)—, a lower alkylene group, a group —S(O)n- (n has the same meanings as described above), or a group —C(=N—OH)—.

The present invention provides the above-mentioned aromatic compound or salt thereof wherein A is a group

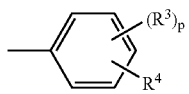

($R^3$, $R^4$ and p have the same meanings as described above).

The present invention provides the above-mentioned aromatic compound or salt thereof wherein A is a group

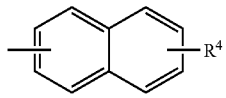

($R^4$ has the same meanings as described above).

The present invention provides the above-mentioned aromatic compound or salt thereof wherein $R^4$ is an imidazolyl lower alkyl group, a 1,2,4-triazolyl lower alkyl group, a 1,2,3-triazolyl lower alkyl group, a 1,2,5-triazolyl lower alkyl group, a pyrazolyl lower alkyl group, a pyrimidinyl lower alkyl group that may have an oxo group as a substituent on the pyrimidine ring, a 3,5-dioxoisoxazolidin-4-ylidene lower alkyl group, a 1,2,4-oxadiazolyl lower alkyl group that may have a lower alkyl group as a substituent on the 1,2,4-oxadiazole ring, a thiazolidinyl lower alkyl group that may have an oxo group as a substituent on the thiazolidine ring, a group

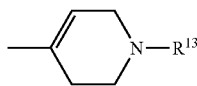

or a group

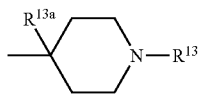

($R^{13}$ and $R^{13a}$ have the same meanings as described above).

The present invention provides the above-mentioned aromatic compound or salt thereof wherein $R^4$ is a group -(T)$_l$-N($R^{14}$)$R^{15}$ (T, $R^{14}$ and $R^{15}$ have the same meanings as described above), and l is 0.

The present invention provides the above-mentioned aromatic compound or salt thereof wherein $R^4$ is a group -(T)$_l$-N($R^{14}$)$R^{15}$ (T, $R^{14}$ and $R^{15}$ have the same meanings as described above), and l is 1.

The present invention provides the above-mentioned aromatic compound or salt thereof wherein $R^4$ is a group -(T)$_l$-N($R^{14}$)$R^{15}$, l is 1, and T is a group —N($R^{17}$)—B$_3$—CO— ($R^{14}$, $R^{15}$, $R^{17}$ and B$_3$ have the same meanings as described above).

The present invention provides the above-mentioned aromatic compound or salt thereof wherein $R^4$ is a group -(T)$_l$-N($R^{14}$)$R^{15}$, l is 1, and T is a group —B$_{19}$—N($R^{18}$)—CO— ($R^{14}$, $R^{15}$, B$_{19}$ and $R^{18}$ have the same meanings as described above).

The present invention provides the above-mentioned aromatic compound or salt thereof wherein $R^4$ is a group -(T)$_l$-N($R^{14}$)$R^{15}$, l is 1, and T is a group —B$_4$—CO— ($R^{14}$, $R^{15}$, and B$_4$ have the same meanings as described above).

The present invention provides the above-mentioned aromatic compound or salt thereof wherein $R^4$ is a group -(T)$_l$-N($R^{14}$)$R^{15}$, l is 1, and T is a group -Q-B$_5$—CO— ($R^{14}$, $R^{15}$, Q and B$_5$ have the same meanings as described above).

The present invention provides the above-mentioned aromatic compound or salt thereof wherein $R^4$ is a group -(T)$_l$-N($R^{14}$)$R^{15}$, l is 1, and T is a group —B$_6$—N($R^{19}$)—B$_7$— ($R^{14}$, $R^{15}$, B$_6$, $R^{19}$ and B$_7$ have the same meanings as described above).

The present invention provides the above-mentioned aromatic compound or salt thereof wherein $R^4$ is a group -(T)$_l$-N($R^{14}$)$R^{15}$, l is 1, and T is a group —CO—B$_8$— ($R^{14}$, $R^{15}$, and B$_8$ have the same meanings as described above).

The present invention provides the above-mentioned aromatic compound or salt thereof wherein $R^4$ is a group -(T)$_l$-N($R^{14}$)$R^{15}$, l is 1, and T is a group —CH(OH)—B$_9$— ($R^{14}$, $R^{15}$, and B$_9$ have the same meanings as described above).

The present invention provides the above-mentioned aromatic compound or salt thereof wherein $R^4$ is a group -(T)$_l$-N($R^{14}$)$R^{15}$, l is 1, and T is a group —CO—B$_{10}$—CO— ($R^{14}$, $R^{15}$, and B$_{10}$ have the same meanings as described above).

The present invention provides the above-mentioned aromatic compound or salt thereof wherein $R^4$ is a group -(T)$_l$-N($R^{14}$)$R^{15}$, l is 1, and T is a group —CH(OH)—B$_{11}$—CO— ($R^{14}$, $R^{15}$, and B$_{11}$ have the same meanings as described above).

The present invention provides the above-mentioned aromatic compound or salt thereof wherein $R^4$ is a group -(T)$_l$-N($R^{14}$)$R^{15}$, l is 1, and T is a group —CO— ($R^{14}$ and $R^{15}$ have the same meanings as described above).

The present invention provides the above-mentioned aromatic compound or salt thereof wherein $R^4$ is a group -(T)$_l$-N($R^{14}$)$R^{15}$, l is 1, and T is a group —SO$_2$— ($R^{14}$ and $R^{15}$ have the same meanings as described above).

The present invention provides the above-mentioned aromatic compound or salt thereof wherein $R^4$ is a group -(T)$_l$-N($R^{14}$)$R^{15}$, l is 1, and T is a group —B$_{23a}$—CO—CO— ($R^{14}$, $R^{15}$ and B$_{23a}$ have the same meanings as described above).

The present invention provides the above-mentioned aromatic compound or salt thereof wherein $R^4$ is a group -(T)$_l$-N($R^{14}$)$R^{15}$, l is 1, and T is a lower alkylene group ($R^{14}$ and $R^{15}$ have the same meanings as described above).

In the above-mentioned aromatic compound represented by the general formula (1) or salt thereof, the aromatic compounds represented by the general formulas (1-1), (1-2), (1-8), (1-9), (1-15), (1-16), (1-29), (1-30), (1-64) and (1-65) or salts thereof are preferable.

Further, those compounds represented by the general formulas (1-1), (1-2), (1-8), (1-9), (1-15), (1-16), (1-29), (1-30), (1-43), (1-44), (1-57), (1-58), (1-64) and (1-65) or salts thereof, wherein Y is a group —O— or a group —N($R^5$)—, A is a group

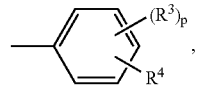

, and $R^4$ is a group -(T)$_l$-N($R^{14}$) $R^{15}$ ($R^3$, $R^4$, $R^5$, $R^{14}$, $R^{15}$, p and l have the same meanings as described above). are more preferable.

The present invention provides the aromatic compounds represented by the general formulas (1-1), (1-2), (1-8), (1-9), (1-15), (1-16), (1-29), (1-30), (1-43), (1-44), (1-57), (1-58), (1-64) and (1-65) or salts thereof, wherein
l is 1, and T is a group —N($R^{17}$)—$B_3$—CO— ($R^{17}$ and $B_3$ have the same meanings as described above).

The present invention provides the aromatic compounds represented by the general formulas (1-1), (1-2), (1-8), (1-9), (1-15), (1-16), (1-29), (1-30), (1-43), (1-44), (1-57), (1-58), (1-64) and (1-65) or salts thereof, wherein
l is 1, and T is a group —$B_4$—CO— ($B_4$ have the same meanings as described above).

The present invention provides the aromatic compounds represented by the general formulas (1-1), (1-2), (1-8), (1-9), (1-15), (1-16), (1-29), (1-30), (1-43), (1-44), (1-57), (1-58), (1-64) and (1-65) or salts thereof, wherein
l is 1, and T is a group —CO—.

The present invention provides the aromatic compounds represented by the general formulas (1-1), (1-2), (1-8), (1-9), (1-15), (1-16), (1-29), (1-30), (1-43), (1-44), (1-57), (1-58), (1-64) and (1-65) or salts thereof, wherein
l is 0.

The present invention particularly provides the aromatic compounds selected from the group consisting of:

N-[6-(4-{[2-(4-piperonylpiperazin-1-yl)-2-oxoethyl]ethylamino}-2-methoxyphenoxy)pyridin-3-yl]-3,4-dichlorobenzamide, N-[6-(4-{[2-(4-piperonylpiperazin-1-yl)-2-oxoethyl]ethylamino}phenoxy)pyridin-3-yl]-4-trifluoromethylbenzamide, N-[6-(4-{[2-(4-piperonylpiperazin-1-yl)-2-oxoethyl]ethylamino}-2-fluorophenoxy)pyridin-3-yl]-4-trifluoromethylbenzamide, N-[6-(4-{[2-(4-piperonylpiperazin-1-yl)-2-oxoethyl]methylamino}-2-fluorophenoxy)pyridin-3-yl]-4-trifluoromethylbenzamide, N-[6-(4-{[2-(4-piperonylpiperazin-1-yl)-2-oxoethyl]methylamino}-2-methoxyphenoxy)pyridin-3-yl]-4-trifluoromethylbenzamide, N-[6-(4-{[2-(4-piperonylpiperazin-1-yl)-2-oxoethyl]ethylamino}-2-methoxyphenoxy)pyridin-3-yl]-4-trifluoromethylbenzamide, N-[6-(4-{[2-(4-piperonylpiperazin-1-yl)-2-oxoethyl]ethylamino}-2-methylphenoxy)pyridin-3-yl]-3,4-dichlorobenzamide, N-[6-(4-{[2-(4-piperonylpiperazin-1-yl)-2-oxoethyl]methylamino}-2-methylphenoxy)pyridin-3-yl]-4-trifluoromethylbenzamide, N-(6-{4-[3-(4-piperonylpiperazin-1-yl)-3-oxopropyl]phenoxy}pyridin-3-yl)-3,4-dichlorobenzenesulfonamide, N-[6-(4-{4-[2-(4-piperonylpiperazin-1-yl)-2-oxoethyl]piperazin-1-yl}phenoxy)pyridin-3-yl]-4-trifluoromethylbenzamide, N-[6-(4-{4-[2-(4-piperonylpiperazin-1-yl)-2-oxoethyl]piperidin-1-yl}phenoxy)pyridin-3-yl]-4-trifluoromethylbenzamide, N-{6-[(4-{4-[2-(4-piperonylpiperazin-1-yl)-2-oxoethyl]piperidin-1-yl}phenyl)methylamino]pyridin-3-yl}-4-trifluoromethylbenzamide, N-[6-(4-{4-[2-(4-benzylpiperazin-1-yl)-2-oxoethyl]piperidin-1-yl}-2-methylphenoxy)pyridin-3-yl]-4-trifluoromethylbenzamide, N-[6-(4-{4-[2-(4-piperonylpiperazin-1-yl)-2-oxoethyl]piperidin-1-yl}-2-methylphenoxy)pyridin-3-yl]-4-trifluoromethylbenzamide, N-[6-(4-{4-[2-(4-piperonylpiperazin-1-yl)-2-oxoethyl]piperidin-1-yl}-2-methylphenoxy)pyridin-3-yl]-3,4-dichlorobenzamide, N-{6-[4-(4-benzylpiperazine-1-carbonyl)-phenoxy]pyridin-3-yl}-4-trifluoromethylbenzamide, N-{6-[4-(4-benzylpiperazine-1-carbonyl)phenoxy]pyridin-3-yl}-3,4-dichlorobenzamide, N-[6-({4-[3-(4-piperonylpiperazin-1-yl)-3-oxopropyl]phenyl}methylamino)pyridin-3-yl]-4-trifluoromethylbenzamide, N-[6-(4-{[2-(4-piperonylpiperazin-1-yl)-2-oxoethyl]ethylamino}-2-fluorophenoxy)pyridin-3-yl]-3,4-dichlorobenzamide, N-[6-(4-{[2-(4-piperonylpiperazin-1-yl)-2-oxoethyl]methylamino}-2-fluorophenoxy)pyridin-3-yl]-3,4-dichlorobenzamide, N-[6-(4-{[2-(4-piperonylpiperazin-1-yl)-2-oxoethyl]methylamino}-2-methoxyphenoxy)pyridin-3-yl]-3,4-dichlorobenzamide, N-[6-(4-{[2-(4-piperonylpiperazin-1-yl)-2-oxoethyl]methylamino}phenoxy)pyridin-3-yl]-3,4-dichlorobenzamide, 1-(6-{4-[3-(4-piperonylpiperazin-1-yl)-3-oxopropyl]phenoxy}pyridin-3-yl)-3-(3,4-dichlorophenyl)-1-ethylurea, N-(6-{4-[3-(4-piperonylpiperazin-1-yl)-3-oxopropyl]phenoxy}pyridin-3-yl)-4-trifluoromethylbenzamide, N-[6-(4-{[2-(4-benzylpiperazin-1-yl)-2-oxoethyl]methylamino}-2-methylphenoxy)pyridin-3-yl]-4-trifluoromethylbenzamide, N-[6-(4-{4-[2-(4-benzylpiperazin-1-yl)-2-oxoethyl]piperidin-1-yl}phenoxy)pyridin-3-yl]-3,4-dichlorobenzamide, N-(6-{4-[3-(4-piperonylpiperazine-1-carbonyl)piperidin-1-yl]phenoxy}pyridin-3-yl)-3,4-dichlorobenzamide, N-[6-(4-{4-[2-(4-benzylpiperazin-1-yl)-2-oxoethyl]piperidin-1-yl}phenoxy)pyridin-3-yl]-4-trifluoromethylbenzamide, N-{6-[(4-{4-[2-(4-benzylpiperazin-1-yl)-2-oxoethyl]piperidin-1-yl}phenyl)methylamino]pyridin-3-yl}-4-trifluoromethylbenzamide, N-(6-{4-[(2-{4-[4-(4-fluorobenzoyl)phenyl]-piperazin-1-yl}-2-oxoethyl)methylamino]-2-methoxyphenoxy}pyridin-3-yl)-4-trifluoromethylbenzamide, 2-(4-piperonylpiperazin-1-yl)-N-{3-methyl-4-[5-(4-trifluoromethylphenoxymethyl)pyridin-2-yloxy]phenyl}-2-oxoacetamide, N-[6-(4-{[2-(4-piperonylpiperazin-1-yl)-2-oxoethyl]methylamino}-2-methylphenoxy)pyridin-3-yl]-2-fluoro-4-trifluoromethylbenzamide, N-[6-(4-{4-[2-(4-piperonylpiperazin-1-yl)-2-oxoethyl]piperidin-1-yl}-2-methoxyphenoxy)pyridin-3-yl]-4-trifluoromethylbenzamide, and 4-(3-{3-methyl-4-[5-(4-trifluoromethyl-benzoylamino)pyridin-2-yloxy]phenyl}-2-oxohexahydropyrimidin-1-yl)benzoic acid ethyl ester, or salts thereof.

The present invention provides processes for preparing the aromatic compound represented by the general formula (1) or a salt thereof according to any one of the processes described in Reaction formulas-1 to 46, 48, 49, 52, 59, 104, 105, 108 to 132 and 135 mentioned below.

The present invention provides a pharmaceutical composition for the treatment of fibrosis, which comprises an aromatic compound represented by the general formula (1A) or a salt thereof:

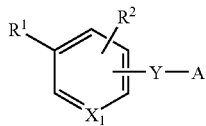
(1A)

[wherein $X_1$ represents a nitrogen atom or a group —CH=,
$R^1$ represents a group —Z—$R^6$,
Z represents a group —N($R^8$)—B—, a group —B—N($R^8$)—, a group —$B_0$—O—, a group

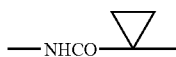

a group —CO—, a group —CH(OH)—, a group

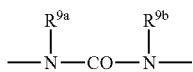

a group —N=CH—, a group

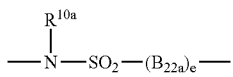

a lower alkenylene group, a group —NHCO—$B_1$—, a group —NHCO—$B_2$—(W)u-, a group —$B_0$—O—$B_{19a}$—, a group

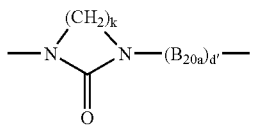

a group

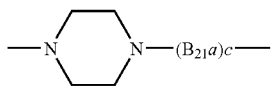

a group

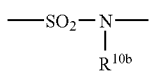

a group —S—, a lower alkynylene group, a lower alkylene group, a group

or a group —CO—NH—$B_{18}$a-, wherein $R^8$ represents a hydrogen atom, a lower alkyl group that may have a lower alkoxy group as a substituent, a lower alkanoyl group, a phenyl lower alkyl group, or a lower alkylsulfonyl group,
B represents a group —CO— or a lower alkylene group,
$B_0$ represents a lower alkylene group,
each of $R^{9a}$ and $R^{9b}$, which are identical or different, represents a hydrogen atom or a lower alkyl group
$R^{10a}$ represents a hydrogen atom or a lower alkyl group,
$B_{22a}$ represents a lower alkylene group or a lower alkenylene group,
e represents 0 or 1,
$B_1$ represents a lower alkenylene group that may have a phenyl group as a substituent,
$B_2$ represents a lower alkylene group that may be substituted by a group selected from the group consisting of a lower alkoxy group and a phenyl group,
W represents an oxygen atom, a group —NH—, or a sulfur atom,
u represents 0 or 1,
$B_{18a}$ represents a lower alkylene group,
$B_{19a}$ represents a lower alkylene group,
$B_{20a}$ represents a lower alkylene group,
$B_{21a}$ represents a lower alkylene group,
$R^{8d}$ represents a hydrogen atom or a lower alkyl group,
k represents 2 or 3,
c represents 0 or 1,
d' represents 0 or 1,
$R^{10b}$ represents a hydrogen atom or a lower alkyl group,
$R^6$ represents a 5- to 15-membered monocyclic, dicyclic, or tricyclic saturated or unsaturated heterocyclic group having 1 to 4 nitrogen atoms, oxygen atoms, or sulfur atoms (wherein, the heterocyclic ring may be substituted by 1 to 3 groups selected from the group consisting of an oxo group; an optionally halogenated lower alkoxy group; an optionally halogenated lower alkyl group; a halogen atom; a lower alkylsulfonyl group; a phenyl group that may be substituted, on the phenyl ring, by an optionally halogenated lower alkyl group; a lower alkylthio group; a pyrrolyl group; a benzoyl group; a lower alkanoyl group; a lower alkoxycarbonyl group; and an amino group that may have a group selected from the group consisting of a lower alkyl group and a lower alkanoyl group as a substituent), an adamantyl group, a naphthyl group (wherein, the naphthalene ring may be substituted by 1 to 3 groups selected from the group consisting of a lower alkyl group, a halogen atom, and an amino group that may have a group selected from the group consisting of a lower alkyl group and a lower alkanoyl group as a substituent), an alkyl group that may have a lower alkoxy group as a substituent, a cycloalkyl group that may be substituted, on the cycloalkyl ring, by a group selected from the group consisting of an amino-substituted lower alkyl group that may have a lower alkyl group on the amino group and a lower alkyl group that may have a halogen atom as a substituent, a lower alkenyl group that may have a halogen atom as a substituent, a lower alkanoyl group, a benzoyl group that may be substituted, on the phenyl ring, by 1 to 3 groups selected from the group consisting of a lower alkyl group that may have a halogen atom as a substituent and a halogen atom, a group

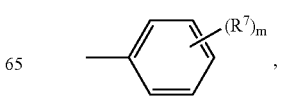

a halogen atom-substituted lower alkyl group, or a cycloalkyl lower alkyl group, $R^7$ represents a hydrogen atom, a phenyl group, a carboxy group, a hydroxyl group, a halogen atom, a lower alkyl group that may have a halogen atom as a substituent, a phenoxy group, a lower alkoxy group that may have a halogen atom as a substituent, a lower alkylenedioxy group, an amino group that may have, as a substituent, a group selected from the group consisting of a lower alkyl group, a lower alkanoyl group, a benzoyl group, and a cycloalkyl group, a cyano group, a lower alkanoyl group that may have a halogen atom as a substituent, a lower alkylsulfonyl group, an aminosulfonyl group, a lower alkoxycarbonyl group, a lower alkanoyloxy group, a 5- or 6-membered saturated or unsaturated heterocyclic group having 1 to 4 nitrogen atoms, oxygen atoms, or sulfur atoms (wherein the heterocyclic ring may be substituted, by an oxo group), or a lower alkoxycarbonyl lower alkyl group, m represents an integer between 1 and 5, wherein when m represents 2 to 5, two to five $R^7$s may be identical or different, $R^2$ represents a hydrogen atom, a halogen atom, or a lower alkyl group, Y represents a group —O—, a group —N($R^5$)—, a group —CO—, a group —CH(OH)—, a lower alkylene group, a group —S(O)n-, or a group —C(=N—OH)—, $R^5$ represents a hydrogen atom, a lower alkyl group, a lower alkanoyl group, a benzoyl group, a phenyl lower alkyl group, or a cycloalkyl group, n represents 0, 1, or 2, A represents a group

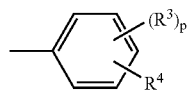

or a group

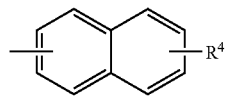

p represents 1 or 2, $R^3$ represents a hydrogen atom, a lower alkoxy group, a halogen atom, a lower alkyl group that may have a halogen atom as a substituent, a lower alkoxycarbonyl group, a carboxy group, a group —CONR$^{11}$R$^{12}$, or a cyano group, wherein each of $R^{11}$ and $R^{12}$, which are identical or different, represents a hydrogen atom, a lower alkyl group, a cycloalkyl group, or a phenyl group, or $R^{11}$ and $R^{12}$, together with the nitrogen atom to which they bind, may bind to each other, directly or via a nitrogen atom, oxygen atom, or sulfur atom to form a 5- to 7-membered saturated heterocyclic ring, $R^4$ represents an imidazolyl lower alkyl group, a 1,2,4-triazolyl lower alkyl group, a 1,2,3-triazolyl lower alkyl group, a 1,2,5-triazolyl lower alkyl group, a pyrazolyl lower alkyl group, a pyrimidinyl lower alkyl group that may have an oxo group as a substituent on the pyrimidine ring, a 3,5-dioxoisoxazolidin-4-ylidene lower alkyl group, a 1,2,4-oxadiazolyl lower alkyl group that may have a lower alkyl group as a substituent on the 1,2,4-oxadiazole ring, a thiazolidinyl lower alkyl group that may have an oxo group as a substituent on the thiazolidine ring, a group

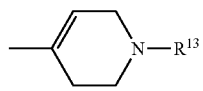

a group

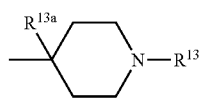

or a group -(T)$_l$-N(R$^{14}$)R$^{15}$, $R^{13}$ represents a hydrogen atom, a lower alkyl group that may have a halogen atom as a substituent, a lower alkanoyl group that may have a halogen atom as a substituent, a lower alkoxycarbonyl group, a phenyl lower alkyl group that may have a lower alkylenedioxy group as a substituent on the phenyl ring, an imidazolyl lower alkyl group, a lower alkoxycarbonyl lower alkyl group, a carboxy lower alkyl group, a benzoyl group, a morpholino-substituted lower alkanoyl group, a piperazinyl carbonyl lower alkyl group that may be substituted, on the piperazine ring, by a phenyl lower alkyl group that may have a lower alkylenedioxy group as a substituent on the phenyl ring, a piperazinyl lower alkanoyl group that may be substituted, on the piperazine ring, by a phenyl lower alkyl group that may have a lower alkylenedioxy group as a substituent on the phenyl ring, a morpholinocarbonyl-substituted lower alkyl group, or an imidazolyl lower alkanoyl group, $R^{13a}$ represents a hydrogen atom or a hydroxyl group, T represents a lower alkylene group, a group —N($R^{17}$)—B$_3$—CO—, a group —(B$_{19}$)$_e$—N($R^8$)—CO—, a group —B$_4$—CO—, a group -Q-B$_5$—CO—, a group —B$_6$—N(R$^{19}$)—B$_7$—CO—, a group —CO—B$_8$—, a group —CH(OH)—B$_9$—, a group —CO—B$_{10}$—CO—, a group —CH(OH)—B$_{11}$—CO—, a group —CO—, a group —SO$_2$—, or a group —B$_{23a}$—CO—CO—, wherein $R^{17}$ represents a hydrogen atom, a lower alkyl group, a cycloalkyl group, a cycloalkylcarbonyl group, a lower alkanoyl group that may have a halogen atom as a substituent, a lower alkenyl group, an amino-substituted lower alkanoyl group that may have a lower alkyl group as a substituent, or a lower alkylsulfonyl group, B$_3$ represents a lower alkylene group, B$_{19}$ represents a lower alkylene group, e represents 0 or 1, $R^{18}$ represents a hydrogen atom or a lower alkyl group, B$_4$ represents a lower alkenylene group or a lower alkylene group that may have a hydroxyl group as a substituent, Q represents an oxygen atom or a group —S(O)n- (wherein n has the same meanings as described above), B$_5$ represents a lower alkylene group, B$_6$ represents a lower alkylene group, $R^{19}$ represents a hydrogen atom or a lower alkanoyl group, B$_7$ represents a lower alkylene group, B$_8$ represents a lower alkylene group, B$_9$ represents a lower alkylene group, B$_{10}$ represents a lower alkylene group, B$_{11}$ represents a lower alkylene group, B$_{23a}$ represents a lower alkylene group, l represents 0 or 1, each of $R^{14}$ and $R^{15}$, which are identical or different represents (1) a hydrogen atom, (2) an alkyl group that may have a hydroxyl group as a substituent, (3) a cycloalkyl group that may have a group selected from the group consisting of a hydroxyl group and a lower alkyl group as a substituent, (4) a phenoxy lower alkyl group, (5) a phenyl group that may be substituted, on the phenyl ring, by 1 to 3 groups selected from the group consisting of a lower alkyl group; a lower alkoxy group that may have a halogen atom as a substituent; a halogen atom; an amino lower alkoxy group that may have a lower alkyl group as a substituent; a hydroxyl group-substituted lower alkyl group; a phenyl lower alkyl group; a lower alkynyl group; an amino group that may have a lower alkylsulfonyl group as a substituent; a lower alkylthio group; a cycloalkyl group; a phenylthio group; an adamantyl group; an anilino group that may have a halogen atom as a substituent on the phenyl ring; a lower alkoxycarbonyl group; a piperazinyl group that may have a lower alkyl group as a substituent on the piperazine ring; a pyrrolidinyl group that may have an oxo group as a substituent on the pyrrolidine ring; a lower alkanoylamino group; a cyano group; and a phenoxy group, (6) a phenoxy group, (7) a phenyl lower alkyl group that may be substituted, on the phenyl ring, by 1 to 3 groups selected from the group consisting of a halogen atom, a lower alkoxy group that may have a halogen atom as a substituent, and a lower alkyl group, (8) a phenyl lower alkyl group that has a lower alkylenedioxy group as a substituent on the phenyl ring, (9) a lower alkanoyl group, (10) a lower alkoxycarbonyl-substituted lower alkyl group, (11) a carboxy-substituted lower alkyl group, (12) an amino group that may have a lower alkanoyl group as a substituent, (13) a 1,2,3,4-tetrahydroquinolyl group that may have 1 to 3 groups selected from the group consisting of an oxo group, a lower alkoxy group, and a lower alkylenedioxy group as a substituent(s) on the tetrahydroquinoline ring, (14) a cycloalkyl lower alkyl group, (15) a piperazinyl lower alkanoyl group that may be substituted, on the piperazine ring, by a phenyl lower alkyl group that may have a lower alkylenedioxy group as a substituent on the phenyl ring, (16) a pyridyl lower alkyl group, (17) an amino group-substituted lower alkyl group that may have a group selected from the group consisting of a lower alkyl group and a lower alkanoyl group as a substituent, (18) a lower alkoxy lower alkyl group, (19) an imidazolyl group, (20) an imidazolyl lower alkyl group, (21) a 1,2,3,4-tetrahydroisoquinolylcarbonyl-substituted lower alkyl group, (22) a piperidinylcarbonyl group that may have a group selected from the group consisting of a lower alkoxycarbonyl group, a phenyl lower alkyl group, and a furyl lower alkyl group as a substituent on the piperidine ring, (23) a thiazolidinyl lower alkanoyl group that may have an oxo group as a substituent on the thiazolidine ring, (24) a piperidinyl group that may be substituted, on the piperidine ring, by a group selected from the group consisting of a lower alkoxycarbonyl group, a phenyl lower alkyl group, a lower alkyl group, a benzoyl group, and a furyl lower alkyl group, (25) a carbonyl lower alkyl group substituted by a group

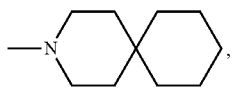

(26) a carbonyl lower alkyl group substituted by a group

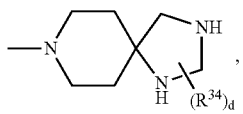

(27) a group —CO—$B_{20}$—N($R^{36}$)$R^{37}$, (26a) a pyrrolidinyl lower alkyl group, (27a) a morpholino lower alkyl group, (28a) a phenyl lower alkenyl group, (29a) an anilinocarbonyl lower alkyl group that may have a lower alkyl group as a substituent on the phenyl ring, (30a) an indolyl group, (31a) a piperazinyl lower alkyl group that may have, as a substituent on the piperazine ring, a group selected from the group consisting of a lower alkyl group and a phenyl lower alkyl group that may have a lower alkylenedioxy group as a substituent on the phenyl ring, (32a) an amidino lower alkyl group that may have a lower alkyl group as a substituent, (33a) a fluorenyl group, (34a) a carbazolyl group that may have a lower alkyl group as a substituent on the carbazole ring, (35a) an amidino group that may have a lower alkyl group as a substituent, (36a) a piperazinyl-substituted oxalyl group that may have 1 to 3 groups selected from the group consisting of a phenyl lower alkyl group (that may have 1 to 3 groups selected from the group consisting of a lower alkylenedioxy group and a lower alkoxy group as a substituent(s) on the phenyl ring) and a pyridyl lower alkyl group as a substituent(s) on the piperazine ring, or (37a) a cyano-substituted lower alkyl group, $R^{34}$ represents an oxo group or a phenyl group, d represents an integer between 0 and 3, $B_{20}$ represents a lower alkylene group, $R^{36}$ and $R^{37}$, together with the nitrogen atom to which they bind, may bind to each other, directly or via a nitrogen atom, oxygen atom, or sulfur atom to form a 5- to 7-membered saturated heterocyclic group, wherein the heterocyclic group may be substituted by 1 to 3 phenyl lower alkyl groups that may have a lower alkylenedioxy group as a substituent on the phenyl ring, $R^{14}$ and $R^{15}$, together with the nitrogen atom to which they bind, may bind to each other, directly or via a nitrogen atom, oxygen atom, or sulfur atom to form a 5- to 10-membered saturated or unsaturated heterocyclic ring; or a group

wherein the heterocyclic ring may be substituted by 1 to 3 groups selected from the group consisting of (28) a phenyl-substituted lower alkyl group, which has 1 to 2 phenyl groups and which may have a pyridyl group on the lower alkyl group, wherein the phenyl ring may be substituted by 1 to 3 groups selected from the group consisting of a lower alkanoyl group, an amino group that may have a lower alkanoyl group as a substituent, a lower alkoxycarbonyl group, a cyano group, a nitro group, a phenyl group, a halogen atom, a lower alkyl group that may have a halogen atom as a substituent, a lower alkoxy group that may have a halogen atom as a substituent, a phenyl lower alkoxy group, a hydroxyl group, and a lower alkylenedioxy group, (29) a carbamoyl group, (30) a pyridyl lower alkyl group that may have, as a substituent(s) on the pyridine ring, 1 to 3 groups selected from the group consisting of a hydroxyl group and a lower alkyl group that may have a hydroxyl group as a substituent, (31) a pyrrolyl lower alkyl group that may have 1 to 3 lower alkyl groups as a substituent(s) on the pyrrole ring, (32) a benzoxazolyl lower alkyl group, (33) a benzothiazolyl lower alkyl group, (34) a furyl lower alkyl group, (35) a benzoyl group that may be substituted, on the phenyl ring, by 1 to 3 groups selected from the group consisting of a cyano group, an amino group that may have a lower alkylsulfonyl group as a substituent, a halogen atom, a lower alkoxy group, a lower alkyl group that may have a halogen atom as a substituent, a thiazolidinyl lower alkyl group that may have an oxo group as a substituent on the thiazolidine ring, a thiazolidinylidene lower alkyl group that may have an oxo group as a substituent on the thiazolidine ring, and a lower alkylenedioxy group, (36) a pyrimidinyl group, (37) a pyrazinyl group, (38) a pyridyl group, (39) a lower alkoxycarbonyl group, (40) a thiazolidinyl lower alkanoyl group that may be substituted, on the thiazolidine ring, by a group selected from the group consisting of an oxo group and a group

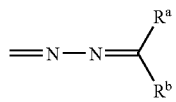

(wherein each of $R^a$ and $R^b$ represents a lower alkyl group), (41) a lower alkyl group that may have a group selected from the group consisting of a hydroxyl group and a halogen atom as a substituent, (42) a lower alkanoyl group that may have a halogen atom as a substituent, (43) a phenyl group that may be substituted, on the phenyl ring, by 1 to 3 groups selected from the group consisting of a carbamoyl group that may have a group selected from the group consisting of a lower alkoxy lower alkyl group and a lower alkyl group, a lower alkoxycarbonyl group, a carboxy group, a cyano group, a phenyl group, a halogen atom, a lower alkyl group that may have a halogen atom as a substituent, a lower alkoxy group that may have a halogen atom as a substituent, a benzoyl group that may have a halogen atom as a substituent on the phenyl ring, a phenyl lower alkyl group that may have a halogen atom as a substituent on the phenyl ring, and a hydroxyl group, (44) a phenyl group that may have a lower alkylenedioxy group as a substituent on the phenyl ring, (45) a naphthyl lower alkyl group, (46) a phenoxy group that may be substituted, on the phenyl ring, by 1 to 3 groups selected from the group consisting of a cyano group, a lower alkyl group that may have a halogen atom as a substituent, and a lower alkoxy group that may have a halogen atom as a substituent, (47) a phenoxy lower alkyl group, (48) a phenyl lower alkoxy group that may be substituted, on the phenyl ring, by 1 to 3 groups selected from the group consisting of a halogen atom, a lower alkyl group that may have a halogen atom as a substituent, and a lower alkoxy group that may have a halogen atom as a substituent, (49) a group —$(B_{12}CO)t$-$N(R^{20})R^{21}$, (50) a group —$(CO)o$-$B_{13}$—$N(R^{22})R^{23}$, (51) a 1,2,3,4-tetrahydronaphthyl-substituted lower alkyl group that may be substituted, on the 1,2,3,4-tetrahydronaphthalene ring, by 1 to 5 lower alkyl groups as a substituent(s), (52) a cycloalkyl group that may have a hydroxyl group as a substituent, (53) a piperidinyl group that may be substituted, on the piperidine ring, by 1 to 3 lower alkyl groups as a substituent(s), (54) a quinolyl lower alkyl group, (55) a 1,2,3,4-tetrazolyl lower alkyl group that may have a group selected from the group consisting of a lower alkyl group and a phenyl lower alkyl group as a substituent on the tetrazole ring, (56) a thiazolyl lower alkyl group that may have a phenyl group as a substituent on the thiazole ring, (57) a benzoyl lower alkyl group that may have 1 to 3 groups selected from the group consisting of a lower alkoxy group and a halogen atom as a substituent(s) on the phenyl ring, (58) a piperidinyl lower alkyl group that may have a lower alkyl group as a substituent on the piperidine ring, (59) an imidazolyl group that may have 1 to 3 phenyl groups as a substituent(s) on the imidazole ring, (60) a benzimidazolyl group that may have 1 to 3 lower alkyl groups as a substituent(s) on the benzimidazole ring, (61) a pyridyl lower alkoxy group, (62) a 1,2,3,4-tetrahydroquinolyl lower alkyl group that may have an oxo group as a substituent on the tetrahydroquinoline ring, (63) a 1,3,4-oxadiazolyl lower alkyl group that may have an oxo group as a substituent on the 1,3,4-oxadiazole ring, (64) a cycloalkyl lower alkyl group, (65) a tetrahydropyranyl group, (66) a thienyl lower alkyl group, (67) a pyrimidinylcarbonyl group that may have an oxo group as a substituent on the pyrimidine ring, (68) a hydroxyl group, (69) a carboxy group, (70) a lower alkoxy lower alkyl group, (71) a lower alkoxy lower alkoxy group, (72) a benzoyloxy group, (73) a lower alkoxycarbonyl lower alkoxy group, (74) a carboxy lower alkoxy group, (75) a phenoxy lower alkanoyl group, (76) a 1,2,3,4-tetrahydroquinolylcarbonyl group that may have an oxo group as a substituent on the tetrahydroquinoline ring, (77) a phenylsulfonyl group, (78) an imidazolyl lower alkanoyl group, (79) an imidazolyl lower alkyl group, (80) a pyridylcarbonyl group, (81) an imidazolylcarbonyl group, (82) a lower alkoxycarbonyl lower alkyl group, (83) a carboxy lower alkyl group, (84) a group —$(O$—$B_{15})s$-$CO$—$N(R^{26})R^{27}$, (85) a group —$N(R^{28})$—$CO$—$B_{16}$—$N(R^{29})R^{30}$, (86) a group —$N(R^{31})$—$B_7$—$CO$—$N(R^{32})R^{33}$, (87) a benzoxazolyl group, (88a) a benzothienyl group, (89a) an oxo group, and (90a) a 1,2,3,4-tetrahydroquinolyl group that may have an oxo group as a substituent on the tetrahydroquinoline ring, $B_{12}$ represents a lower alkylene group, t represents 0 or 1, each of $R^{20}$ and $R^{21}$, which are identical or different, represents a hydrogen atom; a cycloalkyl group; an amino group that may have a lower alkoxycarbonyl group as a substituent; a benzoyl group that may have 1 to 3 lower alkoxy groups as a substituent(s) on the phenyl ring; a lower alkyl group; a lower alkyl group having 1 to 2 phenyl groups that may be substituted, on the phenyl ring, by 1 to 3 groups selected from the group consisting of a lower alkoxycarbonyl group, a cyano group, a nitro group, a phenyl group, a halogen atom, a lower alkyl group that may have a halogen atom as a substituent, a lower alkoxy group that may have a halogen atom as a substituent, and a lower alkylthio group; a phenyl group that may be substituted, on the phenyl ring, by 1 to 3 groups selected from the group consisting of a lower alkoxy group that may have a halogen atom as a substituent and a lower alkyl group that may have a halogen atom as a substituent; a lower alkoxycarbonyl group; a cycloalkyl lower alkyl group; a pyrrolidinyl lower alkyl group that may have 1 to 3 lower alkyl groups that may have a hydroxyl group as a substituent on the pyrrolidine ring; an amino-substituted lower alkyl group that may have a group selected from the group consisting of a phenyl group and a lower alkyl group as a substituent; a 1,2,3,4-tetrahydronaphthyl-substituted lower alkyl group that may have 1 to 5 lower alkyl groups as a substituent(s) on the 1,2,3,4-tetrahydronaphthalene ring; a naphthyl lower alkyl group; a pyridyl lower alkyl group; a quinolyl lower alkyl group; a 1,2,3,4-tetrazolyl lower alkyl group that may have 1 to 3 groups selected from the group consisting of a lower alkyl group and a phenyl lower alkyl group as a substituent(s) on the tetrazole ring; a 1,2,4-triazolyl lower alkyl group; a tetrahydrofuryl lower alkyl group that may have a hydroxyl group as a substituent on the lower alkyl group; a phenoxy lower alkyl group that may have 1 to 3 groups selected from the group consisting of a lower alkyl group and a nitro group as a substituent(s) on the phenyl ring; a phenyl lower alkanoyl group; a lower alkanoyl group that may have a halogen atom as a substituent; an imidazolyl lower alkanoyl group; a lower alkoxycarbonyl lower alkyl group; a pyridyl group; or a carboxy lower alkyl group, or $R^{20}$ and $R^{21}$, together with the nitrogen atom to which they bind, may bind to each other, directly or via a nitrogen atom, oxygen atom, or sulfur atom to form a 5- to 7-membered saturated heterocyclic ring, wherein the heterocyclic ring may be substituted by 1 to 3 groups selected from the group consisting of a lower alkyl group, a phenyl group that may have 1 to 3 groups selected from the group consisting of a halogen atom and a lower alkyl group that may have a halogen atom as a substituent(s) on the phenyl ring, and a phenyl lower alkyl group that may have a lower alkylenedioxy group as a substituent on the phenyl ring, o represents 0 or 1, $B_{13}$ represents a lower alkylene group, each of $R^{22}$ and $R^{23}$, which are identical or different, represents a hydrogen atom, a lower alkyl group, a benzoyl group that may have 1 to 3 lower alkoxy groups as a substituent(s) on the phenyl ring, a phenoxy lower alkyl group that may have a lower alkyl group as a substituent on the phenyl ring, a phenyl lower alkyl group, or a phenyl group, or $R^{22}$ and $R^{23}$, together with the nitrogen atom to which they bind, may bind to each other, directly or via a nitrogen atom, oxygen atom, or sulfur atom to form a 5- to 7-membered saturated heterocyclic ring, wherein the heterocyclic ring may be substituted by 1 to 3 groups selected from the group consisting of a lower alkyl group and a phenyl lower alkyl group that may have a lower alkylenedioxy group as a substituent on the phenyl ring, $B_{15}$ represents a lower alkylene group, s represents 0 or 1, each of $R^{26}$ and $R^{27}$, which are identical or different, represents a hydrogen atom, a lower alkyl group, a phenyl lower alkyl group, or an imidazolyl lower alkyl group, or $R^{26}$ and $R^{27}$, together with the nitrogen atom to which they bind, may bind to each other, directly or via a nitrogen atom, oxygen atom, or sulfur atom to form a 5- to 7-membered saturated heterocyclic ring, wherein the heterocyclic ring may be substituted by 1 to 3 phenyl lower alkyl groups that may have a lower alkylenedioxy group as a substituent on the phenyl ring, as a substituent(s), $R^{28}$ represents a hydrogen atom or a lower alkyl group, $B_{16}$ represents a lower alkylene group, $R^{29}$ and $R^{30}$, together with the nitrogen atom to which they bind, may bind to each other, directly or via a nitrogen atom, oxygen atom, or sulfur atom to form a 5- to 7-membered saturated heterocyclic group, wherein the heterocyclic ring may be substituted by 1 to 3 groups selected from the group consisting of a lower alkyl group, a phenyl group, and a phenyl lower alkyl group that may have a lower alkylenedioxy group as a substituent on the phenyl ring, $R^{31}$ represents a hydrogen atom or a lower alkyl group, $B_{17}$ represents a lower alkylene group, $R^{32}$ and $R^{33}$, together with the nitrogen atom to which they bind, may bind to each other, directly or via a nitrogen atom, oxygen atom, or sulfur atom to form a 5- to 7-membered saturated heterocyclic group, wherein the heterocyclic ring may be substituted by 1 to 3 groups selected from the group consisting of a lower alkyl group, a phenyl group, and a phenyl lower alkyl group that may have a lower alkylenedioxy group as a substituent on the phenyl ring].

Further, the present invention provides the pharmaceutical composition for the treatment of fibrosis, comprising the aromatic compound represented by the general formula (1) or a salt thereof mentioned above.

The present invention provides the above-mentioned pharmaceutical composition for the treatment of fibrosis, comprising the aromatic compound or a salt thereof mentioned above, wherein the aromatic compound is selected from the group consisting of N-[6-(4-{[2-(4-piperonylpiperazin-1-yl)-2-oxoethyl]ethylamino}-2-methoxyphenoxy)pyridin-3-yl]-3,4-dichlorobenzamide, N-[6-(4-{[2-(4-piperonylpiperazin-1-yl)-2-oxoethyl]ethylamino}phenoxy)pyridin-3-yl]-4-trifluoromethylbenzamide, N-[6-(4-{[2-(4-piperonylpiperazin-1-yl)-2-oxoethyl]ethylamino}-2-fluorophenoxy)pyridin-3-yl]-4-trifluoromethylbenzamide, N-[6-(4-{[2-(4-piperonylpiperazin-1-yl)-2-oxoethyl]methylamino}-2-fluorophenoxy)pyridin-3-yl]-4-trifluoromethylbenzamide, N-[6-(4-{[2-(4-piperonylpiperazin-1-yl)-2-oxoethyl]methylamino}-2-methoxyphenoxy)pyridin-3-yl]-4-trifluoromethylbenzamide, N-[6-(4-{[2-(4-piperonylpiperazin-1-yl)-2-oxoethyl]ethylamino}-2-methoxyphenoxy)pyridin-3-yl]-4-trifluoromethylbenzamide, N-[6-(4-{[2-(4-piperonylpiperazin-1-yl)-2-oxoethyl]ethylamino}-2-methylphenoxy)pyridin-3-yl]-3,4-dichlorobenzamide, N-[6-(4-{[2-(4-piperonylpiperazin-1-yl)-2-oxoethyl]methylamino}-2-methylphenoxy)pyridin-3-yl]-4-trifluoromethylbenzamide, N-(6-{4-[3-(4-piperonylpiperazin-1-yl)-3-oxopropyl]phenoxy}pyridin-3-yl)-3,4-dichlorobenzenesulfonamide, N-[6-(4-{4-[2-(4-piperonylpiperazin-1-yl)-2-oxoethyl]piperazin-1-yl}phenoxy)pyridin-3-yl]-4-trifluoromethylbenzamide, N-[6-(4-{4-[2-(4-piperonylpiperazin-1-yl)-2-oxoethyl]piperidin-1-yl}phenoxy)pyridin-3-yl]-4-trifluoromethylbenzamide, N-{6-[(4-{4-[2-(4-piperonylpiperazin-1-yl)-2-oxoethyl]piperidin-1-yl}phenyl)methylamino]pyridin-3-yl}-4-trifluoromethylbenzamide, N-[6-(4-{4-[2-(4-benzylpiperazin-1-yl)-2-oxoethyl]piperidin-1-yl}-2-methylphenoxy)pyridin-3-yl]-4-trifluoromethylbenzamide, N-[6-(4-{4-[2-(4-piperonylpiperazin-1-yl)-2-oxoethyl]piperidin-1-yl}-2-methylphenoxy)pyridin-3-yl]-4-trifluoromethylbenzamide, N-[6-(4-{4-[2-(4-piperonylpiperazin-1-yl)-2-oxoethyl]piperidin-1-yl}-2-methylphenoxy)pyridin-3-yl]-3,4-dichlorobenzamide, N-{6-[4-(4-benzylpiperazine-1-carbonyl)-phenoxy]pyridin-3-yl}-4-trifluoromethylbenzamide, N-{6-[4-(4-benzylpiperazine-1-carbonyl)phenoxy]pyridin-3-yl}-3,4-dichlorobenzamide, N-[6-({4-[3-(4-piperonylpiperazin-1-yl)-3-oxopropyl]phenyl}methylamino)pyridin-3-yl]-4-trifluoromethylbenzamide, N-[6-(4-{[2-(4-piperonylpiperazin-1-yl)-2-oxoethyl]ethylamino}-2-fluorophenoxy)pyridin-3-yl]-3,4-dichlorobenzamide, N-[6-(4-{[2-(4-piperonylpiperazin-1-yl)-2-oxoethyl]methylamino}-2-fluorophenoxy)pyridin-3-yl]-3,4-dichlorobenzamide, N-[6-(4-{[2-(4-piperonylpiperazin-1-yl)-2-oxoethyl]methylamino}-2-methoxyphenoxy)pyridin-3-yl]-3,4-dichlorobenzamide, N-[6-(4-{[2-(4-piperonylpiperazin-1-yl)-2-oxoethyl]methylamino}phenoxy)pyridin-3-yl]-3,4-dichlorobenzamide, 1-(6-{4-[3-(4-piperonylpiperazin-1-yl)-3-oxopropyl]phenoxy}pyridin-3-yl)-3-(3,4-dichlorophenyl)-1-ethylurea, N-(6-{4-[3-(4-piperonylpiperazin-1-yl)-3-oxopropyl]phenoxy}pyridin-3-yl)-4-trifluoromethylbenzamide, N-[6-(4-{[2-(4-benzylpiperazin-1-yl)-2-oxoethyl]methylamino}-2-methylphenoxy)pyridin-3-yl]-4-trifluoromethylbenzamide,
N-[6-(4-{4-[2-(4-benzylpiperazin-1-yl)-2-oxoethyl]piperidin-1-yl}phenoxy)pyridin-3-yl]-3,4-dichlorobenzamide,
N-(6-{4-[3-(4-piperonylpiperazine-1-carbonyl)piperidin-1-yl]phenoxy}pyridin-3-yl)-3,4-dichlorobenzamide,
N-[6-(4-{4-[2-(4-benzylpiperazin-1-yl)-2-oxoethyl]piperidin-1-yl}phenoxy)pyridin-3-yl]-4-trifluoromethylbenzamide,
N-{6-[(4-{4-[2-(4-benzylpiperazin-1-yl)-2-oxoethyl]piperidin-1-yl}phenyl)methylamino]pyridin-3-yl}-4-trifluoromethylbenzamide,
N-(6-{4-[(2-{4-[4-(4-fluorobenzoyl)phenyl]-piperazin-1-yl}-2-oxoethyl)methylamino]-2-methoxyphenoxy}pyridin-3-yl)-4-trifluoromethylbenzamide,
2-(4-piperonylpiperazin-1-yl)-N-{3-methyl-4-[5-(4-trifluoromethylphenoxymethyl)pyridin-2-yloxy]phenyl}-2-oxoacetamide,
N-[6-(4-{[2-(4-piperonylpiperazin-1-yl)-2-oxoethyl]methylamino}-2-methylphenoxy)pyridin-3-yl]-2-fluoro-4-trifluoromethylbenzamide,
N-[6-(4-{4-[2-(4-piperonylpiperazin-1-yl)-2-oxoethyl]piperidin-1-yl}-2-methoxyphenoxy)pyridin-3-yl]-4-trifluoromethylbenzamide, and
4-(3-{3-methyl-4-[5-(4-trifluoromethylbenzoylamino)pyridin-2-yloxy]phenyl}-2-oxohexahydropyrimidin-1-yl)benzoic acid ethyl ester, or salts thereof.

The present invention provides the above-mentioned pharmaceutical composition for the treatment of fibrosis, wherein the fibrosis is lung fibrosis. The present invention provides the above-mentioned pharmaceutical composition for the treatment of fibrosis, wherein the fibrosis is hepatic fibrosis. The present invention provides the above-mentioned pharmaceutical composition for the treatment of fibrosis, wherein the fibrosis is glomerulosclerosis.

Specific examples of each group represented by the general formula (1) are as follows.

Examples of the lower alkynylene group include linear or branched alkynylene groups having 2 to 6 carbon atoms which have 2 to 6 triple bonds such as ethynylene, 1-propynylene, 1-methyl-1-propynylene, 2-methyl-1-propynylene, 2-propynylene, 2-butynylene, 1-butynylene, 3-butynylene, 2-pentynylene, 1-pentynylene, 3-pentynylene, 4-pentynylene, 2-pentyn-4-ynylene, 2-hexynylene, 1-hexynylene, 5-hexynylene, 3-hexynylene, 4-hexynylene, 3,3-diethyl-1-propynylene, 2-ethyl-1-propynylene groups.

Examples of the amino group which may have a substituent selected from the group consisting of a lower alkyl group and a lower alkanoyl group include amino groups which may have 1 or 2 substituents selected from the group consisting of a linear or branched alkyl group having 1 to 6 carbon atoms and a linear or branched alkanoyl group having 1 to 6 carbon atoms such as amino, methylamino, ethylamino, propylamino, isopropylamino, butylamino, tert-butylamino, pentylamino, hexylamino, dimethylamino, diethylamino, dipropylamino, dibutylamino, dipentylamino, dihexylamino, N-methyl-N-ethylamino, N-ethyl-N-propylamino, N-methyl-N-butylamino, N-methyl-N-hexylamino, N-acetylamino, N-formylamino, N-propionylamino, N-butyrylamino, N-isobutyrylamino, N-pentanoylamino, N-tert-butylcarbonylamino, N-hexanoylamino, diacetylamino, N-acetyl-N-methylamino, N-acetyl-N-ethylamino groups.

Examples of the benzoyl group (which may have, on the phenyl ring, 1 to 3 substituents selected from the group consisting of a lower alkyl group which may have a halogen atom as a substituent and a halogen atom) include benzoyl groups (which may have, on the phenyl ring, 1 to 3 substituents selected from the group consisting of a linear or branched alkyl group having 1 to 6 carbon atoms which may have 1 to 3 halogen atoms as substituents and a halogen atom) such as benzoyl, 3,4-difluorobenzoyl, 2-fluorobenzoyl, 3-bromobenzoyl, 4-iodobenzoyl, 4-methylbenzoyl, 2-methylbenzoyl, 3-methylbenzoyl, 2-ethylbenzoyl, 3-ethylbenzoyl, 4-ethylbenzoyl, 4-isopropylbenzoyl, 3-butylbenzoyl, 4-pentylbenzoyl, 4-hexylbenzoyl, 3,4-dimethylbenzoyl, 3,4-diethylbenzoyl, 2,4-dimethylbenzoyl, 2,5-dimethylbenzoyl, 2,6-dimethylbenzoyl, 3,4,5-trimethylbenzoyl, 2-trifluoromethylbenzoyl, 3-trifluoromethylbenzoyl, 4-trifluoromethylbenzoyl, 2-(bromomethyl)benzoyl, 3-(2-chloroethyl)benzoyl, 4-(2,3-dichloropropyl)benzoyl, 4-(4-fluorobutyl)benzoyl, 3-(5-chloropentyl)benzoyl, 4-(5-bromohexyl)benzoyl, 4-(5,6-dibromohexyl)benzoyl, 3,4-di(trifluoromethyl)benzoyl, 3,4-di(4,4,4-trichlorobutyl)benzoyl, 2,4-di(3-chloro-2-methylpropyl)benzoyl, 2,5-di(3-chloropropyl)benzoyl, 2,6-di(2,2,2-trifluoroethyl)benzoyl, 3,4,5-tri(trifluoromethyl)benzoyl, 4-(2,2,2-trichloroethyl)benzoyl, 2-methyl-4-trifluoromethylbenzoyl, 3-ethyl-4-trichloromethylbenzoyl, 2-chloro-4-trifluoromethylbenzoyl, 3-ethyl-4-chlorobenzoyl, 3-fluoro-4-trichloromethylbenzoyl, 2-methyl-3-trifluoromethyl-4-trifluoromethylbenzoyl, 3-fluorobenzoyl, 4-fluorobenzoyl, 2-bromobenzoyl, 4-bromobenzoyl, 2-iodobenzoyl, 3-iodobenzoyl, 2,3-dibromobenzoyl, 2,4-diiodobenzoyl, 2,5-difluorobenzoyl, 2,6-dichlorobenzoyl, 2,4,6-trichlorobenzoyl, 2,4-difluorobenzoyl, 3,5-difluorobenzoyl, 2,6-difluorobenzoyl, 2-chlorobenzoyl, 3-chlorobenzoyl, 4-chlorobenzoyl, 2,3-dichlorobenzoyl, 2,4-dichlorobenzoyl, 2,5-dichlorobenzoyl, 3,4-dichlorobenzoyl, 2,6-dichlorobenzoyl, 3,5-dichlorobenzoyl, 2,4,6-trifluorobenzoyl, 2,4-difluorobenzoyl groups.

Examples of the halogen substituted lower alkyl group include linear or branched alkyl groups having 1 to 6 carbon atoms which have 1 to 3 halogen atoms as substituents such as a trifluoromethyl group, trichloromethyl group, chloromethyl group, bromomethyl group, fluoromethyl group, iodomethyl group, difluoromethyl group, dibromomethyl group, dichloromethyl group, 2-chloroethyl group, 2,2,2-trifluoroethyl group, 2,2,2-trichloroethyl group, 3-chloropropyl group, 2,3-dichloropropyl group, 4,4,4-trichlorobutyl group, 4-fluorobutyl group, 5-chloropentyl group, 3-chloro-2-methylpropyl group, 5-bromohexyl group, and 5,6-dibromohexyl group.

Examples of the lower alkanoyl substituted amino group include linear or branched alkanoyl groups having 2 to 6 carbon atoms which have 1 to 3 halogen atoms as substituents such as a acetyl amino group, propionyl amino group, butyryl amino group, pentanoyl amino group, 2-methylpropionyl amino group and hexanoyl amino group.

Examples of the piperazinyl substituted oxalyl group which may have, on the piperazine ring, 1 to 3 substituents selected from the group consisting of a phenyl lower alkyl group (which may have, on the phenyl ring, 1 to 3 substituents selected from the group consisting of a lower alkylenedioxy group and a lower alkoxy group) and a pyridyl lower alkyl group include piperazinyl substituted oxalyl groups which may have, on the piperazine ring, 1 to 3 substituents selected from the group consisting of a phenylalkyl group of which the alkyl moiety is a linear or branched alkyl group having 1 to 6 carbon atoms (and which may have, on the phenyl ring, 1 to 3 substituents selected from the group consisting of a linear or branched alkylenedioxy group having 1 to 4 carbon atoms and a linear or branched alkoxy group having 1 to 6 carbon atoms) and a pyridylalkyl group of which the alkyl moiety is a linear or branched alkyl group having 1 to 6 carbon atoms such as 4-(3,4-methylenedioxybenzyl)-(1-,2-, or 3-)piperazinyloxalyl, 4-(2-,3-, or 4-pyridylmethyl)-(1-, 2-, or 3-)piperazinyloxalyl, 4-(3,4-dimethoxybenzyl)-(1-, 2-, or 3-)piperazinyloxalyl, 4-(2,3-methylenedioxybenzyl)-(1-,2-, or 3-)piperazinyloxalyl, 4-(3,4-ethylenedioxybenzyl)-(1-,2-, or 3-)piperazinyloxalyl, 4-[2-(2-,3-, or 4-pyridyl)ethyl]-(1-, 2-, or 3-)piperazinyloxalyl, 4-[3-(2-,3-, or 4-pyridyl)propyl-(1-, 2-, or 3-)piperazinyloxalyl, 2,4-bis(2-,3-, or 4-pyridylmethyl)-(1-,2-, or 3-)piperazinyloxalyl, 2-(3,4-methylenedioxybenzyl)-4-(2-,3-, or 4-pyridylmethyl)-(1-,2-, or 3-)piperazinyloxalyl, 2,3,4-tri(2-,3-, or 4-pyridylmethyl)-(1-, 2-, or 3-)piperazinyloxalyl groups.

Examples of the cyano substituted lower alkyl group include cyanoalkyl groups of which the alkyl moiety is a linear or branched alkyl group having 1 to 6 carbon atoms such as a cyanomethyl group, 2-cyanoethyl group, 1-cyanoethyl group, 3-cyanopropyl group, 4-cyanobutyl group, 5-cyanopentyl group, 6-cyanohexyl group, 1,1-dimethyl-2-cyanoethyl group, and 2-methyl-3-cyanopropyl group.

Examples of the carbamoyl group which may have a group selected from the group consisting of a lower alkoxy lower alkyl group and a lower alkyl group include carbamoyl groups which may have 1 or 2 groups selected from the group consisting of a linear or branched alkyl group having 1 to 0.6 carbon atoms which has a linear or branched alkoxy group having 1 to 6 carbon atoms and a linear or branched alkyl group having 1 to 6 carbon atoms such as carbamoyl, N-(2-methoxyethyl)carbamoyl, methylcarbamoyl, ethylcarbamoyl, propylcarbamoyl, isopropylcarbamoyl, butylcarbamoyl, tert-butylcarbamoyl, pentylcarbamoyl, hexylcarbamoyl, dimethylcarbamoyl, diethylcarbamoyl, dipropylcarbamoyl, dibutylcarbamoyl, dipentylcarbamoyl, dihexylcarbamoyl, N-methyl-N-ethylcarbamoyl, N-ethyl-N-propylcarbamoyl, N-methyl-N-butylcarbamoyl, N-methyl-N-hexylcarbamoyl, N-(methoxymethyl)carbamoyl, N-(3-propoxypropyl)carbamoyl, N-(4-butoxybutyl)carbamoyl, N-(4-ethoxybutyl) carbamoyl, N-(5-pentyloxypentyl)carbamoyl, N-(5-methoxypentyl)carbamoyl, N-(6-hexyloxyhexyl)carbamoyl, di(2-methoxyethyl)carbamoyl, N-(2-methoxyethyl)-N-methylcarbamoyl, N-(2-methoxyethyl)-N-ethylcarbamoyl groups.

Examples of the phenyl group which may have, on the phenyl ring, 1 to 3 substituents selected from the group consisting of a halogen atom and a lower alkyl group which may have a halogen atom include phenyl groups which may have, on the phenyl ring, 1 to 3 substituents selected from the group consisting of a halogen atom and a linear or branched alkyl group having 1 to 6 carbon atoms which may have 1 to 3 halogen atoms such as phenyl, 3,4-difluorophenyl, 2-fluorophenyl, 3-bromophenyl, 4-iodophenyl, 4-methylphenyl, 2-methylphenyl, 3-methylphenyl, 2-ethylphenyl, 3-ethylphenyl, 4-ethylphenyl, 4-isopropylphenyl, 3-butylphenyl, 4-pentylphenyl, 4-hexylphenyl, 3,4-dimethylphenyl, 3,4-diethylphenyl, 2,4-dimethylphenyl, 2,5-dimethylphenyl, 2,6-dimethylphenyl, 3,4,5-trimethylphenyl, 2-trifluoromethylphenyl, 3-trifluoromethylphenyl, 4-trifluoromethylphenyl, 2-(bromomethyl)phenyl, 3-(2-chloroethyl) phenyl, 4-(2,3-dichloropropyl)phenyl, 4-(4-fluorobutyl)phenyl, 3-(5-chloropentyl)phenyl, 4-(5-bromohexyl)phenyl, 4-(5,6-dibromohexyl)phenyl, 3,4-di(trifluoromethyl)phenyl, 3,4-di(4,4,4-trichlorobutyl)phenyl, 2,4-di(3-chloro-2-methylpropyl)phenyl, 2,5-di(3-chloropropyl)phenyl, 2,6-di(2,2,2-trifluoroethyl)phenyl, 3,4,5-tri(trifluoromethyl)phenyl, 4-(2,2,2-trichloroethyl)phenyl, 2-methyl-4-trifluoromethylphenyl, 3-ethyl-4-trichloromethylphenyl, 2-chloro-4-trifluoromethylphenyl, 3-ethyl-4-fluorophenyl, 3-fluoro-4-trichloromethylphenyl, 2-methyl-3-trifluoromethyl-4-trifluoromethylphenyl, 3-fluorophenyl, 4-fluorophenyl, 2-bromophenyl, 4-bromophenyl, 2-iodophenyl, 3-iodophenyl, 2,3-dibromophenyl, 2,4-diiodophenyl, 2,5-difluorophenyl, 2,6-dichlorophenyl, 2,4,6-trichlorophenyl, 2,4-difluorophenyl, 3,5-difluorophenyl, 2,6-difluorophenyl, 2-chlorophenyl, 3-chlorophenyl, 4-chlorophenyl, 2,3-dichlorophenyl, 2,4-dichlorophenyl, 2,5-dichlorophenyl, 3,4-dichlorophenyl, 2,6-dichlorophenyl, 3,5-dichlorophenyl, 2,4,6-trifluorophenyl, 2,4-difluorophenyl groups.

Examples of the lower alkenylene group include linear or branched alkenylene groups having 2 to 6 carbon atoms which have 1 to 3 double bonds such as vinylene, 1-propenylene, 1-methyl-1-propenylene, 2-methyl-1-propenylene, 2-propenylene, 2-butenylene, 1-butenylene, 3-butenylene, 3-pentenylene, 1-pentenylene, 2-pentenylene, 4-pentenylene, 1,3-butadienylene, 1,3-pentadienylene, 2-penten-4-ynylene, 2-hexenylene, 1-hexenylene, 5-hexenylene, 3-hexenylene, 4-hexenylene, 3,3-dimethyl-1-propenylene, 2-ethyl-1-propenylene, 1,3,5-hexatrienylene, 1,3-hexadienylene, and 1,4-hexadienylene.

Examples of the lower alkoxy group include linear or branched alkoxy groups having 1 to 6 carbon atoms such as a methoxy group, ethoxy group, propoxy group, isopropoxy group, butoxy group, tert-butoxyl group, pentyloxy group, and hexyloxy group.

Examples of the lower alkyl group include linear or branched alkyl groups having 1 to 6 carbon atoms such as a methyl group, ethyl group, propyl group, isopropyl group, 2,2-dimethylpropyl group, 1-ethylpropyl group, butyl group, isobutyl group, tert-butyl group, isopentyl group, pentyl group, and hexyl group.

Examples of the lower alkyl group which may have a lower alkoxy group as a substituent include, in addition to the above described lower alkyl groups, linear or branched alkyl groups having 1 to 6 carbon atoms which may have a linear or branched alkoxy group having 1 to 6 carbon atoms as a substituent such as a methoxymethyl group, 1-ethoxyethyl group, 2-methoxyethyl group, 2-propoxyethyl group, 3-isopropoxypropyl group, 4-butoxybutyl group, 5-pentyloxypentyl group, 6-hexyloxyhexyl, 1,1-dimethyl-2-methoxyethyl group, 2-methyl-3-ethoxypropyl, and 3-methoxypropyl group.

Examples of the lower alkanoyl group include alkanoyl groups having 1 to 6 carbon atoms such as a formyl group, acetyl group, propionyl group, butyryl group, isobutyryl group, pentanoyl group, tert-butylcarbonyl, and hexanoyl group.

Examples of the phenyl lower alkyl group include phenylalkyl groups of which the alkyl moiety is a linear or branched alkyl group having 1 to 6 carbon atoms such as a benzyl group, 2-phenylethyl group, 1-phenylethyl group, 3-phenylpropyl group, 4-phenylbutyl group, 5-phenylpentyl group, 6-phenylhexyl group, 1,1-dimethyl-2-phenylethyl group, and 2-methyl-3-phenylpropyl group.

Examples of the phenyl lower alkyl group (which may have, on the phenyl ring, 1 to 3 substituents selected from the group consisting of a lower alkylenedioxy group and a lower alkoxy group), include, in addition to the above described phenyl lower alkyl groups, phenylalkyl groups of which the alkyl moiety is a linear or branched alkyl group having 1 to 6 carbon atoms (and which may have, on the phenyl ring, 1 to 3 substituents selected from the group consisting of a linear or branched alkylenedioxy group having 1 to 4 carbon atoms and a linear or branched alkoxy group having 1 to 6 carbon atoms) such as 3,4-methylenedioxybenzyl, 3,4-trimethylenedioxybenzyl, 2-(2,3-ethylenedioxyphenyl)ethyl, 1-(3,4-trimethylenedioxyphenyl)ethyl, 3-(2,3-tetramethylenedioxyphenyl)propyl, 4-(3,4-methylenedioxyphenyl)butyl, 5-(2,3-ethylenedioxyphenyl)pentyl, 6-(3,4-trimethylenedioxyphenyl)hexyl, 1,1-dimethyl-2-(2,3-methylenedioxyphenyl)ethyl, 2-methyl-3-(2,3-ethylenedioxyphenyl)propyl, 2-methoxybenzyl, 2-(2-methoxyphenyl)ethyl, 2-(3-methoxyphenyl)ethyl, 2-(4-methoxyphenyl)ethyl, 4-methoxybenzyl, 1-(2-ethoxyphenyl)ethyl, 3-(3-ethoxyphenyl)propyl, 4-(4-ethoxyphenyl)butyl, 5-(4-isopropoxyphenyl)pentyl, 6-(3-butoxyphenyl)hexyl, 1,1-dimethyl-2-(4-pentyloxyphenyl)ethyl, 2-methyl-3-(4-hexyloxyphenyl)propyl, 3,4-dimethoxybenzyl, 3,4-diethoxybenzyl, 2,4-dimethoxybenzyl, 2,5-dimethoxybenzyl, 2,6-dimethoxybenzyl, 3,4,5-trimethoxybenzyl groups.

Examples of the lower alkylene group include linear or branched alkylene groups having 1 to 6 carbon atoms such as a methylene group, ethylene group, trimethylene group, 2-methyltrimethylene group, 2,2-dimethylethylene group, 2,2-dimethyltrimethylene group, 1-methyltrimethylene group, methylmethylene group, ethylmethylene group, tetramethylene group, pentamethylene group, and hexamethylene group.

Examples of the lower alkenylene group which may have a phenyl group as a substituent include linear or branched alkenylene groups having 2 to 6 carbon atoms which have 1 to 3 double bonds and may have a phenyl group as a substituent such as vinylene, 1-propenylene, 1-methyl-1-propenylene, 2-methyl-1-propenylene, 2-propenylene, 2-butenylene, 1-butenylene, 3-butenylene, 2-pentenylene, 1-pentenylene, 3-pentenylene, 4-pentenylene, 1,3-butadienylene, 1,3-pentadienylene, 2-penten-4-ynylene, 2-hexenylene, 1-hexenylene, 5-hexenylene, 3-hexenylene, 4-hexenylene, 3,3-dimethyl-1-propenylene, 2-ethyl-1-propenylene, 1,3,5-hexatrienylene, 1,3-hexadienylene, 1,4-hexadienylene, 1-phenylvinylene, 3-phenyl-1-propenylene, 3-phenyl-1-methyl-1-propenylene, 3-phenyl-2-methyl-1-propenylene, 1-phenyl-2-propenylene, 1-phenyl-2-butenylene, 3-phenyl-1-butenylene, 1-phenyl-3-butenylene, 5-phenyl-2-pentenylene, 4-phenyl-1-pentenylene, 2-phenyl-3-pentenylene, 1-phenyl-4-pentenylene, 1-phenyl-1,3-butadienylene, 1-phenyl-1,3-pentadienylene, 1-phenyl-2-penten-4-ynylene, 1-phenyl-2-hexenylene, 3-phenyl-1-hexenylene, 4-phenyl-5-hexenylene, 6-phenyl-3-hexenylene, 5-phenyl-4-hexenylene, 1-phenyl-3,3-dimethyl-1-propenylene, 1-phenyl-2-ethyl-1-propenylene, 6-phenyl-1, 3,5-hexatrienylene, 1-phenyl-1,3-hexadienylene, 2-phenyl-1,4-hexadienylene groups.

Examples of the lower alkylene group which may be substituted with a group selected from the group consisting of a lower alkoxy group and a phenyl group include, in addition to the above described lower alkylene groups, linear or branched alkylene groups having 1 to 6 carbon atoms which may be substituted with 1 or 2 groups selected from the group consisting of a linear or branched alkoxy group having 1 to 6 carbon atoms and a phenyl group such as methoxymethylene, 2-phenylethylene, 3-ethoxytrimethylene, 1-propoxy-2-methyltrimethylene, 1-phenyl-2,2-dimethylethylene, 3-phenyl-2, 2-dimethyltrimethylene, 2-butoxy-1-methyltrimethylene, phenylmethylmethylene, 2-pentyloxyethylmethylene, 4-phenyl-2-hexyloxytetramethylene, 3-phenylpentamethylene, 5-phenylhexamethylene, ethoxymethylene, 1-phenylethylene, 3-phenyltrimethylene, 2-phenyl-1-methoxyethylene groups.

Examples of the 5- to 15-membered monocyclic, bicyclic or tricyclic saturated or unsaturated heterocyclic group which has 1 to 4 nitrogen atoms, oxygen atoms or sulfur atoms include pyrrolidinyl, piperidinyl, piperazinyl, morpholino, pyridyl, 1,2,5,6-tetrahydropyridyl, 1,2,4-triazolyl, 1,2,3-triazolyl, 1,2,5-triazolyl, thiazolidinyl, 1,2,3,4-tetrazolyl, thienyl, quinolyl, 1,4-dihydroquinolyl, benzothiazolyl, pyrazyl, pyrimidyl, pyridazyl, 2H-pyrrolyl, pyrrolyl, 1,3,4-oxadiazolyl, tetrahydropyranyl, tetrahydrofuryl, furazanyl, carbostyryl, 3,4-dihydrocarbostyryl, 1,2,3,4-tetrahydroquinolyl, 1,2,3,4-tetrahydroisoquinolyl, indolyl, isoindolyl, indolinyl, benzoimidazolyl, benzoxazolyl, imidazolidinyl, isoquinolyl, quinazolidinyl, quinoxalinyl, cinnolinyl, phthalazinyl, carbazoyl, acridinyl, chromanyl, isoindolinyl, isochromanyl, pyrazolyl, imidazolyl, pyrazolidinyl, phenothiazinyl, benzofuryl, 2,3-dihydrobenzo[b]furyl, benzothienyl, phenoxatiynyl, phenoxadinyl, 4H-chromenyl, 1H-indazolyl, phenazinyl, xanthenyl, thianthrenyl, 2-imidazolinyl, 2-pyrrolinyl, furyl, oxazolyl, isoxazolyl, isoxazolidinyl, thiazolyl, isothiazolyl, pyranyl, 2-thiazolinyl, 2-pyrazolinyl, quinuclidinyl, 1,4-benzoxadinyl, 3,4,-dihydro-2H-1,4-benzoxadinyl, 3,4-dihydro-2H-1,4-benthiazinyl, 1,4-benzothiazinyl, 1,2,3,4-tetrahydroquinoxalinyl, 1,3-dithia-2, 4-dihydronaphthalenyl, phenanthridinyl, 1,4-dithianaphthalenyl, dibenz[b,e]azepine, 6,11-dihydro-5H-dibenz[b,e]azepine groups.

Examples of the halogen atom include a fluorine atom, chlorine atom, bromine atom and iodine atom.

Examples of the lower alkoxy group which may have a halogen atom as a substituent include linear or branched alkoxy groups having 1 to 6 carbon atoms which may have 1 to 3 halogen atoms as substituents such as methoxy, ethoxy, propoxy, isopropoxy, butoxy, tert-butoxy, pentyloxy, hexyloxy, trifluoromethoxy, trichloromethoxy, chloromethoxy, bromomethoxy, fluoromethoxy, iodomethoxy, difluoromethoxy, dibromomethoxy, 2-chloroethoxy, 2,2,2-trifluoroethoxy, 2,2,2-trichloroethoxy, 3-chloropropoxy, 2,3-dichloropropoxy, 4,4,4-trichlorobutoxy, 4-fluorobutoxy, 5-chloropentyloxy, 3-chloro-2-methylpropoxy, 6-bromohexyloxy, 5,6-dichlorohexyloxy groups.

Examples of the lower alkyl group which may have a halogen atom as a substituent include, in addition to the above described lower alkyl groups, linear or branched alkyl groups having 1 to 6 carbon atoms which may have 1 to 3 halogen atoms as substituents such as a trifluoromethyl group, trichloromethyl group, chloromethyl group, dichloromethyl group, bromomethyl group, fluoromethyl group, iodomethyl group, difluoromethyl group, dibromomethyl group, dichloromethyl group, 2-chloroethyl group, 2,2,2-trifluoroethyl group, 2,2,2-trichloroethyl group, 3-chloropropyl group, 2,3-dichloropropyl group, 4,4,4-trichlorobutyl group, 4-fluorobutyl group, 5-chloropentyl group, 3-chloro-2-methylpropyl group, 5-bromohexyl group, and 5,6-dibromohexyl group.

Examples of the lower alkylsulfonyl group include linear or branched alkylsulfonyl groups having 1 to 6 carbon atoms such as a methylsulfonyl group, ethylsulfonyl group, propylsulfonyl group, isopropylsulfonyl group, butylsulfonyl group, tert-butylsulfonyl group, pentylsulfonyl group, and hexylsulfonyl group.

Examples of the phenyl group which may be substituted on the phenyl ring with a lower alkyl group which may have a halogen atom include phenyl groups which may be substituted with 1 to 3 linear or branched alkyl groups having 1 to 6 carbon atoms which may have 1 to 3 halogen atoms such as phenyl, 2-methylphenyl, 3-methylphenyl, 4-methylphenyl, 2-ethylphenyl, 3-ethylphenyl, 4-ethylphenyl, 4-isopropylphenyl, 3-butylphenyl, 4-pentylphenyl, 4-hexylphenyl, 3,4-dimethylphenyl, 3,4-diethylphenyl, 2,4-dimethylphenyl, 2,5-dimethylphenyl, 2,6-dimethylphenyl, 3,4,5-trimethylphenyl, 2-trifluoromethylphenyl, 3-trifluoromethylphenyl, 4-trifluoromethylphenyl, 2-(bromomethyl)phenyl, 3-(2-chloroethyl)

phenyl, 4-(2,3-dichloropropyl)phenyl, 4-(4-fluorobutyl)phenyl, 3-(5-chloropentyl)phenyl, 4-(5-bromohexyl)phenyl, 4-(5,6-dibromohexyl)phenyl, 3,4-di(trifluoromethyl)phenyl, 3,4-di(4,4,4-trichlorobutyl)phenyl, 2,4-di(3-chloro-2-methylpropyl)phenyl, 2,5-di(3-chloropropyl)phenyl, 2,6-di(2,2,2-trifluoroethyl)phenyl, 3,4,5-tri(trifluoromethyl)phenyl, 4-(2,2,2-trichloroethyl)phenyl, 2-methyl-4-trifluoromethylphenyl, 3-ethyl-4-trichloromethyl groups.

Examples of the lower alkylthio group include linear or branched alkylthio groups having 1 to 6 carbon atoms such as a methylthio group, ethylthio group, propylthio group, isopropylthio group, butylthio group, tert-butylthio group, pentylthio group, and hexylthio group.

Examples of the naphthyl group which may be substituted on the naphthalene ring with 1 to 3 substituents selected from the group consisting of a lower alkyl group, a halogen atom, and an amino group which may have a substituent selected from the group consisting of a lower alkyl group and a lower alkanoyl group include naphthyl groups which may have, on the naphthalene ring, 1 to 3 substituents selected from the group consisting of a linear or branched alkyl group having 1 to 6 carbon atoms, a halogen atom, and an amino group which may have 1 or 2 substituents selected from the group consisting of a linear or branched alkyl group having 1 to 6 carbon atoms and a linear or branched alkanoyl group having 1 to 6 carbon atoms such as (1- or 2-)naphthyl, 1-methyl-(2-,3-,4-,5-,6-,7-, or 8-)naphthyl, 2-ethyl-(1-,3-,4-,5-,6-,7-, or 8-)naphthyl, 3-n-propyl-(1-,2-,4-,5-,6-,7-, or 8-)naphthyl, 4-n-butyl-(1-,2-,3-,5-,6-,7-, or 8-)naphthyl, 4-methyl-(1-,2-,3-,5-,6-,7-, or 8-)naphthyl, 5-n-pentyl-(1-,2-,3-,4-,6-,7-, or 8-)naphthyl, 6-n-hexyl-(1-,2-,3-,4-,5-,7-, or 8-)naphthyl, 1,7-dimethyl-(2-,3-,4-,5-,6-, or 8-)naphthyl, 1,2,8-trimethyl-(3-,4-,5-,6-, or 7-)naphthyl, 1-dimethylamino-(2-,3-,4-,5-,6-,7-, or 8-)naphthyl, 2-dimethylamino-(1-,3-,4-,5-,6-,7-, or 8-)naphthyl, 3-methylamino-(1-,2-,4-,5-,6-,7-, or 8-)naphthyl, 5-amino-(1-,2-,3-,4-,6-,7-, or 8-)naphthyl, 5-dimethylamino-(1-,2-,3-,4-,6-,7-, or 8-)naphthyl, 4-(N-methyl-N-ethylamino)-(1-,2-, 3-,5-,6-,7-, or 8-)naphthyl, 1-methyl-2-dimethylamino-(3-,4-,5-,6-,7-, or 8-)naphthyl, 1-chloro-(2-,3-,4-,5-,6-,7-, or 8-)naphthyl, 1-acetylamino-(2-,3-,4-,5-,6-,7-, or 8-)naphthyl groups.

Examples of the alkyl group which may have a lower alkoxy group as a substituent include, in addition to the above described alkyl groups which may have a lower alkoxy group as a substituent, linear or branched alkyl groups having 1 to 8 carbon atoms which may have a linear or branched alkoxy group having 1 to 6 carbon atoms as a substituent such as a heptyl group, 1-ethylpentyl group, octyl group, 7-methoxyheptyl group, 1-ethoxyheptyl group, 2-propoxyl-1-ethylpentyl group, 3-isopropoxyoctyl group, 7-butoxyheptyl group, 8-pentyloxyoctyl group, and 5-hexyloxy-1-ethylpentyl group.

Examples of the amino substituted lower alkyl group include linear or branched alkyl groups having 1 to 6 carbon atoms substituted with an amino group which may have 1 or 2 linear or branched alkyl groups having 1 to 6 carbon atoms such as aminomethyl, 2-aminoethyl, 1-aminoethyl, 3-aminopropyl, 4-aminobutyl, 5-aminopentyl, 6-aminohexyl, 1,1-dimethyl-2-aminoethyl, 2-methyl-3-aminopropyl, methylaminomethyl, 1-ethylaminoethyl, 2-propylaminoethyl, 3-isopropylaminopropyl, 4-butylaminobutyl, 5-pentylaminopentyl, 6-hexylaminohexyl, dimethylaminomethyl, 2-diethylaminoethyl, 2-diisopropylaminoethyl, (N-ethyl-N-propylamino)methyl, 2-(N-methyl-N-hexylamino)ethyl groups.

Examples of the cycloalkyl group include cycloalkyl groups having 3 to 16 carbon atoms such as a cyclopropyl group, cyclobutyl group, cyclopentyl group, cyclohexyl group, cycloheptyl group, cyclooctyl group, cyclononyl group, cyclodecyl group, cycloundecyl group, cyclododecyl group, cyclotridecyl group, cycloteradecyl group, cyclopentadecyl group, and cyclohexadecyl group.

Examples of the cycloalkyl group which may be substituted with a group selected from the group consisting of an amino substituted lower alkyl group which may have a lower alkyl group and a lower alkyl group which may have a halogen as a substituent include cycloalkyl groups having 3 to 16 carbon atoms which may be substituted on the cycloalkyl ring with 1 to 3 groups selected from the group consisting of a linear or branched alkyl group having 1 to 6 carbon atoms substituted with an amino group which may have 1 or 2 linear or branched alkyl groups having 1 to 6 carbon atoms and a linear or branched alkyl group having 1 to 6 carbon atoms which may have 1 to 3 halogen atoms as substituents such as 4-dimethylaminomethylcyclohexyl, 2-(aminomethyl)cyclopropyl, 3-(2-aminomethyl)cyclobutyl, 2-(1-aminoethyl)cyclopentyl, 3-(3-aminopropyl)cyclohexyl, 3-(4-aminobutyl)cycloheptyl, 4-(5-aminopentyl)cyclooctyl, 4-(6-aminohexyl)cyclohexyl, 2-(1,1-dimethyl-2-aminoethyl)cycloheptyl, 3-(2-methyl-3-aminopropyl)cyclopentyl, 3-(methylaminomethyl)cyclohexyl, 2-(1-ethylaminoethyl)cyclooctyl, 2-(2-propylaminoethyl)cyclohexyl, 3-(3-isopropylaminopropyl)cyclopentyl, 4-(4-butylaminobutyl)cycloheptyl, 2-(5-pentylaminopentyl)cyclohexyl, 2-(6-hexylaminohexyl)cyclopentyl, 3-(dimethylaminomethyl)cyclohexyl, 3-[(N-ethyl-N-propylamino)methyl]cycloheptyl, 4-[2-(N-methyl-N-hexylamino)ethyl]cyclooctyl, 4-dimethylaminomethylcyclononyl, 2-(aminomethyl)cyclodecyl, 3-(2-aminomethyl)cycloundecyl, 2-(1-aminoethyl)cyclododecyl, 3-(3-aminopropyl)cyclotridecyl, 3-(4-aminobutyl)cyclotetradecyl, 4-(5-aminopentyl)cyclopentadecyl, 4-(6-aminohexyl)cyclohexadecyl, 2-(1,1-dimethyl-2-aminoethyl)cyclononyl, 3-(2-methyl-3-aminopropyl)cyclodecyl, 3-(methylaminomethyl)cycloundecyl, 2-(1-ethylaminoethyl)cyclododecyl, 2-(2-propylaminoethyl)cyclotridecyl, 3-(3-isopropylaminopropyl)cyclotetradecyl, 4-(4-butylaminobutyl)cyclopentadecyl, 2-(5-pentylaminopentyl)cyclohexadecyl, 2-(6-hexylaminohexyl)cyclononyl, 3-(dimethylaminomethyl)cyclododecyl, 3-[(N-ethyl-N-propylamino)methyl]cyclodecyl, 4-[2-(N-methyl-N-hexylamino)ethyl]cyclohexadecyl, 2,2-dimethylcyclopropyl, 2-trifluoromethylcyclopropyl groups.

Examples of the lower alkenyl group include linear or branched alkenyl groups having 2 to 6 carbon atoms which have 1 to 3 double bonds such as a vinyl group, 1-propenyl group, 1-methyl-1-propenyl group, 2-methyl-1-propenyl group, 2-propenyl group, 2-butenyl group, 1-butenyl group, 3-butenyl group, 2-pentenyl group, 1-pentenyl group, 3-pentenyl group, 4-pentenyl group, 1,3-butadienyl group, 1,3-pentadienyl group, 2-penten-4-ynyl group, 2-hexenyl group, 1-hexenyl group, 5-hexenyl group, 3-hexenyl group, 4-hexenyl group, 3,3-dimethyl-1-propenyl group, 2-ethyl-1-propenyl group, 1,3,5-hexatrienyl group, 1,3-hexadienyl group, and 1,4-hexadienyl group.

Examples of the lower alkenyl group which may have a halogen atom as a substituent include, in addition to the above described lower alkenyl groups, linear or branched alkenyl groups having 2 to 6 carbon atoms which may have 1 to 3 halogen atoms as substituents and 1 to 3 double bonds such as 3,3,3-trifluoro-1-propenyl, 2-bromovinyl, 3-chloro-1-propenyl, 3-iodo-1-methyl-1-propenyl, 3-fluoro-2-methyl-1-propenyl, 2-butenyl, 4,4,3-trichloro-1-butenyl, 4,4-difluoro-3-butenyl, 5-fluoro-2-pentenyl, 5,5,3-tribromo-1-pentenyl, 5-chloro-3-pentenyl, 5,5,5-trifluoro-4-pentenyl, 4-chloro-1,3-butadienyl, 5-fluoro-1,3-pentadienyl, 5-bromo-2-penten- 4-ynyl, 6-fluoro-2-hexenyl, 6,6,5-trifluoro-1-hexenyl, 6-chloro-5-hexenyl, 5-bromo-3-hexenyl, 6-chloro-4-hexenyl, 3,3-dimethyl-2-chloro-1-propenyl, 3-fluoro-2-ethyl-1-propenyl, 6-chloro-1,3,5-hexatrienyl, 6-bromo-1,3-hexadienyl, 6-fluoro-1,4-hexadienyl groups.

Examples of the lower alkylenedioxy group include linear or branched alkylene groups having 1 to 4 carbon atoms such as a methylenedioxy group, ethylenedioxy group, trimethylenedioxy group, and tetramethylenedioxy group.

Examples of the amino group which may have a substituent selected from the group consisting of a lower alkyl group, a lower alkanoyl group, a benzoyl group and a cycloalkyl group include amino groups which may have 1 or 2 substituents selected from the group consisting of a linear or branched alkyl group having 1 to 6 carbon atoms, a linear or branched alkanoyl group having 1 to 6 carbon atoms, a benzoyl group, and a cycloalkyl group having 3 to 16 carbon atoms such as amino, methylamino, ethylamino, propylamino, isopropylamino, butylamino, tert-butylamino, pentylamino, hexylamino, dimethylamino, diethylamino, dipropylamino, dibutylamino, dipentylamino, dihexylamino, N-methyl-N-ethylamino, N-ethyl-N-propylamino, N-methyl-N-butylamino, N-methyl-N-hexylamino, N-methyl-N-acetylamino, N-acetylamino, N-formylamino, N-propionylamino, N-butyrylamino, N-isobutyrylamino, N-pentanoylamino, N-tert-butylcarbonylamino, N-hexanoylamino, N-ethyl-N-acetylamino, N-benzoylamino, N-ethyl-N-benzoylamino, N-methyl-N-benzoylamino, N-acetyl-N-benzoylamino, cyclopropylamino, cyclobutylamino, cyclopentylamino, cyclohexylamino, cycloheptylamino, cyclooctylamino, N-methyl-N-cyclohexylamino, N-methyl-N-cyclopentylamino, N-methyl-N-cycloheptylamino, N-cyclohexyl-N-acetylamino, N-cyclopentyl-N-benzoylamino, cyclononylamino, cyclodecylamino, cyclododecylamino, cyclotridecylamino, cyclotetradecylamino, cyclopentadecylamino, N-methyl-N-cyclohexadecylamino, N-methyl-N-cyclononylamino, N-methyl-N-cyclodecylamino, N-cycloundecyl-N-acetylamino, N-cyclohexadecyl-N-benzoylamino groups.

Examples of the lower alkanoyl group which may have a halogen atom as a substituent include, in addition to the above described lower alkanoyl groups, linear or branched alkanoyl groups having 2-6 carbon atoms which may have 1 to 3 halogen atoms as substituents such as a 2,2,2-trifluoroacetyl group, 2,2,2-trichloroacetyl group, 2-chloroacetyl group, 2-bromoacetyl group, 2-fluoroacetyl group, 2-iodoacetyl group, 2,2-difluoroacetyl group, 2,2-dibromoacetyl group, 3,3,3-trifluoropropionyl group, 3,3,3-trichloropropionyl group, 3-chloropropionyl group, 2,3-dichloropropionyl group, 4,4,4-trichlorobutyryl group, 4-fluorobutyryl group, 5-chloropentanoyl group, 3-chloro-2-methylpropionyl group, 6-bromohexanoyl group, and 5,6-dibromohexanoyl group.

Examples of the lower alkoxycarbonyl group include linear or branched alkoxycarbonyl groups having 1 to 6 carbon atoms such as a methoxycarbonyl group, ethoxycarbonyl group, propoxycarbonyl group, isopropoxycarbonyl group, butoxycarbonyl group, tert-butoxycarbonyl group, pentyloxycarbonyl group, and hexyloxycarbonyl group.

Examples of the lower alkanoyloxy group include linear or branched alkanoyloxy groups having 2 to 6 carbon atoms such as an acetyloxy group, propionyloxy group, butyryloxy group, isobutyryloxy group, pentanoyloxy group, tert-butylcarbonyloxy group, and hexanoyloxy group.

Examples of the 5- or 6-membered saturated or unsaturated heterocyclic group having 1 to 4 nitrogen atoms, oxygen atoms or sulfur atoms include pyrrolidinyl, piperidinyl, piperazinyl, morpholino, thiomorpholino, pyridyl, 1,2,5,6-tetrahydropyridyl, thienyl, pyrazyl, pyrimidyl, pyridazyl, pyrrolyl, 2H-pyrrolyl, imidazolidinyl, pyrazolyl, imidazolyl, pyrazolidinyl, furazanyl, 2-imidazolinyl, imidazolidinyl, 2-pyrrolinyl, furyl, oxazolyl, isoxazolidinyl, isoxazolyl, thiazolyl, isothiazolyl, pyranyl, 2-pyrazolidinyl, 1,2,4-triazolyl, 1,2,3-triazolyl, 1,2,5-triazolyl, thiazolidinyl, 2-thiazolinyl, 1,2,3,4-tetrazolyl, 1,3,4-oxadiazolyl, tetrahydropyranyl, tetrahydrofuryl groups.

Examples of the 5- to 7-membered saturated heterocyclic ring formed by binding $R^{11}$ and $R^{12}$ each other, together with nitrogen atoms bound to them, through or not through a nitrogen atom, a sulfur atom or an oxygen atom, include a pyrrolidinyl group, piperidinyl group, piperazinyl group, morpholino group, thiomorpholino group, and homopiperazinyl group.

Examples of the imidazolyl lower alkyl group include imidazolylalkyl groups of which the alkyl moiety is a linear or branched alkyl group having 1 to 6 carbon atoms such as a (1,2,4 or 5-)imidazolylmethyl group, 2-[(1,2,4 or 5-)imidazolyl]ethyl group, 1-[(1,2,4 or 5-)imidazolyl]ethyl group, 3-[(1,2,4 or 5-)imidazolyl]propyl group, 4-[(1,2,4 or 5-)imidazolyl]butyl group, 5-[(1,2,4 or 5-)imidazolyl]pentyl group, 6-[(1,2,4 or 5-)imidazolyl]hexyl group, 1,1-dimethyl-2-[(1,2,4 or 5-)imidazolyl]ethyl group, and 2-methyl-3-[(1,2,4 or 5-)imidazolyl]propyl group.

Examples of the 1,2,4-triazolyl lower alkyl group include 1,2,4-triazolylalkyl groups of which the alkyl moiety is a linear or branched alkyl group having 1 to 6 carbon atoms such as (1,3, or 5-)1,2,4-triazolylmethyl, 2-[(1,3, or 5-)1,2,4-triazolyl]ethyl, 1-[(1,3, or 5-)1,2,4-triazolyl]ethyl, 3-[(1,3, or 5-)1,2,4-triazolyl]propyl, 4-[(1,3, or 5-)1,2,4-triazolyl]butyl, 5-[(1,3, or 5-)1,2,4-triazolyl]pentyl, 6-[(1,3, or 5-)1,2,4-triazolyl]hexyl, 1,1-dimethyl-2-[(1,3, or 5-)1,2,4-triazolyl]ethyl, 2-methyl-3-[(1,3, or 5-)1,2,4-triazolyl]propyl groups.

Examples of the 1,2,3-triazolyl lower alkyl group include 1,2,3-triazolylalkyl groups of which the alkyl moiety is a linear or branched alkyl group having 1 to 6 carbon atoms such as (1,4, or 5-)1,2,3-triazolylmethyl, 2-[(1,4, or 5-)1,2,3-triazolyl]ethyl, 1-[(1,4, or 5-)1,2,3-triazolyl]ethyl, 3-[(1,4, or 5-)1,2,3-triazolyl]propyl, 4-[(1,4, or 5-)1,2,3-triazolyl]butyl, 5-[(1,4, or 5-)1,2,3-triazolyl]pentyl, 6-[(1,4, or 5-)1,2,3-triazolyl]hexyl, 1,1-dimethyl-2-[(1,4, or 5-)1,2,3-triazolyl]ethyl, 2-methyl-3-[(1,4, or 5-)1,2,3-triazolyl]propyl groups.

Examples of the 1,2,5-triazolyl lower alkyl group include 1,2,5-triazolylalkyl groups of which the alkyl moiety is a linear or branched alkyl group having 1 to 6 carbon atoms such as (1,3, or 4-)1,2,5-triazolylmethyl, 2-[(1,3, or 4-)1,2,5-triazolyl]ethyl, 1-[(1,3, or 4-)1,2,5-triazolyl]ethyl, 3-[(1,3, or 4-)1,2,5-triazolyl]propyl, 4-[(1,3, or 4-)1,2,5-triazolyl]butyl, 5-[(1,3, or 4-)1,2,5-triazolyl]pentyl, 6-[(1,3, or 4-)1,2,5-triazolyl]hexyl, 1,1-dimethyl-2-[(1,3, or 4-)1,2,5-triazolyl]ethyl, 2-methyl-3-[(1,3, or 4-)1,2,5-triazolyl]propyl groups.

Examples of the pyrazolyl lower alkyl group include pyrazolylalkyl groups of which the alkyl moiety is a linear or branched alkyl group having 1 to 6 carbon atoms such as a (1,3,4 or 5-)pyrazolylmethyl group, 2-[(1,3,4 or 5-)1,2,5-pyrazolyl]ethyl group, 1-[(1,3,4 or 5-)pyrazolyl]ethyl group, 3-[(1,3,4 or 5-)pyrazolyl]propyl group, 4-[(1,3,4 or 5-)pyrazolyl]butyl group, 5-[(1,3,4 or 5-)pyrazolyl]pentyl group, 6-[(1,3,4 or 5-)pyrazolyl]hexyl group, 1,1-dimethyl-2-[(1,3,4 or 5-)pyrazolyl]ethyl group, and 2-methyl-3-[(1,3,4 or 5-)pyrazolyl]propyl group.

Examples of the pyrimidinyl lower alkyl group include pyrimidinylalkyl groups which may have 1 to 3 oxo groups as substituents on the pyrimidine ring and of which the alkyl moiety is a linear or branched alkyl group having 1 to 6 carbon atoms such as (2,4,5, or 6-)pyrimidinylmethyl, 2-[(2,4,5, or 6-)pyrimidinyl]ethyl, 1-[(2,4,5, or 6-)pyrimidinyl]ethyl, 3-[(2,4,5, or 6-)pyrimidinyl]propyl, 4-[(2,4,5, or 6-)pyrimidinyl]butyl, 5-[(2,4,5, or 6-)pyrimidinyl]pentyl, 6-[(2,4,5, or 6-)pyrimidinyl]hexyl, 1,1-dimethyl-2-[(2,4,5, or 6-)pyrimidinyl]ethyl, 2-methyl-3-[(2,4,5, or 6-)pyrimidinyl]propyl, [(1,3,4, or 5-)2,6-dioxopyrimidinyl]methyl, [(1,3,4,5, or 6-)2-oxopyrimidinyl]methyl, [(1,2,4, or 5-)6-oxopyrimidinyl]methyl, [(1,2,5, or 6-)4-oxopyrimidinyl]methyl, [(1,3,5, or 6-)2,4-dioxopyrimidinyl]methyl, 2-[(4 or 6-)2,5-dioxopyrimidinyl]ethyl, 1-[(1,3,4, or 5-)2,6-dioxopyrimidinyl]ethyl, 3-[(1,3, or 5-)2,4,6-trioxopyrimidinyl]propyl, 4-[(1,3,4, or 5-)2,6-dioxopyrimidinyl]butyl, 5-[(4 or 6-)2,5-dioxopyrimidinyl]pentyl, 6-[(1,3,5, or 6-)2,4-dioxopyrimidinyl]hexyl, 1,1-dimethyl-2-[(1,3,4, or 5-)2,6-dioxopyrimidinyl]ethyl, 2-methyl-3-[(1,3,4, or 5-)2,6-dioxopyrimidinyl]propyl groups.

Examples of the 3,5-dioxoisoxazolidin-4-ylidene lower alkyl group include 3,5-dioxoisoxazolidin-4-ylidenealkyl groups of which the alkyl moiety is a linear or branched alkyl group having 1 to 6 carbon atoms such as a 3,5-dioxoisoxazolidin-4-ylidenemethyl group, 3,5-dioxoisoxazolidin-4-ylideneethyl group, 3,5-dioxoisoxazolidin-4-ylidenepropyl group, 3,5-dioxoisoxazolidin-4-ylideneisopropyl group, 3,5-dioxoisoxazolidin-4-ylidenebutyl group, 3,5-dioxoisoxazolidin-4-ylidenepentyl group, and 3,5-dioxoisoxazolidin-4-ylidenehexyl group.

Examples of the 1,2,4-oxadiazolyl lower alkyl group which may have a lower alkyl group as a substituent on the 1,2,4-oxadiazol ring include 1,2,4-oxadiazolylalkyl groups which may have a linear or branched alkyl group having 1 to 6 carbon atoms as a substituent on the 1,2,4-oxadiazol ring and of which the alkyl moiety is a linear or branched alkyl group having 1 to 6 carbon atoms such as (3 or 5-)1,2,4-oxadiazolylmethyl, 2-[(3 or 5-)1,2,4-oxadiazolyl]ethyl, 1-[(3 or 5-)1,2,4-oxadiazolyl]ethyl, 3-[(3 or 5-)1,2,4-oxadiazolyl]propyl, 4-[(3 or 5-)1,2,4-oxadiazolyl]butyl, 5-[(3 or 5-)1,2,4-oxadiazolyl]pentyl, 6-[(3 or 5-)1,2,4-oxadiazolyl]hexyl, 1,1-dimethyl-2-[(3 or 5-)1,2,4-oxadiazolyl]ethyl, 2-methyl-3-[(3 or 5-)1,2,4-oxadiazolyl]propyl, 5-methyl-3-(1,2,4-oxadiazolyl)methyl, 3-ethyl-2-[5-(1,2,4-oxadiazolyl)]ethyl, 1-[3-propyl-5-(1,2,4-oxadiazolyl)]ethyl, 3-[5-butyl-3-(1,2,4-oxadiazolyl)]propyl, 4-[3-pentyl-5-(1,2,4-oxadiazolyl)]butyl, 5-[5-hexyl-3-(1,2,4-oxadiazolyl)]pentyl, 6-[3-methyl-5-(1,2,4-oxadiazolyl)]hexyl, 1,1-dimethyl-2-[5-isopropyl-3-(1,2,4-oxadiazolyl)]ethyl, 2-methyl-3-[3-isobutyl-5-(1,2,4-oxadiazolyl)]propyl groups.

Examples of the thiazolydinyl lower alkyl group which may have an oxo group as a substituent on the thiazolydine ring include thiazolydinylalkyl groups which may have 1 to 3 oxo groups as substituents on the thiazolydine ring and of which the alkyl moiety is a linear or branched alkyl group having 1 to 6 carbon atoms such as (2,3,4, or 5-)thiazolidinylmethyl, 2-[(2,3,4, or 5-)thiazolidinyl]ethyl, 1-[(2,3,4, or 5-)thiazolidinyl]ethyl, 3-[(2,3,4, or 5-)thiazolidinyl]propyl, 4-[(2,3,4, or 5-)thiazolidinyl]butyl, 5-[(2,3,4, or 5-)thiazolidinyl]pentyl, 6-[(2,3,4, or 5-)thiazolidinyl]hexyl, 1,1-dimethyl-2-[(2,3,4, or 5-)thiazolidinyl]ethyl, 2-methyl-3-[(2,3,4, or 5-)thiazolidinyl]propyl, 2,4-dioxo-5-thiazolidinylmethyl, 2-[2-oxo-(3,4, or 5-)thiazolidinyl]ethyl, 1-[4-oxo-(2,3, or 5-)thiazolidinyl]ethyl, 3-[5-oxo-(2,3, or 4-)thiazolidinyl]propyl, 4-[2,5-dioxo-(3 or 4-)thiazolidinyl]butyl, S-[2,4,5-trioxo-3-thiazolidinyl]pentyl, 6-[4,5-dioxo-(2 or 3-)thiazolidinyl]hexyl, 1,1-dimethyl-2-[2,4-dioxo-(3 or 5-)thiazolidinyl]ethyl, 2-methyl-3-[2,4-dioxo-(3 or 5-)thiazolidinyl]propyl, 3-[2,4-dioxo-(3 or 5-)thiazolidinyl]propyl groups.

Examples of the phenyl lower alkyl group which may have a lower alkylenedioxy group as a substituent on the phenyl ring include, in addition to the above described phenyl lower alkyl groups, phenylalkyl groups which may have a linear or branched alkylenedioxy group as a substituent on the phenyl ring and of which the alkyl moiety is a linear or branched alkyl group having 1 to 6 carbon atoms such as 3,4-methylenedioxybenzyl, 3,4-trimethylenedioxybenzyl, 2-(2,3-ethylenedioxyphenyl)ethyl, 1-(3,4-trimethylenedioxyphenyl) ethyl, 3-(2,3-tetramethylenedioxyphenyl)propyl, 4-(3,4-methylenedioxyphenyl)butyl, 5-(2,3-ethylenedioxyphenyl)pentyl, 6-(3,4-trimethylenedioxyphenyl)hexyl, 1,1-dimethyl-2-(2,3-methylenedioxyphenyl)ethyl, 2-methyl-3-(3,4-ethylenedioxyphenyl)propyl groups.

Examples of the lower alkoxycarbonyl lower alkyl group include alkoxycarbonylalkyl groups of which the alkoxy moiety is a linear or branched alkoxy group having 1 to 6 carbon atoms and the alkyl moiety is a linear or branched alkyl group having 1 to 6 carbon atoms such as a methoxycarbonylmethyl group, ethoxycarbonylmethyl group, 2-methoxycarbonylethyl group, 2-ethoxycarbonylmethyl group, 1-ethoxycarbonylethyl group, 3-methoxycarbonylpropyl group, 3-ethoxycarbonylpropyl group, 4-ethoxycarbonylbutyl group, 5-isopropoxycarbonylpentyl group, 6-propoxycarbonylhexyl group, 1,1-dimethyl-2-butoxycarbonylethyl group, 2-methyl-3-tert-butoxycarbonylpropyl group, 2-pentyloxycarbonylethyl group, and hexyloxycarbonylmethyl group.

Examples of the carboxy lower alkyl group include carboxyalkyl groups of which the alkyl moiety is a linear or branched alkyl group having 1 to 6 carbon atoms such as a carboxymethyl group, 2-carboxyethyl group, 1-carboxyethyl group, 3-carboxypropyl group, 4-carboxybutyl group, 5-carboxypentyl group, 6-carboxyhexyl group, 1,1-dimethyl-2-carboxyethyl group, and 2-methyl-3-carboxypropyl group.

Examples of the morpholino substituted lower alkanoyl group include morpholino substituted alkanoyl groups of which the alkanoyl moiety is a linear or branched alkanoyl group having 2 to 6 carbon atoms such as a 2-[(2,3 or 4-)morpholino]acetyl group, 3-[(2,3 or 4-)morpholino]propionyl group, 2-[(2,3 or 4-)morpholino]propionyl group, 4-[(2,3 or 4-)morpholino]butyryl group, 5-[(2,3 or 4-)morpholino]pentanoyl group, 6-[(2,3 or 4-)morpholino]hexanoyl group, 2,2-dimethyl-2-[(2,3 or 4-)morpholino]propionyl group, and 2-methyl-3-[(2,3 or 4-)morpholino]propionyl group.

Examples of the piperazinylcarbonyl lower alkyl group which may be substituted on the piperazine ring with a phenyl lower alkyl group which may have a lower alkylenedioxy group as a substituent on the phenyl ring include piperazinylcarbonylalkyl groups which may be substituted on the piperazine ring with 1 to 3 phenylalkyl groups which may have a linear or branched alkylenedioxy group having 1 to 4 carbon atoms and of which the alkyl moiety is a linear or branched alkyl group having 1 to 6 carbon atoms, the piperazinylcarbonylalkyl groups of which the alkyl moiety is a linear or branched alkyl group having 1 to 6 carbon atoms, such as [(1,2, or 3-)piperazinyl]carbonylmethyl, 2-[(1,2, or 3-)piperazinyl]carbonylethyl, 1-[(1,2, or 3-)piperazinyl]carbonylethyl, 3-[(1,2, or 3-)piperazinyl]carbonylpropyl, 4-[(1,2, or 3-)piperazinyl]carbonylbutyl, 5-[(1,2, or 3-)piperazinyl]carbonylpentyl, 6-[(1,2, or 3-)piperazinyl]carbonylhexyl, 1,1-dimethyl-2-[(1,2, or 3-)piperazinyl]carbonylethyl, 2-methyl-3-[(1,2, or 3-)piperazinyl]carbonylpropyl, (4-benzyl-1-piperazinylcarbonyl)methyl, 2-[4-(2-phenylethyl)-1-piperazinylcarbonyl]methyl, 1-[4-(3-phenylpropyl)-1-piperazinylcarbonyl]ethyl, 3-[4-(4-phenylbutyl)-1-piperazinylcarbonyl]propyl, 4-[4-(5-phenylpentyl)-1-piperazinylcarbonyl]butyl, 5-[4-(6-phenylpropyl)-1- piperazinylcarbonyl]pentyl, 6-(4-benzyl-1-piperazinylcarbonyl)hexyl, 1,1-dimethyl-2-(4-benzyl-1-piperazinylcarbonyl)ethyl, 2-methyl-3-(4-benzyl-1-piperazinylcarbonyl)propyl, [4-(3,4-methylenedioxybenzyl)-1-piperazinylcarbonyl]methyl, 2-{4-[2-(2,3-ethylenedioxyphenyl)ethyl]-1-piperazinylcarbonyl}ethyl, 1-{4-[3-(3,4-trimethylenedioxyphenyl)propyl]-1-piperazinylcarbonyl}ethyl, 3-{4-[4-(2,3-tetramethylenedioxyphenyl)butyl]-1-piperazinylcarbonyl}propyl, 4-{4-[5-(3,4-methylenedioxyphenyl)pentyl]-1-piperazinylcarbonyl}butyl, 5-{4-[3-(2,3-ethylenedioxyphenyl)propyl]-1-piperazinylcarbonyl}pentyl, 6-[4-(3,4-trimethylenedioxybenzyl)-1-piperazinylcarbonyl]hexyl, 1,1-dimethyl-2-[4-(2,3-tetramethylenedioxybenzyl)-1-piperazinylcarbonyl]ethyl, 2-methyl-3-[4-(3,4-methylenedioxybenzyl)-1-piperazinylcarbonyl]propyl, (3,4-dibenzyl-1-piperazinylcarbonyl)methyl, (3,4,5-tribenzyl-1-piperazinylcarbonyl)methyl, [2,4-di(3,4-methylenedioxybenzyl)-1-piperazinylcarbonyl])methyl, [2,4,6-tri(3,4-methylenedioxybenzyl)-1-piperazinylcarbonyl]methyl, [3-benzyl-4-(3,4-methylenedioxybenzyl)-1-piperazinylcarbonyl]methyl groups.

Examples of the piperazinyl lower alkanoyl group which may be substituted on the piperazine ring with a phenyl lower alkyl group which may have a lower alkylenedioxy group as a substituent on the phenyl ring include piperazinylalkanoyl groups which may be substituted on the piperazine ring with 1 to 3 phenylalkyl groups which may have a linear or branched alkylenedioxy group having 1 to 4 carbon atoms as a substituent on the phenyl ring and of which the alkyl moiety is a linear or branched alkyl group having 1 to 6 carbon atoms, the piperazinylalkanoyl groups of which the alkanoyl moiety is a linear or branched alkanoyl group having 2 to 6 carbon atoms, such as 2-[(1,2, or 3-)piperazinyl]acetyl, 3-[(1,2, or 3-)piperazinyl]propionyl, 2-[(1,2, or 3-)piperazinyl]propionyl, 4-[(1,2, or 3-)piperazinyl]butyryl, 5-[(1,2, or 3-)piperazinyl]pentanoyl, 6-[(1,2, or 3-)piperazinyl]hexanoyl, 2,2-dimethyl-3-[(1,2, or 3-)piperazinyl]propionyl, 2-methyl-3-[(1,2, or 3-)piperazinyl]propionyl, 2-(4-benzyl-1-piperazinyl)acetyl, 3-[4-(2-phenylethyl)-1-piperazinyl]propionyl, 2-[4-(3-phenylpropyl)-1-piperazinyl]propionyl, 4-[4-(4-phenylbutyl)-1-piperazinyl]butyryl, 5-[4-(5-phenylpentyl)-1-piperazinyl]pentanoyl, 6-[4-(6-phenylpropyl)-1-piperazinyl]hexanoyl, 6-(4-benzyl-1-piperazinyl)hexanoyl, 2,2-dimethyl-3-(4-benzyl-1-piperazinyl)propionyl, 2-methyl-3-(4-benzyl-1-piperazinyl)propionyl, 2-[4-(3,4-methylenedioxybenzyl)-1-piperazinyl])acetyl, 3-{4-[2-(2,3-ethylenedioxyphenyl)ethyl]-1-piperazinyl}propionyl, 2-{4-[3-(3,4-trimethylenedioxyphenyl)propyl]-1-piperazinyl}propionyl, 4-{4-[4-(2,3-tetramethylenedioxyphenyl)butyl]-1-piperazinyl}butyryl, 5-{4-[5-(3,4-methylenedioxyphenyl)pentyl]-1-piperazinyl}pentanoyl, 5-{4-[3-(2,3-ethylenedioxyphenyl)propyl]-1-piperazinyl}pentanoyl, 6-[4-(3,4-trimethylenedioxybenzyl)-1-piperazinyl])hexanoyl, 2,2-dimethyl-3-[4-(2,3-tetramethylenedioxybenzyl)-1-piperazinyl]propionyl, 2-methyl-3-[4-(3,4-methylenedioxybenzyl)-1-piperazinyl]propionyl, 2-(3,4-dibenzyl-1-piperazinyl)acetyl, 2-(3,4,5-tribenzyl-1-piperazinyl)acetyl, 2-[2,4-di(3,4-methylenedioxybenzyl)-1-piperazinyl])acetyl, 2-[2,4,6-tri(3,4-methylenedioxybenzyl)-1-piperazinyl])acetyl, 2[3-benzyl-4-(3,4-methylenedioxybenzyl)-1-piperazinyl])acetyl groups.

Examples of the morpholinocarbonyl substituted lower alkyl group include morpholinocarbonylalkyl groups of which the alkyl moiety is a linear or branched alkyl group having 1 to 6 carbon atoms such as [(2,3, or 4-)morpholino]carbonylmethyl, 2-[(2,3, or 4-)morpholino]carbonylethyl, 1-[(2,3, or 4-)morpholino]carbonylethyl, 3-[(2,3, or 4-)morpholino]carbonylpropyl, 4-[(2,3, or 4-)morpholino]carbonylbutyl, 5-[(2,3, or 4-)morpholino]carbonylpentyl, 6-[(2,3, or 4-)morpholino]carbonylhexyl, 1,1-dimethyl-2-[(2,3, or 4-)morpholino]carbonylethyl, 2-methyl-3-[(2,3, or 4-)morpholino]carbonylpropyl groups.

Examples of the imidazolyl lower alkanoyl group include imidazolylalkanoyl groups of which the alkanoyl moiety is a linear or branched alkanoyl group having 2 to 6 carbon atoms such as a 2-[(1,2,4 or 5-)imidazolyl]acetyl group, 3-[(1,2,4 or 5-)imidazolyl]propionyl group, 2-[(1,2,4 or 5-)imidazolyl]propionyl group, 4-[(1,2,4 or 5-)imidazolyl]butyryl group, 5-[(1,2,4 or 5-)imidazolyl]pentanoyl group, 6-[(1,2,4 or 5-)imidazolyl]hexanoyl group, 2,2-dimethyl-3-[(1,2,4 or 5-)imidazolyl]propionyl group, and 2-methyl-3-[(1,2,4 or 5-)imidazolyl]propionyl group.

Examples of the cycloalkylcarbonyl group include cycloalkylcarbonyl groups of which the cycloalkyl moiety is a cycloalkyl group having 3 to 16 carbon atoms such as a cyclopropylcarbonyl group, cyclobutylcarbonyl group, cyclopentylcarbonyl group, cyclohexylcarbonyl group, cycloheptylcarbonyl group, cyclooctylcarbonyl group, cyclononylcarbonyl group, cyclodecylcarbonyl group, cycloundecylcarbonyl group, cyclododecylcarbonyl group, cyclotridecylcarbonyl group, cyclotetradecylcarbonyl group, cyclopentadecylcarbonyl group, and cyclohexadecylcarbonyl group.

Examples of the amino substituted lower alkanoyl group which may have a lower alkyl group as a substituent include linear or branched alkanoyl groups having 2 to 6 carbon atoms substituted with an amino group which may have 1 or 2 linear or branched alkyl groups having 1 to 6 carbon atoms as substituents such as aminoacetyl, 2-aminopropionyl, 3-aminopropionyl, 4-aminobutyryl, 5-aminopentanoyl, 6-aminohexanoyl, 2,2-dimethyl-3-aminopropionyl, 2-methyl-3-aminopropionyl, methylaminoacetyl, 2-ethylaminopropionyl, 3-propylaminopropionyl, 3-isopropylaminopropionyl, 4-butylaminobutyryl, 5-pentylaminopentanoyl, 6-hexylaminohexanoyl, dimethylaminoacetyl, 3-diisopropylaminopropionyl, (N-ethyl-N-propylamino)acetyl, 2-(N-methyl-N-hexylamino)acetyl groups.

Examples of the lower alkylene group which may have a hydroxyl group as a substituent include, in addition to the above described lower alkylene groups, linear or branched alkylene groups having 1 to 6 carbon atoms which may have 1 to 3 hydroxyl groups as substituents such as 1-hydroxymethylene, 2-hydroxyethylene, 1-hydroxyethylene, 2-hydroxytrimethylene, 3-hydroxytrimethylene, 1-hydroxytrimethylene, 3-hydroxy-2-methyltrimethylene, 1-hydroxy-2-methyltrimethylene, 3-hydroxy-2,2-dimethyltrimethylene, 1-hydroxy-2,2-dimethyltrimethylene, 3-hydroxy-1-methyltrimethylene, 2-hydroxy-1-methyltrimethylene, 1-hydroxymethylmethylene, hydroxymethylmethylene, 2-hydroxymethyltrimethylene, 2-hydroxymethyl-2-methyltrimethylene, (2-hydroxyethyl)methylene, (1-hydroxyethyl)methylene, 4-hydroxytetramethylene, 2-hydroxytetramethylene, 3-hydroxytetramethylene, 1-hydroxytetramethylene, 5-hydroxypentamethylene, 4-hydroxypentamethylene, 3-hydroxypentamethylene, 2-hydroxypentamethylene, 1-hydroxypentamethylene, 6-hydroxyhexamethylene, 5-hydroxyhexamethylene, 4-hydroxyhexamethylene, 3-hydroxyhexamethylene, 2-hydroxyhexamethylene, 1-hydroxyhexamethylene, 1,2-dihydroxytrimethylene, 2,2,4-trihydroxytetramethylene, 1,2,6-trihydroxyhexamethylene, 3,4,5-trihydroxypentamethylene groups.

Examples of the alkyl group which may have a hydroxyl group as a substituent include, in addition to the above described lower alkyl groups, linear or branched alkyl groups having 1 to 16 carbon atoms which have 1 to 3 hydroxyl groups as substituents such as a heptyl group, octyl group, nonyl group, decyl group, undecyl group, dodecyl group, tridecyl group, tetradecyl group, pentadecyl group, 1-methylhexyl group, hexadecyl group, hydroxymethyl group, 2-hydroxyethyl group, 1-hydroxyethyl group, 3-hydroxypropyl group, 2,3-dihydroxypropyl group, 4-hydroxybutyl group, 1,1-dimethyl-2-hydroxyethyl group, 5,5,4-trihydroxypentyl group, 5-hydroxypentyl group, 6-hydroxyhexyl group, 1-hydroxyisopropyl group, and 2-methyl-3-hydroxypropyl group.

Examples of the hydroxyl group substituted alkyl group include linear or branched alkyl groups having 1 to 16 carbon atoms having 1 to 3 hydroxyl groups as substituents such as a hydroxymethyl group, 2-hydroxyethyl group, 1-hydroxyethyl group, 3-hydroxypropyl group, 2,3-dihydroxypropyl group, 4-hydroxybutyl group, 1,1-dimethyl-2-hydroxyethyl group, 5,5,4-trihydroxypentyl group, 5-hydroxypentyl group, 6-hydroxyhexyl group, 1-hydroxyisopropyl group, and 2-methyl-3-hydroxypropyl group.

Examples of the cycloalkyl group which may have a substituent selected from the group consisting of a hydroxyl group and a lower alkyl group include, in addition to the above described cycloalkyl groups, cycloalkyl groups having 3 to 16 carbon atoms which may have 1 to 3 substituents selected from the group consisting of a hydroxyl group and a linear or branched alkyl group having 1 to 6 carbon atoms such as 2-hydroxycyclopropyl, 3-hydroxycyclobutyl, 3-hydroxycyclopentyl, 2-hydroxycyclohexyl, 4-hydroxycyclohexyl, 3-hydroxycycloheptyl, 4-hydroxycyclooctyl, 5-hydroxycyclononyl, 3-hydroxycyclodecyl, 4-hydroxycycloundecyl, 5-hydroxycyclododecyl, 6-hydroxycyclotridecyl, 7-hydroxycyclotetradecyl, 6-hydroxycyclopentadecyl, 8-hydroxycyclohexadecyl, 2,4-dihydroxycyclohexyl, 2,4,6-trihydroxycyclohexyl, 1-methylcyclopentyl, 2-ethylcyclopropyl, 3-n-propylcyclobutyl, 2-n-butylcyclohexyl, 4-n-pentylcycloheptyl, 4-n-hexylcyclooctyl, 2,3-dimethylcyclohexyl, 2,3,4-trimethylcyclohexyl, 2-methyl-4-hydroxycyclohexyl groups.

Examples of the phenoxy lower alkyl group include phenoxyalkyl groups of which the alkyl moiety is a linear or branched alkyl group having 1 to 6 carbon atoms such as a phenoxymethyl group, 2-phenoxyethyl group, 1-phenoxyethyl group, 3-phenoxypropyl group, 4-phenoxybutyl group, 1,1-dimethyl-2-phenoxyethyl group, 5-phenoxypentyl group, 6-phenoxyhexyl group, 1-phenoxyisopropyl group, and 2-methyl-3-phenoxypropyl group.

Examples of the amino lower alkoxy group which may have a lower alkyl group as a substituent include linear or branched alkoxy groups having 1 to 6 carbon atoms substituted with an amino group which may have 1 or 2 linear or branched alkyl groups having 1 to 6 carbon atoms such as aminomethoxy, 2-aminoethoxy, 1-aminoethoxy, 3-aminopropoxy, 4-aminobutoxy, 5-aminopentyloxy, 6-aminohexyloxy, 1,1-dimethyl-2-aminoethoxy, 2-methyl-3-aminopropoxy, methylaminomethoxy, 1-ethylaminoethoxy, 2-propylaminoethoxy, 3-isopropylaminopropoxy, 4-butylaminobutoxy, 5-pentylaminopentyloxy, 6-hexylaminohexyloxy, dimethylaminomethoxy, 2-diethylaminoethoxy, 2-diisopropylaminoethoxy, (N-ethyl-N-propylamino)methoxy, 2-(N-methyl-N-hexylamino)ethoxy groups.

Examples of the hydroxyl group substituted lower alkyl group include linear or branched alkyl groups having 1 to 6 carbon atoms which have 1 to 3 hydroxyl groups as substituents such as a hydroxymethyl group, 1-hydroxyethyl group, 2-hydroxyethyl group, 3-hydroxypropyl group, 2,3-dihydroxypropyl group, 4-hydroxybutyl group, 1,1-dimethyl-2-hydroxyethyl group, 5,5,4-trihydroxypentyl group, 5-hydroxypentyl group, 6-hydroxyhexyl group, 1-hydroxyisopropyl group, and 2-methyl-3-hydroxypropyl group.

Examples of the amino group which may have a lower alkylsulfonyl as a substituent include amino groups which may have 1 or 2 linear or branched alkylsulfonyl groups having 1 to 6 carbon atoms as substituents such as amino, methylsulfonylamino, ethylsulfonylamino, propylsulfonylamino, isopropylsulfonylamino, butylsulfonylamino, tert-butylsulfonylamino, pentylsulfonylamino, hexylsulfonylamino, dimethylsulfonylamino, diethylsulfonylamino, dipropylsulfonylamino, dibutylsulfonylamino, dipentylsulfonylamino, dihexylsulfonylamino, N-methylsulfonyl-N-ethylsulfonylamino, N-ethylsulfonyl-N-propylsulfonylamino, N-methylsulfonyl-N-butylsulfonylamino, N-methylsulfonyl-N-hexylsulfonylamino groups.

Examples of the lower alkynyl group include linear or branched alkynyl groups having 2 to 6 carbon atoms include an ethynyl group, 2-propynyl group, 2-butynyl group, 3-butynyl group, 1-methyl-2-propynyl group, 2-pentynyl group, and 2-hexynyl group.

Examples of the anilino group which may have a halogen atom as a substituent on the phenyl ring include anilino groups which may have 1 to 3 halogen atoms as substituents on the phenyl ring such as anilino, 2-fluoroanilino, 3-fluoroanilino, 4-fluoroanilino, 2-bromoanilino, 3-bromoanilino, 4-bromoanilino, 2-iodoanilino, 3-iodoanilino, 4-iodoanilino, 2,3-dibromoanilino, 2,4-diiodoanilino, 2,5-difluoroanilino, 2,6-dichloroanilino, 2,4,6-trichloroanilino, 2,6-difluoroanilino, 3,5-difluoroanilino, 2,6-difluoroanilino, 2-chloroanilino, 3-chloroanilino, 4-chloroanilino, 2,3-dichloroanilino, 2,4-dichloroanilino, 2,5-dichloroanilino, 3,4-dichloroanilino, 2,6-dichloroanilino, 3,5-dichloroanilino, 2,4,6-trifluoroanilino, 2,4-difluoroanilino, 3,4-difluoroanilino groups.

Examples of the piperazinyl group which may have a lower alkyl group as a substituent on the piperazine ring include piperazinyl groups which may have 1 to 3 linear or branched alkyl groups having 1 to 6 carbon atoms as substituents on the piperazine ring such as a (1-,2- or 3-)piperazinyl group, 4-methyl-(1-,2- or 3-)piperazinyl group, 2,3-dimethyl-(1 or 5-)piperazinyl group, and 2,3,4-trimethyl-(1-,5- or 6-)piperazinyl group.

Examples of the pyrrolidinyl group which may have an oxo group as a substituent on the pyrrolidine ring include pyrrolidinyl groups which may have 1 or 2 oxo groups as substituents on the pyrrolidine ring such as a (1-,2- or 3-)pyrrolidinyl group, 2-oxo-(1-,3-,4- or 5-)pyrrolidinyl group, 3-oxo-(1-,2-, 4- or 5-)pyrrolidinyl group, 2,3-dioxo-(1-,4- or 5-)pyrrolidinyl group, and 2,5-dioxo-(1-,3- or 4-)pyrrolidinyl group.

Examples of the phenyl group which may be substituted on the phenyl ring with 1 to 3 groups selected from the group consisting of a lower alkyl group; a lower alkoxy groups which may have a halogen atom as a substituent; a halogen atom; an amino lower alkoxy group which may have a lower alkyl group as a substituent; a hydroxyl group substituted lower alkyl group; a phenyl lower alkyl group; a lower alkynyl group; an amino group which may have a lower alkylsulfonyl group as a substituent; a lower alkylthio group; a cycloalkyl group; a phenylthio group; an adamantyl group; an anilino group which may have a halogen atom as a substituent on the phenyl ring; a lower alkoxycarbonyl group; a piperazinyl group which may have a lower alkyl group as a substituent on the piperazine ring; a pyrrolidinyl group which may have an oxo group as a substituent on the pyrrolidine ring; a lower alkanoylamino group; a cyano group; and a phenoxy group include phenyl groups which may be substituted on the phenyl ring with 1 to 3 groups selected from the group consisting of a linear or branched alkyl group having 1 to 6 carbon atoms; a linear or branched alkoxy group having 1 to 6 carbon atoms which may have 1 to 3 halogen atoms; a halogen atom; an aminoalkoxy group of which the alkoxy moiety is a linear or branched alkoxy group having 1 to 6 carbon atoms and which may have 1 or 2 linear or branched alkyl groups having 1 to 6 carbon atom as substituents; a linear or branched alkyl group having 1 to 6 carbon atoms which may have 1 to 3 hydroxyl groups as substituents; a phenylalkyl group of which the alkyl moiety is a linear or branched alkyl group having 1 to 6 carbon atoms; a linear or branched alkynyl group having 2 to 6 carbon atoms; an amino group which may have 1 or 2 linear or branched alkylsulfonyl groups having 1 to 6 carbon atoms as substituents; a linear or branched alkylthio group having 1 to 6 carbon atoms; a cycloalkyl group having 3 to 16 carbon atoms; a phenylthio group; an adamantyl group; an anilino group which may have 1 to 3 halogen atoms as substituents on the phenyl ring; a linear or branched alkoxycarbonyl group having 1 to 6 carbon atoms; a piperazinyl group which may have 1 to 3 linear or branched alkyl groups having 1 to 6 carbon atoms as substituents on the piperazine ring; a pyrrolidinyl group which may have 1 or 2 oxo groups as substituents on the pyrrolidine ring; an amino group which may have 1 or 2 linear or branched alkanoyl groups having 2 to 6 carbon atoms; a cyano group; and a phenoxy group such as phenyl, 2-methylphenyl, 3-methylphenyl, 4-methylphenyl, 2-ethylphenyl, 3-ethylphenyl, 4-ethylphenyl, 2-isopropylphenyl, 4-isopropylphenyl, 3-butylphenyl, 4-pentylphenyl, 4-hexylphenyl, 3,4-dimethylphenyl, 3,4-diethylphenyl, 2,4-dimethylphenyl, 2,5-dimethylphenyl, 2,6-dimethylphenyl, 3,4,5-trimethylphenyl, 2-methoxyphenyl, 3-methoxyphenyl, 4-methoxyphenyl, 2-ethoxyphenyl, 3-ethoxyphenyl, 4-ethoxyphenyl, 4-isopropoxyphenyl, 3-butoxyphenyl, 4-pentyloxyphenyl, 4-hexyloxyphenyl, 3,4-dimethoxyphenyl, 3,4-diethoxyphenyl, 2,4-dimethoxyphenyl, 2,5-dimethoxyphenyl, 2,6-dimethoxyphenyl, 3,4,5-trimethoxyphenyl, 2-trifluoromethoxyphenyl, 3-trifluoromethoxyphenyl, 4-trifluoromethoxyphenyl, 2-(bromomethoxy)phenyl, 3-(2-chloroethoxy)phenyl, 4-(2,3-dichloropropoxy)phenyl, 4-(4-fluorobutoxy)phenyl, 3-(5-chloropentyloxy)phenyl, 4-(5-bromohexyloxy)phenyl, 4-(5,6-dibromohexyloxy)phenyl, 3,4-di(trifluoromethoxy)phenyl, 3,4-di(4,4,4-trichlorobutoxy)phenyl, 2,4-di(3-chloro-2-methoxypropyl)phenyl, 2,5-di(3-chloropropoxy)phenyl, 2,6-di(2,2,2-trifluoroethoxy)phenyl, 3,4,5-tri(trifluoromethoxy)phenyl, 4-(2,2,2-trichloroethoxy)phenyl, 2-methyl-4-trifluoromethoxyphenyl, 3-ethyl-4-trichloromethoxyphenyl, 2-methoxy-4-trifluoromethoxyphenyl, 3-ethoxy-4-trichloromethoxyphenyl, 2-methyl-3-trifluoromethoxy-4-trifluoromethoxyphenyl, 2-phenoxyphenyl, 3-phenoxyphenyl, 4-phenoxyphenyl, 2,3-diphenoxyphenyl, 3,4-diphenoxyphenyl, 2,6-diphenoxyphenyl, 3,4,5-triphenoxyphenyl, 2-methyl-4-phenoxyphenyl, 3-ethyl-4-phenoxyphenyl, 2-methoxy-4-phenoxyphenyl, 3-ethoxy-4-phenoxyphenyl, 2-methyl-3-phenoxy-4-trifluoromethoxyphenyl, 2-chlorophenyl, 3-chlorophenyl, 4-chlorophenyl, 2,3-dichlorophenyl, 2,4-dichlorophenyl, 2,5-dichlorophenyl, 3,4-dichlorophenyl, 2,6-dichlorophenyl, 3,5-dichlorophenyl, 2,4,6-trichlorophenyl, 2-fluorophenyl, 3-fluorophenyl, 4-fluorophenyl, 2,5-difluorophenyl, 2,4-difluorophenyl, 3,4-difluorophenyl, 3,5-difluorophenyl, 2,6-difluorophenyl, 2,4,6-trifluorophenyl, 2-bromophenyl, 3-bromophenyl, 4-bromophenyl, 2-iodophenyl, 3-iodophenyl, 4-iodophenyl, 2,3-dibromophenyl, 2,4-diiodophenyl, 4-methylthiophenyl, 4-cyclohexylphenyl, 4-chloro-2-anilinophenyl, 2-(4-chloroanilino)-5-ethoxycarbonylphenyl, 4-[2-(N,N-diethylamino)ethoxy]phenyl, 4-(4-methyl-1-piperazinyl)phenyl, 4-(2-oxo-1-pyrrolidinyl)phenyl, 4-methylsulfonylaminophenyl, 4-(2-hydroxyethyl)phenyl, 4-benzylphenyl, 4-ethinylphenyl, 4-phenylthiophenyl, 4-(1-adamantyl)phenyl, 5-acetylamino-2-chlorophenyl, 3-cyanophenyl, 2-cyanophenyl, 4-cyanophenyl, 2-propanoylaminophenyl, 3,4-dicyanophenyl, 3,4,5-tricyanophenyl groups.

Examples of the phenyl lower alkyl group which may be substituted on the phenyl ring with 1 to 3 groups selected from the group consisting of a halogen atom, a lower alkoxy group which may have a halogen atom as a substituent, and a lower alkyl group include, in addition to the above described phenyl lower alkyl groups, phenylalkyl groups which may be substituted on the phenyl ring with 1 to 3 groups selected from the group consisting of a halogen atom, a linear or branched alkoxy group having 1 to 6 carbon atoms which may have 1 to 3 halogen atoms as substituents, and a linear or branched alkyl group having 1 to 6 carbon atoms, and of which the alkyl moiety is a linear or branched alkyl group having 1 to 6 carbon atoms, such as 4-fluorobenzyl, 2-chlorobenzyl, 3-chlorobenzyl, 4-chlorobenzyl, 2-(2-fluorophenyl)ethyl, 2-(4-fluorophenyl)ethyl, 2-(4-chlorophenyl)ethyl, 3,4-dibromobenzyl, 3,4-diiodobenzyl, 2,4-difluorobenzyl, 2,5-dichlorobenzyl, 2,6-dichlorobenzyl, 3,4,5-trifluorobenzyl, 3-(4-chlorophenyl)propyl, 1-(2-bromophenyl)ethyl, 4-(3-fluorophenyl)butyl, 5-(4-iodophenyl)pentyl, 6-(4-chlorophenyl)hexyl, 1,1-dimethyl-2-(3-fluorophenyl)ethyl, 2-methyl-3-(4-chlorophenyl)propyl, 2-methylbenzyl, 2-(3-methylphenyl)ethyl, 3-(4-methylphenyl)propyl, 1-(2-ethylphenyl)ethyl, 4-(3-ethylphenyl)butyl, 5-(4-ethylphenyl)pentyl, 6-(4-isopropylphenyl)hexyl, 1,1-dimethyl-2-(3-butylphenyl)ethyl, 2-methyl-3-(4-pentylphenyl)propyl, 4-hexylbenzyl, 3,4-dimethylbenzyl, 3,4-diethylbenzyl, 2,4-dimethylbenzyl, 2,5-dimethylbenzyl, 2,6-dimethylbenzyl, 3,4,5-trimethylbenzyl, 2-methoxybenzyl, 2-(2-methoxyphenyl)ethyl, 2-(3-methoxyphenyl)ethyl, 2-(4-methoxyphenyl)ethyl, 4-methoxybenzyl, 1-(2-ethoxyphenyl)ethyl, 3-(3-ethoxyphenyl)propyl, 4-(4-ethoxyphenyl)butyl, 5-(4-isopropoxyphenyl)pentyl, 6-(3-butoxyphenyl)hexyl, 1,1-dimethyl-2-(4-pentyloxyphenyl)ethyl, 2-methyl-3-(4-hexyloxyphenyl)propyl, 3,4-dimethoxybenzyl, 3,4-diethoxybenzyl, 2,4-dimethoxybenzyl, 2,5-dimethoxybenzyl, 2,6-dimethoxybenzyl, 3,4,5-trimethoxybenzyl, 2-trifluoromethoxybenzyl, 3-trifluoromethoxybenzyl, 4-trifluoromethoxybenzyl, 2-[2-(bromomethoxy)phenyl]ethyl, 1-[3-(2-chloroethoxy)phenyl]ethyl, 3-[4-(2,3-dichloropropoxy)phenyl]propyl, 4-[4-(4-fluorobutoxy)phenyl]butyl, 5-[3-(5-chloropentyloxy)phenyl]pentyl, 6-[4-(5-bromohexyloxy)phenyl]hexyl, 1,1-dimethyl-2-[4-(5,6-dibromohexyloxy)phenyl]ethyl, 3,4-di(trifluoromethoxy)benzyl, 3,4-di(4,4,4-trichlorobutoxy)benzyl, 2,4-di(3-chloro-2-methoxypropyl)benzyl, 2,5-di(3-chloropropoxy)benzyl, 2,6-di(2,2,2-trifluoroethoxy)benzyl, 3,4,5-tri(trifluoromethoxy)benzyl, 4-(2,2,2-trichloroethoxy)benzyl, 2-methyl-4-trifluoromethoxybenzyl, 3-ethyl-4-trichloromethoxybenzyl, 2-methoxy-4-trifluoromethoxybenzyl, 3-ethoxy-4-trichloromethoxybenzyl, 2-methyl-3-trifluoromethoxy-4-trifluoromethoxybenzyl, 2-chloro-3-methylbenzyl, 4-fluoro-2-trifluoromethoxybenzyl, 3-chloro-2-methyl-4-methoxybenzyl groups.

Examples of the phenyl lower alkyl group which has a lower alkylenedioxy group as a substituent on the phenyl ring include phenylalkyl groups which has a linear or branched alkylenedioxy group having 1 to 4 carbon atoms on the phenyl ring and of which the alkyl moiety is a linear or branched alkyl group having 1 to 6 carbon atoms such as a 3,4-methylenedioxybenzyl group, 3,4-trimethylenedioxybenzyl group, 2-(2,3-ethylenedioxyphenyl)ethyl group, 1-(3,4-trimethylenedioxyphenyl)ethyl group, 3-(2,3-tetramethylenedioxyphenyl)propyl group, 4-(3,4-methylenedioxyphenyl)butyl group, 5-(2,3-ethylenedioxyphenyl)pentyl group, 6-(3,4-trimethylenedioxyphenyl)hexyl group, 1,1-dimethyl-2-(2,3-methylenedioxyphenyl)ethyl group, and 2-methyl-3-(3,4-ethylenedioxyphenyl)propyl group.

Examples of the amino group which may have a lower alkanoyl group as a substituent include which may have a linear or branched alkanoyl group having 1 to 6 carbon atoms as a substituent such as an amino group, N-acetylamino group, N-formylamino group, N-propionylamino group, N-butyrylamino group, N-isobutyrylamino group, N-pentanoylamino group, N-tert-butylcarbonylamino group, and N-hexanoylamino group.

Examples of the 1,2,3,4-tetrahydroquinolyl group which may have, on the tetrahydroquinoline ring, 1 to 3 substituents selected from the group consisting of an oxo group, a lower alkoxy group, and a lower alkylenedioxy group include 1,2,3,4-tetrahydroquinolyl groups which may have, on the tetrahydroquinoline ring, 1 to 3 substituents selected from the group consisting of an oxo group, a linear or branched alkoxy group having 1 to 6 carbon atoms, and a linear or branched alkylenedioxy group having 1 to 4 carbon atoms such as (1,2,3,4,5,6,7, or 8-)1,2,3,4-tetrahydroquinolyl, 2-oxo-(1,3,4,5,6,7, or 8-)1,2,3,4-tetrahydroquinolyl, 2-oxo-6,7-methylenedioxy-(1,3,4,5, or 8-)1,2,3,4-tetrahydroquinolyl, 4-oxo-(1,2,3,5,6,7, or 8-)1,2,3,4-tetrahydroquinolyl, 2,4-dioxo-(1,3,5,6,7, or 8-)1,2,3,4-tetrahydroquinolyl, 2,4-dioxo-6,7-methylenedioxy-(1,3,5, or 8-)1,2,3,4-tetrahydroquinolyl, 5,6-ethylenedioxy-(1,2,3,4,7, or 8-)1,2,3,4-tetrahydroquinolyl, 7,8-trimethylenedioxy-(1,2,3,4,5, or 6-)1,2,3,4-tetrahydroquinolyl, 6,7-tetramethylenedioxy-(1,2,3,4,5, or 8-)1,2,3,4-tetrahydroquinolyl, 5-methoxy-2-oxo-(1,3,4,6,7, or 8-)1,2,3,4-tetrahydroquinolyl, 2-oxo-6,7-ethylenedioxy-(1,3,4,5, or 8-)1,2,3,4-tetrahydroquinolyl groups.

Examples of the cycloalkyl lower alkyl group include cycloalkylalkyl groups having 3 to 16 carbon atoms of which the alkyl moiety is a linear or branched alkyl group having 1 to 6 carbon atoms such as a cyclopropylmethyl group, cyclohexylmethyl group, 2-cyclopropylethyl group, 1-cyclobutylethyl group, 3-cyclopentylpropyl group, 4-cyclohexylbutyl group, 5-cycloheptylpentyl group, 6-cyclooctylhexyl group, 1,1-dimethyl-2-cyclononylethyl group, 2-methyl-3-cyclodecylpropyl group, cycloundecylmethyl group, 2-cyclododecylethyl group, 1-cyclotridecylethyl group, 3-cyclotetradecylpropyl group, 4-cyclopentadecylbutyl group, and 5-cyclodecylpentyl group.

Examples of the pyridyl lower alkyl group include pyridylalkyl groups of which the alkyl moiety is a linear or branched alkyl group having 1 to 6 carbon atoms such as a (2,3 or 4-)pyridylmethyl group, 2-[(2,3 or 4-)pyridyl]ethyl group, 1-[(2,3 or 4-)pyridyl]ethyl group, 3-[(2,3 or 4-)pyridyl]propyl group, 4-[(2,3 or 4-)pyridyl]butyl group, 1,1-dimethyl-2-[(2,3 or 4-)pyridyl]ethyl group, 5-[(2,3 or 4-)pyridyl]pentyl group, 6-[(2,3 or 4-)pyridyl]hexyl group, 1-[(2,3 or 4-)pyridyl]isopropyl group, and 2-methyl-3-[(2,3 or 4-)pyridyl]propyl group.

Examples of the amino group substituted lower alkyl group which may have a substituent selected from the group consisting of a lower alkyl group and a lower alkanoyl group include linear or branched alkyl groups having 1 to 6 carbon atoms which has an amino group which may have 1 or 2 substituents selected from the group consisting of a linear or branched alkyl group having 1 to 6 carbon atoms and a linear or branched alkanoyl group having 1 to 6 carbon atoms such as aminomethyl, 2-aminoethyl, 1-aminoethyl, 3-aminopropyl, 4-aminobutyl, 5-aminopentyl, 6-aminohexyl, 1,1-dimethyl-2-aminoethyl, 2-methyl-3-aminopropyl, methylaminomethyl, 1-ethylaminoethyl, 2-propylaminoethyl, 3-isopropylaminopropyl, 4-butylaminobutyl, 5-pentylaminopentyl, 6-hexylaminohexyl, dimethylaminomethyl, 2-diisopropylaminoethyl, (N-ethyl-N-propylamino)methyl, 2-(N,N-dimethylamino)ethyl, 2-(N-methyl-N-hexylamino)ethyl, formylaminomethyl, acetylaminomethyl, 1-propionylaminoethyl, 2-acetylaminoethyl, 3-butyrylaminopropyl, 4-pentanoylaminobutyl, 5-hexanoylaminopentyl, 6-acetylaminohexyl, N-methyl-N-acetylaminomethyl, 2-(N-ethyl-N-propanoylamino)ethyl, (N-ethyl-N-butyrylamino)methyl, 2-(N-methyl-N-hexanoylamino)ethyl, 3-(N,N-dimethylamino)propyl groups.

Examples of the lower alkoxy lower alkyl group include linear or branched alkyl groups having 1 to 6 carbon atoms which have a linear or branched alkoxy group having 1 to 6 carbon atoms as a substituent such as a methoxymethyl group, 1-ethoxyethyl group, 2-methoxyethyl group, 2-propoxyethyl group, 3-isopropoxypropyl group, 4-butoxybutyl group, 5-pentyloxypentyl group, 6-hexyloxyhexyl group, 1,1-dimethyl-2-methoxyethyl group, 2-methyl-3-ethoxypropyl group, and 3-methoxypropyl group.

Examples of the 1,2,3,4-tetrahydroisoquinolylcarbonyl substituted lower alkyl group include 1,2,3,4-tetrahydroisoquinolylcarbonyl-alkyl groups of which the alkyl moiety is a linear or branched alkyl group such as (1,2,3,4,5,6,7, or 8-)1,2,3,4-tetrahydroisoquinolylcarbonylmethyl, 2-[(1,2,3,4,5,6,7, or 8-)1,2,3,4-tetrahydroisoquinolyl-carbonyl]ethyl, 1-[(1,2,3,4,5,6,7, or 8-)1,2,3,4-tetrahydroisoquinolylcarbonyl]ethyl, 3-[(1,2,3,4,5,6,7, or 8-)1,2,3,4-tetrahydroisoquinolyl-carbonyl]propyl, 4-[(1,2,3,4,5,6,7, or 8-)1,2,3,4-tetrahydroisoquinolylcarbonyl]butyl, 1,1-dimethyl-2-[(1,2,3,4,5,6,7, or 8-)1,2,3,4-tetrahydroisoquinolylcarbonyl]ethyl, 5-[(1,2,3,4,5,6,7, or 8-)1,2,3,4-tetrahydroisoquinolyl-carbonyl]pentyl, 6-[(1,2,3,4,5,6,7, or 8-)1,2,3,4-tetrahydroisoquinolylcarbonyl]hexyl, 1-[(1,2,3,4,5,6,7, or 8-)1,2,3,4-tetrahydroisoquinolyl-carbonyl]isopropyl, 2-methyl-3-[(1,2,3,4,5,6,7, or 8-)1,2,3,4-tetrahydroisoquinolylcarbonyl]propyl groups.

Examples of the piperidinylcarbonyl group which may have, on the piperidine ring, a substituent selected from the group consisting of a lower alkoxycarbonyl group, a phenyl lower alkyl group, and a furyl lower alkyl group include piperidinylcarbonyl groups which may have, on the piperidine ring, 1 to 3 substituents selected from the group consisting of an alkoxycarbonyl group of which the alkoxy moiety is a linear or branched alkoxy group having 1 to 6 carbon atoms, a phenylalkyl group of which the alkyl moiety is a linear or branched alkyl group having 1 to 6 carbon atoms, and a furylalkyl group of which the alkyl moiety is a linear or branched alkyl group having 1 to 6 carbon atoms such as (1,2,3, or 4-)piperidinylcarbonyl, 1-benzyl-(2,3, or 4-)piperidinylcarbonyl, 1-(2 or 3-)furylmethyl-(2,3, or 4-)piperidinylcarbonyl, 1-(2-phenylethyl)-(2,3, or 4-)piperidinylcarbonyl, 1-{2-[(1 or 2-)furyl]ethyl}-(2,3, or 4-)piperidinylcarbonyl, 1-(1-phenylethyl)-(2,3, or 4-)piperidinyl-carbonyl, 1-{3-[(1 or 2-)furyl]propyl]}-(2,3, or 4-)piperidinylcarbonyl, 1-(3-phenylpropyl)-(2,3, or 4-)piperidinylcarbonyl, 1-{1-[(1 or 2-)furyl]ethyl]}-(2,3, or 4-)piperidinylcarbonyl, 1-(4-phenylbutyl)-(2,3, or 4-)piperidinylcarbonyl, 1-{4-[(1 or 2-)furyl]-butyl]}-(2,3, or 4-)piperidinylcarbonyl, 1-(5-phenylpentyl)-(2,3, or 4-)piperidinylcarbonyl, 1-{5-[(1 or 2-)furyl]

pentyl]}-(2,3, or 4-)piperidinyl-carbonyl, 1-(6-phenylhexyl)-(2,3, or 4-)piperidinyl-carbonyl, 1-{6-[(1 or 2-)furyl]hexyl]}-(2,3, or 4-)piperidinylcarbonyl, 1,2-dibenzyl-(3,4,5, or 6-)piperidinylcarbonyl, 1,3-di(1 or 2-)furylmethyl-(2,4,5, or 6-)piperidinylcarbonyl, 1,3,5-tribenzyl-(2,4, or 6-)piperidinylcarbonyl, 1,2,6-tri(1 or 2-)furylmethyl-(3,4, or 5-)piperidinylcarbonyl, 1-benzyl-3-(1 or 2-)furylmethyl-(2,4,5, or 6-)piperidinylcarbonyl, 1-{1-[(1 or 2-)furyl]ethyl]}-(2,3, or 4-)piperidinylcarbonyl, 1-methoxycarbonyl-(2,3, or 4-)piperidinylcarbonyl, 1-ethoxycarbonyl-(2,3, or 4-)piperidinylcarbonyl, 1-propoxycarbonyl-(2,3, or 4-)piperidinylcarbonyl, 1-butoxycarbonyl-(2,3, or 4-)piperidinylcarbonyl, 1-tert-butoxycarbonyl-(2,3, or 4-)piperidinylcarbonyl, 1-pentyloxycarbonyl-(2,3, or 4-)piperidinylcarbonyl, 1-hexyloxycarbonyl-(2,3, or 4-)piperidinylcarbonyl, 1,2-dimethoxycarbonyl-(3,4,5, or 6-)piperidinylcarbonyl, 1,2,6-triethoxycarbonyl-(3,4, or 5-)piperidinylcarbonyl, 1-(1 or 2-)furylmethyl-3-tert-butoxycarbonyl-(3,4,5, or 6-)piperidinyl-carbonyl, 1-benzyl-2-methoxycarbonyl-(2,4,5, or 6-)piperidinylcarbonyl, 1-(1 or 2-)furylmethyl-2,4-dimethoxycarbonyl-(3,5, or 6-)piperidinylcarbonyl groups.

Examples of the thiazolidinyl lower alkanoyl group which may have an oxo group as a substituent on the thiazolidine ring include thiazolidinylalkanoyl groups which may have 1 to 3 oxo groups as substituents on the thiazolidine ring and of which the alkanoyl moiety is a linear or branched alkanoyl group having 1 to 6 carbon atoms such as 2-[(2,3,4, or 5-)thiazolidinyl]acetyl, 3-[(2,3,4, or 5-)thiazolidinyl]propionyl, 2-[(2,3,4, or 5-)thiazolidinyl]propionyl, 4-[(2,3,4, or 5-)thiazolidinyl]butyryl, 5-[(2,3,4, or 5-)1,2,4-thiazolidinyl]pentanoyl, 6-[(2,3,4, or 5-)thiazolidinyl]hexanoyl, 2,2-dimethyl-3-[(2,3,4, or 5-)thiazolidinyl]propionyl, 2-methyl-3-[(2,3,4, or 5-)thiazolidinyl]propionyl, 2,4-dioxo-(3 or 5-)thiazolidinylacetyl, 3-[2-oxo-(3,4, or 5-)thiazolidinyl]propionyl, 2-[4-oxo-(2,3, or 5-)thiazolidinyl]propionyl, 4-[5-oxo-(2,3, or 4-)thiazolidinyl]butyryl, 5-[2,5-dioxo-(3 or 4-)thiazolidinyl]pentanoyl, 6-[2,4,5-trioxo-3-thiazolidinyl]hexanoyl, 2-[4,5-dioxo-(2 or 3-)thiazolidinyl]acetyl, 2,2-dimethyl-3-[2,4-dioxo-(3 or 5-)thiazolidinyl]propionyl, 2-methyl-3-[2,4-dioxo-(3 or 5-)thiazolidinyl]propionyl groups.

Examples of the piperidinyl group which may be substituted on the piperidine ring with a group selected from the group consisting of a lower alkoxycarbonyl group, a phenyl lower alkyl group, a lower alkyl group, a benzoyl group and a furyl lower alkyl group include piperidinyl groups which may be substituted on the piperidine ring with 1 to 3 groups selected from the group consisting of an alkoxycarbonyl group of which the alkoxy moiety is a linear or branched alkoxy group having 1 to 6 carbon atoms, a phenylalkyl group of which the alkyl moiety is a linear or branched alkyl group having 1 to 6 carbon atoms, a linear or branched alkyl group having 1 to 6 carbon atoms, a benzoyl group, and a furylalkyl group of which the alkyl moiety is a linear or branched alkyl group having 1 to 6 carbon atoms such as (1,2,3, or 4-)piperidinyl, 1-benzyl-(2,3, or 4-)piperidinyl, 1-(2 or 3-)furylmethyl-(2,3, or 4-)piperidinyl, 1-(2-phenylethyl)-(2,3, or 4-)piperidinyl, 1-{2-[(1 or 2-)furyl]ethyl}-(2,3, or 4-)piperidinyl, 1-(1-phenylethyl)-(2,3, or 4-)piperidinyl, 1-{3-[(1 or 2-)furyl]propyl]}-(2,3, or 4-)piperidinyl, 1-(3-phenylpropyl)-(2,3, or 4-)piperidinyl, 1-{1-[(1 or 2-)furyl]ethyl]}-(2,3, or 4-)piperidinyl, 1-(4-phenylbutyl)-(2,3, or 4-)piperidinyl, 1-{4-[(1 or 2-)furyl]butyl]}-(2,3, or 4-)piperidinyl, 1-(5-phenylpentyl)-(2,3, or 4-)piperidinyl, 1-{5-[(1 or 2-)furyl]pentyl]}-(2,3, or 4-)piperidinyl, 1-(6-phenylhexyl)-(2,3, or 4-)piperidinyl, 1-{6-[(1 or 2-)furyl]hexyl]}-(2,3, or 4-)piperidinyl, 1,2-dibenzyl-(3,4,5, or 6-)piperidinyl, 1,3-di(1 or 2-)furylmethyl-(2,4,5, or 6-)piperidinyl, 1,3,5-tribenzyl-(2,4, or 6-)piperidinyl, 1,2,6-tri(1 or 2-)furylmethyl-(3,4, or 5-)piperidinyl, 1-benzyl-3-(1 or 2-)furylmethyl-(2,4,5, or 6-)piperidinyl, 1-{1-[(1 or 2-)furyl]ethyl]}-(2,3, or 4-)piperidinyl, 1-benzoyl-(2,3, or 4-)piperidinyl, 1,2-dibenzoyl-(3,4,5, or 6-)piperidinyl, 1,3,5-tribenzoyl-(2,4, or 6-)piperidinyl, 1-methyl-(2,3, or 4-)piperidinyl, 1-ethyl-(2,3, or 4-)piperidinyl, 1-propyl-(2,3, or 4-)piperidinyl, 1-isopropyl-(2,3, or 4-)piperidinyl, 1-butyl-(2,3, or 4-)piperidinyl, 1-isobutyl-(2,3, or 4-)piperidinyl, 1-tert-butyl-(2,3, or 4-)piperidinyl, 1-pentyl-(2,3, or 4-)piperidinyl, 1-hexyl-(2,3, or 4-)piperidinyl, 1,2-dimethyl-(3,4,5, or 6-)piperidinyl, 1,2,6-trimethyl-(3,4, or 5-)piperidinyl, 1-methyl-3-benzyl-(3,4,5, or 6-)piperidinyl, 1-benzoyl-2-methyl-(2,4,5, or 6-)piperidinyl, 1-(1 or 2-)furylmethyl-2,4-dimethyl-(3,5, or 6-)piperidinyl, 1-methoxycarbonyl-(2,3, or 4-)piperidinyl, 1-ethoxycarbonyl-(2,3, or 4-)piperidinyl, 1-propoxycarbonyl-(2,3, or 4-)piperidinyl, 1-butoxycarbonyl-(2,3, or 4-)piperidinyl, 1-tert-butoxycarbonyl-(2,3, or 4-)piperidinyl, 1-pentyloxycarbonyl-(2,3, or 4-)piperidinyl, 1-hexyloxycarbonyl-(2,3, or 4-)piperidinyl, 1,2-dimethoxycarbonyl-(3,4,5, or 6-)piperidinyl, 1,2,6-triethoxycarbonyl-(3,4, or 5-)piperidinyl, 1-methyl-3-tert-butoxycarbonyl-(3,4,5, or 6-)piperidinyl, 1-benzoyl-2-methoxycarbonyl-(2,4,5, or 6-)piperidinyl, 1-(1 or 2-)furylmethyl-2,4-dimethoxycarbonyl-(3,5, or 6-)piperidinyl, 1-benzyl-2,4-dimethoxycarbonyl-(3,5, or 6-)piperidinyl groups.

Examples of the carbonyl lower alkyl group substituted with a group:

(hereinafter called "A group") include A group substituted carbonylalkyl groups of which the alkyl moiety is a linear or branched alkyl group having 1 to 6 carbon atoms such as an A group substituted carbonylmethyl group, 2-A group substituted carbonylethyl group, 1-A group substituted carbonylethyl group, 3-A group substituted carbonylpropyl group, 4-A group substituted carbonylbutyl group, 1,1-dimethyl-2-A group substituted carbonylethyl group, 5-A group substituted carbonylpentyl group, 6-A group substituted carbonylhexyl group, 1-A group substituted carbonylisopropyl group, and 2-methyl-3-A group substituted carbonylpropyl group.

Examples of the carbonyl lower alkyl group substituted with a group:

wherein $R^{34}$ is an oxo group or phenyl group, and d is an integer of 0 to 3 (hereinafter called "B group"), B group substituted carbonylalkyl groups of which the alkyl moiety is a linear or branched alkyl group having 1 to 6 carbon atoms such as a B group substituted carbonylmethyl group, 2-B group substituted carbonylethyl group, 1-B group substituted carbonylethyl group, 3-B group substituted carbonylpropyl group, 4-B group substituted carbonylbutyl group, 1,1-dimethyl-2-B group substituted carbonylethyl group, 5-B group substituted carbonylpentyl group, 6-B group substituted carbonylhexyl group, 1-B group substituted carbonylisopropyl group, and 2-methyl-3-B group substituted carbonylpropyl group.

Examples of the pyrrolidinyl lower alkyl group include pyrrolidinylalkyl groups of which the alkyl moiety is a linear or branched alkyl group having 1 to 6 carbon atoms such as a (1-,2-, or 3-)pyrrolidinylmethyl group, 2-[(1-,2-, or 3-)pyrrolydinyl]ethyl group, 1-[(1-,2-, or 3-)pyrrolydinyl]ethyl group, 3-[(1-,2-, or 3-)pyrrolydinyl]propyl group, 4-[(1-,2-, or 3-)pyrrolydinyl]butyl group, 5-[(1-, 2-, or 3-)pyrrolydinyl] pentyl group, 6-[(1-,2-, or 3-)pyrrolydinyl]hexyl group, 1,1-dimethyl-2-[(1-,2-, or 3-)pyrrolydinyl]ethyl group, and 2-methyl-3-[(1-,2-, or 3-)pyrrolydinyl]propyl group.

Examples of the morpholino lower alkyl group include morpholinoalkyl groups of which the alkyl moiety is a linear or branched alkyl group having 1 to 6 carbon atoms such as a (2-,3- or 4-)morpholinomethyl group, 2-[(2-,3- or 4-)morpholino]ethyl group, 1-[(2-,3- or 4-)morpholino]ethyl group, 3-[(2-,3- or 4-)morpholino]propyl group, 4-[(2-,3- or 4-)morpholino]butyl group, 5-[(2-,3- or 4-)morpholino]pentyl group, 6-[(2-,3- or 4-)morpholino]hexyl group, 1,1-dimethyl-2-[(2-,3- or 4-)morpholino]ethyl group, and 2-methyl-3-[(2-, 3- or 4-)morpholino]propyl group.

Examples of the phenyl lower alkenyl group include phenylalkenyl groups of which the alkenyl moiety is a linear or branched alkenyl group having 2 to 6 carbon atoms and which have 1 to 3 double bonds such as a styryl group, 3-phenyl-2-propenyl group (trivial name: cinnamyl group), 4-phenyl-2-butenyl group, 4-phenyl-3-butenyl group, 5-phenyl-4-pentenyl group, 5-phenyl-3-pentenyl group, 6-phenyl-5-hexenyl group, 6-phenyl-4-hexenyl group, 6-phenyl-3-hexenyl group, 4-phenyl-1,3-butadienyl group, and 6-phenyl-1,3,5-hexatrienyl group.

Examples of the anilinocarbonyl lower alkyl group which may have a lower alkyl group as a substituent on the phenyl ring include anilinocarbonylalkyl groups of which the alkyl moiety is a linear or branched alkyl group having 1 to 6 carbon atoms and which may have 1 to 3 linear or branched alkyl groups having 1 to 6 carbon atoms as substituents on the phenyl ring such as anilinocarbonylmethyl, 2-anilinocarbonylethyl, 1-anilinocarbonylethyl, 3-anilinocarbonylpropyl, 4-anilinocarbonylbutyl, 5-anilinocarbonylpentyl, 6-anilinocarbonylhexyl, 1,1-dimethyl-2-anilinocarbonylethyl, 2-methyl-3-anilinocarbonylpropyl, (4-methylanilinocarbonyl)methyl, 2-(3-methylanilinocarbonyl)ethyl, 3-(4-methylanilinocarbonyl)propyl, 1-(2-ethylanilinocarbonyl)ethyl, 4-(3-ethylanilinocarbonyl)butyl, 5-(4-ethylanilinocarbonyl) pentyl, 6-(4-isopropylanilinocarbonyl)hexyl, 1,1-dimethyl-2-(3-butylanilinocarbonyl)ethyl, 2-methyl-3-(4-pentylanilinocarbonyl)propyl, 4-hexylanilinocarbonylmethyl, 3,4-dimethylanilinocarbonylmethyl, 3,4-diethylanilinocarbonylmethyl, 2,4-dimethylanilinocarbonylmethyl, 2,5-dimethylanilinocarbonylmethyl, 2,6-dimethylanilinocarbonylmethyl, 3,4,5-trimethylanilinocarbonylmethyl groups.

Examples of the piperazinyl lower alkyl group which may have, on the piperazine ring, a substituent selected from the group consisting of a lower alkyl group and a phenyl lower alkyl group which may have a lower alkylenedioxy group as a substituent on the phenyl ring include piperazinylalkyl groups of which the alkyl moiety is a linear or branched alkyl group having 1 to 6 carbon atoms and which may have, on the piperazine ring, 1 to 3 substituents selected from the group consisting of a linear or branched alkyl group having 1 to 6 carbon atoms and a phenylalkyl group which may have a linear or branched alkylenedioxy group having 1 to 4 carbon atoms as a substituent on the phenyl ring and of which the alkyl moiety is a linear or branched alkyl group having 1 to 6 carbon atoms such as [(1-,2-, or 3-)piperazinyl]methyl, 2-[(1-,2-, or 3-)piperazinyl]ethyl, 1-[(1-,2-, or 3-)piperazinyl] ethyl, 3-[(1-,2-, or 3-)piperazinyl]propyl, 4-[(1-,2-, or 3-)piperazinyl]butyl, 5-[(1-,2-, or 3-)piperazinyl]pentyl, 6-[(1-,2-, or 3-)piperazinyl]hexyl, 1,1-dimethyl-2-[(1-,2-, or 3-)piperazinyl]ethyl, 2-methyl-3-[(1-,2-, or 3-)piperazinyl]propyl, [1-methyl-(2-,3-, or 4-)piperazinyl]methyl, 2-[1-ethyl-(2-,3-, or 4-)piperazinyl]ethyl, 1-[4-propyl-(1-,2-, or 3-)piperazinyl] ethyl, 3-[3-isopropyl-(1-,2-,4-, 5-, or 6-)piperazinyl]propyl, 4-[2-butyl-(1-, 3,4-, 5-, or 6-)piperazinyl]butyl, 5-[1-isobutyl-(2-,3-, or 4-)piperazinyl]pentyl, 3-[4-methyl-(1-, 2-, or 3-)piperazinyl]propyl, 6-[1-tert-butyl-(2-,3-, or 4-)piperazinyl]hexyl, 1,1-dimethyl-2-[4-pentyl-(1-, 2-, or 3-)piperazinyl]ethyl, [1,2-dimethyl-(3-,4-, 5-, or 6-)piperazinyl]methyl, [1,2,6-trimethyl-(3-,4-, or 5-)piperazinyl]methyl, 2-[4-(3,4-methylenedioxybenzyl)-(1-,2-, or 3-)piperazinyl]ethyl groups.

Examples of the amidino lower alkyl group which may have a lower alkyl group as a substituent include amidinoalkyl groups of which the alkyl moiety is a linear or branched alkyl group having 1 to 6 carbon atoms and which may have 1 or 2 linear or branched alkyl groups having 1 to 6 carbon atoms such as an amidinomethyl group, 2-amidinoethyl group, 1-amidinoethyl group, 3-amidinopropyl group, 4-amidinobutyl group, 5-amidinopentyl group, 6-amidinohexyl group, 1,1-dimethyl-2-amidinoethyl group, 2-methyl-3-amidinopropyl group, N,N-dimethylamidinomethyl group, 2-(N,N-dimethylamidino)ethyl group, 1-(N-methylamidino) ethyl group, 3-(N-ethylamidino)propyl group, 4-(N-n-propylamidino)propyl group, 5-(N-n-pentylamidino)pentyl group, 6-(N-n-hexylamidino)hexyl group, and (N-methyl-N-ethylamidino)methyl group.

Examples of the carbazolyl group which may have a lower alkyl group as a substituent on the carbazole ring include carbazolyl groups which may have 1 to 3 linear or branched alkyl groups having 1 to 6 carbon atoms as substituents on the carbazole ring such as (1-,2-, 3-, or 4-)carbazolyl, 9-methyl-(1-,2-, 3-, or 4-)carbazolyl, 9-ethyl-(1-,2-, 3-, or 4-)carbazolyl, 1-ethyl-(2-,3-,4-,5-,6-,7-,8-, or 9-)carbazolyl, 2-n-propyl-(1-,3-,4-, 5-,6-,8-, or 9-)carbazolyl, 3-n-butyl-(1-,2-,4-, 5-,6-,7-,8-, or 9-)carbazolyl, 4-n-pentyl-(1-,2-,3-,5-,6-,7-,8-, or 9-)carbazolyl, 5-n-hexyl-(1-,2-,3-,4-,6-,7-,8-, or 9-)carbazolyl, 6,9-dimethyl-(1-,2-,3-,4-,5-,7-, or 8-)carbazolyl, 1,7,8-trityl-(2-,3-,4-,5-,6-,7-,8-, or 9-)carbazolyl groups.

Examples of the amidino group which may have a lower alkyl group as a substituent include amidino groups which may have 1 or 2 linear or branched alkyl groups having 1 to 6 carbon atoms as substituents such as an amidino group, N,N-dimethylamidino group, N-methylamidino group, N-ethylamidino group, N-n-propylamidino group, N-n-butylamidino group, N-n-pentylamidino group, N-n-hexylamidino group, N,N-diethylamidino group, and N-methyl-N-ethylamidino group.

Examples of the 5- to 7-membered saturated heterocyclic group formed by binding $R^{36}$ and $R^{37}$ each other, together with nitrogen atoms bound to them, through or not through a nitrogen atom, an oxygen atom or a sulfur atom, include a pyrrolidinyl group, piperidinyl group, piperazinyl group, morpholino group, thiomorpholino group, and homopiperazinyl group.

Examples of the 5- to 10-membered saturated or unsaturated heterocyclic group formed by binding $R^{14}$ and $R^{15}$ each other, together with nitrogen atoms bound to them, through or not through a nitrogen atom, an oxygen atom or a sulfur atom, include 1,2,3,4,5,6-hexahydropyrimidinyl, pyrrolidinyl, piperidinyl, piperazinyl, morpholino, thiomorpholino, homopiperazinyl, homopiperidinyl, thiazolidinyl, 1,2,5,6-tetrahydropyridyl, pyrrolyl, pyrazolyl, imidazolyl, 2-pyrrolinyl, 2-imidazolinyl, imidazolidinyl, 2-pyrazolinyl, pyrazolidinyl, 1,2-dihydropyridyl, 1,2-dihydroquinolyl, 1,2,3,4-tetrahydroquinolyl, 1,2,3,4-tetrahydroisoquinolyl, 1,2-dihydroisoquinolyl, indolyl, isoindolyl, indolinyl, isoindolinyl, 3,4-dihydro-2H-1,4-benzoxadinyl, 3,4-dihydro-2H-1,4-benzothiazolidinyl, 1,4-benzothiazinyl, 1,2,3,4-tetrahydroquinoxalinyl, 1,2,3,4-tetrahydrocinnolinyl, 1,2,3,4-tetrahydrophthalazinyl, 1,2,3,4-tetrahydroquinazolinyl, 1,2-dihydroquinoxalinyl, 3,4-dihydroquinoxalinyl, 1,4-dihydroquinoxalinyl, 1,2-dihydrocinnolinyl, 1,2-dihydrophthalazinyl, 3,4-dihydrophthalazinyl, 1,2-dihydroquinazolinyl, 3,4-dihydroquinazolinyl, indazolyl, indazolinyl, 6-azabicyclo[3,2,1]octyl, 3-aza-spiro[5,5]undecyl, thiazolidinyl groups.

Examples of the phenyl lower alkoxy group include phenylalkoxy groups of which the alkoxy moiety is a linear or branched alkoxy group having 1 to 6 carbon atoms such as a benzyloxy group, 2-phenylethoxy group, 1-phenylethoxy group, 3-phenylpropoxy group, 4-phenylbutoxy group, 5-phenylpentyloxy group, 6-phenylhexyloxy group, 1,1-dimethyl-2-phenylethoxy group, and 2-methyl-3-phenylpropoxy group.

Examples of the phenyl substituted lower alkyl group which has 1 or 2 phenyl groups which may be substituted on the phenyl ring with 1 to 3 substituents selected from the group consisting of a lower alkanoyl group, an amino group which may have a lower alkanoyl group as a substituent, a lower alkoxycarbonyl group, a cyano group, a nitro group, a phenyl group, a halogen atom, a lower alkyl group which may have a halogen atom as a substituent, a lower alkoxy group which may have a halogen atom as a substituent, a phenyl lower alkoxy group, a hydroxyl group, and a lower alkylenedioxy groups; and which may have a pyridyl group on the lower alkyl group include, in addition to the above described phenyl lower alkyl groups, phenyl substituted alkyl groups which have 1 or 2 phenyls which may be substituted on the phenyl ring with 1 to 3 substituents selected from the group consisting of a linear or branched alkanoyl group having 1 to 6 carbon atoms, an amino group which may have 1 or 2 linear or branched alkanoyl groups having 1 to 6 carbon atoms as substituents, a linear or branched alkoxycarbonyl group having 1 to 6 carbon atoms, a cyano group, a nitro group, a phenyl group, a halogen atom, a linear or branched alkyl group having 1 to 6 carbon atoms which may have 1 to 3 halogen atoms as substituents, a linear or branched alkoxy group having 1 to 6 carbon atoms which may have 1 to 3 halogen atoms as substituents, a phenylalkoxy groups of which the alkoxy moiety is a linear or branched alkoxy group having 1 to 6 carbon atoms, a hydroxy group, and a linear or branched alkylenedioxy group having 1 to 4 carbon atoms; and which may have a pyridyl group on the alkyl group, of which the alkyl moiety is a linear or branched alkyl group having 1 to 6 carbon atoms, such as 1-phenyl-1-(2,3, or 4-)pyridylmethyl, 1,1-diphenylmethyl, 1,1-di(4-fluorophenyl)methyl, 1-phenyl-1-(4-methoxyphenyl)methyl, 3,4-methylenedioxybenzyl, 3,4-ethylenedioxybenzyl, 3,4-trimethylenedioxybenzyl, 2,5-difluorobenzyl, 2,4-difluorobenzyl, 3,4-difluorobenzyl, 3,5-difluorobenzyl, 2,6-difluorobenzyl, 3-trifluoromethylbenzyl, 2-trifluoromethylbenzyl, 4-trifluoromethylbenzyl, 3,4-dimethoxybenzyl, 3,5-dimethoxybenzyl, 2-chlorobenzyl, 3-chlorobenzyl, 4-chlorobenzyl, 2-methylbenzyl, 3-methylbenzyl, 4-methylbenzyl, 3,4-dimethylbenzyl, 2,3-dimethylbenzyl, 2-methoxybenzyl, 3-methoxybenzyl, 4-cyanobenzyl, 2-cyanobenzyl, 3-cyanobenzyl, 4-methoxybenzyl, 2,3-dichlorobenzyl, 2,4-dichlorobenzyl, 2,5-dichlorobenzyl, 3,4-dichlorobenzyl, 2,6-dichlorobenzyl, 4-fluorobenzyl, 3-fluorobenzyl, 2-fluorobenzyl, 4-nitrobenzyl, 3-nitrobenzyl, 2-nitrobenzyl, 3-trifluoromethoxybenzyl, 4-trifluoromethoxybenzyl, 2-trifluoromethoxybenzyl, 4-methoxycarbonylbenzyl, 3-methoxycarbonylbenzyl, 4-tert-butylbenzyl, 4-ethylbenzyl, 4-isopropylbenzyl, 4-methoxy-3-chlorobenzyl, 2-(4-methoxyphenyl)ethyl, 2-(4-fluorophenyl)ethyl, 2-(4-chlorophenyl)ethyl, 2-(3-methoxyphenyl)ethyl, 2-(4-methylphenyl)ethyl, 4-phenylbenzyl, 3,3-diphenylpropyl, 3-methyl-4-nitrobenzyl, 4-(4-methoxyphenyl)butyl, 2-(4-methylphenyl)ethyl, 4-tert-butoxycarbonylbenzyl, 3-chloro-6-methoxybenzyl, 4-acetylaminobenzyl, 4-nitro-3-methylbenzyl, 4-hydroxybenzyl, 3-hydroxybenzyl, 2-hydroxybenzyl, 4-tert-butyrylbenzyl, 4-benzyloxybenzyl, 4-pivaloylbenzyl, 2-(4-acetylphenyl)ethyl, 1-(3-propionylphenyl)ethyl, 3-(2-butyrylphenyl)propyl, 4-(4-pentanoylphenyl)butyl, 5-(3-hexanoylphenyl)pentyl, 6-(2,4-diacetylphenyl)hexyl, 1,1-dimethyl-2-(2,4,6-triacetylphenyl)ethyl, 2-methyl-3-(3,4-diacetylphenyl)propyl, 2-(4-aminophenyl)ethyl, 1-(3-propionylaminophenyl)ethyl, 3-(2-butyrylaminophenyl)propyl, 4-(4-pentanoylamino)phenylbutyl, 5-(hexanoylaminophenyl)pentyl, 6-(N-acetyl-N-propionylaminophenyl)hexyl, 1,1-dimethyl-2-(3,4-diaminophenyl)ethyl, 2-methyl-3-(3,4,5-triacetylaminophenyl)propyl, 2-(2-ethoxycarbonylphenyl)ethyl, 1-(3-propoxycarbonylphenyl)ethyl, 3-(4-pentyloxycarbonylphenyl)propyl, 4-(3-hexyloxycarbonylphenyl)butyl, 5-(3,4-dimethoxycarbonylphenyl)pentyl, 6-(3,4,5-triethoxycarbonylphenyl)hexyl, 1,1-dimethyl-2-(4-butoxycarbonylphenyl)ethyl, 2-methyl-3-(4-methoxycarbonylphenyl)propyl, 2-(2-cyanophenyl)ethyl, 1-(3-cyanophenyl)ethyl, 3-(4-cyanophenyl)propyl, 4-(2-cyanophenyl)butyl, 5-(3-cyanophenyl)pentyl, 6-(4-cyanophenyl)hexyl, 1,1-dimethyl-2-(2,4-dicyanophenyl)ethyl, 2-methyl-3-(2,4,6-tricyanophenyl)propyl, 2-(2-nitrophenyl)ethyl, 1-(3-nitrophenyl)ethyl, 3-(4-nitrophenyl)propyl, 4-(2-nitrophenyl)butyl, 5-(3-nitrophenyl)pentyl, 6-(4-nitrophenyl)hexyl, 1,1-dimethyl-2-(2,4-dinitrophenyl)ethyl, 2-methyl-3-(2,4,6-trinitrophenyl)propyl, 2-(2-phenylphenyl)ethyl, 1-(3-phenylphenyl)ethyl, 3-(4-phenylphenyl)propyl, 4-(2-phenylphenyl)butyl, 5-(3-phenylphenyl)pentyl, 6-(4-phenylphenyl)hexyl, 1,1-dimethyl-2-(2,4-diphenylphenyl)ethyl, 2-methyl-3-(2,4,6-triphenylphenyl)propyl, 2-(2-fluorophenyl)ethyl, 1-(3-bromophenyl)ethyl, 3-(2-iodophenyl)propyl, 4-(2-bromophenyl)butyl, 5-(3-chlorophenyl)pentyl, 6-(4-bromophenyl)hexyl, 1,1-dimethyl-2-(2,4-dichlorophenyl)ethyl, 2-methyl-3-(2,4,6-trifluorophenyl)propyl, 2-(2-ethylphenyl)ethyl, 1-(3-propylphenyl)ethyl, 3-(4-butylphenyl)propyl, 4-(2-pentylphenyl)butyl, 5-(3-hexylphenyl)pentyl, 6-(4-trifluoromethylphenyl)hexyl, 1,1-dimethyl-2-(2,4-dimethylphenyl)ethyl, 2-methyl-3-[2,4,6-tri(trifluoromethyl)phenyl]propyl, 2-(2-ethoxyphenyl)ethyl, 1-(3-propoxyphenyl)ethyl, 3-(4-butoxyphenyl)propyl, 4-(2-pentyloxyphenyl)butyl, 5-(3-hexyloxyphenyl)pentyl, 6-(4-trifluoromethoxyphenyl)hexyl, 1,1-dimethyl-2-(2,4-dimethoxyphenyl)ethyl, 2-methyl-3-[2,4,6-tri(trifluoromethoxy)phenyl]propyl, 2-(2-benzyloxyphenyl)ethyl, 1-[3-(2-phenylethoxy)phenyl]ethyl, 3-[4-(3-phenylpropoxy)phenyl]propyl, 4-[2-(4-phenylbutoxy)phenyl]butyl, 5-[3-(5-phenylpentyloxy)phenyl]pentyl, 6-[4-(6-phenylhexyloxy)phenyl]hexyl, 1,1-dimethyl-2-(2,4-dibenzyloxyphenyl)ethyl, 2-methyl-3-(2,4,6-tribenzyloxyphenyl)propyl, 2-(2-hydroxyphenyl)ethyl, 1-(3-hydroxyphenyl)ethyl, 3-(4-hydroxyphenyl)propyl, 4-(2- hydroxyphenyl)butyl, 5-(3-hydroxyphenyl)pentyl, 6-(4-hydroxyphenyl)hexyl, 1,1-dimethyl-2-(2,4-dihydroxyphenyl)ethyl, 2-methyl-3-(2,4,6-trihydroxyphenyl)propyl, 2-(3,4-methylenedioxyphenyl)ethyl, 1-(2,3-ethylenedioxyphenyl)ethyl, 3-(3,4-trimethylenedioxyphenyl)propyl, 4-(3,4-tetramethylenedioxyphenyl)butyl, 5-(3,4-methylenedioxyphenyl)pentyl, 6-(3,4-ethylenedioxyphenyl)hexyl, 1,1-dimethyl-2-(3,4-methylenedioxy)ethyl, 2-methyl-3-(3,4-methylenedioxyphenyl)propyl groups.

Examples of the pyridyl lower alkyl group which may have, on the pyridine ring, 1 to 3 substituents selected from the group consisting of a hydroxyl group and a lower alkyl group which may have a hydroxyl group as a substituent include, in addition to the above described pyridyl lower alkyl groups, pyridylalkyl groups which may have, on the pyridine ring, 1 to 3 substituents selected from the group consisting of a hydroxy group and a linear or branched alkyl group having 1 to 6 carbon atoms which may have 1 to 3 hydroxy groups as substituents, and of which the alkyl moiety is a linear or branched alkyl group having 1 to 6 carbon atoms such as [2-methyl-(3,4,5, or 6-)pyridyl]methyl, [2-methyl-3-hydroxy-5-hydroxymethyl-(4 or 6-)pyridyl]methyl, 2-[3-ethyl-(2,4,5, or 6-)pyridyl]ethyl, 1-[4-propyl-(2,3,5, or 6-)pyridyl]ethyl, 3-[2-butyl-(3,4,5, or 6-)pyridyl]propyl, 4-[3-pentyl-(2,4,5, or 6-)pyridyl]butyl, 1,1-dimethyl-2-[4-hexyl-(2,3,5, or 6-)pyridyl]ethyl, 5-[2,3-dimethyl-(4,5, or 6-)pyridyl]pentyl, 6-[2,4,6-trimethyl-(3 or 5-)pyridyl]hexyl, 1-[2-hydroxy-(2,3,5, or 6-)pyridyl]isopropyl, 2-methyl-3-[3-hydroxy-(2,4,5, or 6-)pyridyl]propyl, [2-hydroxy-(3,4,5, or 6-)pyridyl]methyl, 2-[3-hydroxy-(2,4,5, or 6-)pyridyl]ethyl, 1-[4-hydroxy-(2,3,5, or 6-)pyridyl]ethyl, 3-[2-hydroxy-(3,4,5, or 6-)pyridyl]propyl, 4-[3-hydroxy-(2,4,5, or 6-)pyridyl]butyl, 1,1-dimethyl-2-[4-hydroxy-(2,3,5, or 6-)pyridyl]ethyl, 5-[2,3-dihydroxy-(4,5, or 6-)pyridyl]pentyl, 6-[2,4,6-trihydroxy-(3 or 5-)pyridyl]hexyl, [2-hydroxymethyl-(3,4,5, or 6-)pyridyl]methyl, 2-[3-(2-hydroxyethyl)-(2,4,5, or 6-)pyridyl}ethyl, 1-[4-(3-hydroxypropyl)-(2,3,5, or 6-)pyridyl]ethyl, 3-[2-(4-hydroxybutyl)-(3,4,5, or 6-)pyridyl]propyl, 4-[3-(5-hydroxypentyl)-(2,4,5, or 6-)pyridyl]butyl, 1,1-dimethyl-2-[4-(6-hydroxyhexyl)-(2,3,5, or 6-)pyridyl]ethyl, 5-[2,3-di(hydroxymethyl)-(4,5, or 6-)pyridyl]pentyl, 6-[2,4,6-tri(hydroxymethyl)-(3 or 5-)pyridyl]hexyl, 1-[2-hydroxymethyl-(2,3,5, or 6-)pyridyl]isopropyl, 2-methyl-3-[3-(2,3-dihydroxypropyl)-(2,4,5, or 6-)pyridyl]propyl, [2-methyl-3-(2,2,4-trihydroxybutyl)-(4,5, or 6-)pyridyl]methyl, [2-methyl-5-hydroxymethyl-(3,4, or 6-)pyridyl]methyl groups.

Examples of the pyrrolyl lower alkyl group which may have 1 to 3 lower alkyl groups as substituents on the pyrrole ring include pyrrolylalkyl groups which may have 1 to 3 linear or branched alkyl groups having 1 to 6 carbon atoms on the pyrrole and of which the alkyl moiety is a linear or branched alkyl group having 1 to 6 carbon atoms such as [(1,2, or 3-)pyrrolyl]methyl, 2-[(1,2, or 3-)pyrrolyl]ethyl, 1-[(1,2, or 3-)pyrrolyl]ethyl, 3-[(1,2, or 3-)pyrrolyl]propyl, 4-[(1,2, or 3-)pyrrolyl]butyl, 5-[(1,2, or 3-)pyrrolyl]pentyl, 6-[(1,2, or 3-)pyrrolyl]hexyl, 1,1-dimethyl-2-[(1,2, or 3-)pyrrolyl]ethyl, 2-methyl-3-[(1,2, or 3-)pyrrolyl]propyl, [1-methyl-(2 or 3-)pyrrolyl]methyl, 2-[2-ethyl-(1,3,4, or 5-)pyrrolyl]ethyl, 1-[3-propyl-(1, 2, 4, or 5-)pyrrolyl]ethyl, 3-[1-butyl-(2,3, or 4-)pyrrolyl]propyl, 4-[2-pentyl-(1,3,4, or 5-)pyrrolyl]butyl, 5-[3-hexyl-(1,2,4, or 5-)pyrrolyl]pentyl, 6-[1,2-dimethyl-(3,4, or 5-)pyrrolyl]hexyl, 1,1-dimethyl-2-[1,2,3-trimethyl-(4 or 5-)pyrrolyl]ethyl, 2-methyl-3-[1-ethyl-2-methyl-(3,4, or 5-)pyrrolyl]propyl groups.

Examples of the benzoxazolyl lower alkyl group include benzoxazolylalkyl groups of which the alkyl moiety is a linear or branched alkyl group having 1 to 6 carbon atoms such as [(2,4,5,6, or 7-)benzoxazolyl]methyl, 2-[(2,4,5,6, or 7-)benzoxazolyl]ethyl, 1-[(2,4,5,6, or 7-)benzoxazolyl]ethyl, 3-[(2,4,5,6, or 7-)benzoxazolyl]propyl, 4-[(2,4,5,6, or 7-)benzoxazolyl]butyl, 5-[(2,4,5,6, or 7-)benzoxazolyl]pentyl, 6-[(2,4,5,6, or 7-)benzoxazolyl]hexyl, 1,1-dimethyl-2-[(2,4,5,6, or 7-)benzoxazolyl]ethyl, 2-methyl-3-[(2,4,5,6, or 7-)benzoxazolyl]propyl.

Examples of the benzothiazolyl lower alkyl group include benzothiazolylalkyl groups of which the alkyl moiety is a linear or branched alkyl group having 1 to 6 carbon atoms such as [(2,4,5,6, or 7-)benzothiazolyl]methyl, 2-[(2,4,5,6, or 7-)benzothiazolyl]ethyl, 1-[(2,4,5,6, or 7-)benzothiazolyl]ethyl, 3-[(2,4,5,6, or 7-)benzothiazolyl]propyl, 4-[(2,4,5,6, or 7-)benzothiazolyl]butyl, 5-[(2,4,5,6, or 7-)benzothiazolyl]pentyl, 6-[(2,4,5,6, or 7-)benzothiazolyl]hexyl, 1,1-dimethyl-2-[(2,4,5,6, or 7-)benzothiazolyl]ethyl, 2-methyl-3-[(2,4,5,6, or 7-)benzothiazolyl]propyl.

Examples of the furyl lower alkyl group include furylalkyl groups of which the alkyl moiety is a linear or branched alkyl group having 1 to 6 carbon atoms such as a [(2 or 3-)furyl]methyl group, 2-[(2 or 3-)furyl]ethyl group, 1-[(2 or 3-)furyl]ethyl group, 3-[(2 or 3-)furyl]propyl group, 4-[(2 or 3-)furyl]butyl group, 5-[(2 or 3-)furyl]pentyl group, 6-[(2 or 3-)furyl]hexyl group, 1,1-dimethyl-2-[(2 or 3-)furyl]ethyl group, and 2-methyl-3-[(2 or 3-)furyl]propyl group.

Examples of the thiazolidinyl lower alkyl group which may have an oxo group as a substituent on the thiazolidine ring include thiazolidinylalkyl groups which may have 1 to 3 oxo groups as substituents on the thiazolidine ring and of which the alkyl moiety is a linear or branched alkyl group having 1 to 6 carbon atoms such as (2,3,4, or 5-)thiazolidinylmethyl, 2-[(2,3,4, or 5-)thiazolidinyl]ethyl, 1-[(2,3,4, or 5-)thiazolidinyl]ethyl, 3-[(2,3,4, or 5-)thiazolidinyl]propyl, 4-[(2,3,4, or 5-)thiazolidinyl]butyl, 5-[(2,3,4, or 5-)thiazolidinyl]pentyl, 6-[(2,3,4, or 5-)thiazolidinyl]hexyl, 1,1-dimethyl-2-[(2,3,4, or 5-)thiazolidinyl]ethyl, 2-methyl-3-[(2,3,4, or 5-)thiazolidinyl]propyl, [2,4-dioxo-(3 or 5-)thiazolidinyl]methyl, 2-[2-oxo-(3,4, or 5-)thiazolidinyl]ethyl, 1-[4-oxo-(2,3, or 5-)thiazolidinyl]ethyl, 3-[2-oxo-(3,4, or 5-)thiazolidinyl]propyl, 4-[5-oxo-(2,3, or 4-) thiazolidinyl]butyl, 5-[2,5-dioxo-(3 or 4-)thiazolidinyl]pentyl, 6-[2,4,5-trioxo-3-thiazolidinyl]hexyl, 1-[4,5-dioxo-(2 or 3-)thiazolidinyl]ethyl, 2-[4,5-dioxo-(2- or 3-)thiazolidinyl]ethyl, 1,1-dimethyl-2-[2,4-dioxo-(3 or 5-)thiazolidinyl]ethyl, 2-methyl-3-[2,4-dioxo-(3 or 5-)thiazolidinyl]propyl groups.

Examples of the thiazolidinylidene lower alkyl group which may have an oxo group as a substituent on the thiazolidine ring include thiazolidinylidenealkyl groups which may have 1 to 3 oxo groups as substituents on the thiazolidine ring and of which the alkyl moiety is a linear or branched alkyl group having 1 to 6 carbon atoms such as (2,4, or 5-)thiazolidinylidenemethyl, (2,4, or 5-)thiazolidinylideneethyl, (2,4, or 5-)thiazolidinylidenepropyl, (2,4, or 5-)thiazolidinylideneisopropyl, (2,4, or 5-)thiazolidinylidenebutyl, (2,4, or 5-)thiazolidinylidenepentyl, (2,4, or 5-)thiazolidinylidenehexyl, 4,5-dioxo-2-thiazolidinylidenemethyl, 2,5-dioxo-4-thiazolidinylidenemethyl, 2,4-dioxo-5-thiazolidinylidenemethyl, 4-oxo-(2 or 5-)thiazolidinylideneethyl, 5-oxo-(2 or 4-)thiazolidinylidenepropyl, 2-oxo-(4, or 5-)thiazolidinylidenebutyl groups.

Examples of the benzoyl group which may be substituted on the phenyl ring with 1 to 3 groups selected from the group consisting of a cyano group, an amino group which may have a lower alkylsulfonyl group as a substituent, a halogen atom, a lower alkoxy group, a lower alkyl group which may have a halogen atom, a thiazolidinyl lower alkyl group which may have an oxo group as a substituent on the thiazolidine ring, a thiazolidinylidene lower alkyl group which may have an oxo group as a substituent on the thiazolidine ring, and a lower alkylenedioxy group include benzoyl groups which may be substituted on the phenyl ring with 1 to 3 groups selected from the group consisting of a cyano group; an amino group which may have 1 or 2 linear or branched alkylsulfonyl groups having 1 to 6 carbon atoms as substituents; a halogen atom; a linear or branched alkoxy group having 1 to 6 carbon atoms; a linear or branched alkyl group having 1 to 6 carbon atoms which may have 1 to 3 halogen atoms as substituents; a thiazolidinylalkyl group which may have 1 to 3 oxo groups as substituents on the thiazolidine ring and of which the alkyl moiety is a linear or branched alkyl group having 1 to 6 carbon atoms; a thiazolidinylidenealkyl group which may have 1 to 3 oxo groups as substituents on the thiazolidine ring and of which the alkyl moiety is a linear or branched alkyl group having 1 to 6 carbon atoms; and a linear or branched alkylenedioxy group having 1 to 4 carbon atoms such as benzoyl, 4-cyanobenzoyl, 3,4-methylenedioxybenzoyl, 2-aminobenzoyl, 3-aminobenzoyl, 4-aminobenzoyl, 3,4-diaminobenzoyl, 2,4,6-triaminobenzoyl, 4-methoxybenzoyl, 4-trifluoromethylbenzoyl, 4-chlorobenzoyl, 3,4-difluorobenzoyl, 2-fluorobenzoyl, 3-bromobenzoyl, 4-iodobenzoyl, 3,4-dimethoxybenzoyl, 4-fluorobenzoyl, 3-cyanobenzoyl, 2-cyanobenzoyl, 2,3-dicyanobenzoyl, 3,4,5-tricyanobenzoyl, 4-methylbenzoyl, 4-(2,4-dioxothiazolidinylmethyl)benzoyl, 4-(2,4-dioxothiazolidinylidenemethyl)benzoyl, 2-methylbenzoyl, 3-methylbenzoyl, 2-ethylbenzoyl, 3-ethylbenzoyl, 4-ethylbenzoyl, 4-isopropylbenzoyl, 3-butylbenzoyl, 4-pentylbenzoyl, 4-hexylbenzoyl, 3,4-dimethylbenzoyl, 3,4-diethylbenzoyl, 2,4-dimethylbenzoyl, 2,5-dimethylbenzoyl, 2,6-dimethylbenzoyl, 3,4,5-trimethylbenzoyl, 2-methoxybenzoyl, 3-methoxybenzoyl, 2-ethoxybenzoyl, 3-ethoxybenzoyl, 4-ethoxybenzoyl, 4-isopropoxybenzoyl, 3-butoxybenzoyl, 4-pentyloxybenzoyl, 4-hexyloxybenzoyl, 3,4-diethoxybenzoyl, 2,4-dimethoxybenzoyl, 2,5-dimethoxybenzoyl, 2,6-dimethoxybenzoyl, 3,4,5-trimethoxybenzoyl, 2-trifluoromethylbenzoyl, 3-trifluoromethylbenzoyl, 4-trifluoromethylbenzoyl, 2-(bromomethyl)benzoyl, 3-(2-chloroethyl)benzoyl, 4-(2,3-dichloropropyl)benzoyl, 4-(4-fluorobutyl)benzoyl, 3-(5-chloropentyl)benzoyl, 4-(5-bromohexyl)benzoyl, 4-(5,6-dibromohexyl)benzoyl, 3,4-di(trifluoromethyl)benzoyl, 3,4-di(4,4,4-trichlorobutyl)benzoyl, 2,4-di(3-chloro-2-methylpropyl)benzoyl, 2,5-di(3-chloropropyl)benzoyl, 2,6-di(2,2,2-trifluoroethyl)benzoyl, 3,4,5-tri(trifluoromethyl)benzoyl, 4-(2,2,2-trichloroethyl)benzoyl, 2-methyl-4-trifluoromethylbenzoyl, 3-ethyl-4-trichloromethylbenzoyl, 2-methoxy-4-trifluoromethylbenzoyl, 3-ethyl-4-fluorobenzoyl, 3-ethoxy-4-trichloromethylbenzoyl, 2-methyl-3-trifluoromethyl-4-trifluoromethylbenzoyl, 3-fluorobenzoyl, 4-fluorobenzoyl, 2-bromobenzoyl, 4-bromobenzoyl, 2-iodobenzoyl, 3-iodobenzoyl, 2,3-dibromobenzoyl, 2,4-diiodobenzoyl, 2,5-difluorobenzoyl, 2,6-dichlorobenzoyl, 2,4,6-trichlorobenzoyl, 2,4-difluorobenzoyl, 3,4-difluorobenzoyl, 3,5-difluorobenzoyl, 2,6-difluorobenzoyl, 2-chlorobenzoyl, 3-chlorobenzoyl, 4-chlorobenzoyl, 2,3-dichlorobenzoyl, 2,4-dichlorobenzoyl, 2,5-dichlorobenzoyl, 3,4-dichlorobenzoyl, 2,6-dichlorobenzoyl, 3,5-dichlorobenzoyl, 2,4,6-trifluorobenzoyl, 2,4-difluorobenzoyl, 3,4-difluorobenzoyl, 3,4-methylenedioxybenzoyl, 3,4-trimethylenedioxybenzoyl, 2,3-ethylenedioxybenzoyl, 3,4-trimethylenedioxybenzoyl, 2,3-tetramethylenedioxybenzoyl, 2,3-methylenedioxybenzoyl, 3,4-ethylenedioxybenzoyl, 2-methanesulfonylaminobenzoyl groups.

Examples of the thiazolidinyl lower alkanoyl group which may be substituted on the thiazolidine ring with 1 to 3 groups selected from the group consisting of an oxo group and a group of the formula:

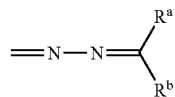

wherein $R^a$ and $R^b$ each represent a lower alkyl group, include thiazolidinylalkanoyl groups which may be substituted on the thiazolidine ring with 1 to 3 substituents selected from the group consisting of an oxo group and a group of the formula:

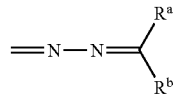

wherein $R^a$ and $R^b$ each represent a linear or branched alkyl group having 1 to 6 carbon atoms, and of which the alkanoyl moiety is a linear or branched alkanoyl group having 2 to 6 carbon atoms such as 2-[(2,3,4, or 5-)thiazolidinyl]acetyl, 3-[(2,3,4, or 5-)thiazolidinyl]propionyl, 2-[(2,3,4, or 5-)thiazolidinyl]propionyl, 4-[(2,3,4, or 5-)thiazolidinyl]butyryl, 5-[(2,3,4, or 5-)thiazolidinyl]pentanoyl, 6-[(2,3,4, or 5-)thiazolidinyl]hexanoyl, 2,2-dimethyl-3-[(2,3,4, or 5-)thiazolidinyl]propionyl, 2-methyl-3-[(2,3,4, or 5-)thiazolidinyl]propionyl, [2,4-dioxo-(3 or 5-)thiazolidinyl]acetyl, 3-[2-oxo-(3, 4, or 5-)thiazolidinyl]propionyl, 2-[4-oxo-(2,3, or 5-)thiazolidinyl]propionyl, 4-[5-oxo-(2,3, or 4-)thiazolidinyl]butyryl, 5-[2,5-dioxo-(3 or 4-)thiazolidinyl]pentanoyl, 6-[2,4,5-trioxo-3-thiazolidinyl]hexanoyl, 2-[4,5-dioxo-(2 or 3-)thiazolidinyl]acetyl, 2,2-dimethyl-3-[2,4-dioxo-(3 or 5-)thiazolidinyl]propionyl, 2-methyl-3-[2,4-dioxo-(3 or 5-)thiazolidinyl]propionyl, 2-[4-oxo-2-isopropylidenehydrazono-(3 or 5-)thiazolidinyl]acetyl, 2-[2-oxo-5-isopropylidenehydrazono-(3 or 4-)thiazolidinyl]acetyl, 2-[2,4-di(isopropylidenehydrazono)-(3 or 5-)thiazolidinyl]acetyl, 3-[2-methylidenehydrazono-(3,4, or 5-)thiazolidinyl]propionyl, 2-[4-ethylidenehydrazono-(2,3, or 5-)thiazolidinyl]-propionyl, 4-[5-propylidenehydrazono-(2,3, or 4-)thiazolidinyl]butyryl, 5-[2,5-di(isopropylidenehydrazono)-(3 or 4-)thiazolidinyl]pentanoyl, 6-[2,4,5-tri(isopropylidenehydrazono)-3-thiazolidinyl]-hexanoyl, 2-[4,5-di(isopropylidenehydrazono)-(2 or 3-)thiazolidinyl]acetyl, 2,2-dimethyl-3-[4-butylidenehydrazono-(2,3, or 5-)thiazolidinyl]-propionyl, 2-methyl-3-[5-pentylidene-(2,3, or 4-)thiazolidinyl]propionyl, 2-(hexylidenehydrazono)-(3,4, or 5-)thiazolidinylacetyl groups.

Examples of the lower alkyl group which may have a substituent selected from the group consisting of a hydroxyl group and a halogen atom include, in addition to the above described lower alkyl groups, linear or branched alkyl groups having 1 to 6 carbon atoms which may have 1 to 3 substituents selected from the group consisting of a hydroxy group and a halogen atom such as hydroxymethyl, 2-hydroxyethyl, 1-hydroxyethyl, 3-hydroxypropyl, 2,3-dihydroxypropyl, 4-hydroxybutyl, 1,1-dimethyl-2-hydroxyethyl, 5,5,4-trihydroxypentyl, 5-hydroxypentyl, 6-hydroxyhexyl, 1-hydroxyisopropyl, 2-methyl-3-hydroxypropyl, trifluoromethyl, trichloromethyl, chloromethyl, bromomethyl, fluoromethyl, iodomethyl, difluoromethyl, dibromomethyl, 2-chloroethyl, 2,2,2-trifluoroethyl, 2,2,2-trichloroethyl, 3-chloropropyl, 2,3-dichloropropyl, 4,4,4-trichlorobutyl, 4-fluorobutyl, 5-chloropentyl, 3-chloro-2-methylpropyl, 5-bromohexyl, 5,6-dibromohexyl, 2-hydroxy-3-fluoropropyl, 2,2-dichloro-3-hydroxybutyl groups.

Examples of the phenyl group which may be substituted on the phenyl ring with 1 to 3 groups selected from the group consisting of a carbamoyl group which may have a group selected from the group consisting of a lower alkoxy lower alkyl group and a lower alkyl group, a lower alkoxycarbonyl group, a carboxy group, a cyano group, a phenyl group, a halogen atom, a lower alkyl group which may have a halogen atom as a substituent, a lower alkoxy group which may have a halogen atom as a substituent, a benzoyl group which may have a halogen atom as a substituent on the phenyl ring, a phenyl lower alkyl group which may have a halogen atom as a substituent on the phenyl ring, and a hydroxyl group include phenyl groups which may be substituted on the phenyl group with 1 to 3 groups selected from the group consisting of a carbamoyl group which may have 1 or 2 groups selected from the group consisting of an alkoxyalkyl group of the alkyl moiety is a linear or branched alkyl group having 1 to 6 carbon atoms and a linear or branched alkyl group having 1 to 6 carbon atoms, a linear or branched alkoxycarbonyl group having 1 to 6 carbon atoms, a carboxy group, a cyano group, a phenyl group, a halogen atom, a linear or branched alkyl group having 1 to 6 carbon atoms which may have 1 to 3 halogen atoms as substituents, a linear or branched alkoxy group having 1 to 6 carbon atoms which may have 1 to 3 halogen atoms as substituents, a benzoyl group which may have 1 to 3 halogen atoms as substituents on the phenyl ring, a phenylalkyl group which may have 1 to 3 halogen atoms as substituents on the phenyl ring and of which the alkyl moiety is a linear or branched alkyl group having 1 to 6 carbon atoms, and a hydroxyl group such as phenyl, 2-methylphenyl, 3-methylphenyl, 4-methylphenyl, 2-ethylphenyl, 3-ethylphenyl, 4-ethylphenyl, 4-isopropylphenyl, 3-butylphenyl, 4-pentylphenyl, 4-hexylphenyl, 3,4-dimethylphenyl, 3,4-diethylphenyl, 2,4-dimethylphenyl, 2,3-dimethylphenyl, 2,5-dimethylphenyl, 2,6-dimethylphenyl, 3,4,5-trimethylphenyl, 2-methoxyphenyl, 3-methoxyphenyl, 4-methoxyphenyl, 2-ethoxyphenyl, 3-ethoxyphenyl, 4-ethoxyphenyl, 4-isopropoxyphenyl, 3-butoxyphenyl, 4-pentyloxyphenyl, 4-hexyloxyphenyl, 3,4-dimethoxyphenyl, 3,4-diethoxyphenyl, 2,4-dimethoxyphenyl, 2,5-dimethoxyphenyl, 2,6-dimethoxyphenyl, 3,4,5-trimethoxyphenyl, 2-trifluoromethoxyphenyl, 3-trifluoromethoxyphenyl, 4-trifluoromethoxyphenyl, 2-(bromomethoxy)phenyl, 3-(2-chloroethoxy)phenyl, 4-(2,3-dichloropropoxy)phenyl, 4-(4-fluorobutoxy)phenyl, 3-(5-chloropentyloxy)phenyl, 4-(5-bromohexyloxy)phenyl, 4-(5,6-dibromohexyloxy)phenyl, 3,4-di(trifluoromethoxy)phenyl, 3,4-di(4,4,4-trichlorobutoxy)phenyl, 2,4-di(3-chloro-2-methoxypropyl)phenyl, 2,5-di(3-chloropropoxy)phenyl, 2,6-di(2,2,2-trifluoroethoxy)phenyl, 3,4,5-tri(trifluoromethoxy)phenyl, 4-(2,2,2-trichloroethoxy)phenyl, 2-methyl-4-trifluoromethoxyphenyl, 3-ethyl-4-trichloromethoxyphenyl, 2-methoxy-4-trifluoromethoxyphenyl, 3-ethoxy-4-trichloromethoxyphenyl, 2-trifluoromethylphenyl, 3-trifluoromethylphenyl, 4-trifluoromethylphenyl, 2-(bromomethyl)phenyl, 3-(2-chloroethyl)phenyl, 4-(2,3-dichloropropyl)phenyl, 4-(4-fluorobutyl)phenyl, 3-(5-chloropentyl)phenyl, 4-(5-bromohexyl)phenyl, 4-(5,6-dibromohexyl)phenyl, 3,4-di(trifluoromethyl)phenyl, 3,4-di(4,4,4-trichlorobutyl)phenyl, 2,4-di(3-chloro-2-methylpropyl)phenyl, 2,5-di(3-chloropropyl)phenyl, 2,6-di(2,2,2-trifluoroethyl)phenyl, 3,4,5-tri(trifluoromethyl)phenyl, 4-(2,2,2-trichloroethyl)phenyl, 2-methyl-4-trifluoromethylphenyl, 3-ethyl-4-trichloromethylphenyl, 2-methoxycarbonylphenyl, 3-methoxycarbonylphenyl, 4-methoxycarbonylphenyl, 2-ethoxycarbonylphenyl, 3-ethoxycarbonylphenyl, 4-ethoxycarbonylphenyl, 4-isopropoxycarbonylphenyl, 3-butoxycarbonylphenyl, 4-tert-butoxycarbonylphenyl, 4-pentyloxycarbonylphenyl, 4-hexyloxycarbonylphenyl, 3,4-dimethoxycarbonylphenyl, 3,4-diethoxycarbonylphenyl, 2,4-dimethoxycarbonylphenyl, 2,5-diethoxycarbonylphenyl, 2,6-dimethoxycarbonylphenyl, 3,4,5-triethoxycarbonylphenyl, 2-cyanophenyl, 3-cyanophenyl, 4-cyanophenyl, 3,4-dicyanophenyl, 3,5-dicyanophenyl, 2,4-dicyanophenyl, 2,5-dicyanophenyl, 2,6-dicyanophenyl, 3,4,5-tricyanophenyl, 2-phenylphenyl, 3-phenylphenyl, 4-phenylphenyl, 3,4-diphenylphenyl, 3,5-diphenylphenyl, 2,4-diphenylphenyl, 2,5-diphenylphenyl, 2,6-diphenylphenyl, 3,4,5-triphenylphenyl, 2-chlorophenyl, 3-chlorophenyl, 4-chlorophenyl, 2,3-dichlorophenyl, 2,4-dichlorophenyl, 2,5-dichlorophenyl, 3,4-dichlorophenyl, 2,6-dichlorophenyl, 3,5-dichlorophenyl, 2,4,6-trichlorophenyl, 2-fluorophenyl, 3-fluorophenyl, 4-fluorophenyl, 2,5-difluorophenyl, 2,4-difluorophenyl, 3,4-difluorophenyl, 3,5-difluorophenyl, 2,6-difluorophenyl, 2,4,6-trifluorophenyl, 2-bromophenyl, 3-bromophenyl, 4-bromophenyl, 2-iodophenyl, 3-iodophenyl, 4-iodophenyl, 2,3-dibromophenyl, 2,4-diiodophenyl, 2-hydroxyphenyl, 3-hydroxyphenyl, 4-hydroxyphenyl, 3,4-dihydroxyphenyl, 3,5-dihydroxyphenyl, 2,4-dihydroxyphenyl, 2,5-dihydroxyphenyl, 2,6-dihydroxyphenyl, 3,4,5-trihydroxyphenyl, 3-benzylphenyl, 2-(2-phenylethyl)phenyl, 4-(1-phenylethyl)phenyl, 2-(3-phenylpropyl)phenyl, 3-(4-phenylbutyl)phenyl, 4-(5-phenylpentyl)phenyl, 2-(6-phenylhexyl)phenyl, 4-(1,1-dimethyl-2-phenylethyl)phenyl, 3-(2-methyl-3-phenylpropyl)phenyl, 2-(4-fluorobenzyl)phenyl, 2-methyl-5-chlorophenyl, 2-methoxy-5-chlorophenyl, 4-(4-fluorobenzoyl)phenyl, 4-(4-fluorobenzyl)phenyl, 3-(2-chlorobenzyl)phenyl, 4-(3-chlorobenzyl)phenyl, 2-(4-chlorobenzyl)phenyl, 3-[2-(4-fluorophenyl)ethyl]phenyl, 4-[2-(4-chlorophenyl)ethyl]phenyl, 2-(3,4-dibromobenzyl)phenyl, 3-(3,4-diiodobenzyl)phenyl, 4-(2,4-difluorobenzyl)phenyl, 2-(2,5-dichlorobenzyl)-phenyl, 3-(2,6-dichlorobenzyl)phenyl, 4-(3,4,5-trifluorobenzyl)phenyl, 2-[3-(4-chlorophenyl)propyl]phenyl, 3-[1-(2-bromophenyl)ethyl]phenyl, 4-[4-(3-fluorophenyl)butyl]phenyl, 2-[5-(4-iodophenyl)pentyl]phenyl, 3-[6-(4-chlorophenyl)hexyl]phenyl, 2-[1,1-dimethyl-2-(3-fluorophenyl)ethyl]phenyl, 4-[2-methyl-3-(4-chlorophenyl)propyl]phenyl, 2,4-dibenzylphenyl, 2,4,6-tribenzylphenyl, 2-chloro-4-cyanophenyl, 3-hydroxy-4-phenylphenyl, 3-ethoxycarbonyl-2-benzoylphenyl, 2-benzyl-4-methyl-6-methoxyphenyl, 4-[(2-methoxyethyl)carbamoyl]phenyl, 3-(N-ethyl-N-isopropylcarbamoyl)phenyl, 4-dimethylcarbamoylphenyl, 2-carboxyphenyl, 3-carboxyphenyl, 4-carboxyphenyl, groups.

Examples of the phenyl group which has a lower alkylenedioxy group as a substituent on the phenyl ring include phenyl groups which has a linear or branched alkylenedioxy group having 1 to 4 carbon atom as a substituent on the phenyl ring such as a 3,4-methylenedioxyphenyl group, 3,4-trimethylenedioxyphenyl group, 2,3-ethylenedioxyphenyl group, 2,3-tetramethylenedioxyphenyl group, 2,3-methylenedioxyphenyl group, 3,4-ethylenedioxyphenyl group, and 2,3-trimethylenedioxyphenyl group.

Examples of the naphthyl lower alkyl group include naphthylalkyl groups of which the alkyl moiety is a linear or branched alkyl group having 1 to 6 carbon atoms such as a (1 or 2-)naphthylmethyl group, 2-[(1 or 2-)naphthyl]ethyl group, 1-[(1 or 2-)naphthyl]ethyl group, 3-[(1 or 2-)naphthyl] propyl group, 4-[(1 or 2-)naphthyl]butyl group, 5-[(1 or 2-)naphthyl]pentyl group, 6-[(1 or 2-)naphthyl]hexyl group, 1,1-dimethyl-2-[(1 or 2-)naphthyl]ethyl group, and 2-methyl-3-[(1 or 2-)naphthyl]propyl group.

Examples of the phenoxy group which may be substituted on the phenyl ring with 1 to 3 groups selected from the group consisting of a cyano group, a lower alkyl group which may have a halogen atom as a substituent, and a lower alkoxy group which may have a halogen atom as a substituent include phenoxy groups which may be substituted on the phenyl group with 1 to 3 groups selected from the group consisting of a cyano group, a linear or branched alkyl group having 1 to 6 carbon atoms which may have 1 to 3 halogen atoms as substituents, and a linear or branched alkoxy group having 1 to 6 carbon atoms which may have 1 to 3 halogen atoms as substituents such as phenoxy, 2-methylphenoxy, 3-methylphenyl, 4-methylphenoxy, 2-ethylphenoxy, 3-ethylphenoxy, 4-ethylphenoxy, 4-isopropylphenoxy, 3-butylphenoxy, 4-pentylphenoxy, 4-hexylphenoxy, 3,4-dimethylphenoxy, 3,4-diethylphenoxy, 2,4-dimethylphenoxy, 2,5-dimethylphenoxy, 2,6-dimethylphenoxy, 3,4,5-trimethylphenoxy, 2-methoxyphenoxy, 3-methoxyphenoxy, 4-methoxyphenoxy, 2-ethoxyphenoxy, 3-ethoxyphenoxy, 4-ethoxyphenoxy, 4-isopropoxyphenoxy, 3-butoxyphenoxy, 4-pentyloxyphenoxy, 4-hexyloxyphenoxy, 3,4-dimethoxyphenoxy, 3,4-diethoxyphenoxy, 2,4-dimethoxyphenoxy, 2,5-dimethoxyphenoxy, 2,6-dimethoxyphenoxy, 3,4,5-trimethoxyphenoxy, 2-trifluoromethoxyphenoxy, 3-trifluoromethoxyphenoxy, 4-trifluoromethoxyphenoxy, 2-(bromomethoxy)phenoxy, 3-(2-chloroethoxy)phenoxy, 4-(2,3-dichloropropoxy)phenoxy, 4-(4-fluorobutoxy)phenoxy, 3-(5-chloropentyloxy)phenoxy, 4-(5-bromohexyloxy)phenoxy, 4-(5,6-dibromohexyloxy)phenoxy, 3,4-di(trifluoromethoxy)phenoxy, 3,4-di(4,4,4-trichlorobutoxy)phenoxy, 2,4-di(3-chloro-2-methoxypropyl)phenoxy, 2,5-di(3-chloropropoxy)phenoxy, 2,6-di(2,2,2-trifluoroethoxy)phenoxy, 3,4,5-tri(trifluoromethoxy)phenoxy, 4-(2,2,2-trichloroethoxy)phenoxy, 2-methyl-4-trifluoromethoxyphenoxy, 3-ethyl-4-trichloromethoxyphenoxy, 2-methoxy-4-trifluoromethoxyphenoxy, 3-ethoxy-4-trichloromethoxyphenoxy, 2-trifluoromethylphenoxy, 3-trifluoromethylphenoxy, 4-trifluoromethylphenoxy, 2-(bromomethyl)phenoxy, 3-(2-chloroethyl)phenoxy, 4-(2,3-dichloropropyl)phenoxy, 4-(4-fluorobutyl)phenoxy, 3-(5-chloropentyl)phenoxy, 4-(5-bromohexyl)phenoxy, 4-(5,6-dibromohexyl)phenoxy, 3,4-di(trifluoromethyl)phenoxy, 3,4-di(4,4,4-trichlorobutyl)phenoxy, 2,4-di(3-chloro-2-methylpropyl)phenoxy, 2,5-di(3-chloropropyl)phenoxy, 2,6-di(2,2,2-trifluoroethyl)phenoxy, 3,4,5-tri(trifluoromethyl)phenoxy, 4-(2,2,2-trichloroethyl)phenoxy, 2-methyl-4-trifluoromethylphenoxy, 3-ethyl-4-trichloromethylphenoxy, 2-cyanophenoxy, 3-cyanophenoxy, 4-cyanophenoxy, 3,5-dicyanophenoxy, 3,4-dicyanophenoxy, 2,3-dicyanophenoxy, 2,4-dicyanophenoxy, 2,5-dicyanophenoxy, 2,6-dicyanophenoxy, 3,4,5-tricyanophenoxy, 2-cyano-4-methylphenoxy, 3-cyano-4-methoxyphenoxy, 3-cyano-5-trifluoromethylphenoxy, 4-cyano-3-trifluoromethoxyphenoxy groups.

Examples of the phenyl lower alkoxy group which may be substituted on the phenyl ring with 1 to 3 groups selected from the group consisting of a halogen atom, a lower alkyl group which may have a halogen atom as a substituent, and a lower alkyloxy group which may have a halogen atom as a substituent include, in addition to the above described phenyl lower alkoxy groups, phenylalkoxy groups which may be substituted on the phenyl ring with 1 to 3 groups selected from the group consisting of a halogen atom, a linear or branched alkyl group having 1 to 6 carbon atoms which may have 1 to 3 halogen atoms as substituents, and a linear or branched alkoxy group having 1 to 6 carbon atoms which may have 1 to 3 halogen atoms as substituents, and of which the alkoxy moiety is a linear or branched alkoxy group having 1 to 6 carbon atoms such as 2,5-difluorobenzyloxy, 2,4-difluorobenzyloxy, 3,4-difluorobenzyloxy, 3,5-difluorobenzyloxy, 2,6-difluorobenzyloxy, 3-trifluoromethylbenzyloxy, 2-trifluoromethylbenzyloxy, 4-trifluoromethylbenzyloxy, 3,4-dimethoxybenzyloxy, 3,5-dimethoxybenzyloxy, 2-chlorobenzyloxy, 3-chlorobenzyloxy, 4-chlorobenzyloxy, 2-methylbenzyloxy, 3-methylbenzyloxy, 4-methylbenzyloxy, 3,4-dimethylbenzyloxy, 2,3-dimethylbenzyloxy, 2-methoxybenzyloxy, 3-methoxybenzyloxy, 4-methoxybenzyloxy, 2,3-dichlorobenzyloxy, 2,4-dichlorobenzyloxy, 2,5-dichlorobenzyloxy, 3,4-dichlorobenzyloxy, 2,6-dichlorobenzyloxy, 4-fluorobenzyloxy, 3-fluorobenzyloxy, 2-fluorobenzyloxy, 3-trifluoromethoxybenzyloxy, 4-trifluoromethoxybenzyloxy, 2-trifluoromethoxybenzyloxy, 4-tert-butylbenzyloxy, 4-ethylbenzyloxy, 4-isopropylbenzyloxy, 4-methoxy-3-chlorobenzyloxy, 2-(4-methoxyphenyl)ethoxy, 2-(4-fluorophenyl)ethoxy, 2-(4-chlorophenyl)ethoxy, 2-(3-methoxyphenyl)ethoxy, 2-(4-methylphenyl)ethoxy, 3-methyl-4-chlorobenzyloxy, 4-(4-methoxyphenyl)butoxy, 2-(4-methylphenyl)ethoxy, 4-tert-butoxybenzyloxy, 3-chloro-6-methoxybenzyloxy, 4-methoxy-3-methylbenzyloxy, 2-(2-fluorophenyl)ethoxy, 1-(3-bromophenyl)ethoxy, 3-(4-iodophenyl)propoxy, 4-(2-bromophenyl)butoxy, 5-(3-chlorophenyl)pentyloxy, 6-(4-bromophenyl)hexyloxy, 1,1-dimethyl-2-(2,4-dichlorophenyl)ethoxy, 2-methyl-3-(2,4,6-trifluorophenyl)propoxy, 2-(2-ethylphenyl)ethoxy, 1-(3-propylphenyl)ethoxy, 3-(4-butylphenyl)propoxy, 4-(2-pentylphenyl)butoxy, 5-(3-hexylphenyl)pentyloxy, 6-(4-trifluoromethylphenyl)hexyloxy, 1,1-dimethyl-2-(2,4-dimethylphenyl)ethoxy, 2-methyl-3-[2,4,6-tri(trifluoromethyl)phenyl]propoxy, 2-(2-ethoxyphenyl)ethoxy, 1-(3-propoxyphenyl)ethoxy, 3-(4-butoxyphenyl)propoxy, 4-(2-pentyloxyphenyl)butoxy, 5-(3-hexyloxyphenyl)pentyloxy, 6-(4-trifluoromethoxyphenyl)hexyloxy, 1,1-dimethyl-2-(2,4-dimethoxyphenyl)ethoxy, 2-methyl-3-[2,4,6-tri(trifluoromethoxy)phenyl]propoxy groups.

Examples of the 1,2,3,4-tetrahydronaphthyl substituted lower alkyl group which may have 1 to 5 lower alkyl groups as substituents on the 1,2,3,4-tetrahydronaphthalene ring include 1,2,3,4-tetrahydronaphthyl substituted alkyl groups which may have 1 to 5 linear or branched alkyl groups having 1 to 6 carbon atoms as substituents on the 1,2,3,4-tetrahydronaphthalene ring, and of which the alkyl moiety is a linear or branched alkyl group having 1 to 6 carbon atoms such as (1,2,5, or 6-)1,2,3,4-tetrahydronaphthylmethyl, 2-[(1,2,5, or 6-)1,2,3,4-tetrahydronaphthyl]ethyl, 1-[(1,2,5, or 6-)1,2,3,4-tetrahydronaphthyl]ethyl, 3-[(1,2,5, or 6-)1,2,3,4-tetrahydronaphthyl]propyl, 4-[(1,2,5, or 6-)1,2,3,4-tetrahydronaphthyl]butyl, 5-[(1,2,5, or 6-)1,2,3,4-tetrahydronaphthyl]pentyl, 6-[(1,2,5, or 6-)1,2,3,4-tetrahydronaphthyl]hexyl, 1,1-dimethyl-2-[(1,2,5, or 6-)1,2,3,4-tetrahydronaphthyl]ethyl, 2-methyl-3-[(1,2,5, or 6-)1,2,3,4-tetrahydronaphthyl]propyl, 1,1,4,4-tetramethyl(2,3,5, or 6-)1,2,3,4-tetrahydronaphthylmethyl, 1,1,4,4,5-pentamethyl(2,3,6,7, or 8-)1,2,3,4-tetrahydronaphthylmethyl, 1,4,4-trimethyl(2,3,5,6,7, or 8-)1,2,3,4-tetrahydronaphthylmethyl, 5,6-dimethyl(2, 3, 7, or 8-)1,2,3,4-tetrahydronaphthylmethyl, 2-[1-methyl-(1,2,3, 4,5,6,7, or 8-)1,2,3,4-tetrahydronaphthyl]ethyl, 1-[2-ethyl-(1,2,3,4,5,6,7, or 8-)1,2,3,4-tetrahydronaphthyl]ethyl, 3-[3-propyl-(1,2,3,4,5,6,7, or 8-)1,2,3,4-tetrahydronaphthyl]

propyl, 4-[(4-butyl-1,2,3,4,5,6,7, or 8-)1,2,3,4-tetrahydronaphthyl]butyl, 5-[5-pentyl-(1,2,3,4,6,7, or 8-)1,2,3,4-tetrahydronaphthyl]pentyl, 6-[6-hexyl-(1,2,3,4,5,7, or 8-)1,2,3,4-tetrahydronaphthyl]hexyl, 1,1-dimethyl-2-[1,7-dimethyl-(1,2,3,4,5,6, or 8-)1,2,3,4-tetrahydronaphthyl]ethyl, 2-methyl-3-[1,1,4-trimethyl-(2,3,4,5,6,7, or 8-)1,2,3,4-tetrahydronaphthyl]propyl groups.

Examples of the piperidinyl group which may have 1 to 3 lower alkyl groups as substituents on the piperidine ring include piperidinyl group which may have 1 to 3 linear or branched alkyl groups having 1 to 6 carbon atoms as substituents on the piperidine ring such as (1,2,3, or 4-)piperidinyl, 1-methyl-(2,3, or 4-)piperidinyl, 1-ethyl-(2,3, or 4-)piperidinyl, 1-propyl-(2,3, or 4-)piperidinyl, 1-isopropyl-(2,3, or 4-)piperidinyl, 1-butyl-(2,3, or 4-)piperidinyl, 1-isobutyl-(2, 3, or 4-)piperidinyl, 1-tert-butyl-(2,3, or 4-)piperidinyl, 1-pentyl-(2,3, or 4-)piperidinyl, 1-hexyl-(2,3, or 4-)piperidinyl, 1,2-dimethyl-(3,4,5, or 6-)piperidinyl, 1,2,6-trimethyl-(3,4, or 5-)piperidinyl groups.

Examples of the quinolyl lower alkyl group include quinolylalkyl groups of which the alkyl moiety is a linear or branched alkyl group having 1 to 6 carbon atoms such as a (2,3,4,5,6,7 or 8-)quinolyl-methyl group, 2-[(2,3,4,5,6,7 or 8-)quinolyl]ethyl group, 1-[(2,3,4,5,6,7 or 8-)quinolyl]ethyl group, 3-[(2,3,4,5,6,7 or 8-)quinolyl]propyl group, 4-[(2,3,4, 5,6,7 or 8-)quinolyl]butyl group, 5-[(2,3,4,5,6,7 or 8-)quinolyl]pentyl group, and 6-[(2,3,4,5,6,7 or 8-)quinolyl]hexyl group.

Examples of the 1,2,3,4-tetrazolyl lower alkyl group which may have, on the tetrazole ring, a substituent selected from the group consisting of a lower alkyl group and a phenyl lower alkyl group include 1,2,3,4-tetrazolylalkyl groups which may have, on the tetrazole ring, a substituent selected from the group consisting of a linear or branched alkyl group having 1 to 6 carbon atoms and of which the alkyl moiety is a linear or branched alkyl group having 1 to 6 carbon atoms, the 1,2,3, 4-tetrazolylalkyl groups of which the alkyl moiety is a linear or branched alkyl group having 1 to 6 carbon atoms, such as [(1 or 0.5-)1,2,3,4-tetrazolyl]methyl, 2-[(1 or 5-)1,2,3,4-tetrazolyl]ethyl, 1-[(1 or 5-)1,2,3,4-tetrazolyl]ethyl, 3-[(1 or 5-)1,2,3,4-tetrazolyl]propyl, 4-[(1 or 5-)1,2,3,4-tetrazolyl]butyl, 5-[(1 or 5-)1,2,3,4,-tetrazolyl]pentyl, 6-[(1 or 5-)1,2,3,4-tetrazolyl]hexyl, 5-[1-methyl-5-(1,2,3,4-tetrazolyl)]pentyl, 6-[1-methyl-5-(1,2,3,4-tetrazolyl)]hexyl, 5-methyl-1-(1,2,3,4-tetrazolyl)methyl, 2-[5-ethyl-1-(1,2,3,4-tetrazolyl)]hexyl, 1,1-dimethyl-2-[(1 or 5-)1,2,3,4-tetrazolyl)]ethyl, 2-methyl-3-[(1 or 5-)1,2,3,4-tetrazolyl]propyl, [1-methyl-5-(1,2,3,4-tetrazolyl)]methyl, [1-ethyl-5-(1,2,3,4-tetrazolyl)]methyl, 2-[1-propyl-5-(1,2,3,4-tetrazolyl)]ethyl, 1-[1-butyl-5-(1,2,3,4-tetrazolyl)]ethyl, 3-[1-pentyl-5-(1,2,3,4-tetrazolyl)]propyl, 3-[5-propyl-1-(1,2,3,4-tetrazolyl)]propyl, 4-[5-butyl-1-(1,2,3,4-tetrazolyl)]butyl, 5-[5-pentyl-1-(1,2,3, 4-tetrazolyl)]pentyl, 6-[5-hexyl-1-(1,2,3,4-tetrazolyl)]hexyl, [1-ethyl-5-(1,2,3,4-tetrazolyl)]methyl, [1-benzyl-5-(1,2,3,4-tetrazolyl)]methyl, 1-[(2-phenylethyl)-5-(1,2,3,4-tetrazolyl)]methyl, 2-[1-(3-phenylpropyl)-5-(1,2,3,4-tetrazolyl)]ethyl, 1-[l-(4-phenylbutyl)-5-(1,2,3,4-tetrazolyl)]ethyl, 3-[1-(5-phenylpentyl)-5-(1,2,3,4-tetrazolyl)]propyl, 4-[l-(6-phenylhexyl)-5-(1,2,3,4-tetrazolyl)]butyl, 5-[1-(1,1-dimethyl-2-phenylethyl)-5-(1,2,3,4-tetrazolyl)]methyl, 6-[1-(2-methyl-3-phenylpropyl)-5-(1,2,3,4-tetrazolyl)]hexyl, 5-benzyl-1-(1,2,3,4-tetrazolyl)methyl, 2-[5-(1-phenylethyl)-1-(1,2,3,4-tetrazolyl)]ethyl, 3-[5-(3-phenylpropyl)-1-(1,2,3,4-tetrazolyl)]propyl, 4-[5-(4-phenylbutyl)-1-(1,2,3,4-tetrazolyl)]butyl, 5-[5-(5-phenylpentyl)-1-(1,2,3,4-tetrazolyl)]pentyl, 6-[5-(6-phenylhexyl)-1-(1,2,3,4-tetrazolyl)]hexyl groups.

Examples of the thiazolyl lower alkyl group which may have a phenyl group as a substituent on the thiazole ring include thiazolylalkyl groups which may have 1 or 2 phenyl groups as substituents on the thiazole ring and of which the alkyl moiety is a linear or branched alkyl group having 1 to 6 carbon atoms such as [(2,4, or 5-)thiazolyl]methyl, 2-[(2,4, or 5-)thiazolyl]ethyl, 1-[(2,4, or 5-)thiazolyl]ethyl, 3-[(2,4, or 5-)thiazolyl]propyl, 4-[(2,4, or 5-)thiazolyl]butyl, 5-[(2,4, or 5-)thiazolyl]pentyl, 6-[(2,4, or 5-)thiazolyl]hexyl, 1,1-dimethyl-2-[(2,4, or 5-)thiazolyl]ethyl, 2-methyl-3-[(2,4, or 5-)thiazolyl]propyl, [2-phenyl-(4 or 5-)thiazolyl]-methyl, 2-[4-phenyl-(2 or 5-)thiazolyl]ethyl, 1-[5-phenyl-(2 or 4-)thiazolyl]ethyl, 3-[2-phenyl-(2 or 5-)thiazolyl]propyl, 4-(2,4-diphenyl-5-thiazolyl)butyl, 5-(2,5-diphenyl-4-thiazolyl)pentyl, 6-(4,5-diphenyl-2-thiazolyl)hexyl, 1,1-dimethyl-2-[2-phenyl-(4 or 5-)thiazolyl]ethyl, 2-methyl-3-[4-phenyl-(2 or 5-)thiazolyl]propyl, [4-phenyl-(2 or 5-)thiazolyl]-methyl, [5-phenyl-(2 or 4-)thiazolyl]methyl, (2,4-diphenyl-5-thiazolyl)methyl, (2,5-diphenyl-4-thiazolyl)methyl, (4,5-diphenyl-2-thiazolyl)methyl groups.

Examples of the benzoyl lower alkyl group which may have, on the phenyl ring, 1 to 3 substituents selected from the group consisting of a lower alkoxy group and a halogen atom include benzoylalkyl groups which may have, on the phenyl ring, 1 to 3 substituents selected from the group consisting of a linear or branched alkoxy group having 1 to 6 carbon atoms and a halogen atom such as benzoylmethyl, 2-benzoylethyl, 1-benzoylethyl, 3-benzoylpropyl, 4-benzoylbutyl, 5-benzoylpentyl, 6-benzoylhexyl, 1,1-dimethyl-2-benzoylethyl, 2-methyl-3-benzoylpropyl, 4-fluorobenzoylmethyl, 2-chlorobenzoylmethyl, 3-chlorobenzoylmethyl, 4-chlorobenzoylmethyl, 2-(4-fluorobenzoyl)ethyl, 2-(4-chlorobenzoyl)ethyl, 3,4-dibromobenzoylmethyl, 3,4-diiodobenzoylmethyl, 2,4-difluorobenzoylmethyl, 2,5-dichlorobenzoylmethyl, 2,6-dichlorobenzoylmethyl, 3,4,5-trifluorobenzoylmethyl, 3-(4-chlorobenzoyl)propyl, 1-(2-bromobenzoyl)ethyl, 4-(3-fluorobenzoyl)butyl, 5-(4-iodobenzoyl)pentyl, 6-(4-chlorobenzoyl)hexyl, 1,1-dimethyl-2-(3-fluorobenzoyl)ethyl, 2-methyl-3-(4-chlorobenzoyl)propyl, 2-methoxybenzoylmethyl, 2-(3-methoxybenzoyl)ethyl, 2-(4-methoxybenzoyl)ethyl, 4-methoxybenzoylmethyl, 1-(2-ethoxybenzoyl)ethyl, 3-(3-ethoxybenzoyl)propyl, 4-(4-ethoxybenzoyl)butyl, 5-(4-isopropoxybenzoyl)pentyl, 6-(3-butoxybenzoyl)hexyl, 1,1-dimethyl-2-(4-pentyloxybenzoyl)ethyl, 2-methyl-3-(4-hexyloxybenzoyl)propyl, 3,4-dimethoxybenzoylmethyl, 3,4-diethoxybenzoylmethyl, 2,4-dimethoxybenzoylmethyl, 2,5-dimethoxybenzoylmethyl, 2,6-dimethoxybenzoylmethyl, 3,4,5-trimethoxybenzoylmethyl, 2-chloro-4-methoxybenzoylmethyl, 3-fluoro-5-ethoxybenzoylmethyl groups.

Examples of the piperidinyl lower alkyl group which may have a lower alkyl group as a substituent on the piperidine ring include piperidinylalkyl groups which may have 1 to 3 linear or branched alkyl groups having 1 to 6 carbon atoms on the piperidine ring and of which the alkyl moiety is a linear or branched alkyl group having 1 to 6 carbon atoms such as [(1,2,3, or 4-)piperidinyl]methyl, 2-[(1,2,3, or 4-)piperidinyl]-ethyl, 1-[(1,2,3, or 4-)piperidinyl]ethyl, 3-[(1,2,3, or 4-)piperidinyl]propyl, 4-[(1,2,3, or 4-)piperidinyl]butyl, 5-[(1,2,3, or 4-)piperidinyl]pentyl, 6-[(1,2,3, or 4-)piperidinyl]hexyl, 1,1-dimethyl-2-[(1,2,3, or 4-)piperidinyl]ethyl, 2-methyl-3-[(1,2,3, or 4-)piperidinyl]propyl, [1-methyl-(2,3, or 4-)piperidinyl]methyl, 2-[1-ethyl-(2,3, or 4-)piperidinyl]ethyl, 1-[4-propyl-(1,2, or 3-)piperidinyl]ethyl, 3-[3-isopropyl-(1,2,4,5, or 6-)piperidinyl]propyl, 4-[2-butyl-(1,3,4,5, or 6-)piperidinyl]butyl, 5-[l-isobutyl-(2,3, or 4-)piperidinyl]pentyl, 6-[1-tert-butyl-(2,3, or 4-)piperidinyl]hexyl, 1,1-dimethyl-2-[4-pentyl-(1,2, or 3-)piperidinyl]ethyl, 2-methyl-3-[1-hexyl-(2,3, or 4-)piperidinyl]propyl, [1,2-dimethyl-(3,4,5, or 6-)piperidinyl]methyl, [1,2,6-trimethyl-(3,4, or 5-)piperidinyl]methyl groups.

Examples of the imidazolyl group which may have 1 to 3 phenyl groups as substituents on the imidazole ring include imidazolyl groups which may have 1 to 3 phenyl groups as substituents on the imidazole ring such as a (1,2,4 or 5-)imidazolyl group, 1-phenyl-(2,4 or 5-)imidazolyl group, 2-phenyl-(1,4 or 5-)imidazolyl group, 4-phenyl-(1,2 or 5-)imidazolyl group, 5-phenyl-(1,2 or 4-)imidazolyl group, 1,2-diphenyl-(4 or 5-)imidazolyl group, 2,4-diphenyl-(1 or 5-)imidazolyl group, 4,5-diphenyl-(1 or 2-)imidazolyl group, 2,5-diphenyl-(1 or 4-)imidazolyl group, and 2,4,5-triphenyl-1-imidazolyl group.

Examples of the benzimidazolyl group which may have 1 to 3 lower alkyl groups as substituents on the benzimidazole ring include benzimidazolyl group which may have 1 to 3 linear or branched alkyl groups having 1 to 6 carbon atoms as substituents on the benzimidazole ring such as (1,2,4,5,6, or 7-)benzimidazolyl, 1-methyl-(2,4,5,6, or 7-)benzimidazolyl, 2-ethyl-(1,4,5,6, or 7-)benzimidazolyl, 4-propyl-(1,2,5,6, or 7-)benzimidazolyl, 5-butyl-(1,2,4,6, or 7-)benzimidazolyl, 6-pentyl-(1,2,4,5, or 7-)benzimidazolyl, 7-hexyl-(1,2,4,5, or 6-)benzimidazolyl, 1-ethyl-(2,4,5,6, or 7-)benzimidazolyl] hexyl, 1-butyl-(2,4,5,6, or 7-)benzimidazolyl, 1-isopropyl-(1,2,4,5,6, or 7-)benzimidazolyl, 1,2-dimethyl-(4,5,6, or 7-)benzimidazolyl, 1-methyl-4-ethyl-(2,5,6, or 7-)benzimidazolyl, 1-propyl-5-methyl-(2,4,6, or 7-)benzimidazolyl, 1,2,5-trimethyl-(2,4,5,6, or 7-)benzimidazolyl groups.

Examples of the pyridyl lower alkoxy group include pyridylalkoxy group of which the alkyl moiety is a linear or branched alkyl group having 1 to 6 carbon atoms such as a (2,3 or 4-)pyridylmethoxy group, 2-[(2,3 or 4-)pyridyl]ethoxy group, 1-[(2,3 or 4-)pyridyl]ethoxy group, 3-[(2,3 or 4-)pyridyl]propoxy group, 4-[(2,3 or 4-)pyridyl]butoxy group, 1-1-dimethyl-2-[(2,3 or 4-)pyridyl]ethoxy group, 5-[(2,3 or 4-)pyridyl]pentyloxy group, 6-[(2,3 or 4-)pyridyl]hexyloxy group, 1-[(2,3 or 4-)pyridyl]isopropoxy group, and 2-methyl-3-[(2,3 or 4-)pyridyl]propoxy group.

Examples of the 1,2,3,4-tetrahydroquinolyl lower alkyl group which may have an oxo group as a substituent on the tetrahydroquinoline ring include 1,2,3,4-tetrahydroquinolylalkyl groups which may have 1 or 2 oxo groups as substituents on the tetrahydroquinoline ring and of which the alkyl moiety is a linear or branched alkyl group having 1 to 6 carbon atoms such as (1,2,3,4,5,6,7, or 8-)1,2,3,4-tetrahydroquinolylmethyl, 2-[(1,2,3,4,5,6,7, or 8-)1,2,3,4-tetrahydroquinolyl]ethyl, 1-[(1,2,3,4,5,6,7, or 8-)1,2,3,4-tetrahydroquinolyl]ethyl, 3-[(1,2,3,4,5,6,7, or 8-)1,2,3,4-tetrahydroquinolyl]propyl, 4-[(1,2,3,4,5,6,7, or 8-)1,2,3,4-tetrahydroquinolyl]butyl, 5-[(1,2,3,4,5,6,7, or 8-)1,2,3,4-tetrahydroquinolyl]pentyl, 6-[(1,2,3,4,5,6,7, or 8-)1,2,3,4-tetrahydroquinolyl]hexyl, 1,1-dimethyl-2-[(1,2,3,4,5,6,7, or 8-)1,2,3,4-tetrahydroquinolyl]ethyl, 2-methyl-3-[(1,2,3,4,5,6,7, or 8-)1,2,3,4-tetrahydroquinolyl]propyl, [2-oxo-(1,3,4,5,6,7, or 8-)1,2,3,4-tetrahydroquinolyl]methyl, [4-oxo-(1,2,3,5,6,7, or 8-)1,2,3,4-tetrahydroquinolyl]methyl, [2,4-dioxo-(1,3,5,6,7, or 8-)1,2,3,4-tetrahydroquinolyl]methyl, 2-[2-oxo-(1,3,4,5,6,7, or 8-)1,2,3,4-tetrahydroquinolyl]ethyl, 3-[4-oxo-(1,2,3,5,6,7, or 8-)1,2,3,4-tetrahydroquinolyl]propyl, 4-[2,4-dioxo-(1,3,5,6,7, or 8-)1,2,3,4-tetrahydroquinolyl]butyl, 5-[2-oxo-(1,3,4,5,6,7, or 8-)1,2,3,4-tetrahydroquinolyl]pentyl, 6-[4-oxo-(1,2,3,5,6,7, or 8-)1,2,3,4-tetrahydroquinolyl]hexyl groups.

Examples of the 1,3,4-oxadiazolyl lower alkyl group which may have an oxo group as a substituent on the oxadiazole ring include 1,3,4-oxadiazolylalkyl groups which may have an oxo group as a substituent on the oxadiazole ring and of which the alkyl moiety is a linear or branched alkyl group having 1 to 6 carbon atoms such as (2 or 5-)1,3,4-oxadiazolylmethyl, 2-[(2 or 5-)1,3,4-oxadiazolyl]ethyl, 1-[(2 or 5-)1,3,4-oxadiazolyl]ethyl, 3-[(2 or 5-)1,3,4-oxadiazolyl]propyl, 4-[(2 or 5-)1,3,4-oxadiazolyl]butyl, 5-[(2 or 5-)1,3,4-oxadiazolyl]pentyl, 6-[(2 or 5-)1,3,4-oxadiazolyl]hexyl, 1,1-dimethyl-2-[(2 or 5-)1,3,4-oxadiazolyl]ethyl, 2-methyl-3-[(2 or 5-)1,3,4-oxadiazolyl]propyl, 2-oxo-[(3 or 5-)1,3,4-oxadiazolyl]methyl, 5-oxo-[(2 or 3-)1,3,4-oxadiazolyl]methyl, 2-[2-oxo-(3 or 5-)(1,3,4-oxadiazolyl)]ethyl, 1-[5-oxo-(2 or 3-)1,3,4-oxadiazolyl]ethyl, 3-[(2 or 5-)1,3,4-oxadiazolyl]propyl, 4-[2-oxo(3 or 5-)1,3,4-oxadiazolyl]butyl, 5-[5-oxo(2 or 3-)1,3,4-oxadiazolyl]pentyl, 6-[2-oxo(3 or 5-)1,3,4-oxadiazolyl]hexyl, 1,1-dimethyl-2-[5-oxo(2 or 3-)1,3,4-oxadiazolyl]ethyl, 2-methyl-3-[2-oxo(3 or 5-)1,3,4-oxadiazolyl]propyl groups.

Examples of the thienyl lower alkyl group include thienylalkyl groups of which the alkyl moiety is a linear or branched alkyl group having 1 to 6 carbon atoms such as a (2 or 3-)thienylmethyl group, 2-[(2 or 3-)thienyl]ethyl group, 1-[(2 or 3-)thienyl]ethyl group, 3-[(2 or 3-)thienyl]propyl group, 4-[(2 or 3-)thienyl]butyl group, 5-[(2 or 3-)thienyl]pentyl group, 6-[(2 or 3-)thienyl]hexyl group, 1,1-dimethyl-2-[(2 or 3-)thienyl]ethyl group, and 2-methyl-3-[(2 or 3-)thienyl]propyl group.

Examples of the pyrimidinylcarbonyl group which may have an oxo group as a substituent on the pyrimidine ring include pyrimidinylcarbonyl groups which may have 1 to 3 oxo groups as substituents on the pyrimidine ring such as a (2,3,4 or 6-)pyrimidinylcarbonyl group, 2,6-dioxo-(1,3,4 or 5-)pyrimidinylcarbonyl group, 2-oxo-(1,3,4,5 or 6-)pyrimidinylcarbonyl group, 6-oxo-(1,2,3,4 or 5-)pyrimidinylcarbonyl group, 4-oxo-(1,2,3,4 or 6-)pyrimidylcarbonyl group, 2,4-dioxo-(1,3,4 or 6-)pyrimidinylcarbonyl group, and 2,4,6-trioxo-(1,3 or 5-)pyrimidylcarbonyl group.

Examples of the lower alkoxy lower alkoxy group include linear or branched alkoxy groups having 1 to 6 carbon atoms which may have a linear or branched alkoxy group having 1 to 6 carbon atoms as a substituent such as a methoxymethoxy group, 1-ethoxyethoxy group, 2-methoxyethoxy group, 2-propoxyethoxy group, 3-isopropoxypropoxy group, 4-butoxybutoxy group, 5-pentyloxypentyloxy group, 6-hexyloxyhexyloxy group, 1,1-dimethyl-2-methoxyethoxy group, 2-methyl-3-ethoxypropoxy group, and 3-methoxypropoxy group.

Examples of the lower alkoxycarbonyl lower alkoxy group include alkoxycarbonylalkoxy groups of which both alkoxy moieties are linear or branched alkoxy groups having 1 to 6 carbon atoms such as methoxycarbonylmethoxy, ethoxycarbonylmethoxy, 2-methoxycarbonylethoxy, 2-ethoxycarbonylethoxy, 1-ethoxycarbonylethoxy, 3-methoxycarbonylpropoxy, 3-ethoxycarbonylpropoxy, 4-ethoxycarbonylbutoxy, 5-isopropoxycarbonylpentyloxy, 6-propoxycarbonylhexyloxy, 1,1-dimethyl-2-butoxycarbonylethoxy, 2-methyl-3-tert-butoxycarbonylpropoxy, 2-pentyloxycarbonylethoxy, hexyloxycarbonylmethoxy groups.

Examples of the carboxy lower alkoxy group include carboxyalkoxy groups of which the alkoxy moiety is a linear or branched alkoxy group having 1 to 6 carbon atoms such as a carboxymethoxy group, 2-carboxyethoxy group, 1-carboxyethoxy group, 3-carboxypropoxy group, 4-carboxybutoxy group, 5-carboxypentyloxy group, 6-carboxyhexyloxy group, 1,1-dimethyl-2-carboxyethoxy group, and 2-methyl-3-carboxypropoxy group.

Examples of the phenoxy lower alkanoyl group include phenoxyalkanoyl groups of which the alkanoyl moiety is a linear or branched alkanoyl group having 2 to 6 carbon atoms such as a 2-phenoxyacetyl group, 3-phenoxypropionyl group, 2-phenoxypropionyl group, 4-phenoxybutyryl group, 5-phenoxypentanoyl group, 6-phenoxyhexanoyl group, 2,2-dimethyl-2-phenoxypropionyl group, and 2-methyl-3-phenoxypropionyl group.

Examples of the 1,2,3,4-tetrahydroquinolylcarbonyl group which may have an oxo group as a substituent on the tetrahydroquinoline ring include 1,2,3,4-tetrahydroquinolylcarbonyl groups which may have 1 or 2 oxo groups as substituents on the tetrahydroquinoline ring such as a [(1,3,4,5,6,7 or 8-)1,2,3,4-tetrahydroquinolyl]carbonyl group, [2-oxo-(1,3,4,5,6,7 or 8-)1,2,3,4-tetrahydroquinolyl]carbonyl group, [4-oxo-(1,2,3,5,6,7 or 8-)1,2,3,4-tetrahydroquinolyl]carbonyl group, and [2,4-dioxo-(1,3,5,6,7 or 8-)1,2,3,4-tetrahydroquinolyl]carbonyl group.

Examples of the 1,2,3,4-tetrahydroquinolyl group which may have an oxo group as a substituent on the tetrahydroquinoline ring include 1,2,3,4-tetrahydroquinolyl groups which may have 1 or 2 oxo groups as substituents on the tetrahydroquinoline ring such as a (1,2,3,4,5,6,7 or 8-)1,2,3,4-tetrahydroquinolyl group, 2-oxo-(1,3,4,5,6,7 or 8-)1,2,3,4-tetrahydroquinolyl group, 4-oxo-(1,2,3,5,6,7 or 8-)1,2,3,4-tetrahydroquinolyl group, and 2,4-dioxo-(1,3,5,6,7 or 8-)1,2,3,4-tetrahydroquinolyl group.

Examples of the amino group which may have a lower alkoxycarbonyl group as a substituent include amino groups which may have a linear or branched chain alkoxycarbonyl group having 1 to 6 carbon atoms such as an amino group, methoxycarbonylamino group, ethoxycarbonylamino group, propoxycarbonylamino group, isopropoxycarbonylamino group, butoxycarbonylamino group, tert-butoxycarbonylamino group, pentyloxycarbonylamino group, and hexyloxycarbonylamino group.

Examples of the benzoyl group which may have 1 to 3 lower alkoxy groups as substituents on the phenyl ring include benzoyl groups which may have 1 to 3 linear or branched alkoxy groups having 1 to 6 carbon atoms as substituents on the phenyl ring such as a benzoyl group, 2-methoxybenzoyl group, 3-methoxybenzoyl group, 4-methoxybenzoyl group, 2-ethoxybenzoyl group, 3-ethoxybenzoyl group, 4-ethoxybenzoyl group, 4-isopropoxybenzoyl group, 3-butoxybenzoyl group, 4-pentyloxybenzoyl group, 4-hexyloxybenzoyl group, 3,4-dimethoxybenzoyl group, 3,4-diethoxybenzoyl group, 2,4-dimethoxybenzoyl group, 2,5-dimethoxybenzoyl group, 2,6-dimethoxybenzoyl group, and 3,4,5-trimethoxybenzoyl group.

Examples of the lower alkyl group which have 1 or 2 phenyls which may have, on the phenyl ring, 1 to 3 substituents selected from the group consisting of a lower alkoxycarbonyl group, a cyano group, a nitro group, a phenyl group, a halogen atom, a lower alkyl group which may have a halogen atom as a substituent, a lower alkoxy group, and a lower alkylthio group include, in addition to the above described phenyl lower alkyl groups, linear or branched alkyl groups which have 1 to 6 carbon atoms which may have, on the phenyl ring, 1 to 3 substituents selected from the group consisting of a linear or branched alkoxycarbonyl group having 1 to 6 carbon atoms, a cyano group, a nitro group, a phenyl group, a halogen atom, a linear or branched alkyl group having 1 to 6 carbon atoms which may have 1 to 3 halogen atoms as substituents, a linear or branched alkoxy group having 1 to 6 carbon atoms which may have 1 to 3 halogen atoms as substituents, and a linear or branched alkylthio group having 1 to 6 carbon atoms such as 1,1-diphenylmethyl, 1,1-di(4-fluorophenyl)methyl, 1-phenyl-1-(4-methoxyphenyl)methyl, 3,3-diphenylpropyl, 2,5-difluorobenzyl, 2,4-difluorobenzyl, 3,4-difluorobenzyl, 3,5-difluorobenzyl, 2,6-difluorobenzyl, 3-trifluoromethylbenzyl, 2-trifluoromethylbenzyl, 4-trifluoromethylbenzyl, 3,4-dimethoxybenzyl, 3,5-dimethoxybenzyl, 2-chlorobenzyl, 3-chlorobenzyl, 4-chlorobenzyl, 2-methylbenzyl, 3-methylbenzyl, 4-methylbenzyl, 3,4-dimethylbenzyl, 2,3-dimethylbenzyl, 2-methoxybenzyl, 3-methoxybenzyl, 4-cyanobenzyl, 2-cyanobenzyl, 3-cyanobenzyl, 4-methoxybenzyl, 2,3-dichlorobenzyl, 2,4-dichlorobenzyl, 2,5-dichlorobenzyl, 3,4-dichlorobenzyl, 2,6-dichlorobenzyl, 4-fluorobenzyl, 3-fluorobenzyl, 2-fluorobenzyl, 4-nitrobenzyl, 3-nitrobenzyl, 2-nitrobenzyl, 3-trifluoromethoxybenzyl, 4-trifluoromethoxybenzyl, 2-trifluoromethoxybenzyl, 4-methoxycarbonylbenzyl, 3-methoxycarbonylbenzyl, 4-tert-butylbenzyl, 4-ethylbenzyl, 4-isopropylbenzyl, 4-methoxy-3-chlorobenzyl, 2-(4-methoxyphenyl)ethyl, 2-(4-fluorophenyl)ethyl, 2-(4-chlorophenyl)ethyl, 2-(3-methoxyphenyl)ethyl, 2-(4-methylphenyl)ethyl, 4-phenylbenzyl, 3,3-diphenylpropyl, 3-methyl-4-nitrobenzyl, 4-(4-methoxyphenyl)butyl, 2-(4-methylphenyl)ethyl, 4-tert-butoxycarbonylbenzyl, 3-chloro-6-methoxybenzyl, 4-nitro-3-methylbenzyl, 4-tert-butyrylbenzyl, 2-(2-ethoxycarbonylphenyl)ethyl, 1-(3-propoxycarbonylphenyl)ethyl, 3-(4-pentyloxycarbonylphenyl)propyl, 4-(3-hexyloxycarbonylphenyl)butyl, 5-(3,4-dimethoxycarbonylphenyl)pentyl, 6-(3,4,5-diethoxycarbonylphenyl)hexyl, 1,1-dimethyl-2-(4-butoxycarbonylphenyl)ethyl, 2-methyl-3-(4-methoxycarbonylphenyl)propyl, 2-(2-cyanophenyl)ethyl, 1-(3-cyanophenyl)ethyl, 3-(4-cyanophenyl)propyl, 4-(2-cyanophenyl)butyl, 5-(3-cyanophenyl)pentyl, 6-(4-cyanophenyl)hexyl, 1,1-dimethyl-2-(2,4-dicyanophenyl)ethyl, 2-methyl-3-(2,4,6-tricyanophenyl)propyl, 2-(2-nitrophenyl)ethyl, 1-(3-nitrophenyl)ethyl, 3-(4-nitrophenyl)propyl, 4-(2-nitrophenyl)butyl, 5-(3-nitrophenyl)pentyl, 6-(4-nitrophenyl)hexyl, 1,1-dimethyl-2-(2,4-dinitrophenyl)ethyl, 2-methyl-3-(2,4,6-trinitrophenyl)propyl, 2-(2-phenylphenyl)ethyl, 1-(3-phenylphenyl)ethyl, 3-(4-phenylphenyl)propyl, 4-(2-phenylphenyl)butyl, 5-(3-phenylphenyl)pentyl, 6-(4-phenylphenyl)hexyl, 1,1-dimethyl-2-(2,4-diphenylphenyl)ethyl, 2-methyl-3-(2,4,6-triphenylphenyl)propyl, 2-(2-fluorophenyl)ethyl, 1-(3-bromophenyl)ethyl, 3-(4-iodophenyl)propyl, 4-(2-bromophenyl)butyl, 5-(3-chlorophenyl)pentyl, 6-(4-bromophenyl)hexyl, 1,1-dimethyl-2-(2,4-dichlorophenyl)ethyl, 2-methyl-3-(2,4,6-trifluorophenyl)propyl, 2-(2-ethylphenyl)ethyl, 1-(3-propylphenyl)ethyl, 3-(4-butylphenyl)propyl, 4-(2-pentylphenyl)butyl, 5-(3-hexylphenyl)pentyl, 6-(4-trifluoromethylphenyl)hexyl, 1,1-dimethyl-2-(2,4-dimethylphenyl)ethyl, 2-methyl-3-[2,4,6-tri(trifluoromethyl)phenyl]propyl, 2-(2-ethoxyphenyl)ethyl, 1-(3-propoxyphenyl)ethyl, 3-(4-butoxyphenyl)propyl, 4-(2-pentyloxyphenyl)butyl, 5-(3-hexyloxyphenyl)pentyl, 6-(4-trifluoromethoxyphenyl)hexyl, 1,1-dimethyl-2-(2,4-dimethoxyphenyl)ethyl, 2-methyl-3-[2,4,6-tri(trifluoromethoxy)phenyl]propyl, 2-methylthiobenzyl, 3-methylthiobenzyl, 4-methylthiobenzyl, 3,4-dimethylthiobenzyl, 2,3-dimethylthiobenzyl, 2-(2-ethylthiophenyl)ethyl, 2-(4-methylthiophenyl)ethyl, 1-(3-propylthiophenyl)ethyl, 3-(4-butylthiophenyl)propyl, 4-(2-pentylthiophenyl)butyl, 5-(3-hexylthiophenyl)pentyl, 6-(4-methylthiophenyl)hexyl, 1,1-dimethyl-2-(2,4-dimethylthiophenyl)ethyl, 2-methyl-3-[2,4,6-trimethylthiophenyl]propyl, 2-methyl-4-cyanobenzyl, 3-ethoxy-4-ethoxycarbonylbenzyl, 4-phenyl- 3-nitrobenzyl, 3-fluoro-4-methoxybenzyl, 4-trifluoromethyl-3-cyanobenzyl, 3-trifluoromethoxy-3-fluorobenzyl groups.

Examples of the phenyl group which may have, on the phenyl ring, 1 to 3 groups selected from the group consisting of a linear or branched alkoxy group having 1 to 6 carbon atoms which may have a halogen atom as a substituent and a linear or branched alkyl group having 1 to 6 carbon atoms which may have a halogen atom as a substituent include phenyl groups which may have, on the phenyl ring, 1 to 3 groups selected from the group consisting of a linear or branched alkoxy group having 1 to 6 carbon atoms which may have 1 to 3 halogen atoms as substituents and a linear or branched alkyl group having 1 to 6 carbon atoms which may have 1 to 3 halogen atoms as substituents such as phenyl, 2-methylphenyl, 3-methylphenyl, 4-methylphenyl, 2-ethylphenyl, 3-ethylphenyl, 4-ethylphenyl, 4-isopropylphenyl, 3-butylphenyl, 4-pentylphenyl, 4-hexylphenyl, 3,4-dimethylphenyl, 3,4-diethylphenyl, 2,4-dimethylphenyl, 2,5-dimethylphenyl, 2,6-dimethylphenyl, 3,4,5-trimethylphenyl, 2-methoxyphenyl, 3-methoxyphenyl, 4-methoxylphenyl, 2-ethoxyphenyl, 3-ethoxyphenyl, 4-ethoxyphenyl, 4-isopropoxyphenyl, 3-butoxyphenyl, 4-pentyloxyphenyl, 4-hexyloxyphenyl, 3,4-dimethoxyphenyl, 3,4-diethoxyphenyl, 2,4-dimethoxyphenyl, 2,5-dimethoxyphenyl, 2,6-dimethoxyphenyl, 3,4,5-trimethoxyphenyl, 2-trifluoromethoxyphenyl, 3-trifluoromethoxyphenyl, 4-trifluoromethoxyphenyl, 2-(bromomethoxy)phenyl, 3-(2-chloroethoxy)phenyl, 4-(2,3-dichloropropoxy)phenyl, 4-(4-fluorobutoxy)phenyl, 3-(5-chloropentyloxy)phenyl, 4-(5-bromohexyloxy)phenyl, 4-(5,6-dibromohexyloxy)phenyl, 3,4-di(trifluoromethoxy)phenyl, 3,4-di(4,4,4-trichlorobutoxy)phenyl, 2,4-di(3-chloro-2-methoxypropyl)phenyl, 2,5-di(3-chloropropoxy)phenyl, 2,6-di(2,2,2-trifluoroethoxy) phenyl, 3,4,5-tri(trifluoromethoxy)phenyl, 4-(2,2,2-trichloroethoxy)phenyl, 2-methyl-4-trifluoromethoxyphenyl, 3-ethyl-4-trichloromethoxyphenyl, 2-methoxy-4-trifluoromethoxyphenyl, 3-ethoxy-4-trichloromethoxyphenyl, 2-trifluoromethylphenyl, 3-trifluoromethylphenyl, 4-trifluoromethylphenyl, 2-(bromomethyl)phenyl, 3-(2-chloroethyl)phenyl, 4-(2,3-dichloropropyl)phenyl, 4-(4-fluorobutyl)phenyl, 3-(5-chloropentyl)phenyl, 4-(5-bromohexyl)phenyl, 4-(5,6-dibromohexyl)phenyl, 3,4-di(trifluoromethyl)phenyl, 3,4-di(4,4,4-trichlorobutyl)phenyl, 2,4-di(3-chloro-2-methylpropyl)phenyl, 2,5-di(3-chloropropyl)phenyl, 2,6-di(2,2,2-trifluoroethyl)phenyl, 3,4,5-tri(trifluoromethyl)phenyl, 4-(2,2,2-trichloroethyl)phenyl, 2-methyl-4-trifluoromethylphenyl, 3-ethyl-4-trichloromethylphenyl groups.

Examples of the pyrrolidinyl lower alkyl group which may have, on the pyrrolidine ring, 1 to 3 lower alkyl groups which may have a hydroxyl group as a substituent include pyrrolidinylalkyl groups which may have, on the pyrrolidine ring, 1 to 3 linear or branched alkyl groups having 1 to 6 carbon atoms which may have 1 to 3 hydroxyl groups as substituents and of which the alkyl moiety is a linear or branched alkyl group having 1 to 6 carbon atoms such as [(1,2, or 3-)pyrrolidinyl] methyl, 2-[(1,2, or 3-)pyrrolidinyl]-ethyl, 1-[(1,2, or 3-)pyrrolidinyl]ethyl, 3-[(1,2, or 3-)pyrrolidinyl]propyl, 4-[(1,2, or 3-)pyrrolidinyl]-butyl, 5-[(1,2, or 3-)pyrrolidinyl]pentyl, 6-[(1,2, or 3-)pyrrolidinyl]hexyl, 1,1-dimethyl-2-[(1,2, or 3-)pyrrolidinyl]ethyl, 2-methyl-3-[(1,2, or 3-)pyrrolidinyl] propyl, [1-methyl-(2 or 3-)pyrrolidinyl]methyl, 2-[2-ethyl-(1,3,4, or 5-)pyrrolidinyl]ethyl, 1-[3-propyl-(1,2,4, or 5-)pyrrolidinyl]ethyl, 3-[1-butyl-(2 or 3-)pyrrolidinyl]propyl, 4-[2-pentyl-(1,3,4, or 5-)pyrrolidinyl]butyl, 5-[3-hexyl-(1,2,4, or 5-)pyrrolidinyl]pentyl, 6-[1,2-dimethyl-(3,4, or 5-)pyrrolidinyl]hexyl, 1,1-dimethyl-2-[1,2,3-trimethyl-(4 or 5-)pyrrolidinyl]ethyl, 2-methyl-3-[1-ethyl-2-methyl-(3,4, or 5-)pyrrolidinyl]propyl, [1-(2-hydroxyethyl)-(2 or 3-)pyrrolidinyl] methyl, [2-hydroxymethyl-(1,3,4, or 5-)pyrrolidinyl]methyl, 2-[2-hydroxymethyl-(1,3,4, or 5-)pyrrolidinyl]ethyl, 1-[3-(3-hydroxypropyl)-(1,2,4, or 5-)pyrrolidinyl]ethyl, 3-[1-(4-hydroxybutyl)-(2 or 3-)pyrrolidinyl]propyl, 4-[2-(5-hydroxypentyl)-(1,3,4, or 5-)pyrrolidinyl]butyl, 5-[3-(6-hydroxyhexyl)-(1,2,4, or 5-)pyrrolidinyl]pentyl, 6-[1,2-dihydroxymethyl-(3,4, or 5-)pyrrolidinyl]hexyl, 1,1-dimethyl-2-[1,2,3-trihydroxymethyl-(4 or 5-)pyrrolidinyl] ethyl, 2-methyl-3-[2-(1,2-hydroxyethyl)-(1,3,4, or 5-)pyrrolidinyl]propyl, [2-(2,3,4-trihydroxybutyl)-(1,3,4, or 5-)pyrrolidinyl]methyl groups.

Examples of the amino substituted lower alkyl group which may have a substituent selected from the group consisting of a phenyl group and a lower alkyl group include linear or branched alkyl groups having 1 to 6 carbon atoms substituted with an amino group which may have 1 or 2 substituents selected from the group consisting of a phenyl group and a linear or branched alkyl group having 1 to 6 carbon atoms such as aminomethyl, 2-aminomethyl, 1-aminoethyl, 3-aminopropyl, 4-aminobutyl, 5-aminopentyl, 6-aminohexyl, 1,1-dimethyl-2-aminoethyl, N,N-diethyl-2-aminoethyl, 2-methyl-3-aminopropyl, methylaminomethyl, 1-ethylaminoethyl, 2-propylaminoethyl, 3-isopropylaminopropyl, 4-butylaminobutyl, 5-pentylaminopentyl, 6-hexylaminohexyl, dimethylaminomethyl, 2-diisopropylaminoethyl, (N-ethyl-N-propylamino)methyl, 2-(N-methyl-N-hexylamino)ethyl, phenylaminomethyl, 1-phenylaminoethyl, 2-phenylaminoethyl, 3-phenylaminopropyl, 4-phenylaminobutyl, 5-phenylaminopentyl, 6-phenylaminohexyl, N-methyl-N-phenylaminomethyl, 2-(N-ethyl-N-phenylamino)ethyl, (N-ethyl-N-phenylamino) methyl, 2-(N-methyl-N-phenylamino)ethyl groups.

Examples of the tetrahydrofuryl lower alkyl group which may have a hydroxyl group as a substituent on the lower alkyl group include tetrahydrofurylalkyl groups which may have a hydroxyl group as a substituent on the lower alkyl group and of which the alkyl moiety is a linear or branched alkyl group having 1 to 6 carbon atoms such as [(2 or 3-)tetrahydrofuryl] methyl, 2-[(2 or 3-)tetrahydrofuryl]ethyl, 1-[(2 or 3-)tetrahydrofuryl]ethyl, 3-[(2 or 3-)tetrahydrotetrahydrofuryl]propyl, 4-[(2 or 3-)tetrahydrofuryl]butyl, 5-[(2 or 3-)tetrahydrofuryl] pentyl, 6-[(2 or 3-)tetrahydrofuryl]hexyl, 1,1-dimethyl-2-[(2 or 3-)tetrahydrofuryl]ethyl, 2-methyl-3-[(2 or 3-)tetrahydrofuryl]propyl, 1-hydroxy-1-[(2 or 3-)tetrahydrofuryl]methyl, 2-hydroxy-2-[(2 or 3-)tetrahydrofuryl]ethyl, 2-hydroxy-1-[(2 or 3-)tetrahydrofuryl]ethyl, 3-hydroxy-3-[(2 or 3-)tetrahydrotetrahydrofuryl]propyl, 4-hydroxy-4-[(2 or 3-)tetrahydrofuryl]butyl, 5-hydroxy-5-[(2 or 3-)tetrahydrofuryl] pentyl, 6-hydroxy-6-[(2 or 3-)tetrahydrofuryl]hexyl, 2-hydroxy-1,1-dimethyl-2-[(2 or 3-)tetrahydrofuryl]ethyl, 3-hydroxy-2-methyl-3-[(2 or 3-)tetrahydrofuryl]propyl groups.

Examples of the phenoxy lower alkyl group which may have, on the phenyl ring, 1 to 3 substituents selected from the group consisting of a lower alkyl group and a nitro group include, in addition to the above described phenoxy lower alkyl groups, phenoxyalkyl groups which may have, on the phenyl ring, 1 to 3 substituents selected from the group consisting of a linear or branched alkyl group having 1 to 6 carbon atoms and a nitro group and of which the alkyl moiety is a linear or branched alkyl group having 1 to 6 carbon atoms such as 2-methylphenoxymethyl, 3-methylphenoxymethyl, 4-methylphenoxymethyl, 3,4-dimethylphenoxymethyl, 2,3-dimethylphenoxymethyl, 3,4,5-trimethylphenoxymethyl, 2-(2-ethylphenoxy)ethyl, 2-(3-methylphenoxy)ethyl, 2-(4-methylphenoxy)ethyl, 1-(3-propylphenoxy)ethyl, 3-(4-butylphenoxy)propyl, 4-(2-pentylphenoxy)butyl, 5-(3-hexylphenoxy)pentyl, 6-(4-methylphenoxy)hexyl, 1,1-dimethyl-2-(2,4-dimethylphenoxy)ethyl, 2-methyl-3-(2,4,6-trimethylphenoxy)propyl, 2-(4-nitro-3-methylphenoxy)ethyl, 4-nitrophenoxymethyl, 3-nitrophenoxymethyl, 2-nitrophenoxymethyl, 2-(2-nitrophenoxy)ethyl, 2-(4-nitrophenoxy)ethyl, 1-(3-nitrophenoxy)ethyl, 3-(4-nitrophenoxy)propyl, 4-(2-nitrophenoxy)butyl, 5-(3-nitrophenoxy)pentyl, 6-(4-nitrophenoxy)hexyl, 1,1-dimethyl-2-(2,4-dinitrophenoxy)ethyl, 2-methyl-3-(2,4,6-trinitrophenoxy)propyl.

Examples of the phenyl lower alkanoyl group include phenylalkanoyl groups of which the alkanoyl moiety is a linear or branched alkanoyl group having 2 to 6 carbon atoms such as a 2-phenylacetyl group, 3-phenylpropionyl group, 2-phenylpropionyl group, 4-phenylbutyryl group, 5-phenylpentanoyl group, 6-phenylhexanoyl group, 2,2-dimethyl-3-phenylpropionyl group, and 2-methyl-3-phenylpropionyl group.

Examples of the 5- to 7-membered saturated heterocyclic group formed by mutually binding $R^{20}$ and $R^{21}$, $R^{22}$ and $R^{23}$, $R^{26}$ and $R^{27}$, $R^{29}$ and $R^{30}$ or $R^{32}$ and $R^{33}$ together with the nitrogen atoms bound to them, through or not through a nitrogen atom, a oxygen atom or a sulfur atom, include a pyrrolidinyl group, piperidinyl group, piperazinyl group, morpholino group, thiomorpholino group, and homopiperazinyl group.

Examples of the phenoxy lower alkyl group which may have a lower alkyl group as a substituent on the phenyl ring include, in addition to the above described phenoxy lower alkyl groups, phenoxyalkyl groups which may have, on the phenyl ring, 1 to 3 linear or branched alkyls having 1 to 6 carbon atoms as substituents and of which the alkyl moiety is a linear or branched alkyl group having 1 to 6 carbon atoms such as 2-methylphenoxymethyl, 3-methylphenoxymethyl, 4-methylphenoxymethyl, 3,4-dimethylphenoxymethyl, 2,3-dimethylphenoxymethyl, 3,4,5-trimethylphenoxymethyl, 2-(2-ethylphenoxy)ethyl, 2-(4-methylphenoxy)ethyl, 1-(3-propylphenoxy)ethyl, 3-(4-butylphenoxy)propyl, 4-(2-pentylphenoxy)butyl, 5-(3-hexylphenoxy)pentyl, 6-(4-methylphenoxy)hexyl, 1,1-dimethyl-2-(2,4-dimethylphenoxy)ethyl, 2-methyl-3-(2,4,6-trimethylphenoxy)propyl groups.

Methods for producing the compound of the present invention will be described below.

The compound of the present invention of the general formula (1) which have various Ys is produced, for example, as shown by the following reaction formulas 1 to 4.

[Reaction formula 1]

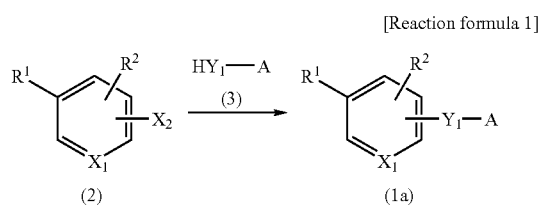

In the formula, $R^1$, $R^2$, $X_1$ and A are the same as described before, $Y_1$ represents an —O— group, an —S— group or an —NH group, and $X_2$ represents a halogen atom.

The reaction between the compound (2) and the compound (3) is generally carried out in an appropriate solvent or without a solvent, and in the presence or absence of a basic compound.

Examples of the inert solvent used include aromatic hydrocarbons such as benzene, toluene, and xylene, ethers such as diethyl ether, tetrahydrofuran, dioxane, monoglyme, and diglyme, halogenated hydrocarbons such as dichloromethane, dichloroethane, chloroform, and carbon tetrachloride, lower alcohols such as methanol, ethanol, isopropanol, butanol, tert-butanol, and ethylene glycol, fatty acids such as acetic acid, esters such as ethyl acetate and methyl acetate, ketones such as acetone and methyl ethyl ketone, acetonitrile, pyridine, dimethylsulfoxide, N,N-dimethylformamide, N-methylpyrrolidone, and hexamethylphosphoric acid triamide, and a mixture thereof.

Examples of the basic compound include carbonates such as sodium carbonate, potassium carbonate, sodium bicarbonate, potassium bicarbonate, and cesium carbonate, metal hydroxides such as sodium hydroxide, potassium hydroxide, and calcium hydroxide, sodium hydride, potassium hydride, potassium, sodium, sodium amide, metal alcoholates such as sodium methylate, sodium ethylate, and sodium n-butoxide, and organic bases such as pyridine, imidazole, N-ethyldiisopropylamine, dimethylaminopyridine, triethylamine, trimethylamine, dimethylaniline, N-methylmorpholine, 1,5-diazabicyclo[4.3.0]nonene-5 (DBN), 1,8-diazabicyclo[5.4.0]undecene-7 (DBU), and 1,4-diazabicyclo[2.2.2]octane (DABCO), and a mixture thereof.

When the reaction is carried out in the presence of a basic compound, the basic compound is used in an amount typically equimolar to the compound (2), and preferably 1 to 10 times of the compound (2) on a molar basis.

The compound (3) is used in an amount typically at least equimolar to the compound (2), and preferably 1 to 10 times of the compound (2) on a molar basis.

The reaction is carried out typically at −30 to 200° C., and preferably at about −30 to 150° C., and is generally completed in about 5 minutes to 80 hours.

To this reaction system, an alkali metal halide such as sodium iodide or potassium iodide may be added, and a phase-transfer catalyst may be added.

Examples of the phase-transfer catalyst include quaternary ammonium salts substituted with a group selected from the group consisting of a linear or branched alkyl group having 1 to 18 carbon atoms, a phenyl lower alkyl group which the alkyl moiety is a linear or branched alkyl group having 1 to 6 carbon atoms and a phenyl group, such as tetrabutylammonium chloride, tetrabutylammonium bromide, tetrabutylammonium fluoride, tetrabutylammonium iodide, tetrabutylammonium hydroxide, tetrabutylammonium hydrogensulfite, tributylmethylammonium chloride, tributylbenzylammonium chloride, tetrapentylammonium chloride, tetrapentylammonium bromide, tetrahexylammonium chloride, benzyldimethyloctylammonium chloride, methyltrihexylammonium chloride, benzyldimethyloctadecanylammonium chloride, methyltridecanylammonium chloride, benzyltripropylammonium chloride, benzyltriethylammonium chloride, phenyltriethylammonium chloride, tetraethylammonium chloride, tetramethylammonium chloride; phosphonium salts substituted with a linear or branched having 1 to 18 carbon atoms such as tetrabutylphosphonium chloride; and pyridinium salts substituted with a linear or branched alkyl group having 1 to 18 carbon atoms such as 1-dodecanylpyridinium chloride. These phase-transfer catalysts are used singly or in a combination of two or more.

Typically the phase-transfer catalyst is used in an amount of 0.1 to 1 times of the compound (2), and preferably 0.1 to 0.5 times of the compound (2).

The compound (1a), wherein $Y_1$ represents an —NH group, may also be produced by reacting the compound (2) with the compound (3) in the presence of an acid in place of a base. Examples of the acid used here include mineral acids such as hydrochloric acid, sulfuric acid, and hydrobromic acid, and organic acids such as acetic acid, trifluoroacetic acid, and p-toluenesulfonic acid. These acids are used singly or as a mixture of two or more.

The compound (1), wherein Y represents an —N($R^5$)— group, and $R^5$ is $R^5$ other than a hydrogen atom, may be produced from the corresponding compound (1) wherein Y represents an —NH— group, as shown in the following reaction formula 2.

[Reaction formula 2]

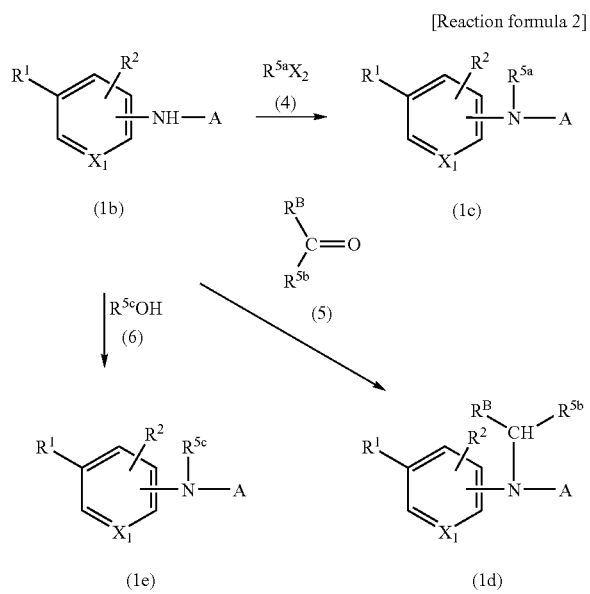

wherein $R^1$, $R^2$, $X_1$, A and $X_2$ are the same as described above, $R^{5a}$ represents a lower alkyl group, phenyl lower alkyl group or cycloalkyl group, $R^{5b}$ represents a hydrogen atom, lower alkyl group, phenyl group or phenyl lower alkyl group, $R^{5c}$ represents a lower alkanoyl group or benzoyl group. $R^B$ represents a hydrogen atom or lower alkyl group, and $R^{5b}$ and $R^B$, together with carbon atoms bound to these groups, may form a cycloalkyl ring by binding each other, provided that the alkyl moiety in the —CHR$^B$R$^{5b}$ group of the compound (1d) has 1 to 6 carbon atoms.

The reaction of the compound (1b) with the compound (4) is carried out under the similar condition as that for the reaction of the compound (2) with the compound (3) as shown by the above described reaction formula 1.

The reaction of the compound (1b) with the compound (5) is carried out, for example, in the presence of a reducing agent without a solvent or with an appropriate solvent. Hereinafter, this method is called "method A".

Examples of the solvent used here include water, lower alcohols such as, methanol, ethanol, isopropanol, butanol, tert-butanol, and ethylene glycol, acetonitrile, fatty acids such as formic acid, and acetic acid, ethers such as diethyl ether, tetrahydrofuran, dioxane, monoglyme, and diglyme, aromatic hydrocarbons such as benzene, toluene, and xylene, and halogenated hydrocarbons such as dichloromethane, dichloroethane, chloroform, and carbon tetrachloride, and a mixture thereof.

Examples of the reducing agent include fatty acids and alkali metal salts thereof such as formic acid, sodium formate, and sodium acetate, hydride reducing agents such as sodium borohydride, sodium cyanoborohydride, sodium triacetyloxyborohydride, and aluminum lithium hydride, or a mixture of these hydride reducing agents, and catalytic hydrogen reducing agents such as palladium black, palladium-carbon, platinum oxide, platinum black, and Raney nickel.

In using a fatty acid or an alkali metal salt thereof such as formic acid, sodium formate, or sodium acetate as a reducing agent, the appropriate reaction temperature is typically from room temperature to about 200° C., and preferably about 50 to about 150° C., and the reaction is completed generally in about 10 minutes to 10 hours. It is preferable to use a fatty acid or an alkali metal salt thereof in a large excess amount with respect to the compound (1b).

In using a hydride reducing agent, the appropriate reaction temperature is typically –80 to 100° C., and preferably –80 to 70° C., and the reaction is completed in general in 30 minutes to 60 hours. The hydride reducing agent is used in an amount typically 1 to 20 times of the compound (1b), and preferably 1 to 6 times of the compound (1b) on a molar basis. Especially in using aluminum lithium hydride as a hydride reducing agent, it is preferable to employ an ether such as diethyl ether, tetrahydrofuran, dioxane, monoglyme, or diglyme, or an aromatic hydrocarbon such as benzene, toluene, or xylene. To the reaction system, an amine such as trimethylamine, triethylamine, and N-ethyldiisopropylamine, or molecular sieves such as Molecular Sieves 3A (MS-3A) or Molecular Sieves 4A (MS-4A) may be added.

In using a catalytic hydrogen reducing agent, the reaction is preferably carried out in a hydrogen atmosphere typically at a normal pressure to about 20 atm, and preferably at a normal atmosphere to about 10 atm, or in the presence of a hydrogen donor such as formic acid, ammonium formate, cyclohexene, or hydrazine hydrate, at a temperature of typically –30 to 100° C., and preferably 0 to 60° C. The above described reaction is in general completed in about 1 to 12 hours. The catalytic hydrogen reducing agent is used typically in an amount of about 0.1% to 40% by weight, and about 1 to 20% by weight based on the compound (1b).

In the reaction of the compound (1b) with the compound (5), the compound (5) is typically used in an amount at least equimolar to the compound (1b), and preferably used in an equal amount to a large excess amount of compound (5) on a molar basis.

When the compound (5), wherein $R^B$ and $R^{5b}$ are mutually bound together with the carbon atoms which bind to these groups to form a cycloalkyl ring, is used as a starting material, and the hydride reducing agent is used to carry out the reaction, cycloalkyloxytrialkylsilane such as [(1-ethoxycyclopropyl)oxy]trimethylsilane may be used in place of the compound (5) as the starting material to produce the above described compound (5) in the reaction system.

The compound (1d) may be produced by reacting the compound (1b) with compound (5) under the reaction condition similar to the reaction condition of the compound (1f) with hydroxylamine of the later described reaction formula 3, and then reducing the resulting compound represented by the general formula:

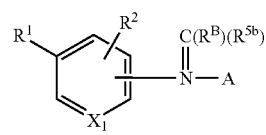

wherein $R^1$, $R^2$, $X_1$, $R^B$ and $R^{5b}$ are the same as described above.

A reaction condition similar to that of the method A may be applied to this reducing reaction.

The reaction of the compound (1b) with the compound (6) is carried out by a method for reacting the compound (1b) with carboxylic acid of the compound (6) in a typical reaction for producing an amide bond. Known reactions for producing an amide bond may be applied to this reaction for producing an amide bond. Specific methods thereof include: (a) a mixed acid anhydride method, specifically, a method of reacting an alkylhalocarboxylic acid with the carboxylic acid (6) to prepare a mixed acid anhydride, and then reacting the amine (1b) with the mixed acid anhydride; (b) an active ester method, specifically, a method of preparing, from the carboxylic acid (6), an active ester such as a phenyl ester, p-nitrophenyl ester, N-hydroxysuccinimide ester, or 1-hydroxybenzotriazole ester, or an active amide with benzoxazoline-2-thione, and then reacting the active ester or amide with the amine (1b); (c) a carbodiimide method, specifically, a method of condensation reaction of wherein the carboxylic acid (6) with the amine (1b) in the presence of an activator such as dicyclohexylcarbodiimide, 1-(3-dimethylaminopropyl)-3-ethylcarbodiimide (WSC), or carbonyldiimidazole; (d) other methods, for example, a method of preparing carboxylic anhydride from the carboxylic acid (6) by the action of a dehydrator such as acetic anhydride, and then reacting the carboxylic anhydride with the amine (1b), a method of reacting an ester of the carboxylic acid (6) with a lower alcohol with the amine (1b) at a high pressure and a high temperature, and a method of reacting an acid halide of the carboxylic acid (6), that is, carboxylic acid halide, with the amine (1b).

The mixed acid anhydride used in the mixed anhydride method (a) described above, may be obtained by a typical Schotten-Baumann reaction, and the compound of the present invention of the general formula (1e) can be produced by reacting the amine (2) with the mixed acid anhydride without isolation.

The Schotten-Baumann reaction described above is carried out in the presence of a basic compound.

The basic compounds used include compounds commonly used in Schotten-Baumann reaction, for example, organic bases such as triethylamine, trimethylamine, pyridine, dimethylaniline, N-ethyldiisopropylamine, dimethylaminopyridine, N-methylmorpholine, 1,5-diazabicyclo[4.3.0]nonene-5 (DBN), 1,8-diazabicyclo[5.4.0]undecene-7, and 1,4-diazabicyclo[2.2.2]octane (DABCO), and inorganic bases such as carbonates such as sodium carbonate, potassium carbonate, sodium bicarbonate, and potassium bicarbonate, metal hydroxides such as sodium hydroxide, potassium hydroxide, and calcium hydroxide, potassium hydride, sodium hydride, potassium, sodium, sodium amide, and metal alcoholates such as sodium methylate and sodium ethylate. These basic compounds are used singly or in a combination of two or more. The reaction is carried out at typically about −20 to 100° C., and preferably about 0 to 50° C., and the reaction time is about 5 minutes to 10 hours, and preferably about 5 minutes to 2 hours.

The resulting mixed acid anhydride is reacted with the amine (1b) at typically about −20 to 150° C., preferably about 10 to 50° C., and the reaction time is about 5 minutes to 10 hours, and preferably about 5 minutes to 5 hours.

The mixed acid anhydride method is, in general, carried out in a solvent. Any of the solvent conventionally used for the mixed acid anhydride method may be used. Specific examples of the solvent include halogenated hydrocarbons such as chloroform, dichloromethane, dichloroethane, and carbon, tetrachloride, aromatic hydrocarbons such as benzene, toluene and xylene, ethers such as diethyl ether, diisopropyl ether, tetrahydrofuran, and dimethoxyethane, esters such as methyl acetate, ethyl acetate, and isopropyl acetate, and aprotic polar solvents such as N,N-dimethylformamide, dimethylsulfoxide, and hexamethylphosphoric acid triamide, and a mixture thereof.

Examples of the alkylhalocarboxylic acid used in the mixed acid anhydride method include methyl chloroformate, methyl bromoformate, ethyl chlorformate, ethyl bromoformate, and isobutyl chloroformate.

In the mixed acid anhydride method, it is typically preferable to use the carboxylic acid (6), alkylhalocarboxylic acid and the amine (1b) equimolar to each other. However, each of alkyl halocarboxylic acid and the carboxylic acid (6) may be used 1 to 1.5 times of the amine (1b) on a molar basis, respectively.

In the above described method (c) of condensation reaction in the presence of an activator, the reaction is carried out in an appropriate solvent in the presence or absence of a basic compound. Any of the solvents and basic compounds used in the reaction in the other methods (d) described above of reacting carboxylic acid halide with the amine may be used for this reaction. It is appropriate to use the activator in an amount typically at least equimolar to the compound (1b), and preferably 1 to 5 times of the compound (1b) on a molar basis. When WSC is used as an activator, the reaction may be carried out advantageously by adding 1-hydroxybenzotriazole and/or an acid such as hydrochloric acid. This reaction is carried out at typically about −20 to 180° C., and preferably about 0 to 150° C., and is completed typically in about 5 minutes to 90 hours.

In the other method (d) described above, wherein the amine (1b) is reacted with carboxylic acid halide, the reaction is carried out in an appropriate solvent in the presence of a basic compound. As such a basic compound, known basic compounds may be widely used, and, for example, any of compounds used for the Shotten-Baumann reaction described above may be used. Examples of the solvent include, in addition to the solvents used in the mixed acid anhydride method described above, alcohols such as methanol, ethanol, isopropanol, propanol, butanol, 3-methoxy-1-butanol, ethyl cellosolve, and methyl cellosolve, acetonitrile, pyridine, acetone, and water. The ratio of the amine (1b) to the carboxylic acid halide in the reaction is not specified and may be appropriately selected in a wide range. Typically, the former may be used in an amount at least about equimolar to the latter, and preferably about 1 to 5 times of the latter on a molar basis. This reaction is carried out at typically about −20 to 180° C., and preferably about 0 to 150° C., and is completed typically in 5 minutes to 50 hours.

Further, the reaction for producing an amide bond shown in the above described reaction formula 2 may be carried out by reacting the carboxylic acid (6) and the amine (1b) in the presence of a condensation agent of a phosphorus compound such as triphenylphosphine, diphenylphosphinyl chloride, phenyl-N-phenylphosphoramide chloridate, diethyl chlorophosphate, diethyl cyanophosphate, diphenylphosphoric acid azide, or bis(2-oxo-3-oxazolidinyl)phosphinic chloride. The condensation agent described above is used singly or in a combination of two or more.

The above described reaction is carried out, in the presence of the solvent and the basic compound which are used in the method for reacting the carboxylic acid halide with the amine (1b) described above, at typically about −20 to 150° C., and preferably about 0 to 100° C., and is completed typically in 5 minutes to about 30 hours. The condensation agent and the carboxylic acid (6) may be used respectively in an amount at least about equimolar to the amine (1b), and preferably about 1 to 2 times of the amine (1b) on a molar basis.

The compound (1), wherein Y represents a —CH(OH)— or —C(=N—OH) group, is produced from the corresponding compound wherein Y represents a —CO— group, as shown in the reaction formula 3.

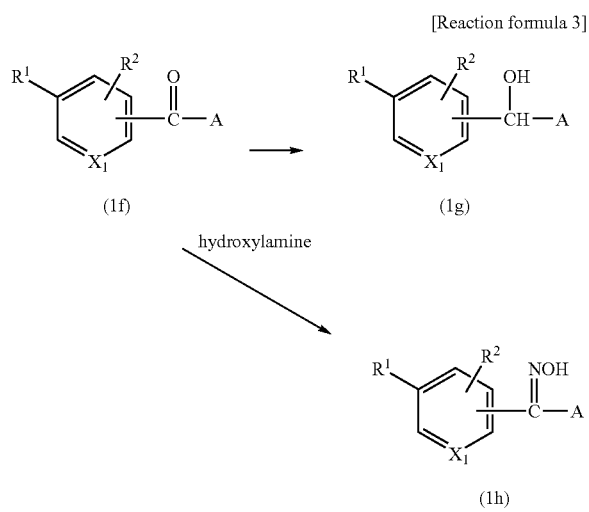

wherein $R^1$, $R^2$, $X_1$ and A are the same as described above.

The compound (1g) is produced by reducing the compound (1f).

In the reducing reaction described above, a reducing method employing a hydride reducing agent is favorably used. Examples of the reducing agent used include aluminum lithium hydride, sodium borohydride, borane, diborane, and lithium borohydride-trimethoxyborane. These reducing agents are used singly or in a mixture of two or more. The reducing agent may be used in an amount typically at least equimolar to the compound (1f), and preferably 1 to 15 times of the compound (1f) on a molar basis. This reducing reaction is typically carried out in an appropriate solvent, for example, water, a lower alcohol such as methanol, ethanol, or isopropanol, an ether such as tetrahydrofuran, diethyl ether, diisopropyl ether, or diglyme, or a halogenated hydrocarbon such as dichloromethane, chloroform, or carbon tetrachloride, or a mixture thereof, at about −60 to 150° C., preferably from about −30 to 100° C., in general for about 10 minutes to 40 hours. In the case where aluminum lithium hydride or borane is used as the reducing agent, it is preferable to use an anhydrous solvent of tetrahydrofuran, diethyl ether, diisopropyl ether, diglyme, or the like.

The compound (1h) is produced by reacting the compound (1f) and hydroxylamine in an appropriate inert solvent in the presence or absence of a basic compound.

Examples of the basic compound used in this reaction include inorganic basic compounds such as sodium hydroxide, potassium hydroxide, calcium hydroxide, sodium carbonate, and potassium carbonate, fatty acid alkali metal salts such as sodium acetate, organic bases such as piperidine, piperidinium acetate, triethylamine, trimethylamine, pyridine, dimethylaniline, N-ethyldiisopropylamine, dimethylaminopyridine, N-methylmorpholine, 1,5-diazabicyclo[4.3.0]nonene-5 (DBN), 1,8-diazabicyclo[5.4.0]undecene-7 (DBU), and 1,4-diazabicyclo[2.2.2]octane (DABCO). These basic compounds may be used singly or in a mixture of two or more.

Any of inert solvents which do not have adverse effects on the reaction may be used. Examples thereof include water, aromatic hydrocarbons such as benzene, toluene, and xylene, ethers such as diethyl ether, tetrahydrofuran, dioxane, monoglyme, and diglyme, halogenated hydrocarbons such as dichloromethane, dichloroethane, chloroform, and carbon tetrachloride, lower alcohols such as methanol, ethanol, isopropanol, butanol, tert-butanol, and ethylene glycol, fatty acids such as acetic acid, esters such as ethyl acetate and methyl acetate, ketones such as acetone and methyl ethyl ketone, acetonitrile, pyridine, dimethyl sulfoxide, N,N-dimethylformamide, and hexamethyl phosphate triamide, and a mixture thereof.

Hydroxylamine is used in an amount typically at least equimolar to the compound (1f), and preferably 1 to 5 times of the compound (1f) on a molar basis. The reaction temperature is typically at room temperature to 200° C., and preferably about 50 to 150° C., and the reaction is in general completed in about 5 minutes to 30 hours.

The compound (1), wherein Y represents an —S(O)n group (n=1 or 2), is produced from the corresponding compound wherein Y represents an —S— group, as shown in the reaction formula 4.

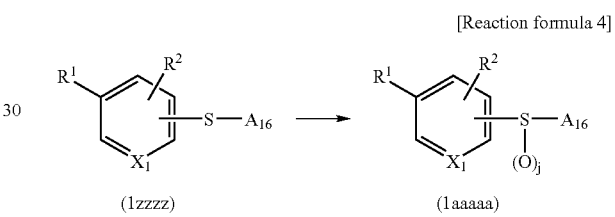

wherein $R^1$, $R^2$, $X_1$ and A are the same as described above, $A_{16}$ represents a -A group or a -$A_{10}$-$T_2$-COOR$^{59a}$ group, $T_2$ represents an —N($R^{17}$)—$B_3$— group, a —$B^{19}$—N($R^{18}$)— group, a —$B_4$— group, a -Q-$B_5$— group, a —$B_6$—N—($R^{19}$)—$B_7$— group, a —CO—$B_{10}$— group, a —CH(OH)—$B_{11}$— group, a —$B_{23a}$—CO— group, or a direct bond, wherein $R^{17}$, $B_3$, $B_{19}$, $R^{18}$, $B_4$, $B_5$, $B_6$, $R^{19}$, $B_7$, $B_{10}$ and $B_{11}$ are the same as described above, $A^{10}$ represents a group of the formula:

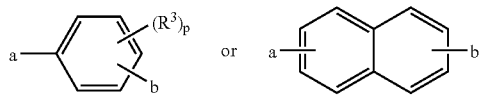

wherein $R^3$ and p are the same as described above, provided that the a is bound to a —S group or a —S(O)j group, and the b is bound to -$T_2$, $R^{59a}$ is a hydrogen atom or a lower alkyl group, and j is 1 or 2.

The reaction for converting the compound (1zzzz) into the compound (1aaaaa) is carried out in an appropriate solvent and in the presence of an oxidizing agent.

Examples of the solvent include water, fatty acids such as formic acid, acetic acid, and trifluoroacetic acid, alcohols such as methanol and ethanol, and halogenated hydrocarbons such as chloroform and dichloromethane, and a mixture thereof.

Examples of the oxidizing agent include peracids such as performic acid, peracetic acid, pertrifluoroacetic acid, perbenzoic acid, m-chloroperbenzoic acid, and o-carboxyperbenzoic acid, hydrogen peroxide, sodium metaperiodate, dichromic acid, dichromates such as sodium dichromate and potassium dichromate, permanganic acid, permanganates such as sodium permanganate and potassium permanganate, and lead salts such as lead tetraacetate. These oxidizing agents are used singly or in a mixture of two or more.

The oxidizing agent is appropriately used in an amount typically at least equimolar to the compound (1zzzz), and preferably 1 to 2 times of the compound (1zzzz) on a molar basis. In the oxidizing reaction which converts a sulfur atom into a sulfonyl group (j=2), it is appropriate to use the oxidizing agent in an amount typically at least two times of the compound (1zzzz), and preferably 2 to 4 times of the compound (1zzzz) on a molar basis.

The above described reaction is carried out at typically −10 to 150° C., and preferably about −10 to 100° C. and is, in general, completed in about 1 to 100 hours.

The compound of the present invention, which has the general formula (1) with various As, is produced, for example, as shown in the following reaction formulas 5 to 36.

The compound (1), wherein A represents a group of the formula:

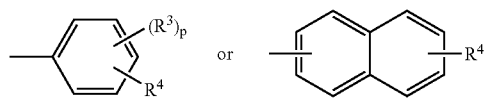

wherein $R^4$ represents an imidazolyl lower alkyl group, a 1,2,4-triazolyl lower alkyl group, a 1,2,3-triazolyl lower alkyl group, a 1,2,5-triazolyl lower alkyl group, a pyrazolyl lower alkyl group, a pyrimidinyl lower alkyl group which may have an oxo group as a substituent on the pyrimidine ring, a 1,2,4-oxadiazolyl lower alkyl group which may have an lower alkyl group as a substituent on the 1,2,4-oxadiazole ring, a thiazolidinyl lower alkyl group which may have an oxo group as a substituent on the thiazolidine ring, or a -(T)$_l$-NR$^{14}$R$^{15}$ group, wherein T is a lower alkylene group and l is 1, is produced by reacting the compound (7) with the compound (8) as shown in the reaction formula 5.

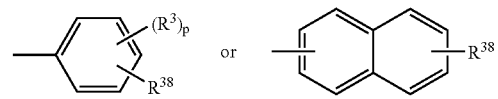

wherein $R^3$ and p are the same as described above, $R^{38}$ represents a —B$_{21}$—R$^{4a}$ group, B$_{21}$ is the same as described above, R$^{4a}$ represents an imidazolyl group, a 1,2,4-triazolyl group, a 1,2,3-triazolyl group, a 1,2,5-triazolyl group, a pyrazolyl group, a pyrimidinyl group which has an oxo group as a substituent on the pyrimidine ring, a 1,2,4-oxadiazolyl group which may have as a lower alkyl group as a substituent on the 1,2,4-oxadiazole ring, a thiazolidinyl group which may have an oxo group as a substituent on the thiazolidine ring, or an —NR$^{14}$R$^{15}$ group, and R$^{14}$ and R$^{15}$ are the same as described above.

The reaction of the compound (7) with the compound (8) is carried out under the reaction condition similar to that of the reaction of the compound (2) with the compound (3) of the above described reaction formula 1.

The compound (1), wherein A represents a group of the formula:

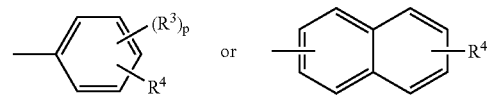

wherein $R^4$ is an imidazolyl lower alkyl group, a 1,2,4-triazolyl lower alkyl group, a 1,2,3-triazolyl lower alkyl group, a 1,2,5-triazolyl lower alkyl group, a pyrazolyl lower alkyl group, a pyrimidinyl lower alkyl group which has an oxo group as a substituent on the pyrimidine ring, a 1,2,4-oxadiazolyl lower alkyl group which has a lower alkyl group as a substituent on the 1,2,4-oxadiazole ring, a thiazolidinyl lower alkyl group which has an oxo group as a substituent on the thiazolidin ring, or a (T)$_l$-NR$^{14}$R$^{15}$ group, wherein T is a lower alkylene group and l is 1, is also produced by reacting the compound (8) with the compound (9) as shown in the reaction formula 6.

[Reaction formula 5]

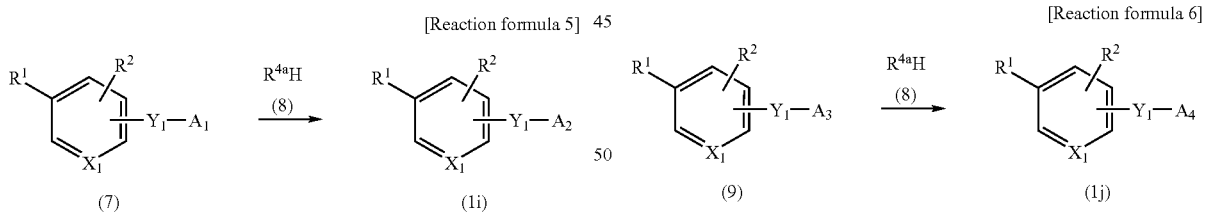

wherein $R^1$, $R^2$ $Y_1$ and $X_1$ are the same as described above, $A_1$ represents a group of the formula:

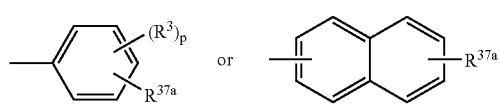

wherein $R^3$ and p are the same as described above, $R^{37a}$ represents a —B$_{21}$—X$_2$ group, B$_{21}$ represents a lower alkylene group, and X$_2$ is the same as described above, and A$_2$ represents a group of the formula:

[Reaction formula 6]

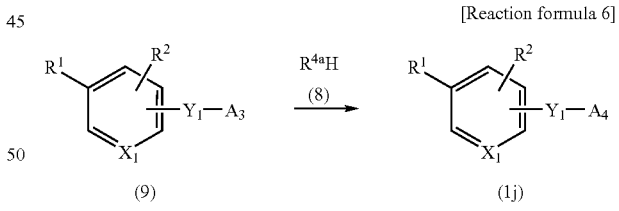

wherein $R^1$, $R^2$, $X_1$ and $Y_1$ and $R^{4a}$ are the same as described above, $A_3$ represents a group of the formula:

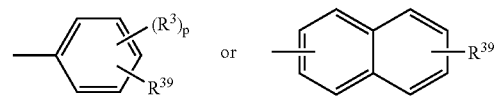

wherein $R^3$ and p are the same as described above, $R^{39}$ represents a (B$_{21}$)$_f$COR$^A$ group, B$_{21}$ is the same as described above, R$^A$ represents a hydrogen atom or a lower alkyl group, and f represents 0 or 1, and A$_4$ represents a group of the formula:

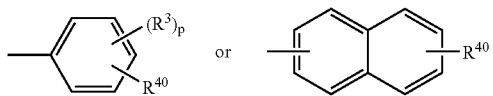

wherein $R^3$ and p are the same as described above, $R^{40}$ represents a —$(B_{21})_f$CHR$^4$R$^{4a}$ group, and $B_{21}$, $R^4$, f and $R^{4a}$ are the same as described above, provided that the alkyl moiety of the —$(B_{21})_f$CHR$^4$R$^{4a}$ group has not more than 6 carbon atoms.

The reaction of the compound (9) with the compound (8) is carried out under the same condition as in the reaction of the compound (1b) with the compound (5) of the above described reaction formula 2.

The compound (1), wherein A represents a group of the formula:

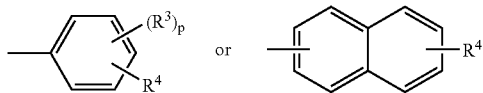

wherein $R^4$ represents a 3,5-dioxoisooxazolidinyl lower alkylidene group which may have an oxo group as a substituent on the 3,5-dioxoisooxazolidine ring, is produced by reacting the compound (11) with the compound (10) as shown in the reaction formula 7.

[Reaction formula 7]

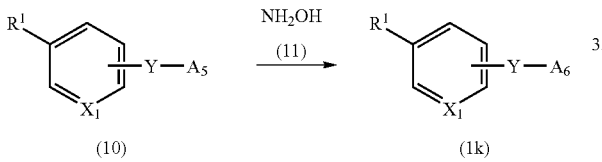

wherein $R^1$, $R^2$, $X_1$ and Y are the same as described above, $A^5$ represents a group of the formula:

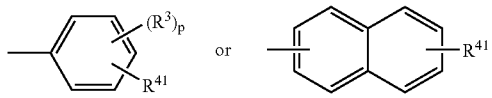

wherein $R^3$ and p are the same as described above, $R^{41}$ represents a —$B_{22}$(CO$_2$R$^4$)(CO$_2$R$^{44}$) group, $B_{22}$ represents a lower alkylidene group, and $R^{43}$ and $R^{44}$ represent a lower alkyl group, and $A^6$ represents a group of the formula:

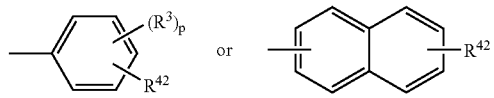

wherein $R^3$ and p are the same as described above, and $R^{42}$ represents

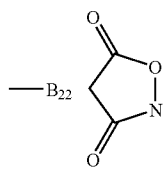

wherein $B_{22}$ is the same as described above.

The reaction of the compound (10) with the compound (11) is carried out under the same condition as that of the reaction which converts the compound (1f) into the compound (1h) of the reaction formula 3.

The compound (1), wherein A represents a group of the formula:

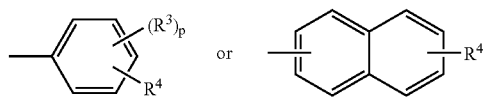

wherein $R^4$ represents a group of the formula:

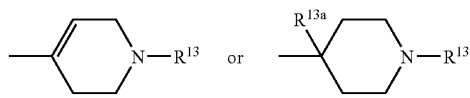

is produced from the compound (13), as shown in the reaction formula 8.

[Reaction formula 8]

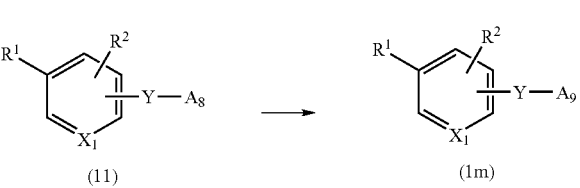

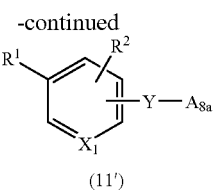

(11')

wherein $R^1$, $R^2$, $X_1$, Y and $R^{13}$ are the same as described above,
$A_7$ represents of the formula:

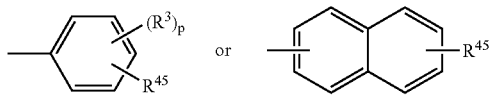

wherein $R^3$ and p are the same as described above, and $R^{45}$ represents a halogen atom,
$A_8$ represents a group of the formula:

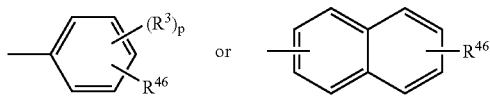

wherein $R^3$ and p are the same as described above, and $R^{46}$ represents

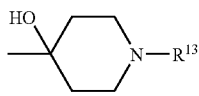

wherein $R^{13}$ is the same as described above,
$A^9$ represents a group of the formula:

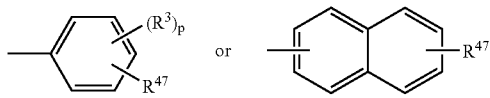

wherein $R^3$ and p are the same as described above, and $R^{47}$ represents a group of the formula:

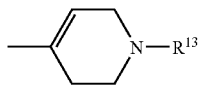

wherein $R^{13}$ is the same as described above, and $A^{8a}$ represents a group of the formula:

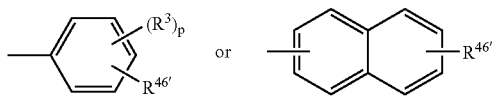

wherein $R^3$ and p are the same as described above, and $R^{46'}$ represents a group

wherein $R^{13}$ is the same as described above.

The reaction of the compound (13) with the compound (12) is carried out in an appropriate inert solvent in the presence of a basic compound.

Examples of the basic compound used here include such as sodium, potassium, magnesium, sodium hydride, sodium amide, metal alcoholates such as sodium methylate, sodium ethylate, and potassium tert-butoxide, and alkyl and aryl lithiums or lithium amides such as methyl lithium, n-butyl lithium, phenyl lithium, and lithium diisopropylamide. These basic compounds are used singly or in a mixture of two or more.

The basic compound is appropriately used in an amount typically at least equimolar to the compound (13), and preferably 1 to 5 times of the compound (13) on a molar basis.

Examples of the inert solvent used include aromatic hydrocarbons such as benzene, toluene, and xylene, ethers such as diethyl ether, tetrahydrofuran, dioxane, monoglyme, and diglyme, aliphatic hydrocarbons such as n-hexane, heptane, and cyclohexane, halogenated hydrocarbons such as chloroform, dichloromethane, dichloroethane, and carbon tetrachloride, dimethylsulfoxide, and N,N-dimethylformamide, and a mixture thereof.

The reaction is carried out at typically about −90 to 150° C., and preferably about −90 to 120° C., and is completed in general in about 10 minutes to 10 hours.

The compound (12) is appropriately used in an amount typically at least equimolar to the compound (13), and preferably 1 to 5 times of the compound (13) on a molar basis.

The reaction which converts the compound (1l) into the compound (1m) is carried out in an appropriate inert solvent and in the presence of an acid.

Examples of the acid used here include mineral acids such as hydrochloric acid, sulfuric acid, and hydrobromic acid, and organic acids such as sulfonic acids including p-toluenesulfonic acid. These acids are used singly or in a mixture of two or more.

It is appropriate to use the acid typically in an amount at least equimolar to the compound (1l), and preferably in an equal amount to a large excess amount with respect to the compound (1l) on a molar basis.

Any of the inert solvents used in the reaction of the compound (13) with the compound (12) may be used in this reaction.

This reaction is suitably carried out at typically room temperature to 200° C., preferably room temperature to about 150° C., and is completed in general in about 1 to 20 hours.

The reaction which converts the compound (1l) into the compound (1l') is carried out in an appropriate solvent and in the presence of an acid and a catalyst.

Examples of the solvent used include water, lower alcohols such as methanol, ethanol, and isopropanol, ketones such as acetone and methyl ethyl ketone, halogenated hydrocarbons such as dichloromethane, dichloroethane, chloroform, and carbon tetrachloride, ethers such as diethyl ether, dimethoxyethane, tetrahydrofuran, diisopropyl ether, diglyme, and 1,4-dioxane, aromatic hydrocarbons such as benzene, toluene, and xylene, acetonitrile, dimethyl sulfoxide, N,N-dimethylacetamide, N,N-dimethylformamide, and N-methylpyrrolidone, and a mixture thereof.

Examples of the acid used here include inorganic acids such as hydrochloric acid, sulfuric acid, and hydrobromic acid, and organic acids such as boron trifluoride diethyl etherate, formic acid, acetic acid, trifluoroacetic acid, and p-toluenesulfonic acid.

Examples of the catalyst include alkylsilane compounds such as triethylsilane.

The acids and the catalysts described above are respectively used typically in an amount about 0.01 to 5 times of the compound (11), and preferably about 0.01 to 1 time of the compound (11) on a molar basis.

The above described reaction is carried out at about room temperature to 200° C., and preferably about room temperature to 150° C., and is completed in general in about 1 to 10 hours.

The reaction which converts the compound (11) into the compound (11') may be carried out in an appropriate solvent and in the presence of a catalytic hydrogen reducing agent.

Examples of the solvent used include water, fatty acids such as acetic acid, alcohols such as methanol, ethanol, and isopropanol, aliphatic hydrocarbons such as n-hexane, alicyclic hydrocarbons such as cyclohexane, ethers such as diethyl ether, dimethoxyethane, tetrahydrofuran, monoglyme, diglyme, and 1,4-dioxane, esters such as methyl acetate, ethyl acetate, and butyl acetate, and aprotic polar solvents such as N,N-dimethylformamide, N,N-dimethylacetamide, N-methylpyrrolidone, and a mixture thereof.

Examples of the catalytic hydrogen reducing agent include palladium, palladium-black, palladium-carbon, palladium hydroxide-carbon, rhodium-alumina, platinum, platinum oxide, copper chromite, Raney nickel, and palladium acetate.

The catalytic hydrogen reducing agent is used typically in an amount of 0.01 to 1 times of the compound (11) on a weight basis.

The above described reaction favorably proceeds at typically about −20 to 100° C., and preferably about 0 to 80° C., and is completed generally in about 0.5 to 20 hours, and the hydrogen pressure is typically at 1 to 10 atm.

It is preferable to add a mineral acid such as hydrochloric acid to this reaction system.

The compound (1), wherein A represents a group of the formula:

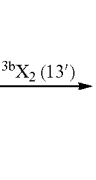 or 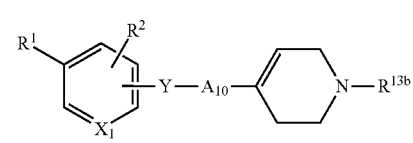

wherein $R^4$ represents a group of the formula:

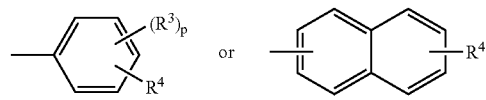 or 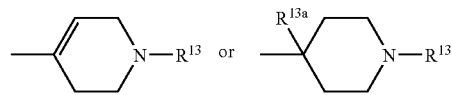

wherein $R^{13}$ represents a group other than a hydrogen atom, is produced from the corresponding compound wherein $R^{13}$ is a hydrogen atom, as shown in the following reaction formula 9.

[Reaction formula 9]

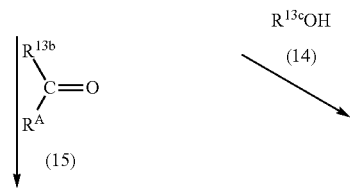

(1n-1) → (1o-1)

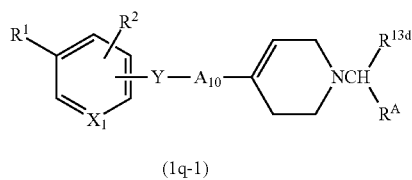

(1q-1)

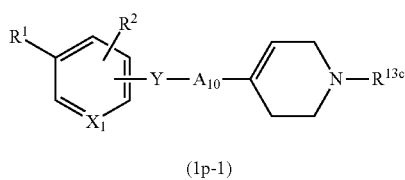

(1p-1)

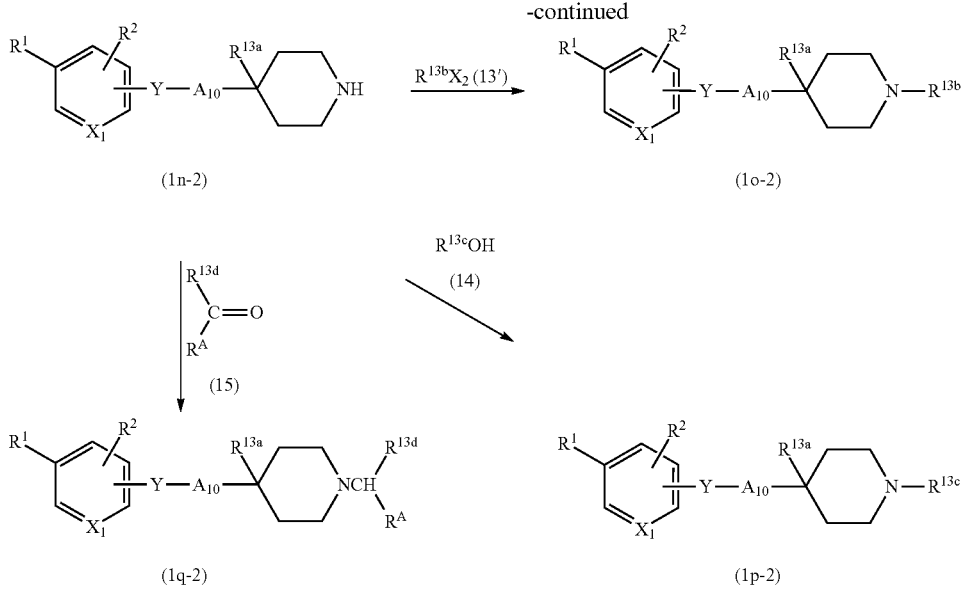

wherein $R^1$, $R^2$, $X_1$, Y, $A_{10}$, $R^A$, $R^{13a}$ and $X_2$ are the same as described above, provided that the a and the b of $A_{10}$ are bound to Y and the piperidinyl group, respectively, $R^{13b}$ represents a lower alkyl group which may have a halogen atom as a substituent, a phenyl lower alkyl group which may have a lower alkylenedioxy group as a substituent on the phenyl ring, an imidazolyl lower alkyl group, a lower alkoxycarbonyl lower alkyl group, a carboxy lower alkyl group, a piperazinylcarbonyl lower alkyl group which may be substituted on the piperazine ring with a phenyl lower alkyl group which may have a lower alkylenedioxy group as a substituent on the phenyl ring, or a morpholinocarbonyl substituted lower alkyl group,
$R^{13c}$ represents a lower alkanoyl group which may have a halogen atom as a substituent, a lower alkoxy carbonyl group, a benzoyl group, a morpholino substituted alkanoyl group, a piperazinyl lower alkanoyl group which may be substituted on the piperazine ring with a phenyl lower alkyl group which may have a lower alkylenedioxy group on the phenyl ring; or an imidazolyl lower alkanoyl group, and
$R^{13d}$ represents a hydrogen atom, a lower alkyl group which may have a halogen atom as a substituent, a phenyl lower alkyl group which may have a lower alkylenedioxy group as a substituent on the phenyl ring, a phenyl group which may have a lower alkylenedioxy group as a substituent on the phenyl ring, an imidazolyl group, an imidazolyl lower alkyl group, a lower alkoxycarbonyl lower alkyl group, a carboxy lower alkyl group, a piperazinylcarbonyl lower alkyl group which may be substituted on the piperazine ring with a phenyl lower alkyl group which may have a lower alkylenedioxy group as a substituent on the phenyl ring, or a morpholinocarbonyl substituted lower alkyl group,
provided that the alkyl moiety of the side chain (—$CHR^A R^{13d}$) of the compound (1q) has not more than 6 carbon atoms.

The reaction of the compound (1n-1) with the compound (13') is carried out under the condition similar to that of the reaction of the compound (1b) with the compound (4) of the above described reaction formula 2.

The reaction of the compound (1n-1) with the compound (14) is carried out under the condition similar to that of the reaction of the compound (1b) with the compound (6) of the above described reaction formula 2.

The reaction of the compound (1n-1) with the compound (15) is carried out under the condition to similar that of the reaction of the compound (1b) with the compound (5) of the above described reaction formula 2.

Also, the reaction of the compound (1n-2) with the compound (13') is carried out under the condition similar to that of the reaction of the compound (1b) with the compound (4) of the above described reaction formula 2, the reaction of the compound (1n-2) with the compound (14) is carried out under the condition similar to that of the reaction of the compound (1b) with the compound (6) of the above described reaction formula 2, and the reaction of the compound (1n-2) with the compound (15) is carried out under the condition to similar that of the reaction of the compound (1b) with the compound (5) of the above described reaction formula 2.

In the reaction formula 9, the hydrolysis of the compounds (1o-1) and (1o-2), wherein $R^{13b}$ represents a lower alkoxycarbonyl lower alkyl group, may produce the corresponding compounds (1o-1) and (1o-2), wherein $R^{13b}$ represents a carboxy lower alkyl group.

In the reaction formula 9, the hydrolysis of compounds (1p-1) and (1p-2), wherein $R^{13c}$ represents a lower alkoxycarbonyl group, may produce the corresponding compounds (1p-1) and (1p-2), wherein $R^{13c}$ is a hydrogen atom.

The hydrolysis reaction (hereinafter this hydrolysis reaction is called "hydrolysis B") may be carried out in an appropriate solvent or without a solvent, in the presence of an acidic or basic compound.

Examples of the solvent used include water, lower alcohols such as methanol, ethanol, isopropanol, and tert-butanol, ketones such as acetone and methyl ethyl ketone, ethers such as diethyl ether, dioxane, tetrahydrofuran, monoglyme, and diglyme, fatty acids such as acetic acid and formic acid, esters such as methyl acetate and ethyl acetate, halogenated hydrocarbons such as chloroform, dichloromethane, dichloroethane, and carbon tetrachloride, dimethylsulfoxide, N,N-dimethylformamide, and hexamethylphosphoric acid triamide, and a mixture thereof.

Examples of the acid include mineral acids such as hydrochloric acid, sulfuric acid, and hydrobromic acid, organic acids such as formic acid, acetic acid, trifluoroacetic acid, sulfonic acids including p-toluenesulfonic acid, and Lewis acids such as boron tribromide and boron trichloride. These acids are used singly or in a mixture of two or more.

Examples of the basic compound include carbonates such as sodium carbonate, potassium carbonate, sodium bicarbonate, and potassium bicarbonate, and metal hydroxides such as sodium hydroxide, potassium hydroxide, calcium hydroxide, and lithium hydroxide. These basic compounds are used singly or in a mixture of two or more.

The hydrolysis reaction is favorably carried out at typically about 0 to about 200° C., and preferably about 0 to 150° C., and is completed in general in about 10 minutes to 50 hours.

The compound (1), wherein A represents a group of the formula:

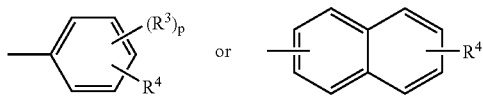

wherein $R^4$ represents a group of the formula:

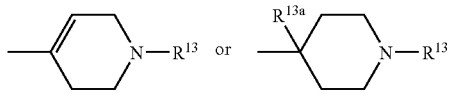

wherein $R^{13}$ represents an imidazolyl lower alkyl group, is produced as shown in the following reaction formula 10.

[Reaction formula 10]

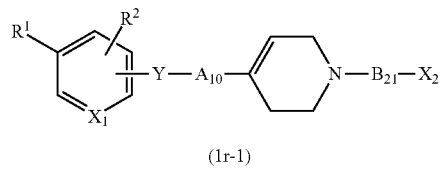

(1r-1)

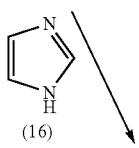

(16)

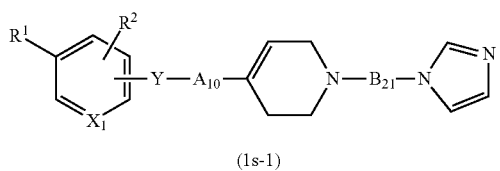

(1s-1)

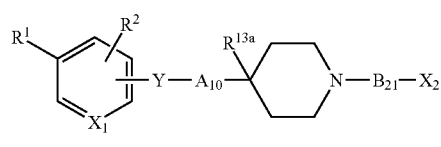

(1r-2)

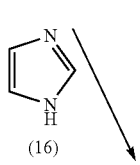

(16)

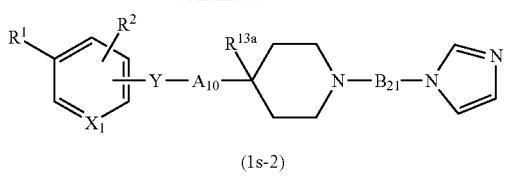

(1s-2)

wherein $R^1$, $R^2$, $X_1$, Y, $A_{10}$, $R^{13a}$, $B_{21}$ and $X_2$ are the same as described above, provided that the a and b of $A_{10}$ are bound to Y and the piperidinyl group, respectively.

The reaction of the compound (1r-1) with the compound (16) with and the reaction of the compound (1r-2) with the compound (16) are carried out under the condition similar to that of the reaction of the compound (2) with the compound (3) of the above described reaction formula 1.

The compound (1), wherein A represents a group of the formula:

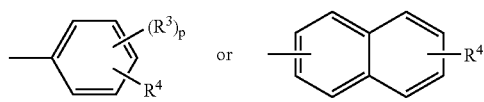

wherein $R^4$ represents a group of the formula:

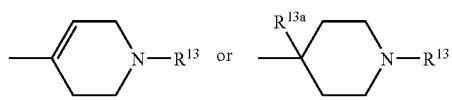

wherein $R^{13}$ represents a morpholino substituted alkanoyl group, a piperazinyl lower alkanoyl group which may be substituted on the piperazine ring with a phenyl lower alkyl group which has a lower alkylenedioxy group as a substituent on the phenyl ring, or an imidazolyl lower alkanoyl group, may be produced from the corresponding compound, wherein $R^{13}$ represents a lower alkanoyl group which may have a halogen atom as a substituent, as shown in the following reaction formula 11.

[Reaction formula 11]

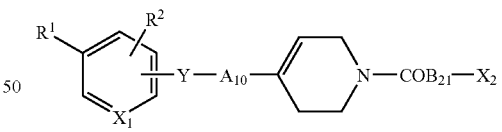

(1t-1)

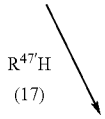

(17)

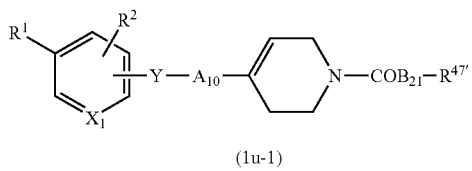

(1u-1)

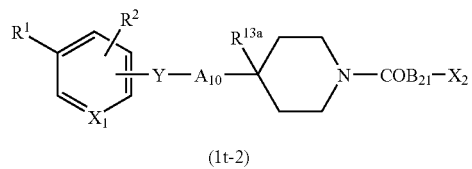

(1t-2)

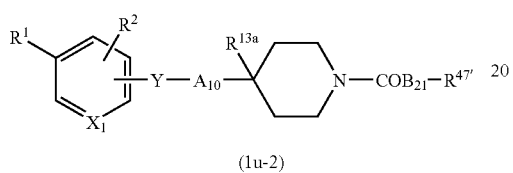

(1u-2)

wherein $R^1$, $R^2$, $X_1$, Y, $R^{13a}$, $B_{21}$ and $X_2$ are the same as described above, and $R^{47'}$ is a morpholino group, a piperazinyl group which may be substituted on the piperazine ring with a phenyl lower alkyl group which may have a lower alkylenedioxy group as a substituent on the phenyl ring, or an imidazolyl group, provided that the a and b of $A_{10}$ are bound to Y and the piperidinyl group, respectively.

The reaction of the compound (1t-1) with the compound (17) and the reaction of the compound (1t-2) with the compound (17) are carried out under the condition similar to that of the reaction of the compound (2) with the compound (3) of the above described reaction formula 1.

The compound (1), wherein A represents a group of the formula:

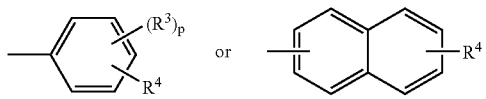

wherein $R^4$ represents a group of the formula:

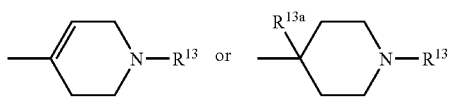

wherein $R^{13}$ represents a piperazinylcarbonyl lower alkyl group which is substituted on the piperazine ring with a phenyl lower alkyl group which may have a lower alkylenedioxy group as a substituent on the phenyl ring, or a morpholinocarbonyl substituted lower alkyl group, is produced from the corresponding compound, wherein $R^{13}$ is a carboxy group, as shown in the following reaction formula 12.

[Reaction formula 12]

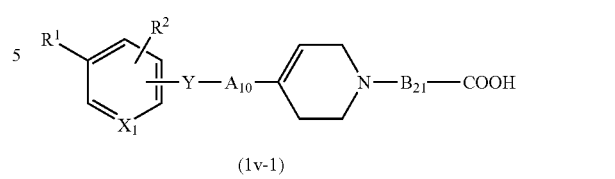

(1v-1)

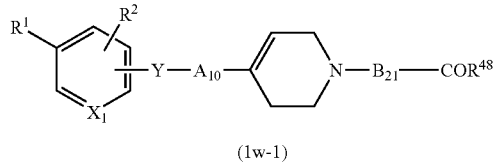

(1w-1)

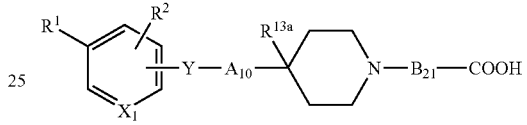

(1v-2)

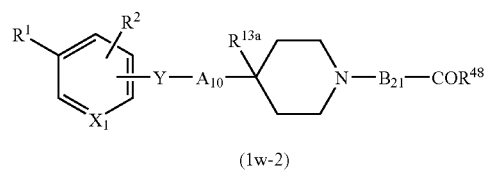

(1w-2)

wherein $R^1$, $R^2$, $X_1$, Y, $A_{10}$, $R^{13a}$, and $B_{21}$ are the same as described above, $R^{48}$ is a piperazinyl group which may be substituted on the piperazine ring with a phenyl lower alkyl group which may have a lower alkylenedioxy group as a substituent on the phenyl ring, or a morpholino group, provided that the a and b of $A_{10}$ are bound to Y and the piperidinyl group, respectively.

The reaction of the compound (1v-1) with the compound (18) and the reaction of the compound (1v-2) with the compound (18) are carried out under the condition similar to that of the reaction of the compound (1b) with the compound (6) of the above described reaction formula 2.

The compound (1), wherein A represents a group of the formula:

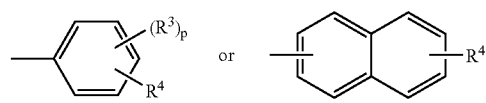

wherein $R^4$ represents -(T)$_t$-NR$^{14}$R$^{15}$, is produced as shown in the reaction formulas 13 and 14.

[Reaction formula 13]

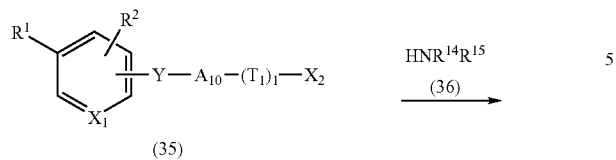

(35)

(1pp)

In the formula, $R^1, R^2, X_1, Y, A_{10}, X_2, l, R^{14}$ and $R^{15}$ are the same as described above, $T_1$ is a lower alkylene group, $-COB_8-$, $-SO_2-$ or a $-CH(OH)-B_9-$, and $B^8$ and $B^9$ are the same as described above, provided that, in the compounds (35) and (1pp), the a and b of $A_{10}$ are bound to Y and $-(T_1)_1$, respectively.

The reaction of the compound (35) with the compound (36) is carried out in the reaction condition similar to that of the reaction of the compound (2) with the compound (3) of the above described reaction formula 1.

The compound (35), wherein l is 0, may also be produced by reacting the corresponding compound (35) with the compound (36) in an appropriate solvent in the presence of a basic compound and a catalyst.

Any of the solvents and basic compounds which are used in the reaction of the compound (2) with the compound (3) of the above described reaction formula 1 may be used here.

Examples of the catalyst to be used include various metal complexes as well as various combinations of a metal complex with ligand. Examples of the metal complex include, for instance, palladium acetate (II), tetrakis(triphenylphosphine) palladium (0), tris(dibenzylideneacetone)dipalladium (0) and the like. Examples of the ligand include, for instance, R-2,2'-bis(diphenylphosphino)-1,1'-binaphthyl (R-BINAP), S-2,2'-bis(diphenylphosphino)-1,1'-binaphthyl (S-BINAP), RAC-2,2'-bis(diphenylphosphino)-1,1'-binaphthyl (RAC-BINAP), t-butylphosphine, 4,5-bis(diphenylphosphino)-9,9-dimethylxanthene and the like.

The catalyst is appropriately used in an amount typically at least equimolar to the compound (35), and preferably 1 to 5 times of the compound (35) on a molar basis.

This reaction is carried out at typically about 0 to 200° C., and preferably about 0 to 150° C., and is completed in general in about 1 to 60 hours. This reaction is called "reaction C" hereinafter.

[Reaction formula 14]

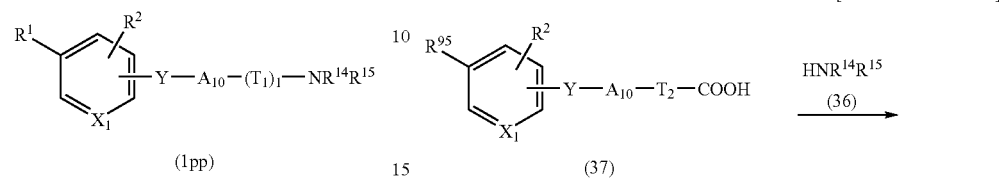

(37)

(1qq)

In the formula, $R^2, X_1, Y, A_{10}, T_2, R^{14}$ and $R^{15}$ are the same as described above, provided that, in the compounds (37) and (1qq), the a and b of $A_{10}$ are bound to Y and $T_2$, respectively, and $R^{95}$ represents $R^1$ or a halogen atom.

The reaction of the compound (37) with the compound (36) is carried out in the reaction condition similar to that of the reaction of the compound (1b) with the compound (6) in the above described reaction formula 2.

The compound (1), wherein A represents a group of the formula:

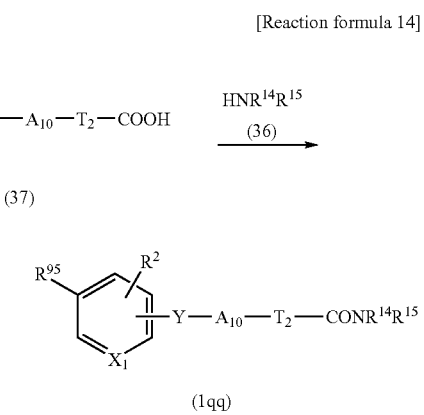

wherein $R^4$ represents $-(T)_l-NR^{14}R^{15}$, and l represents 0, may also be produced by the method shown in the reaction formula 15.

[Reaction formula 15]

(1rr) → (1ss)

(38b)

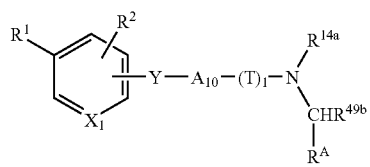

(1ss")

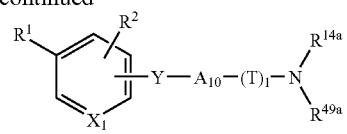

(1ss')

wherein $R^1$, $R^2$, XI, Y, $R^4$, $X_2$, T, l, and $A_{10}$, are the same as described above, $R^{49}$ is the same group as $R^{15}$ defined in (15), (22), (23), (27) and (36a), $R^{49a}$ is $R^{15}$ defined in (2) to (5), (7), (8), (10), (11), (13), (14), (16) to (21), (24), (25), (26), (26a), (27a), (28a), (29a), (30a), (31a), (32a), (33a), (34a), (35a), or (37a), a phenoxycarbonyl group and a lower alkylsulfonyl group, $R^{49b}$ represents a hydrogen atom, an alkyl group which may have a hydroxyl group as a substituent, a phenoxy lower alkyl group, a phenyl lower alkyl group which may be substituted on the phenyl ring with 1 to 3 substituents selected from the group consisting of a halogen atom, a lower alkoxy group which may have a halogen atom as a substituent, and a lower alkyl group, a phenyl group which may be substituted on the phenyl ring with 1 to 3 substituents selected from the group consisting of a halogen atom, a lower alkoxy group which may have a halogen atom as a substituent, and a lower alkyl group, a phenyl lower alkyl group which may have a lower alkylenedioxy group as a substituent on the phenyl ring, a phenyl group which may have a lower alkylenedioxy group on the phenyl ring, a lower alkoxycarbonyl substituted lower alkyl group, a carboxy substituted lower alkyl group, a cycloalkyl lower alkyl group, a cycloalkyl group, a pyridyl lower alkyl group, a pyridyl group, an amino group substituted lower alkyl group which may have a substituent selected from the group consisting of a lower alkyl group and a lower alkanoyl group, a lower alkoxy lower alkyl group, an imidazolyl group, an imidazolyl lower alkyl group, a 1,2,3,4-tetrahydroisoquinolylcarbonyl substituted lower alkyl group, an A group-substituted carbonyl lower alkyl group, a pyrrolidinyl group, a pyrrolidinyl lower alkyl group, a morpholino group, a morpholino lower alkyl group, an anilinocarbonyl lower alkyl group which may have a lower alkyl group as a substituent on the phenyl ring, a piperazinyl group which may have, on the piperazine ring, a substituent selected from the group consisting of a lower alkyl group and a phenyl lower alkyl group which may have a lower alkylenedioxy group as a substituent on the phenyl ring, a piperazinyl lower alkyl group which may have, on the piperazine ring, a substituent selected from the group consisting of a lower alkyl group and a phenyl lower alkyl group which may have a lower alkylenedioxy group as a substituent on the phenyl ring, an amidino group which may have a lower alkyl group as a substituent, an amidino lower alkyl group which may have a lower alkyl group as a substituent, a B group substituted carbonyl lower alkyl group, or a cyano substituted lower alkyl group,
$R^{14a}$ represents a hydrogen atom or a lower alkyl group which may have a hydroxyl group as a substituent, and
$R^{34}$, d, $R^{36}$, $R^{37}$ and $B_{20}$ are the same as described above, provided that, in the compounds (1rr), (1ss), (1ss') and (1ss"), the a and b of $A_{10}$ are bound to Y and N, respectively, and, in the compound (1ss"), the $CHR^AR^{49b}$ moiety of the side chain, (—Y-$A_{10}$N($R^{14a}$)($CHR^AR^{49b}$), has not more than 6 carbon atoms.

The reaction of the compound (1rr) with the compound (38a) is carried out under the condition to similar that of the reaction of the compound (1b) with the compound (4) of the above described reaction formula 2.

The reaction of the compound (1rr) with the compound (38) is carried out under the condition similar to that of the reaction of the compound (1b) with the compound (6) of the above described reaction formula 2.

The reaction of the compound (1rr) with the compound (38b) is carried out under the condition similar to that of the reaction of the compound (1b) with the compound (5) of the above described reaction formula 2 described above.

The compound (1), wherein A represents a group of the formula:

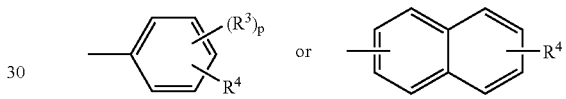

wherein $R^4$ represents a -(T)$_l$-$NR^{14}R^{15}$ group, l represents 1, and T represents a —CH(OH)—$B_9$— group, may also be produced by the method shown in the following reaction formula 16.

[Reaction formula 16]

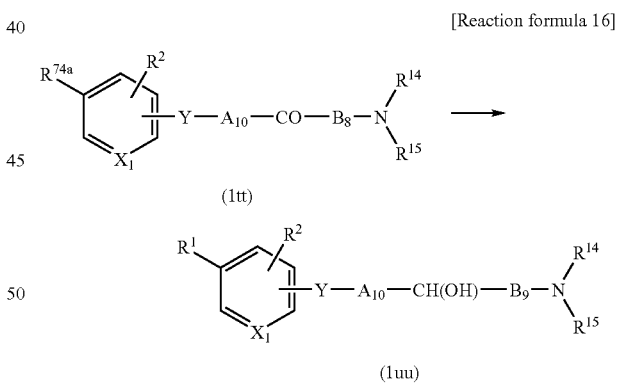

wherein $R^1$, $R^2$, $X_1$, $A_{10}$, Y, $B_8$, $B_9$, $R^{14}$, and $R^{15}$ are the same as described above, provided that, in the compounds (1tt) and (1uu), the a and b of $A_{10}$ are bound to Y and $B_8$ or $B_9$, respectively.

The reaction which converts the compound (1tt) into the compound (1uu) is carried out under the similar condition similar to that of the reaction which converts the compound (1f) into the compound (1g) of the above described reaction formula 3.

The compound (1), wherein A represents a group of the formula:

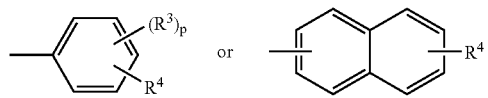

wherein $R^4$ represents a $-(T)_l\text{-}NR^{14}R^{15}$ group, l represents 1, and T represents a $—CH(OH)—B_{11}—CO—$ group, may also be produced by the method shown in the following reaction formula 17.

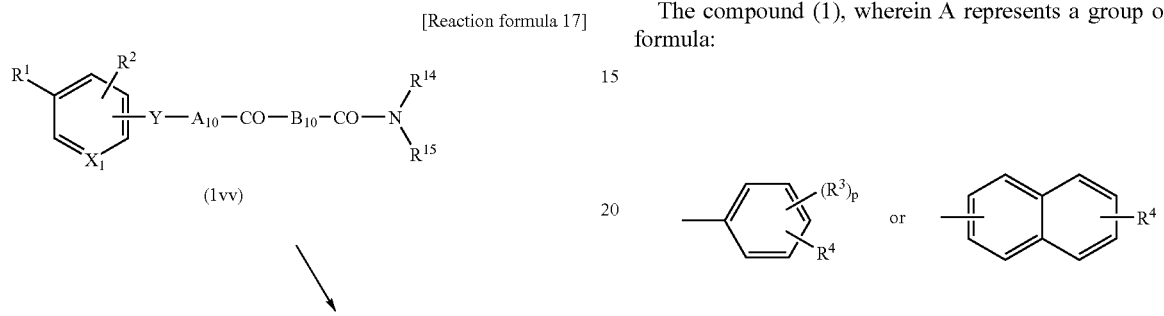

wherein $R^1$, $R^2$, $X_1$, $A_{10}$, $Y$, $B_{10}$, $B_{11}$, $R^{14}$ and $R^{15}$ are the same as described above, provided that, in the compounds (1vv) and (1ww), the a and b of $A_{10}$ are bound to Y and a $—COB_{10}$ or $—CH(OH)B_{11}—$ group, respectively.

The reaction which converts the compound (1vv) into the compound (1ww) is carried out under the condition similar to that of the reaction which converts the compound (1f) into the compound (1g) of the above described reaction formula 3.

The compound (1), wherein A represents a group of the formula:

wherein $R^4$ is a $-(T)_l NR^{14}R^{15}$ group, and $R^{14}$ and $R^{15}$ are bound with each other to form a 5- to 10-membered saturated or unsaturated heterocyclic group which has various substituents thereon, may be produced as shown in the following reaction formulas 18 to 20, 22, 24 to 31, and 34 to 36.

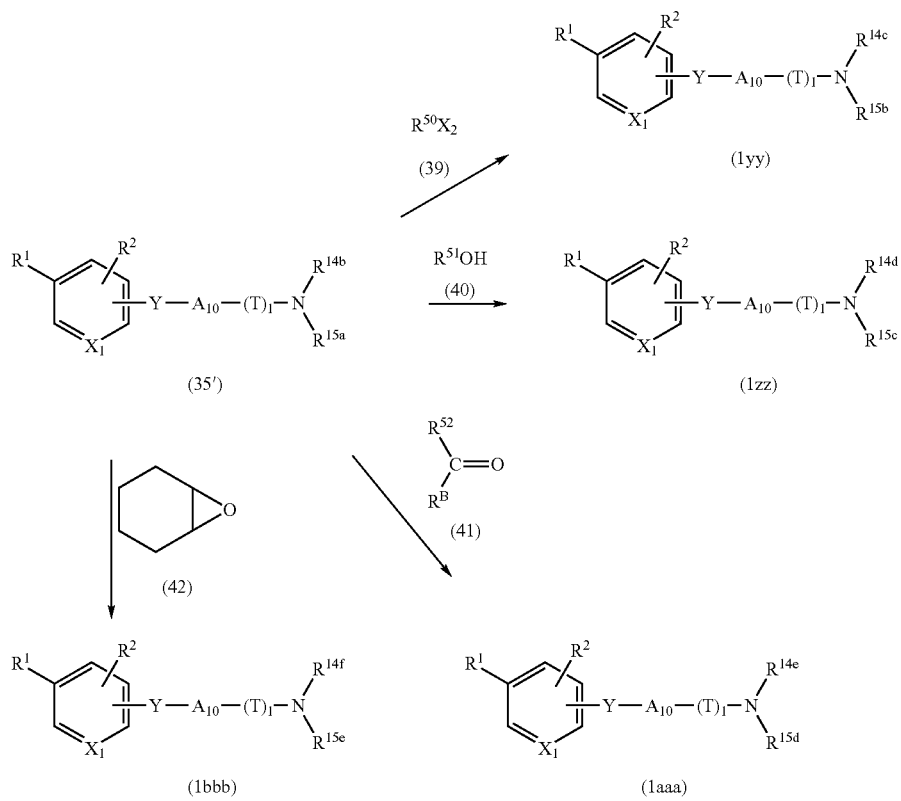

In the formula, $R^1$, $R^2$, $R^B$, $X_1$, Y, T, l, $A_{10}$ and $X_2$ are the same as described above, provided that the a and b of $A_{10}$ are bound to Y and (T)l, respectively;

$R^{14b}$ and $R^{15a}$ represent a 5- to 10-membered saturated or unsaturated heterocyclic group the same as defined for the above described $R^{14}$ and $R^{15}$, except that the heterocyclic group has at least one secondary amine thereon;

$R^{14c}$ and $R^{15b}$ represent a 5- to 10-membered saturated or unsaturated heterocyclic group the same as defined for the above described $R^{14}$ and $R^{15}$, except that the heterocyclic group has at least one tertiary amine thereon substituted with $R^{50}$;

$R^{14d}$ and $R^{15c}$ represent a 5- to 10-membered saturated or unsaturated heterocyclic group the same as defined for the above described $R^{14}$ and $R^{15}$, except that the heterocyclic group has at least one tertiary amine thereon substituted with $R^{51}$;

$R^{14e}$ and $R^{15d}$ represent a 5- to 10-membered saturated or unsaturated heterocyclic group the same as defined for the above described $R^{14}$ and $R^{15}$, except that the heterocyclic group has at least one tertiary amine thereon substituted with a $R^{52}(R^B)CH$— group;

$R^{14f}$ and $R^{15e}$ represent a 5- to 10-membered saturated or unsaturated heterocyclic group the same as defined for the above described $R^{14}$ and $R^{15}$, except that the heterocyclic group has at least one tertiary amine thereon substituted with a group of the formula:

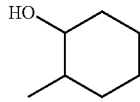

$R^{50}$ is the same substituent of the heterocyclic ring, which is formed by $R^{14}$ and $R^{15}$ bound each other, as the above described (28), (30), (31), (32), (33), (34), (36), (37), (38), (41), (43), (44), (45), (47), (49) (provided that t is 1), (50) (provided that o is 0), (51), (52), (53), (54), (55), (56), (57), (58), (59), (60), (62), (63), (64), (65), (66), (70), (77), (79), (82), (83), (87), (88a), or (90a);

$R^{51}$ is the same substituent of the heterocyclic group, which is formed by $R^{14}$ and $R^{15}$ bound each other, as the above described (35), (39), (40), (42), (50) (provided that o is 1), (67), (75), (76), (77), (78), (80), (81) or (84) (provided that s is 0);

$R^{52}$ is a hydrogen atom, a lower alkyl group which has 1 or 2 phenyls which may be substituted on the phenyl ring with 1 to 3 substituents selected from the group consisting of a lower alkanoyl group, an amino group which may have a lower alkanoyl group as a substituent, a lower alkoxycarbonyl group, a cyano group, a nitro group, a phenyl group, a halogen atom, a lower alkyl group which may have a halogen atom as a substituent, a lower alkoxy group which may have a halogen atom as a substituent, a phenyl lower alkoxy group, a hydroxyl group, and a lower alkylenedioxy group and which may have a pyridyl group on the lower alkyl group, a phenyl group which may be substituted on the phenyl ring with 1 to 3 substituents selected from the group consisting of a lower alkanoyl group, an amino group which have a lower alkanoyl group as a substituent, a lower alkoxycarbonyl group, a cyano group, a nitro group, a phenyl group, a halogen atom, a lower alkyl group which may have a halogen atom as a substituent, a lower alkoxy group which may have a halogen atom as a substituent, a phenyl lower alkoxy group, a hydroxy group, and a lower alkylenedioxy group, a pyridyl lower alkyl group which may be substituted on the pyridine ring with 1 to 3 substituents selected from the group consisting of a hydroxyl group and a lower alkyl group which may have a hydroxyl groups as a substituent, a pyridyl group which may be substituted on the pyridine ring with 1 to 3 substituents selected from the group consisting of a hydroxyl group and a lower alkyl group which may have a hydroxyl group as a substituent, a pyrrolyl lower alkyl group which may have 1 to 3 lower alkyl groups as substituents on the pyrrole ring, a pyrrolyl group which may have 1 to 3 lower alkyl groups as substituents on the pyrrole ring, a benzoxazolyl lower alkyl group, a benzoxazolyl group, a benzthiazolyl lower alkyl group, a benzothiazolyl group, a furyl lower alkyl group, a furyl group, a lower alkyl group which may have a substituent selected from the group consisting of a hydroxyl group and a halogen atom, a naphtyl lower alkyl group, a naphthyl group, a phenoxy lower alkyl group, a —$B_{12}$CO—$NR^{20}R^{21}$ group; a —$B_{13}NR^{22}R^{23}$ group, a 1,2,3,4-tetrahydronaphthyl substituted lower alkyl group which may have 1 to 5 lower alkyl groups as substituents on the 1,2,3,4-tetrahydronaphthalene ring, a 1,2,3,4-tetrahydronaphthyl group which may have 1 to 5 lower alkyl groups as substituents on the 1,2,3,4-tetrahydronaphthalene ring, a quinolyl lower alkyl group, a quinolyl group, a 1,2,3,4-tetrazolyl lower alkyl group which may have, on the tetrazole ring, a substituent selected from the group consisting of a lower alkyl group and a phenyl lower alkyl group, a 1,2,3,4-tetrazolyl group which may have, on the tetrazole ring, a substituent selected from the group consisting of a lower alkyl group and a phenyl lower alkyl group, a thiazolyl lower alkyl group which may have a phenyl group as a substituent on the thiazole ring, a thiazolyl group wherein may have a phenyl group as a substituent on the thiazole ring, a benzoyl lower alkyl group which may have, on the phenyl ring, 1 to 3 substituents selected from the group consisting of a lower alkoxy group and a halogen atom, a piperidinyl lower alkyl group which may have a lower alkoxy group as a substituent on the piperidine ring, a benzoyl lower alkyl group which may have, on the phenyl ring, 1 to 3 substituents selected from the group consisting of a lower alkoxy group and a halogen atom, a piperidinyl group which may have a lower alkyl group on the piperidine ring, a 1,2,3,4-tetrahydroquinolyl lower alkyl group which may have an oxo group as a substituent on the tetrahydroquinoline ring, a 1,2,3,4-tetrahydroquinolyl group which may have an oxo group as a substituent on the tetrahydroquinoline ring, a 1,3,4-oxadiazolyl lower alkyl group which may have an oxo group as a substituent on the 1,3,4-oxadiazole ring, a 1,3,4-oxadiazolyl group which may have an oxo group as a substituent on the 1,3,4-oxadiazole ring, a cycloalkyl lower alkyl group, a cycloalkyl group, a thienyl lower alkyl group, a thienyl group, a lower alkoxy lower alkyl group, a carboxy lower alkyl group, a lower alkoxycarbonyl lower alkyl group, an imidazolyl lower alkyl group, or an imidazolyl group; and $R^B$ and $R^{52}$, together with carbon atoms to which they bind, may form a cycloalkyl group or a tetrahydro-4H-pyranyl group;

provided that the alkyl moiety of the $R^{52}(R^B)CH$— group in the compound (1aaa) has not more than six carbon atoms.

The reaction of the compound (35') with the compound (39) is carried out under the condition similar to that of the reaction of the compound (1b) with the compound (4) of the above described reaction formula 2.

The reaction of the compound (35') with the compound (40) is carried out under the condition similar to that of the reaction of the compound (1b) with the compound (6) of the above described reaction formula 2.

The reaction of the compound (35') with the compound (41) is carried out under the condition similar to that of the reaction of the compound (1b) with the compound (5) of the above described reaction formula 2.

When the reaction is carried out using the compound (41) as a starting material, wherein $R^B$ and $R^{52}$ together with carbon atoms bound to them form a cycloalkyl ring or a tetrahydro-4H-pyran ring using a hydride reducing agent, a cycloalkyloxytrialkylsilane such as [(1-ethoxycyclopropyl)oxy]trimethylsilane may be used as a starting material in place of the compound (41) to generate the above described compound (41) in the reaction system.

The reaction of the compound (35') with the compound (42) is carried out under the condition to similar that of the reaction of the compound (2) with the compound (3) of the above described reaction formula 1.

The compound (35') may also be produced from the compound (1yy), (1zz) or (1aaa) under the reaction condition similar to that of the reaction which converts the compound (1iii') into the compound (1hhh') of the later described reaction formula 24.

[Reaction formula 19]

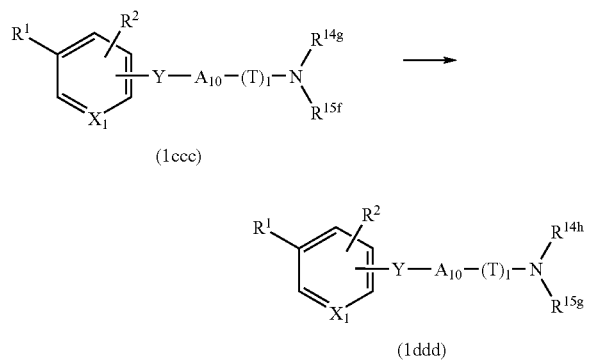

(1ccc)

(1ddd)

In the formula, $R^1$, $R^2$, $X_1$, Y, T, l, $A_{10}$ and $X_2$ are the same as described above, provided that the a and b of $A_{10}$ are bound to Y and (T)l, respectively;
$R^{14g}$ and $R^{15f}$ are a 5- to 10-membered saturated or unsaturated heterocyclic group the same as defined for the above described $R^{14}$ and $R^{15}$, except that the heterocyclic group has at least one tertiary amine thereon substituted with a lower alkoxycarbonyl group; and
$R^{14h}$ and $R^{15g}$ are a 5- to 10-membered saturated or unsaturated heterocyclic group the same as defined for the above described $R^{14}$ and $R^{15}$, except that the heterocyclic group has at least one secondary amine thereon.

The reaction which converts the compound (1ccc) into the compound (1ddd) may be carried out under the reaction condition similar to that of the hydrolysis B described for the above described reaction formula 9.

In the formula, $R^{74a}$ represents a nitro group or a —$R^1$ group, and $R^1$, $R^2$, $X_1$, Y, T, l and $A_{10}$ are the same as described above, provided that the a and b of $A_{10}$ are bound to Y and (T)l, respectively;
$R^{14i}$ and $R^{15h}$ are a 5- to 10-membered saturated or unsaturated heterocyclic group the same as defined for the above described $R^{14}$ and $R^{15}$, except that the heterocyclic group has at least one lower alkoxycarbonyl lower alkoxy group, lower alkoxycarbonyl group, lower alkoxycarbonyl lower alkyl group, or —$(B_{12}CO)t$-$N(R^{20a})R^{51'}$ group thereon;
$R^{14j}$ and $R^{15i}$ are a 5- to 10-membered saturated or unsaturated heterocyclic group the same as defined for the above described $R^{14}$ and $R^{15}$, except that the heterocyclic group has at least one carboxy lower alkoxy group, carboxy group, carboxy lower alkyl group, or —$(B_{12}CO)t$-$N(R^{20a})R^{52'}$ group thereon;
$B_{12}$ and t are the same as described above;
$R^{20a}$ represents a hydrogen atom, a cycloalkyl group, an amino group which have a lower alkoxycarbonyl group as a substituent, a benzoyl group which may have 1 to 3 alkoxy groups as substituents on the phenyl ring, a lower alkyl group, a lower alkyl group which has 1 or 2 phenyls which may be substituted on the phenyl ring with 1 to 3 substituents selected from the group consisting of an lower alkoxycarbonyl group, a cyano group, a nitro group, a phenyl group, a halogen atom, a lower alkyl group which may have a halogen atom as a substituent, a lower alkoxy group which may have a halogen atom as a substituent, and a lower alkylthio group, a phenyl group which may be substituted on the phenyl ring with 1 to 3 groups selected from the group consisting of a lower alkoxy group which may have a halogen atom as a substituent and a lower alkyl group which may have a halogen atom as a substituent, a lower alkoxycarbonyl group, a cycloalkyl lower alkyl group, a pyrrolidinyl lower alkyl group which may have, on the pyrrolidine ring, 1 to 3 lower alkyl groups which may have a hydroxyl group as a substituent, an amino substituted lower alkyl group which may have a substituent selected from the group consisting of a phenyl group and a lower alkyl group, a 1,2,3,4-tetrahydronaphthyl substituted lower alkyl group which may have 1 to 5 lower alkyl groups as substituents on the 1,2,3,4-tetrahydronaphthalene ring, a naphthyl lower alkyl group, a pyridyl lower alkyl group, a quinolyl lower alkyl group, a 1,2,3,4-tetrazolyl lower alkyl group which may have, on the tetrazole ring, 1 to 3 substituents selected from the group consisting of a lower alkyl group and a phenyl lower alkyl group, a 1,2,4-triazolyl lower alkyl group, a tetrahydrofuryl lower alkyl group which may have a hydroxyl group as a substituent on the lower alkyl group, a phenoxy lower alkyl group which may have, on the phenyl ring, 1 to 3 substituents selected from the group consisting of a lower alkyl group and a nitro group, a phenyl lower alkanoyl group, a lower alkanoyl group which may have a halogen atom as a substituent, an imidazolyl lower alkanoyl group, a lower alkoxycarbonyl lower alkyl group, a pyridyl group, or a carboxy lower alkyl group;

[Reaction formula 20]

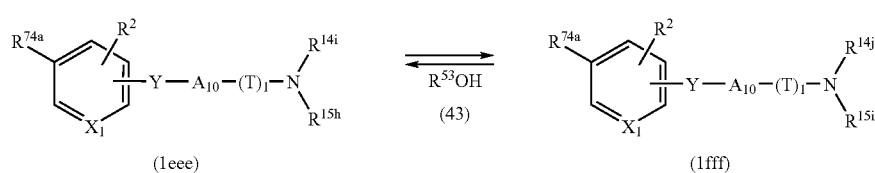

(1eee)      (1fff)

$R^{51'}$ is a lower alkoxycarbonyl group or a lower alkoxycarbonyl lower alkyl group;

$R^{52'}$ is a hydrogen atom or a carboxy lower alkyl group; and $R^{53}$ is a lower alkyl group.

The reaction which converts the compound (1eee) into the compound (1fff) may be carried out under the reaction condition similar to that of the hydrolysis B as described in the above described reaction formula 9.

Any of the reaction conditions for typical esterification reaction may be used for the reaction of the compound (1fff) with the compound (43). For example, the above described reaction is carried out in the presence of a mineral acid such as hydrochloric acid or sulfuric acid, and a halogenation agent such as thionylchloride, phosphorus oxychloride, phosphorus pentachloride, or phosphorus trichloride. The compound (43) is used in large excess over the compound (1fff). The above described reaction favorably proceeds at typically about 0 to 150° C., preferably about 50 to 100° C., and is completed in general in about 1 to 10 hours. The esterification described above may be carried out using a condensation agent such as carbodiimide in the presence of a basic compound such as dimethylaminopyridine. A typical reaction condition for generating an amide bond, which is used in the reaction of the compound (1b) with the compound (6) in the reaction formula 2, may also be used.

The reaction of the compound (1fff) with compound (43) may also be carried out in the presence of the same basic compound and the solvent as those used in the reaction of the compound (2) with the compound (3) of the reaction formula 1. The reaction is carried out at typically about 0 to 100° C., and preferably about 0 to 70° C., and is completed in general in about 1 to 30 hours.

The compound (1eee) may also be produced using a halogenated lower alkyl such as methyl iodide in place of the compound (43) under the condition similar to that of the reaction of the compound (2) with the compound (3) of the reaction formula 1.

[Reaction formula 21]

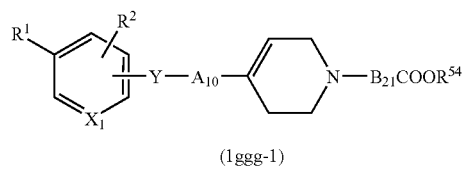

(1ggg-1)

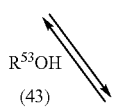

(43)

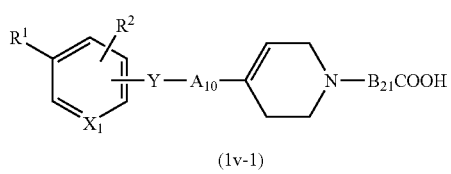

(1v-1)

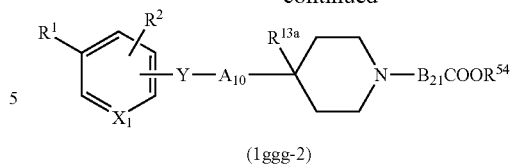

(1ggg-2)

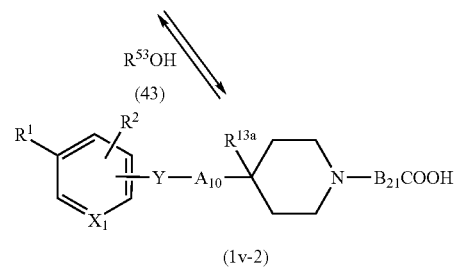

(1v-2)

In the formula, $R^1$, $R^2$, $X_1$, Y, $A_{10}$, $R^{13a}$, $B_{21}$ and $R^{53}$ are the same as described above, and $R^{54}$ is a lower alkyl group, provided that the a and b of $A_{10}$ are bound to Y and the piperidinyl group, respectively.

The reaction which converts the compound (1ggg-1) into the compound (1v-1) and the reaction which converts the compound (1ggg-2) into the compound (1v-2) may be carried out under the reaction condition similar to that of the hydrolysis B described for the above described reaction formula -9, respectively.

The reaction of the compound (1v-1) with the compound (43) and the reaction of the compound (1v-2) with the compound (43) is carried out under the reaction condition similar to that of the reaction of the compound (1fff) with the compound (43) of the above described reaction formula 20.

The compound (1ggg-1) may also be produced using a halogenated lower alkyl such as methyl iodide in place of the compound (43) under the condition similar to that of the reaction of the compound (2) with the compound (3) of the above described reaction formula 1.

Similarly, the compound (1ggg-2) may also be produced using a halogenated lower alkyl such as methyl iodide in place of the compound (43) under the condition similar to that of the reaction of the compound (2) with the compound (3) of the above described reaction formula 1.

[Reaction formula 22]

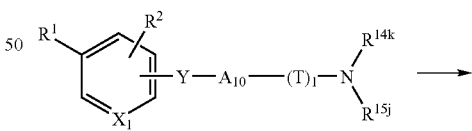

(1hhh)

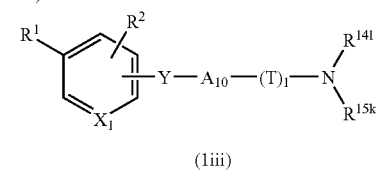

(1iii)

In the formula, $R^1$, $R^2$, $X_1$, Y, T, l and $A_{10}$ are the same as described above, provided that the a and b of $A_{10}$ are bound to Y and (T)l, respectively;

$R^{14k}$ and $R^{15j}$ are a 5- to 10-membered saturated or unsaturated heterocyclic group the same as defined for the above described $R^{14}$ and $R^{15}$, except that the heterocyclic group has at least one —$B_{21}$CONHNH$_2$ group, wherein $B^{21}$ is the same as described above, thereon; and
$R^{14l}$ and $R^{15k}$ are a 5- to 10-membered saturated or unsaturated heterocyclic ring the same as defined for the above described $R^{14}$ and $R^{15}$, except that the heterocyclic group has at least one group of the formula:

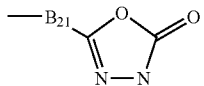

thereon.

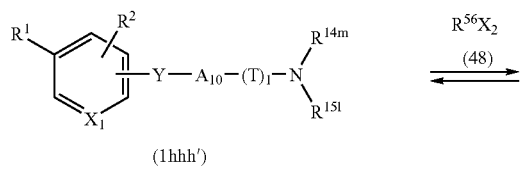

(1hhh')

[Reaction formula 24]

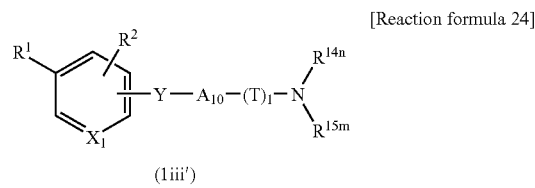

(1iii')

The reaction which converts the compound (1hhh) into compound (1iii) is carried out under the condition similar to that of the reaction of the compound (1b) with the compound (6) of the above described reaction formula 2.

[Reaction formula 23]

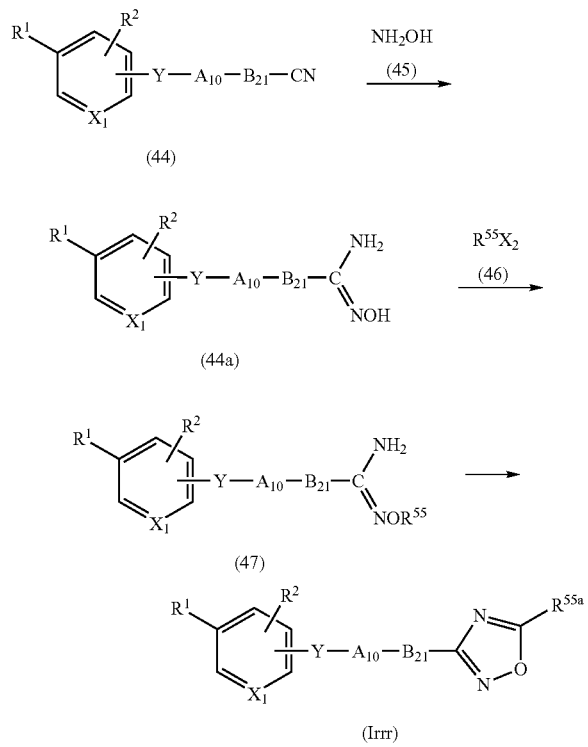

In the formula, $R^1$, $R^2$, $X_1$, Y, $A_{10}$, $B_{21}$ and $X_2$ are the same as described above, the a and b of $A_{10}$ are bound to Y and (T)l, respectively, $R^{55}$ is a lower alkanoyl group, and $R^{55a}$ is a lower alkyl group.

The reaction of the compound (44) with the compound (45) is carried out under the condition to similar that of the reaction which converts the compound (1f) into the compound (1h) of the above described reaction formula 3.

The reaction of the compound (44a) with the compound (46) is carried out under the condition similar to that of the reaction of the compound (2) with the compound (3) of the above described reaction formula 1.

The reaction which converts the compound (47) into the compound (1rrr) is carried out under the condition similar to that of the reaction which converts the compound (1f) into the compound (1h) of the above described reaction formula 3.

In the formula, $R^1$, $R^2$, XI, Y, T, l, $A_{10}$ and $X_2$ are the same as described above, provided that the a and b of $A_{10}$ are bound to Y and (T)l, respectively;
$R^{14m}$ and $R^{15l}$ are a 5- to 10-membered saturated or unsaturated heterocyclic group the same as defined for the above described $R^{14}$ and $R^{15}$, except that the heterocyclic group has at least one hydroxyl group or hydroxyl group substituted lower alkyl group thereon;
$R^{14n}$ and $R^{15m}$ are a 5- to 10-membered saturated or unsaturated heterocyclic group the same as defined for the above described $R^{14}$ and $R^{15}$, except that the heterocyclic group has at least one —$OR^{56}$ group thereon;
$R^{56}$ represents a phenyl group which may be substituted on the phenyl ring with 1 to 3 substituents selected from the group consisting of a cyano group, a lower alkyl group which may have a halogen atom as a substituent, and a lower alkoxy group which may have a halogen atom as a substituent, a phenyl lower alkyl group which may be substituted on the phenyl ring with 1 to 3 substituents selected from the group consisting of a halogen atom, a lower alkyl group which may have a halogen atom as a substituent, and a lower alkoxy group which may have a halogen atom as a substituent, a pyridyl lower alkyl group, a lower alkyl group, a lower alkoxy lower alkyl group, a benzoyl group, a lower alkoxycarbonyl lower alkyl group, a carboxy lower alkyl group; or a —$B_{15}$—CO—$NR^{26}R^{27}$ group, wherein $B_{15}$, $R^{26}$ and $R^{27}$ are the same as described above,
provided that, the $R^{56}$ of the compound (48), which reacts with the above described heterocyclic group substituted with at least one hydroxyl group substituted lower alkyl group of the compound (1hhh'), is an unsubstituted phenyl group or a lower alkyl group.

The reaction of the compound (1hhh') with the compound (48) is carried out under the condition similar to that of the reaction of the compound (2) with the compound (3) of the above described reaction formula 1.

The reaction which converts the compound (1iii') into the compound (1hhh') may be carried out under the condition to similar that of the hydrolysis B described in the above described reaction formula 9.

The compound (1iii') may be converted into the compound (1hhh') by a reduction reaction. This reduction reaction is, for example, carried out in an appropriate solvent in the presence of a catalytic hydrogen reducing agent.

Examples of the solvent used include water, fatty acids such as acetic acid, alcohols such as methanol, ethanol, and isopropanol, aliphatic hydrocarbons such as hexane and cyclohexane, ethers such as dioxane, tetrahydrofuran, diethyl ether, monoglyme, and diglyme, esters such as ethyl acetate and methyl acetate, aprotic polar solvents such as N,N-dimethylformamide, and a mixture thereof.

Examples of the catalytic hydrogen reducing agent used include palladium, palladium black, palladium-carbon, platinum, platinum oxide, copper chromite, and Raney nickel. These reducing agents may be used singly or as a mixture of two or more.

The catalytic hydrogen reducing agent is favorably used generally in an amount of 0.02 to 1 time of the compound (1iii') on a weight basis.

The reaction temperature is typically at about −20 to 100° C., and preferably at about 0 to about 80° C. The reaction is preferably carried out at a hydrogen pressure of typically 1-10 atm, and is completed in general in about 0.5 to 20 hours.

above described $R^{14}$ and $R^{15}$ except that the heterocyclic ring has at least one —$(B_{12}CO)$ $tN(R^{20a})(CHR^A R^{21d})$ group thereon, wherein $B_{12}$, t and $R^{20a}$ are the same as described above;

$R^{21b}$ represents a lower alkyl group, a cycloalkyl group, a lower alkyl group which have 1 or 2 phenyls which may be substituted on the phenyl ring with 1 to 3 substituents selected from the group consisting of a lower alkoxycarbonyl group, a cyano group, a nitro group, a phenyl group, a halogen atom, a lower alkyl group which may have a halogen atom as a substituent, a lower alkoxy group which may have a halogen atom as a substituent and a lower alkylthio group, a phenyl group which may be substituted on the phenyl ring with 1 to 3 groups selected from the group consisting of a lower alkoxy group which may have a halogen atom as a substituent and a lower alkyl group which may have a halogen atom as a substituent, a cycloalkyl lower alkyl group, a pyrrolidinyl lower alkyl group which may have, on the pyrrolidine ring, 1 to 3 lower alkyl groups which may have a hydroxyl group as a substituent, an amino substituted lower alkyl group which may have a substituent selected from the group consisting of a phenyl group and a lower alkyl group, a 1,2,3,4-tetrahydronaphthyl substituted lower alkyl group which may have 1

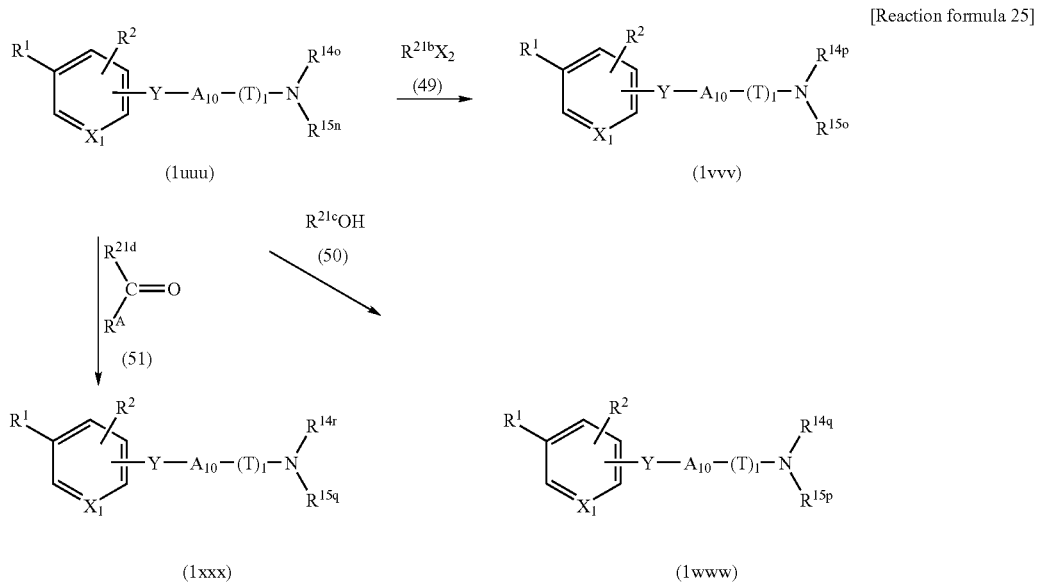

[Reaction formula 25]

In the formula $R^1$, $R^2$, $X_1$, Y, T, l, $A_{10}$, $R^A$ and $X_2$ are the same as described above, provided that the a and b of $A_{10}$ are bound to Y and (T)l, respectively;

$R^{14o}$ and $R^{15n}$ are a 5- to 10-membered saturated or unsaturated heterocyclic group the same as defined for the above described $R^{14}$ and $R^{15}$, except that the heterocyclic group has at least one —$(B_{12}CO)tNHR^{20a}$ group thereon;

$R^{14p}$ and $R^{15o}$ are a 5- to 10-membered saturated or unsaturated heterocyclic group the same as defined for the above described $R^{14}$ and $R^{15}$, except that the heterocyclic group has at least one —$(B_{12}CO)tN(R^{20a})R^{21b}$ group thereon; and $R^{14q}$ and $R^{15p}$ are a 5- to 10-membered saturated or unsaturated heterocyclic group the same as defined for the above described $R^{14}$ and $R^{15}$, except that the heterocyclic group has at least one —$(B_{12}CO)tN(R^{20a})R^{21c}$ group thereon;

$R^{14r}$ and $R^{15q}$ represent a 5- to 10-membered saturated or unsaturated heterocyclic group the same as defined for the to 5 lower alkyl groups as substituents on the 1,2,3,4-tetrahydronaphthalene ring, a naphthyl lower alkyl group, a pyridyl lower alkyl group, a quinolyl lower alkyl group, a 1,2,3,4-tetrazolyl lower alkyl group which may have, on the tetrazole ring, 1 to 3 substituents selected from the group consisting of a lower alkyl group and a phenyl lower alkyl group, a 1,2,4-triazolyl lower alkyl group, a tetrahydrofuryl lower alkyl group which may have a hydroxyl group as a substituent on the lower alkyl group, a phenoxy lower alkyl group which may have, on the phenyl ring, 1 to 3 substituents selected from the group consisting of a lower alkyl group and a nitro group, a lower alkoxycarbonyl lower alkyl group, a pyridyl group, or a carboxy lower alkyl group;

$R^{21c}$ represents a benzoyl group which may have 1 to 3 lower alkoxy groups as substituents on the phenyl ring, a lower alkoxycarbonyl group, a phenyl lower alkanoyl group, a lower alkanoyl group which may have a halogen atom as a substituent or an imidazolyl lower alkanoyl group; and $R^{21d}$ represents a hydrogen atom, a lower alkyl group, a lower alkyl group which have 1 or 2 phenyl groups which may have, on the phenyl ring, 1 to 3 substituents selected from the group consisting of a lower alkoxycarbonyl group, a cyano group, a nitro group, a phenyl group, a halogen atom, a lower alkyl group which may have a halogen atom as a substituent, a lower alkoxy group which may have a halogen atom as a substituent and a lower alkylthio group, a phenyl group which may have, on the phenyl ring, 1 to 3 substituents selected from the group consisting of a lower alkoxycarbonyl group, a cyano group, a nitro group, a phenyl group, a halogen atom, a lower alkyl group which may be substituted with a halogen atom, a lower alkoxy group which may be substituted with a halogen atom and a lower alkylthio group, a cycloalkyl lower alkyl group, a cycloalkyl group, a pyrrolidinyl lower alkyl group which may have, on the pyrrolidine ring, 1 to 3 lower alkyl groups which may have a hydroxyl group as a substituent, a pyrrolidinyl group which may have, on the pyrrolidine ring, 1 to 3 lower alkyl groups which may have a hydroxyl group as a substituent, an amino substituted lower alkyl group which may have a group selected from the group consisting of a phenyl group and a lower alkyl group, a 1,2,3,4-tetrahydronaphthyl substituted lower alkyl group which may have 1 to 5 lower alkyl groups as substituents on the 1,2,3,4-tetrahydronaphthalene ring, a 1,2,3,4-tetrahydronaphthyl group which may have 1 to 5 lower alkyl groups as substituents on the 1,2,3,4-tetrahydronaphthalene ring, a naphthyl lower alkyl group, a naphthyl group, a pyridyl lower alkyl group, a pyridyl group, a quinolyl lower alkyl group, a quinolyl group, a 1,2,3,4-tetrazolyl lower alkyl group which may have, on the tetrazole ring, 1 to 3 substituents selected from the group consisting of a lower alkyl group and a phenyl lower alkyl group, a 1,2,3,4-tetrazolyl group which may have, on the tetrazole ring, 1 to 3 substituents selected from the group consisting of a lower alkyl group and a phenyl lower alkyl group, a 1,2,4-triazolyl lower alkyl group, a 1,2,4-triazolyl group, a tetrahydrofuryl lower alkyl group which may have a hydroxyl group as a substituent on the lower alkyl group, a tetrahydrofuryl group which may have a hydroxyl group as a substituent on the lower alkyl group, a phenoxy lower alkyl group which may have, on the phenyl ring, 1 to 3 substituents selected from the group consisting of a lower alkyl group and a nitro group, a lower alkoxycarbonyl lower alkyl group or a carboxy lower alkyl group;

provided that the alkyl moiety of $CHR^AR^{21d}$ in the side chain $(-(B_{21}CO)tN(R^{20a})(CHR^AR^{21d}))$ has not more than 6 carbon atoms.

The reaction of the compound (1uuu) with the compound (49) is carried out under reaction conditions similar to those of the reaction of the compound (1b) with the compound (4) of the above described reaction formula 2.

The reaction of the compound (1uuu) with the compound (51) is carried out under reaction conditions similar to those of the reaction of the compound (1b) and the compound (5) of the above described reaction formula 2.

The reaction of the compound (1uuu) with the compound (50) is carried out under reaction conditions similar to those of the reaction of the compound (1b) with the compound (6) of the above described reaction formula 2.

[Reaction formula 26]


In the formula, $R^1$, $R^2$, $X_1$, Y, T, l, and $A_{10}$ are the same as described above, provided that the a and b of $A_{10}$ are bound to Y and (T)l, respectively;
$R^{14s}$ and $R^{15r}$ represent a 5- to 10-membered saturated or unsaturated heterocyclic group the same as defined for the above described $R^{14}$ and $R^{15}$, except that the heterocyclic ring has at least one —(CO)$oB_{13}X_2$ group thereon;
$R^{14t}$ and $R^{15s}$ represent a 5- to 10-membered saturated or unsaturated heterocyclic group the same as defined for the above described $R^{14}$ and $R^{15}$, except that the heterocyclic ring has at least one —(CO)o $B_{13}R^{84}$ group thereon; and
$R^{84}$ is an —$NR^{22}R^{23}$ group or an imidazolyl group;
wherein $B_{13}$, o, $X_2$, $R^{22}$ and $R^{23}$ are the same as described above.

The reaction of the compound (1yyy) with the compound (52) is carried out under reaction conditions similar to those of the reaction of the compound (1b) with the compound (4) of the above described reaction formula 2.

[Reaction formula 27]


In the formula, $R^1$, $R^2$, $X_1$, Y, T, l, and $A_{10}$ are the same as described above, provided that the a and b of $A_{10}$ are bound to Y and (T)l, respectively;
$R^{14s'}$ and $R^{15r'}$ represent a 5- to 10-membered saturated or unsaturated heterocyclic group the same as defined for the above described $R^{14}$ and $R^{15}$, except that the heterocyclic ring has at least one —N($R^{28}$)—CO—$B_{16}X_2$ group thereon; and
$R^{14u}$ and $R^{15t}$ represent a 5- to 10-membered saturated or unsaturated heterocyclic group the same as defined for the above described $R^{14}$ and $R^{15}$, except that the heterocyclic ring has at least one —N($R^{28}$)—CO—$B_{16}NR^{29}R^{30}$ group thereon;
wherein $R^{28}$, $B_{16}$, $X_2$, $R^{29}$ and $R^{30}$ represent the same as described above.

The reaction of the compound (1aaaa) with the compound (53) is carried out under reaction conditions similar to those of the reaction of the compound (1b) with the compound (4) of the above described reaction formula 2.

[Reaction formula 28]

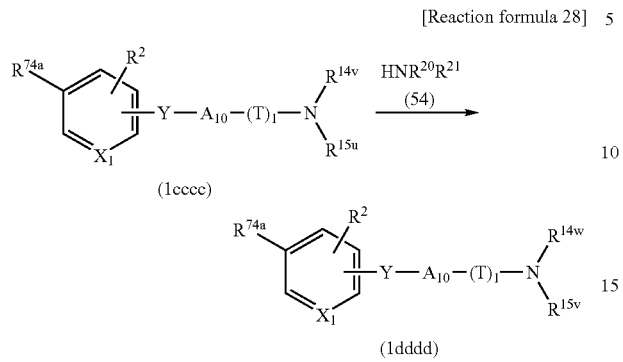

In the formula, $R^{74a}$, $R^2$, $X_1$, Y, T, l, and $A_{10}$ are the same as described above, provided that the a and b of $A_{10}$ are bound to Y and (T)l, respectively;
$R^{14v}$ and $R^{15u}$ represent a 5- to 10-membered saturated or unsaturated heterocyclic group the same as defined for the above described $R^{14}$ and $R^{15}$, except that the heterocyclic ring has at least one —$B_{12}$COOH group thereon; and
$R^{14w}$ and $R^{15v}$ represent a 5- to 10-membered saturated or unsaturated heterocyclic group the same as defined for the above described $R^{14}$ and $R^{15}$, except that the heterocyclic ring has at least one —$B_{12}$CONR$^{20}$R$^{21}$ group thereon;
wherein $B_{12}$, $R^{20}$ and $R^{21}$ are the same as described above.

The reaction of the compound (1cccc) with the compound (54) is carried out under reaction conditions similar to those of the reaction of the compound (1b) with the compound (6) of the above described reaction formula 2.

[Reaction formula 29]

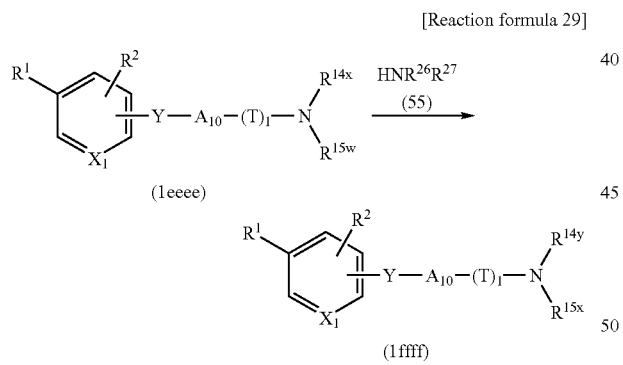

In the formula, $R^1$, $R^2$, $X_1$, Y, T, l, and $A_{10}$ are the same as described above, provided that the a and b of $A_{10}$ are bound to Y and (T)l, respectively;
$R^{14x}$ and $R^{15w}$ represent a 5- to 10-membered saturated or unsaturated heterocyclic group the same as defined for the above described $R^{14}$ and $R^{15}$, except that the heterocyclic ring has at least one —O—$B_{15}$COOH group thereon; and
$R^{14y}$ and $R^{15x}$ represent a 5- to 10-membered saturated or unsaturated heterocyclic group as defined for the above described $R^{14}$ and $R^{15}$, except that the heterocyclic ring has at least one —O—$B_{15}$CONR$^{26}$R$^{27}$ group thereon;
wherein $B_{15}$, $R^{26}$ and $R^{27}$ are the same as described above.

The reaction of the compound (1eeee) with the compound (55) is carried out under reaction conditions similar to those of the reaction of the compound (1b) with the compound (6) of the above described reaction formula 2.

[Reaction formula 30]

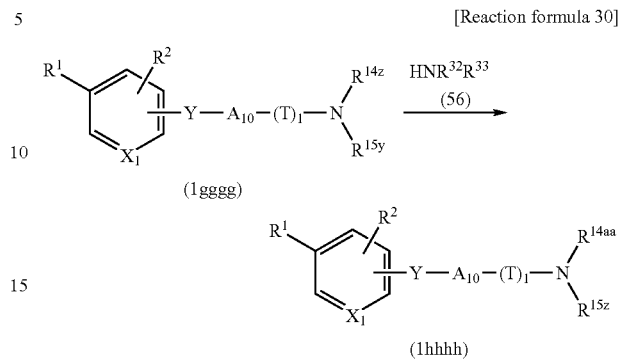

are the same as described above, provided that the a and b of $A_{10}$ are bound to Y and (T)l, respectively;
$R^{14z}$ and $R^{15y}$ represent a 5- to 10-membered saturated or unsaturated heterocyclic group the same as defined for the above described $R^{14}$ and $R^{15}$, except that the heterocyclic ring has at least one —N(R$^{31}$)—$B_{17}$—COOH group thereon; and
$R^{14aa}$ and $R^{15z}$ represent a 5- to 10-membered saturated or unsaturated heterocyclic group the same as defined for the above described $R^{14}$ and $R^{15}$, except that the heterocyclic ring has at least one —N(R$^{31}$)—$B_{17}$CONR$^{32}$R$^{33}$ group thereon;
wherein $R^{31}$, $B_{17}$, and $R^{32}$, $R^{33}$ are the same as described above.

The reaction of the compound (1gggg) with the compound (56) is carried out under reaction conditions similar to those of the reaction of the compound (1b) with the compound (6) of the above described reaction formula 2.

[Reaction formula 31]

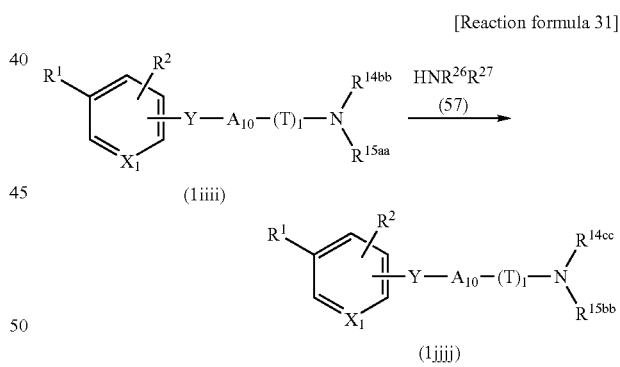

In the formula, $R^1$, $R^2$, $X_1$, Y, T, l, and $A_{10}$ are the same as described above, provided that the a and b of $A_{10}$ are bound to Y and (T)l, respectively;
$R^{14bb}$ and $R^{15aa}$ represent a 5- to 10-membered saturated or unsaturated heterocyclic group the same as defined for the above described $R^{14}$ and $R^{15}$, except that the heterocyclic ring has at least one —COOH group thereon; and
$R^{14cc}$ and $R^{15bb}$ represent a 5- to 10-membered saturated or unsaturated heterocyclic group the same as defined for the above described $R^{14}$ and $R^{15}$, except that the heterocyclic ring has at least one —CONR$^{26}$R$^{27}$ group thereon;
wherein $R^{26}$ and $R^{27}$ are the same as described above.

The reaction of the compound (1iiii) with the compound (57) is carried out under reaction conditions similar to those of the reaction of the compound (1b) with the compound (6) of the above described reaction formula 2.

[Reaction formula 32]

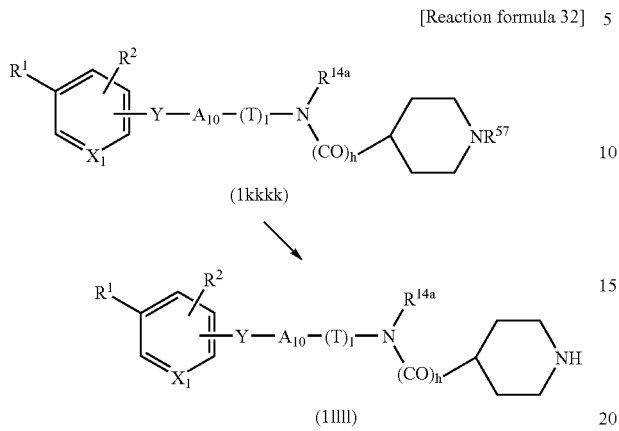

(1kkkk)

(1llll)

In the formula, $R^1$, $R^2$, $X_1$, Y, T, l, $R^{14a}$ and $A_{10}$ are the same as described above, provided that the a and b of $A_{10}$ are bound to Y and (T)l, respectively;

h represents 0 or 1; and
$R^{57}$ represents a lower alkoxycarbonyl group.

The reaction which converts the compound (1kkkk) into the compound (1llll) may be carried out under reaction conditions similar to those of the hydrolysis B described for the above described reaction formula 9.

[Reaction formula 33]

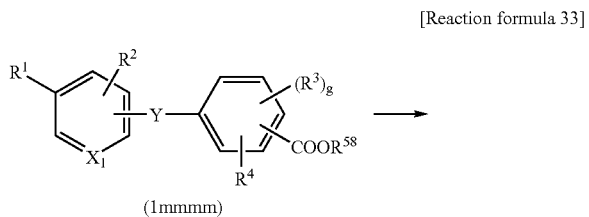

(1mmmm)

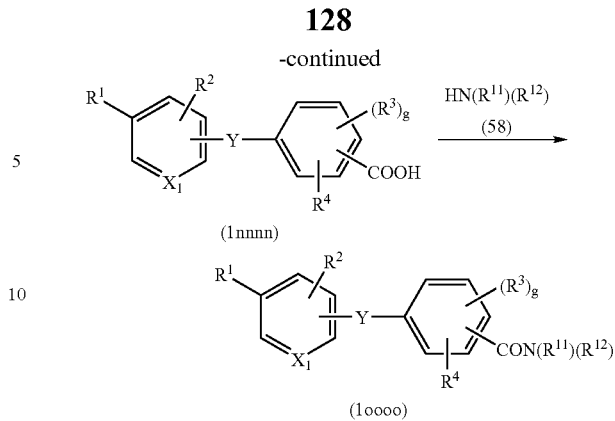

(1nnnn)

(1oooo)

In the formula, $R^1$, $R^2$, $X_1$, $R^3$, $R^4$, Y, $R^{11}$ and $R^{12}$ are the same as described above, $R^{58}$ represents a lower alkyl group, and g represents 0 or 1.

The reaction which converts the compound (1mmmm) into the compound (1nnnn) may be carried out under reaction conditions similar to those of the hydrolysis B described for the above described reaction formula 9.

The reaction of the compound (1nnnn) with the compound (58) is carried out under reaction conditions similar to those of the reaction of the compound (1b) with the compound (6) of the above described reaction formula 2.

[Reaction formula 34]

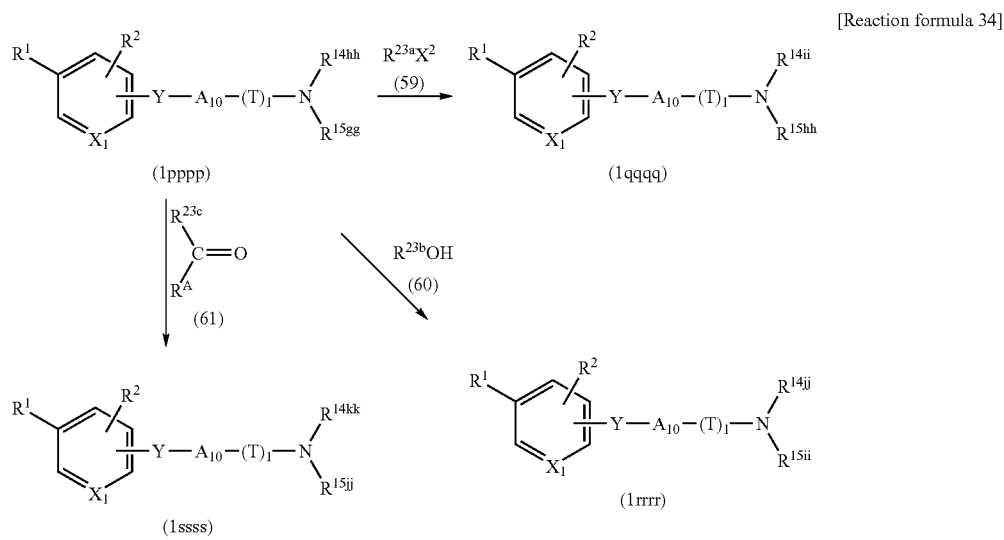

In the formula, $R^1$, $R^2$, $X_1$, Y, T, l, $A_{10}$ and $X_2$ are the same as described above, provided that the a and b of $A_{10}$ are bound to Y and (T)l, respectively;
$R^{14hh}$ and $R^{15gg}$ represent a 5- to 10 membered saturated or unsaturated heterocyclic group the same as defined for the above described $R^{14}$ and $R^{15}$, except that the heterocyclic ring has at least one —(CO)o-$B_{13}$NH($R^{22a}$) group thereon;
$R^{14ii}$ and $R^{15hh}$ represent a 5- to 10-membered saturated or unsaturated heterocyclic group the same as defined for the above described $R^{14}$ and $R^{15}$, except that the heterocyclic ring has at least one —(CO)o-$B_{13}$N($R^{22a}$)$R^{23a}$ group thereon;
$R^{14jj}$ and $R^{15ii}$ represent a 5- to 10-membered saturated or unsaturated heterocyclic group the same as defined for the above described $R^{14}$ and $R^{15}$, except that the heterocyclic ring has at least one —(CO)o-$B_{13}$N($R^{22a}$)$R^{23b}$ group thereon;
$R^{14kk}$ and $R^{15jj}$ represent a 5- to 10-membered saturated or unsaturated heterocyclic group the same as defined for the above described $R^{14}$ and $R^{15}$, except that the heterocyclic ring has at least one —(CO)o-$B_{13}$N($R^{22a}$)(CHR$^A$R$^{23c}$) group thereon, wherein $R^A$, $B_{13}$ and o are the same as described above;

$R^{22a}$ is a hydrogen atom, a lower alkyl group, a benzoyl group which may have 1 to 3 lower alkoxy groups as substituents on the phenyl ring, a phenoxy lower alkyl group which may have a lower alkyl group as a substituent on the phenyl ring, a phenyl lower alkyl group or a phenyl group;

$R^{23a}$ represents a lower alkyl group, a phenoxy lower alkyl group which may have a lower alkyl group as a substituent on the phenyl ring, a phenyl lower alkyl group or a phenyl group;

$R^{23b}$ represents a benzoyl group which may have 1 to 3 lower alkoxy groups as substituents on the phenyl ring; and $R^{23c}$ represents a hydrogen atom, a lower alkyl group, a phenoxy lower alkyl group which may have a lower alkyl group as a substituent on the phenyl ring, a phenyl lower alkyl group or a phenyl group; provided that the alkyl moiety of the —CHR$^A$R$^{23c}$ group in the side chain (—(CO)o-$B_{13}$—N($R^{22a}$)(CHR$^A$R$^{23c}$)) of the compound (1ssss) has not more than 6 carbon atoms.

The reaction of the compound (1pppp) with the compound (59) is carried out under reaction conditions similar to those of the reaction of the compound (1b) with the compound (4) of the above described reaction formula 2.

The reaction of the compound (1pppp) with the compound (61) is carried out under reaction conditions similar to those of the reaction of the compound (1b) with the compound (5) of the above described reaction formula 2.

The reaction of the compound (1pppp) with the compound (60) is carried out under reaction conditions similar to those of the reaction of the compound (1b) with the compound (6) of the above described reaction formula 2.

above described $R^{14}$ and $R^{15}$, except that the heterocyclic ring has at least one —(O—$B_{15}$)s-CON($R^{26a}$)($R^{27a}$) group thereon;

$R^{14nn}$ and $R^{15mm}$ represent a 5- to 10-membered saturated or unsaturated heterocyclic group the same as defined for the above described $R^{14}$ and $R^{15}$, except that the heterocyclic ring has at least one —(O—$B_{15}$)s-CON($R^{26a}$)(CHR$^A$R$^{27b}$) group, wherein $B_{15}$, s and $R^A$ are the same as described above;

$R^{26a}$ represents a hydrogen atom, a lower alkyl group, a phenyl lower alkyl group or an imidazolyl lower alkyl group;

$R^{27a}$ represents a lower alkyl group, a phenyl lower alkyl group or an imidazolyl lower alkyl group; and $R^{27b}$ represents a hydrogen atom, a lower alkyl group, a phenyl lower alkyl group, a phenyl group, an imidazolyl group or an imidazolyl lower alkyl group;

provided that the alkyl moiety of the —CHR$^A$R$^{27b}$ group in the side chain (—(O—$B_{15}$)s-CO($R^{26a}$)(CHR$^A$R$^{27b}$)) of the compound (1vvvv) has not more than 6 carbon atoms.

The reaction of the compound (1tttt) with the compound (62) is carried out under reaction conditions similar to those of the reaction of the compound (1b) with the compound (4) of the above described reaction formula 2.

The reaction of the compound (1tttt) with the compound (63) is carried out under reaction conditions similar to those of the reaction of the compound (1b) with the compound (5) of the above described reaction formula 2.

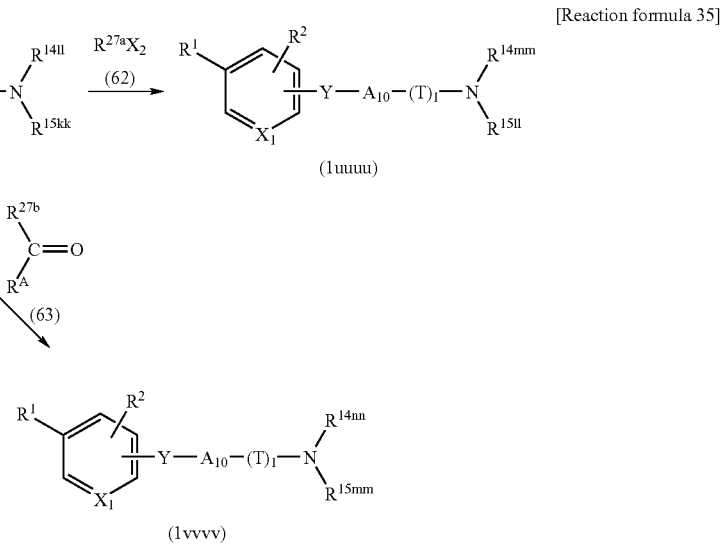

[Reaction formula 35]

In the formula, $R^1$, $R^2$, $X_1$, Y, T, l, $A_{10}$ and $X_2$ are the same as described above, provided that the a and b of $A_{10}$ are bound to Y and (T)l, respectively;

$R^{14ll}$ and $R^{15kk}$ represent a 5- to 10-membered saturated or unsaturated heterocyclic group the same as defined for the above described $R^{14}$ and $R^{15}$, except that the heterocyclic ring has at least one —(O—$B_{15}$)s-CONH($R^{26a}$) group thereon;

$R^{14mm}$ and $R^{15ll}$ represent a 5- to 10-membered saturated or unsaturated heterocyclic group the same as defined for the

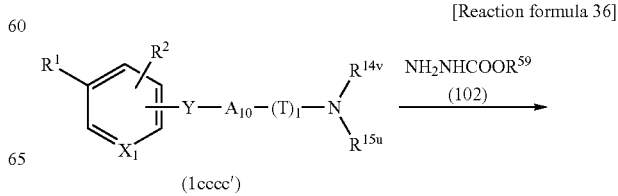

[Reaction formula 36]

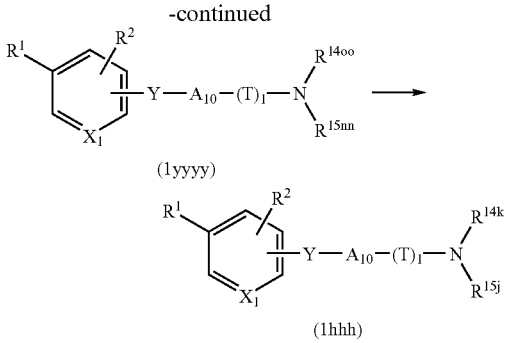

(1yyyy)

(1hhh)

In the formula, $R^1, R^2, X_1, Y, T, l, A_{10}, R^{14v}, R^{15u}, R^{14k}$ and $R^{14j}$ are the same as described above, provided that the a and b of $A_{10}$ are bound to Y and (T)l, respectively;
$R^{59}$ represents a lower alkyl group; and
$R^{14oo}$ and $R^{15nn}$ represent a 5- to 10-membered saturated or unsaturated heterocyclic group the same as defined for the above described $R^{14}$ and $R^{15}$, except that the heterocyclic ring has at least one —$B_{21}$CONHNHCOOR$^{59}$ group, wherein $B_{21}$ is the same as described above.

The reaction of the compound (1cccc') with the compound (102) is carried out under reaction conditions similar to those of the reaction of the compound (1b) with the compound (6) of the above described reaction formula 2.

The reaction which converts the compound (1yyyy) into the compound (1hhh) may be carried out under reaction conditions similar to those of the hydrolysis B described for the above described reaction formula 9.

The compound of the present invention of the general formula (1) having various $R^1$s is produced, for example, as shown by the following reaction formulas 37 to 46.

reaction of the compound (1b) with the compound (4) of the above described reaction formula 2.

The reaction of the compound (19) with the compound (21) is carried out under reaction conditions similar to those of the reaction of the compound (1b) with the compound (5) of the above described reaction formula 2.

The reaction of the compound (19) with the compound (22) is carried out under reaction conditions similar to those of the reaction of the compound (1b) with the compound (6) of the above described reaction formula 2.

[Reaction formula 38]

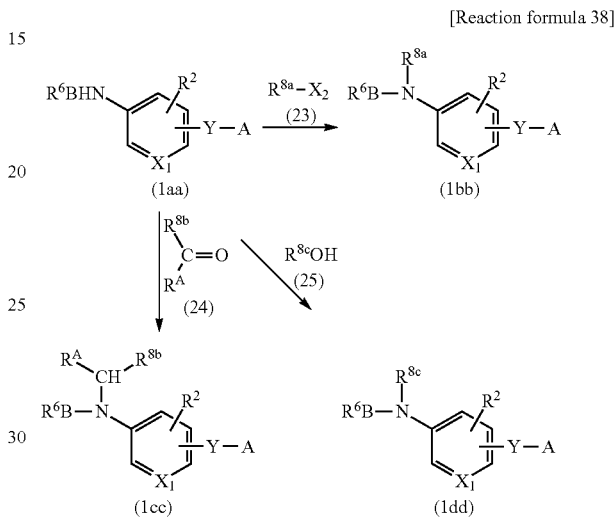

[Reaction formula 37]

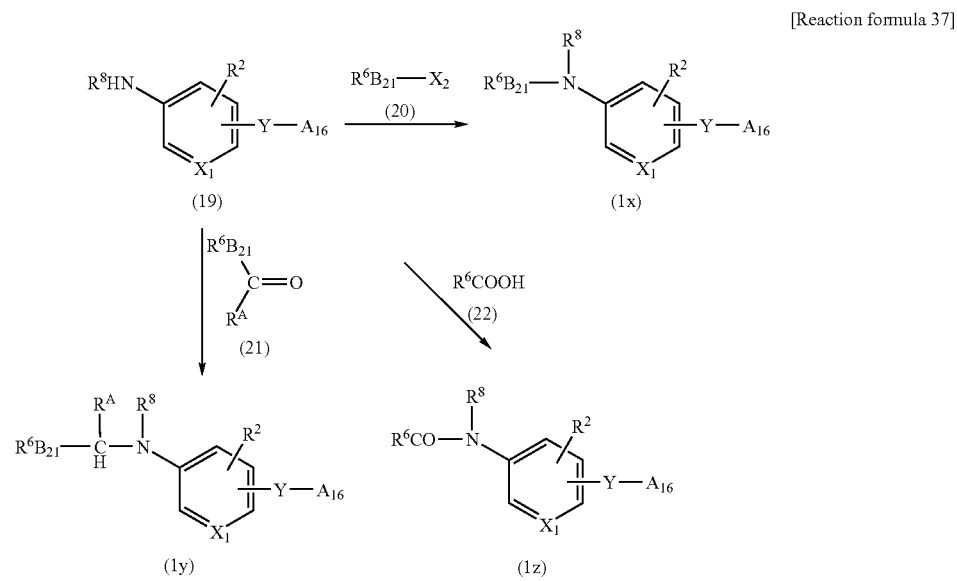

In the formula, $R^2, X_1, Y, A_{16}, R^6, R^6, B_{21}, R^A$ and $X_2$ are the same as described above, provided that the $B_{21}$CHR$^A$ moiety of the ($R^6$—$B_{21}$CHR$^A$—) group of the compound (1y) has not more than 6 carbon atoms.

The reaction of the compound (19) with the compound (20) is carried out under reaction conditions similar to those of the In the formula, $R^2, X_1, Y, A, R^6, B, R^A$ and $X_2$ are the same as described above, $R^{8a}$ represents a lower alkyl group which may have a lower alkoxy group as a substituent, a lower alkylsulfonyl group or a phenyl lower alkyl group, $R^{8b}$ represents a hydrogen atom, a phenyl group, phenyl lower alkyl group or a lower alkyl group which may have a lower alkoxy group as a substituent, and $R^{8c}$ represents a lower alkanoyl group, provided that the alkyl moiety of the —CHR$^A$R$^{8b}$ group of the compound (1cc) has not more than 6 carbon atoms.

The reaction of the compound (1aa) with the compound (23) is carried out under reaction conditions similar to those of the reaction of the compound (1b) with the compound (4) of the above described reaction formula 2.

The reaction of the compound (1aa) with the compound (24) is carried out under reaction conditions similar to those of the reaction of the compound (1b) with the compound (5) of the above described reaction formula 2.

The reaction of the compound (1aa) with the compound (25) is carried out under reaction conditions similar to those of the reaction of the compound (1b) with the compound (6) of the above described reaction formula 2.

[Reaction formula 39]

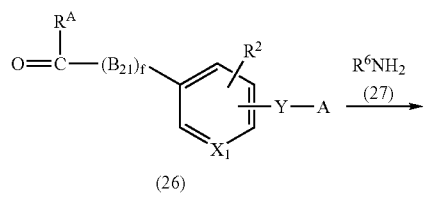

(26)

the (—(B$_{21}$)fCHR$^A$NHR$^6$) group of the compound (1ee) has not more than 6 carbon atoms.

The reaction of the compound (26) with the compound (27) is carried out under reaction conditions similar to those of the reaction of the compound (1b) with the compound (5) of the above described reaction formula 2.

[Reaction formula 40]

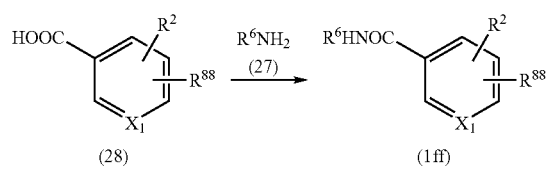

(28) → (1ff)

In the formula, R$^{88}$ represents a —Y-A group or a halogen atom, and R$^2$, X$_1$, Y, A, and R$^6$, are the same as described above.

The reaction of the compound (28) with the compound (27) is carried out under reaction conditions similar to those of the reaction of the compound (1b) with the compound (6) of the above described reaction formula 2.

[Reaction formula 41]

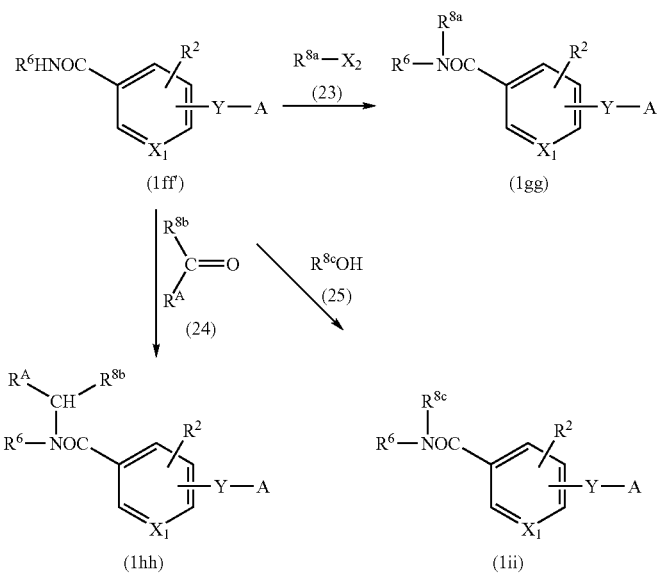

-continued

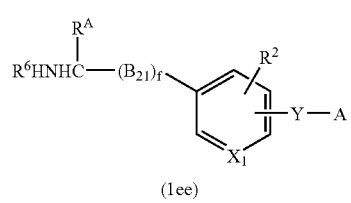

(1ee)

In the formula, R$^2$, X$_1$, Y, A, B$_{21}$, f, R$^A$ and R$^6$ are the same as described above, provided that the (B$_{21}$)fCHR$^A$ moiety of In the formula, R$^2$, X$_1$, Y, A, R$^6$, R$^{8a}$, R$^{8b}$, R$^{8c}$, R$^A$ and X$_2$ are the same as described above, provided that the alkyl moiety of the —CHR$^A$R$^{8b}$ group of the compound (1hh) has not more than 6 carbon atoms.

The reaction of the compound (1ff') with the compound (23) is carried out under reaction conditions similar to those of the reaction of the compound (1b) with the compound (4) of the above described reaction formula 2.

The reaction of the compound (1ff') with the compound (24) is carried out under reaction conditions similar to those of the reaction of the compound (1b) with the compound (5) of the above described reaction formula 2.

The reaction of the compound (1ff) with the compound (25) is carried out under reaction conditions similar to those of the reaction of the compound (1b) with the compound (6) of the above described reaction formula 2.

[Reaction formula 42]

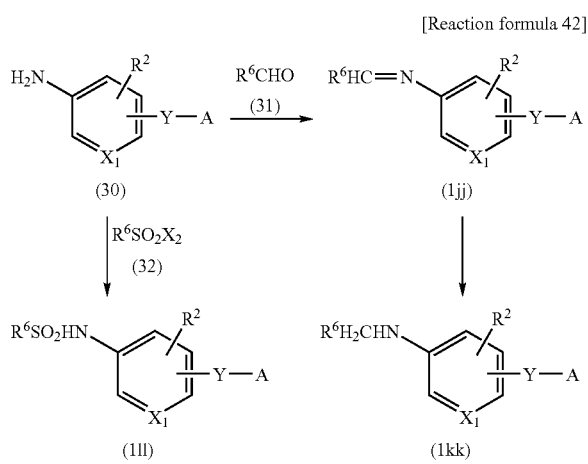

In the formula, $R^2$, $X_1$, Y, A, $R^6$ and $X_2$ are the same as described above.

The reaction which converts the compound (30) into the compound (1jj) may be carried out under reaction conditions similar to those of the reaction which converts the compound (1f) into the compound (1h) of the above described reaction formula 3.

The reaction which converts the compound (1jj) into the compound (1kk) may be carried out under reaction conditions similar to those of the reaction of the compound (1b) with the compound (5) of the above described reaction formula 2.

The reaction of the compound (30) with the compound (32) is carried out under reaction conditions similar to those of the reaction of the compound (1b) with the compound (4) of the above described reaction formula 2.

[Reaction formula 43]

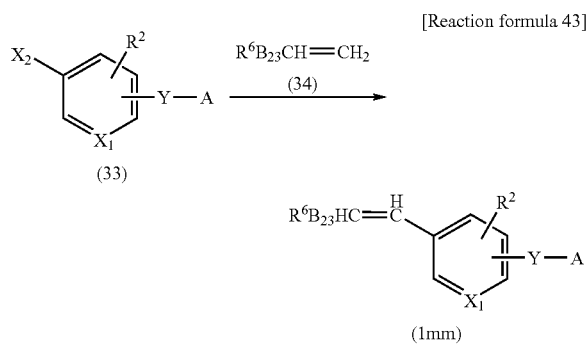

In the formula, $R^2$, $X_1$, Y, A, $X_2$ and $R^6$ are the same as described above, $B_{23}$ represents a lower alkylene group or a lower alkenylene group, and the $B_{23}$—HC=CH— moiety in the side chain ($R^6B_{23}$—HC=CH—) in the compound (1mm) has 1 to 3 double bonds and has not more than 6 carbon atoms.

The reaction of the compound (33) with the compound (34) is carried out in an appropriate inert solvent and in the presence of a condensation agent.

Examples of the inert solvent used in the above described reaction include aromatic hydrocarbons such as benzene, toluene, and xylene, ethers such as diethyl ether, tetrahydrofuran, dioxane, monoglyme, and diglyme, halogenated hydrocarbons such as dichloromethane, dichloroethane, chloroform, and carbon tetrachloride, lower alcohols such as methanol, ethanol, isopropanol, butanol, tert-butanol, and ethylene glycol, fatty acids such as α-dimethylaminoacetic acid and acetic acid, esters such as ethyl acetate and methyl acetate, ketones such as acetone and methyl ethyl ketone, acetonitrile, 1-methyl-2-pyrrolidone, pyridine, dimethyl sulfoxide, dimethylformamide, and hexamethylphosphoric acid triamide, and a mixture thereof.

Examples of the condensation agent include palladium complexes such as bis(benzonitrile)dichloropalladium (II).

The condensation agent is appropriately used in an amount typically 0.01 to 1 times, and preferably 0.01 to 0.5 times of the compound (33) on a molar basis.

The above described reaction favorably proceeds typically at 0 to 200° C., and preferably at about room temperature to about 150° C. and is, in general, completed in about 10 minutes to 20 hours.

The above described reaction proceeds advantageously by adding a alkali metal salt of fatty acid such as sodium acetate to the reaction system.

[Reaction formula 44]

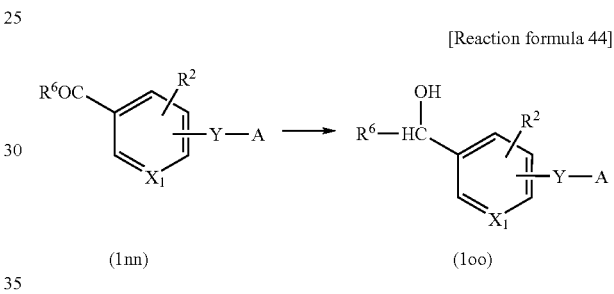

In the formula, $R^{26}$, $X_1$, Y, A and $R^6$ are the same as described above.

The reaction which converts the compound (1nn) into the compound (1oo) may be carried out under reaction conditions similar to those of the reaction which converts the compound (1f) into the compound (1g) of the above described reaction formula 3.

[Reaction formula 45]

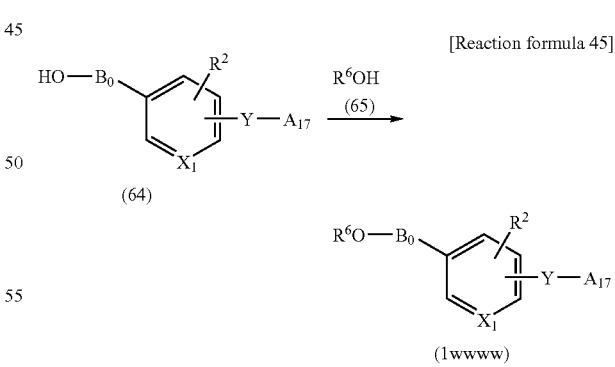

In the formula, $A_{17}$ represents a group of the formula:

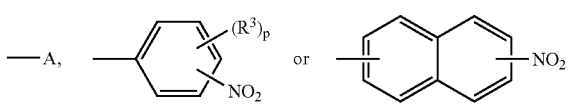

wherein $R^2$, $R^3$, p, $X_1$, Y, A, Bo and $R^6$ are the same as described above.

The reaction of the compound (64) with the compound (65) is carried out in an appropriate solvent in the presence of a condensation agent.

Any of the solvents, which are used in the reaction of carboxylic acid halide with amine (1b) by the method (d) of the formula 2 for reacting the compound (1b) with the compound (6) (reaction which produces an amide bond), may be used in this reaction.

Examples of the condensation agent used include a mixture of an azocarboxylate (such as diethyl azodicarboxylate) with a phosphorus compound (such as triphenylphosphine).

The condensation agent is appropriately used in an amount typically at least equimolar to the compound (64), and preferably 1 to 2 times of the compound (64) on a molar basis.

The compound (65) is appropriately used in an amount typically at least equimolar to the compound (64), and preferably 1 to 2 times of the compound (64) on a molar basis.

The above described reaction favorably proceeds typically at 0 to 200° C., preferably at around 0 to 150° C. and is, in general, completed in around 1 to 10 hours.

[Reaction formula 46]

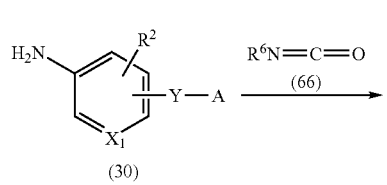

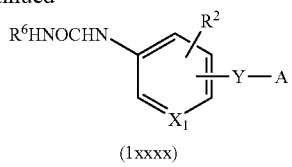

(1xxxx)

In the formula, $R^2$, $X_1$, Y, A, and $R^6$ are the same as described above.

The reaction of the compound (30) with the compound (66) is carried out in the presence or absence of a basic compound, and preferably in the absence of the basic compound in an appropriate solvent or without a solvent.

Any of the inert solvents and the basic compounds, which are used in the reaction of carboxylic acid halide with amine (1b) by the method (d) of the formula 2 for reacting the compound (1b) with the compound (6) (reaction which produces an amide bond), may be used in this reaction.

The compound (66) may be used in an amount typically at least about 1 to 5 times, and preferably about 1 to 3 times of the compound (30) on a molar basis.

The above described reaction is carried out typically at 0 to 200° C., and preferably at around room temperature to 150° C. and is, in general, completed in around 5 minutes to 50 hours.

A boron compound such as a boron trifluoride-diethyl ether complex may be added to the system of the above described reaction.

[Reaction formula 47]

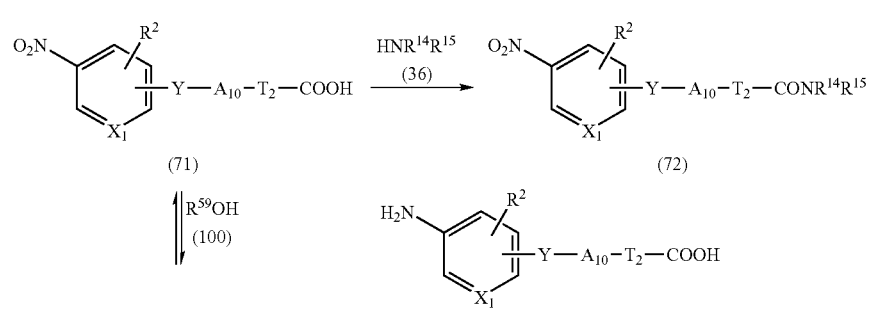

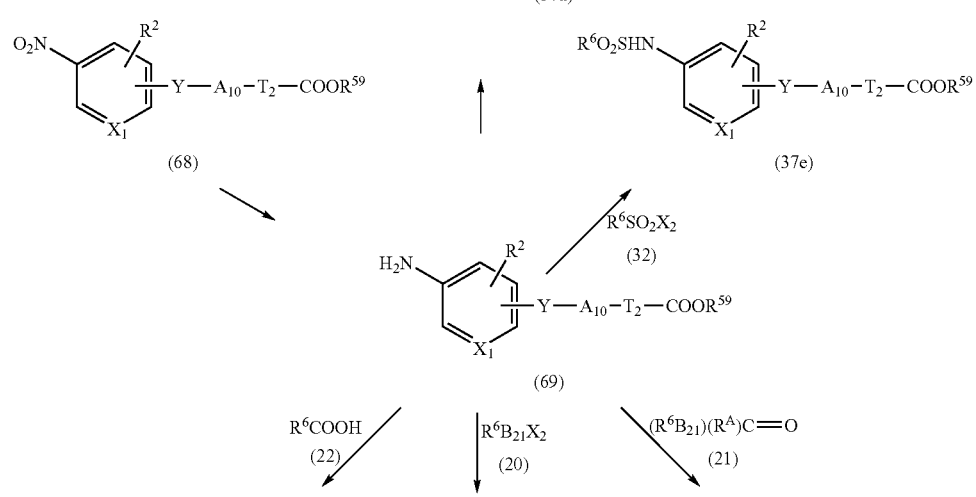

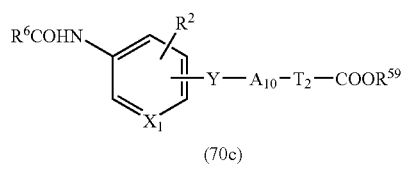 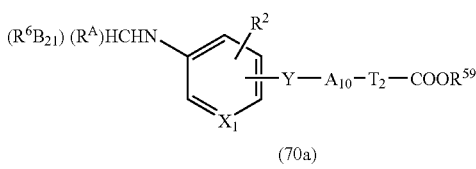

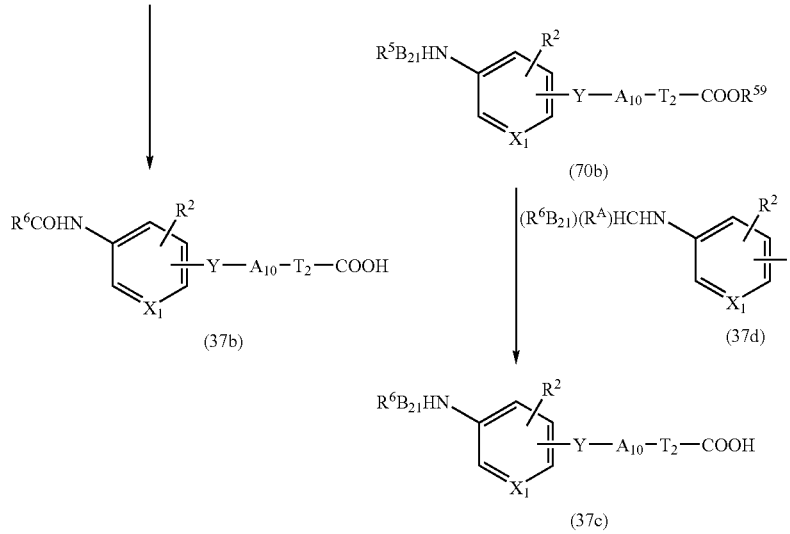

In the formula, $R^2$, $X_1$, $Y$, $T_2$, $A_{10}$, $R^{14}$, $R^{15}$, $B_{21}$, $R^A$, $X_2$, $R^6$ and $R^{59}$ are the same as described above, provided that the a and b of $A_{10}$ are bound to Y and $T_2$, respectively.

The reaction which converts the compound (68) into the compound (71) may be carried out under reaction conditions similar to those of the hydrolysis B described for the above described reaction formula 9.

The reaction of the compound (71) with the compound (100) is carried out under reaction conditions similar to those of the reaction of the compound (1fff) with the compound (43) in formula 20 as described above.

The compound (68) may also be produced using a halogenated lower alkyl group such as methyl iodide in place of the compound (100) in a reaction similar to the reaction of the compound (2) with the compound (3) of the above described reaction formula 1.

The reaction which converts the compound (68) into the compound (69) may be carried out, for example, (1) by reducing the compound (0.68) with a catalytic hydride reducing agent in an appropriate solvent, or (2) by reducing the compound (68) with a reducing agent such as a mixture of a metal or a metal salt with an acid, or a mixture of a metal or a metal salt with an alkali metal hydroxide, a sulfide, an ammonium salt or the like, in an appropriate inert solvent.

Examples of the solvent in using the method (1) include water, acetic acid, alcohols such as methanol, ethanol, and isopropanol, hydrocarbons such as n-hexane and cyclohexane, ethers such as dioxane, tetrahydrofuran, diethyl ether, and diethylene glycol dimethyl ether, esters such as ethyl acetate and methyl acetate, and aprotic polar solvents such as N,N-dimethylformamide, and a mixture thereof. Examples of the catalytic hydride reducing agent used include palladium, palladium black, palladium-carbon, platinum-carbon, platinum, platinum oxide, copper chromite, and Raney nickel. These reducing agents may be used singly or in a mixture of two or more. In general, the reducing agent may be used in an amount 0.02 to 1 times of the compound (68) on a weight basis. The reaction temperature is typically about −20 to 150° C., and preferably about 0 to 100° C., and the hydrogen pressure is typically at 1 to 10 atm. In general, the above described reaction is completed in about 0.5 to 100 hours. An acid such as hydrochloric acid may be added to the above described reaction system.

The reducing agent which may be used in using the method (2) is a mixture of iron, zinc, tin or stannous chloride with a mineral acid such as hydrochloric acid or sulfuric acid; or a mixture of iron, ferrous sulfate, zinc or tin with an alkali metal hydroxide such as sodium hydroxide, a sulfate such as ammonium sulfate or an ammonium salt such as ammonium hydroxide or ammonium chloride. Examples of the inert solvent include water, acetic acid, alcohols such as methanol and ethanol, and ethers such as dioxane, and a mixture thereof. The reaction conditions may be chosen appropriately depending on the reducing agent used. For example, when stannous chloride or hydrochloric acid is used as the reducing agent, the reaction is appropriately carried out advantageously at about 0 to 150° C., and for around 0.5 to 10 hours. The above described reducing agent is used in an amount at least equal molar to the compound (68), and typically 1 to 5 times of the compound (68) on a molar basis.

The reaction of the compound (69) with the compound (20) is carried out under reaction conditions similar to those of the reaction of the compound (1b) with the compound (4) of the above described reaction formula 2.

The reaction of the compound (69) with the compound (22) is carried out under reaction conditions similar to those of the reaction of the compound (1b) with the compound (6) of the above described reaction formula 2.

The reaction of the compound (69) with the compound (21) is carried out under reaction conditions similar to those of the reaction of the compound (1b) with the compound (5) of the above described reaction formula 2.

The reaction which converts the compound (69) into the compound (37a), the reaction which converts the compound (70a) into the compound (37d), the reaction which converts the compound (70b) into the compound (37c) and the reaction which converts the compound (70c) into the compound (37b) may be carried out under reaction conditions similar to those of the hydrolysis B described for the above described reaction formula 9.

The reaction of the compound (71) with the compound (36) is carried out under reaction conditions similar to those of the reaction of the compound (1b) with the compound (6) of the above described reaction formula 2.

The reaction of the compound (69) with the compound (32) is carried out under reaction conditions similar to those of the reaction of the compound (30) with the compound (32) in the reaction formula 42 as described above.

The reaction of the compound (72a) with the compound (74) is carried out under reaction conditions similar to those of the reaction of the compound (1b) with the compound (5) of the above described reaction formula 2.

[Reaction formula 49]

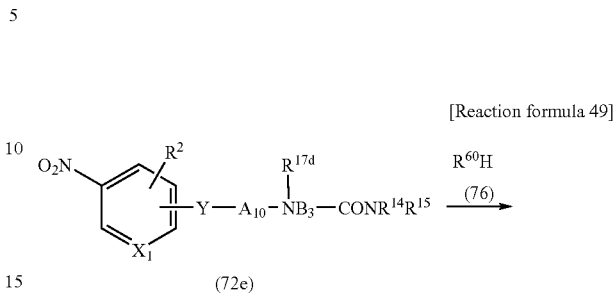

(72e)

[Reaction formula 48]

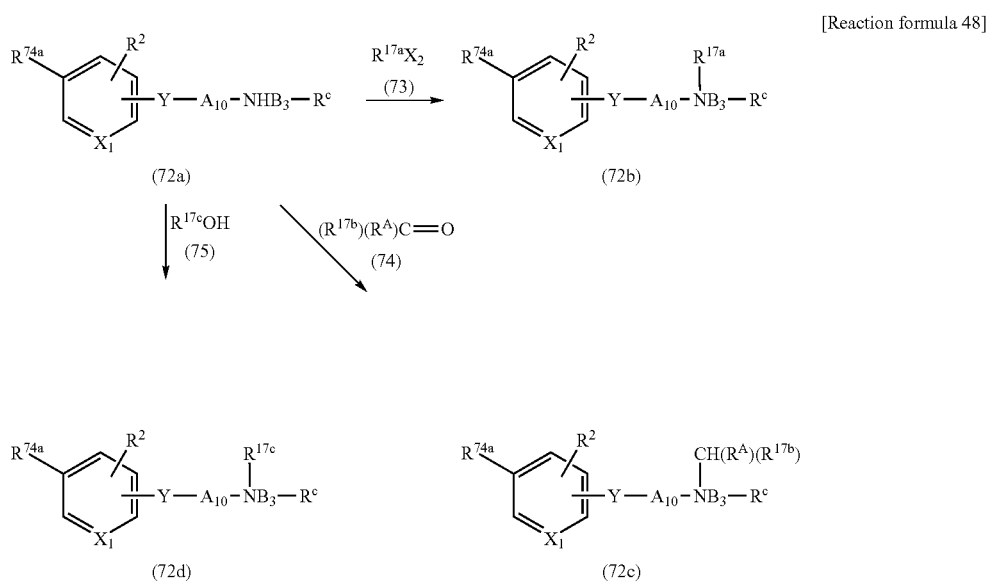

In the formula, $R^2$, $X_1$, $Y$, $A_{10}$, $B_3$, $R^{14}$, $R^{15}$, $R^A$, $R^{74a}$ and $X_2$ are the same as described above;
$R^C$ represents a —$CONR^{14}R^{15}$ group or —$COOR^{59b}$ group, $R^{59b}$ represents a lower alkyl group or a phenyl lower alkyl group;
$R^{17a}$ represents a lower alkyl group, a cycloalkyl group, a lower alkyl sulfonyl group or a lower alkenyl group;
$R^{17b}$ represents a hydrogen atom or a lower alkyl group; and
$R^{17c}$ represents a cycloalkylcarbonyl group, a lower alkanoyl group which may have a halogen atom as a substituent or an amino substituted lower alkanoyl group which may have a lower alkyl group as a substituent; wherein the a of $A_{10}$ is bound to the Y group and the b is bound to an —$NHB_3$—$Rc$ group, —$N(R^{17a})B_3$—$Rc$ group, —$N(CH(R^A)(R^{17b}))B_3$—$Rc$ group or —$N(R^{17c})B_3$—$Rc$ group.

The reaction of the compound (72a) with the compound (73) is carried out under reaction conditions similar to those of the reaction of the compound (1b) with the compound (4) of the above described reaction formula 2.

The reaction of the compound (72a) with the compound (75) is carried out under reaction conditions similar to those of the reaction of the compound (1b) with the compound (6) of the above described reaction formula 2.

-continued

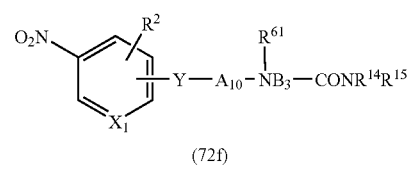

(72f)

In the formula, $R^2$, $X_1$, $Y$, $A_{10}$, $B_3$, $R^{14}$ and $R^{15}$ are the same as described above, $R^{17d}$ represents a lower alkanoyl group which is substituted with a halogen atom, $R^{60}$ represents an amino group which may be substituted with a lower alkyl group, and $R^{61}$ represents an amino substituted lower alkanoyl group which may be substituted with a lower alkyl group, wherein the a of $A_{10}$ is bound to the Y group and the b is bound to an —$N(R^{17d})B_3$—$CONR^{14}R^{15}$ group or —$NR^{61}B_3$—$CONR^{14}R^{15}$ group.

The reaction of the compound (72e) with the compound (76) is carried out under reaction conditions similar to those of the reaction of the compound (2) with the compound (3) in the reaction formula 1 as described above.

[Reaction formula 50]

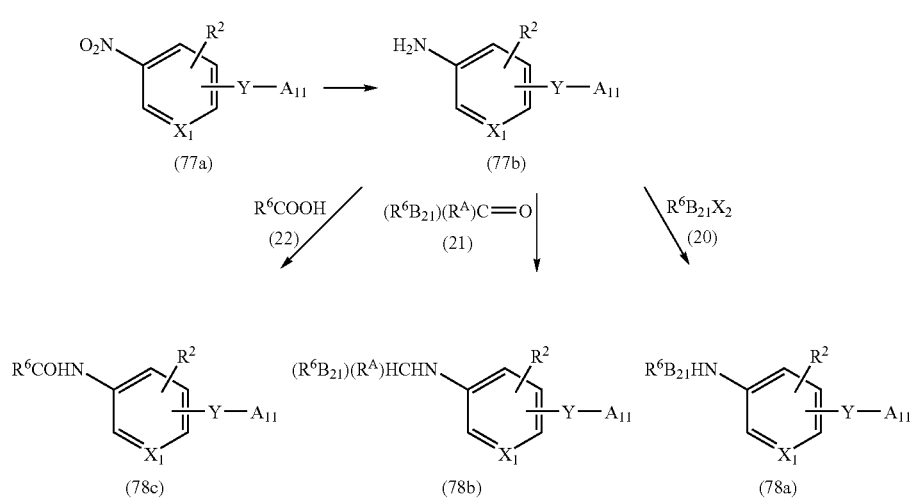

In the formula, $R^2$, $X_1$, $Y$, $R^6$, $B_{21}$, $R^A$ and $X_2$ are the same as described above, and A11 represents a group of the formula:

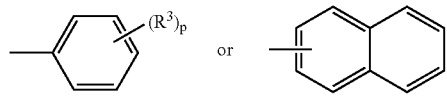

wherein $R^3$ and p are the same as described above, provided that the alkyl moiety in the side chain (—NHCH($R^A$)($B_{21}R^6$) group) of the compound (78b) has not more than 6 carbon atoms.

The reaction which converts the compound (77a) into the compound (77b) may be carried out under reaction conditions similar to those of the reaction which converts the compound (68) into the compound (69) of the above described reaction formula 47.

The reaction of the compound (77b) with the compound (20) is carried out under reaction conditions similar to those of the reaction of the compound (1b) with the compound (4) of the above described reaction formula 2.

The reaction of the compound (77b) with the compound (22) is carried out under reaction conditions similar to those of the reaction of the compound (1b) with the compound (6) of the above described reaction formula 2.

The reaction of the compound (77b) with the compound (21) is carried out under reaction conditions similar to those of the reaction of the compound (1b) with the compound (5) of the above described reaction formula 2.

[Reaction formula 51]

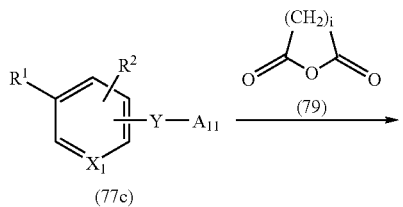

-continued

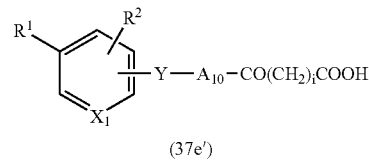

In the formula, $R^1$, $R^2$, $X_1$, $Y$ and $A_{11}$ are the same as described above, and i represents an integer of 2 to 4.

In general, the reaction of the compound (77c) with the compound (79) is called Friedel-Crafts reaction and is carried out in an appropriate solvent in the presence of a Lewis acid.

Any of the Lewis acids typically used in the Friedel-Crafts reaction may be used here. Examples of these Lewis acids include aluminum chloride, zinc chloride, iron chloride, tin chloride, boron tribromide, and concentrated sulfuric acid. These Lewis acids are used singly or in a mixture of two or more. The Lewis acid is used typically in an amount 2 to 6 times of the compound (77c) on a molar basis.

Examples of the solvent used here include aromatic hydrocarbons such as carbon disulfide, nitrobenzene, and chlorobenzene, and halogenated hydrocarbons such as dichloromethane, dichloroethane, carbon tetrachloride, and tetrachloroethane, and a mixture thereof.

The compound (79) is typically used in an amount at least equimolar to the compound (77c), and preferably 1 to 5 times of the compound (77c) on a molar basis.

Typically the above described reaction proceeds favorably at 0 to 120° C., and preferably about 0 to 70° C., and is generally completed in about 0.5 to 24 hours.

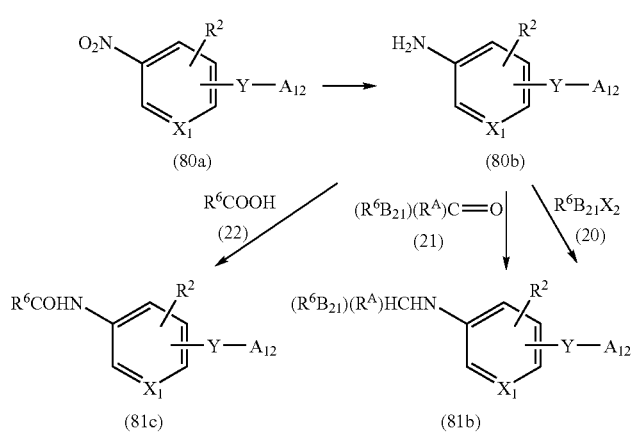

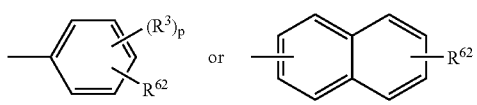

In the formula, $R^2$, $X_1$, Y, $R^6$, $X_2$, $B_{21}$ and $R^A$ are the same as described above. $A_{12}$ represents a group of the formula:

$R^3$ and p are the same as defined above, and $R^{62}$ represents a lower alkanoyl group or a hydroxyl group substituted lower alkyl group, provided that the alkyl moiety in the side chain (NHCH($R^A$)($B_{21}R^6$) group) of the compound (81b) has not more than 6 carbon atoms.

The reaction which converts the compound (80a) into the compound (80b) is carried out under reaction conditions similar to those of the reaction which converts the compound (68) into the compound (69) of the above described reaction formula 47.

The reaction of the compound (80b) with the compound (20) is carried out under reaction conditions similar to those of the reaction of the compound (1b) with the compound (4) of the above described reaction formula 2.

The reaction of the compound (80b) with the compound (22) is carried out under reaction conditions similar to those of the reaction of the compound (1b) with the compound (6) of the above described reaction formula 2.

The reaction of the compound (80b) with the compound (21) is carried out under reaction conditions similar to those of the reaction of the compound (1b) with the compound (5) of the above described reaction formula 2.

[Reaction formula 53]

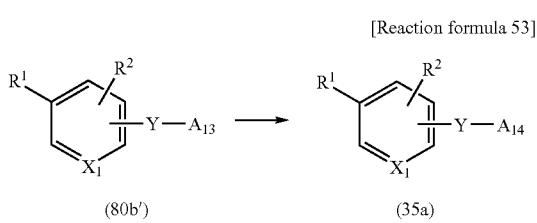

In the formula, $R^1$, $R^2$, $X_1$, and Y are the same as above, $A_{13}$ represents a group of the formula:

[Reaction formula 52]

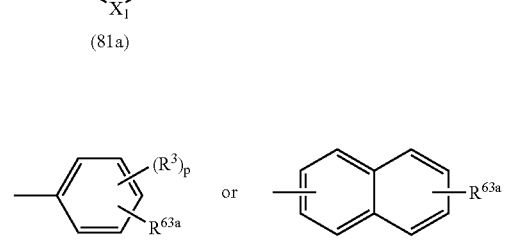

wherein $R^3$ and p are the same as described above, and $R^{63a}$ represents a lower alkanoyl group or a lower alkyl group, and $A_{14}$ represents a group of the formula:

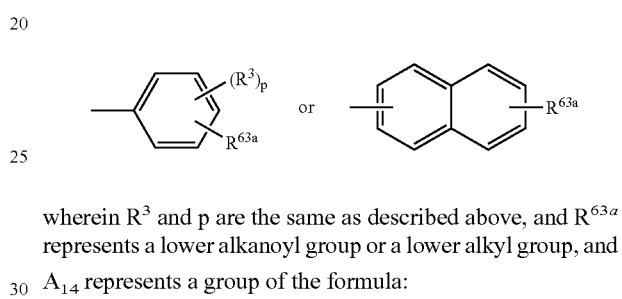

wherein $R^{63b}$ represents a lower alkanoyl group which is substituted with a halogen atom at the α-position or a lower alkyl group which is substituted with a halogen atom at the 2 position.

The reaction which converts the compound (80b') into the compound (35a) is carried out in the presence of a halogenating agent in an appropriate solvent.

Examples of the halogenating agent include halogen atoms such as bromine and chlorine, iodine chloride, sulfuryl chloride, copper compounds such as cupric bromide, and N-halogenated succinic acid imides such as N-bromosuccinic acid imide and N-chlorosuccinic acid imide.

Examples of the solvent used include halogenated hydrocarbons such as dichloromethane, dichloroethane, chloroform, and carbon tetrachloride, fatty acids such as acetic acid and propionic acid, and carbon disulfide.

The halogenated agent is appropriately used in an amount typically 1 to 10 times, and preferably 1 to 5 times of the compound (80b') on a molar basis.

The above described reaction is carried out typically at 0° C. to the boiling point of the solvent, and preferably at about 0 to 100° C., and is completed typically in about 5 minutes to 30 hours.

When an N-halogenated succinic acid imide is used as a halogenated agent, a peroxide such as benzoyl peroxide may be added to the reaction system as a initiator for the radical reaction.

[Reaction formula 54]

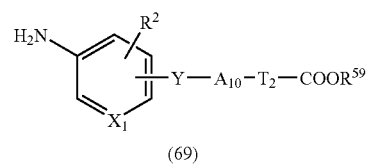

(69)

↓ R⁶⁴OH (82)

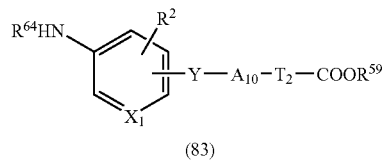

(83)

R⁸ᶜOH (25) ↙   R⁸ᵃX₂ (23) ↓   (R⁸ᵇ)(Rᴬ)C=O (24) ↘

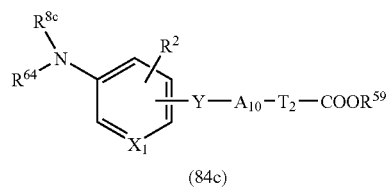

(84c)

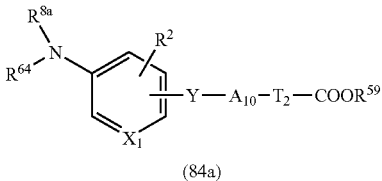

(84a)

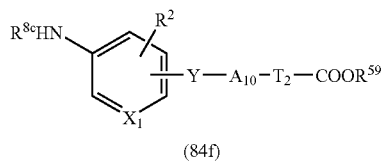

(84f)

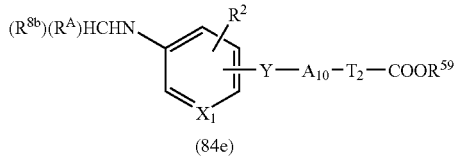

(84b)

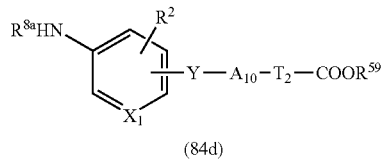

(84d)

In the formula, $R^2$, $X_1$, Y, $A_{10}$, $T_2$, $R^{59}$, $R^{8a}$, $R^{8b}$, $R^{8c}$, $X_2$ and $R^A$ are the same as described above, and $R^{64}$ represents a phenyl lower alkoxycarbonyl group, provided that the alkyl moieties in the side chain (—N(CHR$^A$R$^{8b}$)(R$^{64}$) group) of the compound (84b) and the side chain (—NH(CHR$^A$R$^{8b}$) group) of the compound (84e) have not more than 6 carbon atoms, respectively, and the a and b of $A_{10}$ are bound to the Y group and the $T_2$ group, respectively.

The reaction of the compound (83) with the compound (23) is carried out under reaction conditions similar to those of the reaction of the compound (1b) with the compound (4) of the above described reaction formula 2.

The reaction of the compound (69) with the compound (82), and the reaction of the compound (83) with the compound (25) are carried out under reaction conditions similar to those of the reaction of the compound (1b) with the compound (6) of the above described reaction formula 2.

The reaction of the compound (83) with the compound (24) is carried out under reaction conditions similar to those of the reaction of the compound (1b) with the compound (5) of the above described reaction formula 2.

The reactions which respectively convert the compound (84a) into the compound (84d), the compound (84b) into the compound (84e), and the compound (84c) into the compound (84f) are carried out under reaction conditions similar to those of the reaction which converts the compound (1iii') into the compound (1hhh') by reduction as described for the above described reaction formula 24.

[Reaction formula 55]

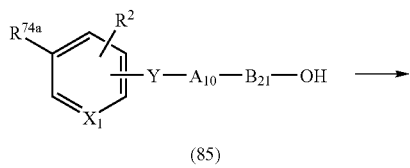

(85)

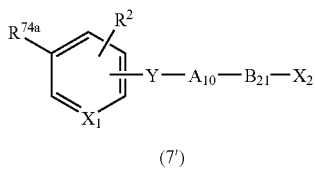

(7')

In the formula, $R^2$, $X_1$, Y, $A_{10}$, $B_{21}$, $R^4$ and $X_2$ are the same as described above, provided that the a and b of $A_{10}$ are bound to the Y group and the $B_{21}$ group, respectively.

The reaction which converts the compound (85) into the compound (7') is carried out by reacting compound (85) to a halogenating agent in an appropriate solvent or without solvent.

Examples of the halogenating agent include mineral acids such as hydrochloric acid and hydrobromic acid, N,N-diethyl-1,2,2-trichlorovinyl azide, phosphorus pentachloride, phosphorus pentabromide, phosphorus oxychloride, sulfonyl halide compounds such as thionyl chloride, mesyl chloride, and tosyl chloride, and a mixture of carbon tetra bromide with triphenylphosphine. The sulfonyl halide compound is used together with a basic compound.

Any of the basic compounds used in the reaction of the compound (2) with the compound (3) of the reaction formula 1 may be used.

Examples of the solvent used include ethers such as dioxane, tetrahydrofuran, and diethyl ether, halogenated hydrocarbons such as chloroform, methylene chloride, and carbon tetrachloride, and dimethylformamide, and a mixture thereof.

When a sulfonyl halide compound is used together with a basic compound as a halogenating agent, the sulfonyl halide compound is appropriately used in an amount typically at least equimolar to the compound (85), and preferably 1 to 2 times of the compound (85) on a molar basis. The basic compound is used typically in a catalytic amount of the compound (85), and preferably in a catalytic amount to an amount equimolar to the compound (85). When another halogenating agent is used, such a halogenating agent is used at least equimolar to the compound (85), and typically used in a large excess amount.

The above described reaction proceeds favorably typically at room temperature to 200° C., and preferably at room temperature to 150° C., and in general is completed in about 1 to 80 hours.

[Reaction formula 56]

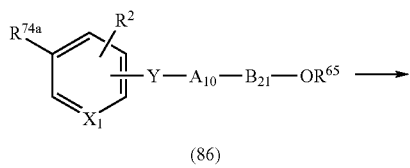

(86)

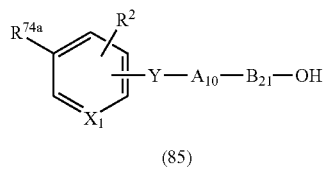

(85)

In the formula, $R^{74a}$, $R^2$, $X_1$, Y, $A_{10}$ and $B_{21}$ are the same as described above, and $R^{65}$ represents a tri-lower alkyl silyl group, provided that the a and b of $A_{10}$ are bound to the Y group and the $B_{21}$ group, respectively.

Here, examples of the tri-lower alkyl silyl group include trialkylsilyl groups of which the alkyl moiety is a linear or branched alkyl group having 1 to 6 carbon atoms such as a tert-butyldimethylsilyl group, trimethylsilyl group, and diethylmethylsilyl group.

The reaction which converts the compound (86) into the compound (85) may be carried out under reaction conditions similar to those of the hydrolysis B described for the above described reaction formula 9.

[Reaction formula 57]

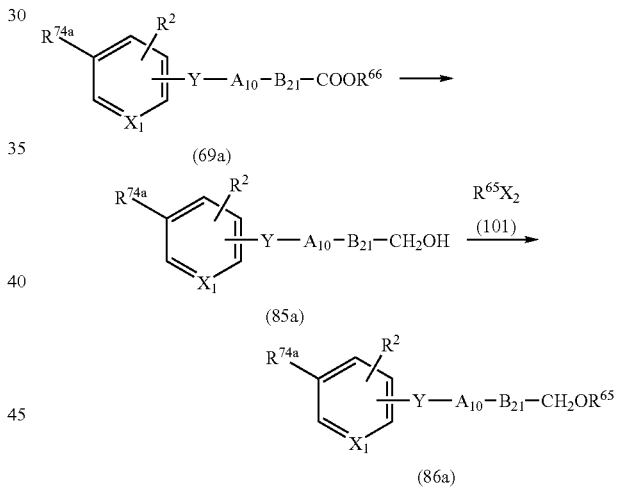

In the formula, $R^{74a}$, $R^2$, $X_1$, Y, $A_{10}$, $B_{21}$, $R^{65}$ and $X_2$ are the same as described above, and $R^{66}$ represents a hydrogen atom, a lower alkyl group or a lower alkoxycarbonyl group, provided that the a and b of $A_{10}$ are bound to Y and $B_{21}$, respectively, and the alkyl moieties in the side chain (—Y-$A_{10}$-$B_{21}$CH$_2$OH) of the compound (85a) and the side chain (—Y-$A_{10}$-$B_{21}$CH$_2$OR$^{65}$) of the compound (86a) have not more than 6 carbon atoms.

The reaction which converts the compound (69a) into the compound (85a) is carried out under the similar reaction conditions as the reaction which converts the compound (1f) into the compound (1g) of the above described reaction formula 3.

The reaction of the compound (85a) with the compound (101) is carried out under reaction conditions similar to those of the reaction which converts the compound (2) into the compound (3) of the above described reaction formula 1.

[Reaction formula 58]

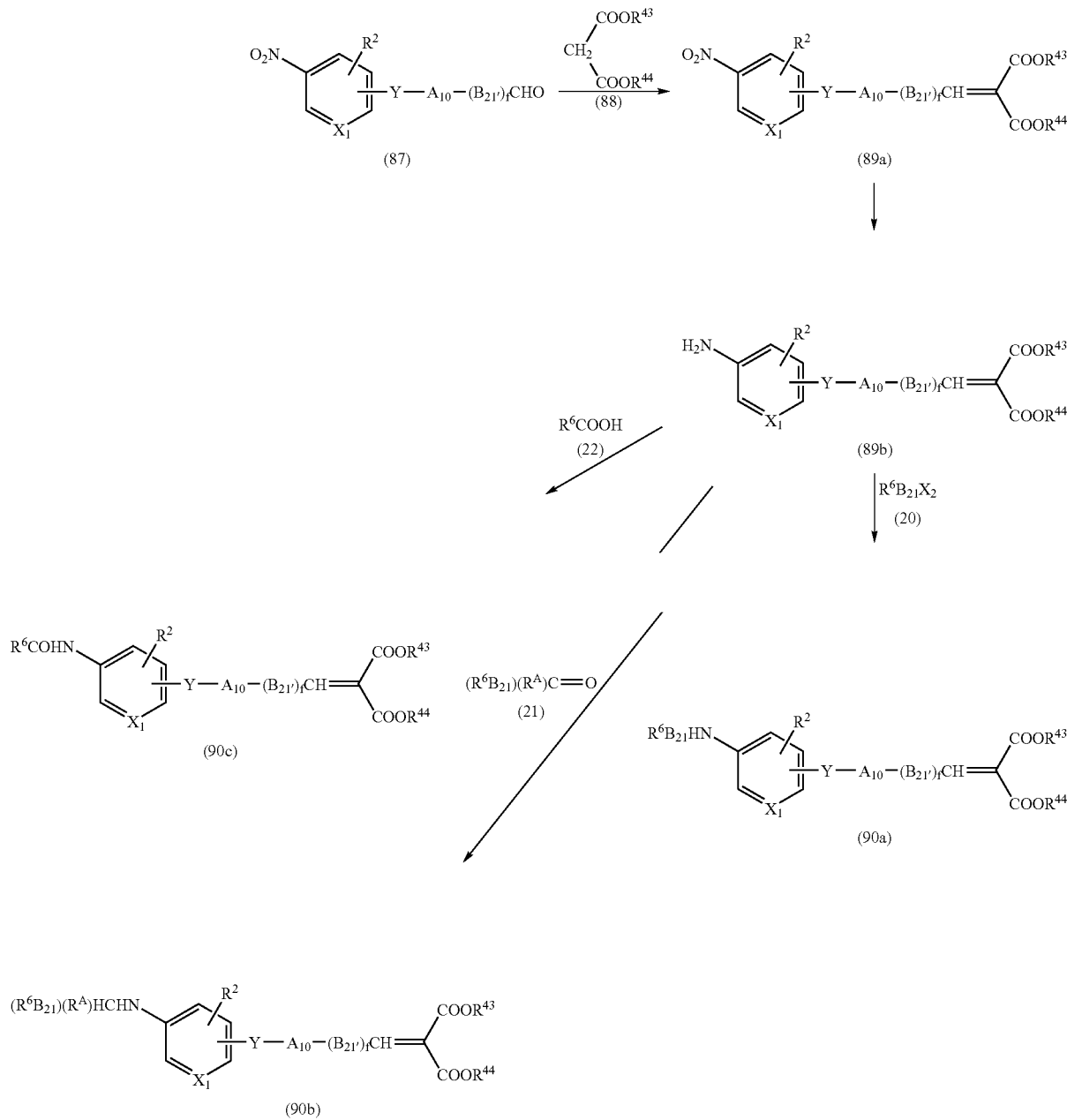

In the formula, $R^2$, $X_1$, Y, $A_{10}$, $B_{21}$, $R^6$, $R^A$, f, $R^{43}$, $R^{44}$ and $X_2$ are the same as described above, and $B_{21'}$ represents a lower alkylene group, provided that the a and b of $A_{10}$ are bound to Y and $B_{21'}$, respectively, and the $(B_{21'})$f-CH=C moiety in the side chain (—Y-$A_{10}$-$(B_{21'})$f-CH=C(COOR$^{43}$)(COOR$^{44}$)) of the compound (90c) and the alkyl moiety in the side chain (—NHCH($R^A$)($B_{21}R^6$)) of the compound (90b) have not more than 6 carbon atoms, respectively.

The reaction of the compound (87) with the compound (88) is carried out under reaction conditions similar to those of the reaction of the compound (1f) and hydroxylamine of the above described reaction formula 3.

The reaction which converts the compound (89a) into the compound (89b) may be carried out under reaction conditions similar to those of the reaction which converts the compound (68) into the compound (69) of the above described reaction formula 47.

The reaction of the compound (89b) with the compound (20) is carried out under reaction conditions similar to those of the reaction of the compound (1b) with the compound (4) of the above described reaction formula 2.

The reaction of the compound (89b) with the compound (22) is carried out under reaction conditions similar to those of the reaction of the compound (1b) with the compound (6) of the above described reaction formula 2.

The reaction of the compound (89b) with the compound (21) is carried out under reaction conditions similar to those of the reaction of the compound (1b) with the compound (5) of the above described reaction formula 2.

[Reaction formula 59]

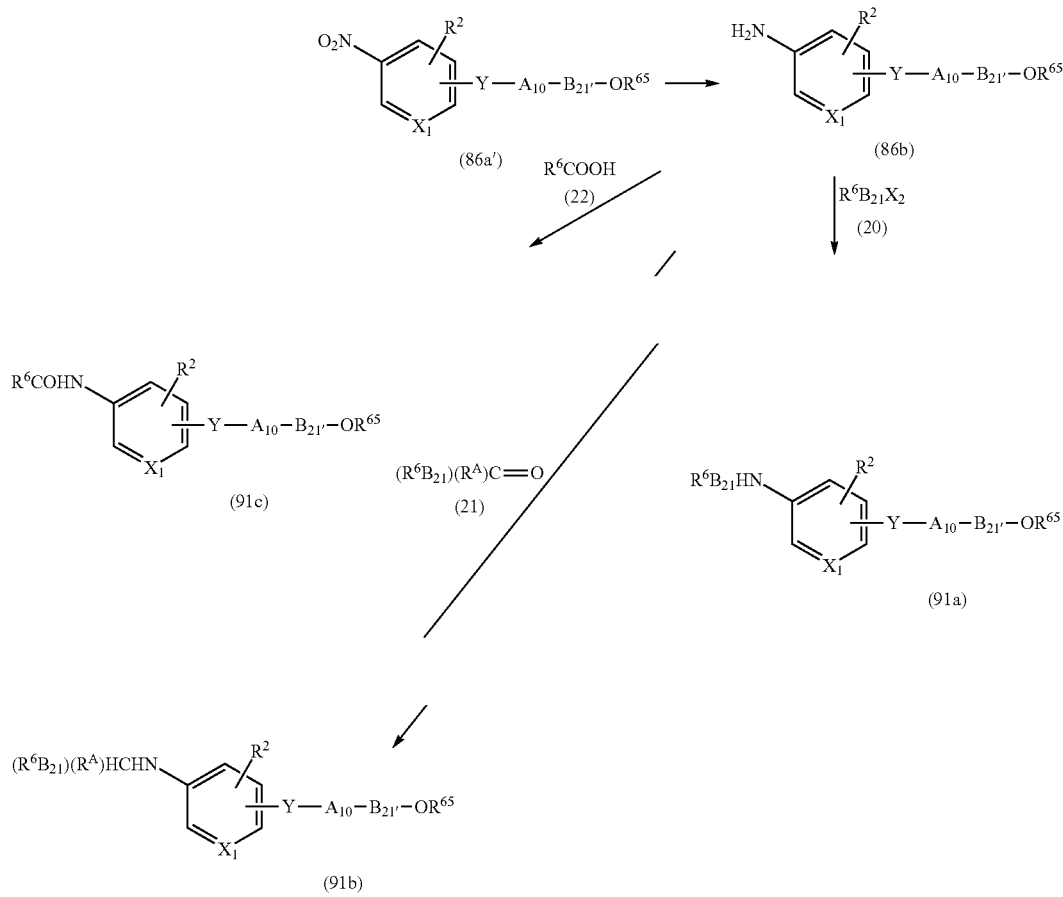

In the formula, $R^2, X_1, Y, A_{10}, B_{21'}, R^{65}, R^6, B_{21}, R^A$ and $X_2$ are the same as defined above, provided that the a and b of $A_{10}$ are bound to the Y group and the $B_{21'}$ group, respectively, and the alkyl moiety in the side chain ($-NHCH(R^A)(B_{21}R^6)$) of the compound (91b) has not more than 6 carbon atoms.

The reaction which converts the compound (86a') into the compound (86b) may be carried out under reaction conditions similar to those of the reaction which converts the compound (68) into the compound (69) of the above described reaction formula 47.

The reaction of the compound (86b) with the compound (20) is carried out under reaction conditions similar to those of the reaction of the compound (1b) with the compound (4) of the above described reaction formula 2.

The reaction of the compound (86b) with the compound (22) is carried out under reaction conditions similar to those of the reaction of the compound (1b) with the compound (6) of the above described reaction formula 2.

The reaction of the compound (86b) with the compound (21) is carried out under reaction conditions similar to those of the reaction of the compound (1b) with the compound (5) of the above described reaction formula 2.

[Reaction formula 60]

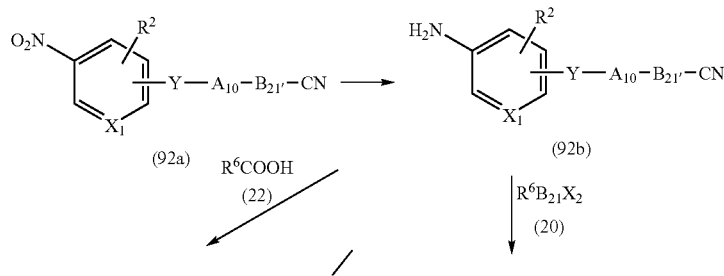

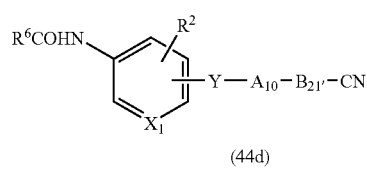

(44d)

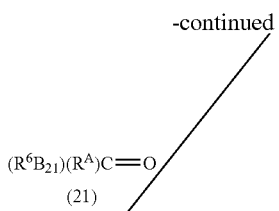

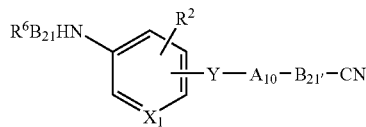

(44b)

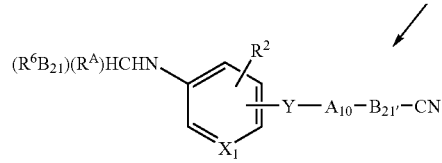

(44c)

In the formula, $R^2$, $X_1$, Y, $A_{10}$, $B_{21}$, $B_{21'}$, $R^6$, $R^A$ and $X_2$ are the same as described above, provided that the a and b of $A_{10}$ are bound to the Y group and the $B_{21'}$ group, respectively, and the alkyl moiety in the side chain (—NHCH($R^A$)($B_{21}R^6$)) of the compound (44c) has not more than 6 carbon atoms.

The reaction which converts the compound (92a) into the compound (92b) may be carried out under reaction conditions similar to those of the reaction which converts the compound (68) into the compound (69) of the above described reaction formula 47.

The reaction of the compound (92b) with the compound (20) is carried out under reaction conditions similar to those of the reaction of the compound (1b) with the compound (4) of the above described reaction formula 2.

The reaction of the compound (92b) with the compound (22) is carried out under reaction conditions similar to those of the reaction of the compound (1b) with the compound (6) of the above described reaction formula 2.

The reaction of the compound (92b) with the compound (21) is carried out under reaction conditions similar to those of the reaction of the compound (1b) with the compound (5) of the above described reaction formula 2.

[Reaction formula 61]

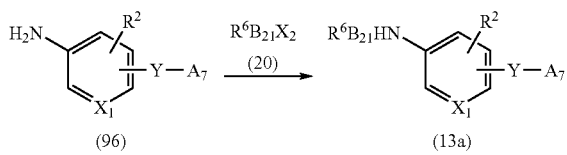

In the formula, $R^2$, $X_1$, and $X_2$ are the same as described above, $R^{67}$ represents an -$A_{10}B_{21}$CN group, -$A_{10}$-$R^{59d}$ group, -$A_{10}$-$T_2$-COO$R^{59a}$ group or -A group, $R^{59d}$ represents a lower alkyl group, $A_{10}$, $B_{21}$, $T_2$ and $R^{59a}$ are the same as described above, and $R^{68}$ represents a nitro group or a halogen atom.

The reaction of the compound (93) with the compound (94) is carried out under reaction conditions similar to those of the reaction of the compound (2) with the compound (3) of the above described reaction formula 1.

[Reaction formula 62]

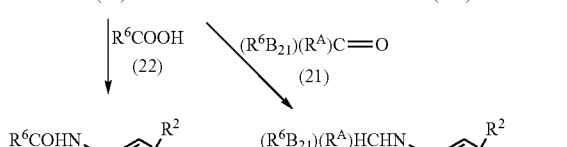

In the formula, $R^2$, $R^{67}$, and $X_1$ are the same as described above.

The reaction which converts the compound (95a) into the compound (95b) may be carried out under reaction conditions similar to those of the reaction which converts the compound (68) into the compound (69) of the above described reaction formula 47.

[Reaction formula 63]

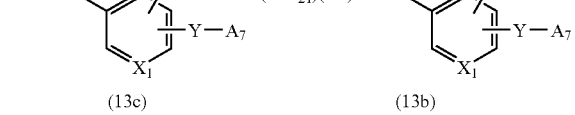

In the formula, $R^2$, $X_1$, Y, $A_7$, $R^6$, $B_{21}$, $R^A$ and $X_2$ are the same as described above, provided that the alkyl moiety in the side chain (—NHCH($R^A$)($B_{21}R^6$)) of the compound (13b) has not more than 6 carbon atoms.

The reaction of the compound (96) with the compound (20) is carried out under reaction conditions similar to those of the reaction of the compound (1b) with the compound (4) of the above described reaction formula 2.

The reaction of the compound (96) with the compound (22) is carried out under reaction conditions similar to those of the reaction of the compound (1b) with the compound (6) of the above described reaction formula 2.

The reaction of the compound (96) with the compound (21) is carried out under reaction conditions similar to those of the reaction of the compound (1b) with the compound (5) of the above described reaction formula 2.

The reaction of the compound (97b) with the compound (22) is carried out under reaction conditions similar to those of the reaction of the compound (1b) with the compound (6) of the above described reaction formula 2.

The reaction of the compound (97b) with the compound (21) is carried out under reaction conditions similar to those of the reaction of the compound (1b) with the compound (5) of the above described reaction formula 2.

[Reaction formula 64]

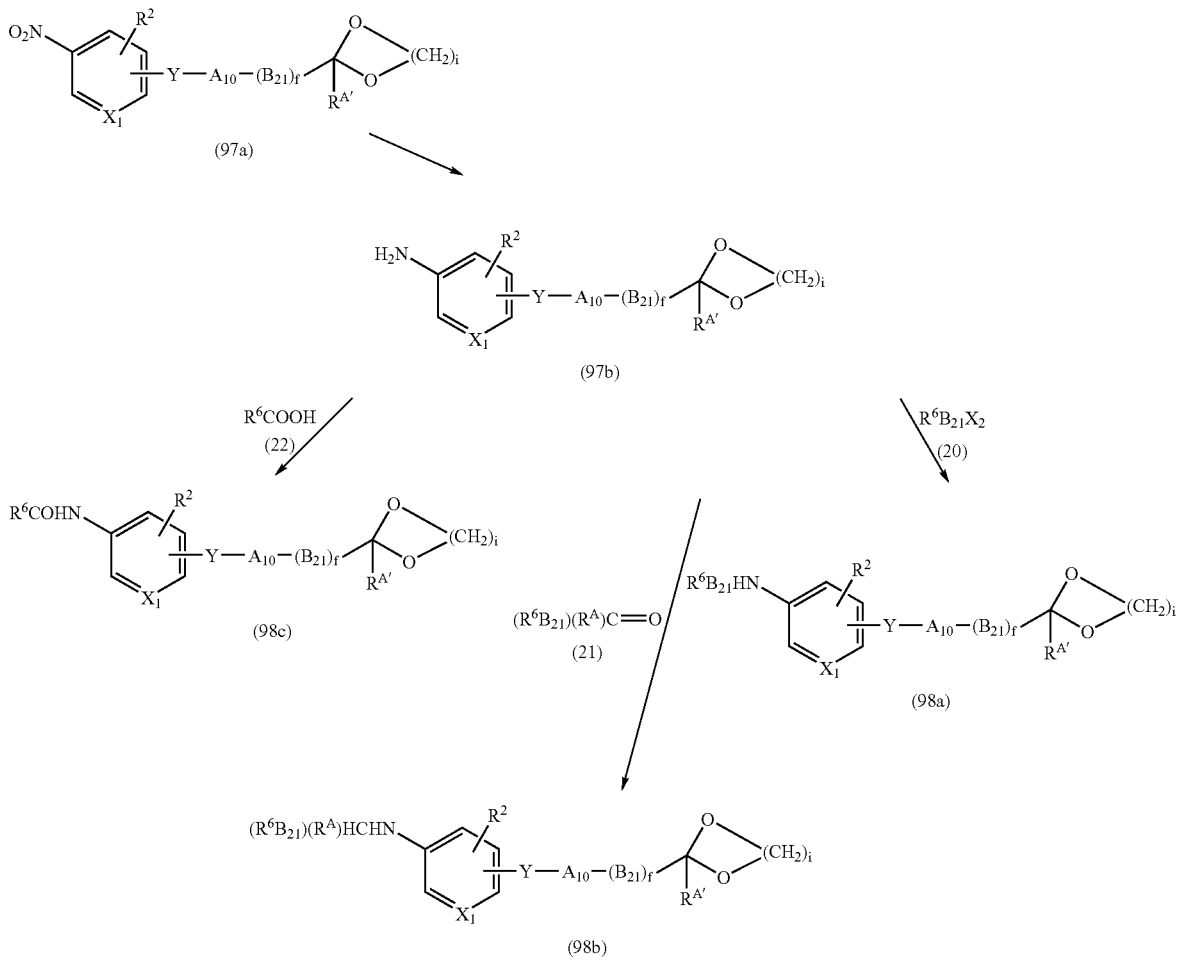

In the formula, $R^2$, $X_1$, Y, $B_{21}$, f, i, $R^6$, $B_{21}$, $A_{10}$, $R^A$ and $X_2$ are the same as described above, and $R^{A'}$ represents a hydrogen atom or a lower alkyl group, provided that the alkyl moiety in the side chain ($-NHCH(R^A)(B_{21}R^6)$) in compound (98b) has not more than 6 carbon atoms, and the a and b of $A_{10}$ are bound to the Y group and the $(B_{21})f$ group, respectively.

The reaction which converts the compound (97a) into the compound (97b) is carried out under reaction conditions similar to those of the reaction which converts the compound (68) into the compound (69) of the above described reaction formula 47.

The reaction of the compound (97b) with the compound (20) is carried out under reaction conditions similar to those of the reaction of the compound (1b) with the compound (4) of the above described reaction formula 2.

[Reaction formula 65]

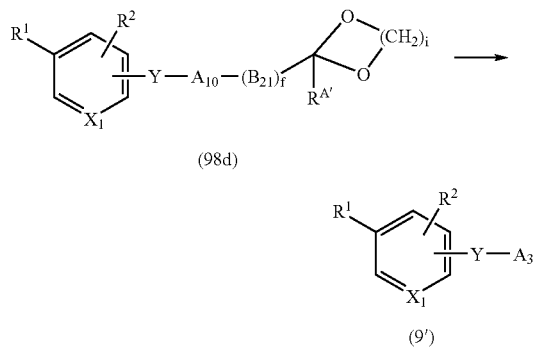

In the formula, $R^1$, $R^2$, $X_1$, Y, $A_{10}$, $B_{21}$, f, $R^{A'}$ and $A_3$ are the same as described above, provided that the a and b of $A_{10}$ are bound to the Y group and the $(B_{21})f$ group, respectively.

The reaction which converts the compound (98d) into the compound (9') may be carried out under reaction conditions similar to those of the hydrolysis B described for the above described reaction formula 9.

[Reaction formula 66]

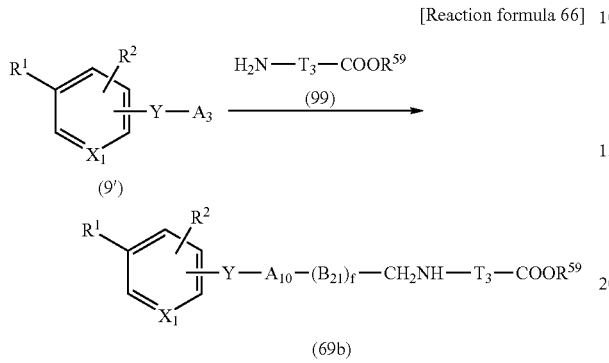

(9')

(69b)

In the formula, $R^1$, $R^2$, $X_1$, Y, $A_3$, $R^{59}$, $A_{10}$, $B_{21}$ and f are the same as described above, $T_3$ represents a direct bond or $B_7$ group, and $B_7$ represents the same as described above, provided that The a and b of $A_{10}$ are bound to the Y group and the $(B_{21})f$ group, respectively.

The reaction of the compound (9') with the compound (99) is carried out under reaction conditions similar to those of the reaction of the compound (1b) with the compound (5) of the above described reaction formula 2.

of the reaction of the compound (1b) with the compound (4) of the above described reaction formula 2.

The reaction of the compound (103) with the compound (38) is carried out under reaction conditions similar to those of the reaction of the compound (1b) with the compound (6) of the above described reaction formula 2.

The reaction of the compound (103) with the compound (38b) is carried out under reaction conditions similar to those of the reaction of the compound (1b) with the compound (5) of the above described reaction formula 2.

[Reaction formula 68]

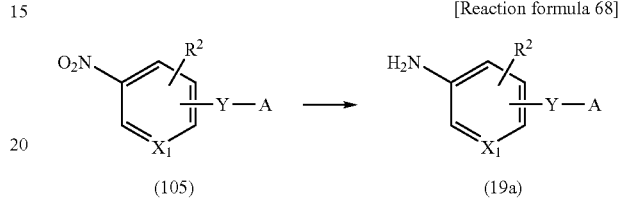

(105)    (19a)

In the formula, $R^2$, $X_1$, Y and A are the same as described above.

The reaction which converts the compound (105) into the compound (19a) is carried out under reaction conditions similar to those of the reaction which converts the compound (68) into the compound (69) of the above described reaction formula 47. The compound (19a) may be used in the following reaction without isolation.

[Reaction formula 67]

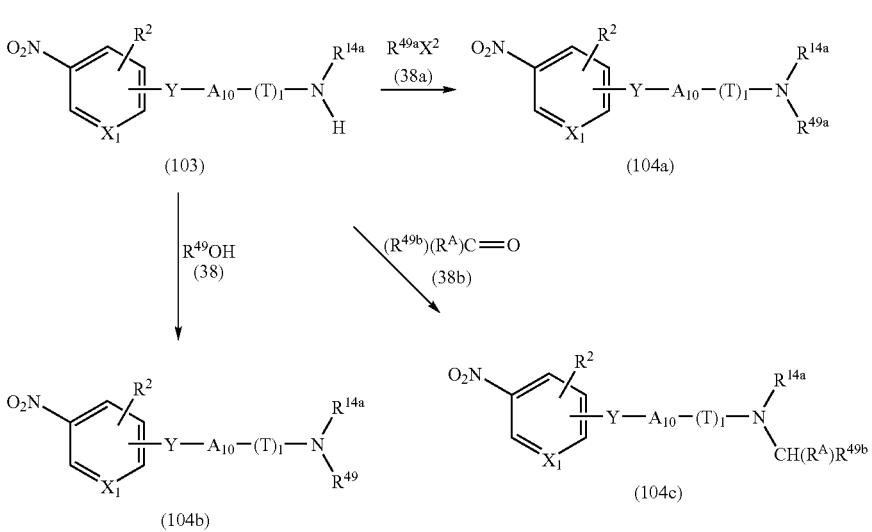

In the formula, $R^2$, $X_1$, Y, $A_{10}$, $R^{14a}$, $R^{49a}$, $R^{49}$, $R^{49b}$, T, 1, $R^A$ and $X_2$ are the same as described above, provided that the $CHR^A$ moiety in the side chain $(-N(R^{14a})(CHR^A R^{49b}))$ of the compound (104c) has not more than 6, the a of $A_{10}$ is bound to the Y group, and the b of $A_{10}$ is bound to a $-NR^{14a}H$ group, $-NR^{14a}R^{49a}$ group, $-NR^{14a}R^{49}$ group, or $-NR^{14a}(CHR^A R^{49b})$ group.

The reaction of the compound (103) with the compound (38a) is carried out under reaction conditions similar to those

[Reaction formula 69]

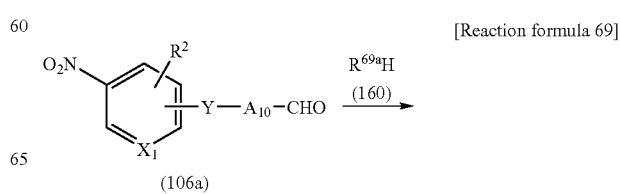

(106a)

-continued

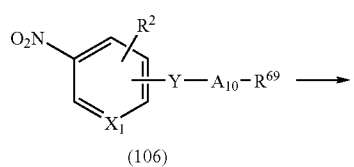

(106)

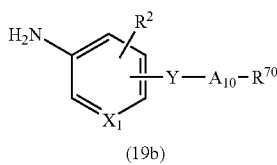

(19b)

In the formula, $R^2$, $X_1$, Y and $A_{10}$ is the same as described above, $R^{69a}$ represents a thiazolidinyl group which may have an oxo group as a substituent on the thiazolidine ring, $R^{69}$ represents a thiazolidinylidene lower alkyl group which may have an oxo group as a substituent on the thiazolidine ring, and $R^{70}$ represents a thiazolidinyl lower alkyl group which may have an oxo group as a substituent on the thiazolidine ring, provided that the a of $A_{10}$ are bound to the Y group and the b of $A_{10}$ is bound to an —$R^{69}$ group or —$R^{70}$ group.

The reaction of the compound (106a) with the compound (160) is carried out under reaction conditions similar to those of the reaction of the compound (87) with the compound (88) of the above described reaction formula 58.

The reaction which converts the compound (106) into the compound (19b) may be carried out under reaction conditions similar to those of the reaction which converts the compound (68) into the compound (69) of the above described reaction formula 47.

[Reaction formula 70]

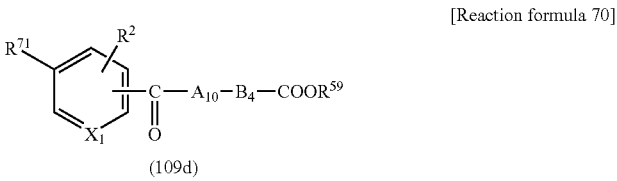

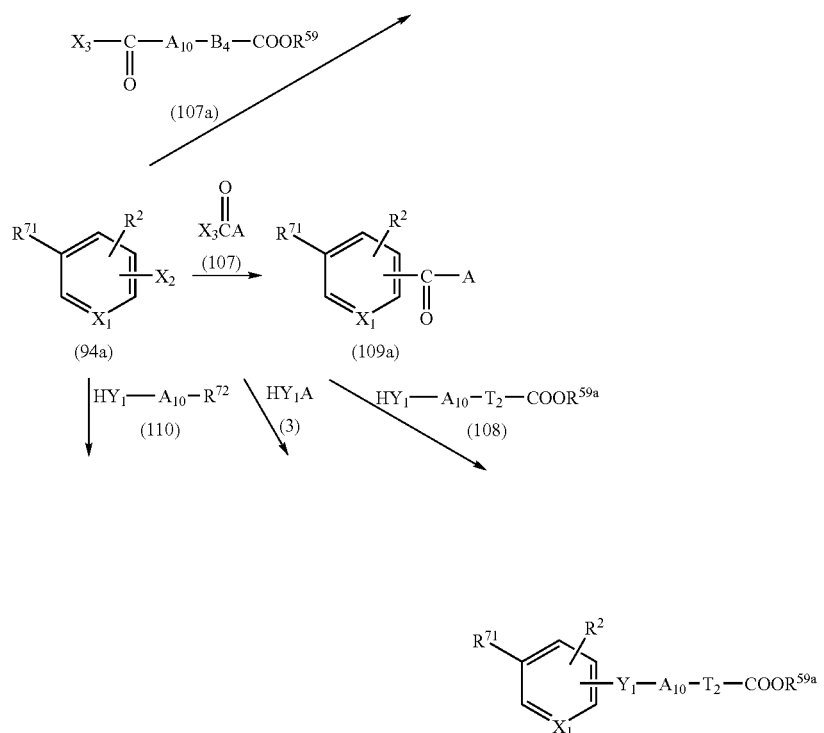

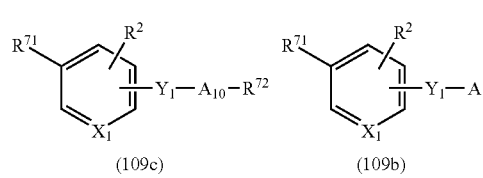

In the formula, $R^2$, $X_1$, $X_2$, A, $Y_1$, $A_{10}$, $T_2$, $R^5$ and $R^{59a}$ are the same as described above, $X_3$ represents a halogen atom, $R^{71}$ represents an —$R^1$ group (wherein $R^1$ is the same as described above), a nitro group or a lower alkoxycarbonyl group, and $R^{72}$ represents a lower alkyl group which may be substituted with a hydroxyl group, a nitro group, an amino group which may be substituted with a lower alkanoyl group, a carboxy lower alkyl group, a —$(B_{21})fC(=O)R^A$ group (wherein $B_{21}$, f and $R^A$ are the same as described above), a lower alkanoyl group, a lower alkoxy group or a hydrogen atom, provided that the a of $A_{10}$ are bound to the $Y_1$ group and the b of $A_{10}$ is bound to a -$T_2$ group or —$R^{72}$ group.

The reaction of the compound (94a) with the compound (107), and the reaction of the compound (94a) with the compound (107a) are carried out in an appropriate solvent and in the presence of a catalyst.

Any of the solvents used in the reaction of the compound (2) with the compound (3) of the above described reaction formula 1 may be used in this reaction.

Examples of the catalyst to be used include various metal complexes as well as various combinations of a metal complex with ligand. Examples of the metal complex include, for instance, palladium acetate (II), tetrakis(triphenylphosphine) palladium (0), tris(dibenzylideneacetone)dipalladium (0) and the like. Examples of the ligand include, for instance, R-2,2'-bis(diphenylphosphino)-1,1'-binaphthyl (R-BINAP), S-2,2'-bis(diphenylphosphino)-1,1'-binaphthyl (S-BINAP), RAC-2,2'-bis(diphenylphosphino)-1,1'-binaphthyl (RAC-BINAP), t-butylphosphine, 4,5-bis(diphenylphosphino)-9,9-dimethylxanthene and the like.

The above described catalyst is appropriately used in an amount typically equimolar to the compound (94a), and preferably 1 to 5 times of the compound (94a) on a molar basis.

The above described reaction is carried out typically at about 0 to 200° C., preferably at about 0 to 150° C., and, in general, is completed in around 30 minutes to 10 hours.

Addition of molecular sieves such as Molecular Sieves 3A (MS3A) or Molecular Sieves 4A (MS4A) or a phosphorus compound such as triphenylphosphine or tri(2-furyl)phosphine makes the reaction proceed advantageously.

The reaction of the compound (94a) with the compound (108), compound (3) or compound (110) is carried out under reaction conditions similar to those of the reaction of the compound (2) with the compound (3) of the above described reaction formula 1.

The compound (109c), wherein $R^{71}$ represents a lower alkoxycarbonyl group, may be converted into the corresponding compound (109c), wherein $R^{71}$ represents a carboxy group, by hydrolyzing under reaction conditions similar to those of the hydrolysis B described for the above described reaction formula 9.

[Reaction formula 71]

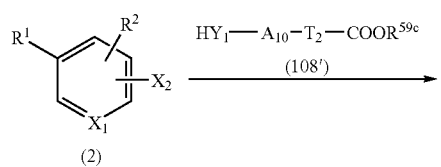

(2)

-continued

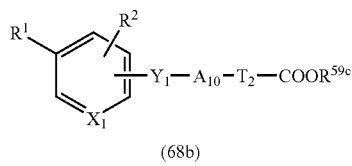

(68b)

In the formula, $R^1$, $R^2$, $X_1$, $X_2$, $Y_1$, $A_{10}$ and $T_2$ are the same as described above, and $R^{59c}$ represents a hydrogen atom, a lower alkyl or a phenyl lower alkyl group, provided that the a and b of $A_{10}$ are bound to a —$Y_1$ group and a -$T_2$ group, respectively.

The reaction of the compound (2) with the compound (108') is carried out under reaction conditions similar to those of the reaction of the compound (2) with the compound (3) of the above described reaction formula 1.

[Reaction formula 72]

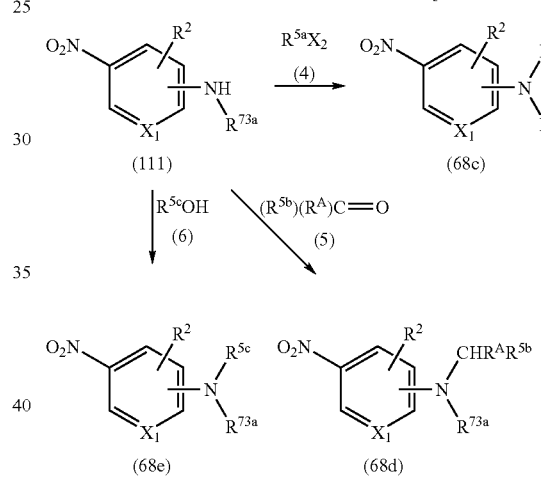

In the formula, $R^2$, $X_1$, $R^{5a}$, $R^{5b}$, $R^A$, $R^{5c}$ and X are the same as described above, and $R^{73a}$ represents a -$A_{10}$-$T_2$-COOR$^{59}$ group (wherein $A_{10}$, $T_2$ and $R^{59}$ are the same as described above) or an -A group (wherein A is the same as described above), provided that the a of $A_{10}$ is bound to an —NH— group, NR$^{5a}$— group, —N(CHR$^A$R$^{5b}$) group or —NR$^{5c}$— group, and the b of $A_{10}$ is bound to a -$T_2$ group, and the alkyl moiety in the side chain (—N(R$^{73a}$)(CHR$^A$R$^{5b}$)) of the compound (68d) has not more than 6 carbon atoms.

The reaction of the compound (111) with the compound (4) is carried out under reaction conditions similar to those of the reaction of the compound (1b) with the compound (4) of the above described reaction formula 2.

The reaction of the compound (111) with the compound (6) is carried out under reaction conditions similar to those of the reaction of the compound (1b) with the compound (6) of the above described reaction formula 2.

The reaction of the compound (111) with the compound (5) is carried out under reaction conditions similar to those of the reaction of the compound (1b) with the compound (5) of the above described reaction formula 2.

[Reaction formula 73]

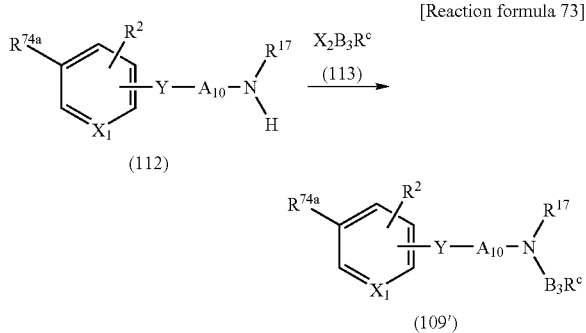

In the formula, $R^2$, $X_1$, Y, $A_{10}$, $X_2$, $R^{17}$, $B_3$, $R^{74a}$ and $R^c$ are the same as described above, provided that the a of $A_{10}$ is bound to a —Y group and the b of $A_{10}$ is bound to an —$NHR^{17}$ group or —$NR^{17}B_3R^c$ group.

The reaction of the compound (112) with the compound (113) is carried out under reaction conditions similar to those of the reaction of the compound (1b) with the compound (4) of the above described reaction formula 2.

[Reaction formula 74]

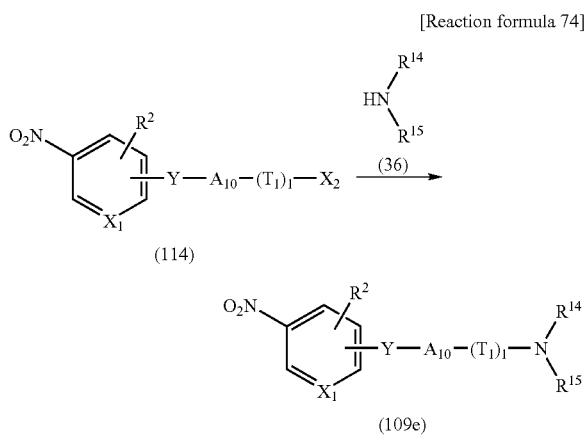

In the formula, $R^2$, $X_1$, Y, $A_{10}$, $T_1$, l, $R^{14}$, and $R^{15}$ are the same as described above, provided that the a and b of $A_{10}$ are bound to an —Y group and a -$(T_1)l$ group, respectively.

The reaction of the compound (114) with the compound (36) is carried out under reaction conditions similar to those of the reaction of the compound (1b) with the compound (5) of the above described reaction formula 2.

The compound (109e), in which l is 0, may also be produced by reacting the corresponding compound (114) with the compound (36) in an appropriate solvent in the presence of a basic compound and a catalyst.

The above described reaction is carried out under reaction conditions similar to those of the reaction C described for the above described reaction formula 13.

[Reaction formula 75]

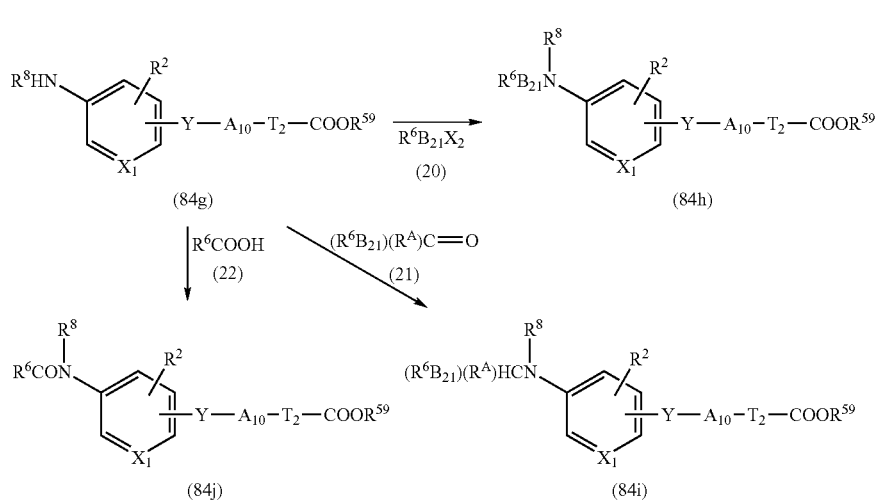

In the formula, $R^2$, $X_1$, Y, $R^8$, $B_{21}$, $R^6$, $A_{10}$, $T_2$, $R^{59}$, $R^A$ and $X_2$ are the same as described above, provided that the $CHR^AB_{21}$ moiety in the side chain (—$N(R^8)(CH(R^A)B_{21}R^6)$) of the compound (84i) has not more than 6 carbon atoms, and the a and b of $A_{10}$ are bound to a —Y group and a -$T_2$ group, respectively.

The reaction of the compound (84g) with the compound (20) is carried out under reaction conditions similar to those of the reaction of the compound (1b) with the compound (4) of the above described reaction formula 2.

The reaction of the compound (84g) with the compound (22) is carried out under reaction conditions similar to those of the reaction of the compound (1b) with the compound (6) of the above described reaction formula 2.

The reaction of the compound (84g) with the compound (21) is carried out under reaction conditions similar to those of the reaction of the compound (1b) with the compound (5) of the above described reaction formula 2.

[Reaction formula 76]

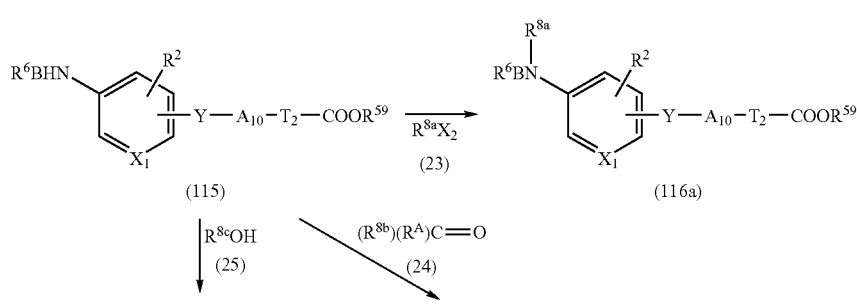

(115) (116a)

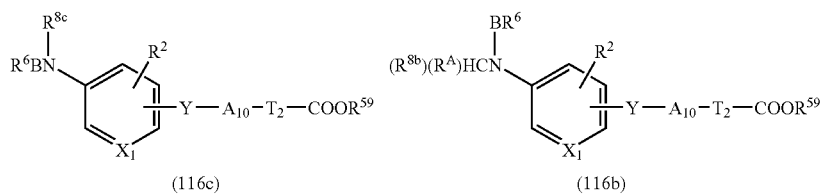

(116c) (116b)

In the formula, $R^2$, $X_1$, Y, $R^{8a}$, $R^{8b}$, $R^{8c}$, B, $R^6$, $A_{10}$, $T_2$, $R^{59}$, $R^A$ and $X_2$ are the same as described above, provided that the $CHR^A$ moiety in the side chain ($-NB(R^6)(CH(R^A)R^{8b})$) of the compound (116b) has not more than 6 carbon atoms, and the a and b of $A_{10}$ are bound to a —Y group and a -$T_2$ group, respectively.

The reaction of the compound (115) with the compound (23) is carried out under reaction conditions similar to those of the reaction of the compound (1b) with the compound (4) of the above described reaction formula 2.

The reaction of the compound (115) with the compound (25) is carried out under reaction conditions similar to those of the reaction of the compound (1b) with the compound (6) of the above described reaction formula 2.

The reaction of the compound (115) with the compound (24) is carried out under reaction conditions similar to those of the reaction of the compound (1b) with the compound (5) of the above described reaction formula 2.

[Reaction formula 77]

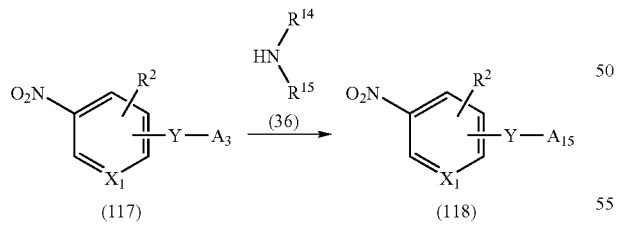

(117) (118)

In the formula, $R^2$, $X_1$, Y, $A_3$, $R^{14}$ and $R^{15}$ are the same as described above, and $A_{15}$ represents a group of the formula:

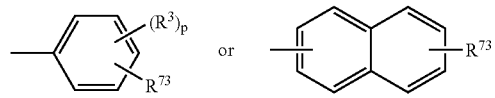

wherein $R^{73}$ represents a —$(B_{21})fCH(R^A)(NR^{14}R^{15})$ group, and $B_{21}$, f and $R^A$ are the same as described above, provided that the $(B_{21})fCH(R^A)$ moiety has not more than 6 carbon atoms.

The reaction of the compound (117) with the compound (36) is carried out under reaction conditions similar to those of the reaction of the compound (1b) with the compound (5) of the above described reaction formula 2.

[Reaction formula 78]

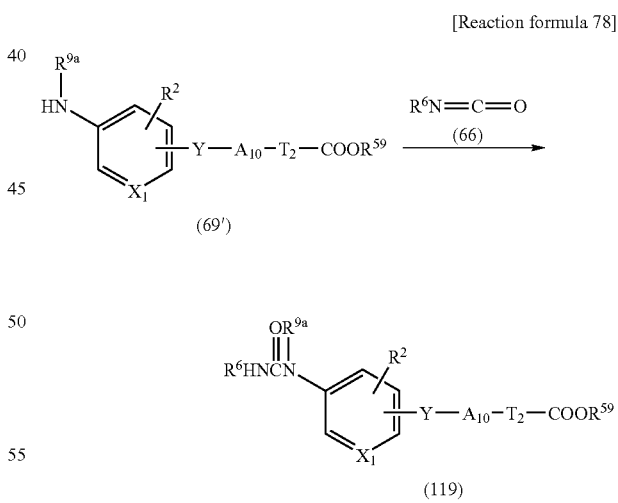

(69') (119)

In the formula, $R^2$, $X_1$, Y, $A_{10}$, $T_2$, $R^6$, $R^{9a}$ and $R^{59}$ are the same as described above, provided that the a and b of $A_{10}$ are bound to a —Y group and a -$T_2$ group, respectively.

The reaction of the compound (69') with the compound (66) is carried out under reaction conditions similar to those of the reaction of the compound (30) with the compound (66) of the above described reaction formula 46.

[Reaction formula 79]

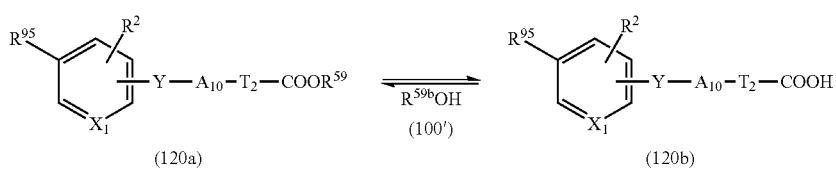

(120a)     (120b)

In the formula, $R^2$, $X_1$, Y, $A_{10}$, $T_2$, $R^{95}$ and $R^{59b}$ are the same as described above, provided that the a and b of $A_{10}$ are bound to a —Y group and a -$T_2$ group, respectively.

The reaction which converts the compound (120a) into the compound (120b) may be carried out under reaction conditions similar to those of the hydrolysis B described for the above described reaction formula 9.

The reaction of the compound (120b) with the compound (100') is carried out under reaction conditions similar to those of the reaction of the compound (1fff) with the compound (43) in the reaction formula 20 described above.

The compound (120a) may also be produced using a lower alkyl halide such as methyl iodide in place of the compound (100') under reaction conditions similar to those of the reaction of the compound (2) with the compound (3) of the above described reaction formula 1.

[Reaction formula 80]

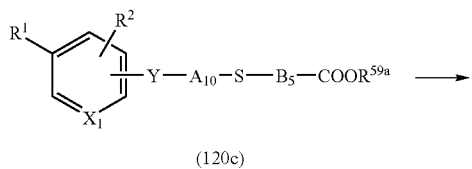

(120c)

-continued

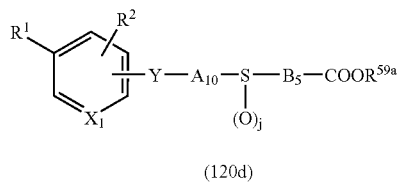

(120d)

In the formula, $R^1$, $R^2$, $X_1$, Y, $A_{10}$, $B_5$, $R^{59a}$ and j are the same as described above, provided that the a and b of $A_{10}$ are bound to a —Y group and a —S group, respectively.

The reaction which converts the compound (120c) into the compound (120d) may be carried out under reaction conditions similar to those of the reaction which converts the compound (1zzzz) into the compound (1aaaaa) in formula 4 described above.

[Reaction formula 81]

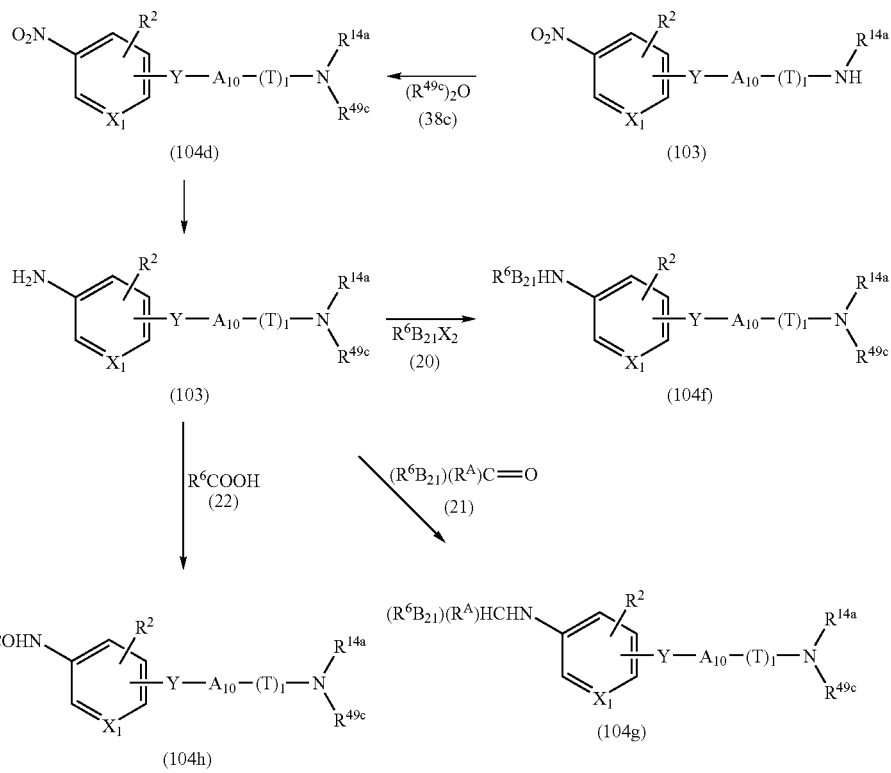

In the formula, $R^2$, $X_1$, Y, $A_{10}$, T, l, $R^6$, $X_2$, $R^A$, $B_{21}$ and $R^{14a}$ are the same as described above, and $R^{49c}$ represents a lower alkoxycarbonyl group, provided that the a and b of $A_{10}$ are bound to a —Y group and a -(T)l group, respectively.

The reaction of the compound (103) with the compound (38c) is carried out under reaction conditions similar to those of the reaction of the compound (2) with the compound (3) of the above described reaction formula 1.

The reaction which converts the compound (104d) into the compound (104e) is carried out under reaction conditions similar to those of the reaction which converts the compound (68) into the compound (69) of the above described reaction formula 47.

The reaction of the compound (104e) with the compound (20) is carried out under reaction conditions similar to those of the reaction of the compound (1b) with the compound (4) of the above described reaction formula 2.

The reaction of the compound (104e) with the compound (22) is carried out under reaction conditions similar to those of the reaction of the compound (1b) with the compound (6) of the above described reaction formula 2.

The reaction of the compound (104e) with the compound (21) is carried out under reaction conditions similar to those of the reaction of the compound (1b) with the compound (5) of the above described reaction formula 2.

[Reaction formula 82]

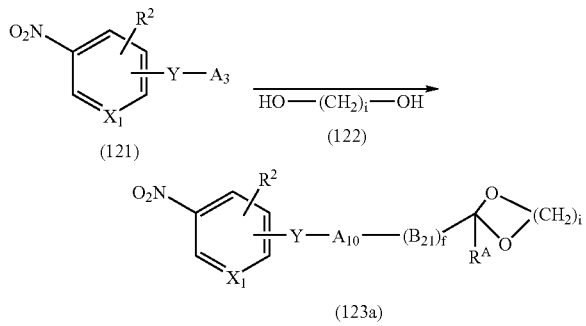

In the formula, $R^2$, $X_1$, Y, $A_3$, $A_{10}$, $B_{21}$, f, $R^A$ and i are the same as described above, provided that the a and b of $A_{10}$ are bound to a —Y group and a —$(B_{21})$f group, respectively, and $(B_{21})$fC($R^A$) in the side chain of the compound (123a) has not more than 6 carbon atoms in total.

The reaction of the compound (121) with the compound (122) may be carried out in an appropriate solvent in the presence of an acid.

Any of the solvents, which are used in the reaction of the compound (2) with the compound (3) of the above described reaction formula 1, may be used in this reaction.

Examples of the acid used include mineral acids such as hydrochloric acid, sulfuric acid, and hydrobromic acid, and organic acids such as acetic acid, trifluoroacetic acid, and sulfonic acids including p-toluenesulfonic acid. These acids may be used singly or in a mixture of two or more. The acid is appropriately used in an amount typically at least 0.01 to 5 times, and preferably 0.01 to 2 times of the compound (121) on a molar basis. The compound (122) is appropriately used in an amount typically at least equimolar to the compound (121), and preferably 1 to 10 times of the compound (121) on a molar basis.

The above described reaction is carried out typically at 0 to 200° C., and preferably at around 0 to 150° C. and, in general, is completed in around 30 minutes to 10 hours.

[Reaction formula 83]

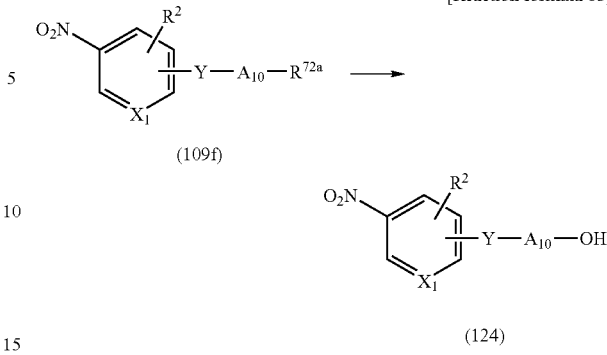

In the formula, $R^2$, $X_1$, Y and $A_{10}$ are the same as described above, and $R^{72a}$ represents a lower alkoxy group, provided that the a of $A_{10}$ is bound to a —Y group and the b of $A_{10}$ is bound to a —$R^{72a}$ group or a hydroxyl group.

The reaction which converts the compound (109f) into the compound (124) may be carried out in an appropriate solvent in the presence of an acid.

In addition to water, any solvents which are used in the reaction of the compound (2) with the compound (3) of the above described reaction formula 1 may be used in this reaction.

Examples of the acid used include mineral acids such as hydrobromic acid, hydrochloric acid, and concentrated sulfuric acid, fatty acids such as formic acid and acetic acid, organic acids such as p-toluenesulfonic acid, Lewis acids such as aluminum chloride, zinc chloride, iron chloride, tin chloride, boron trifluoride, and boron tribromide, iodides such as sodium iodide and potassium iodide, a mixture of the above described Lewis acid with the above described iodide. The acid is appropriately used in an amount typically 0.1 to 5 times, and preferably 0.5 to 3 times of the compound (109f) on a molar basis.

The above described reaction is typically carried out at 0 to 150° C., and preferably at about 0 to 100° C., and, in general, is completed in about 0.5 to 15 hours.

[Reaction formula 84]

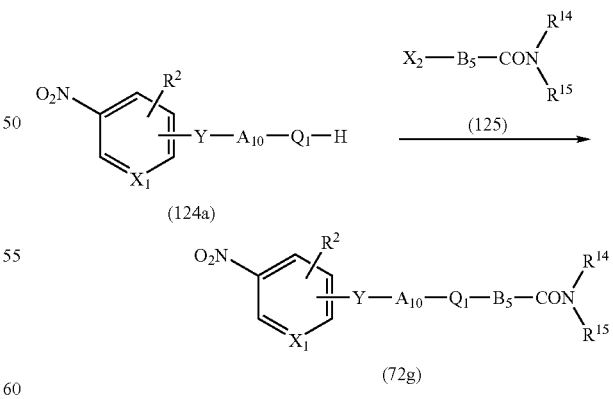

In the formula, $R^2$, $X_1$, Y, $A_{10}$, $B_5$, $X_2$, $R^{14}$, and $R^{15}$ are the same as described above, and $Q_1$ represents an oxygen atom or a sulfur atom, provided that the a and b of $A_{10}$ are bound to a —Y group and a -$Q_1$ group, respectively.

The reaction of the compound (124a) with the compound (125) is carried out under reaction conditions similar to those of the reaction of the compound (2) with the compound (3) of the above described reaction formula 1.

[Reaction formula 85]

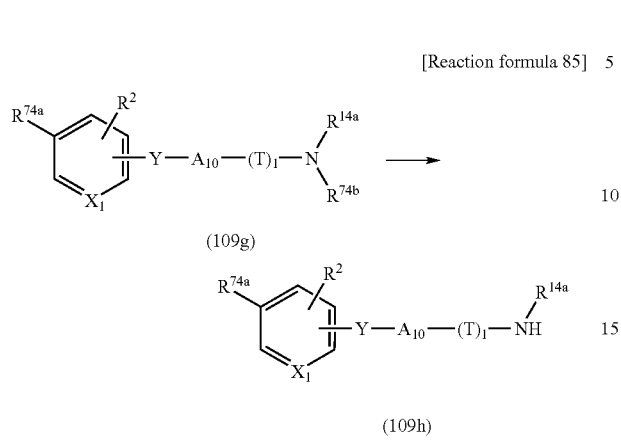

(109g)

(109h)

In the formula, $R^2$, $X_1$, Y, $A_{10}$, $R^{14a}$, $R^{74a}$, T and l are the same as described above, and $R^{74b}$ represents a lower alkanoyl group or a lower alkoxycarbonyl group, provided that the a and b of $A_{10}$ are bound to a —Y group and a -(T)l group, respectively.

The reaction which converts the compound (109g) into the compound (109h) may be carried out under reaction conditions similar to those of the hydrolysis B described for the above described reaction formula 9.

[Reaction formula 86]

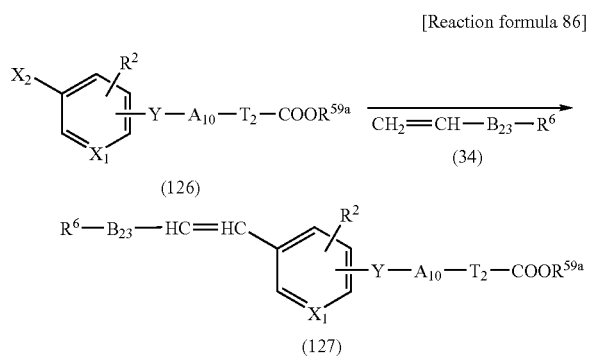

In the formula, $R^2$, $X_1$, Y, $A_{10}$, $T_2$, $X_2$, $R^{59a}$, $B_{23}$ and $R^6$ are the same as described above, provided that the a and b of $A_{10}$ are bound to —Y group and -$T_2$ group, respectively.

The reaction of the compound (126) with the compound (34) is carried out under reaction conditions similar to those of the reaction of the compound (33) with the compound (34) in formula 43 described above.

[Reaction formula 87]

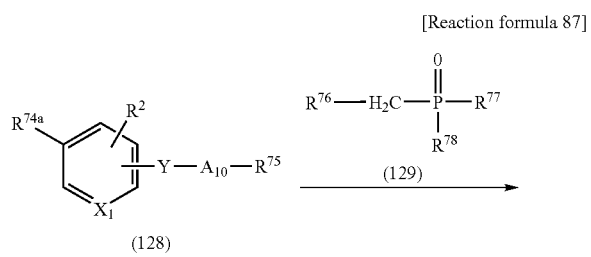

-continued

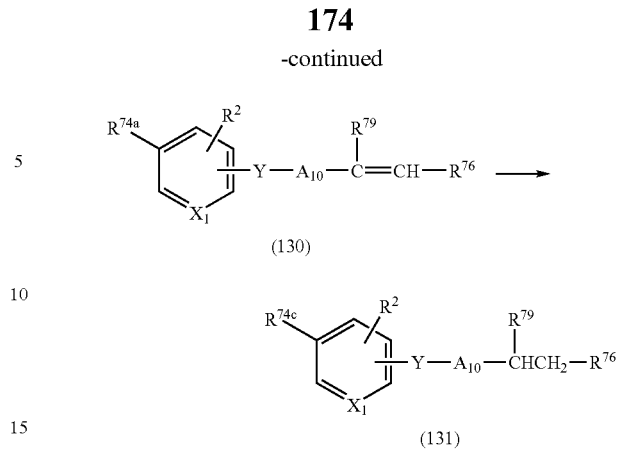

In the formula, $R^2$, $X_1$, Y, $R^{74a}$ and $A_{10}$ are the same as described above, $R^{74c}$ represents an amino group or an —$R^1$ group (wherein $R^1$ is the same as described above), $R^{75}$ represents a lower alkanoyl group, $R^{76}$ represents a lower alkoxycarbonyl group, $R^{77}$ and $R^{78}$ are both lower alkoxy groups, and $R^{79}$ represents a hydrogen atom or a lower alkyl group, provided that the a of $A_{10}$ is bound to a —Y group, and the b of $A_{10}$ is bound to a —$R^{75}$ group, —C($R^{79}$)=CH$R^{76}$ group or —CH($R^{79}$)CH$_2R^{76}$ group, and the C($R^{79}$)=CH moiety or the CH($R^{79}$)CH$_2$ moiety has not more than 6 carbon atoms.

The reaction of the compound (128) with the compound (129) is carried out in an appropriate solvent in the presence of a basic compound.

Any of the conventional solvents which do not affect the reaction may be used. Examples of such a solvent include ethers such as diethyl ether, dioxane, tetrahydrofuran, monoglyme, and diglyme, aromatic hydrocarbons such as benzene, toluene, and xylene, aliphatic hydrocarbons such as n-hexane, heptane, and cyclohexane, amines such as pyridine and N,N-dimethylaniline, aprotic polar solvents such as acetonitrile, N,N-dimethylformamide, dimethyl sulfoxide, and hexamethylphosphoric acid triamide, and alcohols such as methanol, ethanol, and isopropanol, and a mixture thereof.

Examples of the basic compound include metal sodium, metal potassium, sodium hydride, sodium amide, metal hydroxides such as sodium hydroxide, potassium hydroxide, and calcium hydroxide, carbonates such as sodium carbonate, potassium carbonate, and sodium bicarbonate, metal alcoholates such as sodium methylate, sodium ethylate, and potassium tert-butoxide, alkyl and aryl lithiums or lithium amides such as methyl lithium, n-butyryl lithium, phenyl lithium, and lithium diisopropylamide, and organic bases such as pyridine, piperidine, quinoline, trimethylamine, diisopropylethylamine, N,N-dimethylaniline. These basic compounds are used singly or in a mixture of two or more. The basic compound is appropriately used in an amount typically 0.1 to 10 times, and preferably 0.5 to 5 times of the compound (128) on a molar basis.

The compound (129) is appropriately used in an amount typically at least equimolar to the compound (128), and preferably 1 to 5 times of the compound (128) on a molar basis.

The above described reaction is carried out typically at −80 to 150° C., and preferably at about −80 to 120° C. and, in general, is completed in about 0.5 to 40 hours.

When an organic base is used as the basic compound, the reaction proceeds advantageously by adding a lithium salt such as lithium chloride to the reaction system.

The reaction which converts the compound (130) into the compound (131) may be carried out under reaction conditions similar to those of the reaction which converts the compound (68) into the compound (69) of the above described reaction formula 47.

[Reaction formula 88]

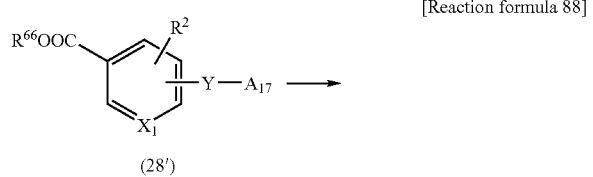

(28')

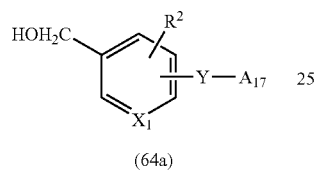

(64a)

In the formula, $R^2$, $X_1$, Y, $R^{66}$ and $A_{17}$ are the same as described above.

The reaction which converts the compound (28') into the compound (64a) is carried out under reaction conditions similar to those of the reaction which converts the compound (1f) into the compound (1g) of the above described reaction formula 3.

[Reaction formula 89]

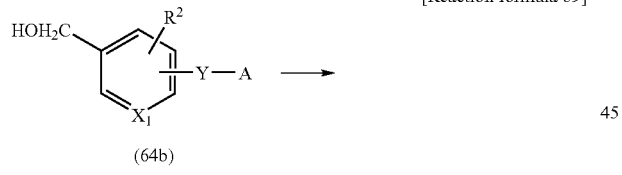

(64b)

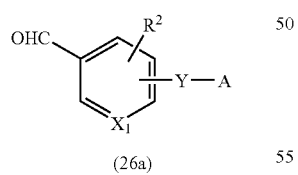

(26a)

In the formula, $R^2$, $X_1$, Y and A are the same as described above.

The reaction which converts the compound (64b) into the compound (26a) is carried out in an appropriate solvent in the presence of an oxidizing agent.

Examples of the solvent include water, fatty acids such as formic acid, acetic acid, trifluoroacetic acid, and propionic acid, esters such as ethyl acetate and methyl acetate, alcohols such as methanol, ethanol, and isopropanol, ethers such as dioxane, tetrahydrofuran, and diethyl ether, ketones such as acetone and methyl ethyl ketone, aromatic hydrocarbons such as benzene, toluene, chlorobenzene, and xylene, and halogenated hydrocarbons such as chloroform and dichloromethane, hexamethylphosphoric acid triamide, N,N-dimethylformamide, dimethyl sulfoxide, and pyridine, and a mixture thereof.

Examples of the oxidizing agent include peracids such as performic acid, peracetic acid, pertrifluoroacetic acid, perbenzoic acid, m-chloroperbenzoic acid, and o-carboxyperbenzoic acid, hydrogen peroxide, sodium metaperiodate, dichromic acid, dichromates such as sodium dichromate and potassium dichromate, manganese dioxide, permanganic acid, permanganates such as sodium permanganate and potassium permanganate, lead salts such as lead tetraacetate, silver oxide, and a Dess-Martin reagent (Dess-Martin periodinane). These oxidizing agents are used singly or in a mixture of two or more. The oxidizing agent is used in an amount typically at least equimolar to the compound (64b), and preferably 1 to 3 times of the compound (64b) on a molar basis.

The above described reaction is carried out typically at −10 to 100° C., and preferably at about 0 to 50° C., and is completed in about 30 minutes to 24 hours.

[Reaction formula 90]

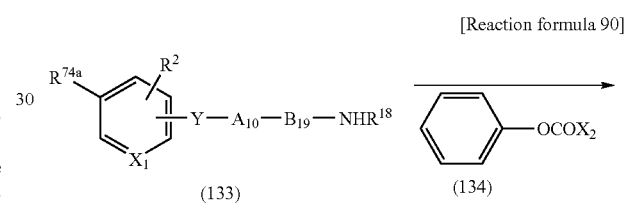

(133)            (134)

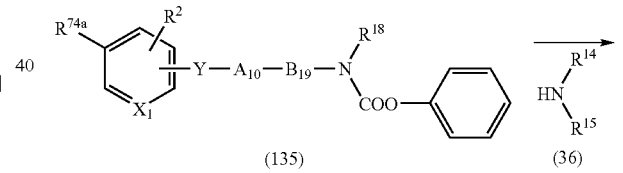

(135)            (36)

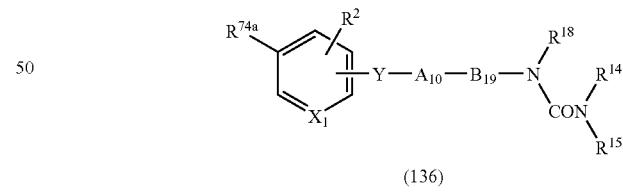

(136)

In the formula, $R^2$, $X_1$, Y, $A_{10}$, $B_{19}$, $R^{18}$, $X_2$, $R^{14}$, $R^{74a}$ and $R^{15}$ are the same as described above, provided that the a and b of $A_{10}$ are bound to a —Y group and a —$B_{19}$ group, respectively.

The reactions between compound (133) with the compound (134), and compound (135) with the compound (36) are carried out under reaction conditions similar to those of the reaction of the compound (2) with the compound (3) of the above described reaction formula 1.

[Reaction formula 91]

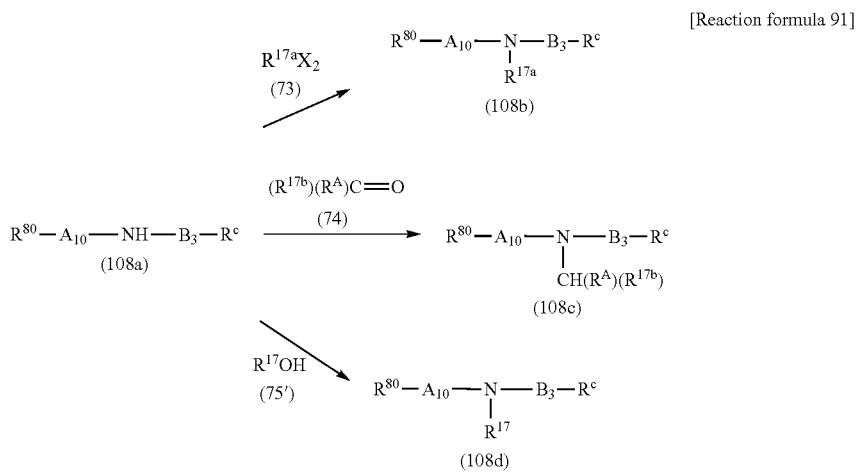

In the formula, $A_{10}$, $B_3$, $R^{17a}$, $R^{17b}$, $R^A$, $R^{17}$, $Y_1$, $R^c$ and $X_2$ are the same as described above, and $R^{80}$ represents a $-Y_1H$ group or a $-OR^{81}$ group, $R^{81}$ represents a protective group for the hydroxyl group, provided that the $CHR^A$ moiety in the side chain ($-N(B_3R^c)(CHR^AR^{17b})$) of the compound (108c) has not more than 6 carbon atoms, the a of $A_{10}$ is bound to a $-R^{80}$ group, and the b is bound to an $-NHB_3R^c$ group, $-N(R^{17a})B_3R^c$ group, $-N(CHR^AR^{17b})B_3R^c$ group or $-N(R_{17})B_3R^c$ group.

Here, examples of the protective group for the hydroxyl group include groups, which are previously mentioned, such as a phenyl lower alkyl group, a lower alkoxy lower alkyl group, tetrahydropyranyl group, tri lower alkylsilyl group, a lower alkanoyl group, and a lower alkyl group.

The reaction of the compound (108a) with the compound (73) is carried out under reaction conditions similar to those of the reaction of the compound (1b) with the compound (4) of the above described reaction formula 2.

The reaction of the compound (108a) with the compound (75') is carried out under reaction conditions similar to those of the reaction of the compound (1b) with the compound (6) of the above described reaction formula 2.

The reaction of the compound (108a) with the compound (74) is carried out under reaction conditions similar to those of the reaction of the compound (1b) with the compound (5) of the above described reaction formula 2.

When the reaction is carried out using the compound (74) as a starting material, wherein $R^A$ and $R^{17b}$ are bound with each other, together with carbon atoms bound to these groups, to form a cycloalkyl ring, and a hydride reducing agent, a cycloalkyloxytrialkylsilane such as [1-ethoxycyclopropyl]oxy]trimethylsilane may be used as a starting material in place of the compound (74) to produce the above described compound (74) in the reaction system.

[Reaction formula 92]

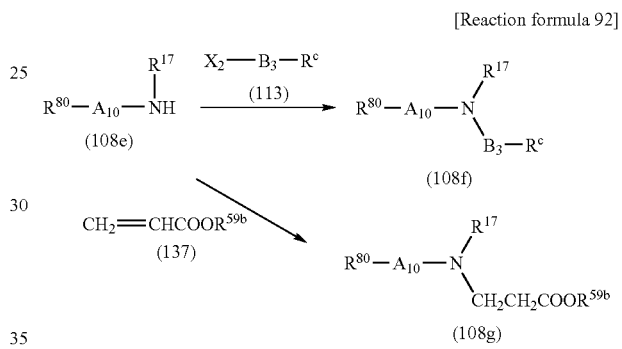

In the formula, $R^{80}$, $A_{10}$, $R^{17}$, $B_3$, $R^c$, $X_2$, and $R^{59b}$ are the same as described above, provided that the a of $A_{10}$ is bound to a $-R^{80}$ group and the b is bound to a $-NHR^{17}$ group, $-N(R^{17})B_3R^c$ group or $-N(R^{17})CH_2CH_2COOR^{59}$ group.

The reaction of the compound (108e) with the compound (113) is carried out under reaction conditions similar to those of the reaction of the compound (1b) with the compound (4) of the above described reaction formula 2.

The reaction of the compound (108e) with the compound (137) is carried out in an appropriate solvent in the presence of an acid.

Any of the solvents used in the reaction of the compound (2) with the compound (3) of the above described reaction formula 1 may be used in this reaction.

Examples of the acid used include mineral acids such as hydrochloric acid, sulfuric acid, and hydrobromic acid, organic acids such as acetic acid, trifluoroacetic acid, and sulfonic acids including p-toluenesulfonic acid, and Lewis acids such as aluminum chloride, zinc chloride, iron chloride, tin chloride, boron tribromide, and a boron trifluoride/diethyl ether complex. These acids may be used singly or in a mixture of two or more. The acid is appropriately used in an amount typically at least 0.01 to 5 times, and preferably 0.1 to 2 times of the compound (108e) on a molar basis. The compound (137) is appropriately used in an amount typically at least equimolar to the compound (108e), and preferably 1 to 10 times of the compound (108e) on a molar basis.

The above described reaction is carried out typically at 0 to 200° C., and preferably at about 0 to 150° C., and, in general, is completed in about 30 minutes to 80 hours.

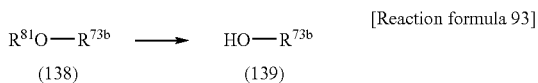

[Reaction formula 93]

In the formula, $R^{81}$ is the same as described above, $R^{73b}$ represents a $-A_{10}-T_2-COOR^{59a}$ or -A group, and $A_{10}$, $T_2$, $R^{59a}$ and A are the same as described above, provided that the a of $A_{10}$ is bound to an $-OR^{81}$ group or a hydroxyl group, and the b of $A_{10}$ is bound to a $-T_2$ group.

When $R^{81}$ of the material compound (138) represents a phenyl lower alkyl group, the reaction which converts the compound (138) into the compound (139) may be carried out under reaction conditions similar to those of the reduction reaction (1) (method using a catalytic hydrogen reducing agent) which is one reaction which converts the compound (68) into the compound (69) of the above described reaction formula 47.

When $R^{81}$ of the material compound (138) represents a tetrahydropyranyl group or tri-lower alkylsilyl group, the reaction which converts the compound (138) into the compound (139) may be carried out under reaction conditions similar to those of the hydrolysis reaction B described for above described reaction formula 9. The reaction which converts the compound (138) into the compound (139) is favorably carried out by hydrolysis using an acid. The acid is appropriately used in an amount typically 1 to 10 times, and preferably 1 to 2 times of the compound (138) on a molar basis.

When $R^{81}$ of the compound (138) represents a tri-lower alkylsilyl group, the compound (138) may be treated with a fluorine compound such as tetra-n-butyl ammonium fluoride, hydrogen fluoride or cesium fluoride.

When $R^{81}$ of the material compound (138) represents a lower alkoxy lower alkyl group or a lower alkyl group, the compound (138) may be treated in an appropriate solvent in the presence of an acid. Examples of the solvent include water, lower alcohols such as methanol, ethanol, and isopropanol, ethers such as dioxane, tetrahydrofuran, and diethyl ether, halogenated hydrocarbons such as dichloromethane, chloroform, and carbon tetrachloride, and polar solvents such as acetonitrile, and a mixture thereof. Examples of the acid used include mineral acids such as hydrochloric acid, sulfuric acid, and hydrobromic acid, fatty acids such as formic acid and acetic acid, sulfonic acids such as p-toluenesulfonic acid, Lewis acids such as boron trifluoride, aluminum chloride, and boron tribromide, iodides such as sodium iodide and potassium iodide, and a mixture of the above described iodide with the above described Lewis acid. The above described reaction is carried out at typically 0 to 200° C., and preferably at about room temperature to 150° C., and, in general, is completed in about 0.5 to 25 hours.

The above described hydrolysis may also be carried out using a basic compound under reaction conditions similar to those of the hydrolysis reaction B described for the above described reaction formula 9. Here, amines such as triethylamine may be used as the basic compound in addition to the basic compounds used in the hydrolysis reaction B.

When $R^{81}$ of the material compound (138) represents a lower alkanoyl group, the reaction which converts the compound (138) into the compound (139) may be carried out under reaction conditions similar to those of the hydrolysis reaction B described for the above described reaction formula 9.

When $R^{73a}$ of the compound (138) represents a group of the formula:

a dehydration reaction takes place under the above described hydrolysis conditions, and sometimes the compound (138), wherein the corresponding $R^{73a}$ represents a group of the formula:

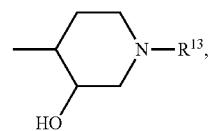

may be obtained.

[Reaction formula 94]

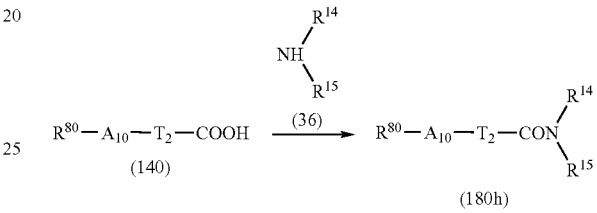

In the formula, $R^{80}$, $A_{10}$, $T_2$, $R^{14}$ and $R^{15}$ are the same as described above, provided that the a and b of $A_{10}$ are bound to a $-R^{80}$ group and a $-T_2$ group, respectively.

The reaction of the compound (140) with the compound (36) is carried out under reaction conditions similar to those of the reaction of the compound (1b) with the compound (6) of the above described reaction formula 2.

[Reaction formula 95]

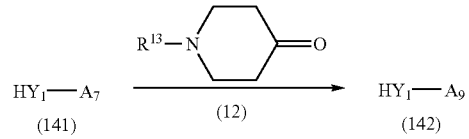

In the formula, $Y_1$, $A_7$, $R^{13}$ and $A_9$ are the same as described above.

The reaction of the compound (141) with the compound (12) is carried out under reaction conditions similar to those of the reaction of the compound (13) with the compound (12) in formula 8 described above.

[Reaction formula 96]

In the formula, $R^{80}$, $A_{10}$, $B_{21}$ and f are the same as described above, provided that the alkyl moiety in the side chain ($-(B_{21})_f-CH_2NH_2$) of the compound (144) has not more than 6 carbon atoms.

The reaction which converts the compound (143) into the compound (144) may be carried out under reaction conditions similar to those of the reaction using a hydride reducing agent which is one reaction of the compound (1b) with the compound (5) of the above described reaction formula 2.

[Reaction formula 97]

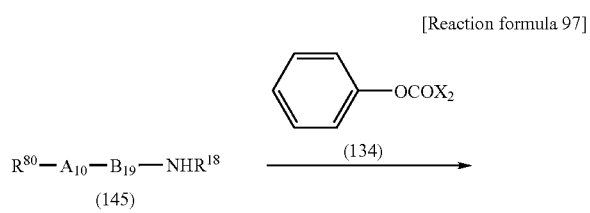

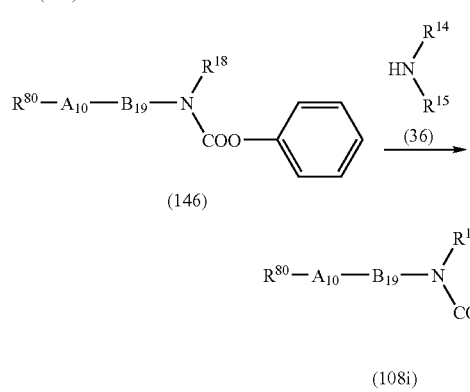

In the formula, $R^{80}$, $A_{10}$, $B_{19}$, $X_2$, $R^{18}$, $R^{14}$ and $R^{15}$ are the same as described above, provided that the a of $A_{10}$ is bound to a —$R^{80}$ group and the b is bound to a —$B_{19}$ group.

The reaction of the compound (145) with the compound (134) is carried out under reaction conditions similar to those of the reaction of the compound (133) with the compound (134) in the reaction formula 90 described above.

The reaction of the compound (146) with the compound (36) is carried out under reaction conditions similar to those of the reaction of the compound (1b) with the compound (6) of the above described reaction formula 2.

[Reaction formula 98]

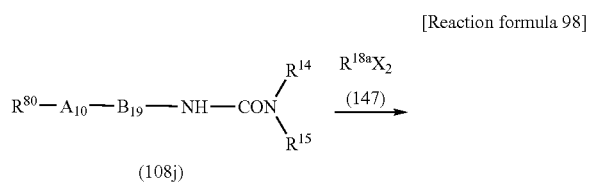

In the formula, $A_{10}$, $B_{19}$, $R^{14}$, $R^{15}$, $R^{80}$ and $X_2$ are the same as described above, and $R^{18a}$ represents a lower alkyl group, provided that the a and b of $A_{10}$ are bound to a —$R^{80}$ group and a —$B_{19}$ group, respectively.

The reaction of the compound (108j) with the compound (147) is carried out under reaction conditions similar to those of the reaction of the compound (1b) with the compound (4) of the above described reaction formula 2.

[Reaction formula 99]

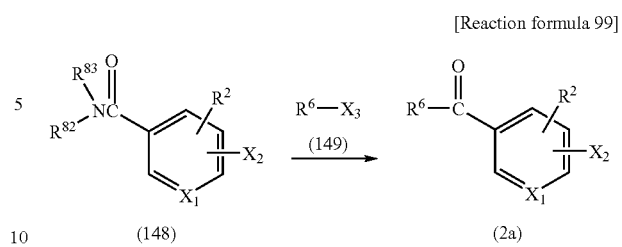

In the formula, $R^2$, $X_1$, $X_2$, $X_3$ and $R^6$ are the same as described above, $R^{82}$ represents a lower alkyl group, and $R^{83}$ represents a lower alkoxy group.

The reaction of the compound (148) with the compound (149) is carried out in an appropriate solvent in the presence of a catalyst.

Any of the solvents used in the reaction of the compound (2) with the compound (3) of the above described reaction formula 1 may be used in this reaction.

Examples of the catalyst include magnesium. The catalyst is appropriately used in an amount typically at least equimolar to the compound (148), and preferably 1 to 5 times of the compound (148) on a molar basis.

The above described reaction is carried out typically at 0 to 200° C., preferably at about 0 to 150° C., and, in general, is completed in about 30 minutes to 10 hours.

[Reaction formula 100]

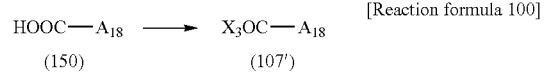

In the formula, $A_{18}$ represents a -A group or -$A_{10}$-$T_2$-COOR$^{59b}$ group, and A, $A_{10}$, $T_2$, $R^{59b}$ and $X_3$ are the same as described above.

The reaction which converts the compound (150) into the compound (107') is carried out under reaction conditions similar to those of the reaction which converts the compound (85) into the compound (7') of the above described reaction formula 55.

[Reaction formula 101]

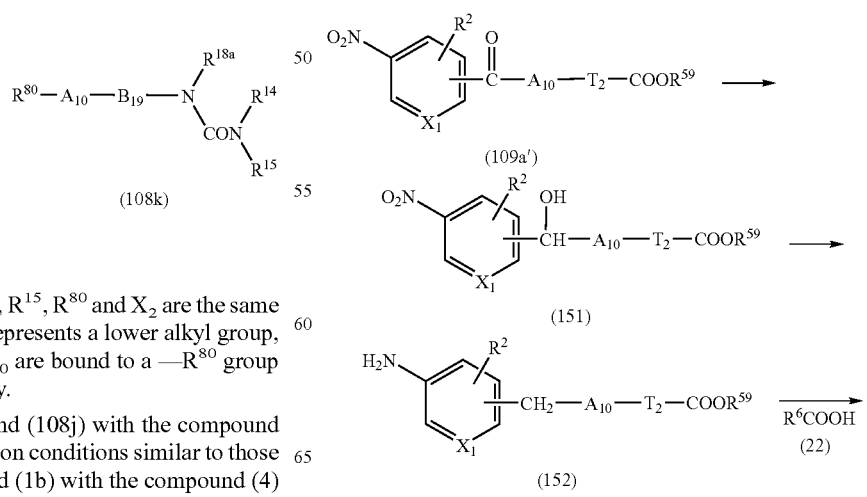

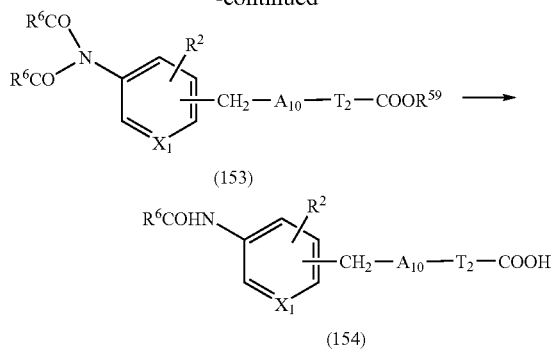

In the formula, $R^2$, $X_1$, $A_{10}$, $T_2$ and $R^6$ are the same as described above, provided that the a of $A_{10}$ is bound to —CO group, —CH(OH) group or —CH$_2$, and the b is bound to a -T$_2$ group.

The reaction which converts the compound (109a') into the compound (151) may be carried out under reaction conditions similar to those of the reaction using a hydride reducing agent which is one reaction of the compound (1b) with the compound (5) of the above described reaction formula 2.

The reaction which converts the compound (151) into the compound (152) is carried out under reaction conditions similar to those of the reaction which converts the compound (68) into the compound (69) of the above described reaction formula 47.

The reaction of the compound (152) with the compound (22) is carried out under reaction conditions similar to those of the reaction of the compound (1b) with the compound (6) of the above described reaction formula 2.

The reaction which converts the compound (153) into the compound (154) may be carried out under reaction conditions similar to those of hydrolysis B reaction described for the above described reaction formula 9.

[Reaction formula 102]

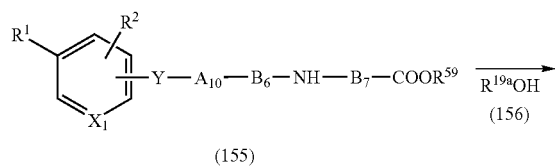

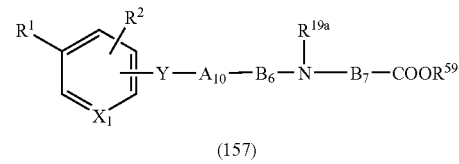

In the formula, $R^1$, $R^2$, $X_1$, Y, $A_{10}$, $B_6$, $B_7$ or $R^{59}$ are the same as described above, and $R^{19a}$ represents a lower alkanoyl group, provided that the a and b of $A_{10}$ are bound to a —Y group and a —B$_6$ group, respectively.

The reaction of the compound (155) with the compound (156) is carried out under reaction conditions similar to those of the reaction of the compound (1b) with the compound (6) of the above described reaction formula 2.

[Reaction formula 103]

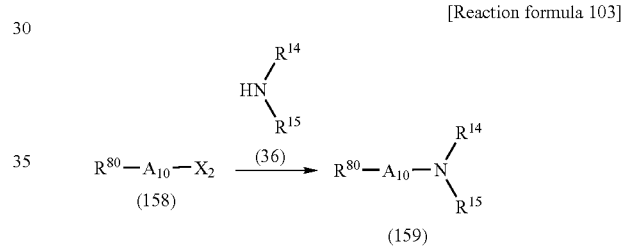

In the formula, $R^{80}$, $A_{10}$, $X_2$, $R^{14}$ and $R^{15}$ are the same as described above.

The reaction of the compound (158) with the compound (36) is carried out under similar reacting conditions as the reaction of the compound (114) with the compound (36) of the above described reaction formula 74 in which l is 0.

[Reaction formula 104]

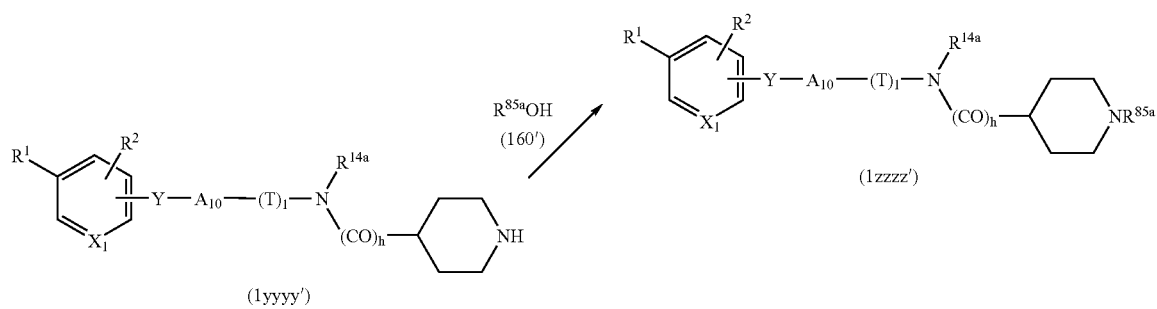

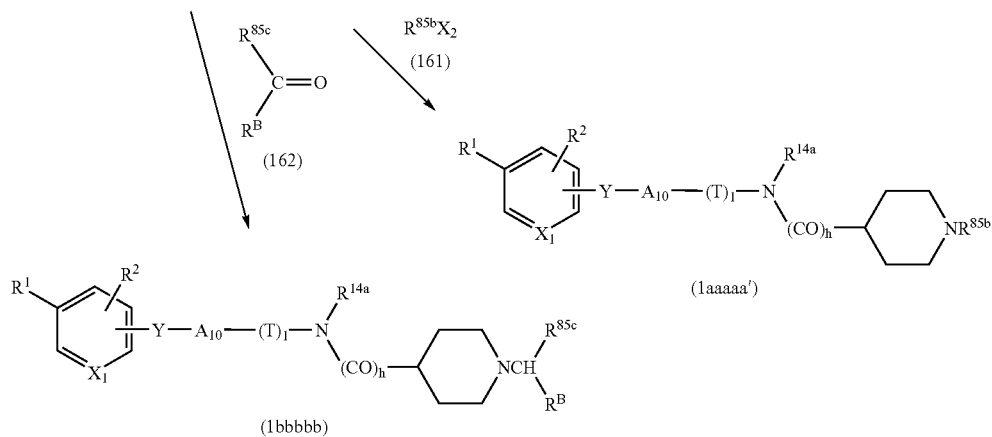

In the formula, $R^1$, $R^2$, Y, $A_{10}$, $R^{14a}$, h, T, l, $R^B$, $X_1$ and $X_2$ are the same as described above, $R^{85a}$ represents a benzoyl group, $R^{85b}$ represents a lower alkoxy carbonyl group, a phenyl lower alkyl group, a lower alkyl group or furyl lower alkyl group, and $R^{85c}$ represents a hydrogen atom, a lower alkyl group, a phenyl group, phenyl lower alkyl group, a furyl group or a furyl lower alkyl group, provided that the —CH($R^B$)$R^{85c}$ group of the compound (1bbbbb) has not more than 6 carbon atoms.

The reaction of the compound (1yyyy') with the compound (160') is carried out under reaction conditions similar to those of the reaction of the compound (1b) with the compound (6) of the above described reaction formula 2.

The reaction of the compound (1yyyy') with the compound (161) is carried out under reaction conditions similar to those of the reaction of the compound (1b) with the compound (4) of the above described reaction formula 2.

The reaction of the compound (1yyyy') with the compound (162) is carried out under reaction conditions similar to those of the reaction of the compound (1b) with the compound (5) of the above described reaction formula 2.

In the formula, $R^2$, $B_0$, Y, $X_1$, $A_{17}$, $R^8$, $X_2$, $X_3$ and $R^6$ are the same as described above, $R^{86}$ represents a lower alkylsulfonyl group, and $R^{87}$ represents a oxygen atom or a —N($R^8$)— group.

The reaction of the compound (165) with the compound (163) is carried out under reaction conditions similar to those of the reaction of the compound (2) with the compound (3) of the above described reaction formula 1.

The reaction which converts the compound (165) into the compound (167) is carried out under reaction conditions similar to those of the reaction which converts the compound (85) into the compound (7') of the above described formula 55.

The reaction of the compound (166) or the compound (167) with the compound (164) is carried out under reaction conditions similar to those of the reaction of the compound (2) with the compound (3) of the above described reaction formula 1.

[Reaction formula 105]

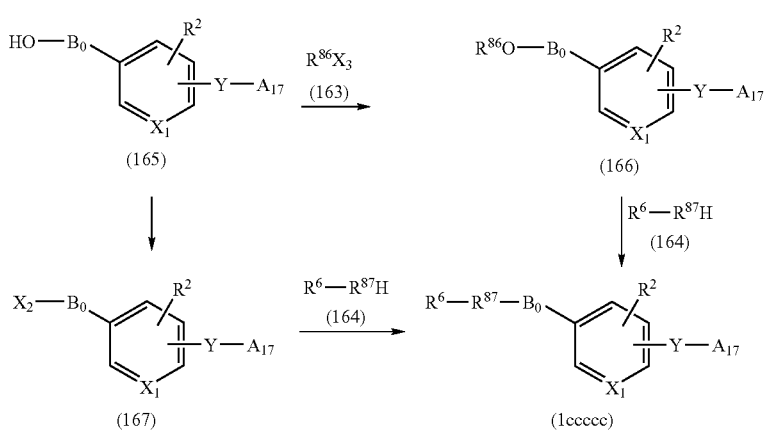

[Reaction formula 106]

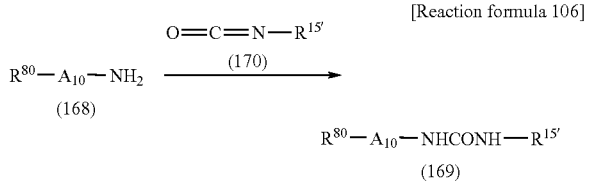

In the formula, $R^{80}$ and $A_{10}$ are the same as described above, $R^{15'}$ represents the same group as (5) in $R^{15}$ described above.

The reaction of the compound (168) with the compound (170) is carried out under reaction conditions similar to those of the reaction of the compound (30) with the compound (66) of the above described reaction formula 46.

[Reaction formula 107]

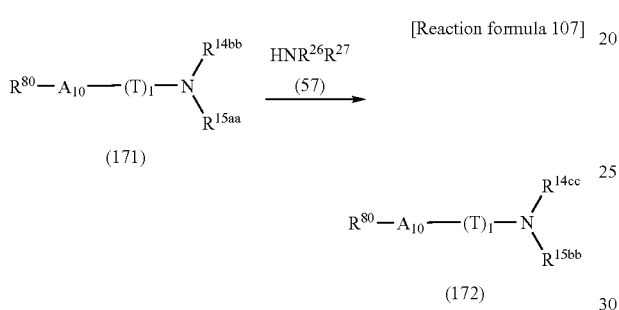

In the formula, $R^{80}$, $A_{10}$, T, l, $R^{14bb}$, $R^{15aa}$, $R^{14cc}$, $R^{15bb}$, $R^{26}$ and $R^{27}$ are the same as described above.

The reaction of the compound (171) with the compound (57) is carried out under reaction conditions similar to those of the reaction of the compound (1iiii) with the compound (57) of the above described reaction formula 31.

[Reaction formula 108]

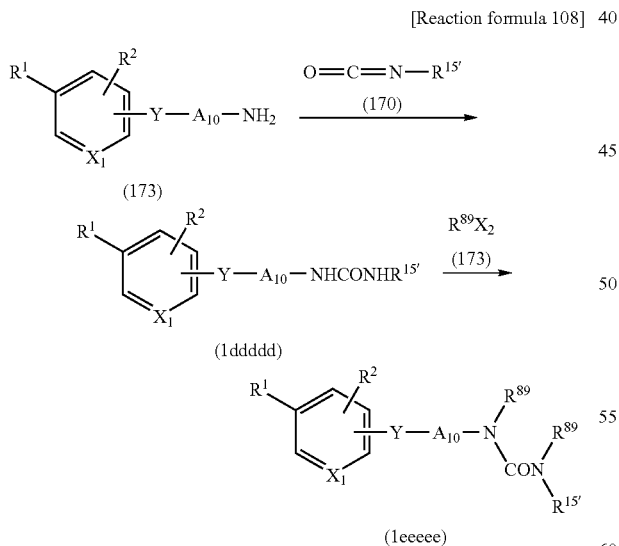

In the formula, $R^1$, $R^2$, $X_1$, Y, $A_{10}$, $R^{15'}$ and $X_2$ are the same as described above, and $R^{89}$ represents a lower alkyl group.

The reaction of the compound (173) with the compound (170) is carried out under reaction conditions similar to those of the reaction of the compound (30) with the compound (66) of the above described reaction formula 46.

The reaction of the compound (1ddddd) with the compound (173) is carried out under reaction conditions similar to those of the reaction of the compound (2) with the compound (3) of the above described reaction formula 1.

[Reaction formula 109]

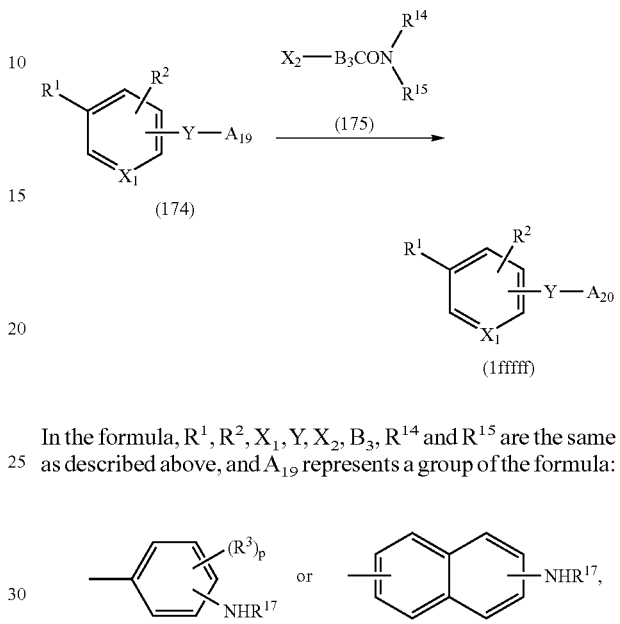

In the formula, $R^1$, $R^2$, $X_1$, Y, $X_2$, $B_3$, $R^{14}$ and $R^{15}$ are the same as described above, and $A_{19}$ represents a group of the formula:

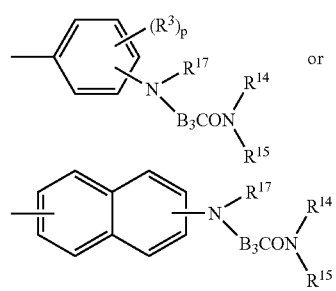

and $A_{20}$ represents a group of the formula:

wherein $R^3$, p, $R^{17}$, $B_3$, $R^{14}$ and $R^{15}$ are the same as described above.

The reaction of the compound (174) with the compound (175) is carried out under reaction conditions similar to those of the reaction of the compound (2) with the compound (3) of the above described reaction formula 1.

[Reaction formula 110]

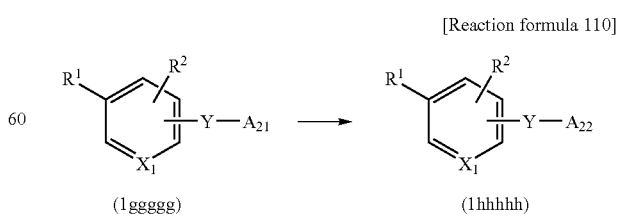

In the formula, $R^1$, $R^2$, $X_1$ and Y are the same as described above, $A_{21}$ represents a group of the formula:

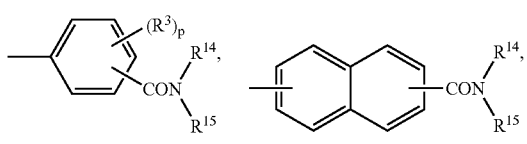
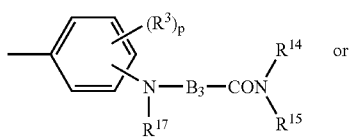
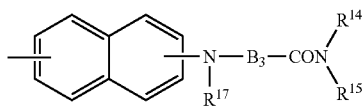

and $A_{22}$ represents a group of the formula:

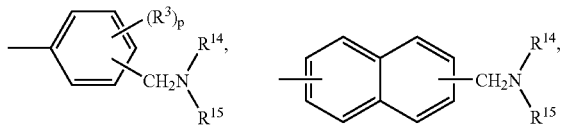
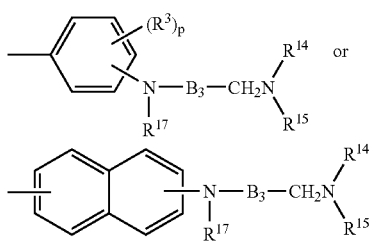

wherein $R^3$, p, $R^{17}$, $B_3$, $R^{14}$ and $R^{15}$ are the same as described above.

The reaction which converts the compound (1ggggg) into the compound (1hhhhh) is carried out under reaction conditions similar to those of the reaction of the compound (1b) with the compound (5) of the above described reaction formula 2 in which a hydrogen reducing agent is used.

[Reaction formula 111]

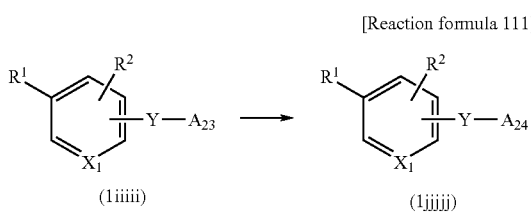

In the formula, $R^1$, $R^2$, $X_1$ and Y are the same as described above, $A_{23}$ represents a group of the formula:

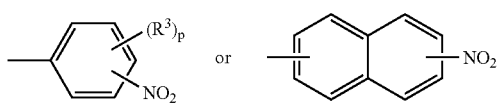

and $A_{24}$ represents a group, of the formula:

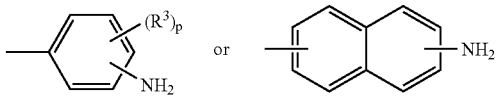

wherein $R^3$ and p are the same as described above.

The reaction which converts the compound (1iiiii) into the compound (1jjjjj) is carried out under reaction conditions similar to those of the reaction which converts the compound (68) into the compound (69) of the above described reaction formula

[Reaction formula 112]

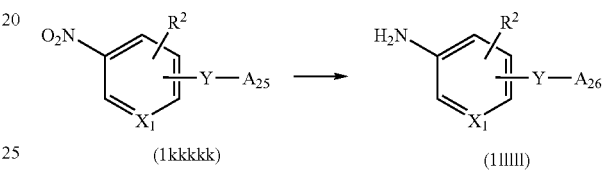

In the formula, $R^2$, $X_1$ and Y are the same as described above, $A_{25}$ represents a group of the formula:

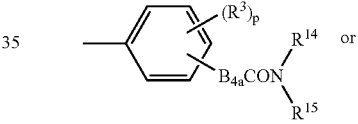
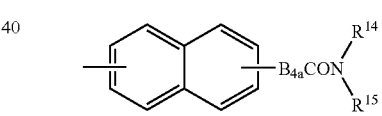

and $A_{26}$ represents a group of the formula:

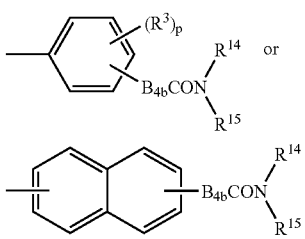

wherein $B_{4a}$ represents a lower alkenylene group, $B_{4b}$ represents a lower alkylene group, and $R^3$, p, $R^{14}$ and $R^{15}$ are the same as described above.

The reaction which converts the compound (1kkkkk) into the compound (1lllll) is carried out under reaction conditions similar to those of the reaction which converts the compound (68) into the compound (69) in the (1) method of formula 47 described above.

[Reaction formula 113]

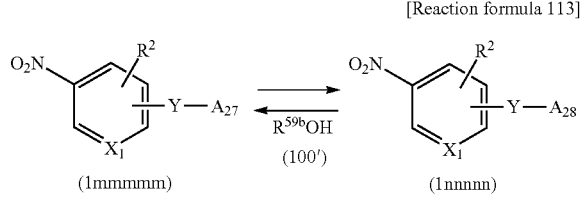

In the formula, $R^2$, $X_1$, Y, and $R^{59b}$ are the same as described above, $A_{28}$ represents a group of the formula:

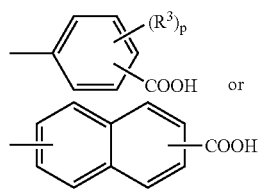

and $A_{27}$ represents a group of the formula:

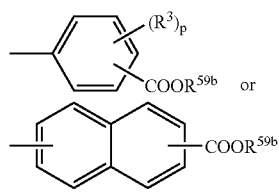

wherein $R^3$, p and $R^{59b}$ are the same as described above.

The reaction which converts the compound (1mmmmm) into the compound (1nnnnn) is carried out under reaction conditions similar to those of the hydrolysis B reaction described for the above described reaction formula 9.

The reaction of the compound (1nnnnn) with the compound (100') is carried out under reaction conditions similar to those of the reaction of the compound (1fff) with the compound (43) of the above described reaction formula 20.

[Reaction formula 114]

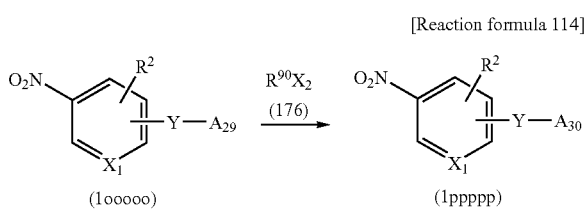

In the formula, $R^2$, $X_1$, $X_2$ and Y are the same as described above, $A_{29}$ represents a group of the formula:

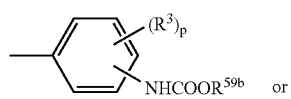

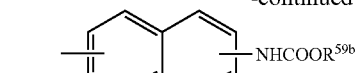

and $A_{30}$ represents

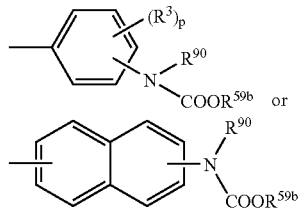

wherein $R^{90}$ represents a lower alkyl group which may have a hydroxyl group as a substituent, and $R^3$, p and $R^{59b}$ are the same as described above.

The reaction of the compound (1ooooo) with the compound (176) is carried out under reaction conditions similar to those of the reaction of the compound (1b) with the compound (4) of the above described reaction formula 2.

[Reaction formula 115]

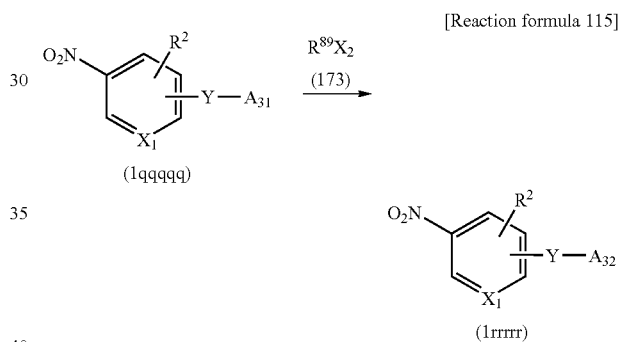

In the formula, $R^2$, $X_1$, $X_2$ and Y are the same as described above, $A_{31}$ represents a group of the formula:

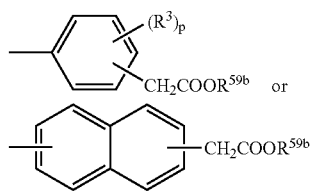

and $A_{32}$ represents

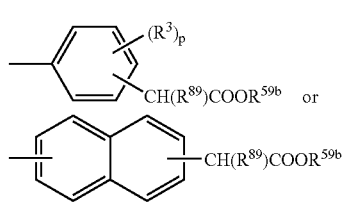

wherein $R^3$, p, $R^{59b}$ and $R^{89}$ are the same as described above.

The reaction of the compound (1qqqqq) with the compound (173) is carried out under reaction conditions similar to those of the reaction of the compound (2) with the compound (3) of the above described reaction formula 1.

[Reaction formula 116]

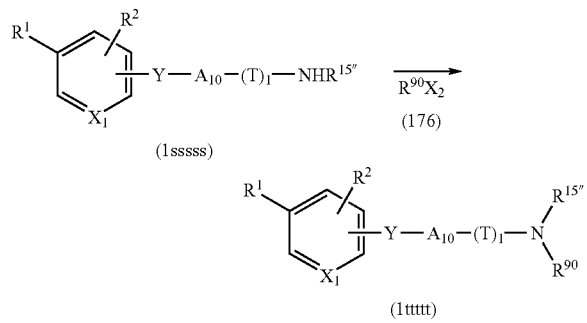

(1sssss)

(1ttttt)

In the formula, $R^1$, $R^2$, $X_1$, Y, $A_{10}$, T, l, $R^{90}$ and $X_2$ are the same as described above.

$R^{15''}$ represents the group (2), (3), (4), (5), (6), (7), (8), (10), (11), (12), (13), (14), (15), (16), (17), (18), (19), (20), (21), (22), (23), (24), (25), (26), (27), (26a), (27a), (28a), (29a), (30a), (31a), (32a), (33a), (34a), (35a), (36a), or (37a), which is defined for the above described $R^{15}$ described above.

The reaction of the compound (1sssss) with the compound (176) is carried out under reaction conditions similar to those of the reaction of the compound (2) with the compound (3) of the above described reaction formula 1.

[Reaction formula 117]

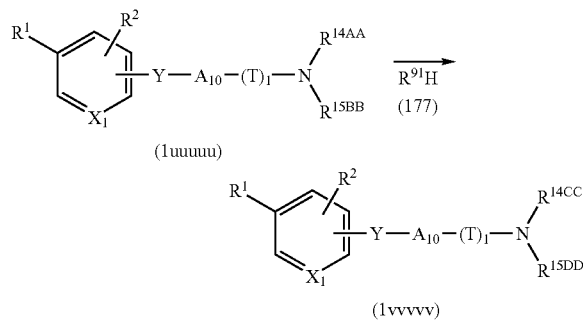

(1uuuuu)

(1vvvvv)

In the formula, $R^1$, $R^2$, $X_1$, Y, $A_{10}$, T and l are the same as described above, $R^{14AA}$ and $R^{15BB}$ represent a 5- to 10-membered saturated or unsaturated heterocyclic group the same as defined for the above described $R^{14}$ and $R^{15}$, except that the heterocyclic ring has at least one —$(B_{12}CO)$t-$N(R^2)$—CO—$B_{16}X_2$ group thereon, $R^{14CC}$ and $R^{15DD}$ represent a 5- to 10-membered saturated or unsaturated heterocyclic group the same as defined for the above described $R^{14}$ and $R^{15}$, except that the heterocyclic ring has at least one —$(B_{12}CO)$t-$N(R^2)$—CO—$B_{16}R^{91}$ group thereon, wherein $B_{12}$, t, $B_{16}$ and $X_2$ are the same as described above, $R^{91}$ represents an imidazolyl group, and $R^{20'}$ represents a hydrogen atom, a cycloalkyl group, an amino group which may have a lower alkoxycarbonyl group as a substituent, a benzoyl group which may have 1 to 3 lower alkoxy groups as substituents on the phenyl ring, a lower alkyl group, a lower alkyl group which have 1 or 2 phenyls which may be substituted on the phenyl ring with 1 to 3 substituents selected from the group consisting of a lower alkoxycarbonyl group, a cyano group, a nitro group, a phenyl group, a halogen atom, a lower alkyl group which may have a halogen atom as a substituent, a lower alkoxy group which may have a halogen atom as a substituent and a lower alkylthio group, a phenyl group which may be substituted on the phenyl ring with 1 to 3 groups selected from the group consisting of a lower alkoxy group which may have a halogen atom as a substituent and a lower alkyl group which may have a halogen atom as a substituent, a lower alkoxycarbonyl group, a cycloalkyl lower alkyl group, a pyrrolidinyl lower alkyl group which may have, on the pyrrolidine ring, 1 to 3 lower alkyl groups which may have a hydroxyl group as a substituent, an amino substituted lower alkyl group which may have a substituent selected from the group consisting of a phenyl group and a lower alkyl group, a 1,2,3,4-tetrahydronaphthyl substituted lower alkyl group which may have 1 to 5 lower alkyl groups as substituents on the 1,2,3,4-tetrahydronaphthalene ring, a naphthyl lower alkyl group, a pyridyl lower alkyl group, a quinolyl lower alkyl group, a 1,2,3,4-tetrazolyl lower alkyl group which may have, on the tetrazole ring, 1 to 3 substituents selected from the group consisting of a lower alkyl group and a phenyl lower alkyl group, a 1,2,4-triazolyl lower alkyl group, a tetrahydrofuryl lower alkyl group which may have a hydroxyl group as a substituent on the lower alkyl group, a phenoxy lower alkyl group which may have, on the phenyl ring, 1 to 3 substituents selected from the group consisting of a lower alkyl group and a nitro group, a phenyl lower alkanoyl group, a lower alkanoyl group which may have a halogen atom as a substituent, an imidazolyl lower alkanoyl group, a lower alkoxycarbonyl lower alkyl group, a pyridyl group or a carboxy lower alkyl group.

The reaction of the compound (1uuuuu) with the compound (177) is carried out under reaction conditions similar to those of the reaction of the compound (1b) with the compound (4) of the above described reaction formula 2.

[Reaction formula 118]

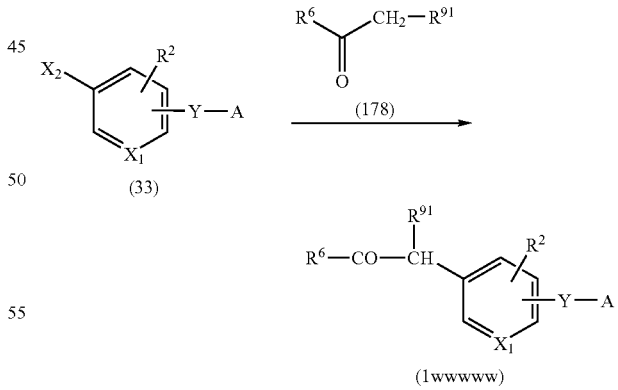

(33)

(1wwwww)

In the formula, $X_1$, $X_2$, $R^{26}$, Y, A and $R^6$ are the same as described above, and $R^{91}$ represents a hydrogen atom or a lower alkyl group.

The reaction of the compound (33) with the compound (178) may also be carried out in an appropriate solvent in the presence of a basic compound and a catalyst. Examples of the inert solvent used include water, aromatic hydrocarbons such as benzene, toluene, and xylene, ethers such as diethyl ether, tetrahydrofuran, dioxane, 2-methoxyethanol, monoglyme, and diglyme, halogenated hydrocarbons such as dichloromethane, dichloroethane, chloroform, and carbon tetrachloride, lower alcohols such as methanol, ethanol, isopropanol, butanol, tert-butanol, and ethylene glycol, fatty acids such as acetic acid, esters such as ethyl acetate and methyl acetate, ketones such as acetone and methyl ethyl ketone, acetonitrile, pyridine, N-methylpyrrolidone, dimethyl sulfoxide, N,N-dimethylformamide, and hexamethylphosphoric acid triamide, and a mixture thereof.

Examples of the basic compound include carbonates such as sodium carbonate, potassium carbonate, sodium bicarbonate, potassium bicarbonate, and cesium carbonate, metal hydroxides such as sodium hydroxide, potassium hydroxide, and calcium hydroxide, potassium phosphate, sodium phosphate, sodium hydride, potassium hydride, potassium, sodium, sodium amide, metal alcoholates such as sodium methylate, sodium ethylate, sodium n-butoxide, sodium tert-butoxide, and potassium tert-butoxide, alkylsilylamide alkali metal salts such as potassium bis(trimethylsilyl)amide, and organic bases such as pyridine, imidazole, N-ethyldiisopropylamine, dimethylaminopyridine, triethylamine, trimethylamine, dimethylaniline, N-methylmorpholine, 1,5-diazabicyclo[4.3.0]nonene-5 (DBN), 1,8-diazabicyclo[5.4.0]undecene-7 (DBU), and 1,4-diazabicyclo[2.2.2]octane (DABCO), and a mixture thereof.

Examples of the catalyst may include palladium compounds such as palladium acetate, bis(tributyltin)/bis(dibenzylideneacetone)palladium, copper iodide/2,2'-bipyridyl, bis(dibenzylidene-acetone)palladium, copper iodide/bis(triphenylphosphine)palladium dichloride, tris(dibenzylideneacetone)dipalladium, R-tris(dibenzylideneacetone)-dipalladium, S-tris(dibenzylideneacetone)dipalladium, palladium (II) acetate, [1,1'-bis(diphenylphosphino)-ferrocene]dichloropalladium (II), and tetrakis (triphenylphosphine)palladium, compounds such as R-2,2'-bis(diphenylphosphino)-1,1'-binaphthyl (R-BINAP), S-2,2'-bis(diphenylphosphino)-1,1'-binaphthyl (S-BINAP), RAC-2,2'-bis(diphenylphosphino)-1,1'-binaphthyl (RAC-BINAP), and 2,2-bis(diphenylimidazolidinyliden), xanthene compounds such as 4,5-bis(diphenylphosphino)-9,9-dimethylxanthene, and borates such as tri-tert-butylphosphine tetrafluoroborate, and a mixture thereof.

The basic compound is appropriately used in an amount at least 0.5 times, and preferably 0.5 to 40 times of the compound (33) on a molar basis. The catalyst is appropriately used in a typical catalyst amount based on the compound (33).

The compound (178) is appropriately used in an amount at least in 0.5 times, and preferably 0.5 to 3 times of the compound (33) on a molar basis.

The above described reaction is carried out typically at room temperature to 200° C., preferably at room temperature to about 150° C., and is completed in about 0.5 to 20 hours.

[Reaction formula 119]

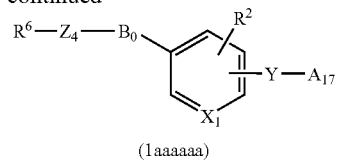

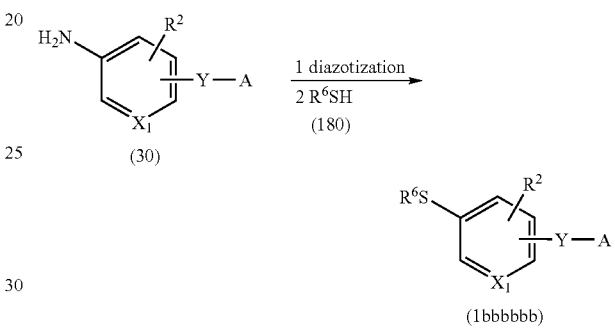

In the formula, $B_o$, $X_1$, $R^2$, Y, $A_{17}$, $R^6$ and $X_2$ are the same as described above, $R^{92}$ represents a $R^6$—$Z_4$— group or $R^6$— group and $Z_4$ represents a lower alkylene group.

The reaction of the compound (64) with the compound (179) may be carried out under reaction conditions similar to those of the reaction of the compound (2) with the compound (3) of the above described reaction formula 1.

[Reaction formula 120]

In the formula $R^2$, $X_1$, Y, A and $R^6$ are the same as described above.

The method for converting the compound (30) into the compound (1bbbbbb) is to obtain a compound (1bbbbbb) by subjecting the compound (30) to diazotization and by reacting the diazonium salt thus obtained with the compound (180).

The diazotization reaction 1. may be carried out in an appropriate solvent in the presence of an acid and a diazotizing agent. Examples of the solvent used in the above described reaction include water and acetonitrile. Examples of the acid used include hydrochloric acid, hydrobromic acid, sulfuric acid, tetrafluoroboric acid, and hexafluorophosophoric acid. Examples of the diazotizing agent include metal nitrites such as sodium nitrite and potassium nitrite, lower alkyl nitrites such as t-butyl nitrite and isoamyl nitrite. The acid is appropriately used in an amount typically about 1 to 10 times of the compound (30), and preferably about 1 to 5 times of the compound (30) on a molar basis. The diazotizing agent is appropriately used in an amount typically at least about equimolar to the compound (30), and preferably 1 to 3 times of the compound (30) on a molar basis. The above described reaction is typically carried out at about 0 to 70° C., and preferably at about 0° C. to room temperature, and is completed in about a few minutes to 5 hours. The reaction 2. of the diazonium salt obtained in the reaction 1. with the compound (180) may be carried out in the similar solvent as in the reaction 1 and in the presence of a basic compound. Any of the basic compounds used in the reaction of the compound (2) with the compound (3) of the above described reaction formula 1 may be used in this reaction. The basic compound is appropriately used in an amount at least equimolar to the compound (30), and preferably 1 to 5 times of the compound (30) on a molar basis. The compound (180) is appropriately used in an amount at least equimolar to the compound (30), and preferably 1 to 5 times of the compound (30) on a molar basis. The above described reaction is carried out typically at about 0 to 70° C., preferably at about 0° C. to room temperature, and is completed in about a few minutes to 5 hours.

The above described reaction is carried out typically at −30 to 200° C., and preferably at 0 to 150° C. and is completed in 0.5 to about 30 hours. A molecular sieve such as Molecular Sieves 3A (MS-3A), Molecular Sieves 4A (MS-4A) or the like may be added to the reaction.

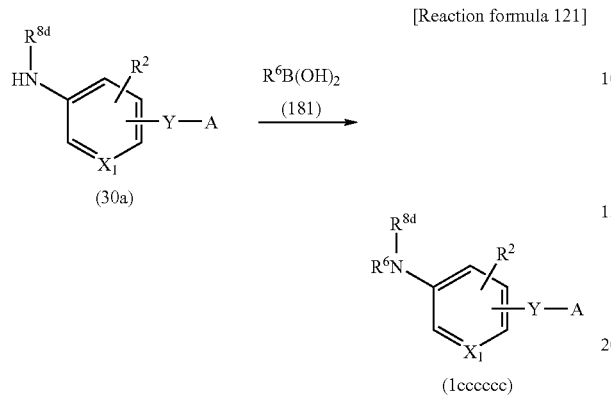

[Reaction formula 121]

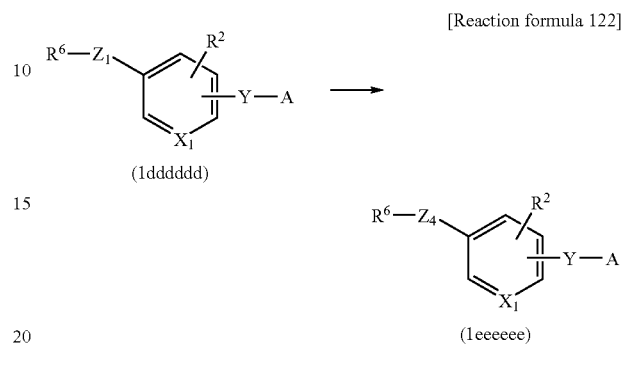

[Reaction formula 122]

In the formula, $X_1$, $R^{8d}$, Y, A, $R^2$ and $R^6$ are the same as described above.

The reaction of the compound (30a) with the compound (181) may be carried out in an appropriate solvent in the presence of an acid and a catalyst. Examples of the inert solvent used include water, aromatic hydrocarbons such as benzene, toluene, and xylene, ethers such as diethyl ether, tetrahydrofuran, dioxane, 2-methoxyethanol, monoglyme, and diglyme, halogenated hydrocarbons such as dichloromethane, dichloroethane, chloroform, and carbon tetrachloride, lower alcohols such as methanol, ethanol, isopropanol, butanol, tert-butanol, and ethylene glycol, fatty acids such as acetic acid, esters such as ethyl acetate and methyl acetate, ketones such as acetone and methyl ethyl ketone, acetonitrile, pyridine, dimethylsulfoxide, N,N-dimethylformamide, and hexamethylphosphoric acid triamide, and a mixture thereof.

Examples of the basic compound include carbonates such as sodium carbonate, potassium carbonate, sodium bicarbonate, potassium bicarbonate, and cesium carbonate, metal hydroxides such as sodium hydroxide, potassium hydroxide, and calcium hydroxide, sodium hydride, potassium hydride, potassium, sodium, sodium amide, metal alcoholates such as sodium methylate, sodium ethylate, sodium n-butoxide, sodium tert-butoxide, and potassium tert-butoxide, organic bases such as pyridine, imidazole, N-ethyldiisopropylamine, dimethylaminopyridine, triethylamine, trimethylamine, dimethylaniline, N-methylmorpholine, 1,5-diazabicyclo[4.3.0]nonene-5 (DBN), 1,8-diazabicyclo[5.4.0]undecene-7 (DBU), and 1,4-diazabicyclo[2.2.2]octane (DABCO), and a mixture thereof.

Examples of the catalyst include palladium compounds such as tetrakis(triphenylphosphine)palladium (0) and dichlorobis(triphenylphosphine)palladium (II), and copper compounds such as copper (II) acetate.

The basic compound is appropriately used in an amount at least equimolar to the compound (30a), and preferably 1 to 5 times of the compound (30a) on a molar basis. The catalyst is appropriately used in an amount 0.001 to 1 times, and preferably 0.01 to 0.5 times of the compound (30a) on a molar basis.

The compound (181) is appropriately used in an amount at least equimolar to the compound (30a), and preferably 1 to 5 times of the compound (30a) on a molar basis.

In the formula, $R^6$, $Z_1$, $X_1$, $R^2$, Y and A are the same as described above. $Z_4$ represents a lower alkylene group.

The reaction which converts the compound (1dddddd) into the compound (1eeeeee) may be carried out in an appropriate solvent in the presence of a catalytic hydrogen reducing agent.

Examples of the solvent used include water, fatty acids such as acetic acid, alcohols such as methanol, ethanol, and isopropanol, aliphatic hydrocarbons such as n-hexane, alicyclic hydrocarbons such as cyclohexane, ethers such as diethyl ether, dimethoxyethane, tetrahydrofuran, monoglyme, diglyme, and 1,4-dioxane, esters such as methyl acetate, ethyl acetate, and butyl acetate, and aprotic polar solvents such as N,N-dimethylformamide, N,N-dimethylacetoamide, and N-methylpyrrolidone, and a mixture thereof.

Examples of the catalytic hydrogen reducing agent include palladium, palladium-black, palladium-carbon, palladium hydroxide-carbon, rhodium-alumina, platinum, platinum oxide, copper chromite, Raney nickel, and palladium acetate.

The above described catalytic hydrogen reducing agent is typically used in an amount 0.01 to 1 times of the compound (1dddddd) on a molar basis.

The above reaction favorably proceeds typically at about −20 to 150° C., and preferably at 0 to 100° C. and, in general, is completed in 0.5 to 20 hours. The hydrogen pressure may be applied typically at 1 to 10 atm.

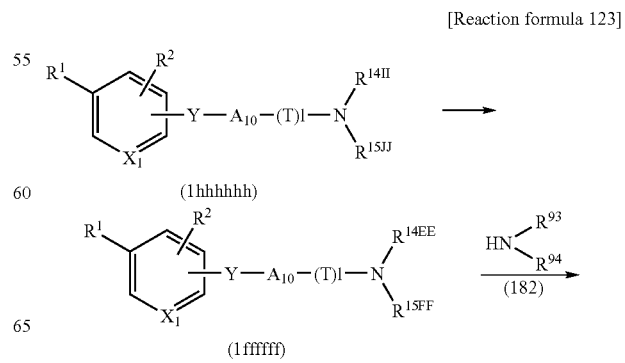

[Reaction formula 123]

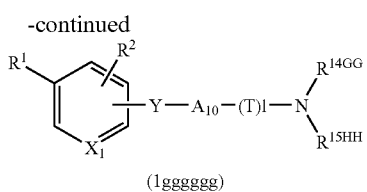

(1ggggggg)

In the formula, $R^1$, $R^2$, Y, $X_1$, $A_{10}$, T and l are the same as described above; $R^{14H}$, and $R^{15JJ}$ represent a 5- to 10-membered saturated or unsaturated heterocyclic group the same as defined for the above described $R^{14}$ and $R^{15}$ except for having at least one phenyl group which has a lower alkoxycarbonyl group on the heterocyclic ring; $R^{14EE}$ and $R^{15FF}$ represent a 5- to 10-membered saturated or unsaturated heterocyclic group the same as defined for the above described $R^{14}$ and $R^{15}$ except for having at least one phenyl group which has a carboxy group on the heterocyclic ring; $R^{14GG}$ and $R^{15HH}$ represent a 5- to 10-membered saturated or unsaturated heterocyclic group the same as defined for the above described $R^{14}$ and $R^{15}$ except for having at least one phenyl group which has a carbamoyl group which may have a group selected from the group consisting of a lower alkoxy lower alkyl group and a lower alkyl group on the heterocyclic ring; and $R^{93}$ and $R^{94}$ represent a hydrogen atom, a lower alkyl group or a lower alkoxy lower alkyl group.

The reaction which converts the compound (1hhhhhh) into the compound (1ffffff) may be carried out under reaction conditions similar to those of the hydrolysis B described for the above described reaction formula 9.

The reaction of the compound (1ffffff) with the compound (182) is carried out under reaction conditions similar to those of the reaction of the compound (1b) with the compound (6) of the above described reaction formula 2.

In the formula, $X_1$, $R^2$, Y, A, $X_2$, k, $X_3$, $R^6$, $B_{20a}$ and d' are the same as described above.

The reaction of the compound (30) with the compound (183) is carried out under reaction conditions similar to those of the reaction of the compound (30) with the compound (66) of the above described reaction formula 46.

The reaction which converts the compound (184) into the compound (1jjjjjj) may be carried out under reaction conditions similar to those of the reaction of the compound (2) with the compound (3) of the above described reaction formula 1.

The reaction of the compound (1jjjjjj) with the compound (185) is carried out under reaction conditions similar to those of the reaction of the compound (2) with the compound (3) of the above described reaction formula 1.

When d' represents 0 in the compound (185), the reaction which converts the compound (1jjjjjj) into the compound (1kkkkkk) may also be carried out in an appropriate solvent in the presence of a halogenated copper such as copper iodide, an alkylglycine such as N,N-dimethylglycine, or an alkali metal phosphate such as potassium phosphate. Any of the solvents used in the reaction of the compound (2) with the compound (3) of the above described reaction formula 1 may be used here. Halogenated copper or alkylglycine is used in a typical catalyst amount. The alkali metal phosphate is appropriately used in an amount typically equimolar to the compound (1jjjjjj), and preferably 1 to 5 times of the compound (1jjjjjj) on a molar basis. The compound (185) is used in an amount typically 0.5 to 5 times, and preferably 0.5 to 3 times of the compound (1jjjjjj) on a molar basis. The above described reaction is carried out typically at about room temperature to 200° C., preferably at about room temperature to 150° C. and is completed in about 1 to 30 hours.

[Reaction formula 124]

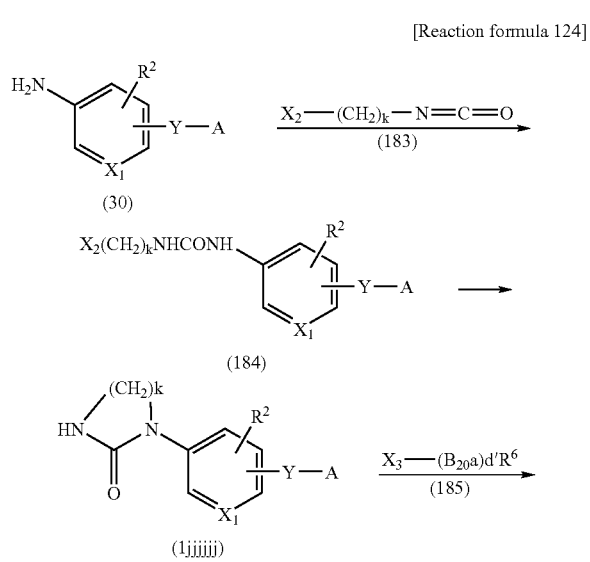

[Reaction formula 125]

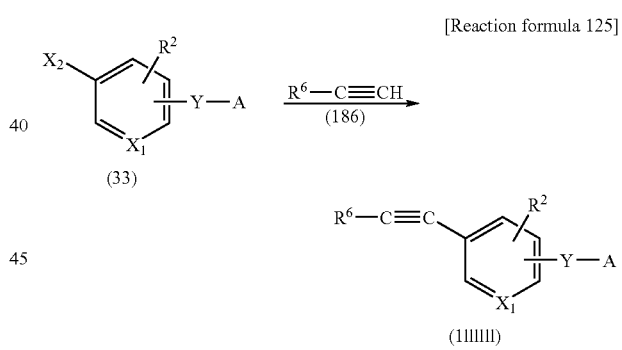

In the formula, $X_2$, $R^2$, $X_1$, Y, A and $R^6$ are the same as described above.

The reaction of the compound (33) with the compound (186) is carried out under reaction conditions similar to those of the reaction of the compound (33) with the compound (178) of the above described reaction formula 118.

[Reaction formula 126]

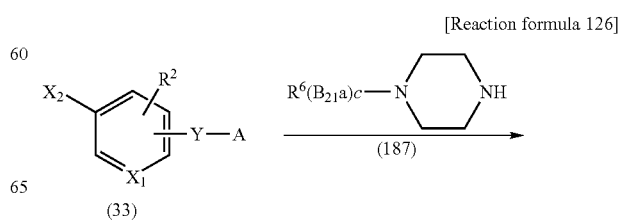

-continued

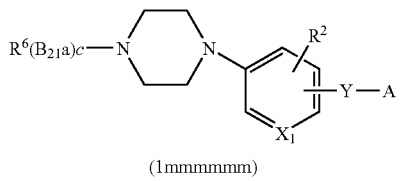

(1mmmmmm)

In the formula, $X_1$, $X_2$, $R^2$, $R^6$, Y, A, $B_{21a}$ and c are the same as described above.

The reaction of the compound (33) with the compound (187) is carried out under reaction conditions similar to those of the reaction of the compound (33) with the compound (178) of the above described reaction formula 118.

[Reaction formula 127]

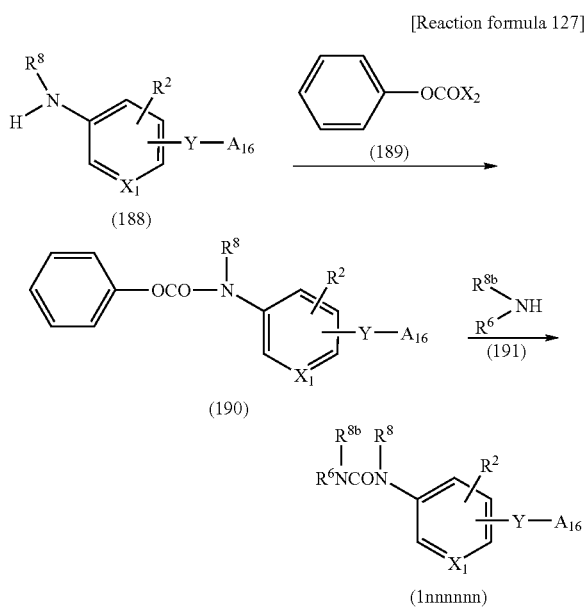

In the formula, $R^8$, $R^2$, XI, Y, $A_{16}$, $X_2$, $R^6$ and $R^{8b}$ are the same as described above.

The reaction of the compound (188) with the compound (189) may be carried out under reaction conditions similar to those of the reaction of the compound (1b) with the compound (6) by the method (d) of the formula 2 in which carboxylic acid halide is reacted with amine.

The reaction of the compound (190) with the compound (191) may be carried out under reaction conditions similar to those of the reaction of the compound (2) with the compound (3) of the above described reaction formula 1.

[Reaction formula 128]

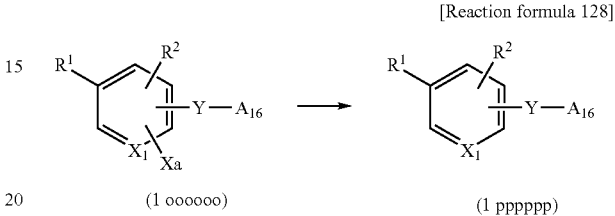

In the formula, $R^1$, $R^2$, $X_1$, Y and $A_{16}$ are the same as described above. Xa represents a halogen atom.

The reaction which converts the compound (1oooooo) into the compound (1pppppp) may be carried out in an appropriate solvent in the presence of a catalytic hydrogenation reducing agent and a hydrogen donor such as formic acid, ammonium formate, cyclohexene, or hydrazine hydrate.

Any solvent and catalytic hydrogenation reducing agent, which are used in the reaction which converts the compound (1dddddd) into the compound (1eeeeee) of the above described reaction formula 122, may be used in the above described reaction.

The above described reaction is carried out under hydrogen atmosphere typically at about 1 atm to 20 atm, and preferably at about 1 atm to 10 atm, and at about −30 to 150° C., and preferably at about 0 to 100° C. In general, the reaction is completed in about 1 to 12 hours.

The catalytic hydrogenation reducing agent is typically used at 0.01 to 40 wt %, and preferably 0.01 to 20 wt % of the compound (1oooooo).

The hydrogen donor is typically used in an amount at least equimolar to the compound (1oooooo), and preferably 1 to 10 times of the compound (1oooooo) on a molar basis.

[Reaction formula 129]

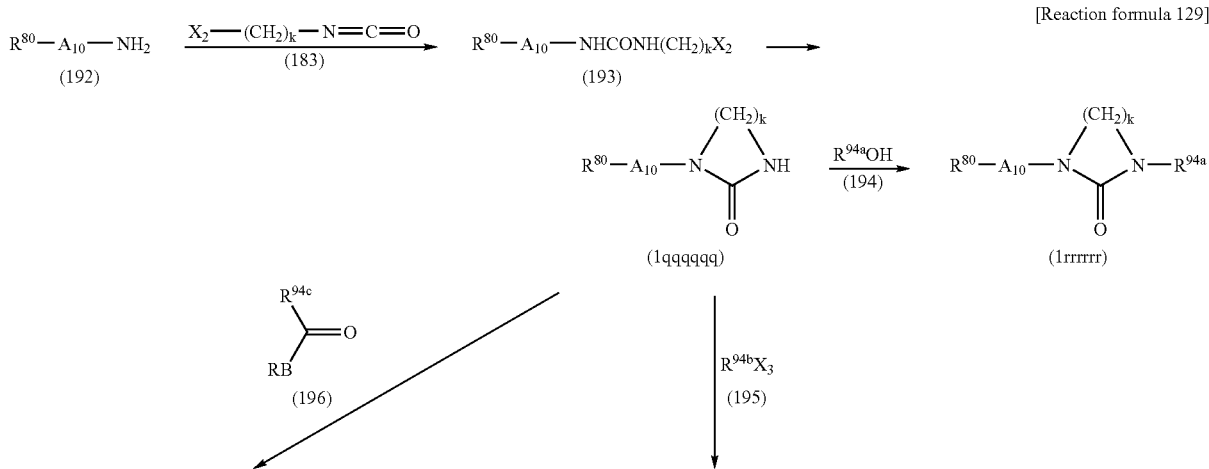

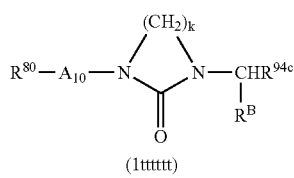

(1tttttt)

-continued

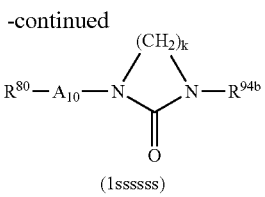

(1ssssss)

In the formula, $A_{10}$, $X_2$, k, $X_3$, $R^{80}$ and $R^B$ are the same as described above; $R^{94a}$ represents a group defined as a substituent (35), (40), (42) or (50), in which o is 1, or (67), (75) to (76), (78), (80) to (81) or (84), in which s is 0, in the case where the above described $R^{14}$ and $R^{15}$ form a heterocyclic ring; $R^{94b}$ represents a group defined as a substituent (28), (30) to (34), (36) to (39), (41), (43) to (45), (47) or (49), in which t is 1, (50), in which o is 0, (52) to (60), (62) to (66), (70), (77), (79), (82) to (83), (87), (88a) or (90a) in the case where the above described $R^{14}$ and $R^{15}$ form a heterocyclic ring; and $R^{94c}$ represents a group defined as a substituent (28), (30) to (34), (39), (41), (45), (47) or (49), in which t is 1, and (50), in which o is 0, (54) to (58), (62) to (64), (66), (70), (79) or (82) to (83) in the case where the above described $R^{14}$ and $R^{15}$ form a heterocyclic ring, a phenyl group which may have, on the phenyl ring, 1 to 3 substituents selected from the group consisting of a lower alkanoyl group, an amino group which may have a lower alkanoyl group as a substituent, a lower alkoxycarbonyl group, a cyano group, a nitro group, a phenyl group, a halogen atom, a lower alkyl group which may have a halogen atom as a substituent, a lower alkoxy group which may have a halogen atom as a substituent, a phenyl lower alkoxy group, a hydroxy group and a lower alkylenedioxy group, a pyridyl group which may have, on the pyridine ring, 1 to 3 substituents selected from the group consisting of a hydroxy group and a lower alkyl group which may have a hydroxyl group as a substituent, a pyrrolyl group which may have 1 to 3 lower alkyl groups as substituents, a benzoxazolyl group, a benzothiazolyl group, a furyl group, a lower alkyl group which may have a substituent selected from the group consisting of a hydroxy group and a halogen atom, a naphthyl group, a 1,2,3,4-tetrahydronaphthyl group which may have 1 to 5 lower alkyl groups as substituents on the 1,2,3,4-tetrahydronaphthalene ring, a quinolyl group, a 1,2,3,4-tetrazolyl group which may have, on the tetrazole ring, a substituent selected from the group consisting of a lower alkyl group and a phenyl lower alkyl group; a thiazolyl group which may have a phenyl group as a substituent on the thiazole ring; a benzoyl group which may have, on the phenyl ring, 1 to 3 substituents selected from the group consisting of a lower alkoxy group and a halogen atom, a piperidinyl group which may have a lower alkyl group as a substituent on the piperidine ring, a 1,2,3,4-tetrahydroquinolyl group which may have an oxo group as a substituent on the tetrahydroquinoline ring, a 1,3,4-oxadiazolyl group which may have an oxo group as a substituent on the 1,3,4 oxadiazole ring, a cycloalkyl group, a thienyl group, or an imidazolyl group.

The reaction of the compound (192) with the compound (183) may be carried out under reaction conditions similar to those of the reaction of the compound (30) with the compound (183) of the above described reaction formula 124.

The reaction which converts the compound (193) into the compound (1qqqqqq) may be carried out under reaction conditions similar to those of the reaction which converts the compound (184) into the compound (1jjjjjj) of the above described reaction formula 124.

The reaction of the compound (1qqqqqq) with the compound (195) may be carried out under reaction conditions similar to those of the reaction of the compound (1b) with the compound (4) of the above described reaction formula 2.

When $R^{94b}$ of the compound (195) represents (36) to (38), (43), (44), (53), (59) to (60), (87), (88a) or (90a), the reaction of the compound (1qqqqqq) with the compound (195) may also be carried out in an appropriate solvent in the presence of a copper halide such as copper iodide, an alkylglycine such as N,N-dimethylglycine, or an alkali metal phosphate such as potassium phosphate. In the above described reaction, any of the solvents used in the reaction of the compound (2) with the compound (3) of the above described reaction formula 1 may be used. The copper halide and alkylglycine are used in a normal catalyst amount. The alkali metal phosphate is appropriately used in an amount typically at least in equimolar to the compound (1qqqqqq), and preferably 1 to 5 times of the compound (1qqqqqq) on a molar basis. The compound (195) is appropriately used in an amount typically 0.5 to 5 times, and preferably 0.5 to 3 times of the compound (1qqqqqq) on a molar basis. The above described reaction is carried out typically at room temperature to 200° C., and preferably about room temperature to 150° C., and is completed in about 1 to 30 hours.

The reaction of the compound (1qqqqqq) with the compound (194) may be carried out under reaction conditions similar to those of the reaction of the compound (1b) with the compound (6) of the above described reaction formula 2.

The reaction of the compound (1qqqqqq) with the compound (196) may be carried out under reaction conditions similar to those of the reaction of the compound (1b) with the compound (5) of the above described formula 2.

[Reaction formula 130]

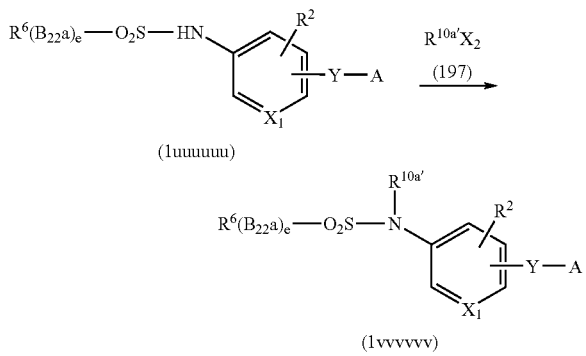

In the formula, $X_1$, Y, A, $R^2$, $R^6$, $B_{22a}$, e and $X_2$ are the same as described above, and $R^{10a'}$ represents a lower alkyl group.

The reaction of the compound (1uuuuuu) with the compound (197) may be carried out under reaction conditions similar to those of the reaction of the compound (1b) with the compound (4) of the above described formula 2.

[Reaction formula 130]

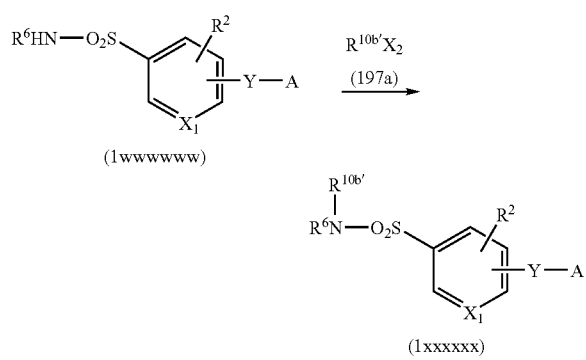

In the formula, $X_1$, Y, A, $R^{26}$, $R^6$ and $X_2$ are the same as described above. $R^{10b'}$ represents a lower alkyl group.

The reaction of the compound (1wwwwww) with the compound (197a) may be carried out under reaction conditions similar to those of the reaction of the compound (1b) with the compound (4) of the above described reaction formula 2.

[Reaction formula 132]

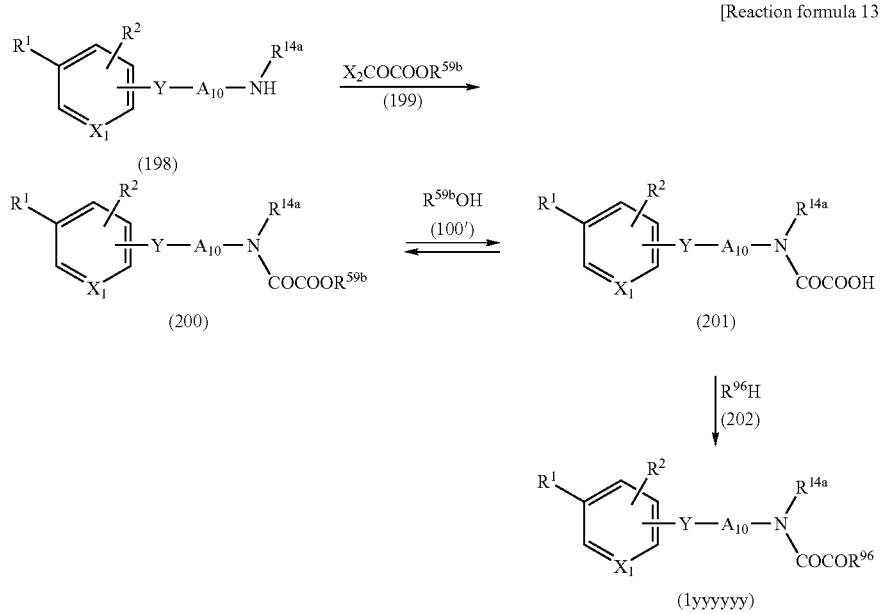

In the formula, $R^1$, $X_1$, $R^2$, Y, $A_{10}$, $X_2$, $R^{14a}$ and $R^{59b}$ are the same as described above, and $R^{96}$ represents a piperazinyl group which may have, on the piperazine ring, 1 to 3 substituents selected from the group consisting of a phenyl lower alkyl group (which may have, on the phenyl ring, 1 to 3 substituents selected from the group consisting of a lower alkylenedioxy group and a lower alkoxy group) and a pyridyl lower alkyl group.

The reaction of the compound (198) with the compound (199) may be carried out under reaction conditions similar to those of the reaction of the compound (2) with the compound (3) of the above described reaction formula 1.

The reaction which converts the compound (200) into the compound (201) may be carried out under reaction conditions similar to those of the hydrolysis B described for the above described reaction formula 9.

The reaction of the compound (201) with the compound (100') is carried out under reaction conditions similar to those of the reaction of the compound (120b) with the compound (100') of the above described reaction formula 79.

The reaction of the compound (201) with the compound (202) is carried out under reaction conditions similar to those of the reaction of the compound (1b) with the compound (6) of the above described reaction formula 2.

The compound (200) may also be produced by the method of the following reaction formula 133:

[Reaction formula 132]

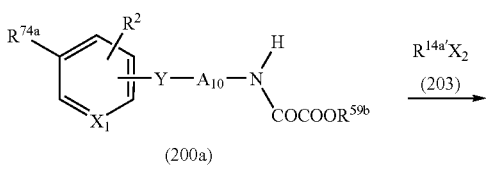

-continued

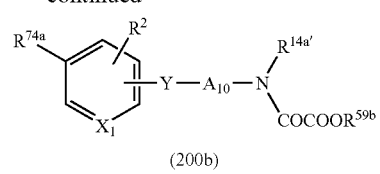

wherein $R^{74a}$, $R^2$, $X_1$, Y, $A_{10}$, $R^{59b}$ and $X_2$ are the same as described above, and $R^{14a'}$ represents a lower alkyl group which may have a hydroxy group as a substituent.

The reaction of the compound (200a) with the compound (203) may be carried out under reaction conditions similar to those of the reaction of the compound (2) with the compound (3) of the above described reaction formula 1.

The compound (3) may also be produced by the method of the following reaction formula 134:

[Reaction formula 134]

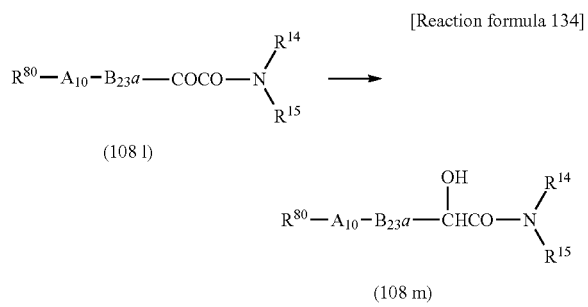

(108 l)

(108 m)

wherein $R^{80}, A_{10}, B_{23a}, R^{14}$ and $R^{15}$ are the same as described above.

The reaction which converts the compound (1081) into the compound (108m) may be carried out under reaction conditions similar to those of the reaction which converts the compound (1f) into the compound (1g) of the above described reaction formula 3.

[Reaction formula 135]

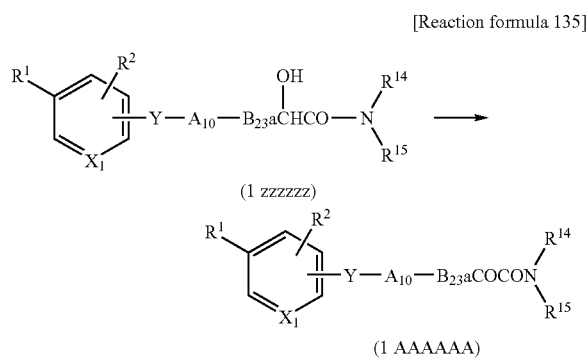

(1 zzzzzz)

(1 AAAAAA)

In the formula, $R^1, R^2, X_1, Y, A_{10}, B_{23a}, R^{14}$ and $R^{15}$ are the same as described above.

The reaction which converts the compound (1zzzzzz) into the compound (1AAAAAA) may be carried out under reaction conditions similar to those of the reaction which converts the compound (64b) into the compound (26a) of the above described reaction formula 89 described above.

Each of the target compounds obtained by the formulas shown above may be isolated and purified by separating the crude reaction product from the reaction mixture after cooling using an isolation procedure such as filtration, concentration, or extraction, and by purifying using a common purification procedure such as column chromatography or re-crystallization.

The compound of the present invention represented by the general formula (1) includes a stereoisomers and an optical isomer.

The compound of the present invention, which has a basic group, may easily form a salt with a common pharmacologically acceptable acid. Examples of such an acid include mineral acids such as hydrochloric acid, hydrobromic acid, nitric acid, sulfuric acid, and phosphoric acid, and organic acids such as methanesulfonic acid, p-toluenesulfonic acid, acetic acid, citric acid, tartaric acid, maleic acid, fumaric acid, malonic acid, and lactic acid.

The compound of the present invention, which has an acidic group, may easily form a salt with a common pharmacologically acceptable basic compound. Examples of such a basic compounds include sodium hydroxide, potassium hydroxide, calcium hydroxide, sodium carbonate, potassium carbonate, sodium bicarbonate, and potassium bicarbonate.

Next, medical formulations which contain the compound of the present invention as an active ingredient will be described.

The above described medical formulations, which are obtained by preparing the compound of the present invention formulated into a common pharmaceutical form, are prepared using a diluent or excipient commonly used such as a filler, expander, binder, moistener, disintegrator, surfactant, or lubricant.

Such medical formulations may be chosen from various forms according to the therapeutic objectives, and typical examples of such formulations include tablets, pills, powders, liquids, suspensions, emulsions, granules, capsules, suppositories, and injections (liquids, suspensions).

Carriers which are used for forming tablets may be chosen widely from the conventional ones, of which examples include excipients such as lactose, saccharose, sodium chloride, glucose, urea, starch, calcium carbonate, kaolin, and crystalline cellulose, binders such as water, ethanol, propanol, simple syrup, a glucose solution, a starch solution, a gelatin solution, carboxymethylcellulose, shellac, methylcellulose, potassium phosphate, and polyvinylpyrrolidone, disintegrators such as dried starch, sodium arginate, agar powder, laminaran powder, sodium bicarbonate, calcium carbonate, polyoxyethylene sorbitan fatty acid ester, sodium lauryl sulfate, stearic acid monoglyceride, starch, and lactose, anti-disintegrators such as saccharose, stearine, cacao butter, and hydrogenated oil, absorbefacients such as quartenary ammonium base and sodium lauryl sulfate, wetting agents such as glycerol and starch, adsorbents such as starch, lactose, kaolin, bentonite, and colloidal silicate, and lubricants such as purified talc, stearate, boric acid powder, and polyethylene glycol.

Further, tablets may be made into conventional coated tablets, for example, sugar-coated tablets, gelatin-coated tablets, enteric-coated tablets, film-coated tablets, or double or multi-layered tablets.

Carriers which are used for forming pills may be chosen widely from the conventional ones, of which examples include excipients such as glucose, lactose, starch, cacao butter, hydrogenated vegetable oil, kaolin, and talc, binders such as gum arabic powder, tragacanth powder, gelatin, and ethanol, and disintegrators such as laminaran and agar.

Carriers which are used for forming suppositories may be chosen widely from the conventional ones, of which examples include polyethylene glycol, cacao butter, higher alcohols, esters of higher alcohols, gelatin, and semi-synthetic glycerides.

The injection preparations in liquid, emulsion and suspension forms are preferably sterilized and isotonic with the blood. Diluents which are used for forming these liquid, emulsion and suspension preparations may be chosen widely from the conventional ones, of which examples include water, ethanol, propylene glycol, ethoxylated isostearyl alcohol, polyoxylated isostearyl alcohol, and polyoxyethylene sorbitan fatty acid ester. In this case, the medical formulations may contain sodium chloride, glucose or glycerol enough to prepare isotonic solutions. Also, conventional solubilizers, buffers, analgestics, and the like, and, as necessary, coloring agents, preservatives, spices, flavors, sweets and the like, or other pharmaceuticals may be added.

Although the amount of the compound of the present invention included in the medical formulation is not limited and may be selected appropriately in a wide range, it is typically preferable that the medical formulation contains the compound of the present invention at 1 to 70 wt %.

The method for administration of the medical formulation of the present invention is not limited and the administration is carried out in accordance with the conditions such as forms of the medical formulation, patient's age, sex, severity of the disease and other conditions. For example, tablets, pills, liquids, suspensions, emulsions, granules and capsules are administered orally. The injection formulations are administered intravenously singly or by mixing with a conventional fluid replacement such as a glucose solution or amino acid solution, or, as necessary, administered singly and intramuscularly, intradermally, subcutaneously or intraperitoneally. The suppositories are administered into the rectum.

The dosage for the above mentioned medical formulation may be chosen appropriately according to the usage, patient's age, sex and severity of the disease and other conditions. Typically, 0.001 to 100 mg per kg body weight per day, preferably 0.001 to 50 mg per kg body weight per day, is administered once or in several times a day.

Since the above described dosage may vary in accordance with various conditions, it may be sufficient with a dosage smaller than in the above described range, or it may be necessary to administer a dosage larger than in the above described range.

The compound of the present invention has a superior effect on suppressing the production of collagen.

The compound of the present invention has lower side effects and is excellent in safety.

EXAMPLES

The present invention is explained in more detail by illustrating Reference Examples, Examples, Formulation Example and Pharmacological Test as follows.

Reference Example 1

Production of 1-(t-butoxycarbonyl)-4-(4-hydroxyphenyl)-1,2,5,6-tetrahydropyridine Step 1

Production of 1-(t-butoxycarbonyl)-4-[(4-methoxymethoxy)phenyl]-4-hydroxypiperidine A solution of 1-bromo-4-methoxymethoxybenzene (5.43 g, 25.0 mmol) in tetrahydrofuran (THF) (100 mL) was stirred at −85° C., and a 2.46 M n-butyllithium hexane solution (10.2 mL, 25.0 mmol) was added dropwise to the stirred solution over 10 minutes. The resulting solution was stirred at the same temperature for 40 minutes. To the reaction solution was added dropwise for 10 minutes a solution of 1-(t-butoxycarbonyl)-4-piperidone (5.20 g, 26.0 mmol) in THF (30 mL). The temperature of the resulting solution was raised to −25° C. over 4 hours, and then the solution was stirred at that temperature for 2 hours. An aqueous solution of saturated ammonium chloride was then added to this solution. The reaction solution was extracted with ethyl acetate and dried over anhydrous magnesium sulfate, after which the solvent was evaporated. The residue was purified by silica gel column chromatography (ethyl acetate:n-hexane=2:3, in ratio by volume; hereinafter the same), to thereby yield 7.63 g of the title compound.

Appearance: Colorless oil $^1$H NMR (CDCl$_3$) δ 1.49 (9H, s), 1.73 (2H, d, J=12.0 Hz), 1.97 (2H, brs), 3.24 (2H, brs), 3.48 (3H, s), 4.00 (2H, brs), 5.17 (2H, s), 7.03 (2H, d, J=9.0 Hz), 7.39 (2H, d, J=9.0 Hz).

Step 2

Production of 1-(t-butoxycarbonyl)-4-(4-hydroxyphenyl)-1,2,5,6-tetrahydropyridine To a solution of 1-(t-butoxycarbonyl)-4-[(4-methoxymethoxy)phenyl]-4-hydroxypiperidine (5.32 g, 15.8 mmol) in toluene (100 mL) was added p-toluenesulfonic acid monohydrate (0.56 g, 2.95 mmol), and the resulting solution was refluxed for 21 hours. The reaction solution was cooled to room temperature, and evaporated under reduced pressure. To this crude product were added ethanol (60 mL) and 2 M hydrochloric acid (40 mL, 80 mmol), and the resulting solution was stirred for 2 hours at 60° C. The reaction solution was again cooled to room temperature, and evaporated under reduced pressure. To the residue were added methanol (100 mL), triethylamine (9.0 mL, 64.6 mmol) and di-t-butyl dicarbonate (5.20 g, 23.8 mmol), and the resulting solution was stirred for 24 hours at room temperature. The solvent was evaporated under reduced pressure, after which to the residue was added 100 mL of ethyl acetate. Insoluble matter was removed by filtration, after which the filtrate was evaporated under reduced pressure. To the residue were added 1,4-dioxane (50 mL) and a 1 M aqueous solution of sodium hydroxide (50 mL, 50 mmol) and stirred for 14 hours at 60° C. To the resulting reaction solution was added at room temperature 2 M hydrochloric acid (25 mL, 50 mmol) to neutralize, and then extracted with ethyl acetate. The ethyl acetate layer was washed with water, dried over anhydrous magnesium sulfate, and evaporated to thereby yield 4.10 g of the title compound.

Appearance: Brown amorphous $^1$H NMR (CDCl$_3$) δ 1.49 (9H, s), 2.47 (2H, brs), 3.62 (2H, t, J=5.5 Hz), 4.05 (2H, brs), 5.91 (1H, brs), 6.81 (2H, d, J=9.0 Hz), 7.25 (2H, d, J=9.0 Hz).

Reference Example 2

Production of methyl 5-(4-benzylpiperazin-1-yl)-2-methoxymethoxybenzoate

To a solution of methyl 5-chloro-2-methoxymethoxybenzoate (1.45 g, 6.29 mmol) and 1-benzylpiperazine (1.66 g, 9.43 mmol) in toluene (50 mL) were added palladium acetate (28 mg, 0.126 mmol), 2,2'-bis(diphenylphosphino)-1,1'-binaphthyl (157 mg, 0.252 mmol) and cesium carbonate (3.07 g, 9.43 mmol), and the resulting solution was refluxed for 3 hours. Water was added to the resulting solution, and extracted with ethyl acetate. The ethyl acetate layer was dried over anhydrous magnesium sulfate, and evaporated. The residue was purified by silica gel column chromatography (ethyl acetate:n-hexane=1:2), to thereby yield 400 mg of the title compound.

Appearance: Yellow oil $^1$H NMR (CDCl$_3$) δ 2.59-2.62 (4H, m), 3.12-3.16 (4H, m), 3.51 (3H, s), 3.57 (2H, s), 3.88 (3H, s), 5.16 (2H, s), 7.01 (1H, dd, J=9.1 Hz, 3.1 Hz), 7.10 (1H, d, J=9.1 Hz), 7.28-7.35 (6H, m).

The following compounds were produced in the same manner as in Reference Example 2.

TABLE 1

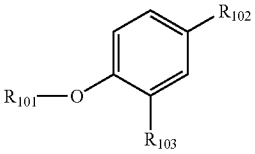

| Reference Example No. | R<sub>101</sub> | R<sub>102</sub> | R<sub>103</sub> | $^1$H NMR (CDCl$_3$) δ ppm |
|---|---|---|---|---|
| 3 | —CH$_2$OCH$_3$ | 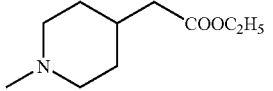 | —H | 1.27(3H, t, J=7.0Hz), 1.43-1.48(2H, m), 1.83(2H, brd, J=13.0Hz), 1.90(1H, m), 2.28(2H, d, J=7.0Hz), 2.66(2H, dt, J=2.5 Hz, 12.0Hz), 3.47(3H, s), 3.50(2H, brd, J=12.0Hz), 4.15(2H, q, J=7.0Hz), 5.10(2H, s), 6.89(2H, d, J=9.0Hz), 6.95(2H, d, J=9.0Hz). |
| 4 | —CH$_2$OCH$_3$ | 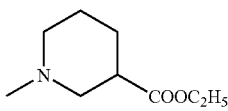 | —H | 1.27(3H, t, J=7.0Hz), 1.57-1.75(2H, m), 1.82(1H, m), 2.00(1H, m), 2.68-2.75(2H, m), 2.93(1H, dd, J=10.0Hz, 12.0 Hz), 3.34(1H, d, J=12.0Hz), 3.48(3H, s), 3.56(1H, brd, J=10.0 Hz), 4.16(2H, q, J=7.0Hz), 5.11(2H, s), 6.91(2H, d, J=9.0 Hz), 6.96(2H, d, J=9.0Hz). |
| 5 | —CH$_3$ | 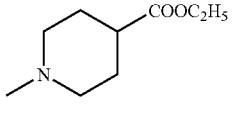 | —H | 1.27(3H, t, J=7.0Hz), 1.91(2H, dq, J=3.0Hz, 13.5Hz), 2.02(2H, dd, J=13.5Hz, 3.0Hz), 2.38(1H, m), 2.69(2H, dt, J=3.0Hz, 12.0 Hz), 3.48(2H, dt, J=12.0Hz, 3.0 Hz), 3.37(3H, s), 4.16(2H, q, J=7.0Hz), 6.83(2H, d, J=9.0Hz), 6.91(2H, d, J=9.0Hz). |
| 6 | —CH$_2$OCH$_3$ | 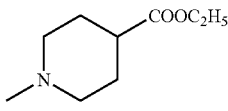 | —CH$_3$ | 1.27(3H, t, J=7.1Hz), 1.82-1.99(4H, m), 2.22(3H, s), 2.33-2.42(1H, m), 2.64-2.73(2H, m), 3.50-3.52(5H, m), 4.15(2H, q, J=7.1Hz), 5.12(2H, s), 6.70(1H, dd, J=8.9Hz, 3.1Hz), 6.78(1H, d, J=3.0Hz), 6.95(1H, d, J=8.7Hz). |
| 7 | —CH$_2$OCH$_3$ | 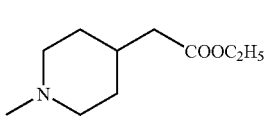 | —OCH$_3$ | 1.27(3H, t, J=7.1Hz), 1.37-1.47(2H, m), 1.81-1.94(3H, m), 2.29(2H, d, J=6.9Hz), 2.64-2.73(2H, m), 3.51(3H, s), 3.54(2H, brs), 3.85(3H, s), 4.15(2H, q, J=7.1Hz), 5.13(2H, s), 6.44(1H, dd, J=8.7Hz, 2.6Hz), 6.56(1H, d, J=2.6Hz), 7.02(1H, d, J=8.7Hz). |
| 8 | —CH$_2$OCH$_3$ | 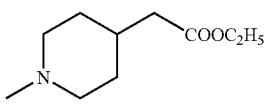 | —CH$_3$ | 1.27(3H, t, J=7.1Hz), 1.37-1.49(2H, m), 1.80-2.04(3H, m), 2.22(3H, s), 227(2H, d, J=6.9 Hz), 2.60-2.68(2H, m), 3.48(3H, s), 3.52(2H, brs), 4.14(2H, q, J=7.1 Hz), 5.11(2H, s), 6.69-6.79(2H, m), 6.94(1H, d, J=8.7Hz). |

TABLE 2

[Structure: O₂N-C₆H₄-O-C₆H₄-R₁₀₄]

| Reference Example No. | R₁₀₄ | ¹H NMR (CDCl₃) δ ppm |
|---|---|---|
| 9 | [1-methylpiperidin-4-yl, N(CH₃)COOC(CH₃)₃] | 1.48(9H, s), 1.76-1.89(4H, m), 2.78(3H, brs), 2.81(2H, brt, J=12.0Hz), 3.71(2H, brd, J=12.0Hz), 4.15(1H, brs), 6.96(2H, d, J=9.0 Hz), 6.98(4H, s), 8.17(2H, d, J=9.0Hz). |
| 10 | [4-methylpiperazin-1-yl with N-COOC(CH₃)₃] | 1.49(9H, s), 3.13(4H, t, J=5.0Hz), 3.60(4H, t, J=5.0Hz), 6.96-7.00(6H, m), 8.18(2H, d, J=9.0Hz). |
| 11 | [1-methylpiperidin-4-yl-O-CH₂-O-CH₃] | 1.79(2H, m), 2.03(2H, m), 2.96(2H, m), 3.41(3H, s), 3.51(2H, m), 3.73(1H, m), 4.74(2H, s), 6.95-6.98(6H, m), 8.17(2H, d, J=9.0Hz). |
| 12 | [1-methylpiperidin-4-yl-COOC₂H₅] | 1.28(3H, t, J=7.0Hz), 1.90(2H, dq, J=4.0 Hz, 13.0Hz), 2.05(2H, dd, J=13.0Hz, 4.0 Hz), 2.45(1H, m), 2.82(2H, dt, J=2.5Hz, 12.0 Hz), 3.62(2H, brd, J=12.5Hz), 4.17(2H, q, J=7.0Hz), 6.95-6.98(6H, m), 8.17(2H, d, J=9.0Hz). |
| 13 | [1-methylpiperidin-4-yl-O-CH₂-COOC₂H₅] | 1.31(3H, t, J=7.0Hz), 1.83(2H, m), 2.05(2H, m), 2.96(1H, m), 3.07(1H, m), 3.46(1H, m), 3.53(1H, m), 3.60(1H, m), 4.16(2H, s), 4.24(2H, q, J=7.0Hz), 6.95-7.01(6H, m), 8.17(2H, d, J=9.0Hz). |

Reference Example 14

Production of methyl 5-(4-benzylpiperazin-1-yl)-2-hydroxybenzoate

To a solution of 400 mg of methyl 5-(4-benzylpiperazin-1-yl)-2-methoxymethoxybenzoate (1.1 mmol) in 1,4-dioxane (20 mL) was added a solution of 4 N hydrogen chloride in 1,4-dioxane (4 mL, 16 mmol), and the resulting solution was stirred for 2 hours at 100° C. The resulting reaction solution was subjected to distillation under reduced pressure to obtain a residue. This residue was purified by silica gel column chromatography (dichloromethane:methanol=30:1), to thereby yield 353 mg of the title compound.

Appearance: Pale yellow powder

¹H NMR (CD₃OD) δ 3.29-3.40 (8H, m), 3.94 (3H, s), 4.39 (2H, s), 6.91 (1H, d, J=8.9 Hz), 7.28 (1H, dd, J=8.9 Hz, 3.0 Hz), 7.42 (1H, d, J=3.0 Hz), 7.49-7.60 (5H, m).

The following compounds were produced in the same manner as in Reference Example 14.

TABLE 3

[Structure: HO-C₆H₃(R₁₀₅)(R₁₀₆)]

| Reference Example No. | R₁₀₅ | R₁₀₆ | Form | ¹H NMR (solvent) δ ppm |
|---|---|---|---|---|
| 15 | —H | [1-methylpiperidin-4-yl-CH₂-COOC₂H₅] | free | (DMSO-d₆) 1.20(3H, t, J=7.0Hz), 1.78(2H, brs), 1.91(2H, brs), 2.10(1H, brs), 2.34(2H, brs), 3.45(2H, brs), 3.55(2H, brs), 4.09(2H, q, J=7.0Hz), 6.88(2H, brs), 7.60(2H, brs), 10.05(1H, brs), 11.75(1H, brs). |

TABLE 3-continued

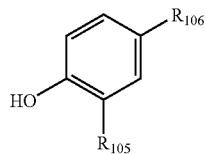

| Reference Example No. | $R_{105}$ | $R_{106}$ | Form | $^1$H NMR (solvent) δ ppm |
|---|---|---|---|---|
| 16 | —H | ![structure with N-methylpiperidine-3-COOC2H5] | free | (DMSO-$d_6$) 1.20(3H, t, J=7.0Hz), 1.64(1H, brs), 1.93(2H, brs), 2.08(2H, brs), 3.30(1H brs), 3.45(2H, brs), 3.48(2H, brs), 4.10(2H, q, J=7.0Hz), 6.88(2H, brs), 7.66(2H, brs), 10.05(1H, brs), 12.60(1H, brs). |
| 17 | —CH$_3$ | ![structure with N-methylpiperidine-4-COOC2H5] | hydrochloride | (DMSO-$d_6$) 1.22(3H, t, J=7.1Hz), 2.03-2.13(4H, m), 2.14(3H, s), 2.75(1H, brs), 3.38-3.57(4H, m), 4.12(2H, q, J=7.1Hz), 6.89(1H, d, J=8.6Hz), 7.46-7.53(2H, m), 9.99(1H, brs). |
| 18 | —OCH$_3$ | ![structure with N-methylpiperidine-4-CH2COOC2H5] | free | (CDCl$_3$) 1.27(3H, t, J=7.1Hz), 1.98-2.18(3H, m), 2.41-2.44(4H, m), 3.30(2H, t, J=12.0Hz), 3.66(2H, d, J=11.9Hz), 3.95(3H, s), 4.15(2H, q, J=7.1Hz), 6.26(1H, brs), 6.96-7.03(2H, m), 7.85(1H, s). |
| 19 | —CH$_3$ | ![structure with N-methylpiperidine-4-CH2COOC2H5] | hydrochloride | (DMSO-$d_6$) 1.20(3H, t, J=7.1Hz), 1.87(4H, brs), 2.14(4H, brs), 2.33(2H, d, J=6.4Hz), 2.52(2H, brs), 3.44(2H, brs), 4.19(2H, q, J=7.1Hz), 6.88(1H, d, J=8.6Hz), 7.46-7.57(2H, m), 9.98(1H, brs), 12.04(1H, brs). |

Reference Example 20

Production of ethyl N-(4-hydroxyphenyl)isonipecotate

To a solution of ethyl N-(4-methoxyphenyl)-isonipecotate (2.63 g, 10 mmol) in dichloromethane (100 mL) was added a solution of 2 M boron tribromide in dichloromethane (20 mL, 40 mmol), and the resulting solution was stirred for 0.5 hours at room temperature. The resulting reaction solution was poured into ice water, then an aqueous solution of 1 M sodium hydroxide (110 mL) was added to the solution. After stirring, the resulting solution was separated. The organic layer was washed with water, dried over anhydrous magnesium sulfate, and evaporated under reduced pressure to thereby yield 2.43 g of the title compound.

Appearance: Yellow oil $^1$H NMR (CDCl$_3$) δ 1.27 (3H, t, J=7.0 Hz), 1.91 (2H, m), 2.02 (2H, brd, J=11.5 Hz), 2.38 (1H, m), 2.68 (2H, dt, J=2.0 Hz, 11.5 Hz), 3.46 (2H, dt, J=12.0 Hz, 3.0 Hz), 4.16 (2H, q, J=7.0 Hz), 4.45 (1H, brs), 6.75 (2H, d, J=9.0 Hz), 6.86 (2H, d, J=9.0 Hz).

The following compounds were produced in the same manner as in Reference Example 20.

Reference Example 21

4-(2-Fluoro-4-nitrophenoxy)phenol $^1$H NMR (DMSO-$d_6$) δ 6.80-7.10 (5H, m), 8.04 (1H, ddd, J=1.4 Hz, 2.7 Hz, 9.2 Hz), 8.29 (1H, dd, J=2.7 Hz, 10.9 Hz), 9.59 (1H, s)

Reference Example 22

1-Benzyl-3-(4-hydroxyphenyl)imidazolidin-2-one $^1$H NMR (DMSO-$d_6$) δ 3.18-3.40 (2H, m), 3.61-3.80 (2H, m), 4.35 (2H, s), 6.71 (2H, d, J=8.8 Hz), 7.15-7.48 (7H, m), 9.10 (1H, s).

Reference Example 23

Production of 2-(4-hydroxyphenylamino)-1-(4-piperonylpiperazin-1-yl)ethanone

To a solution of N-(4-hydroxyphenyl)glycine (11.38 g, 68.1 mmol) in N,N-dimethylformamide (DMF) (150 mL) were added under ice cooling 1-piperonylpiperazine (15.0 g, 68.1 mmol), 1-hydroxybenzotriazole monohydrate (10.43 g, 68.1 mmol) and 1-ethyl-3-(3-dimethylaminopropyl)carbodiimide hydrochloride (15.66 g, 81.7 mmol), and the resulting solution was stirred for 30 minutes under ice cooling and for 4.5 hours at room temperature. The reaction solution was concentrated under reduced pressure. To the residue was added a saturated sodium bicarbonate solution (400 mL), and extracted with ethyl acetate (400 mL). The ethyl acetate layer was washed with a saturated sodium bicarbonate solution and brine. The ethyl acetate layer was dried over anhydrous magnesium sulfate, and evaporated, to leave the resulting product solidified in a powdered form. Ethyl acetate was added, and the resulting product was filtered off and washed with ethyl acetate, to thereby yield 18.58 g of the title compound.

Appearance: Brown powder $^1$H NMR (DMSO-$d_6$) δ 2.30 (2H, brs), 2.36 (2H, brs), 3.40 (2H, s), 3.47 (4H, t, J=14.5 Hz), 4.03 (2H, d, J=7.0 Hz), 4.90 (1H, brs), 5.99 (2H, s), 6.49 (2H, d, J=8.9 Hz), 6.54 (2H, d, J=8.9 Hz), 6.75 (1H, dd, J=8.0 Hz, 1.1 Hz), 6.85 (1H, d, J=8.0 Hz), 6.87 (1H, s), 8.42 (1H, s).

The following compounds were produced in the same manner as in Reference Example 23.

Reference Example 24

6-Chloro-N-(3,4-dichlorophenyl)nicotinamide $^1$H NMR (CDCl$_3$) δ 7.64 (1H, d, J=8.9 Hz), 7.72 (1H, dd, J=8.7 Hz, 2.3 Hz), 7.73 (1H, dd, J=8.3 Hz, 0.7 Hz), 8.12 (1H, d, J=2.3 Hz), 8.35 (1H, dd, J=8.3 Hz, 2.5 Hz), 8.95 (1H, dd, J=2.5 Hz, 0.7 Hz), 10.71 (1H, brs).

Reference Example 25

4-(4-Piperonylpiperazine-1-carbonyl)-1-(4-hydroxyphenyl)pyrrolidin-2-one $^1$H NMR (CDCl$_3$) δ 2.43-2.45 (4H, m), 2.73-2.95 (2H, m), 3.45 (2H, s), 3.49-3.54 (4H, m), 3.65-3.72 (1H, m), 3.78-3.87 (1H, m), 4.17-4.23 (1H, m), 5.96 (2H, s), 6.71-6.80 (4H, m), 6.84-6.85 (1H, m), 7.29 (2H, d, J=8.9 Hz).

TABLE 4

| Reference Example No. | Xa$_1$ | Xa$_2$ | R$_{107}$ | R$_{108}$ | Form | $^1$H NMR (solvent) δ ppm |
|---|---|---|---|---|---|---|
| 26 | —NH— | —CH$_2$— | —H | benzyl | free | (CDCl$_3$) 2.46-2.48(4H, m), 3.45(2H, t, J=5.0Hz), 3.54(2H, s), 3.68(2H, t, J=5.0Hz), 3.82(2H, s), 6.53(2H, d, J=8.7 Hz), 6.70(2H, d, J=8.7Hz), 7.27-7.34(5H, m). |
| 27 | —CH$_2$— | —CH$_2$— | —H | benzyl | free | (CDCl$_3$) 2.30-2.33(2H, m), 2.41-2.45(2H, m), 2.55-2.60(2H, m), 2.85-2.91(2H, m), 3.36-3.40(2H, m), 3.52(2H, s), 3.62-3.66(2H, m), 5.10(1H, brs), 6.74-6.77(2H, m), 7.03(2H, d, J=8.6 Hz), 7.27-7.32(5H, m). |
| 28 | —CH$_2$— | —CH$_2$— | —H | piperonyl | hydrochloride | (DMSO-$d_6$) 2.56-3.47(10H, m), 4.01-4.07(1H, m), 4.18-4.48(3H, m), 6.07(2H, s), 6.65-6.68(2H, m), 7.00-7.03(4H, m), 7.21(1H, s), 9.18(1H, brs), 11.04(1H, brs). |
| 29 | —O— | —CH$_2$— | —H | piperonyl | free | (CDCl$_3$) 2.31-2.50(4H, m), 3.41(2H, s), 3.52-3.72(4H, m), 4.63(2H, s), 5.94(2H, s), 6.25(1H, brs), 6.70(2H, d, J=9.1 Hz), 6.69-6.77(1H, m), 6.73(1H, s), 6.77(2H, d, J=9.1Hz), 6.83(1H, d, J=0.9Hz). |
| 30 | —O— | —CH$_2$— | —H | benzyl | free | (CDCl$_3$) 2.40-2.52(4H, m), 3.51(2H, s), 3.53-3.73(4H, m), 4.63(2H, s), 5.89(1H, brs), 6.70(2H, d, J=9.2Hz), 6.78(2H, d, J=9.2Hz), 7.22-7.43(5H, m). |
| 31 | —CH(OH)— | none | —H | benzyl | free | (CDCl$_3$) 1.89-2.03(1H, m), 2.21-2.32(1H, m), 2.32-2.57(2H, m), 3.00-3.18(1H, m), 3.20-3.35(1H, m), 3.40(1H, d, J=13.1Hz), 3.46(1H, d, J=13.1 Hz), 3.60-3.83(2H, m), 5.13(1H, s), 6.71(2H, d, J=8.6Hz), 7.09(2H, d, J=8.6Hz), 7.18-7.35(5H, m). |
| 32 | none | none | —H | 3-pyridyl | free | (DMSO-$d_6$) 3.18-3.35(4H, m), 3.64(4H, brs), 6.82(2H, d, J=8.4Hz), 7.21-7.37(4H, m), 8.02-8.03(1H, m), 8.32 (1H, d, J=2.4Hz), 9.90(1H, brs). |
| 33 | —CH$_2$— | —CO— | —H | —CO$_2$C(CH$_3$)$_3$ | free | (CDCl$_3$) 1.44(9H, s), 2.93-3.15(4H, m), 3.32(2H, t, J=5.2Hz), 3.50(2H, t, J=5.2Hz), 3.97(2H, s), 5.48(1H, brs), 6.81(2H, d, J=8.6Hz), 7.11(2H, d, J=8.6Hz). |
| 34 | —NH— | —CH$_2$— | —CH$_3$ | piperonyl | free | (CDCl$_3$) 2.20(3H, s), 2.41-2.46(4H, m), 3.44(4H, brs), 3.67(2H, t, J=4.8Hz), 3.81(2H, s), 4.34(1H, brs), 4.52(1H, |

TABLE 4-continued

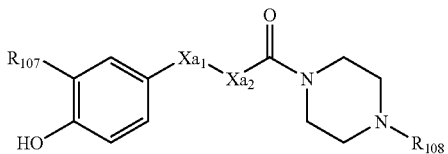

| Reference Example No. | Xa₁ | Xa₂ | R₁₀₇ | R₁₀₈ | Form | ¹H NMR (solvent) δ ppm |
|---|---|---|---|---|---|---|
| | | | | | | brs), 5.95(2H, s), 6.37(1H, dd, J=8.4 Hz, 2.6Hz), 6.44(1H, d, J=2.8Hz), 6.64(1H, d, J=8.4Hz), 6.70-6.77(2H, m), 6.85(1H, s). |

Reference Example 35

Production of ethyl(4-hydroxy-3-methylphenylamino)acetate

Potassium carbonate (5.04 g, 36.5 mmol) was added at room temperature to a solution of 4-amino-o-cresol (3.00 g, 24.4 mmol) and ethyl bromoacetate (2.70 mL, 24.4 mmol) in DMF (30 mL). The resulting solution was stirred at room temperature for 1.5 hours. Water was added to the reaction mixture, and extracted with ethyl acetate. The ethyl acetate layer was washed with brine. The ethyl acetate layer was dried over anhydrous sodium sulfate, and evaporated. The residue was purified by silica gel column chromatography (n-hexane:ethyl acetate=3:1), to thereby yield 5.10 g of the title compound.

Appearance: Yellow solid $^1$H NMR (CDCl$_3$) δ 1.28 (3H, t, J=7.1 Hz), 2.19 (3H, s), 3.84 (2H, s), 3.95 (1H, brs), 4.22 (2H, q, J=7.1 Hz), 4.59 (1H, brs), 6.36 (1H, dd, J=8.4 Hz, 2.9 Hz), 6.44 (1H, d, J=2.9 Hz), 6.63 (1H, d, J=8.4 Hz).

The following compounds were produced in the same manner as in Reference Example 35.

Reference Example 36

Ethyl(3-hydroxyphenylamino)acetate $^1$H NMR (CDCl$_3$) δ 1.30 (3H, t, J=7.1 Hz), 3.88 (2H, s), 4.25 (2H, q, J=7.1 Hz), 4.29 (1H, brs), 4.85 (1H, s), 6.08-6.10 (1H, m), 6.18-6.24 (2H, m), 7.01-7.07 (1H, m)

Reference Example 37

Benzyl(4-hydroxy-3-methoxyphenylamino)acetate $^1$H NMR (CDCl$_3$) δ 3.81 (3H, s), 3.92 (2H, brs), 4.01 (1H, brs), 5.09 (1H, brs), 5.20 (2H, s), 6.11 (1H, dd, J=8.4 Hz, 2.6 Hz), 6.23 (1H, d, J=2.6 Hz), 6.76 (1H, d, J=8.4 Hz), 7.31-7.38 (5H, m).

Reference Example 38 t-Butyl[3-(4-benzyloxy-3-methylphenyl)-2-oxotetrahydropyrimidin-1-yl]acetate $^1$H NMR (CDCl$_3$) δ 1.47 (9H, s), 2.04-2.21 (2H, m), 2.25 (3H, s), 3.45 (2H, t, J=5.9 Hz), 3.67 (2H, t, J=5.9 Hz), 4.04 (2H, s), 5.06 (2H, s), 6.82 (1H, d, J=8.6 Hz), 7.01 (1H, dd, J=2.6 Hz, 8.6 Hz), 7.06-7.12 (1H, m), 7.26-7.48 (5H, m).

TABLE 5

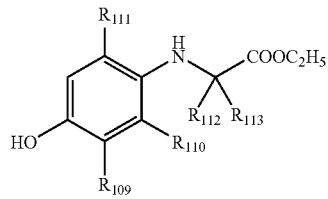

| Reference Example No. | R₁₀₉ | R₁₁₀ | R₁₁₁ | R₁₁₂ | R₁₁₃ | ¹H NMR (CDCl₃) δ ppm or MS |
|---|---|---|---|---|---|---|
| 39 | —CH₃ | —CH₃ | —H | —H | —H | ¹H NMR 1.30(3H, t, J=7.1Hz), 2.14(3H, s), 2.20(3H, s), 3.87(2H, s), 4.24(2H, q, J=7.1Hz), 4.42(1H, brs), 6.29(1H, d, J=8.6 Hz), 6.58(1H, d, J=8.6Hz). |
| 40 | —F | —H | —F | —H | —H | ¹H NMR 1.30(3H, t, J=7.1Hz), 3.85(2H, s), 4.25(2H, q, J=7.1Hz), 4.77(1H, s), 6.37(1H, dd, J=7.9Hz, 11.8Hz), 6.73(1H, dd, J=7.9Hz, 11.6Hz). |
| 41 | —CH₃ | —H | —CH₃ | —H | —H | ¹H NMR 1.30(3H, t, J=7.1Hz), 2.15(3H, s), 2.19(3H, s), 3.84(1H, brs), 3.89(2H, s), 4.17(1H, brs), 4.25(2H, q, J=7.1Hz), 6.28(1H, s), 6.57(1H, s). |

TABLE 5-continued

[Structure: phenol with R109, R110 substituents, and NH-C(R112)(R113)-COOC2H5 group with R111]

| Reference Example No. | $R_{109}$ | $R_{110}$ | $R_{111}$ | $R_{112}$ | $R_{113}$ | $^1$H NMR (CDCl$_3$) δ ppm or MS |
|---|---|---|---|---|---|---|
| 42 | —H | —CH$_3$ | —CH$_3$ | —H | —H | MS 223(M$^+$) |
| 43 | —OCH$_3$ | —H | —H | —H | —H | $^1$H NMR 1.29(3H, t, J=7.1Hz), 3.82(3H, s), 3.85(2H, s), 4.23(2H, q, J=7.1Hz), 5.26(1H, brs), 6.11(1H, dd, J=8.4Hz, 2.6 Hz), 6.25(1H, d, J=2.6Hz), 6.76(1H, d, J=8.4Hz). |
| 44 | —F | —H | —H | —H | —H | $^1$H NMR 1.30(3H, t, J=7.1Hz), 3.83(2H, s), 4.08(1H, brs), 4.24(2H, q, J=7.1Hz), 4.62(1H, d, J=3.3Hz), 6.30-6.41(2H, m), 6.85(1H, t, J=8.9Hz). |
| 45 | —H | —H | —H | —CH$_3$ | —CH$_3$ | $^1$H NMR 1.20(3H, t, J=7.1Hz), 1.48(6H, s), 4.15(2H, q, J=7.1Hz), 6.60-6.69(4H, m). |
| 46 | —CH$_3$ | —H | —H | —CH$_3$ | —H | $^1$H NMR 1.24(3H, t, J=7.3Hz), 1.44(3H, d, J=6.9Hz), 2.18(3H, s), 3.80(1H, brs), 4.03(1H, q, J=6.9Hz), 4.17(2H, q, J=7.3 Hz), 4.25(1H, brs), 6.37(1H, dd, J=8.4Hz, 3.0Hz), 6.45(1H, d, J=2.8Hz), 6.62(1H, d, J=8.4Hz). |
| 47 | —H | —H | —H | —CH$_3$ | —H | $^1$H NMR 1.24(3H, t, J=7.1Hz), 1.44(3H, d, J=6.7Hz), 3.88(1H, brs), 4.04(1H, q, J=6.9Hz), 4.17(2H, q, J=7.1Hz), 4.59(1H, brs), 6.54(2H, d, J=8.9Hz), 6.68(2H, d, J=8.9Hz). |
| 48 | —CF$_3$ | —H | —H | —H | —H | MS 263(M$^+$) |

TABLE 6

[Structure: benzene ring with R114—O—, R115, R116, R117 substituents, and N(R118)-CH2-COOC2H5 group]

| Reference Example No. | $R_{114}$ | $R_{115}$ | $R_{116}$ | $R_{117}$ | $R_{118}$ | $^1$H NMR (solvent) δ ppm or MS |
|---|---|---|---|---|---|---|
| 49 | O$_2$N—(3-fluoro-4-methylphenyl) | —H | —H | —H | —H | $^1$H NMR (DMSO-d$_6$) 1.18(3H, t, J=7.1Hz), 3.89(2H, d, J=6.2 Hz), 4.11(2H, q, J=7.1Hz), 6.14(1H, t, J=6.2Hz), 6.62(2H, d, J=8.8Hz), 6.90(1H, t, J=9.0 Hz), 6.97(2H, d, J=8.8Hz), 8.03(1H, dd, J=2.6Hz, 9.0Hz), 8.24(1H, dd, J=2.6Hz, 10.9Hz). |
| 50 | O$_2$N—(6-methyl-5-nitropyridin-2-yl) | —H | —F | —H | —F | —CH$_3$ | $^1$H NMR (CDCl$_3$) 1.29(3H, t, J=7.1Hz), 3.07(3H, s), 4.03(2H, s), 4.22(2H, q, J=7.1Hz), 6.22-6.35(2H, m), 7.15(1H, d, J=9.0 Hz), 8.49(1H, dd, J=2.8Hz, 9.0 Hz), 9.01(1H, d, J=2.8Hz). |

TABLE 6-continued

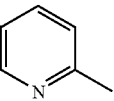

| Reference Example No. | $R_{114}$ | $R_{115}$ | $R_{116}$ | $R_{117}$ | $R_{118}$ | $^1$H NMR (solvent) δ ppm or MS |
|---|---|---|---|---|---|---|
| 51 | 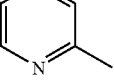 | —F | —F | —H | —CH$_3$ | $^1$H NMR (CDCl$_3$) 1.28(3H, t, J=7.1Hz), 3.05(3H, s), 4.06(2H, s), 4.20(2H, q, J=7.1Hz), 6.72(1H, td, J=2.2Hz, 9.0Hz), 6.90(1H, td, J=1.8Hz, 9.4Hz), 7.11(1H, d, J=9.0Hz), 8.50(1H, dd, J=2.7Hz, 9.0Hz), 9.02(1H, d, J=2.7Hz). |
| 52 | O$_2$N—pyridine-CH$_3$ | —H | —H | —H | —SO$_2$CH$_3$ | $^1$H NMR (CDCl$_3$) 1.31(3H, t, J=7.1Hz), 3.17(3H, s), 4.25(2H, q, J=7.1Hz), 4.47(2H, s), 7.09(1H, d, J=8.9Hz), 7.20(2H, d, J=8.7Hz), 7.60(2H, d, J=8.9Hz), 8.51(1H, dd, J=9.1Hz, 2.8Hz), 9.03(1H, d, J=2.8Hz). |
| 53 | O$_2$N—pyridine-CH$_3$ | —CH$_3$ | —H | —H | —SO$_2$CH$_3$ | $^1$H NMR (CDCl$_3$) 1.31(3H, t, J=7.1Hz), 2.16(3H, s), 3.17(3H, s), 4.25(2H, q, J=7.1Hz), 4.46(2H, s), 7.07(1H, dd, J=9.1Hz, 0.7Hz), 7.08(1H, d, J=7.3Hz), 7.40(1H, d, J=2.6Hz), 7.44(1H, dd, J=7.3Hz, 2.6Hz), 8.50(1H, dd, J=9.1Hz, 2.8Hz), 9.01(1H, dd, J=2.8Hz, 0.7Hz). |
| 54 | —H | —CF$_3$ | —H | —H | —C$_2$H$_5$ | MS 291(M$^+$) |

TABLE 7

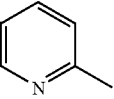

| Reference Example No. | $R_{119}$ | $R_{120}$ | $R_{121}$ | $^1$H NMR (CDCl$_3$) δ ppm |
|---|---|---|---|---|
| 55 | 4-CF$_3$Ph— | —H | —H | 1.30(3H, t, J=7.1Hz), 3.89(2H, d, J=4.6Hz), 3.95(2H, s), 4.20(1H, brs), 4.25(2H, q, J=7.1Hz), 6.62(2H, d, J=8.9Hz), 6.77(1H, d, J=8.4Hz), 6.97(2H, d, J=8.9Hz), 7.27(2H, d, J=7.9Hz), 7.39(1H, dd, J=8.4Hz, 2.5Hz), 7.54(2H, d, J=7.9Hz), 8.03(1H, d, J=2.5Hz). |
| 56 | 4-CF$_3$PhO— | —H | —SO$_2$CH$_3$ | 1.30(3H, t, J=7.1Hz), 3.15(3H, s), 4.23(2H, q, J=7.1Hz), 4.45(2H, s), 5.06(2H, s), 6.99-7.04(3H, m), 7.16(2H, d, J=8.9Hz), 7.54(2H, d, J=8.9Hz), 7.56(2H, d, J=9.2Hz), 7.79-7.83(1H, m), 8.23(1H, d, J=2.0Hz). |
| 57 | 4-CF$_3$PhO— | —CH$_3$ | —SO$_2$CH$_3$ | 1.30(3H, t, J=7.1Hz), 2.19(3H, s), 3.16(3H, s), 4.24(2H, q, J=7.1Hz), 4.44(2H, s), 5.05(2H, s), 6.96-7.07(4H, m), 7.36(1H, dd, J=8.7Hz, 2.6Hz), 7.42(1H, d, J=2.3Hz), |

TABLE 7-continued

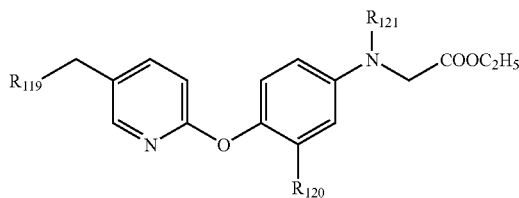

| Reference Example No. | R₁₁₉ | R₁₂₀ | R₁₂₁ | ¹H NMR (CDCl₃) δ ppm |
|---|---|---|---|---|
| | | | | 7.56(2H, d, J=8.9Hz), 7.80(1H, dd, J=8.6 Hz, 2.3Hz), 8.20(1H, d, J=2.3Hz). |

(Ph means a benzene ring having 1 to 4 free valences. Hereinafter Ph indicates the same meaning.)

Reference Example 58 t-Butyl(3-cyano-4-hydroxyphenylamino)acetate

MS 248 (M⁺).

Reference Example 59

Production of 2-[4-(2-fluoro-4-nitrophenoxy)phenoxy]-1-(4-piperonylpiperazin-1-yl)ethanone Potassium carbonate (0.350 g, 2.53 mmol) was added to a solution of 4-(2-fluoro-4-nitrophenoxy)phenol (0.420 g, 1.69 mmol) and 1-chloroacetyl-4-piperonylpiperazine (0.500 g, 1.70 mmol) in DMF (8 mL). The resulting reaction mixture was stirred for 40 minutes at 100° C. Water was added to the reaction mixture, and extracted with ethyl acetate. The ethyl acetate layer was washed with brine, dried over anhydrous sodium sulfate, and evaporated, to thereby yield 0.860 of the title compound.

Appearance: Brown oil
¹H NMR (CDCl₃) δ 2.50-2.60 (4H, m), 3.43 (2H, s), 3.50-3.70 (4H, m), 4.71 (2H, s), 5.95 (2H, s), 6.65-6.75 (2H, m), 6.80-7.05 (6H, m), 7.94 (1H, dd, J=2.3 Hz, 9.1 Hz), 8.06 (1H, dd, J=2.3 Hz, 10.4 Hz).

The following compound was produced in the same manner as in Reference Example 59.

Reference Example 60

2-[4-(2-fluoro-4-nitrophenoxy)phenylamino]-1-(4-piperonylpiperazin-1-yl)ethanone ¹H NMR (DMSO-d₆) δ 2.25-2.40 (4H, m), 3.43 (2H, s), 3.45-3.50 (4H, m), 3.90 (2H, d, J=5.1 Hz), 5.75 (1H, t, J=5.1 Hz), 5.99 (2H, s), 6.70-6.75 (3H, m), 6.80-7.00 (5H, m), 8.05 (1H, ddd, J=1.4 Hz, 2.7 Hz, 10.5 Hz), 8.27 (1H, dd, J=2.7 Hz, 11.0 Hz).

Reference Example 61

Production of methyl 3-(4-benzyloxyphenylamino)-propionate

Under nitrogen, 4-benzyloxyaniline (13.0 g, 65 mmol) was dissolved by heating at 70° C., and a boron trifluoride-diethyl ether complex (0.82 mL, 6.5 mmol) was added dropwise at the same temperature to the dissolved solution. Methyl acrylate (5.85 mL, 65 mmol) was then slowly added dropwise to the resulting solution. This solution was stirred for 10 hours at 70° C. After cooling with ice, ethyl acetate was added to the reaction mixture and washed with aqueous 1 N sodium hydroxide and brine. The organic layer was dried over anhydrous magnesium sulfate, evaporated, and the residue was purified by silica gel column chromatography (n-hexane:ethyl acetate=5:1), to thereby yield 17.5 g of the title compound.

Appearance: Brown powder
¹H NMR (CDCl₃) δ 2.60 (2H, t, J=6.4 Hz), 3.39 (2H, t, J=6.4 Hz), 3.69 (3H, s), 3.77 (1H, brs), 4.98 (2H, s), 6.58 (2H, d, J=8.9 Hz), 6.85 (2H, d, J=8.9 Hz), 7.30-7.44 (5H, m).

Reference Example 62

Production of ethyl 3-(4-Methoxyphenylamino)propionate 3-(4-hydroxyphenylamino)propionic acid (4.00 g, 20.5 mmol) was added to 48% hydrobromic acid (50 mL), and the resulting solution was stirred for 2.5 hours at 100° C. After concentration under reduced pressure, ethanol (10 mL) was added to the residue, and concentrated under reduced pressure. A saturated sodium bicarbonate solution was added to the residue, and extracted with dichloromethane. The dichloromethane layer was dried over anhydrous sodium sulfate and evaporated. The residue was purified by silica gel column chromatography (n-hexane:ethyl acetate=2:1), to thereby yield 1.27 g of the title compound.

Appearance: Yellow oil
¹H NMR (CDCl₃) δ 1.27 (3H, t, J=7.2 Hz), 2.59 (2H, t, J=6.4 Hz), 3.38 (2H, t, J=6.4 Hz), 4.15 (2H, q, J=7.2 Hz), 6.55 (2H, d, J=8.8 Hz), 6.70 (2H, d, J=8.8 Hz).

Reference Example 63

Production of ethyl[(3-fluoro-4-hydroxyphenyl)methylamino]acetate

Ethyl(3-fluoro-4-hydroxyphenylamino)acetate (1.06 g, 5.1 mmol) was dissolved in methanol (150 mL) and the resulting solution was cooled with ice. To the resulting solution were added aqueous 37% formaldehyde (1.5 mL), sodium triacetoxyborohydride (1 g, 16 mmol) and acetic acid (0.9 mL, 15 mmol), and then stirred at room temperature under a nitrogen atmosphere for 14 hours. The solvent was evaporated under reduced pressure. Water was added to the residue, and the resulting solution was neutralized with a saturated sodium bicarbonate solution and extracted with ethyl acetate. The organic layer was washed with brine, and then dried over anhydrous sodium sulfate. The solvent was evaporated under reduced pressure, and the residue was purified by silica gel column chromatography (ethyl acetate:n-hexane=1:2), to thereby yield 0.93 g of the title compound.

Appearance: Light brown oil $^1$H NMR (CDCl$_3$) δ 1.24 (3H, t, J=7.1 Hz), 3.00 (3H, s), 3.98 (2H, s), 4.17 (2H, q, J=7.1 Hz), 4.68 (1H, brs), 6.31-6.52 (2H, m), 6.87 (1H, t, J=8.9 Hz).

The following compounds were produced in the same manner as in Reference Example 63.

Reference Example 64

Ethyl(methyl{4-[5-(4-trifluoromethylbenzyl)pyridin-2-yloxy]phenyl}amino)acetate $^1$H NMR (CDCl$_3$) δ 1.25 (3H, t, J=7.1 Hz), 3.07 (3H, s), 3.95 (2H, s), 4.04 (2H, s), 4.18 (2H, q, J=7.1 Hz), 6.69 (2H, d, J=9.1 Hz), 6.75 (1H, d, J=8.5 Hz), 7.00 (2H, d, J=9.1 Hz), 7.27 (2H, d, J=8.1 Hz), 7.39 (1H, dd, J=8.5 Hz, 2.5 Hz), 7.54 (2H, d, J=8.1 Hz), 8.04 (1H, d, J=2.5 Hz).

Reference Example 65

Ethyl[(4-hydroxy-2-trifluoromethylphenyl)methylamino]-acetate

MS 277 (M$^+$).

TABLE 8

| Reference Example No. | R$_{122}$ | R$_{123}$ | R$_{124}$ | R$_{125}$ | M | $^1$H NMR (CDCl$_3$) δ ppm |
|---|---|---|---|---|---|---|
| 66 | —H | —H | —CH$_3$ | —CH$_3$ | 1 | 3.00(3H, s), 3.71(3H, s), 4.01(2H, s), 4.55(1H, brs), 6.62(2H, d, J=9.2Hz), 6.75(2H, d, J=9.2Hz). |
| 67 | Benzyl | —H | —CH$_3$ | —CH$_3$ | 2 | 2.51-2.57(2H, m), 2.86(3H, s), 3.56-3.62(2H, m), 3.66(3H, s), 5.00(2H, s), 6.72(2H, d, J=9.1 Hz), 6.91(2H, d, J=9.1Hz), 7.30-7.45(5H, m). |
| 68 | —H | —F | —C$_2$H$_5$ | —C$_2$H$_5$ | 1 | 1.18(3H, t, J=7.1Hz), 1.26(3H, t, J=7.1Hz), 3.38(2H, q, J=7.1 Hz) 3.94(2H, s), 4.19(2H, q, J=7.1Hz), 4.61(1H, brs), 6.30-6.35 (1H, m), 6.43(1H, dd, J=13.7Hz, 3.0Hz), 6.86(1H, t, J=8.9Hz). |
| 69 | —H | —OCH$_3$ | —C$_2$H$_5$ | —C$_2$H$_5$ | 1 | 1.17(3H, t, J=7.1Hz), 1.25(3H, t, J=7.1Hz), 3.39(2H, q, J=7.1 Hz), 3.85(3H, s), 3.95(2H, s), 4.18(2H, q, J=7.1Hz), 5.30(1H, brs), 6.21(1H, dd, J=8.6Hz, 2.8 Hz), 6.33(1H, d, J=2.8Hz), 6.79(1H, d, J=8.7Hz). |
| 70 | 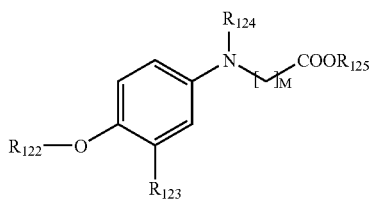 | —CH$_3$ | —C$_2$H$_5$ | —C$_2$H$_5$ | 1 | 1.23(3H, t, J=7.1Hz), 1.28(3H, t, J=7.1Hz), 2.08(3H, s), 3.47(2H, q, J=7.1Hz), 4.01(2H, s), 4.22(2H, q, J=7.1Hz), 6.40-6.59(2H, m), 6.81-7.00(2H, m), 8.43(1H, dd, J=9.1Hz, 2.8Hz), 9.06(1H, d, J=2.8Hz). |
| 71 | O$_2$N-pyridyl | —CH$_3$ | —CH$_3$ | —C$_2$H$_5$ | 1 | 1.27(3H, t, J=7.1Hz), 2.10(3H, s), 3.08(3H, s), 4.06(2H, s), 4.21(2H, q, J=7.1Hz), 6.50-6.62(2H, m), 6.85-6.99(2H, m), 8.43(1H, dd, J=9.1Hz, 2.8Hz), 9.05(1H, d, J=2.8Hz). |
| 72 | O$_2$N-pyridyl | —OCH$_3$ | —CH$_3$ | —C$_2$H$_5$ | 1 | 1.27(3H, t, J=7.1Hz), 3.11(3H, s), 3.74(3H, s), 4.07(2H, s), 4.21(2H, q, J=7.1Hz), 6.27(1H, dd, J=8.7Hz, 2.8Hz), 6.34(1H, d, J=2.8Hz), 6.95-7.01(2H, m), 8.42(1H, dd, J=9.2Hz, 3.0Hz), 9.03(1H, d, J=2.8Hz). |

TABLE 8-continued

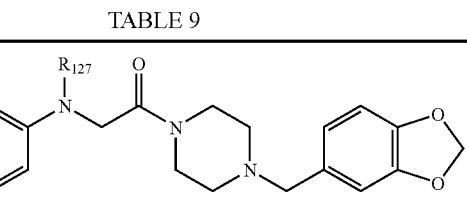

| Reference Example No. | $R_{122}$ | $R_{123}$ | $R_{124}$ | $R_{125}$ | M | $^1$H NMR (CDCl$_3$) δ ppm |
|---|---|---|---|---|---|---|

(M means the number of the methylene groups. Hereinafter M indicates the same meaning.)

TABLE 9

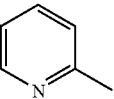

| Reference Example No. | $R_{126}$ | $R_{127}$ | $^1$H NMR (CDCl$_3$) δ ppm |
|---|---|---|---|
| 73 | —H | —CH$_3$ | 2.41(4H, brs), 2.88(3H, s), 3.42(2H, s), 3.50(2H, brs), 3.60(2H, brs), 3.94(2H, s), 5.92(2H, s), 6.55-6.69(4H, m), 6.72(2H, s), 6.82(1H, s), 7.47(1H, brs). |
| 74 | —H | —C$_2$H$_5$ | 1.05(3H, t, J=7.1Hz), 2.44(4H, brs), 3.25(2H, q, J=7.1Hz), 3.46(2H, s), 3.60(4H, brs), 3.91(2H, s), 5.94(2H, s), 6.63(4H, s), 6.72-6.74(2H, m), 6.82(1H, s), 7.43(1H, brs). |
| 75 | 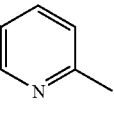 | —CH$_3$ | 2.44(4H, brs), 3.06(3H, s), 3.44(2H, s), 3.49(2H, brs), 3.63(2H, brs), 4.11(2H, s), 5.94(2H, s), 6.69-6.77(4H, m), 6.85(1H, s), 6.92-7.02(3H, m), 8.41(1H, dd, J=9.1Hz, 2.8Hz), 9.04(1H, d, J=3.0Hz). |
| 76 | O$_2$N-pyridyl | —C$_2$H$_5$ | 1.20(3H, t, J=7.1Hz), 2.42-2.46(4H, m), 3.44-3.51(6H, m), 3.64(2H, q, J=7.1Hz), 4.06(2H, s), 5.95(2H, s), 6.67(2H, d, J=9.2Hz), 6.74(2H, brs), 6.85(1H, brs), 6.94(1H, d, J=9.1Hz), 6.99(2H, d, J=9.1Hz), 8.42(1H, dd, J=9.1Hz, 2.8Hz), 9.05(1H, d, J=2.8Hz). |

Reference Example 77

Production of 1-(4-piperonylpiperazin-1-yl)-2-[cyclopropyl(4-hydroxyphenyl)amino]ethanone To a solution of 1-(4-piperonylpiperazin-1-yl)-2-(4-hydroxyphenylamino)ethanone (1.00 g, 2.7 mmol) in methanol (10 mL) were added acetic acid (1.55 mL, 27 mmol), molecular sieves 3A1/16 (1.00 g), [(1-ethoxycyclopropyl)oxy]trimethylsilane (0.653 mL, 3.2 mmol) and sodium cyanoborohydride (770 mg, 12 mmol). The resulting solution was stirred for 16 hours at 60° C. This reaction solution was filtered and concentrated, and to the residue were added ethyl acetate and water. The aqueous layer was adjusted to pH 10 using aqueous 6 N sodium hydroxide. This layer was stirred for some time, and once insoluble matter had dissolved, the ethyl acetate layer was removed, and washed with aqueous 2 N sodium hydroxide and a saturated sodium bicarbonate solution, then dried over anhydrous magnesium sulfate. The solvent was evaporated, to thereby yield 770 mg of the title compound.

Appearance: White powder $^1$H NMR (CDCl$_3$) δ 0.54-0.59 (2H, m), 0.72-0.79 (2H, m), 2.39-2.45 (4H, m), 2.70-2.77 (1H, m), 3.44 (2H, s), 3.48-3.51 (2H, m), 3.57-3.60 (2H, m), 4.12 (2H, s), 5.95 (2H, s), 6.62-6.67 (2H, m), 6.74-6.85 (5H, m).

The following compound was produced in the same manner as in Reference Example 77.

Reference Example 78

Ethyl{cyclopropyl[3-methyl-4-(5-nitropyridin-2-yloxy)phenyl]amino}acetate $^1$H NMR (CDCl$_3$) δ 0.66-0.72 (2H, m), 0.83-0.89 (2H, m), 1.26 (3H, t, J=7.3 Hz), 2.10 (3H, s), 2.71-2.79 (1H, m), 4.08-4.22 (4H, m), 6.77-6.82 (2H, m), 6.91-6.95 (2H, m), 8.40-8.45 (1H, m), 9.05 (1H, d, J=2.8 Hz).

Reference Example 79

Production of ethyl[(3-hydroxyphenyl)methylamino]-acetate

Potassium bicarbonate (1.42 mL, 14.19 mmol) was added to a solution of ethyl(3-hydroxyphenylamino)acetate (2.77 g, 14.19 mmol) in DMF (15 mL). To the resulting solution was further added methyl iodide (1.77 mL, 28.38 mmol), and then stirred at room temperature for 18 hours. To the resulting reaction solution was added brine (150 mL), and the obtained mixture was extracted with ethyl acetate (150 mL). The ethyl acetate layer was dried over anhydrous sodium sulfate, after which solvent was evaporated, to thereby yield 2.48 g of the title compound.

Appearance: Pale yellow oil $^1$H NMR (CDCl$_3$) δ 1.24 (3H, t, J=7.1 Hz), 3.04 (3H, s), 4.03 (2H, s), 4.18 (2H, q, J=7.1 Hz), 5.17 (1H, brs), 6.17-6.27 (3H, m), 7.04-7.10 (1H, m).

The following compounds were produced in the same manner as in Reference Example 79.

TABLE 10

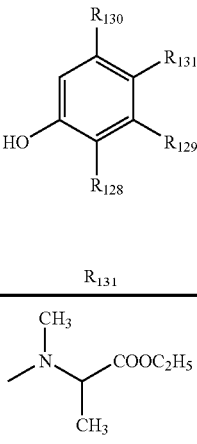

| Reference Example No. | R$_{128}$ | R$_{129}$ | R$_{130}$ | R$_{131}$ | $^1$H NMR (CDCl$_3$) δ ppm or MS |
|---|---|---|---|---|---|
| 80 | —H | —H | —H | 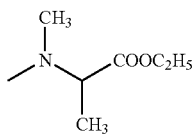 | $^1$H NMR 1.22(3H, t, J=7.1Hz), 1.43(3H, d, J=7.1Hz), 2.83(3H, s), 4.16(2H, q, J=7.1Hz), 4.33(1H, q, J=7.1Hz), 4.84(1H, brs), 6.75(4H, s). |
| 81 | —CH$_3$ | —H | —H | 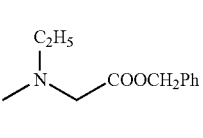 | $^1$H NMR 1.23(3H, t, J=7.3Hz), 1.42(3H, d, J=7.1Hz), 2.22(3H, s), 2.82(3H, s), 4.08-4.21(2H, m), 4.30 (1H, s), 4.33(1H, q, J=7.1Hz), 6.58(1H, dd, J=8.6Hz, 3.0Hz), 6.65(1H, d, J=2.8Hz), 6.68(1H, d, J=8.6Hz). |
| 82 | —OCH$_3$ | —H | —H | 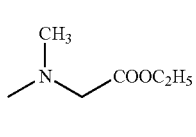 | $^1$H NMR 1.17(3H, t, J=7.1Hz), 3.39(2H, q, J=7.1Hz), 3.75(3H, s), 4.00(2H, brs), 5.11(1H, brs), 5.15 (2H, s), 6.21(1H, dd, J=8.6Hz, 2.8 Hz), 6.27(1H, d, J=2.8Hz), 6.77(1H, d, J=8.6Hz), 7.27-7.37(5H, m). |
| 83 | —F | —H | —F | 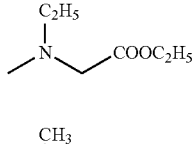 | $^1$H NMR 1.24(3H, t, J=7.1Hz), 2.92(3H, s), 3.93(2H, s), 4.15(2H, q, J=7.1Hz), 4.96(1H, d, J=2.8Hz), 6.70(1H, d, J=8.2Hz, 12.9Hz), 6.77(1H, d, J=8.1Hz, 12.2Hz). |
| 84 | —CH$_3$ | —H | —CH$_3$ | 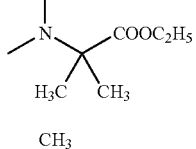 | $^1$H NMR 0.99(3H, t, J=7.1Hz), 1.21(3H, t, J=7.1Hz), 2.18(3H, s), 2.24(3H, s), 3.10(2H, q, J=7.1Hz), 3.68(2H, s), 4.11(2H, q, J=7.1Hz), 4.47(1H, s), 6.59(1H, s), 6.94(1H, s). |
| 85 | —H | —H | —H | 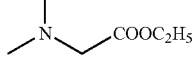 | $^1$H NMR 1.26(3H, t, J=7.3Hz), 1.33(6H, s), 2.80(3H, s), 4.18(2H, q, J=7.3Hz), 5.15(1H, brs), 6.71(2H, d, J=8.9Hz), 7.00(2H, d, J=8.9 Hz). |
| 86 | —H | —CH$_3$ | —CH$_3$ | 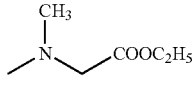 | MS 237(M$^+$) |
| 87 | —CH$_3$ | —H | —CH$_3$ | 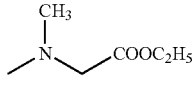 | $^1$H NMR 1.24(3H, t, J=7.1Hz), 2.19(3H, s), 2.24(3H, s), 2.79(3H, s), 3.64(2H, s), 4.15(2H, q, J=7.1Hz), 4.45(1H, brs), 6.59(1H, s), 6.89(1H, s). |

TABLE 10-continued

[Structure: phenol with HO, and substituents R130 (position 4), R131 (position 3), R129 (position 2), R128 (position 6... actually ortho to OH)]

| Reference Example No. | R$_{128}$ | R$_{129}$ | R$_{130}$ | R$_{131}$ | $^1$H NMR (CDCl$_3$) δ ppm or MS |
|---|---|---|---|---|---|
| 88 | —CF$_3$ | —H | —H | —N(CH$_3$)CH$_2$COOC$_2$H$_5$ | MS 277(M$^+$) |
| 89 | —CN | —H | —H | —N(CH$_3$)CH$_2$COOC(CH$_3$)$_3$ | MS 262(M$^+$) |

TABLE 11

[Structure: O$_2$N-pyridine-O-phenyl-N(R$_{135}$)-(CH$_2$)$_M$-COOR$_{136}$, with R$_{134}$, R$_{133}$, R$_{132}$ substituents on phenyl]

| Reference Example No. | R$_{132}$ | R$_{133}$ | R$_{134}$ | R$_{135}$ | R$_{136}$ | M | $^1$H NMR (CDCl$_3$) δ ppm |
|---|---|---|---|---|---|---|---|
| 90 | —H | —H | —H | —C$_2$H$_5$ | —C$_2$H$_5$ | 1 | 1.24(3H, t, J=7.1Hz), 1.28(3H, t, J=7.0Hz), 3.48(2H, q, J=7.1Hz), 4.02(2H, s), 4.21(2H, q, J=7.0Hz), 6.67(2H, d, J=8.9Hz), 6.95(1H, d, J=9.1Hz), 7.00(2H, d, J=8.9Hz), 8.42(1H, dd, J=2.8Hz, 9.1Hz), 9.06(1H, d, J=2.8Hz). |
| 91 | —H | —H | —H | —CH$_3$ | —C$_2$H$_5$ | 1 | 1.27(3H, t, J=7.2Hz), 3.10(3H, s), 4.07(2H, s), 4.20(2H, q, J=7.2Hz), 6.71(2H, d, J=9.2Hz), 6.95(1H, d, J=9.1Hz), 7.02(2H, d, J=9.2Hz), 8.43(1H, dd, J=2.8Hz, 9.1Hz), 9.05(1H, d, J=2.8Hz). |
| 92 | —F | —H | —H | allyl | —C$_2$H$_5$ | 1 | 1.29(3H, t, J=7.1Hz), 4.02(4H, brs), 4.23(2H, q, J=7.1Hz), 5.21-5.30(2H, m), 5.84-5.94(1H, m), 6.40-6.52(2H, m), 7.01-7.08(2H, m), 8.47(1H, dd, J=8.9Hz, 2.8Hz), 9.03(1H, d, J=2.6 Hz). |
| 93 | —F | —H | —F | —C$_2$H$_5$ | —C$_2$H$_5$ | 1 | 1.22(3H, t, J=7.1Hz), 1.27(3H, t, J=7.1Hz), 3.37(2H, q, J=7.1Hz), 4.02(2H, s), 4.20(2H, q, J=7.1Hz), 6.77(1H, dd, J=8.1Hz, 12.3Hz), 6.92(1H, dd, J=7.3Hz, 12.7Hz), 7.09(1H, d, J=9.0Hz), 8.49(1H, dd, J=2.8Hz, 9.0Hz), 9.02(1H, d, J=2.8Hz). |
| 94 | —F | —F | —H | —CH$_3$ | —C(CH$_3$)$_3$ | 0 | 1.45(9H, s), 3.26(3H, s), 6.90-7.11(2H, m), 7.16(1H, d, J=9.0Hz), 8.53(1H, dd, J=2.8Hz, 9.0Hz), 9.01(1H, d, J=2.8Hz). |

TABLE 12

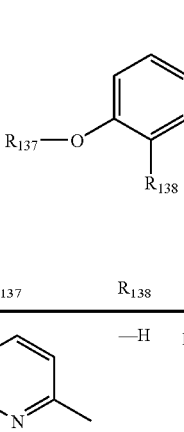

| Reference Example No. | R₁₃₇ | R₁₃₈ | R₁₃₉ | Xa₃ | Xa₄ | ¹H NMR (CDCl₃) δ ppm |
|---|---|---|---|---|---|---|
| 95 | O₂N-[6-methylpyridin-3-yl] | —H | piperonyl | none | —CH₂— | 2.44(8H, brs), 2.96(2H, s), 3.30(3H, s), 3.38(2H, s), 5.92(2H, s), 6.72(2H, brs), 6.82(1H, s), 7.09(1H, d, J=9.1Hz), 7.20(2H, d, J=8.9Hz), 7.29(2H, d, J=8.9Hz), 8.51(1H, dd, J=9.1Hz, 2.8Hz), 9.04(1H, d, J=2.8Hz). |
| 96 | [2-methyltetrahydropyran-2-yl] | —H | benzyl | none | none | 1.55-1.80(3H, m), 1.81-2.15(3H, m), 2.23(4H, t, J=5.0Hz), 3.16(3H, s), 3.20(4H, t, J=5.0Hz), 3.42(2H, s), 3.55-3.69(1H, m), 3.85-4.00(1H, m), 5.36(1H, t, J=3.2Hz), 6.99(4H, s), 7.16-7.36(5H, m). |
| 97 | —H | —CH₃ | piperonyl | —CH₂— | none | 2.18(3H, s), 2.38-2.42(4H, m), 2.89(3H, s), 3.41(2H, s), 3.50(2H, brs), 3.61(2H, brs), 3.95(2H, brs), 5.93(2H, s), 6.44-6.57(3H, m), 6.73-6.76(2H, m), 6.83(1H, s). |

TABLE 13

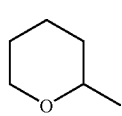

| Reference Example No. | R₁₄₀ | ¹H NMR (CDCl₃) δ ppm |
|---|---|---|
| 98 | —NO₂ | 1.07(3H, t, J=7.1Hz), 2.15(3H, s), 3.38(3H, s), 4.19(2H, q, J=7.1Hz), 7.06-7.20(4H, m), 8.51(1H, dd, J=9.1Hz, 2.8Hz), 8.97(1H, d, J=2.8Hz). |
| 99 | 4-CF₃PhOCH₂— | 1.07(3H, t, J=7.1Hz), 2.18(3H, s), 3.36(3H, s), 4.08(2H, q, J=7.1Hz), 5.04(2H, s), 6.97(1H, d, J=8.6Hz), 7.01-7.13(4H, m), 7.16(1H, d, J=2.3Hz), 7.57(2H, d, J=8.6Hz), 7.80(1H, dd, J=8.6Hz, 2.3Hz), 8.17(1H, d, J=2.3Hz). |

Reference Example 100

Production of ethyl[acetyl(3-fluoro-4-hydroxyphenyl)amino]acetate

Ethyl(3-fluoro-4-hydroxyphenylamino)acetate (0.84 g, 4 mmol) was dissolved in N,N-dimethylacetamide (4 mL). To the resulting solution was added acetyl chloride (0.6 mL, 10 mmol), and the resulting solution was stirred at room temperature for 1 hour. Water (1 mL), methanol (10 mL) and saturated sodium carbonate (10 mL) were added, and the mixture was stirred at room temperature for 1 hour. Water was added to the solution. 10% hydrochloric acid was employed to turn the solution acidic, and then the solution was extracted with ethyl acetate. The organic layer was washed with water and brine, then dried over anhydrous sodium sulfate. The solvent was evaporated under reduced pressure, and the obtained residue was purified by silica gel column chromatography (ethyl acetate:n-hexane=2:1), to thereby yield 0.84 g of the title compound.

Appearance: Colorless powder $^1$H NMR (CDCl$_3$) δ 1.28 (3H, t, J=7.3 Hz), 1.94 (3H, s), 4.20 (2H, q, J=7.3 Hz), 4.32 (2H, s), 6.02 (1H, brs), 6.99-7.07 (2H, m), 7.13-7.18 (1H, m).

The following compounds were produced in the same manner as in Reference Example 100.

TABLE 14

| Reference Example No. | $R_{141}$ | $R_{142}$ | M | $^1$H NMR (CDCl$_3$) δ ppm |
|---|---|---|---|---|
| 101 | —H | —CH$_3$ | 1 | 1.26(3H, t, J=7.1Hz), 1.92(3H, s), 2.24(3H, s), 4.19(2H, q, J=7.1Hz), 4.32(2H, s), 5.38(1H, brs), 6.78(1H, d, J=8.4Hz), 7.04(1H, dd, J=8.4Hz, 2.5Hz), 7.10(1H, d, J=2.5Hz). |
| 102 | —H | —H | 2 | 1.21(3H, t, J=7.2Hz), 1.83(3H, s), 2.56(2H, t, J=7.4Hz), 3.97(2H, t, J=7.4Hz), 4.06(2H, q, J=7.2Hz), 6.05(1H, brs), 6.87(2H, d, J=8.7Hz), 7.03(2H, d, J=8.7Hz). |
| 103 | benzyl | —H | 1 | 1.26(3H, t, J=7.1Hz), 1.91(3H, s), 4.18(2H, q, J=7.1Hz), 4.33(2H, s), 5.07(2H, s), 6.98(2H, d, J=8.9Hz), 7.26(2H, d, J=8.9Hz), 7.35-7.45 (5H, m). |
| 104 | 3,4-dichlorobenzoyl-NH-(structure) | —H | 1 | 1.24(3H, t, J=7.1Hz), 1.89(3H, s), 4.15(2H, q, J=7.1Hz), 4.32(2H, s), 6.95(2H, d, J=8.9Hz), 7.12(1H, t, J=9.0Hz), 7.27-7.32(3H, m), 7.52-7.60(1H, m), 7.70-7.80(2H, m), 7.99(1H, s), 8.05(1H, s). |

TABLE 15

| Reference Example No. | $R_{143}$ | $^1$H NMR (CDCl$_3$) δ ppm |
|---|---|---|
| 105 | —C$_2$H$_5$ | 1.09(3H, t, J=7.4Hz), 2.20(2H, q, J=7.4Hz), 2.40-2.45(4H, m), 3.43(4H, brs), 3.61(2H, brs), 4.47(2H, s), 5.94(2H, s), 6.70-6.76(2H, m), 6.84(1H, s), 7.08(1H, d, J=9.0Hz), 7.19(2H, d, J=8.7Hz), 7.52(2H, d, J=8.7Hz), 8.51(1H, dd, J=2.8Hz, 9.0Hz), 9.04(1H, d, J=2.8Hz). |
| 106 | —CH$_2$Cl | 2.40-2.48(4H, m), 3.43(4H, s), 3.62(2H, brs), 3.97(2H, s), 4.49(2H, s), 5.95(2H, s), 6.70-6.77(2H, m), 6.84(1H, s), 7.11(1H, d, J=9.0 Hz), 7.23(2H, d, J=8.7Hz), 7.59(2H, d, J=8.7Hz), 8.52(1H, dd, J=2.8Hz, 9.0Hz), 9.04(1H, d, J=2.8Hz). |
| 107 | cyclopropyl | 0.65-1.52(5H, m), 2.43(4H, brs), 3.43(4H, brs), 3.61(2H, brs), 4.50(2H, brs), 5.95(2H, s), 6.72-6.75(2H, m), 6.84(1H, s), 7.08(1H, |

TABLE 15-continued

| Reference Example No. | $R_{143}$ | $^1$H NMR (CDCl$_3$) δ ppm |
|---|---|---|
| | | d, J=9.1Hz), 7.20(1H, d, J=8.8Hz), 7.59(2H, d, J=8.8Hz), 8.50(1H, dd, J=2.9Hz, 9.1Hz), 9.04(1H, d, J=2.9Hz). |

TABLE 16

| Reference Example No. | $R_{144}$ | $^1$H NMR (CDCl$_3$) δ ppm |
|---|---|---|
| 108 | —H | 1.44(3H, t, J=7.1Hz), 4.43(2H, q, J=7.1Hz), 5.05(2H, s), 6.93(1H, d, J=8.6Hz), 7.02(2H, d, J=8.6Hz), 7.17(2H, d, J=8.9Hz), 7.56(2H, d, J=8.4Hz), 7.69(2H, d, J=8.9Hz), 7.79(1H, dd, J=8.4Hz, 2.5Hz), 8.22(1H, d, J=2.5Hz), 8.90(1H, brs). |
| 109 | —CH$_3$ | 1.44(3H, t, J=7.1Hz), 2.19(3H, s), 4.43(2H, q, J=7.1Hz), 5.03(2H, s), 6.94(1H, d, J=8.4Hz), 7.02(2H, d, J=8.4Hz), 7.07(1H, d, J=8.6 Hz), 7.51-7.58(4H, m), 7.78(1H, dd, J=8.6Hz, 2.5Hz), 8.20(1H, d, J=2.5Hz), 8.84(1H, brs). |

Reference Example 110

Production of (6-chloropyridin-3-yl)(4-trifluoromethylphenyl)methanone

Under an argon gas flow, half of a solution of 4-bromobenzotrifluoride (1.20 g, 5.33 mmol) in THF (6 mL) was added to magnesium (156 mg, 6.41 mmol). The resulting solution was stirred, and further 1,2-dibromoethane (3 drops) was added. Once the reaction began, the balance of the 4-bromobenzotrifluoride in THF solution was added dropwise, and once dropping had finished, the resulting solution was stirred for 30 minutes at 60° C. A solution of 6-chloro-N-methoxy-N-methylnicotinamide (990 mg, 5.36 mmol) in THF (3 mL) was charged into a separate reaction vessel, into which the above reaction solution was added dropwise under an argon gas flow and ice cooling. After dropping had finished, the resulting solution was stirred for 30 minutes at room temperature, and then heated to reflux for 1 hour. The reaction solution was cooled with ice, then aqueous ammonium chloride and water were added. The resulting solution was extracted with ethyl acetate, and washed with brine. The ethyl acetate layer was dried over anhydrous magnesium sulfate, evaporated, and the residue was purified by silica gel column chromatography (n-hexane:ethyl acetate=10:1), to thereby yield 610 mg of the title compound.

Appearance: White powder
$^1$H NMR (CDCl$_3$) δ 7.52 (1H, d, J=8.3 Hz), 7.80 (2H, d, J=8.0 Hz), 7.90 (2H, d, J=8.0 Hz), 8.11 (1H, dd, J=8.3 Hz, 2.0 Hz), 8.77 (1H, d, J=2.0 Hz).

Reference Example 111

Production of ethyl 3-[4-(4-nitrophenoxy)phenyl]-propionate

To a solution of ethyl 3-(4-hydroxyphenyl)-propionate (6.00 g, 30.9 mmol) in DMF (60 mL) were added 4-fluoronitrobenzene (6.54 g, 46.3 mmol) and potassium carbonate (5.12 g, 37.1 mmol). The resulting reaction solution was stirred for 1 hour at 80° C. To the reaction solution was added water and extracted with ethyl acetate. The resulting ethyl acetate layer was washed with water and then with brine. The ethyl acetate layer was dried over anhydrous magnesium sulfate, evaporated, and the residue was purified by silica gel column chromatography (n-hexane:ethyl acetate=5:1), to thereby yield 9.64 g of the title compound.

Appearance: Pale yellow oil
$^1$H NMR (CDCl$_3$) δ 1.23 (3H, t, J=7.1 Hz), 2.62 (2H, t, J=7.7 Hz), 2.96 (2H, t, J=7.7 Hz), 4.12 (2H, q, J=7.1 Hz), 6.93-7.06 (4H, m), 7.24 (2H, d, J=8.5 Hz), 8.17 (2H, d, J=9.2 Hz).

The following compounds were produced in the same manner as in Reference Example 111.

TABLE 17

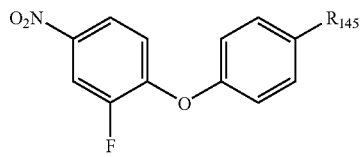

| Reference Example No. | $R_{145}$ | $^1$H NMR (solvent) δ ppm |
|---|---|---|
| 112 | —Ac | (DMSO-$d_6$) 2.58(3H, s), 7.26(2H, d, J=8.8Hz), 7.40(1H, t, J=8.4Hz), 8.04(2H, d, J=8.8Hz), 8.15(1H, ddd, J=1.4Hz, 2.6Hz, 8.4Hz), 8.39(1H, dd, J=2.6Hz, 10.7Hz). |
| 113 | —CH$_2$COOCH$_3$ | (DMSO-$d_6$) 3.63(3H, s), 3.72(2H, s), 7.11-7.17(3H, m), 7.38(2H, d, J=8.4Hz), 8.09(1H, ddd, J=1.4Hz, 2.7Hz, 9.1Hz), 8.33(1H, dd, J=2.7Hz, 10.2Hz). |
| 114 | —(CH$_2$)$_2$COOC$_2$H$_5$ | (CDCl$_3$) 1.22(3H, t, J=7.1Hz), 2.62(2H, t, J=7.6Hz), 2.96(2H, t, J=7.6Hz), 4.12(2H, q, J=7.1Hz), 6.92(1H, dd, J=9.0Hz, 8.0Hz), 6.99(2H, d, J=8.6Hz), 7.24(2H, d, J=8.6Hz), 7.90-8.00(1H, m), 8.06(1H, dd, J=10.3Hz, 2.7Hz). |
| 115 | —NHAc | (DMSO-$d_6$) 2.05(3H, s), 7.07(1H, t, J=8.6Hz), 7.16(2H, d, J=9.0Hz), 7.67(2H, d, J=9.0Hz), 8.06(1H, ddd, J=1.4Hz, 2.7Hz, 8.6Hz), 8.31(1H, dd, 2.7Hz, 10.9Hz), 10.06(1H, s). |
| 116 | —SCH$_2$COOC$_2$H$_5$ | (CDCl$_3$) 1.24(3H, t, J=7.1Hz), 3.62(2H, s), 4.18(2H, q, J=7.1Hz), 6.95-7.05(3H, m), 7.49(2H, d, J=8.8Hz), 8.00(1H, ddd, J=1.5Hz, 2.6Hz, 9.1Hz), 8.08(1H, dd, J=2.6Hz, 10.2Hz). |
| 117 | —OCH$_3$ | (DMSO-$d_6$) 3.77(3H, s), 6.90-7.10(3H, m), 7.16(2H, d, J=9.1Hz), 8.03(1H, ddd, J=1.4Hz, 2.6Hz, 9.2Hz), 8.27(1H, dd, J=2.6Hz, 10.9Hz). |
| 118 | —H | (CDCl$_3$) 6.95(1H, dd, J=9.0Hz, 8.0Hz), 7.07(2H, d, J=7.9Hz), 7.24(2H, t, J=7.9Hz), 7.42(2H, t, J=7.9Hz), 7.91-8.02(1H, m), 8.07(1H, dd, J=10.3Hz, 2.7Hz). |
| 119 | —(CH$_2$)$_3$COOC$_2$H$_5$ | (CDCl$_3$) 1.25(3H, t, J=7.1Hz), 1.88-2.03(2H, m), 2.32(2H, t, J=7.4Hz), 2.66(2H, t, J=7.4Hz), 4.12(2H, q, J=7.1Hz), 6.91(1H, dd, J=9.0Hz, 8.0Hz), 6.99(2H, d, J=8.5Hz), 7.22(2H, d, J=8.5Hz), 7.91-7.98(1H, m), 8.06(1H, dd, J=10.3Hz, 2.7Hz) |
| 120 | —CHO | (DMSO-$d_6$) 7.33(2H, d, J=8.7Hz), 7.47(1H, t, J=9.0Hz), 8.00(2H, d, J=8.7Hz), 8.16(1H, ddd, J=1.4Hz, 2.7Hz, 9.0Hz), 8.40(1H, dd, J=2.7Hz, 10.6Hz), 9.99(1H, s). |
| 121 | —COOC$_2$H$_5$ | (DMSO-$d_6$) 1.32(3H, t, J=7.1Hz), 4.31(2H, q, J=7.1Hz), 7.26(2H, d, J=8.9Hz), 7.41(1H, t, J=8.4Hz), 8.03(2H, d, J=8.9Hz), 8.14(1H, ddd, J=1.4Hz, 2.6Hz, 8.4Hz), 8.39(1H, dd, J=2.6Hz, 10.6Hz). |

(Ac means an acetyl group. Hereinafter Ac indicates the same meaning.)

TABLE 18

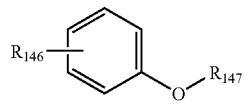

| Reference Example No. | $R_{146}$ | $R_{147}$ | $^1$H NMR (solvent) δ ppm |
|---|---|---|---|
| 122 | 4-NO$_2$ | ![structure]COOC$_2$H$_5$ | (DMSO-$d_6$) 1.33(3H, t, J=7.1Hz), 4.32(2H, q, J=7.1Hz), 7.24-7.31(4H, m), 8.05(2H, d, J=8.9Hz), 8.29(2H, d, J=9.3Hz). |
| 123 | 4-NO$_2$ | ![structure with CH$_3$, N, COOCH$_3$] | (CDCl$_3$) 3.10(3H, s), 3.75(3H, s), 4.10(2H, s), 6.71(2H, d, J=9.2Hz), 6.96(2H, d, J=9.2Hz), 6.98(2H, d, J=9.2Hz), 8.17(2H, d, J=9.2Hz). |

TABLE 18-continued

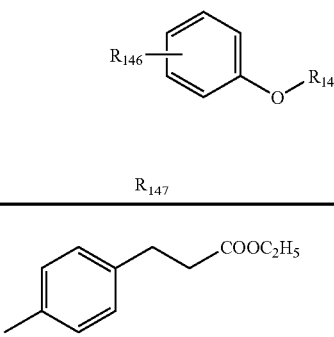

| Reference Example No. | $R_{146}$ | $R_{147}$ | $^1$H NMR (solvent) δ ppm |
|---|---|---|---|
| 124 | 2-NO$_2$ | (4-methylphenyl)-CH$_2$CH$_2$-COOC$_2$H$_5$ | (CDCl$_3$) 1.22(3H, t, J=7.1Hz), 2.60(2H, t, J=7.7Hz), 2.93(2H, t, J=7.7Hz), 4.11(2H, q, J=7.1Hz), 6.92-6.99(3H, m), 7.13-7.23(3H, m), 7.45(1H, dt, J=1.6Hz, 8.2Hz), 7.92(1H, dd, J=8.2Hz, 1.6Hz). |
| 125 | 4-NO$_2$ | N-Boc-tetrahydropyridinyl-(4-methylphenyl) | (CDCl$_3$) 1.50(9H, s), 2.53(2H, brs), 3.66(2H, m), 4.10(2H, brs), 6.05(1H, brs), 7.02(2H, d, J=9.0Hz), 7.06(2H, d, J=8.5Hz), 7.43(2H, d, J=8.5Hz), 8.21(2H, d, J=9.0Hz). |
| 126 | 4-NO$_2$ | (3-methylphenyl)-CH$_2$CH$_2$-COOC$_2$H$_5$ | (CDCl$_3$) 1.21(3H, t, J=7.1Hz), 2.61(2H, t, J=7.7Hz), 2.95(2H, t, J=7.7Hz), 4.10(2H, q, J=7.1Hz), 6.88-6.94(2H, m), 6.98(2H, d, J=9.2Hz), 7.08(1H, d, J=7.6Hz), 7.32(1H, t, J=7.6Hz), 8.18(2H, d, J=9.2Hz). |
| 127 | 4-NO$_2$ | (2-methylphenyl)-CH$_2$CH$_2$-COOCH$_3$ | (CDCl$_3$) 2.58(2H, t, J=7.7Hz), 2.87(2H, t, J=7.7Hz), 3.62(3H, s), 6.89-7.01(3H, m), 7.13-7.37(3H, m), 8.18(2H, d, J=9.2Hz). |

TABLE 19

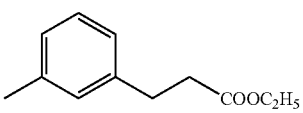

| Reference Example No. | $R_{148}$ | $R_{149}$ | $R_{150}$ | $^1$H NMR (CDCl$_3$) δ ppm |
|---|---|---|---|---|
| 128 | —H | —H | —C$_2$H$_5$ | 1.41(3H, t, J=7.3Hz), 4.40(2H, q, J=7.3Hz), 7.09(1H, d, J=8.9Hz), 7.22-7.26(2H, m), 8.14-8.17(2H, m), 8.52(1H, dd, J=8.9Hz, 3.0Hz), 9.04(1H, d, J=3.0Hz). |
| 129 | —H | —H | —CH$_3$ | 3.94(3H, s), 7.10(1H, d, J=8.9Hz), 7.22-7.26(2H, m), 8.13-8.16(2H, m), 8.52(1H, dd, J=8.9Hz, 2.7Hz), 9.04(1H, d, J=2.7Hz). |
| 130 | —F | —H | —CH$_3$ | 3.95(3H, s), 7.18(1H, d, J=8.8Hz), 7.29-7.35(1H, m), 7.87-7.96(2H, m), 8.54(1H, dd, J=8.8Hz, 2.6Hz), 8.99(1H, d, J=2.6Hz). |
| 131 | —F | —H | —C$_2$H$_5$ | 1.41(3H, t, J=7.1Hz), 4.41(2H, q, J=7.1Hz), 7.18(1H, d, J=9.1Hz), 7.29-7.35(1H, m), 7.88-7.96(2H, m), 8.54(1H, dd, J=9.1Hz, 2.8Hz), 8.99(1H, d, J=2.8Hz). |
| 132 | —CH$_3$ | —H | —CH$_3$ | 2.21(3H, s), 3.93(3H, s), 7.08-7.15(2H, m), 7.97(1H, dd, J=8.4Hz, 2.2Hz), 8.02(1H, d, J=2.2Hz), 8.52(1H, dd, J=8.9Hz, 2.7Hz), 9.01(1H, d, J=2.7Hz). |
| 133 | —OCH$_3$ | —H | —C$_2$H$_5$ | 1.41(3H, t, J=7.1Hz), 3.80(3H, s), 4.40(2H, q, J=7.1Hz), 7.09(1H, d, J=8.9Hz), 7.21(1H, d, J=8.2Hz), 7.71-7.77(2H, m), 8.49(1H, dd, J=8.9Hz, 2.8Hz), 8.97(1H, d, J=2.8 H). |

TABLE 19-continued

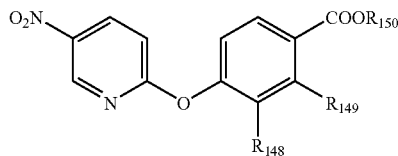

| Reference Example No. | $R_{148}$ | $R_{149}$ | $R_{150}$ | $^1$H NMR (CDCl$_3$) δ ppm |
|---|---|---|---|---|
| 134 | —H | —OCH$_3$ | —CH$_3$ | 3.90(3H, s), 3.91(3H, s), 6.77-6.81(2H, m), 7.11(1H, dd, J=9.1Hz, 0.5Hz), 7.91-7.95(1H, m), 8.53(1H, dd, J=9.1Hz, 2.7Hz), 9.06(1H, d, J=2.7Hz). |
| 135 | —H | —CH$_3$ | —CH$_3$ | 2.64(3H, s), 3.91(3H, s), 7.02-7.10(3H, m), 8.03-8.06(1H, m), 8.52(1H, dd, J=8.9Hz, 2.7Hz), 9.05(1H, dd, J=2.7Hz, 0.5Hz). |
| 136 | —Cl | —H | —CH$_3$ | 3.95(3H, s), 7.17-7.20(1H, m), 7.31(1H, d, J=8.6Hz), 8.03-8.07(1H, m), 8.20(1H, d, J=2.0Hz), 8.55(1H, dd, J=9.1Hz, 2.8Hz), 8.98(1H, dd, J=2.8Hz, 0.5Hz). |
| 137 | —F | —F | —CH$_3$ | 3.97(3H, s), 7.06-7.16(1H, m), 7.21(1H, dd, J=0.3Hz, 9.0Hz), 7.77-7.88(1H, m), 8.56(1H, dd, J=2.8Hz, 9.0 Hz), 8.99(1H, dd, J=0.3Hz, 2.8Hz) |

TABLE 20

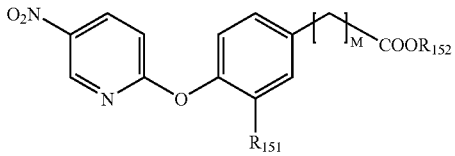

| Reference Example No. | $R_{151}$ | $R_{152}$ | M | $^1$H NMR (CDCl$_3$) δ ppm |
|---|---|---|---|---|
| 138 | —H | —CH$_3$ | 2 | 2.64-2.70(2H, m), 2.97-3.02(2H, m), 3.69(3H, s), 7.01 7.10(3H, m), 7.26-7.30(2H, m), 8.47(1H, dd, J=8.9Hz, 2.6Hz), 9.04(1H, d, J=2.6Hz). |
| 139 | —OCH$_3$ | —C$_2$H$_5$ | 2 | 1.26(3H, t, J=7.1Hz), 2.67(2H, t, J=7.5Hz), 2.99(2H, t, J=7.5Hz), 3.74(3H, s), 4.16(2H, q, J=7.1Hz), 6.76-6.91(2H, m), 7.02(1H, d, J=9.1Hz), 7.06(1H, d, J=8.0 Hz), 8.45(1H, dd, J=9.1Hz, 2.6Hz), 9.01(1H, d, J=2.6 Hz). |
| 140 | —H | —CH$_3$ | 1 | 3.67(2H, s), 3.72(3H, s), 7.04(1H, d, J=8.9Hz), 7.12(2H, d, J=8.6Hz), 7.38(2H, d, J=8.6Hz), 8.45-8.50(1H, m), 9.04(1H, d, J=3.0Hz). |
| 141 | —H | —C$_2$H$_5$ | 2 | 1.23(3H, t, J=7.1Hz), 2.63(2H, t, J=7.8Hz), 2.97(2H, t, J=7.8Hz), 4.11(2H, q, J=7.1Hz), 7.00(1H, d, J=9.1 Hz), 7.06(2H, d, J=8.5Hz), 7.26(2H, d, J=8.5Hz), 8.45(1H, dd, J=9.1Hz, 2.8Hz), 9.02(1H, d, J=2.8Hz). |
| 142 | —OCH$_3$ | —CH$_3$ | 2 | 2.66-2.71(2H, m), 2.97-3.02(2H, m), 3.70(3H, s), 3.74(3H, s), 6.83-6.88(2H, m), 7.01-7.08(2H, m), 8.45(1H, dd, J=9.1Hz, 2.8Hz), 9.01(1H, d, J=2.8Hz). |
| 143 | —OC$_2$H$_5$ | —C$_2$H$_5$ | 2 | 1.15(3H, t, J=7.0Hz), 1.26(3H, t, J=7.1Hz), 2.53-2.72(2H, m), 2.87-3.05(2H, m), 3.98(2H, q, J=7.0Hz), 4.15(2H, q, J=7.1Hz), 6.73-6.93(2H, m), 7.02(1H, d, J=9.0Hz), 7.07(1H, d, J=8.0Hz), 8.45(1H, dd, J=9.0Hz, 2.8Hz), 9.01(1H, d, J=2.8Hz). |
| 144 | —F | —C$_2$H$_5$ | 2 | 1.26(3H, t, J=7.1Hz), 2.57-2.71(2H, m), 2.89-3.06(2H, m), 4.15(2H, q, J=7.1Hz), 6.98-7.21(4H, m), 8.50(1H, dd, J=9.0Hz, 2.8Hz), 9.01(1H, d, J=2.8Hz). |
| 145 | —H | —C$_2$H$_5$ | 4 | 1.26(3H, t, J=7.3Hz), 1.60-1.80(4H, m), 2.30-2.40(2H, m), 2.60-2.75(2H, m), 4.13(2H, q, J=7.3Hz), 7.01(1H, d, J=9.0Hz), 7.06(2H, d, J=8.6Hz), 7.25(2H, d, J=8.6 Hz), 8.46(1H, dd, J=9.0Hz, 3.0Hz), 9.04(1H, d, J=3.0 Hz). |

TABLE 21

| Reference Example No. | R₁₅₃ | R₁₅₄ | M | ¹H NMR (CDCl₃) δ ppm or MS |
|---|---|---|---|---|
| 146 | —CH₃ | —H | 1 | ¹H NMR 1.32(3H, t, J=7.1Hz), 2.08(3H, s), 3.90(2H, d, J=5.3Hz), 4.15-4.39(3H, m), 6.39-6.59(2H, m), 6.81-7.01(2H, m), 8.44(1H, dd, J=9.1Hz, 2.8Hz), 9.05(1H, dd, J=2.8Hz, 0.4Hz). |
| 147 | —CH₃ | —Ac | 1 | ¹H NMR 1.29(3H, t, J=7.1Hz), 1.99(3H, s), 2.17(3H, s), 4.22(2H, q, J=7.1Hz), 4.38(2H, s), 7.05-7.12(2H, m), 7.22-7.28(2H, m), 7.31(1H, s), 8.50(1H, d, J=9.0Hz), 9.01(1H, s). |
| 148 | —H | —H | 1 | ¹H NMR 1.32(3H, t, J=7.1Hz), 3.91(2H, d, J=5.4Hz), 4.27(2H, q, J=7.1Hz), 4.37(1H, t, J=5.4Hz), 6.66(2H, d, J=8.9Hz), 6.96(1H, d, J=9.1Hz), 6.98(2H, d, J=8.9Hz), 8.43(1H, dd, J=2.8Hz, 9.1Hz), 9.05(1H, d, J=2.8Hz). |
| 149 | —H | —Ac | 2 | ¹H NMR 1.23(3H, t, J=7.1Hz), 1.90(3H, s), 2.62(2H, t, J=7.3Hz), 4.03(2H, t, J=7.3Hz), 4.08(2H, q, J=7.1Hz), 7.10(1H, d, J=9.0Hz), 7.21-7.28(4H, m), 8.52(1H, dd, J=2.8Hz, 9.0Hz), 9.04(1H, d, J=2.8Hz). |
| 150 | —F | —C₂H₅ | 1 | ¹H NMR 1.21-1.32(6H, m), 3.47(2H, q, J=7.1Hz), 4.01(2H, s), 4.23(2H, q, J=7.1Hz), 6.38-6.49(2H, m), 7.01-7.07(2H, m), 8.46(1H, dd, J=9.1Hz, 2.8Hz), 9.03(1H, d, J=2.8Hz). |
| 151 | —OCH₃ | —C₂H₅ | 1 | ¹H NMR 1.25(3H, t, J=7.1Hz), 1.28(3H, t, J=7.1Hz), 3.50(2H, q, J=7.1Hz), 3.72(3H, s), 4.03(2H, s), 4.22(2H, q, J=7.1Hz), 6.23(1H, dd, J=8.9Hz, 2.8Hz), 6.30(1H, d, J=2.6Hz), 6.95-6.99(2H, m), 8.42(1H, dd, J=9.1Hz, 2.8Hz), 9.04(1H, d, J=2.8Hz). |
| 152 | —F | —CH₃ | 1 | ¹H NMR 1.28(3H, t, J=7.1Hz), 3.09(3H, s), 4.06(2H, s), 4.21(2H, q, J=7.1Hz), 6.42-6.54(2H, m), 7.03-7.10(2H, m), 8.47(1H, dd, J=9.1Hz, 2.8Hz), 9.03(1H, d, J=2.8Hz). |
| 153 | —OCH₃ | —H | 1 | ¹H NMR 1.32(3H, t, J=7.1Hz), 3.72(3H, s), 3.92(2H, d, J=5.3Hz), 4.27(2H, q, J=7.1Hz), 4.41(1H, brt), 6.19(1H, dd, J=8.4Hz, 2.5Hz), 6.29(1H, d, J=2.5Hz), 6.96-7.00(2H, m), 8.42(1H, dd, J=9.1Hz, 2.8Hz), 9.03(1H, d, J=2.8Hz). |
| 154 | —F | —Ac | 1 | ¹H NMR 1.30(3H, t, J=7.1Hz), 2.02(3H, s), 4.23(2H, q, J=7.1Hz), 4.38(2H, s), 7.16-7.33(4H, m), 8.54(1H, dd, J=9.1Hz, 2.8Hz), 9.01(1H, dd, J=2.8Hz, 0.5Hz). |
| 155 | —F | —H | 1 | ¹H NMR 1.32(3H, t, J=7.1Hz), 3.89(2H, d, J=5.3Hz), 4.28(2H, q, J=7.1Hz), 4.35-4.55(1H, m), 6.31-6.50(2H, m), 6.91-7.11(2H, m), 8.47(1H, dd, J=9.1Hz, 2.8Hz), 9.02(1H, d, J=2.8Hz, 0.4Hz). |
| 156 | —CF₃ | —CH₃ | 1 | MS 399(M⁺) |
| 157 | —CF₃ | —C₂H₅ | 1 | MS 413(M⁺) |

TABLE 22

| Reference Example No. | R₁₅₅ | R₁₅₆ | R₁₅₇ | R₁₅₈ | R₁₅₉ | M | ¹H NMR or MS |
|---|---|---|---|---|---|---|---|
| 158 | —H | —H | —H | —CH₃ | —CH₃ | 1 | ¹H NMR (CDCl₃) δ 3.10(3H, s), 3.74(3H, s), 4.09(2H, s), 6.72(2H, d, J=9.1Hz), 6.96(1H, d, J=9.0 |

TABLE 22-continued

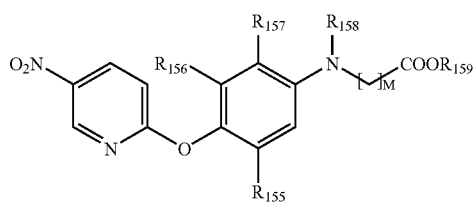

| Reference Example No. | $R_{155}$ | $R_{156}$ | $R_{157}$ | $R_{158}$ | $R_{159}$ | M | $^1$H NMR or MS |
|---|---|---|---|---|---|---|---|
| | | | | | | | Hz), 7.03(2H, d, J=9.1Hz), 8.43(1H, dd, J=9.0Hz, 2.9Hz), 9.06(1H, d, J=2.9Hz). |
| 159 | —H | —H | —H | —Ac | —C$_2$H$_5$ | 1 | $^1$H NMR (DMSO-d$_6$) δ 1.20(3H, t, J=7.1Hz), 1.87(3H, s), 4.12(2H, q, J=7.1Hz), 4.37(2H, s), 7.28-7.35(3H, m), 7.48(2H, d, J=8.7 Hz), 8.65(1H, dd, J=2.9Hz, 9.1 Hz), 9.05(1H, d, J=2.9Hz). |
| 160 | —H | —H | —H | —CH$_3$ | —CH$_3$ | 2 | $^1$H NMR (CDCl$_3$) δ 2.59-2.64(2H, m), 2.96(3H, s), 3.67-3.72(5H, m), 6.76(2H, d, J=9.1Hz), 6.97(1H, d, J=9.1Hz), 7.05(2H, d, J=8.9 Hz), 8.43(1H, dd, J=9.1Hz, 3.0 Hz), 9.06(1H, d, J=2.8Hz). |
| 161 | —F | —H | —F | —H | —C$_2$H$_5$ | 1 | $^1$H NMR (CDCl$_3$) δ 1.32(3H, t, J=7.1Hz), 3.91(2H, d, J=5.5Hz), 4.28(2H, q, J=7.1Hz), 4.57-4.71(1H, m), 6.43(1H, dd, J=7.9 Hz, 11.6Hz), 6.94(1H, dd, J=7.0 Hz, 11.0Hz), 7.08(1H, d, J=9.0 Hz), 8.49(1H, dd, J=2.8Hz, 9.0 Hz), 9.01(1H, d, J=2.8Hz). |
| 162 | —F | —F | —H | —CH$_3$ | —C(CH$_3$)$_3$ | 0 | $^1$H NMR (CDCl$_3$) δ 1.51(9H, s), 3.30(3H, s), 6.95-7.10(2H, m), 7.21(1H, d, J=9.1Hz), 8.54(1H, dd, J=2.8Hz, 9.1Hz), 9.00(1H, d, J=2.8Hz). |
| 163 | —CH$_3$ | —H | —CH$_3$ | —C$_2$H$_5$ | —C$_2$H$_5$ | 1 | $^1$H NMR (CDCl$_3$) δ 1.08(3H, t, J=7.1Hz), 1.24(3H, t, J=7.1Hz), 2.07(3H, s), 2.28(3H, s), 3.21(2H, q, J=7.1Hz), 3.78(2H, s), 4.15 (2H, q, J=7.1Hz), 6.86(1H, s), 6.95(1H, d, J=9.1Hz), 7.07(1H, s), 8.45(1H, dd, J=9.1Hz, 2.8 Hz), 9.06(1H, d, J=2.8Hz). |
| 164 | —COOCH$_3$ | —H | —H | —C$_2$H$_5$ | —C(CH$_3$)$_3$ | 1 | MS 431(M$^+$) |
| 165 | —CH$_3$ | —H | —CH$_3$ | —CH$_3$ | —C$_2$H$_5$ | 1 | $^1$H NMR (CDCl$_3$) δ 1.27(3H, t, J=7.1Hz), 2.08(3H, s), 2.28(3H, s), 2.89(3H, s), 3.73(2H, s), 4.19(2H, q, J=7.1Hz), 6.85(1H, s), 6.96 (1H, d, J=9.1Hz), 7.01(1H, s), 8.45(1H, dd, J=9.1Hz, 2.8Hz), 9.06(1H, d, J=2.8Hz). |
| 166 | —CN | —H | —H | —CH$_3$ | —C(CH$_3$)$_3$ | 1 | MS 384(M$^+$) |
| 167 | —H | —H | —CF$_3$ | —C$_2$H$_5$ | —C$_2$H$_5$ | 1 | MS 413(M$^+$) |

TABLE 23

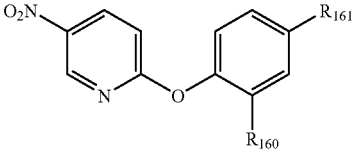

| Reference Example No. | R₁₆₀ | R₁₆₁ | $^1$H NMR (CDCl$_3$) δ ppm |
|---|---|---|---|
| 168 | —H | 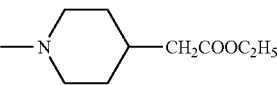 (N-piperidinyl-CH₂COOC₂H₅) | 1.27(3H, t, J=7.0Hz), 1.41-1.48(2H, m), 1.85(2H, brd, J=13.0Hz), 1.95(1H, m), 2.29(2H, d, J=7.0Hz), 2.76(2H, dt, J=2.5Hz, 12.0Hz), 3.65(2H, brd, J=12.0Hz), 4.16(2H, q, J=7.0Hz), 6.96-6.99(3H, m), 7.03(2H, d, J=9.0Hz), 8.44(1H, dd, J=9.0Hz, 3.0Hz), 9.05(1H, d, J=3.0Hz). |
| 169 | —H | morpholino | 3.16-3.19(4H, m), 3.86-3.89(4H, m), 6.94-7.01(3H, m), 7.05-7.11(2H, m), 8.45(1H, dd, J=9.2Hz, 3.0Hz), 9.05(1H, d, J=3.0Hz). |
| 170 | —H | 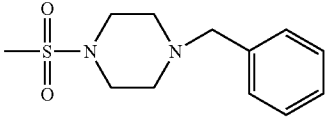 | 2.47-2.62(4H, m), 2.96-3.14(4H, m), 3.49(2H, s), 7.11(1H, d, J=9.0Hz), 7.19-7.37(7H, m), 7.81(2H, d, J=8.7 Hz), 8.52(1H, dd, J=9.0Hz, 2.0Hz), 9.02(1H, d, J=2.0Hz). |
| 171 | —H | 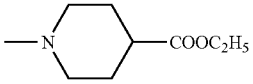 (N-piperidinyl-COOC₂H₅) | 1.28(3H, t, J=7.0Hz), 1.90(2H, dq, J=4.0Hz, 11.5Hz), 2.04(2H, brd, J=13.0 Hz), 2.43(1H, m), 2.82(2H, dt, J=3.0 Hz, 12.0Hz), 3.63(2H, dt, J=13.0Hz, 3.0Hz), 4.17(2H, q, J=7.0Hz), 6.97-6.99(3H, m), 7.04(2H, d, J=9.0Hz), 8.44(1H, dd, J=9.0Hz, 3.0Hz), 9.05(1H, d, J=3.0Hz). |
| 172 | —H | 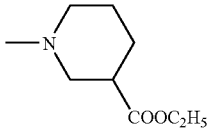 | 1.28(3H, t, J=7.0Hz), 1.70(2H, m), 1.84(1H, m), 2.04(1H, m), 2.69(1H, m), 2.86(1H, m), 3.08(1H, dd, J=12.0Hz, 10.0Hz), 3.46(1H, brd, J=12.0Hz), 3.69(1H, dd, J=12.0Hz, 4.0Hz), 4.18(2H, q, J=7.0Hz), 6.97-7.05(5H, m), 8.45(1H, dd, J=9.0Hz, 3.0Hz), 9.06(1H, d, J=3.0Hz). |
| 173 | —COOCH₃ | 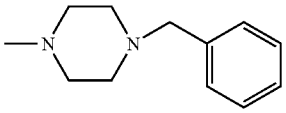 | 2.61-2.64(4H, m), 3.24-3.28(4H, m), 3.58(2H, s), 3.68(3H, s), 7.03-7.16(3H, m), 7.26-7.36(5H, m), 7.54(1H, d, J=2.8 Hz), 8.46(1H, dd, J=9.1Hz, 2.8Hz), 8.97(1H, d, J=2.8Hz). |
| 174 | —H | 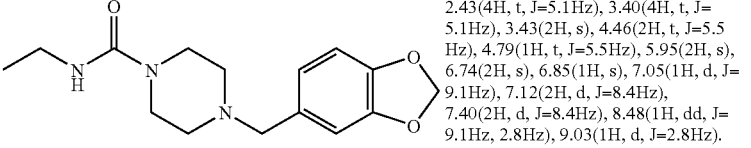 | 2.43(4H, t, J=5.1Hz), 3.40(4H, t, J=5.1Hz), 3.43(2H, s), 4.46(2H, t, J=5.5 Hz), 4.79(1H, t, J=5.5Hz), 5.95(2H, s), 6.74(2H, s), 6.85(1H, s), 7.05(1H, d, J=9.1Hz), 7.12(2H, d, J=8.4Hz), 7.40(2H, d, J=8.4Hz), 8.48(1H, dd, J=9.1Hz, 2.8Hz), 9.03(1H, d, J=2.8Hz). |
| 175 | —CH₃ | —NHCOCOOC₂H₅ | 1.33(3H, t, J=7.1Hz), 2.07(3H, s), 4.32(2H, q, J=7.1Hz), 7.15(1H, d, J=8.7Hz), 7.27(1H, dd, J=9.2Hz, 0.5 Hz), 7.63(1H, dd, J=8.6Hz, 2.5Hz), 7.71(1H, d, J=2.5Hz), 8.62(1H, dd, J=9.1Hz, 2.8Hz), 9.01(1H, dd, J=2.8Hz, 0.5Hz), 10.82(1H, brs). |

TABLE 24

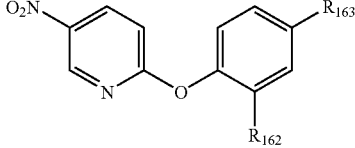

| Reference Example No. | R₁₆₂ | R₁₆₃ | ¹H NMR(solvent) δ ppm |
|---|---|---|---|
| 176 | —H | —Ac | (CDCl₃) 2.60(3H, s), 7.10–9.00(7H, m). |
| 177 | —H | —CHO | (CDCl₃) 7.14(1H, d, J=9.0 Hz), 7.35(2H, d, J=8.7 Hz), 8.00(2H, d, J=8.7 Hz), 8.54(1H, dd, J=9.0 Hz, 1.8 Hz), 9.04(1H, d, J=1.8 Hz), 10.03(1H, s). |
| 178 | —H | —C₂H₅ | (CDCl₃) 1.28(3H, t, J=7.6 Hz), 2.70(2H, q, J=7.6 Hz), 7.01(1H, dd, J=9.1 Hz, 0.7 Hz), 7.07(2H, d, J=8.7 Hz), 7.28(2H, d, J=8.7 Hz), 8.46(1H, dd, J=9.1 Hz, 2.8 Hz), 9.05(1H, dd, J=2.8 Hz, 0.7 Hz). |
| 179 | —CH₃ | —CHO | (CDCl₃) 2.25(3H, s), 7.14(1H, d, J=8.9 Hz), 7.24(1H, d, J=8.2 Hz), 7.81(1H, dd, J=8.2 Hz, 2.0 Hz), 7.85(1H, s), 8.53(1H, dd, J=8.9 Hz, 2.6 Hz), 9.00(1H, d, J=2.6 Hz), 10.00(1H, s). |
| 180 | —H | 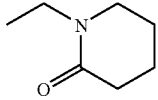 | (CDCl₃) 1.70–1.93(4H, m), 2.45–2.56(2H, m), 3.22–3.36(2H, m), 4.62(2H, s), 7.03(1H, d, J=9.2 Hz), 7.12(2H, d, J=8.6 Hz), 7.35(2H, d, J=8.6 Hz), 8.47 (1H, dd, J=9.2 Hz, 2.6 Hz), 9.04(1H, d, J=2.6 Hz). |
| 181 | —H | 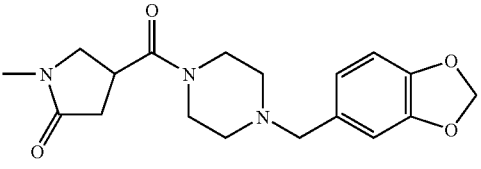 | (CDCl₃) 2.46–2.47(4H, m), 2.77–2.99(2H, m), 3.46(2H, s), 3.51–3.57(4H, m), 3.64 3.73(1H, m), 3.90–3.96(1H, m), 4.30–4.36(1H, m), 5.96(2H, s), 6.75–6.86(3H, m), 7.04(1H, d, J=9.1 Hz), 7.17(2H, d, J=9.1 Hz), 7.70(2H, d, J=8.9 Hz), 8.48(1H, dd, J=2.8 Hz, 9.1 Hz), 9.03(1H, d, J=2.8 Hz). |
| 182 | —H | 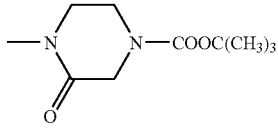 | (CDCl₃) 1.51(9H, s), 3.80(4H, m), 4.27(2H, s), 7.07(1H, d, J=9.1 Hz), 7.21(2H, dd, J=6.8 Hz, 2.1 Hz), 7.38(2H, dd, J=6.8 Hz, 2.1 Hz), 8.49(1H, dd, J=9.1 Hz, 2.8 Hz), 9.04(1H, d, J=2.8 Hz). |
| 183 | —H | 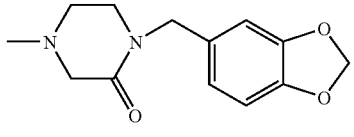 | (CDCl₃) 3.35–3.55(4H, m), 3.96(2H, s), 4 58(2H, s), 5.96(2H, s), 6.73–6.78(2H, m), 6.81(1H, s), 6.91(2H, d, J=9.1 Hz), 7.00(1H, d, J=9.1 Hz), 7.09(2H, d, J=9.1 Hz), 8.45(1H, dd, J=9.1 Hz, 2.8 Hz), 9.04(1H, d, J=2.8 Hz). |
| 184 | —H | —NHCONHPh | (DMSO-d6) 6.96(1H, t, J=6.5 Hz), 7.14(2H, d, J=8.8 Hz), 7.21(1H, d, J=9.1 Hz), 7.27(2H, t, J=8.3Hz), 7.45(2H, d, J=8.3 Hz), 7.52(2H, d, J=8.8 Hz), 8.60(1H, dd, J=2.8 Hz, 9.1 Hz), 8.70(1H, s), 8.77(1H, s), 9.02(1H, d, J=2.8 Hz). |

TABLE 25

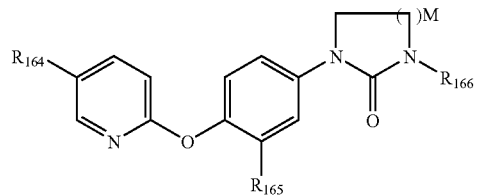

| Reference Example No. | $R_{164}$ | $R_{165}$ | $R_{166}$ | M | mp(° C.) or $^1$H NMR(solvent) δ ppm |
|---|---|---|---|---|---|
| 185 | —NO$_2$ | —CH$_3$ | piperonyl | 2 | mp 142.0–143.0 |
| 186 | —NO$_2$ | —H | benzyl | 1 | $^1$H NMR(DMSO-d$_6$) 3.36(2H, t, J=8.1 Hz), 3.84(2H, t, J=8.1 Hz), 4.40(2H, s), 7.15–7.25(3H, m), 7.26–7.34(3H, m), 7.35–7.41(2H, m), 7.61–7.71(2H, m), 8.59(1H, dd, J=2.9 Hz, 9.1 Hz), 9.02(1H, d, J=9.1 Hz). |
| 187 | —NO$_2$ | —CH$_3$ | piperonyl | 1 | $^1$H NMR(DMSO-d$_6$) 2.05(3H, s), 3.29–3.41(2H, m), 3.71–3.88(2H, m), 4.29(2H, s), 5.60(2H, s), 6.74–6.81(1H, m), 6.82–6.92(2H, m), 7.09(1H, d, J=8.8 Hz), 7.21(1H, d, J=9.1 Hz), 7.49(1H, d, J=2.6 Hz, 8.8 Hz), 7.51–7.57(1H, m), 8.60(1H, d, J=9.1 Hz), 9.00(1H, d, J=2.9 Hz). |
| 188 | —NO$_2$ | —CH$_3$ | 3,4-(CH$_3$O)$_2$PhOH$_2$— | 2 | $^1$H NMR(CDCl$_3$) 2.00–2.15(2H, m), 2.14(3H, s), 3.31(2H, t, J=6.0 Hz), 3.73(2H, d, J=6.0 Hz), 3.88(3H, s), 3.89(3H, s), 4.57(2H, s), 6.83(1H, d, J=8.1 Hz), 6.87(1H, dd, J=1.9 Hz, 8.1 Hz), 6.91(1H, d, J=1.9 Hz), 6.98–7.06(2H, m), 7.20(1H, dd, J=2.4 Hz, 8.6 Hz), 7.29(1H, d, J=2.4 Hz), 8.46(1H, dd, J=2.8 Hz, 9.1 Hz), 9.04(1H, d, J=2.8 Hz). |
| 189 | —NO$_2$ | —CH$_3$ | —CH$_2$COOC(CH$_3$)$_3$ | 2 | $^1$H NMR(ODds) 1.48(9H, s), 2.12(3H, s), 2.12–2.24(2H, m), 3.48(2H, t, J=5.9 Hz), 3.77(2H, t, J=5.9 Hz), 4.05(2H, s), 6.92–7.06(2H, m), 7.17(1H, dd, J=2.6 Hz, 8.6 Hz), 8.45(1H, dd, J=2.9 Hz, 9.1 Hz), 9.04(1H, d, J=2.9 Hz). |
| 190 | —Br | —CH$_3$ | piperony | 2 | $^1$H NMR(CDCl$_3$) 1.94–2.18(2H, m), 2.15(3H, s), 3.30(2H, d, J=6.0 Hz), 3.71(2H, d, J=6.0 Hz), 4.52(2H, s), 5.95(2H, s), 6.69–6.82(3H, m), 6.88(1H, s), 7.00(1H, d, J=8.6 Hz), 7.15(1H, dd, J=2.6 Hz, 8.6 Hz), 7.24(1H, d, J=2.6 Hz), 7.73(1H, dd, J=2.5 Hz, 8.6 Hz), 8.20(1H, d, J=2.5 Hz). |
| 191 | —Br | —CH$_3$ | 3,4-(CH$_3$O)$_2$PhCH$_2$— | 2 | $^1$H NMR(CDCl$_3$) 1.95–2.11(2H, m), 2.14(3H, s), 3.30(2H, t, J=5.9 Hz), 3.70(2H, t, J=5.9 Hz), 3.88(3H, s), 3.88(3H, a), 4.56(2H, s), 6.74–6.92(4H, s), 7.00(1H, d, J=8.5 Hz), 7.15(1H, dd, J=2.4 Hz, 8.5 Hz), 7.24(1H, d, J=2.4 Hz), 7.73(1H, dd, J=2.6 Hz, 8.8 Hz), 8.19(1H, dd, J=0.5 Hz, 2.6 Hz). |

TABLE 26

(Structure: 5-nitro-2-(O-R₁₆₇)pyridine)

| Reference Example No. | R₁₆₇ | ¹H NMR(CDCl₃) δ ppm or MS |
|---|---|---|
| 192 | 3-methylphenyl-N(CH₃)-CH₂-COOC₂H₅ | ¹H NMR 1.24(3H, t, J=7.1 Hz), 3.07(3H, s), 4.05(2H, s), 4.18(2H, q, J=7.1 Hz), 6.44–6.45(1H, m), 6.49–6.53(1H, m), 6.57–6.61(1H, m), 6.97(1H, d, J=9.1 Hz), 7.25–7.31(1H, m), 8.44(1H, dd, J=9.1 Hz, 2.8 Hz), 9.07(1H, d, J=2.8 Hz). |
| 193 | 3-methylphenyl-COOCH₃ | ¹H NMR 3.93(3H, s), 7.08–7.11(1H, m), 7.26–7.40(1H, m), 7.51–7.57(1H, m), 7.83–7.84(1H, m), 7.96–8.00(1H, m), 8.49–8.53(1H, m), 9.02–9.03(1H, m). |
| 194 | 3-methylcinnamoyl-piperazinyl-CH₂-benzodioxole | MS 488(M+) |
| 195 | 6-methyl-2-naphthyl-COOCH₃ | ¹H NMR 4.00(3H, s), 7.14(1H, d, J=8.9 Hz), 7.37(1H, dd, J=8.9 Hz, 2.3 Hz), 7.67(1H, d, J=2.3 Hz), 7.87(1H, d, J=8.6 Hz), 8.04(1H, d, J=8.9 Hz), 8.11(1H, dd, J=8.6 Hz, 1.7 Hz), 8.51–8.55(1H, m), 8.64(1H, brs), 9.05(1H, d, 2.8 Hz). |
| 196 | 4-methyl-1-naphthyl-COOCH₃ | ¹H NMR 4.03(3H, s), 7.20(1H, d, J=9.1 Hz), 7.31(1H, d, J=8.1 Hz), 7.51–7.57(1H, m), 7.65–7.71(1H, m), 7.94(1H, d, J=8.4 Hz), 8.29(1H, d, J=8.1 Hz), 8.55(1H, dd, J=9.1 Hz, 2.8 Hz), 8.99(1H, d, J=2.8 Hz), 9.05(1H, d, J=8.7 Hz). |
| 197 | 6-methyl-1-naphthyl-COOC₂H₅ | ¹H NMR 1.47(3H, t, J=7.1 Hz), 4.49(2H, t, J=7.1 Hz), 7.11(1H, d, J=8.9 Hz), 7.42(1H, dd, J=9.4 Hz, 2.5 Hz), 7.52–7.58(1H, m), 7.67(1H, d, J=2.5 Hz), 7.99(1H, d, J=8.2 Hz), 8.21(1H, dd, J=7.3 Hz, 1.2 Hz), 8.51(1H, dd, J=9.1 Hz, 2.8 Hz), 9.04–9.08(2H, m). |
| 198 | 3,4-dimethylphenyl-tetrahydropyrimidinone-CH₂-C(O)-piperazinyl-CH₂-benzodioxole | ¹H NMR(CDCl₃) 2.11(3H, s), 2.19(2H, t, J=5.9 Hz), 2.34–2.50(4H, m), 3.42(2H, s), 3.40–3.47(2H, m), 3.51(2H, t, J=5.9 Hz), 3.56–3.76(2H, m), 3.78(2H, t, J=5.7 Hz), 4.20(2H, s), 5.94(2H, 69–6.77(2H, m), 6.84(1H, d, J=1.0 Hz), 6.96–7.02(2H, m), 7.17(1H, dd, J=2.6 Hz, 8.5 Hz), 7.24–7.28(1H, m), 8.45(1H, dd, J=2.8 Hz, 9.1 Hz), 9.04(1H, d, J=2.8 Hz). |

TABLE 27

| Reference Example No. | $R_{168}$ | $R_{169}$ | M | $^1$H NMR(solvent) δ ppm |
|---|---|---|---|---|
| 199 | —H | benzyl | 2 | (CDCl$_3$) 2.36–2.45(4H, m), 2.63–2.68(2H, m), 2.99–3.05(2H, m), 3.41–3.45(2H, m), 3.52(2H, s), 3.64–3.67(2H, m), 7.01–7.11(3H, m), 7.29–7.34(7H, m), 8.47(1H, dd, J=9.1 Hz, 2.8 Hz), 9.05(1H, d, J=2.8 Hz). |
| 200 | —H | piperonyl | 2 | (CDCl$_3$) 2.33–2.41(4H, m), 2.62–2.67(2H, m), 2.98–3.04(2H, m), 3.39–3.43(4H, m), 3.62–3.65(2H, m), 5.94(2H, s), 6.73–6.77(2H, m), 6.84(1H, s), 7.00–7.10(3H, m), 7.26–7.31(2H, m), 8.44–8.48(1H, m), 9.03(1H, dd, J=3.0 Hz, 0.5 Hz). |
| 201 | —F | benzyl | 0 | (CDCl$_3$) 2.49(4H, brs), 3.49–3.56(4H, m), 3.79(2H, brs), 7.15(1H, d, J=8.9 Hz), 7.24–7.38(8H, m), 8.53(1H, dd, J=9.1 Hz, 2.8 Hz), 8.99(1H, d, J=2.8 Hz). |
| 202 | —H | benzyl | 0 | (DMSO-d$_6$) 2.41(4H, brs), 3.33(2H, brs), 3.52(4H, brs), 7.24–7.27(8H, m), 7.50(2H, d, J=7.9 Hz), 8.64(1H, dd, J=9.1 Hz, 2.8 Hz), 9.04(1H, d, J=2.8 Hz). |
| 203 | —H | 4-CH$_3$OPhCH$_2$— | 0 | (CDCl$_3$) 2.46(4H, brs), 3.44–3.90(4H, m), 3.49(2H, s), 3.81(3H, s), 6.85–6.89(2H, m), 7.06(1H, d, J=8.9 Hz), 7.18–7.27(4H, m), 7.48–7.53(2H, m), 8.48–8.52(1H, m), 9.03(1H, d, J=2.8 Hz). |
| 204 | —H | piperonyl | 0 | (CDCl$_3$) 2.46(4H, brs), 3.46(2H, s), 3.52(2H, brs), 3.77(2H, brs), 5.95(2H, s), 6.75(2H, s), 6.86(1H, s), 7.07(1H, dd, J=9.1 Hz, 0.5 Hz), 7.20(2H, d, J=8.6 Hz), 7.51(2H, d, J=8.6 Hz), 8.50(1H, dd, J=8.9 Hz, 2.8 Hz), 9.03(1H dd, J=2.8 Hz, 0.5 Hz). |
| 205 | —H | 3-pyridyl | 0 | (CDCl$_3$) 3.27(4H, brs), 3.84(4H, brs), 7.08–7.12(1H, m), 7.21–7.27(4H, m), 7.54–7.59(2H, m), 8.16–8.18(1H, m), 8.34(1H, brs), 8.52(1H, dd, J=9.1 Hz, 2.8 Hz), 9.05(1H, dd, J=2.8 Hz, 0.5 Hz). |

TABLE 28

| Reference Example No. | $Xa_5$ | $R_{170}$ | M | $^1$H NMR(CDCl$_3$) δ ppm |
|---|---|---|---|---|
| 206 | —O— | piperonyl | 1 | 2.43(4H, brs), 3.42(2H, s), 3.58(2H, t, J=5.0 Hz), 3.64(2H, t, J=5.0 Hz), 4.70(2H, s), 5.95(2H, s), 6.70–6.79(2H, m), 6.84(1H, d, J=0.6 Hz), 7.01(3H, d, J=91 Hz), 7.09(2H, d, J==9.1 Hz), 8.46(1H, dd, J=9.1 Hz, 2.8 Hz), 9.04(1H, d, J=2.8 Hz). |
| 207 | —CH(OH)— | benzyl | 0 | 1.90–2.05(1H, m), 2.21–2.68(3H, m), 3.11–3.25(1H, m), 3.28–3.40(1H, m), 3.45(2H, s), 3.73(2H, t, J=5.1 Hz), 4.77(1H, d, J=6.3 Hz), 5.24(1H, d, J=6.3 Hz), 7.04(1H, d, J=8.9 Hz), 7.16(2H, d, J=8.7 Hz), 7.2 1–7.35(5H, m), 7.38(2H, d, J=8.7 Hz), 8.48(1H, dd, J=8.9 Hz, 2.8 Hz), 9.03(1H, d, J=2.8 Hz). |

TABLE 28-continued

[Structure: O₂N-pyridine-O-phenyl-Xa₅-[CH]ₘ-C(=O)-N-piperazine-N-R₁₇₀]

| Reference Example No. | Xa₅ | R₁₇₀ | M | ¹H NMR(CDCl₃) δ ppm |
|---|---|---|---|---|
| 208 | cyclopropyl-N(CH₃)— | piperonyl | 1 | 0.65–0.70(2H, m), 0.81–0.88(2H, m), 2.41–2.48(4H, m), 2.77–2.85(1H, m), 3.45(2H, s), 3.49–3.52(2H, m), 3.60–3.63(2H, m), 4.20(2H, s), 5.95(2H, s), 6.71–6.78(2H, m), 6.86(1H, brs), 6.90–7.02(5H, m), 8.39–8.44(1H, m), 9.06(1H, d, J=2.8 Hz). |
| 209 | —O— | benzyl | 1 | 2.45(4H, t, J=4.5 Hz), 3.52(2H, s), 3.59(2H, t, J=4.9 Hz), 3.65(2H, t, J=4.9 Hz), 4.70(2H, s), 7.00(2H, d, J=9.2 Hz), 7.01(1H, d, J=9.0 Hz), 7.08(2H, d, J=9.2 Hz), 7.21–7.40(5H, m), 8.46(1H, dd, J=9.0 Hz, 2.8 Hz), 9.04(1H, d, J=2.8 Hz). |
| 210 | —N(CH₃)— | benzyl | 0 | 2.32(4H, brs), 3.24(3H, s), 3.28(4H, brs), 3.48(2H, brs), 7.04(1H, d, J=9.1 Hz), 7.11(2H, d, J=9.0 Hz), 7.15(2H, d, J=9.0 Hz), 7.22–7.40(5H, m), 8.48(1H, dd, J=9.1 Hz, 2.8 Hz), 9.04(1H, d, J=2.8 Hz). |

TABLE 29

[Structure: R₁₇₁-pyridine-O-phenyl(R₁₇₂)-Xa₅-C(R₁₇₃)(R₁₇₄)-COOR₁₇₅]

| Reference Example No. | R₁₇₁ | R₁₇₂ | Xa₆ | R₁₇₃ | R₁₇₄ | R₁₇₅ | ¹H NMR(CDCl₃) δ ppm or MS |
|---|---|---|---|---|---|---|---|
| 211 | —NO₂ | —H | —N(CH₃)— | —CH₃ | —H | —C₂H₅ | ¹H NMR 1.25(3H, t, J=7.1 Hz), 1.50(3H, d, J=7.1 Hz), 2.93(3H, s), 4.18(2H, q, J=7.1 Hz), 4.48(1H, q, J=7.3 Hz), 6.82(2H, d, J=9.2 Hz), 6.97(1H, d, J=9.1 Hz), 7.03(2H, d, J=9.0Hz), 8.43(1H, dd, J=9.1 Hz, 2.8 Hz), 9.06(1H, d, J=2.8 Hz). |
| 212 | —NO₂ | —H | —N(CH₃)— | —CH₃ | —CH₃ | —C₂H₅ | ¹H NMR 1.24(3H, t, J=7.1 Hz), 1.46(6H, s), 2.94(3H, s), 4.18(2H, q, J=7.1 Hz), 6.97(1H, dd, J=9.1 Hz, 0.5 Hz), 7.00–7.08(4H, m), 8.45(1H, dd, J=9.1 Hz, 3.0 Hz), 9.05(1H, dd, J=2.8 Hz, 0.5 Hz). |
| 213 | —NO₂ | —CH₃ | —N(CH₃)— | —CH₃ | —H | —C₂H₅ | ¹H NMR 1.26(3H, t, J=7.1 Hz), 1.49(3H, d, J=7.3 Hz), 2.10(3H, s), 2.91(3H, s), 4.13–4.24(2H, m), 4.48(1H, q, J=7.3 Hz), 6.64–6.68(2H, m), 6.91–6.96(2H, m), 8.43(1H, dd, J=9.1 Hz, 2.8 Hz), 9.06(1H, dd, J= |

TABLE 29-continued

[Structure: R₁₇₁-pyridine-O-phenyl(R₁₇₂)-Xa₅-C(R₁₇₃)(R₁₇₄)-COOR₁₇₅]

| Reference Example No. | R₁₇₁ | R₁₇₂ | Xa₆ | R₁₇₃ | R₁₇₄ | R₁₇₅ | ¹H NMR(CDCl₃) δ ppm or MS |
|---|---|---|---|---|---|---|---|
| 214 | —NO₂ | —H | none | —CH₃ | —CH₃ | —CH₃ | 2.8 Hz, 0.5 Hz). MS 316(M+) |
| 215 | —Br | —OCH₃ | —CH₂— | —H | —H | —C₂H₅ | ¹H NMR 1.26(3H, t, J=7.1 Hz), 2.63–2.68 (2H, m), 2.94–3.00(2H, m), 3.75(3H, s), 4.15(2H, q, J=7.1 Hz), 6.80.6.86(3H, m), 7.03(1H, d, J=7.9 Hz), 7.73(1H, dd, J=8.7 Hz, 2.6 Hz), 8.16(1H, dd, J=2.6 Hz, 0.7 Hz). |
| 216 | 3,4-Cl₂PhCH₂NHCO— | —H | —CH₂— | —H | —H | —C₂H₅ | MS 472(M+) |
| 217 | 4-CF₃PhCH₂NHCO— | —H | —CH₂— | —H | —H | —C₂H₅ | MS 472(M+) |

TABLE 30

[Structure: R₁₇₆-pyridine-O-R₁₇₇]

| Reference Example No. | R176 | R177 | ¹H NMR(CDCl₃) δ ppm or MS |
|---|---|---|---|
| 218 | 4-CF₃PhCO— | [phenyl with OCH₃, CH₂CH₂COOC₂H₅] | ¹H NMR 1.26(3H, t, J=7.1 Hz), 2 64–2.69(2H, m), 2.95–3.01(2H, m), 3.76(3H, s), 4.15(2H, q, J=7.1 Hz), 6.83–6.89(2H, m), 7.03–7.10(2H, m), 7.73–7.76(2H, m), 7.86–7.89(2H, m), 8.21(1H, dd, J=8.6 Hz, 2.5 Hz), 8.55(1H, dd, J=2.5 Hz, 0.7 Hz). |
| 219 | 3,4-Cl₂PhNHCO— | [phenyl with OCH₃, N(CH₂CH₃)CH₂COOCH₂Ph] | ¹H NMR 1.20(3H, t, J=7.1 Hz), 3.44(2H, q, J=7.1 Hz), 3.56(3H, s), 4.04(2H, s), 5.17(2H, s), 6.15–6.18(2H, m), 6.83(1H, d, J=8.7 Hz), 6.88(1H, d, J=8.9 Hz), 7.29–7.35(6H, m), 7.44(1H, dd, J=8.7 Hz, 2.5 Hz), 7.82(1H, d, J=2.3 Hz), 8.10(1H, dd, J=8.7 Hz, 2.5 Hz), 8.59(1H, d, J=2.5 Hz), 8.72(1H, brs). |
| 220 | 3,4-Cl₂PhNHCO— | [2,4,6-trimethylphenyl-N(CH₃)CH₂COOC₂H₅] | MS 501(M+) |
| 221 | 4-CF₃PhNHCO— | [2,4,6-trimethylphenyl-N(CH₃)CH₂COOC₂H₅] | MS 501(M+) |

TABLE 30-continued

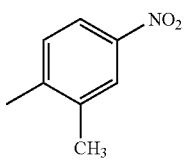

| Reference Example No. | R176 | R177 | $^1$H NMR(CDCl$_3$) δ ppm or MS |
|---|---|---|---|
| 222 | —COOC$_2$H$_5$ | 4-NO2Ph- | $^1$H NMR 1.40(3H, t, J=7.1 Hz), 4.40(2H, q, J=7.1 Hz), 7.08(1H, d, J=8.6 Hz), 7.32(2H, d, J=9.0 Hz), 8.31(2H, d, J=9.0 Hz), 8.37(1H, dd, J=8.6 Hz, 2.3 Hz), 8.82(1H, d, J=2.3 Hz). |
| 223 | 4-CF$_3$PhNHCO— | 4-CHOPh- | MS 386(M+) |
| 224 | —COOC$_2$H$_5$ | 3-methyl-4-nitrophenyl | $^1$H NMR 1.39(3H, t, J=7.1 Hz), 2.28(3H, s), 4.39(2H, q, J=7.1 Hz), 7.07(1H, dd, J=8.6 Hz, 0.5 Hz), 7.21(LH, d, J=8.9 Hz), 8.13(1H, dd, J=8.9 Hz, 2.8 Hz), 8.20(1H, d, J=2.8 Hz), 8.36(1H, dd, J=8.6 Hz, 2.3 Hz), 8.78(1H, dd, J=2.8 Hz, 0.5 Hz). |

(CHOPh means a formylphenyl group. Hereinafter CHOPh indicates the same meaning.)

TABLE 31

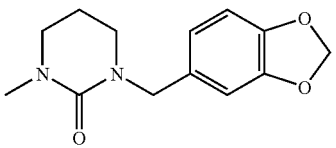

| Reference Example No. | R$_{178}$ | R$_{179}$ | R$_{180}$ | Form | mp(° C.) or $^1$H NMR (solvent) δ ppm |
|---|---|---|---|---|---|
| 225 | 4-CF$_3$PhNHCO— | —CH$_3$ | —NHCOCOOC$_2$H$_5$ | free | $^1$H NMR(DMSO-d$_6$) 1.33(3H t J=7.1 Hz), 2.08(3H.s5, 4.33(2H, q, J=7.1 Hz), 7.12(1H, d, J=8.7 Hz), 7.17(1H, d, J=8.6 Hz), 7.63(1H, dd, J=8.7 Hz, 2.5 Hz), 7.72–7.75(3H, m), 7.98(2H, d, J=8.7 Hz), 8.37(1H, dd, J=8.6 Hz, 2.5 Hz), 8.69(1H, d, J=2.5 Hz), 10.62(1H, brs), 10.81(1H, brs). |
| 226 | 3,4-Cl$_2$PhNHCO— | —CH$_3$ | (N-methyl-benzodioxolylmethyl-tetrahydropyrimidinone) | hydro-bromide | mp 132.0–134.0 |
| 227 | —NO$_2$ | —CH$_3$ | (1-methylpiperidin-4-yl-COOC$_2$H$_5$) | free | $^1$H NMR(CDCl$_3$) 1.28(3H, t, J=7.1 Hz), 1.86–1.95(2H, m), 2.02–2.06(2H, m), 2.10(3H, s), 2.40–2.48(1H, m), 2.76–2.85(2H, m), 3.61–3.65(2H, m), 4.17(2H, q, J=7.1 Hz), 6.79–6.97(4H, m), 8.43(1H, dd, J=9.1 Hz, 3.0 Hz), 9.04(1H, d, J=2.8 Hz). |

TABLE 31-continued

[Structure: pyridine with R178 at 5-position, linked via O to phenyl ring with R180 (para) and R179 (ortho to O)]

| Reference Example No. | R178 | R179 | R180 | Form | mp(° C.) or ¹H NMR (solvent) δ ppm |
|---|---|---|---|---|---|
| 228 | —NO₂ | —OCH₃ | [1-methylpiperidin-4-yl-CH₂-COOC₂H₅] | free | ¹H NMR(CDCl₃) 1.28(3H, t, J=7.1 Hz), 1.41–1.50(2H, m), 1.84–2.04(3H, m), 2.30(2H, d, J=6.9 Hz), 2.78(2H, dd, J=12.0 Hz, 9.7 Hz), 3.65(2H, d, J=12.4 Hz), 3.73(3H, s), 4.16(2H, q, J=7.3 Hz), 6.53(1H, dd, J=8.7 Hz, 2.6 Hz), 6.59 (1H, d, J=2.6 Hz), 6.96–7.02(2H, m), 8.42(1H, dd, J=9.1 Hz, 2.8 Hz), 9.03(1H, d, J=2.8 Hz). |
| 229 | —NO₂ | —CH₃ | [1-methylpiperidin-4-yl-CH₂-COOC₂H₅] | free | ¹H NMR(CDCl₃) 1.27(3H, t, J=7.1 Hz), 1.37–1.49(2H, m), 1.83–2.03(3H, m), 2.10(3H, s), 2.29(2H, d, J=6.9 Hz), 2.74(2H, dd, J=12.2 Hz, 10.1 Hz), 3.64(2H, d, J=12.4 Hz), 4.15(2H, q, J=7.3 Hz), 6.77–6.83(2H, m), 6.91–6.97(2H, m), 8.42(1H, dd, J=9.1Hz, 2.8 Hz), 9.02(1H, d, J=2.8 Hz). |

TABLE 32

[Structure: pyridine with R181 at 5-position, linked via O to phenyl ring with substituents R182, R183, R184, R185]

| Reference Example No. | R181 | R182 | R183 | R184 | R185 | ¹H NMR(CDCl₃) δ ppm or MS |
|---|---|---|---|---|---|---|
| 230 | —Br | —CH₃ | —H | —H | [N(CH₃)-CH₂-C(O)-piperazinyl-CH₂-benzo[1,3]dioxole] | ¹H NMR 2.09(3H, s), 2.41–2.45(4H, m), 3.01(3H, s), 3.43(2H, s), 3.49(2H, brs), 3.63(2H, brs), 4.07 (2H, brs), 5.93(2H, m), 6.51–6.56(2H, m), 6.68–6.77(3H, m), 6.85–6.91(2H, m), 7.68(1H, dd, J=8.7 Hz, 2.5 Hz), 8.19(1H, d, J=2.5 Hz). |
| 231 | 3,4-Cl₂PhNHCO— | —H | —CF3 | —H | —N(CH₃)CH₂COOC₂H₅ | MS 541(M+) |
| 232 | 4-CF₃PhNHCO— | —H | —CF3 | —H | —N(CH₃)CH₂COOC₂H₅ | MS 541(M+) |
| 233 | 3,4-Cl₂PhCH₂NHCO— | —H | —CF3 | —H | —N(CH₃)CH₂COOC₂H₅ | MS 555(M+) |
| 234 | 4-CF3CH₂NHCO— | —H | —CF3 | —H | —N(CH₃)CH₂COOC₂H₅ | MS 555(M+) |

TABLE 32-continued

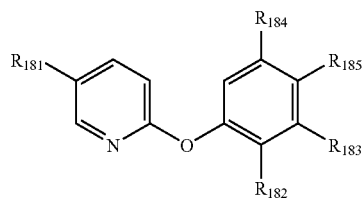

| Reference Example No. | $R_{181}$ | $R_{182}$ | $R_{183}$ | $R_{184}$ | | $^1$H NMR(CDCl$_3$) δ ppm or MS |
|---|---|---|---|---|---|---|
| 235 | —Br | —F | —H | —F | —N(CH$_3$)CH$_2$COOC$_2$H$_5$ | $^1$H NMR 1.26(3H, t, J=7.1 Hz), 2.99(3H, s), 4.03(2H, s), 4.18 (2H, q J=7.1 Hz), 6.76(1H, d, J=8.2 Hz, 12.1 Hz), 6.84–6.95(2H, m), 7.77(1H, dd, J=2.6 Hz, 8.7 Hz), 8.17(1H, d, J=2.6 Hz). |

TABLE 33

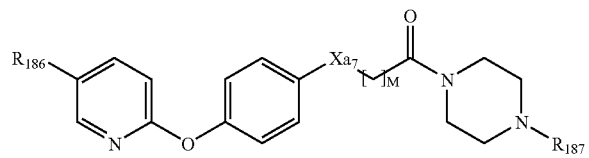

| Reference Example No. | $R_{186}$ | $Xa_7$ | $R_{187}$ | M | $^1$H NMR(solvent) δ ppm |
|---|---|---|---|---|---|
| 236 | —COOC$_2$H$_5$ | —CH$_2$— | piperonyl | 1 | (DMSO-d$_6$) 1.31(3H, t, J=7.0 Hz), 2.28(4H, brs), 2.60–2.66(2H, m), 2.80–2.86(2H, m), 3.38(2H, s), 3.40–3.46(4H, m), 4.31(2H, q, J=7.0 Hz), 5.98(2H, s), 6.72–6.76(1H, m), 6.84(2H, d, J=8.4 Hz), 7.06–7.11(3H, m), 7.30(2H, d, J=8.4 Hz), 8.30(1H, dd, J=8.6 Hz, 2.4 Hz), 8.68(1H, d, J=2.4 Hz). |
| 237 | —COOC$_2$H$_5$ | none | benzyl | 0 | (CDCl$_3$) 1.39(3H, t, J=7.3 Hz), 2.48(4H, brs), 3.55–3.91(6H, m), 4.38(2H, q, J=7.3 Hz), 6.97(1H, d, J=8.6 Hz), 7.17–7.19(2H, m), 7.20 7.34(5H, m), 7.46–7.49(2H, m), 8.31(1H, dd, J=8.6 Hz, 2.4 Hz), 8.82(1H, d, J=2.4 Hz). |
| 238 | —Br | —N(CH$_3$)— | piperonyl | 1 | (CDCl$_3$) 2.41–2.45(4H, m), 3.03(3H, s), 3.43(2H, s), 3.47–3.51(2H, m), 3.61 3.65(2H, m), 4.09(2H, s), 5.95(2H, s), 6.68–6.85(6H, m), 6.96–7.02(2H, m), 7.70(1H, dd, J=8.7 Hz, 2.5 Hz), 8.20(1H, d, J=2.5 Hz). |
| 239 | —Br | —CH$_2$— | piperonyl | 1 | (CDCl$_3$) 2.31–2.41(4H, m), 2.59–2.65(2H, m), 2.95–3.00(2H, m), 3.38–3.42(4H, m), 3.61–3.65(2H, m), 5.95(2H, s), 6.70–6.77(2H, m), 6.81–6.84(2H, m), 7.01–7.06(2H, m), 7.22–7.27(2H, m), 7.76(1H, dd, J=8.7 Hz, 2.6 Hz), 8.20–8.21(1H, m). |
| 240 | —Br | none | benzyl | 0 | (CDCl$_3$) 2.47(4H, brs), 3.49–3.55(6H, m), 6.86(1H, d, J=8.6 Hz), 7.14(2H, d, J=8.6 Hz), 7.28–7.33(5H, m), 7.45(2H, d, J=8.6 Hz), 7.80(1H, dd, J=8.6 Hz, 2.5 Hz), 8.22(1H, d, J=2.5 Hz). |

TABLE 33-continued
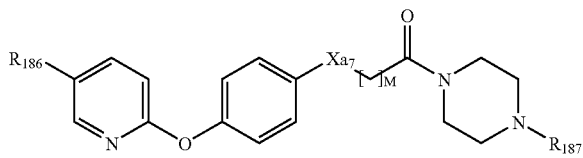
| Reference Example No. | $R_{186}$ | $Xa_7$ | $R_{187}$ | M | $^1$H NMR(solvent) δ ppm |
|---|---|---|---|---|---|
| 241 | —COOCH3- | N(CH$_3$)— | piperonyl | 1 | (CDCl$_3$) 2.41–2.45(4H, m), 3.04(3H, s), 3.43(2H, s), 3.47–3.49(2H, m), 3.63(2H, s), 3.91(3H, s), 4.10(2H, s), 5.95(2H, s), 6.69–6.75(4H, m), 6.84(1H, dd, J=8.7 Hz, 0.7 Hz) 6.85(1H, brs), 7.02(2H, d, J=9.2 Hz), 8.21(1H, dd, J=8.7 Hz, 2.5 Hz), 8.82(1H, dd, J=2.5 Hz, 0.7 Hz). |
| 242 | COOC$_2$H$_5$ | none | piperonyl | 0 | (CDCl$_3$) 1.39(3H, t, J=7.1 Hz), 2.45(4H, brs), 3.45(2H, s), 3.54–3.75(4H, m), 4.38(2H, q, J=7.1 Hz), 5.95(2H, s), 6.71–6.75(2H, m), 6.86(1H, s), 6.97(1H, d, J=8.6 Hz), 7.19(2H, d, J=8.6 Hz), 7.48(2H, d, J=8.7 Hz), 8.30(1H, dd, J=2.3 Hz, 8.6 Hz), 8.82(1H, d, J=2.3 Hz). |
TABLE 34
| Reference Example No. | Chemical Structure | MS(M+) |
|---|---|---|
| 243 | 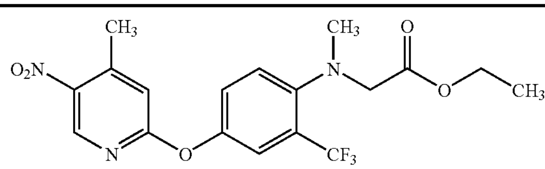 | 413 |
| 244 | 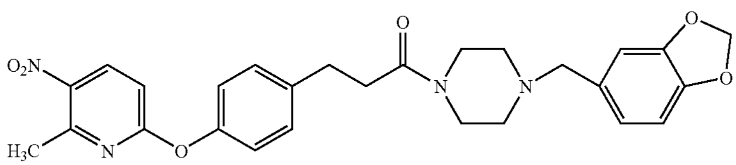 | 504 |
| 245 | 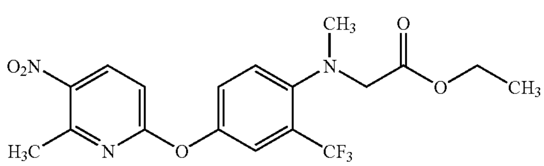 | 413 |
| 246 | 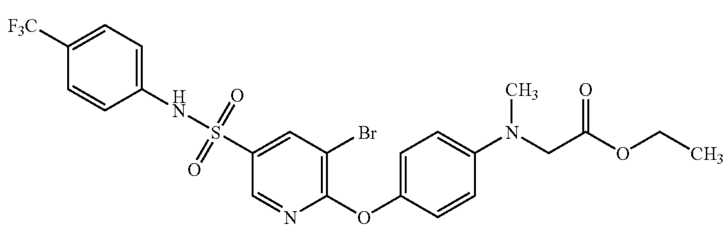 | 574 |

Reference Example 247

Production of 4-(5-nitropyridin-2-yloxy)phenylamine

To a solution of sodium hydroxide (730 mg, 18.25 mmol) in methanol was added 4-aminophenol (2.00 g, 18.32 mmol). After the resulting mixture was made to dissolve, methanol was evaporated under reduced pressure. To the residue was added DMF (20 mL), and then 2-chloro-5-nitropyridine (2.91 g, 18.35 mmol). The reaction solution was stirred for 1.5 hours at 70° C., and then concentrated under reduced pressure. Water was added to the residue, and the resulting solution was extracted with ethyl acetate. The ethyl acetate layer was washed with brine. The ethyl acetate layer was dried over anhydrous magnesium sulfate, after which solvent was evaporated, and the residue was purified by silica gel column chromatography (n-hexane:ethyl acetate=1:1), to thereby yield 3.37 g of the title compound.

Appearance: Black-red powder $^1$H NMR (DMSO-$d_6$) δ 5.10 (2H, s), 6.61 (2H, d, J=8.9 Hz), 6.85 (2H, d, J=8.9 Hz), 7.08 (1H, d, J=9.0 Hz), 8.55 (1H, dd, J=9.0 Hz, 3.0 Hz), 9.01 (1H, d, J=3.0 Hz).

The following compounds were produced in the same manner as in Reference Example 247.

TABLE 35

| Reference Example No. | Chemical Structure | $^1$H NMR(solvent) δ ppm |
|---|---|---|
| 248 | (structure: 4-CF₃-benzyl-pyridine-O-phenyl-NH₂) | (DMSO-$d_6$) 4.03(2H, s), 6.96(1H, d, J=8.4 Hz), 7.10(2H, d, J=8.9 Hz), 7.17(2H, d, J=8.9 Hz), 7.48(2H, d, J=8.1 Hz), 7.66(2H, d, J=8.1 Hz), 7.71(1H, dd, J=8.4 Hz, 2.5 Hz), 8.08(1H, d, J=2.5 Hz), 9.12(2H, brs). |
| 249 | (structure: O₂N-pyridine-O-phenyl-CH₂CH(OH)C(O)-piperazine-COOC(CH₃)₃) | (CDCl₃) 1.47(9H, s), 2.94(2H, d, J=5.1 Hz), 3.10–3.80(9H, m), 4.62(1H, d, J=5.1 Hz), 7.03(1H, d, J=9.1 Hz), 7.10(2H, d, J=8.5 Hz), 7.31(2H, d, J=8.5 Hz), 8.46(1H, dd, J=9.1 Hz, 2.8 Hz), 9.01(1H, d, J=2.8 Hz). |

TABLE 36

O₂N-pyridine-O-phenyl-R₁₈₈

| Reference Example No. | R₁₈₈ | $^1$H NMR(solvent) δ ppm |
|---|---|---|
| 250 | —CH₂OH | (CDCl₃) 4.74(2H, s), 7.04(1H, d, J=8.9 Hz), 7.13–7.18(2H, m), 7.46(2H, d, J=8.3 Hz), 8.48(1H, dd, J=8.9 Hz, 2.6 Hz), 9.03(1H, d, J=2.6 Hz). |
| 251 | —(CH₂)₂OH | (CDCl₃) 2.91(2H, t, J=6.6 Hz), 3.91(2H, t, J=6.6 Hz), 7.03(1H, d, J=9.2 Hz), 7.09–7.13(2H, m), 7.32(2H, d, J=8.6 Hz), 8.47(1H, dd, J=9.2 Hz, 3.0 Hz), 9.04(1H, d, J=3.0 Hz). |
| 252 | —(CH₂)₂COOH | (CDCl₃) 2.73(2H, t, J=7.9 Hz), 3.01(2H, t, J=7.9 Hz), 7.03(1H, d, J=8.9 Hz), 7.09(2H, d, J=8.6 Hz), 7.30(2H, d, J=8.6 Hz), 8.47(1H, dd, J=9.2 Hz, 3.0 Hz), 9.04(1H, d, J=2.6 Hz). |
| 253 | —(CH₂)₃COOH | (DMSO-$d_6$) 2.01(2H, dq, J=15.0 Hz, 7.2 Hz), 2.46(2H, t, J=7.2 Hz), 2.72(2H, t, J=7.2 Hz), 7.02(1H, d, J=8.6 Hz), 7.08(2H, d, J=8.6 Hz), 7.27(2H, d, J=8.6 Hz), 8.46(1H, dd, J=8.6 Hz, 3.0 Hz), 9.04(1H, d, J=3.0 Hz). |

Reference Example 254

Production of ethyl 3-[4-(3-nitrophenoxy)phenyl]-propionate

Under argon, to a solution of 3-iodonitrobenzene (3.00 g, 12.0 mmol) in pyridine (15 mL) were added ethyl 3-(4-hydroxyphenyl)propionate (2.81 g, 14.5 mmol), copper oxide (3.35 g, 42.2 mmol), and potassium carbonate (4.16 g, 30.1 mmol), and the resulting solution was heated to reflux for 40 hours. The reaction solution was concentrated under reduced pressure. Water and ethyl acetate were added to the residue, and once insoluble matter had been filtered off, and the filtrate was extracted with ethyl acetate out. The ethyl acetate layer was washed with 1 M hydrochloric acid, water and a saturated sodium bicarbonate solution, and then washed with brine. The ethyl acetate layer was dried over anhydrous magnesium sulfate, evaporated, and the residue was purified by silica gel column chromatography (n-hexane:ethyl acetate=9:1→6:1), to thereby yield 1.12 g of the title compound.

Appearance: Pale yellow oil $^1$H NMR (CDCl$_3$) δ 1.23 (3H, t, J=7.1 Hz), 2.62 (2H, t, J=7.7 Hz), 2.95 (2H, t, J=7.7 Hz), 4.12 (2H, q, J=7.1 Hz), 6.96 (2H, d, J=8.6 Hz), 7.22 (2H, d, J=8.6 Hz), 7.29 (1H, dd, J=8.2 Hz, 2.3 Hz), 7.43 (1H, t, J=8.2 Hz), 7.74 (1H, s), 7.90 (1H, dd, J=8.2 Hz, 2.3 Hz).

Reference Example 255

Production of 1-(t-butoxycarbonyl)-4-[4-(4-nitrophenoxy)phenyl]piperazine

Potassium carbonate (15.7 g, 114 mmol) was added to a solution of 2-chloro-5-nitropyridine (4.50 g, 28.4 mmol) and 1-(4-hydroxyphenyl)piperazine dihydrochloride (7.13 g, 28.4 mmol) in DMF (80 mL). The resulting solution was stirred at room temperature for 8 hours. To this reaction solution was added di-t-butyl dicarbonate (6.81 g, 31.2 mmol), and stirred at room temperature for 2.5 days. To the reaction solution was charged with ethyl acetate, washed with water, and dried with anhydrous magnesium sulfate, and evaporated. The residue was purified by silica gel column chromatography (ethyl acetate:n-hexane=1:3), to thereby yield 7.05 g of the title compound.

Appearance: Yellow needles $^1$H NMR (CDCl$_3$) δ 1.49 (9H, s), 3.15 (4H, t, J=5.0 Hz), 3.59 (4H, t, J=5.0 Hz), 6.98 (2H, d, J=9.0 Hz), 7.00 (1H, d, J=9.0 Hz), 7.07 (2H, d, J=9.0 Hz), 8.45 (1H, dd, J=9.0 Hz, 2.5 Hz), 9.05 (1H, d, J=2.5 Hz).

Reference Example 256

Production of (ethyl{3-methoxy-4-[5-(4-trifluoromethylphenylcarbamoyl)pyridin-2-yloxy]phenyl}amino)acetate Benzyl[ethyl(4-hydroxy-3-methoxyphenyl)amino]acetate (9.46 g, 30 mmol) and 6-chloro-N-(4-trifluoromethylphenyl) nicotinamide (9.02 g, 30 mmol) were dissolved in DMF (100 mL). To the resulting solution was added potassium carbonate (6.22 g, 45 mmol), and then stirred for 12 hours at 120° C. The reaction solution was concentrated under reduced pressure. To the residue was added ethyl acetate and extracted with water. The pH of the aqueous layer was adjusted from 3 to 4 with 1 M hydrochloric acid, after which the mixture was extracted with ethyl acetate. The organic layer was washed with brine and dried over anhydrous magnesium sulfate, and evaporated to thereby yield 4.2 g of the title compound.

Appearance: Brown powder $^1$H NMR (DMSO-d$_6$) δ 1.19 (3H, t, J=7.1 Hz), 3.40 (2H, q, J=7.1 Hz), 3.63 (3H, s), 4.01 (2H, s), 6.17 (1H, d, J=8.9 Hz), 6.22 (1H, brs), 6.25 (1H, d, J=2.5 Hz), 6.87-6.90 (2H, m), 7.53 (2H, d, J=8.6 Hz), 7.76 (2H, d, J=8.4 Hz), 8.18 (1H, dd, J=8.7 Hz, 2.3 Hz), 8.67 (1H, d, J=2.1 Hz), 8.88 (1H, brs).

Reference Example 257

Production of ethyl methyl[2,5-difluoro-4-(5-nitropyridin-2-yloxy)phenyl]aminoacetate To a solution of ethyl(2,5-difluoro-4-hydroxyphenyl)aminoacetate (1.1 g, 4.8 mmol) in DMF (25 mL) were added sodium bicarbonate (0.44 g, 5.2 mmol) and methyl iodide (1.69 mL, 28.6 mmol), and the resulting reaction solution was stirred for 2 days at room temperature. Water was added to the reaction mixture, and extracted with ethyl acetate. Once the ethyl acetate layer had been washed with water, the ethyl acetate layer was dried with anhydrous magnesium sulfate, and evaporated. The residue was dissolved in DMF (30 mL), and to this resulting solution were added potassium carbonate (0.72 g, 5.2 mmol) and 2-chloro-5-nitropyridine (0.79 g, 5.0 mmol). The reaction solution was stirred for 2.5 days at room temperature. Water was added to the reaction mixture, and extracted with ethyl acetate. The ethyl acetate layer was washed with water, and dried over anhydrous magnesium sulfate. The solvent was then evaporated, and the residue was purified by silica gel chromatography (n-hexane:ethyl acetate=8:1), to thereby yield 1.41 g of the title compound.

Appearance: Yellow oil $^1$H NMR (CDCl$_3$) δ 1.27 (3H, t, J=7.1 Hz), 3.01 (3H, s), 4.05 (2H, s), 4.19 (2H, q, J=7.1 Hz), 6.77 (1H, dd, J=8.2 Hz, 12.2 Hz), 6.92 (1H, dd, J=7.2 Hz, 12.8 Hz), 8.49 (1H, dd, J=2.8 Hz, 9.0 Hz), 9.02 (1H, d, J=2.8 Hz).

The following compounds were produced in the same manner as in Reference Example 257.

TABLE 37

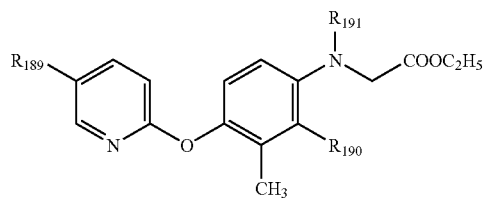

| Reference Example No. | R$_{189}$ | R$_{190}$ | R$_{191}$ | $^1$H NMR(CDCl$_3$) δ ppm |
|---|---|---|---|---|
| 258 | —NO$_2$ | —CH$_3$ | —CH$_3$ | 1.27(3H, t, J=7.1 Hz), 2.05(3H, s), 2.29(3H, s), 2.87(3H, s), 3.71(2H, s), 4.18(2H, q, J=7.1 Hz), 6.87(1H, d, J=8.7 Hz), 6.97(1H, dd, J=9.1 Hz, 0.3 Hz), 7.08(1H, d, J=8.7 Hz), 8.45(1H, dd, J=9.1 Hz, 2.8 Hz), 9.04(1H, dd, J=2.8 Hz, 0.3 Hz). |

TABLE 37-continued

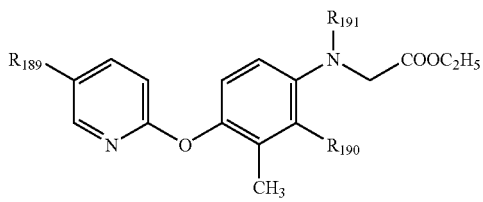

| Reference Example No. | $R_{189}$ | $R_{190}$ | $R_{191}$ | $^1$H NMR(CDCl$_3$) δ ppm |
|---|---|---|---|---|
| 259 | 4-CF$_3$PhCO— | —H | —C$_2$H$_5$ | 1.23(3H, t, J=7.1 Hz), 1.28(3H, t, J=7.1 Hz), 2.12(3H, s), 3.46(2H, q, J=7.1 Hz), 4.01(2H, s), 4.21(2H, q, J=7.1 Hz), 6.49–6.53(2H, m), 6.92–6.96(2H, m), 7.73–7.77(2H, m), 7.86–7.89(2H, m), 8.17(1H, dd, J=8.7 Hz, 2.5 Hz), 8.59(1H, dd, J=2.5 Hz, 0.7 Hz). |

Reference Example 260

Production of ethyl 4-{3-[3-methyl-4-(5-nitropyridin-2-yloxy)phenyl]-2-oxotetrahydropyrimidin-1-yl}benzoate Under a nitrogen atmosphere, to a solution of ethyl 4-[3-(4-benzyloxy-3-methyl)phenyl-2-oxotetrahydropyrimidin-1-yl]benzoate (1.82 g, 3.1 mmol) in ethanol-DMF (70 mL-30 mL) was added 10% palladium-carbon (0.4 g), and the resulting solution was stirred under a hydrogen atmosphere for 4 hours at room temperature. The resulting solution was filtered through Celite, and ethanol was evaporated under reduced pressure so as to give a DMF (30 mL) solution. To this solution was added 2-chloro-5-nitropyridine (0.52 g, 3.3 mmol) and stirred under a nitrogen atmosphere for 14 hours at room temperature, and then for 3 hours at 40° C. Water was added to the reaction mixture, and extracted with ethyl acetate. The ethyl acetate layer was washed with water, dried over anhydrous magnesium sulfate, and evaporated. The residue was purified by silica gel chromatography (n-hexane: ethyl acetate=10:1), to thereby yield 1.8 g of the title compound.

Appearance: White powder
$^1$H NMR (CDCl$_3$) δ 1.39 (3H, t, J=7.1 Hz), 2.14 (3H, s), 2.21-2.40 (2H, m), 3.75-3.97 (4H, m), 4.36 (2H, q, J=7.1 Hz), 7.01 (1H, d, J=9.1 Hz), 7.06 (1H, d, J=8.6 Hz), 7.23 (1H, dd, J=2.6 Hz, 8.6 Hz), 7.32 (1H, d, J=2.6 Hz), 7.40-7.49 (2H, m), 7.97-8.07 (2H, m), 8.46 (1H, dd, J=2.8 Hz, 9.1 Hz), 9.04 (1H, d, J=2.8 Hz).

Reference Example 261

Production of 3-[4-(5-nitropyridin-2-ylsulfanyl)phenyl]propionic acid

To a solution of 2-chloro-5-nitropyridine (1.74 g, 11.0 mmol) and 4-mercaptohydrocinnamic acid (2.00 g, 11.0 mmol) in DMF (30 mL) was added potassium carbonate (4.55 g, 32.9 mmol), and the resulting solution was stirred for 1 hour at 80° C. To the reaction solution were added water and concentrated hydrochloric acid, and then cooled with ice. The precipitated solid matter was collected by filtration, to thereby yield 3.29 g of the title compound.

Appearance: Pale yellow powder
$^1$H NMR (DMSO-d$_6$) δ 2.60 (2H, t, J=7.5 Hz), 2.91 (2H, t, J=7.5 Hz), 7.07 (1H, d, J=9.0 Hz), 7.43 (2H, d, J=8.2 Hz), 7.57 (2H, d, J=8.2 Hz), 8.39 (1H, dd, J=2.8 Hz, 9.0 Hz), 9.17 (1H, d, J=2.8 Hz), 12.19 (1H, s).

Reference Example 26

Production of ethyl 3-[3-methoxy-4-(5-nitropyridin-2-ylamino)phenyl]propionate

To 2-chloro-5-nitropyridine (3.11 g, 20 mmol) were added ethyl 3-(4-amino-3-methoxyphenyl)propionate (4.38 g, 20 mmol) and acetic acid (10 mL), and the resulting solution was stirred for 13 hours at 100° C. To the reaction solution were added ethyl acetate and water. The ethyl acetate layer was separated, washed with brine, a saturated sodium bicarbonate solution and brine, and dried over anhydrous magnesium sulfate. The solvent was evaporated, and the residue was purified by silica gel column chromatography (n-hexane: ethyl acetate=2:1), to thereby yield 3.78 g of the title compound.

Appearance: Yellow powder
$^1$H NMR (CDCl$_3$) δ 1.26 (3H, t, J=7.1 Hz), 2.61-2.67 (2H, m), 2.93-2.99 (2H, m), 3.89 (3H, s), 4.15 (2H, q, J=7.1 Hz), 6.73 (1H, d, J=9.2 Hz), 6.81-6.87 (2H, m), 7.43 (1H, brs), 7.92 (1H, d, J=8.1 Hz), 8.23 (1H, dd, J=9.2 Hz, 2.8 Hz), 9.11 (1H, d, J=2.8 Hz).

The following compounds were produced in the same manner as in Reference Example 262.

TABLE 38

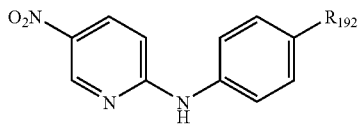

| Reference Example No. | R192 | ¹H NMR(solvent) δ ppm |
|---|---|---|
| 263 | —COOC$_2$H$_5$ | (DMSO-d$_6$) 1.32(3H, t, J=7.1 Hz), 4.29(2H, q, J=7.1 Hz), 7.01(1H, d, J=9.3 Hz), 7.89(2H, d, J=8.9 Hz), 8.36(1H, dd, J=2.9 Hz, 9.3 Hz), 9.09(1H, d, J=2.9 Hz), 10.43(1H, s). |
| 264 | —(CH$_2$)$_2$COOC$_2$H$_5$ | (CDCl$_3$) 1.25(3H, t, J=7.1 Hz), 2.64(2H, t, J=7.6 Hz), 2.97(2H, t, J=7.6 Hz), 4.14(2H, q,.J=7.1 Hz), 6.73(1H, d, J=9.3 Hz), 7.20–7.40(4H, m), 8.23(1H, dd, J=2.7 Hz, 9.3 Hz), 9.07(1H, d, J=2.7 Hz). |
| 265 | —N(piperazine)N—CH$_2$COOC$_2$H$_5$ | (CDCl$_3$) 1.30(3H, t, J=7.1 Hz), 2.77(4H, t, J=5.0 Hz), 3.28(4H, t, J=5.0 Hz), 3.28(2H, s), 4.22(2H, q, J=7.1 Hz), 6.61(1H, d, J=9.4 Hz), 6.95(2H, d, J=9.0 Hz), 7.11(1H, brs), 7.22(2H, d, J=9.0 Hz), 8.18(1H, dd, J=9.4 Hz, 2.5 Hz), 9.05(1H, d, J=2.5 Hz). |
| 266 | —N(piperidine)—CH$_2$COOC$_2$H$_5$ | (CDCl$_3$) 1.28(3H, t, J=7.1 Hz), 1.32–1.60(2H, m), 1.75–2.12(3H, m), 2.29(2H, d, J=6.9 Hz), 2.77(2H, td, J=12 4 Hz, 2.4 Hz), 3.68(2H, d, J=12.4 Hz), 4.16(2H, q, 7.1 Hz), 6.60(1H, d, J=9.2 Hz), 6.96(2H, d, J=8.9 Hz), 7.16(1H, brs), 7.20(2H, d, J=8.9 Hz), 8.18(1H, dd, J=9.2 Hz, 2.6 Hz), 9.05(1H, d, J=2.6 Hz). |

Reference Example 267

Production of 4-[(5-nitro-2-pyridyl)oxy]benzaldehyde ethylene acetal

To a solution of 4-[(5-nitro-2-pyridyl)oxy]benzaldehyde (5.00 g, 20.5 mmol) in benzene (100 mL) were added ethylene glycol (2.28 mL, 41.0 mmol) and p-toluenesulfonic acid (0.50 g), and the resulting solution was heated to reflux for 3 hours while removing water with a Dean-Stark. The reaction solution was washed with a saturated sodium bicarbonate solution, and subsequently washed with brine. The benzene layer was dried over anhydrous magnesium sulfate, and evaporated, to thereby yield 5.88 g of the title compound.

Appearance: Yellow powder

¹H NMR (CDCl$_3$) δ 4.00-4.19 (4H, m), 5.83 (1H, s), 7.00 (1H, d, J=9.0 Hz), 7.15 (2H, d, J=8.5 Hz), 7.55 (2H, d, J=8.5 Hz), 8.45 (1H, dd, J=9.0 Hz, 2.0 Hz), 9.01 (1H, d, J=2.0 Hz).

The following compound was produced in the same manner as in Reference Example 267.

Reference Example 268

4-(2-Fluoro-4-nitrophenoxybenzaldehyde ethylene acetal

¹H NMR (DMSO-d$_6$) δ 3.90-4.10 (4H, m), 5.76 (1H, s), 7.15-7.25 (3H, m), 7.54 (2H, d, J=8.7 Hz), 8.10 (1H, ddd, J=1.3 Hz, 2.7 Hz, 9.1 Hz), 8.35 (1H, dd, J=2.7 Hz, 10.8 Hz).

Reference Example 269

Production of t-butyl[4-(5-nitropyridin-2-yloxy)phenyl]carbamate

To a solution of 4-(5-nitropyridin-2-yloxy)phenylamine (2.97 g, 12.85 mmol) in THF was added di-t-butyl dicarbonate (5.60 g, 25.66 mmol), and the resulting solution was stirred under reflux for 4 hours. The reaction solution was concentrated under reduced pressure. Water was added to the residue, and extracted with ethyl acetate. The ethyl acetate layer was washed with brine, dried over anhydrous magnesium sulfate, evaporated, and to the resulting product was added diethyl ether. The obtained white powder was filtered, and the resulting product was washed with diethyl ether, to thereby yield 3.04 g of the title compound.

Appearance: Yellow powder

¹H NMR (CDCl$_3$) δ 1.53 (9H, s), 6.53 (1H, brs), 7.00 (1H, d, J=9.2 Hz), 7.09 (2H, d, J=8.9 Hz), 7.45 (2H, d, J=8.9 Hz), 8.46 (1H, dd, J=9.2 Hz, 3.0 Hz), 9.03 (1H, d, J=3.0 Hz).

Reference Example 270

Production of 5-[3-methyl-4-(5-nitropyridin-2-yloxy)benzylidene]thiazolidine-2,4-dione To a solution of 3-methyl-4-(5-nitropyridin-2-yloxy)benzaldehyde (600 mg, 2.32 mmol) in toluene (35 mL) were added 2,4-thiazolidinedione (270 mg, 2.31 mmol) and piperidine acetate (135 mg, 0.93 mmol). The resulting solution was attached to a Dean Stark, and stirred under reflux for 1.5 hours. After being left to cool for 17 hours at room temperature, the precipitated yellow powder was filtered, to thereby yield 600 mg of the title compound.

Appearance: Yellow powder

¹H NMR (DMSO-d$_6$) δ 2.15 (3H, s), 7.33 (1H, d, J=8.4 Hz), 7.35 (1H, d, J=9.1 Hz), 7.52 (1H, dd, J=8.4 Hz, 2.0 Hz), 7.59 (1H, d, J=2.0 Hz), 7.79 (1H, s), 8.65 (1H, dd, J=9.1 Hz, 3.0 Hz), 9.02 (1H, d, J=3.0 Hz), 12.63 (1H, brs)

The following compounds were produced in the same manner as in Reference Example 270.

TABLE 39

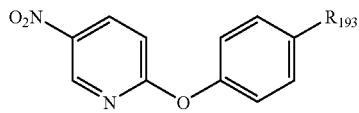

| Reference Example No. | $R_{193}$ | $^1$H NMR(solvent) δ ppm |
|---|---|---|
| 271 | ![structure: ethylidene thiazolidinedione]  | (DMSO-$d_6$) 7.35(1H, d, J=9.0 Hz), 7.42(2H, d, J=8.6 Hz), 7.71(2H, d, J=8.6 Hz), 7.84(1H, s), 8.65(1H, dd, J=9.0 Hz, 2.9 Hz), 9.04(1H, d, J=2.9 Hz), 12.64(1H, brs). |
| 272 | —CH=C(COOCH$_3$)$_2$ | (CDCl$_3$) 3.87(6H, s), 7.09(1H, d, J=9.0 Hz), 7.20(2H, d, J=8.5 Hz), 7.53(2H, d, J=8.5 Hz), 7.77(1H, s), 8.51(1H, dd, J=9.0 Hz, 2.8 Hz), 9.04(1H, d, J=2.8 Hz). |

Reference Example 273

Production of N-[4-(2-fluoro-4-nitrophenoxy)phenyl]-N-[2-(4-piperonylpiperazin-1-yl)-2-oxyethyl]acetamide To a solution of N-[4-(2-fluoro-4-nitrophenoxy)phenyl]acetamide (0.800 g, 2,76 mmol) in DMF (5 mL) was added 60% sodium hydride (0.118 g, 2.95 mmol). The resulting solution was stirred for 10 minutes at room temperature, after which a solution of 1-chloroacetyl-4-piperonylpiperazine (0.870 g, 2.96 mmol) in DMF (4 mL) was added to the reaction solution. The reaction solution was stirred for 2 hours at 60° C., and then for 1 hour at 100° C. Water was added to the reaction mixture, and extracted with ethyl acetate. The ethyl acetate layer was washed with brine, dried over anhydrous sodium sulfate, evaporated, and the residue was purified by silica gel column chromatography (dichloromethane:methanol=5:1), to thereby yield 0.730 g of the title compound.

Appearance: Yellow oil $^1$H NMR (DMSO-$d_6$) δ 1.82 (3H, s), 2.20-2.40 (4H, m), 3.30-3.50 (6H, m), 4.43 (2H, s), 5.98 (2H, s), 6.70-6.85 (3H, m), 7.20-7.30 (3H, m), 7.48 (2H, d, J=8.8 Hz), 8.12 (1H, ddd, J=1.4 Hz, 2.7 Hz, 10.5 Hz), 8.36 (1H, dd, J=2.7 Hz, 10.7 Hz).

The following compound was produced in the same manner as in Reference Example 273.

Reference Example 274

3-(4-Benzyloxy-3-methylphenyl)-1-[2-oxo-2-(4-piperonylpiperazin-1-yl)ethyl]tetrahydropyrimidin-2-one $^1$H NMR (DMSO-$d_6$) δ 1.92-2.08 (2H, m), 2.15 (3H, s), 2.22-2.40 (4H, m), 3.25-3.49 (8H, m), 3.56 (2H, d, J=5.6 Hz), 4.08 (2H, s), 5.09 (2H, s), 5.97 (2H, s), 6.74 (1H, dd J=1.3 Hz, 7.9 Hz), 6.84 (1H, d, J=7.9 Hz), 6.85 (1H, d, J=1.3 Hz), 6.91 (1H, d, J=8.7 Hz), 6.95 (1H, dd, J=2.5 Hz, 8.6 Hz), 7.01 (1H, d, J=2.5 Hz), 7.28-7.34 (1H, m), 7.36-7.41 (2H, m), 7.42-7.48 (2H, m).

Reference Example 275

Production of 2-dimethylamino-N-[4-(5-nitropyridin-2-yloxy)phenyl]-N-[2-(4-piperonylpiperazin-1-yl)-2-oxoethyl]acetamide To a solution of 2-chloro-N-[4-(5-nitropyridin-2-yloxy)phenyl]-N-[2-(4-piperonylpiperazin-1-yl)-2-oxoethyl]acetamide (0.300 g, 0.528 mmol) in acetonitrile (3 mL) was added at room temperature dimethylamine (0.150 mL, 1.63 mmol), and the resulting solution was stirred for 2 hours at 50° C. Water was added to the reaction mixture, and extracted with ethyl acetate. The ethyl acetate layer was washed with brine, dried over anhydrous sodium sulfate, evaporated, and the residue was purified by silica gel column chromatography (dichloromethane:methanol=10:1), to thereby yield 0.270 g of the title compound.

Appearance: Yellow powder $^1$H NMR (CDCl$_3$) δ 2.29 (6H, s), 2.40-2.45 (4H, m), 3.02 (2H, s), 3.40-3.46 (4H, m), 3.61 (2H, s), 4.48 (2H, s), 5.95 (2H, s), 6.70-6.77 (2H, m), 6.84 (1H, s), 7.09 (1H, d, J=9.0 Hz), 7.19 (2H, d, J=8.7 Hz), 7.51 (2H, d, J=8.7 Hz), 8.51 (1H, dd, J=2.8 Hz, 9.0 Hz), 9.04 (1H, d, J=2.8 Hz).

Reference Example 276

Production of methyl 2-[4-(5-nitropyridin-2-yloxy)phenyl]propionate

To a solution of methyl 2-[4-(5-nitropyridin-2-yloxy)phenyl]acetate (0.50 g, 1.7 mmol) in DMF (10 mL) were added 60% sodium hydride (0.153 g, 3.8 mmol) and methyl iodide (0.13 mL, 2.1 mmol), and the resulting reaction solution was stirred for 1 hour at 0° C. To the reaction solution was added saturated aqueous ammonium chloride, and extracted with ethyl acetate. The ethyl acetate layer was washed with water and saturated aqueous sodium chloride. The ethyl acetate layer was dried over anhydrous magnesium sulfate, evaporated, and the residue was purified by silica gel chromatography (n-hexane:ethyl acetate=8:1), to thereby yield 0.32 g of the title compound.

Appearance: Colorless oil $^1$H NMR (CDCl$_3$) δ 1.54 (3H, d, J=7.4 Hz), 3.69 (3H, s), 3.78 (1H, q, J=7.2 Hz), 7.03 (1H, d, J=9.1 Hz), 7.09-7.15 (2H, m), 7.36-7.41 (2H, m), 8.48 (1H, dd, J=9.1, 2.8 Hz), 9.05 (1H, d, J=2.8 Hz).

Reference Example 277

Production of ethyl 3-{3-methoxy-4-[methyl(5-nitropyridin-2-yl)amino]phenyl}propionate To a solution of ethyl 3-[3-methoxy-4-(5-nitropyridin-2-ylamino)phenyl]propionate (3.70 g, 11 mmol) in DMF (60 mL) were added under ice-cooling sodium hydride (60%, 490 mg, 12 mmol) and methyl iodide (0.77 mL, 12 mmol), and the resulting reaction solution was stirred for 2 hours gradually warming up to room temperature. The reaction solution was concentrated under reduced pressure. To the residue was added ethyl acetate, washed with water and brine, and then dried with anhydrous magnesium sulfate. The solvent was evaporated, to thereby yield 4.27 g of the title compound.

Appearance: Yellow oil substance $^1$H NMR (CDCl$_3$) δ 1.27 (3H, t, J=7.1 Hz), 2.66-2.71 (2H, m), 2.98-3.04 (2H, m), 3.46 (3H, s), 3.78 (3H, s), 4.17 (2H, q, J=7.1 Hz), 6.12 (1H, brd, J=9.5 Hz), 6.87-6.90 (2H, m), 7.11-7.14 (1H, m), 7.97-8.02 (1H, m), 9.11 (1H, d, J=2.7 Hz).

The following compounds were produced in the same manner as in Reference Example 277.

TABLE 40

| Reference Example No. | R194 | R195 | $^1$H NMR(solvent) δ ppm |
|---|---|---|---|
| 278 | —CH$_3$ | —COOC$_2$H$_5$ | (DMSO-d$_6$) 1.34(3H, t, J=7.1 Hz), 3.56(3H, s), 4.34(2H, q, J=7.1 Hz), 6.70(1H, d, J=9.5 Hz), 7.55(2H, d, J=8.6 Hz), 8.06(2H, d, J=8.6 Hz), 8.21(1H, dd, J=2.8 Hz, 9.5 Hz), 9.05(1H, d, J=2.8 Hz). |
| 279 | —CH$_3$ | —(CH$_2$)$_2$COOC$_2$H$_5$ | (CDCl$_3$) 1.26(3H, t, J=7.1 Hz), 2.67(2H, t, J=7.6 Hz), 3.01(2H, t, J=7.6 Hz), 3.55(3H, s), 4.15(2H, q, J=7.1 Hz), 6.32(1H, d, J=9.5 Hz), 7.17(2H, d, J=8.3 Hz), 7.32(2H, d, J=8.3 Hz), 8.01(1H, dd, J=2.7 Hz, 9.5 Hz), 9.11(1H, d, J=2.7 Hz). |
| 280 | benzyl | —(CH$_2$)$_2$COOC$_2$H$_5$ | (CDCl$_3$) 1.24(3H, t, J=7.2 Hz), 2.64(2H, t, J=7.7 Hz), 2.97(2H, t, J=7.7 Hz), 4.14(2H, q, J=7.2 Hz), 5.27(2H, s), 6.26(1H, d, J=9.5 Hz), 7.06(2H, d, J=8.3 Hz), 7.20–7.30(7H, m), 8.02(1H, dd, J=2.7 Hz, 9.5 Hz), 9.12(1H, d, J=2.7 Hz). |
| 281 | —CH$_3$ |  —N⌒N—CH$_2$COOC$_2$H$_5$ | (CDCl$_3$) 1.30(3H, t, J=7.1 Hz), 2.78(4H, t, J=5.0 Hz), 3.30(2H, s), 3.31(4H, t, J=5.0 Hz), 3.53(3H, s), 4.22(2H, q, J=7.1 Hz), 6.30(1H, d, J=9.5 Hz), 6.99(2H, d, J=8.9 Hz), 7.12(2H, d, J=8.9 Hz), 7.99(1H, dd, J=9.5 Hz, 2.8 Hz), 9.10(1H, d, J=2.8 Hz). |
| 282 | —CH$_3$ | —N⌒CH$_2$COOC$_2$H$_5$ | (CDCl$_3$) 1.28(3H, t, J=7.1 Hz), 1.45(2H, qd, J=12.2 Hz, 3.7 Hz), 1.80-2.17(3H, m), 2.30(2H, d, J=6.9 Hz), 2.80(2H, td, J=12.2 Hz, 2.3 Hz), 3.52(3H, s), 3.72(2H, d, J=12.4 Hz), 4.16(2H, q, J=7.1 Hz), 6.30(1H, d, J=9.5 Hz), 6.98(2H, d, J=8.9 Hz), 7.10(2H, d, J=8.9 Hz), 7.98(1H, dd, J=9.5 Hz, 2.8 Hz), 9.10(1H, d, J=2.8 Hz). |

TABLE 41

| Reference Example No. | R196 | 1H NMR(CDCl3) δ ppm |
|---|---|---|
| 283 | —(CH2)2CH3 | 0.93(3H, t, J=7.4 Hz), 1.60–1.70(2H, m), 2.35–2.43(4H, m), 2.66(2H, t, J=8.1 Hz), 3.03(2H, t, J=8.1 Hz), 3.42(2H, s), 3.43–3.45(2H, m), 3.62–3.65(2H, m), 3.96(2H, t, J=7.7 Hz), 5.95(2H, s), 6.16(1H, d, J=9.5 Hz), 6.70–6.80(2H, m), 6.84(1H, d, J=1.3 Hz), 7.14(2H, d, J=8.3 Hz), 7.33(2H, d, J=8.3 Hz), 7.96(1H, dd, J=2.8 Hz, 9.5 Hz), 9.08(1H, d, J=2.8 Hz). |
| 284 | cyclopentyl | 1.30–1.40(2H, m), 1.55–1.65(4H, m), 1.95–2.00(2H, m), 2.35 2.45(4H, m), 2.67(2H, t, J=7.4 Hz), 3.04(2H, t, J=7.4 Hz), 3.42(2H, s), 3.43–3.47(2H, m), 3.55–3.68(2H, m), 5.185.28(1H, m), 5.88(1H, d, J=9.5 Hz), 5.95(2H, s), 6.70–6.78(2H, m), 6.84(1H, s), 7.04(2H, d, J=8.2 Hz), 7.34(2H, d, J=8.2 Hz), 7.92(1H, dd, J=2.8 Hz, 9.5 Hz), 9.09(1H, d, J=2.8 Hz). |

TABLE 42

| Reference Example No. | Chemical Structure | 1H NMR(solvent) δ ppm |
|---|---|---|
| 285 | 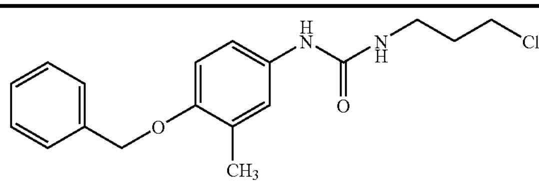 | (CDCl3) 1.91–2.06(2H, m), 2.27(3H, s), 3.31–3.44(2H, m), 3.58(2H, t, J=6.3 Hz), 4.69–4.85(1H, m), 5.07(2H, s), 6.04(1H, s), 6.84(1H, d, J=10.1 Hz), 7.O1(1H, dd, J=8.5 Hz, 2.5 Hz), 7.04(1H, d, J=2.5 Hz), 7.30–7.36(1H, m), 7.37–7.46(4H, m). |
| 286 | 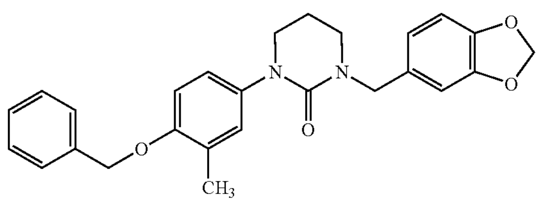 | (CDCl3) 1.96–2.11(2H, m), 2.27(3H, s), 3.20–3.34(2H, m), 3.56–3.68(2H, m) 4 50(2H, s), 5.07(2H, s), 5.94(2H, s), 6.72–6.80(2H, m), 6.84(1H, d, J=8.6 Hz), 6.88(1H, d, J=1.2 Hz), 7.04(1H, dd, J=2.6 Hz, 8.6 Hz), 7.11(1H, d, J=2.6 Hz), 7.28–7.34(1H, m), 7.35–7.41(2H, m), 7.42–7.48(2H, m). |
| 287 | 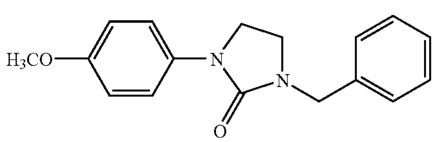 | (DMSO-d6) 3.20–3.40(2H, m), 3.71(3H, s), 3.64–3.83(2H, m), 4.36(2H, s), 6.84–6.95(2H, m), 7.22–7.41(5H, m), 7.42–7.53(2H, m). |
| 288 | 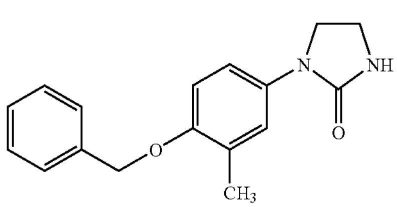 | (DMSO-d6) 2.18(3H, s), 3.35(2H, t, J=8.7 Hz), 3.69–3.84(2H, m), 5.05(2H, s), 6.74(1H, s), 6.93(1H, d, J=8.9 Hz),7.23(1H, dd, J=2.8 Hz, 8.9 Hz), 7.27–7.48(6H, m). |
| 289 | 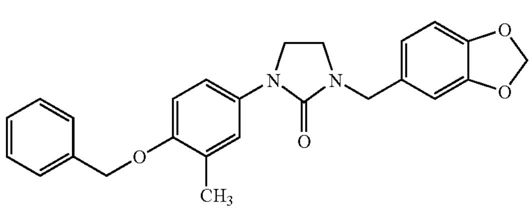 | (CDCl3) 2.29(3H, s), 3.28–3.39(2H, m), 3.68–3.8 1(2H, m), 4.36(2H, s), 5.06(2H, s), 5.95(2H, s), 6.77(2H, s), 6.78–6.91(2H, m), 7.20–7.35(2H, m), 7.36–7.51(5H, m). |

TABLE 42-continued

| Reference Example No. | Chemical Structure | ¹H NMR(solvent) δ ppm |
|---|---|---|
| 290 | (structure) | (CDCl$_3$) 1.93–2.12(2H, m), 2.27(3H, s), 3.28(2H, t, J=5.9 Hz), 3.63(2H, t, J=5.9 Hz), 3.88(6H, s), 4.55 (2H, s), 5.07(2H, s), 6.71–6.92(4H, m), 6.96–7.08(1H, m), 7.11(1H, d, J=2.1 Hz), 7.25–7.51(5H, m). |

Reference Example 291

Production of N-[4-(5-nitropyridin-2-yloxy)phenyl]-2-(4-piperonylpiperazin-1-yl)acetamide A solution of (4-piperonylpiperazin-1-yl)acetic acid (13.9 g, 50 mmol) was suspended in DMF (400 mL), and to the resulting suspension were added 1-hydroxybenzotriazole monohydrate (8.42 g, 55 mmol), 1-ethyl-3-(3-dimethylaminopropyl)carbodiimide hydrochloride (10.5 g, 55 mmol) and 4-(5-nitropyridin-2-yloxy)phenylamine (11.6 g, 50 mmol) under ice cooling. The resulting solution was stirred for 6 hours at room temperature. The reaction solution was concentrated under reduced pressure. To the residue was added ethyl acetate, and washed with a saturated sodium bicarbonate solution and brine. The organic layer was left for standing overnight at room temperature, and the resulting precipitated crystals were collected by suction filtration, to thereby yield 12.8 g of the title compound.
Appearance: White powder
¹H NMR (CDCl$_3$) δ 2.53 (4H, brs), 2.64-2.65 (4H, m), 3.15 (2H, s), 3.46 (2H, s), 5.95 (2H, s), 6.76 (2H, brs), 6.86 (1H, s), 7.04 (1H, d, J=9.1 Hz), 7.14 (2H, d, J=8.7 Hz), 7.67 (2H, d, J=8.9 Hz), 8.47 (1H, dd, J=9.1 Hz, 2.8 Hz), 9.03 (1H, d, J=2.8 Hz), 9.24 (1H, brs).

Reference Example 292

Production of ethyl{methanesulfonyl[3-methoxy-4-(5-nitropyridin-2-yloxy)phenyl]amino}acetate A solution of ethyl[3-methoxy-4-(5-nitropyridin-2-yloxy)phenylamino]acetate (2.43 g, 7.00 mmol) was dissolved in THF (15 mL), dichloromethane (20 mL) and DMF (10 mL), and to the resulting solution were added triethylamine (1.95 mL, 13.99 mmol), 4-dimethylaminopyridine (0.86 g, 7.00 mmol) and methanesulfonyl chloride (1.08 mL, 13.99 mmol) under ice cooling. The resulting solution was stirred for 14 hours at 30° C. Water was added to the reaction mixture, and extracted with dichloromethane. The dichloromethane layer was washed with water and brine. The dichloromethane layer was dried over anhydrous magnesium sulfate, evaporated, and the residue was purified by silica gel column chromatography (ethyl acetate:n-hexane=1:2), to thereby yield 1.10 g of the title compound.
Appearance: Yellow oil
¹H NMR (CDCl$_3$) δ 1.32 (3H, t, J=7.3 Hz), 3.18 (3H, s), 3.75 (3H, s), 4.26 (2H, q, J=7.3 Hz), 4.49 (2H, s), 7.09 (1H, d, J=9.1 Hz), 7.15 (2H, d, J=1.2 Hz), 7.25 (1H, s), 8.48 (1H, dd, J=9.1 Hz, 2.8 Hz), 8.98 (1H, d, J=2.8 Hz).

The following compounds were produced in the same manner as in Reference Example 292.

TABLE 43

| Reference Example No. | Chemical Structure | ¹H NMR(solvent) δ ppm or MS |
|---|---|---|
| 293 | (structure) | ¹H NMR(DMSO-d$_6$) 3.00(3H, s), 5.17(2H, s), 7.05(1H, d, J=8.4 Hz), 7.12(2H, d, J=8.9 Hz), 7.19–7.26(4H, m), 7.67(2H, d, J=8.9 Hz), 7.95(1H, dd, J=8.4 Hz, 2.5 Hz), 8.25(1H, d, J=2.3 Hz), 9.69(1H, brs). |
| 294 | (structure) | ¹H NMR(CDCl$_3$) 2.18(3H, s), 3.04(3H, s), 5.04(2H, s), 6.56(1H, brs), 6.96(1H, d, J=8.6 Hz), 7.01–7.09(4H, m), 7.15(1H, d, J=2.6 Hz), 7.56(2H, d, J=8.4 Hz), 7.79(1H, dd, J=8.6 Hz, 2.5 Hz), 8.19(1H, d, J=2.5 Hz). |

TABLE 43-continued

| Reference Example No. | Chemical Structure | $^1$H NMR(solvent) δ ppm or MS |
|---|---|---|
| 295 | [structure: methanesulfonamide-pyridine-O-phenyl-CH2CH2-COOC2H5] | MS 364(M+) |

Reference Example 296

Production of 3-[4-(5-nitropyridin-2-yloxy)phenyl]-n-propanol

To a solution of 3-[4-(5-nitropyridin-2-yloxy)phenyl]propionic acid (2.64 g, 9.2 mmol) in THF (50 mL) was added dropwise a 1 M borane-THF complex THF solution (38.4 mL, 38.4 mmol) under ice cooling. The reaction solution was stirred for 2 hours at room temperature. Water was added to the reaction mixture, and extracted with ethyl acetate, and the ethyl acetate layer was washed with water and then brine. The ethyl acetate layer was dried over anhydrous magnesium sulfate, after which solvent was evaporated, and the residue was purified by silica gel column chromatography (n-hexane:ethyl acetate=1:1), to thereby yield 1.17 g of the title compound.

Appearance: Green oil
$^1$H NMR (CDCl$_3$) δ 1.90-1.96 (2H, m), 2.73-2.79 (2H, m), 3.69-3.74 (2H, m), 7.00-7.09 (3H, m), 7.26-7.30 (2H, m), 8.44-8.49 (1H, m), 9.05 (1H, d, J=2.6 Hz).

Reference Example 297

Production of 2-{4-[3-(t-butyldimethylsilanyloxy)propyl]phenoxy}-5-nitropyridine To a solution of 3-[4-(5-nitropyridin-2-yloxy)phenyl]-n-propanol (1.17 g, 4.3 mmol) in DMF (10 mL) were added imidazole (580 mg, 8.5 mmol) and t-butylchlorodimethylsilane (640 mg, 4.2 mmol), and the resulting solution was stirred for 13 hours at room temperature. Water was added to the reaction mixture, and extracted with diethyl ether, and the diethyl ether layer was washed with water and then brine. The diethyl ether layer was dried over anhydrous magnesium sulfate, evaporated, and the residue was purified by silica gel column chromatography (n-hexane:ethyl acetate=5:1), to thereby yield 1.14 g of the title compound.

Appearance: Pale yellow powder
$^1$H NMR (CDCl$_3$) δ 0.07 (6H, s), 0.92 (9H, s), 1.84-1.89 (2H, m), 2.69-2.75 (2H, m), 3.66 (2H, t, J=6.3 Hz), 6.99-7.08 (3H, m), 7.27 (2H, d, J=7.6 Hz), 8.46 (1H, dd, J=8.9 Hz, 3.0 Hz), 9.05 (1H, d, J=3.0 Hz).

The following compound was produced in the same manner as in Reference Example 297.

Reference Example 298

2-{4-[2-(t-Butyldimethylsilanyloxy)ethyl]phenoxy}-5-nitropyridine $^1$H NMR (CDCl$_3$) δ 0.00 (6H, s), 0.88 (9H, s), 2.86 (2H, t, J=6.9 Hz), 3.84 (2H, t, J=6.9 Hz), 7.00 (1H, d, J=9.2 Hz), 7.05-7.08 (2H, m), 7.26-7.31 (2H, m), 8.46 (1H, dd, J=9.2 Hz, 3.0 Hz), 9.05 (1H, d, J=3.0 Hz).

Reference Example 299

Production of ethyl 4-[4-(5-nitropyridin-2-yloxy)phenyl]butanoate

To a solution of 4-[4-(5-nitropyridin-2-yloxy)phenyl]butanoic acid (9.98 g, 33.01 mmol) in dichloromethane were added ethanol (5.59 mL, 99.01 mmol), 4-dimethylaminopyridine (400 mg, 3.27 mmol), triethylamine (13.81 mL, 99.08 mmol) and 1-ethyl-3-(3-dimethylaminopropyl)carbodiimide hydrochloride (7.6 g, 39.65 mmol) under ice cooling, and the resulting solution was stirred for 20 minutes under ice cooling and then for 1 hour at room temperature. The reaction solution was concentrated under reduced pressure. Water was added to the residue, and extracted with ethyl acetate, and the ethyl acetate layer was washed with 1 N hydrochloric acid, a saturated sodium bicarbonate solution and brine. The ethyl acetate layer was dried over anhydrous magnesium sulfate, evaporated, and the residue was purified by silica gel column chromatography (n-hexane:ethyl acetate=5:1), to thereby yield 6.77 g of the title compound.

Appearance: Colorless oil
$^1$H NMR (CDCl$_3$) δ 1.27 (3H, t, J=7.0 Hz), 1.99 (2H, dt, J=15.0 Hz, 7.5 Hz), 2.36 (2H, t, J=7.5 Hz), 2.70 (2H, t, J=7.5 Hz), 4.14 (2H, q, J=7.0 Hz), 7.01 (1H, d, J=9.0 Hz), 7.08 (2H, d, J=8.5 Hz), 7.26 (2H, d, J=8.5 Hz), 8.46 (1H, dd, J=9.0 Hz, 3.0 Hz), 9.04 (1H, d, J=3.0 Hz).

Reference Example 300

Production of methyl 3-[4-(5-nitropyridin-2-ylsulfanyl)phenyl]propionate

To a solution of 3-[4-(5-nitropyridin-2-ylsulfanyl)phenyl] propionic acid (86.0 g, 0.283 mmol) in DMF (1 mL) were added potassium carbonate (59.0 mg, 0.424 mmol) and methyl iodide (0.0260 mL, 0.424 mmol), and the resulting solution was stirred for 1 hour at room temperature. Water was added to the reaction mixture, and then cooled with ice. The precipitated solid matter was collected by filtration, to thereby yield 76.9 mg of the title compound.

Appearance: Light brown powder
$^1$H NMR (DMSO-d$_6$) δ 2.70 (2H, t, J=7.6 Hz), 2.94 (2H, t, J=7.6 Hz), 3.60 (3H, s), 7.07 (1H, d, J=8.9 Hz), 7.43 (2H, d, J=8.1 Hz), 7.57 (2H, d, J=8.1 Hz), 8.39 (1H, dd, J=2.7 Hz, 8.9 Hz), 9.17 (1H, d, J=2.7 Hz).

Reference Example 301

Production of ethyl(Z)-3-[4-(5-nitro-2-pyridyloxy)phenyl]-2-butenoate

To a suspension of 60% sodium hydride (1.28 g, 32.0 mmol) in THF (80 mL) was added dropwise a solution of triethyl phosphonoacetate (8.71 g, 38.8 mmol) in THF (40 mL) under ice cooling, and the resulting solution was stirred for 10 minutes at the same temperature. To the reaction solution was added 4-[(5-nitro-2-pyridyl)oxy]acetophenone (5.90 g, 22.8 mmol) and the resulting solution was stirred at the same temperature for 10 minutes, and then stirred at room temperature for 60 hours. To the reaction solution was added saturated ammonium chloride and extracted with ethyl acetate. The ethyl acetate layer was washed with a saturated sodium bicarbonate solution, and then washed with brine. The ethyl acetate layer was dried over anhydrous magnesium sulfate, evaporated, and the residue was purified by silica gel column chromatography (n-hexane:ethyl acetate=5:1), to thereby yield 1.17 g of the title compound.

Appearance: Colorless needles $^1$H NMR (CDCl$_3$) δ 1.13 (3H, t, J=7.1 Hz), 2.20 (3H, d, J=1.4 Hz), 4.02 (2H, q, J=7.1 Hz), 5.93 (1H, q, J=1.4 Hz), 7.02 (1H, d, J=9.0 Hz), 7.12 (2H, d, J=8.6 Hz), 7.29 (2H, d, J=8.6 Hz), 8.45 (1H, dd, J=9.0 Hz, 2.8 Hz), 9.03 (1H, d, J=2.8 Hz).

The following compounds were produced in the same manner as in Reference Example 301.

Reference Example 302

Ethyl(E)-3-{4-[4-(3,4-dichlorobenzoylamino)-2-fluorophenoxy]phenyl}acrylate

Melting point: 166-167° C.

acetone)palladium (0) (27.2 mg, 0.0472 mmol) and tri(2-furyl)phosphine (43.9 mg, 0.189 mmol), and subsequently added a solution of 4-[2-ethoxycarbonyl)ethyl]benzoyl chloride (0.379 g, 1.57 mmol) in toluene (5 mL). The resulting reaction solution was stirred for 4 hours at 80° C. To the reaction solution was added saturated aqueous potassium fluoride and stirred for 0.5 hours at room temperature. Insoluble matter was then filtered off. The filtrate was extracted with ethyl acetate, and the ethyl acetate layer was washed with brine. The ethyl acetate layer was dried over anhydrous magnesium sulfate, evaporated, and the residue was purified by silica gel column chromatography (n-hexane→n-hexane:ethyl acetate=4:1), to thereby yield 0.323 g of the title compound.

Appearance: Pale yellow powder $^1$H NMR (CDCl$_3$) δ 1.22 (3H, t, J=7.1 Hz), 2.65 (2H, t, J=7.7 Hz), 3.03 (2H, t, J=7.7 Hz), 4.12 (2H, q, J=7.1 Hz), 7.34 (2H, d, J=8.3 Hz), 8.00 (2H, d, J=8.3 Hz), 8.18 (1H, d, J=8.5 Hz), 8.65 (1H, dd, J=8.5 Hz, 2.6 Hz), 9.49 (1H, d, J=2.6 Hz).

Reference Example 307

Production of ethyl 3-[4-(4-aminophenoxy)phenyl]propionate

To a suspension of 5% palladium-carbon (0.50 g) in ethanol (50 mL) was added ethyl 3-[4-(4-nitrophenoxy)phenyl]propionate (5.00 g, 15.9 mmol), and the resulting solution was subjected to catalytic reduction at atmospheric pressure

TABLE 44

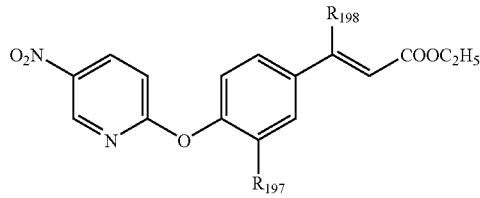

| Reference Example No. | R$_{197}$ | R$_{198}$ | $^1$H NMR(CDCl$_3$) δ ppm or MS |
|---|---|---|---|
| 303 | —H | —H | $^1$H NMR 1.35(3H, t, J=7.1 Hz), 4.28(2H, q, J=7.1 Hz), 6.43(1H, d, J=16.0 Hz), 7.09(1H, d, J=8.9 Hz), 7.20(2H, d, J=8.7 Hz), 7.62(2H, d, J=8.7 Hz), 7.70(1H, d, J=16.0 Hz), 8.50(1H, dd, J=8.9 Hz, 2.5 Hz), 9.04(1H, d, J=2.5 Hz). |
| 304 | —H | —CH$_3$ | $^1$H NMR 1.31(3H, t, J=7.1 Hz), 2.58(3H, d, J=1.2 Hz), 4.21(2H, q, J=7.1 Hz), 6.14(1H, q, J=1.2 Hz), 7.05(1H, d, J=9.0 Hz), 7.16(2H, d, J=8.7 Hz), 7.55(2H, d, J=8.7 Hz), 8.48(1H, dd, J=9.0 Hz, 2.8 Hz), 9.03(1H, d, J=2.8 Hz). |
| 305 | —CH$_3$ | —H | MS 328(M+) |

Reference Example 306

Production of ethyl 3-[4-(5-nitropyridine-2-carbonyl)phenyl]propionate

A solution of bis(tributyltin) (1.37 g, 2.36 mmol) in toluene (7 mL) was added under an argon atmosphere to 2-chloro-5-nitropyridine (0.325 g, 2.05 mmol), bis(dibenzylideneacetone)palladium (0) (18.1 mg, 0.0315 mmol), tri(2-furyl)phosphine (29.3 mg, 0.126 mmol) and molecular sieves 4A (1.90 g), and the resulting solution was heated to reflux for 1 hour. To the reaction solution was added bis(dibenzylideneand at room temperature. Once the absorption of hydrogen had stopped, the catalyst was removed by filtration, and the filtrate was concentrated under reduced pressure, to thereby yield 4.52 g of the title compound.

Appearance: Light brown oil $^1$H NMR (CDCl$_3$) δ 1.22 (3H, t, J=7.1 Hz), 2.57 (2H, t, J=7.8 Hz), 2.88 (2H, t, J=7.8 Hz), 3.55 (2H, brs), 4.10 (2H, q, J=7.1 Hz), 6.64 (2H, d, J=8.8 Hz), 6.78-6.86 (4H, m), 7.08 (2H, d, J=8.6 Hz).

The following compounds were produced in the same manner as in Reference Example 307.

TABLE 45

$R_{199}-O-\text{Ph}-R_{200}$

| Reference Example No. | $R_{199}$ | $R_{200}$ | $^1$H NMR(CDCl$_3$) δ ppm |
|---|---|---|---|
| 308 | 4-NH$_2$Ph— | 2-(CH$_2$)$_2$COOCH$_3$ | 2.66(2H, t, J=7.8 Hz), 3.00(2H, t, J=7.8 Hz), 3.54(2H, brs), 3.63(3H, s), 6.65(2H, d, J=8.8 Hz), 6.70(1H, d, J=8.1 Hz), 6.79(2H, d, J=8.8 Hz), 6.94(1H, t, J=8.1 Hz), 7.08(1H, t, J=8.1 Hz), 7.19(1H, d, J=8.1 Hz). |
| 309 | 4-NH$_2$Ph— | 3-(CH$_2$)$_2$COOC$_2$H$_5$ | 1.21(3H, t, J=7.2 Hz), 2.56(2H, t, J=7.9 Hz), 2.87(2H, t, J=7.9 Hz), 3.54(2H, brs), 4.10(2H, q, J=7.2 Hz), 6.66(2H, d, J=8.8 Hz), 6.70–6.76(2H, m), 6.79–6.87(3H, m), 7.16(1H, t, J=7.8 Hz). |
| 310 | 2-NH$_2$Ph— | 4-(CH$_2$)$_2$COOC$_2$H$_5$ | 1.22(3H, t, J=7.2 Hz), 2.56(2H, t, J=7.8 Hz), 2.89(2H, t, J=7.8 Hz), 3.55(2H, brs), 4.11(2H, q, J=7.2 Hz), 6.72(1H, t, J=7.8 Hz), 6.79–6.92(4H, m), 6.93(1H, t, J=7.8 Hz), 7.12(2H, d, J=8.5 Hz). |
| 311 | 4-NH$_2$Ph— | 4-COOC$_2$H$_5$ | 1.37(3H, t, J=7.1 Hz), 4.36(2H, q, J=7.1 Hz), 4.00–4.50(2H, m), 6.78(2H, d, J=8.9 Hz), 6.89–6.95(4H, m), 7.97(2H, d, J=8.9 Hz). |
| 312 | 3-NH$_2$Ph— | 4-(CH$_2$)$_2$COOC$_2$H$_5$ | 1.22(3H, t, J=7.2 Hz), 2.59(2H, t, J=7.8 Hz), 2.91(2H, t, J=7.8 Hz), 3.65(2H, brs), 4.12(2H, q, J=7.2 Hz), 6.29(1H, t, J=2.2 Hz), 6.32–6.41(2H, m), 6.92(2H, d, J=8.6 Hz), 7.06(1H, t, J=8.0 Hz), 7.13(2H, d, J=8.6 Hz). |
| 313 | 5-amino-2-methylpyridin-yl (H$_2$N-pyridine-CH$_3$) | 3-COOCH$_3$ | 3.56(2H, brs), 3.89(3H, s), 6.80(1H, dd, J=8.6 Hz, 0.7 Hz), 7.11(1H, dd, J=8.6 Hz, 3.0 Hz), 7.25–7.29(1H, m), 7.39–7.44(1H, m), 7.69–7.72(2H, m), 7.78–7.82(1H, m). |

TABLE 46

H$_2$N—Ph(F)—O—Ph—R$_{201}$

| Reference Example No. | $R_{201}$ | Form | $^1$H NMR(solvent) δ ppm |
|---|---|---|---|
| 314 | —Ac | hydrochloride | (DMSO-d$_6$) 2.53(3H, s), 3.30–4.20(3H, m), 6.88(1H, d, J=8.8 Hz), 6.99–7.05(3H, m), 7.22(1H, t, J=8.8 Hz), 7.96(1H, d, J=8.9 Hz). |
| 315 | —CH$_2$COOCH$_3$ | free | (CDCl$_3$) 3.57(2H, s), 3.60–3.80(5H, m), 6.41(1H, ddd, J=1.2 Hz, 2.6 Hz, 8.6 Hz), 6.50(1H, dd, J=2.6 Hz, 12.0 Hz), 6.80–6.95(3H, m), 7.18(2H, d, J=8.4 Hz). |
| 316 | —(CH$_2$)$_2$COOC$_2$H$_5$ | free | (CDCl$_3$) 1.21(3H, t, J=7.1 Hz), 2.56(2H, t, J=7.8 Hz), 2.87(2H, t, J=7.8 Hz), 3.66(2H, brs), 4.10(2H, q, J=7.1 Hz), 6.34–6.43(1H, m), 6.48(1H, dd, J=12.0 Hz, 2.7 Hz), 6.77–6.93(3H, m), 7.08(2H, d, J=8.7 Hz). |
| 317 | —H | free | (CDCl$_3$) 3.66(2H, brs), 6.35–6.44(1H, m), 6.49(1H, dd, J=12.0 Hz, 2.7 Hz), 6.83–6.96(3H, m), 7.O1(1H, dd, J=9.0 Hz, 8.0 Hz), 7.26(2H, d, J=8.0 Hz). |
| 318 | —(CH$_2$)$_3$COOC$_2$H$_5$ | free | (CDCl$_3$) 1.23(3H, t, J=7.1 Hz), 1.83–1.97(2H, m), 2.28(2H, t, J=7.5 Hz), 2.57(2H, t, J=7.6 Hz), 3.66(2H, brs), |

TABLE 46-continued

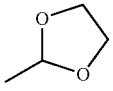

| Reference Example No. | $R_{201}$ | Form | $^1$H NMR(solvent) δ ppm |
|---|---|---|---|
| 319 | —COOC$_2$H$_5$ | free | 4.09(2H, q, J=7.1 Hz), 6.34–6.43(1H, m), 6.48(1H, dd, J=12.0 Hz, 2.7 Hz), 6.81(2H, d, J=8.5 Hz), 6.88(1H, dd, J=9.0 Hz, 8.0 Hz), 7.05(2H, d, J=8.5 Hz). (DMSO-d$_6$) 1.29(3H, t, J=7.1 Hz), 4.27(2H, q, J=7.1 Hz), 5.42(2H, brs), 6.41(1H, dt, J=1.6 Hz, 8.6 Hz), 6.50(1H, dd, J=2.5 Hz, 13.3 Hz), 6.90–7.00(3H, m), 7.91(2H, d, J=9.7 Hz). |
| 320 | —NHCH$_2$COOC$_2$H$_5$ | free | (CDCl$_3$) 1.29(3H, t, J=7.1 Hz), 3.62(2H, s), 3.86(2H, s), 4.12(1H, s), 4.23(2H, q, J=7.1 Hz), 6.35–6.39(1H, m), 6.48(1H, dd, J=2.7 Hz, 12.1 Hz), 6.55(2H, d, J=8.9 Hz), 6.80–6.85(3H, m). |
| 321 | ![dioxolane] | free | (CDCl$_3$) 3.70(2H, brs), 3.95–4.15(4H, m), 5.76(1H, s), 6.38–6.42(1H, m), 6.49(1H, dd, J=2.7 Hz, 14.7 Hz), 6.85–6.93(3H, m), 7.39(2H, d, J=8.7 Hz). |

TABLE 47

| Reference Example No. | $R_{202}$ | $R_{203}$ | $R_{204}$ | $^1$H NMR (CDCl$_3$) δppm |
|---|---|---|---|---|
| 322 | —H | —H | —C$_2$H$_5$ | 1.38(3H, t, J=7.3Hz), 4.35(2H, q, J=7.3Hz), 6.82(1H, d, J=8.6Hz), 7.04-7.14(3H, m), 7.75(1H, d, J=3.0Hz), 8.01-8.04(2H, m). |
| 323 | —H | —H | —CH$_3$ | 3.30(2H, brs), 3.89(3H, s), 6.82(1H, d, J=8.6 Hz), 7.04-7.13(3H, m), 7.75(1H, d, J=3.0Hz), 8.02(2H, dd, J=6.6Hz, 2.0Hz). |
| 324 | —F | —H | —CH$_3$ | 357(2H, brs), 3.91(3H, s), 6.87(1H, d, J=8.6Hz), 7.10-7.23(2H, m), 7.64(1H, d, J=3.0Hz), 7.80-7.82(1H, m), 7.83-7.85(1H, m). |
| 325 | —F | —H | —C$_2$H$_5$ | 1.38(3H, t, J=7.1Hz), 4.37(2H, q, J=7.1Hz), 6.87(1H, d, J=8.6Hz), 7.12(1H, dd, J=8.6Hz, 3.0 Hz), 7.15-7.22(1H, m), 7.64(1H, d, J=3.0Hz), 7.81-7.86(2H, m). |
| 326 | —CH$_3$ | —H | —CH$_3$ | 2.29(3H, s), 3.56(2H, brs), 3.89(3H, s), 6.79(1H, d, J=8.6Hz), 6.92(1H, d, J=8.6Hz), 7.11(1H, dd, J=8.6 Hz, 3.0Hz), 7.71(1H, d, J=3.0Hz), 7.85(1H, dd, J=8.6Hz, 2.4Hz), 7.94(1H, d, J=2.4Hz). |
| 327 | —OCH$_3$ | —H | —C$_2$H$_5$ | 1.38(3H, t, J=7.1Hz), 3.55(2H, brs), 3.85(3H, s), 4.37(2H, q, J=7.1Hz), 6.79-6.83(1H, m), 7.02-7.10(2H, m), 7.63-7.67(3H, m). |
| 328 | —H | —OCH$_3$ | —CH$_3$ | 3.63(2H, brs), 3.86(6H, s), 6.54-6.58(1H, m), 6.68(1H, d, J=2.2Hz), 6.81-6.84(1H, m), 7.13(1H, dd, J=8.6 Hz, 3.0Hz), 7.77(1H, dd, J=3.0Hz, 0.5Hz), 7.83(1H, d, J=8.9Hz). |
| 329 | —H | —CH$_3$ | —CH$_3$ | 2.58(3H, s), 3.63(2H, brs), 3.86(3H, s), 6.80-6.88(3H, m), 7.13(1H, dd, J=8.6Hz, 3.0Hz), 7.75(1H, d, J=3.0Hz), 7.92-7.96(1H, m). |
| 330 | —Cl | —H | —CH$_3$ | 3.62(2H, brs), 3.91(3H, s), 6.88(1H, d, J=8.6Hz), 7.08-7.15(2H, m), 7.68(1H, d, J=3.0Hz), 7.91(1H, dd, J=8.6Hz, 2.1Hz), 8.13(1H, d, J=2.1Hz). |

TABLE 48

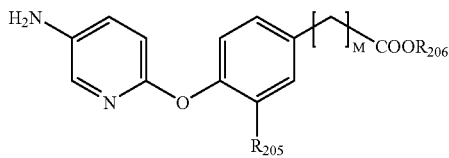

| Reference Example No. | R205 | R206 | M | ¹H NMR (CDCl₃) δppm or MS |
|---|---|---|---|---|
| 331 | —H | —CH₃ | 2 | MS 272(M⁺) |
| 332 | —OCH₃ | —C₂H₅ | 2 | ¹H NMR 1.25(3H, t, J=7.1Hz), 2.63(2H, t, J=7.5Hz), 2.94(2H, t, J=7.5Hz), 3.43(2H, brs), 3.77(3H, s), 4.14(2H, q, J=7.1Hz), 6.71-6.86(3H, m), 6.98(1H, d, J=8.0Hz), 7.06(1H, dd, J=8.6Hz, 2.9Hz), 7.65(1H, d, J=2.9Hz). |
| 333 | —H | —CH₃ | 1 | ¹H NMR 3.60(2H, s), 3.69(3H, s), 6.76(1H, d, J=8.6Hz), 6.99-7.10(3H, m), 7.24-7.27(2H, m), 7.71(1H, d, J=3.0 Hz). |
| 334 | —H | —C₂H₅ | 2 | ¹H NMR 1.21(3H, t, J=7.1Hz), 2.58(2H, t, J=7.7Hz), 2.90(2H, t, J=7.7Hz), 4.11(2H, q, J=7.1Hz), 6.72(1H, d, J=8.6Hz), 6.95(2H, d, J=8.5Hz), 7.05(1H, dd, J=8.6Hz, 3.0Hz), 7.14(2H, d, J=8.5Hz), 7.68(1H, d, J=3.0Hz). |
| 335 | —OCH₃ | —CH₃ | 2 | ¹H NMR 2.62-2.68(2H, m), 2.91-2.97(2H, m), 3.45(2H, brs), 3.69(3H, s), 3.77(3H, s), 6.74-6.79(2H, m), 6.82(1H, d, J=1.8Hz), 6.98(1H, d, J=7.9Hz), 7.04-7.26(1H, m), 7.64(1H, d, J=3.0Hz). |
| 336 | —OC₂H₅ | —C₂H₅ | 2 | ¹H NMR 1.20(3H, t, J=7.0Hz), 1.25(3H, t, J=7.1Hz), 2.51-2.68(2H, m), 2.81-3.01(2H, m), 3.19-3.63(2H, m), 3.98(2H, q, J=7.0Hz), 4.14(2H, q, J=7.1Hz), 6.69-6.83(3H, m), 6.95-7.09(2H, m), 7.60-7.67(1H, m). |
| 337 | —F | —C₂H₅ | 2 | ¹H NMR 1.25(3H, t, J=7.1Hz), 2.52-2.71(2H, m), 2.86-3.02(2H, m), 3.47(2H, brs), 4.14(2H, q, J=7.1Hz), 6.81(1H, d, J=8.6Hz), 6.93-7.04(2H, m), 7.05-7.13(2H, m), 7.63(1H, d, J=2.9Hz). |
| 338 | —H | —C₂H₅ | 4 | ¹H NMR 1.25(3H, t, J=7.2Hz), 1.55-1.80(4H, m), 2.32(2H, t, J=7.0Hz), 2.60(2H, t, J=7.0Hz), 3.49(2H, brs), 4.12(2H, q, J=7.2Hz), 6.74(1H, d, J=8.5Hz), 6.97(2H, d, J=8.5Hz), 7.06(1H, dd, J=8.5Hz, 3.0Hz), 7.14(2H, d, J=8.5Hz), 7.71(1H, d, J=3.0Hz). |
| 339 | —H | —C₂H₅ | 3 | ¹H NMR 1.26(3H, t, J=7.5Hz), 1.94(2H, dt, J=15.0 Hz, 7.5Hz), 2.33(2H, t, J=7.5Hz), 2.63(2H, t, J=7.5 Hz), 3.50(2H, brs), 4.13(2H, q, J=7.0Hz), 6.75(1H, d, J=8.5Hz), 6.98(2H, d, J=8.5Hz), 7.07(1H, dd, J=8.5 Hz, 3.0Hz), 7.15(2H, d, J=8.5Hz), 7.72(1H, d, J=3.0 Hz). |

TABLE 49

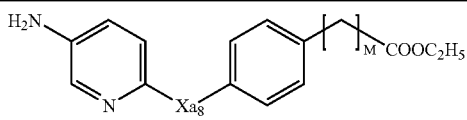

| Reference Example No. | Xa₈ | M | Form | ¹H NMR (solvent) δppm |
|---|---|---|---|---|
| 340 | —NH— | 2 | free | (CDCl₃) 1.24(3H, t, J=7.1Hz), 2.60(2H, t, J=7.6Hz), 2.90(2H, t, J=7.6Hz), 3.35(2H, brs), 4.13(2H, q, J=7.1Hz), 6.16(1H, brs), 6.77(1H, d, J=8.6Hz), 6.98(1H, dd, J=2.9Hz, 8.6Hz), 7.00-7.15(4H, m), 7.78(1H, d, J=2.9Hz). |
| 341 | —N(CH₃)— | 0 | hydrochloride | (DMSO-d₆) 1.30(3H, t, J=7.1Hz), 3.43(3H, s), 4.28(2H, q, J=7.1Hz), 7.03(1H, d, J=9.1Hz), 7.30(2H, d, J=8.6Hz), 7.55(1H, d, J=9.1Hz), 7.93(2H, d, J=8.6Hz), 8.05(1H, s). |
| 342 | —N(CH₃)— | 2 | free | (CDCl₃) 1.24(3H, t, J=7.2Hz), 2.63(2H, t, J=7.7Hz), 2.95(2H, t, J=7.7Hz), 3.53(3H, s), 4.14(2H, q, J=7.2Hz), 6.52(1H, d, J=9.5Hz), 7.07(1H, dd, J= |

TABLE 49-continued

| Reference Example No. | Xa₈ | M | Form | ¹H NMR (solvent) δppm |
|---|---|---|---|---|
| | | | | 2.7Hz, 9.5Hz), 7.10(2H, d, J=8.3Hz), 7.22(2H, d, J=8.3Hz), 7.83(1H, d, J=2.7Hz). |
| 343 | —N(CH₂Ph)— | 2 | dihydrochloride | (CDCl₃) 1.22(3H, t, J=7.1Hz), 2.57(2H, t, J=7.7Hz), 2.90(2H, t, J=7.7Hz), 4.11(2H, q, J=7.1Hz), 5.28(2H, s), 6.65(1H, d, J=8.8Hz), 7.08(2H, d, J=7.8Hz), 7.15-7.24(7H, m), 8.27(1H, d, J=8.8Hz), 8.80(1H, s). |
| 344 | —CO— | 2 | free | (CDCl₃) 1.21(3H, t, J=7.1Hz), 2.63(2H, t, J=7.7Hz), 2.98(2H, t, J=7.7Hz), 4.10(2H, q, J=7.1Hz), 7.18(2H, brs), 7.27(2H, d, J=8.1Hz), 7.32(1H, d, J=8.3Hz), 7.88-7.99(3H, m), 8.27(1H, s). |

(—CO— means a group of $\overset{O}{\underset{}{\|}}$ . Hereinafter —CO— indicates the same meaning.)

TABLE 50

| Reference Example No. | R₂₀₇ | R₂₀₈ | R₂₀₉ | M | ¹H NMR (solvent) δppm |
|---|---|---|---|---|---|
| 345 | —H | —H | —C(CH₃)₃ | 0 | (CDCl₃) 1.51(9H, s), 3.49(2H, brs), 6.41(1H, brs), 6.72(1H, d, J=8.6Hz), 7.00(2H, d, J=8.9Hz), 7.06(1H, dd, J=8.6Hz, 3.0Hz), 7.32(2H, d, J=8.9Hz), 7.69(1H, d, J=3.0Hz). |
| 346 | —H | —Ac | —C₂H₅ | 1 | (CDCl₃) 1.27(3H, t, J=7.1Hz), 1.94(3H, s), 3.60(2H, brs), 4.18(2H, q, J=7.1Hz), 4.35(2H, s), 6.82(1H, d, J=8.6Hz), 7.07(2H, d, J=8.8Hz), 7.12(1H, dd, J=3.0Hz, 8.6Hz), 7.31(2H, d, J=8.8Hz), 7.73(1H, d, J=3.0Hz). |
| 347 | —H | —Ac | —C₂H₅ | 2 | (CDCl₃) 1.23(3H, t, J=7.1Hz), 1.85(3H, s), 2.57(2H, t, J=7.4Hz), 3.60(2H, s), 3.98(2H, t, J=7.4Hz), 4.07(2H, q, J=7.1Hz), 6.82(1H, d, J=8.6Hz), 7.08(2H, d, J=8.8Hz), 7.10-7.15(3H, m), 7.74(1H, d, J=3.0Hz). |
| 348 | —CH₃ | —Ac | —C₂H₅ | 1 | (CDCl₃) 1.28(3H, t, J=7.1Hz), 1.95(3H, s), 2.23(3H, s), 3.52(2H, s), 4.19(2H, q, J=7.1Hz), 4.34(2H, s), 6.73(1H, d, J=8.6Hz), 6.91(1H, d, J=8.4Hz), 7.05-7.15(2H, m), 7.20(1H, s), 7.66(1H, s). |
| 349 | —H | —CH₃ | —CH₃ | 1 | (CDCl₃) 3.05(3H, s), 3.45(2H, brs), 3.72(3H, s), 4.05(2H, s), 6.67(3H, d, J=9.0Hz), 6.98(2H, d, J=2.0Hz), 7.04(1H, dd, J=8.6Hz, 3.0Hz), 7.69(1H, d, J=2.0Hz). |
| 350 | —H | —CH₃ | —C₂H₅ | 1 | (CDCl₃) 1.25(3H, t, J=7.1Hz), 3.05(3H, s), 3.45(2H, brs), 4.03(2H, s), 4.18(2H, q, J=7.1Hz), 6.65-6.69(3H, m), 6.96(2H, d, J=9.0Hz), 7.04(1H, dd, J=2.9Hz, 8.6Hz), 7.69(1H, d, J=2.9Hz). |
| 351 | —H | —C₂H₅ | —C₂H₅ | 1 | (CDCl₃) 1.20(3H, t, J=7.2Hz), 1.26(3H, t, J=7.2Hz), 3.40-3.46(4H, m), 3.99(2H, s), 4.19(2H, q, J=7.2Hz), 6.63(2H, d, J=9.1Hz), 6.67(1H, |

TABLE 50-continued

Structure: H₂N-pyridine-O-phenyl(R₂₀₇)-N(R₂₀₈)-(CH₂)ₘ-COOR₂₀₉

| Reference Example No. | R₂₀₇ | R₂₀₈ | R₂₀₉ | M | ¹H NMR (solvent) δppm |
|---|---|---|---|---|---|
| | | | | | d, J=8.6Hz), 6.95(2H, d, J=9.1Hz), 7.04(1H, dd, J=3.2Hz, 8.6Hz), 7.69(1H, d, J=3.2Hz). |
| 352 | —CH₃ | —CH₃ | —C₂H₅ | 1 | (CDCl₃) 1.26(3H, t, J=7.1Hz), 2.13(3H, s), 3.05(3H, s), 3.41(2H, brs), 4.02(2H, s), 4.19(2H, q, J=7.1Hz), 6.46-6.68(3H, m), 6.89(1H, d, J=8.6Hz), 7.03(1H, dd, J=8.6Hz, 3.0Hz), 7.67(1H, d, J=3.0Hz). |
| 353 | —OCH₃ | —CH₃ | —C₂H₅ | 1 | (CDCl₃) 1.26(3H, t, J=7.1Hz), 3.07(3H, s), 3.42(2H, brs), 3.75(3H, s), 4.04(2H, s), 4.19(2H, q, J=7.1Hz), 6.24(1H, dd, J=8.7Hz, 2.8Hz), 6.33(1H, d, J=2.8Hz), 6.67(1H, d, J=8.6Hz), 6.95(1H, d, J=8.7Hz), 7.02(1H, dd, J=8.6Hz, 3.0Hz), 7.63(1H, d, J=2.8Hz). |
| 354 | —OCH₃ | —C₂H₅ | —C₂H₅ | 1 | (DMSO-d₆) 1.13(3H, t, J=7.1Hz), 1.20(3H, t, J=7.1Hz), 3.41(2H, q, J=7.1Hz), 3.63(3H, s), 4.09-4.17(4H, m), 4.81(2H, brs), 6.11(1H, dd, J=8.7Hz, 2.8Hz), 6.26(1H, d, J=2.8Hz), 6.55(1H, d, J=8.6Hz), 6.79(1H, d, J=8.7Hz), 6.99(1H, dd, J=8.7Hz, 3.0Hz), 7.40(1H, d, J=2.3Hz). |

TABLE 51

Structure: H₂N-phenyl-O-phenyl-R₂₁₀

| Reference Example No. | R₂₁₀ | ¹H NMR (CDCl₃) δppm |
|---|---|---|
| 355 | 4-methylpiperazinyl-COOC(CH₃)₃ | 1.48(9H, s), 3.04(4H, t, J=5.0Hz), 3.54(2H, brs), 3.57(4H, t, J=5.0Hz), 6.65(2H, d, J=9.0Hz), 6.82(2H, d, J=9.0Hz), 6.88(4H, ABq, J=9.0Hz). |
| 356 | 1-methylpiperidin-4-yl-O-CH₂-O-CH₃ | 1.78(2H, m), 2.03(2H, m), 2.86(2H, m), 3.39(3H, s), 3.42(2H, m), 3.52(2H, brs), 3.70(1H, m), 4.72(2H, s), 6.64(2H, d, J=9.0Hz), 6.82(2H, d, J=9.0Hz), 6.88(4H, ABq, J=9.0Hz). |
| 357 | 1-methylpiperidin-4-yl-COOC₂H₅ | 1.27(3H, t, J=7.0Hz), 1.88(2H, dq, J=3.5Hz, 12.5Hz), 2.03(2H, dd, J=12.5Hz, 3.0Hz), 2.40(1H, m), 2.72(2H, dt, J=2.5Hz, 12.0Hz), 3.51-3.53(4H, m), 4.16(2H, q, J=7.0Hz), 6.65(2H, d, J=8.5Hz), 6.82(2H, d, J=8.5Hz), 6.88(4H, s). |
| 358 | 1-methylpiperidin-4-yl-N(CH₃)-COOC(CH₃)₃ | 1.48(9H, s), 1.74(2H, brd, J=11.5Hz), 1.85(2H, m), 2.74(2H, m), 2.77(3H, s), 3.53(2H, brs), 3.60(2H, brd, J=12.0Hz), 4.12(1H, brs), 6.65(2H, d, J=8.5Hz), 6.82(2H, d, J=8.5Hz), 6.87(4H, s). |
| 359 | 1-methylpiperidin-4-yl-O-CH₂-COOC₂H₅ | 1.30(3H, t, J=7.0Hz), 1.81(2H, m), 2.03(2H, m), 2.84(1H, m), 2.95(1H, m), 3.35(1H, m), 3.44(1H, m), 3.54(3H, m), 4.15(2H, s), 4.23(2H, q, J=7.0Hz), 6.65(2H, d, J=9.0Hz), 6.82(2H, d, J=9.0Hz), 6.88(4H, s). |

TABLE 51-continued

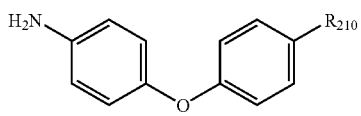

| Reference Example No. | $R_{210}$ | $^1$H NMR (CDCl$_3$) δppm |
|---|---|---|
| 360 | 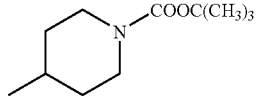 | 1.48(9H, s), 1.60(2H, m), 1.80(2H, m), 2.59(1H, m), 2.78(2H, brs), 3.57(2H, brs), 4.23(2H, brs), 4.12(1H, brs), 6.67(2H, d, J=9.0Hz), 6.86(2H, d, J=9.0Hz), 6.87(2H, d, J=9.0Hz), 7.09(2H, d, J=9.0Hz). |

TABLE 52

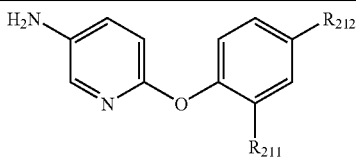

| Reference Example No. | $R_{211}$ | $R_{212}$ | $^1$H NMR (CDCl$_3$) δppm or MS |
|---|---|---|---|
| 361 | —H | —Ac | $^1$H NMR 2.50(3H, s), 3.60(2H, brs), 6.80-7.90(7H, m). |
| 362 | —H | —NHCONHPh | $^1$H NMR 3.55(2H, s), 6.76(1H, d, J=8.6Hz), 6.89(1H, s), 6.95-7.02(3H, m), 7.03-7.12(2H, m), 7.21-7.36(6H, m), 6.68(1H, d, J=2.9Hz). |
| 363 | —H | 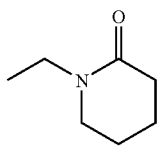 | $^1$H NMR 1.70-1.90(4H, m), 2.18(2H, brs), 2.40-2.50(2H, m), 3.13-3.29(2H, m), 4.56(2H, s), 6.76(1H, d, J=8.6Hz), 7.01(2H, d, J=8.6Hz), 7.09(1H, dd, J=8.6Hz, 3.0Hz), 7.23(2H, d, J=8.6Hz), 7.72(1H, d, J=3.0Hz). |
| 364 | —H | —CH(CH$_3$)COOCH$_3$ | MS 272(M$^+$) |
| 365 | —H | —C(CH$_3$)$_2$COOCH$_3$ | MS 286(M$^+$) |
| 366 | —H | 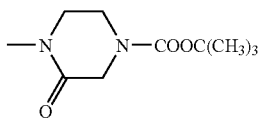 | $^1$H NMR 1.50(9H, s), 3.55(2H, brs), 3.72(2H, m), 3.78(2H, m), 4.25(2H, s), 6.80(1H, d, J=8.6Hz), 7.08(2H, d, J=8.9Hz), 7.10(1H, dd, J=8.6Hz, 3.0Hz), 7.24(2H, d, J=8.9Hz), 7.72(1H, d, J=3.0Hz). |
| 367 | —H | 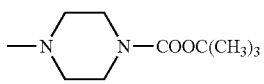 | $^1$H NMR 1.48(9H, s), 3.07(4H, brs), 3.47(2H, brs), 3.57(4H, t, J=5.0Hz), 6.72(1H, d, J=8.5Hz), 6.92(2H, d, J=9.0Hz), 7.00(2H, d, J=9.0Hz), 7.06(1H, dd, J=8.5Hz, 3.0Hz), 7.70(1H, d, J=3.0Hz). |
| 368 | —H | 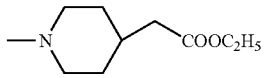 | $^1$H NMR 1.27(3H, t, J=7.0Hz), 1.44(2H, dq, J=4.0Hz, 12.5Hz), 1.83(2H, brd, J=13.0Hz), 1.91(1H, m), 2.28(2H, d, J=7.0Hz), 2.70(2H, dt, J=2.5Hz, 12.0Hz), 3.46(2H, brs), 3.57(2H, brd, J=12.0Hz), 4.15(2H, q, J=7.0Hz), 6.69(1H, d, J=8.5Hz), 6.92(2H, d, J=9.0Hz), 6.97(2H, d, J=9.0Hz), 7.05(2H, dd, J=8.5Hz, 3.0Hz), 7.70(1H, d, J=3.0Hz). |
| 369 | —CH$_3$ | 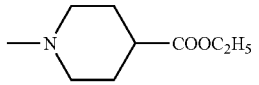 | $^1$H NMR 1.27(3H, t, J=7.1Hz), 1.86-2.05(4H, m), 2.14(3H, s), 2.35-2.44(1H, m), 2.69-2.79(2H, m), 3.43(2H, brs), 3.55-3.59(2H, m), 4.16(2H, q, J=7.1Hz), 6.62(1H, d, J=8.6Hz), 6.74-6.82(2H, m), 6.89(1H, d, J=8.6Hz), 7.03(1H, dd, J=8.6Hz, 3.0Hz), 7.68(1H, d, J=3.0Hz). |

TABLE 52-continued

Structure: H₂N-pyridine-O-phenyl(R₂₁₁, R₂₁₂)

| Reference Example No. | R₂₁₁ | R₂₁₂ | ¹H NMR (CDCl₃) δppm or MS |
|---|---|---|---|
| 370 | —OCH₃ | piperidine-CH₂-COOC₂H₅ | ¹H NMR 1.27(3H, t, J=7.1Hz), 1.38-1.50(2H, m), 1.87-2.06(3H, m), 2.29(2H, d, J=7.1Hz), 2.69-2.77(2H, m), 3.42(2H, brs), 3.58(2H, d, J=12.2Hz), 3.75(3H, s), 4.15(2H, q, J=7.1Hz), 6.49(1H, dd, J=8.6Hz, 2.6Hz), 6.59(1H, d, J=2.6Hz), 6.70(1H, d, J=8.6Hz), 6.96(1H, d, J=8.6Hz), 7.04(1H, dd, J=8.6Hz, 3.0Hz), 7.65(1H, d, J=3.0Hz). |
| 371 | —CH₃ | piperidine-CH₂-COOC₂H₅ | ¹H NMR 1.27(3H, t, J=7.1Hz), 1.37-1.49(2H, m), 1.80-2.04(3H, m), 2.13(3H, s), 2.28(2H, d, J=6.9 Hz), 2.69(2H, dd, J=12.0Hz, 9.9Hz), 3.41-3.59(4H, m), 4.15(2H, q, J=7.3Hz), 6.60(1H, d, J=8.6Hz), 6.73-6.81(2H, m), 6.88(1H, d, J=8.6Hz), 7.02(1H, dd, J=8.6Hz, 3.0Hz), 7.66(1H, d, J=2.8 Hz). |

TABLE 53

Structure: H₂N-pyridine-O-phenyl(R₂₁₃)

| Reference Example No. | R₂₁₃ | ¹H NMR (CDCl₃) δppm |
|---|---|---|
| 372 | 1,3-dioxolan-2-yl | 3.51(2H, brs), 3.94-4.12(4H, m), 5.78(1H, s), 6.73(1H, d, J=8.6Hz), 6.99-7.09(3H, m), 7.43(2H, d, J=8.5Hz), 7.70(1H, d, J=2.7Hz). |
| 373 | —(CH₂)₃—O—Si(CH₃)₂—C(CH₃)₃ | 0.05(6H, s), 0.91(9H, s), 1.77-1.88(2H, m), 2.62-2.68(2H, m), 3.62-3.66(2H, m), 6.73(1H, d, J=8.9 Hz), 6.95-7.17(5H, m), 7.72(1H, d, J=3.0Hz). |
| 374 | —(CH₂)₂—O—Si(CH₃)₂—C(CH₃)₃ | −0.07(6H, s), 0.81(9H, s), 2.73(2H, t, J=7.3Hz), 3.72(2H, t, J=7.3Hz), 6.66(1H, dd, J=8.6Hz, 0.7 Hz), 6.88-6.92(2H, m), 6.99(1H, dd, J=8.6Hz, 3.0 Hz), 7.10(2H, d, J=8.6Hz), 7.64(1H, d, J=3.0Hz). |
| 375 | morpholino | 3.09-3.13(4H, m), 3.84-3.87(4H, m), 6.71(1H, d, J=8.6Hz), 6.90(2H, d, J=8.9Hz), 7.02(2H, d, J=9.2 Hz), 7.05(1H, dd, J=8.6Hz, 3.0Hz), 7.69(1H, d, J=3.0Hz) |
| 376 | thiazolidine-2,4-dione-5-yl-CH₂ | 3.12(1H, dd, J=14.2Hz, 9.8Hz), 3.52(1H, dd, J=14.2Hz, 3.8Hz), 3.70(2H, s), 4.51(1H, dd, J=9.8 Hz, 3.8Hz), 6.78(1H, d, J=8.6Hz), 7.02(2H, d, J=8.6Hz), 7.09(1H, dd, J=8.6Hz, 3.1Hz), 7.20(2H, d, J=8.6Hz), 7.71(1H, d, J=3.1Hz), 7.98(1H, brs). |
| 377 | —CH=C(COOCH₃)₂ | 3.84(3H, s), 3.85(3H, s), 6.82(1H, d, J=8.3Hz), 7.03(2H, d, J=8.9Hz), 7.02-7.10(1H, m), 7.42(2H, d, J=8.9Hz), 7.70-7.76(2H, m). |

TABLE 53-continued

Structure: H₂N-pyridine-O-phenyl-R₂₁₃ (5-amino-2-(4-R₂₁₃-phenoxy)pyridine)

| Reference Example No. | R₂₁₃ | ¹H NMR (CDCl₃) δppm |
|---|---|---|
| 378 | 1-methylpiperidine-4-COOC₂H₅ | 1.27(3H, t, J=7.0Hz), 1.88(2H, m), 2.02(2H, m), 2.40(1H, m), 2.75(2H, dt, J=3.0Hz, 12.0Hz), 3.46(2H, brs), 3.56(2H, dt, J=13.0Hz, 3.0Hz), 4.15(2H, q, J=7.0Hz), 6.70(1H, d, J=8.5Hz), 6.92(2H, d, J=9.0Hz), 6.98(2H, d, J=9.0Hz), 7.05(1H, dd, J=8.5Hz, 3.0Hz), 7.70(1H, d, J=3.0 Hz). |
| 379 | 1-methylpiperidine-3-COOC₂H₅ | 1.28(3H, t, J=7.0Hz), 1.66-1.72(2H, m), 1.82(1H, m), 2.01(1H, m), 2.68(1H, m), 2.78(1H, m), 2.99(1H, dd, J=12.0Hz, 10.0Hz), 3.39(1H, brd, J=12.0 Hz), 3.47(2H, brs), 3.62(1H, dd, J=12.0Hz, 4.0 Hz), 4.17(2H, q, J=7.0Hz), 6.70(1H, d, J=8.5Hz), 6.94(2H, d, J=Hz), 6.98(2H, d, J=9.0Hz), 7.06(1H, dd, J=8.5Hz, 3.0Hz), 7.70(1H, d, J=3.0 Hz). |
| 380 | —CH(CH₃)CH₂COOC₂H₅ | 1.18(3H, t, J=7.2Hz), 1.27(3H, d, J=7.0Hz), 2.43-2.60(2H, m), 3.19-3.29(1H, m), 3.48(2H, brs), 4.06(2H, q, J=7.2Hz), 6.72(1H, d, J=8.7Hz), 6.96(2H, d, J=8.6Hz), 7.05(1H, dd, J=8.7Hz, 3.0 Hz), 7.16(2H, d, J=8.6Hz), 7.70(1H, d, J=3.0Hz). |

TABLE 54

Structure: H₂N-pyridine-O-R₂₁₄ (5-amino-2-(O-R₂₁₄)pyridine)

| Reference Example No. | R₂₁₄ | ¹H NMR (CDCl₃) δppm or MS |
|---|---|---|
| 381 | 3-(3-methylphenyl)-1-[4-(1,3-benzodioxol-5-ylmethyl)piperazin-1-yl]propan-1-one moiety | MS 460(M⁺) |
| 382 | 2-hydroxy-2-(4-methylphenyl)-1-(4-benzylpiperazin-1-yl)ethanone moiety | ¹H NMR 1.90-2.03(1H, m), 2.20-2.55(3H, m), 3.11-3.25(1H, m), 3.25-3.38(1H, m), 3.43(2H, s), 3.57(2H, s), 3.60-3.88(2H, m), 4.70(1H, d, J=6.5 Hz), 5.18(1H, d, J=6.5Hz), 6.76(1H, d, J=8.6Hz), 7.02(2H, d, J=8.5Hz), 7.08(1H, dd, J=8.5Hz, 3.0Hz), 7.20-7.35(7H, m), 7.73(1H, dd, J=3.1Hz, 0.5Hz). |
| 383 | N-methyl-N-(4-methylphenyl)-4-benzylpiperazine-1-carboxamide moiety | ¹H NMR 2.25(4H, t, J=5.0Hz), 3.19(3H, s), 3.22(4H, t, J=5.0Hz), 3.43(2H, s), 3.56(2H, brs), 6.77(1H, d, J=8.6Hz), 7.00(2H, d, J=9.2Hz), 7.05(2H, d, J=9.2Hz), 7.09(1H, dd, J=8.6Hz, 2.8Hz), 7.17-7.35(5H, m), 7.72(1H, d, J=2.8Hz). |

TABLE 54-continued

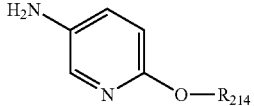

| Reference Example No. | R$_{214}$ | $^1$H NMR (CDCl$_3$) δppm or MS |
|---|---|---|
| 384 | 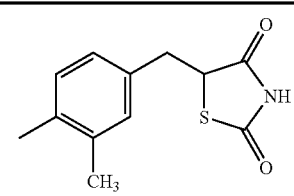 | $^1$H NMR 2.20(3H, s), 3.07(1H, dd, J=14.2Hz, 10.1Hz), 3.50(2H, brs), 3.52(1H, dd, J=14.2Hz, 3.8Hz), 4.51(1H, dd, J=10.1Hz, 3.8Hz), 6.73(1H, d, J=8.5Hz), 6.90(1H, d, J=8.5Hz), 7.03(1H, dd, J=8.5Hz, 3.0Hz), 7.08(1H, dd, J=8.5Hz, 3.0Hz), 7.10(1H, d, J=3.0Hz), 7.67(1H, d, J=3.0Hz), 8.10(1H, brs). |
| 385 | 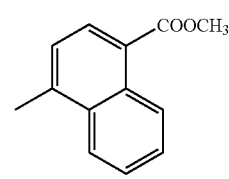 | $^1$H NMR 3.62(2H, brs), 3.97(3H, s), 6.86(1H, d, J=8.6Hz), 7.12(1H, dd, J=8.6Hz, 3.0Hz), 7.32(1H, dd, J=8.9Hz, 2.5Hz), 7.41(1H, d, J=2.1Hz), 7.72-7.75(2H, m), 7.92(1H, d, J=8.9Hz), 8.02(1H, dd, J=8.6Hz, 1.7Hz), 8.56(1H, s). |
| 386 | 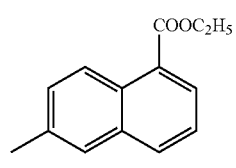 | $^1$H NMR 3.63(2H, brs), 3.98(3H, s), 6.90(1H, d, J=8.6Hz), 6.94(1H, d, J=8.2Hz), 7.15(1H, dd, J=8.7Hz, 3.0Hz), 7.54-7.57(1H, m), 7.62-7.68(1H, m), 7.77(1H, d, J=3.0Hz), 8.18(1H, d, J=8.2Hz), 8.32-8.35(1H, m, 9.03(1H, d, J=8.7Hz). |
| 387 | (6-methyl-naphthalene-1-COOC$_2$H$_5$) | $^1$H NMR 1.45(3H, t, J=7.1Hz), 3.57(2H, brs), 4.47(2H, q, J=7.1Hz), 6.83(1H, d, J=8.6Hz), 7.12(1H, dd, J=8.6Hz, 3.1Hz), 7.38(1H, dd, J=9.4Hz, 2.6Hz), 7.43-7.49(2H, m), 7.75(1H, d, J=3.0Hz), 7.89(1H, d, J=8.2Hz), 8.10(1H, dd, J=7.3Hz, 1.3Hz), 8.93(1H, d, J=9.4Hz). |

TABLE 55

| Reference Example No. | R$_{215}$ | R$_{216}$ | R$_{217}$ | Xa$_9$ | Xa$_{10}$ | $^1$H NMR (CDCl$_3$) δppm or MS |
|---|---|---|---|---|---|---|
| 388 | —H | —CH$_3$ | piperonyl | —CH$_2$— | —CH$_2$— | MS 474(M$^+$) |
| 389 | —H | —F | benzyl | none | none | $^1$H NMR 2.46(4H, brs), 3.54(6H, brs), 6.83(1H, d, J=8.7Hz), 7.09(1H, dd, J=8.6Hz, 3.0Hz), 7.16-7.36(8H, m), 7.61(1H, d, J=3.0Hz). |
| 390 | —H | —OCH$_3$ | piperonyl | —CH$_2$— | —CH$_2$— | $^1$H NMR 2.31-2.41(4H, m), 2.59-2.65(2H, m), 2.92-2.98(2H, m), 3.41(4H, brs), 3.62-3.65(2H, m), 3.76(3H, s), 5.95(2H, s), 6.71-6.79(4H, m), 6.83-6.85(2H, m), 6.97(1H, d, J=8.1Hz), 7.06(1H, dd, J=8.7Hz, 3.0Hz), 7.63(1H, d, J=2.8Hz). |

TABLE 55-continued

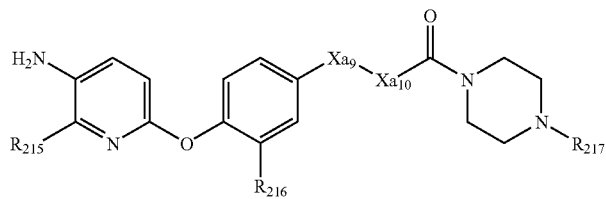

| Reference Example No. | $R_{215}$ | $R_{216}$ | $R_{217}$ | $Xa_9$ | $Xa_{10}$ | $^1$H NMR (CDCl$_3$) δppm or MS |
|---|---|---|---|---|---|---|
| 391 | —H | —H | —COOC(CH$_3$)$_3$ | —CH$_2$— | —CH(OH)— | $^1$H NMR 1.47(9H, s), 2.81-2.98(2H, m), 3.01-3.20(1H, m), 3.29(3H, brs), 3.39(2H, brs), 3.51(2H, brs), 3.58-3.78(3H, m), 4.58(1H, q, J=7.0Hz), 6.75(1H, d, J=8.8 Hz), 6.99(2H, d, J=8.6Hz), 7.07(1H, dd, J=8.8Hz, 3.0 Hz), 7.19(2H, d, J=8.6Hz), 7.67(1H, d, J=3.0Hz). |
| 392 | —CH$_3$ | —H | piperonyl | —CH$_2$— | —CH$_2$— | MS 474(M$^+$) |

TABLE 56

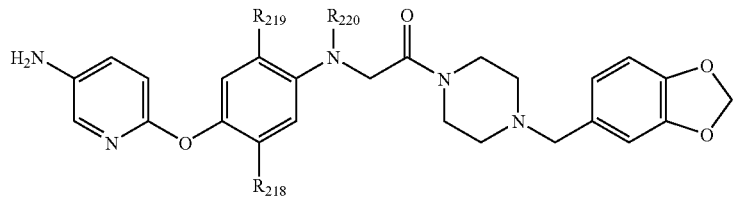

| Reference Example No. | $R_{218}$ | $R_{219}$ | $R_{220}$ | $^1$H NMR (CDCl$_3$) δppm or MS |
|---|---|---|---|---|
| 393 | —H | —H | —H | $^1$H NMR 2.42-2.49(4H, m), 3.42-3.48(4H, m), 3.66-3.72(2H, m), 3.86(2H, d, J=4.3 Hz), 4.82(1H, t, J=4.3Hz), 5.96(2H, s), 6.62(2H, d, J=8.8Hz), 6.68(1H, d, J=8.6 Hz), 6.73-6.78(2H, m), 6.86(1H, d, J=1.0 Hz), 6.95(1H, d, J=8.8Hz), 7.05(1H, dd, J=3.0Hz, 8.6Hz), 7.69(1H, d, J=3.0Hz) |
| 394 | —H | —H | —Ac | $^1$H NMR 1.94(3H, s), 2.45-2.55(4H, m), 3.45-3.70(8H, m), 4.42(2H, s), 5.95(2H, s), 6.75-6.85(3H, m), 6.92(1H, s), 7.04(2H, d, J=8.8Hz), 7.12(1H, dd, J=3.0Hz, 8.6 Hz), 7.36(2H, d, J=8.8Hz), 7.72(1H, d, J=3.0Hz). |
| 395 | —H | —H | —COC$_2$H$_5$ | $^1$H NMR 1.06(3H, t, J=7.5Hz), 2.17(2H, q, J=7.5Hz), 2.40-2.45(4H, m), 3.41(4H, s), 3.59(2H, s), 4.42(2H, s), 5.94(2H, s), 6.70-6.75(2H, m), 6.80-6.85(2H, m), 7.04(2H, d, J=8.7Hz), 7.11(1H, dd, J=3.1 Hz, 8.6Hz), 7.36(2H, d, J=8.7Hz), 7.72(1H, d, J=3.1Hz). |
| 396 | —H | —H | ![cyclopropyl ketone structure] | $^1$H NMR 0.60-1.55(5H, m), 2.39(4H, brs), 3.42(4H, brs), 3.55(2H, brs), 4.46(2H, brs), 5.94(2H, s), 6.69-6.75(2H, m), 6.77-6.85(2H, m), 7.00-7.15(2H, m), 7.40-7.46(2H, m), 7.72(1H, s). |
| 397 | —H | —H | cyclopropyl | $^1$H NMR 0.60-0.66(2H, m), 0.77-0.83(2H, m), 2.42-2.44(4H, m), 2.77-2.79(1H, m), 3.43-3.52(6H, m), 3.59-3.62(2H, m), |

TABLE 56-continued

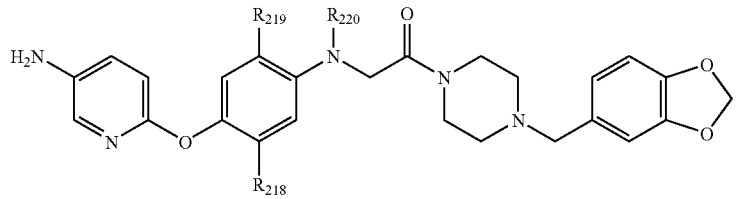

| Reference Example No. | R<sub>218</sub> | R<sub>219</sub> | R<sub>220</sub> | $^1$H NMR (CDCl$_3$) δppm or MS |
|---|---|---|---|---|
| | | | | 4.16(2H, s), 5.95(2H, s), 6.66(1H, d, J=8.6 Hz), 6.75(2H, s), 6.86-6.97(5H, m), 7.03(1H, dd, J=8.6Hz, 2.8Hz), 7.70(1H, d, J=2.8 Hz). |
| 398 | —CH$_3$ | —CH$_3$ | —C$_2$H$_5$ | MS 517(M$^+$) |
| 399 | —COOCH$_3$ | —H | —C$_2$H$_5$ | MS 547(M$^+$) |

TABLE 57

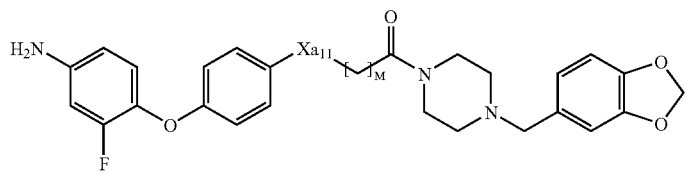

| Reference Example No. | Xa$_{11}$ | M | $^1$H NMR (CDCl$_3$) δppm |
|---|---|---|---|
| 400 | —NH— | 0 | 2.40-2.50(4H, m), 3.40-3.55(6H, m), 3.68(2H, brs), 5.95(2H, s), 6.27(1H, s), 6.30-6.55(2H, m), 6.65-6.95(5H, m), 7.20-7.30(2H, m). |
| 401 | —NH— | 1 | 2.40-2.50(4H, m), 3.35-3.45(4H, m), 3.55-3.70(4H, m), 3.83(2H, d, J=4.4Hz), 4.72(1H, t, J=4.4Hz), 5.95(2H, s), 6.30-6.40(1H, m), 6.45-6.60(3H, m), |
| 402 | —N(Ac)— | 1 | 1.91(3H, s), 2.40-2.50(4H, m), 3.45-3.75(8H, m), 4.41(2H, s), 5.94(2H, s), 6.40-6.52(2H, m), 6.70-6.75(2H, m), 6.80-6.95(4H, m), 7.28(2H, d, J=9.0Hz). |
| 403 | —O— | 1 | 2.41(4H, brs), 3.42(2H, s), 3.50-3.80(6H, m), 4.63(2H, s), 5.94(2H, s), 6.40(1H, ddd, J=1.2Hz, 2.6Hz, 7.4Hz), 6.50(1H, dd, J=2.6Hz, 12.1Hz), 6.65-6.75(2H, m), 6.80-6.95(6H, m). |

Reference Example 404

Production of methyl 3-[(4-hydroxyphenyl)methylamino]-propionate

Methyl 3-[(4-benzyloxyphenyl)methylamino]-propionate (27.3 g, 91.1 mmol) was dissolved in ethanol (300 mL), and the resulting solution was cooled with ice and 10% palladium-carbon (3.0 g) was added. The resulting solution was stirred for 4.5 hours at room temperature under a hydrogen atmosphere. The reaction solution was filtered through Celite to remove insoluble matter, and the filtrate was concentrated under reduced pressure to thereby yield 19.1 g of the title compound.

Appearance: Red oil
$^1$H NMR (CDCl$_3$) δ 2.51-2.56 (2H, m), 2.83 (3H, brs), 3.57 (2H, brs), 3.66 (3H, s), 4.99 (1H, brs), 6.71-6.74 (4H, m).

The following compounds were produced in the same manner as in Reference Example 404.

Reference Example 405

Ethyl[acetyl(4-hydroxyphenyl)amino]acetate $^1$H NMR (CDCl$_3$) δ 1.26 (3H, t, J=7.1 Hz), 1.92 (3H, s), 4.19 (2H, q, J=7.1 Hz), 4.34 (2H, s), 6.16 (1H, s), 6.87 (2H, d, J=8.8 Hz), 7.21 (2H, d, J=8.8 Hz).

TABLE 58

| Reference Example No. | Chemical Structure | mp (° C.) or ¹H NMR (CDCl₃) δppm |
|---|---|---|
| 406 | 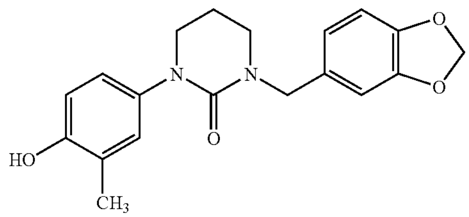 | mp 172.0-173.0 |
| 407 | 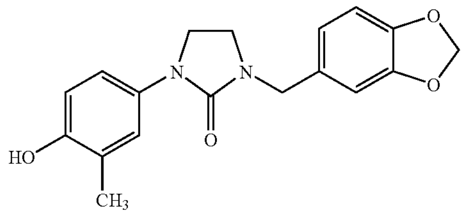 | ¹H NMR 2.24(3H, s), 3.25-3.39(2H, m), 3.66-3.81(2H, m), 4.36(2H, s), 4.93(1H, s), 5.95(2H, s), 6.71(1H, d, J=8.6Hz), 6.77(2H, d, J=0.6Hz), 6.83(1H, s), 7.15(1H, dd, J=2.8 Hz, 8.6Hz), 7.32(1H, d, J=2.8 Hz). |
| 408 | 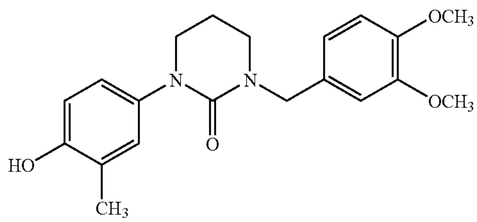 | ¹H NMR 1.94-2.12(2H, m), 2.08(3H, s), 3.29(2H, t, J=6.0Hz), 3.58(2H, t, J=6.0Hz), 3.89(3H, s), 3.93(3H, s), 4.57(2H, s), 6.34(1H, d, J=8.4Hz), 6.71(1H, dd, J=2.6 Hz, 8.4Hz), 6.75-6.93(3H, m), 6.96(1H, d, J=1.3Hz), 7.61(1H, s). |
| 409 | 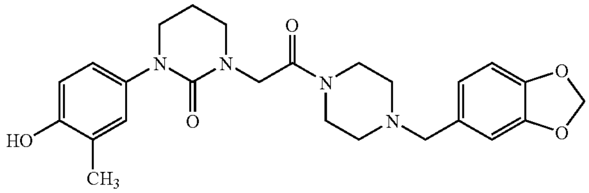 | ¹H NMR 2.07(3H, s), 2.09-2.18(2H, m), 2.37-2.50(4H, m), 3.41(2H, s), 3.43-3.54(4H, m), 3.54-3.68(4H, m), 4.22(2H, s), 5.94(2H, s), 6.35(1H, d, J=8.4Hz), 6.62-6.77(3H, m), 6.83(1H, d, J=1.1 Hz), 6.88(1H, d, J=2.4Hz). |
| 410 | 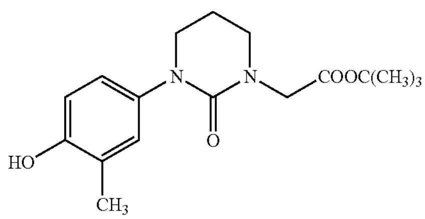 | ¹H NMR 1.49(9H, s), 2.07(3H, s), 2.07-2.21(2H, m), 3.45(2H, t, J=5.9Hz), 3.61(2H, t, J=5.9Hz), 4.07(2H, s), 6.33(1H, d, J=8.4Hz), 6.71(1H, dd, J=2.6Hz, 8.4Hz), 6.87(1H, d, J=2.6Hz), 7.26(1H, s). |

Reference Example 411

Production of [4-(5-aminopyridin-2-yloxy)phenyl](4-piperonylpiperazin-1-yl)methanone

[4-(5-nitropyridin-2-yloxy)phenyl](4-piperonylpiperazin-1-yl)methanone (0.36 g, 0.78 mmol) was dissolved in a mixed solvent consisting of ethanol (5 mL) and THF (5 mL). To the resulting solution was added 5% platinum-carbon (0.06 g), and stirred at room temperature under a hydrogen atmosphere. Two hours later, the 5% platinum-carbon was removed by filtration, and the solvent was evaporated under reduced pressure, to thereby yield 0.32 g of the title compound.

Appearance: Pale yellow amorphous powder

¹H NMR (CDCl₃) δ 2.43 (4H, brs), 3.44 (2H, s), 3.58 (6H, brs), 5.95 (2H, s), 6.74 (2H, s), 6.80 (1H, d, J=8.6 Hz), 6.85 (1H, s), 7.05 (2H, d, J=8.6 Hz), 7.10 (1H, dd, J=8.6 Hz, 3.0 Hz), 7.40 (2H, d, J=8.7 Hz), 7.74 (1H, d, J=2.6 Hz).

The following compounds were produced in the same manner as in Reference Example 411.

Reference Example 412

4-[5-(4-Trifluoromethylphenoxymethyl)pyridin-2-yloxy]phenylamine

¹H NMR (CDCl₃) δ 3.63 (2H, brs), 5.02 (2H, s), 6.70 (2H, d, J=8.9 Hz), 6.88 (1H, d, J=8.4 Hz), 6.94 (2H, d, J=8.9 Hz), 7.01 (2H, d, J=8.6 Hz), 7.55 (2H, d, J=8.4 Hz), 7.72 (1H, dd, J=8.4 Hz, 2.5 Hz), 8.22 (1H, d, J=2.3 Hz).

Reference Example 413

3-Methyl-4-[5-(4-trifluoromethylphenoxymethyl)pyridin-2-yloxy]phenylamine $^1$H NMR (CDCl$_3$) δ 2.08 (3H, s), 3.58 (2H, brs), 5.02 (2H, s), 6.65 (1H, dd, J=8.2 Hz, 2.8 Hz), 6.60 (1H, d, J=2.8 Hz), 6.83-6.87 (2H, m), 7.02 (2H, d, J=8.9 Hz), 7.56 (2H, d, J=9.1 Hz), 7.72 (1H, dd, J=8.6 Hz, 2.5 Hz), 8.21 (1H, d, J=2.5 Hz).

Reference Example 414

2-{[4-(4-Aminophenoxy)phenyl]methylamino}-1-(4-piperonylpiperazin-1-yl)ethanone $^1$H NMR (CDCl$_3$) δ 2.41 (4H, t, J=5.1 Hz), 2.99 (3H, s), 3.42 (2H, s), 3.48 (2H, t, J=4.8 Hz), 3.50 (2H, brs), 3.62 (2H, t, J=4.8 Hz), 4.04 (2H, s), 5.95 (2H, s), 6.61-6.68 (4H, m), 6.73-6.88 (7H, m).

Reference Example 415

2-{[3-(5-Aminopyridin-2-yloxy)phenyl]methylamino}-1-(4-piperonylpiperazin-1-yl)ethanone $^1$H NMR (CDCl$_3$) δ 2.40 (4H, t, J=4.9 Hz), 3.00 (3H, s), 3.41 (2H, s), 3.44-3.46 (2H, m), 3.51 (2H, brs), 3.59-3.61 (2H, m), 4.06 (2H, s), 5.95 (2H, s), 6.35-6.45 (3H, m), 6.70-6.74 (3H, m), 6.85 (1H, s), 7.05 (1H, dd, J=8.6 Hz, 3.1 Hz), 7.12-7.18 (1H, m), 7.73 (1H, d, J=3.1 Hz).

TABLE 59

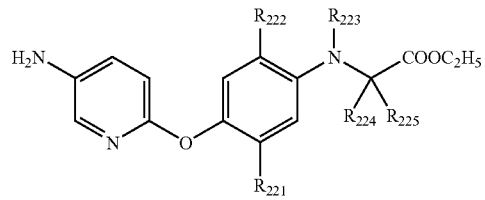

| Reference Example No. | R$_{221}$ | R$_{222}$ | R$_{223}$ | R$_{224}$ | R$_{225}$ | $^1$H NMR (CDCl$_3$) δppm or MS |
|---|---|---|---|---|---|---|
| 416 | —H | —H | —CH$_3$ | —CH$_3$ | —CH$_3$ | $^1$H NMR 1.25(3H, t, J=7.1Hz), 1.38(6H, s), 2.86(3H, s), 3.50(2H, brs), 4.17(2H, q, J=7.1Hz), 6.73(1H, dd, J=8.6Hz, 0.3Hz), 6.93(2H, d, J=9.1Hz), 7.02-7.09(3H, m), 7.73(1H, d, J=3.0Hz). |
| 417 | —F | —H | —CH$_3$ | —H | —H | $^1$H NMR 1.26(3H, t, J=7.1Hz), 3.05(3H, s), 3.44(2H, brs), 4.02(2H, s), 4.19(2H, q, J=7.1Hz), 6.38-6.51(2H, m), 6.75(1H, d, J=8.6 Hz), 7.01-7.13(2H, m), 7.63(1H, d, J=3.0Hz). |
| 418 | —F | —H | —C$_2$H$_5$ | —H | —H | $^1$H NMR 1.16-1.30(6H, m), 3.43(2H, brs), 3.43(2H, q, J=7.1Hz), 3.98(2H, s), 4.21(2H, q, J=7.1Hz), 6.33-6.47(2H, m), 6.75(1H, d, J=8.6 Hz), 6.99-7.09(2H, m), 7.64(1H, d, J=3.0Hz). |
| 419 | —F | —H | —(CH$_2$)$_2$CH$_3$ | —H | —H | $^1$H NMR 0.95(3H, t, J=7.4Hz), 1.27(3H, t, J=7.3Hz), 1.59-1.70(2H, m), 3.31(2H, t, J=7.6z), 3.45(2H, brs), 3.99(2H, s), 4.20(2H, q, J=7.1Hz), 6.32-6.45(2H, m), 6.75(1H, dd, J=8.7Hz, 0.7Hz), 7.04(1H, t, J=9.1Hz), 7.05(1H, dd, J=7.4Hz, 5.8Hz), 7.64(1H, dd, J=3.0Hz, 0.7Hz). |
| 420 | —F | —H | —Ac | —H | —H | $^1$H NMR 1.29(3H, t, J=7.1Hz), 1.98(3H, s), 3.55(2H, brs), 4.21(2H, q, J=7.1Hz), 4.35(2H, s), 6.87(1H, d, J=8.7Hz), 7.10-7.29(4H, m), 7.63(1H, d, J=3.0Hz). |
| 421 | —H | —CF$_3$ | —C$_2$H$_5$ | —H | —H | MS 383(M$^+$) |

TABLE 60

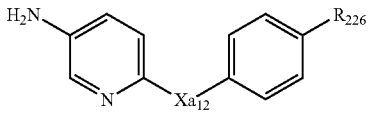

| Reference Example No. | Xa₁₂ | R₂₂₆ | ¹H NMR (CDCl₃) δppm |
|---|---|---|---|
| 422 | —O— | —CH₂CN | 3.54(2H, brs), 3.72(2H, s), 6.79(1H, d, J=8.5Hz), 7.06(2H, d, J=8.9Hz), 7.09(1H, dd, J=8.5Hz, 3.0Hz), 7.30(2H, d, J=8.9Hz), 7.71(1H, d, J=3.0Hz). |
| 423 | —O— | 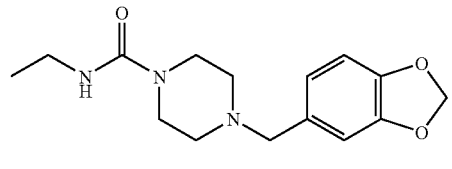 | 2.41(4H, t, J=5.1Hz), 3.38(4H, t, J=5.1Hz), 3.42(2H, s), 3.54(2H, brs), 4.37(2H, d, J=5.1Hz), 4.72(1H, t, J=5.1Hz), 5.94(2H, s), 6.74(2H, s), 6.77(1H, d, J=8.7Hz), 6.85(1H, s), 7.01(2H, d, J=8.5Hz), 7.08(1H, dd, J=8.7Hz, 3.0Hz), 7.28(2H, d, J=8.5Hz), 7.68(1H, d, J=2.8Hz). |
| 424 | —O— | 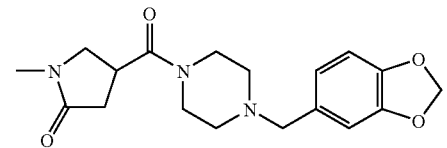 | 2.45-2.47(4H, m), 2.73-2.98(2H, m), 3.45(2H, s), 3.49-3.72(7H, m), 3.85-3.91(1H, m), 4.24-4.30(1H, m), 5.96(2H, s), 6.74-6.78(3H, m), 6.86(1H, s), 7.05-7.11(3H, m), 7.53-7.58(2H, m), 7.70(1H, d, J=3.0Hz). |
| 425 | —O— | 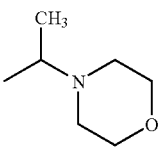 | 1.35(3H, d, J=6.6Hz), 2.37-2.52(4H, m), 3.31(1H, q, J=6.6Hz), 3.67-3.72(4H, m), 6.76(1H, d, J=8.6Hz), 6.99(2H, d, J=8.3Hz), 7.08(1H, dd, J=8.6Hz, 2.3Hz), 7.27(2H, d, J=8.4 Hz), 7.72(1H, d, J=3.0Hz). |
| 426 | —N(CH₃)— | 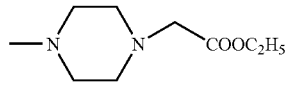 | 1.30(3H, t, J=7.1Hz), 2.76(4H, t, J=5.0Hz), 3.24(4H, t, J=5.0Hz), 3.28(3H, s), 3.35(4H, s), 4.21(2H, q, J=7.1Hz), 6.42(1H, dd, J=8.8Hz, 0.7 Hz), 6.83(1H, dd, J=8.8Hz, 2.9Hz), 6.92(2H, d, J=8.9Hz), 7.10(2H, d, J=8.9Hz), 7.79(1H, dd, J=2.9Hz, 0.7 Hz). |
| 427 | —N(CH₃)— | 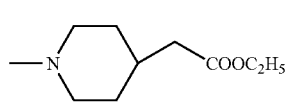 | 1.28(3H, t, J=7.1Hz), 1.46(2H, qd, J=12.3Hz, 3.6Hz), 1.77-2.10(3H, m), 2.29(2H, d, J=6.9Hz), 2.73(2H, td, J=12.3Hz, 2.4Hz), 3.23(2H, brs), 3.35(3H, s), 3.63(2H, d, J=12.3Hz), 4.15(2H, q, 4=7.1Hz), 6.41(1H, d, J=8.9Hz), 6.82(1H, dd, 4=8.9Hz, 3.0 Hz), 6.92(2H, d, J=8.9Hz), 7.09(2H, d, 4=8.9Hz), 7.79(1H, d, J=2.5Hz). |
| 428 | —O— | 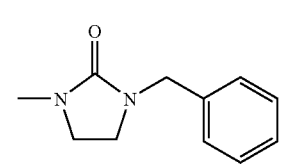 | 3.28-3.42(2H, m), 3.43-3.59(2H, m), 3.71-3.88(2H, m), 4.47(2H, s), 6.73(1H, d, 4=8.6Hz), 7.01-7.11(3H, m), 7.25-7.39(5H, m), 7.51-7.59(2H, m), 7.70(1H, d, 4=2.9Hz). |

TABLE 61

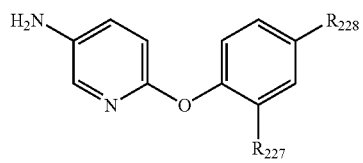

| Reference Example No. | R227 | R228 | 1H NMR (CDCl3) δppm or MS |
|---|---|---|---|
| 429 | —F | (butyryl-piperazinyl-methyl-benzodioxole) | MS 478(M+) |
| 430 | —CH3 | (methyl-oxo-tetrahydropyrimidinyl-methyl-benzodioxole) | 1H NMR 1.96-2.11(2H, m), 2.19(3H, s), 3.29(2H, t, J=5.9Hz), 3.46(2H, s), 3.68(2H, t, J=5.9Hz), 4.52(2H, s), 5.95(2H, s), 6.67(1H, d, J=8.6Hz), 6.73-6.81(2H, m), 6.88(1H, s), 6.93(1H, d, J=8.6Hz), 7.05(1H, dd, J=3.0Hz, 8.6Hz), 7.09(1H, dd, J=2.6Hz, 8.6 Hz), 7.18-7.22(1H, m), 7.00(1H, d, J=3.0Hz). |
| 431 | —CH3 | (methyl-oxo-tetrahydropyrimidinyl-methyl-dimethoxyphenyl) | 1H NMR 1.99-2.11(2H, m), 2.19(3H, s), 3.29(2H, t, J=6.0Hz), 3.47(2H, s), 3.68(2H, d, J=6.0Hz), 3.88(3H, s), 3.88(3H, s), 4.56(2H, s), 6.68(1H, d, J=8.6Hz), 6.82(1H, d, J=8.1Hz), 6.86(1H, dd, J=1.8Hz, 8.1Hz), 6.91(1H, d, J=1.8Hz), 6.93(1H, d, J=8.6Hz), 7.05(1H, dd, J=3.0Hz, 8.6 Hz), 7.09(1H, dd, J=2.6Hz, 8.6Hz), 7.19(1H, d, J=2.6Hz), 7.69(1H, d, J=3.0Hz). |
| 432 | —CH3 | (methyl-oxo-tetrahydropyrimidinyl-acetyl-piperazinyl-methyl-benzodioxole) | 1H NMR 2.10-2.21(2H, m), 2.35-2.48(4H, m), 3.42(2H, s), 3.43-3.54(6H, m), 3.57-3.66(2H, m), 3.73(2H, t, J=5.7 Hz), 4.21(2H, s), 5.95(2H, s), 6.66(1H, d, J=8.6Hz), 6.69-6.77(2H, m), 6.84(1H, d, J=1.2Hz), 6.92(1H, d, J=8.6Hz), 7.02-7.09(2H, m), 7.17(1H, d, J=2.4 Hz), 7.69(1H, d, J=2.8Hz). |
| 433 | —CH3 | (methyl-oxo-tetrahydropyrimidinyl-phenyl-COOC2H5) | 1H NMR 1.38(3H, t, J=7.1Hz), 2.19(3H, s), 2.19-2.38(2H, m), 3.47(2H, s), 3.73-3.93(4H, m), 4.36(2H, q, J=7.1 Hz), 6.67(1H, d, J=8.6Hz), 6.94(1H, d, J=8.6Hz), 7.05(1H, dd, J=3.0Hz, 8.6 Hz), 7.12(1H, dd, J=2.6Hz, 8.6Hz), 7.22(1H, d, J=2.6Hz), 7.40-7.48(2H, m), 7.69(1H, d, J=3.0Hz), 7.95-8.04(2H, m). |
| 434 | —CH3 | (methyl-oxo-tetrahydropyrimidinyl-CH2-COOC(CH3)3) | 1H NMR 1.47(9H, s), 2.05-2.24(5H, m), 3.34-3.54(4H, m), 3.77(2H, t, J=5.8 Hz), 4.04(2H, s), 6.65(1H, d, J=8.6Hz), 6.90(1H, d, J=8.6Hz), 6.99-7.10(2H, m), 7.17(1H, d, J=2.4Hz), 7.68(1H, d, J=3.0Hz). |

TABLE 62

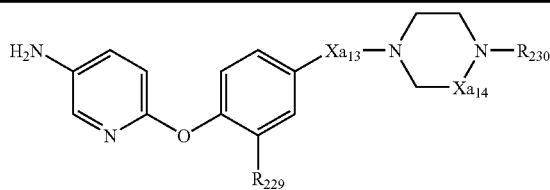

| Reference Example No. | R229 | Xa13 | R230 | Xa14 | ¹H NMR (CDCl₃) δppm |
|---|---|---|---|---|---|
| 435 | —H | —CO— | 3-pyridyl | —CH₂— | 3.23(4H, brs), 3.62(2H, brs), 3.81(4H, brs), 6.83(1H, d, J=8.6 Hz), 7.09(2H, d, J=8.6Hz), 7.12(1H, dd, J=8.6Hz, 3.1Hz), 7.20-7.21(2H, m), 7.45(2H, d, J=8.7 Hz), 7.55(1H, d, J=3.0Hz), 8.14-8.17(1H, m), 8.31-8.33(1H, m). |
| 436 | —H | none | piperonyl | —CO— | 3.37(4H, s), 3.48(2H, brs), 3.90(2H, s), 4.57(2H, s), 5.95(2H, s), 6.72(1H, dd, J=8.5Hz, 0.7Hz), 6.74-6.78(2H, m), 6.78-6.82(1H, m), 6.86(2H, d, J=9.1Hz), 7.02(2H, d, J=9.1Hz), 7.06(1H, dd, J=8.5Hz, 2.9Hz), 7.69(1H, d, J=2.9Hz). |
| 437 | —COOCH₃ | none | benzyl | —CH₂— | 2.58-2.62(4H, m), 3.14-3.18(4H, m), 3.61(2H, s), 3.65(3H, s), 6.63(1H, d, J=8.7Hz), 6.95(1H, d, J=8.9Hz), 7.12-7.18(2H, m), 7.25-7.36(5H, m), 7.41(1H, d, J=3.0Hz), 7.51(1H, d, J=2.8Hz). |
| 438 | —H | —CH₂— | —COOC(CH₃)₃ | —CH₂— | 1.45(9H, s), 2.36-2.40(4H, m), 3.40-3.44(4H, m), 3.47(2H, s), 3.56(2H, brs), 6.76(1H, d, J=8.6Hz), 6.97-7.02(2H, m), 7.08(1H, dd, J=8.6Hz, 3.0Hz), 7.25-7.29(2H, m), 7.71(1H, d, J=3.0Hz). |
| 439 | —H | —CO— | benzyl | —CH₂— | 2.38(4H, brs), 3.33(2H, brs), 3.50(4H, brs), 5.17(2H, brs), 6.82(1H, d, J=8.6Hz), 6.96(2H, d, J=8.7Hz), 7.10(1H, dd, J=8.6Hz, 3.0Hz), 7.27-7.33(5H, m), 7.36(2H, d, J=8.7Hz), 7.57(1H, d, J=3.0 Hz). |
| 440 | —H | —CO— | 4-CH₃OPhCH₂— | —CH₂— | 2.44(4H, brs), 3.48(2H, s), 3.59(4H, brs), 3.81(3H, s), 6.80(1H, dd, J=8.6Hz, 0.7Hz), 6.85-6.89(2H, m), 7.03-7.08(2H, m), 7.11(1H, dd, J=8.6Hz, 3.0Hz), 7.21-7.26(2H, m), 7.38-7.43(2H, m), 7.73-7.75(1H, m). |
| 441 | —H | —SO₂— | benzyl | —CH₂— | 2.42-2.57(4H, m), 2.91-3.10(4H, m), 3.47(2H, s), 3.63(2H, brs), 6.83(1H, d, J=8.6Hz), 7.07-7.14(3H, m), 7.18-7.31(5H, m), 7.68(2H, d, J=8.8 Hz), 7.74(1H, d, J=2.0Hz). |

TABLE 63

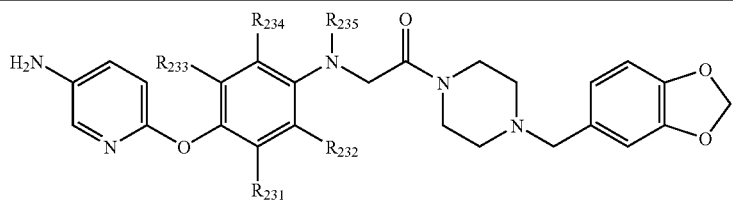

| Reference Example No. | R231 | R232 | R233 | R234 | R235 | ¹H NMR (CDCl₃) δppm |
|---|---|---|---|---|---|---|
| 442 | —F | —H | —H | —H | —H | 2.43-2.48(4H, m), 3.44-3.47(6H, m), 3.67-3.68(2H, m), 3.82(2H, d, J=4.1Hz), 4.96(1H, brs), 5.96(2H, s), 6.36-6.43(2H, m), |

TABLE 63-continued

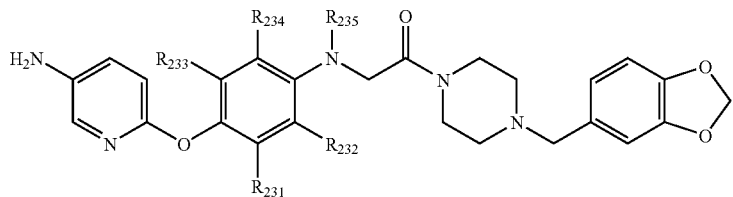

| Reference Example No. | $R_{231}$ | $R_{232}$ | $R_{233}$ | $R_{234}$ | $R_{235}$ | $^1$H NMR (CDCl$_3$) δppm |
|---|---|---|---|---|---|---|
| | | | | | | 6.71-6.78(3H, m), 6.86(1H, brs), 6.97-7.03(1H, m), 7.06(1H, dd, J=8.7Hz, 3.0 Hz), 7.63(1H, d, J=3.0Hz). |
| 443 | —F | —H | —H | —H | —CH$_3$ | 2.43-2.45(4H, m), 3.01(3H, s), 3.44(2H, s), 3.47(2H, brs), 3.63(2H, brs), 4.07(2H, s), 5.95(2H, s), 6.39-6.50(2H, m), 6.72-6.76(3H, m), 6.85(1H, s), 7.00-7.08(2H, m), 7.63(1H, dd, J=3.0Hz, 0.5Hz). |
| 444 | —F | —H | —H | —H | —C$_2$H$_5$ | 1.18(3H, t, J=7.1Hz), 2.43(4H, t, J=5.0 Hz), 3.37-3.48(8H, m), 3.63(2H, brs), 4.01(2H, s), 5.95(2H, s), 6.35-6.46(2H, m), 6.72-6.77(3H, m), 6.85(1H, s), 6.99(1H, d, J=8.9Hz), 7.05(1H, dd, J=8.7Hz, 3.0Hz), 7.63(1H, d, J=3.0Hz). |
| 445 | —F | —H | —H | —F | —CH$_3$ | 2.33-2.49(4H, m), 2.93(3H, s), 3.38-3.68(8H, m), 4.00(2H, s), 5.95(2H, s), 6.71-6.77(2H, s), 6.78-6.82(2H, m), 6.83-6.91(2H, m), 7.08(1H, dd, J=2.9Hz, 8.6Hz), 7.62(1H, d, J=2.9Hz). |
| 446 | —F | —H | —H | —F | —C$_2$H$_5$ | 1.11(3H, t, J=7.1Hz), 2.31-2.49(4H, m), 3.29(2H, q, J=7.1Hz), 3.41(2H, s), 3.42-3.69(6H, m), 3.96(2H, s), 6.70-6.78(2H, m), 6.79-6.91(4H, m), 7.08(1H, dd, J=2.9Hz, 8.6Hz), 7.62(1H, d, J=2.9Hz). |
| 447 | —F | —H | —F | —H | —CH$_3$ | 2.36-2.52(4H, m), 3.01(3H, s), 3.34-3.54(6H, m), 3.55-3.71(2H, m), 4.05(2H, s), 5.95(2H, s), 6.18-6.29(2H, m), 6.70-6.79(2H, m), 6.82(1H, d, J=8.6Hz), 6.85(1H, d, J=0.98 Hz), 7.07(1H, dd, J=2.9Hz, 8.6Hz), 7.59(1H, d, J=2.9Hz). |
| 448 | —F | —F | —H | —H | —CH$_3$ | 2.29-2.55(4H, m), 2.95(3H, s), 3.30-3.75(8H, m), 4.01(2H, s), 5.95(2H, s), 6.60-6.95(6H, m), 7.09(1H, dd, J=3.0Hz, 8.6Hz), 7.62(1H, d, J=3.0Hz). |
| 449 | —CH$_3$ | —CH$_3$ | —H | —H | —CH$_3$ | 2.11(3H, s), 2.25(3H, s), 2.36-2.42(4H, m), 2.66(3H, s), 3.41(2H, s), 3.45(2H, brs), 3.53-3.56(2H, m), 3.61-3.64(2H, m), 3.73(2H, s), 5.95(2H, s), 6.67(1H, d, J=8.7Hz), 6.70-6.85(4H, m), 6.95(1H, d, J=8.7Hz), 7.03-7.08(1H, m), 7.67(1H, d, J=3.0Hz). |
| 450 | —CH$_3$ | —H | —H | —H |  | 0.62-0.66(2H, m), 0.76-0.83(2H, m), 2.12(3H, s), 2.40-2.46(4H, m), 2.73-2.81(1H, m), 3.43(2H, s), 3.48-3.63(4H, m), 4.15(2H, s), 5.94(2H, s), 6.58(1H, d, J=8.7Hz), 6.68-6.77(4H, m), 6.87(2H, d, J=8.6Hz), 7.01(1H, dd, J=8.7Hz, 3.0Hz), 7.67(1H, d, J=3.0Hz). |

TABLE 64

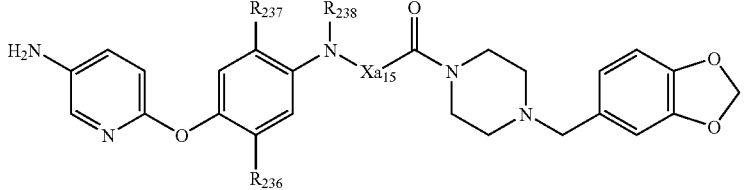

| Reference Example No. | R236 | R237 | R238 | Xa15 | ¹H NMR (CDCl₃) δppm or MS |
|---|---|---|---|---|---|
| 451 | —CH₃ | —H | —H | —CO— | ¹H NMR 2.20(3H, s), 2.48-2.54(4H, m), 3.44(4H, s), 3.67-3.75(2H, m), 4.23-4.27(2H, m), 5.95(2H, s), 6.68-6.78(3H, m), 6.86(1H, brs), 6.95(1H, d, J=8.7Hz), 7.07(1H, dd, J=8.6Hz, 3.0Hz), 7.37(1H, dd, J=8.7Hz, 2.6Hz), 7.52(1H, d, J=2.5Hz), 7.66(1H, d, J=3.0Hz), 9.13(1H, brs). |
| 452 | —CH₃ | —H | —CH₃ | —CO— | ¹H NMR 2.21-2.31(7H, m), 3.28-3.40(9H, m), 3.53(2H, brs), 5.93(2H, s), 6.66-6.80(4H, m,) 6.91(1H, d, J=8.6Hz), 7.03-7.12(3H, m), 7.66(1H, d, J=3.0Hz). |
| 453 | —H | —H | —SO₂CH₃ | —CH₂— | ¹H NMR 2.41(4H, brs), 3.19(3H, s), 3.34-3.38(2H, m), 3.42(2H, s), 3.57-3.60(4H, m), 4.51(2H, s), 5.95(2H, s), 6.70-6.77(2H, m), 6.80(1H, d, J=8.6Hz), 6.84(1H, brs), 7.02(2H, d, J=8.7Hz), 7.10(1H, dd, J=8.6Hz, 3.0Hz), 7.59(2H, d, J=8.7Hz), 7.71(1H, d, J=3.0Hz). |
| 454 | —CH₃ | —H | —SO₂CH₃ | —CH₂— | ¹H NMR 2.21(3H, s), 2.41(4H, brs), 3.20(3H, s), 3.34-3.38(2H, m), 3.42(2H, s), 3.53(2H, brs), 3.59-3.61(2H, m), 4.51(2H, s), 5.94(2H, s), 6.70-6.77(3H, m), 6.83(1H, brs), 6.90(1H, d, J=8.6Hz), 7.09(1H, dd, J=8.6Hz, 3.0Hz), 7.36(1H, dd, J=8.6Hz, 2.1Hz), 7.42(1H, d, J=2.3Hz), 7.66(1H, d, J=3.0Hz). |
| 455 | —CF₃ | —H | —C₂H₅ | —CH₂— | MS 557(M⁺) |
| 456 | —CF₃ | —H | —CH₃ | —CH₂— | MS 543(M⁺) |
| 457 | —CN | —H | —CH₃ | —CH₂— | MS 500(M⁺) |
| 458 | —OCH₃ | —H | —SO₂CH₃ | —CH₂— | ¹H NMR 2.48(4H, brs), 3.26(3H, s), 3.42-3.66(8H, m), 3.82(3H, s), 4.58(2H, s), 5.99(2H, s), 6.77-6.79(2H, m), 6.81-6.88(2H, m), 7.06-7.30(4H, m), 7.67(1H, d, J=2.3Hz). |
| 459 | —CH₃ | —CH₃ | —CH₃ | —CH₂— | MS 503(M⁺) |

TABLE 65

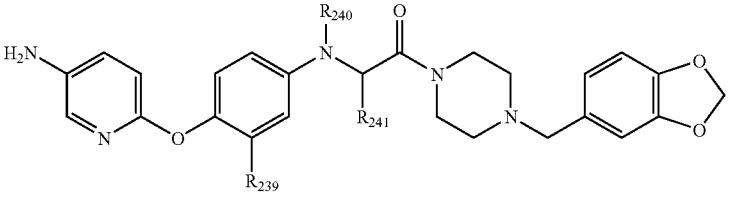

| Reference Example No. | R239 | R240 | R241 | ¹H NMR (CDCl₃) δppm |
|---|---|---|---|---|
| 460 | —H | —CH₃ | —H | 2.40-2.44(4H, m), 3.00(3H, s), 3.49(4H, brs), 3.63(2H, brs), 4.05(2H, s), 5.95(2H, s), 6.67(1H, d, J=8.6Hz), 6.69(2H, d, J=9.1Hz), 6.74(2H, brs), 6.85(1H, brs), 6.97(2H, d, J=9.1Hz), 7.03(1H, dd, J=8.6Hz, 3.0Hz), 7.68(1H, d, J=3.0Hz). |
| 461 | —H | —CH₃ | —CH₃ | 1.28(3H, d, J=6.6Hz), 2.14-2.21(1H, m), 2.28-2.35(2H, m), 2.47-2.49(1H, m), 2.75(3H, s), 3.24-3.54(3H, m), 3.38(2H, s), 3.45(2H, s), 3.78-3.84(1H, m), 4.54(1H, q, J=6.8Hz), 5.93(2H, s), 6.68-6.75(5H, m), 6.82(1H, s), 6.99(2H, d, J=9.1Hz), 7.05(1H, dd, J=8.6Hz, 3.0Hz), 7.69(1H, dd, J=3.1Hz, 0.7Hz). |

TABLE 65-continued

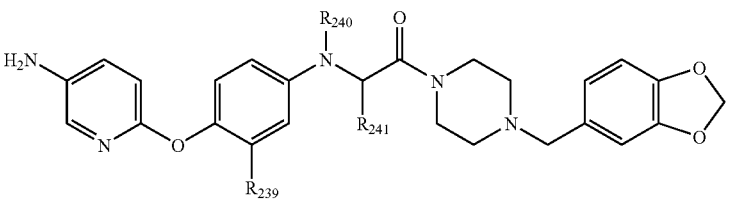

| Reference Example No. | R<sub>239</sub> | R<sub>240</sub> | R<sub>241</sub> | ¹H NMR (CDCl₃) δppm |
|---|---|---|---|---|
| 462 | —CH₃ | —CH₃ | —CH₃ | 1.28(3H, d, J=6.6Hz), 2.15(3H, s), 2.15-2.21(1H, m), 2.33-2.36(2H, m), 2.49(1H, brs), 2.74(3H, s), 3.25-3.55(3H, m), 3.39(2H, s), 3.42(2H, s), 3.80(1H, brs), 4.55(1H, q, J=6.4 Hz), 5.93(2H, s), 6.55-6.59(2H, m), 6.64(1H, dd, J=8.6Hz, 0.5Hz), 6.69-6.75(2H, m), 6.83(1H, brs), 6.90(1H, d, J=8.7 Hz), 7.04(1H, dd, J=8.7Hz, 3.0Hz), 7.67(1H, dd, J=3.0 Hz, 0.7Hz). |
| 463 | —OCH₃ | —CH₃ | —H | 2.31-2.50(4H, m), 3.02(3H, s), 3.31-3.57(6H, m), 3.58-3.70(2H, m), 3.76(3H, s), 4.06(2H, s), 5.95(2H, s), 6.24(1H, dd, J=8.7Hz, 2.8Hz), 6.37(1H, d, J=2.8Hz), 6.68(1H, d, J=8.6Hz), 6.69-6.79(2H, m), 6.85(1H, s), 6.94(1H, d, J=8.7 Hz), 7.02(1H, dd, J=8.6Hz, 3.0Hz), 7.65(1H, d, J=3.0 Hz). |
| 464 | —OCH₃ | —C₂H₅ | —H | 1.18(3H, t, J=7.0Hz), 2.31-2.51(4H, m), 3.28-3.70(10H, m), 3.74(3H, s), 4.01(2H, s), 5.95(2H, s), 6.22(1H, dd, J=8.7Hz, 2.8Hz), 6.35(1H, d, J=2.8Hz), 6.68(1H dd, J=8.7Hz, 0.5Hz), 6.69-6.79(2H, m), 6.81-6.88(1H, m), 6.93(1H, d, J=8.7Hz), 7.03(1H, dd, J=8.7Hz, 3.0Hz), 7.65(1H, dd, J=3.0Hz, 0.5Hz). |
| 465 | —CH₃ | —CH₃ | —H | 2.13(3H, s), 2.42(4H, t, J=3.0Hz), 2.99(3H, s), 3.35-3.57(6H, m), 3.58-3.70(2H, m), 4.05(2H, s), 5.95(2H, s), 6.53(1H, dd, J=8.8Hz, 3.1Hz), 6.57(1H, d, J=3.1Hz), 6.60(1H, d, J=8.8Hz), 6.71-6.78(2H, m), 6.85(1H, brs), 6.88(1H, d, J=8.7Hz), 7.02(1H, dd, J=8.7Hz, 3.0Hz), 7.67(1H, d, J=3.0Hz). |
| 466 | —CH₃ | —C₂H₅ | —H | 1.15(3H, t, J=7.0Hz), 2.12(3H, s), 2.42(4H, t, J=5.1Hz), 3.27-3.70(10H, m), 4.00(2H, s), 5.95(2H, s), 6.46-6.57(2H, m), 6.60(1H, dd, J=8.7Hz, 0.5Hz), 6.69-6.78(2H, m), 6.82-6.90(2H, m), 7.02(1H, dd, J=8.7Hz, 3.0Hz), 7.68(1H, dd, J=3.0Hz, 0.5Hz). |
| 467 | —CH₃ | —Ac | —H | 1.95(3H, s), 2.23(3H, s), 2.31-2.52(4H, m), 3.29-3.70(8H, m), 4.43(2H, s), 5.94(2H, s), 6.69-6.79(3H, m), 6.84(1H, s), 6.92(1H, d, J=8.5Hz), 7.10(1H, dd, J=8.6Hz, 3.0Hz), 7.19(1H, dd, J=8.5Hz, 2.5Hz), 7.28(1H, d, J=2.2Hz), 7.68(1H, d, J=2.5Hz). |

TABLE 66

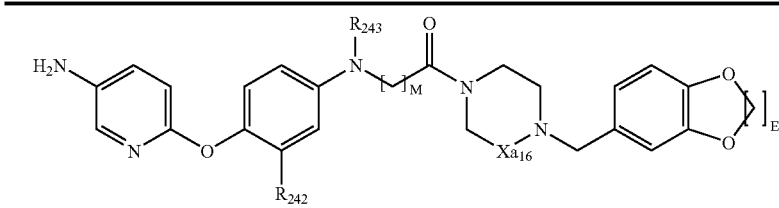

| Reference Example No. | R<sub>242</sub> | R<sub>243</sub> | Xa<sub>16</sub> | M | E | ¹H NMR (solvent) δppm |
|---|---|---|---|---|---|---|
| 468 | —OCH₃ | —H | —CH₂— | 1 | 1 | (DMSO-d₆) 2.32-2.40(4H, m), 3.32(2H, brs), 3.50(4H, brs), 3.61(3H, s), 3.88(2H, brs), 4.88(2H, brs), 5.44(1H, brs), 5.99(2H, s), 6.15(1H, dd, J=8.6Hz, 2.5Hz), 6.44(1H, d, J=2.3Hz), 6.51(1H, d, J=8.6Hz), 6.71-6.88(4H, m), 6.98(1H, dd, J=8.6Hz, 2.8 Hz), 7.40(1H, d, J=2.6Hz). |
| 469 | —OCH₃ | —H | —CH₂— | 1 | 2 | (DMSO-d₆) 2.32(2H, brs), 2.40(2H, brs), 3.39(2H, s), 3.49(4H, brs), 3.61(3H, s), 3.89(2H, brd), 4.22(4H, s), 4.82(2H, brs), 5.44(1H, brt), 6.15(1H, dd, J=8.6Hz, 2.5 |

TABLE 66-continued

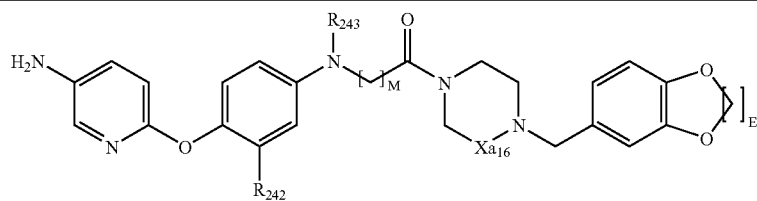

| Reference Example No. | $R_{242}$ | $R_{243}$ | $Xa_{16}$ | M | E | $^1$H NMR (solvent) δppm |
|---|---|---|---|---|---|---|
| | | | | | | Hz), 6.44-6.52(2H, m), 6.70-6.81(4H, m), 6.98(1H, dd, J=8.7Hz, 3.0Hz), 7.39(1H, d, J=2.8Hz). |
| 470 | —H | —CH$_3$ | —CH$_2$— | 2 | 1 | (CDCl$_3$) 2.35(4H, tt, J=5.0Hz, 5.0Hz), 2.52-2.58(2H, m), 2.91(3H, s), 3.36-3.39(4H, m), 3.59-3.62(2H, m), 3.65-3.73(4H, m), 5.93(2H, s), 6.64-6.76(5H, m), 6.83(1H, d, J=1.0Hz), 6.97(2H, d, J=9.1Hz), 7.03(1H, dd, J=8.6Hz, 3.1Hz), 7.66(1H, dd, J=3.1 Hz, 0.5Hz). |
| 471 | —CH$_3$ | —CH$_3$ | —CO— | 1 | 1 | (CDCl$_3$) 2.12(3H, s), 2.88-3.10(3H, m), 3.26(2H, t, J=5.3Hz), 3.40(2H, brs), 3.60-3.90(2H, m), 4.00-4.15(2H, m), 4.20-4.40(2H, m), 4.52(2H, s), 5.95(2H, s), 6.53(1H, dd, J=8.5Hz, 3.0Hz), 6.60(1H, s), 6.60(1H, d, J=8.5Hz), 6.71(1H, d, J=8.5 Hz), 6.74(1H, s), 6.76(1H, d, J=8.5Hz), 6.88(1H, d, J=8.8Hz), 7.02(1H, dd, J=8.5 Hz, 2.8Hz), 7.66(1H, d, J=2.8Hz). |
| 472 | —OCH$_3$ | —C$_2$H$_5$ | —CO— | 1 | 1 | (CDCl$_3$) 1.17(3H, t, J=7.0Hz), 3.20-3.31(2H, m), 3.40-3.60(2H, m), 3.41(2H, q, J=7.0Hz), 3.61-3.82(2H, m), 3.74(3H, s), 4.02(2H, s), 4.30(2H, s), 4.50(2H, s), 5.95(2H, s), 6.24(1H, dd, J=8.7Hz, 2.8Hz), 6.40(1H, s), 6.68(1H, d, J=8.6Hz), 6.70(1H, dd, J=7.9Hz, 1.5Hz), 6.76(1H, d, J=1.5Hz), 6.76(1H, d, J=7.9Hz), 6.93(1H, d, J=8.6Hz), 7.03(1H, dd, J=8.5 Hz, 2.8Hz), 7.64(1H, d, J=2.8Hz). |

(E means the number of the methylene groups.
Hereinafter E indicates the same meaning.)

TABLE 67

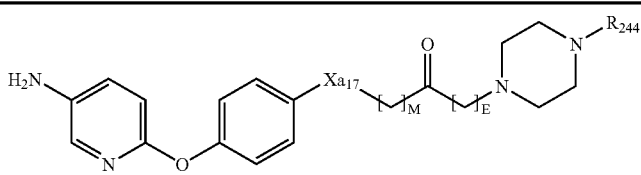

| Reference Example No. | $Xa_{17}$ | M | E | $R_{244}$ | Form | mp (° C.) or $^1$H NMR (CDCl$_3$) δppm |
|---|---|---|---|---|---|---|
| 473 | —CH$_2$— | 1 | 0 | benzyl | free | $^1$H NMR 2.33-2.43(4H, m), 2.57-2.63 (2H, m), 2.91-2.97(2H, m), 3.38-3.42(4H, m), 3.50(2H, s), 3.62-3.65(2H, m), 6.75(1H, dd, J=8.6Hz, 0.5Hz), 6.95-7.00(2H, m), 7.07(1H, dd, J=8.6Hz, 3.0Hz), 7.15-7.20(2H, m), 7.28-7.33(5H, m), 7.70(1H, dd, J=3.0Hz, 0.5Hz). |
| 474 | —CH$_2$— | 1 | 0 | piperonyl | trihydro-chloride | mp 179-180 dec |
| 475 | —O— | 1 | 0 | piperonyl | free | $^1$H NMR 2.41(4H, brs), 3.42(2H, s), 3.48(2H, brs), 3.50-3.70(4H, m), 4.65(2H, s), 5.95(2H, s), 6.72(1H, d, J=8.6Hz), 6.74(2H, brs), 6.85(1H, brs), 6.91(2H, d, J=9.2Hz), 7.00(2H, d, J=9.2Hz), 7.06(1H, dd, |

TABLE 67-continued

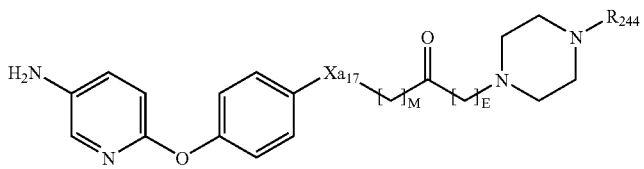

| Reference Example No. | $Xa_{17}$ | M | E | $R_{244}$ | Form | mp (° C.) or $^1$H NMR (CDCl$_3$) δppm |
|---|---|---|---|---|---|---|
| | | | | | | J=8.6Hz, 3.0Hz), 7.69(1H, d, J=3.0Hz). |
| 476 | —O— | 1 | 0 | benzyl | free | $^1$H NMR 2.44(4H, t, J=5.0Hz), 3.51(4H, s), 3.58(2H, t, J=5.0Hz), 3.64(2H, t, J=5.0Hz), 4.65(2H, s), 6.72(1H, d, J=8.5Hz), 6.92(2H, d, J=9.2Hz), 7.00(2H, d, J=9.2Hz), 7.06(1H, dd, J=8.5Hz, 3.0Hz), 7.22-7.35(5H, m), 7.69(1H, d, J=3.0 Hz). |
| 477 | —NH— | 0 | 1 | piperonyl | free | $^1$H NMR 2.51(4H, brs), 2.62-2.63(4H, m), 3.12(2H, s), 3.45(2H, s), 3.52(2H, brs), 5.94(2H, s), 6.74(1H, dd, J=8.7 Hz, 0.7Hz), 6.75(2H, brs), 6.85(1H, s), 7.03(2H, d, J=8.9Hz), 7.07(1H, dd, J=8.7Hz, 3.0Hz), 7.54(2H, d, J=9.1Hz), 7.69(1H, dd, J=3.0Hz, 0.7Hz), 9.10(1H, brs). |
| 478 | —N(CH$_3$)— | 0 | 1 | piperonyl | free | $^1$H NMR 2.44(8H, brs), 2.93(2H, s), 3.24(3H, s), 3.38(2H, s), 3.62(2H, brs), 5.92(2H, s), 6.72(2H, brs), 6.80-6.84(2H, m), 7.06(2H, d, J=9.1Hz), 7.12(1H, dd, J=8.6Hz, 3.1Hz), 7.15(2H, d, J=8.9Hz), 7.73(1H, d, J=3.0Hz). |

TABLE 68

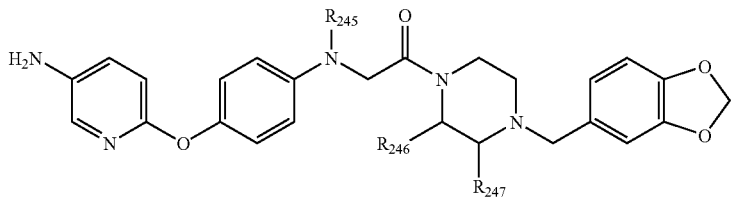

| Reference Example No. | $R_{245}$ | $R_{246}$ | $R_{247}$ | $^1$H NMR (CDCl$_3$) 67 ppm |
|---|---|---|---|---|
| 479 | —CH$_3$ | —H | —CH$_3$ | 1.12(3H, d, J=6.3Hz), 2.10-2.12(1H, m), 2.47(1H, brs), 2.67-2.72(1H, m), 2.80-3.11(6H, m), 3.47-3.60(3H, m), 3.84-4.10(4H, m), 5.94(2H, s), 6.64-6.74(5H, m), 6.85(1H, brs), 6.94-6.98(2H, m), 7.00-7.05(1H, m), 7.68(1H, d, J=2.8Hz). |
| 480 | —CH$_3$ | —CH$_3$ | —H | 1.28-1.37(3H, m), 1.94-2.03(1H, m), 2.11-2.15(1H, m), 2.63-2.67(1H, m), 2.79-2.82(1H, m), 2.95-3.00(4H, m), 3.30-3.46(5H, m), 4.03-4.69(3H, m), 5.94(2H, s), 6.66(1H, d, J=8.7H), 6.68(2H, d, J=9.1H), 6.74(2H, brs), 6.87(1H, brs), 6.96(2H, d, J=9.1Hz), 7.03(1H, dd, J=8.7Hz, 3.0Hz), 7.68(1H, d, J=3.0Hz). |
| 481 | —CH$_2$H$_5$ | —H | —CH$_3$ | 1.11-1.18(6H, m), 2.04-2.13(1H, m), 2.45-2.47(1H, m), 2.66-2.73(1H, m), 2.85-3.64(8H, m), 3.84-4.11(4H, m), 5.94(2H, s), 6.64-6.69(3H, m), 6.74(2H, brs), 6.85(1H, brs), 6.93-6.96(2H, m), 7.03(1H, dd, J=8.7Hz, 3.0Hz), 7.69(1H, d, J=3.0Hz). |
| 482 | —C$_2$H$_5$ | —CH$_3$ | —H | 1.15(3H, t, J=7.1Hz), 1.26-1.70(3H, m), 1.94-2.04(1H, m), 2.14-2.17(1H, m), 2.63-2.67(1H, m), 2.80(1H, brs), 3.01-3.59(8H, m), 3.73-4.71(3H, m), 5.95(2H, s), 6.63-6.70(3H, m), 6.74(2H, brs), 6.87(1H, brs), 6.95(2H, d, J=9.1Hz), 7.03(1H, dd, J=8.6Hz, 3.0Hz), 7.69(1H, dd, J=3.0Hz, 0.7Hz). |

TABLE 69

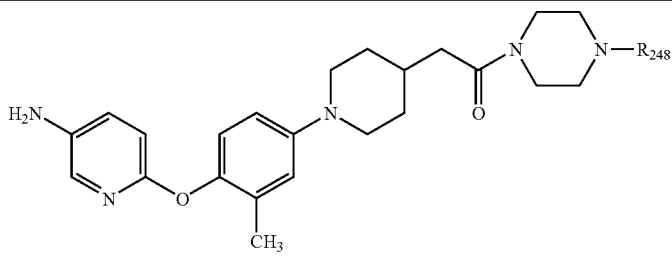

| Reference Example No. | R248 | ¹H NMR (CDCl₃) δppm |
|---|---|---|
| 483 | piperonyl | 1.36-1.46(2H, m), 1.82-1.99(3H, m), 2.13(3H, s), 2.28(2H, d, J=6.8 Hz), 2.41(4H, brs), 2.70(2H, t, J=12.0Hz), 3.41-3.76(10H, m), 5.94(2H, s), 6.59-6.89(7H, m), 7.03(1H, dd, J=8.6Hz, 3.0Hz), 7.67-7.69(1H, m). |
| 484 | benzyl | 1.33-1.42(2H, m), 1.82-1.98(3H, m), 2.04(3H, s), 2.28(2H, d, J=6.8 Hz), 2.41-2.45(4H, m), 2.70(2H, t, J=12.0Hz), 3.51-3.78(10H, m), 6.60(1H, d, J=8.6Hz), 6.69-6.92(3H, m), 7.03(1H, dd, J=8.6Hz, 3.0Hz), 7.28-7.33(5H, m), 7.67(1H, d, J=2.5Hz). |

TABLE 70

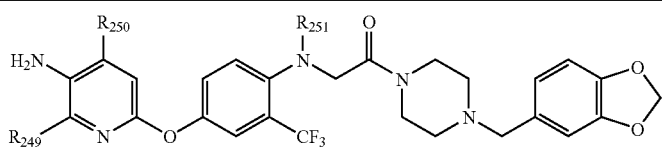

| Reference Example No. | R249 | R250 | R251 | MS (M⁺) |
|---|---|---|---|---|
| 485 | —H | H | —C₂H₅ | 557 |
| 486 | —H | —CH₃ | —CH₃ | 557 |
| 487 | —CH₃ | —H | —CH₃ | 557 |

Reference Example 488

Production of ethyl[4-(4-amino-2-fluorophenoxy)phenylsulfanyl]acetate

To a solution of ethyl[4-(2-fluoro-4-nitrophenoxy)phenylsulfanyl]acetate (4.93 g, 14.0 mmol) in ethanol (100 mL) was added tin chloride dihydrate (9.50 g, 42.1 mmol), and the resulting solution was stirred for 8 hours at 50° C. Water was added to the reaction mixture and extracted with ethyl acetate. The ethyl acetate layer was washed with 1 M hydrochloric acid, a saturated sodium bicarbonate solution, and brine, dried over anhydrous sodium sulfate, and evaporated, to thereby yield 3.45 g of the title compound.

Appearance: Brown oil

¹H NMR (CDCl₃) δ 1.20 (3H, t, J=7.1 Hz), 3.53 (2H, s), 3.80-4.20 (4H, m), 6.37-6.45 (1H, m), 6.49 (1H, dd, J=2.6 Hz, 12.0 Hz), 6.80-7.00 (3H, m), 7.38 (2H, d, J=8.9 Hz).

The following compounds were produced in the same manner as in Reference Example 488.

Reference Example 489

2-{Allyl[4-(5-aminopyridin-2-yloxy)-3-fluorophenyl]amino}-1-(4-piperonylpiperazin-1-yl)ethanone ¹H NMR (CDCl₃) δ 2.44-2.46 (4H, m), 3.44 (4H, brs), 3.44 (2H, s), 3.83 (2H, brs), 3.98 (2H, d, J=4.8 Hz), 4.03 (2H, s), 5.16-5.30 (2H, m), 5.82-5.95 (1H, m), 5.95 (2H, s), 6.35-6.46 (2H, m), 6.71-6.74 (3H, m), 6.85-6.87 (1H, m), 6.96-7.07 (2H, m), 7.63-7.64 (1H, m).

Reference Example 490

(E)-3-[3-(5-Aminopyridin-2-yloxy)phenyl]-1-(4-piperonylpiperazin-1-yl)propenone

MS 458 (M⁺).

Reference Example 491

Production of methyl 3-[4-(5-aminopyridin-2-ylsulfanyl)phenyl]propionate

To a solution of methyl 3-[4-(5-nitropyridin-2-ylsulfanyl)phenyl]propionate (2.97 g, 9.33 mmol) in methanol (50 mL) were added sodium borohydride (0.590 g, 15.6 mmol) and 10% palladium-carbon (1.80 g), and the resulting solution was stirred for 24 hours at room temperature under a hydrogen atmosphere at atmospheric pressure. The reaction solution was filtered through Celite, and to the resulting filtrate was added concentrated hydrochloric acid (1.5 mL), and concentrated under reduced pressure. To the residue was added a saturated sodium bicarbonate solution, and extracted with ethyl acetate, and the ethyl acetate layer was washed with brine. The ethyl acetate layer was dried over anhydrous magnesium sulfate, and evaporated, to thereby yield 2.49 g of the title compound.

Appearance: Yellow powder
$^1$H NMR (CDCl$_3$) δ 2.62 (2H, t, J=7.6 Hz), 2.93 (2H, t, J=7.6 Hz), 3.67 (3H, s), 6.87 (1H, dd, J=2.9 Hz, 8.4 Hz), 6.98 (1H, d, J=8.4 Hz), 7.15 (2H, d, J=8.2 Hz), 7.35 (2H, d, J=8.2 Hz), 8.01 (1H, d, J=2.9 Hz).

Reference Example 492

Production of ethyl 3-[4-(5-aminopyridin-2-yloxy)phenyl]acrylate

To a solution of ethyl 3-[4-(5-nitropyridin-2-yloxy)phenyl]acrylate (2.02 g, 6.43 mmol) in methanol (100 mL) were added zinc (6.3 g, 96.3 mmol) and ammonium chloride (710 mg, 13.27 mmol). The resulting reaction solution was stirred for 2.5 hours under reflux, then acetic acid (5 mL) was added, and stirred for 20 minutes under reflux. Insoluble matter was filtered off through Celite, after which the filtrate was concentrated under reduced pressure. To the residue was added 5% potassium hydrogensulfate (150 mL), the mixture was extracted with dichloromethane, and the dichloromethane layer was washed with a saturated sodium bicarbonate solution and brine. The dichloromethane layer was dried over anhydrous magnesium sulfate, and evaporated, to thereby yield 1.78 g of the title compound.
Appearance: Yellow oil
$^1$H NMR (CDCl$_3$) δ 1.34 (3H, t, J=7.1 Hz), 3.58 (2H, brs), 4.26 (2H, q, J=7.1 Hz), 6.35 (1H, dd, J=16.0 Hz, 2.0 Hz), 6.81 (1H, d, J=8.6 Hz), 7.05 (2H, d, J=8.6 Hz), 7.10 (1H, dd, J=8.6 Hz, 3.0 Hz), 7.50 (2H, d, J=8.6 Hz), 7.66 (1H, dd, J=16.0 Hz, 3.0 Hz), 7.73 (1H, d, J=3.0 Hz).

Reference Example 493

Production of 3-(4-(5-amino-4-methylpyridin-2-yloxy)phenyl)-1-(4-piperonylpiperazin-1-yl)propan-1-one 3-(4-hydroxyphenyl)-1-(4-piperonylpiperazin-1-yl)propan-1-one (0.38 g, 1.0 mmol) was dissolved in DMF (6 mL). To the resulting solution was added 60% sodium hydride (0.05 g, 1.2 mmol) and 2-chloro-4-methyl-5-nitropyridine (0.196 g, 1.1 mmol), and the resulting reaction solution was stirred overnight at room temperature. To the reaction solution was added saturated aqueous ammonium chloride, and extracted with ethyl acetate. The ethyl acetate layer was washed with water and brine. The ethyl acetate layer was dried over anhydrous magnesium sulfate, evaporated, and the residue was purified by silica gel column chromatography (ethyl acetate), to thereby yield the intermediate product 3-(4-(4-methyl-5-nitropyridin-2-yloxy)phenyl)-1-(4-piperonylpiperazin-1-yl)propan-1-one. The 3-(4-(4-methyl-5-nitropyridin-2-yloxy)phenyl)-1-(4-piperonylpiperazin-1-yl)propan-1-one was dissolved in a mixed solvent consisting of ethanol (4 mL) and dioxane (1 mL). To this solution was added 10% palladium-carbon (0.034 g), and the resulting solution was subjected to catalytic reduction for 8 hours at atmospheric pressure and room temperature. The catalyst was removed by filtration, and the filtrate was concentrated under reduced pressure, and the residue was purified by silica gel chromatography (dichloromethane:methanol=20:1), to thereby yield 0.22 g of the title compound.
Appearance: Slightly yellow oil
$^1$H NMR (CDCl$_3$) δ 2.18 (3H, s), 2.30-2.45 (4H, m), 2.56-2.63 (2H, m), 2.91-2.97 (2H, m), 3.30-3.50 (6H, m), 3.55-3.70 (2H, m), 5.95 (2H, s), 6.65-6.80 (3H, m), 6.84 (1H, s), 6.95-7.05 (2H, m), 7.15-7.20 (2H, m), 7.64 (1H, s).

Reference Example 494

Production of ethyl 3-{4-[4-(3,4-dichlorobenzoylamino)-phenoxy]phenyl}propionate A solution of 3,4-dichlorobenzoyl chloride (3.65 g, 17.4 mmol) was added dropwise under ice cooling to a solution of ethyl 3-[4-(4-aminophenoxy)phenyl]propionate (4.52 g, 15.9 mmol) and triethylamine (2.65 mL, 19.0 mmol) in THF (80 mL), and the resulting solution was stirred for 1 hour at the same temperature. Water was added to the reaction mixture, and extracted with ethyl acetate. The ethyl acetate layer was washed with a saturated sodium bicarbonate solution and brine. The ethyl acetate layer was dried over anhydrous magnesium sulfate and evaporated. The residue was recrystallized from water-containing ethanol to thereby yield 6.67 g of the title compound.
Appearance: Colorless needles
Melting point: 139-141° C.
The following compounds were produced in the same manner as in Reference Example 494.

Reference Example 495

Ethyl 3-[4-(5-phenoxycarbonylaminopyridin-2-yloxy)phenyl]propionate

MS 406 (M$^+$).

TABLE 71

| Reference Example No. | Xa$_{18}$ | R$_{252}$ | mp (° C.) or $^1$H NMR (CDCl$_3$) δ ppm |
|---|---|---|---|
| 496 | p-phenylene | 2-(CH$_2$)$_2$COOCH$_3$ | mp 117-119 |
| 497 | p-phenylene | 3-(CH$_2$)$_2$COOC$_2$H$_5$ | mp 111-113 |
| 498 | o-phenylene | 4-(CH$_2$)$_2$COOC$_2$H$_5$ | mp 72-73 |
| 499 | m-phenylene | 4-(CH$_2$)$_2$COOC$_2$H$_5$ | $^1$H NMR 1.22(3H, t, J=7.2 Hz), 2.59 (2H, t, J=7.7 Hz), 2.91(2H, t, J=7.7 Hz), 4.10(2H, q, J=7.2 Hz), 6.78(1H, dt, J=8.1 Hz, 1.1 Hz), 6.93 (2H, d, J= |

TABLE 71-continued

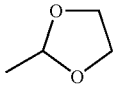

| Reference Example No. | Xa₁₈ | R₂₅₂ | mp (° C.) or ¹H NMR (CDCl₃) δ ppm |
|---|---|---|---|
| | | | 8.5 Hz), 7.14(2H, d, J=8.5 Hz), 7.20-7.36(3H, m), 7.52(1H, d, J=8.3 Hz), 7.64(1H, dd, J=8.3 Hz, 2.1 Hz), 7.81(1H, brs), 7.91(1H, d, J=2.1 Hz). |

TABLE 72

| Reference Example No. | R₂₅₃ | R₂₅₄ | mp (° C.) or ¹H NMR (solvent) δ ppm |
|---|---|---|---|
| 500 | —F | —H | mp 168-169 |
| 501 | —H | —COOC₂H₅ | mp 144-145 |
| 502 | —F | —COOC₂H₅ | mp 145-146 |
| 503 | —F | —CH₂COOCH₃ | mp 127-129 |
| 504 | —F | —(CH₂)₂COOC₂H₅ | mp 131-133 |
| 505 | —F | —(CH₂)₃COOC₂H₅ | mp 110-111 |
| 506 | —F | —SCH₂COOC₂H₅ | ¹H NMR (CDCl₃) 1.23(3H, t, J=7.1 Hz), 3.56(2H, s), 4.15(2H, q, J=7.1 Hz), 6.90(2H, d, J=8.7 Hz), 7.08(1H, t, J=8.7 Hz), 7.20-7.30(1H, m), 7.42(2H, d, J 8.7 Hz), 7.58(1H, d, J=8.3 Hz), 7.65-7.80(2H, m), 7.82(1H, s), 7.96(1H, d, J=2.1 Hz). |
| 507 | —F | —NHCH₂COOC₂H₅ | ¹H NMR (DMSO-d₆) 1.19(3H, t, J=7.1 Hz), 3.87(2H, d, J 6.4 Hz), 4.11(2H, q, J=7.1 Hz), 5.93(1H, t, J=6.4 Hz), 6.56(2H, d, J=9.0 Hz), 6.81(2H, d, J 9.0 Hz), 6.98(1H, t, J=9.2 Hz), 7.44-7.47 (1H, m), 7.82-7.86(2H, m), 7.93(1H, dd, J=2.0 Hz, 8.4 Hz), 8.20(1H, d, J=2.0 Hz), 10.50(1H, s). |
| 508 | —H | —Br | ¹H NMR (DMSO-d₆) 6.96(2H, d, J=9.0 Hz), 7.08(2H, d, J=9.0 Hz), 7.55(2H, d, J=8.5 Hz), 7.79(2H, d, J=8.5 Hz), 7.83(1H, d, J=8.5 Hz), 7.94(1H, dd, J=8.5 Hz, 2.0 Hz), 8.21(1H, d, J=2.0 Hz), 10.44(1H, brs). |
| 509 | —F | —Ac | mp 143 |
| 510 | —F | (2-methyl-1,3-dioxolan-2-yl) | ¹H NMR (CDCl₃) 4.00-4.15(4H, m), 5.78(1H, s), 6.96(2H, d, J=8.7 Hz), 7.00-7.10(1H, m), 7.20-7.30(1H, m), 7.43(2H, d, J=8.7 Hz), 7.57(1H, d, J=8.3 Hz), 7.82(1H, s), 7.95(1H, d, J=2.1 Hz). |

TABLE 73

| Reference Example No. | R255 | R256 | R257 | ¹H NMR (CDCl₃) δ ppm |
|---|---|---|---|---|
| 511 | —Cl | —Cl | 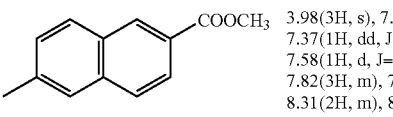 | 3.98(3H, s), 7.06(1H, d, J=8.7 Hz), 7.33-7.37(1H, m), 7.56-7.59(2H, m), 7.70-7.73(1H, m), 7.80(1H, d, J=8.5 Hz), 7.95-8.07(4H, m), 8.23-8.30(2H, m), 8.60(1H, s). |
| 512 | —CF₃ | —H | 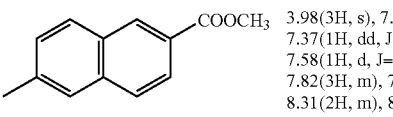 | 3.98(3H, s), 7.07-7.10(1H, m), 7.37(1H, dd, J=8.9 Hz, 2.3 Hz), 7.58(1H, d, J=2.3 Hz), 7.76-7.82(3H, m), 7.93-8.08(5H, m), 8.27-8.31(2H, m), 8.60(1H, s). |
| 513 | —Cl | —Cl | 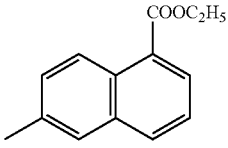 | 1.46(3H, t, J=7.1 Hz), 4.47(2H, q, J=7.1 Hz), 7.04(1H, d, J=8.7 Hz), 7.41(1H, dd, J=9.4 Hz, 2.5 Hz), 7.47-7.60(3H, m), 7.70(1H, dd, J=N. 8.4 Hz, 2.1 Hz), 7.82(1H, brs), 7.94(1H, d, J=8.6 Hz), 7.98(1H, d, J=2.1 Hz), 8.14(1H, dd, J=7.3 Hz, 1.2 Hz), 8.20-8.27(2H, m), 8.92(1H, d, J=9.4 Hz). |
| 514 | —CF₃ | —H | 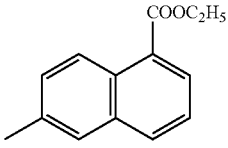 | 1.46(3H, t, J=7.1 Hz), 4.47(2H, q, J=7.1 Hz), 7.04(1H, d, J=8.7 Hz), 7.40(1H, dd, J=9.4 Hz, 2.5 Hz), 7.47-7.53(1H, m), 7.59(1H, d, J=2.5 Hz), 7.75(2H, d, J=8.2 Hz), 7.92-8.00(4H, m), 8.14(1H, dd, J=7.3 Hz, 1.2 Hz), 8.23-8.29(2H, m), 8.97(1H, d, J=9.4 Hz). |
| 513 | —Cl | —Cl | 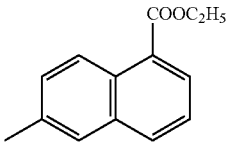 | 4.00(3H, s), 7.09(1H, d, J=9.6 Hz), 7.16(1H, d, J=8.1 Hz), 7.50-7.57(2H, m), 7.62-7.72(2H, m), 7.98(2H, d, J=2.1 Hz), 8.15-8.29(4H, m), 9.01(1H, d, J=8.7 Hz). |

TABLE 74

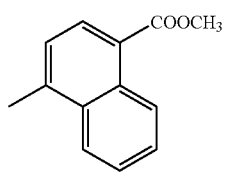

| Reference Example No. | R258 | ¹H NMR (CDCl₃) δ ppm |
|---|---|---|
| 516 | —COOCH₃ | 3.91(3H, s), 7.03(1H, d, J=8.9 Hz), 7.15-7.18(2H, m), 7.58(1H, d, J=8.3 Hz), 7.69-7.73(1H, m), 7.89(1H, brs), 7.99(1H, d, J=2.0 Hz), 8.06-8.09(2H, m), 8.23-8.30(2H, m). |
| 517 | —COOC₂H₅ | 1.39(3H, t, J=7.3 Hz), 4.37(2H, q, J=7.3 Hz), 7.02(1H, d, J=8.6 Hz), 7.15-7.18(2H, m), 7.57(1H, d, J=8.6 Hz), 7.70-7.73(1H, m), 7.97-7.99 (2H, m), 8.06-8.09(2H, m), 8.23-8.30(2H, m). |
| 518 | —CH₂COOCH₃ | 3.63(2H, s), 3.71(3H, s), 6.94(1H, d, J=8.9 Hz), 7.07(2H, d, J=8.2 Hz), 7.30(2H, d, J=8.6 Hz), 7.55(1H, d, J=8.6 |

TABLE 74-continued

| Reference Example No. | R_{258} | ¹H NMR (CDCl₃) δ ppm |
|---|---|---|
| | | Hz), 7.70(1H, dd, J=8.2 Hz, 2.0 Hz), 7.97-8.08(2H, m), 8.17(1H, dd, J=8.9 Hz, 2.6 Hz), 8.24(1H, d, J=2.6 Hz). |
| 519 | —(CH₂)₂COOCH₃ | 2.62-2.67(2H, m), 2.93-2.98(2H, m), 3.68(3H, s), 6.93(1H, d, J=8.9 Hz), 7.03-7.06(2H, m), 7.20-7.23(2H, m), 7.56(1H, d, J=8.3 Hz), 7.68-7.72 (1H, m), 7.96-7.98(2H, m), 8.17(1H, dd, J=8.9 Hz, 2.6 Hz), 8.24(1H, d, J=2.6 Hz). |
| 520 | —(CH₂)₃COOC₂H₅ | 1.26(3H, t, J=7.0 Hz), 1.96(2H, dt, J=15.0 Hz, 7.5 Hz), 2.34(2H, t, J=7.5 Hz), 2.66(2H, t, J=7.5 Hz), 4.13(2H, q, J=7.0 Hz), 6.93(1H, d, J=8.8 Hz), 7.04(1H, d, J=8.6 Hz), 7.20(2H, d, J=8.6 Hz), 7.56(1H, d, J=8.3 Hz), 7.70(1H, dd, J=8.3 Hz, 2.0 Hz), 7.89(1H, s), 7.98(1H, d, J=2.0 Hz), 8.16(1H, dd, J=8.8 Hz, 2.6 Hz), 8.24(1H, d, J=2.6 Hz). |
| 521 | —(CH₂)₄COOC₂H₅ | 1.26(3H, t, J=7.2 Hz), 1.60-1.75(4H, m), 2.33(2H, t, J=7.0 Hz), 2.64(2H, t, J=7.0 Hz), 4.13(2H, q, J=7.2 Hz), 6.94(1H, d, J=8.9 Hz), 7.04(2H, d, J=8.5 Hz), 7.20(2H, d, J=8.5 Hz), 7.58(1H, d, J=8.3 Hz), 7.70(1H, dd, J=8.3 Hz, 2.3 Hz), 7.78(1H, brs), 7.98(1H, d, J=2.3 Hz), 8.16(1H, dd, J=8.9 Hz, 2.6 Hz), 8.24(1H, d, J=2.6 Hz). |
| 522 | —CH₂CN | 3.76(2H, s), 7.00(1H, d, J=8.8 Hz), 7.16(2H, d, J=8.7 Hz), 7.37(2H, d, J=8.7 Hz), 7.58(1H, d, J=8.4 Hz), 7.70(1H, dd, J=8.4 Hz, 2.1 Hz), 7.81(1H, s), 7.98(1H, d, J=2.1 Hz), 8.20(1H, dd, J=8.8 Hz, 2.3 Hz), 8.25(1H, d, J=2.3 Hz). |
| 523 | —NHCOOC(CH₃)₃ | 1.52(9H, s), 6.49(1H, brs), 6.90(1H, d, J=8.6 Hz), 7.05(2H, d, J=8.9 Hz), 7.37(2H, d, J=8.9 Hz), 7.56(1H, d, J=8.6 Hz), 7.69(1H, dd, J=8.6 Hz, 2.3 Hz), 7.92(1H, brs), 7.97(1H, d, J=2.3 Hz), 8.14(1H, dd, J=8.6 Hz, 2.6 Hz), 8.22(1H, d, J=2.6 Hz). |
| 524 | —CH═C(COOCH₃)₂ | 3.85(3H, s), 3.86(3H, s), 7.02(1H, d, J=8.8 Hz), 7.13(2H, d, J=8.5 Hz), 7.46(2H, d, J=8.5 Hz), 7.59(1H, d, J=8.2 Hz), 7.70(1H, dd, J=8.2 Hz, 2.0 Hz), 7.74(1H, s), 7.88(1H, brs), 7.97(1H, d, J=2.0 Hz), 8.22(1H, dd, J=8.8 Hz, 2.5 Hz), 8.24(1H, d, J=2.5 Hz). |

TABLE 75

| Reference No. | R_{259} | R_{260} | R_{261} | ¹H NMR(solvent) δ ppm |
|---|---|---|---|---|
| 525 | —OCH₃ | —H | —COOC₂H₅ | (CDCl₃) 1.40(3H, t, J=7.1 Hz), 3.81(3H, s), 4.39(2H, q, J=7.1 Hz), 6.99-7.02(1H, m), 7.16(1H, d, J=8.1 Hz), 7.56(1H, d, J=8.4 Hz), 7.67-7.72(3H, m), 7.97-8.01(2H, m), 8.17 8.22(2H, m). |
| 526 | —CH₃ | —H | —COOCH₃ | (CDCl₃) 2.24(3H, s), 3.91(3H, s), 6.97-7.01(1H, m), 7.07(1H, d, J=8.4 Hz), 7.57(1H, d, J=8.4 Hz), 7.69-7.73(1H, m), 7.91(1H, dd, J=8.4 Hz, 2.4 Hz), 7.97 7.99(3H, m), 8.21-8.26 (2H, m). |
| 527 | —Cl | —H | —COOCH₃ | (CDCl₃) 3.93(3H, s), 7.08(1H, d, J=8.7 Hz), 7.26(1H, d, J=1.7 Hz), 7.56(1H, d, J=8.2 |

TABLE 75-continued

| Reference No. | $R_{259}$ | $R_{260}$ | $R_{261}$ | $^1$H NMR(solvent) δ ppm |
|---|---|---|---|---|
| | | | | Hz), 7.69-7.73(1H, m), 7.95-7.99 (2H, m), 8.10(1H, brs), 8.15(1H, d, J=2.0 Hz), 8.22-8.24(1H, m), 8.27(1H, d, J=2.8 Hz). |
| 528 | —F | —H | —COOCH$_3$ | (CDCl$_3$) 3.92(3H, s), 7.07(1H, dd, J=7.8 Hz, 1.8 Hz), 7.25-7.31(1H, m), 7.56(1H, d, J=8.4 Hz), 7.71(1H, dd, J=8.2 Hz, 21 Hz), 7.82-7.89(2H, m), 7.97(1H, d, J=2.1 Hz), 8.08(1H, brs), 8.21-8.25(2H, m). |
| 529 | —H | —OCH$_3$ | —COOCH$_3$ | (CDCl$_3$) 3.83(3H, s), 3.87(3H, s), 6.70(1H, dd, J=8.6 Hz, 2.2 Hz), 6.74(1H, d, J=2.2 Hz), 7.01(1H, d, J=8.6 Hz), 7.56(1H, d, J=8.1 Hz), 7.75(1H, dd, J=8.6 Hz, 2.2 Hz), 7.87(1H, d, J=8.6 Hz), 8.01(1H, d, J=2.2 Hz), 8.25-8.33(3H, m). |
| 530 | —H | —CH$_3$ | —COOCH$_3$ | (CDCl$_3$) 2.63(3H, s), 3.91(3H, s), 6.98 7.05(3H, m), 7.60(1H, d, J=8.4 Hz), 7.75(1H, dd, J=8.4 Hz, 2.2 Hz), 7.97-8.03(3H, m), 8.23-8.28(1H, m), 8.30-8.32(1H, m). |
| 531 | —H | —COOCH$_3$ | —H | (DMSO-d$_6$) 3.85(3H, s), 7.17(1H, d, J=8.9 Hz), 7.43-7.47 (1H, m), 7.56-7.62(2H, m), 7.78-7.86(2H, m), 7.93-7.97(1H, m), 8.22 8.27(2H, m), 8.50(1H, d, J=2.3 Hz), 10.60(1H, s). |

TABLE 76

| Reference Example No. | $R_{262}$ | $R_{263}$ | $R_{264}$ | $^1$H NMR (CDCl$_3$) δ ppm |
|---|---|---|---|---|
| 532 | —OCH$_3$ | —H | —COOC$_2$H$_5$ | 1.40(3H, t, J=7.1 Hz), 3.82(3H, s), 4.39(2H, q, J=7.1 Hz), 7.00–7.03(1H, m), 7.17(1H, d, J=8.1 Hz), 7.68 7.76(4H, m), 8.01(2H, d, J=8.1 Hz), 8.16(1H, brs), 8.22–8.25(2H, m). |
| 533 | —OCH$_3$ | —H | —(CH$_2$)$_2$COOCH$_3$ | 2.63–2.69(2H, m), 2.93–2.99(2H, m), 3.69(3H, s), 3.74 (3H, s), 6.78–6.84(2H, m), 6.93(1H, d, J=8.7 Hz), 7.03(1H, d, J=8.1 Hz), 7.73(2H, d, J=8.1 Hz), 7.96–7.99(3H, m), 8.14–8.20(2H, m). |
| 534 | —CH$_3$ | —H | —COOCH$_3$ | 2.25(3H, s), 3.91(3H, s), 6.99–7.03(1H, m), 7.07(1H, d, J=8.4 Hz), 7.75–7.78(2H, m), 7.88–7.92(1H, m), 7.98–8.01(4H, m), 8.26–8.29(2H, m). |
| 535 | —Cl | —H | —COOCH$_3$ | 3.93(3H, s), 7.09(1H, d, J=8.7 Hz), 7.24–7.27(1H, m), 7.76(2H, d, J=8.7 Hz), 7.96–8.03(4H, m), 8.16(1H, d, J=2.1 Hz), 8.24(1H, d, J=2.6 Hz), 8.29(1H, dd, J=8.7 Hz, 2.6 Hz). |
| 536 | —F | —H | —COOCH$_3$ | 3.92(3H, s), 7.08(1H, d, J=8.7 Hz), 7.26–7.32(1H, m), 7.75(2H, d, J=8.4 |

TABLE 76-continued

[Structure: 4-(trifluoromethyl)benzamide linked via NH to pyridine (with R264, R263, R262 substituted phenoxy group)]

| Reference Example No. | R262 | R263 | R264 | ¹H NMR (CDCl₃) δ ppm |
|---|---|---|---|---|
| | | | | Hz), 7.83–7.90(2H, m), 7.98(3H, d, J= 8.2 Hz), 8.22–8.28(2H, m). |
| 537 | —H | —OCH₃ | —COOCH₃ | 3.87(3H, s), 3.88(3H, s), 6.71(1H, dd, J= 8.6 Hz, 2.2 Hz), 6.77(1H, d, J=2.2 Hz), 704(1H, d, J=8.9 Hz), 7.77(2H, d, J=8.1 Hz), 7.88(1H, d, J=8.6 Hz), 8.02 (2H, d, J=8.1 Hz), 8.17(1H, brs), 8.29 8.35(2H, m). |
| 538 | —H | —CH₃ | —COOCH₃ | 2.63(3H, s), 3.91(3H, s), 6.98–7.06(3H, m), 7.79(2H, d, J=8.1 Hz), 8.00–8.04(4H, m), 8.27–8.34(2H, m). |
| 539 | —H | —COOCH₃ | —H | 3.91(3H, s), 6.99–7.04(1H, m), 7.32–7.37(1H, m), 7.45–7.50(1H, m), 7.74–7.80(3H, m), 7.86–7.90(1H, m), 7.96 8.01(3H, m), 8.22–8.27(2H, m). |

TABLE 77

[Structure: substituted benzamide (R265, R266, R267) linked via NH to pyridine-O-phenyl(R268)]

| Reference Example No. | R265 | R266 | R267 | R268 | ¹H NMR (CDCl₃) δ ppm or mp (□) |
|---|---|---|---|---|---|
| 540 | —CF₃ | —H | —H | CH₃-CH(CH₂COOC₂H₅)- | ¹H NMR 1.17(3H, t, J=7.1Hz), 1.26(3H, d, J=7.0 Hz), 2.44-2.61(2H, m), 3.19-3.29(1H, m), 4.05(2H, q, J=7.1 Hz), 6.88(1H, d, J=8.8 Hz), 7.01(2H, d, J=8.5 Hz), 7.19(2H, d, J=8.5 Hz), 7.68(2H, d, J=8.3 Hz), 7.94(2H, d, J=8.3 Hz), 8.15(1H, dd, J=8.8 Hz, 2.7Hz), 8.23(1H, d, J=2.7 Hz), 8.29(1H, brs). |
| 541 | —Cl | —Cl | —H | CH₃-CH(CH₂COOC₂H₅)- | ¹H NMR 1.17(3H, t, J=7.1 Hz), 1.26(3H, d, J=7.0 Hz), 2.43-2.60(2H, m), 3.18-3.28(1H, m), 4.05(2H, q, J=7.1 Hz), 6.85(1H, d, J=8.9 Hz), 6.99(2H, d, J=8.4 Hz), 7.18(2H, d, J=8.4 Hz), 7.48(1H, d, J=8.3 Hz), 7.66(1H, dd, J=8.3 Hz, 2.0 Hz), 7.92(1H, d, J=2.0 Hz), 8.10(1H, dd, J=8.9 Hz, 2.7 Hz), 8.20(1H, d, J=2.7 Hz), 8.39(1H, brs). |
| 542 | —CF₃ | —H | —H | CH=CH-COOC₂H₅ (trans) | ¹H NMR 1.35(3H, t J=7.1 Hz), 4.27(2H, q, J=7.1 Hz), 6.39(1H, dd, J=16.0 Hz, 2.6 Hz), 7.03(1H, d, J=8.9 Hz), 7.16(2H, d, J=8.8 Hz), 7.56(2H, d, J=8.8Hz), 7.68(1H, dd, J=16.0 Hz, 3.2 Hz), 7.77(2H, d, J=8.1 Hz), 7.93(1H, brs), 8.01(2H, d, J=8.1Hz), 8.26(1H, dd, J=8.9 Hz, 2.6Hz), 8.29(1H, d, J=2.6 Hz). |
| 543 | —CF₃ | —H | —H | —CH₂COOCH₃ | ¹H NMR 3.62(2H, s), 3.70(3H, s), 6.94(1H, d, J=8 7 Hz) 7.05-7.09(2H, m), |

TABLE 77-continued

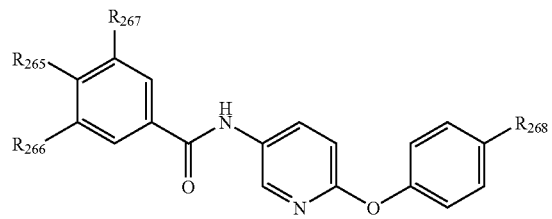

| Reference Example No. | $R_{265}$ | $R_{266}$ | $R_{267}$ | $R_{268}$ | $^1$H NMR (CDCl$_3$) δ ppm or mp (□) |
|---|---|---|---|---|---|
| 544 | —CF$_3$ | —H | —H | —(CH$_2$)$_2$COOC$_2$H$_5$ | 7.26-7.32(2H, m), 7.72(2H, d, J=8.6 Hz), 7.97(2H, d, J=8.2 Hz), 8.17-8.26(3H, m). $^1$H NMR 1.25(3H, t, J=7.1 Hz), 2.62(2H, t, J=7.7 Hz), 2.95(2H, t, J=7.7 Hz), 4.13(2H, q, J=7.1 Hz), 6.94(1H, d, J= 8.8 Hz), 7.04(2H, d, J=8.6 Hz), 7.22(2H, d, J=8.6 Hz), 7.75(2H, d, J=8.3 Hz), 7.98(2H, d, J=8.3 Hz), 8.03 (1H, brs), 8.19(1H, dd, J=8.8 Hz, 2.6Hz), 8.26(1H, d, J=2.6 Hz). |
| 545 | —Cl | —Cl | —H | —(CH$_2$)$_2$O—Si(CH$_3$)$_2$—C(CH$_3$)$_3$ | $^1$H NMR 0.01(6H, s), 0.89(9H, s), 2.83(2H, t, J=6.9 Hz), 3 82(2H t J=6.9 Hz), 6.92(1H, d, J=8.9 Hz), 7.05(2H, dd, J=6.3 Hz, 2.0 Hz), 7.24(2H, d, J=8.6 Hz), 7.58(1H, d, J=8.3 Hz), 7.71(1H, dd, J=8.3 Hz, 2.0 Hz), 7.80(1H, brs), 7.98(1H, d, J=2.0 Hz), 8.15-8.19(1H, m), 8.25(1H, d, J=2.6 Hz). |
| 546 | —Cl | —Cl | —H | —(CH$_2$)$_3$O—Si(CH$_3$)$_2$—C(CH$_3$)$_3$ | $^1$H NMR 0.07(6H, s), 0.91(9H, s), 1.82-1.87(2H, m), 2.65-2.71(2H, m), 3.63-3.68(2H, m), 6.92(1H, d, J=8.9 Hz), 7.02-7.05(2H, m), 7.21(2H, d, J=8.6Hz), 7.57(1H, d, J=8.3 Hz), 7.68-7.72(1H, m), 7.86(1H, brs), 7.97(1H, d, J=2.CHz), 8.14-8.18(1H, m), 8.24(1H, d, J=2.3 Hz). |
| 547 | —H | —F | —CF$_3$ | —COOC$_2$H$_5$ | mp 133-134 |

TABLE 78

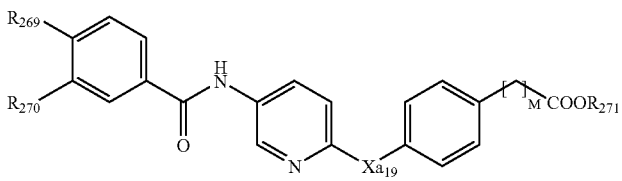

| Reference Example No. | $R_{269}$ | $R_{270}$ | $Xa_{19}$ | $R_{271}$ | M | mp (° C.) or $^1$H NMR (solvent) δ ppm |
|---|---|---|---|---|---|---|
| 548 | —Cl | —Cl | —S— | —CH$_3$ | 2 | mp 141-142 |
| 549 | —Cl | —Cl | —NH— | —C$_2$H$_5$ | 2 | mp 170-171 |
| 550 | —Cl | —Cl | —N(CH$_3$)— | —C$_2$H$_5$ | 2 | $^1$H NMR (DMSO-d$_6$) 1.17(3H, t, J=7.1 Hz), 2.63(2H, t, J=7.7 Hz), 2.85(2H, t, J=7.7 Hz), 3.36(3H, s), 4.07(2H, d, J= 7.1 Hz), 6.56(1H, d, J=9.5 Hz), 7.18(2H, d, J=8.3 Hz), 7.27(2H, d, J= 8.3 Hz), 7.75-7.95(3H, m), 8.20(1H, s), 8.47(1H, s), 10.26(1H, s). |
| 551 | —CF$_3$ | —H | —N(CH$_3$)— | —C$_2$H$_5$ | 0 | mp 135-136 |
| 552 | —CF$_3$ | —H | —N(CH$_3$)— | —C$_2$H$_5$ | 2 | $^1$H NMR (CDCl$_3$) 1.26(3H, t, J=7.2 Hz), 2.65(2H, t, J=8.0 Hz), 2.97(2H, t, J=8.0 Hz), 3.45(3H, s), 4.16(2H, q, J= 7.2 Hz), 6.57(1H, d, J=9.1 Hz), 7.18(2H, d, J=8.3 Hz), 7.24(2H, d, J= 8.3 Hz), 7.35-7.45(1H, m), 7.65- |

TABLE 78-continued

[Structure: R269, R270-substituted benzamide linked via NH to pyridine with Xa19 to phenyl-(CH2)M-COOR271]

| Reference Example No. | R269 | R270 | Xa19 | R271 | M | mp (° C.) or ¹H NMR (solvent) δ ppm |
|---|---|---|---|---|---|---|
| | | | | | | 7.78(3H, m), 7.98(2H, d, J=8.1 Hz), 8.28(1H, d, J=2.5 Hz). |
| 553 | —Cl | —Cl | —N(CH₂Ph)— | —C₂H₅ | 2 | ¹H NMR (CDCl₃) 1.23(3H, t, J=7.2 Hz), 2.61(2H, t, J=7.6 Hz), 2.92(2H, t, J=7.6 Hz), 4.12(2H, q, J=7.2 Hz), 5.20(2H, s), 6.54(1H, d, J=9.1 Hz), 7.10-7.30(8H, m), 7.53(1H, d, J=8.4 Hz), 7.60-7.75(3H, m), 7.94(1H, d, J=1.3 Hz), 8.22(1H, d, J=2.3 Hz). |
| 554 | —Cl | —H | —O— | —CH₃ | 0 | ¹H NMR (CDCl₃) 3.91(3H, s), 7.04(1H, d, J=9.9 Hz), 7.17(2H, d, J=8.6 Hz), 7.49(2H, d, J=8.6 Hz), 7.79(1H, brs), 7.83(2H, d, J=8.6 Hz), 8.08(2H, d, J=8.6 Hz), 8.27-8.29(2H, m). |
| 555 | —CF₃ | —H | —O— | —C₂H₅ | 0 | ¹H NMR (CDCl₃) 1.39(3H, t, J=7.3 Hz), 4.37(2H, q, J=7.3 Hz), 7.04(1H, dd, J=8.3 Hz, 1.3 Hz), 7.15-7.19(2H, m), 7.78(2H, d, J=8.3 Hz), 7.91(1H, brs), 8.00(2H, d, J=6.9 Hz), 8.07-8.10(2H, m), 8.27-8.31(2H, m). |
| 556 | —H | —OCF₃ | —O— | —CH₃ | 0 | ¹H NMR (CDCl₃) 3.91(3H, s), 7.02(1H, d, J=8.7 Hz), 7.16(2H, d, J=8.7 Hz), 7.42(1H, d, J=8.2 Hz), 7.53(1H, t, J=8.1 Hz), 7.76-7.81(2H, m), 8.05-8.08(3H, m), 8.25-8.31(2H, m). |
| 557 | —H | —CF₃ | —O— | —C₂H₅ | 0 | ¹H NMR (CDCl₃) 1.39(3H, t, J=7.2 Hz), 4.37(2H, q, J=7.2 Hz), 7.40(1H, d, J=8.7 Hz), 7.09-7.20(2H, m), 7.66(1H, t, J=7.8 Hz), 7.76-7.90(1H, m), 8.00(1H, brs), 8.00-8.10(3H, m), 8.10-8.18(1H, m), 8.20-8.35(2H, m). |

TABLE 79

[Structure: 3,4-dichlorobenzamide linked via NH to pyridine with R272, -O- to phenyl-N(R273)-(CH2)M-COOC2H5]

| Reference Example No. | R272 | R273 | M | mp (° C.) or ¹H NMR (CDCl₃) δ ppm |
|---|---|---|---|---|
| 558 | —H | —Ac | 1 | mp 178-179 |
| 559 | —H | —Ac | 2 | ¹H NMR 1.22(3H, t, J=7.2 Hz), 1.86(3H, s), 2.58(2H, t, J=7.3 Hz), 3.99(2H, t, J=7.3 Hz), 4.07(2H, q, J=7.2 Hz), 7.02(1H, d, J=8.9 Hz), 7.15-7.20(4H, m), 7.58(1H, d, J=8.4 Hz), 7.75(1H, dd, J=2.1 Hz, 8.4 Hz), 8.02(1H, d, J=2.1 Hz), 8.24(1H, dd, J=2.7 Hz, 8.9 Hz), 8.28(1H, s), 8.32(1H, d, J=2.7 Hz). |
| 560 | —H | —CH₃ | 1 | ¹H NMR 1.26(3H, t, J=7.1 Hz), 3.06(3H, s), 4.04(2H, s), 4.18(2H, q, J=7.1 Hz), 6.68(2H, d, J=9.1 Hz), 6.85(1H, d, J=8.9 Hz), 7.00(2H, d, J=9.1 Hz), 7.55(1H, d, J=8.4 Hz), 7.70(1H, dd, J=1.9 Hz, 8.4 Hz), 7.94(1H, s), 7.97(1H, d, J=1.9 Hz), 8.10(1H, dd, J=2.6 Hz, 8.9 Hz), 8.21(1H, d, J=2.6 Hz). |
| 561 | —H | —C₂H₅ | 1 | ¹H NMR 1.22(3H, t, J=7.1 Hz), 1.27(3H, t, J=7.1 Hz), 3.46(2H, q, J=7.1 Hz), 4.01(2H, s), 4.20(2H, q, J=7.1 Hz), 6.64(2H, d, J=9.1 Hz), 6.86(1H, d, J=8.9 Hz), 6.98(2H, d, J=9.1 Hz), 7.56(1H, d, J=8.4 Hz), 7.70(1H, dd, J=1.9 Hz, 8.4 Hz), 7.82(1H, s), 7.97(1H, d, J=1.9 Hz), 8.11(1H, dd, J=2.6 Hz, 8.9 Hz), 8.22(1H, d, J=2.6 Hz). |

TABLE 79-continued

| Reference Example No. | $R_{272}$ | $R_{273}$ | M | mp (° C.) or $^1$H NMR (CDCl$_3$) δ ppm |
|---|---|---|---|---|
| 562 | —OCH$_3$ | —OH$_3$ | 1 | $^1$H NMR 1.25(3H, t, J=7.1 Hz), 3.03(3H, s), 3.65(3H, s), 4.01(2H, s), 4.17(2H, q, J=7.1 Hz), 6.16(1H, d, J=8.7 Hz), 6.21(1H, s), 6.76(1H, d, J=8.9 Hz), 6.88 (1H, d, J=8.6 Hz), 7.43(1H, d, J=8.4 Hz), 7.67(1H, d, J=8.4 Hz), 7.94(1H, d, J=1.8 Hz), 8.02(1H, d, J=8.9 Hz), 8.13(1H, d, J=2.3 Hz), 8.88(1H, s). |
| 563 | —OCH$_3$ | —C$_2$H$_5$ | 1 | $^1$H NlMR 1.21(3H, t, J=7.1 Hz), 1.27(3H, t, J=7.1 Hz), 3.44(2H, q, J=7.1 Hz), 3.68(3H, s), 3.98(2H, s), 4.20(2H, q, J=7.1 Hz), 6.17(1H, dd, J=8.9 Hz, 3.C Hz), 6.24(1H, d, J=2.8 Hz), 6.81(1H, d, J=8.9 Hz), 6.91(1H, d, J=8.7 Hz), 7.48(1H, d, J=8.4 Hz), 7.68(1H, dd, J=8.4 Hz, 2.2 Hz), 7.96(1H, d, J=2.C Hz), 8.04(1H, dd, J=8.9 Hz, 2.8 Hz), 8.15(1H, d, J=2.3 Hz), 8.34(1H, s). |
| 564 | —CH$_3$ | —Ac | 1 | $^1$H NMR 1.26(3H, t, J=7.1 Hz), 1.96(3H, s), 2.22(3H, s), 4.20(2H, q, J=7.1 Hz), 4.37(2H, s), 6.99(1H, d, J=8.9 Hz), 7.07(1H, d, J=8.4 Hz), 7.19(1H, dd, J=2.4 Hz, 8.4 Hz), 7.59(1H, d, J=8.4 Hz), 7.72(1H, d, J=8.4 Hz), 7.90-8.12(2H, m), 8.21(1H, dd, J=2.C Hz, 8.4 Hz), 8.27(1H, s). |
| 565 | —CH$_3$ | —CH$_3$ | 1 | $^1$H NMR 1.26(3H, t, J=7.1 Hz), 2.12(3H, s), 3.06(3H, s), 4.04(2H, s), 4.20(2H, q, J=7.1 Hz), 6.49-6.61(2H, m), 6.83(1H, d, J=8.9 Hz), 6.93(1H, d, J=8.5 Hz), 7.57(1H, d, J=8.5 Hz), 7.70(1H, dd, J=8.5 Hz, 2.1 Hz), 7.73(1H, d, J=2.1 Hz), 7.97 (1H, d, J=2.1 Hz), 8.12(1H, dd, J=8.9 Hz, 2.8 Hz), 8.21(1H, d, J=2.8 Hz). |
| 566 | —F | —Ac | 1 | hu 1H NMR 1.29(3H, t, J=7.1 Hz), 2.00(3H, s), 4.21(2H, q, J=7.1 Hz), 4.37(2H, s), 7.09(1H, dd, J=7.9 Hz, 1.8 Hz), 7.18-7.32(3H, m), 7.59(1H, d, J=8.4 Hz), 7.72 (1H, dd, J=8.3 Hz, 2.1 Hz), 7.83(1H, brs), 7.99(1H, d, J=2.C Hz), 8.20-8.24(2H, m). |
| 567 | —F | —CH$_3$ | 1 | $^1$H NMR 1.27(3H, t, J=7.1 Hz), 3.06(3H, s), 4.04(2H, s), 4.20(2H, q, J=7.1 Hz), 6.40-6.52(2H, m), 6.96(1H, d, J=9.2 Hz), 7.07(1H, t, J=9.1 Hz), 7.57(1H, d, J=8.2 Hz), 7.70(1H, dd, J=8.2 Hz, 2.0 Hz), 7.82(1H, brs), 7.97(1H, d, J=2.1 Hz), 8.138.19(2H, m). |
| 568 | —F | —C$_2$H$_5$ | 1 | $^1$H NMR 1.23(3H, t, J=7.1 Hz), 1.28(3H, t, J=7.1 Hz), 3.45(2H, q, J=7.1 Hz), 4.00(2H, s), 4.22(2H, q, J=7.1 Hz), 6.37-6.48(2H, m), 6.97(1H, d, J=8.7 Hz), 7.05(1H, t, J=9.1 Hz), 7.57(1H, d, J=8.4 Hz), 7.70(1H, dd, J=8.4 Hz, 2.2 Hz), 7.79(1H, brs), 7.98(1H, d, J=2.C Hz), 8.13-8.20(2H, m). |

TABLE 80

| Reference Example No. | $R_{274}$ | $R_{275}$ | M | E | mp (° C.) or $^1$H NMR (CDCl$_3$) δ ppm |
|---|---|---|---|---|---|
| 569 | —H | —Ac | 1 | 2 | mp 163-164 |
| 570 | —H | —Ac | 2 | 2 | $^1$H NMR 1.22(3H, t, J=7.2 Hz), 1.87(3H, s), 2.59(2H, t, J=7.3 Hz), 4.00(2H, t, J=7.3 Hz), 4.08(2H, q, J=7.2 Hz), 7.03(1H, d, J=8.8 Hz), 7.19(4H, s), 7.78(2H, d, J=8.3 Hz), 7.95(1H, brs), 8.01(2H, d, J=8.3 Hz), 8.27(1H, d, J=8.8 Hz), 8.31(1H, s). |
| 571 | —H | —CH$_3$ | 1 | 1 | $^1$H NMR 3.06(3H, s), 3.73(3H, s), 4.07(2H, s), 6.68(2H, d, J=9.1 Hz), 6.86 (1H, d, J=8.9 Hz), 7.00(2H, d, J=9.1 Hz), 7.74(2H, d, J=8.0 Hz), 7.98(2H, d, J=8.0 Hz), 8.07(1H, s), 8.15(1H, dd, J=8.9 Hz, 2.5 Hz), 8.24(1H, d, J=2.5 Hz). |
| 572 | —H | —C$_2$H$_5$ | 1 | 2 | $^1$H NMR 1.18(3H, t, J=7.1 Hz), 1.25(3H, t, J=7.1 Hz), 3.41(2H, q, J=7.1 Hz), 3.98(2H, s), 4.17(2H, q, J=7.1 Hz), 6.59(2H, d, J=9.1 Hz), 6.79(1H, d, J=8.7 Hz), |

TABLE 80-continued

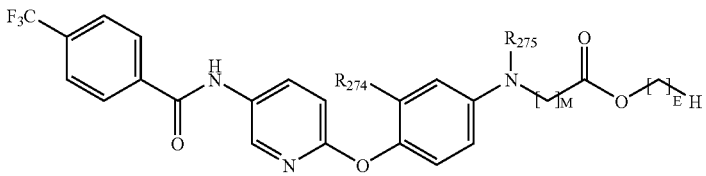

| Reference Example No. | $R_{274}$ | $R_{275}$ | M | E | mp (° C.) or $^1$H NMR (CDCl$_3$) δ ppm |
|---|---|---|---|---|---|
| | | | | | 6.92(2H, d, J=9.1 Hz), 7.64(2H, d, J=8.4 Hz), 7.94(2H, d, J=8.1 Hz), 8.07(1H, dd, J=8.9 Hz, 2.6 Hz), 8.22(1H, d, J=2.8 Hz), 8.75(1H, s). |
| 573 | —OCH$_3$ | —CH$_3$ | 1 | 2 | $^1$H NMR 1.24(3H, t, J=7.1 Hz), 3.03(3H, s), 3.65(3H, s), 4.01(2H, s), 4.17 (2H, q, J=7.1 Hz), 6.17(1H, dd, J=8.7 Hz, 2.6 Hz), 6.24(1H, d, J=2.5 Hz), 6.77(1H, d, J=8.9 Hz), 6.89(1H, d, J=8.7 Hz), 7.63(2H, d, J=8.3 Hz), 7.96(2H, d, J=8.1 Hz), 8.06(1H, d, J=8.7 Hz), 8.16(1H, d, J=2.5 Hz), 8.91(1H, s). |
| 574 | —OCH$_3$ | —C$_2$H$_5$ | 1 | 2 | $^1$H NMR 1.19(3H, t, J=7.1 Hz), 1.26(3H, t, J=7.1 Hz), 3.42(2H, q, J=7.1 Hz), 3.64(3H, s), 3.97(2H, s), 4.18(2H, q, J=7.1 Hz), 6.14(1H, dd, J=8.7 Hz, 2.8 Hz), 6.21(1H, d, J=2.8 Hz), 6.76(1H, d, J=8.9 Hz), 6.87(1H, d, J=8.7 Hz), 7.62(2H, d, J=8.4 Hz), 7.96(2H, d, J=8.3 Hz), 8.05(1H, dd, J=8.9 Hz, 2.5 Hz), 8.18(1H, d, J=2.6 Hz), 9.01(1H, s). |
| 575 | —CH$_3$ | —Ac | 1 | 2 | $^1$H NMR 1.25(3H, t, J=7.0 Hz), 1.93(3H, s), 2.21(3H, s), 4.18(2H, q, J=7.0 Hz), 4.35(2H, s), 6.98(1H, d, J=8.7 Hz), 7.06(1H, d, J=8.5 Hz), 7.18(1H, d, J=8.5 Hz), 7.23-7.28(1H, m), 7.75(2H, d, J=7.8 Hz), 8.02(2H, d, J=7.8 Hz), 8.22-8.33(2H, m). |
| 576 | —CH$_3$ | —CH$_3$ | 1 | 2 | $^1$H NMR 1.26(3H, t, J=7.1 Hz), 2.11(3H, s), 3.05(3H, s), 4.04(2H, s), 4.19 (2H, q, J=7.1 Hz), 6.46-6.60(2H, m), 6.80(1H, d, J=8.9 Hz), 6.91(1H, d, J=8.5 Hz), 7.74(2H, d, J=8.4 Hz), 7.98(2H, d, J=8.2 Hz), 8.07(1H, s), 8.15 (1H, dd, J=8.9 Hz, 2.7 Hz), 8.23(1H, d, J=2.7 Hz). |
| 577 | —F | —Ac | 1 | 2 | $^1$H NMR 1.28(3H, t, J=7.1 Hz), 1.98(3H, s), 4.20(2H, q, 7.1 Hz), 4.36 (2H, s), 7.09(1H, dd, J=6.4 Hz, 3.5 Hz), 7.13-7.32(3H, m), 7.77(2H, d, J=8.3 Hz), 8.01(2H, d, J=8.1 Hz), 8.12(1H, s), 8.23-8.28(2H, m). |
| 578 | —F | —CH$_3$ | 1 | 2 | $^1$H NMR 1.27(3H, t, J=7.1 Hz), 3.07(3H, s), 4.04(2H, s), 4.20(2H, q, J=7.1 Hz), 6.41-6.53(2H, m), 6.98(1H, d, J=9.7 Hz), 7.07(1H, t, J=9.1 Hz), 7.76 (2H, d, J=8.6 Hz), 7.84(1H, s), 7.99(2H, d, J=8.1 Hz), 8.19-8.21(2H, m). |
| 579 | —F | —C$_2$H$_5$ | 1 | 2 | $^1$H NMR 1.20-1.31(6H, m), 3.45(2H, q, J=7.3 Hz), 4.00(2H, s), 4.22(2H, q, J=7.1 Hz), 6.37-6.49(2H, m), 6.97-7.09(2H, m), 7.76-7.79(3H, m), 7.99(2H, d, J=7.9 Hz), 8.19-8.21(2H, m). |

Reference Example 580

Production of ethyl 3-{4-[5-(3,4-dichlorobenzoylamino)-pyridin-2-yloxy]-3-methoxyphenyl}propionate Under ice cooling, to a solution of ethyl 3-(4-(5-aminopyridin-2-yloxy)-3-methoxyphenyl)propionate (1.43 g, 4.5 mmol) in dichloromethane (30 mL) was added pyridine (0.44 mL, 5.4 mmol), and then 3,4-dichlorobenzoyl chloride (0.99 g, 4.7 mmol). The resulting solution was stirred for 1 hour under ice cooling, and then for 10 hours at room temperature. To the resulting reaction solution was added 10% hydrochloric acid, and extracted with dichloromethane. The dichloromethane layer was washed with water, dried over anhydrous magnesium sulfate, and evaporated. To the residue was added diethyl ether, and stirred. The precipitates were collected by filtration. After washing with water and diethyl ether, the precipitates were air dried at 60° C., to thereby yield 0.52 g of the title compound.

Appearance: White powder $^1$H NMR (CDCl$_3$) δ 1.26 (3H, t, J=7.1 Hz), 2.56-2.79 (2H, m), 2.91-3.09 (2H, m), 3.75 (3H, s), 4.15 (2H, q, J=7.1 Hz), 6.75 (3H, m), 7.10 (1H, d, J=8.0 Hz), 7.56 (1H, d, J=8.2 Hz), 7.99 (1H, d, J=8.1 Hz), 8.17 (1H, s), 8.69 (1H, d, J=9.2 Hz), 8.79 (1H, s), 9.52 (1H, brs).

The following compounds were produced in the same manner as in Reference Example 580.

TABLE 81

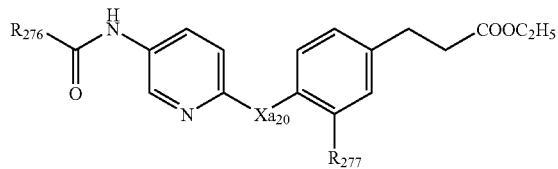

| Reference Example No. | $R_{276}$ | $R_{277}$ | $Xa_{20}$ | $^1$H NMR (CDCl$_3$) δ ppm |
|---|---|---|---|---|
| 581 | 3,4-Cl$_2$Ph— | —H | —CO— | 1.23(3H, t, J=7.2 Hz), 2.64(2H, t, J=7.6 Hz), 3.01(2H, t, J=7.6 Hz), 4.12(2H, q, J=7.2 Hz), 7.30(2H, d, J=8.2 Hz), 7.57 (1H, d, J=8.3 Hz), 7.73(1H, dd, J=8.3 Hz, 2.2 Hz), 7.95-8.04 (3H, m), 8.09(1H, d, J=8.6 Hz), 8.16(1H, brs), 8.41(1H, dd, J=8.6 Hz, 2.6 Hz), 8.80(1H, d, J=2.6 Hz). |
| 582 | 4-CF$_3$Ph— | —OC$_2$H$_5$ | —O— | 1.22(3H, t, J=6.9 Hz), 1.26(3H, t, J=7.2 Hz), 2.51-2.73(2H, m), 2.87-3.06(2H, m), 4.02(2H, q, J=6.9 Hz), 4.15(2H, q, J=7.2 Hz), 6.71-6.96(3H, m), 7.17(1H, d, J=7.9 Hz), 7.75(2H, d, J=7.6 Hz), 8.43(2H, d, J=7.6 Hz), 9.15-9.32(1H, m), 9.42(1H, s), 11.14(1H, brs). |
| 583 | 3,4-Cl$_2$Ph— | —F | —O— | 1.26(3H, t, J=7.1 Hz), 2.53-2.70(2H, m), 2.85-3.03(2H, m), 4.15(2H, q, J=7.1 Hz), 6.97-7.09(3H, m), 7.10-7.19(1H, m), 7.58(1H, d, J=8.3 Hz), 7.70(1H, dd, J=8.3 Hz, 2.1 Hz), 7.72 (1H, brs), 7.97(1H, d, J=2.1 Hz), 8.15-8.23(2H, m). |
| 584 | PhCH$_2$O— | —H | —O— | 1.25(3H, t, J=7.1 Hz), 2.53-2.71(2H, m), 2.84-3.04(2H, m), 4.14(2H, q, J=7.1 Hz), 6.51-6.64(1H, m), 6.88(1H, d, J=8.8 Hz), 6.98-7.06(2H, m), 7.17-7.24(2H, m), 7.30-7.43(5H, m), 7.87-8.02(1H, m), 8.05(1H, d, J=2.5 Hz). |
| 585 | 4-CF$_3$Ph— | —F | —O— | 1.26(3H, t, J=7.1 Hz), 2.56-2.71(2H, m), 2.89-3.02(2H, m), 4.15(2H, q, J=7.1 Hz), 6.97-7.08(3H, m), 7.10-7.19(1H, m), 7.77(2H, d, J=8.2 Hz), 7.82(1H, brs), 7.99(2H, d, J=8.2 Hz), 8.17-8.26(2H, m). |

TABLE 82

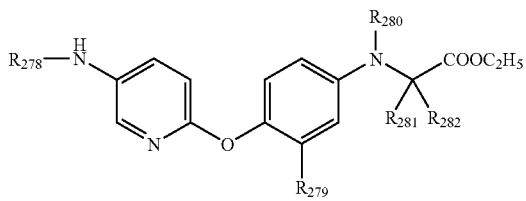

| Reference Example No. | $R_{278}$ | $R_{279}$ | $R_{280}$ | $R_{281}$ | $R_{282}$ | $^1$H NMR (CDCl$_3$) δ ppm |
|---|---|---|---|---|---|---|
| 586 | 4-CF$_3$PhCO— | —F | —(CH$_2$)$_2$CH$_3$ | —H | —H | 0.96(3H, t, J=7.3 Hz), 1.28(3H, t, J=7.1 Hz), 1.63-1.74(2H, m), 3.32(2H, t, J=7.6 Hz), 4.01(2H, s), 4.21(2H, q, J=7.1 Hz), 6.35-6.47(2H, m), 6.97(1H, d, J=7.8 Hz), 7.01(1H, t, J=8.9 Hz), 7.77(2H, d, J=8.2 Hz), 7.81(1H, s), 7.99(2H, d, J=8.2 Hz), 8.198.22(2H, m). |
| 587 | 4-CF$_3$PhCO— | —H | —CH$_3$ | —CH$_3$ | —CH$_3$ | 1.25(3H, t, J=7.1 Hz), 1.42(6H, s), 2.91(3H, s), 4.18(2H, q, J=7.1 Hz), 6.92(1H, d, J=8.7 Hz), 7.00(2H, d, J=9.2 Hz), 7.07(2H, d, J=9.1 Hz), 7.77(2H, d, J=8.2 Hz), |

TABLE 82-continued

[Structure: R278-NH-pyridine-O-phenyl(R279)-N(R280)-C(R281)(R282)-COOC2H5]

| Reference Example No. | R278 | R279 | R280 | R281 | R282 | ¹H NMR (CDCl₃) δ ppm |
|---|---|---|---|---|---|---|
| | | | | | | 7.81(1H, a), 8.00(2H, d, J=8.1 Hz), 8.20(1H, dd, J=8.7 Hz, 2.8 Hz), 8.28(1H, d, J=2.5 Hz). |
| 588 | 3,4-Cl₂PhSO₂— | —F | —CH₃ | —H | —H | 1.29(3H, t, J=7.1 Hz), 3.05(3H, s), 4.03(2H, s), 4.22(2H, q, J=7.1 Hz), 6.38-6.49(2H, m), 6.82(1H, brs), 6.88(1H, d, J=8.7 Hz), 7.02(1H, t, J=8.8 Hz), 7.48(1H, dd, J=8.4, 1.6 Hz), 7.52(1H, d, J=8.4 Hz), 7.57(1H, dd, J=8.7 Hz, 2.6 Hz), 7.70(1H, d, J=2.6 Hz), 7.82(1H, d, J=1.8 Hz). |

Reference Example 589

Production of ethyl 4-[5-(3,4-dimethylbenzoylamino)-pyridin-2-yloxy]benzoate

To a solution of ethyl 4-(5-aminopyridin-2-yloxy)benzoate (14.15 g, 54.8 mmol) in DMF (100 mL) were added 3,4-dimethylbenzoic acid (8.23 g, 54.8 mmol), 1-hydroxybenzotriazole monohydrate (8.4 g, 54.8 mmol), 1-ethyl-3-(3-dimethylaminopropyl)carbodiimide hydrochloride (12.6 g, 65.7 mmol) under ice cooling, and then stirred for 30 minutes under ice cooling and for 17 hours at room temperature. The reaction solution was concentrated under reduced pressure. To the residue was added water (200 mL), and extracted with ethyl acetate (250 mL). The ethyl acetate layer was washed with a saturated sodium bicarbonate solution and brine, dried over anhydrous magnesium sulfate, and evaporated. The residue was purified by silica gel column chromatography (n-hexane:ethyl acetate=2:1), to thereby yield 16.15 g of the title compound.

Appearance: White powder

¹H NMR (CDCl₃) δ 1.39 (3H, t, J=7.1 Hz), 2.33 (6H, s), 4.37 (2H, q, J=7.1 Hz), 6.99 (1H, d, J=9.7 Hz), 7.15 (2H, d, J=8.7 Hz), 7.24 (1H, d, J=7.7 Hz), 7.59 (1H, dd, J=7.7 Hz, 2.0 Hz), 7.65 (1H, d, J=2.0 Hz), 7.90 (1H, brs), 8.07 (2H, d, J=8.7 Hz), 8.25-8.35 (2H, m).

The following compounds were produced in the same manner as in Reference Example 589.

TABLE 83

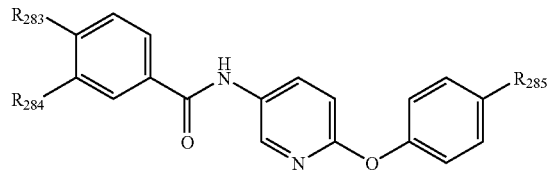

| Reference Example No. | R283 | R284 | R285 | ¹H NMR (CDCl₃) δ ppm |
|---|---|---|---|---|
| 590 | —Cl | —Cl | —Ac | 2.58(3H, s), 7.19(1H, d, J=8.7 Hz), 7.22(2H, d, J=8.7 Hz), 6.06(2H, s), 7.84(1H, d, J=8.4 Hz), 7.97(1H, dd, J=8.4 Hz, 2.1 Hz), 8.01(1H, d, J=8.7 Hz), 8.24(1H, d, J=2.1 Hz), 8.28(1H, dd, J=8.7 Hz, 2.6 Hz), 8.56(1H, d, J=2.6 Hz), 10.64(1H, brs). |
| 591 | —CN | —H | —COOCH₃ | 3.92(3H, s), 7.05(1H, d, J=8.9 Hz), 7.18(2H, d, J=8.6 Hz), 7.81(2H, d, J=8.6 Hz), 7.90(1H, brs), 8.00(2H, d, J=8.6 Hz), 8.08(2H, d, J=8.6 Hz), 8.27(1H, dd, J=8.6 Hz, 2.6 Hz), 8.30(1H, d, J=2.3 Hz). |

Reference Example 592

Production of ethyl 3-{4-[5-(3,4-dichlorobenzoylamino)-pyridin-2-yloxy]-3-ethoxyphenyl}propionate To a solution of ethyl 3-[3-ethoxy-4-(5-nitropyridin-2-yloxy)phenyl]propionate (0.82 g, 2.3 mmol) in ethanol (40 mL) was added 10% palladium-carbon (0.15 g) under a nitrogen atmosphere, and the resulting solution was stirred under a hydrogen atmosphere at atmospheric pressure for 1 hour at room temperature. The palladium-carbon was removed by filtration, and the filtrate was concentrated. The obtained filtrate (0.58 g) was dissolved in dichloromethane (30 mL), and to the resulting solution were added pyridine (0.17 mL, 2.1 mmol) and 3,4-dichlorobenzoyl chloride (0.39 g, 1.84 mmol) under ice cooling. The resulting solution was stirred under ice cooling for 1 hour, and then stirred for 12 hours at room temperature. The reaction solution was made acidic by adding 10% hydrochloric acid, and extracted with dichloromethane. The dichloromethane layer was washed with a saturated sodium bicarbonate solution, dried over anhydrous magnesium sulfate, and evaporated, to thereby yield 0.94 g of the title compound.

Appearance: Yellow amorphous powder $^1$H NMR (CDCl$_3$) δ 1.18 (3H, t, J=7.0 Hz), 1.26 (3H, t, J=7.1 Hz), 2.53-2.71 (2H, m), 2.86-3.01 (2H, m), 3.98 (2H, q, i=7.0 Hz), 4.15 (2H, q, J=7.1 Hz), 6.78-6.88 (2H, m), 6.95 (1H, d, J=8.8 Hz), 7.06 (1H, d, J=7.9 Hz), 7.58 (1H, d, J=8.3 Hz), 7.65-7.77 (2H, m), 7.98 (1H, d, J=2.1 Hz), 8.14 (1H, dd, J=8.8 Hz, 2.7 Hz), 8.19 (1H, d, J=2.3 Hz).

The following compound was produced in the same manner as in Reference Example 592.

Reference Example 593

N-{6-(4-(3-hydroxypropyl)phenoxy]pyridin-3-yl}-4-trifluoromethylbenzamide $^1$H NMR (CDCl$_3$) δ 1.86-1.97 (2H, m), 2.70-2.75 (2H, m), 3.68-3.73 (2H, m), 6.95 (1H, d, J=8.7 Hz), 7.03-7.08 (2H, m), 7.23 (2H, d, J=8.4 Hz), 7.77 (2H, d, J=8.2 Hz), 7.84 (1H, brs), 7.99 (2H, d, J=8.2 Hz), 8.20-8.23 (1H, m), 8.26 (1H, d, J=2.6 Hz).

Reference Example 594

Production of methyl 2-(4-{5-[3-(3,4-dichlorophenyl)-ureido]pyridin-2-yloxy}phenyl)acetate To a solution of methyl 2-[4-(5-aminopyridin-2-yloxy)phenyl]acetate (0.44 g, 1.7 mmol) in dichloromethane (7 mL) was added 3,4-dichlorophenylisocyanate (0.353 g, 1.9 mmol), and the resulting reaction solution was stirred for 1 hour at room temperature. To the reaction solution was added diisopropyl ether. Insoluble matter was removed by filtration, to thereby yield 0.60 g of the title compound.

Appearance: White powder $^1$H NMR (DMSO-d$_6$) δ 3.63 (3H, s), 3.69 (2H, s), 6.99-7.05 (3H, m), 7.26-7.30 (2H, m), 7.35 (1H, dd, J=8.8, 2.4 Hz), 7.52 (1H, d, J=8.8 Hz), 7.86 (1H, d, J=2.4 Hz), 7.98 (1H, dd, J=8.8, 2.8 Hz), 8.18 (1H, d, J=2.7. Hz), 8.91 (1H, s), 9.10 (1H, s).

The following compounds were produced in the same manner as in Reference Example 594.

TABLE 84

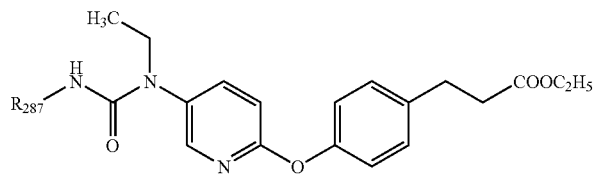

| Reference Example No. | R$_{286}$ | MS (M$^+$) |
|---|---|---|
| 595 | —H | 459 |
| 596 | —CH$_3$ | 473 |

TABLE 85

| Reference Example No. | R$_{287}$ | $^1$H NMR (CDCl$_3$) δ ppm or MS |
|---|---|---|
| 597 | 4-CF$_3$Ph— | $^1$H NMR 1.18(3H, t, J=7.1 Hz), 1.25(3H, t, J=7.1 Hz), 2.62-2.68(2H, m), 2.96-3.01(2H, m), 3.76(2H, q, J=7.1 Hz), 4.14(2H, q, J=7.1 Hz), 6.17(1H, brs), 7.05(1H, dd, J=8.7 Hz, 0.7 Hz), 7.11(2H, d, J=8.6 Hz), 7.28(2H, d, J=8.6 Hz), 7.40(2H, d, J=8.7 Hz), 7.49(2H, d, J=8.6 Hz), 7.63(1H, dd, J=8.7 Hz, 2.6 Hz), 8.14(1H, dd, J=2.6 Hz, 0.7 Hz). |
| 598 | 3,4-Cl$_2$Ph— | MS 501(M$^+$) |

TABLE 86

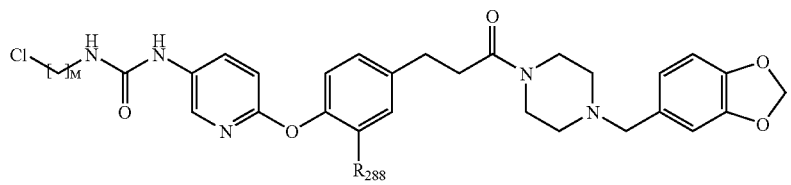

| Reference Example No. | R288 | M | ¹H NMR (CDCl₃) δ ppm |
|---|---|---|---|
| 599 | —H | 3 | 1.90-2.11(2H, m), 2.28-2.50(4H, m), 2.5 1-2.72(2H, m), 2.82-3.07(2H, m), 3.28-3.51(4H, m), 3.52-3.78(4H, m), 5.255.40(1H, m), 5.96(2H, s), 6.69-6.81(2H, m), 6.82-6.94(2H, m), 6.95-7.08(2H, m), 7.09-7.26(3H, m), 7.88-8.07(2H, m). |
| 600 | —H | 2 | 2.20-2.46(4H, m), 2.52-2.70(2H, m), 2.82-3.02(2H, m), 3.28 3.50(4H, m), 3.51-3.72(6H, m), 5.52-5.71(1H, m), 5.95(1H, s), 6.68-6.78(2H, m), 6.80-6.89(2H, m), 6.91(2H, d, J=8.4 Hz), 7.17(2H, d, J=8.4 Hz), 7.36(1H, s), 7.89-8.01(2H, m). |
| 601 | —OCH₃ | 3 | 1.85-2.08(2H, m), 2.27-2.46(4H, m), 2.55-2.71(2H, m), 2.88-3.03(2H, m), 3.30-3.46(6H, m), 3.56(2H, t, J=6.3 Hz), 3.63(2H, t, J=4.9 Hz), 3.71(3H, s), 5.20-5.36(1H, m), 5.95(2H, s), 6.68-6.89(6H, m), 7.00(1H, d, J=8.0 Hz), 7.15(1H, s), 7.87(1H, d, J= . 2.4 Hz), 7.92(1H, dd J=2.8 Hz, 8.8 Hz). |
| 602 | —OCH₃ | 2 | 2.25-2.49(4H, m), 2.58-2.72(2H, m), 2.87-3.05(2H, m), 3.30 3.71(1CH, m), 3.71(3H, s), 5.40-5.52(1H, m), 5.95(2H, s), 6.66-6.91(6H, m), 7.00(1H, d, J=8.0 Hz), 7.07(1H, s), 7.85-7.99 (2H, m). |

TABLE 87

| Reference Example No. | Chemical Structure | ¹H NMR (solvent) δ ppm |
|---|---|---|
| 603 | 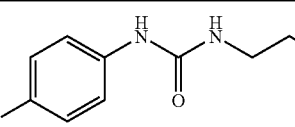 | (DMSO-d₆) 3.38(2H, t, J=6.1 Hz), 3.63(2H, t, J=6.1 Hz), 3.68(3H, s), 6.27(1H, t, J=6.1 Hz), 6.76-6.84(2H, m), 7.22 7.31(2H, m), 8.41(1H, s). |
| 604 | 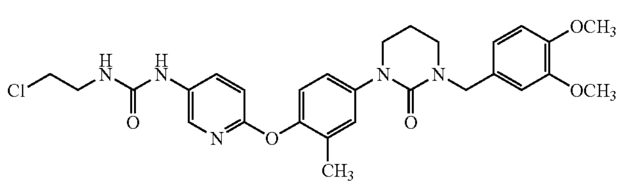 | (CDCl₃) 2.002.20(5H, m), 3.27-3.47 (4H, m), 3.48-3.60(2H, m), 3.61-3.78 (2H, m), 3.88(3H, s), 3.89(3H, s), 4.59 (2H, s), 5.94-6.12(1H, m), 6.66(1H, d, J=8.8 Hz), 6.83(1H, d, J=8.6 Hz), 6.80 6.92(3H, m), 7.04(1H, dd, J=2.6 Hz, 8.6 Hz), 7.19(1H, d, J=2.6 Hz), 7.50(1H, d, J=2.8 Hz, 8.8 Hz), 7.73(1H. s), 7.95(1H, d, J= 2.8 Hz). |
| 605 | 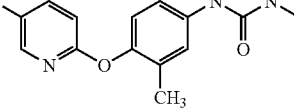 | (CDCl₃) 1.76-1.93(2H, m), 2.00-2.20(5H, m), 3.11-3.28(2H, m), 3.29-3.41 (2H, m), 3.42-3.57(2H, m), 3.60-3.78 (2H, m), 3.87(3H, s), 3.88(3H, s), 4.57 (2H, s), 5.70-5.88(1H, m), 6.67(1H, d, J=8.8 Hz), 6.83(1H, d, J=8.6 Hz), 6.86(3H, m), 7.04(1H, dd, J=2.6 Hz, 8.6 Hz), 7.17(1H. d, J=2.6 Hz), 7.56(1H, dd, J=2.8 Hz, 8.8 Hz), 7.68(1H, s), 7.93(1H, d, J= 2.8 Hz). |

Reference Example 606

Production of methyl 3-(4-{5-[3-(4-trifluoromethyl-phenyl)ureido]pyridin-2-yloxy}phenyl)propionate Methyl 3-[4-(5-nitropyridin-2-yloxy)phenyl]propionate (1.00 g, 3.3 mmol) was dissolved in a mixed solvent consisting of THF (1 mL) and ethanol (120 mL). To the resulting solution was added 10% palladium-carbon (100 mg), and stirred for 23 hours at room temperature under a hydrogen atmosphere. The reaction solution was filtered and the filtrate was concentrated. To the residue were added THF (20 mL), triethylamine (0.917 mL, 6.6 mmol) and phenyl 4-trifluoromethylisocyanate (0.61 mL, 4.3 mmol), and the resulting solution was stirred for 20 hours at room temperature. The reaction solution was evaporated under reduced pressure. The residue was washed with ethyl acetate, to thereby yield 850 mg of the title compound.

Appearance: White powder $^1$H NMR (DMSO-$d_6$) δ 2.62-2.68 (2H, m), 2.83-2.88 (2H, m), 3.60 (3H, s), 6.97-7.02 (3H, m), 7.24 (2H, d, J=8.4 Hz), 7.65-7.69 (4H, m), 7.99 (1H, dd, J=8.9 Hz, 2.8 Hz), 8.19 (1H, d, J=2.8 Hz), 8.88 (1H, s), 9.20 (1H, s).

Reference Example 607

Production of methyl 3-fluoro-4-{5-[(4-trifluoromethyl-benzylidene)amino]pyridin-2-yloxy}benzoate Methyl 4-(5-aminopyridin-2-yloxy)-3-fluorobenzoate (2.0 g, 7.63 mmol) was dissolved in methanol (50 mL). To the resulting solution was added 4-trifluoromethylbenzaldehyde (1.04 mL, 7.63 mmol), and refluxed for 6 hours. The reaction solution was cooled to room temperature, and the resulting precipitated crystals were collected by suction filtration. The collected crystals were washed with methanol, to thereby yield 2.81 g of the title compound.

Appearance: Pale grey powder $^1$H NMR (DMSO-$d_6$) δ 3.89 (3H, s), 7.32 (1H, d, J=8.7 Hz), 7.48-7.54 (1H, m), 7.85-7.92 (4H, m), 8.01 (1H, dd, J=8.7 Hz, 2.6 Hz), 8.13-8.16 (3H, m), 8.86 (1H, s).

The following compounds were produced in the same manner as in Reference Example 607.

TABLE 88

| Reference Example No. | $R_{289}$ | $R_{290}$ | $R_{291}$ | $R_{292}$ | $^1$H NMR (solvent) δ ppm |
|---|---|---|---|---|---|
| 608 | —CF$_3$ | —H | —H | —CH$_3$ | (DMSO-$d_6$) 3.86(3H, s), 7.24-7.30(3H, m), 7.92(2H, d, J=8.1 Hz), 7.98-8.05(3H, m), 8.16(2H, d, J=8.1 Hz), 8.24(1H, d, J=2.1 Hz), 8.88(1H, s). |
| 609 | —CF$_3$ | —H | —H | —C$_2$H$_5$ | (DMSO-$d_6$) 1.33(3H, t, J=7.1 Hz), 4.32(2H, q, J=7.1 Hz), 7.24-7.30(3H, m), 7.92(2H, d, J=8.3 Hz), 8.00(1H, dd, J=8.7 Hz, 2.6 Hz), 8.02(2H, d, J=8.7 Hz), 8.16(2H, d, J=7.9 Hz), 8.24(1H, d, J=2.6 Hz), 8.88(1H, s). |
| 610 | —Cl | —Cl | —F | —CH$_3$ | (DMSO-$d_6$) 3.89(3H, s), 7.21(1H, d, J=8.6 Hz), 7.48-7.54 (1H, m), 7.80-7.94(4H, m), 7.97(1H, dd, J=8.7 Hz, 2.8 Hz), 8.12-8.15(2H, m), 8.75(1H, s). |
| 611 | —Cl | —Cl | —F | —C$_2$H$_5$ | (CDCl$_3$) 1.40(3H, t, J=7.1 Hz), 4.39(2H, q, J=7.1 Hz), 7.09(1H, d, J=8.6 Hz), 7.26 7.35(1H, m), 7.55-7.57(1H, m), 7.66-7.73(2H, m), 7.86-7.92(2H, m), 8.02-8.03(2H, m), 8.40(1H, s). |

Reference Example 612

Production of ethyl 4-{5-[1-(4-trifluoromethylphenyl)-ethylideneamino]pyridin-2-yloxy}benzoate Ethyl 4-(5-aminopyridin-2-yloxy)benzoate (16.0 g, 62 mmol) was dissolved in toluene (300 mL). To the resulting solution were added 4-trifluoromethylacetophenone (11.7 g, 62 mmol) and (±)-camphor-10-sulfonic acid (1.08 g, 4.65 mmol), and refluxed overnight. The reaction solution was concentrated under reduced pressure, to thereby yield 26.5 g of the title compound.

Appearance: Dark green oil $^1$H NMR (CDCl$_3$) δ 1.35-1.41 (3H, m), 2.34 (3H, s), 4.36 (2H, d, J=7.1 Hz), 7.01-7.31 (4H, m), 7.70-7.77 (3H, m), 8.01-8.11 (4H, m).

Reference Example 613

Production of methyl 4-[5-(4-trifluoromethylbenzyl-amino)pyridin-2-yloxy]benzoate Methyl 4-{5-[(4-trifluoromethylbenzylidene)-amino]pyridin-2-yloxy}benzoate (2.64 g, 6.59 mmol) was suspended in methanol (25 mL), and to the resulting suspension was slowly added sodium borohydride (1.25 g, 33.0 mmol). The resulting solution was stirred at room temperature for 3 days. The reaction solution was concentrated under reduced pressure. To the residue was added ethyl acetate, and washed with water and brine. The organic layer was dried over anhydrous magnesium sulfate, and evaporated. The residue was washed with diethyl ether, to thereby yield 2.65 g of the title compound.

Appearance: White powder $^1$H NMR (CDCl$_3$) δ 3.89 (3H, s), 4.16 (1H, brs), 4.42 (2H, s), 6.84 (1H, d, J=8.7 Hz), 7.01 (1H, dd, J=8.6 Hz, 3.0 Hz), 7.05 (2H, d, J=8.4 Hz), 7.49 (2H, d, J=8.4 Hz), 7.62 (2H, d, J=8.3 Hz), 7.67 (1H, d, J=3.1 Hz), 8.01 (2H, d, J=8.6 Hz).

The following compounds were produced in the same manner as in Reference Example 613.

yloxy)phenyl]propionate (2.1 g, 7.3 mmol) in ethanol (20 mL), and the resulting solution was stirred for 2 hours at 40° C. To the resulting reaction solution was added sodium borohydride (0.55 g, 15.7 mmol) under ice cooling, and stirred at the same temperature for 1 hour. To the solution was added water and extracted with ethyl acetate. The ethyl acetate layer was washed with water, dried over anhydrous magnesium sulfate. The solvent was evaporated, and the residue was purified by silica gel column chromatography (n-hexane:ethyl acetate=4:1), to thereby yield 2.71 g of the title compound.

Appearance: Colorless oil $^1$H NMR (CDCl$_3$) δ 1.24 (3H, t, J=7.1 Hz), 2.50-2.68 (2H, m), 2.81-3.01 (2H, m), 3.71-4.20 (3H, m), 4.28 (2H, s), 6.76 (1H, d, J=8.7 Hz), 6.88-7.02 (3H, m), 7.06-7.23 (3H, m), 7.41 (1H, d, J=8.2 Hz), 7.46 (1H, d, J=2.0 Hz), 7.60 (1H, d, J=3.0 Hz).

TABLE 89

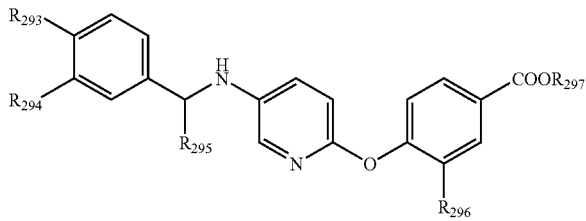

| Reference Example No. | $R_{293}$ | $R_{294}$ | $R_{295}$ | $R_{296}$ | $R_{297}$ | $^1$H NMR (CDCl$_3$) δ ppm |
|---|---|---|---|---|---|---|
| 614 | —CF$_3$ | —H | —H | —H | —C$_2$H$_5$ | 1.37(3H, t, J=7.1 Hz), 4.19(1H, brs), 4.35(2H, q, J=7.1 Hz), 4.41(2H, brs), 6.83(1H, d, J=8.7 Hz), 7.01(1H, dd, J=8.6 Hz, 3.0 Hz), 7.04(2H, d, J=8.6 Hz), 7.48(2H, d, J=8.1 Hz), 7.61(2H, d, J=8.3 Hz), 7.66(1H, d, J=3.0 Hz), 8.02(2H, d, J=8.7 Hz). |
| 615 | —CF$_3$ | —H | —CH$_3$ | —H | —C$_2$H$_5$ | 1.37(3H, t, J=7.1 Hz), 1.56(3H, d, J=6.8 Hz), 4.06(1H, brs), 4.34(2H, q, J=7.1 Hz), 4.49(1H, q, J=6.6 Hz), 6.75(1H, d, J=8.7 Hz), 6.87(1H, dd, J=8.7 Hz, 3.0 Hz), 7.01(2H, d, J=8.6 Hz), 7.47(2H, d, J=8.1 Hz), 7.53(1H, d, J=3.0 Hz), 7.60(2H, d, J=8.3 Hz), 8.00(2H, d, J=8.7 Hz). |
| 616 | —CF$_3$ | —H | —H | —F | —CH$_3$ | 3.90(3H, s), 4.40(2H, brs), 6.89(1H, d, J=8.1 Hz), 7.03(1H, dd, J=8.7 Hz, 3.0 Hz), 7.15-7.21(1H, m), 7.47(2H, d, J=8.1 Hz), 7.55(1H, d, J=3.0 Hz), 7.61(2H, d, J=8.1 Hz), 7.80-7.84(2H, m). |
| 617 | —Cl | —Cl | —H | —F | —CH$_3$ | 3.91(3H, s), 4.29(2H, brs), 6.88(1H, d, J=8.7 Hz), 7.02(1H, dd, J=8.7 Hz, 3.0 Hz), 7.15-7.21(2H, m), 7.41(1H, d, J=8.3 Hz), 7.46(1H, d, J=2.0 Hz), 7.53(1H, d, J=3.0 Hz), 7.81-7.84(2H, m). |

Reference Example 618

Production of ethyl 3-{4-[5-(3,4-dichlorobenzylamino)-pyridin-2-yloxy]phenyl}propionate A solution of 3,4-dichlorobenzaldehyde (1.28 g, 7.3 mmol) was added to a solution of ethyl 3-[4-(5-aminopyridin-2-

The following compounds were produced in the same manner as in Reference Example 618.

TABLE 90

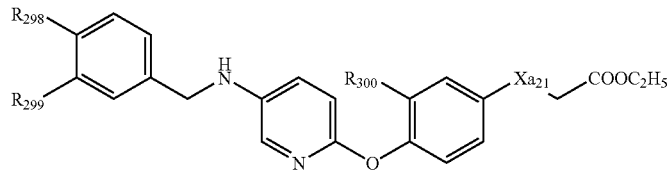

| Reference Example No. | $R_{298}$ | $R_{299}$ | $R_{300}$ | $Xa_{21}$ | $^1$H NMR (CDCl$_3$) δ ppm |
|---|---|---|---|---|---|
| 619 | —CF$_3$ | —H | —H | —CH$_2$— | 1.24(3H, t, J=7.3 Hz), 2.60(2H, t, J=8.1 Hz), 2.92(2H, t, J=8.1 Hz), 4.13(2H, q, J=7.3 Hz), 4.39(2H, s), 6.76(1H, d, J=8.7 Hz), 6.97(2H, d, J=8.4 Hz), 6.98(1H, dd, J=8.6 Hz, 3.1 Hz), 7.17(2H, d, J=8.4 Hz), 7.47(2H, d, J=8.1 Hz), 7.60(2H, d, J=7.9 Hz), 7.61(1H, d, J=3.1 Hz). |
| 620 | —Cl | —Cl | —OCH$_3$ | —CH$_2$— | 1.25(3H, t, J=7.1 Hz), 2.65-2.74(2H, m), 2.94(2H, t, J=8.2 Hz), 3.76(3H, s), 3.93(1H, brs), 4.14(2H, q, J=7.1 Hz), 4.22-4.34(2H, m), 6.70-6.85(3H, m), 6.85-7.02(2H, m), 7.10-7.25(1H, m), 7.39 (1H, d, J=8.2 Hz), 7.44(1H, d, J=2.C Hz), 7.53(1H, d, J=2.7 Hz). |
| 621 | —CF$_3$ | —H | —OCH$_3$ | —CH$_2$— | 1.25(3H, t, J=7.1 Hz), 2.52-2.68(2H, m), 2.81-3.01(2H, m), 3.76 (3H, s), 3.93(1H, brs), 4.14(2H, q, J=7.1 Hz), 4.30-4.40(2H, m), 6.72-6.84(3H, m), 6.96(1H, d, J=8.0 Hz), 6.98(1H, dd, J=8.0 Hz, 3.0 Hz), 7.40(2H, d, J=8.0 Hz), 7.55(1H, d, J=3.0 Hz), 7.59 (2H, d, J=8.0 Hz). |
| 622 | —Cl | —Cl | —OC$_2$H$_5$ | —CH$_2$— | 1.18(3H, t, J=7.0 Hz), 1.25(3H, t, J=7.1 Hz), 2.52-2.69(2H, m), 2.82-3.00(2H, m), 3.81-4.02(3H, m), 4.14(2H, q, J=7.1 Hz), 4.27 (2H, d, J=4.7 Hz), 6.72-6.82(3H, m), 6.93-7.02(2H, m), 7.18 (1H, dd, J=8.2 Hz, 2.0 Hz), 7.39(1H, d, J=8.4 Hz), 7.45(1H, d, J=2.0 Hz), 7.52(1H, d, J=3.0 Hz). |
| 623 | —CF$_3$ | —H | —OC$_2$H$_5$ | —CH$_2$— | 1.18(3H, t, J=7.0 Hz), 1.25(3H, t, J=7.1 Hz), 2.51-2.72(2H, m), 2.83-3.01(2H, m), 3.87-4.06(3H, m), 4.16(2H, q, J=7.1 Hz), 4.30-4.42(2H, m), 6.72-6.83(3H, m), 6.94-7.02(2H, m), 7.46(2H, d, J=8.1 Hz), 7.54(1H, d, J=3.0 Hz), 7.59(2H, d, J=8.1 Hz). |
| 624 | —Cl | —Cl | —F | —CH$_2$— | 1.12-1.35(3H, m), 2.50-2.74(2H, m), 2.93(2H, t, J=7.7 Hz), 3.95 (1H, brs), 4.05-4.20(2H, m), 4.27 (2H, s), 6.82(1H, d, J=8.4 Hz), 6.90-7.15(4H, m), 7.18(1H, dd, J=8.2 Hz, 2.0 Hz),7.35-7.60(3H, m). |
| 625 | —CF$_3$ | —H | —F | —CH$_2$— | 1.13-1.35(3H, m), 2.65-2.70(2H, m), 2.93(2H, t, J=7.7 Hz), 4.01 (1H, brs), 4.05-4.23(2H, m), 4.37(2H, s), 6.82(1H, d, J=8.8 Hz), 6.90-7.15(4H, m), 7.37-7.55(3H, m), 7.55-7.70(2H, m). |
| 626 | —Cl | —Cl | —H | —N(Ac)- | 1.27(3H, t, J=7.1 Hz), 1.94(3H, s), 4.10(1H, brs), 4.19(2H, q, J=7.1 Hz), 4.31(2H, s), 4.34(2H, s), 6.84(1H, d, J=8.5 Hz), 7.00(1H, dd, J=8.5 Hz, 3.0 Hz), 7.06(2H, d, J=8.7 Hz), 7.20(1H, dd, J=8.2 Hz, 2.2 Hz), 7.31(2H, d, J=8.7 Hz), 7.42(1H, d, J=8.2 Hz), 7.47(1H, d, J=2.2 Hz), 7.62(1H, d, J=3.0 Hz). |
| 627 | —CF$_3$ | —H | —H | —N(Ac)- | 1.27(3H, t, J=7.1 Hz), 1.93(3H, s), 4.15(1H, brs), 4.18(2H, q, J=7.1 Hz), 4.34(2H, s), 4.35-4.50(2H, m), 6.83(1H, d, J=8.6 Hz), 7.01(1H, dd, J=8.6 Hz, 3.0 Hz), 7.06(2H, d, J=8.9 Hz), 7.31(2H, d, J=8.9 Hz), 7.48(2H, d, J=8.1 Hz), 7.62(2H, d, J=8.1 Hz), 7.64(1H, d, J=3.6 Hz). |

Reference Example 628

Production of ethyl 3-(4-{5-[benzyloxycarbonyl(2-methoxyethyl)amino]pyridin-2-yloxy}phenyl)propionate Under a nitrogen atmosphere, to a solution of ethyl 3-[4-(5-benzyloxycarbonylaminopyridin-2-yloxy)phenyl]propionate (1.7 g, 4.0 mmol) in DMF (50 mL) was added 60% sodium hydride (0.19 g, 4.9 mmol) under ice cooling, and the resulting solution was stirred for 35 minutes at the same temperature. 2-Bromoethylmethyl ether (0.4 mL, 4.2 mmol) was added dropwise to the solution. The reaction solution was stirred for 2 hours under ice cooling, and then stirred for 2 days at room temperature. To the reaction solution was added water, and extracted with ethyl acetate. The ethyl acetate layer was washed with water, and then dried over anhydrous magnesium sulfate. The solvent was evaporated, and the residue was purified by silica gel column chromatography (n-hexane:ethyl acetate=4:1), to thereby yield 1.6 g of the title compound.

Appearance: Pale yellow oil $^1$H NMR (CDCl$_3$) δ 1.25 (3H, t, J=7.1 Hz), 2.57-2.70 (2H, m), 2.89-3.02 (2H, m), 3.52 (2H, t, J=5.4 Hz), 3.79 (2H, t, J=5.4 Hz), 4.14 (2H, q, J=7.1 Hz), 5.14 (2H, brs), 6.87 (1H, d, J=8.7 Hz), 6.89-7.10 (2H, m), 7.11-7.41 (7H, m), 7.47-7.69 (1H, m), 8.10 (1H, brs).

The following compounds were produced in the same manner as in Reference Example 628.

Reference Example 629

Ethyl[(4-{5-[(3,4-dichlorophenyl)methylamino]pyridin-2-yloxy}-2-trifluoromethylphenyl)ethylamino]acetate

MS 541 (M$^+$).

palladium-carbon was filtered off through Celite, and the filtrate was evaporated to yield 1.23 g of the title compound.

Appearance: Blue oil $^1$H NMR (CDCl$_3$) δ 1.24 (3H, t, J=7.1 Hz), 2.55-2.68 (2H, m), 2.87-2.98 (2H, m), 3.20-3.31 (2H, m), 3.56-3.66 (2H, m), 4.13 (2H, q, J=7.1 Hz), 6.77 (1H, d, J=8.7 Hz), 6.93-7.01 (2H, m), 7.03 (1H, dd, J=8.7 Hz, 3.0 Hz), 7.13-7.22 (2H, m), 7.66 (1H, d, J=3.0 Hz).

The following compound was produced in the same manner as in Reference Example 636.

Reference Example 637

Ethyl 3-[4-(5-ethylaminopyridin-2-yloxy)phenyl]-propionate $^1$H NMR (CDCl$_3$) δ 1.29-1.32 (6H, m), 2.55-2.67 (2H, m), 2.87-2.99 (2H, m), 3.14 (2H, q, J=7.1 Hz), 4.13 (2H, q, J=7.1 Hz), 6.77 (1H, d, J=8.7 Hz), 6.89-7.02 (3H, m), 7.09-7.25 (3H, m), 7.63 (1H, d, J=3.0 Hz).

TABLE 91

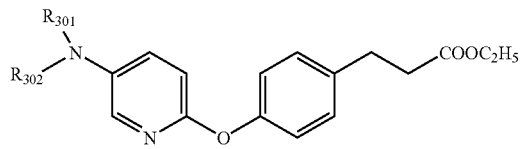

| Reference Example No. | R$_{301}$ | R$_{302}$ | $^1$H NMR (CDCl$_3$) δ ppm or MS |
|---|---|---|---|
| 630 | 4-CF$_3$PhCH$_2$— | —(CH$_2$)$_2$OCH$_3$ | $^1$H NMR 1.24(3H, t, J=7.1 Hz), 2.54-2.67(2H, m), 2.76-2.98(2H, m), 4.13(2H, q, J=7.1 Hz), 4.61(2H, s), 6.76(1H, d, J=8.9 Hz), 6.93-7.01(2H, m), 7.07(1H, dd, J=8.9 Hz, 3.3 Hz), 7.12-7.20 (2H, m), 7.33(2H, d, J=8.0 Hz), 7.56(2H, d, J=8.0 Hz), 7.65 (1H, d, J=2.9 Hz). |
| 631 | 4-CF$_3$PhCH$_2$— | —C$_2$H$_5$ | $^1$H NMR 1.09-1.32(6H, m), 2.53-2.66(2H, m), 2.84-2.98(2H, m), 3.45 (2H, q, J=7.1 Hz), 4.13(2H, q, J=7.1 Hz), 4.49(2H, s), 6.77 (1H, d, J=8.5 Hz), 6.93-7.01(2H, m), 7.02-7.09(1H, m), 7.12-7.20(2H, m), 7.11-7.39(2H, m), 7.53-7.61(2H, m), 7.66 (1H, d, J=3.0 Hz). |
| 632 | PhCH$_2$OCO— | —C$_2$H$_5$ | $^1$H NMR 1.15(3H, t, J=7.1 Hz), 1.25(3H, t, J=7.1 Hz), 2.54-2.71(2H, m), 2.83-3.04(2H, m), 3.69(2H, q, J=7.1 Hz), 4.14(2H, q, J=7.1 Hz), 5.14(2H, brs), 6.88(1H, d, J=8.7 Hz), 7.02-7.11(2H, m), 7.18-7.40(7H, m), 7.44-7.59(1H, m), 7.98-8.08(1H, m). |
| 633 | 4-CF$_3$PhCH$_2$— | —SO$_2$CH$_3$ | MS 522(M$^+$) |
| 634 | 3,4-Cl$_2$PhCH$_2$— | —SO$_2$CH$_3$ | MS 522(M$^+$) |
| 635 | 3,4-Cl$_2$Ph— | —CH$_3$ | MS 444(M$^+$) |

Reference Example 636

Production of ethyl 3-{4-[5-(2-methoxyethylamino)-pyridin-2-yloxy]phenyl}propionate To a solution of ethyl 3-(4-{5-[benzyloxycarbonyl(2-methoxyethyl)amino]pyridin-2-yloxy}phenyl}propionate (1.82 g, 3.8 mmol) in ethanol-ethyl acetate (10 mL-10 mL) was added under a nitrogen atmosphere 10% palladium-carbon (0.2 g), and the resulting solution was stirred for 3 hours under a hydrogen atmosphere at atmospheric pressure. The

Reference Example 638

Production of ethyl 3-(3-methoxy-4-{5-[methyl-(4-trifluoromethylbenzyl)amino]pyridin-2-yloxy}phenyl)-propionate To a solution of ethyl 3-{3-methoxy-4-[5-(4-trifluoromethylbenzylamino]pyridin-2-yloxy}phenyl]-propionate (0.8 g, 1.7 mmol) in methanol (15 mL) were added a 37% aqueous formaldehyde solution (0.38 mL, 5.1 mmol) and acetic acid (0.1 mL, 1,7 mmol). The reaction solution was stirred for 30 minutes at room temperature. After that, sodium cyanoborohydride (0.24 g, 3.4 mmol) was added to the reaction solution under ice cooling, and the mixture was stirred under ice cooling for 40 minutes. To the reaction solution was added water, and extracted with ethyl acetate. The ethyl acetate layer was washed with water, and then dried over anhydrous magnesium sulfate. The solvent was evaporated, and the residue was purified by silica gel column chromatography (n-hexane:ethyl acetate=4:1), to thereby yield 0.62 g of the title compound.

Appearance: Pale yellow oil $^1$H NMR (CDCl$_3$) δ 1.25 (3H, t, J=7.1 Hz), 2.52-2.70 (2H, m), 2.87-3.02 (5H, m), 3.77 (3H, s), 4.14 (2H, q, J=7.1 Hz), 4.40-4.50 (2H, m), 6.74-6.86 ((3H, m), 6.97 (1H, d, J=8.0 Hz), 7.11 (1H, dd, J=8.9 Hz, 3.2 Hz), 7.34 (2H, d, J=8.1 Hz), 7.57 (2H, d, J=8.1 Hz), 7.65 (1H, d, J=3.2 Hz).

The following compounds were produced in the same manner as in Reference Example 638.

TABLE 92

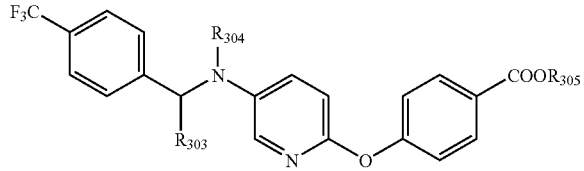

| Reference Example No. | R$_{303}$ | R$_{304}$ | R$_{305}$ | $^1$H NMR (CDCl$_3$) δ ppm |
|---|---|---|---|---|
| 639 | —H | —CH$_3$ | —CH$_3$ | 3.07(3H, s), 3.89(3H, s), 4.56(2H, s), 6.87(1H, d, J=8.9 Hz), 7.06(2H, d, J=8.6 Hz), 7.13(1H, dd, J=8.9 Hz, 3.3 Hz), 7.35(2H, d, J=8.1 Hz), 7.60(2H, d, J=8.3 Hz), 7.75(1H, d, J=3.1 Hz), 8.02(2H, d, J=8.6 Hz). |
| 640 | —H | —C$_2$H$_5$ | —C$_2$H$_5$ | 1.24(3H, t, J=7.1 Hz), 1.37(3H, t, J=7.1 Hz), 3.49(2H, q, J=7.1 Hz), 4.35(2H, q, J=7.1 Hz), 4.53(2H, s), 6.84(1H, d, J=8.9 Hz), 7.05(2H, d, J=8.6 Hz), 7.06(1H, dd, J=8.9 Hz, 3.1 Hz), 7.36(2H, d, J=8.4 Hz), 7.58(2H, d, J=8.3 Hz), 7.69(1H, d, J=3.1 Hz), 8.02(2H, d, J=8.6 Hz). |
| 641 | —CH$_3$ | —CH$_3$ | —C$_2$H$_5$ | 1.38(3H, t, J=7.1 Hz), 1.59(3H, d, J=6.9 Hz), 2.74(3H, s), 4.36(2H, q, J=7.1 Hz), 4.49(1H, q, J=6.9 Hz), 6.89(1H, d, J=8.9 Hz), 7.08 (2H, d, J=8.9 Hz), 7.24(1H, dd, J=8.9 Hz, 3.1 Hz), 7.43(2H, d, J=8.6 Hz), 7.61(2H, d, J=8.3 Hz), 7.84(1H, d, J=3.1 Hz), 8.03(2H, d, J=8.9 Hz). |

TABLE 93

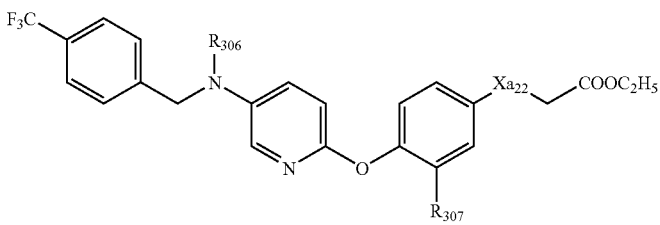

| Reference Example No. | R$_{306}$ | R$_{307}$ | Xa$_{22}$ | $^1$H NMR (CDCl$_3$) δ ppm |
|---|---|---|---|---|
| 642 | —CH$_3$ | —H | —CH$_2$— | 1.24(3H, t, J=7.1Hz), 2.60(2H, t, J=7.8Hz), 2.92(2H, t, J=7.8Hz), 3.02(3H, s), 4.12(2H, q, J=7.1Hz), 4.51(2H, s), 6.79(1H, d, J=8.9Hz), 6.97(2H, d, J=8.4Hz), 7.10(1H, dd, J=8.9Hz, 3.3 Hz), 7.17(2H, d, J=8.3Hz), 7.34(2H, d, J=8.1Hz), 7.58(2H, d, J=8.3Hz), 7.69(1H, d, J=3.1Hz). |
| 643 | —CH$_3$ | —H | —N(Ac)— | 1.27(3H, t, J=7.1Hz), 1.94(3H, s), 3.06(3H, s), 4.18(2H, q, J=7.1Hz), 4.34(2H, s), 4.55(2H, s), 6.87(1H, d, J=8.9Hz), 7.07(2H, d, J=8.7Hz), 7.13(1H, dd, J=8.9Hz, 3.1Hz), 7.31(2H, d, J=8.7 Hz), 7.35(2H, d, J=8.0Hz), 7.59(2H, d, J=8.0Hz), 7.72(1H, d, J=3.1Hz). |
| 644 | —CH$_3$ | —F | —CH$_2$— | 1.25(3H, t, J=7.1Hz), 2.55-2.70(2H, m), 2.93(2H, t, J=7.9Hz), 3.00(3H, s), 4.13(2H, q, J=7.1Hz), 4.49(2H, s), 6.86(1H, d, J=8.9Hz), 6.90-7.16(4H, m), 7.33(2H, d, J=8.1Hz), 7.57(2H, d, J=8.1Hz), 7.62(1H, d, J=3.2Hz). |

TABLE 93-continued

| Reference Example No. | R₃₀₆ | R₃₀₇ | Xa₂₂ | ¹H NMR (CDCl₃) δ ppm |
|---|---|---|---|---|
| 645 | —CH₃ | —OC₂H₅ | —CH₂— | 1.19(3H, t, J=7.0Hz), 1.25(3H, t, J=7.1Hz), 2.50-2.69(2H, m), 2.81-2.99(2H, m), 2.98(3H, s), 3.98(2H, q, J=7.0Hz), 4.14(2H, q, J=7.1Hz), 4.48(2H, s), 6.68-6.88(3H, m), 7.00(1H, d, J=8.0Hz), 7.11(1H, dd, J=8.0Hz, 3.0Hz), 7.33(2H, d, J=8.0Hz), 7.56(2H, d, J=8.0Hz), 7.64(1H, d, J=3.0Hz). |
| 646 | —C₂H₅ | —F | —CH₂— | 1.19(3H, t, J=7.1Hz), 1.10-1.35(3H, m), 2.50-2.70(2H, m), 2.93(2H, t, J=8.0Hz), 3.43(2H, q, J=7.1Hz), 4.02-4.22(2H, m), 4.47(2H, s), 6.83(1H, d, J=9.0Hz), 6.88-7.15(4H, m), 7.34(2H, d, J=8.0Hz), 7.41-7.70(3H, m). |
| 647 | —C₂H₅ | —OCH₃ | —CH₂— | 1.18(3H, t, J=7.0Hz), 1.25(3H, t, J=7.1Hz), 2.57-2.68(2H, m), 2.88-2.99(2H, m), 3.42(2H, q, J=7.0Hz), 3.77(3H, s), 4.14(2H, q, J=7.1Hz), 4.42-4.50(2H, m), 6.72-6.86((3H, m), 6.97(1H, d, J=8.0Hz), 7.05(1H, dd, J=9.0Hz, 3.2Hz), 7.30-7.38(2H, m), 7.51-7.59(2H, m), 7.60(1H, d, J=3.2Hz). |
| 648 | —C₂H₅ | —OC₂H₅ | —CH₂— | 1.17(3H, t, J=7.0Hz), 1.18(3H, t, J=7.0Hz), 1.25(3H, t, J=7.1Hz), 2.55-2.69(2H, m), 2.84-2.98(2H, m), 3.42(2H, q, J=7.1Hz), 3.97(2H, q, J=7.0Hz), 4.13(2H, q, J=7.0Hz), 4.46(2H, s), 6.71-6.82(3H, m), 6.99(1H, d, J=8.0Hz), 7.05(1H, dd, J=8.9Hz, 3.1Hz), 7.34(2H, d, J=8.0Hz), 7.55(2H, d, J=8.0Hz), 7.59(1H, d, J=3.1Hz). |

TABLE 94

| Reference Example No. | R₃₀₈ | R₃₀₉ | Xa₂₃ | ¹H NMR (CDCl₃) δ ppm |
|---|---|---|---|---|
| 649 | —CH₃ | —H | —N(Ac)— | 1.27(3H, t, J=7.1Hz), 1.94(3H, s), 3.03(3H, s), 4.19(2H, q, J=7.1Hz), 4.34(2H, s), 4.43(2H, s), 6.87(1H, d, J=9.0Hz), 7.03-7.11(1H, m), 7.07(2H, d, J=8.7Hz), 7.13(1H, dd, J=9.0Hz, 3.1Hz), 7.27-7.35(1H, m), 7.31(2H, d, J=8.7Hz), 7.40(1H, d, J=8.2Hz), 7.71(1H, d, J=3.1Hz). |
| 650 | —CH₃ | —F | —CH₂— | 1.15-1.30(3H, m), 2.53-2.70(2H, m), 2.93(2H, t, J=7.9Hz), 2.97(3H, s), 4.02-4.20(2H, m), 4.37(2H, s), 6.86(1H, d, J=8.9Hz), 6.91-7.18(5H, m), 7.32(1H, d, J=2.0Hz), 7.38(1H, d, J=8.2Hz), 7.61(1H, d, J=2.9Hz). |
| 651 | —CH₃ | —OCH₃ | —CH₂— | 1.25(3H, t, J=7.1Hz), 2.55-2.75(2H, m), 2.85-3.05(2H, m), 2.95(3H, s), 3.77(3H, s), 4.14(2H, q, J=7.1Hz), 4.36(2H, s), 6.71-6.88(3H, m), 6.98(1H, d, J=8.1Hz), 7.00-7.15(2H, m), 7.32(1H, d, J=2.0Hz), 7.38(1H, d, J=8.1Hz), 7.64(1H, d, J=3.1Hz). |
| 652 | —CH₃ | —OC₂H₅ | —CH₂— | 1.19(3H, t, J=7.0Hz), 1.25(3H, t, J=7.1Hz), 2.55-2.72(2H, m), 2.84-3.01(5H, m), 3.98(2H, q, J=7.0Hz), 4.14(2H, q, J=7.1Hz), 4.29-4.40(2H, |

TABLE 94-continued

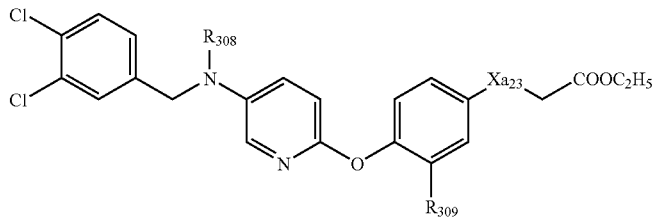

| Reference Example No. | R_{308} | R_{309} | Xa_{23} | ¹H NMR (CDCl₃) δ ppm |
|---|---|---|---|---|
| | | | | m), 6.74-6.83(3H, m), 7.00(1H, d, J=8.0Hz), 7.06(1H, dd, J=8.2Hz, 2.0Hz), 7.10(1H, dd, J= 9.0Hz, 3.2Hz), 7.31(1H, d, J=2.0Hz), 7.37(1H, d, J=8.2Hz), 7.63(1H, d, J=3.2Hz). |
| 653 | —C₂H₅ | —F | —CH₂— | 1.17(3H, t, J=7.1Hz), 1.20-1.30(3H, m), 2.50-2.72(2H, m), 2.93(2H, t, J=7.8Hz), 3.40(2H, q, J= 7.1Hz), 4.00-4.22(2H, m), 4.36(2H, s), 6.83(1H, d, J=8.9Hz), 6.85-7.15(5H, m), 728-7.32(1H, m), 7.37(1H, d, J=8.2Hz), 7.56(1H, d, J=3.2Hz). |
| 654 | —C₂H₅ | —OCH₃ | —CH₂— | 1.16(3H, t, J=7.1Hz), 1.21-1.35(3H, m), 2.50-2.75(2H, m), 2.82-3.05(2H, m), 3.39(2H, q, J=7.1 Hz), 3.77(3H, s), 4.05-4.25(2H, m), 4.35(2H, s), 6.68-6.88(3H, m), 6.90-7.00(1H, m), 7.00-7.11(2H, m), 7.31(1H, d, J=2.0Hz), 7.37(1H, d, J=8.2 Hz), 7.59(1H, d, J=3.0Hz). |
| 655 | —C₂H₅ | —OC₂H₅ | —CH₂— | 1.11-1.22(6H, m), 1.25(3H, t, J=7.1Hz), 2.56-2.67(2H, m), 2.86-2.97(2H, m), 3.39(2H, q, J=7.1 Hz), 3.97(2H, q, J=7.0Hz), 4.14(2H, q, J=7.1 Hz), 4.34(2H, s), 6.73-6.82(3H, m), 6.99(1H, d, J= 8.0Hz), 7.02-7.10(2H, m), 7.32(1H, d, J=1.9 Hz), 7.36(1H, d, J=8.2Hz), 7.58(1H, d, J=3.1 Hz). |

Reference Example 656

Production of ethyl 3-(4-(5-(3,4-dichlorophenylamino)pyridin-2-yloxy)phenyl)propionate Triethylamine (1.2 mL, 8.4 mmol) was added to a suspension of ethyl 3-(4-(5-aminopyridin-2-yloxy)phenyl)propionate (1.2 g, 4.2 mmol), 3,4-dichlorophenylboronic acid (1.6 g, 8.4 mmol), anhydrous copper acetate (0.762 g, 4.2 mmol) and molecular sieves 4A (5 g) in dichloromethane (24 mL), and the resulting reaction solution was stirred overnight at room temperature. After the resulting solution was filtered through Celite, the filtrate was concentrated under reduced pressure. The residue was purified by silica gel chromatography (n-hexane:ethyl acetate=4:1), to thereby yield 1.5 g of the title compound.

Appearance: Slightly brown solid

¹H NMR (CDCl₃) δ 1.25 (3H, t, J=7.1 Hz), 2.60-2.66 (2H, m), 2.93-2.99 (2H, m), 4.14 (2H, q, J=7.1 Hz), 5.52 (1H, brs), 6.71 (1H, dd, J=8.7 Hz, 2.7 Hz), 6.90 (1H, d, J=8.7 Hz), 6.97 (1H, d, J=2.7 Hz), 7.04-7.08 (2H, m), 7.21-7.26 (3H, m), 7.49 (1H, dd, J=8.7 Hz, 2.9 Hz), 8.01 (1H, d, J=2.8 Hz).

The following compound was produced in the same manner as in Reference Example 656.

Reference Example 657

Ethyl({4-[5-(3,4-dichlorophenylamino)pyridin-2-yloxy]-2-trifluoromethylphenyl}ethylamino)acetate

MS 527 (M⁺).

Reference Example 658

Production of ethyl 4-[3-(4-benzyloxy-3-methyl)phenyl-2-oxotetrahydropyrimidin-1-yl]benzoate Under a nitrogen atmosphere, to a solution of 1-(4-benzyloxy-3-methyl)phenyltetrahydropyrimidin-2-one (0.5 g, 1.7 mmol) in dioxane (5 mL) were added copper (I) iodide (16 mg, 0.08 mmol) and N,N-dimethylglycine hydrochloride (47 mg, 0.34 mmol). The resulting solution was stirred for 5 minutes, and then ethyl 4-iodobenzoate (0.39 g, 1.4 mmol) and potassium (III) phosphate (1.04 g, 4.9 mmol) were added to the reaction mixture. The resulting solution was stirred for 20 hours at 100° C., after which the resulting solution was sprinkled with silica gel. The residue was purified by silica gel chromatography (n-hexane:ethyl acetate=3:1→dichloromethane:methanol=40:1), to thereby yield 0.43 g of the title compound.

Appearance: White powder

¹H NMR (DMSO-d₆) δ 1.30 (3H, t, J=7.1 Hz), 2.08-2.22 (5H, m), 3.66 (2H, t, J=5.9 Hz), 3.81 (2H, t, J=5.9 Hz), 4.28 (2H, q, J=7.1 Hz), 5.10 (2H, s), 6.86-7.14 (3H, m), 7.26-7.51 (7H, m), 7.82-7.92 (2H, m).

Reference Example 659

Production of ethyl(E)-3-(3-methoxy-4{-5-[2-(4-trifluoromethylphenyl)vinyl]pyridin-2-yloxy}phenyl)propionate To ethyl 3-[4-(5-bromopyridin-2-yloxy)-3-methoxyphenyl]propionate (610 mg, 1.6 mmol) were added 4-trifluoromethylstyrene (0.332 mL, 2.2 mmol), dichlorobis(benzonitrile)

palladium (II) (33 mg, 0.082 mmol), N,N-dimethylglycine hydrochloride (17 mg, 0.16 mmol), sodium acetate (263 mg, 3.2 mmol) and N-methylpyrrolidone (5 mL) under an argon atmosphere. The resulting solution was stirred under an argon atmosphere for 17 hours at 130° C. To the reaction solution was added ethyl acetate and filtered. The filtrate was washed with water, and then dried over anhydrous sodium sulfate. The solvent was evaporated, and the residue was purified by silica gel column chromatography (n-hexane:ethyl acetate=3: 1), to thereby yield 500 mg of the title compound.

Appearance: Pale yellow oil $^1$H NMR (CDCl$_3$) δ 1.27 (3H, t, J=7.1 Hz), 2.64-2.69 (2H, m), 2.95-3.01 (2H, m), 3.76 (3H, s), 4.05 (2H, q, J=7.1 Hz), 6.71-6.88 (2H, m), 6.95 (1H, d, J=8.6 Hz), 6.98-7.08 (2H, m), 7.11 (1H, d, J=16.5 Hz), 7.56-7.63 (4H, m), 7.87-7.91 (1H, m), 8.23 (1H, d, J=2.3 Hz).

The following compound was produced in the same manner as in Reference Example 659.

Reference Example 660

Ethyl 3-(4-{5-[(E)-2-(3,4-dichlorophenyl)vinyl]pyridin-2-yloxy}-3-methoxyphenyl)propionate $^1$H NMR (CDCl$_3$) δ 1.26 (3H, t, J=7.1 Hz), 2.63-2.69 (2H, m), 2.94-3.00 (2H, m), 3.76 (3H, s), 4.15 (2H, q, J=7.1 Hz), 6.81-6.90 (3H, m), 6.93 (1H, d, J=8.6 Hz), 6.99 (1H, d, J=15.3 Hz), 7.06 (1H, d, J=9.1 Hz), 7.27-7.31 (1H, m), 7.40 (1H, d, J=8.2 Hz), 7.55 (1H, d, J=2.0 Hz), 7.82-7.86 (1H, m), 8.19 (1H, d, J=2.5 Hz).

Reference Example 661

Production of ethyl{4-[4-(3,4-dichlorobenzoylamino)-2-fluorophenoxy]benzenesulfonyl}acetate To a solution of ethyl{4-[4-(3,4-dichlorobenzoylamino)-2-fluorophenoxy]phenylsulfanyl}-acetate (1.20 g, 2.43 mmol) in dichloromethane (20 mL) was added m-chloroperbenzoic acid (1.45 g, 6.06 mmol) at 0° C. The resulting solution was stirred for 2 hours at room temperature. To the reaction solution was added methanol and stirred for some time. To the resulting solution was then added water, and extracted with dichloromethane. The dichloromethane layer was washed with a saturated sodium bicarbonate solution and brine, dried over anhydrous sodium sulfate, and evaporated. The obtained residue was purified by silica gel column chromatography (n-hexane:ethyl acetate=1:1), to thereby yield 1.28 g of the title compound.

Appearance: Yellow amorphous powder $^1$H NMR (CDCl$_3$) δ 1.22 (3H, t, J=7.1 Hz), 4.11 (2H, s), 4.16 (2H, q, J=7.1 Hz), 7.06 (2H, d, J=8.9 Hz), 7.19 (1H, t, J=8.7 Hz), 7.30 (1H, d, J=8.7 Hz), 7.59 (1H, d, J=8.3 Hz), 7.71 (1H, dd, J=2.0 Hz, 8.3 Hz), 7.75-7.85 (1H, m), 7.86-7.95 (3H, m), 7.98 (1H, d, J=2.0 Hz).

Reference Example 662

Production of methyl 3-{4-[5-(3,4-dichlorobenzoylamino)pyridine-2-sulfinyl]phenyl}propionate To a solution of methyl 3-{4-[5-(3,4-dichlorobenzoylamino)pyridin-2-ylsulfanyl]phenyl}propionate (1.00 g, 2.17 mmol) in dichloromethane (20 mL) was added m-chloroperbenzoic acid (0.620 g, 2.60 mmol) at 0° C. The resulting solution was stirred for 1 hour at 0° C. To the reaction solution was added methanol and stirred for some time. To the resulting solution was then added water, and extracted with dichloromethane. The dichloromethane layer was washed with water, a saturated sodium bicarbonate solution and brine, dried over anhydrous sodium sulfate, and evaporated. The obtained residue was recrystallized from ethanol 3 times, to thereby yield 0.790 g of the title compound.

Appearance: White powder

Melting point: 164-166° C.

Reference Example 663

Production of methyl 3-{4-[5-(3,4-dichlorobenzoylamino)pyridine-2-sulfonyl]phenyl}propionate To a solution of methyl 3-{4-[5-(3,4-dichlorobenzoylamino)pyridin-2-ylsulfanyl]phenyl}-propionate (1.00 g, 2.17 mmol) in dichloromethane (20 mL) was added m-chloroperbenzoic acid (1.29 g, 5.42 mmol) at 0° C. The resulting solution was stirred for 1.5 hours at 0° C. To the reaction solution was added methanol and stirred for some time. To the resulting solution was then added water, and extracted with dichloromethane. The dichloromethane layer was washed with brine, dried over anhydrous sodium sulfate, and evaporated. The obtained residue was recrystallized from ethanol, to thereby yield 0.890 g of the title compound.

Appearance: White powder

Melting point: 165-166° C.

Reference Example 664

Production of ethyl{4-[4-(3,4-dichlorobenzoylamino)-2-fluorophenoxy]benzenesulphenyl}acetate To a solution of ethyl{4-[4-(3,4-dichloro-benzoylamino)-2-fluorophenoxy]phenylsulfanyl}acetate (0.800 g, 1.61 mmol) in methanol (20 mL) was added a 31% hydrogen peroxide solution (2.08 mL, 18.5 mmol). The resulting solution was refluxed for 16 hours. The reaction solution was cooled with ice, and the resulting precipitated solid was collected by filtration, to thereby yield 0.651 g of the title compound.

Appearance: White powder $^1$H NMR (DMSO-d$_6$) δ 1.13 (3H, t, J=7.1 Hz), 3.90-4.10 (4H, m), 7.14 (2H, d, J=8.8 Hz), 7.34 (1H, t, J=9.0 Hz), 7.55-7.65 (1H, m), 7.72 (2H, d, J=8.8 Hz), 7.84 (1H, d, J=8.4 Hz), 7.90-8.00 (2H, m), 8.22 (1H, d, J=2.0 Hz), 10.63 (1H, s).

Reference Example 665

Production of ethyl 3-(4-{5-[4-(trifluoromethyl)phenyl-carbamoyl]pyridin-2-yloxy}phenyl)butyrate To a suspension of 60% sodium hydride (0.133 g, 3.3 mmol) in THF (6 mL) was added dropwise triethylphosphono acetate (0.53 mL, 2.7 mmol) under ice cooling, and the resulting solution was stirred for 1 hour at room temperature. To the reaction solution was added a solution of 6-(4-acetylphenoxy)-N-[4-(trifluoromethyl)phenyl]nicotinamide (0.53 g, 1.3 mmol) in THF (6 mL), and the resulting solution was stirred for 10 hours at 60° C. To the reaction solution was added saturated aqueous ammonium chloride, and extracted with ethyl acetate. The ethyl acetate layer was washed with brine, dried over anhydrous magnesium sulfate, evaporated, and the residue was purified by silica gel chromatography (n-hexane:ethyl acetate=4:1), to thereby yield 0.57 g of the intermediate product ethyl 3-(4-{5-[4-(trifluoromethyl)phenyl-carbamoyl]pyridin-2-yloxy}phenyl)-2-butenoate. 10% palladium-carbon (0.057 g) was suspended in a mixed solvent consisting of ethanol (8 mL) and dioxane (2 mL), and to this suspension was added ethyl 3-(4-{5-[4-(trifluoromethyl)phenylcarbamoyl]pyridin-2-yloxy}phenyl)-2-butenoate (0.57 g, 1.2 mmol). The resulting product was subjected to catalytic reduction at atmospheric pressure and room temperature. Once the absorption of hydrogen had stopped, the catalyst was removed by filtration, and the filtrate was concentrated under reduced pressure, to thereby yield 0.56 g of the title compound.

Appearance: White solid $^1$H NMR (CDCl$_3$) δ 1.21 (3H, t, J=7.1 Hz), 1.33 (3H, d, J 7.0 Hz), 2.51-2.67 (2H, m), 3.28-3.37 (1H, m), 4.10 (2H, q, J=7.1 Hz), 7.00 (1H, d, J=8.6 Hz), 7.07-7.12 (2H, m), 7.26-7.31 (2H, m), 7.60-7.65 (2H, m), 7.73-7.77 (2H, m), 7.81 (1H, brs), 8.21 (1H, dd, J=8.6, 2.6 Hz), 8.68 (1H, d, J=2.3 Hz).

The following compound was produced in the same manner as in Reference Example 665.

Reference Example 666

Ethyl 2-methyl-3-{4-[5-(4-trifluoromethylphenylcarbamoyl)pyridin-2-yloxy]phenyl}propionate

MS 472 (M$^+$)

Reference Example 667

Production of 3,4-dichloro-N-{6-[4-(N-hydroxycarbamimidoylmethyl)phenoxy]pyridin-3-yl}benzamide To a solution of 3,4-dichloro-N-[6-(4-cyanomethylphenoxy)pyridin-3-yl]benzamide (700 mg, 1.76 mmol) in ethanol (30 mL) were added water (2 mL), hydroxylamine (420 mg, 12.71 mmol) and potassium carbonate (1.76 g, 12.73 mmol). Under argon, the resulting solution was stirred under reflux for 4 hours. The resulting reaction solution was concentrated under reduced pressure. To the residue was added water, and extracted with ethyl acetate. The ethyl acetate layer was washed with brine, dried over anhydrous magnesium sulfate, evaporated, and the residue was purified by silica gel column chromatography (dichloromethane:methanol=10:1), to thereby yield 510 mg of the title compound.

Appearance: White powder $^1$H NMR (DMSO-d$_6$) δ 3.27 (2H, s), 5.41 (2H, brs), 7.03 (2H, d, J=8.4 Hz), 7.05 (1H, d, J=8.8 Hz), 7.31 (2H, d, J=8.4 Hz), 7.84 (1H, d, J=8.4 Hz), 7.94 (1H, dd, J=8.4 Hz, 2.0 Hz), 8.18 (1H, dd, J=8.8 Hz, 2.6 Hz), 8.22 (1H, d, J=2.0 Hz), 8.46 (1H, d, J=2.6 Hz), 8.88 (1H, s), 10.53 (1H, s).

Reference Example 668

Production of 3,4-dichloro-N-{6-[4-(N-acetoxy-carbamimidoylmethyl)phenoxy]pyridin-3-yl}benzamide To a solution of 3,4-dichloro-N-{6-[4-(N-hydroxycarbamimidoylmethyl)phenoxy]pyridin-3-yl}benzamide (510 mg, 1.18 mmol) in dioxane (8 mL) was added potassium carbonate (163 mg, 1.18 mmol). While stirring under ice cooling, to the resulting solution was added dropwise acetyl chloride (0.084 mL, 1.18 mmol), and the resulting solution was stirred for 15 minutes at room temperature. To the reaction solution was added THF (10 mL), and then water, and extracted with ethyl acetate. The ethyl acetate layer was washed with brine, dried over anhydrous magnesium sulfate, evaporated. The residue was washed with ethyl acetate, to yield 340 mg of the title compound.

Appearance: White powder $^1$H NMR (DMSO-d$_6$) δ 2.05 (3H, s), 3.35 (2H, s), 6.43 (2H, brs), 7.06 (1H, d, J=9.0 Hz), 7.06 (2H, d, J=8.6 Hz), 7.36 (2H, d, J=8.6 Hz), 7.84 (1H, d, J=8.3 Hz), 7.94 (1H, dd, J=8.3 Hz, 2.0 Hz), 8.18 (1H, dd, J=9.0 Hz, 2.5 Hz), 8.22 (1H, d, J=2.0 Hz), 8.47 (1H, d, J=2.5 Hz), 10.54 (1H, s).

Reference Example 669

Production of 4-{4-[4-(3,4-dichlorobenzoylamino)-2-fluorophenoxy]phenyl}-4-oxobutyric acid To a suspension consisting of 3,4-dichloro-3'-fluoro-4'-phenoxybenzanilide (5.05 g, 13.4 mmol) and succinic anhydride (1.48 g, 14.8 mmol) in 1,2-dichloroethane (25 mL) was added aluminum chloride (6.26 g, 47.0 mmol) under ice cooling, and the resulting mixture was stirred at the same temperature for 5 minutes, and then at room temperature for 1.5 hours. The resulting reaction solution was poured into ice water, and the resulting solid was collected by filtration. To the solid was added 50% aqueous acetone (200 mL), and the resulting solution was refluxed for 0.5 hours, then cooled. The obtained solid was collected by filtration, to thereby yield 6.30 g of the title compound.

Appearance: White powder

Melting point: 205-208° C.

Reference Example 670

Production of ethyl 3-{4-[hydroxy(5-nitro-2-pyridyl)-methyl]phenyl}propionate

To a solution of ethyl 3-[4-(5-nitropyridine-2-carbonyl)phenyl]propionate (1.52 g, 4.63 mmol) in dichloromethane (15 mL) and ethanol (15 mL) was added sodium borohydride (0.175 g, 4.63 mmol) under ice cooling, and the resulting solution was stirred at the same temperature for 1 hour. The reaction solution was concentrated under reduced pressure. The residue was dissolved in water and ethyl acetate. To the solution was added acetic acid and extracted with ethyl acetate. The ethyl acetate layer was washed with a saturated sodium bicarbonate solution and brine, and then dried over anhydrous magnesium sulfate. The solvent was evaporated, and the residue was purified by silica gel column chromatography (n-hexane:ethyl acetate=3:1), to thereby yield 0.264 g of the title compound.

Appearance: Brown powder $^1$H NMR (CDCl$_3$) δ 1.19 (3H, t, J=7.2 Hz), 2.56 (2H, t, J=7.8 Hz), 2.91 (2H, t, J=7.8 Hz), 4.09 (2H, q, J=7.2 Hz), 4.35 (1H, brs), 5.84 (1H, s), 7.17 (2H, d, J=8.1 Hz), 7.26 (2H, d, J=8.1 Hz), 7.46 (1H, d, J=8.7 Hz), 8.40 (1H, dd, J=8.7 Hz, 2.5 Hz), 9.36 (1H, d, J=2.5 Hz).

The following compound was produced in the same manner as in Reference Example 670.

Reference Example 671 t-Butyl 4-[2-hydroxy-3-(4-hydroxyphenyl)propionyl]-piperazine-1-carboxylate $^1$H NMR (CDCl$_3$) δ 1.47 (9H, s), 1.62 (1H, brs), 2.85 (2H, d, J=6.0 Hz), 3.00-3.80 (8H, m), 4.56 (1H, t, J=6.0 Hz), 5.35 (1H, brs), 6.74 (2H, d, J=8.4 Hz), 7.06 (2H, d, J=8.4 Hz).

Reference Example 672

Production of ethyl 3-(4-{5-[bis(3,4-dichlorobenzoyl)-amino]-2-pyridylmethyl}phenyl)propionate To a suspension of 10% palladium-carbon (27 mg) in ethanol (5 mL) were added a solution of ethyl 3-{4-(hydroxy(5-nitro-2-pyridyl)-methyl]phenyl}propionate (0.264 g, 0.799 mmol) and 0.5 M hydrogen chloride in ethanol (2 mL), and the resulting solution was subjected to catalytic reduction at atmospheric pressure at 50° C. Once the absorption of hydrogen had stopped, the catalyst was removed by filtration, and the filtrate was concentrated under reduced pressure. The residue was suspended in THF (5 mL), and triethylamine (0.267 mL, 2.40 mmol) was added. To the solution was added dropwise a solution of 3,4-dichlorobenzoyl chloride (0.255 g, 0.879 mmol) in THF (1 mL) under ice cooling, and stirred for 1 hour at the same temperature. To the resulting solution was added water and extracted with ethyl acetate. The ethyl acetate layer was washed with a saturated sodium bicarbonate solution and brine, dried over anhydrous magnesium sulfate, and evaporated. The residue was purified by silica gel column chromatography (n-hexane:ethyl acetate=5:1), to thereby yield 0.177 g of the title compound.

Appearance: Pale yellow oil
$^1$H NMR (CDCl$_3$) δ 1.20 (3H, t, J=7.2 Hz), 2.56 (2H, t, J=7.8 Hz), 2.89 (2H, t, J=7.8 Hz), 4.09 (2H, q, J=7.2 Hz), 6.99 (1H, s), 7.17 (2H, d, J=8.2 Hz), 7.35 (2H, d, J=8.2 Hz), 7.42 (1H, d, J=8.6 Hz), 7.43-7.56 (2H, m), 7.63 (1H, dd, J=8.6 Hz, 2.1 Hz), 7.85-7.94 (2H, m), 8.15 (1H, d, J=2.0 Hz), 8.20-8.32 (2H, m), 8.57 (1H, d, J=2.5 Hz).

Reference Example 673

Production of ethyl 3-(4-(5-(N-(4-(trifluoromethyl)-phenyl)sulfamoyl)pyridin-2-yloxy)phenyl)propionate To a solution of ethyl 3-(4-(3-bromo-5-(N-(4-(trifluoromethyl)phenyl)sulfamoyl)pyridin-2-yloxy)phenyl)propionate (0.41 g, 0.7 mmol) in ethanol (10 mL) were added 10% palladium-carbon (0.041 g) and ammonium formate (0.226 g, 3.6 mmol), and the resulting solution was heated to reflux for 2 hours. The catalyst was removed by filtration, and the filtrate was concentrated under reduced pressure. The residue was then purified by silica gel chromatography (n-hexane:ethyl acetate=4:1), to thereby yield 0.28 g of the title compound.

Appearance: White solid
$^1$H NMR (CDCl$_3$) δ 1.24 (3H, t, J=7.1 Hz), 2.60-2.66 (2H, m), 2.93-2.99 (2H, m), 4.14 (2H, q, J=7.1 Hz), 6.95 (1H, d, J=8.8 Hz), 7.01-7.05 (2H, m), 7.20-7.26 (3H, m), 7.50-7.54 (3H, m), 8.03 (1H, dd, J=8.8 Hz, 2.6 Hz), 8.59 (1H, d, J=2.6 Hz).

Reference Example 674

Production of 1-(4-methoxyphenyl)imidazolin-2-one

To a suspension of 1-(2-chloroethyl)-3-(4-methoxyphenyl)urea (7.0 g, 30.6 mmol) in t-butanol (120 mL) was added potassium t-butoxide (6.4 g, 57.0 mmol) under a nitrogen atmosphere. The resulting solution was stirred for 10 minutes, and then potassium t-butoxide (3.0 g, 26.7 mmol) was added. This solution was stirred for 10 minutes, and then potassium t-butoxide (4.3 g, 38.3 mmol) was added. The resulting solution was stirred for 16 hours at room temperature. The pH was adjusted to between 2 and 3 with 10% hydrochloric acid, and the solvent was evaporated under reduced pressure. To the residue were added water (100 mL) and ethyl acetate (100 mL), and stirred for 1 hour at room temperature. Resulting precipitates were filtered, washed with diethyl ether, and then dried under reduced pressure, to thereby yield 5.1 g of the title compound.

Appearance: White powder
$^1$H NMR (DMSO-d$_6$) δ 3.29-3.44 (2H, m), 3.70 (3H, s), 3.71-3.88 (2H, m), 6.77 (1H, s), 6.81-6.95 (2H, m), 7.35-7.50 (2H, m).

The following compounds were produced in the same manner as in Reference Example 674.

Reference Example 675

1-(4-Benzyloxy-3-methylphenyl)tetrahydropyrimidin-2-one $^1$H NMR (DMSO-d$_6$) δ 1.81-1.96 (2H, m), 2.16 (3H, s), 3.11-3.25 (2H, m), 3.51 (2H, t, J=5.6 Hz), 5.09 (2H, s), 6.42 (1H, s), 6.91 (1H, d, J=8.7 Hz), 6.98 (1H, dd, J=2.6 Hz, 8.7 Hz), 7.04 (1H, d, J=2.6 Hz), 7.28-7.34 (1H, m), 7.36-7.41 (2H, m), 7.42-7.48 (2H, m).

TABLE 95

| Reference Example No. | R$_{310}$ | M | mp(° C.) or $^1$H NMR (CDCl$_3$) δ ppm |
|---|---|---|---|
| 676 | —H | 1 | mp 162.0-163.0 |
| 677 | —H | 2 | mp 179.0-180.0 |
| 678 | —OCH$_3$ | 1 | $^1$H NMR 2.29-2.45(4H, m), 2.59-2.69(2H, m), 2.91-3.04(2H, m), 3.34-3.47(4H, m), 3.53-3.69(4H, m), 3.75(3H, s), 3.85-3.96(2H, m), 4.58(1H, s), 5.95(2H, s), 6.69-6.78(2H, m), 6.79-6.89(3H, m), 6.91(1H, d, J=9.0Hz), 7.02(1H, d, J=8.0Hz), 7.99(1H, d, J=2.9Hz), 8.25(1H, dd, J=2.9Hz, 9.0Hz). |
| 679 | —OCH$_3$ | 2 | mp 140.0-141.5 |

TABLE 96

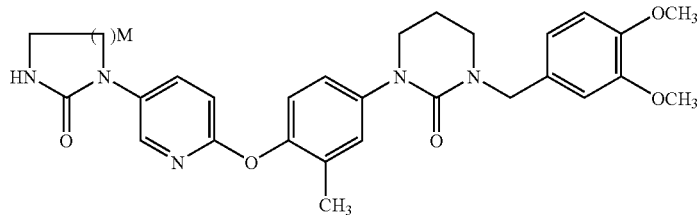

| Reference Example No. | M | $^1$H NMR (CDCl$_3$) δ ppm |
|---|---|---|
| 680 | 1 | 1.98-2.14(2H, m), 2.18(3H, s), 3.30(2H, d, J=6.0Hz), 3.51-3.66(2H, m), 3.67-3.78(2H, m), 3.80-4.05(8H, m), 4.57(2H, s), 4.79(1H, s), 6.78-6.94(4H, m), 6.99(1H, d, J=8.6Hz), 7.13(1H, dd, J=2.6Hz, 8.6Hz), 7.22(1H, d, J=2.6Hz), 8.05(1H, d, J=2.9Hz), 8.22(1H, dd, J=2.9Hz, 9.0Hz). |
| 681 | 2 | 1.91-2.15(4H, m), 2.18(3H, s), 3.18-3.36(2H, m), 3.37-3.51(2H, m), 3.58-3.78(2H, m), 3.88(3H, s), 3.88(3H, s), 4.56(2H, s), 4.89(1H, s), 6.76-6.94(4H, m), 7.00(1H, d, J=8.7Hz), 7.13(1H, dd, J=2.6Hz, 8.7Hz), 7.23(1H, d, J=2.6Hz), 7.67(1H, dd, J=2.8Hz, 8.8Hz), 8.08(1H, d, J=2.8Hz). |

Reference Example 682

Production of 3-{4-[4-(3,4-dichlorobenzoylamino)-phenoxy]phenyl}propionic acid

To a solution of ethyl 3-{4-[4-(3,4-dichlorobenzoylamino)phenoxy]phenyl}propionate (6.00 g, 13.1 mmol) in THF (60 mL) and ethanol (30 mL) were added 5 M aqueous sodium hydroxide (3.14 mL, 15.7 mmol) and water (30 mL) and the resulting solution was refluxed for 1 hour. The reaction solution was cooled with ice. To the reaction solution were added 5 M hydrochloric acid (4.0 mL, 20.0 mmol) and water (100 mL). The obtained solid was collected by filtration, and recrystallized from water-containing acetone, to thereby yield 5.60 g of the title compound.

Appearance: White powder

Melting point: 188-190° C.

The following compounds were produced in the same manner as in Reference Example 682.

TABLE 97

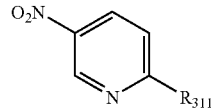

| Reference Example No. | R$_{311}$ | $^1$H NMR (solvent) δ ppm or MS |
|---|---|---|
| 683 | ![structure] | $^1$H NMR (CDCl$_3$) 1.51(3H, d, J=7.1Hz), 2.12(3H, s), 2.91(3H, s), 4.49(1H, q, J=7.1Hz), 6.71-6.75(2H, m), 6.95-7.00(2H, m), 8.45(1H, dd, J=9.1Hz, 2.8Hz), 9.04(1H, dd, J=2.8Hz, 0.5Hz). |
| 684 | ![structure] | MS 300(M$^+$) |
| 685 | ![structure] | $^1$H NMR (DMSO-d$_6$) 7.39(1H, td, J=2.0Hz, 8.9 Hz), 7.50(1H, d, J=9.0Hz), 7.78(1H, td, J=2.1 Hz, 8.9Hz), 8.70(1H, dd, J=2.8Hz, 9.0Hz), 9.04(1H, d, J=2.8Hz), 11.35-11.91(1H, m). |
| 686 | ![structure] | $^1$H NMR (CDCl$_3$) 2.72-2.77(2H, m), 2.98-3.03(2H, m), 3.74(3H, s), 6.85-6.89(2H, m), 7.03(1H, d, J=9.1Hz), 7.06-7.09(1H, m), 8.45(1H, dd, J=9.1Hz, 2.8Hz), 9.01.(1H, d, J=2.8Hz). |

TABLE 97-continued

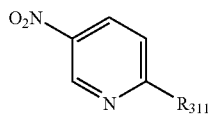

| Reference Example No. | R_{311} | $^1$H NMR (solvent) δ ppm or MS |
|---|---|---|
| 687 | ![structure: 4-(methylamino)phenyl-CH2CH2-COOH] | $^1$H NMR (DMSO-d$_6$) 2.52(2H, t, J=7.6Hz), 2.80(2H, t, J=7.6Hz), 6.86(1H, d, J=9.4Hz), 7.21(2H, d, J=8.5Hz), 7.58(2H, d, J=8.5Hz), 8.26(1H, dd, J=2.9Hz, 9.4Hz), 9.01(1H, d, J=2.9Hz), 10.06(1H, s). |
| 688 | ![structure: 3-methoxyphenyl-N(CH3)-CH2-COOH] | $^1$H NMR (DMSO-d$_6$) 2.96(3H, s), 4.09(2H, s), 6.44-6.49(2H, m), 6.56(1H, dd, J=8.3Hz, 2.4Hz), 7.15(1H, d, J=9.1Hz), 7.20-7.26(1H, m), 8.59(1H, dd, J=9.1Hz, 2.8Hz), 9.05(1H, d, J=2.8Hz). |
| 689 | ![structure: 4-methoxyphenyl-N(CH3)-CH(CH3)-COOH] | $^1$H NMR (CDCl$_3$) 1.53(3H, d, J=7.1Hz), 2.93(3H, s), 4.51(1H, q, J=7.1Hz), 6.87(2H, d, J=9.2Hz), 6.98(1H, d, J=9.1Hz), 7.05(2H, d, J=9.1Hz), 8.44(1H, dd, J=9.1Hz, 2.8Hz), 9.05(1H, d, J=2.6Hz). |
| 690 | ![structure: 4-methoxyphenyl-N(CH3)-CH2CH2-COOH] | $^1$H NMR (CDCl$_3$) 2.63-2.69(2H, m), 2.97(3H, s), 3.68(2H, t, J=7.1Hz), 6.81(2H, d, J=9.1Hz), 6.98(1H, d, J=9.1Hz), 7.05(2H, d, J=9.2Hz), 8.44(1H, dd, J=9.1Hz, 2.8Hz), 9.06(1H, d, J=2.8Hz). |
| 691 | ![structure: 4-(dimethylamino)benzoic acid] | $^1$H NMR (DMSO-d$_6$) 3.55(3H, s), 6.67(1H, d, J=9.5Hz), 7.52(2H, d, J=8.5Hz), 8.04(2H, d, J=8.5Hz), 8.21(1H, dd, J=2.8Hz, 9.5Hz), 9.05(1H, d, J=2.8Hz), 13.10(1H, brs). |
| 692 | ![structure: 1-(3-methyl-4-methoxyphenyl)piperidin-4-yl-CH2-COOH] | $^1$H NMR (DMSO-d$_6$) 1.28-1.32(2H, m), 1.75-1.79(3H, m), 2.01(3H, s), 2.19(2H, d, J=6.8Hz), 2.65(2H, t, J=12.0Hz), 3.65(2H, d, J=12.4Hz), 6.80-6.96(3H, m), 7.15(1H, d, J=9.2Hz), 8.58(1H, dd, J=9.1Hz, 2.8Hz), 9.01(1H, d, J=2.8Hz), 10.71(1H, brs). |
| 693 | ![structure: 3-fluoro-4-methoxyphenyl-CH2CH2-COOH] | MS 306(M$^+$) |

TABLE 98

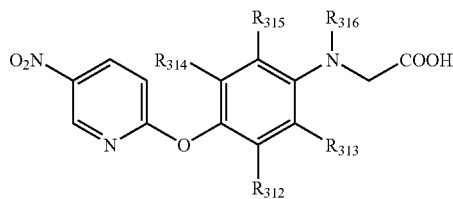

| Reference Example No. | $R_{312}$ | $R_{313}$ | $R_{314}$ | $R_{315}$ | $R_{316}$ | $^1$H NMR (solvent) δ ppm |
|---|---|---|---|---|---|---|
| 694 | —F | —H | —H | —H | —CH$_3$ | (CDCl$_3$) 3.09(3H, s), 4.12(2H, s), 6.45-6.57(2H, m), 7.05-7.12(2H, m), 8.47(1H, dd, J=9.1Hz, 2.8Hz), 9.02(1H, dd, J=2.8Hz, 0.7Hz). |
| 695 | —F | —H | —H | —H | —C$_2$H$_5$ | (CDCl$_3$) 1.25(3H, t, J=7.1Hz), 3.47(2H, q, J=7.1Hz), 4.06(2H, s), 6.42-6.53(2H, m), 7.04-7.10(2H, m), 8.47(1H, dd, J=9.1Hz, 2.8Hz), 9.02(1H, dd, J=2.8Hz, 0.5Hz). |
| 696 | —F | —H | —H | —H | allyl | (CDCl$_3$) 4.03(2H, d, J=5.0Hz), 4.09(2H, s), 5.25-5.32(2H, m), 5.82-5.96(1H, m), 6.44-6.56(2H, m), 7.04-7.10(2H, m), 8.47(1H, dd, J=9.1Hz, 2.8Hz), 9.02(1H, d, J=2.6Hz). |
| 697 | —F | —H | —H | —F | —CH$_3$ | (DMSO-d$_6$) 2.94(3H, s), 4.04(3H, s), 6.92(1H, dd, J=8.5Hz, 12.9Hz), 7.30(1H, dd, J=7.5Hz, 13.7Hz), 7.35(1H, d, J=9.1Hz), 8.63(1H, dd, J=2.8Hz, 9.1Hz), 9.04(1H, d, J=2.8Hz), 12.41-12.82(1H, m). |
| 698 | —F | —H | —H | —F | —C$_2$H$_5$ | (DMSO-d$_6$) 1.10(3H, t, J=7.0Hz), 3.12-3.48(2H, m), 4.01(2H, s), 6.90(1H, dd, J=8.4Hz, 13.1Hz), 7.29(1H, dd, J=7.6Hz, 13.7Hz), 7.35(1H, d, J=9.0Hz), 8.63(1H, dd, J=2.8Hz, 9.0Hz), 9.04(1H, d, J=2.8Hz), 12.41-12.70(1H, m). |
| 699 | —F | —H | —F | —H | —CH$_3$ | (DMSO-d$_6$) 2.96(3H, s), 4.26(2H, s), 6.41-6.61(2H, m), 7.43(1H, d, J=9.1Hz) 8.65(1H, dd, J=2.8Hz, 9.1Hz), 9.05(1H, d, J=2.8Hz), 12.56-12.90(1H, m). |
| 700 | —CH$_3$ | —CH$_3$ | —H | —H | —CH$_3$ | (CDCl$_3$) 2.07(3H, s), 2.32(3H, s), 2.85(3H, s), 3.76(2H, s), 6.91(1H, d, J=8.7Hz), 7.00(1H, dd, J=9.1Hz, 0.6Hz), 7.09(1H, d, J=8.7Hz), 8.46(1H, dd, J=9.1Hz, 2.8 Hz), 9.04(1H, dd, J=2.8Hz, 0.6Hz). |
| 701 | —CH$_3$ | —H | —H | —CH$_3$ | —C$_2$H$_5$ | (DMSO-d$_6$) 0.98(3H, t, J=7.1Hz), 1.98(3H, s), 2.20(3H, s), 3.09(2H, q, J=7.1 Hz), 3.70(2H, s), 6.91(1H, s), 7.06(1H, s), 7.18(1H, d, J=9.1Hz), 8.59(1H, dd, J=9.1 Hz, 2.9Hz), 9.03(1H, d, J=2.9Hz), 12.30(1H, brs). |
| 702 | —H | —H | —H | —H | —SO$_2$CH$_3$ | (DMSO-d$_6$) 3.17(3H, s), 4.43(2H, s), 7.29(2H, d, J=8.7Hz), 7.31(1H, d, J=9.1 Hz), 7.55(2H, d, J=8.9Hz), 8.64(1H, dd, J=9.1Hz, 2.8Hz), 9.05(1H, d, J=2.8Hz). |
| 703 | —CH$_3$ | —H | —H | —H | —SO$_2$CH$_3$ | (DMSO-d$_6$) 2.09(3H, s), 3.11(3H, s), 4.42(2H, s), 7.20(1H, d, J=8.6Hz), 7.31(1H, d, J=9.1Hz), 7.37(1H, dd, J=8.6 Hz, 2.5Hz), 7.44(1H, d, J=2.3Hz), 8.64(1H, dd, J=9.1Hz, 2.8Hz), 9.03(1H, d, J=2.8Hz), 12.88(1H, brs). |

TABLE 99

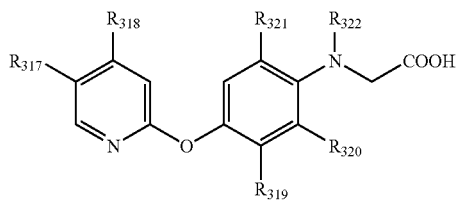

| Reference Example No. | $R_{317}$ | $R_{318}$ | $R_{319}$ | $R_{320}$ | $R_{321}$ | $R_{322}$ | $^1$H NMR (solvent) δ ppm or MS |
|---|---|---|---|---|---|---|---|
| 704 | —NO$_2$ | —H | —CH$_3$ | —H | —CH$_3$ | —CH$_3$ | MS 331(M$^+$) |
| 705 | —NO$_2$ | —H | —CF$_3$ | —H | —H | —CH$_3$ | MS 371(M$^+$) |
| 706 | —NO$_2$ | —H | —CF$_3$ | —H | —H | —C$_2$H$_5$ | MS 385(M$^+$) |
| 707 | —NO$_2$ | —CH$_3$ | —H | —CF$_3$ | —H | —CH$_3$ | MS 385(M$^+$) |
| 708 | —NO$_2$ | —H | —F | —F | —H | —CH$_3$ | $^1$H NMR (DMSO-d$_6$) 2.98(3H, s), 4.05(2H, s), 6.64-6.88(1H, m), 6.96-7.20 (1H, m), 7.38(1H, d, J=9.1 Hz), 8.64(1H, dd, J=2.7Hz, 9.1Hz), 9.04(1H, d, J=2.7 Hz) 12.24-12.95(1H m). |
| 709 | —NO$_2$ | —H | —OCH$_3$ | —H | —H | —SO$_2$CH$_3$ | $^1$H NMR (DMSO-d$_6$) 3.16(3H, s), 3.70(3H, s), 4.45(2H, s), 7.10-7.30(4H, m), 8.61(1H, dd, J=9.1Hz, 2.8Hz), 9.02(1H, d, J=2.8 Hz), 12.97(1H, brs). |
| 710 | —Br | —H | —F | —H | —F | —CH$_3$ | $^1$H NMR (DMSO-d$_6$) 2.92(3H, s), 4.01(2H, s), 6.80-6.93(1H, m), 7.11(1H, d, J=8.8Hz), 7.14-7.26(1H, m), 8.06(1H, dd, J=2.6Hz, 8.8Hz), 8.25(1H, d, J=2.6 Hz), 12.18-12.89(1H, m). |
| 711 | 4-CF$_3$PhCH$_2$— | —H | —H | —H | —H | —CH$_3$ | $^1$H NMR (CDCl$_3$) 3.04(3H, s), 3.93(2H, s), 4.04(2H, s), 6.69(2H, d, J=9.1Hz), 6.70(1H, d, J=8.5Hz), 6.97(2H, d, J=9.1Hz), 7.25(2H, d, J=8.6Hz), 7.39(1H, dd, J=8.5Hz, 2.5 Hz), 7.52(2H, d, J=8.6Hz), 8.09(1H, d, J=2.5Hz), 11.26(1H, brs). |
| 712 | 4-CF$_3$PhOCH$_2$— | —H | —H | —H | —H | —SO$_2$CH$_3$ | $^1$H NMR (DMSO-d$_6$) 3.11(3H, s), 4.40(2H, s), 5.18(2H, s), 7.12(1H, d, J= 8.9Hz), 7.15-7.23(4H, m), 7.49(2H, d, J=8.9Hz), 7.67(2H, d, J=8.6Hz), 7.98(1H, dd, J=8.4Hz, 2.5 Hz), 8.28(1H, d, J=2.0Hz), 12.41(1H, brs). |
| 713 | 4-CF$_3$PhOCH$_2$— | —H | —CH$_3$ | —H | —H | —SO$_2$CH$_3$ | $^1$H NMR (DMSO-d$_6$) 2.06(3H, s), 3.18(3H, s), 3.89(2H, s), 5.15(2H, s), 7.02 (1H, d, J=8.4Hz), 7.07(1H, d, J=8.6Hz), 7.21(2H, d, J= 8.4Hz), 7.44(1H, dd, J=8.6 Hz, 2.6Hz), 7.49(1H, d, J= 2.3Hz), 7.67(2H, d, J=8.9 Hz), 7.95(1H, dd, J=8.4Hz, 2.5Hz), 8.24(1H, d, J=2.5 Hz). |

TABLE 100

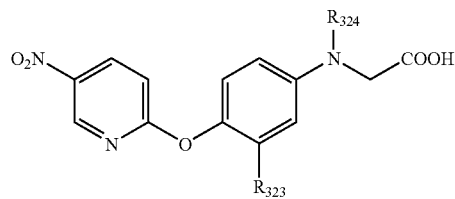

| Reference Example No. | $R_{323}$ | $R_{324}$ | $^1$H NMR (solvent) δ ppm |
|---|---|---|---|
| 714 | —H | —H | (DMSO-d$_6$) 3.35(1H, brs), 3.84(2H, s), 6.63(2H, d, J=8.9Hz), 6.96(2H, d, J=8.9Hz), 7.14(1H, d, J=9.1Hz), 8.59(1H, dd, J=2.9Hz, 9.1Hz), 9.05(1H, d, J=2.9Hz). |
| 715 | —H | —CH$_3$ | (CDCl$_3$) 3.09(3H, s), 4.11(2H, s), 6.74(2H, d, J=9.1Hz), 6.97(1H, dd, J=9.1Hz, 0.5Hz), 7.04(2H, d, J=9.1Hz), 8.43(1H, dd, J=9.1Hz, 2.8Hz), 9.04(1H, dd, J=2.8Hz, 0.5Hz). |
| 716 | —H | —C$_2$H$_5$ | (CDCl$_3$) 1.24(3H, t, J=7.1Hz), 3.48(2H, q, J=7.1Hz), 4.07(2H, s), 6.73(2H, d, J=9.2Hz), 6.98(1H, d, J=9.1Hz), 7.04(2H, d, J=9.2Hz), 8.44(1H, dd, J=9.1Hz, 2.8Hz), 9.05(1H, d, J=2.8Hz). |
| 717 | —OCH$_3$ | —H | (DMSO-d$_6$) 3.62(3H, s), 3.83(2H, s), 6.13(1H, dd, J=8.6Hz, 2.5Hz), 6.41(1H, d, J=2.5Hz), 6.90(1H, d, J=8.6Hz), 7.09(1H, d, J=8.6Hz), 8.54(1H, dd, J=9.1Hz, 3.0Hz), 9.00(1H, d, J=3.0Hz). |
| 718 | —OCH$_3$ | —CH$_3$ | (DMSO-d$_6$) 3.00(3H, s), 3.65(3H, s), 4.12(2H, s), 6.21(1H, dd, J=8.8Hz, 2.8Hz), 6.39(1H, d, J=2.8Hz), 6.96(1H, d, J=8.8Hz), 7.11(1H, d, J=9.1Hz), 8.54(1H, dd, J=9.1Hz, 2.8Hz), 9.00(1H, d, J=2.8Hz), 12.57(1H, s). |
| 719 | —OCH$_3$ | —C$_2$H$_5$ | (DMSO-d$_6$) 1.13(3H, t, J=7.0Hz), 3.42(2H, q, J=7.0Hz), 3.64(3H, s), 4.05(2H, s), 6.14(1H, dd, J=8.8Hz, 2.8Hz), 6.31(1H, d, J=2.8Hz), 6.95(1H, d, J=8.8Hz), 7.12(1H, d, J=9.1Hz), 8.53(1H, dd, J=9.1Hz, 2.8Hz), 9.00(1H, d, J=2.8Hz), 12.59(1H, brs). |
| 720 | —CH$_3$ | —Ac | (DMSO-d$_6$) 1.86(3H, s), 2.08(3H, s), 4.26(2H, s), 7.05-7.50(4H, m), 8.63(1H, dd, J=9.1Hz, 2.9Hz), 9.02(1H, dd, J=2.9Hz, 0.4Hz), 12.72(1H, brs). |
| 721 | —CH$_3$ | —H | (CDCl$_3$) 2.09(3H, s), 3.98(2H, s), 5.26(1H, brs), 6.50-6.55(2H, m), 6.92(1H, d, J=8.4Hz), 6.98(1H, d, J=8.1Hz), 8.45(1H, dd, J=8.1Hz, 2.8Hz), 9.04(1H, d, J=2.8Hz). |
| 722 | —CH$_3$ | —CH$_3$ | (DMSO-d$_6$) 1.99(3H, s), 2.97(3H, s), 4.09(2H, s), 6.52(1H, dd, J=8.8Hz, 3.0Hz), 6.59(1H, d, J=3.0Hz), 6.92(1H, d, J=8.8Hz), 7.13(1H, dd, J=9.1Hz, 0.3Hz), 8.57(1H, dd, J=9.1Hz, 2.9Hz), 9.01(1H, d, J=2.9Hz), 12.54(1H, brs). |
| 723 | —CH$_3$ | —C$_2$H$_5$ | (DMSO-d$_6$) 1.11(3H, t, J=7.0Hz), 1.98(3H, s), 3.89(2H, q, J=7.0Hz), 4.02(2H, s), 6.44(1H, dd, J=8.8Hz, 2.9Hz), 6.51(1H, d, J=2.9Hz), 6.90(1H, d, J=8.8Hz), 7.13(1H, d, J=9.1Hz), 8.56(1H, dd, J=9.1Hz, 2.9Hz), 9.01(1H, d, J=2.9Hz), 12.53(1H, brs). |
| 724 | —CH$_3$ | ![cyclopropyl] | (DMSO-d$_6$) 0.54-0.59(2H, m), 0.80-0.87(2H, m), 2.02(3H, s), 2.64-2.71(1H, m), 4.11(2H, s), 6.77-6.81(1H, m), 6.85(1H, d, J=2.8Hz), 6.96(1H, d, J=8.7Hz), 7.17(1H, dd, J=9.2Hz, 0.5Hz), 8.59(1H, dd, J=9.1Hz, 3.0Hz), 9.04(1H, dd, J=3.0Hz, 0.5Hz), 12.56(1H, brs). |
| 725 | —F | —H | (DMSO-d$_6$) 3.82(2H, s), 6.43(1H, dd, J=8.7Hz, 2.8Hz), 6.53(1H, dd, J=13.4Hz, 2.6Hz), 7.07(1H, t, J=8.9Hz), 7.28(1H, dd, J=9.1Hz, 0.5Hz), 8.61(1H, dd, J=9.1Hz, 2.8Hz), 9.03(1H, dd, J=2.8Hz, 0.5Hz). |

TABLE 101

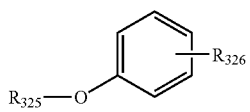

| Reference Example No. | R₃₂₅ | R₃₂₆ | mp(° C.) or $^1$H NMR (solvent) δ ppm |
|---|---|---|---|
| 726 | 4-NO₂Ph— | 4-N(CH₃)CH₂COOH | $^1$H NMR (CDCl₃) 3.10(3H, s), 4.13(2H, s), 6.74(2H, d, J=9.2 Hz), 6.95(2H, d, J=9.2Hz), 7.00(2H, d, J=9.2Hz), 8.17(2H, d, J=9.2Hz). |
| 727 | 3,4-diCl-C₆H₃-C(O)NH-C₆H₄-(4-Me)- | 2-(CH₂)₂COOH | mp 157-159 |
| 728 | 3,4-diCl-C₆H₃-C(O)NH-C₆H₄-(4-Me)- | 3-(CH₂)₂COOH | mp 192-194 |
| 729 | 3,4-diCl-C₆H₃-C(O)NH-C₆H₃-(2-Me)- | 4-(CH₂)₂COOH | $^1$H NMR (CDCl₃) 2.67(2H, t, J=7.7Hz), 2.94(2H, t, J=7.7Hz), 6.78(1H, dd, J=8.2Hz, 1.2Hz), 6.97(2H, d, J=8.6Hz), 7.02-7.19(2H, m), 7.20(2H, d, J=8.6 Hz), 7.48(1H, d, J=8.3Hz), 7.56(1H, dd, J=8.3Hz, 2.1Hz), 7.84(1H, d, J=2.1Hz), 8.38(1H, brs), 8.49(1H, dd, J=8.3Hz, 2.1 Hz), 10.46(1H, brs). |
| 730 | 3,4-diCl-C₆H₃-C(O)NH-C₆H₃-(3-Me)- | 4-(CH₂)₂COOH | $^1$H NMR (CDCl₃) 2.67(2H, t, J=7.6Hz), 2.93(2H, t, J=7.6Hz), 6.78(1H, dt, J=8.1Hz, 1.2Hz), 6.95(2H, d, J=8.5Hz), 7.16(2H, d, J=8.5Hz), 7.22-7.34(3H, m), 7.53(1H, d, J=8.3Hz), 7.64(1H, dd, J=8.3Hz, 2.1Hz), 7.73(1H, brs), 7.90(1H, d, J=2.1Hz), 10.23(1H, brs). |
| 731 | 3,4-diCl-C₆H₃-NHC(O)N(C₂H₅)-(6-Me-pyridin-3-yl)- | 4-(CH₂)₂COOH | $^1$H NMR (DMSO-d₆) 1.05(3H, t, J=7.1Hz), 2.56(2H, t, J=7.6 Hz), 2.84(2H, t, J=7.6Hz), 3.64 (2H, q, J=7.1Hz), 7.05-7.10(3H, m), 7.28(2H, d, J=8.6Hz), 7.45(2H, brs), 7.76-7.80(2H, m), 8.08(1H, dd, J=2.8Hz, 0.5Hz), 8.27(1H, brs), 12.10(1H, brs). |
| 732 | 4-F₃C-C₆H₄-NHC(O)N(C₂H₅)-(6-Me-pyridin-3-yl)- | 4-(CH₂)₂COOH | $^1$H NMR (DMSO-d₆) 1.06(3H, t, J=7.1Hz), 2.53-2.59(2H, m), 2.81-2.87(2H, m), 3.67(2H, q, J=7.1Hz), 7.05-7.10(3H, m), 7.29(2H, d, J=8.7Hz), 7.56(2H, d, J=8.7Hz), 7.66(2H, d, J=8.7 Hz), 7.78(1H, dd, J=8.6Hz, 2.8 Hz), 8.09(1H, d, J=2.8Hz), 8.41(1H, brs), 12.14(1H, brs). |

TABLE 102

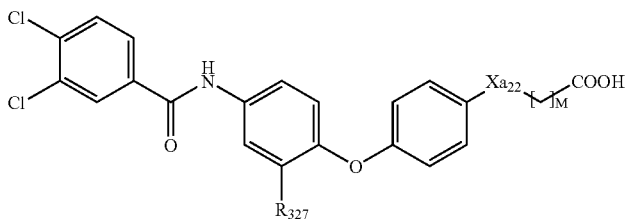

| Reference Example No. | $R_{327}$ | $Xa_{24}$ | M | Form | mp(° C.) or $^1$H NMR (DMSO-$d_6$) δ ppm |
|---|---|---|---|---|---|
| 733 | —H | none | 0 | free | mp 252-255 |
| 734 | —F | none | 0 | free | mp 257-259 |
| 735 | —F | none | 1 | free | mp 204-206 |
| 736 | —F | none | 2 | free | mp 173-174 |
| 737 | —F | none | 3 | free | mp 175-177 |
| 738 | —F | —S— | 1 | Na salt | $^1$H NMR 3.86(2H, s), 6.86(2H, d, J=8.7Hz), 7.15(1H, t, J=9.0Hz), 7.25(2H, d, J=8.7Hz), 7.55(1H, d, J=9.0Hz), 7.80(1H, d, J=8.4Hz), 7.91(1H, dd, J=2.4Hz, 13.3Hz), 7.98(1H, dd, J=2.0Hz, 8.4Hz), 8.25(1H, d, J=2.0Hz). |
| 739 | —F | —SO— | 1 | free | $^1$H NMR 3.79(1H, d, J=14.3Hz), 3.97(1H, d, J=14.3Hz), 7.12(2H, d, J=8.8Hz), 7.33(1H, t, J=9.1Hz), 7.55-7.65(1H, m), 7.71(2H, d, J=8.8Hz), 7.84(1H, d, J=8.4Hz), 7.90-7.95(2H, m), 8.20(1H, d, J=2.0Hz), 10.63(1H, s), 13.20(1H, brs). |
| 740 | —F | —SO$_2$— | 1 | free | mp 214-216 |
| 741 | —F | —N(Ac)— | 1 | free | $^1$H NMR 1.80(3H, s), 4.22(2H, s), 7.00(1H, d, J=8.9Hz), 7.25-7.30(1H, m), 7.38(2H, d, J=8.9 Hz), 7.50-7.60(1H, m), 7.84(1H, d, J=8.4Hz), 7.90-7.96(2H, m), 8.21(1H, d, J=2.0Hz), 10.61(1H, s), 12.68(1H, s). |
| 742 | —F |  | 0 | free | mp 241-243 |

(—SO— means a group of

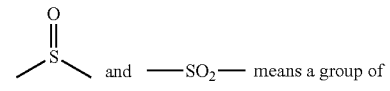

and —SO$_2$— means a group of

. Hereinafter —SO— and —SO$_2$— indicate the same meanings.)

TABLE 103

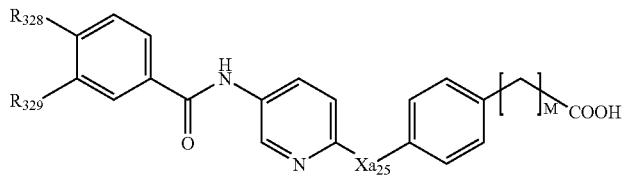

| Reference Example No. | $R_{328}$ | $R_{329}$ | $Xa_{25}$ | M | mp(° C.) or $^1$H NMR (DMSO-$d_6$) δ ppm |
|---|---|---|---|---|---|
| 743 | —Cl | —Cl | —CO— | 2 | $^1$H NMR 2.60(2H, t, J=7.6Hz), 2.91(2H, t, J=7.6Hz), 7.39(2H, d, J=8.2Hz), 7.82-8.20(4H, m), 8.07(1H, d, J=8.6Hz), 8.25(1H, dd, J=7.5Hz, 2.1Hz), 8.45(1H, dd, J=8.6Hz, 2.5Hz), 9.03(1H, d, J=2.5 Hz), 10.91(1H, s), 12.16(1H, brs). |
| 744 | —Cl | —Cl | —S— | 2 | mp 201-202 |
| 745 | —Cl | —Cl | —SO— | 2 | mp 202-205 |
| 746 | —Cl | —Cl | —SO$_2$— | 2 | mp 172-173 |

TABLE 103-continued

Structure: R328, R329-substituted benzamide linked via C(=O)NH to pyridine (with Xa25 at 6-position) connected to phenyl-[M]-COOH

| Reference Example No. | R328 | R329 | Xa25 | M | mp(° C.) or ¹H NMR (DMSO-d₆) δ ppm |
|---|---|---|---|---|---|
| 747 | —Cl | —Cl | —NH— | 2 | ¹H NMR 2.76(2H, t, J=7.6Hz), 3.20-3.40 (2H, m), 6.86(1H, d, J=8.8Hz), 7.12(2H, d, J=8.3Hz), 7.52(2H, d, J=8.3Hz), 7.83(1H, d, J=8.4Hz), 7.90-7.96(2H, m), 8.21(1H, d, J=1.3Hz), 8.45(1H, d, J=2.4 Hz), 9.03(1H, brs), 10.37(1H, s), 12.11(1H, brs). |
| 748 | —Cl | —Cl | —N(CH₃)— | 2 | mp 158-160 |
| 749 | —CF₃ | —H | —N(CH₃)— | 0 | mp 240-243 |
| 750 | —CF₃ | —H | —N(CH₃)— | 2 | ¹H NMR 2.57(2H, t, J=7.5Hz), 2.84(2H, t, J=7.5Hz), 3.38(3H, s), 6.61(1H, d, J=9.1 Hz), 7.22(2H, d, J=8.3Hz), 7.29(2H, d, J=8.3Hz), 7.80-7.85(1H, m), 7.91(2H, d, J=8.3Hz), 8.15(2H, d, J=8.3Hz), 8.51(1H, d, J=2.5Hz), 10.42(1H, s), 12.10(1H, brs). |
| 751 | —Cl | —Cl | —N(CH₂Ph)— | 2 | ¹H NMR 2.53(2H, t, J=7.9Hz), 2.80(2H, t, J=7.9Hz), 5.21(2H, s), 6.63(1H, d, J=9.1 Hz), 7.15-7.30(9H, m), 7.75-7.95(3H, m), 8.19(1H, d, J=2.1Hz), 8.45(1H, d, J=2.5 Hz), 10.34(1H, s), 12.10(1H, brs). |

TABLE 104

Structure: R330, R331, R332-substituted benzamide linked via C(=O)NH to pyridine (with O at 6-position) connected to phenyl-[M]-COOH

| Reference Example No. | R330 | R331 | R332 | M | mp(° C.) or ¹H NMR (DMSO-d₆) δ ppm |
|---|---|---|---|---|---|
| 752 | —H | —CN | —H | 0 | ¹H NMR 7.18-7.21(3H, m), 7.98(2H, d, J=8.2Hz), 8.05(2H, d, J=8.9Hz), 8.13(2H, d, J=8.2Hz), 8.28(1H, dd, J=8.6Hz, 2.6Hz), 8.57(1H, d, J=2.6 Hz), 10.70(1H, s), 12.87(1H, brs). |
| 753 | —Cl | —Cl | —H | 0 | ¹H NMR 7.17-7.22(3H, m), 7.85(1H, d, J=8.2Hz), 7.94-8.01(3H, m), 8.23-8.29(2H, m), 8.55(1H, d, J=2.6 Hz), 10.01(1H, s), 12.87(1H, brs). |
| 754 | —H | —Cl | —H | 0 | ¹H NMR 7.16-7.21(3H, m), 7.63(2H, d, J=8.6Hz), 7.97-8.02(4H, m), 8.28(1H, dd, J=8.6Hz, 2.6Hz), 8.57(1H, d, J=2.6Hz), 10.53(1H, s), 12.86(1H, brs). |
| 755 | —H | —CF₃ | —H | 0 | ¹H NMR 7.18-7.22(3H, m), 7.93-8.00(4H, m), 8.18(2H, d, J=8.4Hz), 8.30(1H, dd, J=8.9Hz, 2.7Hz), 8.58(1H, d, J=2.7Hz), 10.69(1H, s), 12.91(1H, brs). |
| 756 | —CH₃ | —CH₃ | —H | 0 | ¹H NMR 2.30(3H, s), 2.31(3H, s), 7.16(1H, d, J=8.9 Hz), 7.18(2H, d, J=8.7Hz), 7.31(1H, d, J=7.6Hz), 7.72(1H, d, J=7.6Hz), 7.77(1H, s), 7.98(2H, d, J=8.7 Hz), 8.28(1H, dd, J=8.9Hz, 2.7Hz), 8.58(1H, d, J=2.7Hz), 10.35(1H, s), 12.88(1H, brs). |
| 757 | —CF₃ | —H | —F | 0 | mp 238-239 |
| 758 | —OCF₃ | —H | —H | 0 | ¹H NMR 7.18-7.22(3H, m), 7.61-7.81(2H, m), 7.89-8.06(4H, m), 8.28(1H, dd, J=8.7Hz, 2.6Hz), 8.57(1H, d, J=2.3Hz), 10.62(1H, s), 12.95(1H, brs). |
| 759 | —CF₃ | —H | —H | 0 | ¹H NMR 7.11-7.22(3H, m), 7.70-7.85(1H, m), 7.90-8.05(3H, m), 8.2-8.35(3H, m), 8.56(1H, d, J=2.4Hz), 10.70(1H, s), 12.90(1H, brs). |

TABLE 104-continued

[Structure: R330, R331, R332 substituted benzamide linked via NH to pyridine (with N) connected via O to phenyl-(CH2)M-COOH]

| Reference Example No. | R330 | R331 | R332 | M | mp(° C.) or ¹H NMR (DMSO-d₆) δ ppm |
|---|---|---|---|---|---|
| 760 | —H | —CF₃ | —H | 1 | ¹H NMR 3.59(2H, s), 7.04-7.10(3H, m), 7.27-7.33(2H, m), 7.94(2H, d, J=8.4Hz), 8.17(2H, d, J=8.1Hz), 8.21-8.25(1H, m), 8.51(1H, d, J=2.6Hz), 10.64(1H, s), 12.43(1H, brs). |
| 761 | —Cl | —Cl | —H | 1 | ¹H NMR 3.59(2H, s), 7.04-7.09(3H, m), 7.27-7.32(2H, m), 7.83(1H, d, J=8.4Hz), 7.95(1H, dd, J=8.4Hz, 2.1 Hz), 8.18-8.23(2H, m), 8.48(1H, d, J=2.6Hz), 10.55(1H, s), 12.37(1H, brs). |
| 762 | —Cl | —Cl | —H | 2 | ¹H NMR 2.51-2.58(2H, m), 2.81-2.86(2H, m), 7.01-7.06(3H, m), 7.26(2H, d, J=8.6Hz), 7.84(1H, d, J=8.4Hz), 7.93-7.97(1H, m), 8.16-8.23(2H, m), 8.47(1H, d, J=2.7Hz), 10.54(1H, s), 12.13(1H, brs). |
| 763 | —H | —CF₃ | —H | 2 | ¹H NMR 2.56(2H, t, J=7.5Hz), 2.84(2H, t, J=7.5 Hz), 7.03(2H, d, J=8.6Hz), 7.05(1H, d, J=8.8Hz), 7.27(2H, d, J=8.6Hz), 7.93(2H, d, J=8.2Hz), 8.17(2H, d, J=8.2Hz), 8.21(1H, dd, J=8.8Hz, 2.6 Hz), 8.50(1H, d, J=2.6Hz), 10.63(1H, s), 12.16(1H, s). |

TABLE 105

[Structure: 3,4-dichlorobenzamide linked via NH to pyridine connected via O to phenyl (with R333, R334 substituents)-(CH2)M-COOH]

| Reference Example No. | R333 | R334 | M | ¹H NMR (DMSO-d₆) δ ppm |
|---|---|---|---|---|
| 764 | —OCH₃ | —H | 0 | 3.76(3H, s), 7.09(1H, d, J=8.9Hz), 7.23(1H, d, J=8.1 Hz), 7.59-7.63(2H, m), 7.84(1H, d, J=8.4Hz), 7.93-7.96(1H, m), 8.16-8.22(2H, m), 8.39(1H, d, J=2.7Hz), 10.53(1H, s), 13.00(1H, brs). |
| 765 | —H | —OCH₃ | 0 | 3.80(3H, s), 6.69(1H, dd, J=8.4Hz, 2.2Hz), 6.90(1H, d, J=2.2Hz), 7.17(1H, d, J=8.9Hz), 7.73(1H, d, J=8.4Hz), 7.85(1H, d, J=8.4Hz), 7.97(1H, dd, J=8.4Hz, 2.2Hz), 8.23-8.28(2H, m), 8.56(1H, d, J=2.4Hz), 10.62(1H, s), 12.56(1H, brs). |
| 766 | —CH₃ | —H | 0 | 2.18(3H, s), 7.09-7.16(2H, m), 7.79-7.97(4H, m), 8.21-8.26(2H, m), 8.47(1H, d, J=2.2Hz), 10.57(1H, s), 12.86(1H, brs). |
| 767 | —H | —CH₃ | 0 | 2.53(3H, s), 6.97-7.04(2H, m), 7.16(1H, d, J=8.7Hz), 7.77-7.98(3H, m), 8.23-8.27(2H, m), 8.54(1H, d, J=2.6 Hz), 10.62(1H, s), 12.79(1H, brs). |
| 768 | —F | —H | 0 | 7.24(1H, d, J=8.9Hz), 7.39-7.45(1H, m), 7.70-8.05(4H, m), 8.23-8.28(2H, m), 8.46(1H, d, J=2.6Hz), 10.64(1H, s), 13.55(1H, brs). |
| 769 | —Cl | —H | 0 | 7.25(1H, d, J=8.9Hz), 7.39(1H, d, J=8.6Hz), 7.84(1H, d, J=8.4Hz), 7.93-7.97(2H, m), 8.06(1H, d, J=2.0Hz), 8.22(1H, d, J=2.0Hz), 8.25-8.29(1H, m), 8.47(1H, d, J=2.6Hz), 10.61(1H, s), 13.31(1H, brs). |
| 770 | —OCH₃ | —H | 2 | 2.50-2.65(2H, m), 2.71-2.92(2H, m), 3.67(3H, s), 6.81(1H, dd, J=8.1Hz, 1.9Hz), 6.95(1H, d, J=8.9Hz), 6.99-7.05(2H, m), 7.82(1H, d, J=8.4Hz), 7.93(1H, dd, J=8.4 Hz, 2.0Hz), 8.10(1H, dd, J=8.9Hz, 2.7Hz), 8.20(1H, d, J=2.0Hz), 8.35(1H, m), 10.47(1H, s), 12.15(1H, brs). |

TABLE 105-continued

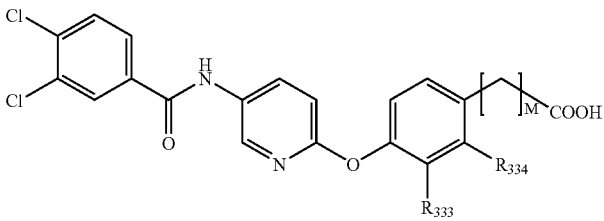

| Reference Example No. | R333 | R334 | M | $^1$H NMR (DMSO-$d_6$) δ ppm |
|---|---|---|---|---|
| 771 | —OC$_2$H$_5$ | —H | 2 | 1.06(3H, t, J=7.0Hz), 2.51-2.62(2H, m), 2.74-2.88(2H, m), 3.94(2H, q, J=7.0Hz), 6.80(1H, dd, J=8.1Hz, 1.8 Hz), 6.92-7.04(3H, m), 7.82(1H, d, J=8.4Hz), 7.93(1H, dd, J=8.4Hz, 2.0Hz), 8.11(1H, dd, J=8.9Hz, 2.7Hz), 8.20(1H, d, J=2.0Hz), 8.36(1H, d, J=2.7Hz), 10.47(1H, s), 12.14(1H, brs). |
| 772 | —F | —H | 2 | 2.50-2.67(2H, m), 2.75-2.93(2H, m), 7.03-7.29(4H, m), 7.82(1H, d, J=8.4Hz), 7.93(1H, dd, J=8.4Hz, 2.0Hz), 8.12-8.24(2H, m), 8.39(1H, d, J=2.5Hz), 10.53(1H, s), 12.18(1H, brs). |

TABLE 106

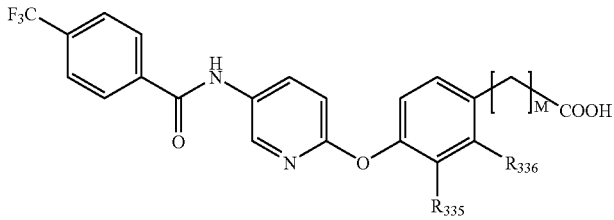

| Reference Example No. | R335 | R336 | M | $^1$H NMR (DMSO-$d_6$) δ ppm |
|---|---|---|---|---|
| 773 | —OCH$_3$ | —H | 0 | 3.76(3H, s), 7.10(1H, d, J=8.9Hz), 7.23(1H, d, J=8.1 Hz), 7.59-7.64(2H, m), 7.93(2H, d, J=8.1Hz), 8.15-8.23(3H, m), 8.42(1H, d, J=2.2Hz), 10.60(1H, s), 13.00(1H, brs). |
| 774 | —H | —OCH$_3$ | 0 | 3.80(3H, s), 6.69(1H, dd, J=8.6Hz, 2.2Hz), 6.90(1H, d, J=2.2Hz), 7.17(1H, d, J=8.6Hz), 7.73(1H, d, J=8.4 Hz), 7.95(2H, d, J=8.4Hz), 8.18(2H, d, J=8.4Hz), 8.29(1H, dd, J=8.6Hz, 2.7Hz), 8.58(1H, d, J=2.7Hz), 10.69(1H, s), 12.51(1H, brs). |
| 775 | —CH$_3$ | —H | 0 | 1.99(3H, s), 7.09-7.17(2H, m), 7.79-7.83(1H, m), 7.91-7.95(3H, m), 8.12-8.18(2H, m), 8.27(1H, dd, J=8.9Hz, 2.7Hz), 8.49(1H, d, J=2.7Hz), 10.64(1H, s), 12.87(1H, brs). |
| 776 | —H | —CH$_3$ | 0 | 2.54(3H, s), 6.98-7.05(2H, m), 7.17(1H, d, J=8.7Hz), 7.87-7.97(3H, m), 8.13-8.19(2H, m), 8.26-8.30(1H, m), 8.57(1H, d, J=2.8Hz), 10.70(1H, s), 12.81(1H, brs). |
| 777 | —F | —H | 0 | 7.26(1H, d, J=8.9Hz), 7.40-7.46(1H, m), 7.82-7.85(2H, m), 7.94(2H, d, J=8.2Hz), 8.17(2H, d, J=8.2Hz), 8.30(1H, dd, J=8.9Hz, 2.1Hz), 8.49(1H, d, J=2.1Hz), 10.70(1H, s), 13.39(1H, brs). |
| 778 | —Cl | —H | 0 | 7.14(1H, d, J=8.9Hz), 7.19(1H, d, J=8.2Hz), 7.82-7.86(1H, m), 7.92(2H, d, J=8.4Hz), 7.96(1H, d, J=1.8 Hz), 8.20(2H, d, J=8.2Hz), 8.29(1H, dd, J=8.9Hz, 2.6 Hz), 8.47(1H, d, J=2.6Hz), 10.86(1H, s). |
| 779 | —OCH$_3$ | —H | 2 | 2.57-2.63(2H, m), 2.83-2.89(2H, m), 3.69(3H, s), 6.84(1H, dd, J=8.1Hz, 1.8Hz), 6.97(1H, d, J=8.9Hz), 7.01-7.04(2H, m), 7.92(2H, d, J=8.4Hz), 8.14-8.18(3H, m), 8.40(1H, d, J=2.5Hz), 10.58(1H, s). |
| 780 | —OC$_2$H$_5$ | —H | 2 | 1.06(3H, t, J=7.0Hz), 2.47-2.67(2H, m), 2.72-2.91(2H, m), 3.94(2H, q, J=7.0Hz), 6.80(1H, dd, J=8.0Hz, 1.8 Hz), 6.94-7.05(3H, m), 7.91(2H, d, J=8.3Hz), 8.09-8.19(3H, m), 8.38(1H, d, J=2.6Hz), 10.55(1H, s), 12.14(1H, brs) |

TABLE 106-continued

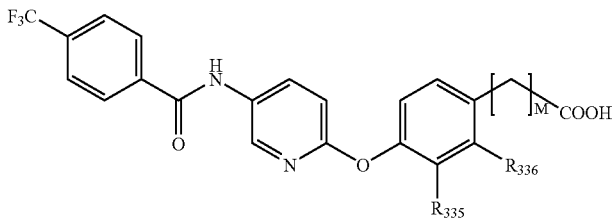

| Reference Example No. | $R_{335}$ | $R_{336}$ | M | $^1$H NMR (DMSO-$d_6$) δ ppm |
|---|---|---|---|---|
| 781 | —F | —H | 2 | 2.49-2.63(2H, m), 2.71-2.93(2H, m), 7.09(1H, dd, J=8.3 Hz, 1.5Hz), 7.14(1H, d, J=8.9Hz), 7.17-7.28(2H, m), 7.92(2H, d, J=8.2Hz), 8.15(2H, d, J=8.2Hz), 8.21(1H, dd, J=8.9Hz, 2.7Hz), 8.38-8.44(1H, m), 10.60(1H, s), 12.17(1H, brs). |

TABLE 107

| Reference Example No. | $R_{337}$ | $R_{338}$ | $R_{339}$ | $^1$H NMR (DMSO-$d_6$) δ ppm |
|---|---|---|---|---|
| 782 | —Cl | —Cl | 6-methylnaphthalen-2-yl-COOH | 7.20(1H, d, J=8.7Hz), 7.40(1H, dd, J=8.7Hz, 2.3Hz), 7.60-7.67(1H, m), 7.82-8.03(4H, m), 8.15(1H, d, J=8.9Hz), 8.26-8.32(2H, m), 8.56-8.60(2H, m), 10.78(1H, s). |
| 783 | —CF$_3$ | —H | 6-methylnaphthalen-2-yl-COOH | 7.18(1H, d, J=8.7Hz), 7.36(1H, dd, J=8.7Hz, 2.3Hz), 7.63(1H, d, J=2.0Hz), 7.84-8.11(5H, m), 8.23(2H, d, J=8.1Hz), 8.34(1H, dd, J=8.9Hz, 2.5Hz), 8.54-8.60(2H, m), 10.98(1H, s). |
| 784 | —Cl | —Cl | 6-methylnaphthalen-1-yl-COOH | 7.19(1H, d, J=8.7Hz), 7.47(1H, dd, J=9.4Hz, 2.5Hz), 7.57-7.63(1H, m), 7.73(1H, d, J=2.5Hz), 7.85(1H, d, J=8.4Hz), 7.96(1H, dd, J=8.4Hz, 2.0Hz), 8.10-8.14(2H, m), 8.23-8.28(2H, m), 8.52(1H, d, J=2.5Hz), 8.92(1H, d, J=9.4Hz), 10.60(1H, s), 13.20(1H, brs). |
| 785 | —CF$_3$ | —H | 6-methylnaphthalen-1-yl-COOH | 7.20(1H, d, J=8.7Hz), 7.48(1H, dd, J=9.4Hz, 2.6Hz), 7.57-7.63(1H, m), 7.73(1H, d, J=2.5Hz), 7.94(2H, d, J=8.2Hz), 8.11-8.19(4H, m), 8.29(1H, dd, J=8.7Hz, 2.6Hz), 8.55(1H, d, J=2.5Hz), 8.93(1H, d, J=9.4Hz), 10.68(1H, s), 13.21(1H, brs). |
| 786 | —Cl | —Cl | 4-methylnaphthalen-1-yl-COOH | 7.24(1H, d, J=8.1Hz), 7.32(1H, d, J=8.7Hz), 7.58-7.64(1H, m), 7.69-7.77(1H, m), 7.85(1H, d, J=8.4Hz), 7.97(1H, dd, J=8.4Hz, 2.1Hz), 8.06-8.12(1H, m), 8.20-8.23(2H, m), 8.30(1H, dd, J=8.7Hz, 2.6Hz), 8.48(1H, d, J=2.6Hz), 9.02(1H, d, J=8.7Hz), 10.63(1H, s), 13.11(1H, brs). |
| 787 | —Cl | —Cl | 3-methylphenyl-COOH | 7.17(1H, d, J=8.9Hz), 7.38-7.43(1H, m), 7.53-7.59(2H, m), 7.76-7.86(2H, m), 7.93-7.97(1H, m), 8.22-8.27(2H, m), 8.51(1H, d, J=2.0Hz), 10.60(1H, s), 13.15(1H, brs). |

TABLE 108

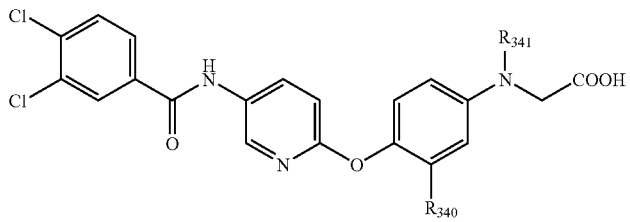

| Reference Example No. | R340 | R341 | ¹H NMR (solvent) δ ppm |
|---|---|---|---|
| 788 | —H | —Ac | (DMSO-d₆) 1.85(3H, s), 4.26(2H, s), 7.13(1H, d, J=8.8Hz), 7.19(2H, d, J=8.7Hz), 7.42(2H, d, J=8.7Hz), 7.85(1H, d, J=8.4Hz), 7.95(1H, dd, J=1.9Hz, 8.4Hz), 8.20-8.24(2H, m), 8.51(1H, d, J=2.5Hz), 12.77(1H, brs). |
| 789 | —H | —CH₃ | (DMSO-d₆) 2.98(3H, s), 4.01(2H, s), 6.65(1H, d, J=9.1Hz), 6.90-6.95(3H, m), 7.82(1H, d, J=8.4Hz), 7.94(1H, dd, J=2.1Hz, 8.4Hz), 8.13(1H, dd, J=2.7Hz, 8.9Hz), 8.22(1H, d, J=2.1Hz), 8.43(1H, d, J=2.7Hz), 10.54(1H, s). |
| 790 | —H | —C₂H₅ | (DMSO-d₆) 1.11(3H, t, J=7.1Hz), 3.39(2H, q, J=7.1Hz), 4.01(2H, s), 6.58(2H, d, J=9.1Hz), 6.90-6.95(3H, m), 7.81(1H, d, J=8.4Hz), 7.92(1H, dd, J=2.0Hz, 8.4Hz), 8.11(1H, dd, J=2.7Hz, 8.9Hz), 8.19(1H, d, J=2.0Hz), 8.41(1H, d, J=2.7Hz), 10.48(1H, s), 12.53(1H, brs). |
| 791 | —OCH₃ | —CH₃ | (DMSO-d₆) 3.01(3H, s), 3.67(3H, s), 4.12(2H, s), 6.20(1H, dd, J=8.7Hz, 2.8Hz), 6.39(1H, d, J=2.8Hz), 6.85-6.94(2H; m), 7.83(1H, d, J=8.4Hz), 7.94(1H, dd, J=8.4Hz, 2.1Hz), 8.08(1H, dd, J=8.7Hz, 2.6Hz), 8.21(1H, d, J=2.0Hz), 8.36(1H, d, J=2.5Hz), 10.47(1H, s), 12.58(1H, brs). |
| 792 | —OCH₃ | —C₂H₅ | (DMSO-d₆) 1.15(3H, t, J=7.1Hz), 3.43(2H, q, J=7.1Hz), 3.65(3H, s), 4.06(2H, s), 6.13(1H, dd, J=8.7Hz, 2.6Hz), 6.30(1H, d, J=2.6Hz), 6.87-6.91(2H, m), 7.83(1H, d, J=8.4Hz), 7.94(1H, dd, J=8.4Hz, 2.0Hz), 8.08(1H, dd, J=8.9Hz, 2.6Hz), 8.21(1H, d, J=2.0Hz), 8.36(1H, d, J=2.6Hz), 10.48(1H, s), 12.58(1H, brs). |
| 793 | —CH₃ | —Ac | (DMSO-d₆) 1.84(3H, s), 2.11(3H, s), 4.23(2H, s), 7.05-7.10(2H, m), 7.20-7.25(1H, m), 7.32(1H, d, J=2.2Hz), 7.75-7.85(1H, m), 7.92(1H, dd, J=2.2Hz, 8.4Hz), 8.10-8.20(2H, m), 8.43(1H, d, J=2.6Hz), 10.53(1H, s), 12.66(1H, brs). |
| 794 | —CH₃ | —CH₃ | (DMSO-d₆) 2.01(3H, s), 2.97(3H, s), 4.07(2H, s), 6.49(1H, dd, J=8.8Hz, 3.0Hz), 6.57(1H, d, J=3.0Hz), 6.85(1H, d, J=8.8Hz), 6.90(1H, d, J=8.9Hz), 7.82(1H, d, J=8.4Hz), 7.93(1H, dd, J=8.4Hz, 2.0Hz), 8.11(1H, dd, J=8.9Hz, 2.7Hz), 8.20(1H, d, J=2.0Hz), 8.39(1H, d, J=2.7Hz), 10.47(1H, s), 12.51(1H, brs). |
| 795 | —F | —Ac | (CDCl₃ + DMSO-d₆) 1.99(3H, s), 4.35(2H, s), 7.03(1H, d, J=8.9Hz), 7.21-7.31(3H, m), 7.57(1H, d, J=8.4Hz), 7.90(1H, dd, J=8.4Hz, 2.1Hz), 8.19(1H, d, J=2.0Hz), 8.32(1H, dd, J=8.9Hz, 2.6Hz), 8.46(1H, d, J=2.5Hz), 10.12(1H, s). |
| 796 | —F | —CH₃ | (CDCl₃ + DMSO-d₆) 3.04(3H, s), 3.98(2H, s), 6.40-6.49(2H, m), 6.90(1H, d, J=8.9Hz), 7.02(1H, t, J=8.7Hz), 7.52(1H, d, J=8.4Hz), 7.85(1H, dd, J=8.4Hz, 2.1Hz), 8.14(1H, d, J=2.0Hz), 8.23(1H, dd, J=8.9Hz, 2.6Hz), 8.34(1H, d, J=2.5Hz), 9.77(1H, s). |
| 797 | —F | —C₂H₅ | (CDCl₃) 1.26(3H, t, J=7.1Hz), 3.44(2H, q, J=7.1Hz), 4.03(2H, s), 6.39-6.52(2H, m), 6.96(1H, d, J=9.7Hz), 7.06(1H, t, J=8.9Hz), 7.55(1H, d, J=8.4Hz), 7.69(1H, dd, J=8.6Hz, 2.1Hz), 7.96-7.97(2H, m), 8.15-8.18(2H, m). |

TABLE 109

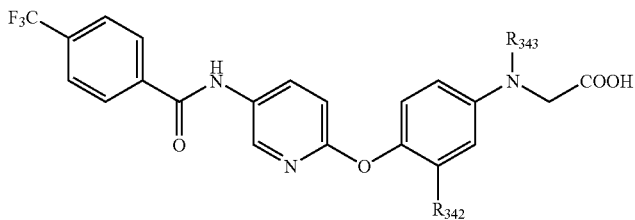

| Reference Example No. | $R_{342}$ | $R_{343}$ | $^1$H NMR (solvent) δ ppm |
|---|---|---|---|
| 798 | —H | —Ac | (DMSO-$d_6$) 1.85(3H, s), 4.26(2H, s), 7.13(1H, d, J=8.8Hz), 7.18(2H, d, J=8.7Hz), 7.42(2H, d, J=8.7Hz), 7.94(2H, d, J=8.2Hz), 8.16(2H, d, J=8.2Hz), 8.25(1H, dd, J=2.5 Hz, 8.8Hz), 8.54(1H, d, J=2.5Hz), 10.66(1H, s), 12.70(1H, brs). |
| 799 | —H | —$CH_3$ | (DMSO-$d_6$) 2.99(3H, s), 4.09(2H, s), 6.67(2H, d, J=9.0Hz), 6.96(3H, d, J=9.0Hz), 7.93(2H, d, J=8.2Hz), 8.16(2H, d, J=8.2Hz), 8.12-8.20(1H, m), 8.46(1H, d, J=2.3Hz), 10.59(1H, s), 12.58(1H, brs). |
| 800 | —H | —$C_2H_5$ | (DMSO-$d_6$) 1.13(3H, t, J=7.1Hz), 3.38(2H, q, J=7.1Hz), 4.00(2H, s), 6.65(1H, d, J=8.9Hz), 6.73(1H, d, J=8.9Hz), 6.92-6.97(3H, m), 7.93(2H, d, J=8.1Hz), 8.15-8.18(3H, m), 8.46(1H, s), 10.59(1H, s). |
| 801 | —$OCH_3$ | —$CH_3$ | (DMSO-$d_6$) 3.01(3H, s), 3.67(3H, s), 4.12(2H, s), 6.20(1H, dd, J=8.7Hz, 2.6Hz), 6.39(1H, d, J=2.5Hz), 6.83-6.95(2H, m), 7.93(2H, d, J=8.3Hz), 8.09-8.17(3H, m), 8.38(1H, d, J=2.6Hz), 10.56(1H, s), 12.58(1H, brs). |
| 802 | —$OCH_3$ | —$C_2H_5$ | (DMSO-$d_6$) 1.15(3H, t, J=7.1Hz), 3.43(2H, q, J=7.1Hz), 3.66(3H, s), 4.06(2H, s), 6.14(1H, dd, J=8.7Hz, 2.6Hz), 6.31(1H, d, J=2.8Hz), 6.88-6.92(2H, m), 7.93(2H, d, J=8.4Hz), 8.09-8.17(3H, m), 8.39(1H, d, J=2.5Hz), 10.55(1H, s), 12.59(1H, brs). |
| 803 | —$CH_3$ | —Ac | (DMSO-$d_6$) 1.84(3H, s), 2.11(3H, s), 4.23(2H, s), 7.05-7.10(2H, m), 7.23(1H, dd, J=2.4Hz, 8.5Hz), 7.33(1H, d, J=2.4Hz), 7.86(1H, d, J=8.3Hz), 7.91(2H, d, J=8.3Hz), 8.14(2H, d, J=8.3Hz), 8.20(1H, dd, J=2.7Hz, 8.9Hz), 8.45(1H, d, J=2.7Hz), 10.61(1H, s), 12.67(1H, brs). |
| 804 | —$CH_3$ | —$CH_3$ | (DMSO-$d_6$) 2.01(3H, s), 2.97(3H, s), 4.06(2H, s), 6.49(1H, dd, J=8.8Hz, 3.1Hz), 6.57(1H, d, J=2.9Hz), 6.85(1H, d, J=8.8Hz), 6.91(1H, d, J=8.9Hz), 7.91(2H, d, J=8.3Hz), 8.04-8.23(3H, m), 8.41(1H, d, J=2.6Hz), 10.56(1H, s), 12.11-12.98(1H, m). |
| 805 | —F | —Ac | (CDCl$_3$) 1.96(3H, s), 4.32(2H, s), 7.09-7.31(4H, m), 7.75(2H, d, J=8.4Hz), 8.02(2H, d, J=8.3Hz), 8.20(1H, d, J=2.6 Hz), 8.40(1H, dd, J=8.9Hz, 2.6Hz), 8.44(1H, s). |
| 806 | —F | —$CH_3$ | (CDCl$_3$ + DMSO-$d_6$) 3.08(3H, s), 4.02(2H, s), 6.47-6.52(2H, m), 6.92(1H, d, J=8.7Hz), 7.06(1H, t, J=9.0Hz), 7.73(2H, d, J=8.4Hz), 8.11(2H, d, J=8.4Hz), 8.26(1H, dd, J=8.7Hz, 2.5Hz), 8.39(1H, d, J=2.5Hz), 9.76(1H, s). |
| 807 | —F | —$C_2H_5$ | (CDCl$_3$ + DMSO-$d_6$) 1.23(3H, t, J=7.1Hz), 3.45(2H, q, J=7.1Hz), 3.97(2H, s), 6.39-6.48(2H, m), 6.91(1H, d, J=8.7 Hz), 7.04(1H, t, J=9.1Hz), 7.73(2H, d, J=7.9Hz), 8.12(2H, d, J=7.9Hz), 8.25(1H, d, J=9.1Hz), 8.42(1H, d, J=2.5Hz), 9.92(1H, s). |
| 808 | —F | —$(CH_2)_2CH_3$ | (CDCl$_3$ + DMSO-$d_6$) 0.96(3H, t, J=7.2Hz), 1.61-1.72(2H, m), 3.33(2H, t, J=7.6Hz), 3.99(2H, s), 6.37-6.48(2H, m), 6.93(1H, d, J=8.8Hz), 7.04(1H, t, J=9.1Hz), 7.73(2H, d, J=8.1Hz), 8.09(2H, d, J=8.1Hz), 8.26(1H, dd, J=8.9Hz, 2.6Hz), 8.36(1H, d, J=2.5Hz), 9.45(1H, s). |

TABLE 110

[Structure: R344, R345-substituted benzamide linked via NH to pyridine with O-phenyl-R346]

| Reference Example No. | R344 | R345 | R346 | ¹H NMR (solvent) δ ppm |
|---|---|---|---|---|
| 809 | —Cl | —Cl | —N(Ac)(CH$_2$)$_2$COOH | (DMSO-d$_6$) 1.71(3H, s), 2.39(2H, t, J=7.5Hz), 3.78(2H, t, J=7.5Hz), 7.08(1H, d, J=8.8Hz), 7.14(2H, d, J=8.6Hz), 7.31(2H, d, J=8.6Hz), 7.80(1H, d, J=8.4Hz), 7.91(1H, dd, J=2.1Hz, 8.4Hz), 8.15-8.21(2H, m), 8.49(1H, d, J=2.5Hz), 10.55(1H, s), 12.20(1H, brs) |
| 810 | —CF$_3$ | —H | —N(Ac)(CH$_2$)$_2$COOH | (DMSO-d$_6$) 1.71(3H, s), 2.40(2H, t, J=7.3Hz), 3.78(2H, t, J=7.3Hz), 7.09(1H, d, J=8.7Hz), 7.14(2H, d, J=8.1Hz), 7.31(2H, d, J=8.1Hz), 7.90(2H, d, J=8.1Hz), 8.12(2H, d, J=8.1Hz), 8.21(1H, d, J=8.7Hz), 8.52(1H, s), 10.63(1H, s), 12.25(1H, brs). |
| 811 | —Cl | —Cl | —CH(CH$_3$)CH$_2$COOH | (CDCl$_3$-CD$_3$OD) 1.26(3H, d, J=7.0Hz), 2.42-2.61(2H, m), 3.17-3.28(1H, m), 6.84(1H, d, J=8.9Hz), 6.98(2H, d, J=8.5Hz), 7.20(2H, d, J=8.5Hz), 7.50(1H, d, J=8.4Hz), 7.73(1H, dd, J=8.5Hz, 2.1Hz), 8.01(1H, d, J=2.1Hz), 8.14(1H, d, J=2.7Hz), 8.26(1H, dd, J=8.9Hz, 2.7Hz). |
| 812 | —CF$_3$ | —H | —CH(CH$_3$)CH$_2$COOH | (CDCl$_3$-CD$_3$OD) 1.28(3H, d, J=7.0Hz), 2.44-2.61(2H, m), 3.18-3.29(1H, m), 6.88(1H, d, J=8.9Hz), 7.00(2H, d, J=8.5Hz), 7.20(2H, d, J=8.5Hz), 7.70(2H, d, J=8.2Hz), 7.99(2H, d, J=8.2Hz), 8.17(1H, d, J=2.6Hz), 8.28(1H, dd, J=8.9Hz, 2.6Hz). |
| 813 | —CF$_3$ | —H | —CH=CHCOOH (trans) | (DMSO-d$_6$) 6.49(1H, d, J=16.0Hz), 7.15(3H, d, J=8.8Hz), 7.61(1H, d, J=16.0Hz), 7.74(2H, d, J=8.8Hz), 7.94(2H, d, J=8.3Hz), 8.17(2H, d, J=8.3Hz), 8.26(1H, dd, J=8.8Hz, 2.7Hz), 8.55(1H, d, J=2.7Hz), 10.67(1H, s), 12.36(1H, s). |
| 814 | —CF$_3$ | —H | —C(CH$_3$)$_2$N(CH$_3$)$_2$ COOH | (CDCl$_3$) 1.34(6H, s), 2.79(3H, s), 6.98(1H, d, J=8.9Hz), 7.10(2H, d, J=8.9Hz), 7.21(2H, d, J=9.1Hz), 7.76(2H, d, J=8.2Hz), 8.01(2H, d, J=8.1Hz), 8.10(1H, brs), 8.24(1H, dd, J=8.7Hz, 2.6Hz), 8.31(1H, d, J=2.3Hz). |

TABLE 111

[Structure: R347, R348-substituted benzyl-N(R349)-pyridine-O-phenyl(R350)-(CH$_2$)$_M$COOH]

| Reference Example No. | R347 | R348 | R349 | R350 | M | ¹H NMR (solvent) δ ppm |
|---|---|---|---|---|---|---|
| 815 | —Cl | —Cl | —H | —F | 0 | (DMSO-d$_6$) 4.29(2H, d, J=5.6Hz), 6.46(1H, t, J=5.9Hz), 6.94(1H, d, J=8.7Hz), 7.15(1H, dd, J=8.7Hz, 3.0Hz), 7.20(1H, d, J=8.3Hz), |

TABLE 111-continued

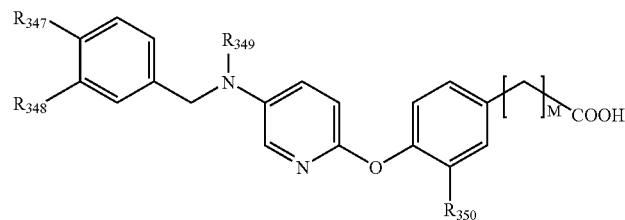

| Reference Example No. | $R_{347}$ | $R_{348}$ | $R_{349}$ | $R_{350}$ | M | $^1$H NMR (solvent) δ ppm |
|---|---|---|---|---|---|---|
| | | | | | | 7.36(1H, dd, J=8.3Hz, 1.8Hz), 7.47(1H, d, J=2.8Hz), 7.59(1H, d, J=8.3Hz), 7.63(1H, d, J=2.0Hz), 7.72-7.77(2H, m). |
| 816 | —CF$_3$ | —H | —H | —F | 0 | (DMSO-d$_6$) 4.37(2H, d, J=5.3Hz), 6.47(1H, brs), 6.89(1H, d, J=8.7Hz), 7.06-7.12(1H, m), 7.13(1H, dd, J=8.7Hz, 3.0Hz), 7.45(1H, d, J=3.0Hz), 7.58(2H, d, J=8.1Hz), 7.65-7.69(2H, m), 7.70(2H, d, J=8.1Hz). |
| 817 | —CF$_3$ | —H | —CH$_3$ | —H | 0 | (DMSO-d$_6$) 3.03(3H, s), 4.66(2H, s), 6.82(2H, d, J=8.7Hz), 6.87(1H, d, J=8.9Hz), 7.29(1H, dd, J=8.9Hz, 3.3Hz), 7.45(2H, d, J=8.1Hz), 7.68-7.72(3H, m), 7.82(2H, d, J=8.7Hz). |
| 818 | —CF$_3$ | —H | —C$_2$H$_5$ | —H | 0 | (DMSO-d$_6$) 1.13(3H, t, J=7.1Hz), 3.49(2H, q, J=7.1Hz), 4.61(2H, s), 6.81(2H, d, J=8.6Hz), 6.84(1H, d, J=8.9Hz), 7.22(1H, dd, J=8.9Hz, 3.3Hz), 7.47(2H, d, J=8.1Hz), 7.62(1H, d, J=3.3Hz), 7.70(2H, d, J=8.3Hz), 7.80(2H, d, J=8.7Hz). |
| 819 | —Cl | —Cl | —CH$_3$ | —OCH$_3$ | 2 | (CDCl$_3$) 2.66(2H, t, J=7.7Hz), 2.93(2H, t, J=7.7Hz), 2.95(3H, s), 3.75(3H, s), 4.35(2H, s), 6.68-6.88(3H, m), 6.90-7.00(1H, m), 7.00-7.17(2H, m), 7.31(1H, d, J=2.0Hz), 7.37(1H, d, J=8.2Hz), 7.65(1H, d, J=3.0Hz), 8.21(1H, brs). |
| 820 | —CF$_3$ | —H | —CH$_3$ | —OCH$_3$ | 2 | (DMSO-d$_6$) 2.41-2.62(2H, m), 2.69-2.85(2H, m), 2.96(3H, s), 3.64(3H, s), 4.58(2H, s), 6.70-6.79(2H, m), 6.88(1H, d, J=8.0Hz), 6.95(1H, d, J=1.8Hz), 7.25(1H, dd, J=9.2Hz, 3.2Hz), 7.42(2H, d, J=8.0Hz), 7.52(1H, d, J=3.2Hz), 7.67(2H, d, J=8.0Hz), 11.64-12.51(1H, m). |
| 821 | —Cl | —Cl | —CH$_3$ | —OC$_2$H$_5$ | 2 | (DMSO-d$_6$) 1.03(3H, t, J=7.0Hz), 2.53(2H, t, J=7.6Hz), 2.78(2H, t, J=7.6Hz), 3.89(2H, q, J=7.0Hz), 4.49(2H, s), 6.70-6.80(2H, m), 6.88(1H, d, J=8.0Hz), 6.92(1H, d, J=1.9Hz), 7.19(1H, dd, J=8.3Hz, 2.0Hz), 7.26(1H, dd, J=9.0Hz, 3.2Hz), 7.45(1H, d, J=2.0Hz), 7.52(1H, d, J=3.2Hz), 7.56(1H, d, J=8.3Hz), 11.81-12.30(1H, m). |
| 822 | —Cl | —Cl | —CH$_3$ | —F | 2 | (DMSO-d$_6$) 2.55(2H, t, J=7.6Hz), 2.80(2H, t, J=7.6Hz), 2.96(3H, s), 4.50(2H, s), 6.92(1H, d, J=8.9Hz), 7.00-7.22(4H, m), 7.22-7.38(1H, m), 7.38-7.40(1H, m), 7.40-7.55(2H, m), 12.10(1H, brs). |
| 823 | —Cl | —Cl | —C$_2$H$_5$ | —F | 2 | (CDCl$_3$) 1.17(3H, t, J=7.0Hz), 2.66(2H, t, J=7.7Hz), 2.93(2H, t, J=7.7Hz), 3.40(2H, q, J=7.0Hz), 4.36(2H, s), 6.72-6.86(1H, m), 6.90-7.15(5H, m), 727-7.35(1H, m), 7.36(1H, d, J=8.2Hz), 7.59(1H, d, J=3.2Hz). |

TABLE 112

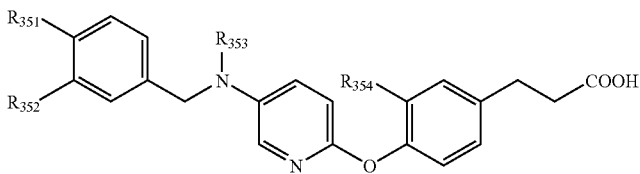

| Reference Example No. | $R_{351}$ | $R_{352}$ | $R_{353}$ | $R_{354}$ | $^1$H NMR (solvent) δ ppm |
|---|---|---|---|---|---|
| 824 | —CF$_3$ | —H | —CH$_3$ | —H | (DMSO-d$_6$) 2.50-2.54(2H, m), 2.79(2H, t, J=7.6Hz), 3.02(3H, s), 4.64(2H, s), 6.86(1H, d, J=8.9Hz), 6.89(2H, d, J=8.4Hz), 7.19(2H, d, J=8.7Hz), 7.29(1H, dd, J=8.9Hz, 3.3Hz), 7.44(2H, d, J=7.9 Hz), 7.69(2H, d, J=7.9Hz), 7.64(1H, d, J=3.1Hz). |
| 825 | —CF$_3$ | —H | —CH$_3$ | —OC$_2$H$_5$ | (DMSO-d$_6$) 1.03(3H, t, J=7.0Hz), 2.47-2.59(2H, m), 2.71-2.83(2H, m), 2.97(3H, s), 3.89(2H, q, J=7.0 Hz), 4.59(2H, s), 6.69-6.79(2H, m), 6.88(1H, d, J= 8.0Hz), 6.91(1H, d, J=1.9Hz), 7.26(1H, dd, J=9.0 Hz, 3.1Hz), 7.41(2H, d, J=8.0Hz), 7.52(1H, d, J= 3.1Hz), 7.66(2H, d, J=8.0Hz), 11.85-12.31(1H, m). |
| 826 | —CF$_3$ | —H | —CH$_3$ | —F | (CDCl$_3$) 2.67(2H, t, J=7.7Hz), 2.94(2H, t, J=7.7 Hz), 3.00(3H, s), 4.49(2H, s), 6.86(1H, d, J=8.9Hz), 6.90-7.16(4H, m), 7.33(2H, d, J=8.1Hz), 7.57(2H, d, J=8.1Hz), 7.64(1H, d, J=3.1Hz). |
| 827 | —CF$_3$ | —H | —C$_2$H$_5$ | —H | (DMSO-d$_6$) 1.11(3H, t, J=7.0Hz), 2.42-2.57(2H, m), 2.71-2.82(2H, m), 3.47(2H, q, J=7.0Hz), 4.58(2H, s), 6.82(1H, d, J=8.9Hz), 6.84-6.91(2H, m), 7.13-7.21(2H, m), 7.20(1H, dd, J=8.9Hz, 3.1Hz), 7.45(2H, d, J=8.1Hz), 7.57(1H, d, J=3.1Hz), 7.68(2H, d, J=8.1Hz), 12.06(1H, brs). |
| 828 | —Cl | —Cl | —C$_2$H$_5$ | —OCH$_3$ | (CDCl$_3$) 1.16(3H, t, J=7.1Hz), 2.55-2.78(2H, m), 2.94(2H, t, J=7.7Hz), 3.39(2H, q, J=7.1Hz), 3.77(3H, s), 4.35(2H, s), 6.70-6.88(3H, m), 6.92-7.13(3H, m), 7.32(1H, d, J=2.0Hz), 7.36(1H, d, J= 8.2Hz), 7.59(1H, d, J=3.1Hz). |
| 829 | —CF$_3$ | —H | —C$_2$H$_5$ | —OCH$_3$ | (DMSO-d$_6$) 1.09(3H, t, J=7.0Hz), 2.48-2.61(2H, m), 2.72-2.86(2H, m), 3.40(2H, q, J=7.0Hz), 3.64(3H, s),4.54(2H, s), 6.73(1H, d, J=9.0Hz), 6.74(1H, dd, J=8.0Hz, 1.9Hz), 6.87(1H, d, J=8.0Hz), 6.95(1H, d, J=1.9Hz), 7.18(2H, dd, J=9.0Hz, 3.2Hz), 7.39-7.49(3H, m), 7.62-7.71(2H, m), 11.90-12.31(1H, m). |
| 830 | —Cl | —Cl | —C$_2$H$_5$ | —OC$_2$H$_5$ | (DMSO-d$_6$) 0.95-1.11(6H, m), 2.41-2.57(2H, m), 2.77(2H, t, J=7.7Hz), 3.29-3.47(2H, m), 3.88(2H, q, J=7.0Hz), 4.44(2H, s), 6.73(1H, dd, J=8.0Hz, 1.9 Hz), 6.74(1H, d, J=9.0Hz), 6.88(1H, d, J=8.0Hz), 6.91(1H, d, J=1.9Hz), 7.15-7.24(2H, m), 7.41-7.48 (2H, m), 7.55(1H, d, J=8.2Hz), 11.60-12.50(1H, m). |
| 831 | —CF$_3$ | —H | —C$_2$H$_5$ | —OC$_2$H$_5$ | (DMSO-d$_6$) 1.02(3H, t, J=7.0Hz), 1.08(3H, t, J= 7.0Hz), 2.46-2.59(2H, m), 2.71-2.83(2H, m), 3.43(2H, q, J=7.0Hz), 3.89(2H, q, J=7.0Hz), 6.69-6.78(2H, m), 6.87(1H, d, J=8.0Hz), 6.91(1H, d, J=1.8Hz), 7.19(1H, dd, J=9.0Hz, 3.2Hz), 7.39-7.49(3H, m), 7.61-7.69(2H, m), 11.92-12.22(1H, m). |
| 832 | —CF$_3$ | —H | —C$_2$H$_5$ | —F | (CDCl$_3$) 1.19(3H, t, J=7.1Hz), 2.67(2H, t, J=7.7 Hz), 2.93(2H, t, J=7.7Hz), 3.43(2H, q, J=7.1Hz), 4.48(2H, s), 6.83(1H, d, J=9.0Hz), 6.90-7.20(4H, m), 7.34(2H, d, J=8.2Hz), 7.50-7.65(3H, m) |

TABLE 113

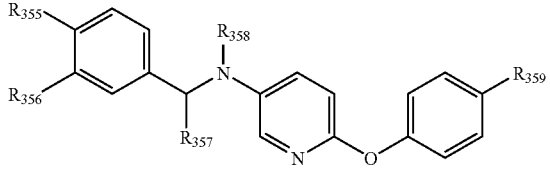

| Reference Example No. | R355 | R356 | R357 | R358 | R359 | Form | ¹H NMR (solvent) δ ppm |
|---|---|---|---|---|---|---|---|
| 833 | —CF₃ | —H | —CH₃ | —H | —COOH | free | (DMSO-d₆) 1.45(3H, d, J=6.8Hz), 4.61(1H, dt, J=6.8Hz, 6.8Hz), 6.53(1H, d, J=6.8Hz), 6.85(1H, d, J=8.6Hz), 6.97(2H, d, J=8.7Hz), 7.04(1H, dd, J=8.7Hz, 3.0Hz), 7.51(1H, d, J=3.0Hz), 7.62(2H, d, J=8.3Hz), 7.70(2H, d, J=8.3Hz), 7.89(2H, d, J=8.9Hz), 12.79(1H, brs). |
| 834 | —CF₃ | —H | —CH₃ | —CH₃ | —COOH | free | (DMSO-d₆) 1.54(3H, d, J=6.8Hz), 2.73(3H, s), 5.23(1H, q, J=6.8Hz), 7.00(1H, d, J=8.9Hz), 7.05(2H, d, J=8.7Hz), 7.46(1H, dd, J=9.1Hz, 3.3Hz), 7.54(2H, d, J=8.1Hz), 7.72(2H, d, J=8.4Hz), 7.84(1H, d, J=3.3Hz), 7.93(2H, d, J=8.6Hz) |
| 835 | —CF₃ | —H | —H | —CH₃ | 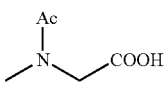 | dihydrochloride | (DMSO-d₆) 1.81(3H, s), 3.05(3H, s), 4.22(2H, s), 4.67(2H, s), 6.95(1H, d, J=8.7Hz), 7.04(2H, d, J=8.6Hz) 7.28-7.40(1H, m), 7.35(2H, d, J=8.6Hz), 7.45(2H, d, J=8.1Hz), 7.62-7.80(1H, m), 7.70(2H, d, J=8.1Hz). |
| 836 | —Cl | —Cl | —H | —CH₃ | 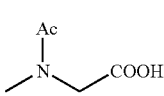 | dihydrochloride | (CDCl₃) 1.81(3H, s), 3.02(3H, s), 4.23(2H, s), 4.57(2H, s), 6.95(1H, d, J=8.8Hz), 7.04(2H, d, J=8.7Hz), 7.22(1H, dd, J=8.2Hz, 2.0Hz), 7.32-7.40(1H, m), 7.35(2H, d, J=8.7Hz), 7.51(1H, d, J=2.0Hz), 7.59(1H, d, J=8.2Hz), 7.71(1H, d, J=3.0Hz). |
| 837 | —CF₃ | —H | —H | —(CH₂)₂OCH₃ | —(CH₂)₂COOH | free | (DMSO-d₆) 2.43-2.57(2H, m), 2.71-2.82(2H, m), 3.25(3H, s), 3.48-3.58(2H, m), 3.59-3.68(2H, m), 4.66(2H, s), 6.80(1H, d, J=8.9Hz), 6.83-6.90(2H, m), 7.11-7.25(3H, m), 7.44(2H, d, J=8.0Hz), 7.56(1H, d, J=3.1Hz), 7.67(2H d J=8.0Hz), 12.09(1H, brs). |

TABLE 114

Structure: R360, R361-substituted phenyl—Xa26—pyridine(N)—O—phenyl(R362)—Xa27—COOH

| Reference Example No. | R360 | R361 | R362 | Xa26 | Xa27 | $^1$H NMR (solvent) δ ppm or MS |
|---|---|---|---|---|---|---|
| 838 | —Cl | —Cl | —OCH$_3$ | —CH=CH— (trans) | —CH$_2$— | $^1$H NMR (DMSO-d$_6$) 2.57-2.63(2H, m), 2.83-2.88(2H, m), 3.68(3H, s), 6.84(1H, dd, J=8.1Hz, 1.7Hz), 6.98-7.05(3H, m), 7.20(1H, d, J=16.5Hz), 7.36(1H, d, J=16.5Hz), 7.54-7.65(2H, m), 7.87(1H, d, J=1.8 Hz), 8.07-8.11(1H, m), 8.22(1H, d, J=2.1Hz), 12.20(1H, brs). |
| 839 | —CF$_3$ | —H | —OCH$_3$ | —CH=CH— (trans) | —CH$_2$— | $^1$H NMR (DMSO-d$_6$) 2.58-2.63(2H, m), 2.83-2.89(2H, m), 3.68(3H, s), 6.82-6.86(1H, m), 6.99-7.06(3H, m), 7.31(1H, d, J=16.5Hz), 7.41(1H, d, J=16.5 Hz), 7.71-7.81(4H, m), 8.15(1H, dd, J=8.7Hz, 2.5Hz), 8.27(1H, d, J=2.1Hz), 12.18(1H, brs). |
| 840 | —CF$_3$ | —H | —OCH$_3$ | —CO— | —CH$_2$— | $^1$H NMR (DMSO-d$_6$) 2.57-2.63(2H, m), 2.83-2.89(2H, m), 3.70(3H, s), 6.86(1H, dd, J=8.1Hz, 2.0Hz), 7.06-7.15(3H, m), 7.90-7.97(4H, m), 8.18-8.22(1H, m), 8.50(1H, dd, J=2.5Hz, 0.7Hz), 12.19(1H, brs). |
| 841 | —CF$_3$ | —H | —CH$_3$ | —CO— | —N(C$_2$H$_5$)— | $^1$H NMR (CDCl$_3$) 1.23(3H, t, J=7.1Hz), 2.12(3H, s), 3.46(2H, q, J=7.1Hz), 4.04(2H, s), 5.77(1H, brs), 6.55-6.59(2H, m), 6.97(2H, d, J=8.7Hz), 7.73-7.89(4H, m), 8.17-8.21(1H, m), 8.58(1H, d, J=2.3Hz). |
| 842 | —Cl | —Cl | —H | —NHCONH— | none | MS 431(M$^+$) |

TABLE 115

Structure: HOOC—pyridine(N)—O—phenyl(R363, R364)

| Reference Example No. | R363 | R364 | Form | $^1$H NMR (solvent) δ ppm |
|---|---|---|---|---|
| 843 | —H | N(CH$_3$)-CH$_2$-C(=O)-piperazine-CH$_2$-(benzo[1,3]dioxole) | hydrochloride | (DMSO-d$_6$) 2.94(3H, s), 3.10-3.59(7H, m), 4.02-4.39(5H, m), 6.07(2H, s), 6.68(2H, d, J=9.1Hz), 6.74-7.06(5H, m), 7.25(1H, brs), 8.23(1H, dd, J=8.7 Hz, 2.3Hz), 8.65(1H, d, J=2.3Hz), 11.23(1H, brs). |
| 844 | —H | —NO$_2$ | free | (CDCl$_3$) 7.13(1H, d, J=8.5 Hz), 7.35(2H, d, J=9.1Hz), 8.33(2H, d, J=9.1Hz), 8.41(1H, dd, J=8.5Hz, 2.5 Hz), 8.89(1H, d, J=2.5Hz). |

TABLE 115-continued

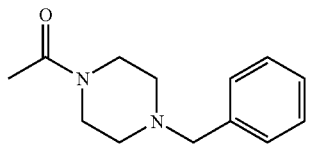

| Reference Example No. | R363 | R364 | Form | ¹H NMR (solvent) δ ppm |
|---|---|---|---|---|
| 845 | —H | 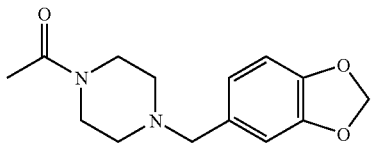 | free | (DMSO-d₆) 2.47(4H, brs), 3.31-3.53(6H, m), 7.16(1H, d, J=8.6Hz), 7.23-7.34(7H, m), 7.45-7.48(2H, m), 8.31(1H, dd, J=8.6Hz, 2.4 Hz), 8.68(1H, d, J=2.4Hz), 13.20(1H, brs). |
| 846 | —H | | free | (DMSO-d₆) 3.36-3.55(8H, m), 3.58(2H, s), 6.00(2H, s), 6.78-6.92(3H, m), 7.17(1H, d, J=8.6Hz), 7.26(2H, d, J=8.6Hz), 7.48(2H, d, J=8.4Hz), 8.31(1H, dd, J=2.3 Hz, 8.6Hz), 8.68(1H, d, J=2.2Hz). |
| 847 | —H | | free | (DMSO-d₆) 2.50(4H, brs), 2.63-2.68(2H, m), 2.81-2.86(2H, m), 3.48-3.61(6H, 6.01(2H, s), 6.81-6.90(2H, m), 6.96(1H, s), 7.06-7.10(3H, m), 7.30(2H, d, J=8.6Hz), 8.25-8.33(1H, m), 8.66(1H, d, J=2.7Hz), 12.58(1H, brs). |
| 848 | —CH₃ | —NO₂ | free | (DMSO-d₆) 2.22(3H, s), 7.28(1H, dd, J=8.6Hz, 0.7 Hz), 7.40(1H, d, J=8.9Hz), 8.14(1H, dd, J=8.9Hz, 2.8 Hz), 8.28(1H, d, J=2.6Hz), 8.36(1H, dd, J=8.6Hz, 2.3 Hz), 8.65(1H, dd, J=2.3 Hz, 0.7Hz). |

TABLE 116

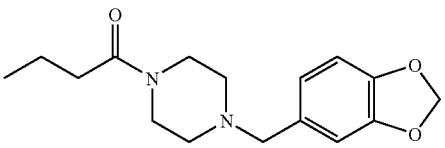

| Reference Example No. | R365 | R366 | R367 | ¹H NMR (solvent) δ ppm |
|---|---|---|---|---|
| 849 | —NO₂ | —CH₃ | —H | (DMSO-d₆) 2.06(3H, s), 7.14(1H, d, J=8.6 Hz), 7.26(1H, d, J=9.1 Hz), 7.64(1H, dd, J=8.7 Hz, 2.5 Hz), 7.74(1H, d, J=2.5 Hz), 8.62(1H, dd, J=9.1 Hz, 3.0 Hz), 9.02(1H, d, J=2.8 Hz), 10.75(1H, brs). |
| 850 | —NO₂ | —CH₃ | —CH₃ | (DMSO-d₆) 2.09(3H, s), 3.26(3H, s), 7.20-7.36(4H, m), 8.64(1H, dd, J=9.1 Hz, 2.8 Hz), 9.03(1H, d, J=2.6 Hz). |
| 851 | 4-CF₃PhNHCO— | —CH₃ | —H | (DMSO-d₆) 2.08(3H, s), 7.11(1H, d, J=8.7 Hz), 7.16(1H, d, J=8.7 Hz), 7.64(1H, dd, J=8.7 Hz, 2.5 Hz), 7.72-7.75(3H, m), 7.98(2H, d, J=8.6 Hz), 8.37(1H, dd, J= |

TABLE 116-continued

[Structure: pyridine with R365 at 5-position, linked via O to phenyl bearing R366, with N(R367)-C(=O)-COOH group]

| Reference Example No. | R365 | R366 | R367 | ¹H NMR (solvent) δ ppm |
|---|---|---|---|---|
| 852 | 4-CF₃PhOCH₂— | —H | —H | 8.7 Hz, 2.5 Hz), 8.69(1H, d, J=2.5 Hz), 10.62(1H, brs), 10.74(1H, brs). (DMSO-d₆) 5.17(2H, s), 7.06(1H, d, J=8.4 Hz), 7.13(2H, d, J=8.9 Hz), 7.21(2H, d, J=8.6 Hz), 7.67(2H, d, J=8.4 Hz), 7.79(2H, d, J=9.1 Hz), 7.95(1H, dd, J=8.4 Hz, 2.5 Hz), 8.25(1H, d, J 2.0 Hz), 10.78(1H, brs). |
| 853 | 4-CF₃PhOCH₂— | —CH₃ | —H | (CDCl₃) 2.18(3H, s), 5.05(2H, s), 7.01 7.08(5H, m), 7.51-7.58(4H, m), 7.83 7.87(1H, m), 8.20(1H, d, J=2.1 Hz), 9.02(1H, brs). |
| 854 | 4-CF₃PhOCH₂— | —CH₃ | —CH₃ | (DMSO-d₆) 2.09(3H, s), 3.25(3H, s), 5.17(2H, s), 7.10(1H, d, J=8.4 Hz), 7.11(1H, d, J=8.4 Hz), 7.17-7.23(3H, m), 7.32(1H, d, J=2.3 Hz), 7.67(2H, d, J=8.7 Hz), 7.98(1H, dd, J=8.4 Hz, 2.3 Hz), 8.24(1H, d, J=2.3 Hz). |

TABLE 117

[Structure: pyridine with R368 at 5-position, linked via O to phenyl bearing R369, with N(R370)-CH₂-COOH group]

| Reference Example No. | R368 | R369 | R370 | ¹H NMR (solvent) δ ppm |
|---|---|---|---|---|
| 855 | 3,4-Cl₂PhSO₂NH— | —F | —CH₃ | (DMSO-d₆) 2.96(3H, s), 4.11(2H, s), 6.43(1H, dd, J=8.9 Hz, 2.1 Hz), 6.58(1H, dd, J=14.4 Hz, 3.0 Hz), 6.97-7.02(2H, m), 7.53(1H, dd, J=8.9 Hz, 2.8 Hz), 7.63(1H, dd, J=8.4 Hz, 2.1 Hz), 7.77(1H, d, J=2.5 Hz), 7.86(1H, d, J=8.6 Hz), 7.88(1H, d, J=2.1 Hz), 10.40(1H, s), 12.61(1H, brs). |
| 856 | 3,4-Cl₂PhNHCO— | —OCH₃ | —C₂H₅ | (CDCl₃) 1.26(3H, t, J=7.1 Hz), 3.45(2H, q, J=7.1 Hz), 3.69(3H, s), 4.08(2H, s), 6.24(1H, dd, J=8.7 Hz, 2.8 Hz), 6.31(1H, d, J=2.6 Hz), 6.95(1H, d, J=8.7 Hz), 7.00(1H, d, J=8.7 Hz), 7.29-7.50(1H, m), 7.55(1H, dd, J=8.9 Hz, 2.5 Hz), 7.88(1H, d, J 2.5 Hz), 8.24(1H, dd, J=8.7 Hz, 2.5 Hz), 8.56(1H, brs), 8.73(1H, d, J=2.0 Hz). |

Reference Example 857

Production of 3-{4-[5-(3,4-dichlorobenzylmethylamino)-pyridin-2-yloxy]phenyl}propionic acid To a solution of ethyl 3-{4-[5-(3,4-dichlorobenzylamino)pyridin-2-yloxy]phenyl}propionate (1.63 g, 3.7 mmol) in ethanol (30 mL) were added 37% aqueous formaldehyde (2.0 mL, 22 mmol) and acetic acid (0.21 mL, 3.7 mmol), and the resulting solution was stirred at room temperature for 1 hour. To this solution was then added sodium cyanoborohydride (0.46 g, 7.3 mmol) at 0° C., and the resulting solution was stirred at the same temperature for 1 hour. To this solution was added water and extracted with ethyl acetate. The ethyl acetate layer was washed with water, and then dried over anhydrous magnesium sulfate. The solvent was evaporated, and the residue was purified by silica gel column chromatography (n-hexane:ethyl acetate=5:1), to thereby yield 1.55 g of ethyl 3-{4-[5-(3,4-dichlorobenzylmethylamino)-pyridin-2-yloxy]phenyl}propionate. This product was dissolved in ethanol (40 mL), and to the resulting solution was added 10% aqueous sodium hydroxide (2.7 mL, 6.7 mmol) and stirred at room temperature for 2 hours. The resulting solution was then acidified by adding 10% hydrochloric acid, and extracted with ethyl acetate. The ethyl acetate layer was washed with water, dried over anhydrous magnesium sulfate, and evaporated, to thereby yield 1.44 g of the title compound.

Appearance: Colorless oil $^1$H NMR (DMSO-$d_6$) δ 2.38-2.60 (2H, m), 2.78 (2H, t, J=7.6 Hz), 4.52 (2H, s), 6.81-6.92 (3H, m), 7.12-7.23 (3H, m), 7.28 (1H, dd, J=8.9 Hz, 3.3 Hz), 7.48 (1H, d, J=1.9 Hz), 7.57 (1H, d, J=8.2 Hz), 7.63 (1H, d, J=3.3 Hz), 11.70-12.40 (1H, m).

The following compound was produced in the same manner as in Reference Example 857.

Reference Example 858

3-(4-{5-[(3,4-Dichlorobenzyl)ethylamino]pyridin-2-yloxy}phenyl)propionic acid $^1$H NMR (DMSO-$d_6$) δ 1.09 (3H, t, J=6.9 Hz), 2.37-2.59 (2H, m), 2.64-2.83 (2H, m), 3.45 (2H, q, J=6.9 Hz), 4.48 (2H, s), 6.82 (1H, d, J=8.9 Hz), 6.85-6.92 (2H, m), 7.12-7.25 (4H, m), 7.48 (1H, d, J=1.8 Hz), 7.54-7.61 (2H, m), 11.77-12.38 (1H, m).

Reference Example 859

Production of N-[2-(4-formylphenoxy)-5-pyridyl]-3,4-dichlorobenzamide

To a solution of 4-[(5-amino-2-pyridyl)oxy]benzaldehyde ethylene acetal (5.27 g, 20.4 mmol) and triethylamine (3.41 mL, 24.5 mmol) in THF (80 mL) was added dropwise a solution of 3,4-dichlorobenzoyl chloride (4.49 g, 21.4 mmol) in THF (30 mL) under ice cooling. The resulting solution was stirred for 2 hours at the same temperature. The reaction solution was concentrated under reduced pressure, to the residue, 80% acetic acid (55 mL) was added, and the mixture was heated at 80° C. with stirring for 1 hour. The reaction solution was concentrated under reduced pressure and to the residue was added water, and extracted with ethyl acetate. The ethyl acetate layer was washed with a saturated sodium bicarbonate solution and brine, dried over anhydrous magnesium sulfate, and evaporated. The obtained solid was recrystallized from isopropanol, to thereby yield 5.63 g of the title compound.

Appearance: Pale yellow powder $^1$H NMR (CDCl$_3$) δ 7.05 (1H, d, J=8.7 Hz), 7.24 (2H, d', J=8.7 Hz), 7.57 (1H, d, J=8.4 Hz), 7.70 (1H, dd, J=8.4 Hz, 2.1 Hz), 7.82-7.93 (3H, m), 7.97 (1H, d, J=2.1 Hz), 8.25 (1H, dd, J=8.7 Hz, 2.7 Hz), 8.29 (1H, d, J=2.7 Hz), 9.96 (1H, s).

Reference Example 860

Production of ethyl{4-[5-(3,4-dichlorobenzoylamino)-pyridin-2-yloxy]benzylamino}acetate A solution of N-[2-(4-formylphenoxy)-5-pyridyl]-3,4-dichlorobenzamide (1.00 g, 2.58 mmol), glycine ethyl ester hydrochloride (0.400 g, 2.84 mmol) and sodium acetate (0.230 g, 2.84 mmol) in methanol (20 mL) was stirred for 30 minutes at 60° C. The reaction solution was cooled with ice, and then sodium cyanoborohydride (0.180 g, 2.84 mmol) was added. The resulting solution was stirred at the same temperature for 1 hour. To the reaction solution was added 5 M hydrochloric acid (2 mL) and concentrated under reduced pressure. To the residue was added a saturated sodium bicarbonate solution, and extracted with dichloromethane. The dichloromethane layer was washed with brine, dried over anhydrous sodium sulfate, and evaporated. The residue was purified by silica gel column chromatography (n-hexane:ethyl acetate=1:2), to thereby yield 0.752 g of the title compound.

Appearance: Yellow oil $^1$H NMR (CDCl$_3$) δ 1.27 (3H, t, J=7.1 Hz), 3.43 (2H, s), 3.81 (2H, s), 4.20 (2H, q, J=7.1 Hz), 6.95 (1H, d, J=8.8 Hz), 7.09 (2H, d, J=8.5 Hz), 7.36 (2H, d, J=8.5 Hz), 7.57 (1H, d, J=8.3 Hz), 7.71 (1H, dd, J=2.1 Hz, 8.3 Hz), 7.84 (1H, s), 7.98 (1H, d, J=2.1 Hz), 8.18 (1H, dd, J=2.7 Hz, 8.8 Hz), 8.24 (1H, d, J=2.7 Hz).

Reference Example 861

Production of (acetyl{4-[5-(3,4-dichlorobenzoylamino)-pyridin-2-yloxy]benzyl}amino)acetic acid To a solution of ethyl{4-[5-(3,4-dichloro-benzoylamino)pyridin-2-yloxy]benzylamino}acetate (0.811 g, 1.59 mmol) in dichloromethane (5 mL) were added triethylamine (0.332 mL, 2.39 mmol) and acetyl chloride (0.136 mL, 1.91 mmol) at room temperature. The resulting solution was stirred for 1 hour at the same temperature. To the reaction solution was added water, and extracted with dichloromethane. The dichloromethane layer was washed with brine, dried over anhydrous sodium sulfate, and evaporated, to thereby yield 0.785 g of residue. This residue was dissolved in ethanol (5 mL). To the resulting solution was added 5 M aqueous sodium hydroxide (0.350 mL, 1.75 mmol) at room temperature and stirred at the same temperature for 14 hours. To the resulting reaction solution were added 5 M hydrochloric acid (0.400 mL) and water, and extracted with dichloromethane. The dichloromethane layer was washed with brine, dried over anhydrous sodium sulfate, and evaporated, to thereby yield 0.776 g of the title compound.

Appearance: White amorphous powder $^1$H NMR (DMSO-$d_6$ at 375 K) δ 2.10 (3H, s), 4.02 (2H, s), 4.60 (2H, s), 7.03 (1H, d, J=8.8 Hz), 7.11 (2H, d, J=8.2 Hz), 7.32 (2H, d, J=8.2 Hz), 7.78 (1H, d, J=8.4 Hz), 7.97 (1H, dd, J=2.1 Hz, 8.4 Hz), 8.10-8.30 (2H, m), 8.53 (1H, d, J=2.6 Hz), 10.23 (1H, s).

Reference Example 862

Production of 1-(4-piperonylpiperazin-1-yl)-2-{methyl-[3-methyl-4-(5-nitropyridin-2-yloxy)phenyl]amino}-ethanone To a solution of {methyl[3-methyl-4-(5-nitropyridin-2-yloxy)phenyl]amino}acetic acid (0.93 g, 2.9 mmol) in DMF (40 mL) were added 1-ethyl-3-(3-dimethylaminopropyl)carbodiimide hydrochloride (0.67 g, 3.5 mmol), 1-hydroxybenzotriazole monohydrate (0.54 g, 3.5 mmol), and 1-piperonylpiperazine (0.68 g, 3.08 mmol). The reaction mixture was stirred for 15 hours at room temperature under a nitrogen atmosphere. To the resulting solution was added water and extracted with ethyl acetate. The ethyl acetate layer was washed with water and then dried over anhydrous magnesium sulfate. The solvent was evaporated, and the residue was purified by silica gel column chromatography (n-hexane:ethyl acetate=2:1→dichloromethane:methanol=100:1), to thereby yield 1.2 g of the title compound.

Appearance: Yellow powder
Melting point: 142-143° C.

The following compounds were produced in the same manner as in Reference Example 862.

TABLE 118

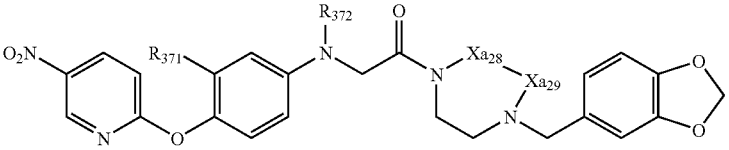

| Reference Example No. | $R_{371}$ | $R_{372}$ | $Xa_{28}$ | $Xa_{29}$ | $^{1}$H NMR (CDCl$_3$) δ ppm |
|---|---|---|---|---|---|
| 863 | —CH$_3$ | —CH$_3$ | —CH$_2$— | —CO— | 2.09(3H, s) 3.04(3H, s), 3.22 3.39(2H, m), 3.60-3.90(2H, m), 4.11(2H, s), 4.19-4.40(2H, m), 4.53(2H s) 5 95(2H, s), 6.51-6.62(2H, m), 6.68-6.80(3H, m), 6.92(1H, d, J=8.6 Hz), 6.94(1H, d, J=9.0 Hz), 8.42(1H, dd, J=9.0 Hz, 2.6 Hz), 9.04(1H, d, J=2.6 Hz). |
| 864 | —OCH$_3$ | —C$_2$H$_5$ | —CH$_2$— | —CO— | 1.21(3H, t, J=6.7 Hz), 3.20-3.33(2H, m), 3.46(2H, q, J=6.7 Hz), 3.71(3H, s), 3.65-3.85(2H, m), 4.07 (2H, s), 4.29(2H, s), 4.52(2H, s), 5.96(2H, s), 6.23 (1H, dd, J=8.7 Hz, 2.6 Hz), 6.39(1H, d, J=2.6 Hz), 6.65-6.85(3H, m), 6.97(2H, d, J=8.7 Hz), 8.41 (1H, dd, J=9.0 Hz, 2.8 Hz), 9.02(1H, d, J=2.8 Hz). |
| 865 | —H | —CH$_3$ | —CH$_2$— | —CH(CH$_3$)— | 1.12-1.16(3H, m), 2.08-2.16(1H, m), 2.46-2.53(1H, m), 2.71-2.73(1H, m), 2.85-3.48(6H, m), 3.54-3.59 (1H, m), 3.84-4.19(4H, m), 5 94(2H, s), 6.68-6.74 (4H, m), 6.85(1H, brs), 6.94(1H, d, J=9.1 Hz), 7.01 (2H, d, J=8.9 Hz), 8.41(1H, dd, J=9.1 Hz, 2.8 Hz), 9.05(1H, d, J=2.8 Hz). |
| 866 | —H | —C$_2$H$_5$ | —CH$_2$— | —CH(CH$_3$)— | 1.13-1.28(6H, m), 2.08-2.16(1H, m), 2.47-2.50(1H, m), 2.7 1-2.75(1H, m), 2.86-3.35(3H, m), 3.41-3.49 (2H, m), 3.58-3.62(1H, m), 3.85-4.16(4H, m), 5.94 (2H, s), 6.67(2H, d, J=9.1 Hz), 6 .74(2H, brs), 6.85(1H, brs) 6.94(1H, d, J=9.1 Hz), 6.99(2H, d, J=9.1 Hz), 8.41(1H, dd, J=9.1 Hz, 3.0 Hz), 9.05(1H, d, J=2.5 Hz). |
| 867 | —H | —CH$_3$ | —CH(CH$_3$)— | —CH$_2$— | 1.29-1.40(3H, m), 1.96-2.06(1H, m), 2.17(1H, brs), 2.65-2.70(1H, m), 2.81-2.86(1H, m), 2.96-3.06(4H, m), 3.32-3.49(3H m), 3.97-4.71(3H, m), 5.95(2H, s), 6.70(2H, d, J=9.2 Hz), 6.74-6.75(2H, m), 6.87 (1H, brs), 6.94(1H, dd, J=9.1 Hz, 0.5 Hz), 7.01(2H, d, J=9.2 Hz), 8.41(1H, dd, J=9.1 Hz, 2.8 Hz), 9.05(1H, dd, J= 2.8 Hz, 0.5 Hz). |
| 868 | —H | —C$_2$H$_5$ | —CH(CH$_3$)— | —CH$_2$— | 1.20(3H, t, J=7.1 Hz), 1.26-1.40(3H, m), 1.98-2.05(1H, m), 2.16 2.17(1H, m), 2.65-2.69(1H, m), 2.81-2.85(1H, m), 3.02-3.56(6H, m), 4.03-4.71 (3H, m), 5.94(2H, s), 6.66(2H, d, J=9.2 H) 6 74-6.75(2H, m), 6.87(1H, brs5, 6.94(1H, dd, J=9.1 Hz, 0.7 Hz), 6.99(2H, d, J=9.1 Hz), 8.41(1H, dd, J=9.1 Hz, 2.8 Hz), 9.05(1H, dd, J=2.8 Hz, 0.7 Hz). |

TABLE 119

[Structure: O2N-pyridine-O-phenyl(R373, R374)-N(R375)-C(=O)-CH2-piperazine-CH2-benzodioxole]

| Reference Example No. | R373 | R374 | R375 | 1H NMR (solvent) δ ppm or MS |
|---|---|---|---|---|
| 869 | —COOCH3 | —H | —C2H5 | MS 577(M+) |
| 870 | —OCH3 | —H | —H | 1H NMR (DMSO-d6) 2.32-2.40(4H, m), 3.42(2H, s), 3.50(4H, brs), 3.63(3H, s), 3.92(2H, d, J=4.6 Hz), 5.65(1H, t, J=4.8 Hz), 5.99(2H, s), 6.22(1H, dd, J=8.6 Hz, 2.5 Hz), 6.51(1H, d, J=2.5 Hz), 6.76(1H, dd, J=7.9 Hz, 1.5 Hz), 6.84-6.91(3H, m), 7.07(1H, dd, J=9.1 Hz, 0.5 Hz), 8.54(1H, dd, J=9.1 Hz, 2.8 Hz), 9.00(1H, dd, J=2.8 Hz, 0.5 Hz). |
| 871 | —OCH3 | —H | —CH3 | 1H NMR (CDCl3) 2.35-2.52(4H, m), 3.07(3H, s), 3.44(2H, s), 3.41-3.55(2H, m) 3.56-3.70(2H, m), 3 73(3H, s), 5.95(2H, s), 6.24(1H, dd, J=8.8 Hz, 218 Hz), 6.35(1H, d, J=2.8 Hz), 6.64-6.79(2H, m), 6.85(1H, s), 6.89-7.04(2H, m), 8.41(1H, dd, J=9.1 Hz, 2.8 Hz), 9.03(1H, d, J=2.8 Hz). |
| 872 | —OCH3 | —H | —C2H5 | 1H NMR (CDCl3) 1.22(3H, t, J=7.0 Hz), 2.33-2.52(4H, m), 3.49-3.58(6H, m), 3.59-3.69(2H, m), 3.72(3H, s), 4.06(2H, s), 5.95(2H, s), 6.22(1H, dd, J=8.8 Hz, 2.7 Hz), 6.33(1H, d, J=2.7 Hz), 6.69 6.79(2H, m), 6.85(1H, s), 6.95(1H, d, J=9.1 Hz), 6.96 (1H, d, J=8.8 Hz), 8.41(1H, dd, J=9.1 Hz, 2.8 Hz), 9.04(1H, d, J=2.8 Hz). |
| 873 | —CH3 | —H | —H | 1H NMR (CDCl3) 2.08(3H, s), 2.43-2.48(4H, m), 3.45-3.48 (4H, m), 3.67-3.71(2H, m), 3.86(2H, d, J=4.1 Hz), 4.93(1H, t, J=4.1Hz), 5.96(2H, s), 6.47-6.52(2H, m), 6.71-6.78(2H, m), 6.86-6.96(3H, m), 8.44(1H, dd, J=9.1 Hz, 2.8 Hz), 9.05(1H, d, J=2.8 Hz). |
| 874 | —CH3 | —H | —Ac | 1H NMR (CDCl3) 1.98(3H, s), 2.16(3H s) 2.32-2.51(4H, m), 3.35-3.48(4H, m), 3.53-3.69(2H, m), 4.46(2H, s), 5.95(2H, s), 6.65-6.79(2H, m), 6.85(1H, s), 7.08(2H, d, J=8.7 Hz), 7.27-7.34 (1H, m) 7.35-7.42(1H, m), 8.51(1H, dd, J=9.0 Hz, 2.8 Hz), 9.02 (1H, dd, J=2.8 Hz, 0.3 Hz). |
| 875 | —CH3 | —H | —C2H5 | 1H NMR (CDCl3) 1.20(3H, t, J=7.1 Hz), 2.08(3H s), 2.37-2.55(4H, m), 3.37-3.72(8H, m), 4.05(2H, s), 5.95(2H, s), 6.42-6.58(2H, m), 6.63-6.79(2H, m), 6.81-6.99(3H, m), 8.42(1H, dd, J=9.1 Hz, 2.8 Hz), 9.05(1H, d, J=2.8 Hz). |
| 876 | —CH3 | —H | cyclopropyl | 1H NMR (CDCl3) 0.64-0.69(2H, m), 0.80-0.87(2H, m), 2.09 (3H, s), 2.41-2.49(4H, m), 2.76-2.84(1H, m), 3.44(2H, s), 3.49-3.52(2H, m), 3.60-3.64(2H, m), 4.18(2H, s), 5.95(2H, s), 6.71-6.93(7H, m), 8.39-8.44(1H, m), 9.05-9.06(1H, m). |
| 877 | —CH3 | —CH3 | —CH3 | 1H NMR (CDCl3) 2.05(3H, s), 2.28(3H, s), 2.37-2.43(4H, m), 2.72(3H, s), 3.42(2H, s), 3.52 3.56(2H, m), 3.62-3.65(2H, m), 3.77(2H, s), 5.95(2H, s), 6.71-6.77(2H, m), 6.85-6.90(2H, m), 6.97-7.06(2H, m), 8.45(1H, dd, J=9.1 Hz, 3.0 Hz), 9.04(1H, dd, J=3.0 Hz, 0.5 Hz). |

TABLE 120

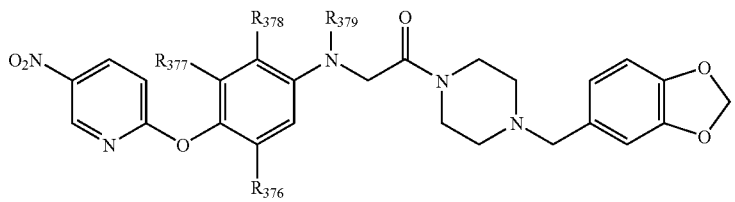

| Reference Example No. | $R_{376}$ | $R_{377}$ | $R_{378}$ | $R_{379}$ | $^1$H NMR (solvent) δ ppm or MS |
|---|---|---|---|---|---|
| 878 | —CH$_3$ | —H | —CH$_3$ | —C$_2$H$_5$ | MS 547(M$^+$) |
| 879 | —F | —H | —H | —H | $^1$H NMR (CDCl$_3$) 2.44-2.49(4H, m), 3.43-3.45(2H, m), 3.45 (2H, s), 3.68-3.71(2H, m), 3.84(2H, d, J=4.1 Hz), 5.12(1H, brs), 5.96(2H, s), 6.40-6.45(2H, m), 6.71-6.80(2H, m), 6.85(1H, brs), 7.02(1H, t, J=8.5 Hz), 7.05(1H, dd, J=9.1 Hz, 0.5 Hz), 8.46(1H, dd, J=9.1 Hz, 2.8 Hz), 9.02(1H, dd, J=2.8 Hz, 0.7 Hz). |
| 880 | —F | —H | —H | —CH$_3$ | $^1$H NMR (CDCl$_3$) 2.44(4H, brs), 3.06(3H s) 3.45(2H, s), 3.45-3.47(2H, m), 3.62-3.64(2H, m), 4.11(2H s) 5.95(2H, s), 6.40-6.51(2H, m), 6.71-6.78(2H, m), 6.85(1H, brs), 7.04(1H, d, J=9.1 Hz), 7.05(1H, t, J=8.9 Hz), 8.46(1H, dd, J 9.1 Hz, 2.8 Hz), 9.02(1H, d, J=2.3 Hz) |
| 881 | —F | —H | —H | —C$_2$H$_5$ | $^1$H NMR (CDCl$_3$) 1.22(3H, t, J=7.2 Hz), 2.45(4H, brs), 3.40-3.49 (4H, m), 3.45(2H, s), 3.65(2H, brs), 4.05(2H s) 5.95 (2H, s), 6.37-6.46(2H, m), 6.74-6.75(2H, m), 6.86(1H, brs), 6.99-7.06 (2H, m), 8.45(1H, dd, J=9.1 Hz, 2.8 Hz), 9.03(1H, d, J=2.5 Hz). |
| 882 | —F | —H | —H | allyl | $^1$H NMR (CDCl$_3$) 2.46(4H, brs), 3.45(2H, s), 3.48(2H, brs), 3.65(2H, brs), 4.00(2H, d, J=5.0 Hz), 4.07(2H, s), 5.19-5.29(2H, m), 5.82-5.94(1H, m), 5.95(2H, s), 6.37-6.47(2H, m), 6.71-6.78 (2H, m), 6.86-6.87(1H, m), 6.98-7.05(2H, m), 8.45(1H, dd, J=9.1 Hz, 2.8 Hz), 9.02(1H, dd, J=2.8 Hz, 0.5 Hz) |
| 883 | —F | —H | —F | —CH$_3$ | $^1$H NMR (CDCl$_3$) 2.33-2.49(4H, m), 2.99(3H, s), 3.43(2H, s), 3.37-3.50(2H, m), 3.51-3.68(2H, m) 4.10(2H, s), 5.95(2H, s), 6.69-6.78(2H, m), 6.81(1H, dd, J=8.2 Hz, 12.1 Hz), 6.85(1H, d, J=0.96 Hz), 6.90(1H, dd, J=7.1 Hz, 12.8 Hz), 7.09(1H, d, J=9.1 Hz), 8.49(1H, dd, J=2.8 Hz, 9.0 Hz), 9.01(1H, d, J=2.8 Hz). |
| 884 | —F | —H | —F | —C$_2$H$_5$ | $^1$H NMR (CDCl$_3$) 1.17(3H, t, J=7.1Hz), 2.30-2.52(4H, m), 3.35 (2H, q, J=7.1Hz), 3.37-3.70(6H, m), 4.04(2H, s), 5.95(2H, s), 6.68-6.78(2H, m), 6.82(1H, dd, J=8.0 Hz, 12.1 Hz), 6.83-6.88 (1H, m), 6.91(1H, dd, J=7.2 Hz, 12.5 Hz), 7.09(1H, d, J=9.0 Hz), 8.49(1H, dd, J=2.8 Hz, 9.0 Hz), 9.02(1H, d, J=2.8Hz). |
| 885 | —F | —F | —H | —CH$_3$ | $^1$H NMR (DMSO-d$_6$) 2.20-2.45(4H, m), 2.91(3H, s), 3.34-3.53 (6H, m), 4.31(2H, s), 5.98(2H, s), 6.47(2H, d, J=11.8 Hz), 6.70-6.79(1H, m), 6.80-6.91(2H, m), 7.42(1H, d, J=9.1 Hz), 8.64(1H, dd, J 2 .8 Hz, 9.1 Hz), 9.05(1H, d, J=2.8 Hz). |
| 886 | —CH$_3$ | —H | —CH$_3$ | —CH$_3$ | MS 533(M$^+$) |
| 887 | —CF$_3$ | —H | —H | —C$_2$H$_5$ | MS 587(M$^+$) |
| 888 | —CF$_3$ | —H | —H | —CH$_3$ | MS 573(M$^+$) |
| 889 | —H | —F | —F | —CH$_3$ | $^1$H NMR (CDCl$_3$) 2.30-2.52(4H, m), 3.01(3H, s), 3.43(2H, s), 3.38-3.71(4H, m), 4.10(2H, s), 5.95(2H, s), 6.65-6.81(3H, m), 6.82-6.96(2H, m), 7.10(1H, d, J=9.1 Hz), 8.49(1H, dd, J=2.8 Hz, 9.1 Hz), 9.01(1H, d, J=2.8 Hz). |

TABLE 121

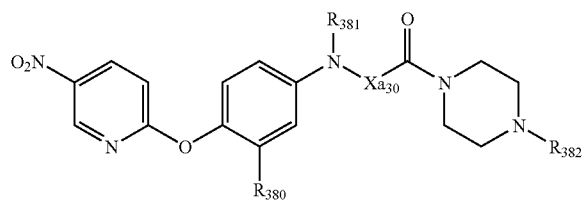

| Reference Example No. | $R_{380}$ | $R_{381}$ | $Xa_{30}$ | $R_{382}$ | mp (° C.) or $^1$H NMR (CDCl$_3$) δ ppm |
|---|---|---|---|---|---|
| 890 | —CH$_3$ | —CH$_3$ | —CH$_2$— | benzyl | $^1$H NMR 2.12(3H, s), 2.40-2.55(4H, m), 3.04(3H, s), 3.45-3.55(2H, m), 3.54(2H, s), 3.60-3.70 (2H, m), 4.10(2H, s), 6.50-6.61(2H, m), 6.91(1H, d, J=8.5 Hz), 6.92(1H, d, J=9.1 Hz), 7.22-7.40(5H, m), 8.42(1H, dd, J=9.1 Hz, 2.8 Hz), 9.05(1H, d, J=2.8 Hz). |
| 891 | —CH$_3$ | —C$_2$H$_5$ | —CH$_2$— | benzyl | mp 134-136 |
| 892 | —H | —CH$_3$ | —CH$_2$CH$_2$— | piperonyl | $^1$H NMR 2.34-2.41(4H, m), 2.56-2.61 (2H, m), 2.97(3H, s), 3.39-3.42(4H, m), 3.60-3.64 (2H, m), 3.71-3.76(2H, m), 5.94(2H, s), 6.72-6.76 (5H, m), 6.83(1H, brs), 6.97(1H, d, J=9.1 Hz), 7.02 (1H, d, J=9.1 Hz), 8.43(1H, dd, J=9.1 Hz, 2.8 Hz), 9.04(1H, d, J=2.8 Hz). |
| 893 | —CH$_3$ | —CH$_3$ | —CH(CH$_3$)— | piperonyl | $^1$H NMR 1.31(3H, d, J=6.6 Hz), 2.11 (3H, s), 2.17-2.49(4H, m), 2.78(3H, s), 3.31-3.56(3H, m), 3.39(2H, s), 3.77(1H, brs), 4.57(1H, q, J=6.6 Hz), 5.94(2H, s), 6.60-6.63(2H, m), 6.68-6.75(2H, m), 6.83(1H, brs), 6.93-6.98(2H, m), 8.44(1H, dd, J=9.1 Hz, 2.8 Hz), 9.05(1H, d, J=2.8 Hz). |
| 894 | —H | —CH$_3$ | —CH(CH$_3$)— | piperonyl | $^1$H NMR 1.32(3H, d, J=6.6 Hz), 2.19-2.50(4H, m), 2.80(3H, s), 3.30-3.56(3H, m), 3.32(2H, s), 3.78(1H, brs), 4.58(1H, q, J=6.6 Hz), 5.93(2H, s), 6.68-6.82 (3H, m), 6.77(2H, d, J=9.1 Hz), 6.98(1H, dd, J=8.6 Hz, 0.5 Hz), 7.04(2H, d, J=9.2 Hz), 8.44(1H, dd, J=9.1 Hz, 2.8 Hz), 9.05(1H, dd, J=2.8 Hz, 0.5 Hz). |
| 895 | —CH$_3$ | —H | —CO— | piperonyl | $^1$H NMR 2.15(3H, s), 2.49-2.55(4H, m), 3.45(2H, s), 3.71-3.75(2H, m), 4.25-4.28(2H, m), 5.96(2H, s), 6.75(2H, brs), 6 86(1H, brs), 7.04(1H, d, J=9.1 Hz), 7.06(1H, d, J=8.6 Hz), 7.49(1H, dd, J=8.7 Hz, 2.6 Hz), 7.61(1H, d, J=2.5 Hz), 8.48(1H, dd, J=9.1 Hz, 2.8 Hz), 9.02(1H, d, J=2.8 Hz), 9.23(1H, brs). |
| 896 | —CH$_3$ | —CH$_3$ | —CO— | piperonyl | $^1$H NMR 2.15(3H, s), 2.25-2.33(4H, m), 3.33-3.42(9H, m), 5.93(2H, s), 6.66-6.79(3H, m) 7.04-7.21(4H, m), 8.51(1H, dd, J=9.1 Hz, 2.8 Hz), 8.99(1H, dd, J=2.8 Hz, 0.5 Hz). |

TABLE 122
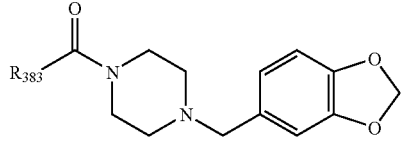
| Reference Example No. | R₃₈₃ | ¹H NMR (CDCl₃) δ ppm or MS |
|---|---|---|
| 897 | 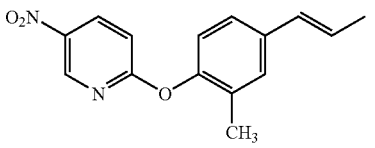 | MS 502(M⁺) |
| 898 | 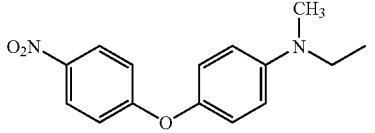 | ¹H NMR 2.44(4H, brs), 3.07(3H, s), 3.44(2H, s), 3.47-3.51 (2H, m), 3.62-3.66(2H, m), 4.12(2H, s), 5.95 (2H, s), 6.67-6.75(4H, m), 6.86(1H, s), 6.93-6.99(4H, m), 8.16(2H, d, J=9.2 Hz). |
| 899 | 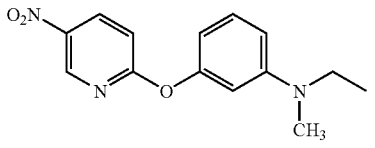 | ¹H NMR 2.42(4H, t, J=4.9 Hz), 3.04(3H, s), 3.42(2H, s), 3.44(2H, t, J=4.9 Hz), 3.62(2H, t, J=4.9 Hz), 4.11(2H, s), 5.95(2H, s), 6.42-6.44(1H, m), 6.50-6.51 (1H, m), 6.54-6.58(1H, m), 6.70-6.77(2H, m), 6.84(1H, m), 6.96(1H, d, J=9.1 Hz), 7.24-7.30(1H, m), 8.43(1H, dd, J=9.1 Hz, 2.8 Hz), 9.08(1H, d, J=2.8 Hz). |
| 900 | 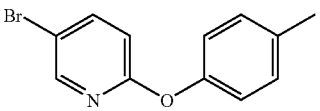 | ¹H NMR 2.44(4H, brs), 3.44(2H, s), 3.55(2H, brs), 3.73(2H, brs), 5.95(2H, s), 6.74(2H, s), 6.85(1H, s), 6.86(1H, d, J=8.6 Hz), 7.14(2H, d, J=8.6 Hz), 7.46(2H, d, J=8.6 Hz), 7.79(1H, dd, J=8.7 Hz, 2.5 Hz), 8.22(1H, d, J=2.5 Hz). |
| 901 | 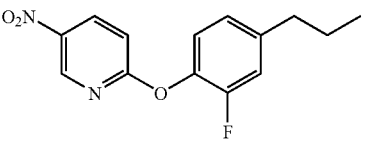 | MS 508(M⁺) |
| 902 | 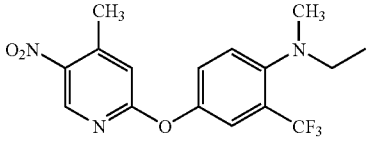 | MS 587(M⁺) |
| 903 | 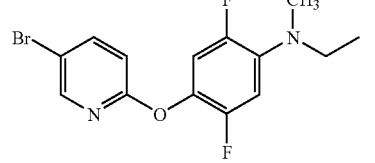 | ¹H NMR 2.31-2.50(4H, m), 2.96(3H, s), 3.42(2H, s), 3.40-3.52(2H, m), 3.53-3.67(2H, m), 4.05(2H, s), 5.95(2H, s), 6.65-6.95(6H, m), 7.77(1H, dd, J=2.5 Hz, 8.7 Hz), 8.16(1H, dd, J=0.5 Hz, 2.5 Hz). |

TABLE 123

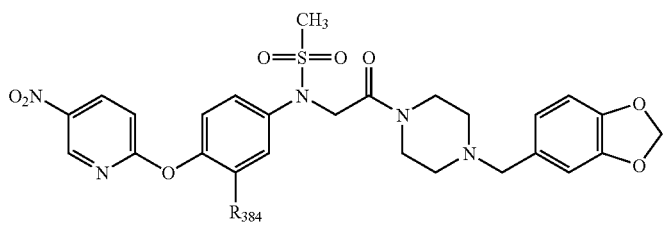

| Reference Example No. | $R_{384}$ | $^1$H NMR (CDCl$_3$) δ ppm |
|---|---|---|
| 904 | —H | 2.29-2.34(4H, m), 3.15(3H, s), 3.34-3.43(6H, m), 4.63(2H, s), 5.98(2H, s), 6.72-6.76(1H, m), 6.83-6.86(2H, m), 7.27(2H, d, J=8.9 Hz), 7.31(1H, d, J=9.3 Hz), 7.54(2H, d, J=8.9 Hz), 8.64(1H, dd, J=9.2 Hz, 2.8 Hz), 9.05(1H, d, J=2.8 Hz). |
| 905 | —CH$_3$ | 2.15(3H, s), 2.42-2.43(4H, m), 3.22(3H, s), 3.39-3.41(2H, m), 3.43(2H, s), 3.61-3.63(2H, m), 4.56(2H, s), 5.94(2H, s), 6.70-6.77(2H, m), 6.84(1H, brs), 7.06(1H, d, J 8.2 Hz), 7.07(1H, d, J=9.1 Hz), 7.48 7.52(2H, m), 8.49(1H, dd, J=9.1 Hz, 2.8 Hz), 9.01(1H, d, J=2.8 Hz). |
| 906 | —OCH$_3$ | 2.42-2.46(4H, m), 3.24(3H, s), 3.40(2H, brs), 3.43(2H, s), 3.63(2H, brs), 3.74(3H, s), 4.58(2H, s), 5.94(2H, s), 6.70-6.77(2H, m), 6.84(1H, s), 7.06-7.14(2H, m), 7.23-7.28(1H, m), 7.32(1H, d, J=2.3 Hz), 8.47(1H, dd, J=9.1 Hz, 2.8 Hz), 8.98(1H, d, J=2.8 Hz). |

TABLE 124

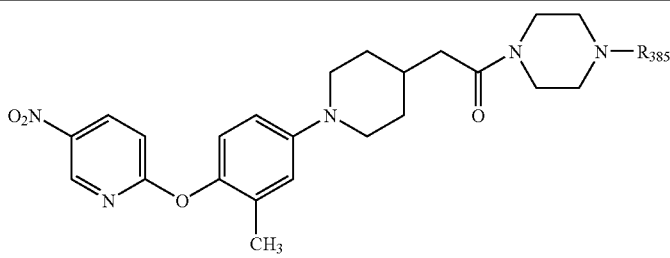

| Reference Example No. | $R_{385}$ | $^1$H NMR (CDCl$_3$) δ ppm |
|---|---|---|
| 907 | piperonyl | 1.33-1.46(2H, m), 1.86-2.OO(3H, m), 2.10(3H, s), 2.29(2H, d, J=6.8 Hz), 2.39-2.43 (4H, m), 2.75(2H, t, J=12.2 Hz), 3.40-3.48(4H, m), 3.62-3.66(4H, m), 5.94(2H, s), 6.73-6.85(5H, m), 6.91-6.96(2H, m), 8.43(1H, dd, J=9.1 Hz, 3.0 Hz), 9.04(1H, d, J=2.8 Hz). |
| 908 | benzyl | 1.35-1.46(2H, m), 1.86-2.00(3H, m), 2.10(3H, s), 2.29(2H, d, J=6.8 Hz), 2.41-2.45 (4H, m), 2.75(2H, t, J=12.2 Hz), 3.47-3.53(4H, m), 3.61-3.65(4H, m), 6.79-6.96(4H, m), 7.24-7.33(5H, m), 8.43(1H, dd, J= 9.1 Hz, 2.8 Hz), 9.05(1H, d, J=2.8 Hz). |

Reference Example 909

Production of (4-benzylpiperazin-1-yl){4-[methyl(5-nitropyridin-2-yl)amino]phenyl}methanone To a solution of 4-[methyl-(5-nitropyridin-2-yl)amino] benzoic acid (0.800 g, 2.93 mmol) and 1-benzylpiperazine (0.542 g, 3.08 mmol) in DMF (15 mL) were added triethylamine (1.02 mL, 7.32 mmol) and diethyl cyanophosphonate (0.593 mL, 3.52 mmol), and the resulting solution was stirred for 3 hours. To the resulting reaction solution was added water and extracted with ethyl acetate. The ethyl acetate layer was washed with brine, dried over anhydrous sodium sulfate, evaporated, and the residue was purified by silica gel column chromatography (ethyl acetate), to thereby yield 1.25 g of the title compound.

Appearance: Yellow amorphous powder $^1$H NMR (CDCl$_3$) δ 2.25-2.65 (4H, m), 3.49 (2H, brs), 3.56 (2H, s), 3.57 (3H, s), 3.81 (2H, brs), 6.43 (1H, d, J=9.5 Hz), 7.25-7.35 (7H, m), 7.53 (2H, d, J=8.4 Hz), 8.06 (1H, dd, J=2.8 Hz, 9.5 Hz), 9.12 (1H, d, J=2.8 Hz).

The following compounds were produced in the same manner as in Reference Example 909.

TABLE 125

[Structure: O₂N-pyridine-Xa₃₁-phenyl(R₃₈₄)-Xa₃₂-C(O)-piperazine-CH₂-benzodioxole, repeated M times]

| Reference Example No. | Xa₃₁ | R₃₈₆ | Xa₃₂ | M | $^1$H NMR (DMSO-d$_6$) δ ppm |
|---|---|---|---|---|---|
| 910 | —NH— | —H | —CH$_2$— | 1 | 2.20-2.30(4H, m), 2.59(2H, t, J=7.3 Hz), 2.78(2H, t, J=7.3 Hz), 3.35(2H, s), 3.36-3.45(4H, m), 5.98(2H, s), 6.72 (1H, dd, J=1.3 Hz, 7.9 Hz), 6.80-6.90(3H, m), 7.21(2H, d, J= 8.4 Hz), 7.57(2H, d, J=8.4 Hz), 8.26(1H, dd, J= 2.9 Hz, 9.3 Hz), 9.01(1H, d, J=2.9 Hz), 10.06(1H, s). |
| 911 | —O— | —H | —NH— | 1 | 2.32(2H, brs), 2.39(2H, brs), 3.41(2H, s), 3.50(4H, brs), 3.91(2H, d, J 5.2 Hz), 5.68(1H, t, J=5.2 Hz), 5.99(2H, s), 6.70(2H, d, J=8.9 Hz), 6.74-6.77(1H, m), 6.83-6.88 (2H, m), 6.94(2H, d, J=8.9 Hz), 7.11(1H, d, J=9.1 Hz), 8.56(1H, dd, J 2.9 Hz, 9.1 Hz), 9.02(1H, d, J= 2.9 Hz). |
| 912 | —O— | —OCH$_3$ | —NH— | 2 | 2.48(2H, brs), 2.49(2H, brs), 3.39(2H, s), 3.50(4H, brs), 3.63(3H, s), 3.92(2H, d, J=4.8 Hz), 4.22(4H, s), 5.65(1H, brt), 6.22(1H, dd, J= 8.6 Hz, 2.5 Hz), 6.51(1H, d, J=2.5 Hz), 6.73-6.81(3H, m), 6.89(1H, d, J 8.6 Hz), 7.07(1H, d, J=9.1 Hz), 8.54(1H, dd, J=9.1 Hz, 2.8 Hz), 9.00(1H, d, J=2.8 Hz). |

Reference Example 913

Production of N-(4-(5-nitropyridin-2-yloxy)phenyl]-N-[2-(4-piperonylpiperazin-1-yl)-2-oxoethyl]acetamide To a solution of ethyl{acetyl[4-(5-nitropyridin-2-yloxy)phenyl]amino}acetate (2.30 g, 6.40 mmol) in ethanol (50 mL) was added 5 M aqueous sodium hydroxide (1.92 mL, 9.60 mmol), and the resulting solution was stirred at room temperature for 30 minutes. To this reaction solution were added 5 M hydrochloric acid (2 mL) and water, and extracted with ethyl acetate. The ethyl acetate layer was washed with brine, dried over anhydrous sodium sulfate, evaporated, and the obtained residue was purified by silica gel column chromatography (n-hexane:ethyl acetate=1:1), to thereby yield 1.68 g of an oil. To a solution of this oil in DMF (10 mL) were added 1-piperonylpiperazine (1.29 g, 5.86 mmol), triethylamine (1.85 mL, 13.3 mmol) and diethyl cyanophosphonate (1.07 mL, 6.36 mmol), and the resulting solution was stirred for 1 hour at room temperature. To this reaction solution was added water and extracted with ethyl acetate. The ethyl acetate layer was washed with brine, dried over anhydrous sodium sulfate, evaporated, and the residue was purified by silica gel column chromatography (dichloromethane:methanol=30:1), to thereby yield 2.21 g of the title compound.

Appearance: Yellow amorphous powder $^1$H NMR (CDCl$_3$) δ 1.98 (3H, s), 2.40-2.50 (4H, m), 3.40-3.45 (4H, m), 3.62 (2H, brs), 4.48 (2H, s), 5.94 (2H, s), 6.70-6.76 (2H, m), 6.85 (1H, s), 7.09 (1H, d, J=9.1 Hz), 7.20 (2H, d, J=8.7 Hz), 7.51 (2H, d, J=8.7 Hz), 8.51 (1H, dd, J=2.8 Hz, 9.1 Hz), 9.04 (1H, d, J=2.8 Hz).

The following compounds were produced in the same manner as in Reference Example 913.

TABLE 126

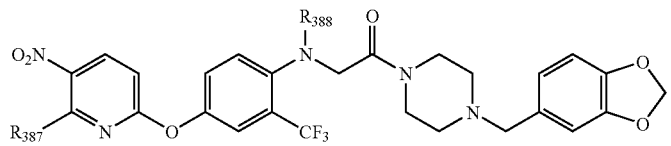

| Reference Example No. | R₃₈₇ | R₃₈₈ | MS (M⁺) |
|---|---|---|---|
| 914 | —CH$_3$ | —CH$_3$ | 587 |
| 915 | —H | —C$_2$H$_5$ | 587 |

Reference Example 916

Production of 3-[3-methoxy-4-(5-nitropyridin-2-yloxy)phenyl]-1-(4-piperonylpiperazin-1-yl)propan-1-one 3-[3-methoxy-4-(5-nitropyridin-2-yloxy)phenyl]propionic acid (3.18 g, 10 mmol) was dissolved in dichloromethane (30 mL). To the resulting solution were added thionyl chloride (0.88 mL, 12 mmol) and DMF (1 drop), and refluxed for 2 hours. The reaction solution was concentrated under reduced pressure, and the residue was dissolved in dichloromethane (20 mL). To the resulting solution were added triethylamine (1.67 mL, 12 mmol) and a solution of 1-piperonylpiperazine (2.20 g, 10 mmol) in dichloromethane (30 mL) under ice cooling, and the resulting solution was stirred for 1 hour at 0° C. The resulting reaction solution was washed with water and brine. The organic layer was dried over anhydrous magnesium sulfate, and evaporated. The residue was recrystallized from ethyl acetate, to thereby yield 4.95 g of the title compound.

Appearance: Pale yellow powder $^1$H NMR (CDCl$_3$) δ 2.33-2.42 (4H, m), 2.63-2.69 (2H, m), 2.97-3.03 (2H, m), 3.42 (4H, brs), 3.62-3.66 (2H, m), 3.74 (3H, s), 5.95 (2H, s), 6.73-6.75 (2H, m), 6.85-6.90 (3H, m), 7.04 (1H, d, J=9.1 Hz), 7.06 (1H, d, J=7.9 Hz), 8.45 (1H, dd, J=9.1 Hz, 2.8 Hz), 9.01 (1H, d, J=2.8 Hz).

The following compound was produced in the same manner as in Reference Example 916.

Reference Example 917

6-Chloro-N-(4-trifluoromethylphenyl)nicotinamide $^1$H NMR (DMSO-d$_6$) 67.74 (1H, d, J=8.4 Hz), 7.76 (2H, d, J=8.7 Hz), 8.00 (2H, d, J=8.7 Hz), 8.38 (1H, dd, J=8.7 Hz, 2.5 Hz), 8.97 (1H, d, J=2.5 Hz), 10.80 (1H, brs).

Reference Example 918

Production of 3-{3-methoxy-4-[methyl(5-nitropyridin-2-yl)amino]phenyl}-1-(4-piperonylpiperazin-1-yl)propan-1-one To a solution of ethyl 3-{3-methoxy-4-[methyl-(5-nitropyridin-2-yl)amino]phenyl}propionate (3.85 g, 11 mmol) in ethanol (80 mL) was added 2 N aqueous sodium hydroxide (6.4 mL, 13 mmol), and the resulting solution was stirred at room temperature for 2.5 hours. To the resulting reaction solution was added 6 N hydrochloric acid (2.2 mL, 13 mmol), and the solvent was removed under reduced pressure. To the residue were added THF (80 mL) and N,N'-carbonyldiimidazole (2.08 g, 13 mmol), and the resulting solution was stirred at room temperature for 3 hours. To the resulting reaction solution were added 1-piperonylpiperazine (2.60 g, 12 mmol) and DMF (40 mL), and stirred at room temperature for 21 hours. The solvent was evaporated under reduced pressure, and the residue was extracted with ethyl acetate. The ethyl acetate layer was washed with a saturated sodium bicarbonate solution, dried over anhydrous magnesium sulfate, evaporated, and the residue was purified by silica gel column chromatography (ethyl acetate), to thereby yield 4.59 g of the title compound.

Appearance: Yellow powder $^1$H NMR (CDCl$_3$) δ 2.36-2.43 (4H, m), 2.64-2.70 (2H, m), 2.99-3.05 (2H, m), 3.42-3.46 (7H, m), 3.63-3.67 (2H, m), 3.77 (3H, s), 5.95 (2H, s), 6.12 (1H, brd, J=9.1 Hz), 6.70-6.77 (2H, m), 6.85-6.90 (3H, m), 7.12 (1H, d, J=8.1 Hz), 7.97-8.01 (1H, m), 9.11 (1H, d, J=2.6 Hz).

Reference Example 919

Production of 5-{methyl[2-oxo-2-(4-piperonylpiperazin-1-yl)ethyl]amino}-2-(5-nitropyridin-2-yloxy)-benzonitrile To a solution of t-butyl 2-((3-cyano-4-(5-nitropyridin-2-yloxy)phenyl)(methyl)amino)acetate (1.2 g, 3.1 mmol) in dichloromethane (12 mL) was added trifluoroacetic acid (12 mL), and the resulting reaction solution was stirred at room temperature for 5 hours. The solvent was evaporated, and water was added to the residue, and extracted with ethyl acetate. The ethyl acetate layer was dried over anhydrous magnesium sulfate, and evaporated, to thereby yield crude 2-((3-cyano-4-(5-nitropyridin-2-yloxy)phenyl)(methyl)amino)-acetic acid. To a solution of this compound in DMF (24 mL) were added 1-ethyl-3-(3-dimethylaminopropyl)-carbodiimide hydrochloride (659 mg, 3.4 mmol), 1-hydroxybenzotriazole monohydrate (526 mg, 3.4 mmol) and 1-piperonylpiperazine (757 mg, 3.4 mmol), and the resulting reaction solution was stirred for 8 hours at room temperature. Water was added to the reaction solution and extracted with ethyl acetate. The ethyl acetate layer was then washed with, in order, saturated aqueous sodium bicarbonate solution, water and brine. The ethyl acetate layer was dried over anhydrous magnesium sulfate, and evaporated. The residue was purified by silica gel chromatography (ethyl acetate), to thereby yield 412 g of the title compound.

Appearance: Yellow amorphous powder $^1$H NMR (CDCl$_3$) δ 2.40-2.55 (4H, m), 3.09 (3H, s), 3.45-3.50 (4H, m), 3.55-3.70 (2H, m), 4.14 (2H, s), 5.95 (2H, s), 6.70-6.80 (2H, m), 6.80-6.95 (3H, m), 7.10-7.20 (2H, m), 8.50 (1H, dd, J=9.1 Hz, 2.8 Hz), 8.99 (1H, d, J=2.8 Hz).

Reference Example 920

Production of 2-{(2,3-difluoro-4-t-butoxycarbonylamino)phenoxy}-5-nitropyridine

To a solution of {2,3-difluoro-4-(5-nitropyridin-2-yloxy)}benzoic acid (1.22 g, 4.1 mmol) in t-butanol (50 mL) were added diphenylphosphorylazide (0.98 mL, 4.5 mmol) and triethylamine (0.63 mL, 4.5 mmol), and the resulting solution was refluxed for 4 hours under a nitrogen atmosphere. After cooling, water was added to the reaction solution and extracted with ethyl acetate. The ethyl acetate layer was washed with water, dried over anhydrous magnesium sulfate, and evaporated. The residue was purified by silica gel column chromatography (n-hexane:ethyl acetate=6:1), to thereby yield 1.2 g of the title compound.

Appearance: White powder $^1$H NMR (CDCl$_3$) δ 1.54 (9H, s), 6.59-6.78 (1H, m), 6.90-7.04 (1H, m), 7.13 (1H, d, J=9.0 Hz), 7.84-8.02 (1H, m), 8.51 (1H, dd, J=2.8 Hz, 9.0 Hz), 8.99 (1H, d, J=2.8 Hz).

Reference Example 921

Production of 3,4-dichloro-N-[3-fluoro-4-(4-formylphenoxy)phenyl]benzamide 3,4-Dichloro-N-[4-(4-[1,3]dioxolane-2-ylphenoxy)-3-fluorophenyl]benzamide (17.4 g, 38.9 mmol) was added to 80% acetic acid, and the resulting solution was stirred for 1.5 hours at 80° C. The reaction solution was concentrated under reduced pressure, wherein the obtained residue was recrystallized from 80% ethanol to thereby yield 12.8 g of the title compound.
Appearance: Pale yellow powder
$^1$H NMR (DMSO-$d_6$) δ 7.13 (2H, d, J=8.6 Hz), 3.40 (1H, t, J=9.0 Hz), 7.63 (1H, d, J=9.0 Hz), 7.85 (1H, d, J=8.4 Hz), 7.90-8.00 (4H, m), 8.22 (1H, d, J=1.9 Hz), 9.93 (1H, s), 10.67 (1H, s).

Reference Example 922

Production of N-[6-(4-aminophenoxy)pyridin-3-yl]-3,4-dichlorobenzamide dihydrochloride t-Butyl{4-[5-(3,4-dichlorobenzoylamino)-pyridin-2-yloxy]phenyl}carbamate (4.31 g, 9.09 mmol) was dissolved in a mixed solution of chloroform-methanol-ethyl acetate. The resulting solution was concentrated to a volume of about 20 mL. To the residue solution was added a solution of 4 N hydrogen chloride in ethyl acetate (70 mL), and left to cool for 2 hours at room temperature. The precipitated white powder was filtered, and washed with ethyl acetate, to thereby yield 4.04 g of the title compound.
Appearance: White powder
$^1$H NMR (DMSO-$d_6$) δ 5.20 (2H, brs), 7.14 (1H, d, J=8.5 Hz), 7.25 (2H, d, J=8.9 Hz), 7.42 (2H, d, J=8.9 Hz), 7.84 (1H, d, J=8.5 Hz), 7.97 (1H, dd, J=8.5 Hz, 2.0 Hz), 8.24 (1H, dd, J=8.5 Hz, 2.6 Hz), 8.25 (1H, d, J=2.0 Hz), 8.51 (1H, d, J=2.6 Hz), 10.65 (1H, s).

The following compounds were produced in the same manner as in Reference Example 922.

Reference Example 926

Production of 4-(tetrahydropyran-2-yloxy)benzylamine

To a solution of lithium aluminum hydride (2.66 g, 70 mmol) in THF (200 mL) was added dropwise under ice cooling a solution of 4-(tetrahydropyran-2-yloxy)benzonitrile in THF (70 mL). The resulting solution was then refluxed for 1 hour. The resulting reaction solution was again cooled with ice, and then to the solution was added dropwise, in order, water (2.66 mL), 1 N aqueous sodium hydroxide (2.66 mL) and water (7.98 mL). Insoluble matter was removed by filtration. The filtrate was concentrated under reduced pressure, after which the residue was purified by silica gel column chromatography (chloroform:methanol=7:1), to thereby yield 11.41 g of the title compound.
Appearance: Colorless oil
$^1$H NMR (CDCl$_3$) δ 1.56 (2H, s), 1.45-1.78 (3H, m), 1.78-2.12 (3H, m), 3.53-3.66 (1H, m), 3.80 (2H, s), 3.84-3.99 (1H, m), 5.41 (1H, t, J=3.2 Hz), 7.02 (2H, d, J=8.7 Hz), 7.22 (2H, d, J=8.7 Hz).

Reference Example 927

Production of 4-(2-fluoro-4-nitrophenoxy)phenylamine hydrochloride

N-[4-(2-fluoro-4-nitrophenoxy)phenyl]-acetamide (1.00 g, 3.45 mmol) was added to 6 M hydrochloric acid (10 mL), and the resulting solution was refluxed for 2 hours. The resulting reaction solution was concentrated under reduced pressure, to thereby yield 0.910 g of the title compound.

TABLE 127

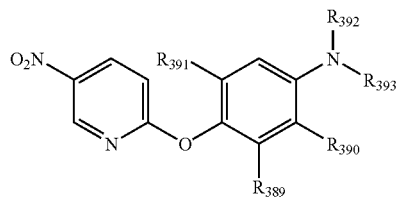

| Reference Example No. | $R_{389}$ | $R_{390}$ | $R_{391}$ | $R_{392}$ | $R_{393}$ | $^1$H NMR (CDCl$_3$) δ ppm or MS |
|---|---|---|---|---|---|---|
| 923 | —F | —H | —F | —H | —CH$_3$ | $^1$H NMR 2.83(3H, d, J=5.2 Hz), 3.90-4.05 (1H, m), 6.18-6.27(2H, m), 7.15(1H, d, J=9.0 Hz), 8.49(1H, dd, J=2.8 Hz, 9.0 Hz), 9.02(1H, d, J=2.8Hz). |
| 924 | —F | —F | —H | —H | —CH$_3$ | $^1$H NMR 2.92(3H, d, J=3.8 Hz), 3.90-4.16 (1H, m), 6.46(1H, td, J=2.2 Hz, 8.8 Hz), 6.89(1H, td, J 2.4 Hz, 7.8 Hz), 7.08(1H, d, J=9.0 Hz), 8.49(1H, dd, J=2.8 Hz, 9.0 Hz), 9.02(1H, d, J=2.8 Hz). |
| 925 | —COOCH$_3$ | —H | —H | —CH$_2$COOH | —C$_2$H$_5$ | MS 375(M$^+$) |

Appearance: Pale yellow powder $^1$H NMR (DMSO-d$_6$) δ 3.40-4.00 (2H, m), 7.18 (1H, t, J=8.7 Hz), 7.24 (2H, d, J=8.9 Hz), 7.32 (2H, d, J=8.9 Hz), 8.10 (1H, ddd, J=1.4 Hz, 2.6 Hz, 8.9 Hz), 8.35 (1H, dd, J=2.6 Hz, 10.8 Hz).

Reference Example 928

Production of {4-[5-(3,4-dichlorobenzoylamino)pyridin-2-yloxy]phenyl}carbamate phenyl ester To a suspension of N-[6-(4-aminophenoxy)pyridin-3-yl]-3,4-dichlorobenzamide dihydrochloride (700 mg, 1.57 mmol) in THF (20 mL) was added triethylamine (1.1 mL, 7.89 mmol). To the resulting solution was then added dropwise phenyl chlorocarbonate (0.39 mL, 3.14 mmol) under ice cooling. The resulting reaction solution was stirred for 1 hour at room temperature. Water was added to the residue, and extracted with ethyl acetate. The ethyl acetate layer was washed with a saturated sodium bicarbonate solution and brine. The ethyl acetate layer was dried over anhydrous magnesium sulfate, and evaporated, whereupon the residue solidified into a powder. The powder was filtered, and washed with diethyl ether, to thereby yield 470 mg of the title compound.

Appearance: White powder $^1$H NMR (DMSO-d$_6$) δ 7.04 (1H, d, J=8.9 Hz), 7.11 (2H, d, J=8.9 Hz), 7.19-7.31 (3H, m), 7.38-7.49 (2H, m), 7.53 (2H, d, J=8.0 Hz), 7.84 (1H, d, J=8.4 Hz), 7.95 (1H, dd, J=8.4 Hz, 2.0 Hz), 8.18 (1H, dd, J=8.9 Hz, 2.2 Hz), 8.22 (1H, d, J=2.0 Hz), 8.47 (1H, d, J=2.2 Hz), 10.26 (1H, s), 10.54 (1H, s).

The following compounds were produced in the same manner as in Reference Example 928.

Reference Example 932

Production of 4-piperonylpiperazine-1-carboxylic acid [4-(2-fluoro-4-nitrophenoxy)phenyl]amide To a solution of [4-(2-fluoro-4-nitrophenoxy)phenyl]carbamate phenyl ester (0.700 g, 1.90 mmol) in DMF (15 mL) was added 1-piperonylpiperazine (0.460 g, 2.09 mmol), and the resulting solution was stirred for 2 hours at room temperature. water was added to the resulting reaction solution, and extracted with ethyl acetate. The ethyl acetate layer was washed with brine. The ethyl acetate layer was dried over anhydrous sodium sulfate, and evaporated, to thereby yield 0.939 g of the title compound.

Appearance: Yellow oil $^1$H NMR (DMSO-d$_6$) δ 2.30-2.40 (4H, m), 3.35-3.50 (6H, m), 6.00 (2H, s), 6.70-6.90 (2H, m), 7.00-7.15 (2H, m), 7.55 (2H, d, J=9.1 Hz), 8.05-8.10 (1H, m), 8.30 (1H, dd, J=2.8 Hz, 10.9 Hz), 9.31 (1H, s).

The following compounds were produced in the same manner as in Reference Example 932.

Reference Example 933

Ethyl 3-(4-{5-[3-(3,4-dichlorophenyl)-3-ethylureido]-pyridin-2-yloxy}phenyl)propionate

MS 501 (M$^+$).

TABLE 128

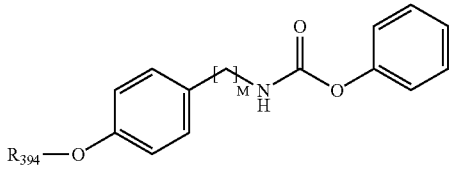

| Reference Example No. | R$_{394}$ | M | $^1$H NMR (solvent) δ ppm |
|---|---|---|---|
| 929 | 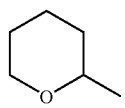 | 0 | (DMSO-d$_6$) 7.08(1H, t, J=8.7 Hz), 7.15-7.30(5H, m), 7.35-7.50(2H, m), 7.60(2H, d, J=8.9 Hz), 8.07(1H, dd, J=1.1 Hz, 9.0 Hz), 8.31(1H, dd, J 2.6 Hz, 10.9 Hz), 10.36(1H, s). |
| 930 | 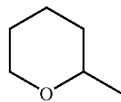 | 0 | (CDCl$_3$) 1.50 1.80(3H, m), 1.80-2.15(3H, m), 3.55-3.67(1H, m), 3.85-4.00(1H, m), 5.37(1H, t, J=3.3 Hz), 6.83(1H, brs), 7.03(2H, d, J 9.1 Hz), 7.14-7.30(3H, m), 7.30-7.47(4H, m). |
| 931 | | 1 | (CDCl$_3$) 1.50-1.79(3H, m), 1.79-2.15(3H, m), 3.55 3.60(1H, m), 3.82-4.00(1H, m), 3.39(2H, d, J=6.0 Hz), 5.26(1H, brs), 5.42(1H, t, J=3.1 Hz), 7.05(2H, d, J=8.7 Hz), 7.27(2H, d, J=8.7 Hz), 7.10-7.40(5H, m). |

TABLE 129

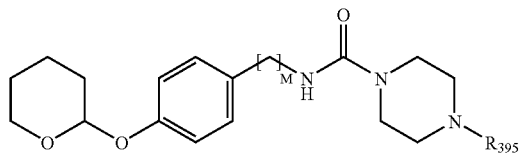

| Reference Example No. | $R_{395}$ | M | $^1$H NMR (CDCl$_3$) δ ppm |
|---|---|---|---|
| 934 | benzyl | 0 | 1.50-1.87(3H, m), 1.87-2.15(3H, m), 2.48(4H, t, J=5.1 Hz), 3.48(4H, t, J=5.1 Hz), 3.54(2H, s), 3.50-3.65(1H, m), 3.85-4.00(1H, m), 5.34(1H, t, J=3.2 Hz), 6.21(1H, brs), 6.98(2H, d, J 8.9 Hz), 7.22(2H, d, J=8.9 Hz), 7.25-7.38 (5H, m). |
| 935 | piperonyl | 1 | 1.48-1.77(3H, m), 1.77-2.11(3H, m), 2.40(4H, t, J=5.0 Hz), 3.36(4H, t, J=5.0 Hz), 3.41(2H, s), 3.50-3.67(1H, m), 3.81-3.96(1H, m), 4.34(2H, d, J=5.1 Hz), 4.61(1H, t, J=5.1 Hz), 5.40(1H, t, J 3.2 Hz), 5.94(2H, s), 6.74(2H, s), 6.84(1H, s), 7.00(2H, d, J=8.6 Hz), 7.22(2H, d, J=8.6 Hz). |

Reference Example 936

Production of 4-piperonylpiperazine-1-carboxylic acid 4-hydroxybenzylamide

To a solution of 4-piperonylpiperazine-1-carboxylic acid 4-(tetrahydropyran-2-yloxy)benzylamide (1.1 g, 2.43 mmol) in methanol (50 mL) was added p-toluenesulfonic acid monohydrate (1.0 g, 5.26 mmol), and the resulting solution was stirred for 1 hour at room temperature. The resulting reaction solution was concentrated under reduced pressure. Water was added to the residue, and extracted with ethyl acetate. The ethyl acetate layer was washed with a saturated sodium bicarbonate solution and brine. The ethyl acetate layer was dried over anhydrous magnesium sulfate, and evaporated, to thereby yield 330 mg of the title compound.
Appearance: White powder
$^1$H NMR (CDCl$_3$) δ 2.41 (4H, t, J=5.0 Hz), 3.37 (4H, t, J=5.0 Hz), 3.42 (2H, s), 4.32 (2H, d, J=5.2 Hz), 4.68 (1H, t, J=5.2 Hz), 5.94 (2H, s), 6.15 (1H, brs), 6.70-6.80 (2H, m), 6.75 (2H, d, J=8.6 Hz), 6.84 (1H, s), 7.13 (2H, d, J=8.6 Hz).

The following compound was produced in the same manner as in Reference Example 936.

Reference Example 937

4-Benzylpiperazine-1-carboxylic acid (4-hydroxyphenyl)methylamide hydrochloride $^1$H NMR (DMSO-d$_6$) δ 2.69-2.91 (2H, m), 3.03 (3H, s), 2.92-3.23 (4H, m), 3.68 (2H, d, J=13.7 Hz), 4.26 (2H, s), 6.75 (2H, d, J=8.7 Hz), 6.98 (2H, d, J=8.7 Hz), 7.45 (3H, brs), 7.54 (2H, brs), 9.52 (1H, s).

Reference Example 938

Production of 3,4-dichloro-N-{6-[4-(3-hydroxypropyl)-phenoxy]pyridin-3-yl}benzamide To 2-{4-[3-(t-butyldimethylsilanyloxy)propyl]phenoxy}-5-nitropyridine (950 mg, 1.8 mmol) were added acetic acid (10 mL) and water (5 mL), and the resulting solution was stirred for 1 hour at room temperature. The resulting reaction solution was concentrated under reduced pressure. Water was added to the residue, and extracted with ethyl acetate. The ethyl acetate layer was washed with a saturated sodium bicarbonate solution and brine. The ethyl acetate layer was dried over anhydrous magnesium sulfate, and evaporated. The residue was recrystallized from ethyl acetate, to thereby yield 520 mg of the title compound.
Appearance: White prisms
$^1$H NMR (DMSO-d$_6$) δ 1.70-1.78 (2H, m), 2.59-2.65 (2H, m), 3.32-3.47 (2H, m), 4.46-4.49 (1H, m), 7.00-7.05 (3H, m), 7.23 (2H, d, J=8.2 Hz), 7.84 (1H, d, J=8.2 Hz), 7.95 (1H, dd, J=8.3 Hz, 2.0 Hz), 8.16-8.22 (2H, m), 8.48 (1H, d, J=2.6 Hz), 10.54 (1H, s).

The following compound was produced in the same manner as in Reference Example 938.

Reference Example 939

3,4-Dichloro-N-{6-[4-(2-hydroxyethyl)phenoxy]pyridin-3-yl}benzamide $^1$H NMR (DMSO-d$_6$) δ 2.73 (2H, t, J=6.9 Hz), 3.59-3.66 (2H, m), 4.65 (1H, t, J=5.3 Hz), 7.00-7.06 (3H, m), 7.25 (2H, d, J=8.3 Hz), 7.84 (1H, d, J=8.3 Hz), 7.95 (1H, dd, J=8.3 Hz, 2.0 Hz), 8.16-8.23 (2H, m), 8.47 (1H, d, J=2.6 Hz), 10.54 (1H, s).

Reference Example 940

Production of 3,4-dichloro-N-{6-[4-(5-hydroxypentyl)-phenoxy]pyridin-3-yl}benzamide To a solution of ethyl 5-{4-[5-(3,4-dichloro-benzoylamino)pyridin-2-yloxy]phenyl}pentanoate (8.79 g, 18.0 mmol) in THF (140 mL) was added sodium borohydride (3.14 g, 144 mmol), and the resulting solution was refluxed for 3 hours under a nitrogen atmosphere. The resulting reaction solution was cooled with ice, and treated with 1 N hydrochloric acid. The resulting solution was extracted with ethyl acetate. The ethyl acetate layer was washed with a saturated sodium bicarbonate solution and brine. The ethyl acetate layer was dried over anhydrous magnesium sulfate, and evaporated. The residue was purified by silica gel column chromatography (n-hexane:ethyl acetate=1:2), to thereby yield 7.07 g of the title compound.

Appearance: White powder $^1$H NMR (CDCl$_3$) δ 1.25-1.75 (7H, m), 2.62 (2H, t, J=7.6 Hz), 3.65 (2H, t, J=6.6 Hz), 6.92 (1H, d, J=8.5 Hz), 7.02 (2H, d, J=8.5 Hz), 7.19 (2H, d, J=8.5 Hz), 7.56 (1H, d, J=8.5 Hz), 7.69 (1H, dd, J=8.5 Hz, 2.0 Hz), 7.93 (1H, s), 7.97 (1H, d, J=2.0 Hz), 8.15 (1H, dd, J=8.5 Hz, 2.5 Hz), 8.22 (1H, d, J=2.5 Hz).

The following compounds were produced in the same manner as in Reference Example 940.

TABLE 130

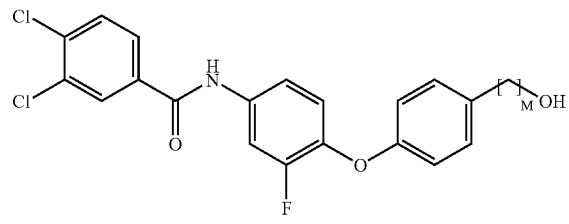

| Reference Example No. | M | mp (° C.) |
|---|---|---|
| 941 | 1 | 162–163 |
| 942 | 2 | 104–105 |
| 943 | 3 | 111–113 |
| 944 | 4 | 102–104 |

Reference Example 948

Production of 4-cyano-N-[6-(4-hydroxymethylphenoxy)-pyridin-3-yl]benzamide

A suspension of 4-[5-(4-cyanobenzoylamino)-pyridin-2-yloxy]benzoic acid (1.80 g, 5.01 mmol) in THF (20 mL) was cooled with ice-common salt, and to the solution was added triethylamine (0.77 mL, 5.51 mmol), and then ethyl chlorformate (0.53 mL, 5.51 mmol). The resulting solution was stirred at room temperature. Thirty minutes later, the reaction solution was filtered and insoluble matter was removed. The resulting filtrate was poured while stirring under ice cooling into an aqueous solution of sodium borohydride (0.95 g, 25.05 mmol) in 80% methanol (40 mL). After stirring for 30 minutes at room temperature, water (200 mL) was added to the reaction solution. The obtained mixture was extracted with ethyl acetate (200 mL). The ethyl acetate layer was washed with brine, dried over anhydrous sodium sulfate, and evaporated under reduced pressure. The residue was recrystallized from a mixed solution of ethyl acetate-n-hexane, to thereby yield 1.26 g of the title compound.

Appearance: Slightly yellow powder $^1$H NMR (DMSO-d$_6$) δ 4.50 (2H, d, J=5.3 Hz), 5.19 (1H, t, J=5.6 Hz), 7.04-7.09 (3H, m), 7.35 (2H, d, J=8.6 Hz), 8.04 (2H, d, J=8.9 Hz), 8.12 (2H, d, J=8.6 Hz), 8.21 (1H, dd, J=8.9 Hz, 2.6 Hz), 8.49 (1H, d, J 2.3 Hz), 11.63 (1H, s).

The following compounds were produced in the same manner as in Reference Example 948.

TABLE 131

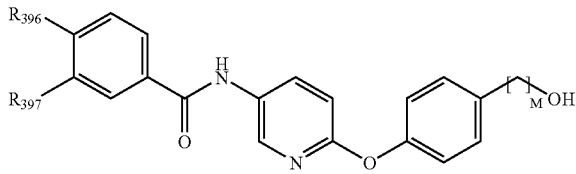

| Reference Example No. | R$_{396}$ | R$_{397}$ | M | $^1$H NMR (DMSO-d$_6$) δ ppm |
|---|---|---|---|---|
| 945 | —Cl | —Cl | 1 | 4.49(2H, d, J=5.6 Hz), 5.17(1H, brs), 7.03- 7.08(3H, m), 7.35(2H, d, J=8.6 Hz), 7.84(1H, d, J=8.6 Hz), 7.93- 7.97(1H, m), 8.17- 8.22(2H, m), 8.47(1H, d, J=2.6 Hz), 10.53(1H, s). |
| 946 | —CF$_3$ | —H | 1 | 4.50(2H, d, J=5.7 Hz), 5.18(1H, t, J=5.7 Hz), 7.04- 7.09(3H, m), 7.35 (2H, d, J=8.4 Hz), 7.93(2H, d, J=8.4 Hz), 8.15- 8.24(3H, m), 8.50(1H, d, J=2.7 Hz), 10.61(1H, s). |
| 947 | —Cl | —Cl | 4 | 1.35- 1.70(4H, m), 2.59(2H, t, J=7.5 Hz), 3.42(2H, q, J= 6.0 Hz), 4.37 (1H, t, J=5.5 Hz), 7.02(2H, d, J=8.2 Hz), 7.04(1H, d, J=8.6 Hz), 7.22 (2H, d, J=8.2 Hz), 7.84(1H, d, J=8.2 Hz), 7.94(1H, dd, J=8.2 Hz, 2.0 Hz), 8.18(1H, dd, J=8.9 Hz, 2.6 Hz), 8.22(1H, d, J=2.0 Hz), 8.47(1H, d, J=2.6 Hz), 10.53(1H, s). |

Reference Example 949

4-Chloro-N-[6-(4-hydroxymethylphenoxy)pyridin-3-yl]benzamide $^1$H NMR (DMSO-$d_6$) δ 4.50 (2H, d, J=5.3 Hz), 5.18 (1H, t, J=5.6 Hz), 7.03-7.08 (3H, m), 7.35 (2H, d, J=8.6 Hz), 7.63 (2H, d, J=8.6 Hz), 8.00 (2H, d, J=8.6 Hz), 8.20 (1H, dd, J=8.9 Hz, 2.6 Hz), 8.48 (1H, d, J=2.3 Hz), 10.46 (1H, s).

silica gel column chromatography (n-hexane:ethyl acetate=10:1), to thereby yield 1.34 g of the title compound.

Appearance: White powder $^1$H NMR (CDCl$_3$) δ 2.08 (3H, d, J=6.9 Hz), 5.26 (1H, q, J=6.9 Hz), 7.05 (1H, d, J=9.1 Hz), 7.15 (2H, d, J=8.6 Hz), 7.53 (2H, d, J=8.7 Hz), 8.49 (1H, dd, J=9.1 Hz, 2.8 Hz), 9.04 (1H, d, J=2.8 Hz).

TABLE 132

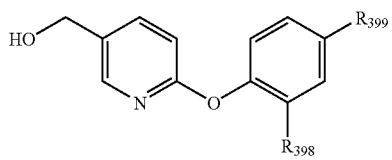

| Reference Example No. | $R_{398}$ | $R_{399}$ | $^1$H NMR (CDCl$_3$) δ ppm |
|---|---|---|---|
| 950 | —H | —NO$_2$ | 4.71(2H, s), 7.05(1H, d, J=8.4 Hz), 7.25(2H, d, J=8.9 Hz), 7.83(1H, dd, J=8.3 Hz, 2.3 Hz), 8.19(1H, d, J=2.5 Hz), 8.27(2H, d, J=8.9 Hz). |
| 951 | —CH$_3$ | —NO$_2$ | 2.30(4H, brs), 4.67(2H, s), 7.02(1H, d, J=8.41 Hz,), 7.12(1H, d, J=8.90 Hz), 7.80(1H, dd, J=8.41 Hz, 2.47 Hz), 8.05 8.17(3H, m). |
| 952 | —H | ![structure] | 2.45(4H, brs), 3.45(2H, s), 3.57(2H, brs), 3.69(2H, brs), 4.67(2H, s), 5.95(2H, s), 6.74-6.77(2H, m), 6.85(1H, s), 6.94(1H, d, J=8.4 Hz), 7.14(2H, d, J=8.4 Hz), 7.44 (2H, d, J=8 .4 Hz), 7.76(1H, dd, J=2.5 Hz, 8.4 Hz), 8.16(1H, d, J=2.5 Hz). |
| 953 | —H | ![structure] | 1.96(1H, brs), 2.40-2.44(4H, m), 3.02(3H, s), 3.43(2H, brs), 3.47-3.49(2H, m), 3.62(2H, brs), 4.07(2H, s), 4.62 (2H, s), 5.94(2H, s), 6.68-6.77(4H, m), 6.81(1H, d, J=8.6 Hz), 6.85(1H, brs), 6.99(2H, d, J=9.2 Hz), 7.66(1H, dd, J=8.4 Hz, 2.5 Hz), 8.13(1H, d, J=2.5 Hz). |
| 954 | —H | ![structure] | 1.75-2.01(1H, m), 2.22-2.50(4H, m), 2.51-2.70 (2H, m), 2.88-3.07(2H, m), 3.30-3.51(4H, m), 3.52-3.78(2H, m), 4.67(2H, s), 5.96(2H, s), 6.69-6.81(2H, m), 6.83-6.88(1H, m), 6.91(1H, d, J=8.4 Hz), 7.01-7.11(2H, m), 7.19-7.29(2H, m), 7.74(1H, dd, J=2.5 Hz, 8.4 Hz), 8.16(1H, dd, J=0.5 Hz, 2.5 Hz). |

Reference Example 955

Production of 2-[4-(1-bromoethyl)phenoxy]-5-nitropyridine 2-(4-ethylphenoxy)-5-nitropyridine (7.33 g, 30 mmol) was dissolved in carbon tetrachloride (100 mL), and to the resulting solution were added N-bromosuccimide (5.34 g, 30 mmol) and benzoyl peroxide (0.73 g, 3 mmol). This solution was refluxed overnight under a nitrogen atmosphere. The reaction solution was allowed to cool, after which insoluble matter was removed by filtration. The resulting filtrate was washed with a saturated sodium bicarbonate solution and brine. The organic layer was dried over anhydrous magnesium sulfate, and evaporated. The residue was purified by

Reference Example 956

Production of N-[6-(4-chloromethylphenoxy)pyridin-3-yl]-4-trifluoromethylbenzamide To a solution of N-[6-(4-hydroxymethylphenoxy)pyridin-3-yl]-4-trifluoromethylbenzamide (3.06 g, 7.9 mmol) in dichloromethane (90 mL) was added thionyl chloride (1.7 mL, 23.3 mmol), and the resulting solution was stirred for 4 hours at room temperature. To the residue was added a saturated sodium bicarbonate solution, and extracted with ethyl acetate. The ethyl acetate layer was washed with a saturated sodium bicarbonate solution and brine, dried over anhydrous magnesium sulfate, and evaporated. The residue was washed with diethyl ether, to thereby yield 2.95 g of the title compound.

Appearance: White powder $^1$H NMR (CDCl$_3$) δ 4.61 (2H, s), 7.00 (1H, d, J=8.9 Hz), 7.11-7.14 (2H, m), 7.41-7.44 (2H, m), 7.77 (2H, d, J=8.4 Hz), 7.89 (1H, brs), 8.00 (2H, d, J=8.4 Hz), 8.22-8.28 (2H, m).

The following compounds were produced in the same manner as in Reference Example 956.

Reference Example 957

3,4-Dichloro-N-[4-(4-chloromethylphenoxy)-3-fluorophenyl]benzamide $^1$H NMR (CDCl$_3$) δ 4.58 (2H, s), 6.95 (2H, d, J=8.6 Hz), 7.10 (1H, t, J=8.6 Hz), 7.20-7.30 (1H, m), 7.30-7.40 (3H, m), 7.59 (1H, d, J=8.3 Hz), 7.65-7.78 (2H, m), 7.96 (1H, d, J=2.1 Hz).

Reference Example 963

Production of 3,4-dichloro-N-{6-[4-(5-chloropentyl)-phenoxy]pyridin-3-yl}benzamide hydrochloride To 3,4-dichloro-N-{6-[4-(5-hydroxypentyl)-phenoxy]pyridin-3-yl}benzamide (6.83 g, 15.34 mmol) was added thionyl chloride (35 mL). The resulting solution was stirred for 20 minutes at room temperature, followed by stirring for 1 hour at 50° C. Excess thionyl chloride was evaporated, after which to the resulting residue was added ethyl acetate (100 mL). The obtained white powder was filtered, and washed with ethyl acetate, to thereby yield 6.98 g of the title compound.

Appearance: White powder $^1$H NMR (DMSO-d$_6$) δ 1.33-1.50 (2H, m), 1.50-1.68 (2H, m), 1.68-1.85 (2H, m), 2.59 (2H, t, J=7.6 Hz), 3.64 (2H, t, J=6.6 Hz), 7.02 (2H, d, J=8.5 Hz), 7.03 (1H, d, J=9.0 Hz), 7.23 (2H, d, J=8.5 Hz), 7.83 (1H, d, J=8.5 Hz), 7.97 (1H, dd, J=8.5 Hz, 2.0 Hz), 8.20 (1H, dd, J=9.0 Hz, 2.5 Hz), 8.25 (1H, d, J=2.0 Hz), 8.50 (1H, d, J=2.5 Hz), 10.63 (1H, s)

The following compounds were produced in the same manner as in Reference Example 963.

TABLE 133

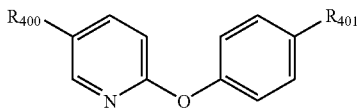

| Reference Example No. | R$_{400}$ | R$_{401}$ | $^1$H NMR (CDCl$_3$) δ ppm |
|---|---|---|---|
| 958 | —NO$_2$ | —CH$_2$Cl | 4.63(2H, s), 7.06(1H, d, J=8.9 Hz), 7.16(2H, dd, J=6.6 Hz, 2.0 Hz), 7.47 (2H, d, J=8.3 Hz), 8.47-8.51(1H, m), 9.04(1H, d, J=2.6 Hz) |
| 959 | 3,4-Cl$_2$PhCONH— | —CH$_2$Cl | 4.59(2H, s), 6.95(1H, d, J=8.9 Hz), 7.10(2H, d, J=8.6 Hz), 7.40 (2H, d, J=8.6 Hz), 7.54(1H, d, J=8.2 Hz), 7.71-7.75(1H, m), 7.99 (1H, d, J=2.3 Hz), 8.18-8.22 (2H, m), 8.30(1H, d, J=2.6 Hz). |
| 960 | 4-CNPhCONH— | —CH$_2$Cl | 4.60(2H, s), 6.99(1H, d, J=8.9 Hz), 7.12(2H, d, J=8.6 Hz), 7.42 (2H, d, J=8.6 Hz), 7.79(2H, d, J=8.3 Hz), 7.97-8.00(3H, m), 8.21 (1H, dd, J=8.9 Hz, 2.6 Hz), 8.27 (1H, d, J=2.6 Hz). |
| 961 | 4-ClPhCONH— | —CH$_2$Cl | 4.61(2H, s), 6.99(1H, d, J=9.6 Hz), 7.12(2H, d, J=8.3 Hz), 7.42 (2H, d, J=8.3 Hz), 7.48(2H, d, J=8.3 Hz), 7.75(1H, brs), 7.85 (2H, d, J=8.3 Hz), 8.20-8.25 (2H, m). |
| 962 | —CH$_2$Cl | ![structure] | 2.41-2.45(4H, m), 3.03(3H, s), 3.43 (2H, brs), 3.49(2H, brs), 3.63(2H, brs), 4.08(2H, s), 4.54 (2H, s), 5.94 (2H, s), 6.70(2H, d, J=9.2 Hz), 6.73-6.77(2H, m), 6.82(1H, d, J=8.6 Hz), 6.85(1H, brs), 7.00(2H, d, J=9.2 Hz), 7.67(1H, dd, J=8.6 Hz, 2.5 Hz), 8.15(1H, d, J=2.5Hz). |

(CNPh means a cyanophenyl group. Hereinafter CNPh indicates the same meaning.)

TABLE 134

[Structure: benzamide with R402, R403 substituents on phenyl ring, connected via C(=O)NH to a pyridine, which is linked via O to a phenyl ring bearing a -(CH2)M-Cl group]

| Reference Example No. | $R_{402}$ | $R_{403}$ | M | Form | $^1$H NMR (solvent) δ ppm |
|---|---|---|---|---|---|
| 964 | —Cl | —Cl | 2 | free | (CDCl$_3$) 3.04-3.10(2H, m), 3.69-3.75(2H, m), 6.95(1H, d, J=8.6 Hz), 7.06-7.09(2H, m), 7.24(2H, d, J=8.2 Hz), 7.56(1H, d, J=8.2 Hz), 7.69(1H, dd, J=8.2 Hz, 2.0 Hz), 7.93(1H, brs), 7.97(1H, d, J=2.0 Hz), 8.15-8.19(1H, m), 8.24(1H, d, J=2.6 Hz). |
| 965 | —Cl | —Cl | 3 | free | (CDCl$_3$) 2.04-2.12(2H, m), 2.76-2.81(2H, m), 3.53-3.58(2H, m), 6.94(1H, d, J 8.9 Hz), 7.04-7.07(2H, m), 7.20-7.26(2H, m), 7.56(1H, d, J=8.1 Hz), 7.70(1H, dd, J=8.4 Hz, 2.2 Hz), 7.90 (1H, brs), 7.97(1H, d, J=2.2 Hz), 8.14-8.18(1H, m), 8.24(1H, d, J=2.7 Hz). |
| 966 | —CF$_3$ | —H | 3 | free | (CDCl$_3$) 2.04-2.14(2H, m), 2.75-2.81(2H, m), 3.53-3.57(2H, m), 6.93(1H, d, J=8.7 Hz), 7.03-7.07(2H, m), 7.20-7.23(2H, m), 7.73(2H, d, J=8.2 Hz), 7.97(2H, d, J=8.2 Hz), 8.09(1H, brs), 8.16-8.21(1H, m), 8.25(1H, d, J=2.6 Hz). |
| 967 | —Cl | —Cl | 4 | hydrochloride | (DMSO-d$_6$) 1.60-1.85(4H, m), 2.62(2H, t, J=6.3 Hz), 3.68(2H, t, J=6.3 Hz), 7.03(2H, d, J=8.5 Hz), 7.04(1H, d, J 9.0 Hz), 7.24(2H, d, J=8.5 Hz), 7.83(1H, d, J=8.6 Hz), 7.97(1H, dd, J=8.6 Hz, 2.0 Hz), 8.20(1H, dd, J=9.0 Hz, 2.7 Hz), 8.25(1H, d, J=2.2 Hz), 8.50(1H, d, J=2.7 Hz), 10.64(1H, s). |

Reference Example 968

Production of N-{6-[4-(2-bromoacetyl)phenoxy]pyridin-3-yl}-3,4-dichlorobenzamide N-[6-(4-acetylphenoxy)pyridin-3-yl]-3,4-dichlorobenzamide (4.0 g, 10 mmol) was dissolved in chloroform (200 mL). To the resulting solution was added copper bromide (5.76 g, 25 mmol), and refluxed overnight. The resulting reaction solution was filtered, and the filtrate was washed with saturated sodium thiosulfate solution and brine. The organic layer was dried over anhydrous magnesium sulfate, and evaporated. To the filtered product from the earlier step was added ethyl acetate, and washed with saturated sodium thiosulfate water and brine. The organic layer was dried over anhydrous magnesium sulfate, and evaporated. The residues were combined for purification by silica gel column chromatography (n-hexane:ethyl acetate=3:1), to thereby yield 1.86 g of the title compound.

Appearance: White powder $^1$H NMR (CDCl$_3$) δ 4.43 (2H, s), 7.06 (1H, d, J=8.7 Hz), 7.21 (2H, d, J=8.9 Hz), 7.57 (1H, d, J=8.4 Hz), 7.72 (1H, dd, J=8.4 Hz, 2.0 Hz), 7.99 (1H, d, J=2.0 Hz), 8.03 (2H, d, J=8.9 Hz), 8.09 (1H, brs), 8.27 (1H, dd, J=8.7 Hz, 2.8 Hz), 8.32 (1H, d, J=2.2 Hz).

The following compound was produced in the same manner as in Reference Example 968.

Reference Example 969

N-{4-[4-(2-Bromoacetyl)phenoxy]-3-fluorophenyl}-3,4-dichlorobenzamide $^1$H NMR (DMSO-D$_6$) δ 4.88 (2H, s), 7.06 (2H, d, J=8.9 Hz), 7.30-7.50 (1H, m), 7.60-7.70 (1H, m), 7.80-8.20 (5H, m), 8.22 (1H, d, J=2.0 Hz), 10.67 (1H, brs).

Reference Example 970

Production of 4'-[4-(3-bromopropyl)phenoxy]-3,4-dichloro-3'-fluorobenzanilide

To a suspension of 3,4-dichloro-3'-fluoro-4'-[4-(3-hydroxypropyl)phenoxy]benzanilide (2.32 g, 5.34 mmol) in dichloromethane (46 mL) were added carbon tetrabromide (2.13 g, 6.41 mmol) and triphenylphosphine (1.54 g, 5.88 mmol), and the resulting solution was stirred for 12 hours at room temperature. The reaction solution was concentrated under reduced pressure, and the residue was purified by silica gel column chromatography (n-hexane:ethyl acetate=5:1), to thereby yield 2.41 g of the title compound.

Appearance: White powder $^1$H NMR (CDCl$_3$) δ 2.08-2.11 (2H, m), 2.73 (2H, t, J=7.3 Hz), 3.38 (2H, t, J=6.5 Hz), 6.88 (2H, d, J=8.5 Hz), 7.02 (1H, dd, J=9.0 Hz, 8.0 Hz), 7.13 (2H, d, J=8.5 Hz), 7.17-7.28 (1H, m), 7.54 (1H, d, J=8.3 Hz), 7.60-7.74 (2H, m), 7.85 (1H, brs), 7.93 (1H, d, J=2.0 Hz).

The following compounds were produced in the same manner as in Reference Example 970.

TABLE 135

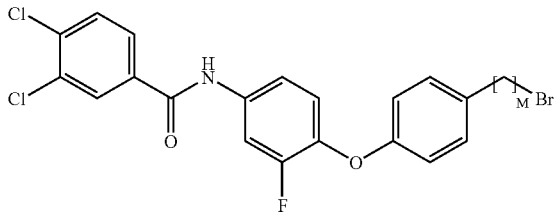

| Reference Example No. | M | $^1$H NMR (CDCl$_3$) δ ppm |
|---|---|---|
| 971 | 2 | 3.13(2H, t, J=7.5 Hz), 3.55(2H, t, J=7.5 Hz), 6.91(2H, d, J=6.6 Hz), 7.08(1H, t, J=8.7 Hz), 7.15(2H, d, J 6.6 Hz), 7.18-7.25(1H, m), 7.56(1H, d, J=8.3 Hz), 7.65-7.75(2H, m), 7.90-8.00(2H, m). |
| 972 | 4 | 1.67-1.79(2H, m), 1.81-1.94(2H, m), 2.60(2H, t, J=7.5 Hz), 3.40(2H, t, J=6.6 Hz), 6.88(2H, d, J=8.6 Hz), 7.02(1H, dd, J=9.0 Hz, 8.0 Hz), 7.11(2H, d, J 8.6 Hz), 7.14-7.21(1H, m), 7.55(1H, d, J=8.3 Hz), 7.60-7.73(2H, m), 7.78(1H, brs), 7.93(1H, d, J=1.9 Hz). |

Reference Example 973

Production of t-butyl 4-[4-(5-nitropyridin-2-yloxy) benzyl]piperazine-1-carboxylate To a solution of 2-(4-chloromethylphenoxy)-5-nitropyridine (12.32 g, 47 mmol) in DMF (120 mL) were added triethylamine (19.4 mL, 140 mmol) and t-butyl piperazine-1-carboxylate (11.27 g, 61 mmol), and the resulting solution was stirred for 3 hours at 50° C. Water was added to the residue, and extracted with ethyl acetate. The ethyl acetate layer was washed with water and brine. The ethyl acetate layer was dried over anhydrous magnesium sulfate, and evaporated. The residue was purified by silica gel column chromatography (n-hexane:ethyl acetate=1:1), to thereby yield 11.26 g of the title compound.
Appearance: Yellow powder
$^1$H NMR (CDCl$_3$) δ 1.46 (9H, s), 2.40-2.44 (4H, m), 3.43-3.46 (4H, m), 3.54 (2H, s), 7.04 (1H, d, J=8.9 Hz), 7.09-7.14 (2H, m), 7.38-7.44 (2H, m), 8.48 (1H, dd, J=8.9 Hz, 2.8 Hz), 9.05 (1H, d, J=2.8 Hz).
The following compound was produced in the same manner as in Reference Example 973.

Reference Example 974

4-{1-[4-(5-Nitropyridin-2-yloxy)phenyl]ethyl}morpholine $^1$H NMR (CDCl$_3$) δ 1.38 (3H, d, J=6.8 Hz), 2.36-2.54 (4H, m), 3.37 (1H, q, J=6.8 Hz), 3.69-3.72 (4H, m), 7.02 (1H, dd, J=9.1 Hz, 0.5 Hz), 7.11 (2H, d, J=8.6 Hz), 7.40 (2H, d, J=8.5 Hz), 8.47 (1H, dd, J=9.1 Hz, 2.8 Hz), 9.06 (1H, dd, J=2.8 Hz, 0.5 Hz).

Reference Example 975

Production of methanesulfonic acid 6-(4-nitrophenoxy)-pyridin-3-ylmethyl ester

[6-(4-nitrophenoxy)pyridin-3-yl]methanol (6.1 g, 24.8 mmol) was dissolved in dichloromethane (150 mL), and to the resulting solution was added triethylamine (4.15 mL, 29.8 mmol) under ice cooling. To the resulting solution was added dropwise methanesulfonic acid chloride (2.11 mL, 27.3 mmol), and then stirred under a nitrogen atmosphere for 30 minutes at 0° C. The reaction solution was washed with a saturated sodium bicarbonate solution and brine. The organic layer was dried over anhydrous magnesium sulfate, and evaporated. To the residue was added a mixed solvent (50 mL) of n-hexane:ethyl acetate=1:1. The precipitated crystals were removed by suction filtration, to thereby yield 7.9 g of the title compound.
Appearance: White powder
$^1$H NMR (CDCl$_3$) δ 3.04 (3H, s), 5.23 (2H, s), 7.09 (1H, d, J=8.4 Hz), 7.29 (2H, d, J=9.1 Hz), 7.88 (1H, dd, J=8.4 Hz, 2.5 Hz), 8.23 (1H, d, J=2.3 Hz), 8.28 (2H, d, J 10=9.1 Hz).
The following compounds were produced in the same manner as in Reference Example 975.

TABLE 136

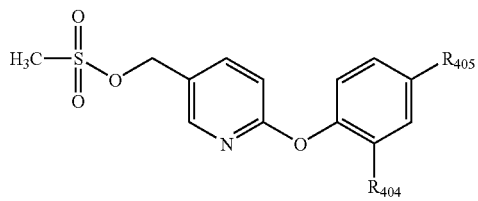

| Reference Example No. | $R_{404}$ | $R_{405}$ | $^1$H NMR (CDCl$_3$) δ ppm |
|---|---|---|---|
| 976 | —CH$_3$ | —NO$_2$ | 2.29(3H, s), 3.03(3H, s), 5.22(2H, s), 7.08(1H, dd, J=8.4 Hz, 0.5 Hz), 7.18(1H, |

TABLE 136-continued

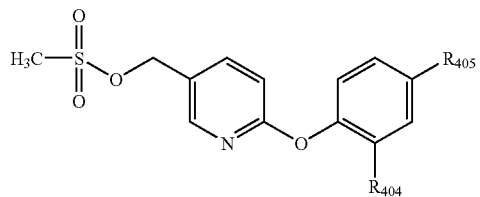

| Reference Example No. | R404 | R405 | 1H NMR (CDCl3) δ ppm |
|---|---|---|---|
| | | | d, J=8.9 Hz), 7.86(1H, dd, J=8.4 Hz, 2.5 Hz), 8.11(1H, dd, J=8.9 Hz, 2.8 Hz), 8.17(1H, dd, J=2.5 Hz, 0.5 Hz), 8.19(1H, d, J=2.8 Hz). |
| 977 | —H | (acetylpiperazinyl-methyl-benzodioxole) | 2.65(4H, brs), 3.01(3H, s), 3.65-3.75(6H, m), 5.22(2H, s), 5.97(2H, s), 6.79(2H, s), 6.92(1H, s), 7.00(1H, d, J=8.4 Hz), 7.18(2H, d, J=8.6 Hz), 7.47(2H, d, J=8.7 Hz), 7.81(1H, dd, J=2.5 Hz, 8.4 Hz), 8.20(1H, d, J=2.0 Hz). |

Reference Example 978

Production of 2-(4-nitrophenoxy)-5-(4-trifluoromethyl-phenoxymethyl)pyridine

Methanesulfonic acid 6-(4-nitrophenoxy)-pyridin-3-ylmethyl ester (4.86 g, 15 mmol) was dissolved in DMF (250 mL), and to the resulting solution were added 4-hydroxybenzotrifluoride (2.92 g, 18 mmol) and potassium carbonate (3.11 g, 22.5 mmol). The resulting solution was stirred under a nitrogen atmosphere for 1 hour at 50° C. The reaction solution was concentrated under reduced pressure. To the residue was added ethyl acetate, and washed with a saturated sodium bicarbonate solution and brine. The organic layer was dried over anhydrous magnesium sulfate, and evaporated. The residue was purified by silica gel column chromatography (dichloromethane:methanol=80:1), to thereby yield 5.8 g of the title compound.

Appearance: Pale yellow powder

1H NMR (CDCl3) δ 5.09 (2H, s), 7.02-7.10 (3H, m), 7.26-7.31 (2H, m), 7.56-7.59 (2H, m), 7.88 (1H, dd, J=8.4 Hz, 2.5 Hz), 8.25-8.31 (3H, m).

The following compound was produced in the same manner as in Reference Example 978.

Reference Example 979

2-(2-Methyl-4-nitrophenoxy)-5-(4-trifluoromethyl-phenoxymethyl)pyridine

1H NMR (CDCl3) δ 2.31 (3H, s), 5.07 (2H, s), 7.03 (2H, d, J=8.6 Hz), 7.08 (1H, d, J=8.4 Hz), 7.17 (1H, d, J=8.9 Hz), 7.57 (2H, d, J=8.4 Hz), 7.87 (1H, dd, J=8.4 Hz, 2.5 Hz), 8.10 (1H, dd, J=8.9 Hz, 2.8 Hz), 8.18 (1H, d, J=2.6 Hz), 8.21 (1H, d, J=2.5 Hz).

Example 1

Production of N-{6-[4-(4-benzylpiperazine-1-carbonyl)-phenoxy]pyridin-3-yl}-4-trifluoromethylbenzamide To a solution of 4-[5-(4-trifluoromethyl-benzoylamino)pyridin-2-yloxy]benzoic acid (1.19 g, 2.3 mmol) in DMF (30 mL) were added 1-ethyl-3-(3-dimethylaminopropyl)carbodiimide hydrochloride (530 mg, 2.8 mmol), 1-hydroxybenzotriazole monohydrate (370 mg, 2.7 mmol) and benzylpiperazine (0.475 mL, 2.7 mmol) under ice cooling. The resulting solution was stirred for 1 day gradually warming up to room temperature. To the residue was added a saturated sodium bicarbonate solution and extracted with ethyl acetate. The ethyl acetate layer was washed with a saturated sodium bicarbonate solution and brine, dried over anhydrous magnesium sulfate, and evaporated. The residue was purified by silica gel column chromatography (methanol:chloroform=1:19), to thereby yield 800 mg of the title compound.

Appearance: White needles

1H NMR (CDCl3) δ 2.46 (4H, brs), 3.55 (2H, s), 3.72 (4H, brs), 6.96 (1H, d, J=8.9 Hz), 7.10-7.13 (2H, m), 7.28-7.40 (7H, m), 7.74 (2H, d, J=8.3 Hz), 8.02 (2H, d, J=8.3 Hz), 8.16-8.21 (1H, m), 8.32 (1H, d, J=2.6 Hz), 8.53 (1H, brs).

The following compounds were produced in the same manner as in Example 1.

TABLE 137
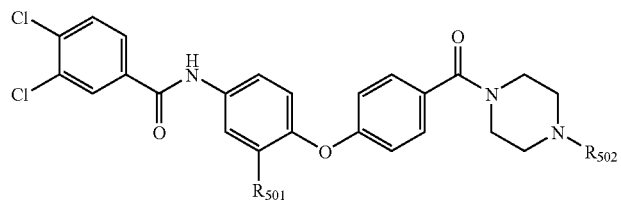
| Example No. | R₅₀₁ | R₅₀₂ | Form | mp (° C.) |
|---|---|---|---|---|
| 2 | —H | —CH₃ | hydrochloride | 175–176 |
| 3 | —H | benzyl | hydrochloride | 187–189 |
| 4 | —H | piperonyl | free | 182–183 |
| 5 | —H | —COOC(CH₃)₃ | free | 217–220 |
| 6 | —H | —Ac | free | 152–154 |
| 7 | —H | —(CH₂)₂CH | hydrochloride | 153–155 |
| 8 | —F | benzyl | free | 172–173 |
| 9 | —F | piperonyl | free | 170–171 |
TABLE 138
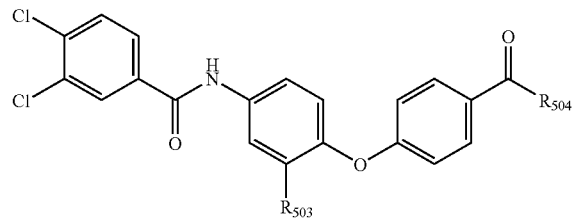
| Example No. | R₅₀₃ | R₅₀₄ | Form | mp (° C.) |
|---|---|---|---|---|
| 10 | —H | morpholino | free | 189–192 |
| 11 | —F | morpholino | free | 203–204 |
| 12 | —F | | free | 210–211 |
| 13 | —F | | hydrochloride | 233–235 |
| 14 | —F | | hydrochloride | 247–249 |
| 15 | —H | | free | 174–175 |
| 16 | —H | ![](N-methylpiperidinyl-N-methyl-N-phenethylamine) | hydrochloride | 213–216 |

TABLE 139

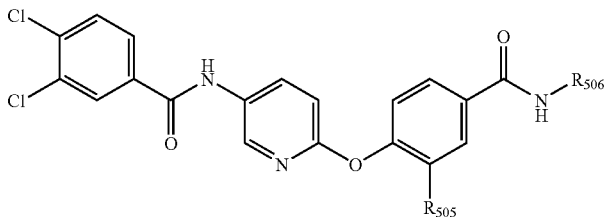

| Example No. | R505 | R506 | ¹H NMR (DMSO-d₆) δppm |
|---|---|---|---|
| 17 | —CH₃ | —NHAc | 1.92(3H, s), 2.17(3H, s), 7.13(1H, d, J=8.2Hz), 7.14(1H, d, J=8.9Hz), 7.74(1H, dd, J=8.2Hz, 2.2 Hz), 7.84(1H, d, J=8.2Hz), 7.84(1H, d, J=2.2Hz), 7.95(1H, dd, J=8.2Hz, 2.2Hz), 8.22(1H, d, J=2.2 Hz), 8.23(1H, dd, J=8.9Hz, 2.6Hz), 8.46(1H, d, J=2.6Hz), 9.89(1H, s), 10.24(1H, s), 10.57(1H, s). |
| 18 | —H | cyclopropyl | 0.51-0.60(2H, m), 0.66-0.74(2H, m), 2.80-2.89(1H, m), 7.10-7.20(3H, m), 7.81-7.89(3H, m), 7.95(1H, dd, J=8.4Hz, 2.1Hz), 8.19-8.28(2H, m), 8.42(1H, brd), 8.52(1H, d, J=2.7Hz), 10.59(1H, s). |
| 19 | —H | cyclohexyl | 1.06-1.19(1H, m), 1.21-1.36(4H, m), 1.55-1.65(1H, m), 1.69-1.78(2H, m), 1.78-1.87(2H, m), 3.69-3.80(1H, m), 7.10-7.20(3H, m), 7.85(1H, d, J=8.4 Hz), 7.86-7.92(2H, m), 7.95(1H, dd, J=8.4Hz, 2.1 Hz), 8.17(1H, brd), 8.20-8.29(2H, m), 8.52(1H, d, J=2.7Hz), 10.58(1H, s). |
| 20 | —H | cyclopentyl | 1.46-1.60(4H, m), 1.63-1.76(2H, m), 1.82-1.94(2H, m), 4.17-4.28(1H, m), 7.10-7.20(3H, m), 7.85(1H, d, J=8.4Hz), 7.87-7.92(2H, m), 7.95(1H, dd, J=8.4Hz, 2.1Hz), 8.19-8.28(3H, m), 8.52(1H, d, J=2.6Hz), 10.58(1H, s). |
| 21 | —H | cycloheptyl | 1.36-1.71(10H, m), 1.80-1.90(2H, m), 3.88-4.00(1H, m), 7.10-7.20(3H, m), 7.85(1H, d, J=8.4Hz), 7.86-7.92(2H, m), 7.95(1H, dd, J=8.4Hz, 2.1Hz), 8.17-8.28(3H, m), 8.51(1H, d, J=2.6Hz), 10.58(1H, s). |
| 22 | —H | cyclododecanyl | 1.20-1.57(20H, m), 1.61-1.73(2H, m), 4.08-4.21(1H, m), 7.10-7.21(3H, m), 7.85(1H, d, J=8.4Hz), 7.88-7.92(2H, m), 7.95(1H, dd, J=8.4Hz, 2.1Hz), 8.09(1H, brd), 8.20-8.29(2H, m), 8.51(1H, d, J=2.7 Hz), 10.58(1H, s). |
| 23 | —H | cyclooctyl | 1.44-1.65(8H, m), 1.65-1.80(6H, m), 3.98-4.09(1H, m), 7.10-7.20(3H, m), 7.85(1H, d, J=8.4Hz), 7.88-7.92(2H, m), 7.95(1H, dd, J=8.4Hz, 2.1Hz), 8.17-8.27(3H, m), 8.51(1H, d, J=2.7Hz), 10.58(1H, s). |
| 24 | —H | cyclopropyl-methyl | 0.19-0.26(2H, m), 0.38-0.47(2H, m), 0.99-1.09(1H, m), 3.12-3.19(2H, m), 7.12-7.21(3H, m), 7.85(1H, d, J=8.4Hz), 7.89-7.94(2H, m), 7.95(1H, dd, J=8.4Hz, 2.1Hz), 8.21-8.29(2H, m), 8.53(1H, d, J=2.8Hz), 8.54(1H, brt), 10.60(1H, s). |
| 25 | —H | —(CH₂)₂NHAc | 1.81(3H, s), 3.15-3.24(2H, m), 3.24-3.33(2H, m), 7.10-7.20(3H, m), 7.80-8.00(5H, m), 8.20-8.26(2H, m), 8.48(1H, brt), 8.52(1H, d, J=2.6Hz), 10.59(1H, s). |

TABLE 140

| Example No. | R507 | Form | ¹H NMR (solvent) δppm or MS |
|---|---|---|---|
| 26 | morpholino | hydro-chloride | ¹H NMR (DMSO-d₆) 3.50-3.65(8H, m), 7.13-7.19(3H, m), 7.47(2H, d, J=8.6Hz), 7.84(1H, d, J=8.2Hz), 7.97(1H, dd, J=8.3Hz, 2.0Hz), 8.23-8.27(2H, m), 8.54(1H, d, J=2.6Hz), 10.63(1H, s). |

TABLE 140-continued

[Structure: 3,4-dichloro-N-(6-(4-(C(=O)R₅₀₇)phenoxy)pyridin-3-yl)benzamide scaffold]

| Example No. | R₅₀₇ | Form | ¹H NMR (solvent) δppm or MS |
|---|---|---|---|
| 27 | [4-methyl-1,4-diazepan-1-yl connected via CH₂ to benzo[1,3]dioxol-5-yl] | free | ¹H NMR (CDCl₃) 1.81-1.95(2H, m), 2.59-2.77(4H, m), 3.51-3.57(4H, m), 3.75(2H, brs), 5.94(2H, s), 6.71-6.75(2H, m), 6.83-6.93(2H, m), 7.05-7.10(2H, m), 7.32-7.37(2H, m), 7.54(1H, d, J=8.2Hz), 7.79(1H, dd, J=8.3Hz, 2.0Hz), 8.06-8.10(2H, m), 8.30(1H, s), 8.96(1H, s). |
| 28 | [2-benzyl-1,4-dimethylpiperazine] | free | MS 574(M+) |
| 29 | [1-methyl-4-(4-trifluoromethylphenyl)-1,2,3,6-tetrahydropyridine] | free | MS 611(M+) |
| 30 | —NH(CH₂)₂OCH₃ | free | ¹H NMR (DMSO-d₆) 3.32(3H, s), 3.39-3.48(4H, m), 7.15-7.20(3H, m), 7.85(1H, d, J=8.3Hz), 7.86-7.92(2H, m), 7.95(1H, dd, J=8.4Hz, 2.1Hz), 8.20-8.26(2H, m), 8.50(1H, brt), 8.52(1H, d, J=2.5Hz), 10.59(1H, s). |
| 31 | [4-(dimethylamino)-1-benzoylpiperidine] | free | MS 601(M⁺ − 1) |
| 32 | [N-methyl-cyclohexylmethylamine] | free | ¹H NMR (DMSO-d₆) 0.86-0.99(2H, m), 1.10-1.27(3H, m), 1.50-1.65(2H, m), 1.65-1.78(4H, m), 3.06-3.15(2H, m), 7.11-7.22(3H, m), 7.85(1H, d, J=8.4Hz), 7.88-7.92(2H, m), 7.95(1H, dd, J=8.4Hz, 2.1Hz), 8.20-8.28(2H, m), 8.40(1H, brt), 8.52(1H, d, J=2.7Hz), 10.58(1H, s). |
| 33 | —NH(CH₂)₂OPh | free | ¹H NMR (DMSO-d₆) 3.63(2H, t, J=5.8Hz), 4.12(2H, t, J=5.9Hz), 6.90-7.01(3H, m), 7.13-7.24(3H, m), 7.26-7.35(2H, m), 7.85(1H, d, J=8.4 Hz), 7.90-8.00(3H, m), 8.20-8.30(2H, m), 8.52(1H, d, J=2.6Hz), 8.69(1H, brt), 10.59(1H, s). |
| 34 | [4-(methylamino)-1-benzylpiperidine] | free | MS 574(M+) |
| 35 | [4-methyl-1-benzyl-1,4-diazepane] | free | ¹H NMR (CDCl₃) 1.80-1.96(2H, m), 2.61-2.79(4H, m), 3.45-3.57(2H, m), 3.62-3.67(2H, m), 3.75-3.77(2H, m), 6.94(1H, d, J=8.6Hz), 7.08-7.13(2H, m), 7.24-7.41(7H, m), 7.56(1H, d, J=8.6Hz), 7.76(1H, dd, J=8.6Hz, 2.0Hz), 8.04(1H, d, J=2.0 Hz), 8.07-8.14(1H, m), 8.29(1H, d, J=2.0Hz), 8.39(1H, s). |

TABLE 141

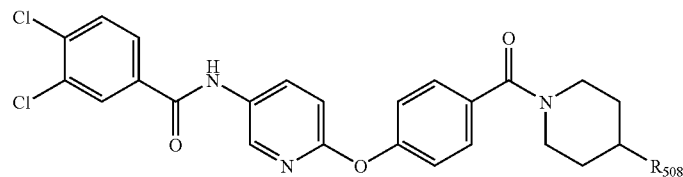

| Example No. | R₅₀₈ | Property |
|---|---|---|
| 36 | ![piperazine-acetyl-benzyl] | mp 221-224° C. |
| 37 | ![piperazine-acetyl-methylenedioxybenzyl] | mp 228-230° C. |
| 38 | ![morpholine-acetyl] | mp 193-194° C. |
| 39 | —N(CH₃)COOC(CH₃)₃ | $^1$H NMR (CDCl₃) δ 1.47(9H, s), 1.45-1.81(4H, m), 2.73(3H, s), 2.90(2H, brs), 4.10(2H, brs), 4.75(1H, brs), 6.95(1H, d, J=8.7Hz), 7.11(2H, d, J=8.7 Hz), 7.39(2H, d, J=8.7Hz), 7.55(1H, d, J=8.2 Hz), 7.77(1H, dd, J=8.2Hz, 2.0Hz), 8.05(1H, d, J=2.0Hz), 8.14(1H, dd, J=8.7Hz, 2.6Hz), 8.30(1H, d, J=2.6Hz), 8.77(1H, s). |
| 40 | —OPh | MS 560(M⁺ − 1) |
| 41 | 4-CF₃PhO— | MS 629(M⁺) |
| 42 | 4-CF₃OPhO— | MS 644(M⁺ − 1) |
| 43 | 4-CNPhO— | MS 586(M⁺) |
| 44 | —C₂H₅ | MS 496(M⁺ − 1) |
| 45 | —COOC₂H₅ | $^1$H NMR (CDCl₃) δ 1.27(3H, t, J=7.0Hz), 1.73(2H, brs), 1.95(2H, brs), 2.58(1H, m), 3.08(2H, brs), 3.86(1H, brs), 4.16(2H, q, J=7.0Hz), 4.50(1H, brs), 6.97(1H, d, J=9.0Hz), 7.12(2H, d, J=8.5Hz), 7.40(2H, d, J=8.5Hz), 7.57(1H, d, J=8.5Hz), 7.75(1H, dd, J=8.5Hz, 2.0Hz), 8.03(1H, d, J=2.0Hz), 8.16(1H, dd, J=9.0Hz, 3.0Hz), 8.30(1H, d, J=3.0Hz), 8.34(1H, brs). |
| 46 | —(CH₂)₂N(CH₃)Ph | MS 602(M⁺) |
| 47 | 2-FPhCH₂O— | MS 592(M⁺ − 1) |
| 48 | PhCH₂O— | MS 574(M⁺ − 1) |
| 49 | cyclohexyl | MS 550(M⁺ − 1) |
| 50 | 4-ClPh— | MS 580(M⁺ + 1) |
| 51 | —Ph | MS 544(M⁺ − 1) |
| 52 | —CHPh₂ | MS 635(M⁺) |
| 53 | 2-NH₂PhCO— | MS 587(M⁺ − 1) |
| 54 | 4-CH₃OPhCONH— | MS 617(M⁺ − 1) |
| 55 | —NHCOPh | MS 587(M⁺ − 1) |
| 56 | 4-CF₃PhCH₂O— | mp 186-187° C. |
| 57 | 4-ClPhCH₂O— | mp 176-177° C. |

TABLE 142

[Structure: 3,4-dichlorobenzamide linked to pyridine-O-phenyl-C(O)-piperidine-R509]

| Example No. | R509 | MS |
|---|---|---|
| 58 | [1,4-dimethyl-2-methylpiperazine] | 580(M⁺ − 1) |
| 59 | [1-methyl-4-phenylimidazole] | 610(M⁺ − 1) |
| 60 | [1,4-dimethyl-1,4-diazepane] | 580(M⁺ − 1) |
| 61 | [1-methyl-2-methyl-benzimidazole] | 598(M⁺ − 1) |
| 62 | [N,N-dimethyl-2-(1,2,4-triazol-1-yl)ethylamine] | 592(M⁺ − 1) |
| 63 | Ph(CH₂)₂N(CH₃)— | 600(M⁺ − 2) |
| 64 | Ph₂CH(CH₂)₂N(CH₃)— | 691(M⁺ − 1) |
| 65 | 4-CH₃SPh(CH₂)₂N(CH₃)— | 648(M⁺) |
| 66 | [N,N-dimethyl-2-(3-methyl-4-nitrophenoxy)ethylamine] | 678(M⁺ + H) |
| 67 | [N,N-dimethyl-2-(tetrahydrofuran-2-yl)-2-hydroxyethylamine] | 613(M⁺ + H) |
| 68 | 4-CH₃OPh(CH₂)₄N(CH₃)— | 660(M⁺) |
| 69 | 4-CH₃Ph(CH₂)₂N(CH₃)— | 617(M⁺ + H) |
| 70 | PhO(CH₂)₂N(CH₃)— | 618(M⁺) |
| 71 | PhN(CH₃)(CH₂)₂N(CH₃)— | 631(M⁺) |
| 72 | [N-methyl-N-(2-cyclohexylethyl)amine] | 608(M⁺) |
| 73 | —O(CH₂)₂Ph | 588(M⁺ − 1) |
| 74 | [3-pyridyl-CH₂-O-CH₃] | 575(M⁺ − 1) |

TABLE 142-continued

| Example No. | R509 | MS |
|---|---|---|
| 75 | [4-pyridyl-CH₂-O-CH₃] | 576(M⁺) |
| 76 | 4-ClPhCH₂— | 594(M⁺ + 1) |
| 77 | 4-CF₃PhNH— | 644(M⁺) |

TABLE 143

[Structure: 3,4-dichlorobenzamide linked to pyridine-O-phenyl-C(O)-piperidine-R510]

| Example No | R510 | MS |
|---|---|---|
| 78 | 4-CH3PhO(CH₂)₂N(CH₃)— | 633(M⁺ + H). |
| 79 | Ph(CH₂)₃N(CH₃)— | 616(M⁺) |
| 80 | 2-phenylmorpholino | 630(M⁺) |
| 81 | 4-CH₃PhCH₂— | 572(M⁺ − 1) |
| 82 | morpholino | 554(M⁺) |
| 83 | 4-CH₃OPhCH₂O— | 606(M⁺ + H) |
| 84 | 3-ClPhCH₂O— | 608(M⁺ − 1) |
| 85 | 2-ClPhCH₂O— | 608(M⁺ − 1) |
| 86 | 3,4-Cl₂PhCH₂O— | 644(M⁺ + 1) |
| 87 | 3-CH₃OPhCH₂O— | 604(M⁺ − 1) |
| 88 | 3,5-(CH₃O)₂PhCH₂O— | 634(M⁺ − 1) |
| 89 | 4-CH₃PhCH₂O— | 588(M⁺ − 1) |
| 90 | 3-CH₃PhCH₂O— | 588(M⁺ − 1) |
| 91 | 2-CH₃PhCH₂O— | 588(M⁺ − 1) |
| 92 | 3,4-(CH₃)₂PhCH₂O— | 602(M⁺ − 1) |
| 93 | 4-FPhCH₂O— | 592(M⁺ − 1) |
| 94 | 3-FPhCH₂O— | 592(M⁺ − 1) |
| 95 | 3,5-F₂PhCH₂O— | 610(M⁺ − 1) |
| 96 | 2-CF₃PhCH₂O— | 642(M⁺ − 1) |
| 97 | 4-CF₃OPhCH₂O— | 658(M⁺ − 1) |
| 98 | 3-CF₃OPhCH₂O— | 658(M⁺ − 1) |
| 99 | 2-CF₃OPhCH₂O— | 658(M⁺ − 1) |
| 100 | [3-chloro-4-methoxybenzyl-O-CH₃] | 638(M⁺ − 1) |

TABLE 144

Structure: 4-(trifluoromethyl)benzamide linked to pyridine, pyridine-O-phenyl-C(=O)-R511

| Example No. | R511 | mp (° C.) or $^1$H NMR (CDCl$_3$) δppm |
|---|---|---|
| 101 | 4-benzyl-piperazin-1-yl-carbonyl-(1-methylpiperidin-4-yl) | mp 218-220 |
| 102 | 4-(1,3-benzodioxol-5-ylmethyl)piperazin-1-yl-carbonyl-(1-methylpiperidin-4-yl) | mp 227-231 |
| 103 | 4-benzyl-1-methylpiperidin-4-yl | $^1$H NMR 1.09-1.30(1H, m), 1.60-1.87(4H, m), 2.55-2.95(4H, m), 3.80(1H, brs), 4.59(1H, brs), 6.92(1H, d, J=8.7Hz), 7.05-7.35(9H, m), 7.71(2H, d, J=8.6Hz), 8.04(2H, d, J=8.1Hz), 8.14(1H, dd, J=8.9Hz, 2.6 Hz), 8.34(1H, d, J=2.6Hz), 8.99(1H, s). |
| 104 | 1-methyl-4-(ethoxycarbonyl)piperidin-4-yl | $^1$H NMR 1.27(3H, t, J=7.0Hz), 1.74(2H, brs), 1.95(2H, brs), 2.58(1H, m), 3.08(2H, brs), 3.92(1H, brs), 4.17(2H, q, J=7.0Hz), 4.51(1H, brs), 7.01(1H, d, J=9.0Hz), 7.16(2H, d, J=8.5Hz), 7.44(2H, d, J=8.5Hz), 7.78(2H, d, J=8.0Hz), 7.88(1H, brs), 8.01(2H, d, J=8.0Hz), 8.24(1H, dd, J=9.0Hz, 3.0Hz), 8.32(1H, d, J=3.0Hz) |
| 105 | 1-(tert-butoxycarbonyl)-4-(dimethylamino)piperidin-4-yl | $^1$H NMR 1.46(9H, s), 1.50-1.90(4H, m), 2.35-3.00(2H, m), 2.89(3H, s), 4.10-4.70(3H, m), 6.99(1H, d, J=8.7Hz), 7.14(2H, d, J=8.3Hz), 7.40(2H, d, J=8.3Hz), 7.76(2H, d, J=8.1Hz), 8.03(2H, d, J=8.1Hz), 8.22(1H, dd, J=8.7Hz, 2.6Hz), 8.33(1H, d, J=2.6Hz), 8.34(1H, brs). |

TABLE 145

Structure: 3,4-dichlorobenzamide-pyridine-O-phenyl-C(=O)-piperazine-N-R512

| Example No. | R512 | $^1$H NMR (CDCl$_3$) δppm or MS |
|---|---|---|
| 106 | 4-CH$_3$OPhCH(Ph)— | MS 665(M$^+$ − 1) |
| 107 | 4-CH$_3$OPhCOCH$_2$— | $^1$H NMR 2.63(4H, brs), 3.65(4H, brs), 3.82(2H, s), 3.88(3H, s), 6.92-6.98(3H, m), 7.12(2H, d, J=8.7Hz), 7.41(2H, d, J=8.7Hz), 7.56(1H, d, J=8.2Hz), 7.75(1H, dd, J=8.2Hz, 2.1Hz), 7.97(2H, d, J=8.9Hz), 8.03(1H, d, J=2.0Hz), 8.16(1H, dd, J=8.9Hz, 2.8Hz), 8.30(1H, d, J= |

TABLE 145-continued

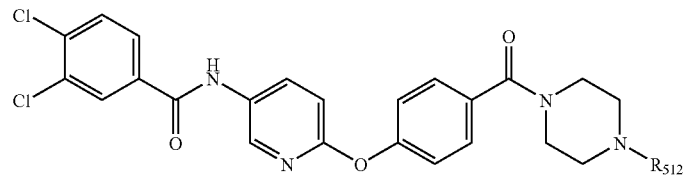

| Example No. | $R_{512}$ | $^1$H NMR (CDCl$_3$) δppm or MS |
|---|---|---|
| | | 2.8Hz), 8.39(1H, s). |
| 108 | 4-ClPhCOCH$_2$— | $^1$H NMR 2.63(4H, brs), 3.66(4H, brs), 3.83(2H, s), 6.97(1H, d, J=8.7Hz), 7.13(2H, d, J=8.6 Hz), 7.39-7.47(4H, m), 7.56(1H, d, J=8.4Hz), 7.74(1H, dd, J=8.2Hz, 2.1Hz), 7.94(2H, d, J=8.6Hz), 8.02(1H, d, J=2.0Hz), 8.16(1H, dd, J=8.7Hz, 2.8Hz), 8.30(1H, d, J=2.8Hz), 8.37(1H s). |
| 109 | 3-pyridyl | $^1$H NMR 3.20(4H, brs), 3.78(4H, brs), 6.93(1H, d, J=8.7Hz), 7.11(2H, d, J=8.6Hz), 7.19-7.21(2H, m), 7.39(2H, d, J=8.6Hz), 7.46(1H, d, J=8.4Hz), 7.76(1H, dd, J=8.4Hz, 2.0Hz), 8.03(1H, d, J=2.0Hz), 8.11-8.25(3H, m), 8.36(1H, d, J=2.5Hz), 9.81(1H, s). |
| 110 | —CH$_2$CONHPh | MS 603(M$^+$) |
| 111 | 2-pyridyl | MS 547(M$^+$) |
| 112 | 4-pyridyl | MS 547(M$^+$) |
| 113 | ![pyrazine] | MS 548(M$^+$) |
| 114 | ![pyrimidine] | MS 548(M$^+$) |
| 115 | —(CH$_2$)$_4$Ph | MS 603(M$^+$ + H) |
| 116 | —CH(C$_2$H$_5$)$_2$ | MS 540(M$^+$) |
| 117 | —CH(CH$_3$)$_2$ | MS 511(M$^+$ − 1) |
| 118 | —(CH$_2$)$_2$N(CH$_3$)$_2$ | MS 540(M$^+$ − 1) |

TABLE 146

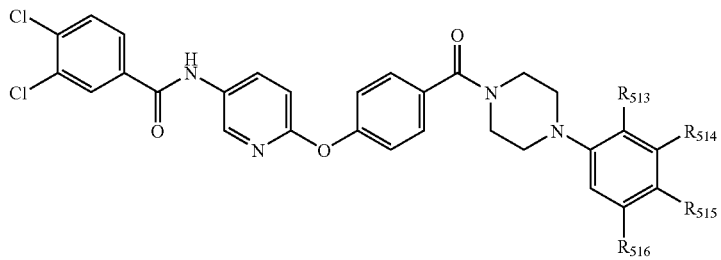

| Example No. | $R_{513}$ | $R_{514}$ | $R_{515}$ | $R_{516}$ | MS (M$^+$) |
|---|---|---|---|---|---|
| 119 | —F | —H | —H | —H | 564 |
| 120 | —Cl | —H | —H | —H | 582 |
| 121 | —CF$_3$ | —H | —H | —H | 614 |
| 122 | —OCH$_3$ | —H | —H | —H | 576 |
| 123 | —CH$_3$ | —H | —H | —H | 560 |
| 124 | —H | —CF$_3$ | —H | —H | 614 |
| 125 | —H | —Cl | —H | —H | 582 |
| 126 | —H | —OCH$_3$ | —H | —H | 576 |
| 127 | —H | —CH$_3$ | —H | —H | 560 |
| 128 | —H | —H | —CN | —H | 571 |
| 129 | —H | —H | —OCF$_3$ | —H | 630 |
| 130 | —H | —H | —CO$_2$C(CH$_3$)$_3$ | —H | 646 |

TABLE 146-continued

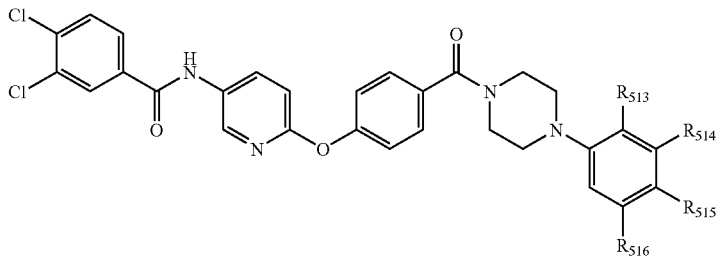

| Example No. | R₅₁₃ | R₅₁₄ | R₅₁₅ | R₅₁₆ | MS (M⁺) |
|---|---|---|---|---|---|
| 131 | —H | —H | —F | —H | 564 |
| 132 | —H | —H | —Cl | —H | 580 |
| 133 | —H | —H | —OCH₃ | —H | 576 |
| 134 | —H | —H | —CH₃ | —H | 560 |
| 135 | —H | —H | —CF₃ | —H | 614 |
| 136 | —H | —H | —Ph | —H | 622 |
| 137 | —Cl | —Cl | —H | —H | 616 |
| 138 | —CH₃ | —CH₃ | —H | —H | 574 |
| 139 | —H | —CH₃ | —CH₃ | —H | 574 |
| 140 | —F | —H | —F | —H | 582 |
| 141 | —OCH₃ | —H | —H | —Cl | 612 |

TABLE 147

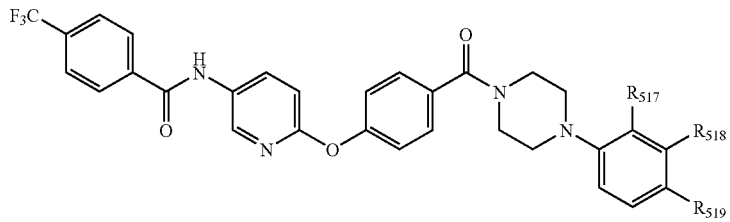

| Example No. | R₅₁₇ | R₅₁₈ | R₅₁₉ | mp (° C.) or ¹H NMR (CDCl₃) δppm |
|---|---|---|---|---|
| 142 | —H | —H | —H | ¹H NMR 3.20(4H, brs), 3.79(4H, brs), 6.89-6.96(3H, m), 7.00(1H, d, J=8.9Hz), 7.14-7.19(2H, m), 7.27-7.33(2H, m), 7.43-7.48(2H, m), 7.76(2H, d, J=8.1Hz), 8.02(2H, d, J=8.1Hz), 8.23(1H, dd, J=8.9Hz, 2.7Hz), 8.31-8.34(2H, m). |
| 143 | —F | —H | —H | mp 193-194 |
| 144 | —Cl | —H | —H | ¹H NMR 3.07(4H, brs), 3.82(4H, brs), 7.00-7.06(3H, m), 7.18(2H, d, J=8.4Hz), 7.22-7.26(1H, m), 7.38-7.41(1H, m), 7.48(2H, d, J=8.6Hz), 7.77(2H, d, J=8.1Hz), 8.04(2H, d, J=8.1Hz), 8.24(1H, dd, J=8.9Hz, 2.4Hz), 8.30(1H, brs), 8.35(1H, d, J=2.4Hz). |
| 145 | —H | —Cl | —H | ¹H NMR 3.19(4H, brs), 3.76(4H, brs), 6.77-6.81(1H, m), 6.86-6.88(2H, m), 6.99(1H, d, J=8.9 Hz), 7.13-7.22(3H, m), 7.40-7.45(2H, m), 7.73(2H, d, J=8.4Hz), 8.02(2H, d, J=8.4Hz), 8.21(1H, dd, J=8.9Hz, 2.7Hz), 8.34(1H, d, J=2.7Hz), 8.56(1H, s). |
| 146 | —H | —CH₃ | —H | ¹H NMR 2.31(3H, s), 3.15(4H, brs), 3.74(4H, brs), 6.71-6.73(3H, m), 6.97(1H, d, J=8.9Hz), 7.11-7.18(3H, m), 7.42(2H, d, J=8.1Hz), 7.72(2H, d, J=8.1Hz), 8.01(2H, d, J=8.1Hz), 8.18-8.21(1H, m), 8.34(1H, brs), 8.54(1H, brs). |
| 147 | —H | —OCH₃ | —H | ¹H NMR 3.07(4H, brs), 3.73(4H, brs), 3.88(3H, s), 6.88-7.08(5H, m), 7.13-7.17(2H, m), 7.42-7.47(2H, m), 7.75(2H, d, J=8.4Hz), 8.03(2H, d, J=7.8 Hz), 8.21(1H, dd, J=8.9Hz, 2.4Hz), 8.34(1H, d, J=2.4Hz), 8.45(1H, brs). |
| 148 | —H | —CF₃ | —H | mp 174-177 |
| 149 | —H | —H | —OH | mp 241-242 |
| 150 | —H | —H | —OCH₃ | ¹H NMR 3.06(4H, brs), 3.63-3.91(7H, m), 6.83-6.93(4H, m), 6.99(1H, d, J=8.6Hz), 7.15(2H, d, J=8.4Hz), 7.44(2H, d, J=8.4Hz), 7.75(2H, d, J= |

TABLE 147-continued

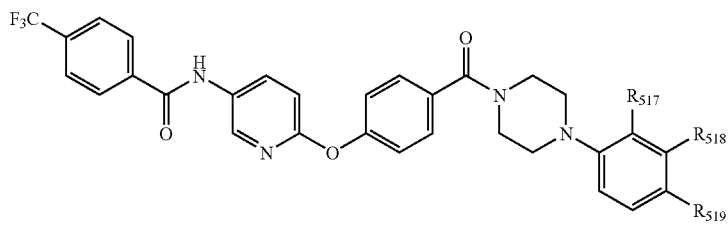

| Example No. | $R_{517}$ | $R_{518}$ | $R_{519}$ | mp (° C.) or $^1$H NMR (CDCl$_3$) δppm |
|---|---|---|---|---|
| | | | | 8.4Hz), 8.02(2H, d, J=8.1Hz), 8.22(1H, dd, J=8.9Hz, 2.4Hz), 8.33(1H, d, J=2.4Hz), 8.40(1H, brs). |
| 151 | —H | —H | —CN | $^1$H NMR 3.23(4H, brs), 3.79(4H, brs), 7.01(1H, d, J=8.9Hz), 7.12-7.19(5H, m), 7.33-7.39(1H, m), 7.43-7.48(2H, m), 7.74(2H, d, J=8.4Hz), 8.02(2H, d, J=8.4Hz), 8.23(1H, dd, J=8.9Hz, 2.7Hz), 8.35(1H, d, J=2.7Hz), 8.47(1H, s). |

TABLE 148

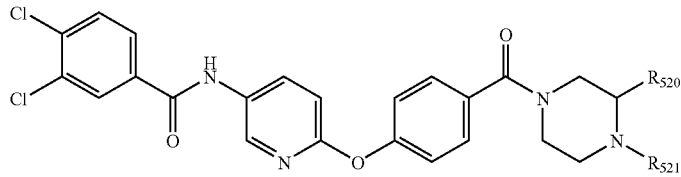

| Example No. | $R_{520}$ | $R_{521}$ | $^1$H NMR (solvent) δppm or MS |
|---|---|---|---|
| 152 | —H | piperonyl | $^1$H NMR (CDCl$_3$) 2.38-2.45(4H, m), 3.45(2H, s), 3.49-3.74(4H, m), 5.95(2H, s), 6.74(2H, s), 6.85(1H, s), 6.97(1H, d, J=8.6Hz), 7.10(2H, d, J=8.9Hz), 7.41(2H, d, J=8.9Hz), 7.58(1H, d, J=8.3Hz), 7.74(1H, dd, J=8.3Hz, 2.0Hz), 8.02(1H, d, J=2.3Hz), 8.13-8.20(2H, m), 8.29(1H, d, J=2.6Hz). |
| 153 | —H | —COOC(CH$_3$)$_3$ | $^1$H NMR (DMSO-d$_6$) 1.41(9H, s), 3.39-3.50(8H, m), 7.13-7.19(3H, m), 7.45-7.48(2H, m), 7.84(1H, d, J=8.4Hz), 7.95(1H, dd, J=8.4Hz, 2.1Hz), 8.21-8.26(2H, m), 8.52(1H, d, J=2.3Hz), 10.58(1H, s). |
| 154 | —H | 2-naphthylmethyl | MS 611(M$^+$ + 1) |
| 155 | —H | 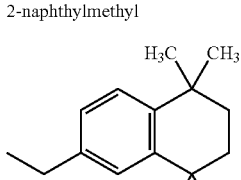 | MS 671(M$^+$ + 1) |
| 156 | —H | 1-naphthylmethyl | MS 611(M$^+$ + H) |
| 157 | —CH$_3$ | 3,4-(CH$_3$O)$_2$PhCH$_2$— | MS 633(M$^+$ + 1) |
| 158 | —H | 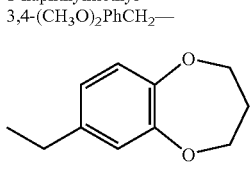 | MS 631(M$^+$ − 1) |
| 159 | —H | —CH(CH$_3$)Ph | MS 573(M$^+$ − 1) |

TABLE 148-continued
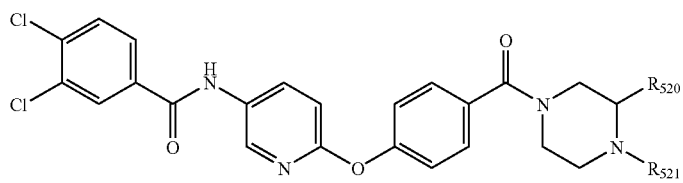
| Example No. | $R_{520}$ | $R_{521}$ | $^1$H NMR (solvent) δppm or MS |
|---|---|---|---|
| 160 | —H | 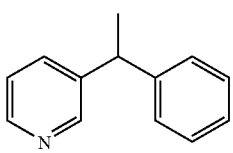 | MS 637(M$^+$) |
| 161 | —H | (4-FPh)$_2$CH— | MS 671(M$^+$ − 1) |
| 162 | —H | —(CH$_2$)$_3$CH$_3$ | MS 526(M$^+$) |
| 163 | —H | —(CH$_2$)$_3$Ph | MS 588(M$^+$) |
| 164 | —H | cyclopentyl | MS 538(M$^+$) |
| 165 | —H | cycloheptyl | MS 565(M$^+$ − 1) |
TABLE 149
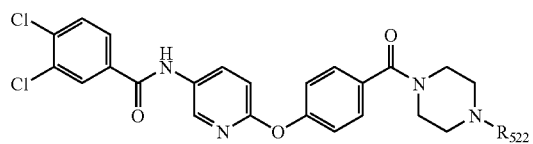
| Example No. | $R_{522}$ | MS |
|---|---|---|
| 166 | 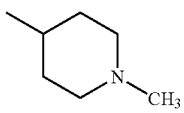 | 567(M$^+$) |
| 167 | 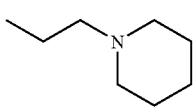 | 581(M$^+$) |
| 168 | 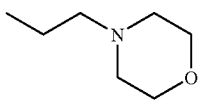 | 583(M$^+$) |
| 169 | 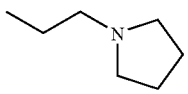 | 567(M$^+$) |
TABLE 149-continued
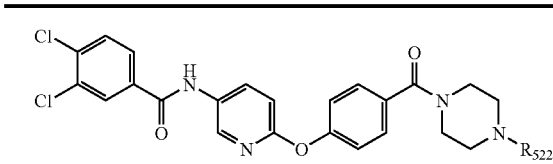
| Example No. | $R_{522}$ | MS |
|---|---|---|
| 170 | 4-pyridylmethyl | 561(M$^+$) |
| 171 | 2-pyridylmethyl | 562(M$^+$ + H) |
| 172 | 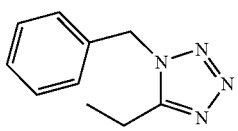 | 643(M$^+$ + H) |
| 173 | 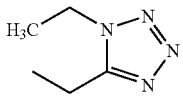 | 580(M$^+$) |
| 174 | 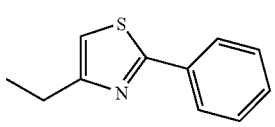 | 643(M$^+$) |

TABLE 150

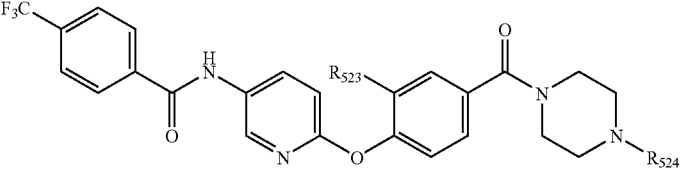

| Example No. | R$_{523}$ | R$_{524}$ | mp (° C.) or $^1$H NMR (solvent) δppm |
|---|---|---|---|
| 175 | —H | 3-pyridyl | $^1$H NMR (CDCl$_3$) 3.21(4H, brs), 3.78(4H, brs), 6.98(1H, d, J=8.7Hz), 7.13-7.21(4H, m), 7.41-7.44(2H, m), 7.70(2H, d, J=8.1Hz), 8.02(2H, d, J=8.1Hz), 8.12-8.14(1H, m), 8.20-8.27(2H, m), 8.35(1H, d, J=2.6Hz), 8.99(1H, s). |
| 176 | —H | 2-pyridyl | mp 222-224 |
| 177 | —F | 3-pyridyl | $^1$H NMR (CDCl$_3$) 3.21(4H, brs), 3.79(4H, brs), 7.05(1H, d, J=8.4Hz), 7.20-7.30(5H, m), 7.71(2H, d, J=8.2Hz), 8.00(2H, d, J=8.2Hz), 8.14(1H, brs), 8.21-8.25(3H, m), 8.78(1H, s). |
| 178 | —H |  | mp 205-206 |
| 179 | —H | 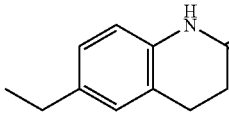 | $^1$H NMR (DMSO-d$_6$) 2.38(4H, brs), 2.43(2H, t, J=7.5Hz), 2.86(2H, t, J=7.5Hz), 3.41(2H, s), 7.5Hz), 2.86(2H, t, J=7.5Hz), 3.41(2H, s), 3.45(4H, brs), 6.80(1H, d, J=7.9Hz), 7.06(1H, d, J=7.9Hz), 7.10(1H, s), 7.15(1H, d, J=8.8Hz), 7.17(2H, d, J=8.4Hz), 7.44(2H, d, J=8.4Hz), 7.94(2H, d, J=8.0Hz), 8.17(2H, d, J=8.0Hz), 8.26(1H, dd, J=8.8Hz, 2.6Hz), 8.54(1H, d, J=2.6Hz), 10.06(1H, s), 10.68(1H, s). |
| 180 | —H | 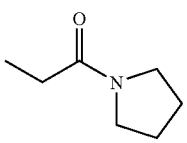 | $^1$H NMR (CDCl$_3$) 1.71-2.05(4H, m), 2.58(4H, brs), 3.16(2H, s), 3.36-3.53(4H, m), 3.55(2H, brs), 3.74(2H, brs), 7.00(1H, d, J=8.9Hz), 7.14(2H, d, J=8.6Hz), 7.42(2H, d, J=8.6Hz), 7.76(2H, d, J=8.1Hz), 8.04(2H, d, J=8.1Hz), 8.26(1H, dd, J=8.9Hz, 2.6Hz), 8.34(1H, d, J=2.6Hz), 8.50(1H, s). |
| 181 | —H | —COOC(CH$_3$)$_3$ | $^1$H NMR (CDCl$_3$) 1.48(9H, s), 3.45(4H, brs), 3.58(4H, brs), 6.99(1H, d, J=8.7Hz), 7.15(2H, d, J=8.7Hz), 7.41(2H, d, J=8.7Hz), 7.74(2H, d, J=8.2Hz), 8.02(2H, d, J=8.2Hz), 8.21(1H, dd, J=8.7Hz, 2.6Hz), 8.33(1H, d, J=2.6Hz), 8.43(1H, brs). |
| 182 | —H | —CH$_2$COOC$_2$H$_5$ | $^1$H NMR (CDCl$_3$) 1.28(3H, t, J=7.1Hz), 2.61(4H, brs), 3.26(2H, s), 3.57(2H, brs), 3.78(2H, brs), 4.19(2H, q, J=7.1Hz), 6.97(1H, d, J=8.7Hz), 7.12(2H, d, J=8.7Hz), 7.40(2H, d, J=8.7Hz), 7.74(2H, d, J=8.1Hz), 8.03(2H, d, J=8.1Hz), 8.19(1H, dd, J=8.7Hz, 2.6Hz), 8.33(1H, d, J=2.6Hz), 8.61(1H, brs). |
| 183 | —H | —CH$_2$CONHNHCOOC(CH$_3$)$_3$ | $^1$H NMR (CDCl$_3$) 1.46(9H, s), 2.60(4H, brs), 3.17(2H, s), 3.67(4H, brs), 6.48(1H, brs), 7.00(1H, d, J=8.7Hz), 7.14(2H, d, J=8.5Hz), 7.41(2H, d, J=8.5Hz), 7.75(2H, d, J=8.1Hz), 8.02(2H, d, J=8.1Hz), 8.24(1H, dd, J=8.7Hz, 2.6Hz), 8.33(1H, d, J=2.6Hz), 8.53(2H, s). |

TABLE 151

| Example No. | R525 | R526 | R527 | R528 | R529 | Form | mp (° C.) or ¹H NMR (solvent) δppm |
|---|---|---|---|---|---|---|---|
| 184 | —Cl | —Cl | —H | —F | 3-pyridyl | free | ¹H NMR (CDCl₃) 3.21(4H, brs), 3.79(4H, brs), 7.02(1H, d, J=8.7Hz), 7.18-7.28(5H, m), 7.49(1H, d, J=8.2Hz), 7.74(1H, dd, J=8.2Hz, 1.7Hz), 8.00(1H, d, J=1.7Hz), 8.13(1H, brs), 8.17-8.21(1H, m), 8.26(2H, d, J=2.3Hz), 9.33(1H, brs). |
| 185 | —H | —Cl | —H | —H | 4-CNPhCH₂— | free | mp 199-201 |
| 186 | —OCF₃ | —H | —H | —H | 3-pyridyl-methyl | free | ¹H NMR (CDCl₃) 2.43-2.55(4H, m), 3.43-3.71(6H, m), 6.90(1H, d, J=8.7Hz), 7.05-7.08(2H, m), 7.25-7.46(5H, m), 7.66-7.69(1H, m), 7.82-7.88(2H, m), 8.15(1H, dd, J=8.9Hz, 2.8 Hz), 8.36(1H, d, J=2.5Hz), 8.48(1H, dd, J=4.8Hz, 1.7 Hz), 8.51(1H, d, J=1.7Hz), 9.84(1H, s). |
| 187 | —CF₃ | —H | —H | —H | 4-CNPhCH₂— | free | mp 193-197 |
| 188 | —F | —H | —CF₃ | —H | 4-CNPhCH₂— | oxalate | mp 136-139 |
| 189 | —CH₃ | —CH₃ | —H | —H | —COOC(CH₃)₃ | free | ¹H NMR (CDCl₃) 1.48(9H, s), 2.34(6H, s), 3.46(4H, brs), 3.60(4H, brs), 6.99(1H, d, J=8.7Hz), 7.14-7.17 (2H, m), 7.23-7.26(1H, m), 7.42-7.47(2H, m), 7.61(1H, dd, J=7.8Hz, 2.0Hz), 7.67 (1H, d, J=2.0Hz), 7.93 (1H, brs), 8.25-8.31(2H, m). |

TABLE 152

| Example No. | R530 | R531 | R532 | R533 | R534 | MS |
|---|---|---|---|---|---|---|
| 190 | —Cl | —H | —H | —H | —H | 594(M⁺) |
| 191 | —OCH₃ | —H | —H | —H | —H | 590(M⁺) |
| 192 | —CH₃ | —H | —H | —H | —H | 574(M⁺) |
| 193 | —F | —H | —H | —H | —H | 578(M⁺) |
| 194 | —NO₂ | —H | —H | —H | —H | 603(M⁺ − 2) |
| 195 | —CF₃ | —H | —H | —H | —H | 628(M⁺) |
| 196 | —OCF₃ | —H | —H | —H | —H | 645(M⁺ + 1) |
| 197 | —H | —Cl | —H | —H | —H | 595(M⁺ + 1) |
| 198 | —H | —F | —H | —H | —H | 579(M⁺ + 1) |
| 199 | —H | —NO₂ | —H | —H | —H | 605(M⁺) |
| 200 | —H | —CF₃ | —H | —H | —H | 628(M⁺) |
| 201 | —H | —OCF₃ | —H | —H | —H | 644(M⁺) |

TABLE 152-continued

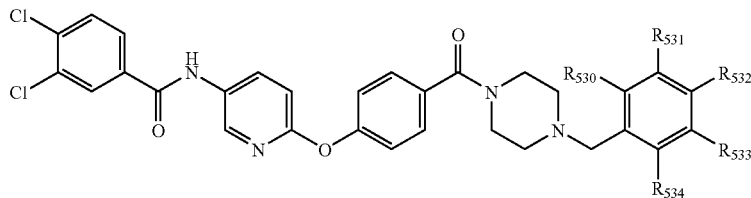

| Example No. | $R_{530}$ | $R_{531}$ | $R_{532}$ | $R_{533}$ | $R_{534}$ | MS |
|---|---|---|---|---|---|---|
| 202 | —H | —COOCH$_3$ | —H | —H | —H | 618(M$^+$) |
| 203 | —H | —H | —Cl | —H | —H | 594(M$^+$) |
| 204 | —H | —H | —F | —H | —H | 578(M$^+$) |
| 205 | —H | —H | —NO$_2$ | —H | —H | 605(M$^+$) |
| 206 | —H | —H | —COOCH$_3$ | —H | —H | 618(M$^+$) |
| 207 | —H | —H | —Ph | —H | —H | 636(M$^+$) |
| 208 | —H | —H | —C$_2$H$_5$ | —H | —H | 588(M$^+$) |
| 209 | —Cl | —Cl | —H | —H | —H | 630(M$^+$) |
| 210 | —Cl | —H | —Cl | —H | —H | 630(M$^+$) |
| 211 | —H | —F | —H | —F | —H | 596(M$^+$) |
| 212 | —H | —OCH$_3$ | —H | —OCH$_3$ | —H | 622(M$^+$ + 2) |
| 213 | —F | —H | —F | —H | —H | 596(M$^+$) |
| 214 | —H | —Cl | —Cl | —H | —H | 630(M$^+$) |
| 215 | —F | —H | —H | —H | —F | 596(M$^+$) |
| 216 | —Cl | —H | —H | —H | —Cl | 630(M$^+$) |
| 217 | —F | —H | —H | —F | —H | 596(M$^+$) |
| 218 | —Cl | —H | —H | —Cl | —H | 629(M$^+$ + 1) |
| 219 | —H | —Cl | —OCH$_3$ | —H | —H | 624(M$^+$) |

TABLE 153

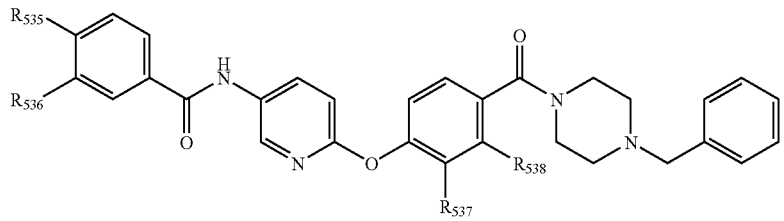

| Example No. | $R_{535}$ | $R_{536}$ | $R_{537}$ | $R_{538}$ | mp (° C.) or $^1$H NMR (CDCl$_3$) δppm |
|---|---|---|---|---|---|
| 220 | —Cl | —Cl | —H | —H | mp 164-166 |
| 221 | —Cl | —Cl | —F | —H | $^1$H NMR 2.46(4H, brs), 3.39-3.82(6H, m), 7.00(1H, d, J=8.9Hz), 7.13-7.33(8H, m), 7.52(1H, d, J=8.4Hz), 7.72(1H, dd, J=8.4Hz, 2.0Hz), 8.00(1H, d, J=2.0Hz), 8.15(1H, dd, J=8.9Hz, 2.6Hz), 8.23(1H, d, J=2.6Hz), 8.61(1H, brs). |
| 222 | —CF$_3$ | —H | —F | —H | $^1$H NMR 2.44(4H, brs), 3.42-3.78(6H, m), 6.97(1H, d, J=8.7Hz), 7.09-7.36(8H, m), 7.66(2H, d, J=8.1Hz), 7.96(2H, d, J=8.1Hz), 8.16(1H, dd, J=8.7Hz, 2.5Hz), 8.26(1H, d, J=2.5Hz), 9.04(1H, brs). |
| 223 | —Cl | —Cl | —Cl | —H | $^1$H NMR 2.47(4H, brs), 3.42-3.83(6H, m), 7.00(1H, d, J=8.9Hz), 7.17(1H, d, J=8.2Hz), 7.25-7.33(6H, m), 7.46(1H, d, J=1.8Hz), 7.53(1H, d, J=8.4Hz), 7.74(1H, dd, J=8.4Hz, 2.1Hz), 8.01(1H, d, J=2.1Hz), 8.17(1H, dd, J=8.9Hz, 2.6Hz), 8.25(1H, d, J=2.6Hz), 8.64(1H, brs). |
| 224 | —CF$_3$ | —H | —Cl | —H | $^1$H NMR 2.47(4H, brs), 3.42-3.82(6H, m), 7.02(1H, d, J=8.9Hz), 7.19(1H, d, J=8.4Hz), 7.27-7.33(6H, m), 7.47(1H, d, J=1.8Hz), 7.73(2H, d, J=8.4Hz), 8.00(2H, d, J=7.9Hz), 8.20-8.26(2H, m), 8.46(1H, brs). |
| 225 | —Cl | —Cl | —CH$_3$ | —H | $^1$H NMR 2.15(3H, s), 2.45(4H, brs), 3.46-3.75(6H, m), 6.85(1H, d, J=8.9Hz), 6.95(1H, d, J=8.4 Hz), 7.13-7.33(7H, m), 7.50(1H, d, J=8.6Hz), 7.75(1H, dd, J=8.4Hz, 2.2Hz), 8.03(1H, d, J=2.2Hz), 8.08(1H, dd, J=8.9Hz, 3.0Hz), 8.27(1H, d, J=3.0Hz), 9.06(1H, s). |

TABLE 153-continued

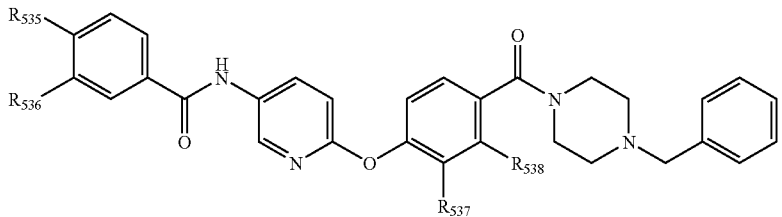

| Example No. | $R_{535}$ | $R_{536}$ | $R_{537}$ | $R_{538}$ | mp (° C.) or ¹H NMR (CDCl₃) δppm |
|---|---|---|---|---|---|
| 226 | —CF₃ | —H | —CH₃ | —H | ¹H NMR 2.17(3H, s), 2.44(4H, brs), 3.40-3.82(6H, m), 6.88(1H, d, J=8.9Hz), 6.98(1H, d, J=8.1 Hz), 7.14-7.18(1H, m), 7.23-7.33(6H, m), 7.70(2H, d, J=8.4Hz), 8.01(2H, d, J=8.1Hz), 8.15(1H, dd, J=8.9Hz, 2.7Hz), 8.30(1H, d, J=2.7Hz), 8.90(1H, brs). |
| 227 | —Cl | —Cl | —OCH₃ | —H | mp 197-199 |
| 228 | —CF₃ | —H | —OCH₃ | —H | mp 152-154 |
| 229 | —Cl | —Cl | —H | —CH₃ | mp 182-183 |
| 230 | —CF₃ | —H | —H | —CH₃ | mp 188-190 |
| 231 | —Cl | —Cl | —H | —OCH₃ | mp 196-198 |
| 232 | —CF₃ | —H | —H | —OCH₃ | ¹H NMR 2.32-2.50(4H, m), 3.30(2H, brs), 3.53(2H, s), 3.70-3.81(5H, m), 6.61-6.65(2H, m), 6.91(1H, d, J=8.9Hz), 7.11-7.15(1H, m), 7.26-7.36(5H, m), 7.72(2H, d, J=8.4Hz), 8.05-8.13(3H, m), 8.36(1H, d, J=2.4Hz), 9.07(1H, s). |

TABLE 154

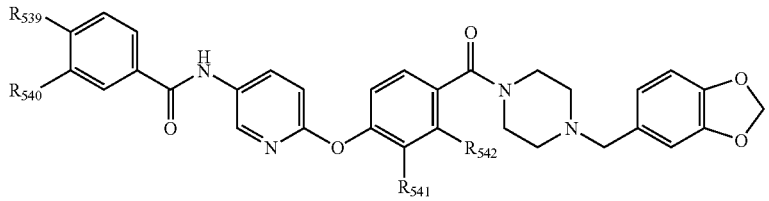

| Example No. | $R_{539}$ | $R_{540}$ | $R_{541}$ | $R_{542}$ | Form | mp (° C.) or ¹H NMR (solvent) δppm |
|---|---|---|---|---|---|---|
| 233 | —CF₃ | —H | —H | —H | hydrochloride | ¹H NMR (DMSO-d₆) 2.90-3.70(6H, m), 3.80-4.60(2H, m), 4.24(2H, brs), 6.07(2H, s), 6.98(1H, d, J=8.0Hz), 7.05(1H, dd, J=8.0 Hz, 1.5Hz), 7.16(1H, d, J=8.7Hz), 7.20(2H, d, J=8.6Hz), 7.27(1H, s), 7.52(2H, d, J=8.6 Hz), 7.93(2H, d, J=8.3Hz), 8.21(2H, d, J=8.3Hz), 8.30(1H, dd, J=8.7Hz, 2.6Hz), 8.60(1H, d, J=2.6Hz), 10.80(1H, s). |
| 234 | —Cl | —Cl | —F | —H | free | ¹H NMR (CDCl₃) 2.42(4H, brs), 3.37-3.79(6H, m), 5.94(2H, s), 6.70-6.77(2H, m), 6.84(1H, brs), 6.96(1H, d, J=8.7Hz), 7.10-7.22(3H, m), 7.47(1H, d, J=8.2Hz), 7.72(1H, dd, J=8.2Hz, 2.0Hz), 7.99(1H, d, J=2.0Hz), 8.12(1H, dd, J=8.9Hz, 2.6Hz), 8.25(1H, d, J=2.6Hz), 9.14(1H, brs). |
| 235 | —CF₃ | —H | —F | —H | free | ¹H NMR (CDCl₃) 2.41(4H, brs), 3.37-3.79(6H, m), 5.94(2H, s), 6.69-6.76(2H, m), 6.84(1H, s), 6.99(1H, d, J=8.9Hz), 7.10-7.26(3H, m), 7.67(2H, d, J=8.1Hz), 7.97(2H, d, J=8.1 Hz), 8.17(1H, dd, J=8.9Hz, 2.5Hz), 8.26(1H, d, J=2.5Hz), 8.89(1H, brs). |
| 236 | —Cl | —Cl | —Cl | —H | free | ¹H NMR (CDCl₃) 2.45(4H, brs), 3.38-3.81(6H, m), 5.95(2H, s), 6.71-6.78(2H, m), 6.85(1H, s), 7.01(1H, d, J=8.7Hz), 7.17-7.30(2H, m), 7.45-7.47(1H, m), 7.54(1H, d, J=8.4Hz), 7.70-7.74(1H, m), 8.00(1H, d, J=1.8Hz), 8.17(1H, dd, J=8.9Hz, 2.6Hz), 8.24(1H, d, J=2.6Hz), 8.48(1H, s). |
| 237 | —CF₃ | —H | —Cl | —H | free | ¹H NMR (CDCl₃) 2.45(4H, brs), 3.40-3.81(6H, m), 5.95(2H, s), 6.71-6.77(2H, m), 6.85(1H, s), 7.03(1H, d, J=8.6Hz), 7.20(1H, d, J=8.2 |

TABLE 154-continued

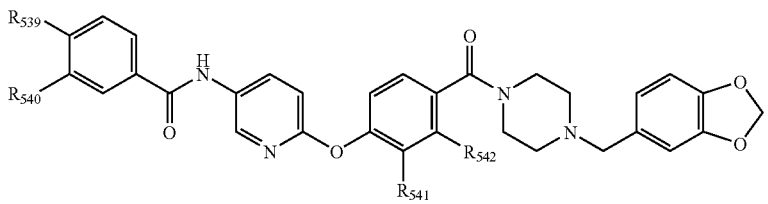

| Example No. | $R_{539}$ | $R_{540}$ | $R_{541}$ | $R_{542}$ | Form | mp (° C.) or $^1$H NMR (solvent) δppm |
|---|---|---|---|---|---|---|
| | | | | | | Hz), 7.28-7.31(1H, m), 7.48(1H, d, J=2.0Hz), 7.74(2H, d, J=8.4Hz), 8.00(2H, d, J=8.2 Hz), 8.21-8.26(2H, m), 8.34(1H, brs). |
| 238 | —CF$_3$ | —H | —CH$_3$ | —H | free | $^1$H NMR (CDCl$_3$) 2.16(3H, s), 2.42(4H, brs), 3.44-3.70(6H, m), 5.94(2H, s), 6.70-6.77(2H, m), 6.85-6.89(2H, m), 6.97(1H, d, J=8.4Hz), 7.14-7.23(2H, m), 7.69(2H, d, J=8.1Hz), 8.01(2H, d, J=8.1Hz), 8.13-8.17(1H, m), 8.30(1H, d, J=2.7Hz), 8.97(1H, brs). |
| 239 | —Cl | —Cl | —OCH$_3$ | —H | free | mp 194-196 |
| 240 | —CF$_3$ | —H | —OCH$_3$ | —H | free | mp 134-136 |
| 241 | —CF$_3$ | —H | —H | —CH$_3$ | free | mp 199-201 |
| 242 | —CF$_3$ | —H | —H | —OCH$_3$ | free | mp 192-193 |

TABLE 155

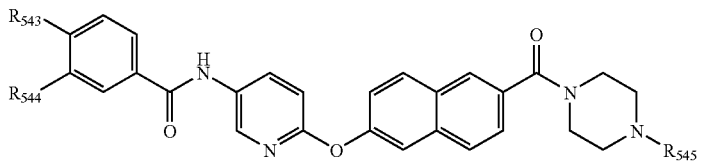

| Example No. | $R_{543}$ | $R_{544}$ | $R_{545}$ | $^1$H NMR (CDCl$_3$) δppm |
|---|---|---|---|---|
| 243 | —Cl | —Cl | benzyl | 2.39-2.62(4H, m), 3.42-3.91(6H, m), 6.94(1H, d, J=8.9Hz), 7.28-7.33(6H, m), 7.41(1H, dd, J=8.4Hz, 1.6Hz), 7.50-7.53(2H, m), 7.72 7.75(2H, m), 7.81-7.84(2H, m), 8.02(1H, d, J=2.1Hz), 8.14(1H, dd, J=8.9Hz, 2.7Hz), 8.28(1H, d, J=2.7Hz), 8.66(1H, s). |
| 244 | —Cl | —Cl | piperonyl | 2.41-2.74(4H, m), 3.42-3.91(6H, m), 5.94(2H, s), 6.73(2H, brs), 6.84(1H, brs), 6.97(1H, d, J=8.9Hz), 7.29-7.33(1H, m), 7.42(1H, d, J=8.2Hz), 7.52-7.57(2H, m), 7.71-7.85(4H, m), 8.02(1H, d, J=2.0Hz), 8.18(1H, dd, J=8.9 Hz, 2.8Hz), 8.28(1H, d, J=2.8Hz), 8.48(1H, brs). |
| 245 | —Cl | —Cl | 3-pyridyl | 3.25(4H, brs), 3.82(4H, brs), 7.01(1H, d, J=8.7Hz), 7.21-7.22(2H, m), 7.35(1H, dd, J=8.9Hz, 2.3Hz), 7.47-7.50(1H, m), 7.52-7.56(2H, m), 7.74(1H, dd, J=8.2Hz, 2.0Hz), 7.80(1H, d, J=8.6Hz), 7.86-7.91(2H, m), 8.01(1H, d, J=2.0Hz), 8.13-8.15(1H, m), 8.18-8.22(1H, m), 8.29-8.31(2H, m), 8.42(1H, brs). |
| 246 | —CF$_3$ | —H | benzyl | 2.35-2.58(4H, m), 3.37-3.87(6H, m), 6.96(1H, d, J=8.9Hz), 7.28-7.34(6H, m), 7.41(1H, dd, J=8.4Hz, 1.5Hz), 7.52(1H, d, J=2.0Hz), 7.64-7.76(3H, m), 7.83(2H, d, J=9.1Hz), 8.00(2H, d, J=8.2Hz), 8.19(1H, dd, J=8.9 Hz, 2.6Hz), 8.30(1H, d, J=2.6Hz), 8.68(1H, brs). |
| 247 | —CF$_3$ | —H | piperonyl | 2.30-2.58(4H, m), 3.35-3.87(6H, m), 5.94(2H, s), 6.70-6.77(2H, m), 6.85(1H, brs), 6.95(1H, d, J=8.7Hz), 7.31(1H, dd, J=8.9Hz, 2.1 Hz), 7.39(1H, d, J=8.4Hz), 7.51(1H, brs), 7.66-7.83(5H, m), 7.99(2H, d, J=8.1Hz), 8.17(1H, dd, J=8.7Hz, 2.3Hz), 8.30(1H, brs), 8.89(1H, brs). |

TABLE 155-continued

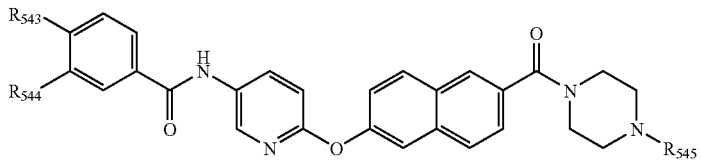

| Example No. | R543 | R544 | R545 | 1H NMR (CDCl3) δppm |
|---|---|---|---|---|
| 248 | —CF3 | —H | 3-pyridyl | 3.22(4H, brs), 3.79(4H, brs), 6.99(1H, d, J= 8.7Hz), 7.17-7.23(2H, m), 7.33(1H, dd, J= 8.9Hz, 2.3Hz), 7.45(1H, dd, J=8.4Hz, 1.5 Hz), 7.54(1H, d, J=2.3Hz), 7.66(2H, d, J= 8.4Hz), 7.76-7.86(3H, m), 7.99(2H, d, J=8.1 Hz), 8.13(1H, brs), 8.21-8.25(1H, m), 8.28(1H, brs), 8.33(1H, d, J=2.5Hz), 9.13(1H, s). |

TABLE 156

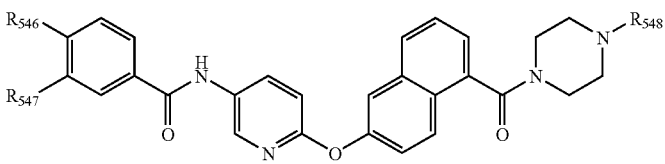

| Example No. | R546 | R547 | R548 | 1H NMR (CDCl3) δppm |
|---|---|---|---|---|
| 249 | —Cl | —Cl | benzyl | 2.27-2.34(2H, m), 2.58-2.61(2H, m), 3.20-3.29(2H, m), 3.53(2H, s), 3.90-3.99(2H, m), 6.91(1H, d, J=8.7Hz), 7.29-7.32(7H, m), 7.39-7.45(1H, m), 7.53-7.56(2H, m), 7.71-7.81(3H, m), 8.00-8.04(2H, m), 8.25(1H, d, J=2.6Hz), 8.47(1H, s). |
| 250 | —Cl | —Cl | piperonyl | 2.25-2.31(2H, m), 2.55-2.59(2H, m), 3.22(2H, brs), 3.44(2H, s), 3.86-4.01(2H, m), 5.94(2H, s), 6.69-6.76(2H, m), 6.84-6.91(2H, m), 7.25-7.29(2H, m), 7.38-7.44(1H, m), 7.52-7.55(2H, m), 7.71-7.80(3H, m), 7.97-8.03(2H, m), 8.24(1H, d, J=2.8Hz), 8.60(1H, s). |
| 251 | —CF3 | —H | benzyl | 2.27-2.34(2H, m), 2.57-2.61(2H, m), 3.23-3.25(2H, m), 3.53(2H, s), 3.89-3.98(2H, m), 6.96(1H, d, J=8.7Hz), 7.27-7.31(7H, m), 7.40-7.45(1H, m), 7.55(1H, d, J=2.3Hz), 7.72-7.83 (4H, m), 8.00(2H, d, J=8.1Hz), 8.12(1H, dd, J= 8.9Hz, 2.8Hz), 8.30(1H, d, J=2.6Hz), 8.40(1H, brs). |
| 252 | —CF3 | —H | piperonyl | 2.25-2.31(2H, m), 2.55-2.58(2H, m), 3.23(2H, m), 3.43(2H, s), 3.85-4.00(2H, m), 5.94(2H, s), 6.70-6.76(2H, m), 6.84(1H, s), 6.96(1H, d, J= 8.9Hz), 7.28-7.31(2H, m), 7.40-7.46(1H, m), 7.55(1H, d, J=2.5Hz), 7.72-7.83(4H, m), 8.00(2H, d, J=7.9Hz), 8.12(1H, dd, J=8.9 Hz, 2.6Hz), 8.30(1H, d, J=2.6Hz), 8.44(1H, brs). |

TABLE 157

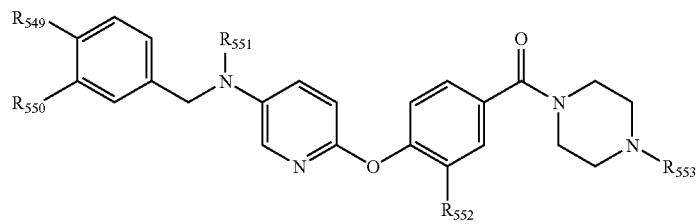

| Example No. | R549 | R550 | R551 | R552 | R553 | Form | $^1$H NMR (solvent) δppm |
|---|---|---|---|---|---|---|---|
| 253 | —CF$_3$ | —H | —CH$_3$ | —H | 3-pyridyl | free | (CDCl$_3$) 3.06(3H, s), 3.22(4H, brs), 3.81(4H, brs), 4.55(2H, s), 6.87(1H, d, J=8.9Hz), 7.09(2H, d, J=8.7 Hz), 7.14(1H, dd, J=8.9Hz, 3.3 Hz), 7.19-7.21(2H, m), 7.35(2H, d, J=7.9Hz), 7.44(2H, d, J=8.7 Hz), 7.60(2H, d, J=8.1Hz), 7.74(1H, d, J=3.0Hz), 8.14-8.17(1H, m), 8.31-8.33(1H, m). |
| 254 | —CF$_3$ | —H | —H | —F | benzyl | free | (CDCl$_3$) 2.46(4H, brs), 3.54(6H, brs), 4.11(1H, brs), 4.38(2H, brs), 6.85(1H, d, J=8.7Hz), 7.01(1H, dd, J=8.7Hz, 3.1Hz), 7.16-7.25(3H, m), 7.28-7.33(5H, m), 7.46(2H, d, J=8.1Hz), 7.52(1H, d, J=2.6Hz), 7.60(2H, d, J=8.1Hz). |
| 255 | —CF$_3$ | —H | —CH$_3$ | —H | piperonyl | hydrochloride | (DMSO-d$_6$) 2.49-2.52(2H, m), 3.06(5H, brs), 3.35(4H, brs), 4.22(2H, brs), 4.68(2H, brs), 6.07(2H, s), 6.94-7.05(5H, m), 7.23(1H, brs), 7.32(1H, dd, J=8.9 Hz, 3.3Hz), 7.43-7.46(4H, m), 7.69-7.72(3H, m), 11.23(1H, brs). |
| 256 | —Cl | —Cl | —H | —F | benzyl | free | (CDCl$_3$) 2.47(4H, brs), 3.49-3.68(6H, m), 4.29(2H, brs), 6.86(1H, d, J=8.7Hz), 7.01(1H, dd, J=8.7 Hz, 3.0Hz), 7.17-7.22(4H, m), 7.32(5H, brs), 7.41(1H, d, J=8.3 Hz), 7.45(1H, d, J=1.8Hz), 7.51(1H, d, J=3.0Hz). |
| 257 | —CF$_3$ | —H | —CH$_3$ | —H | 4-CH$_3$OPhCH$_2$— | hydrochloride | (DMSO-d$_6$) 2.49-2.52(2H, m), 3.06(5H, brs), 3.32-3.38(4H, m), 3.78(3H, s), 4.27(2H, d, J=4.1 Hz), 4.68(2H, brs), 6.96(1H, d, J=8.9Hz), 7.00-7.05(4H, m), 7.32(1H, dd, J=8.9Hz, 3.3Hz), 7.43-7.49(6H, m), 7.68-7.72(3H, m), 10.72(1H, brs). |
| 258 | —CF$_3$ | —H | —CH$_3$ | —H | 4-pyridylmethyl | hydrochloride | (DMSO-d$_6$) 2.49-2.52(2H, m), 3.05-3.44(9H, m), 4.26(2H, brs), 4.68(2H, brs), 6.96(1H, d, J=8.9 Hz), 7.03(2H, d, J=8.7Hz), 7.32(1H, dd, J=8.9Hz, 3.3Hz), 7.42-7.47(4H, m), 7.68-7.72(5H, m), 8.71(2H, dd, J=4.6Hz, 1.5 Hz). |

TABLE 158

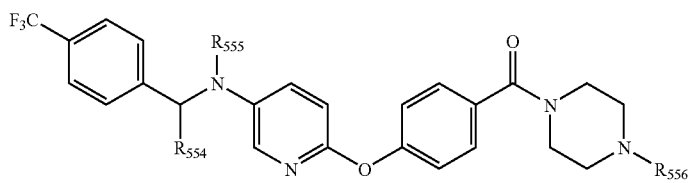

| Example No. | R554 | R555 | R556 | Form | $^1$H NMR (solvent) δppm |
|---|---|---|---|---|---|
| 259 | —CH$_3$ | —H | benzyl | hydrochloride | (DMSO-d$_6$) 1.44(3H, d, J=6.8Hz), 2.44-2.52(2H, m), 3.08-3.15(2H, m), 3.30-3.38(4H, |

TABLE 158-continued

| Example No. | R554 | R555 | R556 | Form | $^1$H NMR (solvent) δppm |
|---|---|---|---|---|---|
| | | | | | m), 4.33(2H, brs), 4.55-4.62(1H, m), 6.51(1H, d, J=6.3Hz), 6.82(1H, d, J=8.7Hz), 6.97(2H, d, J=8.7Hz), 7.04(1H, dd, J=8.7 Hz, 3.0Hz), 7.41(2H, d, J=8.6Hz), 7.45-7.47(4H, m), 7.57(2H, brs), 7.61(2H, d, J=8.3 Hz), 7.69(2H, d, J=8.4Hz), 10.99(1H, brs). |
| 260 | —CH₃ | —CH₃ | benzyl | free | (CDCl₃) 1.58(3H, d, J=6.9Hz), 2.46(4H, brs), 2.72(3H, s), 3.46-3.53(6H, m), 4.97(1H, q, J=6.9Hz), 6.86(1H, d, J=8.9Hz), 7.07(2H, d, J=8.6Hz), 7.23(1H, dd, J=8.9Hz, 3.3Hz), 7.27-7.36(5H, m), 7.40(2H, d, J=8.6Hz), 7.43(2H, d, J=7.3Hz), 7.60(2H, d, J=8.3 Hz), 7.82(1H, d, J=3.3Hz). |
| 261 | —CH₃ | —CH₃ | piperonyl | free | (CDCl₃) 1.58(3H, d, J=6.9Hz), 2.43(4H, brs), 2.72(3H, s), 3.44(2H, s), 3.48-3.68(4H, m), 4.97(1H, q, J=6.9Hz), 5.95(2H, s), 6.74(2H, brs), 6.85(1H, brs), 6.87(1H, d, J=9.1Hz), 7.07(2H, d, J=8.7Hz), 7.23(1H, dd, J=8.9 Hz, 3.3Hz), 7.40(2H, d, J=8.6Hz), 7.43(2H, d, J=7.9Hz), 7.60(2H, d, J=8.3Hz), 7.82(1H, d, J=3.1Hz). |
| 262 | —CH₃ | —H | piperonyl | hydro-chloride | (DMSO-d₆) 1.44(3H, d, J=6.8Hz), 2.49-2.52(2H, m), 3.01-3.06(2H, m), 3.29-3.45(4H, m), 4.23(2H, brs), 4.58-4.62(1H, m), 6.07(2H, s), 6.51(1H, d, J=6.6Hz), 6.82(1H, d, J=8.7 Hz), 6.96-6.99(4H, m), 7.04(1H, dd, J=8.7 Hz, 3.0Hz), 7.20(1H, brs), 7.41(2H, d, J=8.6 Hz), 7.46(1H, d, J=3.0Hz), 7.61(2H, d, J=8.3Hz), 7.69(2H, d, J=8.4Hz), 10.99(1H, brs). |
| 263 | —H | —C₂H₅ | benzyl | hydro-chloride | (DMSO-d₆) 1.14(3H, d, J=6.9Hz), 2.50-2.51(2H, m), 3.11(2H, brs), 3.35(4H, brs), 3.51(2H, q, J=6.9Hz), 4.33(2H, brs), 4.63(2H, brs), 6.94(1H, d, J=8.9Hz), 7.03(2H, d, J=8.6Hz), 7.25(1H, dd, J=8.9 Hz, 3.3Hz), 7.42-7.48(7H, m), 7.57(2H, brs), 7.62(1H, d, J=3.1Hz), 7.70(2H, d, J=8.1 Hz), 11.03(1H, brs). |
| 264 | —H | —C₂H₅ | piperonyl | hydro-chloride | (DMSO-d₆) 1.14(3H, d, J=6.9Hz), 2.50-2.51(2H, m), 3.06(2H, brs), 3.36(4H, brs), 3.52(2H, q, J=6.9Hz), 4.22(2H, brs), 4.64(2H, brs), 6.07(2H, s), 6.94(1H, d, J=8.9 Hz), 6.99(2H, brs), 7.03(2H, d, J=8.6Hz), 7.23(1H, brs), 7.25(1H, dd, J=8.9Hz, 3.3 Hz), 7.42-7.49(4H, m), 7.62(1H, d, J=3.1 Hz), 7.71(2H, d, 4=8.1Hz), 11.29(1H, brs). |

TABLE 159

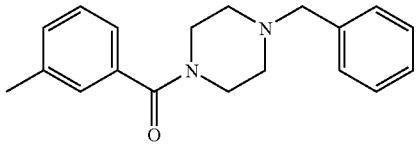

| Example No. | R557 | R558 | $^1$H NMR (solvent) δppm |
|---|---|---|---|
| 265 | 3,4-Cl₂PhCONH— | | (CDCl₃) 2.39-2.49(4H, m), 3.39-3.79(6H, m), 6.87(1H, d, J=8.9 Hz), 7.06-7.15(3H, m), 7.27-7.37(6H, m), 7.51(1H, d, J=8.4 Hz), 7.74-7.78(1H, m), 8.01-8.05(2H, m), 8.28(1H, d, J=2.6 Hz), 9.10(1H, brs). |

TABLE 159-continued

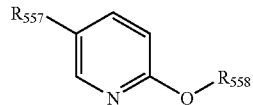

| Example No. | R557 | R558 | 1H NMR (solvent) δppm |
|---|---|---|---|
| 266 | 3,4-Cl2PhCONH— | 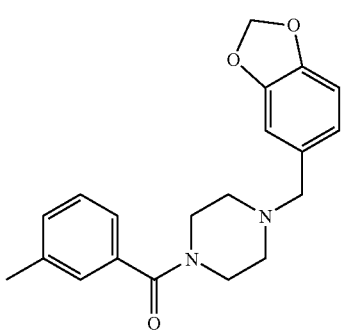 | (CDCl3) 2.37-2.48(4H, m), 3.43-3.75(6H, m), 5.94(2H, s), 6.70-6.77(2H, m), 6.84(1H, brs), 6.92(1H, d, J=8.9Hz), 7.09-7.17(3H,.m), 7.34-7.40(1H, m), 7.55(1H, d, J=8.4Hz), 7.73-7.77(1H, m), 8.04(1H, d, J=2.1 Hz), 8.09(1H, dd, J=8.9Hz, 2.8 Hz), 8.28(1H, d, J=2.8Hz), 8.63(1H, brs). |
| 267 | 4-CF3PhCH2N(CH3)— | 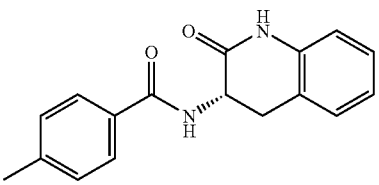 | (DMSO-d6) 3.03-3.13(5H, m), 4.69-4.75(3H, m), 6.88-6.98(3H, m), 7.06(2H, d, J=8.6Hz), 7.16-7.23(2H, m), 7.33(1H, dd, J=9.1 Hz, 3.1Hz), 7.46(2H, d, J=8.3 Hz), 7.69-7.73(3H, m), 7.91(2H, d, J=8.7Hz), 8.61(1H, d, J=8.1 Hz), 10.35(1H, brs). |
| 268 | 4-CF3PhCH2N(CH3)— | 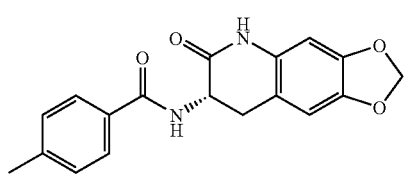 | (DMSO-d6) 2.89-3.06(2H, m), 3.06(3H, s), 4.61-4.72(3H, m), 5.96(2H, s), 6.50(1H, s), 6.84(1H, s), 6.97(1H, d, J=8.9Hz), 7.06(2H, d, J=8.7Hz), 7.33(1H, dd, J=8.9Hz, 3.3Hz), 7.46(2H, d, J=8.1Hz), 7.69-7.73(3H, m), 7.89(2H, d, J=8.7Hz), 8.56(1H, d, J=8.3Hz), 10.15(1H, brs). |
| 269 | 3,4-Cl2PhCONH— | 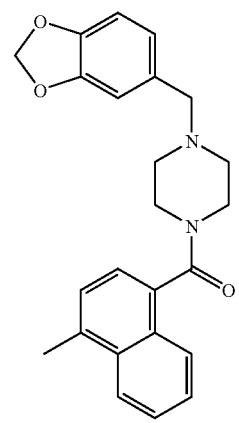 | (CDCl3) 2.28-2.30(2H, m), 2.58-2.60(2H, m), 3.25-3.29(2H, m), 3.44(2H, s), 3.92-3.98(2H, m), 5.94(2H, s), 6.73(2H, s), 6.84(1H, s), 6.96(1H, d, J=8.7Hz), 7.14(1H, d, J=7.8Hz), 7.37(1H d, J=7.8Hz), 7.50-7.59(3H, m), 7.73(1H, dd, J=8.2Hz, 2.1Hz), 7.83(1H, dd, J=7.6Hz, 3.0Hz), 8.03(1H, d, J=2.1Hz), 8.06-8.13(2H, m), 8.17(1H, s), 8.24(1H, d, J=3.0Hz). |

TABLE 160

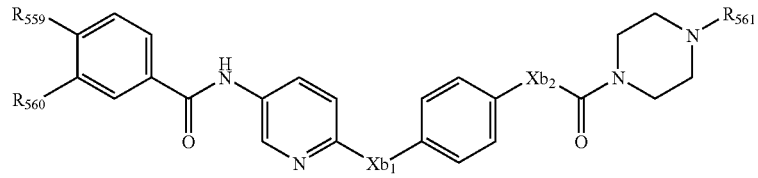

| Example No. | R559 | R560 | Xb1 | Xb2 | R561 | Form | mp (° C.) or ¹H NMR (DMSO-d₆) δppm |
|---|---|---|---|---|---|---|---|
| 270 | —Cl | —Cl | —O— | 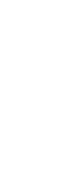 | piperonyl | free | ¹H NMR (at 375 K) 2.00(3H, brs), 2.30-2.38(4H, m), 3.34-3.43(6H, m), 4.12(2H, s), 4.51(2H, brs), 5.91(2H, s), 6.73(1H, d, J=7.9Hz), 6.77(1H, d, J=7.9Hz), 6.81(1H, s), 6.98(1H, d, J=8.8Hz), 7.05(2H, d, J=8.2Hz), 7.26(2H, d, J=8.2Hz), 7.73(1H, d, J=8.4Hz), 7.91(1H, dd, J=2.1Hz, 8.4Hz), 8.12-8.18(3H, m), 8.48(1H, d, J=2.6Hz), 10.17(1H, s). |
| 271 | —Cl | —Cl | —O— | 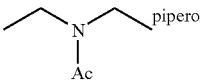 | benzyl | free | ¹H NMR (at 375 K) 2.00(3H, brs), 2.33-2.40(4H, m), 3.38-3.42(4H, m), 3.49-3.53(2H, m), 4.13(2H, s), 4.51(2H, brs), 6.98(1H, d, J=8.8Hz), 7.02-7.10(2H, m), 7.16-7.30(7H, m), 7.73(1H, d, J=8.4Hz), 7.91(1H, dd, J=8.4Hz, 2.1Hz), 8.11-8.17(2H, m), 8.48(1H, d, J=2.5Hz), 10.17(1H, s). |
| 272 | —CF₃ | —H | —O— | —CH=CH— (trans) | benzyl | free | ¹H NMR 2.39(4H, brs), 3.52(2H, s), 3.58(2H, brs), 3.71(2H, brs), 7.13(1H, d, J=8.9Hz), 7.14(2H, d, J=8.7Hz), 7.24(1H, d, J=15.3Hz), 7.18-7.41(5H, m), 7.50(1H, d, J=15.3Hz), 7.76(2H, d, J=8.7Hz), 7.94(2H, d, J=8.3Hz), 8.17(2H, d, J=8.3Hz), 8.25(1H, dd, J=8.9Hz, 2.7Hz), 8.54(1H, d, J=2.7Hz), 10.66(1H, s). |
| 273 | —CF₃ | —H | —O— | —CH=CH— (trans) | piperonyl | free | ¹H NMR 2.37(4H, brs), 3.42(2H, s), 3.58(2H, brs), 3.70(2H, brs), 5.99(2H, s), 6.76(1H, dd, J=8.0Hz, 2.4Hz), 6.85(1H, d, J=8.0Hz), 6.88(1H, d, J=1.5Hz), 7.13(1H, d, J=8.9Hz), 7.14(2H, d, J=8.7Hz), 7.20(1H, d, J=15.4Hz), 7.50(1H, d, J=15.4Hz), 7.76(2H, d, J=8.7Hz), 7.94(2H, d, J=8.2Hz), 8.17(2H, d, J=8.2Hz), 8.25(1H, dd, J=8.9Hz, 2.6Hz), 8.54(1H, d, J=2.6Hz), 10.65(1H, s). |
| 274 | —CF₃ | —H | —N(CH₃)— | none | piperonyl | dihydrochloride | ¹H NMR 2.98-3.12(2H, m), 3.12-3.36(2H, m), 3.50(3H, s), 3.71-4.68(6H, m), 6.06(2H, s), 6.93-7.06(3H, m), 7.26(1H, s), 7.42(2H, d, J=8.3Hz), 7.53(2H, d, J=8.3Hz), 7.92(2H, d, J=8.3Hz), 8.12(1H, d, J=9.2Hz), 8.20(2H, d, J=8.3Hz), 8.67(1H, s), 10.79(1H, s), 11.47(1H, brs). |
| 275 | —CF₃ | —H | —N(CH₃)— | none | benzyl | free | mp 213-214 |

TABLE 161
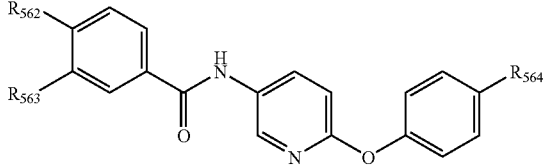
| Example No. | R562 | R563 | R564 | mp (° C.) or ¹H NMR (CDCl₃) δppm |
|---|---|---|---|---|
| 276 | —Cl | —Cl | 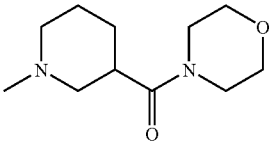 | ¹H NMR 1.62-1.80(2H, m), 1.82-1.87(2H, m), 2.71(1H, dt, J=3 Hz, 11.0Hz), 2.84(1H, brs), 2.94(1H, t, J=11.0Hz), 3.55-3.70(10H, m), 6.89(1H, d, J=9.0 Hz), 6.93(2H, dd, J=7.0Hz, 2.0 Hz), 7.02(2H, dd, J=7.0Hz, 2.0 Hz), 7.56(1H, d, J=8.0Hz), 7.71(1H, dd, J=9.0Hz, 2.0Hz), 7.99(1H, d, J=2.0Hz), 8.10(1H, s), 8.15(1H, dd, J=9.0Hz, 2.5 Hz), 8.25(1H, d, J=2.5Hz). |
| 277 | —Cl | —Cl | 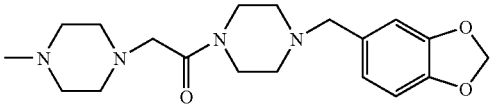 | ¹H NMR 2.38-2.42(4H, m), 2.62-2.67(4H, m), 3.14-3.17(4H, m), 3.22(2H, s), 3.42(2H, s), 3.61-3.63(4H, m), 5.95(2H, s), 6.70-6.75+2H, m), 7.03(2H, d, J=8.0 Hz), 7.55(1H, d, J=8.0Hz), 7.70(1H, brs), 7.73(2H, d, J=8.0 Hz), 8.01(1H, s), 8.15(1H, brd, J=9.0Hz), 8.27(1H, d, J=2.5 Hz). |
| 278 | —Cl | —Cl | 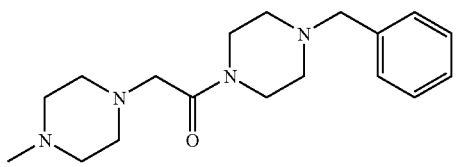 | ¹H NMR 2.40-2.45(4H, m), 2.60-2.64(4H, m), 3.13(4H, brs), 3.20(2H, brs), 3.48(2H, brs), 3.62(4H, brs), 6.85-6.91(3H, m), 7.01(2H, d, J=8.0Hz), 7.26-7.32(5H, m), 7.52(1H, d, J=8.5 Hz), 7.70(1H, brs), 7.74(1H, dd, J=8.5Hz, 2.0Hz), 8.03(1H, d, J=2.0Hz), 8.15(1H, brd, J=9.0, Hz), 8.29(1H, d, J=2.5Hz). |
| 279 | —H | —CF₃ | 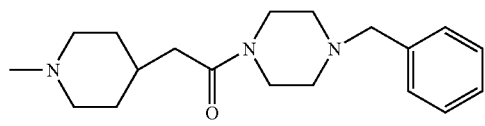 | mp 180-183 |
| 280 | —H | —CF₃ | 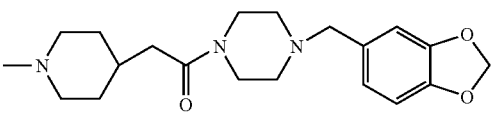 | mp 197-199 |
| 281 | —H | —CF₃ | 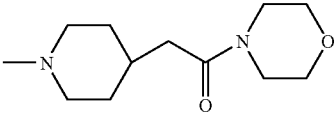 | mp 133-135 |

TABLE 162
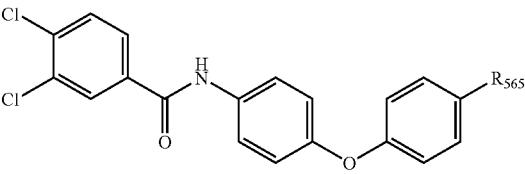
| Example No. | R565 | Form | mp(° C.) |
|---|---|---|---|
| 282 | 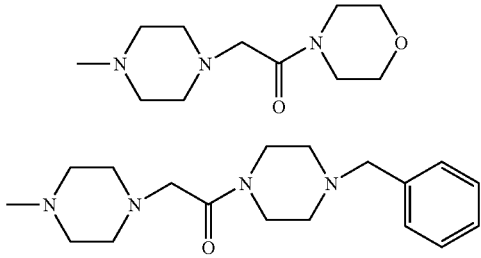 | free | 108–110 |
| 283 | 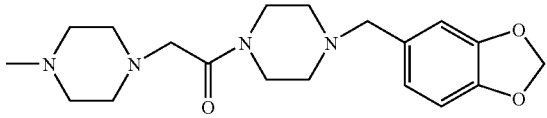 | free | 136–138 |
| 284 | 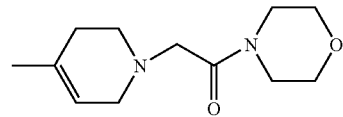 | free | 133–136 |
| 285 | 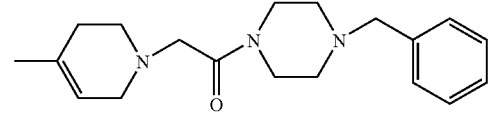 | free | 147–151 |
| 286 | 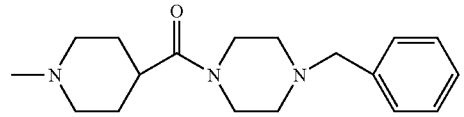 | dihydrochloride | 180–183 |
| 287 | 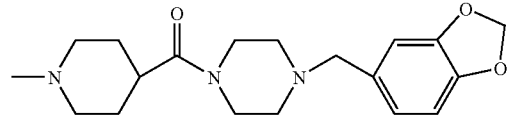 | free | 111–113 |
| 288 | 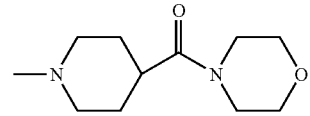 | free | 111–113 |
| 289 | 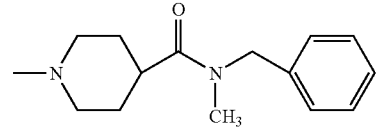 | free | 246–249 |
| 290 | 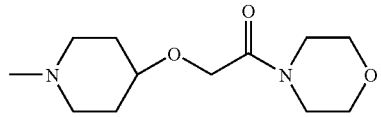 | free | 148–151 |
| 291 |  | free | 120–121 |

TABLE 163

| Example No. | R₅₆₆ | Form | mp(° C.) |
|---|---|---|---|
| 292 | | free | 83–86 |
| 293 | | free | 130–133 |
| 294 | | free | 145–146 |
| 295 | | trihydrochloride | 180–185 |
| 296 | | free | 184–186 |
| 297 | | free | 173–176 |
| 298 | | free | 181–183 |
| 299 | | free | 166–170 |

TABLE 164

[Structure: 3,4-dichloro-N-(4-(4-R567-phenoxy)phenyl)benzamide]

| No. | R567 | mp(° C.) |
|-----|------|----------|
| 300 | (1-methylpiperidin-4-yl)carbonyl-(4-benzylpiperazin-1-yl) | 102–104 |
| 301 | (1-methylpiperidin-4-yl)carbonyl-(4-(benzo[d][1,3]dioxol-5-ylmethyl)piperazin-1-yl) | 106–109 |
| 302 | (1-methylpiperidin-4-yl)carbonyl-morpholino | 261–264 |
| 303 | 1-methyl-N-benzyl-N-methylpiperidine-4-carboxamide | 173–175 |
| 304 | 2-(4-methylpiperidin-1-yl)-1-morpholinoethanone | 164–166 |
| 305 | 2-(1-methylpiperidin-4-yl)-1-(4-benzylpiperazin-1-yl)ethanone | 158–160 |
| 306 | (1-methylpiperidin-3-yl)carbonyl-(4-benzylpiperazin-1-yl) | 174–176 |
| 307 | (1-methylpiperidin-3-yl)carbonyl-(4-(benzo[d][1,3]dioxol-5-ylmethyl)piperazin-1-yl) | 206–207 |
| 308 | 2-(4-methylpiperazin-1-yl)-1-morpholinoethanone | 165–166 |
| 309 | 2-(4-methyl-3-oxopiperazin-1-yl)-1-(4-benzylpiperazin-1-yl)ethanone | 164–167 |

TABLE 164-continued

[Structure: 3,4-dichlorobenzamide linked through NH to 4-phenoxyphenyl, with R₅₆₇ on the distal phenyl]

| No. | R₅₆₇ | mp(° C.) |
|---|---|---|
| 310 | [1-methyl-3-oxopiperazin-4-yl]-CH₂-C(O)-morpholine | 188–190 |
| 311 | [1-methyl-3-oxopiperazin-4-yl]-CH₂-C(O)-[piperazine]-CH₂-[1,3-benzodioxol-5-yl] | 130–132 |

TABLE 165

[Structure: 4-(trifluoromethyl)benzamide linked through NH to a pyridine ring, which is connected via O to a phenyl bearing R₅₆₈ and a piperazine substituted with R₅₆₉]

| Example No. | R₅₆₈ | R₅₆₉ | mp(° C.) or ¹H NMR(CDCl₃) δ ppm |
|---|---|---|---|
| 312 | —H | propanoyl-piperazine-CH₂-phenyl (benzyl) | mp 166–167 |
| 313 | —H | propanoyl-piperazine-CH₂-(1,3-benzodioxol-5-yl) | mp 157–158 |
| 314 | —H | propanoyl-morpholine | mp 218–219 |
| 315 | CH₃C(O)NH-cyclopropyl | benzyl | ¹H NMR 0.25–0.31(2H, m), 0.61–0.69(2H, m), 2.67–2.73(1H, m), 2.86(4H, brs), 3.18(4H, brs), 3.83(2H, s), 6.80–6.92(3H, m), 7.16–7.62(8H, m), 8.11(2H, d, J=8.1 Hz), 8.39(1H, dd, J=8.9 Hz, 2.6 Hz), 8.45(1H, d, J=2.5 Hz), 10.23(1H, s), 10.93(1H, brs). |
| 316 | —CONHPh | benzyl | ¹H NMR 3.07(4H, brs), 3.26(4H, brs), 3.98(2H, s), 6.83–7.59(14H, m), 7.65(2H, d, J=8.3 Hz), 8.06(2H, d, J=8.1 Hz), 8.37(1H, d, J=2.6 Hz), 8.49(1H, dd, J=8.9 Hz, 2.6 Hz), 9.30(1H, s), 9.71(1H, brs). |

TABLE 165-continued

[Structure: 4-(trifluoromethyl)benzamide linked to pyridine-O-phenyl-piperazine with R568 on phenyl and R569 on piperazine]

| Example No. | R568 | R569 | mp(° C.) or ¹H NMR(CDCl₃) δ ppm |
|---|---|---|---|
| 317 | [1-acetylpyrrolidin-yl group] | benzyl | ¹H NMR 1.87(4H, brs), 2.72(4H, brs), 3.19(4H, brs), 3.40(4H, brs), 3.69(2H, s), 6.58(1H, d, J=8.7 Hz), 6.80(1H, s), 6.92(1H, d, J=9.2 Hz), 7.02(1H, d, J=8.9 Hz), 7.26–7.34(5H, m), 7.57(2H, d, J=7.9 Hz), 7.90(1H, d, J=7.1 Hz), 8.05(2H, d, J=8.1 Hz), 8.40(1H, s), 9.73(1H, s). |

TABLE 166

[Structure: 4-(trifluoromethyl)benzamide linked to pyridine-Xb3-phenyl-piperazine-XB4-C(=O)-piperazine-Xb5-R570]

| Example No. | Xb3 | Xb4 | Xb5 | R570 | mp(° C.) or ¹H NMR (CDCl₃) δ ppm |
|---|---|---|---|---|---|
| 318 | —O— | >CH—N< | | benzyl | mp 162–163 |
| 319 | —O— | >CH—N< | | piperonyl | mp 136–137 |
| 320 | —O— | >CH—N< | —O— | none | mp 176–177 |
| 321 | —N(CH₃)— | >N—N< | | benzyl | ¹H NMR 2.43(4H, brs), 2.67(4H, t, J=4.8 Hz), 3.22(4H, t, J=4.8 Hz), 3.24(2H, s), 3.42(3H, s), 3.52(2H, s), 3.63(4H, brs), 6.46 (1H, d, J=9.1 Hz), 6.95(2H, d, J=8.9 Hz), 7.15(2H, d, J=8.9 Hz), 7.20–7.40(5H, m), 7.65–7.80(2H, m), 7.74(2H, d, J=8.2 Hz), 7.98(2H, d, J=8.2 Hz), 8.26(1H, d, J=2.5 Hz). |
| 322 | —N(CH₃)— | >N—N< | | piperonyl | ¹H NMR 2.41(4H, brs), 2.67(4H, t, J=4.8 Hz), 3.22(4H, t, J=5.1 Hz), 3.24(2H, s), 3.42(5H, s), 3.62(4H, t, J=4.5 Hz), 5.94(2H, s) 6 46(1H, d, J=9.1 Hz), 6.74(2H, s), 6.85(1H, s), 6.95(2H, d, J=8.9 Hz), 7.15(2H, d, J=8.9 Hz), 7.65–7.75(1H, m), 7.74(2H, d, J=8.1 Hz), 7.83(1H, brs), 7.99(2H, d, J=8.1 Hz), 8.26(1H, d, J=2.5 Hz). |

TABLE 166-continued

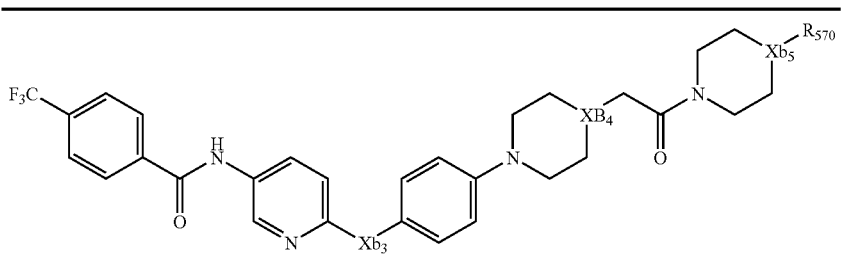

| Example No. | Xb₃ | Xb₄ | Xb₅ | R₅₇₀ | mp(° C.) or ¹H NMR (CDCl₃) δ ppm |
|---|---|---|---|---|---|
| 323 | —N(CH₃)— | (piperidine-CH) | (N-methylpiperazine) | benzyl | ¹H NMR 1.31–1.52(2H, m), 1.88(2H, d, J=12.3 Hz), 1.88–2.15(1H, m), 2.29(2H, d, J=6.7 Hz), 2.44(4H, t, J=5.1 Hz), 2.76(2H, t, J=11.2 Hz), 3.42(3H, s), 3.49(2H, t, J=4.9 Hz), 3.53(2H, s), 3.59–3.78(4H, m), 6.47(1H, d, J=9.1 Hz), 6.96(2H, d, J=8.9 Hz), 7.13 (2H, d, J=8.9 Hz), 7.20–7.41(5H, m), 7.61–7.78(2H, m), 7.75(2H, d, J=8.1 Hz), 7.98 (2H, d, J=8.1 Hz), 8.25(1H, d, J=2.3 Hz). |
| 324 | —N(CH₃)— | (piperidine-CH) | (N-methylpiperazine) | piperonyl | ¹H NMR 1.30–1.51(2H, m), 1.88(2H, d, J=2.9 Hz), 1.98–2.11(1H, m), 2.29(2H, d, J=6.7 Hz), 2.41(4H, m), 2.76(2H, t, J=11.2 Hz), 3.42(3H, s), 3.43(2H, s), 3.49(2H, t, J=4.8 Hz) 3.55–3.78(4H, m), 5.95(2H, s), 6.47(1H, d, J=9.0 Hz), 6.74(2H, s), 6.86(1H, s), 6.96(2H, d, J=8.9 Hz), 7.13(2H, d, J=8.9 Hz), 7.70(1H, brs), 7.71(1H, dd, J=9.0 Hz, 2.7 Hz), 7.75(2H, d, J=8.2 Hz), 7.99(2H, d, J=8.2 Hz), 8.26(1H, d, J=2.7 Hz). |

TABLE 167

| Example No. | Xb₆ | M | R₅₇₁ | Form | δ mp(° C.) or ¹H NMR |
|---|---|---|---|---|---|
| 325 | —N(Ac)— | 1 | 4-methyl-1-(2-phenylethyl)piperazine | hydro-chloride | mp 214–216 |
| 325 | —N(Ac)— | 1 | 1-benzyl-4-methylpiperazine | free | ¹H NMR(DMSO-d₆) δ 1.77(3H, s), 2.25–2.34(4H, m), 3.30–3.50(6H, m), 4.40 (2H, s), 6.97(2H, d, J=8.8 Hz), 7.22–7.35(6H, m), 7.36(2H, d, J=8.8 Hz), 7.53–7.59(1H, m), 7.84(1H, d, J=8.3 Hz), 7.89–7.95(2H, m), 8.20(1H, d, J=2.2 Hz), 10.61(1H s). |
| 327 | none | 1 | 1-benzyl-4-methylpiperazine | free | mp 178–179 |

TABLE 167-continued

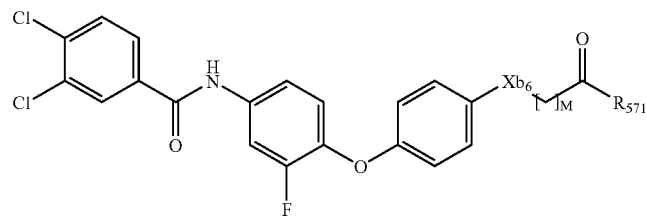

| Example No. | Xb6 | M | R571 | Form | δ mp(° C.) or ¹H NMR |
|---|---|---|---|---|---|
| 328 | none | 1 | morpholino | free | mp 196–198 |
| 329 | none | 1 | (N-methylpiperazinyl-CH2-benzodioxole) | free | mp 197–198 |
| 330 | none | 3 | morpholino | free | mp 144–146 |
| 331 | none | 3 | (N-methylpiperazinyl-CH2-phenyl) | hydrochloride | mp 194–196 |
| 332 | none | 3 | (N-methylpiperazinyl-CH2-benzodioxole) | hydrochloride | mp 205–206 |
| 333 | —S— | 1 | (N-methylpiperazinyl-CH2-benzodioxole) | | ¹H NMR(CDCl₃) δ 2.35–2.45(4H, m), 3.42(2H, s), 3.42–3.48(2H, m), 3.58(2H, brs), 3.65(2H, s), 5.94(2H, s), 6.72–6.75(2H, m), 6.84(1H, d, J=1.1 Hz), 6.89(2H, d, J=8.8 Hz), 7.00–7.10(1H, m), 7.19–7.25(1H, m), 7.42(2H, d, J=8.8 Hz), 7.58(1H, d, J=8.3 Hz), 7.65–7.76(2H, m), 7.98(1H, s), 7.99(1H, s). |
| 334 | —SO— | 1 | (N-methylpiperazinyl-CH2-benzodioxole) | free | mp 133–135 |
| 335 | —SO₂— | 1 | (N-methylpiperazinyl-CH2-benzodioxole) | free | mp 125–128 |
| 336 | CH=CH- (trans) | 0 | (N-methylpiperazinyl-CH2-benzodioxole) | free | mp 169–171 |

TABLE 168

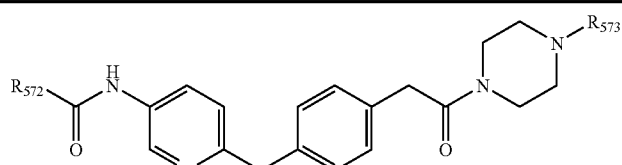

| Example No. | R572 | R573 | ¹H NMR(solvent) δ ppm |
|---|---|---|---|
| 337 | 4-CF₃Ph— | benzyl | (CDCl₃) 2.302.34(2H, m), 2.39–2.43(2H, m), 3.46–3.49(4H, m), 3.62–3.66(2H, m), 3.69(2H, |

TABLE 168-continued

[Structure: R572-C(=O)-NH-pyridine-O-phenyl-CH2-C(=O)-N(piperazine)-R573]

| Example No. | R572 | R573 | 1H NMR(solvent) δ ppm |
|---|---|---|---|
| | | | s), 6.94(1H, d, J=8.7 Hz), 7.03–7.08(2H, m), 7.19–7.35(7H, m), 7.75(2H, d, J=8.2 Hz), 8.00(2H, d, J=8.2 Hz), 8.21(1H, dd, J=8.7 Hz, 2.8 Hz), 8.26(1H, s), 8.29(1H, d, J=2.8 Hz). |
| 338 | 4-CF3Ph— | piperonyl | (CDCl3) 2.28–2.32(2H, m), 2.36–2.39(2H, m), 3.39(2H, s), 3.45–3.49(2H, nO, 3.60–3.64(2H, m), 3.68(2H, s), 5.94(2H, s), 6.69–6.76(2H, m), 6.83(1H, brs), 6.92(1H, d, J=8.7 Hz), 7.01–7.06(2H, m), 7.17–7.22(2H, m), 7.72(2H, d, J=8.4 Hz), 8.00(2H, d, J=8.1 Hz), 8.17–8.21(1H, m), 8.29(1H, d, J=2.6 Hz), 8.49(1H, brs). |
| 339 | 3,4-Cl2Ph— | benzyl | (CDCl3) 2.31–2.34(2H, m), 2.38–2.42(2H, m), 3.46–3.50(4H, m), 3.62–3.65(2H, m), 3.69(2H, s), 6.90(1H, d, J=8.9 Hz), 7.00–7.05(2H, m), 7.17–7.23(2H, m), 7.28–7.35(5H, m), 7.54(1H, d, J=8.2 Hz), 7.73(1H, dd, J=8.4 Hz, 2.1 Hz), 7.99(1H, d, J=2.1 Hz), 8.12–8.17(1H, m); 8.28(1H, d, J=2.8 Hz), 8.44(1H, brs). |
| 340 | 3,4-Cl2Ph— | 3-pyridyl | (CDCl3) 3.02–3.06(2H, m), 3.13–3.17(2H, m), 3.63–3.67(2H, m), 3.76–3.82(4H, m), 6.91(1H, d, J=8.9 Hz), 7.02–7.07(2H, m), 7.17–7.24(4H, m), 7.52(1H, d, J=8.4 Hz), 7.737.76(1H, m), 8.01(1H, d, J=2.0 Hz), 8.11–8.13(1H, m), 8.18(1H, dd, J=8.9 Hz, 2.8 Hz), 8.23–8.25(2H, m), 8.95(1H, brs). |
| 341 | 3,4-Cl2Ph— | piperonyl | (CDCl3) 2.28–2.39(4H, m), 3.39(2H, s), 3.46-3.49(2H, m), 3.60–3.64(2H, m), 3.69(2H, s), 5.94(2H, s), 6.69–6.76(2H, m), 6.82–6.83(1H, m), 6.89(1H, d, J=8.9 Hz), 6.99–7.04(2H, m), 7.15–7.21(2H, m), 7.53(1H, d, J=8.4 Hz), 7.71–7.75(1H, m), 7.99(1H, d, J=2.1 Hz), 8.14(1H, dd, J=8.9 Hz, 2.6 Hz), 8.28(1H, d, J=2.6 Hz), 8.56(1H, s). |
| 342 | 3,4-Cl2PhNH— | piperonyl | (DMSO-d6) 2.20–2.35(4H, m), 3.38(2H, s), 3.40-3.55(4H, m), 3.69(2H, s), 5.98(2H, s), 6.70-6.76(1H, m), 6.76–6.86(2H, m), 6.97–7.00(3H, m), 7.02–7.24(2H, m), 7.35(1H, dd, J=8.8 Hz, 2.5 Hz), 7.52(1H, d, J=8.8 Hz), 7.86(1H, d, J=2.5 Hz), 7.98(1H, dd, J=8.8 Hz, 2.8 Hz), 8.19(1H, d, J=2.6 Hz), 8.89(1H, s), 9.08(1H, s). |

TABLE 169

[Structure: 3,4-Cl2-C6H3-C(=O)-NH-phenyl(F)-O-phenyl-CH2CH2-C(=O)-NH-R574]

| Example No. | R574 | 1H NMR(DMSO-d6) δ ppm or MS |
|---|---|---|
| 343 | —H | 1H NMR 2.33(2H, t, J=7.7 Hz), 2.77(2H, t, J=7.7 Hz), 6.75(1H, brs), 6.87(2H, d, J=8.6 Hz), 7.15–7.23(3H, m), 7.28(1H, brs), 7.54(1H, d, J=8.7 Hz), 7.85(1H, d, J=8.4 Hz), 7.89(1H, dd, J=13.2 Hz, 2.4 Hz), 7.94(1H, dd, J=8.4 Hz, 2.0 Hz), 8.21(1H, d, J=2.0 Hz), 10.57(1H, s). |
| 344 | —CH3 | MS 460(M+) |
| 345 | —C2H5 | 1H NMR 0.97(3H, t, J=7.2 Hz), 2.32(2H, t, J=7.8 Hz), |

TABLE 169-continued

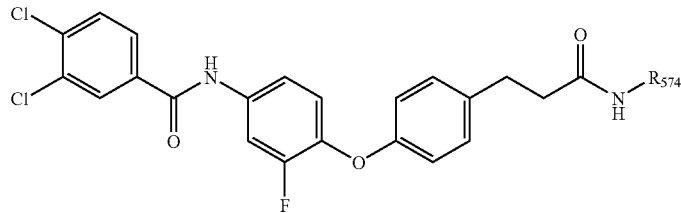

| Example No. | $R_{574}$ | $^1$H NMR(DMSO-$d_6$) δ ppm or MS |
|---|---|---|
| | | 2.77(2H, t, J=7.8 Hz), 3.00–3.08(2H, m), 6.87(2H, d, J=8.6 Hz), 7.14–7.21(3H, m), 7.54(1H, d, J=9.8 Hz), 7.78(1H, brt), 7.85(1H, d, J=8.4 Hz), 7.89(1H, dd, J=13.2 Hz, 2.3 Hz), 7.94(1H, dd, J=8.4 Hz, 2.1 Hz), 8.21(1H, d, J=2.1 Hz), 10.57(1H, s). |
| 346 | —CH(CH$_3$)$_2$ | $^1$H NMR 1.00(6H, d, J=6.6 Hz), 2.30(2H, t, J=7.7 Hz), 2.77(2H, t, J=7.7 Hz), 3.75–3.86(1H, m), 6.87(2H, d, J=8.6 Hz), 7.137.20(3H, m), 7.54(1H, d, J=8.9 Hz), 7.65(1H, brd), 7.85(1H, d, J=8.4 Hz), 7.89(1H, dd, J=13.1 Hz, 2.5 Hz), 7.94(1H, dd, J=8.4 Hz, 2.1 Hz), 8.22(1H, d, J=2.1 Hz), 10.58(1H, s). |
| 347 | —CH$_2$CH(CH$_3$)$_2$ | $^1$H NMR 0.78(6H, d, J=6.7 Hz), 1.56–1.68(1H, m), 2.36(2H, t, J=7.6 Hz), 2.78(2H, t, J=7.6 Hz), 2.81–2.87(2H, m), 6.87(2H, d, J=8.6 Hz), 7.10–7.22(3H, m), 7.54(1H, d, J=8.9 Hz), 7.77(1H, brt), 7.85(1H, d, J=8.4 Hz), 7.89(1H, dd, J=13.2 Hz, 2.4 Hz), 7.94(1H, dd, J=8.4 Hz, 2.1 Hz), 8.21(1H, d, J=2.1 Hz), 10.57(1H, s). |
| 348 | —(CH$_2$)$_3$CH$_3$ | $^1$H NMR 0.84(3H, t, J=7.3 Hz), 1.15–1.27(2H, m), 1.27–1.38(2H, m), 2.33(2H, t, J=7.7 Hz), 2.77(2H, t, J=7.7 Hz), 2.97–3.05(2H, m), 6.87(2H, d, J=8.6 Hz), 7.11–7.21(3H, m), 7.50–7.58(1H, m), 7.74(1H, brt), 7.85(1H, d, J=8.4 Hz), 7.89(1H, dd, J=13.2 Hz, 2.4 Hz), 7.94(1H, dd, J=8.4 Hz, 2.1 Hz), 8.21(1H, d, J=2.1 Hz), 10.57(1H, s). |
| 349 | cyclopropyl | $^1$H NMR 0.26–0.37(2H, m), 0.51–0.63(2H, m), 2.29(2H, t, J=7.7 Hz), 2.53–2.61(1H, m), 2.76(2H, t, J=7.7 Hz), 6.87(2H, d, J=8.6 Hz), 7.10–7.23(3H, m), 7.54(1H, d, J=8.6 Hz), 7.80–8.00(4H, m), 8.21(1H, d, J=2.1 Hz), 10.57(1H, s). |
| 350 | cyclopentyl | $^1$H NMR 1.21–1.34(2H, m), 1.41–1.51(2H, m), 1.51–1.63(2H, m), 1.68–1.80(2H, m), 2.31(2H, t, J=7.7 Hz), 2.76(2H, t, J=7.7 Hz), 3.90–3.99(1H, m), 6.87(2H, d, J=8.6 Hz), 7.14–7.21(3H, m), 7.50–7.57(1H, m), 7.72(1H, brd), 7.85(1H, d, J=8.4 Hz), 7.89(1H, dd, J=13.2 Hz, 2.4 Hz), 7.94(1H, dd, J=8.4 Hz, 2.1 Hz), 8.22(1H, d, J=2.1 Hz), 10.58(1H, s). |
| 351 | cyclohexyl | $^1$H NMR 1.00–1.15(3H, m), 1.15–1.28(2H, m), 1.48–1.58(1H, m), 1.58–1.70(4H, m), 2.31(2H, t, J=7.6 Hz), 2.77(2H, t, J=7.6 Hz), 3.44–3.53(1H, m), 6.87(2H, d, J=8.6 Hz), 7.11–7.23(3H, m), 7.50–7.57(1H, m), 7.62(1H, brd), 7.85(1H, d, J=8.4 Hz), 7.89(1H, dd, J=13.2 Hz, 2.4 Hz), 7.94(1H, dd, J=8.4 Hz, 2.1 Hz), 8.21(1H, d, J=2.1 Hz), 10.57(1H, s). |

TABLE 170

| Example No. | $R_{575}$ | $^1$H NMR(DMSO-$d_6$) δ ppm |
|---|---|---|
| 352 | cycloheptyl | 1.28–1.40(4H, m), 1.40–1.61(6H, m), 1.63–1.77(2H, m), 2.31(2H, t, J=7.6 Hz), 2.76(2H, t, J=7.6 Hz), 3.64–3.74(1H, m), 6.87(2H, d, J=8.6 Hz), 7.11–7.23(3H, m), 7.54(1H, d, J=9.1 Hz), 7.67(1H, brd), 7.85(1H, d, J=8.4 Hz), 7.89(1H, dd, J=13.2 Hz, 2.4 Hz), 7.94(1H, dd, J=8.4 Hz, 2.1 Hz), 8.21(1H, d, J=2.1 Hz), 10.57(1H, s). |
| 353 | cyclooctyl | 1.30–1.65(14H, m), 2.31(2H, t, J=7.6 Hz), 2.76(2H, t, J=7.6 Hz), 3.69–3.80(1H, m), 6.87(2H, d, J=8.6 Hz), 7.10–7.22(3H, m), 7.54(1H, d, J=8.9 Hz), 7.65(1H, brd), 7.85(1H, d, J=8.4 Hz), 7.89(1H, dd, J=13.2 Hz, 2.3 Hz), 7.94(1H, dd, J=8.4 Hz, 2.0 Hz), 8.21(1H, d, J=2.0 Hz), 10.57(1H, s). |
| 354 | cyclododecanyl | 1.10–1.41(20H, m), 1.41–1.54(2H, m), 2.32(2H, t, J=7.5 Hz), 2.77(2H, t, J=7.5 Hz), 3.79–3.88(1H, m), 6.86(2H, d, J=8.6 Hz), 7.10–7.21(3H, m), 7.48–7.57(2H, m), 7.85(1H, d, J=8.4 Hz), 7.89(1H, dd, J=13.1 Hz, 2.5 Hz), 7.94(1H, dd, J=8.4 Hz, 2.1 Hz), 8.21(1H, d, J=2.1 Hz), 10.58(1H, s). |

TABLE 170-continued

| Example No. | R$_{575}$ | $^1$H NMR(DMSO-d$_6$) δ ppm |
|---|---|---|
| 355 | cyclopropylmethyl | 0.06–0.16(2H, m), 0.28–0.42(2H, m), 0.78–0.90(1H, m), 2.35(2H, t, J=7.7 Hz), 2.78(2H, t, J=7.7 Hz), 2.84–2.97(2H, m), 6.87(2H, d, J=8.5 Hz), 7.12–7.27(3H, m), 7.54(1H, d, J=8.8 Hz), 7.85(1H, d, J=8.4 Hz), 7.87(1H, brt), 7.89(1H, dd, J=13.2 Hz, 2.3 Hz), 7.94(1H, dd, J=8.4 Hz, 2.0 Hz), 8.21(1H, d, J=2.0 Hz), 10.57(1H, s). |
| 356 | cyclohexylmethyl | 0.71–0.86(2H, m), 1.03–1.20(3H, m), 1.22–1.34(1H, m), 1.50–1.69(5H, m), 2.35(2H, t, J=7.6 Hz), 2.78(2H, t, J=7.6 Hz), 2.80–2.90(2H, m), 6.86(2H, d, J=8.6 Hz), 7.12 7.23(3H, m), 7.54(1H, d, J=8.9 Hz), 7.73(1H, brt), 7.85(1H, d, J=8.4 Hz), 7.89(1H, dd, J=13.2 Hz, 2.4 Hz), 7.94(1H, dd, J=8.4 Hz, 2.1 Hz), 8.21(1H, d, J=2.1 Hz), 10.57(1H, s). |
| 357 | piperonyl | 2.41(2H, t, J=7.6 Hz), 2.81(2H, t, J=7.6 Hz), 4.15(2H, d, J=5.9 Hz), 5.96(2H, s), 6.63(1H, d, J=8.0 Hz), 6.74(1H, d, J=1.4 Hz), 6.80(1H, d, J=8.0 Hz), 6.87(2H, d, J=8.8 Hz), 7.14–7.23(3H, m), 7.54(1H, d, J=9.8 Hz), 7.85(1H, d, J=8.4 Hz), 7.89(1H, dd, J=13.2 Hz, 2.4 Hz), 7.94(1H, dd, J=8.4 Hz, 2.1 Hz), 8.22(1H, d, J=2.1 Hz), 8.25(1H, brt), 8.40–8.46(2H, m), 10.58(1H, s). |
| 358 | —CH(CH$_3$)Ph | 1.30(3H, d, J=7.0 Hz), 2.40(2H, t, J=7.5 Hz), 2.78(2H, t, J=7.5 Hz), 3.86–3.96(1H, m), 6.82–6.99(2H, m), 7.12 7.24(6H, m), 7.24–7.31(2H, m), 7.55(1H, dd, J=8.9 Hz, 1.2 Hz), 7.85(1H, d, J=8.4 Hz), 7.90(1H, dd, J=13.2 Hz, 2.5 Hz), 7.94(1H, dd, J=8.4 Hz, 2.1 Hz), 8.22(1H, d, J=2.1 Hz), 8.24(1H, brd), 10.59(1H, s). |

TABLE 171

| Example No. | R$_{576}$ | $^1$H NMR(DMSO-d$_6$) δ ppm or MS |
|---|---|---|
| 359 | 2-pyridylmethyl | MS 537(M+) |
| 360 | 3-pyridylmethyl | $^1$H NMR 2.44(2H, t, J=7.6 Hz), 2.82(2H, t, J=7.6 Hz), 4.27(2H, d, J=5.9 Hz), 6.86(2H, dd, J=6.7 Hz, 1.9 Hz), 7.14–7.22(3H, m), 7.25–7.32(1H, m), 7.46–7.58(2H, m), 7.85(1H, d, J=8.4 Hz), 7.90(1H, dd, J=13.2 Hz, 2.5 Hz), 7.94(1H, dd, J=8.4 Hz, 2.1 Hz), 8.22(1H, d, J=2.1 Hz), 8.38(1H, brt), 8.40–8.46(2H, m), 10.58(1H, s). |
| 361 | 4-pyridylmethyl | MS 537(M+) |
| 362 | -(CH$_2$)2NHAc | $^1$H NMR 1.78(3H, s), 2.34(2H, t, J=7.8 Hz), 2.78(2H, t, J=7.8 Hz), 2.96–3.10(4H, m), 6.83–6.91(2H, m), 7.14–7.23(3H, m), 7.54(1H, dd, J=8.9 Hz, 1.3 Hz), 7.80–7.98(5H, m), 8.21(1H, d, J=2.1 Hz), 10.58(1H, s). |
| 363 | —CH(CH$_3$)(CH$_2$)4CH$_3$ | $^1$H NMR 0.84(3H, t, J=7.0 Hz), 0.96(3H, d, J=6.6 Hz), 1.08–1.34(8H, m), 2.32(2H, t, J=7.2 Hz), 2.77(2H, t, J=7.2 Hz), 3.65–3.76(1H, m), 6.82 6.89(2H, m), 7.12–7.21(3H, m), 7.50–7.60(2H, m), 7.85(1H, d, J=8.4 Hz), 7.89(1H, dd, J=13.2 Hz, 2.5 Hz), 7.94(1H, dd, J=8.3 Hz, 2.1 Hz), 8.21(1H, d, J=2.1 Hz), 10.58(1H, s). |
| 364 | -(CH$_2$)2OCH$_3$ | $^1$H NMR 2.35(2H, t, J=7.7 Hz), 2.77(2H, t, J=7.7 Hz), 3.13–3.22(2H, m), 3.22(3H, s), 3.29(2H, t, J=5.8 Hz), 6.82–6.92(2H, m), 7.13–7.23(3H, m), 7.54(1H, d, J=8.9 Hz)7.85(1H, d, J=8.4 Hz), 7.85-7.92(2H, m), 7.94(1H, dd, J=8.4 Hz, 2.0 Hz), 8.21(1H, d, J=2.0 Hz), 10.57(1H, s). |

TABLE 171-continued

[Structure: 3,4-dichlorobenzamide linked to fluorophenyl-O-phenyl-CH2CH2C(O)NH-R575]

| Example No. | R576 | ¹H NMR(DMSO-d6) δ ppm or MS |
|---|---|---|
| 365 | [1-butyl-imidazole] | MS 554(M+) |
| 366 | [4-methyl-1-benzyl-piperidine] | MS 619(M+) |

TABLE 172

[Structure: 3,4-dichlorobenzamide linked to phenyl(R577)-O-phenyl-CH2CH2C(O)-R578]

| Example No. | R577 | R578 | mp(° C.) or MS |
|---|---|---|---|
| 367 | —H | morpholino | mp 160–162 |
| 368 | —F | morpholino | mp 150–151 |
| 369 | —F | [1-methyl-4-(4-trifluoromethylphenyl)-1,2,3,6-tetrahydropyridine] | MS 657(M⁺ + H) |
| 370 | —F | [4-(dimethylamino)-1-benzoylpiperidine] | MS 646(M⁺ − 1) |
| 371 | —F | 4-CH₃OPh(CH₂)₂N(C₂H₅)— | MS 608(M+) |
| 372 | —F | 4-CH₃OPhCH₂N(C₂H₅)— | MS 594(M+) |
| 373 | —F | 3,4-(CH₃O)₂PhCH₂N(CH₂CH₂CH₃)— | MS 638(M+) |

TABLE 173

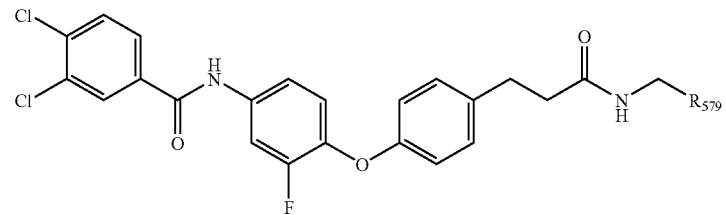

| Example No. | $R_{579}$ | $^1$H NMR(DMSO-$d_6$) δ ppm |
|---|---|---|
| 374 | Ph— | 2.39–2.49(2H, m), 2.78–2.88(2H, m), 4.18–4.30(2H, m), 6.87(2H, d, J=8.6 Hz), 7.02–7.33(8H, m), 7.55(1H, d, J=8.9 Hz), 7.85(1H, d, J=8.4 Hz), 7.90(1H, dd, J=13.2 Hz, 2.4 Hz), 7.94(1H, dd, J=8.4 Hz, 2.0 Hz), 8.22(1H, d, J=2.0 Hz), 8.32(1H, brt), 10.58(1H, s). |
| 375 | 4-FPh— | 2.43(2H, t, J=7.6 Hz), 2.82(2H, t, J=7.6 Hz), 4.22(2H, d, J=5.9 Hz), 6.87(2H, d, J=8.6 Hz), 7.04–7.12(2H, m), 7.12 7.24(5H, m), 7.55(1H, d, J=9.0 Hz), 7.85(1H, d, J=8.4 Hz), 7.90(1H, dd, J=13.2 Hz, 2.4 Hz), 7.94(1H, dd, J=8.4 Hz, 2.1 Hz), 8.22(1H, d, J=2.1 Hz), 8.32(1H, brt), 10.58(1H, s). |
| 376 | 3,4-(CH$_3$O)$_2$Ph— | 2.42(2H, t, J=7.6 Hz), 2.82(2H, t, J=7.6 Hz), 3.70(3H, s), 3.71(3H, s), 4.18(2H, d, J=5.8 Hz), 6.67(1H, d, J=8.4 Hz), 6.77–6.90(4H, m), 7.15–7.23(3H, m), 7.55(1H, d, J=9.0 Hz), 7.85(1H, d, J=8.4 Hz), 7.89(1H, dd, J=13.2 Hz, 2.4 Hz), 7.94(1H, dd, J=8.4 Hz, 2.1 Hz), 8.21(1H, d, J=2.0 Hz), 8.25(1H, brt), 10.58(1H, s). |
| 377 | 2-ClPh— | 2.48(2H, t, J=7.5 Hz), 2.83(2H, t, J=7.5 Hz), 4.30(2H, d, J=5.9 Hz), 6.88(2H, d, J=8.6 Hz), 7.08–7.15(1H, m), 7.15-7.32(5H, m), 7.38–7.46(1H, m), 7.51–7.59(1H, m), 7.85(1H, d, J=8.4 Hz), 7.90(1H, dd, J=13.2 Hz, 2.4 Hz), 7.94(1H, dd, J=8.4 Hz, 2.1 Hz), 8.22(1H, d, J=2.0 Hz), 8.34(1H, brt), 10.58(1H, s). |
| 378 | 3-ClPh— | 2.45(2H, t, J=7.5 Hz), 2.83(2H, t, J=7.5 Hz), 4.25(2H, d, J=6.0 Hz), 6.87(2H, d, J=8.6 Hz), 7.07–7.12(1H, m), 7.12-7.21(3H, m), 7.21–7.25(1H, m), 7.25–7.33(2H, m), 7.55(1H, d, J=9.0 Hz), 7.85(1H, d, J=8.4 Hz), 7.90(1H, dd, J=13.2 Hz, 2.4 Hz), 7.94(1H, dd, J=8.4 Hz, 2.1 Hz), 8.22(1H, d, J=2.1 Hz), 8.37(1H, brt), 10.58(1H, s). |
| 379 | 4-ClPh— | 2.44(2H, t, J=7.5 Hz), 2.82(2H, t, J=7.5 Hz), 4.22(2H, d, J=6.0 Hz), 6.87(2H, d, J=8.6 Hz), 7.14(2H, d, J=8.4 Hz), 7.16–7.22(3H, m), 7.29–7.34(2H, m), 7.55(1H, d, J=8.1 Hz), 7.85(1H, d, J=8.4 Hz), 7.90(1H, dd, J=13.2 Hz, 2.5 Hz), 7.94(1H, dd, J=8.4 Hz, 2.1 Hz), 8.21(1H, d, J=2.1 Hz), 8.34(1H, brt), 10.58(1H, s). |
| 380 | 2-CH$_3$Ph— | 2.21(3H, s), 2.44(2H, t, J=7.5 Hz), 2.82(2H, t, J=7.5 Hz), 4.21(2H, d, J=5.7 Hz), 6.87(2H, d, J=8.6 Hz), 7.00–7.07(1H, m), 7.07–7.23(6H, m), 7.55(1H, d, J=9.0 Hz), 7.85(1H, d, J=8.4 Hz), 7.90(1H, dd, J=13.2 Hz, 2.4 Hz), 7.94(1H, dd, J=8.4 Hz, 2.1 Hz), 8.16(1H, brt), 8.22(1H, d, J=2.1 Hz), 10.58(1H, s). |
| 381 | 4-CH$_3$OPh— | 2.41(2H, t, J=7.6 Hz), 2.81(2H, t, J=7.6 Hz), 3.71(3H, s), 4.17(2H, d, J=5.8 Hz), 6.80–6.91(4H, m), 7.07(2H, d, J=8.5 Hz), 7.13–7.25(3H, m), 7.55(1H, d, J=8.5 Hz), 7.85(1H, d, J=8.4 Hz), 7.90(1H, dd, J=13.2 Hz, 2.4 Hz), 7.94(1H, dd, J=8.4 Hz, 2.1 Hz), 8.21(1H, d, J=2.1 Hz), 8.24(1H, brt), 10.58(1H, s). |

TABLE 174

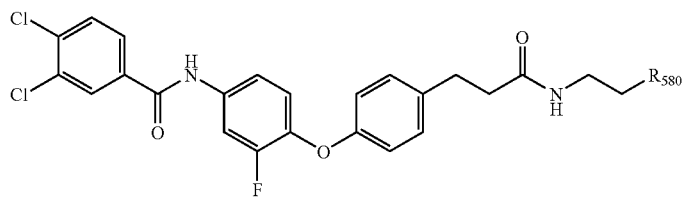

| Example No. | $R_{580}$ | $^1$H NMR(DMSO-$d_6$) δ ppm |
|---|---|---|
| 382 | Ph— | 2.33(2H, t, J=7.7 Hz), 2.66(2H, t, J=7.3 Hz), 2.77(2H, t, J=7.7 Hz), 3.20–3.29(2H, m), 6.87(2H, d, J=8.6 Hz), |

TABLE 174-continued

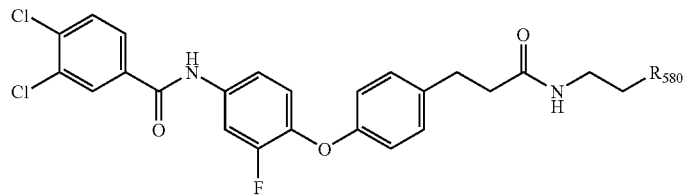

| Example No. | R580 | 1H NMR(DMSO-d6) δ ppm |
|---|---|---|
| | | 7.12–7.22(6H, m), 7.23–7.30(2H, m), 7.54(1H, dd, J=Ph–8.9 Hz, 1.1 Hz), 7.85(1H, d, J=8.4 Hz), 7.85–7.91(2H, m), 7.94(1H, dd, J=8.4 Hz, 2.1 Hz), 8.21(1H, d, J=2.1 Hz), 10.57(1H, s). |
| 383 | 4-FPh— | 2.33(2H, t, J=7.7 Hz), 2.65(2H, t, J=7.2 Hz), 2.76(2H, t, J=7.7 Hz), 3.30–3.37(2H, m), 6.87(2H, d, J=8.5 Hz), 7.04–7.11(2H, m), 7.13–7.22(5H, m), 7.54(1H, d, J=9.1 Hz), 7.85(1H, d, J=8.4 Hz), 7.80–7.92(2H, m), 7.94(1H, dd, J=8.4 Hz, 2.0 Hz), 8.21(1H, d, J=2.0 Hz), 10.58(1H, s). |
| 384 | 4-ClPh— | 2.32(2H, t, J=7.6 Hz), 2.66(2H, t, J=7.1 Hz), 2.76(2H, t, J=7.6 Hz), 3.18–3.27(2H, m), 6.87(2H, d, J=8.5 Hz), 7.10–7.22(5H, m), 7.31(2H, d, J=8.3 Hz), 7.54(1H, d, J=8.9 Hz), 7.84(1H, d, J=8.4 Hz), 7.85–7.92(2H, m), 7.94(1H, dd, J=8.4 Hz, 2.0 Hz), 8.2 i(1H, d, J=2.0 Hz), 10.57(1H, s). |
| 385 | 3-CH3OPh— | 2.33(2H, t, J=7.7 Hz), 2.64(2H, t, J=7.3 Hz), 2.78(2H, t, J=7.7 Hz), 3.18–3.27(2H, m), 3.72(3H, s), 6.70 6.78(3H, m), 6.87(2H, d, J=8.6 Hz), 7.12 7.23(4H, m), 7.54(1H, dd, J=8.9 Hz, 1.2 Hz), 7.85(1H, d, J=8.4 Hz), 7.85–7.92(2H, m), 7.94(1H, dd, J=8.4 Hz, 2.1 Hz), 8.21(1H, d, J=2.0 Hz), 10.57(1H, s). |
| 386 | 4-CH3OPh— | 2.33(2H, t, J=7.6 Hz), 2.59(2H, t, J=7.2 Hz), 2.77(2H, t, J=7.6 Hz), 3.16–3.24(2H, m), 3.71(3H, s), 6.83(2H, d, J=8.5 Hz), 6.87(2H, d, J=8.5 Hz), 7.07(2H, d, J=8.4 Hz), 7.13–7.23(3H, m), 7.54(1H, d, J=8.5 Hz), 7.80–7.98(4H, m), 8.21(1H, d, J=1.8 Hz), 10.57(1H, s). |
| 387 | PhO— | 2.38(2H, t, J=7.7 Hz), 2.79(2H, t, J=7.7 Hz), 3.38 3.43(2H, m), 3.94(2H, t, J=5.7 Hz), 6.79–6.85(2H, m), 6.89–6.96(3H, m), 7.12–7.20(3H, m), 7.23–7.31(2H, m), 7.50–7.57(1H, m), 7.85(1H, d, J=8.4 Hz), 7.89(1H, dd, J=13.2 Hz, 2.4 Hz), 8.10(1h, brt), 8.22(1H, d, J=2.1 Hz), 10.58(1H, s). |
| 388 | PhCH2— | 1.60–1.70(2H, m), 2.36(2H, t, J=7.4 Hz), 2.49–2.55(2H, m), 2.79(2H, t, J=7.4 Hz), 3.00–3.08(2H, m), 6.83 6.90(2H, m), 7.10–7.21(6H, m), 7.2 1–7.29(2H, m), 7.53(1H, d, J=2.1 Hz), 10.57(1H, s). |

TABLE 175

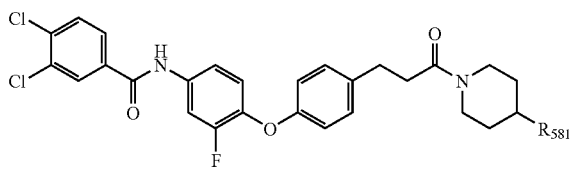

| Example No. | R581 | MS |
|---|---|---|
| 389 | —CHPh2 | 681(M+ + 1) |
| 390 | —NHCOPh | 633(M+) |
| 391 | —O(CH2)2Ph | 634(M+) |
| 392 | —(CH2)2N(CH3)Ph | 647(M+) |
| 393 | 4-methyl-2-phenylmorpholinyl | 675(M+) |
| 394 | morpholino | 599(M+) |

TABLE 175-continued

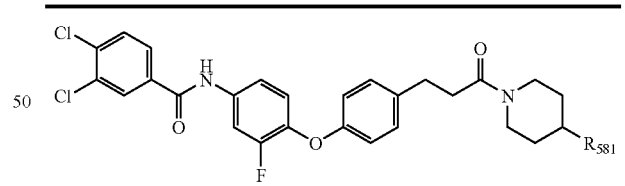

| Example No. | R581 | MS |
|---|---|---|
| 395 | 1,2-dimethylpiperazinyl | 626(M+) |
| 396 | cyclohexyl | 596(M+) |

TABLE 175-continued

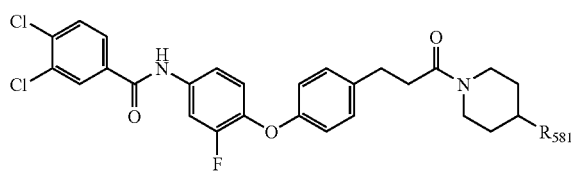

| Example No. | R<sub>581</sub> | MS |
|---|---|---|
| 397 | (1-methyl-4-phenyl-imidazole) | 656(M+) |
| 398 | (1-methyl-4-methyl-1,4-diazepane) | 626(M+) |
| 399 | 4-CH₃OPhCONH— | 664(M$^+$ + 1) |

TABLE 175-continued

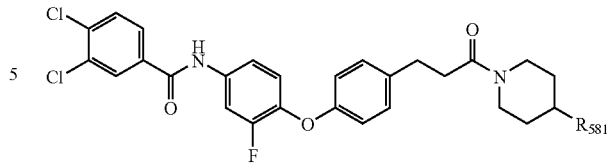

| Example No. | R$_{581}$ | MS |
|---|---|---|
| 400 | (1-methyl-2-methyl-benzimidazole) | 644(M+) |
| 401 | (3-methoxymethyl-pyridine) | 620(M$^+$ − 1) |
| 402 | (4-methoxymethyl-pyridine) | 623(M$^+$ + 2) |

TABLE 176

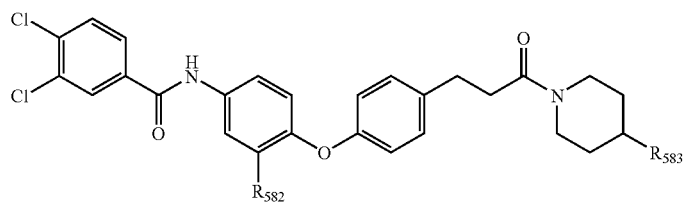

| Example No. | R$_{582}$ | R$_{583}$ | Property |
|---|---|---|---|
| 403 | —H | 4-CF₃OPhNH— | mp 91–95° C. |
| 404 | —F | 4-CF₃OPhNH— | mp 145–147° C. |
| 405 | —H | 4-CF₃PhO— | mp 118–121° C. |
| 406 | —H | 4-CF₃OPhO— | mp 126–127° C. |
| 407 | —F | 4-CF₃PhO— | mp 129–134° C. |
| 408 | —H | 4-CNPhO— | mp 148–149° C. |
| 409 | —F | 4-CNPhO— | mp 147–150° C. |
| 410 | —F | 4-CF₃OPhO— | $^1$H NMR(CDCl₃) δ 1.69–1.85(4H, m), 2.62(2H, t, J=7.5 Hz), 2.90(2H, t, J=7.5 Hz), 3.36(1H, m), 3.57–3.67(3H, m), 4.47(1H, m), 6.85 6.90(4H, m), 7.00(1H, t, J=8.5 Hz), 7.10(2H, d, J=8.5 Hz), 7.13(2H, d, J=8.5 Hz), 7.30(1H, brd, J=8.5 Hz), 7.52(1H, d, J=8.5 Hz), 7.69–7.75(2H, m), 7.98(1H, d, J=2.0 Hz), 8.80(1H, s). |
| 411 | —F | PhO— | MS 606(M+) |
| 412 | —F | 4-ClPhCH₂— | MS 638(M+) |
| 413 | —F | 4-CH₃PhCH₂— | MS 618(M+) |
| 414 | —F | 4-ClPh— | MS 626(M+) |
| 415 | —F | Ph— | MS 590(M+) |
| 416 | —F | 2-NH2PhCO— | MS 633(M+) |

TABLE 177

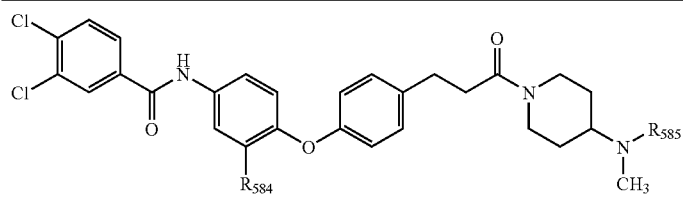

| Example No. | R584 | R585 | Form | mp(° C.) or MS |
|---|---|---|---|---|
| 417 | —F | —H | free | MS 543(M+) |
| 418 | —F | —(CH$_2$)$_2$OPh | free | MS 664(M$^+$ + H) |
| 419 | —F | —(CH$_2$)$_2$Ph | free | MS 648(M$^+$ + H) |
| 420 | —F | —(CH$_2$)$_2$N(C$_2$H$_5$)$_2$ | free | MS 643(M$^+$ + H) |
| 421 | —H | —(CH$_2$)$_2$Ph | fumarate | mp 148–151 |
| 422 | —F | —(CH$_2$)$_3$Ph | free | MS 661(M+) |
| 423 | —F | —(CH$_2$)$_2$CHPh$_2$ | free | MS 737(M+) |
| 424 | —F | propyl-triazole | free | MS 638(M+) |
| 425 | —F | 4-CH$_3$SPh(CH$_2$)$_2$— | free | MS 692(M$^+$ − 1) |
| 426 | —F | 4-CH$_3$PhO(CH$_2$)$_2$— | free | MS 678(M$^+$ + H) |
| 427 | —F | propoxy-methyl-nitrophenyl | free | MS 723(M$^+$ + H) |
| 428 | —F | 4-CH$_3$OPh(CH$_2$)4- | free | MS 705(M+) |
| 429 | —F | tetrahydrofuryl-CH(OH)CH$_2$CH$_3$ | free | MS 658(M$^+$ + H) |
| 430 | —F | 4-CH$_3$Ph(CH$_2$)$_2$— | free | MS 661(M+) |
| 431 | —F | —(CH$_2$)$_2$N(CH$_3$)Ph | free | MS 676(M+) |
| 432 | —F | cyclohexyl-(CH$_2$)$_3$— | free | MS 653(M+) |

TABLE 178

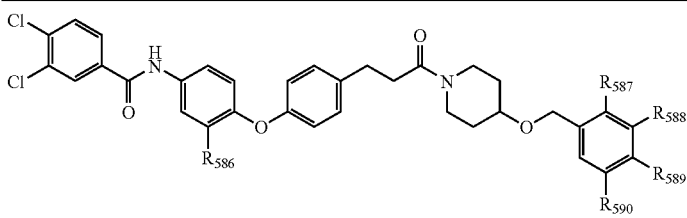

| Example No. | R586 | R587 | R588 | R589 | R590 | mp(°) or MS |
|---|---|---|---|---|---|---|
| 433 | —H | —H | —H | —CF$_3$ | —H | mp 124–126 |
| 434 | —F | —H | —H | —CF$_3$ | —H | mp 132–134 |
| 435 | —F | —H | —H | —Cl | —H | MS 654(M+) |
| 436 | —F | —F | —H | —H | —H | MS 638(M+) |
| 437 | —F | —H | —H | —H | —H | MS 620(M+) |
| 438 | —F | —H | —H | —OCH$_3$ | —H | MS 651(M$^+$ + H) |
| 439 | —F | —H | —Cl | —H | —H | MS 656(M+) |
| 440 | —F | —Cl | —H | —H | —H | MS 654(M) |

TABLE 178-continued

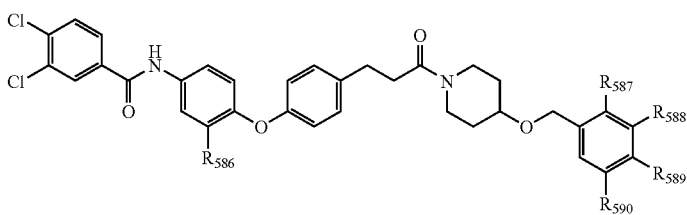

| Example No. | R586 | R587 | R588 | R589 | R590 | mp(°) or MS |
|---|---|---|---|---|---|---|
| 441 | —F | —H | —Cl | —Cl | —H | MS 690(M+) |
| 442 | —F | —H | —OCH3 | —H | —H | MS 650(M+) |
| 443 | —F | —H | —OCH3 | —H | —OCH3 | MS 680(M+) |
| 444 | —F | —H | —H | CH3 | —H | MS 635(M+ + H) |
| 445 | —F | —H | —OH3 | —H | —H | MS 636(M+ + 2) |
| 446 | —F | —CH3 | —H | —H | —H | MS 635(M+ + H) |
| 447 | —F | —H | —OH3 | —CH3 | —H | MS 648(M+) |
| 448 | —F | —H | —H | —F | —H | MS 638(M+) |
| 449 | —F | —H | —F | —H | —H | MS 638(M+) |
| 450 | —F | —H | —F | —H | —F | MS 656(M+) |
| 451 | —F | —CF3 | —H | —H | —H | MS 688(M+) |
| 452 | —F | —H | —H | —OCF3 | —H | MS 705(M+ + H) |
| 453 | —F | —H | —OCF3 | —H | —H | MS 704(M+) |
| 454 | —F | —OCF3 | —H | —H | —H | MS 704(M+) |
| 455 | —F | —H | —Cl | —OCH3 | —H | MS 685(M+ + H) |

TABLE 179

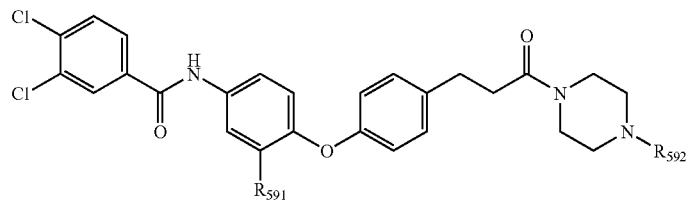

| Example No. | R591 | R592 | Property |
|---|---|---|---|
| 456 | —H | —CH2CONHPh | $^1$H NMR(CDCl$_3$) δ 2.45(2H, brt, J=5.0 Hz), 2.55(2H, brt, J=5.0 Hz), 2.63(2H, t, J=7.5 Hz), 2.96(2H, t, J=7.5 Hz), 3.11(2H, s), 3.47(2H, brs), 3.70(2H, brs), 6.93(2H, d, J=8.5 Hz), 6.98(2H, d, J=8.5 Hz), 7.13(1H, t, J=8.5 Hz), 7.15(1H, d, J=8.5 Hz), 7.34(2H, t, J=8.5 Hz), 7.52–7.59(5H, m), 7.73(1H, dd, J=8.5 Hz, 2.0 Hz), 7.99(1H, d, J=2.0 Hz), 8.28(1H, s), 8.92(1H, s). |
| 457 | —F | —CH2CONHPh | $^1$H NMR(CDCl$_3$) δ 2.39(2H, brs), 2.51(2H, brs), 2.61(2H, t, J=7.5 Hz), 2.93(2H, t, J=7.5 Hz), 3.08(2H, s), 3.43(2H, brs), 3.67(2H, brs), 6.88(2H, d, J=8.5 Hz), 7.03(1H, t, J=8.5 Hz), 7.11–7.15(3H, m), 7.30–7.35(3H, m), 7.51–7.54(3H, m), 7.70(1H, dd, J=9.0 Hz, 2.0 Hz), 7.74(1H, dd, J=8.5 Hz, 2.0 Hz), 8.00(1H, d, J=2.0 Hz), 8.74(1H, s), 8.93(1H, s). |
| 458 | —F | —(CH2)3Ph | MS 633(M+) |
| 459 | —F | —(CH2)4Ph | MS 647(M+) |
| 460 | —F | —CH(C2H5)2 | MS 586(M+ + 1) |
| 461 | —F | —CH(CH3)2 | MS 556(M+ − 1) |
| 462 | —F | —(CH2)3CH3 | MS 571(M+) |
| 463 | —F | —(CH2)2N(CH3)2 | MS 585(M+ − 1) |
| 464 | —F | —COOC(CH3)3 | mp 155–157° C. |
| 465 | —F | —CH2COPh | MS 633(M+) |
| 466 | —H | 3-pyridyl | mp 153–155° C. |
| 467 | —F | 3-pyridyl | mp 183–185° C. |
| 468 | —F | 2-pyridyl | MS 591(M+ − 1) |
| 469 | —F | 4-pyridyl | MS 592(M+) |

TABLE 179-continued

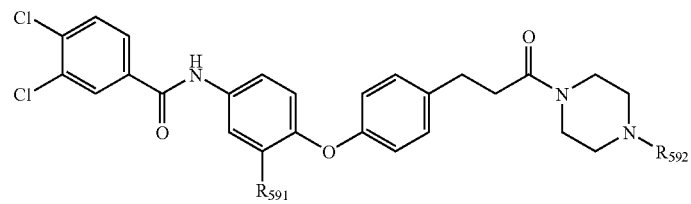

| Example No. | R591 | R592 | Property |
|---|---|---|---|
| 470 | —F | 3-methylpyrazinyl | MS 593(M+) |
| 471 | —F | 2-methylpyrimidinyl | MS 593(M+) |

TABLE 180

| Example No. | R593 | R594 | MS |
|---|---|---|---|
| 472 | —CH3 | benzyl | 619(M+) |
| 473 | 2-pyridylmethyl | —H | 606(M+) |
| 474 | 3-pyridylmethyl | —H | 606(M+) |
| 475 | 4-pyridylmethyl | —H | 605(M+ − 1) |
| 476 | cyclopentyl | —H | 583(M+) |
| 477 | cycloheptyl | —N | 611(M+) |
| 478 | 4-methyl-1-methylpiperidinyl | —H | 612(M+) |
| 479 | N-propylpiperidinyl | —H | 627(M+ + H) |
| 480 | N-propylmorpholinyl | —H | 628(M+) |
| 481 | N-propylpyrrolidinyl | —H | 612(M+) |
| 482 | 2-quinolylmethyl | —H | 657(M+ + H) |
| 483 | 1-benzyl-5-ethyltetrazolyl | —H | 686(M+ − 1) |
| 484 | 1-ethyl-5-ethyltetrazolyl | —H | 625(M+) |
| 485 | 4-ethyl-2-phenylthiazolyl | —H | 688(M+) |

TABLE 181

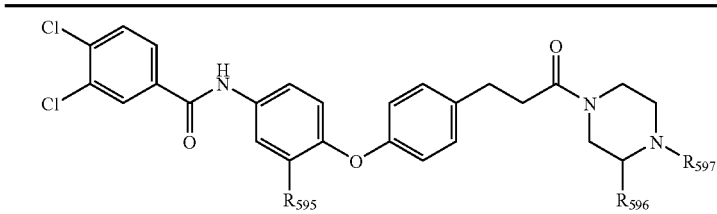

| Example No. | R595 | R596 | R597 | Form | mp (° C.) or MS |
|---|---|---|---|---|---|
| 486 | —H | —H | —COOC(CH3)3 | free | mp 188–189 |
| 487 | —H | —H | —CH3 | free | mp 189–191 |
| 488 | —H | —H | benzyl | fumarate | mp 190–192 |
| 489 | —F | —H | —(CH2)2Ph | hydrochloride | mp 191–200 |

TABLE 181-continued

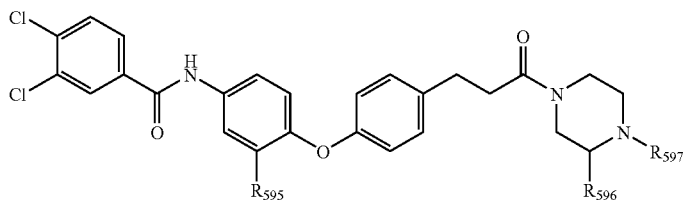

| Example No. | R595 | R596 | R597 | Form | mp (° C.) or MS |
|---|---|---|---|---|---|
| 490 | —F | —H | piperonyl | hydrochloride | mp 226–228 |
| 491 | —F | —H | (see structure) | free | MS 714(M+ − 1) |
| 492 | —F | —H | 1-naphthylmethyl | free | MS 655(M+) |
| 493 | —F | —CH3 | 3,4-(CH3O)2PhCH2— | free | MS 679(M+) |
| 494 | —F | —H | (see structure) | free | MS 678(M+ + 1) |
| 495 | —F | —H | —CH(CH3)Ph | free | MS 619(M+) |
| 496 | —F | —H | (see structure) | free | MS 682(M+) |
| 497 | —F | —H | (4-FPh)2CH— | free | MS 717(M+) |
| 498 | —F | —H | 4-CH3OPhCH(Ph)— | free | MS 711(M+) |

TABLE 182

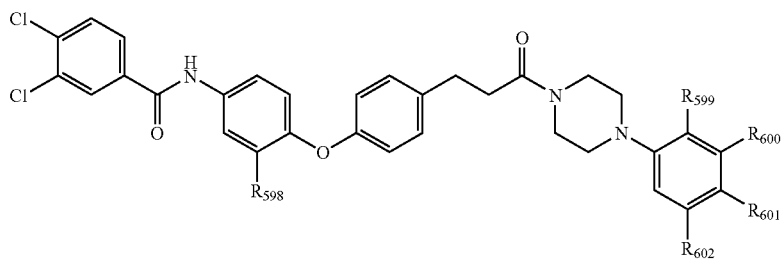

| Example No. | R598 | R599 | R600 | R601 | R602 | Form | mp(° C.) or MS |
|---|---|---|---|---|---|---|---|
| 499 | —F | —H | —H | —OCF3 | —H | hydrochloride | mp 118–121 |
| 500 | —F | —H | —H | —CN | —H | free | mp 190–192 |
| 501 | —H | —H | —H | —OCF3 | —H | hydrochloride | mp 148–149 |
| 502 | —H | —H | —H | —ON | —H | free | mp 186–188 |
| 503 | —F | —CF3 | —H | —H | —H | free | MS 659(M+) |
| 504 | —F | —H | —CF3 | —H | —H | free | MS 659(M+) |
| 505 | —F | —H | —H | —COOC(CH3)3 | —H | free | MS 691(M+) |
| 506 | —F | —H | —H | —F | —H | free | MS 609(M+) |
| 507 | —F | —OCH3 | —H | —H | —H | free | MS 621(M+) |
| 508 | —F | —Cl | —H | —H | —H | free | MS 625(M+) |
| 509 | —F | —H | —H | —Cl | —H | free | MS 627(M+) |
| 510 | —F | —H | —Cl | —H | —H | free | MS 625(M+) |

TABLE 182-continued

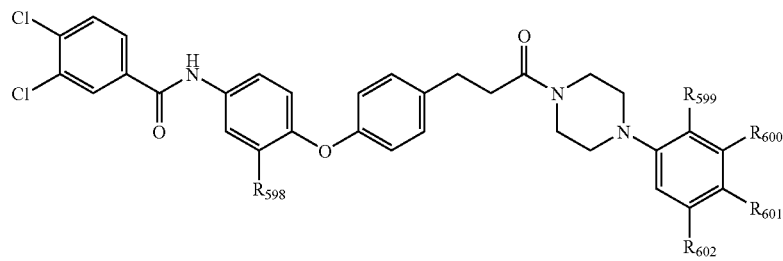

| Example No. | $R_{598}$ | $R_{599}$ | $R_{600}$ | $R_{601}$ | $R_{602}$ | Form | mp(° C.) or MS |
|---|---|---|---|---|---|---|---|
| 511 | —F | —Cl | —Cl | —H | —H | free | MS 661(M+) |
| 512 | —F | —H | H | —OCH$_3$ | —H | free | MS 621(M+) |
| 513 | —F | —H | —OCH$_3$ | —H | —H | free | MS 621(M+) |
| 514 | —F | —H | —H | —CH$_3$ | —H | free | MS 605(M+) |
| 515 | —F | —H | —CH$_3$ | —H | —H | free | MS 605(M+) |
| 516 | —F | —CH$_3$ | —H | —H | —H | free | MS 605(M+) |
| 517 | —F | —CH$_3$ | —CH$_3$ | —H | —H | free | MS 619(M+) |
| 518 | —F | —H | —CH$_3$ | —CH$_3$ | —H | free | MS 619(M+) |
| 519 | —F | —H | —H | —CF$_3$ | —H | free | MS 659(M+) |
| 520 | —F | —H | —H | -Ph | —H | free | MS 667(M+) |
| 521 | —F | —F | —H | —H | —H | free | MS 609(M+) |
| 522 | —F | —F | —H | —F | —H | free | MS 627(M+) |
| 523 | —F | —OCH$_3$ | —H | —H | —Cl | free | MS 657(M+) |

TABLE 183

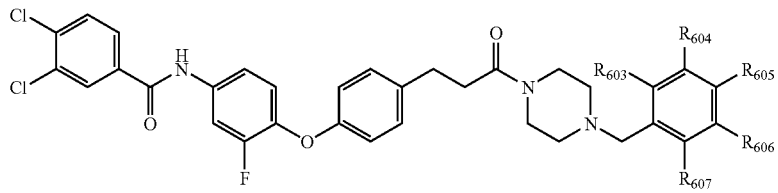

| Example No. | $R_{603}$ | $R_{604}$ | $R_{605}$ | $R_{606}$ | $R_{607}$ | Form | mp(° C.) or MS |
|---|---|---|---|---|---|---|---|
| 524 | —H | —H | —H | —H | —H | fumarate | mp 168–170 |
| 525 | —H | —H | —Cl | —H | —H | free | MS 638(M$^+$ − 1) |
| 526 | —H | —Cl | —H | —H | —H | free | MS 639(M+) |
| 527 | —Cl | —H | —H | —H | —H | free | MS 641(M$^+$ + 2) |
| 528 | —Cl | —Cl | —H | —H | —H | free | MS 675(M$^+$ + 2) |
| 529 | —Cl | —H | —Cl | —H | —H | free | MS 673(M+) |
| 530 | —Cl | —H | —H | —Cl | —H | free | MS 673(M+) |
| 531 | —H | —Cl | —Cl | —H | —H | free | MS 676(W+) |
| 532 | —H | —OCH$_3$ | —H | —H | —H | free | MS 635(M+) |
| 533 | —OCH$_3$ | —H | —H | —H | —H | free | MS 635(M+) |
| 534 | —H | —OCH$_3$ | —H | —OCH$_3$ | —H | free | MS 665(M+) |
| 535 | —H | —CH$_3$ | —H | —H | —H | free | MS 619(M+) |
| 536 | —CH$_3$ | —H | —H | —H | —H | free | MS 619(M+) |
| 537 | —H | —CH$_3$ | —CH$_3$ | H | —H | free | MS 633(M+) |
| 538 | —H | —H | F | —H | —H | free | MS 623(M+) |
| 539 | —H | —F | —H | —H | H | free | MS 623(M+) |
| 540 | —F | —H | H | —H | —H | free | MS 623(M+) |
| 541 | —F | —H | —F | —H | —H | free | MS 641(M+) |
| 542 | —F | —H | —H | —H | —F | free | MS 641(M+) |
| 543 | —H | —H | —NO$_2$ | —H | —H | free | MS 650(M+) |
| 544 | —H | —NO$_2$ | —H | —H | —H | free | MS 650(M+) |
| 545 | —NO$_2$ | —H | —H | —H | —H | free | MS 650(M+) |
| 546 | —H | —CF$_3$ | —H | —H | —H | free | MS 673(M+) |
| 547 | —H | —H | —ON | —H | —H | free | MS 630(M+) |
| 548 | —H | —OCF$_3$ | —H | —H | —H | free | MS 689(M+) |
| 549 | —H | —H | —COOOH$_3$ | —H | —H | free | MS 664(M$^+$ + 1) |
| 550 | —H | —H | —O(CH$_3$)$_3$ | —H | —H | free | MS 661(M+) |
| 551 | —H | —H | —OCH$_2$Ph | —H | —H | free | MS 710(M$^+$ − 1) |
| 552 | —H | —H | —Ph | —H | —H | free | MS 681(M+) |
| 553 | —Cl | —H | —H | —H | —Cl | MS free | 675(M$^+$ + 2) |
| 554 | —F | —H | —H | —F | —H | free | MS 641(M+) |
| 555 | —H | —F | —H | —F | —H | free | MS 641(M+) |

TABLE 183-continued

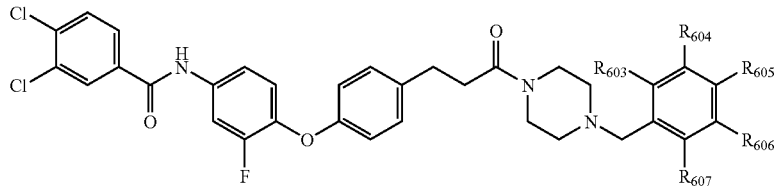

| Example No. | $R_{603}$ | $R_{604}$ | $R_{605}$ | $R_{606}$ | $R_{607}$ | Form | mp(° C.) or MS |
|---|---|---|---|---|---|---|---|
| 556 | —H | —H | —CF$_3$ | —H | —H | free | MS 674(M$^+$ − 1) |
| 557 | —H | —H | —OCF$_3$ | —H | —H | free | MS 689(M+) |
| 558 | —OCF$_3$ | —H | —H | —H | —H | free | MS 689(M+) |
| 559 | —H | —COOCH$_3$ | —H | —H | —H | free | MS 663(M+) |
| 560 | —H | —H | —C$_2$H$_5$ | —H | —H | free | MS 633(M+) |
| 561 | —H | —H | —CH(CH$_3$)$_2$ | —H | —H | free | MS 647(M+) |
| 562 | —H | —Cl | —OCH$_3$ | —H | —H | free | MS 669(M+) |

TABLE 184

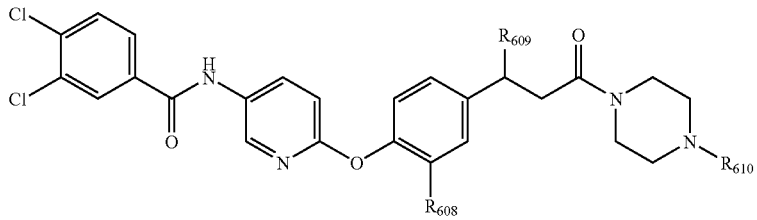

| Example No. | $R_{608}$ | $R_{609}$ | $R_{610}$ | Form | mp(° C.) or $^1$H NMR(solvent) δ ppm |
|---|---|---|---|---|---|
| 563 | —H | —CH$_3$ | piperonyl | free | mp 147–149 |
| 564 | —H | —H | piperonyl | free | mp 138–140 |
| 565 | —H | —CH$_3$ | benzyl | free | mp 150–152 |
| 566 | —H | —H | benzyl | free | $^1$H NMR(CDCl$_3$) 2.34–2.42(4H, m), 2.58–2.64(2H, m), 2.91–2.96(2H, m), 3.40–3.43(2H, m), 3.51(2H, s), 3.60–3.64(2H, m), 6.93(1H, d, J=8.9 Hz), 7.01–7.04(2H, m), 7.20(2H, d, J=8.6 Hz), 7.27–7.33(5H, m), 7.56(1H, d, J=8.3Hz), 7.71–7.75(1H, m), 8.00(1H, d, J=2.0 Hz), 8.16-8.27(3H, m). |
| 567 | —OCH$_3$ | —H | piperonyl | free | mp 142.0–144.5 |
| 568 | —F | —H | piperonyl | free | mp 156.5–157.5 |
| 569 | —H | —H | —COOC(CH$_3$)$_3$ | free | $^1$H NMR(CDCl$_3$) 1.46(9H, s), 2.62–2.67(2H, m), 2.96–3.01(2H, m), 3.33–3.39(6H, m), 3.57–3.60(2H, m), 6.94–6.97(1H, m), 7.05(2H, d, J=8.4 Hz), 7.23(2H, d, J=8.4 Hz), 7.57(1H, d, J=8.1 Hz), 7.71–7.75(1H, m), 8.00(1H, d, J=2.2 Hz), 8.13(1H, brs), 8.21–8.24(2H, m). |
| 570 | —OC$_2$H$_5$ | —H | piperonyl | oxalate | $^1$H NMR(DMSO-d$_6$) 1.06(3H, t, J=6.9 Hz), 2.39–2.86(8H, m), 3.40–3.60(4H, m), 3.65(2H, s), 3.70–5.20(4H, m), 6.00(2H, s), 6.76–6.84(2H, m), 6.85–7.02(5H, m), 7.82(1H, d, J=8.4 Hz), 7.92(1H, m), 8.03(1H, m), 8.20(1H, d, J=2.0 Hz), 8.35(1H, d, J=2.5 Hz), 10.47(1H, s). |

TABLE 185

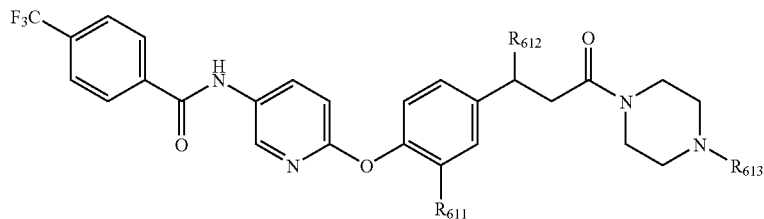

| Example No. | $R_{611}$ | $R_{612}$ | $R_{613}$ | Form | mp (° C.) or $^1$HNMR (CDCl$_3$) δppm |
|---|---|---|---|---|---|
| 571 | —H | —CH$_3$ | piperonyl | hydrochloride | mp 218-220 |
| 572 | —H | —CH$_3$ | benzyl | free | mp 142-144 |
| 573 | —OCH$_3$ | —H | benzyl | free | $^1$HNMR 2.34-2.40 (4H, m), 2.58-2.63 (2H, m), 2.89-2.94 (2H, m), 3.39-3.42 (2H, m), 3.50 (2H, s), 3.58-3.61 (2H, m), 3.70 (3H, s), 6.75-6.80 (2H, m), 6.91 (1H, d, J=8.7Hz), 7.00 (1H, d, J=7.9Hz), 7.24-7.35 (5H, m), 7.69 (2H, d, J=8.1Hz), 7.98 (2H, d, J=8.1Hz), 8.14-8.18 (1H, m), 8.23 (1H, d, J=2.3Hz), 8.59 (1H, s). |
| 574 | —OCH$_3$ | —H | piperonyl | free | $^1$HNMR 2.31-2.37 (4H, m), 2.57-2.63 (2H, m), 2.88-2.94 (2H, m), 3.37-3.41 (4H, m), 3.57-3.60 (2H, m), 3.70 (3H, s), 5.93 (2H, s), 6.69-6.80 (4H, m), 6.84 (1H, brs), 6.90 (1H, d, J=8.9Hz), 7.00 (1H, d, J=7.9Hz), 7.69 (2H, d, J=8.1Hz), 7.98 (2H, d, J=8.1Hz), 8.14-8.19 (1H, m), 8.24 (1H, d, J=2.5Hz), 8.67 (1H, s). |
| 575 | —F | —H | piperonyl | free | mp 170.5-171.0 |
| 576 | —H | —H | —COOC(CH$_3$)$_3$ | free | $^1$HNMR 1.46 (9H, s), 2.66 (2H, t, J=6.5Hz), 2.97 (2H, t, J=6.5Hz), 3.25-3.48 (6H, m), 3.51-3.65 (2H, m), 6.95 (1H, d, J=9.7Hz), 7.04 (2H, d, J=8.4Hz), 7.22 (2H, d, J=8.4Hz), 7.75 (2H, d, J=8.2Hz), 8.01 (2H, d, J=8.2Hz), 8.18-8.33 (3H, m). |
| 577 | —OC$_2$H$_5$ | —H | piperonyl | hydrochloride | mp 147.5-149.0 |

TABLE 186

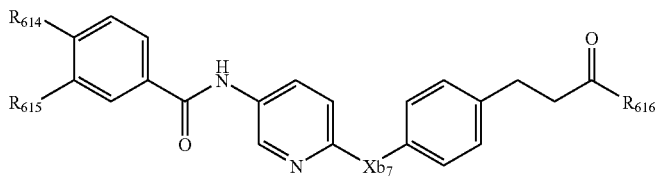

| Example No. | $R_{614}$ | $R_{615}$ | $R_{616}$ | $Xb_7$ | Form | mp (° C.) or $^1$HNMR |
|---|---|---|---|---|---|---|
| 578 | —Cl | —Cl | morpholino | —O— | free | $^1$HNMR (CDCl$_3$) δ 2.60-2.66 (2H, m), 2.96-3.02 (2H, m), 3.37-3.41 (2H, m), 3.55-3.64 (6H, m), 6.96 (1H, d, J=8.4Hz), 7.06 (2H, d, J=8.6Hz), 7.23-7.26 (2H, m), 7.58 (1H, d, J=8.4Hz), 7.70-7.74 (1H, m), 7.86 (1H, brs), 7.99 (1H, d, J=1.9Hz), 8.19-8.25 (2H, m). |

TABLE 186-continued
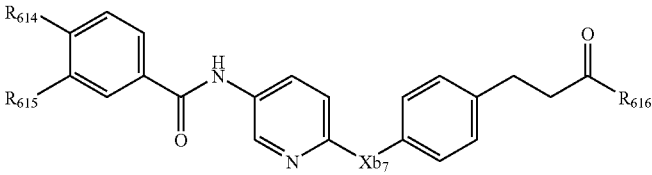
| Example No. | R_614 | R_615 | R_616 | Xb_7 | Form | mp (° C.) or ¹HNMR |
|---|---|---|---|---|---|---|
| 579 | —Cl | —Cl | 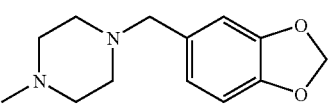 | —NH— | free | mp 141-142 |
| 580 | —Cl | —Cl | 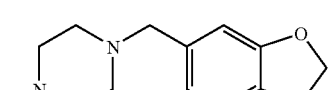 | —S— | free | mp 169-170 |
| 581 | —Cl | —Cl | 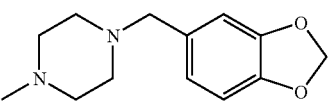 | —SO_2— | free | mp 154-156 |
| 582 | —CF_3 | —H | 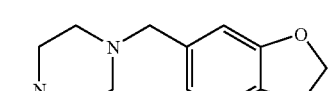 | —N(CH_3)— | free | mp 175-176 |
| 583 | —Cl | —Cl | 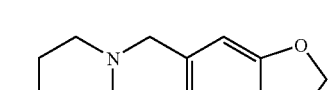 | —N(CH_2Ph)— | free | mp 171-173 |
| 584 | —Cl | —Cl | 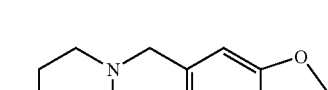 | —N(CH_2Ph)— | free | mp 144-146 |
| 585 | —Cl | —Cl | 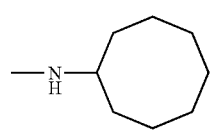 | —CO— | free | mp 129-132 |
| 586 | —Cl | —Cl |  | —O— | free | mp 208-210 |
| 587 | —Cl | —Cl | —NH(CH_2)_2OPh | —O— | free | mp 129-132 |

TABLE 186-continued

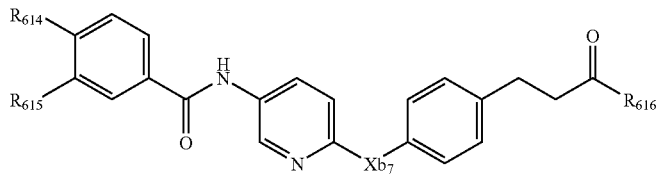

| Example No. | $R_{614}$ | $R_{615}$ | $R_{616}$ | $Xb_7$ | Form | mp (° C.) or $^1$HNMR |
|---|---|---|---|---|---|---|
| 588 | —Cl | —Cl | 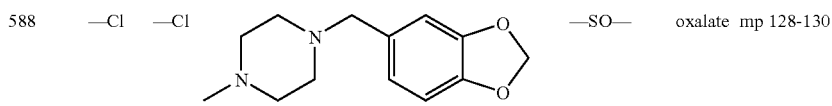 | —SO— | oxalate | mp 128-130 |

TABLE 187

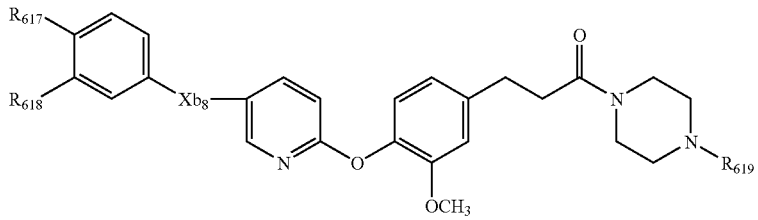

| Example No. | $R_{617}$ | $R_{618}$ | $Xb_8$ | $R_{619}$ | $^1$HNMR (CDCl$_3$) δppm |
|---|---|---|---|---|---|
| 589 | —Cl | —Cl | —CH=CH— (trans) | piperonyl | 2.33-2.42 (4H, m), 2.62-2.68 (2H, m), 2.96-3.O1 (2H, m), 3.40-3.44 (4H, m), 3.62-3.66 (2H, m), 3.76 (3H, s), 5.95 (2H, s), 6.71-6.77 (2H, m), 6.82-7.07 (7H, m), 7.28-7.32 (1H, m), 7.38-7.46 (1H, m), 7.57 (1H, d, J=2.0Hz), 7.83-7.87 (1H, m), 8.19 (1H, d, J=2.3Hz). |
| 590 | —CF$_3$ | —H | —CH=CH— (trans) | piperonyl | 2.33-2.42 (4H, m), 2.62-2.68 (2H, m), 2.96-3.02 (2H, m), 3.40-3.43 (4H, m), 3.63-3.66 (2H, m), 3.76 (3H, s), 5.94 (2H, s) 6.71-6.7941 (2H, m), 6.82-6.89 (3H, m), 6.95 (1H, d, J=8.7Hz), 7.00 (1H, d, J=16.5Hz), 7.05-7.14 (2H, m), 7.55-7.62 (4H, m), 7.86-7.90 (1H, m), 8.22 (1H, d, J=2.3Hz). |
| 591 | —CF$_3$ | —H | —CO— | benzyl | 2.38-2.43 (4H, m), 2.63-2.68 (2H, m), 2.97-3.02 (2H, m), 3.43 (2H, brs), 3.51 (2H, s), 3.65 (2H, brs), 3.76 (3H, s), 6.84-6.89 (2H, m), 7.04-7.09 (2H, m), 7.27-7.31 (5H, m), 7.73-7.88 (4H, m), 8.19-8.22 (1H, m), 8.55 (1H, brs). |
| 592 | —CF$_3$ | —H | —CO— | piperonyl | 2.35-2.39 (4H, m), 2.62-2.68 (2H, m), 2.96-3.02 (2H, m), 3.41-3.44 (4H, m), 3.62-3.65 (2H, m), 3.76 (3H, s), 5.95 (2H, s), 6.74-6.89 (5H, m), 7.04-7.09 (2H, m), 7.73-7.88 (4H, m), 8.19-8.22 (1H, m), 8.55 (1H, brs). |
| 593 | —CF$_3$ | —H | —CO— | 3-pyridyl | 2.69-2.75 (2H, m), 3.01-3.06 (2H, m), 3.14-3.20 (4H, m), 3.59-3.62 (2H, m), 3.77 (3H, s), 3.80-3.84 (2H, m), 6.86-6.92 (2H, m), 7.04-7.11 (2H, m), 7.18-7.20 (2H, m), 7.75 (2H, d, J=8.4Hz), 7.87 (2H, d, J=8.1Hz), 8.15 (1H, t, J=3.0Hz), 8.20 (1H, dd, J=8.7Hz, 2.3Hz), 8.30 (1H, t, J=1.8Hz), 8.53 (1H, d, J=2.3Hz). |

TABLE 188

[Structure: R620-pyridyl-O-phenyl-(CH2)M-C(O)-piperazine-N-R621]

| Example No. | R620 | R621 | M | ¹HNMR (solvent) δppm |
|---|---|---|---|---|
| 594 | 3,4-Cl₂PhNHCON(C₂H₅)— | 4-pyridyl-methyl | 2 | (CDCl₃) 1.16 (3H, t, J=7.1Hz), 2.35-2.45 (4H, m), 2.62-2.67 (2H, m), 2.97-3.03 (2H, m), 3.42-3.46 (2H, m), 3.51 (2H, s), 3.64-3.68 (2H, m), 3.73 (2H, q, J=7.1Hz), 6.07 (1H, d, J=5.0Hz), 7.04 (1H, d, J=8.7Hz), 7.09-7.14 (3H, m), 7.25-7.30 (5H, m), 7.52 (1H, d, J=2.6Hz), 7.61 (1H, dd, J=8.7Hz, 2.6Hz), 8.11 (1H, d, J=2.6Hz), 8.54 (2H, d, J=5.9Hz). |
| 595 | 4-CF₃PhNHCON(C₂H₅)— | piperonyl | 2 | (CDCl₃) 1.18 (3H, t, J=7.1Hz), 2.32-2.41 (4H, m), 2.61-2.67 (2H, m), 2.97-3.03 (2H, m), 3.39-3.43 (4H, m), 3.61-3.65 (2H, m), 3.75 (2H, q, J=7.1Hz), 5.94 (2H, s), 6.15 (1H, brs), 6.72-6.76 (2H, m), 6.83 (1H, d, J=0.7Hz), 7.05 (1H, dd, J=8.7Hz, 0.5Hz), 7.11 (2H, d, J=8.6Hz), 7.29 (2H, d, J=8.6Hz), 7.40 (2H, d, J=8.6Hz), 7.49 (2H, d, J=8.7Hz), 7.63 (1H, dd, J=8.7Hz, 2.8Hz), 8.14 (1H, dd, J=2.8Hz, 0.5Hz). |
| 596 | 4-CF₃PhNHCON(C₂H₅)— | 4-pyridyl-methyl | 2 | (CDCl₃) 1.18 (3H, t, J=7.1Hz), 2.35-2.45 (4H, m), 2.62-2.68 (2H, m), 2.98-3.03 (2H, m), 3.42-3.46 (2H, m), 3.51 (2H, s), 3.66 (2H, t, J=5.0Hz), 3.75 (2H, q, J=7.1Hz), 6.18 (1H, brs), 7.05 (1H, dd, J=8.7Hz, 0.5Hz), 7.11 (2H, d, J=8.4Hz), 7.25-7.31 (4H, m), 7.40 (2H, d, J=8.7Hz), 7.49 (2H, d, J=8.7Hz), 7.63 (1H, dd, J=8.7Hz, 2.8Hz), 8.13 (1H, dd, J=2.6Hz, 0.5Hz), 8.53-8.55 (2H, m). |
| 597 | 4-CF₃PhNHCON(C₂H₅)— | 2-pyridyl | 2 | (CDCl₃) 1.17 (3H, t, J=7.1Hz), 2.68-2.74 (2H, m), 3.02-3.07 (2H, m), 3.46-3.53 (6H, m), 3.70-3.78 (4H, m), 6.12 (1H, brs), 6.62-6.67 (2H, m), 7.04 (1H, d, J=8.7Hz), 7.12 (2H, d, J=8.6Hz), 7.31 (2H, d, J=8.6Hz), 7.40 (2H, d, J=8.7Hz), 7.45-7.52 (3H, m), 7.60 (1H, dd, J=8.7Hz, 2.6Hz), 8.07 (1H, d, J=2.5Hz), 8.16-8.19 (1H, m). |

TABLE 189

[Structure: R622,R623-phenyl-C(O)NH-pyridyl-O-phenyl-R624,R625]

| Example No. | R622 | R623 | R624 | R625 | mp (° C.) or ¹HNMR (CDCl₃) δppm |
|---|---|---|---|---|---|
| 598 | —Cl | —Cl | —H | 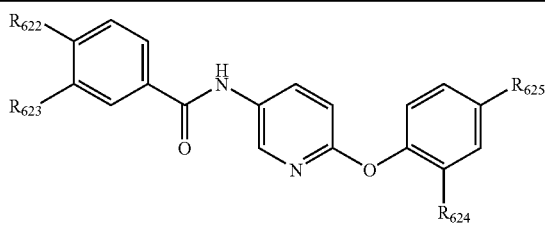 | mp 169-171 |

TABLE 189-continued

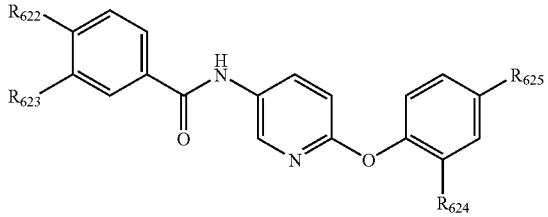

| Example No. | R622 | R623 | R624 | R625 | mp (° C.) or ¹HNMR (CDCl₃) δppm |
|---|---|---|---|---|---|
| 599 | —Cl | —Cl | —H | 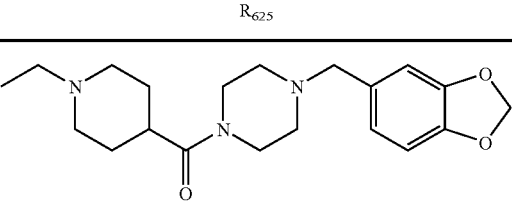 | mp 158-160 |
| 600 | —Cl | —Cl | —H | 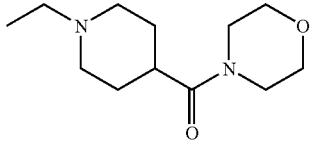 | mp 183-186 |
| 601 | —CF₃ | —H | —F | 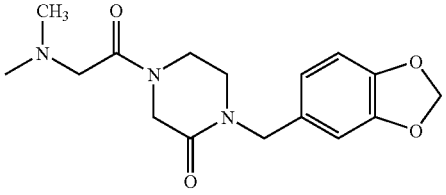 | ¹HNMR 3.00 (3H, s), 3.20-3.36 (2H, m), 3.57-3.80 (2H, m), 4.07 (2H, s), 4.14-4.34 (2H, m), 4.51 (2H, s), 5.94 (2H, s), 6.32-6.50 (2H, m), 6.65-6.80 (3H, m), 6.92 (1H, d, J=9.4Hz), 7.02 (1H, t, J=8.8Hz), 7.71 (2H, d, J=8.1Hz), 7.98 (2H, d, J=8.1Hz), 8.10-8.20 (1H, m), 8.18 (1H, s), 8.30 (1H, s). |
| 602 | —CF₃ | —H | —H | 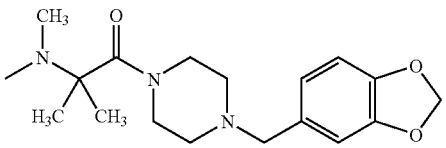 | ¹HNMR 1.45 (6H, s), 2.14 (2H, brs), 2.33 (2H, brs), 2.87 (3H, s), 3.32 (2H, s), 3.63 (2H, brs), 3.92 (2H, brs), 5.93 (2H, s), 6.68-6.75 (2H, m), 6.82 (1H, d, J=1.0Hz), 6.92 (2H, d, J=9.2Hz), 6.93 (1H, d, J=9.1Hz), 7.00 (2H, d, J=9.2Hz), 7.77 (2H, d, J=8.1Hz), 7.81 (1H, s), 8.00 (2H, d, J=8.1Hz), 8.19 (1H, dd, J=8.7Hz, 2.8Hz), 8.26 (1H, d, J=2.1Hz). |
| 603 | —CF₃ | —H | —OCH₃ | 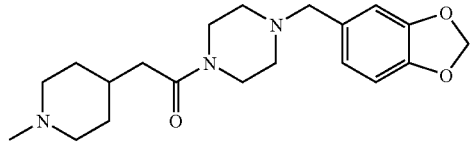 | ¹HNMR 1.33-1.45 (2H, m), 1.82-1.96 (3H, m), 2.28 (2H, d, J=6.8Hz), 2.39-2.41 (4H, m), 2.72 (2H, t, J=10.1Hz), 3.43 (2H, s), 3.48 (2H, brs), 3.57-3.62 (4H, m), 3.72 (3H, s), 5.95 (2H, s), 6.48 (1H, dd, J=8.7Hz, 2.5Hz), 6.56 (1H, d, J=2.5Hz), 6.71-6.77 (2H, m), 6.86(2H, d, J=8.6Hz), 6.97 (1H, d, J=8.6Hz), 7.70 (2H, d, J=8.4Hz), 8.00 (2H, d, J=8.1Hz), 8.13 (1H, dd, J=8.7Hz, 2.6Hz), 8.22 (1H, d, J=2.5Hz), 8.40 (1H, s). |

TABLE 190

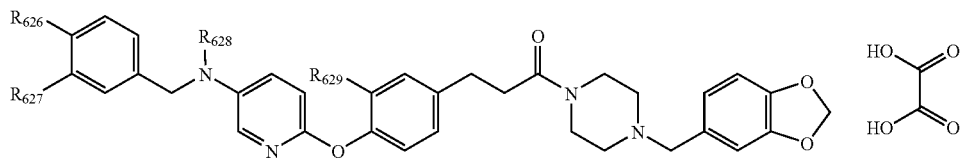

| Example No. | $R_{626}$ | $R_{627}$ | $R_{628}$ | $R_{629}$ | mp (° C.) or $^1$HNMR (DMSO-$d_6$) δppm |
|---|---|---|---|---|---|
| 604 | —CF$_3$ | —H | —CH$_3$ | —OC$_2$H$_5$ | $^1$HNMR 1.03 (3H, t, J=6.9Hz), 2.52-2.68 (6H, m), 2.69-2.82 (2H, m), 3.39-3.61 (4H, m), 3.72 (2H, s), 3.89 (2H, q, J=6.9Hz), 4.00-5.90 (4H, m), 6.01 (2H, s), 6.74 (1H, dd, J=8.0Hz, 1.8Hz), 6.76 (1H, d, J=8.9Hz), 6.82 (1H, dd, J=8.0Hz, 1.3Hz), 6.84-6.97 (4H, m), 7.26 (1H, dd, J=9.0Hz, 3.1Hz), 7.41 (2H, d, J=8.0Hz), 7.50 (1H, d, J=3.1Hz), 7.65 (2H, d, J=8.0Hz). |
| 605 | —CF$_3$ | —H | —C$_2$H$_5$ | —OC$_2$H$_5$ | $^1$HNMR 1.02 (3H, t, J=6.9Hz), 1.08 (3H, t, J=6.9Hz), 2.53-2.84 (8H, m), 3.43 (2H, q, J=6.9Hz), 3.46-3.62 (4H, m), 3.72 (2H, s), 3.88 (2H, q, J=6.9Hz), 4.30-5.90 (4H, m), 6.01 (2H, s), 6.69-6.78 (2H, m), 6.82 (1H, dd, J=8.0Hz, 1.4Hz), 6.83-6.97 (4H, m), 7.19 (1H, dd, J=9.0Hz, 3.1Hz), 7.37-7.48 (3H, m), 7.65 (2H, d, J=8.1Hz). |
| 606 | —Cl | —Cl | —CH$_3$ | —H | $^1$HNMR 2.48-2.67 (6H, m), 2.68-2.82 (2H, m), 2.98 (3H, s), 3.37-3.62 (4H, m), 3.70 (2H, s), 4.50-5.90 (4H, m), 6.01 (2H, s), 6.78-6.95 (6H, m), 7.13-7.23 (3H, m), 7.28 (1H, dd, J=9.0Hz, 3.3Hz), 7.48 (1H, d, J=2.0Hz), 7.57 (1H, d, J=8.3Hz), 7.61 (1H, d, J=3.1Hz). |
| 607 | —Cl | —Cl | —C$_2$H$_5$ | —H | $^1$HNMR 1.09 (3H, t, J=6.9Hz), 2.48-2.66 (6H, m), 2.69-2.82 (2H, m), 3.35-3.59 (6H, m), 3.67 (2H, s), 4.00-5.90 (4H, m), 6.00 (2H, s), 6.76-6.94 (6H, m), 7.13-7.25 (4H, m), 7.47 (1H, d, J=1.9Hz), 7.52-7.61 (2H, m). |
| 608 | —CF$_3$ | —H | —CH$_3$ | —F | $^1$HNMR 2.50-2.72 (6H, m), 2.72-2.88 (2H, m), 2.98 (3H, s), 3.32-3.61 (4H, m), 3.70 (2H, brs), 4.67 (2H, s), 6.00 (2H, s), 6.80 (1H, dd, J=7.9Hz, 1.4Hz), 6.85-6.95 (3H, m), 6.98-7.11 (2H, m), 7.11-7.22 (1H, m), 7.29 (1H, dd, J=9.0Hz, 3.1Hz), 7.41 (2H, d, J=8.0Hz), 7.50 (1H, d, J=3.1Hz), 7.66 (2H, d, J=8.0Hz). |
| 609 | —Cl | —Cl | —C$_2$H$_5$ | —F | $^1$HNMR 1.00-1.20 (3H, m), 2.46-2.72 (6H, m), 2.72-2.89 (2H, m), 3.29-3.61 (6H, m), 3.71 (2H, brs), 4.46 (2H, s), 6.01 (2H, s), 6.81 (1H, dd, J=8.0Hz, 1.4Hz), 6.85-6.95 (3H, m), 6.98-7.11 (2H, m), 7.13-7.28 (3H, m), 7.45 (1H, d, J=3.1Hz), 7.46 (1H, d, J=1.9Hz), 7.56 (1H, d, J=8.3Hz). |
| 610 | —Cl | —Cl | —CH$_3$ | —OC$_2$H$_5$ | $^1$HNMR 1.02 (3H, t, J=6.9Hz), 2.42-2.81 (8H, m), 2.94 (3H, s), 3.00-4.30 (10H, m), 4.49 (2H, s), 6.00 (2H, s), 6.71-6.83 (3H, m), 6.84-6.95 (4H, m), 7.18 (1H, dd, J=8.3Hz, 2.0Hz), 7.26 (1H, dd, J=9.0Hz, 3.2Hz), 7.44 (1H, d, J=2.0Hz), 7.50 (1H, d, J=3.0Hz), 7.55 (1H, d, J=8.3Hz). |
| 611 | —Cl | —Cl | —C$_2$H$_5$ | —OC$_2$H$_5$ | $^1$HNMR 1.01 (3H, t, J 7.0Hz), 1.06 (3H, t, J=7.0Hz), 2.40-2.83 (8H, m), 2.90-4.50 (14H, m), 6.00 (2H, s), 6.70-6.82 (3H, m), 6.84-6.95 (4H, m), 7.15-7.24 (2H, m), 7.39-7.48 (2H, m), 7.55 (1H, d, J=8.3Hz). |
| 612 | —Cl | —Cl | —C$_2$H$_5$ | —OCH$_3$ | mp 91.0-96.5 dec |
| 613 | —CF$_3$ | —H | —C$_2$H$_5$ | —F | mp 104-107 |

TABLE 191

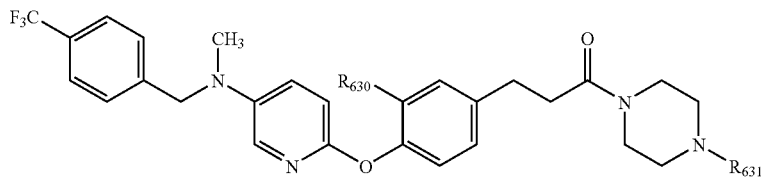

| Example No. | R630 | R631 | Form | ¹HNMR (solvent) δppm |
|---|---|---|---|---|
| 614 | —H | piperonyl | free | (CDCl₃) 2.30-2.34 (2H, m), 2.36-2.40 (2H, m), 2.56-2.62 (2H, m), 2.91-2.96 (2H, m), 3.01 (3H, s), 3.37-3.40 (4H, m), 3.60-3.64 (2H, m), 4.50 (2H, s), 5.94 (2H, s), 6.72-6.73 (2H, m), 6.80 (1H, d, J=8.9Hz), 6.84 (1H, brs), 6.98 (2H, d, J=8.6Hz), 7.11 (1H, dd, J=8.9Hz, 3.3Hz), 7.18 (2H, d, J=8.4Hz), 7.34 (2H, d, J=7.9Hz), 7.58 (2H, d, J=8.3Hz), 7.70 (1H, d, J=3.3Hz). |
| 615 | —H | 3-pyridyl | free | (CDCl₃) 2.63-2.69 (2H, m), 2.95-3.01 (5H, m), 3.08-3.18 (4H, m), 3.54-3.58 (2H, m), 3.78-3.81 (2H, m), 4.50 (2H, s), 6.79 (1H, d, J=8.9Hz), 6.99 (2H, d, J=8.6Hz), 7.10 (1H, dd, J=8.9Hz, 3.1Hz), 7.17-7.22 (4H, m), 7.34 (2H, d, J=8.1Hz), 7.58 (2H, d, J=7.9Hz), 7.67 (1H, d, J=2.8Hz), 8.12-8.14 (1H, m), 8.29-8.30 (1H, m). |
| 616 | —H | 4-pyridylmethyl | free | (CDCl₃) 2.33 (2H, t, J=5.0Hz), 2.41 (2H, t, J=5.1Hz), 2.57-2.63 (2H, m), 2.92-2.97 (2H, m), 3.02 (3H, s), 3.41 (2H, t, J=5.0Hz), 3.50 (2H, s), 3.65 (2H, t, J=5.1Hz), 4.51 (2H, s), 6.80 (1H, d, J=8.9Hz), 6.98 (2H, d, J=8.4Hz), 7.11 (1H, dd, J=8.9Hz, 3.1Hz), 7.18 (2H, d, J=8.4Hz), 7.27 (2H, d, J=5.6Hz), 7.34 (2H, d, J=8.3Hz), 7.58 (2H, d, J=8.3Hz), 7.69 (1H, d, J=3.1Hz), 8.55 (2H, d, J=5.8Hz). |
| 617 | —H | benzyl | hydrochloride | (DMSO-d₆) 2.64-2.69 (2H, m), 2.75-2.81 (2H, m), 2.92-3.02 (5H, m), 3.23-3.32 (2H, m), 3.41-3.51 (2H, m), 4.02-4.08 (1H, m), 4.31 (2H, brs), 4.43-4.48 (1H, m), 4.64 (2H, brs), 6.86 (1H, d, J=9.1Hz), 6.90 (2H, d, J=8.6Hz), 7.20 (2H, d, J=8.4Hz), 7.29 (1H, dd, J=9.1Hz, 3.1Hz), 7.42-7.47 (5H, m), 7.56-7.57 (2H, m), 7.62 (1H, d, J=3.1Hz), 7.69 (2H, d, J=8.1Hz), 11.08 (1H, brs). |
| 618 | —OCH₃ | piperonyl | hydrochloride | (DMSO-d₆) 2.59-3.09 (6H, m), 2.97 (3H, s), 3.16-3.61 (4H, m), 3.65 (3H, s), 3.97-4.13 (1H, m), 4.14-4.28 (2H, m), 4.38-4.51 (1H, m), 4.58 (2H, s), 6.06 (2H, s), 6.72-6.80 (2H, m), 6.89 (1H, d, J=8.0Hz), 6.93-7.03 (3H, m), 7.18 (1H, s), 7.26 (1H, dd, J=9.0Hz, 3.2Hz), 7.42 (2H, d, J=8.0Hz), 7.49 (1H, d, J=3.1Hz), 7.67 (2H, d, J=8.0Hz), 10.81 (1H, brs). |

TABLE 192

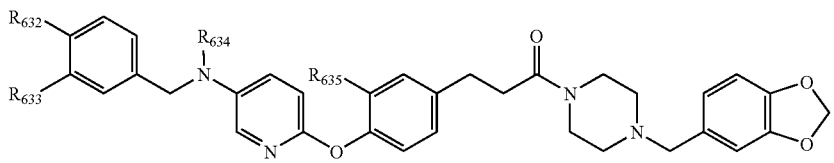

| Example No. | R632 | R633 | R634 | R635 | Form | ¹HNMR (DMSO-d₆) δppm |
|---|---|---|---|---|---|---|
| 619 | —CF₃ | —H | —C₂H₅ | —H | TsOH salt | 1.11 (3H, t, J=6.9Hz), 2.28 (3H, s), 2.54-3.02 (7H, m), 3.17-3.48 (3H, m), 3.47 (2H, q, J=6.9Hz), 3.97-4.12 (1H, m), 4.15-4.31 (2H, m), 4.38-4.52 (1H, m), 4.58 (2H, s), 6.07 (2H, s), 6.78- |

TABLE 192-continued

| Example No. | $R_{632}$ | $R_{633}$ | $R_{634}$ | $R_{635}$ | Form | $^1$HNMR (DMSO-$d_6$) δppm |
|---|---|---|---|---|---|---|
| 620 | —CF$_3$ | —H | —(CH$_2$)$_2$OCH$_3$ | —H | TsOH salt | 7.26 (11H, m), 7.39-7.49 (4H, m), 7.53 (1H, d, J=3.1Hz), 7.68 (2H, d, J=8.2Hz), 9.45-9.69 (1H, m) 2.27 (3H, s), 2.52-3.03 (7H, m), 3.24 (3H, s), 3.17-3.70 (10H, m), 3.95-4.13 (1H, m), 4.15-4.32 (2H, m), 4.36-4.54 (1H, m), 4.66 (2H, s), 6.07 (2H, s), 6.80 (1H, d, J=8.9Hz), 6.83-7.07 (5H, m), 7.10 (2H, d, J=7.8Hz), 7.13-7.26 (3H, m), 7.37-7.49 (4H, m), 7.52 (1H, d, J=3.1Hz), 7.67 (2H, d, J=8.1Hz), 9.46-9.69 (1H, m). |
| 621 | —Cl | —Cl | —CH$_3$ | —OCH$_3$ | hydrochloride | 2.60-3.15 (7H, m), 2.94 (3H, s), 3.15-3.38 (2H, m), 3.38-3.60 (1H, m), 3.65 (3H, s), 4.07 (1H, d, J=15.7Hz), 4.20 (2H, brs), 4.38-4.60 (1H, m), 4.48 (2H, s), 6.06 (2H, s), 6.73-6.81 (2H, m), 6.90 (1H, d, J=8.0Hz), 6.93-7.05 (3H, m), 7.16-7.24 (2H, m), 7.29 (1H, dd, J=8.9Hz, 3.2Hz), 7.47 (1H, d, J=1.9Hz), 7.50 (1H, d, J=3.1Hz), 7.56 (1H, d, J=8.2Hz), 11.10 (1H, brs). |
| 622 | —Cl | —Cl | —CH$_3$ | —F | hydrochloride | 2.58-3.17 (7H, m), 2.96 (3H, s), 3.18-3.38 (2H, m), 3.38-3.70 (1H, m), 4.00-4.18 (1H, m), 4.20 (2H, brs), 4.33-4.60 (1H, m), 4.50 (2H, s), 6.06 (2H, s), 6.92 (1H, d, J=9.0Hz), 6.95-7.14 (4H, m), 7.16-7.25 (3H, m), 7.31 (1H, dd, J=9.0Hz, 3.1Hz), 7.47 (1H, d, J=1.9Hz), 7.51 (1H, d, J=3.1Hz), 7.56 (1H, d, J=8.2Hz), 11.10 (1H, brs). |
| 623 | —CF$_3$ | —H | —C$_2$H$_5$ | —OCH$_3$ | hydrochloride | 1.09 (3H, t, J=6.9Hz), 2.58-3.11 (8H, m), 3.15-3.58 (4H, m), 3.64 (3H, s), 3.94-4.12 (1H, m), 4.14-4.28 (2H, m), 4.36-4.50 (1H, m), 4.54 (2H, s), 6.69-6.79 (2H, m), 6.88 (1H, d, J=8.0Hz), 6.92-7.02 (3H, m), 7.12-7.24 (2H, m), 7.37-7.49 (3H, m), 7.67 (2H, d, J=8.1Hz), 10.77 (1H, brs). |

TABLE 193

| Example No. | $R_{636}$ | $R_{637}$ | $R_{638}$ | $R_{639}$ | $R_{640}$ | $R_{641}$ | Form | mp (° C.) or $^1$HNMR |
|---|---|---|---|---|---|---|---|---|
| 624 | Ya$_2$ | —H | —H | Ya$_1$ | —H | —H | hydrochloride | $^1$HNMR (DMSO-$d_6$) δ2.56-2.72 (2H, m), 2.73-2.94 (3H, m), 2.96-3.10 (1H, m), 3.12-3.52 (4H, m), 3.91-4.07 (1H, m), 4.10-4.26 (2H, m), 4.33-4.48 (1H, m), 6.05 (2H, s), 6.82 (1H, d, J=8.2Hz), 6.89-7.02 (4H, m), 7.09 (1H, t, J=7.6Hz), 7.14-7.25 (2H, m), 7.35 (1H, d, J=7.6Hz), 7.74 (2H, d, J=9.0Hz), |

TABLE 193-continued
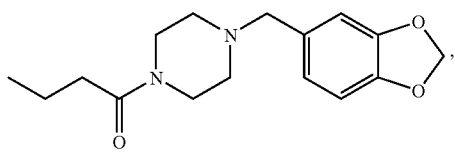
| Example No. | R₆₃₆ | R₆₃₇ | R₆₃₈ | R₆₃₉ | R₆₄₀ | R₆₄₁ | Form | mp (° C.) or ¹HNMR |
|---|---|---|---|---|---|---|---|---|
| | | | | | | | | 7.81 (1H, d, J=8.4Hz), 7.94 (1H, dd, J=8.4Hz, 2.1Hz), 8.22 (1H, d, J=2.1Hz), 10.45 (1H, s), 11.15 (1H, brs). |
| 625 | Ya₂ | —H | —H | —H | Ya₁ | —H | oxalate | mp 134-143 |
| 626 | —H | —H | Ya₂ | —H | —H | Ya₁ | fumarate | mp 123-126 |
| 627 | —H | Ya₂ | —H | —H | —H | Ya₁ | hydrochloride | mp 141-153 |
In the above-mentioned Table, Y$_{a1}$ means a group of
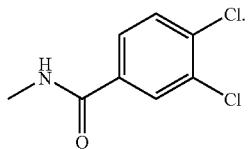
and Y$_{a2}$ means a group of
TABLE 194
| Example No. | R₆₄₂ | MS (M⁺ + H) |
|---|---|---|
| 628 |  | 540 |
| 629 |  | 574 |
| 630 | morpholino | 528 |
TABLE 194-continued
| Example No. | R₆₄₂ | MS (M⁺ + H) |
|---|---|---|
| 631 |  | 574 |
| 632 |  | 673 |
| 633 |  | 513 |
| 634 |  | 543 |
| 635 | | 632 |
| 636 | | 555 |

TABLE 194-continued

Structure: 3,4-dichlorobenzamide–pyridine–O–phenyl–N(Et)–CH2–C(=O)–R642

| Example No. | R642 | MS (M+ + H) |
|---|---|---|
| 637 | 1-methylpyrrolidin-3-yloxy-(4-OCF3-phenyl) | 689 |
| 638 | (4-methylmorpholin-2-yl)methyl-(4-ethylpiperazin-1-yl) | 655 |
| 639 | (4-methylmorpholin-2-yl)methyl-piperidin-1-yl | 626 |

TABLE 195

Structure: 3,4-dichlorobenzamide–pyridine–O–phenyl–N(Et)–CH2–C(=O)–N(R643)(R644)

| Example No. | R643 | R644 | MS (M+ + H) |
|---|---|---|---|
| 640 | —CH3 | cyclohexyl | 554 |
| 641 | —H | cyclohexyl | 540 |
| 642 | —C2H5 | —Ph | 562 |
| 643 | —CH3 | 4-CH3Ph— | 562 |
| 644 | —H | cycloheptyl | 554 |
| 645 | —H | cyclooctyl | 569 |
| 646 | —H | benzyl | 548 |
| 647 | —H | 2-ClPhCH2— | 584 |
| 648 | —H | 3-ClPhCH2— | 584 |
| 649 | —H | 4-ClPhCH2— | 584 |
| 650 | —CH3 | Ph(CH2)2— | 577 |
| 651 | —CH3 | 3,4-(CH3O)2PhCH2— | 623 |
| 652 | —CH3 | benzyL | 562 |
| 653 | —C2H5 | benzyl | 576 |
| 654 | —H | PhOCH2CH(CH3)— | 593 |
| 655 | —C2H5 | cyclohexyl | 569 |
| 656 | —H | —C2H5 | 486 |
| 657 | —H | —(CH2)2CH3 | 500 |
| 658 | —H | —(CH2)2OCH3 | 516 |
| 659 | —C2H5 | cyclohexylmethyl | 583 |
| 660 | —H | 4-CH3OPhCH2— | 578 |
| 661 | —H | 4-CH3OPh(CH2)2— | 593 |
| 662 | —H | 4-CF3OPhCH2— | 632 |
| 663 | —H | 4-CF3OPh— | 618 |
| 664 | —H | 4-ClPh(CH2)2— | 598 |
| 665 | —H | piperonyl | 592 |
| 666 | —H | —(CH2)2OPh | 579 |
| 667 | —H | cyclopentyl | 527 |
| 668 | —H | cyclohexylmethyl | 554 |
| 669 | —H | 4-hydroxycyclohexan-1-yl | 556 |
| 670 | —H | 4-FPhCH2— | 566 |
| 671 | —H | —CH(CH3)Ph | 562 |
| 672 | —H | —(CH2)3Ph | 576 |
| 673 | —H | —Ph | 534 |
| 674 | —H | 4-CH3OPh— | 564 |
| 675 | —H | —(CH2)2Ph | 562 |
| 676 | —H | 3-PhOPh— | 627 |

TABLE 195-continued

| Example No. | R643 | R644 | MS (M+ + H) |
|---|---|---|---|
| 677 | —H | 4-PhOPh— | 627 |
| 678 | —H | 2-CH3OPh(CH2)2— | 593 |
| 679 | —H | 2-FPh(CH2)2— | 580 |

TABLE 196

Structure: 3,4-dichlorobenzamide–pyridine–O–phenyl–N(Et)–CH2–C(=O)–N(R645)(R646)

| Example No. | R645 | R646 | MS (M+ + H) |
|---|---|---|---|
| 680 | —H | 4-methyl-1-benzylpiperidinyl | 632 |
| 681 | —H | —CH(CH3)2 | 501 |
| 682 | —CH3 | (2-propylpyridin-yl) | 578 |
| 683 | —(CH2)2OH | —(CH2)2OH | 547 |
| 684 | —CH3 | —(CH2)2N(CH3)2 | 544 |
| 685 | —H | —(CH2)3CH3 | 515 |
| 686 | —H | cyclopropyl | 499 |
| 687 | —H | 2-pyridylmethyl | 550 |
| 688 | —H | 3-pyridylmethyl | 550 |
| 689 | —H | —CH2CH(CH3)2 | 515 |
| 690 | —H | cyclopropylmethyl | 513 |
| 691 | —H | 1-butylimidazolyl | 567 |
| 692 | —H | 1-butylpyrrolidinyl | 570 |
| 693 | —H | 4-propylmorpholinyl | 572 |

TABLE 197

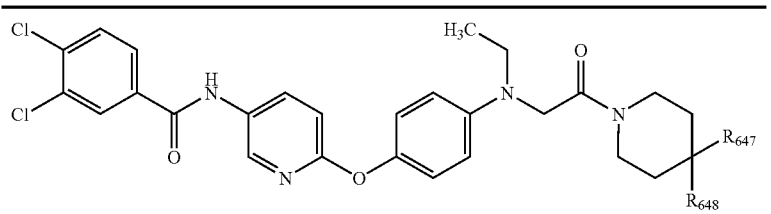

| Example No. | R₆₄₇ | R₆₄₈ | ¹HNMR or MS |
|---|---|---|---|
| 694 | —H | 4-CF₃OPhO— | MS 702 (M⁺ + H) |
| 695 | —H | benzyl | MS 617 (M⁺ + H) |
| 696 | —OH | 4-ClPh— | MS 654 (M⁺ + H) |
| 697 | —H | —H | MS 526 (M⁺ + H) |
| 698 | —H | —Ph | MS 602 (M⁺ + H) |
| 699 | —H | piperonyl | ¹HNMR (CDCl₃) δ1.11-1.16 (5H, m), 1.65-1.71 (3H, m), 2.48 (2H, d, J=6.4Hz), 2.54-2.58 (1H, m), 2.95-3.04 (1H, m), 3.35 (2H, q, J=7.1Hz), 3.84-3.89 (1H, m), 4.01 (2H, s), 4.52-4.57 (1H, m), 5.93 (2H, s), 6.56-6.63 (4H, m), 6.73 (1H, d, J=7.8Hz), 6.79 (1H, d, J=8.7Hz), 6.92 (2H, d, J=9.1Hz), 7.52 (1H, d, J=8.4Hz), 7.72 (1H, dd, J=8.4Hz, 2.0Hz), 7.99 (1H, d, J=2.0Hz), 8.04 (1H, dd, J=8.9Hz, 2.8Hz), 8.26 (1H, d, J=2.5Hz), 8.56 (1H, brs). |
| 700 | —H | N-methylpiperidinyl | MS 610 (M⁺ + H) |
| 701 | —H | 4-CH₃OPhCONH— | MS 676 (M⁺ + H) |
| 702 | —H | —N(CH₃)CH₂Ph | MS 646 (M⁺ + H) |
| 703 | —H | 4-CH₃PhO(CH₂)₂N(CH₃)— | MS 690 (M⁺ + H) |
| 704 | —OH | —Ph | MS 619 (M⁺ + H) |
| 705 | —H | 4-CNPhO— | MS 644 (M⁺ + H) |
| 706 | —H | 2-ClPhCH₂— | MS 653 (M⁺ + H) |
| 707 | —CH₂(CH₂)₃CH₂— | | MS 595 (M⁺ + H) |

TABLE 198

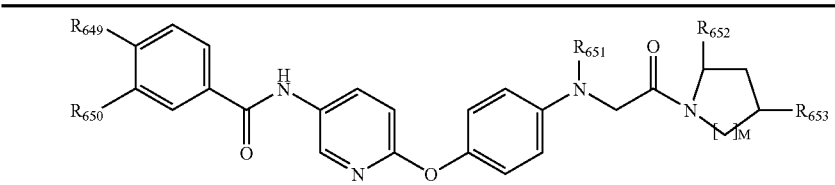

| Example No. | R₆₄₉ | R₆₅₀ | R₆₅₁ | R₆₅₂ | R₆₅₃ | M | ¹HNMR (solvent) δppm |
|---|---|---|---|---|---|---|---|
| 708 | —Cl | —Cl | —CH₃ | —CONH₂ | —H | 1 | (DMSO-d₆) 1.79-2.02 (4H, m), 2.96 (3H, s), 3.37-3.67 (3H, m), 4.19 (2H, s), 6.61-6.70 (2H, m), 6.89-6.95 (3H, m), 7.83 (1H, d, J=8.4Hz), 7.94 (1H, dd, J=8.4Hz, 2.0Hz), 8.13 (1H, dd, J=8.9Hz, 2.6Hz), 8.22 (1H, d, J=2.0Hz), 8.43 (1H, d, J=2.6Hz), 10.51 (1H, s). |
| 709 | —Cl | —Cl | —CH₃ | —H | benzyl | 2 | (CDCl₃) 1.18-1.26 (2H, m), 1.57 (3H, brs), 1.58-1.74 (2H, m), 2.49-2.58 (2H, m), 3.83 (1H, d, J=13.5Hz), 4.08 (2H, s), 4.56 (1H, d, J=13.5Hz), 6.40 (1H, d, J=8.9Hz), 6.67 (2H, d, J=9.1Hz), 6.98 (2H, d, J=9.1Hz), 7.12-7.32 (5H, m), 7.56 (1H, d, J=8.4Hz), 7.71 (1H, dd, J=8.4Hz, 2.1Hz), 7.98 (1H, d, J=2.1Hz), 8.03-8.10 (2H, m), 8.24 (1H, d, J=2.6Hz). |

TABLE 198-continued

| Example No. | $R_{649}$ | $R_{650}$ | $R_{651}$ | $R_{652}$ | $R_{653}$ | M | $^1$HNMR (solvent) δppm |
|---|---|---|---|---|---|---|---|
| 710 | —CF$_3$ | —H | —C$_2$H$_5$ | —H | piperonyl | 2 | (CDCl$_3$) 1.12-1.17 (5H, m), 1.64-1.71 (3H, m), 2.48 (2H, d, J=6.6Hz), 2.53-2.58 (1H, m), 2.94-3.03 (1H, m), 3.37 (2H, q, J=7.1Hz), 3.84-3.89 (1H, m), 4.01 (2H, s), 4.53-4.58 (1H, m), 5.93 (2H, s), 6.56-6.63 (4H, m), 6.73 (1H, d, J=7.8Hz), 6.82 (1H, d, J=8.9Hz), 6.95 (2H, d, J=9.1Hz), 7.72 (2H, d, J=8.3Hz), 7.99 (2H, d, J=8.1Hz), 8.10 (1H, dd, J=8.9Hz, 2.8Hz), 8.27 (1H, d, J=2.6Hz), 8.37 (1H, brs). |
| 711 | —Cl | —Cl | —CH$_3$ | —H | piperonyl | 2 | (CDCl$_3$) 1.03-1.17 (2H, m), 1.64-1.74 (3H, m), 2.46-2.57 (3H, m), 2.97-3.04 (4H, m), 3.80-3.85 (1H, m), 4.07 (2H, s), 4.51-4.55 (1H, m), 5.92 (2H, s), 6.56-6.63 (4H, m), 6.73 (1H, d, J=7.8Hz), 6.79 (1H, d, J=8.9Hz), 6.94 (2H, d, J=8.9Hz), 7.52 (1H, d, J=8.4Hz), 7.71 (1H, dd, J=8.4Hz, 2.1Hz), 7.98 (1H, d, J=2.1Hz), 8.04 (1H, d, J=8.9Hz), 8.25 (1H, d, J=2.3Hz), 8.49 (1H, brs). |
| 712 | —CF$_3$ | —H | —CH$_3$ | —H | piperonyl | 2 | (CDCl$_3$) 1.09-1.17 (2H, m), 1.67-1.70 (3H, m), 2.47-2.52 (3H, m), 2.94-3.03 (4H, m), 3.80-3.85 (1H, m), 4.06 (2H, s), 4.50-4.55 (1H, m), 5.92 (2H, s), 6.55-6.65 (4H, m), 6.73 (1H, d, J=7.9Hz), 6.81 (1H, d, J=8.9Hz), 6.95 (2H, d, J=8.9Hz), 7.70 (2H, d, J=8.1Hz), 7.99 (2H, d, J=8.1Hz), 8.09 (1H, dd, J=8.9Hz, 2.1Hz), 8.26 (1H, d, J=2.6Hz), 8.48 (1H, brs). |

TABLE 199

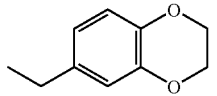

| Example No. | $R_{654}$ | $R_{655}$ | $R_{656}$ | $^1$HNMR (solvent) δppm |
|---|---|---|---|---|
| 713 | —OCH$_3$ | —CH$_3$ | (ethyl-benzodioxane) | (CDCl$_3$) 2.38-2.43 (4H, m), 2.95 (3H, s), 3.40 (2H, s), 3.47-3.58 (4H, m), 3.63 (3H, s), 4.05 (2H, s), 4.24 (4H, s), 6.12 (1H, dd, J=8.7Hz, 2.6Hz), 6.21 (1H, d, J=2.6Hz), 6.74-6.87 (5H, m), 7.44 (1H, d, J=8.4Hz), 7.69 (1H, dd, J=8.4Hz, 2.0Hz), 7.96 (1H, d, J=2.0Hz), 8.02 (1H, dd, J=8.9Hz, 2.6Hz), 8.19 (1H, d, J=2.6Hz), 9.00 (1H, s). |
| 714 | —F | —CH$_3$ | 3-furylmethyl | (DMSO-d$_6$) 2.32 (2H, brs), 2.41 (2H, brs), 2.93 (3H, s), 3.37 (2H, s), 3.44 (4H, brs), 4.29 (2H, s), 6.40-6.44 (2H, m), 6.56 (1H, dd, J=14.5Hz, 2.8Hz), 7.01-7.08 (2H, m), 7.58 (1H, s), 7.62 (1H, s), 7.84 (1H, d, J=8.4Hz), 7.94 (1H, dd, J=8.4Hz, 2.0Hz), 8.16 (1H, dd, J=8.9Hz, 2.8Hz), 8.22 (1H, d, J=2.0Hz), 8.39 (1H, d, J= |

TABLE 199-continued

[Structure: 3,4-dichlorobenzamide-N-pyridine-O-phenyl(R654)-N(R655)-CH2-C(=O)-piperazine-N-R656]

| Example No. | R654 | R655 | R656 | ¹HNMR (solvent) δppm |
|---|---|---|---|---|
| | | | | 2.6Hz), 10.53 (1H, s). |
| 715 | —F | —CH₃ | 6-ethyl-2,3-dihydro-1,4-benzodioxin-2-yl | (DMSO-d₆) 2.30 (2H, brs), 2.39 (2H, brs), 2.93 (3H, s), 3.38 (2H, s), 3.44 (4H, brs), 4.22 (4H, s), 4.28 (2H, s), 6.41 (1H, dd, J=8.6Hz, 2.2Hz), 6.56 (1H, dd, J=14.4Hz, 2.8Hz), 6.76-6.81 (3H, m), 7.01-7.08 (2H, m), 7.84 (1H, d, J=8.4Hz), 7.94 (1H, dd, J=8.4Hz, 2.0Hz), 8.16 (1H, dd, J=8.9Hz, 2.8Hz), 8.22 (1H, d, J=2.0Hz), 8.39 (1H, d, J=2.5Hz), 10.53 (1H, s). |
| 716 | —H | —CH₃ | 3-furylmethyl | (CDCl₃) 2.42 (4H, brs), 2.97 (3H, s), 3.40 (2H, s), 3.50 (2H, brs), 3.61 (2H, brs), 4.07 (2H, s), 6.38 (1H, d, J=1.5Hz), 6.63 (2H, d, J=9.1Hz), 6.80 (1H, d, J=8.9Hz), 6.95 (2H, d, J=9.1Hz), 7.34 (1H, s), 7.40 (1H, t, J=1.5Hz), 7.52 (1H, d, J=8.4Hz), 7.70 (1H, dd, J=8.4Hz, 2.0Hz), 7.97 (1H, d, J=2.0Hz), 8.04 (1H, dd, J=8.9Hz, 2.6Hz), 8.24 (1H, d, J=2.6Hz), 8.42 (1H, s). |
| 717 | —OCH₃ | —CH₃ | 3-furylmethyl | (CDCl₃) 2.40-2.44 (4H, m), 2.96 (3H, s), 3.39 (2H, s), 3.49-3.63 (4H, m), 3.63 (3H, s), 4.06 (2H, s), 6.12 (1H, dd, J=8.7Hz, 2.6Hz), 6.22 (1H, d, J=2.5Hz), 6.38 (1H, s), 6.76 (1H, d, J=8.7Hz), 6.86 (1H, d, J=8.7Hz), 7.33-7.47 (3H, m), 7.69 (1H, dd, J=8.4Hz, 2.0Hz), 7.96-8.04 (2H, m), 8.20 (1H, d, J=2.3Hz), 8.92 (1H, s). |

TABLE 200

[Structure: 3,4-dichlorobenzamide-N-pyridine-O-phenyl(R657)-N(R658)-CH2-C(=O)-piperazine-N-R659]

| Example No. | R657 | R658 | R659 | Property |
|---|---|---|---|---|
| 718 | —CH₃ | —CH₃ | 3-furylmethyl | mp 116.5-118.0° C. |
| 719 | —H | —C₂H₅ | 2-pyrimidinyl | MS 606 (M⁺ + H) |
| 720 | —H | —C₂H₅ | 2-benzoxazolyl | MS 645 (M⁺ + H) |

TABLE 200-continued

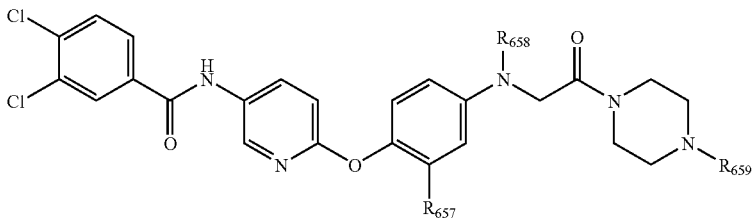

| Example No. | R$_{657}$ | R$_{658}$ | R$_{659}$ | Property |
|---|---|---|---|---|
| 721 | —H | —C$_2$H$_5$ | (5-methyl-1,3-benzodioxole) | $^1$HNMR (CDCl$_3$) δ1.16 (3H, t, J=7.1Hz), 3.04 (4H, brs), 3.40 (2H, q, J=7.1Hz), 3.66-3.76 (4H, m), 4.07 (2H, s), 5.91 (2H, s), 6.36 (1H, dd, J=8.4Hz, 2.5Hz), 6.55 (1H, d, J=2.3Hz), 6.66 (2H, d, J=9.1Hz), 6.73 (1H, d, J=8.4Hz), 6.83 (1H, d, J=8.9Hz), 6.96 (2H, d, J=8.9Hz), 7.54 (1H, d, J=8.4Hz), 7.71 (1H, dd, J=8.4Hz, 2.1Hz), 7.98 (1H, d, J=2.1Hz), 8.07 (1H, dd, J=8.9Hz, 2.6Hz), 8.22 (1H, brs), 8.24 (1H, d, J=2.5Hz). |
| 722 | —H | —CH$_3$ | (5-methyl-1,3-benzodioxole) | $^1$HNMR (CDCl$_3$) δ3.00-3.03 (7H, m), 3.64 (2H, brs), 3.75 (2H, brs), 4.12 (2H, s), 5.91 (2H, s), 6.36 (1H, dd, J=8.4Hz, 2.5Hz), 6.55 (1H, d, J=2.3Hz), 6.68 (2H, d, J=9.1Hz), 6.73 (1H, d, J=8.4Hz), 6.83 (1H, d, J=8.9Hz), 6.98 (2H, d, J=9.1Hz), 7.54 (1H, d, J=8.4Hz), 7.71 (1H, dd, J=8.4Hz, 2.1Hz), 7.98 (1H, d, J=2.1Hz), 8.07 (1H, dd, J=8.9Hz, 2.8Hz), 8.22 (1H, brs), 8.23 (1H, d, J=3.0Hz). |
| 723 | —H | —C$_2$H$_5$ | (6-ethyl-1,4-benzodioxane) | $^1$HNMR (DMSO-d$_6$) δ1.11 (3H, t, J=7.1Hz), 2.31 (2H, brs), 2.38 (2H, brs), 3.22-3.58 (8H, m), 4.16 (2H, s), 4.21 (4H, s), 6.56 (2H, d, J=9.0Hz), 6.71-6.85 (3H, m), 6.90 (2H, d, J=9.0Hz), 6.93 (1H, d, J=8.9Hz), 7.83 (1H, d, J=8.4Hz), 7.95 (1H, dd, J=8.4Hz, 2.0Hz), 8.12 (1H, dd, J=8.9Hz, 2.6Hz), 8.22 (1H, d, J=2.0Hz), 8.43 (1H, d, J=2.6Hz), 10.51 (1H, s). |
| 724 | —H | —C$_2$H$_5$ | (7-ethyl-benzodioxepine) | $^1$HNMR (CDCl$_3$) δ1.13 (3H, t, J=7.0Hz), 2.10-2.25 (2H, m), 2.42 (4H, brs), 3.34 (2H, q, J=7.0Hz), 3.42 (2H, s), 3.50 (2H, brs), 3.61 (2H, brs), 4.01 (2H, s), 4.11-4.31 (4H, m), 6.59 (2H, d, J=9.2Hz), 6.79 (1H, d, J=8.9Hz), 6.82-6.98 (5H, m), 7.51 (1H, d, J=8.4Hz), 7.70 (1H, dd, J=8.4Hz, 2.0Hz), 7.98 (1H, d, J=2.8Hz), 8.03 (1H, dd, J=8.9Hz, 2.8Hz), 8.24 (1H, d, J=2.8Hz), 8.54 (1H, s). |

TABLE 201

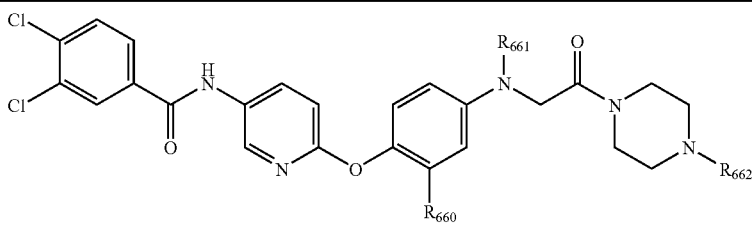

| Example No. | R$_{660}$ | R$_{661}$ | R$_{662}$ | mp (° C.) or $^1$HNMR (solvent) δppm |
|---|---|---|---|---|
| 725 | —CH$_3$ | —Ac | piperonyl | mp 216-217 |
| 726 | —CH$_3$ | —Ac | benzyl | $^1$HNMR (DMSO-d$_6$) 1.82 (3H, s), 2.09 (3H, s), 2.28-2.36 (4H, m), 3.35-3.50 (6H, m), 4.44 (2H, s), 7.05-7.10 (2H, m), 7.20-7.32 (7H, |

TABLE 201-continued

[Structure: 3,4-dichlorobenzamide linked to pyridine-O-phenyl(R660) with N(R661)-CH2-C(O)-piperazine-R662]

| Example No. | R660 | R661 | R662 | mp (° C.) or ¹HNMR (solvent) δppm |
|---|---|---|---|---|
| 727 | —H | —C₂H₅ | 3-pyridyl | m), 7.82 (1H, d, J=8.5Hz), 7.92 (1H, dd, J=1.9Hz, 8.5Hz), 8.15-8.20 (2H, m), 8.42 (1H, d, J=2.5Hz), 10.53 (1H, s). ¹HNMR (DMSO-d₆) 1.13 (3H, t, J=7.1Hz), 3.21 (2H, brs), 3.29 (2H, brs), 3.37 (2H, q, J=7.1Hz), 3.51-3.78 (4H, m), 4.26 (2H, s), 6.60 (2H, d, J=9.0Hz), 6.92 (2H, d, J=9.0Hz), 6.94 (1H, d, J=8.9Hz), 7.23 (1H, dd, J=8.5Hz, 4.6Hz), 7.36 (1H, dd, J=8.5Hz, 1.6Hz), 7.83 (1H, d, J=8.5Hz), 7.94 (1H, dd, J=8.5Hz, 2.0Hz), 8.03 (1H, d, J=4.6Hz), 8.12 (1H, dd, J=8.9Hz, 2.8Hz), 8.22 (1H, d, J=2.0Hz), 8.34 (1H, d, J=2.8Hz), 8.43 (1H, d, J=2.8Hz), 10.51 (1H, s). |
| 728 | —F | —C₂H₅ | piperonyl | mp 149-151 |
| 729 | —F | —CH₃ | piperonyl | mp 199-201 |
| 730 | —F | —Ac | piperonyl | mp 233-235 |
| 731 | —OCH₃ | —CH₃ | piperonyl | ¹HNMR (CDCl₃) 2.41-2.43 (4H, m), 3.02 (3H, s), 3.42 (2H, s), 3.49-3.62 (4H, m), 3.72 (3H, s), 4.08 (2H, s), 5.95 (2H, s), 6.21 (1H, dd, J=8.7Hz, 2.6Hz), 6.32 (1H, d, J=2.8Hz), 6.73-6.77 (2H, m), 6.84 (2H, t, J=4.5Hz), 6.95 (1H, d, J=8.7Hz), 7.54 (1H, d, J=8.4Hz), 7.70 (1H, dd, J=8.2Hz, 2.0Hz), 7.97 (2H, d, J=2.0Hz), 8.05-8.09 (1H, m), 8.19 (1H, d, J=2.5Hz). |
| 732 | —H | —CH₃ | 3-pyridylmetyl | ¹HNMR (CDCl₃) 2.40-2.42 (4H, m), 2.93 (3H, s), 3.44 (2H, s), 3.48-3.58 (4H, m), 4.06 (2H, s), 6.58 (2H, d, J=9.1Hz), 6.74 (1H, d, J=8.9Hz), 6.90 (2H, d, J=9.1Hz), 7.25-7.30 (1H, m), 7.43 (1H, d, J=8.4Hz), 7.66-7.73 (2H, m), 7.97 (1H, d, J 2.0Hz), 8.03 (1H, dd, J=8.9Hz, 2.6Hz), 8.25 (1H, d, J=2.5Hz), 8.47-8.51 (2H, m), 9.59 (1H, s). |
| 733 | —H | —CH₃ | 4-methylphenyl-CH₂-4-fluorophenyl | ¹HNMR (DMSO-d₆) 2.96 (3H, s), 3.07-3.15 (4H, m), 3.59 (4H, brs), 3.83 (2H, s), 4.31 (2H, s), 6.66 (2H, d, J=9.1Hz), 6.88-6.95 (5H, m), 7.05-7.13 (4H, m), 7.20-7.24 (2H, m), 7.83 (1H, d, J=8.4Hz), 7.95 (1H, dd, J=8.4Hz, 2.0Hz), 8.12 (1H, dd, J=8.9Hz, 2.8Hz), 8.22 (1H, d, J=2.0Hz), 8.43 (1H, d, J=2.5Hz), 10.50 (1H, s). |

TABLE 202

[Structure: 3,4-dichlorobenzamide linked to pyridine-O-phenyl(R663) with N(Et)-CH2-C(O)-piperazine-R664]

| Example No. | R663 | R664 | MS or ¹HNMR |
|---|---|---|---|
| 734 | —H | —CHPh₂ | MS 694 (M⁺ + H) |
| 735 | —H | 3-CH₃OPh— | MS 634 (M⁺ + H) |

TABLE 202-continued

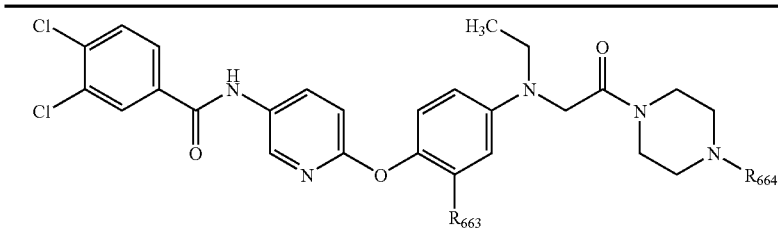

| Example No. | R_663 | R_664 | MS or ¹HNMR |
|---|---|---|---|
| 736 | —H | 4-CH₃OPh— | MS 634 (M⁺ + H) |
| 737 | —H | 3,4-(CH₃)₂Ph— | MS 632 (M⁺ + H) |
| 738 | —H | 2,3-Cl₂Ph— | MS 673 (M⁺ + H) |
| 739 | —H | 2,4-F₂Ph— | MS 640 (M⁺ + H) |
| 740 | —H | 2-CH₃OPh— | MS 634 (M⁺ + H) |
| 741 | —H | 3-CF₃Ph— | MS 671 (M⁺ + H) |
| 742 | —H | 2-ClPh— | MS 639 (M⁺ + H) |
| 743 | —H | 4-CF₃Ph— | MS 671 (M⁺ + H) |
| 744 | —H | —Ph | MS 604 (M⁺ + H) |
| 745 | —H | 2-pyridylmethyl | MS 619 (M⁺ + H) |
| 746 | —H | 2-pyridyl | MS 605 (M⁺ + H) |
| 747 | —H | —(CH₂)₃Ph | MS 646 (M⁺ + H) |
| 748 | —H | —(CH₂)₄Ph | MS 660 (M⁺ + H) |
| 749 | —H | —(CH₂)₂N(CH₃)₂ | MS 599 (M⁺ + H) |
| 750 | —H | cyclopentyl | MS 596 (M⁺ + H) |
| 751 | —H | 4-methyl-1-methylpiperidinyl | MS 625 (M⁺ + H) |
| 752 | —H | 4-propylmorpholinyl | MS 641 (M⁺ + H) |
| 753 | —H | —CH(CH₃)Ph | MS 634 (M⁺ + H) |
| 754 | —H | —(CH₂)₂Ph | MS 632 (M⁺ + H) |
| 755 | —H | —CH₂CONHPh | MS 661 (M⁺ + H) |
| 756 | —H | —(CH₂)₃N(CH₃)₂ | MS 613 (M⁺ + H) |
| 757 | —H | 4-ethyl-1-methylpiperidinyl | MS 639 (M⁺ + H) |
| 758 | —H | —CH₃ | MS 542 (M⁺ + H) |
| 759 | —OCH₃ | —H | ¹HNMR (CDCl₃) δ1.26 (3H, t, J=6.9Hz), 2.70 (1H, brs), 2.82-2.87 (4H, m), 3.33 (2H, q, J=6.9Hz), 3.49-3.57 (4H, m), 3.62 (3H, s), 4.00 (2H, s), 6.09 (1H, d, J=8.7Hz), 6.20 (1H, s), 6.73 (1H, d, J=8.7Hz), 6.83 (1H, d, J=8.6Hz), 7.42 (1H, d, J=8.3HZ), 7.70 (1H, d, J=7.4Hz), 7.97-8.03 (2H, m), 8.23 (1H, s), 9.26 (1H, brs). |

TABLE 203

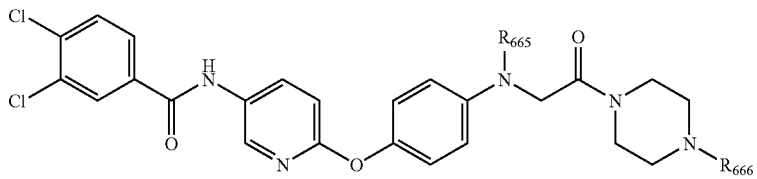

| Example No. | R_665 | R_666 | Form | ¹HNMR (DMSO-d₆) δppm |
|---|---|---|---|---|
| 760 | —Ac | piperonyl | hydro-chloride | 1.84 (3H, s), 2.83-3.14 (2H, m), 3.23-3.32 (2H, m), 4.02 (1H, d, J=13.6Hz), 4.18-4.27 (2H, m), 4.40 (1H, d, J=13.6Hz), 4.50-4.60 (2H, |

TABLE 203-continued

Structure: 3,4-dichlorobenzamide-pyridine-O-phenyl-N(R665)-CH2-C(O)-piperazine-N-R666

| Example No. | R665 | R666 | Form | $^1$HNMR (DMSO-d$_6$) δppm |
|---|---|---|---|---|
| | | | | m), 6.07 (2H, s), 6.96-7.03 (2H, m), 7.10-7.25 (4H, m), 7.43 (2H, d, J=8.8Hz), 7.85 (1H, d, J=8.4Hz), 7.98 (1H, dd, J=2.0Hz, 8.4Hz), 8.24 (1H, dd, J=2.6Hz, 8.9Hz), 8.26 (1H, d, J=2.0Hz), 8.54 (1H, d, J=2.6Hz), 10.69 (1H, s), 11.07 (1H, brs). |
| 761 | —Ac | benzyl | hydro-chloride | 1.84 (3H, s), 2.90-3.17 (2H, m), 3.23-3.35 (2H, m), 4.03 (1H, d, J=14.4Hz), 4.28-4.43 (3H, m), 4.50-4.62 (2H, m), 7.13 (1H, d, J=8.8Hz), 7.17 (2H, d, J=8.8Hz), 7.40-7.50 (5H, m), 7.58-7.62 (2H, m), 7.85 (1H, d, J=8.4Hz), 8.00 (1H, dd, J=2.0Hz, 8.4Hz), 8.20-8.29 (2H, m), 8.54 (1H, d, J=2.6Hz), 10.70 (1H, s), 11.21 (1H, s). |
| 762 | —C$_2$H$_5$ | 3-furylmethyl | trihydro-chloride | 1.11 (3H, t, J=7.1Hz), 2.75-3.30 (3H, m), 3.30-3.50 (2H, m), 3.40 (2H, q, J=7.1Hz), 3.51-3.72 (1H, m), 3.95-4.15 (1H, m), 4.22 (2H, s), 4.30-4.62 (3H, m), 6.80-6.85 (1H, m), 6.89 (2H, d, J=8.9Hz), 7.00 (1H, d, J=8.9Hz), 7.01 (2H, d, J=8.9Hz), 7.70-7.80 (1H, m), 7.84 (1H, d, J=8.5Hz), 7.88 (1H, s), 7.99 (1H, dd, J=8.5Hz, 2.0Hz), 8.19 (1H, dd, J=8.9Hz, 2.7Hz), 8.27 (1H, d, J=2.0Hz), 8.50 (1H, d, J=2.7Hz), 10.69 (1H, s). |
| 763 | —C$_2$H$_5$ | 4-pyridylmethyl | tetrahydro-chloride | 1.11 (3H, t, J=7.0Hz), 3.00-3.60 (6H, m), 3.41 (2H, q, J=7.0Hz), 3.90 (2H, brs), 4.42 (2H, brs), 4.63 (2H, brs), 6.82 (2H, d, J=8.8Hz), 6.98 (3H, d, J=8.8Hz), 7.84 (1H, d, J=8.4Hz), 7.98 (1H, dd, J=8.4Hz, 2.0Hz), 8.17 (1H, dd, J=8.9Hz, 2.6Hz), 8.22-8.39 (3H, m), 8.49 (1H, d, J=2.5Hz), 8.99 (2H, d, J=6.2Hz), 10.67 (1H, s). |
| 764 | —CH$_3$ | 6-ethylbenzothiazol-2-yl | dihydro-chloride | 2.94 (3H, s), 2.80-3.22 (3H, m), 3.22-3.70 (3H, m), 3.95-4.60 (6H, m), 6.68 (2H, d, J=9.1Hz), 6.92 (2H, d, J=9.1Hz), 6.95 (1H, d, J=8.9Hz), 7.79 (1H, dd, J=8.4Hz, 1.6Hz), 7.84 (1H, d, J=8.4Hz), 7.96 (1H, dd, J=8.4Hz, 2.0Hz), 8.14 (1H, dd, J=8.9Hz, 2.3Hz), 8.20 (1H, d, J=8.4Hz), 8.24 (1H, d, J=2.0Hz), 8.40 (1H, d, J=1.6Hz), 8.44 (1H, d, J=2.3Hz), 9.51 (1H, s), 10.57 (1H, s). |

TABLE 204

Structure: R667,R668-benzamide-pyridine-O-phenyl(R669)-N(R670)-CH2-C(O)-piperazine-N-R671 · maleic acid

| Example No. | R667 | R668 | R669 | R670 | R671 | mp (° C.) or $^1$HNMR (solvent) δppm |
|---|---|---|---|---|---|---|
| 765 | —Cl | —Cl | —H | —CH$_3$ | piperonyl | mp 198-200 |
| 766 | —Cl | —Cl | —H | —C$_2$H$_5$ | benzyl | $^1$HNMR (DMSO-d$_6$) 1.12 (3H, t, J=7.1Hz), 2.98 (4H, brs), 3.34 (2H, q, J=7.1Hz), 3.20-3.50 (2H, m), 3.67 (2H, brs), 4.10 (2H, brs), |

TABLE 204-continued

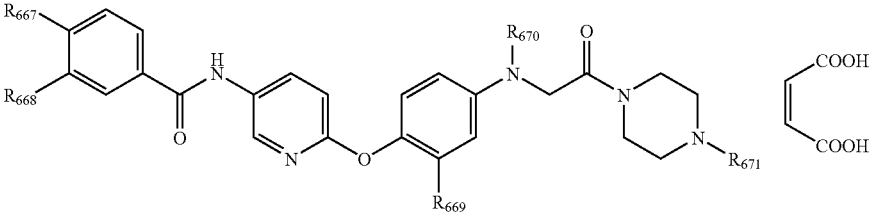

| Example No. | $R_{667}$ | $R_{668}$ | $R_{669}$ | $R_{670}$ | $R_{671}$ | mp (° C.) or $^1$HNMR (solvent) δppm |
|---|---|---|---|---|---|---|
| | | | | | | 4.23 (2H, s), 6.11 (2H, s), 6.59 (2H, d, J=9.2Hz), 6.91 (2H, d, J=9.2Hz), 6.94 (1H, d, J=8.9Hz), 7.45 (5H, s), 7.84 (1H, d, J=8.4Hz), 7.94 (1H, dd, J=8.4Hz, 2.6Hz), 8.12 (1H, dd, J=8.9Hz, 2.6Hz), 8.22 (1H, d, J=2.0Hz), 8.43 (1H, d, J=2.6Hz), 10.51 (1H, s). |
| 767 | —Cl | —Cl | —H | —CH$_3$ | 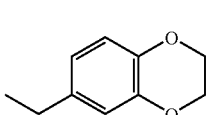 | $^1$HNMR (DMSO-d$_6$) 2.94 (3H, s), 3.05 (4H, brs), 3.40 (2H, brs), 3.63 (2H, brs), 4.04 (2H, brs), 4.26 (4H, s), 4.31 (2H, brs), 6.09 (2H, s) 6.65 (2H, d, J=9.1Hz), 6.82-7.06 (6H, m), 7.84 (1H, d, J=8.4Hz), 7.94 (1H, dd, J=8.4Hz, 2.0Hz), 8.12 (1H, dd, J=8.8Hz, 2.5Hz), 8.22 (1H, d, J=2.0Hz), 8.43 (1H, d, J=2.5Hz), 10.51 (1H, s). |
| 768 | —Cl | —Cl | —OCH$_3$ | —C$_2$H$_5$ | piperonyl | mp 172-177 |
| 769 | —CF$_3$ | —H | —H | —C$_2$H$_5$ | benzyl | $^1$HNMR (CDCl$_3$+CD$_3$OD) 1.13 (3H, t, J=6.9Hz), 3.08 (4H, brs), 3.36 (2H, q, J=6.9Hz), 3.85 (4H, brs), 4.09 (2H, s), 4.18 (2H, s), 6.31 (2H, s), 6.73 (2H, d, J=8.9Hz), 6.87 (1H, d, J=9.2Hz), 6.98 (2H, d, J=8.9Hz), 7.40-7.44 (5H, m), 7.73 (2H, d, J=8.4Hz), 8.07 (2H, d, J=8.3Hz), 8.27 (2H, d, J=7.4Hz), 9.63 (1H, s). |
| 770 | —CF$_3$ | —H | —H | —CH$_3$ | 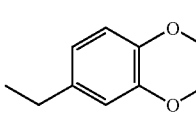 | $^1$HNMR (DMSO-d$_6$) 2.94 (3H, s), 2.95 (4H, brs), 3.33 (4H, brs), 4.03 (2H, brs), 4.26 (4H, s), 4.31 (2H, brs), 6.09 (2H, s), 6.65 (2H, d, J=9.2Hz), 6.85-7.03 (6H, m), 7.93 (2H, d, J=8.2Hz), 8.14 (1H, dd, J=8.9Hz, 2.5Hz), 8.16 (2H, d, J=8.2Hz), 8.45 (1H, d, J=2.5Hz), 10.59 (1H, s). |

TABLE 205

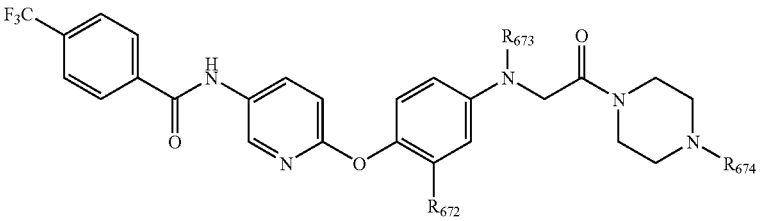

| Example No. | $R_{672}$ | $R_{673}$ | $R_{674}$ | mp (° C.) or $^1$HNMR (solvent) δppm |
|---|---|---|---|---|
| 771 | —H | —Ac | benzyl | mp 161-162 |
| 772 | —CH$_3$ | —Ac | piperonyl | $^1$HNMR (DMSO-d$_6$) 1.82 (3H, s), 2.10 (3H, s), 2.23-2.36 (4H, m), 3.33-3.45 (6H, m), 4.44 (2H, s), 5.96 (2H, s), 6.72 (1H, d, J=8.0Hz), |

TABLE 205-continued

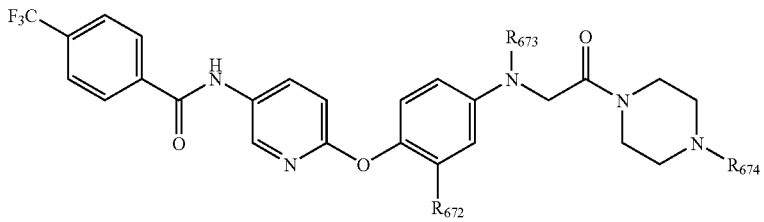

| Example No. | $R_{672}$ | $R_{673}$ | $R_{674}$ | mp (° C.) or $^1$HNMR (solvent) δppm |
|---|---|---|---|---|
| | | | | 6.82 (1H, d, J=8.0Hz), 6.84 (1H, s), 7.02-7.10 (2H, m), 7.23 (1H, d, J=8.6Hz), 7.33 (1H, s), 7.91 (2H, d, J=8.4Hz), 8.14 (2H, d, J=8.4Hz), 8.20 (1H, d, J=8.6Hz), 8.45 (1H, s), 10.60 (1H, s). |
| 773 | —CH$_3$ | —Ac | benzyl | $^1$HNMR (DMSO-d$_6$) 1.82 (3H, s), 2.10 (3H, s), 2.30-2.37 (4H, m), 3.35-3.45 (4H, m), 3.47 (2H, s), 4.44 (2H, s), 7.03-7.10 (2H, m), 7.20-7.35 (7H, m), 7.91 (2H, d, J=8.4Hz), 8.14 (2H, d, J=8.4Hz), 8.21 (1H, dd, J=2.5Hz, 8.9Hz), 8.45 (1H, d, J=2.5Hz), 10.60 (1H, s). |
| 774 | —H | —C$_2$H$_5$ | piperonyl | mp 178-180 |
| 775 | —F | —C$_2$H$_5$ | piperonyl | mp 170-172 |
| 776 | —F | —CH$_3$ | piperonyl | mp 220-221 |
| 777 | —OCH$_3$ | —CH$_3$ | piperonyl | $^1$HNMR (CDCl$_3$) 2.38-2.42 (4H, m), 2.96 (3H, s), 3.41 (2H, s), 3.47-3.58 (4H, m), 3.64 (3H, s), 4.05 (2H, s), 5.94 (2H, s), 6.13 (1H, dd, J=8.9Hz, 2.8Hz), 6.24 (1H, d, J=2.8Hz), 6.70-6.89 (5H, m), 7.64 (2H, d, J=8.3Hz), 7.96 (2H, d, J=8.1Hz), 8.06 (1H, dd, J=8.9Hz, 2.6Hz), 8.20 (1H, d, J=2.6Hz), 8.93 (1H, s). |
| 778 | —OCH$_3$ | —CH$_3$ | ![ethyl-benzodioxine] | $^1$HNMR (CDCl$_3$) 2.38-2.42 (4H, m), 2.96 (3H, s), 3.40 (2H, s), 3.47-3.57 (4H, m), 3.98 (3H, s), 4.05 (2H, s), 4.24 (4H, s), 6.13 (1H, dd, J=8.9Hz, 2.8Hz), 6.23 (1H, d, J=2.6Hz), 6.73-6.88 (5H, m), 7.63 (2H, d, J=8.3Hz), 7.97 (2H, d, J=8.1Hz), 8.07 (1H, dd, J=8.9Hz, 2.6Hz), 8.20(1H, d, J=2.5Hz), 9.11 (1H, s). |
| 779 | —F | —CH$_3$ | ![ethyl-benzodioxine] | $^1$HNMR (DMSO-d$_6$) 2.30 (2H, brs), 2.39 (2H, brs), 2.93 (3H, s), 3.38 (2H, s), 3.44 (4H, brs), 4.22 (4H, s), 4.28 (2H, s), 6.40-6.43 (1H, m), 6.56 (1H, dd, J=14.2Hz, 2.6Hz), 6.73-6.81 (3H, m), 7.02-7.08 (2H, m), 7.93 (2H, d, J=8.6Hz), 8.14-8.21 (3H, m), 8.49 (1H, d, J=2.6Hz), 10.61 (1H, s). |
| 780 | —F | —CH$_3$ | 3-furylmethyl | $^1$HNMR (DMSO-d$_6$) 2.32 (2H, s), 2.41 (2H, s), 2.93 (3H, s), 3.37 (2H, s), 3.44 (4H, brs), 4.29 (2H, s), 6.40-6.44 (2H, m), 6.55 (1H, dd, J=14.5Hz, 2.8Hz), 7.02-7.08 (2H, m), 7.58 7.62 (2H, m), 7.93 (2H, d, J=8.4Hz), 8.14-8.21 (3H, m), 8.41 (1H, d, J=2.6Hz), 10.61 (1H, s). |

TABLE 206

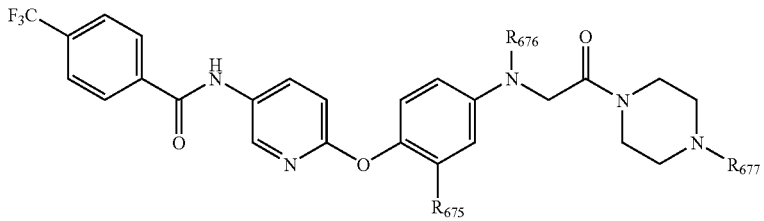

| Example No. | $R_{675}$ | $R_{676}$ | $R_{677}$ | mp (° C.) or ¹HNMR (solvent) δppm |
|---|---|---|---|---|
| 781 | —OCH₃ | —C₂H₅ | (6-ethyl-2,3-dihydro-1,4-benzodioxin) | ¹HNMR (CDCl₃) 1.16 (3H, t, J=6.9Hz), 2.38-2.43 (4H, m), 3.33-3.62 (8H, m), 3.66 (3H, s), 4.02 (2H, s), 4.26 (4H, s), 6.14 (1H, dd, J=8.7Hz, 2.6Hz), 6.25 (1H, d, J=2.6Hz), 6.75-6.90 (5H, m), 7.66 (2H, d, J=8.3Hz), 8.01 (2H, d, J=8.3Hz), 8.09 (1H, dd, J=9.1Hz, 2.8Hz), 8.26 (1H, d, J=2.6Hz), 9.19 (1H, s). |
| 782 | —F | —Ac | piperonyl | ¹HNMR (DMSO-d₆) 1.88 (3H, s), 2.33 (4H, brs), 3.40 (2H, s), 3.40 (4H, brs), 4.50 (2H, s), 5.99 (2H, s), 6.73-6.76 (1H, m), 6.83-6.86 (2H, m), 7.21 (1H, d, J=8.9Hz), 7.32-7.49 (3H, m), 7.94 (2H, d, J=8.3Hz), 8.16 (2H, d, J=8.1Hz), 8.25 (1H, dd, J=8.9Hz, 2.6Hz), 8.46 (1H, d, J=2.6Hz), 10.66 (1H, s). |
| 783 | —H | —CH₃ | 3-furylmethyl | ¹HNMR (CDCl₃) 2.44 (4H, brs), 2.99 (3H, s), 3.40 (2H, s), 3.50 (2H, t, J=4.9Hz), 3.62 (2H, t, J=4.9Hz), 4.07 (2H, s), 6.38 (1H, d, J=1.0Hz), 6.67 (2H, d, J=9.1Hz), 6.84 (1H, d, J=8.8Hz), 6.98 (2H, d, J=9.1Hz), 7.34 (1H, s), 7.40 (1H, t, J=1.6Hz), 7.73 (2H, d, J=8.2Hz), 7.99 (2H, d, J=8.2Hz), 8.11 (1H, dd, J=8.8Hz, 2.6Hz), 8.24 (1H, s), 8.25 (1H, d, J=2.6Hz). |
| 784 | —OCH₃ | —C₂H₅ | 3-furylmethyl | mp 174-176 |
| 785 | —OCH₃ | —CH₃ | 3-furylmethyl | mp 160-164 |
| 786 | —CH₃ | —CH₃ | —COOC(CH₃)₃ | ¹HNMR (CDCl₃) 1.47 (9H, s), 2.12 (3H, s), 3.01 (3H, s), 3.30-3.71 (8H, m), 4.09 (2H, s), 6.44-6.66 (2H, m), 6.83 (1H, d, J=8.9Hz), 6.93 (1H, d, J=8.4Hz), 7.75 (2H, d, J=8.1Hz), 7.94 (1H, s), 7.99 (2H, d, J=8.1Hz), 8.15 (1H, d, J=9.2Hz), 8.22 (1H, s). |
| 787 | —H | —C₂H₅ | (5-methyl-1,3-benzodioxol) | ¹HNMR (CDCl₃) 1.18 (3H, t, J=7.1Hz), 3.03 (4H, brs), 3.43 (2H, q, J=7.1Hz), 3.67-3.77 (4H, m), 4.08 (2H, s), 5.91 (2H, s), 6.36 (1H, dd, J=8.4Hz, 2.3Hz), 6.55 (1H, d, J=2.5Hz), 6.68-6.75 (3H, m), 6.87 (1H, d, J=8.7Hz), 7.00 (2H, d, J=8.9Hz), 7.75 (2H, d, J=8.4Hz), 7.98 (1H, brs), 7.99 (2H, d, J=8.3Hz), 8.13 (1H, dd, J=8.7Hz, 2.6Hz), 8.25 (1H, d, J=2.6Hz) |

TABLE 207

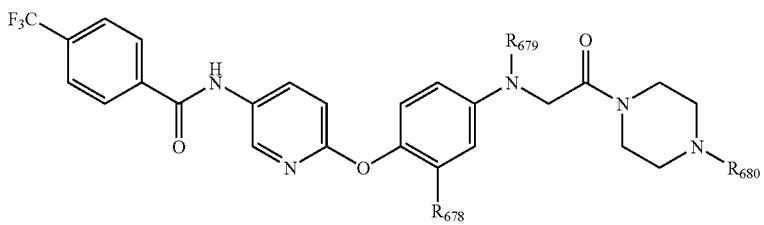

| Example No. | $R_{678}$ | $R_{679}$ | $R_{680}$ | Form | mp (° C.) or ¹HNMR (solvent) δppm |
|---|---|---|---|---|---|
| 788 | —F | —(CH₂)₂CH₃ | piperonyl | free | ¹HNMR (CDCl₃) 0.94 (3H, t, J=7.3Hz), 1.58-1.69 (2H, m), 2.45 (4H, brs), 3.29 (2H, t, J=7.6Hz), 3.45 (2H, s), 3.49 (2H, brs), 3.64 (2H, brs), 4.05 (2H, s), 5.95 (2H, s), 6.34- |

TABLE 207-continued

[Structure: 4-(trifluoromethyl)benzamide-pyridine-O-phenyl(R678)-N(R679)-CH2-C(O)-piperazine-N-R680]

| Example No. | R678 | R679 | R680 | Form | mp (° C.) or ¹HNMR (solvent) δppm |
|---|---|---|---|---|---|
| | | | | | 6.44 (2H, m), 6.75 (2H, s), 6.86 (1H, s), 6.96 (1H, d, J=8.9Hz), 7.03 (1H, t, J=9.1Hz), 7.76 (2H, d, J=8.2Hz), 7.86 (1H, brs), 8.00 (2H, d, J=8.1Hz), 8.16-8.22 (2H, m). |
| 789 | —H | —CH₃ | 5-methyl-benzo[d][1,3]dioxol-yl | free | ¹HNMR (CDCl₃) 3.02 (7H, brs), 3.64 (2H, brs), 3.75 (2H, brs), 4.12 (2H, s), 5.91 (2H, s), 6.36 (1H, dd, J=8.4Hz, 2.5Hz), 6.55 (1H, d, J=2.5Hz), 6.70 (2H, d, J=9.1Hz), 6.73 (1H, d, J=8.3Hz), 6.85 (1H, d, J=8.9Hz), 6.99 (2H, d, J=9.2Hz), 7.73 (2H, d, J=8.3Hz), 7.98 (2H, d, J=8.3Hz), 8.12 (1H, dd, J=9.1Hz, 2.8Hz), 8.15 (1H, brs), 8.24 (1H, d, J=2.5Hz). |
| 790 | —OCH₃ | —CH₃ | 4-(4-FPhCO)Ph— | free | ¹HNMR (CDCl₃) 3.03 (3H, s), 3.39 (4H, brs), 3.70 (3H, s), 3.71-3.79 (4H, m), 4.14 (2H, s), 6.23 (1H, dd, J=8.9Hz, 2.8Hz), 6.36 (1H, d, J=2.6Hz), 6.81-6.96 (4H, m), 7.09-7.17 (2H, m), 7.68 (2H, d, J=8.4Hz), 7.72-7.78 (4H, m), 7.99 (2H, d, J=8.3Hz), 8.09 (1H, dd, J=8.9Hz, 2.8Hz), 8.21 (1H, d, J=2.6Hz), 8.53 (1H, s). |
| 791 | —OCH₃ | —C₂H₅ | 4-(4-FPhCO)Ph— | free | ¹HNMR (CDCl₃) 1.17 (3H, t, J=6.9Hz), 3.37-3.42 (6H, m), 3.67 (3H, s), 3.71-3.76 (4H, m), 4.08 (2H, s), 6.19 (1H, dd, J=8.9Hz, 2.8Hz), 6.33 (1H, d, J=2.6Hz), 6.77-6.92 (4H, m), 7.09-7.15 (2H, m), 7.64 (2H, d, J=8.3Hz), 7.71-7.77 (4H, m), 7.98 (2H, d, J=8.1Hz), 8.07 (1H, dd, J=8.9Hz, 2.6Hz), 8.23 (1H, d, J=2.6Hz), 8.83 (1H, s). |
| 792 | —CH₃ | —CH₃ | 3-furylmethyl | hydrochloride | mp 158.5-161.0 |

TABLE 208

[Structure: R681,R682-benzamide-pyridine-O-phenyl-N(Ac)-CH2CH2-C(O)-piperazine-N-R683 · HCl]

| Example No. | R681 | R682 | R683 | ¹H NMR (DMSO-d₆) δppm |
|---|---|---|---|---|
| 793 | —Cl | —Cl | piperonyl | 1.74(3H, s), 2.19-2.34(4H, m), 2.54(2H, t, J=7.7 Hz), 3.32-3.46(6H, m), 3.76(2H, t, J=7.7Hz), 5.96(2H, s), 6.72(1H, d, J=7.9Hz), 6.77-6.85(2H, m), 7.11(1H, d, J=8.8Hz), 7.17(2H, d, J=8.6Hz), 7.31(2H, d, J=8.6Hz), 7.83(1H, d, J=8.4Hz), 7.93(1H, dd, J=8.4Hz, 2.1Hz), 8.17-8.25(2H, m), 8.51(1H, d, J=2.4Hz), 10.57(1H, s). |

TABLE 208-continued

![structure: R681/R682-benzamide-pyridine-O-phenyl-N(Ac)-CH2CH2-C(O)-piperazine-R683, HCl]

| Example No. | R681 | R682 | R683 | ¹H NMR (DMSO-d₆) δppm |
|---|---|---|---|---|
| 794 | —Cl | —Cl | benzyl | 1.74(3H, s), 2.25-2.37(4H, m), 2.54(2H, t, J=7.7 Hz), 3.36-3.42(4H, m), 3.46(2H, s), 3.76(2H, t, J=7.7Hz), 7.11(1H, d, J=8.8Hz), 7.16(2H, d, J=8.6 Hz), 7.20-7.31(5H, m), 7.34(2H, d, J=8.6Hz), 7.83(1H, d, J=8.4Hz), 7.93(1H, dd, J=8.4Hz, 2.1 Hz), 8.19-8.25(2H, m), 8.51(1H, d, J=2.5Hz), 10.57(1H, s). |
| 795 | —CF₃ | —H | piperonyl | 1.74(3H, s), 2.20-2.35(4H, m), 2.54(2H, t, J=7.7 Hz), 3.34-3.42(6H, m), 3.76(2H, t, J=7.7Hz), 5.96(2H, s), 6.72(1H, d, J=7.8Hz), 6.78-6.86(2H, m), 7.12(1H, d, J=8.8Hz), 7.17(2H, d, J=8.5Hz), 7.35(2H, d, J=8.5Hz), 7.92(2H, d, J=8.2Hz), 8.15(2H, d, J=8.2Hz), 8.24(1H, dd, J=8.8Hz, 2.5 Hz), 8.54(1H, d, J=2.5Hz), 10.65(1H, s). |
| 796 | —CF₃ | —H | benzyl | 1.74(3H, s), 2.18-2.36(4H, m), 2.54(2H, t, J=7.7 Hz), 3.35-3.45(4H, m), 3.46(2H, s), 3.76(2H, t, J=7.7Hz), 7.12(1H, d, J=8.8Hz), 7.17(2H, d, J=8.6 Hz), 7.20-7.33(5H, m), 7.34(2H, d, J=8.6Hz), 7.92(2H, d, J=8.3Hz), 8.15(2H, d, J=8.3Hz), 8.24(1H, dd, J=8.8Hz, 2.5Hz), 8.54(1H, d, J=2.5 Hz), 10.65(1H, s). |

TABLE 209

![structure: R684/R685-benzyl-N(CH3)-pyridine-O-phenyl-N(Ac)-CH2-C(O)-piperazine-R686, HCl]

| Example No. | R684 | R685 | R686 | ¹H NMR (DMSO-d₆) δppm |
|---|---|---|---|---|
| 797 | —Cl | —Cl | benzyl | 1.80(3H, s), 3.02(3H, s), 2.70-3.40(5H, m), 3.41-3.68(1H, m), 3.88-4.10(1H, m), 4.32(2H, brs), 4.25-4.50(1H, m), 4.50(2H, d, J=3.8Hz), 4.57(2H, s), 6.94(1H, d, J=8.9Hz), 7.02(2H, d, J=8.7Hz), 7.22(1H, dd, J=8.2Hz, 2.0Hz), 7.34(1H, dd, J=8.9 Hz, 3.2Hz), 7.36(2H, d, J=8.7Hz), 7.42-7.49(3H, m), 7.50(1H, d, J=2.0Hz), 7.55-7.64(1H, m), 7.62 (2H, d, J=8.2Hz), 7.66(1H, d, J=6.1Hz). |
| 798 | —Cl | —Cl | piperonyl | 1.81(3H, s), 2.75-3.40(5H, m), 3.02(3H, s), 3.43-3.67(1H, m), 3.90-4.10(1H, m), 4.22(2H, brs), 4.30-4.50(1H, m), 4.50(2H, d, J=4.6Hz), 4.57(2H, s), 6.07(2H, s), 6.94(2H, d, J=8.8Hz), 6.97-7.07(1H, m), 7.02(2H, d, J=8.9Hz), 7.22(1H, dd, J=8.3Hz, 1.8Hz), 7.24(1H, s), 7.34(1H, dd, J=8.8Hz, 3.0Hz), 7.36(2H, d, J=8.9Hz), 7.50(1H, d, J=1.8Hz), 7.60(1H, d, J=8.3Hz), 7.67(1H, d, J=3.0Hz). |
| 799 | —CF₃ | —H | benzyl | 1.80(3H, s), 3.05(3H, s), 2.70-3.40(5H, m), 3.41-3.68(1H, m), 3.90-4.08(1H, m), 4.22-4.45(1H, m), 4.32(2H, brs), 4.50(2H, d, J=3.5Hz), 4.67(2H, s), 6.94(1H, d, J=8.9Hz), 7.02(2H, d, J=8.8Hz), 7.34(1H, dd, J=8.9Hz, 3.3Hz), 7.36(2H, d, J=8.8 Hz), 7.39-7.50(5H, m), 7.54-7.64(2H, m), 7.67(1H, d, J=3.3Hz), 7.70(2H, d, J=8.1Hz). |
| 800 | —CF₃ | —H | piperonyl | 1.80(3H, s), 2.70-3.40(5H, m), 3.05(3H, s), 3.43-3.65(1H, m), 3.90-4.09(1H, m), 4.22(2H, s), 4.29-4.48(1H, m), 4.50(2H, d, J=4.8Hz), 4.67(2H, s), 6 07(2H, s), 6.94(1H, d, J=8.9Hz), 7.00(2H, d, J=7.0Hz), 7.02(2H, d, J=8.8Hz), 7.24(1H, d, J=1.1 Hz), 7.35(1H, dd, J=8.9Hz, 2.3Hz), 7.36(2H, d, J= |

TABLE 209-continued

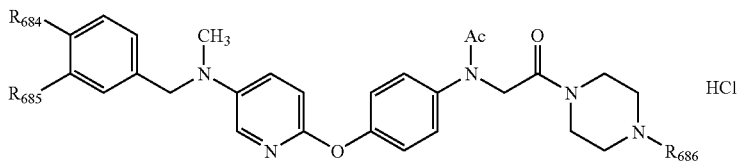

| Example No. | R684 | R685 | R686 | 1H NMR (DMSO-d6) δppm |
|---|---|---|---|---|
| | | | | 8.8Hz), 7.45(2H, d, J=8.1Hz), 7.67(1H, d, J=3.3 Hz), 7.70(2H, d, J=8.1Hz). |

TABLE 210

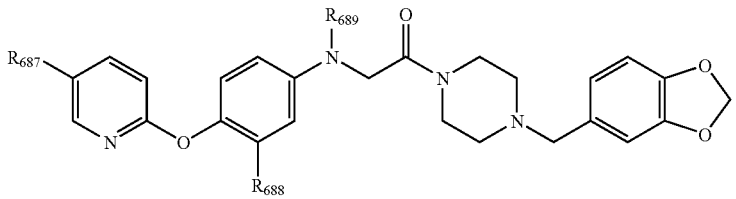

| Example No. | R687 | R688 | R689 | 1H NMR (CDCl3) δppm |
|---|---|---|---|---|
| 801 | 4-CF3PhCO— | —CH3 | —C2H5 | 1.19(3H, t, J=7.1Hz), 2.11(3H, s), 2.42-2.45(4H, m), 3.39-3.53(6H, m), 3.63-3.66(2H, m), 4.04(2H, s), 5.95(2H, s), 6.50-6.54(2H, m), 6.71-6.77(2H, m), 6.85(1H, s), 6.90-6.95(2H, m), 7.75(2H, d, J=8.2Hz), 7.87(2H, d, J=8.1Hz), 8.17(1H, dd, J=8.7Hz, 2.5Hz), 8.59(1H, d, J=2.0Hz). |
| 802 | 3,4-Cl2PhNHCO— | —OCH3 | —C2H5 | 1.19(3H, t, J=7.1Hz), 2.42(4H, brs), 3.42(2H, q, J=7.1Hz), 3.43(2H, s), 3.51(2H, s), 3.62(2H, brs), 3.68(3H, s), 4.04(2H, s), 5.95(2H, s), 6.17(1H, dd, J=8.7Hz, 2.6Hz), 6.28(1H, d, J=2.6Hz), 6.73-6.74(2H, m), 6.85(1H, brs), 6.88(1H, d, J=8.6Hz), 6.90(1H, d, J=8.7Hz), 7.37(1H, d, J=8.7Hz), 7.47(1H, dd, J=8.7Hz, 2.5Hz), 7.86(1H, d, J=2.5Hz), 8.11(1H, dd, J=8.6Hz, 2.5Hz), 8.31(1H, brs), 8.58(1H, d, J=2.3Hz). |
| 803 | 4-CF3PhNHCO— | —OCH3 | —C2H5 | 1.19(3H, t, J=7.1Hz), 2.42(4H, brs), 3.38-3.47(4H, m), 3.51(2H, brs), 3.62(2H, brs), 3.68(3H, s), 4.05(2H, s), 5.94(2H, s), 6.17(1H, dd, J=8.7Hz, 2.8Hz), 6.29(1H, d, J=2.8Hz), 6.73-6.74(2H, m), 6.84(1H, brs), 6.89(1H, d, J=8.7Hz), 6.91(1H, d, J=8.7Hz), 7.58(2H, d, J=8.7Hz), 7.76(2H, d, J=8.7Hz), 8.13(1H, dd, J=8.7Hz, 2.5Hz), 8.44(1H, brs), 8.64(1H, d, J=2.5Hz). |
| 804 | 3,4-Cl2PhNHCONH— | —CONHCH3 | —C2H5 | 1.07(3H, t, J=7.0Hz), 2.30-2.45(4H, m), 2.85(3H, d, J=4.9Hz), 3.33(2H, q, J=7.0Hz), 3.38(2H, s), 3.38-3.50(2H, m), 3.50-3.65(2H, m), 4.01(2H, s), 5.95(2H, s), 6.55-6.65(1H, m), 6.69-6.84(5H, m), 7.14(1H, d, J=3.1Hz), 7.25-7.35(2H, m), 7.35-7.45(1H, m), 7.65(1H, d, J=1.5Hz), 7.72(1H, d, J=2.6Hz), 7.84(1H, dd, J=8.9Hz, 2.7Hz), 8.02(1H, s), 8.61(1H, s). |
| 805 | 4-CF3PhCH2— | —H | —CH3 | 2.42(4H, t, J=5.1Hz), 3.02(1H, s), 3.43(2H, s), 3.48(2H, brs), 3.63(2H, brs), 3.95(2H, s), 4.06(2H, s), 5.94(2H, s), 6.70(2H, d, J=9.0Hz), 6.73(2H, s), 6.74(1H, d, J=10.0Hz), 6.84(1H, s), 7.00(2H, d, J=9.0Hz), 7.27(2H, d, J=8.1Hz), 7.38(1H, dd, J=8.4Hz, 2.5Hz), 7.54(2H, d, J=8.1Hz), 8.03(1H, d, J=2.5Hz). |

TABLE 211

| Example No. | R690 | R691 | R692 | R693 | ¹H NMR (solvent) δppm |
|---|---|---|---|---|---|
| 806 | 4-CF₃PhNHCO— | —CH₃ | —H | piperonyl | (CDCl₃) 2.17(3H, s), 2.49-2.54(4H, m), 3.45(2H, s), 3.71-3.75(2H, m), 4.26(2H, brs), 5.96(2H, s), 6.75(2H, brs), 6.86(1H, brs), 7.02(1H, d, J=8.7Hz), 7.06(1H, d, J=8.7Hz), 7.47(1H, dd, J=8.7Hz, 2.5Hz), 7.58(1H, d, J=2.3Hz), 7.63(2H, d, J=8.4Hz), 7.75(2H, d, J=8.3Hz), 7.84(1H, brs), 8.22(1H, dd, J=8.7 Hz, 2.6Hz), 8.64(1H, d, J=2.5Hz), 9.20(1H, brs). |
| 807 | 4-CF₃PhOCH₂— | —H | —H | piperonyl | (CDCl₃) 2.51-2.54(4H, m), 3.45(2H, s), 3.71-3.75(2H, m), 4.27-4.29(2H, m), 5.05(2H, s), 5.95(2H, s), 6.85(2H, brs), 6.86(1H, brs), 6.96(1H, d, J=8.4Hz), 7.02(2H, d, J=8.6Hz), 7.14(2H, d, J=8.9Hz), 7.56(2H, d, J=8.6Hz), 7.64(2H, d, J=8.9Hz), 7.78(1H, dd, J=8.4Hz, 2.3Hz), 8.22(1H, d, J=2.3Hz), 9.21(1H, brs). |
| 808 | 4-CF₃PhOCH₂— | —H | —H | 4-pyridylmethyl | (CDCl₃) 2.52-2.58(4H, m), 3.55(2H, s), 3.74-3.77(2H, m), 4.29-4.32(2H, m), 5.04(2H, s), 6.96(1H, d, J=8.4 Hz), 7.02(2H, d, J=8.4Hz), 7.15(2H, d, J=8.9Hz), 7.26-7.30(2H, m), 7.56(2H, d, J=8.6 Hz), 7.64(2H, d, J=9.1Hz), 7.78(1H, dd, J=8.6Hz, 2.5Hz), 8.22(1H, d, J=2.0Hz), 8.56-8.58(2H, m), 9.24(1H, brs). |
| 809 | 4-CF₃PhOCH₂— | —CH₃ | —CH₃ | piperonyl | a mixture of the rotational isomers (DMSO-d₆) 2.07-2.43(7H, m), 3.24-3.57(11H, m), 5.17(2H, brs), 5.95-5.99(2H, m), 6.66-6.89(3H, m), 7.07-7.12(2H, m), 7.16-7.37(4H, m), 7.66(2H, d, J=8.4Hz), 7.85-8.00(1H, m), 8.22(1H, d, J=2.0 Hz). |
| 810 | 4-CF₃PhOCH₂— | —CH₃ | —CH₃ | 3,4-(CH₃O)₂PhCH₂— | a mixture of the rotational isomers (DMSO-d₆) 2.07-2.43(7H, m), 3.26-3.75(15H, m), 5.17(2H, brs), 6.70-6.91(3H, m), 7.07-7.12(2H, m), 7.16-7.37(4H, m), 7.66(2H, d, J=8.9 Hz), 7.95-8.00(1H, m), 8.22(1H, d, J=2.0Hz). |

TABLE 212

| Example No. | R694 | ¹H NMR (CDCl₃) δppm |
|---|---|---|
| 811 | piperonyl | 2.18(3H, s), 2.49-2.54(4H, m), 3.45(2H, s), 3.70-3.74(2H, m), 4.23-4.27(2H, m), 5.03(2H, s), 5.95(2H, s), 6.71- |

TABLE 212-continued

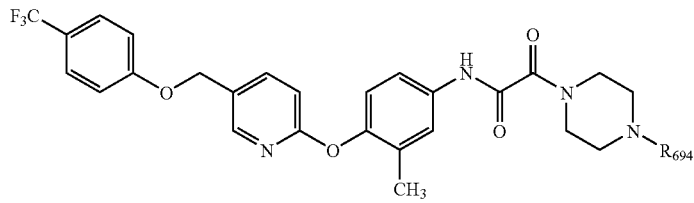

| Example No. | R_694 | $^1$H NMR (CDCl$_3$) δppm |
|---|---|---|
| | | 6.78(2H, m), 6.86(1H, brs), 6.92(1H, d, J=8.6Hz), 7.00-7.06(3H, m), 7.44(1H, dd, J=8.7Hz, 2.6Hz), 7.54-7.58(3H, m), 7.77(1H, dd, J=8.6Hz, 2.5Hz), 8.20(1H, d, J=2.3Hz), 9.20(1H, brs). |
| 812 | 3,4-(CH$_3$O)$_2$PhCH$_2$— | 2.18(3H, s), 2.50-2.55(4H, m), 3.48(2H, s), 3.71-3.75(2H, m), 3.88(3H, s), 3.90(3H, s), 4.24-4.28(2H, m), 5.03(2H, s), 6.79-6.86(2H, m), 6.88(1H, brs), 6.93(1H, d, J=8.4Hz), 7.00-7.06(3H, m), 7.44(1H, dd, J=8.6Hz, 2.6Hz), 7.54-7.58(3H, m), 7.77(1H, dd, J=8.4Hz, 2.5Hz), 8.20(1H, d, J=2.5Hz), 9.19(1H, brs). |
| 813 | 4-pyridylmethyl | 2.18(3H, s), 2.52-2.58(4H, m), 3.55(2H, s), 3.73-3.77(2H, m), 4.27-4.31(2H, m), 5.03(2H, s), 6.93(1H, d, J=8.4Hz), 7.00-7.06(3H, m), 7.28(2H, d, J=5.9Hz), 7.44(1H, dd, J=8.7Hz, 2.6Hz), 7.54-7.57(3H, m), 7.77(1H, dd, J=8.4Hz, 2.3Hz), 8.19(1H, d, J=2.1Hz), 8.56(2H, d, J=5.9Hz), 9.23(1H, brs). |

TABLE 213

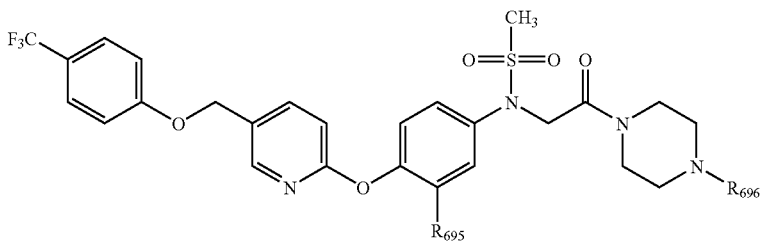

| Example No. | R_695 | R_696 | $^1$H NMR (CDCl$_3$) δppm |
|---|---|---|---|
| 814 | —H | piperonyl | 2.42(4H, brs), 3.21(3H, s), 3.37(2H, brs), 3.42(2H, s), 3.62(2H, brs), 4.54(2H, s), 5.06(2H, s), 5.94(2H, s), 6.70-6.77(2H, m), 6.83(1H, brs), 6.98-7.04(3H, m), 7.14(2H, d, J=8.7Hz), 7.56(2H, d, J=8.7Hz), 7.62(2H, d, J=8.9Hz), 7.81(1H, dd, J=8.4Hz, 2.3Hz), 8.23(1H, d, J=2.1Hz). |
| 815 | —H | 4-pyridylmethyl | 2.48(4H, brs), 3.21(3H, s), 3.41(2H, brs), 3.53(2H, s), 3.65(2H, brs), 4.55(2H, s), 5.06(2H, s), 7.01(1H, d, J=8.2Hz), 7.03(2H, d, J=8.4Hz), 7.14(2H, d, J=8.9Hz), 7.26-7.28(2H, m), 7.57(2H, d, J=8.7Hz), 7.62(2H, d, J=8.7Hz), 7.81(1H, dd, J=8.4Hz, 2.3Hz), 8.23(1H, d, J=2.1Hz), 8.56(2H, d, J=5.6Hz). |
| 816 | —CH$_3$ | piperonyl | 2.18(3H, s), 2.41-2.44(4H, m), 3.22(3H, s), 3.36-3.39(2H, m), 3.43(2H, s), 3.60-3.64(2H, m), 4.54(2H, s), 5.05(2H, s), 5.94(2H, s), 6.73-6.74(2H, m), 6.84(1H, brs), 6.97(1H, d, J=8.4Hz), 7.02(1H, d, J=8.6Hz), 7.04(2H, d, J=8.6Hz), 7.45(1H, dd, J=8.6Hz, 2.6Hz), 7.49(1H, d, J=2.5Hz), 7.56(2H, d, J=8.4Hz), 7.80(1H, dd, J=8.6Hz, 2.5Hz), 8.20(1H, d, J=2.0Hz). |
| 817 | —CH$_3$ | 3,4-(CH$_3$O)$_2$PhCH$_2$— | 2.18(3H, s), 2.44(4H, brs), 3.22(3H, s), 3.38-3.40(2H, m), 3.46(2H, s), 3.63-3.65(2H, m), 3.87(3H, s), 3.89(3H, s), 4.55(2H, s), 5.04(2H, s), 6.81(2H, brs), 6.87(1H, brs), 6.98(1H, d, J=8.6Hz), 7.02(1H, d, J=8.4Hz), 7.04(2H, d, J=8.4Hz), 7.45(1H, dd, J=8.6Hz, 2.6Hz), 7.49(1H, d, J=2.6Hz), 7.56(2H, d, J=8.4Hz), 7.80(1H, dd, J=8.4Hz, 2.5Hz), 8.20(1H, d, J=2.3Hz). |

TABLE 214
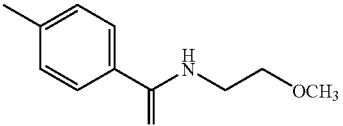
| Example No. | R₆₉₇ | R₆₉₈ | mp (° C.) |
|---|---|---|---|
| 818 | 4-CF₃PhCO— | 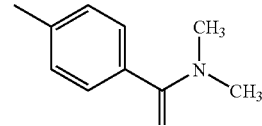 | 207.0-209.0 |
| 819 | 4-CF₃PhCO— | 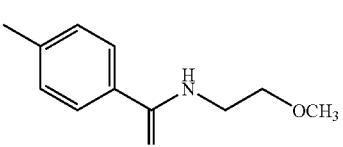 | 237.0-238.0 |
| 820 | 3,4-Cl₂PhSO₂— | 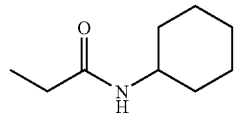 | 115.0-116.0 |
| 821 | 3,4-Cl₂PhNHCO— | —CH₂CONHPh | 147.0-148.0 |
| 822 | 3,4-Cl₂PhNHCO— | 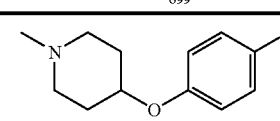 | 207.0-208.0 |
TABLE 215
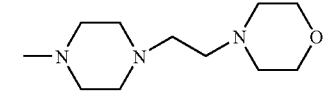
| Example No. | R₆₉₉ | ¹H NMR or MS |
|---|---|---|
| 823 |  | ¹NMR (DMSO-d₆) δ 1.40-1.80(2H, m), 1.80-2.10 (2H, m), 2.93(3H, s), 3.15-3.50(2H, m), 3.60-3.90(2H, m), 4.31(2H, s), 4.60-4.70(1H, m), 6.35-6.45(1H, m), 6.54(1H, dd, J=14.4Hz, 2.6Hz), 6.96-7.11(4H, m), 7.27-7.31(2H, m), 7.52(1H, dd, J=8.7Hz, 2.7Hz), 7.63(1H, dd, J=8.5Hz, 2.1Hz), 7.76(1H, d, J=2.7 Hz), 7.84-7.88(2H, m), 10.39(1H, brs). |
| 824 |  | MS 682(M⁺ + H) |

TABLE 215-continued

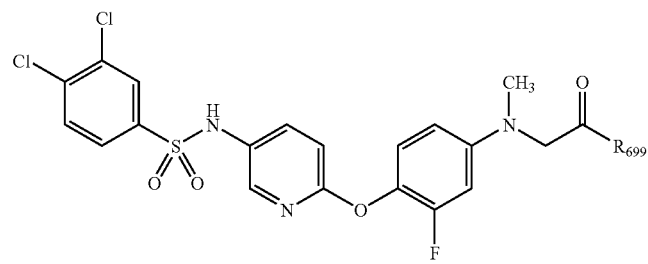

| Example No. | R_699 | ¹H NMR or MS |
|---|---|---|
| 825 | H₃C-N(CH₃)-CH₂CH₂-(2-pyridyl) | MS 618(M⁺ + H) |
| 826 | —N[CH₂CH(CH₃)₂]₂ | MS 611(M⁺ + H) |
| 827 | 3-methylthiazolidine | MS 571(M⁺ + H) |
| 828 | N-methyl-(3,3,5-trimethylcyclohexyl)methylamine | MS 635(M⁺ + H) |
| 829 | —N[(CH₂)₃N(CH₃)₂]₂ | MS 669(M⁺ + H) |
| 830 | 1-methyl-4-(4-pyridyl)piperazine | MS 645(M⁺ + H) |
| 831 | 1-methyl-4-[4-(trifluoromethyl)phenyl]piperazine | MS 712(M⁺ + H) |
| 832 | N-methyl-cyclododecylamine | MS 665(M⁺ + H) |
| 833 | 1,3,5-trimethylpiperidine (3,5-dimethyl-1-methylpiperidine) | MS 595(M⁺ + H) |
| 834 | 2-[(1-methylpiperidin-4-yl)carbonyl]-N-(methylsulfonyl)aniline | MS 764(M⁺ + H) |

TABLE 216

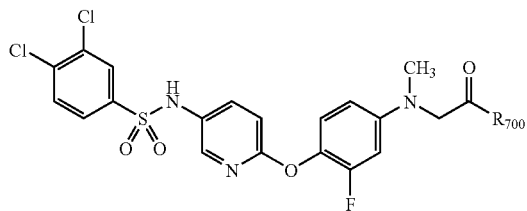

| Example No. | R$_{700}$ | MS (M$^+$ + H) |
|---|---|---|
| 835 | (N-spiro[5.5]undecane) | 635 |
| 836 | —N(CH$_2$CH=CHPh)CH$_2$CH$_2$N(C$_2$H$_5$)$_2$ | 714 |
| 837 | —NH-C(CH$_3$)(cyclopentyl) | 581 |
| 838 | 4-CF$_3$OPhCH$_2$NH— | 673 |
| 839 | —NH-CH$_2$-cyclopropyl | 553 |
| 840 | —NH(CH$_2$)$_5$OH | 585 |
| 841 | —NHCH(CH$_3$)COOCH$_3$ | 585 |
| 842 | 3,5-F$_2$PhCH$_2$N(C$_2$H$_5$)— | 653 |
| 843 | 4-CH$_3$PhNHCOCH$_2$N(CH$_3$)— | 660 |
| 844 | 3,4-(CH$_3$O)$_2$PhCH$_2$N(C$_2$H$_5$)— | 677 |
| 845 | 4-CH$_3$PhCH$_2$N(C$_2$H$_5$)— | 631 |
| 846 | —NH-(5-indolyl) | 614 |
| 847 | 4-phenethyl-1,4-diazepan-1-yl | 686 |
| 848 | 3,4-Cl$_2$Ph— | 714 |
| 849 | 4-(4-chlorophenyl)-4-hydroxypiperidin-1-yl | 695 |
| 850 | 4-benzhydrylpiperazin-1-yl | 734 |

TABLE 216-continued

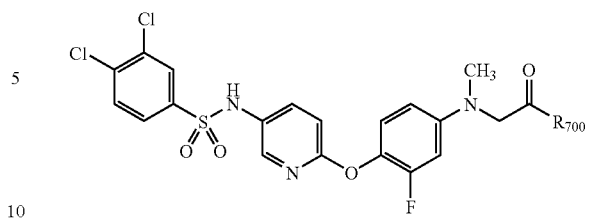

| Example No. | R$_{700}$ | MS (M$^+$ + H) |
|---|---|---|
| 851 | —N(CH$_2$Ph)CH$_2$CH$_2$CN | 642 |
| 852 | —N(C$_2$H$_5$)CH(CH$_3$)$_2$ | 569 |
| 853 | —NHC(CH$_3$)$_2$CH$_2$Ph | 631 |
| 854 | 3-CNPhNH— | 600 |
| 855 | 3,5-F$_2$PhNH— | 611 |

TABLE 217

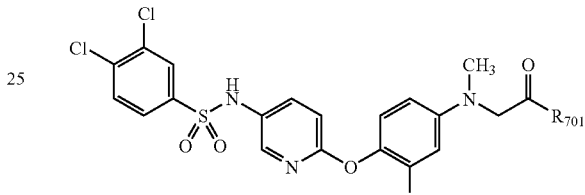

| Example No. | R$_{701}$ | MS (M + H) |
|---|---|---|
| 856 | 4-(benzothiophen-4-yl)piperazin-1-yl | 700 |
| 857 | 4-morpholinopiperidin-1-yl | 652 |
| 858 | 4-hydroxypiperidin-1-yl | 583 |
| 859 | 4-(2-imidazol-1-yl-ethyl)piperazin-1-yl | 662 |
| 860 | 4-(4-methylpiperazin-1-yl)piperidin-1-yl | 665 |
| 861 | 4-(pyridin-4-yl)-1,4-diazepan-1-yl | 659 |
| 862 | 4-(2-pyridin-4-yl-ethyl)piperazin-1-yl | 673 |

TABLE 217-continued

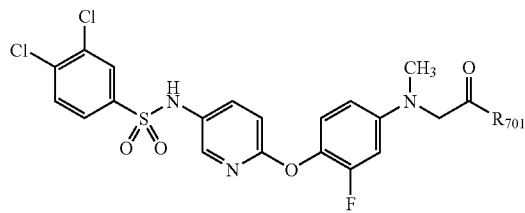

| Example No. | R₇₀₁ | MS (M + H) |
|---|---|---|
| 863 | (N-methylpiperazinyl-CH2-C(O)-NH-2-pyridyl) | 702 |
| 864 | (8-methylamino-5-methoxy-3,4-dihydroquinolin-2(1H)-one) | 674 |
| 865 | (6-methylamino-5-methoxy-3,4-dihydroquinolin-2(1H)-one) | 674 |
| 866 | (2-chloro-3-methylamino-5-acetamidophenyl) | 666 |

TABLE 218

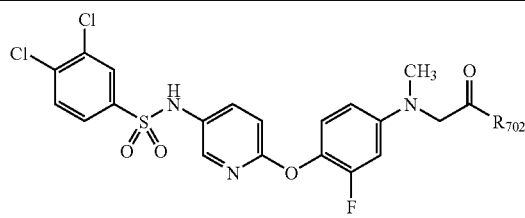

| Example No. | R₇₀₂ | MS (M⁺ + H) |
|---|---|---|
| 867 | (1-methylpyrrolidin-3-yl)-3,4-dihydroquinolin-2(1H)-one | 698 |
| 868 | CH₃NH-CH2CH2CH2-N(4-methylpiperazinyl) | 639 |

TABLE 218-continued

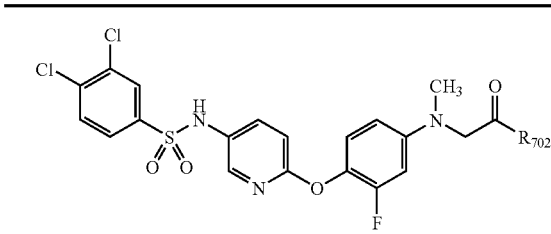

| Example No. | R₇₀₂ | MS (M⁺ + H) |
|---|---|---|
| 869 | 1-methylpiperidin-4-yl-COOC₂H₅ | 639 |
| 870 | 1-methyl-4-benzyl-4-hydroxypiperidine | 673 |
| 871 | 1-methyl-3-acetamidopyrrolidine | 610 |
| 872 | CH₃NH-CH2CH2-pyrrolidin-1-yl | 596 |
| 873 | CH₃NH-CH2-C(=NH)-NH2 | 555 |
| 874 | CH₃NH-C(=NH)-N(CH₃)2 | 569 |
| 875 | 2-methylamino-9H-fluorene | 663 |
| 876 | 9-ethyl-3-methylamino-carbazole | 692 |

TABLE 219

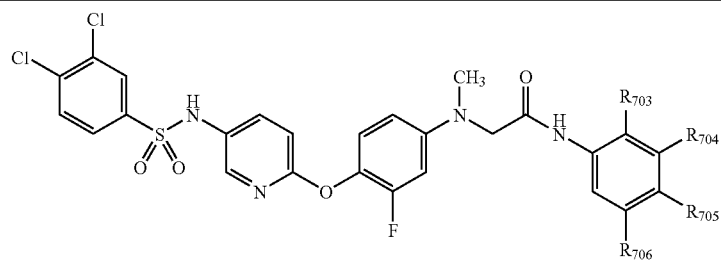

| Example No. | $R_{703}$ | $R_{704}$ | $R_{705}$ | $R_{706}$ | MS ($M^+ + H$) |
|---|---|---|---|---|---|
| 877 | —H | —H | —OCF$_3$ | —H | 659 |
| 878 | —H | —H | —CH$_3$ | —H | 589 |
| 879 | —OCH$_3$ | —OCH$_3$ | —H | —H | 635 |
| 880 | —H | —H | —SCH$_3$ | —H | 621 |
| 881 | —CH(CH$_3$)$_2$ | —H | —H | —H | 617 |
| 882 | —H | —H | cyclohexyl | —H | 657 |
| 883 | —NHPh | —H | —Cl | —H | 702 |
| 884 | 4-ClPhNH— | —H | —H | —COOC$_2$H$_5$ | 774 |
| 885 | —H | —H | —O(CH$_2$)$_2$N(C$_2$H$_5$)$_2$ | —H | 690 |
| 886 | —H | —H | 1,4-dimethylpiperazinyl | —H | 673 |
| 887 | —H | —H | 1-methyl-2-oxopyrrolidinyl | —H | 658 |
| 888 | —H | —H | —NHSO$_2$CH$_3$ | —H | 668 |
| 889 | —H | —H | —(CH$_2$)$_2$OH | —H | 619 |
| 890 | —H | —H | —(CH$_2$)$_4$CH$_3$ | —H | 645 |
| 891 | —H | —H | benzyl | —H | 665 |
| 892 | —H | —H | —SPh | —H | 683 |
| 893 | —H | —H | adamantyl | —H | 709 |

TABLE 220

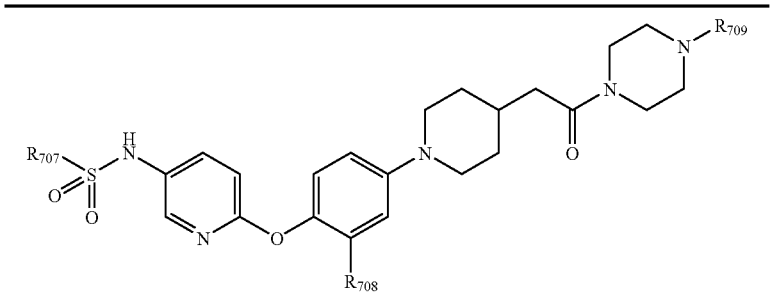

| Example No. | $R_{707}$ | $R_{708}$ | $R_{709}$ | $^1$H NMR (CDCl$_3$) δppm |
|---|---|---|---|---|
| 894 | 4-CF$_3$Ph— | —CH$_3$ | piperonyl | 1.34-1.42(2H, m), 1.80-1.98(3H, m), 2.03(3H, s), 2.29(2H, d, J=6.6Hz), 2.41(4H, brs), 2.65(2H, t, J=12.0Hz), 3.43(2H, s), 3.49- |

TABLE 220-continued

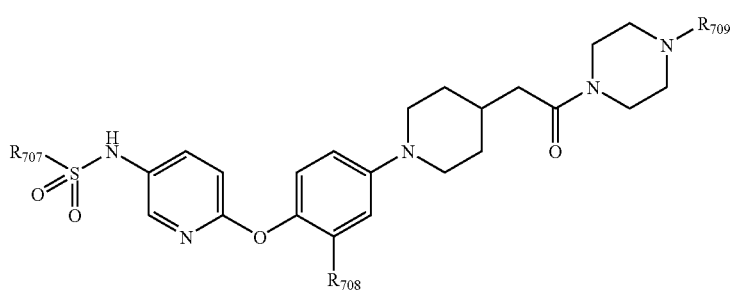

| Example No. | $R_{707}$ | $R_{708}$ | $R_{709}$ | $^1$H NMR (CDCl$_3$) δppm |
|---|---|---|---|---|
| | | | | 3.65(6H, m), 5.94(2H, s), 6.69-6.87(8H, m), 7.56(1H, dd, J=8.9Hz, 2.8Hz), 7.68(2H, d, J=8.6Hz), 7.76-7.85(3H, m). |
| 895 | 3,4-Cl$_2$Ph— | —CH$_3$ | piperonyl | 1.34-1.39(2H, m), 1.79-1.98(3H, m), 2.04(3H, s), 2.29(2H, d, J=6.6Hz), 2.41(4H, brs), 2.64(2H, t, J=11.9Hz), 3.43(2H, s), 3.49-3.65(6H, m), 5.94(2H, s), 6.70-6.88(7H, m), 7.45-7.50(3H, m), 7.55(1H, dd, J=8.9Hz, 2.8Hz), 7.78-7.82(2H, m). |
| 896 | 4-CF$_3$Ph— | —CH$_3$ | benzyl | 1.34-1.43(2H, m), 1.80-2.01(3H, m), 2.03(3H, s), 2.29(2H, d, J=6.6Hz), 2.43(4H, brs), 2.65(2H, t, J=12.0Hz), 3.49-3.65(8H, m), 6.70-6.76(3H, m), 6.86(1H, d, J=8.7Hz), 7.26-7.32(6H, m), 7.55(1H, dd, J=8.7Hz, 2.6Hz), 7.68(2H, d, J=8.6Hz), 7.76(1H, d, J=2.8Hz), 7.84(2H, d, J=8.4Hz). |
| 897 | 3,4-Cl$_2$Ph— | —CH$_3$ | benzyl | 1.27-1.39(2H, m), 1.79-2.01(3H, m), 2.04(3H, s), 2.29(2H, d, J=6.8Hz), 2.43(4H, brs), 2.64(2H, t, J=11.9Hz), 3.53-3.66(8H, m), 6.69-6.76(3H, m), 6.86(1H, d, J=8.7Hz), 7.29-7.32(6H, m), 7.44-7.50(2H, m), 7.55(1H, dd, J=8.7Hz, 2.6Hz), 7.79-7.82(2H, m). |
| 898 | 4-CF$_3$Ph— | —H | 3,4-Cl$_2$Ph— | 1.34-1.46(2H, m), 1.83-2.02(3H, m), 2.34(2H, d, J=6.8Hz), 2.67(2H, t, J=12.0Hz), 3.15-3.17(4H, m), 3.55-3.65(4H, m), 3.78-3.80(2H, m), 6.72-6.97(7H, m), 7.26-7.31(2H, m), 7.56(1H, dd, J=8.9Hz, 2.8Hz), 7.70(2H, d, J=8.24Hz), 7.78-7.86(3H, m). |
| 899 | 4-CF$_3$Ph— | —H | 4-CF$_3$Ph— | 1.35-1.47(2H, m), 1.83-2.02(3H, m), 2.36(2H, d, J=6.8Hz), 2.67(2H, t, J=12.0Hz), 3.28-3.30(4H, m), 3.57(2H, d, J=12.2Hz), 3.68(2H, brs), 3.82(2H, brs), 6.76(1H, d, J=8.7Hz), 6.87-6.96(7H, m), 7.50(2H, d, J=8.6Hz), 7.56(1H, dd, J=8.9Hz, 2.8Hz), 7.69(2H, d, J=8.4Hz), 7.80-7.86(3H, m). |
| 900 | 3,4-Cl$_2$Ph— | —H | 4-CF$_3$Ph— | 1.34-1.47(2H, m), 1.83-2.02(3H, m), 2.35(2H, d, J=6.8Hz), 2.68(2H, t, J=12.0Hz), 3.29-3.31(4H, m), 3.58(2H, d, J=12.2Hz), 3.68(2H, brs), 3.83(2H, brs), 6.79(1H, d, J=8.7Hz), 6.88-6.98(7H, m), 7.50-7.59(5H, m), 7.79(1H, d, J=2.8Hz), 7.83-7.84(1H, m). |

TABLE 221

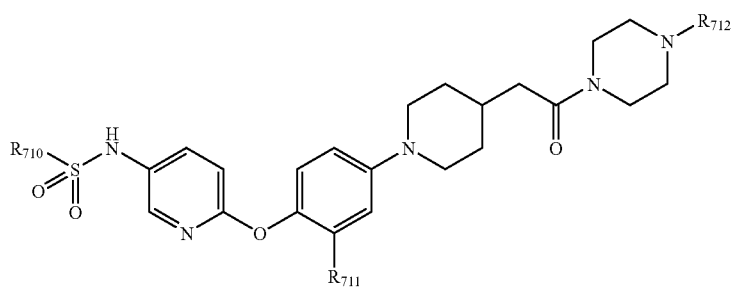

| Example No. | $R_{710}$ | $R_{711}$ | $R_{712}$ | $^1$H NMR (CDCl$_3$) δppm |
|---|---|---|---|---|
| 901 | 3,4-Cl$_2$Ph— | —H | 3,4-Cl$_2$Ph— | 1.34-1.46(2H, m), 1.82-2.02(3H, m), 2.35(2H, d, J=6.6Hz), 2.66(2H, t, J=12.0Hz), 3.16-3.17(4H, m), 3.57(2H, d, J=12.2Hz), 3.65(2H, brs), 3.80(2H, brs), 6.72-6.78(2H, m), 6.87-6.97(6H, m), 7.29(1H, d, J=8.9Hz), 7.49(2H, s), 7.57(1H, dd, J=8.7Hz, 2.6Hz), 7.81-7.84(2H, m). |
| 902 | 4-CF$_3$Ph— | —CH$_3$ | 3,4-Cl$_2$Ph— | 1.34-1.46(2H, m), 1.82-2.01(3H, m), 2.03(3H, s), 2.35(2H, d, J=6.8Hz), 2.67(2H, t, J=12.0 Hz), 3.15-3.17(4H, m), 3.58(2H, d, J=12.2Hz), 3.65(2H, brs), 3.79(2H, brs), 6.70-6.76(4H, m), 6.86(1H, d, J=8.6Hz), 6.96(1H, d, J=2.8Hz), 7.29(1H, d, J=8.7Hz), 7.53-7.57(1H, m), 7.68(2H, d, J=8.2Hz), 7.77(1H, d, J=2.5Hz), 7.84(2H, d, J=8.2Hz), 8.05(1H, s). |
| 903 | 4-CF$_3$Ph— | —H | piperonyl | 1.27-1.41(2H, m), 1.83-2.05(3H, m), 2.29(2H, d, J=6.8Hz), 2.40-2.44(4H, m), 2.66-2.75(2H, m), 3.44-3.56(4H, m), 3.65-3.74(4H, m), 5.95(2H, s), 6.75-6.99(8H, m), 7.57(1H, dd, J=8.9Hz, 2.8Hz), 7.71-7.74(4H, m), 7.85(2H, d, J=8.2Hz). |
| 904 | 3,4-Cl$_2$Ph— | — | benzyl | 1.31-1.40(2H, m), 1.80-2.05(3H, m), 2.29(2H, d, J=6.8Hz), 2.62-2.71(2H, m), 3.53-3.58(6H, m), 3.66(2H, brs), 6.79(1H, d, J=8.7Hz), 6.88-6.98(4H, m), 7.31(5H, brs), 7.50(2H, s), 7.56 (1H, dd, J=8.9Hz, 2.8Hz), 7.77-7.84(3H, m). |
| 905 | 4-CF$_3$Ph— | —H | benzyl | 1.30-1.43(2H, m), 1.80-2.04(3H, m), 2.28(2H, d, J=6.8Hz), 2.42-2.46(4H, m), 2.62-2.70(2H, m), 3.47-3.58(6H, m), 3.66(2H, brs), 6.78(1H, d, J=8.7Hz), 6.87-6.97(4H, m), 7.26-7.32(6H, m), 7.56(1H, dd, J=8.9Hz, 2.8Hz), 7.68-7.77(3H, m), 7.83-7.86(2H, m). |
| 906 | 3,4-Cl$_2$Ph— | —H | piperonyl | 1.33-1.39(2H, m), 1.79-2.00(3H, m), 2.30(2H, d, J=6.8Hz), 2.42-2.44(4H, m), 2.65(2H, t, J=10.4Hz), 3.43(2H, s), 3.49-3.57(4H, m), 3.65(2H, brs), 5.94(2H, s), 6.74-6.77(3H, m), 6.84-6.97(5H, m), 7.49-7.59(3H, m), 7.81-7.85(3H, m). |
| 907 | 4-CF$_3$Ph— | —OCH$_3$ | piperonyl | 1.33-1.44(2H, m), 1.82-1.95(3H, m), 2.29(2H, d, J=6.8Hz), 2.41(4H, brs), 2.70(2H, t, J=12.2 Hz), 3.43-3.64(8H, m), 3.67(3H, s), 5.94(2H, s), 6.46(1H, dd, J=8.7Hz, 2.6Hz), 6.54(1H, d, J=2.5Hz), 6.70-6.78(4H, m), 6.85(1H, s), 6.92(1H, d, J=8.6Hz), 7.55(1H, dd, J=8.7 Hz, 2.6Hz), 7.67(2H, d, J=8.4Hz), 7.74(1H, d, J=2.6Hz), 7.84(2H, d, J=8.2Hz). |

TABLE 222

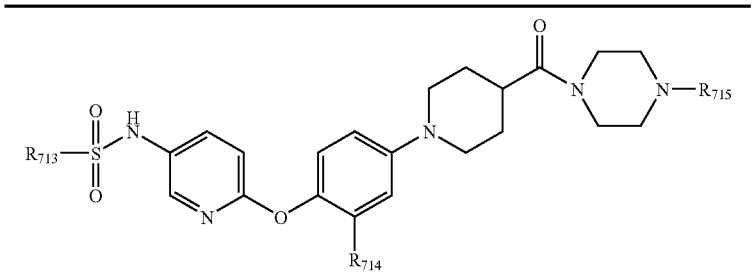

| Example No. | $R_{713}$ | $R_{714}$ | $R_{715}$ | $^1$H NMR (CDCl$_3$) δppm |
|---|---|---|---|---|
| 908 | 3,4-Cl$_2$Ph— | —H | benzyl | 1.76-1.99(4H, m), 2.45-2.73(7H, m), 3.53(4H, brs), 3.66(4H, brs), 6.75(1H, d, J=8.7Hz), 6.87-6.97(4H, m), 7.29-7.59(9H, m), 7.83(2H, d, J=2.0Hz). |
| 909 | 4-CF$_3$Ph— | —H | benzyl | 1.77-1.99(4H, m), 2.45(4H, brs), 2.53-2.76(3H, m), 3.54(4H, brs), 3.65-3.69(4H, m), 6.81(1H, d, J=8.7Hz), 6.90-6.99(4H, m), 7.28-7.34(6H, m), 7.57(1H, dd, J=8.9Hz, 2.8Hz), 7.71-7.75(3H, m), 7.85(2H, d, J=8.2Hz). |
| 910 | 4-CF$_3$Ph— | —CH$_3$ | piperonyl | 1.75-1.96(4H, m), 2.04(3H, s), 2.44(4H, brs), 2.53-2.73(3H, m), 3.43(2H, s), 3.53(2H, brs), 3.63(4H, brs), 5.94(2H, s), 6.70-6.89(8H, m), 7.56(1H, dd, J=8.9Hz, 2.8Hz), 7.67(2H, d, J=8.6Hz), 7.78(1H, d, J=2.6Hz), 7.84(2H, d, J=8.2Hz). |
| 911 | 4-CF$_3$Ph— | —CH$_3$ | benzyl | 1.75-2.02(4H, m), 2.03(3H, s), 2.45(4H, brs), 2.55-2.72(3H, m), 3.53(4H, brs), 3.66(4H, brs), 6.72-6.77(3H, m), 6.87(1H, d, J=8.6Hz), 7.25-7.31(6H, m), 7.56(1H, dd, J=8.7Hz, 2.6Hz), 7.66(2H, d, J=8.2Hz), 7.78-7.86(3H, m). |
| 912 | 3,4-Cl$_2$Ph— | —CH$_3$ | piperonyl | 1.76-1.98(4H, m), 2.04(3H, s), 2.44(4H, brs), 2.54-2.72(3H, m), 3.43(2H, s), 3.54(2H, brs), 3.63-3.67(4H, m), 5.94(2H, s), 6.70-6.89(8H, m), 7.44-7.59(3H, m), 7.80(2H, d, J=2.0Hz). |
| 913 | 3,4-Cl$_2$Ph— | —CH$_3$ | benzyl | 1.77-1.97(4H, m), 2.07(3H, s), 2.45(4H, brs), 2.53-2.75(3H, m), 3.54(4H, brs), 3.66(4H, brs), 6.75-6.81(3H, m), 6.90(1H, d, J=8.6Hz), 7.26-7.33(6H, m), 7.51-7.58(3H, m), 7.72(1H, d, J=2.6Hz), 7.79(1H, s). |
| 914 | 3,4-Cl$_2$Ph— | —H | piperonyl | 1.76-1.99(4H, m), 2.44(4H, brs), 2.54-2.74(3H, m), 3.43(2H, s), 3.54(2H, brs), 3.63-3.67(4H, m), 5.94(2H, s), 6.74-6.98(8H, m), 7.45-7.59(3H, m), 7.81-7.84(3H, m). |
| 915 | 4-CF$_3$Ph— | —H | piperonyl | 1.76-1.80(2H, m), 1.91-1.95(2H, m), 2.43(4H, brs), 2.59-2.73(3H, m), 3.43(2H, s), 3.54(2H, brs), 3.62(4H, brs), 5.94(2H, s), 6.72-6.75(3H, m), 6.84-6.96(5H, m), 7.57(1H, dd, J=8.7Hz, 2.8Hz), 7.66(2H, d, J=8.4Hz), 7.82-7.87(4H, m). |

TABLE 223

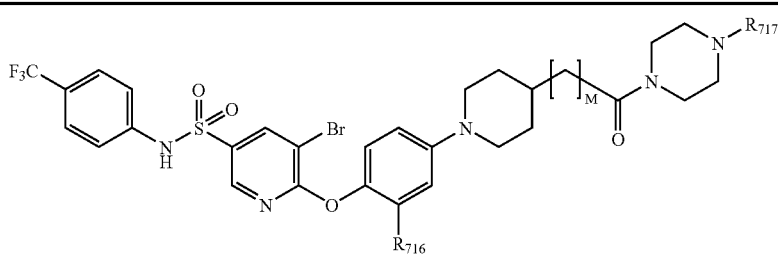

| Example No. | $R_{716}$ | $R_{717}$ | M | $^1$H NMR (CDCl$_3$) βppm |
|---|---|---|---|---|
| 916 | —H | piperonyl | 1 | 1.31-1.45(2H, m), 1.82-2.02(3H, m), 2.33(2H, d, J=6.8Hz), 2.43(4H, brs), 2.69(2H, t, J=12.0Hz), 3.43(2H, s), 3.51-3.67(6H, m), 5.93(2H, s), 6.73-6.99(8H, m), 7.28(2H, d, J=8.6Hz), 7.50(2H, d, J= |

TABLE 223-continued

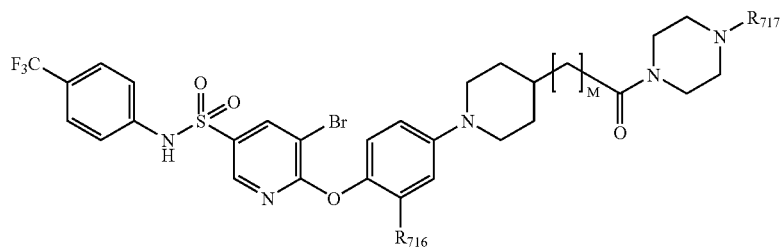

| Example No. | R716 | R717 | M | ¹H NMR (CDCl₃) βppm |
|---|---|---|---|---|
|  |  |  |  | 8.6Hz), 8.28(1H, d, J=2.1Hz), 8.43(1H, d, J=2.1 Hz). |
| 917 | —H | benzyl | 1 | 1.34-1.44(2H, m), 1.82-2.00(3H, m), 2.32(2H, d, J=6.8Hz), 2.43-2.47(4H, m), 2.69(2H, t, J=12.0Hz), 3.51-3.67(8H, m), 6.88(2H, d, J=9.2Hz), 6.98(2H, d, J=9.2Hz), 7.25-7.32(8H, m), 7.50(2H, d, J=8.6 Hz), 8.28(1H, d, J=2.3Hz), 8.43(1H, d, J=2.1Hz). |
| 918 | —CH₃ | piperonyl | 1 | 1.31-1.45(2H, m), 1.82-2.00(3H, m), 2.02(3H, s), 2.33(2H, d, J=6.8Hz), 2.43(4H, brs), 2.68(2H, t, J=11.9Hz), 3.41-3.67(8H, m), 5.92(2H, s), 6.73-6.92(7H, m), 7.25-7.30(2H, m), 7.50(2H, d, J=8.6 Hz), 8.30(1H, d, J=2.3Hz), 8.41(1H, d, J=2.3Hz). |
| 919 | —CH₃ | benzyl | 1 | 1.37-1.40(2H, m), 1.83-2.01(3H, m), 2.03(3H, s), 2.31(2H, d, J=6.9Hz), 2.43-2.47(4H, m), 2.70(2H, t, J=12.0Hz), 3.51-3.67(8H, m), 6.74-6.80(2H, m), 6.91(1H, d, J=8.6Hz), 7.24-7.33(8H, m), 7.52(2H, d, J=8.4Hz), 8.29(1H, d, J=2.1Hz), 8.42(1H, d, J=2.3Hz). |
| 920 | —H | piperonyl | 0 | 1.79-2.03(4H, m), 2.45(4H, brs), 2.57-2.76(3H, m), 3.44(2H, s), 3.55(2H, brs), 3.66(4H, brs), 5.94(2H, s), 6.72-6.78(2H, m), 6.85-7.00(6H, m), 7.28(2H, d, J=8.6Hz), 7.50(2H, d, J=8.6Hz), 8.28(1H, d, J=2.1 Hz), 8.42(1H, d, J=2.1Hz). |

TABLE 224

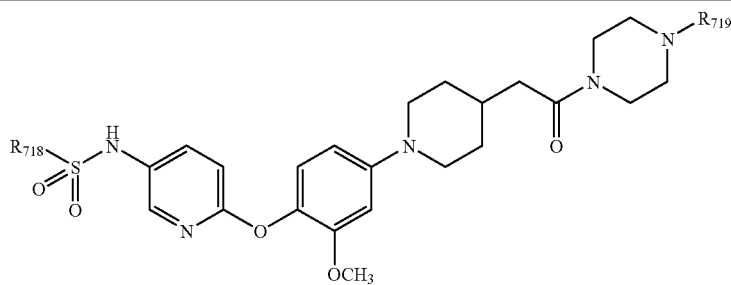

| Example No. | R718 | R719 | ¹H NMR (CDCl₃) δppm |
|---|---|---|---|
| 921 | 3,4-Cl₂Ph— | piperonyl | 1.37-1.44(2H, m), 1.81-2.02(3H, m), 2.30(2H, d, J=6.8 Hz), 2.42(4H, brs), 2.69(2H, t, J=11.9Hz), 3.43(2H, s), 3.43-3.65(6H, m), 3.68(3H, s), 5.94(2H, s), 6.46(1H, dd, J=8.7Hz, 2.5Hz), 6.54(1H, d, J=2.3Hz), 6.73-6.76(3H, m), 6.85(1H, s), 6.93(1H, d, J=8.6Hz), 7.44-7.57(3H, m), 7.79-7.83(3H, m). |
| 922 | 4-CF₃Ph— | benzyl | 1.37-1.44(2H, m), 1.81-2.02(3H, m), 2.29(2H, d, J=6.8 Hz), 2.42-2.46(4H, m), 2.69(2H, t, J=12.0Hz), 3.48-3.63(8H, m), 3.67(3H, s), 6.46(1H, dd, J=8.7Hz, 2.6 Hz), 6.54(1H, d, J=2.6Hz), 6.75(1H, d, J=8.9Hz), 6.92(1H, d, J=8.7Hz), 7.26-7.36(6H, m), 7.54(1H, dd, J=8.7Hz, 2.8Hz), 7.67(2H, d, J=8.6Hz), 7.75(1H, d, J=2.8Hz), 7.83(2H, d, J=8.1Hz). |
| 923 | 3,4-Cl₂Ph— | benzyl | 1.37-1.44(2H, m), 1.81-2.02(3H, m), 2.30(2H, d, J=6.8 Hz), 2.42-2.46(4H, m), 2.69(2H, t, J=11.9Hz), 3.50 3.66(8H, m), 3.67(3H, s), 6.45(1H, dd, J=8.7Hz, 2.5 Hz), 6.54(1H, d, J=2.5Hz), 6.74(1H, d, J=8.7Hz), 6.93(1H, d, J=8.6Hz), 7.26-7.32(5H, m), 7.43-7.56(3H, m), 7.79-7.83(3H, m). |

TABLE 225

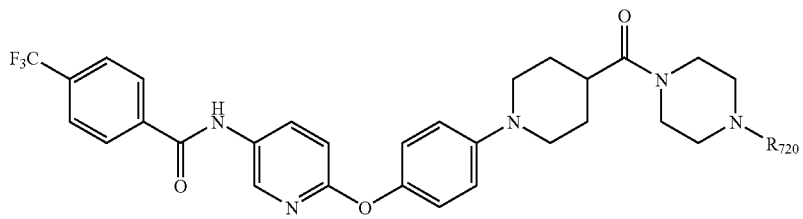

| Example No. | R<sub>720</sub> | $^1$H NMR (CDCl$_3$) δppm |
|---|---|---|
| 924 | benzyl | 1.63-1.77(2H, m), 1.81-1.98(2H, m), 2.44(4H, brs), 2.53-2.72(3H, m), 3.53(4H, brs), 3.65-3.69(4H, m), 6.90-7.04(5H, m), 7.26-7.33(5H, m), 7.74(2H, d, J=8.2Hz), 7.99(2H, d, J=8.2Hz), 8.14-8.19(2H, m), 8.27(1H, d, J=2.6Hz). |
| 925 | piperonyl | 1.64-1.77(2H, m), 1.89-1.97(2H, m), 2.39-2.41(4H, m), 2.56-2.75(3H, m), 3.43(2H, s), 3.52-3.69(6H, m), 5.94(2H, s), 6.70-6.77(2H, m), 6.85-7.04(6H, m), 7.74(2H, d, J=8.2Hz), 7.99(2H, d, J=8.2Hz), 8.14-8.18(2H, m), 8.27(1H, d, J=2.5Hz). |

The following compounds were made in the same manner as in Reference Example 918.

TABLE 226

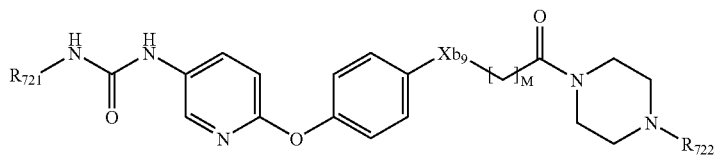

| Example No. | R<sub>721</sub> | Xb<sub>9</sub> | R<sub>722</sub> | M | $^1$H NMR (CDCl$_3$) δppm |
|---|---|---|---|---|---|
| 926 | 4-CF$_3$Ph— | —CH$_2$— | benzyl | 1 | 2.38-2.44(4H, m), 2.63-2.68(2H, m), 2.89-2.95(2H, m), 3.45-3.49(2H, m), 3.52(2H, s), 3.64-3.68(2H, m), 6.85(1H, d, J=8.9 Hz), 6.93-6.98(2H, m), 7.08-7.13(2H, m), 7.28-7.36(5H, m), 7.44-7.51(4H, m), 7.96 (1H, d, J=2.5Hz), 8.00-8.04(1H, m), 8.14(1H, s), 8.18(1H, s). |
| 927 | 3,4-Cl$_2$Ph— | —CH(CH$_3$)— | piperonyl | 0 | 1.47(3H, d, J=6.8Hz), 2.00-2.15(1H, m), 2.25-2.50(3H, m), 3.36(2H, s), 3.36-3.80(4H, m), 3.98(1H, q, J=6.8Hz), 5.93(2H, s), 6.65-6.75(2H, m), 6.79(1H, d, J=1.2Hz), 6.89(1H, d, J=8.8Hz), 7.02-7.06(2H, m), 7.16-7.33(4H, m), 7.57(1H, d, J=2.4Hz), 7.91(1H, d, J=2.7Hz), 8.00(1H, brs), 8.05-8.10(2H, m). |
| 928 | 3,4-Cl$_2$Ph— | —C(CH$_3$)$_2$— | piperonyl | 0 | 1.55(6H, s), 1.80-2.15(2H, m), 2.20-2.55(2H, m), 2.95-3.20(2H, m), 3.31(2H, s), 3.50-3.90(2H, m), 5.91(2H, s), 6.60-6.72(2H, m), 6.76(1H, d, J=1.3Hz), 6.90(1H, d, J=8.9Hz), 7.07-7.33(6H, m), 7.58(1H, d, J=2.4Hz), 7.88(1H, d, J=2.7Hz), 8.09-8.11(2H, m), 8.17(1H, dd, J=8.9Hz, 2.8Hz). |

TABLE 227

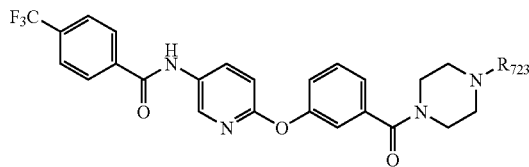

| Example No. | R<sub>723</sub> | $^1$H NMR (CDCl$_3$) δppm |
|---|---|---|
| 929 | benzyl | 2.33-2.55(4H, m), 3.36-3.79(6H, m), 6.89(1H, d, J=8.7Hz), 7.07-7.15(3H, m), 7.24-7.38(6H, m), 7.67-7.70(2H, m), 8.00(2H, d, J=7.9Hz), 8.09-8.13(1H, m), 8.32(1H, d, J=2.3Hz), 9.05(1H, brs). |

TABLE 227-continued

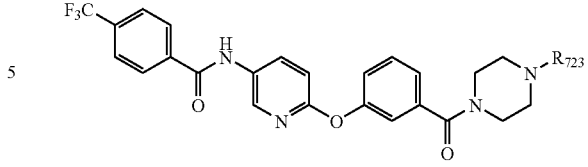

| Example No. | R<sub>723</sub> | $^1$H NMR (CDCl$_3$) δppm |
|---|---|---|
| 930 | piperonyl | 2.36-2.44(4H, m), 3.37-3.76(6H, m), 5.93(2H, s), 6.69-6.75(2H, m), 6.83(1H, brs), 6.86(1H, d, J=8.7Hz), 7.04-7.06(2H, m), 7.10-7.14(1H, m), 7.27-7.36(1H, m), 7.65(2H, d, J=8.4Hz), 7.99 (2H, d, J=8.1Hz), 8.07-8.12(1H, m), 8.34(1H, d, J=2.6Hz), 9.41(1H, s). |

TABLE 228

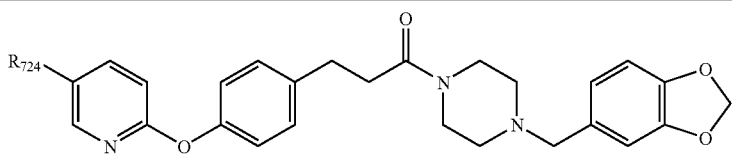

| Example No. | R<sub>724</sub> | $^1$H NMR (CDCl$_3$) δppm |
|---|---|---|
| 931 | 4-CF$_3$PhCH$_2$N(SO$_2$CH$_3$)— | 2.31-2.41(4H, m), 2.58-2.64(2H, m), 2.94-2.97(2H, m), 2.99(3H, s), 3.38-3.41(4H, m), 3.60-3.65(2H, m), 4.85(2H, s), 5.94(2H, s), 6.65-6.75(2H, m), 6.83-6.87(2H, m), 6.95-7.05(2H, m), 7.20-7.30(2H, m), 7.38-7.41(2H, m), 7.52(1H, dd, J=8.8Hz, 2.8Hz), 7.54-7.57(2H, m), 8.04(1H, d, J=2.3Hz). |
| 932 | 3,4-Cl$_2$PhCH$_2$N(SO$_2$CH$_3$)— | 2.25-2.45(4H, m), 2.59-2.65(2H, m), 2.94-3.05(5H, m), 3.30-3.45(4H, m), 3.55-3.70(2H, m), 4.74(2H, s), 5.95(2H, s), 6.65-6.80(2H, m), 6.84-6.89(2H, m), 7.02-7.15(3H, m), 7.23-7.30(3H, m), 7.30-7.40(2H, m), 8.03(1H, d, J=2.7Hz). |
| 933 | 3,4-Cl$_2$PhCH$_2$NHCO— | 2.25-2.45(4H, m), 2.59-2.65(2H, m), 2.94-3.00(2H, m), 3.37-3.41(4H, m), 3.59-3.65(2H, m), 4.58(2H, d, J=5.9 Hz), 5.94(2H, s), 6.50-6.65(1H, m), 6.65-6.80(2H, m), 6.84(1H, s), 6.94(1H, d, J=8.6Hz), 7.03-7.06(2H, m), 7.17(1H, dd, J=8.2Hz, 2.0Hz), 7.22-7.26(2H, m), 7.38-7.42(2H, m), 8.14(1H, dd, J=8.6Hz, 2.5Hz), 8.57(1H, d, J=2.3Hz). |
| 934 | 3,4-Cl$_2$PhNHCON(C$_2$H$_5$)— | 1.17(3H, t, J=7.1Hz), 2.32-2.42(4H, m), 2.61-2.67(2H, m), 2.97-3.03(2H, m), 3.39-3.43(4H, m), 3.61-3.65(2H, m), 3.74(2H, q, J=7.1Hz), 5.94(2H, s), 6.00(1H, brs), 6.70-6.85(3H, m), 7.05(1H, d, J=8.7 Hz), 7.09-7.13(3H, m), 7.26-7.31(3H, m), 7.52(1H, d, J=2.5Hz), 7.61(1H, dd, J=8.7Hz, 2.8Hz), 8.12(1H, d, J=2.4Hz). |
| 935 | 3,4-Cl$_2$PhN(CH$_3$)— | 2.25-2.45(4H, m), 2.59-2.65(2H, m), 2.95-3.00(2H, m), 3.25(3H, s), 3.38-3.42(4H, m), 3.61-3.65(2H, m), 5.94(2H, s), 6.55-6.65(1H, m), 6.65-6.80(2H, m), 6.80-6.85(2H, m), 6.89-6.93(1H, m), 7.06-7.10(2H, m), 7.20-7.27(3H, m), 7.45-7.50(1H, m), 8.01(1H, d, J=2.4Hz). |
| 936 | 3,4-Cl$_2$PhNH— | 2.31-2.41(4H, m), 2.59-2.65(2H, m), 2.94-3.00(2H, m), 3.37-3.41(4H, m), 3.61-3.65(2H, m), 5.61(1H, brs), 5.94(2H, s), 6.69-6.80(3H, m), 6.84(1H, s), 6.90(1H, d, J=8.7Hz), 6.96(1H, d, J=2.7Hz), 7.04-7.07(2H, m), 7.21-7.25(3H, m), 7.49(1H, dd, J=8.7Hz, 2.9Hz), 8.00(1H, d, J=2.8Hz). |
| 937 | 4-CF$_3$PhCH$_2$NHCO— | 2.31-2.40(4H, m), 2.59-2.65(2H, m), 2.95-3.01(2H, m), 3.38-3.41(4H, m), 3.60-3.64(2H, m), 4.70(2H, d, J=5.8 Hz), 5.94(2H, s), 6.35-6.50(1H, m), 6.70-6.77(2H, m), 6.84(1H, s), 6.95(1H, d, J=8.6Hz), 7.03-7.07(2H, m), 7.23-7.26(2H, m), 7.44-7.47(2H, m), 7.59-7.62(2H, m), 8.14(1H, dd, J=8.6Hz, 2.5Hz), 8.57(1H, d, J=2.4 Hz). |

TABLE 228-continued

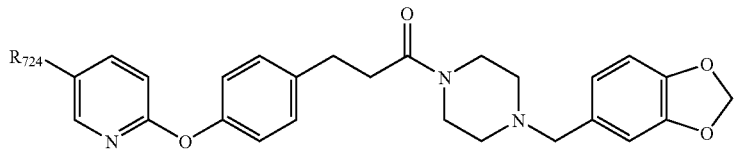

| Example No. | $R_{724}$ | $^1$H NMR (CDCl$_3$) δppm |
|---|---|---|
| 938 | 3,4-Cl$_2$PhN(C$_2$H$_5$)CONH— | 1.17(3H, t, J=7.1Hz), 2.30-2.40(4H, m), 2.57-2.63(2H, m), 2.92-2.98(2H, m), 3.37-3.40(4H, m), 3.60-3.64(2H, m), 3.77(2H, q, J=7.1Hz), 5.94(2H, s), 6.65-6.80(2H, m), 6.81-6.85(2H, m), 6.98-7.00(2H, m), 7.17-7.21(3H, m), 7.45(1H, d, J=2.4Hz), 7.57(1H, d, J=8.5Hz), 7.85-7.91(2H, m). |

TABLE 229

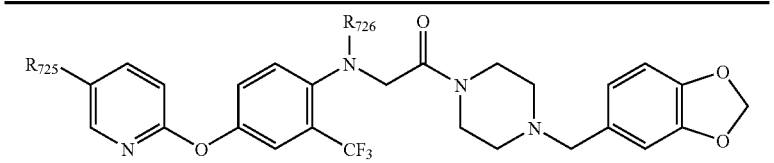

| Example No. | $R_{725}$ | $R_{726}$ | $^1$H NMR (CDCl$_3$) δppm |
|---|---|---|---|
| 939 | 3,4-Cl$_2$PhNHCO— | —CH$_3$ | 2.30-2.50(4H, m), 2.78(3H, s), 3.42(2H, s), 3.50-3.65(4H, m), 3.82(2H, s), 5.95(2H, s), 6.65-6.75(2H, m), 6.85(1H, s), 7.05(1H, d, J=8.6 Hz), 7.26-7.30(1H, m), 7.39-7.43(2H, m), 7.49-7.53(2H, m), 7.88(1H, d, J=2.4Hz), 8.24(1H, dd, J=8.6Hz, 2.5Hz), 8.31(1H, brs), 8.66(1H, d, J=2.4Hz). |
| 940 | 4-CF$_3$PhNHCO— | —CH$_3$ | 2.30-2.45(4H, m), 2.78(3H, s), 3.41(2H, s), 3.55-3.59(4H, m), 3.82(2H, s), 5.94(2H, s), 6.65-6.80(2H, m), 6.85(1H, s), 7.05(1H, d, J=8.6 Hz), 7.26-7.30(1H, m), 7.41(1H, d, J=2.8Hz), 7.51(1H, d, J=8.8Hz), 7.59-7.63(2H, m), 7.77-7.80(2H, m), 8.26(1H, dd, J=8.6Hz, 2.5Hz), 8.54(1H, brs), 8.66(1H, d, J=2.2Hz). |
| 941 | 3,4-Cl$_2$PhCH$_2$NHCO— | —CH$_3$ | 2.30-2.45(4H, m), 2.80(3H, s), 3.42(2H, s), 3.50-3.65(4H, m), 3.81(2H, s), 4.59(2H, d, J=5.9 Hz), 5.95(2H, s), 6.50-6.60(1H, m), 6.65-6.80(2H, m), 6.85(1H, s), 7.01(1H, d, J=8.6 Hz), 7.18(1H, dd, J=8.2Hz, 2.0Hz), 7.30(1H, dd, J=8.8Hz, 2.7Hz), 7.39-7.43(3H, m), 7.54(1H, d, J=8.8Hz), 8.18(1H, dd, J=8.6Hz, 2.5Hz), 8.56(1H, d, J=2.4Hz). |
| 942 | 4-CF$_3$PhCH$_2$NHCO— | —CH$_3$ | 2.30-2.45(4H, m), 2.80(3H, s), 3.42(2H, s), 3.50-3.65(4H, m), 3.81(2H, s), 4.70(2H, d, J=5.9 Hz), 5.94(2H, s), 6.50-6.65(1H, m), 6.70-6.80(2H, m), 6.85(1H, s), 7.00(1H, d, J=8.6 Hz), 7.29(1H, dd, J=8.8Hz, 2.7Hz), 7.39-7.62(6H, m), 8.18(1H, dd, J=8.6Hz, 2.5Hz), 8.57(1H, d, J=2.4Hz). |
| 943 | 3,4-Cl$_2$PhN(CH$_3$)— | —C$_2$H$_5$ | 1.02(3H, t, J=7.1Hz), 2.35-2.40(4H, m), 3.22(2H, q, J=7.1Hz), 3.27(3H, s), 3.40(2H, s), 3.45-3.60(4H, m), 3.85(2H, s), 5.94(2H, s), 6.64(1H, dd, J=8.9Hz, 2.9Hz), 6.65-6.75(2H, m), 6.84(1H, s), 6.90(1H, d, J=2.8Hz), 6.96(1H, d, J=8.7Hz), 7.22-7.26(1H, m), 7.26-7.35(1H, m), 7.42(1H, d, J=2.8Hz), 7.50(1H, dd, J=8.7Hz, 2.9Hz), 7.66(1H, d, J=8.8Hz), 8.00(1H, d, J=2.6Hz). |

TABLE 230

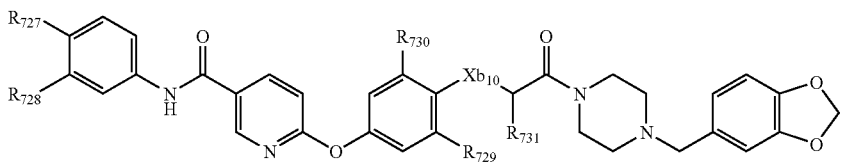

| Example No. | $R_{727}$ | $R_{728}$ | $R_{729}$ | $R_{730}$ | $R_{731}$ | $Xb_{10}$ | $^1$H NMR (CDCl$_3$) δppm |
|---|---|---|---|---|---|---|---|
| 944 | —Cl | —Cl | —CH$_3$ | —CH$_3$ | —H | —N(CH$_3$)— | 2.30(6H, s), 2.32-2.45(4H, m), 2.83(3H, s), 3.30-3.45(4H, m), 3.55-3.70(2H, m), 3.83(2H, s), 5.94(2H, s), 6.69-6.76(4H, m), 6.83(1H, s), 6.96(1H, d, J=8.6Hz), 7.40(1H, d, J=8.7Hz), 7.50(1H, dd, J=8.8Hz, 2.5Hz), 7.87(1H, d, J=2.4Hz), 8.19(1H, dd, J=8.6Hz, 2.5Hz), 8.31(1H, brs), 8.68(1H, d, J=2.2 Hz). |
| 945 | —CF$_3$ | —H | —CH$_3$ | —CH$_3$ | —H | —N(CH$_3$)— | 2.30-2.45(10H, m), 2.86(3H, s), 3.30-3.45(4H, m), 3.55-3.70(2H, m), 3.84(2H, s), 5.94(2H, s), 6.65-6.78(4H, m), 6.84(1H, s), 6.99(1H, d, J=8.6Hz), 7.60-7.65(2H, m), 7.70-7.78(2H, m), 8.07(1H, brs), 8.21(1H, dd, J=8.6Hz, 2.6Hz), 8.70(1H, d, J=2.5Hz). |
| 946 | —CF$_3$ | —H | —H | —H | —H | —CH(CH$_3$)— | 1.30-1.36(3H, m), 2.10-2.40(4H, m), 2.47-2.67(2H, m), 3.25-3.45(5H, m), 3.50-3.65(2H, m), 5.93(2H, s), 6.65-6.75(2H, m), 6.83(1H, d, J=0.9Hz), 7.01(1H, dd, J=8.6Hz, 0.6Hz), 7.06-7.15(2H, m), 7.25-7.30(2H, m), 7.60-7.64(2H, m), 7.74-7.78(2H, m), 8.14(1H, brs), 8.22(1H, dd, J=8.6 Hz, 2.6Hz), 8.67-8.68(1H, m). |
| 947 | —CF$_3$ | —H | —H | —H | —CH$_3$ | —CH$_2$— | 1.14-1.17(3H, m), 1.95-2.10(1H, m), 2.15-2.45(3H, m), 2.55-2.70(1H, m), 2.85-3.05(2H, m), 3.15-3.45(4H, m), 3.45-3.70(2H, m), 5.92-5.94(2H, m), 6.65-6.85(3H, m), 6.95-7.06(3H, m), 7.10-7.30(2H, m), 7.59-7.63(2H, m), 7.75-7.79(2H, m), 8.24(1H, dd, J=8.6Hz, 2.6Hz), 8.40(1H, brs), 8.71(1H, d, J=2.4Hz). |

TABLE 231

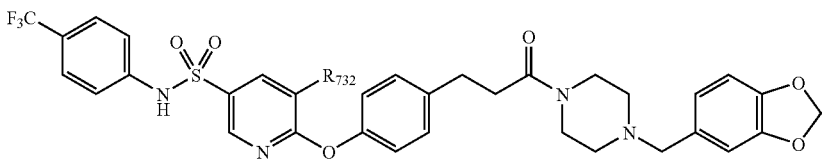

| Example No. | $R_{732}$ | $^1$H NMR (DMSO-d$_6$) δppm |
|---|---|---|
| 948 | —Br | 2.20-2.35(4H, m), 2.59-2.65(2H, m), 2.79-2.85(2H, m), 3.20-3.60(6H, m), 5.99(2H, s), 6.73-6.77 (1H, m), 6.83-6.86(2H, m), 7.07-7.10(2H, m), 7.27-7.34(4H, m), 7.62-7.65(2H, m), 8.44-8.48(2H, m), 10.90(1H, brs). |
| 949 | —H | 2.20-2.35(4H, m), 2.59-2.65(2H, m), 2.78-2.84(2H, m), 3.38-3.44(6H, m), 5.98(2H, s), 6.72-6.76 (1H, m), 6.82-6.86(2H, m), 7.04-7.08(2H, m), 7.17(1H, d, J=8.8 Hz), 7.26-7.33(4H, m), 7.61-7.65(2H, m), 8.17(1H, dd, J=8.7 Hz, 2.6 Hz), 8.55(1H, d, J=2.6 Hz), 10.98(1H, brs). |

Example 950

Production of 3,4-dichloro-N-{6-[4-(4-phenethylpiperazine-1-carbonyl)phenoxy]pyridin-3-yl}benzamide To a solution of ethyl 4-(5-aminopyridin-2-yloxy)benzoate (690 mg, 2.7 mmol) in THF (10 mL) were added triethylamine (0.73 mL, 5.3 mmol) and 3,4-dichlorobenzoyl chloride (570 mg, 2.7 mmol) under ice cooling, and the resulting solution was stirred for 1 hour under ice cooling. This reaction solution was concentrated under reduced pressure, and to the residue was added ethyl acetate. The resulting solution was washed with water, 1 N hydrochloric acid and brine, and then dried over anhydrous magnesium sulfate. The solvent was evaporated, and the residue was washed, when hot, with n-hexane:dichloromethane=1:2. The product was dissolved in THF (20 mL). To the residue was added 1 N aqueous sodium hydroxide (2.9 mL, 2.9 mmol), and this solution was stirred for 5 hours at 100° C. THF was evaporated, and the aqueous layer was made to have a pH of 3 with 1 N hydrochloric acid. Precipitated matter was collected by filtration, and dried. The resulting product was dissolved in DMF (10 mL), and 1-phenethylpiperazine (200 mg, 1.1 mmol), 1-ethyl-3-(3-dimethylaminopropyl)carbodiimide hydrochloride (240 mg, 1.3 mmol) and 1-hydroxybenzotriazole monohydrate (170 mg, 1.3 mmol) were added to the solution. The resulting solution was stirred for 1 day at room temperature. This reaction solution was concentrated under reduced pressure, and to the residue was added chloroform. The resulting solution was washed with water, and then dried over anhydrous magnesium sulfate. The solvent was evaporated, and the residue was purified by silica gel column chromatography (methanol:chloroform=1:99), to thereby yield 310 mg of the title compound.

Appearance: White powder $^1$H NMR (CDCl$_3$) δ 2.54 (4H, brs), 2.62-2.68 (2H, m), 2.79-2.85 (2H, m), 3.60-3.73 (4H, m), 6.95 (1H, d, J=8.9 Hz), 7.09-7.23 (5H, m), 7.27-7.33 (2H, m), 7.37-7.41 (2H, m), 7.55 (1H, d, J=8.3 Hz), 7.74-7.78 (1H, m), 8.04 (1H, d, J=2.0 Hz), 8.11-8.15 (1H, m), 8.31 (1H, d, J=2.6 Hz), 8.57 (1H, brs).

The following compounds were produced in the same manner as in Example 950.

TABLE 232

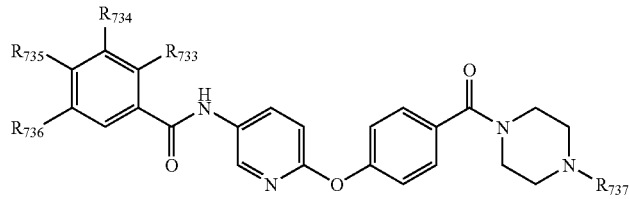

| Example No. | R$_{733}$ | R$_{734}$ | R$_{735}$ | R$_{736}$ | R$_{737}$ | MS (M$^+$+H) |
|---|---|---|---|---|---|---|
| 951 | —CH$_3$ | —F | —H | —H | 4-CNPhCH$_2$— | 550 |
| 952 | —H | —F | —F | —H | 4-CNPhCH$_2$— | 554 |
| 953 | —H | —Cl | —H | —Cl | 4-CNPhCH$_2$— | 586 |
| 954 | —H | —OCF$_3$ | —H | —H | 4-CNPhCH$_2$— | 602 |
| 955 | —CH$_3$ | —F | —H | —H | 2-pyridylmethyl | 526 |
| 956 | —H | —CH$_3$ | —CH$_3$ | —H | 2-pyridylmethyl | 522 |
| 957 | —H | —F | —F | —H | 2-pyridylmethyl | 530 |
| 958 | —H | —Cl | —H | —Cl | 2-pyridylmethyl | 530 |
| 959 | —H | —CF$_3$ | —H | —H | 2-pyridylmethyl | 562 |
| 960 | —H | —H | —Cl | —H | 2-pyridylmethyl | 528 |
| 961 | —H | —CF$_3$ | —H | —F | 2-pyridylmethyl | 580 |
| 962 | —H | —OCF$_3$ | —H | —H | 2-pyridylmethyl | 578 |
| 963 | —CH$_3$ | —F | —H | —H | 3-pyridylmethyl | 526 |
| 964 | —H | —CH$_3$ | —CH$_3$ | —H | 3-pyridylmethyl | 522 |
| 965 | —H | —F | —F | —H | 3-pyridylmethyl | 530 |
| 966 | —H | —Cl | —H | —Cl | 3-pyridylmethyl | 562 |
| 967 | —H | —CF$_3$ | —H | —H | 3-pyridylmethyl | 562 |
| 968 | —H | —H | —Cl | —H | 3-pyridylmethyl | 528 |
| 969 | —H | —CF$_3$ | —H | —F | 3-pyridylmethyl | 580 |
| 970 | —CH$_3$ | —F | —H | —H | 4-pyridylmethyl | 526 |
| 971 | —H | —CH$_3$ | —CH$_3$ | —H | 4-pyridylmethyl | 522 |
| 972 | —H | —F | —F | —H | 4-pyridylmethyl | 530 |
| 973 | —H | —Cl | —H | —Cl | 4-pyridylmethyl | 562 |
| 974 | —H | —CF$_3$ | —H | —H | 4-pyridylmethyl | 562 |
| 975 | —H | —H | —Cl | —H | 4-pyridylmethyl | 528 |
| 976 | —H | —CF$_3$ | —H | —F | 4-pyridylmethyl | 580 |
| 977 | —H | —OCF$_3$ | —H | —H | 4-pyridylmethyl | 578 |
| 978 | —CH$_3$ | —F | —H | —H | piperonyl | 569 |
| 979 | —H | —CH$_3$ | —CH$_3$ | —H | piperonyl | 565 |
| 980 | —H | —F | —F | —H | piperonyl | 573 |
| 981 | —H | —Cl | —H | —Cl | piperonyl | 605 |
| 982 | —H | —CF$_3$ | —H | —H | piperonyl | 605 |
| 983 | —H | —CF$_3$ | —H | —F | piperonyl | 623 |

TABLE 233

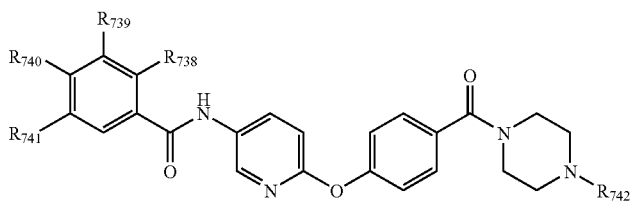

| Example No. | $R_{738}$ | $R_{739}$ | $R_{740}$ | $R_{741}$ | $R_{742}$ | MS (M$^+$+H) |
|---|---|---|---|---|---|---|
| 984 | —H | —OCF$_3$ | —H | —H | piperonyl | 621 |
| 985 | —H | —CH$_3$ | —CH$_3$ | —H | benzyl | 521 |
| 986 | —H | —F | —F | —H | benzyl | 529 |
| 987 | —CH$_3$ | —F | —H | —H | 4-AcNHPhCH$_2$— | 582 |
| 988 | —H | —CH$_3$ | —CH$_3$ | —H | 4-AcNHPhCH$_2$— | 578 |
| 989 | —H | —F | —F | —H | 4-AcNHPhCH$_2$— | 586 |
| 990 | —H | —Cl | —H | —Cl | 4-AcNHPhCH$_2$— | 618 |
| 991 | —H | —CF$_3$ | —H | —H | 4-AcNHPhCH$_2$— | 618 |
| 992 | —H | —H | —Cl | —H | 4-AcNHPhCH$_2$— | 584 |
| 993 | —H | —CF$_3$ | —H | —F | 4-AcNHPhCH$_2$— | 636 |
| 994 | —H | —OCF$_3$ | —H | —H | 4-AcNHPhCH$_2$— | 634 |
| 995 | —CH$_3$ | —F | —H | —H | 2,3-(CH$_3$)$_2$PhCH$_2$— | 553 |
| 996 | —H | —CH$_3$ | —CH$_3$ | —H | 2,3-(CH$_3$)$_2$PhCH$_2$— | 549 |
| 997 | —H | —F | —F | —H | 2,3-(CH$_3$)$_2$PhCH$_2$— | 557 |
| 998 | —H | —Cl | —H | —Cl | 2,3-(CH$_3$)$_2$PhCH$_2$— | 589 |
| 999 | —H | —CF$_3$ | —H | —H | 2,3-(CH$_3$)$_2$PhCH$_2$— | 589 |
| 1000 | —H | —H | —Cl | —H | 2,3-(CH$_3$)$_2$PhCH$_2$— | 555 |
| 1001 | —H | —CF$_3$ | —H | —F | 2,3-(CH$_3$)$_2$PhCH$_2$— | 607 |
| 1002 | —H | —OCF$_3$ | —H | —H | 2,3-(CH$_3$)$_2$PhCH$_2$— | 605 |
| 1003 | —CH$_3$ | —F | —H | —H | 3-furylmethyl | 515 |
| 1004 | —H | —CH$_3$ | —CH$_3$ | —H | 3-furylmethyl | 511 |
| 1005 | —H | —F | —F | —H | 3-furylmethyl | 519 |
| 1006 | —H | —Cl | —H | —Cl | 3-furylmethyl | 551 |
| 1007 | —H | —CF$_3$ | —H | —H | 3-furylmethyl | 551 |
| 1008 | —H | —H | —Cl | —H | 3-furylmethyl | 517 |
| 1009 | —H | —Cl | —Cl | —H | 3-furylmethyl | 551 |
| 1010 | —H | —CF$_3$ | —H | —F | 3-furylmethyl | 569 |
| 1011 | —H | —OCF$_3$ | —H | —H | 3-furylmethyl | 567 |
| 1012 | —CH$_3$ | —F | —H | —H | 3-pyridyl | 512 |
| 1013 | —H | —CH$_3$ | —CH$_3$ | —H | 3-pyridyl | 508 |
| 1014 | —H | —F | —F | —H | 3-pyridyl | 516 |
| 1015 | —H | —Cl | —H | —Cl | 3-pyridyl | 548 |
| 1016 | —H | —CF$_3$ | —H | —H | 3-pyridyl | 548 |
| 1017 | —H | —CF$_3$ | —H | —F | 3-pyridyl | 566 |
| 1018 | —H | —OCF$_3$ | —H | —H | 3-pyridyl | 564 |

TABLE 234

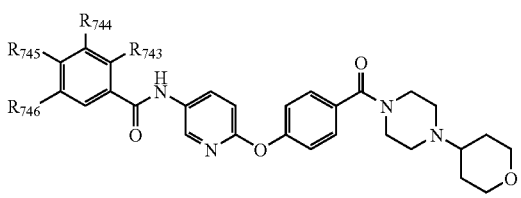

| Example No. | $R_{743}$ | $R_{744}$ | $R_{745}$ | $R_{746}$ | MS (M$^+$+H) |
|---|---|---|---|---|---|
| 1019 | —CH$_3$ | —F | —H | —H | 519 |
| 1020 | —H | —CH$_3$ | —CH$_3$ | —H | 515 |
| 1021 | —H | —F | —F | —H | 523 |
| 1022 | —H | —Cl | —H | —Cl | 555 |
| 1023 | —H | —CF$_3$ | —H | —H | 555 |
| 1024 | —H | —H | —Cl | —H | 521 |
| 1025 | —H | —Cl | —Cl | —H | 555 |
| 1026 | —H | —CF$_3$ | —H | —F | 573 |
| 1027 | —H | —OCF$_3$ | —H | —H | 571 |

TABLE 235

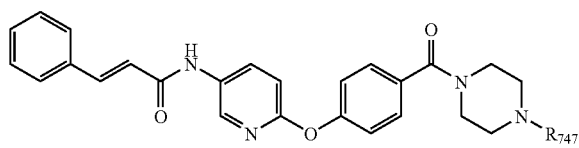

| Example No. | $R_{747}$ | MS (M$^+$+H) |
|---|---|---|
| 1028 | 4-CNPhCH$_2$— | 544 |
| 1029 | 2-pyridylmethyl | 520 |
| 1030 | 3-pyridylmethyl | 520 |
| 1031 | 4-pyridylmethyl | 520 |
| 1032 | 4-AcNHPhCH$_2$— | 576 |
| 1033 | 2,3-(CH$_3$)$_2$PhCH$_2$— | 547 |
| 1034 | 3-furylmethyl | 509 |
| 1035 | 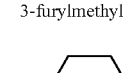 | 513 |

Example 1036

Production of 2-{3-methyl-4-[5-(4-trifluoromethylbenzoyl)pyridin-2-yloxy]phenylamino}-1-(4-piperonylpiperazin-1-yl)ethanone To a solution of 2-chloro-5-(4-trifluoromethylbenzoyl)pyridine (1.00 g, 3.5 mmol) in DMF (30 mL) were added N-(4-hydroxy-3-methylphenyl)glycine ethyl ester (0.81 g, 3.9 mmol), cesium carbonate (1.71 g, 5.2 mmol) and copper (I) iodide (200 mg, 1.05 mmol), and the resulting solution was stirred for 3.5 hours at 60° C. under an argon atmosphere. The resulting reaction solution was filtered and concentrated. To the residue was added water and extracted with ethyl acetate. The ethyl acetate layer was washed with water and then dried over anhydrous magnesium sulfate. The solvent was evaporated, and the residue was purified by silica gel column-chromatography (n-hexane:ethyl acetate=3:1), to thereby yield 1.20 g of a yellow oil. The yellow oil was dissolved in THF (23 mL), and to the solution was added 1 M aqueous sodium hydroxide (3.9 mL, 3.9 mmol). The resulting solution was stirred for 3 hours at room temperature. This reaction solution was cooled with ice, and made to have a pH of 1 with 6 M hydrochloric acid. The resulting solution was extracted with ethyl acetate, and the ethyl acetate layer was washed with water and then dried over anhydrous magnesium sulfate. The solvent was evaporated under reduced pressure, to thereby yield 1.04 g of a yellow oil. This yellow oil was dissolved in DMF (20 mL), and to the resulting solution were added 1-piperonylpiperazine (530 mg, 2.4 mmol), 1-ethyl-3-(3-dimethylaminopropyl)carbodiimide hydrochloride (560 mg, 2.9 mmol) and 1-hydroxybenzotriazole monohydrate (390 mg, 2.6 mmol), and the resulting solution was stirred for 15 hours at room temperature. The reaction solution was concentrated under reduced pressure, and to the residue was added water, and extracted with ethyl acetate. The ethyl acetate layer was washed with water, dried over anhydrous magnesium sulfate, evaporated, and the residue was purified by silica gel column chromatography (n-hexane:ethyl acetate=1:2→ethyl acetate), to thereby yield 280 mg of a yellow oil. To this oil was added diethyl ether and left to stand. Precipitated matter was collected by filtration, to thereby yield 220 mg of the title compound.

Appearance: Yellow powder $^1$H NMR (CDCl$_3$) δ 2.11 (3H, s), 2.43-2.48 (4H, m), 3.45-3.48 (4H, m), 3.67-3.71 (2H, m), 3.86 (2H, d, J=4.1 Hz), 4.90 (1H, t, J=4.1 Hz), 5.96 (2H, s), 6.49-6.53 (2H, m), 6.71-6.78 (2H, m), 6.86-6.97 (3H, m), 7.75 (2H, d, J=8.1 Hz), 7.87 (2H, d, J=8.1 Hz), 8.18 (1H, dd, J=8.7 Hz, 2.5 Hz), 8.58 (1H, d, J=2.1 Hz).

The following compound was produced in the same manner as in Example 1036.

Example 1037

6-(4-{[2-(4-Piperonylpiperazin-1-yl)-2-oxoethyl]methylamino}-2,5-difluorophenoxy)-N-(4-trifluoromethylphenyl)nicotinamide hydrobromide Melting point: 224.5-226.0° C.

Example 1038

Production of N-(6-{2-methyl-4-[methyl-(2-oxo-2-piperazin-1-ylethyl)amino]phenoxy}pyridin-3-yl)-3,4-dichlorobenzamide To a solution of methyl{4-[5-(3,4-dichlorobenzoylamino)-pyridin-2-yloxy]-3-methylphenyl}aminoacetic acid (1.59 g, 3.5 mmol) in DMF (60 mL) were added 1-ethyl-3-(3-dimethylaminopropyl)carbodiimide hydrochloride (0.79 g, 4.1 mmol), 1-hydroxybenzotriazole monohydrate (0.63 g, 4.1 mmol), and 1-t-butyloxycarbonylpiperazine (0.68 g, 3.6 mmol). The resulting solution was stirred for 15 hours at room temperature under a nitrogen atmosphere. Water was added to the solution, and extracted with ethyl acetate. The ethyl acetate layer was washed with a saturated sodium bicarbonate solution and then the ethyl acetate layer was dried over anhydrous magnesium sulfate. The solvent was evaporated, and the residue was purified by silica gel column chromatography (n-hexane:ethyl acetate=2:1→3:2), to thereby yield an amide product. This amide product was dissolved in THF (20 mL). To the solution was then added 10% hydrochloric acid (10 mL), and the resulting solution was stirred for 14 hours at room temperature. To this reaction solution was added a saturated sodium bicarbonate solution to make the solution neutral, and extracted with ethyl acetate. The ethyl acetate layer was dried over anhydrous magnesium sulfate, evaporated, and the residue was purified by silica gel column chromatography (dichloromethane:methanol=50:1→20:1), to thereby yield 0.38 g of the title compound.

Appearance: Colorless amorphous powder $^1$H NMR (CDCl$_3$) δ 2.10 (3H, s), 2.75-2.94 (4H, m), 2.99 (3H, s), 3.40-3.70 (4H, m), 4.08 (2H, s), 6.46-6.59 (2H, m), 6.79 (1H, d, J=8.9 Hz), 6.89 (1H, d, J=8.6 Hz), 7.55 (1H, d, J=8.4 Hz), 7.71 (1H, dd, J=8.4 Hz, 2.1 Hz), 7.98 (1H, d, J=2.1 Hz), 8.03-8.14 (2H, m), 8.23 (1H, d, J=2.6 Hz).

Example 1039

Production of N-(6-{4-[3-(4-piperonylpiperazin-1-yl)-3-oxopropyl]phenoxy}pyridin-3-yl)-4-trifluoromethylbenzamide To a solution of 3-[4-(5-aminopyridin-2-yloxy)phenyl]-1-(4-piperonylpiperazin-1-yl)propan-1-one trihydrochloride (200 mg, 0.35 mmol) in THF (4 mL) were added triethylamine (0.243 mL, 1.8 mmol) and 4-trifluoromethylbenzoyl chloride (0.055 mL, 0.37 mmol), and the resulting solution was stirred for 1 hour at room temperature. Water was added to the residue, and extracted with ethyl acetate. The ethyl acetate layer was washed with water and brine, dried over anhydrous magnesium sulfate, evaporated, and the residue was recrystallized from diethyl ether, to thereby yield 170 mg of the title compound.

Appearance: White powder

Melting point: 140-141° C.

$^1$H NMR (CDCl$_3$) δ 2.32-2.40 (4H, m), 2.59-2.65 (2H, m), 2.93-2.99 (2H, m), 3.41 (4H, brs), 3.60-3.64 (2H, m), 5.94 (2H, s), 6.71-6.77 (2H, m), 6.85 (1H, s), 6.96 (1H, d, J=8.9 Hz), 7.05 (2H, d, J=8.4 Hz), 7.22 (2H, d, J=8.4 Hz), 7.76 (2H, d, J=8.4 Hz), 8.01 (2H, d, J=8.4 Hz), 8.11-8.14 (1H, m), 8.23 (1H, dd, J=8.9 Hz, 2.7 Hz), 8.28 (1H, d, J=2.7 Hz).

A crude titled product (77.4 g) obtained using the same procedures was recrystallized from ethyl acetate (400 mL), to thereby yield 49.66 g of the title compound.

Appearance: White powder; Melting point: 142-144° C.

The following compounds were produced in the same manner as in Example 1039.

TABLE 236

Structure: 3,4-dichlorobenzamide-NH-phenyl-O-phenyl-Xb₁₁-[ring]-Xb₁₂-R₇₄₈

| Example No. | Xb₁₁ | Xb₁₂ | R₇₄₈ | mp (° C.) or ¹H NMR |
|---|---|---|---|---|
| 1040 | >N– | >N– | —COOC(CH₃)₃ | mp 197-199 |
| 1041 | >N– | >CH– | —OCH₂OCH₃ | mp 152-154 |
| 1042 | >N– | >CH– | —COOC₂H₅ | mp 189-190 |
| 1043 | >N– | >CH– | —N(CH₃)COOC(CH₃)₃ | mp 146 147 |
| 1044 | >CH– | >N– | —COOC(CH₃)₃ | mp 192-193 |
| 1045 | >N– | >CH– | —OCH₂COOC₂H₅ | ¹H NMR (CDCl₃) δ 1.30(3H, t, J=7.0 Hz), 1.75-1.81(2H, m), 2.03(2H, brs), 2.85-2.90(2H, m), 3.45-3.49(2H, m), 3.56(1H, m), 4.15(2H, s), 4.23(2H, q, J=7.0 Hz), 6.90-6.95(6H, m), 7.50-7.53(3H, m), 7.69(1H, dd, J=8.5 Hz, 2.0 Hz), 7.95(1H, d, J=2.0 Hz), 8.04(1H, brs). |

TABLE 237

Structure: R₇₄₉,R₇₅₀-benzamide-NH-phenyl(R₇₅₁)-O-phenyl-Xb₁₃-(CH₂)ₘ-C(O)-piperazine-CH₂-benzodioxole

| Example No. | R₇₄₉ | R₇₅₀ | R₇₅₁ | Xb₁₃ | M | Form | mp (° C.) or ¹H NMR |
|---|---|---|---|---|---|---|---|
| 1046 | —Cl | —Cl | —F | —N(Ac)— | 1 | free | ¹H NMR (DMSO-d₆) δ 1.78(3H, s), 2.22-2.38 (4H, m), 3.30-3.50(6H, m), 4.41(2H, s), 5.98(2H, s), 6.74(1H, d, J=8.1 Hz), 6.80-6.86(2H, m), 6.98(2H, d, J=8.8 Hz), 7.29(1H, t, J=9.2 Hz), 7.38 (2H, d, J=8.8 Hz), 7.58(1H, d, J=9.2 Hz), 7.84(1H, d, J=8.4 Hz), 7.90-7.96(2H, m), 8.21(1H, d, J=1.8 Hz), 10.61(1H, s). |
| 1047 | —Cl | —Cl | —F | —NH— | 0 | free | mp 224-228 |
| 1048 | —Cl | —Cl | —F | —NH— | 1 | dihydrochloride | mp 174-178 |
| 1049 | —CF₃ | —H | —H | —N(CH₃)— | 1 | free | ¹H NMR (CDCl₃) δ 2.45(4H, brs), 3.03(3H, s), 3.46(2H, s), 3.52(2H, brs), 3.64(2H, brs), 4.08(2H, s), 5.95(2H, s), 6.67(2H, d, J=9.1 Hz), 6.74-6.78(2H, m), 6.87(1H, s), 6.92-6.97(4H, m), 7.52(2H, d, J=8.9 Hz), 7.74-7.81(3H, m), 7.98(2H, d, J=8.2 Hz). |

TABLE 237-continued

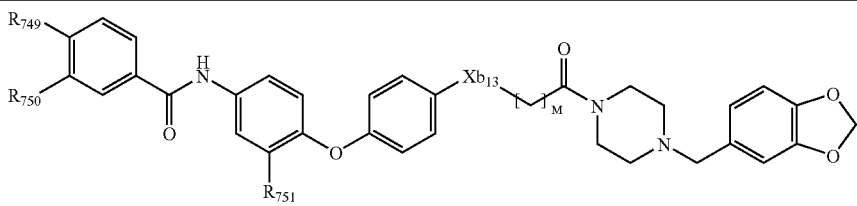

| Example No. | $R_{749}$ | $R_{750}$ | $R_{751}$ | $Xb_{13}$ | M | Form | mp (° C.) or $^1$H NMR |
|---|---|---|---|---|---|---|---|
| 1050 | —Cl | —Cl | —H | —N(CH$_3$)— | 1 | free | $^1$H NMR (CDCl$_3$)δ 2.49(4H, brs), 3.02(3H, s), 3.50(2H, s), 3.55(2H, brs), 3.66(2H, brs), 4.08(2H, s), 5.96(2H, s), 6.67(2H, d, J=9.1 Hz), 6.74-6.78(2H, m), 6.88-6.96(5H, m), 7.50(2H, d, J=8.9 Hz), 7.56(1H, d, J=8.4 Hz), 7.70(1H, dd, J=8.4 Hz, 2.1 Hz), 7.83(1H, s), 7.97(1H, d, J=2.1 Hz). |
| 1051 | —Cl | —Cl | —F | —O— | 1 | hydrochloride | $^1$H NMR (DMSO-d$_6$)δ 2.83-2.95(1H, m), 2.97-3.12(2H, m), 3.23-3.56(3H, m), 3.95-4.06(1H, m), 4.18-4.29(2H, m), 4.33-4.44 (1H, m), 4.75-4.92(2H, m), 6.07(2H, s), 6.90-6.96(4H, m), 6.97-7.04(2H, m), 7.11 (1H, t, J=9.1 Hz), 7.15-7.22(1H, m), 7.52(1H, d, J=9.1 Hz), 7.84(1H, d, J=8.4 Hz), 7.88(1H, d, J=13.3 Hz), 7.94(1H, dd, J=8.4 Hz, 1.9 Hz), 8.23(1H, d, J=1.9 Hz), 10.60 |

TABLE 238

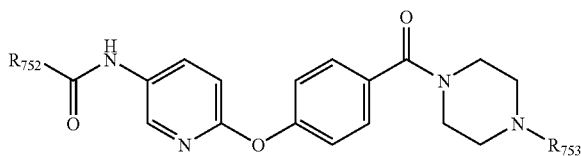

| Example No. | $R_{752}$ | $R_{753}$ | mp (° C.) or $^1$H NMR (CDCl$_3$) δppm |
|---|---|---|---|
| 1052 | 4-ClPh— | benzyl | mp 187-190 |
| 1053 | 3-ClPh— | benzyl | $^1$H NMR 2.38(4H, brs), 3.34-3.71(6H, m), 6.86(1H, d, J=8.8 Hz), 7.00-7.05(2H, m), 7.19-7.36(8H, m), 7.43-7.47(1H, m), 7.69-7.73(1H, m), 7.83(1H, t, J = 1.8 Hz), 8.08(1H, dd, J=8.8 Hz, 2.8 Hz), 8.24(1H, d, J=2.6 Hz), 8.51(1H, brs). |
| 1054 | 4-CH$_3$Ph— | 4-CH$_3$OPhCH$_2$— | $^1$H NMR 2.32-2.50(7H, m), 3.44-3.79(9H, m), 6.84-6.92(3H, m), 7.06-7.11(2H, m), 7.20-7.23(4H, m), 7.34-7.39(2H, m), 7.79(2H, d, J=8.3 Hz), 8.16-8.21(1H, m), 8.35(1H, d, J=2.8 Hz), 8.76(1H, brs). |
| 1055 | 2-naphthyl | 4-CH$_3$OPhCH$_2$— | $^1$H NMR 2.41(4H, brs), 3.46-3.80(6H, m), 3.81(3H, s), 6.83-6.90(2H, m), 6.95(1H, d, J=8.7 Hz), 7.10(2H, d, J=8.7 Hz), 7.22(2H, d, J=8.6 Hz), 7.38(2H, d, J=8.7 Hz), 7.52-7.63(2H, m), 7.88-7.97(4H, m), 8.27(1H, dd, J=8.7 Hz, 2.8 Hz), 8.41-8.43(2H, m), 8.80(1H, brs). |
| 1056 | 4-ClPh— | 4-CH$_3$OPhCH$_2$— | $^1$H NMR 2.43(4H, brs), 3.48-3.77(6H, m), 3.80(3H, s), 6.83-6.89(2H, m), 6.96(1H, d, J=8.9 Hz), 7.10-7.15(2H, m), 7.22(2H, d, J=8.6 Hz), 7.38-7.48(4H, m), 7.82-7.87(2H, m), 8.17-8.21(2H, m), 8.30(1H, d,J=2.6 Hz). |
| 1057 | 3-ClPh— | 4-CH$_3$OPhCH$_2$— | $^1$H NMR 2.41(4H, brs), 3.46-3.76(6H, m), 3.79(3H, s), 6.83-6.89(3H, m), 7.05(2H, d, J=8.4 Hz), 7.21(2H, d, J=8.6 Hz), 7.31-7.48(4H, m), 7.77(1H, d, J=7.8 Hz), 7.90(1H, s), 8.08-8.12(1H, m), 8.35(1H, d, J=2.5 Hz), 9.26(1H, brs). |
| 1058 | 4-CF$_3$OPh— | benzyl | mp 152-153 |
| 1059 | 2,4-Cl$_2$Ph— | benzyl | mp 196-197 |
| 1060 | 2,3-F$_2$Ph— | benzyl | mp 172-175 |
| 1061 | 4-ClPh— | piperonyl | $^1$H NMR 2.45(4H, brs), 3.45(2H, s), 3.45-3.75(4H, m), 5.95(2H, s), 6.74-6.77(2H, m), 6.86(1H, s), 6.99(1H, d, J=8.9 Hz), 7.14(2H, d, J=8.7 Hz), 7.42-7.51(4H, m), 7.84(2H, d, J=8.7 Hz), 7.91(1H, brs), 8.22(1H, dd, J=8.7 Hz, 2.8 Hz), 8.29(1H, d, 2.1 Hz) |

TABLE 238-continued

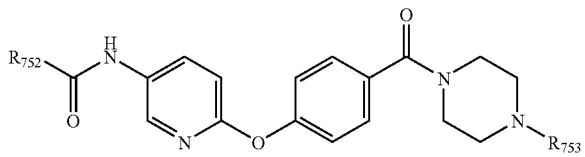

| Example No. | R$_{752}$ | R$_{753}$ | mp (° C.) or $^1$H NMR (CDCl$_3$) δppm |
|---|---|---|---|
| 1062 | 4-ClPh— | 3-pyridyl | $^1$H NMR 3.24(4H, brs), 3.49-3.82(4H, m), 7.02(1H, d, J=8.7 Hz), 7.16-7.24(4H, m), 7.48(2H, d, J=8.9 Hz), 7.49(2H, d, J=8.7 Hz), 7.85(2H, d, J=8.7 Hz), 8.04(1H, brs), 8.15-8.17(1H, m), 8.24(1H, dd, J=8.7 Hz, 2.8 Hz), 8.31-8.32(2H, m). |

TABLE 239

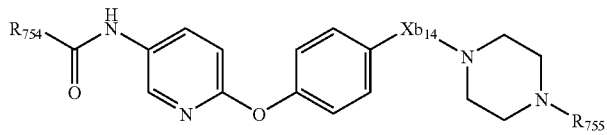

| Example No. | R$_{754}$ | R$_{755}$ | Xb$_{14}$ | Form | Property |
|---|---|---|---|---|---|
| 1063 | 3-CF$_3$OPh— | benzyl | —CO— | maleate | mp 155-157° C. |
| 1064 | 3,5-Cl$_2$Ph— | benzyl | —CO— | dihydrochloride | $^1$H NMR (DMSO-d$_6$)δ 3.15-3.54(8H, m), 4.36(2H, s), 7.15-7.22(3H, m), 7.47-7.60(7H, m), 7.90-7.91(1H, m), 8.00(1H, s), 8.01(1H, s), 8.22-8.27(1H, m), 8.54(1H, d, J=2.2 Hz), 10.69(1H, s). |
| 1065 | PhCH=CH— (trans) | benzyl | —CO— | free | MS 518(M$^+$) |
| 1066 | PhCH=CH— (trans) | piperonyl | —CO— | free | $^1$H NMR (CDCl$_3$)δ 2.45(4H, brs), 3.44(2H, s), 3.52(2H, brs), 3.76(2H, brs), 5.95 (2H, s), 6.60(1H, d, J=15.5 Hz), 6.74-6.77(2H, m), 6.85(1H, s), 6.95(1H, d, J=8.7 Hz), 7.12(2H, d, J=8.6 Hz), 7.38-7.45(5H, m), 7.53-7.56(2H, m), 7.74(1H, brs), 7.77(1H, d, J=15.5 Hz), 8.21(1H, d, J=8.4 Hz), 8.25(1H, d, J=2.5 Hz). |
| 1067 | PhCH=CH— (trans) | 3-pyridyl | —CO— | free | $^1$H NMR (CDCl$_3$)δ 3.20(4H, brs), 3.79(4H, brs), 6.67(1H, d, J=15.7 Hz), 6.92(1H, d, J=8.7 Hz), 7.10-7.21(4H, m), 7.33-7.46(7H, m), 7.73(1H, d, J=15.7 Hz), 8.11-8.31(4H, m), 9.30(1H, s). |
| 1068 | 3,4-Cl$_2$Ph— | benzyl | —SO$_2$— | hydrochloride | mp 253-256° C. |
| 1069 | 4-CF$_3$Ph— | benzyl | —SO$_2$— | hydrochloride | mp 249-251° C. |

TABLE 240

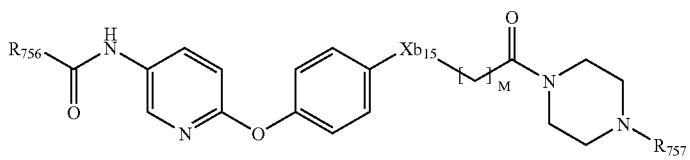

| Example No. | R$_{756}$ | R$_{757}$ | Xb$_{15}$ | M | $^1$H NMR (solvent) δppm |
|---|---|---|---|---|---|
| 1070 | 3,4-Cl$_2$Ph— | benzyl | —CH(OH)— | 0 | (CDCl$_3$)1.95-2.15(1H, m), 2.15-2.40(3H, m), 3.42(2H, s), 3.49(4H, brs), 5.42(1H, d, |

TABLE 240-continued

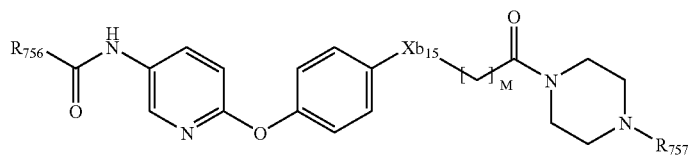

| Example No. | R<sub>756</sub> | R<sub>757</sub> | Xb<sub>15</sub> | M | $^1$H NMR (solvent) δppm |
|---|---|---|---|---|---|
| | | | | | J=6.6 Hz), 5.61(1H, d, J=6.6 Hz), 7.08(1H, d, J=8.9 Hz), 7.09(2H, d, J=8.6 Hz), 7.15-7.43(5H, m), 7.38(2H, d, J=8.6 Hz), 7.85(1H, d, J=8.4 Hz), 7.95(1H, dd, J=8.4 Hz, 2.0 Hz), 8.20(1H, dd, J=8.9 Hz, 2.7 Hz), 8.23(1H, d, J=2.3 Hz), 8.50(1H, d, J=2.7 Hz), 10.57(1H, s). |
| 1071 | 4-CF$_3$Ph— | benzyl | —CH(OH)— | 0 | (CDCl$_3$)1.90-2.05(1H, m), 2.22-2.57(3H, m), 3.10-3.40(2H, m), 3.44(2H, s), 3.58-3.85(2H, m), 4.75(1H, d, J=6.4 Hz), 5.21(1H, d, J=6.4 Hz), 6.96(1H, d, J=8.9 Hz), 7.12(2H, d, J=8.6 Hz), 7.20-7.38(5H, m), 7.32(2H, d, J=8.6 Hz), 7.78(2H, d, J=8.1 Hz), 7.92(1H, brs), 8.00(2H, d, J=8.1 Hz), 8.22(1H, dd, J=8.9 Hz, 2.5 Hz), 8.29(1H, d, J=2.5 Hz). |
| 1072 | 4-CF$_3$Ph— | piperonyl | —O— | 1 | (DMSO-d$_6$)2.32(2H, brs), 2.40(2H, brs), 3.41(2H, s), 3.46(4H, brs), 4.81(2H, s), 5.99(2H, s), 6.73-6.88(3H, m), 6.94(2H, d, J=9.2 Hz), 7.02(1H, d, J=8.7 Hz), 7.05(2H, d, J=9.2 Hz), 7.93(2H, d, J=8.4 Hz), 8.16(2H, d, J=8.4 Hz), 8.19(1H, dd, J=8.7 Hz, 2.7 Hz), 8.47(1H, d, J=2.7 Hz), 10.60(1H, s). |
| 1073 | 4-CF$_3$Ph— | benzyl | —O— | 1 | (CDCl$_3$)2.35-2.53(4H, m), 3.51(2H, s), 3.56(2H, t, J=5.0 Hz), 3.62(2H, t, J=5.0 Hz), 4.64(2H, s), 6.90(1H, d, J=8.8 Hz), 6.92(2H, d, J=9.0 Hz), 7.04(2H, d, J=9.0 Hz), 7.21-7.41(5H, m), 7.73(2H, d, J=8.1 Hz), 8.00(2H, d, J=8.1 Hz), 8.18(1H, dd, J=8.8 Hz, 2.6 Hz), 8.27(1H, d, J=2.6 Hz), 8.32(1H, brs). |
| 1074 | 3-ClPh— | piperonyl | none | 2 | (CDCl$_3$)2.31-2.38(4H, m), 2.58-2.64(2H, m), 2.90-2.96(2H, m), 3.37-3.40(4H, m), 3.59-3.62(2H, m), 5.94(2H, s), 6.70 6.77(2H, m), 6.84(1H, s), 6.92(1H, d, J=8.9 Hz), 7.03(2H, d, J=8.4 Hz), 7.20(2H, d, J=8.4 Hz), 7.38-7.44(1H, m), 7.50-7.54(1H, m), 7.77(1H, d, J=7.8 Hz), 7.87-7.88(1H, m), 8.21(1H, dd, J=8.9 Hz, 2.7 Hz), 8.28(1H, d, J=2.7 Hz), 8.36(1H, s). |

TABLE 241

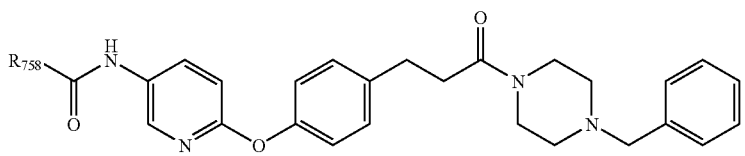

| Example No. | R<sub>758</sub> | mp (° C.) or H NMR |
|---|---|---|
| 1075 | 3-ClPh— | $^1$H NMR (CDCl$_3$)δ 2.33-2.38(4H, m), 2.55-2.61(2H, m), 2.86-2.91(2H, m), 3.37-3.41(2H, m), 3.49(2H, s), 3.56-3.60(2H, m), 6.87(1H, d, J=8.9 Hz), 6.97-7.01(2H, m), 7.14(2H, d, J=8.6 Hz), 7.25-7.37(6H, m), 7.45-7.48(1H, m), 7.75-7.79(1H, m), 7.87(1H, t, J=1.8 Hz), 8.18(1H, dd, J=8.9 Hz, 2.8 Hz), 8.32(1H, d, J=2.8 Hz), 9.06(1H, brs). |
| 1076 | 4-ClPh— | mp 136-139 |
| 1077 | 2-ClPh— | $^1$H NMR (CDCl$_3$)δ 2.32-2.41(4H, m), 2.56-2.61(2H, m), 2.90-2.96(2H, m), 3.37-3.41(2H, m), 3.50(2H, s), 3.58-3.61(2H, m), 6.92(1H, d, J=8.7 Hz), 7.03(2H, d, J=8.4 Hz), 7.19-7.43(10H, m), 7.69-7.72(1H, m), 8.21-8.27(3H, m). |
| 1078 | Ph— | $^1$H NMR (CDCl$_3$)δ 2.36(4H, brs), 2.56-2.61(2H, m), 2.89-2.95(2H, m), 3.36-3.41(2H, m), 3.49(2H, s), 3.58-3.62(2H, m), 6.99(1H, d, J= |

TABLE 241-continued

| Example No. | R$_{758}$ | mp (° C.) or H NMR |
|---|---|---|
| | | 8.7 Hz), 7.01(2H, d, J=8.1 Hz), 7.18(2H, d, J=8.1 Hz), 7.26-7.55(8H, m), 7.87(2H, d, J=6.6 Hz), 8.20(1H, d, J=8.7 Hz), 8.28(1H, brs), 8.50(1H, brs). |
| 1079 | 4-CNPh— | $^1$H NMR (CDCl$_3$)δ 2.33-2.41(4H, m), 2.56-2.62(2H, m), 2.87-2.92(2H, m), 3.38-3.42(2H, m), 3.50(2H, s), 3.56-3.60(2H, m), 6.91(1H, d, J=8.9 Hz), 6.98-7.01(2H, m), 7.14-7.19(2H, m), 7.25-7.35(5H, m), 7.71-7.75(2H, m), 7.99-8.02(2H, m), 8.17-8.29(2H, m), 8.75-8.97(1H, m). |
| 1080 | 3-CH$_3$OPh— | $^1$H NMR (CDCl$_3$)δ 2.33-2.41(4H, m), 2.56-2.62(2H, m), 2.90-2.95(2H, m), 3.38-3.42(2H, m), 3.51(2H, s), 3.60-3.63(2H, m), 3.83(3H, s), 6.90(1H, d, J=8.7 Hz), 7.00-7.09(3H, m), 7.18(2H, d, J=8.6 Hz), 7.26-7.44(8H, m), 8.19-8.23(1H, m), 8.29(1H, d, J=2.8 Hz), 8.48(1H, brs). |
| 1081 | 4-CH$_3$Ph— | $^1$H NMR (CDCl$_3$)δ 2.33-2.40(7H, m), 2.56-2.62(2H, m), 2.90-2.95(2H, m), 3.38-3.41(2H, m), 3.49(2H, s), 3.59-3.62(2H, m), 6.89(1H, d, J=8.7 Hz), 7.01(2H, d, J=8.6 Hz), 7.16-7.32(9H, m), 7.78(2H, d, J=8.2 Hz), 8.18-8.22(1H, m), 8.27(1H, d, J=2.6 Hz), 8.33-8.44(1H, m). |
| 1082 | 2-CH$_3$Ph— | $^1$H NMR (CDCl$_3$)δ 2.32-2.40(4H, m), 2.48(3H, s), 2.55-2.60(2H, m), 2.89-2.95(2H, m), 3.37-3.40(2H, m), 3.50(2H, s), 3.57-3.60(2H, m), 6.89-6.92(1H, m), 7.00-7.05(2H, m), 7.18-7.47(10H, m), 7.45(1H, d, J=2.2 Hz), 8.04(1H, brs), 8.23-8.25(2H, m). |
| 1083 | 4-CH$_3$OPh— | $^1$H NMR (CDCl$_3$)δ 2.31-2.38(4H, m), 2.54-2.60(2H, m), 2.87-2.93(2H, m), 3.37-3.40(2H, m), 3.48(2H, s), 3.58-3.61(2H, m), 3.82(3H, s), 6.84-6.90(3H, m), 6.99(2H, d, J=8.4 Hz), 7.15(2H, d, J=8.6 Hz), 7.25-7.32(5H, m), 7.85(2H, d, J=8.9 Hz), 8.17(1H, dd, J=8.9 Hz, 2.7 Hz), 8.28(1H, d, J=2.7 Hz), 8.73(1H, brs). |
| 1084 | 2-CH$_3$OPh— | $^1$H NMR (CDCl$_3$)δ 2.33-2.42(4H, m), 2.58-2.64(2H, m), 2.93-2.99(2H, m), 3.38-3.42(2H, m), 3.49(2H, s), 3.61-3.65(2H, m), 4.02(3H, s), 6.89-6.92(1H, m), 7.01-7.32(11H, m), 7.47-7.53(1H, m), 8.23-8.29(3H, m), 9.76(1H, s). |
| 1085 | 2-naphthyl | mp 156-159 |
| 1086 | 4-CF$_3$Ph— | $^1$H NMR (DMSO-d$_6$)δ 2.30-2.32(4H, m), 2.59-2.65(2H, m), 2.79-2.84(2H, m), 3.44-3.47(6H, m), 7.02(2H, d, J=8.6 Hz), 7.05(1H, d, J=9.1 Hz), 7.25-7.35(7H, m), 7.93(2H, d, J=8.3 Hz), 8.16(2H, d, J=8.3 Hz), 8.21(1H, dd, J=8.9 Hz, 2.6 Hz), 8.49(1H, d, J=2.6 Hz), 10.62(1H, brs). |

TABLE 242

| Example No. | R$_{759}$ | R$_{760}$ | Form | mp (° C.) or $^1$H NMR |
|---|---|---|---|---|
| 1087 | 4-CF$_3$OPh— | benzyl | maleate | mp 144-146 |
| 1088 | 3-CF$_3$OPh— | benzyl | maleate | mp 125-128 |
| 1089 | 4-CF$_3$OPh— | piperonyl | free | mp 187-190 |
| 1090 | 2-CF$_3$OPh— | piperonyl | free | $^1$H NMR (CDCl$_3$)δ 2.31-2.39(4H, m), 2.57-2.63(2H, m), 2.91-2.97(2H, m), 3.37-3.40(4H, m), 3.58-3.62(2H, m), 5.93(2H, s), 6.70-6.76(2H, m), 6.84(1H, s), 6.93(1H, d, J=8.9 Hz), 7.03-7.07(2H, m), 7.19-7.23(2H, m), 7.32-7.36(1H, m), 7.40-7.46(1H, m), 7.53-7.59(1H, m), 7.99-8.03(1H, m), 8.20(1H, dd, J=8.9 Hz, 2.7 Hz), 8.27(1H, d, J=2.7 Hz), 8.55(1H, brs). |
| 1091 | 3-CF$_3$OPh— | piperonyl | free | $^1$H NMR (CDCl$_3$)δ 2.30-2.36(4H, m), 2.55-2.61(2H, m), 2.86-2.92(2H, m), 3.37-3.40(4H, m), 3.56-3.60(2H, m), 5.93(2H, s), 6.69-6.76(2H, m), 6.83(1H, s), 6.88-6.92(1H, m), 6.98-7.02(2H, m), 7.14-7.18(2H, m), |

TABLE 242-continued

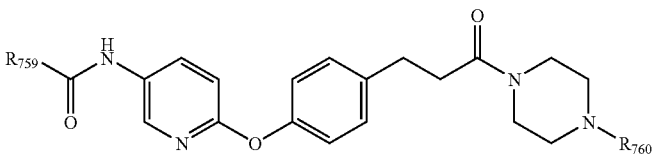

| Example No. | R₇₅₉ | R₇₆₀ | Form | mp (° C.) or ¹H NMR |
|---|---|---|---|---|
| 1092 | 3,5-Cl₂Ph— | piperonyl | dihydro-chloride | 7.36-7.40(1H, m), 7.44-7.52(1H, m), 7.78-7.85(2H, m), 8.19(1H, dd, J=8.9 Hz, 2.7 Hz), 8.29-8.31(1H, m), 8.78-8.92(1H, m). ¹H NMR (DMSO-d₆)δ 2.69-3.33(10H, m), 3.99-4.11(1H, m), 4.23(2H, s), 4.44-4.49(1H, m), 6.07(2H, s), 6.97-7.07(5H, m), 7.20-7.30(3H, m), 7.89-8.00(1H, m), 8.00(2H, d, J=1.8 Hz), 8.19(1H, dd, J=8.9 Hz, 2.6 Hz), 8.48(1H, d, J=2.3 Hz), 10.64(1H, s). |
| 1093 | PhCH=CH— (trans) | piperonyl | free | ¹H NMR (CDCl₃)δ 2.05-3.38(9H, m), 3.69-4.71(5H, m), 5.96(2H, s), 6.72-6.79(2H, m), 6.95-7.05(4H, m), 7.13-7.23(3H, m), 7.35-7.37(3H, m), 7.51-7.54(2H, m), 7.70-7.76(1H, m), 8.41(1H, d, J=2.3 Hz), 8.50(1H, d, J=8.7 Hz), 8.95(1H, brs). |
| 1094 | 2-naphthyl | piperonyl | free | ¹H NMR (CDCl₃)δ 2.28-2.34(4H, m), 2.55-2.61(2H, m), 2.89-2.95(2H, m), 3.38(4H, brs), 3.58(2H, brs), 5.92(2H, s), 6.69-6.76(2H, m), 6.83(1H, s), 6.92(1H, d, J=8.6 Hz), 7.02(2H, d, J=8.4 Hz), 7.18(2H, d, J=8.4 Hz), 7.51-7.61(2H, m), 7.86-7.94(4H, m), 8.27(1H, dd, J=8.6 Hz, 2.7 Hz), 8.33-8.38(2H, m), 8.55(1H, brs). |
| 1095 | 4-ClPh— | piperonyl | free | ¹H NMR (CDCl₃)δ 2.31-2.41(4H, m), 2.59-2.65(2H, m), 2.94-3.00(2H, m), 3.38-3.41(4H, m), 3.63(2H, brs), 5.94(2H, s), 6.71-6.77(2H, m), 6.85(1H, s), 6.95(1H, d, J=8.9 Hz), 7.05(2H, d, J=8.4 Hz), 7.23(2H, d, J=8.4 Hz), 7.48(2H, d, J=8.6 Hz), 7.82-7.89(3H, m), 8.19-8.25(2H, m). |

TABLE 243

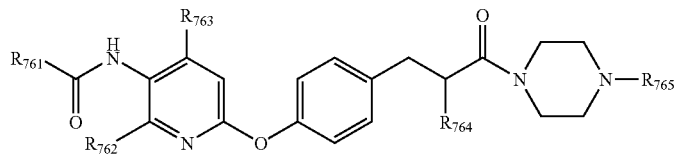

| Example No. | R₇₆₁ | R₇₆₂ | R₇₆₃ | R₇₆₄ | R₇₆₅ | ¹H NMR (CDCl₃) δppm |
|---|---|---|---|---|---|---|
| 1096 | 4-CF₃Ph— | —H | —H | —OH | —COOC(CH₃)₃ | 1.44(9H, s), 2.82-3.00(2H, m), 3.00-3.80(9H, m), 4.60(1H, t, J=6.5 Hz), 6.97(1H, d, J=8.8 Hz), 7.06(2H, d, J=8.6 Hz), 7.24(2H, d, J=8.6 Hz), 7.75(2H, d, J=8.1 Hz), 8.00(2H, d, J=8.1 Hz), 8.07(1H, brs), 8.18(1H, d, J=2.6 Hz), 8.27(1H, dd, J=8.8 Hz, 2.6 Hz). |
| 1097 | 4-CF₃Ph— | —H | —CH₃ | —H | piperonyl | 2.32(3H, s), 2.32-2.40(4H, m), 2.59-2.64(2H, m), 2.93-2.98(2H, m), 3.30-3.45(4H, m), 3.55-3 70(2H, m), 5.94(2H, s), 6.65-6.75(2H, m), 6.82-6.84(2H, m), 7.03-7.07(2H, m), 7.20-7.24(2H, m), 7.72(1H, brs), 7.75-7.79(2H, m), 8.00-8.04(2H, m), 8.30(1H, s). |
| 1098 | 4-CF₃Ph— | —CH₃ | —H | —H | piperonyl | 2.31-2.40(4H, m), 2.47(3H, s), 2.59-2.65(2H, m), 2.94-3.00(2H, m), 3.38-3.41(4H, m), 3.60-3.65(2H, m), 5.94(2H, s), 6.68-6.77(3H, m), 6.84(1H, s), 7.04-7.08(2H, m), 7.20-7.24(2H, m), |

TABLE 243-continued

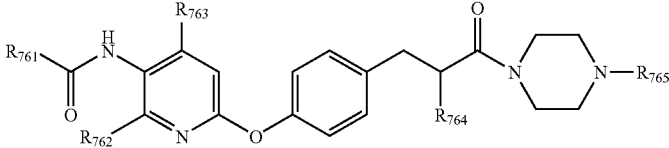

| Example No. | $R_{761}$ | $R_{762}$ | $R_{763}$ | $R_{764}$ | $R_{765}$ | $^1$H NMR (CDCl$_3$) δppm |
|---|---|---|---|---|---|---|
| 1099 | 3,4-Cl$_2$Ph— | —CH$_3$ | —H | —H | piperonyl | 7.63(1H, brs), 7.77-7.80(2H, m), 7.99-8.11(3H, m). 2.25-2.40(4H, m), 2.45(3H, s), 2.58-2.64(2H, m), 2.92-2.98(2H, m), 3.38-3.41(4H, m), 3.60-3.64(2H, m), 5.94(2H, s), 6.66-6.76(3H, m), 6.84(1H, s), 7.03-7.07(2H, m), 7.18-7.22(2H, m), 7.59(1H, d, J=8.3 Hz), 7.67(1H, brs), 7.72(1H, dd, J=8.4 Hz, 2.0 Hz), 7.98-8.02(2H, m). |
| 1100 | 3,4-Cl$_2$Ph— | —H | —cH$_3$ | —H | piperonyl | 2.31(3H, s), 2.31-2.40(4H, m), 2.58-2.64(2H, m), 2.92-2.98(2H, m), 3.37-3.41(4H, m), 3.60-3.64(2H, m), 5.94(2H, s), 6.65-6.75(2H, m), 6.80-6.84(2H, m), 7.03-7.06(2H, m), 7.20-7.24(2H, m), 7.58(1H, d, J=8.3 Hz), 7.64(1H, brs), 7.73(1H, dd, J=8.3 Hz, 1.8 Hz), 8.01(1H, d, J=1.9 Hz), 8.26(1H, s). |

TABLE 244

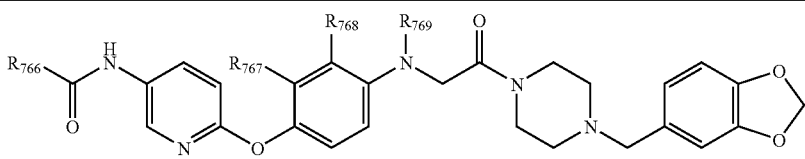

| Example No. | $R_{766}$ | $R_{767}$ | $R_{768}$ | $R_{769}$ | mp (° C.) or $^1$H NMR (solvent) δppm |
|---|---|---|---|---|---|
| 1101 | 4-CF$_3$Ph— | —H | —H | —Ac | mp 189-191 |
| 1102 | 3,4-Cl$_2$Ph— | —H | —H | —COC$_2$H$_5$ | mp 204-206 |
| 1103 | 3,4-Cl$_2$Ph— | —H | —H | —H | mp 188-189 |
| 1104 | 3,4-Cl$_2$Ph— | —H | —H | cyclopropyl ketone | $^1$H NMR (DMSO-d$_6$)0.60-0.70(2H, m), 0.75-0.80(2H, m), 1.42(1H, m), 2.25-2.35(4H, m), 3.35-3.45(6H, m), 4.49(2H, s), 5.98(2H, s), 6.74(1H, d, J=7.9 Hz), 6.84(1H, d, J=7.9 Hz), 6.86(1H, s), 7.12(1H, d, J=8.8 Hz), 7.18(2H, d, J=8.6 Hz), 7.47(2H, d, J=8.6 Hz), 7.84(1H, d, J=8.4 Hz), 7.95(1H, dd, J=8.4 Hz, 2.0 Hz), 8.20-8.23(2H, m),8.51(1H, d, J=2.5 Hz), 10.58(1H, s). |
| 1105 | 4-CF$_3$Ph— | —H | —H | —CH$_3$ | $^1$H NMR (DMSO-d$_6$)2.31-2.39(4H, m), 2.94(3H, s), 3.31(2H, s), 3.42(4H, brs), 4.24(2H, s), 5.99(2H, s), 6.64(2H, d, J=9.1 Hz), 6.76(1H, dd, J=7.9 Hz, 1.2 Hz), 6.84-6.96(5H, m), 7.93(2H, d, J=8.3 Hz), 8.13(1H, s), 8.16(2H, d, J=8.6 Hz), 8.45(1H, d, J=2.5 Hz), 10.58(1H, s). |
| 1106 | 3,4-Cl$_2$Ph— | —H | —H | cyclopropyl | $^1$H NMR (CDCl$_3$)0.57-0.62(2H, m), 0.75-0.82(2H, m), 2.37-2.49(4H, m), 2.70-2.74(1H, m), 3.45(2H, s), 3.49-3.59(4H, m), 4.17(2H, s), 5.95(2H, s), 6.74-6.94(8H, m), 7.49(1H, d, J=8.2 Hz), 7.67-7.71(1H, m), 7.95(1H, d, J=2.1 Hz), 8.00(1H, dd, J=8.9 Hz, 2.6 Hz), 8.24(1H, d, J=2.6 Hz), 8.59(1H, brs). |

TABLE 244-continued

[Structure: R766-C(=O)-NH-(pyridine)-O-(phenyl with R767, R768)-N(R769)-C(=O)-CH2-piperazine-CH2-(benzodioxole)]

| Example No. | R766 | R767 | R768 | R769 | mp (° C.) or ¹H NMR (solvent) δppm |
|---|---|---|---|---|---|
| 1107 | 4-CF₃Ph— | —H | —H | (cyclopropyl) | ¹H NMR (CDCl₃)0.57-0.62(2H, m), 0.74-0.81(2H, m), 2.35-2.47(4H, m), 2.66-2.74(1H, m), 3.44(2H, s), 3.47-3.57(4H, m), 4.16(2H, s), 5.94(2H, s), 6.70-6.94(8H, m), 7.66(2H, d, J=8.2 Hz), 7.95(2H, d, J=8.0 Hz), 8.04(1H, dd, J=8.9 Hz, 2.6 Hz), 8.25(1H, d, J=2.6 Hz), 8.80(1H, s). |
| 1108 | 4-CF₃Ph— | —CH₃ | —CH₃ | —CH₃ | ¹H NMR (CDCl₃)2.09(3H, s), 2.26(3H, s), 2.39(4H, brs), 2.67(3H, s), 3.41(2H, s), 3.53-3.63(4H, m), 3.74(2H, s), 5.94(2H, s), 6.71-6.77(2H, m), 6.85-6.90(3H, m), 6.98(1H, d, J=8.7 Hz), 7.75(2H, d, J=8.2 Hz), 7.98-8.01(3H, m), 8.18(1H, dd, J=8.9 Hz, 2.8 Hz), 8.25(1H, d, J=2.3 Hz). |
| 1109 | 3,4-Cl₂Ph— | —CH₃ | —CH₃ | —CH₃ | ¹H NMR (CDCl₃)2.09(3H, s), 2.25(3H, s), 2.37-2.40(4H, m), 2.66(3H, s), 3.41(2H, s), 3.53-3.63(4H, m), 3.73(2H, s), 5.94(2H, s), 6.70-6.77(2H, m), 6.84-6.89(3H, m), 6.96(1H, d, J=8.7 Hz), 7.56(1H, d, J=8.2 Hz), 7.70-7.74(1H, m), 7.99(1H, d, J=2.0 Hz), 8.10-8.16(2H, m), 8.24(1H, d, J=2.8 Hz). |

TABLE 245

[Structure: R770-C(=O)-NH-(pyridine)-O-(phenyl with R771)-N(R772)-C(=O)-CH2-piperazine-CH2-(benzodioxole)]

| Example No. | R770 | R771 | R772 | Form | mp (° C.) or ¹H NMR (solvent) δppm |
|---|---|---|---|---|---|
| 1110 | 4-CF₃Ph— | —OCH₃ | —C₂H₅ | free | mp 142.6-146.5 |
| 1111 | 4-CF₃Ph— | —CH₃ | —C₂H₅ | hydro-chloride | mp 173-175 dec |
| 1112 | 3,4-Cl₂Ph— | —CH₃ | —C₂H₅ | hydro-chloride | mp 168.5-171.0 |
| 1113 | 2,3-Cl₂Ph— | —CH₃ | —CH₃ | free | ¹H NMR (CDCl₃)2.12(3H, s), 2.41-2.45(4H, m), 3.01(3H, s), 3.43(2H, s), 3.50(2H, brs), 3.63(2H, brs), 4.07(2H, s), 5.95(2H, s), 6.52-6.58(2H, m), 6.71-6.77(2H, m), 6.81-6.93(3H, m), 7.32(1H, t, J=7.8 Hz), 7.56-7.61(2H, m), 7.68(1H, brs), 8.16(1H, dd, J=8.7 Hz, 2.8 Hz), 8.20(1H, d, J=2.2 Hz). |
| 1114 | 3,4-Cl₂Ph— | —OCH₃ | —H | free | ¹H NMR (DMSO-d₆)2.32-2.40(4H, m), 3.42(2H, s), 3.51(4H, brs), 3.63(3H, s), 3.91(2H, d, J=4.8 Hz), 5.54(1H, t, J=4.8 Hz), 5.99(2H, s), 6.21(1H, dd, J=8.6 Hz, 2.5 Hz), 6.50(1H, d, J=2.5 Hz), 6.76(1H, dd, J=7.9 Hz, 1.5 Hz), 6.82-6.88(4H, m), 7.82(1H, d, J=8.4 Hz), 7.94(1H, dd, J=8.4 Hz, 2.0 Hz), 8.07(1H, dd, J=8.9 Hz, 2.6 Hz), 8.21(1H, d, J=2.2 Hz), 8.37(1H, d, J=2.5 Hz), 10.44(1H, s). |
| 1115 | 4-CF₃Ph— | —OCH₃ | —H | free | ¹H NMR (CDCl₃)2.32-2.40(4H, m), 3.42(2H, s), 3.50(4H, brs), 3.63(3H, s), 3.91(2H, d, J=4.6 Hz), 5.55(1H, brt), 5.99(2H, s), 6.20(1H, dd, J=8.6 Hz, 2.5 Hz), 6.49(1H, d, J=2.3 Hz), 6.74-6.88(5H, m), 7.92(2H, d, J=8.4 Hz), 8.07-8.17(3H, m), 8.38(1H, d, J=2.3 Hz), 10.53(1H, s). |

TABLE 245-continued

| Example No. | R770 | R771 | R772 | Form | mp (° C.) or ¹H NMR (solvent) δppm |
|---|---|---|---|---|---|
| 1116 | 4-CF₃Ph— | —CH₃ |  | free | ¹H NMR (CDCl₃)0.59-0.64(2H, m), 0.76-0.82(2H, m), 2.08(3H, s), 2.37-2.47(4H, m), 2.69-2.77(1H, m), 3.44(2H, s), 3.48-3.59(4H, m), 4.16(2H, s), 5.94(2H, s), 6.67-6.77(5H, m), 6.86(2H, d, J=8.6 Hz), 7.70(2H, d, J=8.2 Hz), 7.97(2H, d, J=8.1 Hz), 8.08(1H, dd, J=8.9 Hz, 2.8 Hz), 8.23(1H, d, J=2.8 Hz), 8.39(1H, brs). |
| 1117 | 3,4-Cl₂Ph— | —CH₃ |  | free | ¹H NMR (CDCl₃)0.59-0.65(2H, m), 0.76-0.83(2H, m), 2.08(3H, s), 2.38-2.48(4H, m), 2.71-2.78(1H, m), 3.44(2H, s), 3.49-3.59(4H, m), 4.17(2H, s), 5.95(2H, s), 6.67-6.77(5H, m), 6.85-6.88(2H, m), 7.53(1H, d, J=8.2 Hz), 7.68-7.72(1H, m), 7.96(1H, d, J=2.0 Hz), 8.02-8.07(1H, m), 8.22-8.26(2H, m). |
| 1118 |  | —CH₃ | —CH₃ | free | ¹H NMR (CDCl₃)0.83-0.85(2H, m), 1.07-1.08(2H, m), 1.46-1.63(1H, m), 2.10(3H, s), 2.41-2.44(4H, m), 3.00(3H, s), 3.43(2H, s), 3.47-3.49(2H, m), 3.63(2H, brs), 4.06(2H, s), 5.94(2H, s), 6.51-6.55(2H, m), 6.70-6.77(3H, m), 6.85(1H, brs), 6.89(1H, d, J=8.4 Hz), 7.44-7.64(1H, m), 8.01-8.04(1H, m), 8.08(1H, d, J=2.3 Hz). |

TABLE 246

| Example No. | R773 | R774 | R775 | Form | ¹H NMR (solvent) δppm |
|---|---|---|---|---|---|
| 1119 | 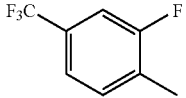 | —CH₃ | —CH₃ | hydro-chloride | (DMSO-d₆)2.01(3H, s), 2.80-3.18(3H, m), 2.93(3H, s), 3.35(3H, s), 3.38-3.62(1H, m), 3.95-4.50(4H, m), 4.27(2H, s), 6.08(2H, s), 6.49(1H, dd, J=8.7 Hz, 2.7 Hz), 6.58(1H, d, J=2.7 Hz), 6.83(1H, d, J=8.7 Hz), 6.92(1H, d, J=8.9 Hz), 7.02(2H, s), 7.21(1H, s), 7.74(1H, d, J=8.4 Hz), 7.90(1H, d, J=8.4 Hz), 7.88-7.95(1H, m), 8.11(1H,dd, J=8.9 Hz, 2.7 Hz), 8.36(1H, d, J=2.7 Hz), 10.71(1H, s). |
| 1120 | 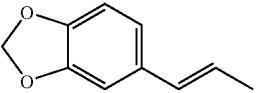 | —CH₃ | —CH₃ | free | (CDCl₃)2.11(3H, s), 2.42(4H, brs), 3.00(3H, s), 3.43(2H, s), 3.47-3.49(2H, m), 3.63(2H, brs), 4.07(2H, s), 5.95(2H, s), 6.01(2H, s), 6.37(1H, d, J=15.2 Hz), 6.52-6.56(2H, m), 6.74-6.85(5H, m), 6.91(1H, d, J=8.6 Hz), 7.00-7.02(2H, m), 7.49(1H, brs), 7.65(1H, d, J=15.3 Hz), 8.16-8.17(2H, m). |
| 1121 | 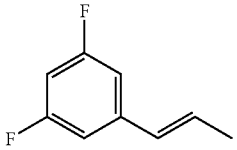 | —CH₃ | —CH₃ | free | (CDCl₃)2.09(3H, s), 2.42-2.43(4H, m), 3.00(3H, s), 3.43(2H, s), 3.47-3.50(2H, m), 3.63(2H, brs), 4.08(2H, s), 5.95(2H, s), 6.49-6.61(3H, m), 6.70-6.91(6H, m), 7.01-7.03(2H, m), 7.63(1H, d, J=15.3 Hz), 7.98(1H, brs), 8.16-8.19(2H, m). |

TABLE 246-continued

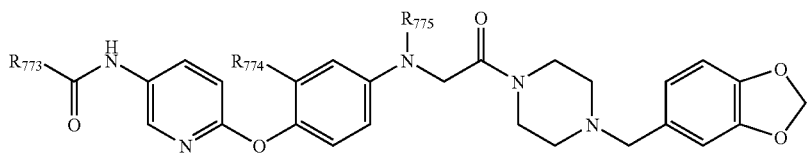

| Example No. | R₇₇₃ | R₇₇₄ | R₇₇₅ | Form | ¹H NMR (solvent) δppm |
|---|---|---|---|---|---|
| 1122 | 4-CF₃Ph-thiazole (2-(4-CF₃Ph)-4,5-dimethylthiazole) | —CH₃ | —CH₃ | free | (CDCl₃)2.17(3H, s), 2.43(4H, brs), 2.82(3H, s), 3.01(3H, s), 3.44(2H, s), 3.50(2H, brs), 3.63(2H, brs), 4.08(2H, s), 5.95(2H, s), 6.53-6.57(2H, m), 6.74(2H, brs), 6.81(1H, d, J=8.9 Hz), 6.85(1H, s), 6.92(1H, d, J=8.6 Hz), 7.52(1H, brs), 7.73(2H, d, J=8.3 Hz), 8.04-8.09(3H, m), 8.18(1H, d, J=2.8 Hz). |
| 1123 | 4-CF₃Ph— | | —F | allyl | free | (CDCl₃)2.45(4H, brs), 3.45(2H, s), 3.45(2H, brs), 3.64(2H, brs), 3.99(2H, d, J=5.1 Hz), 4.05(2H, s), 5.18-5.28(2H, m), 5.83-5.93(1H, m), 5.95(2H, s), 6.36-6.47(2H, m), 6.75(2H, s), 6.86-6.87(1H, m), 6.96(1H, d, J=9.1 Hz), 7.03(1H, t, J=8.9 Hz), 7.75-7.78(3H, m), 7.99(2H, d, J=8.1 Hz), 8.15-8.22(2H, m). |
| 1124 | 2,2-dimethylcyclopropyl | —CH₃ | —CH₃ | free | (CDCl₃)0.83-0.87(1H, m), 1.19-1.22(7H, m), 1.37-1.42(1H, m), 2.10(3H, s), 2.41-2.44(4H, m), 3.00(3H, s), 3.43(2H, s), 3.48(2H, brs), 3.63(2H, brs), 4.06(2H, s), 5.94(2H, s), 6.51-6.56(2H, m), 6.70-6.77(3H, m), 6.85-6.91(2H, m), 7.40(1H, brs), 8.05-8.06(2H, m) |

TABLE 247

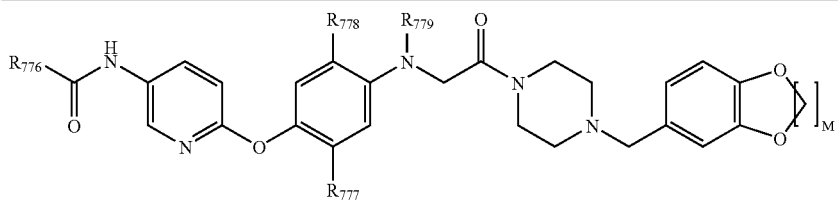

| Example No. | R₇₇₆ | R₇₇₇ | R₇₇₈ | R₇₇₉ | M | mp (° C.) or ¹H NMR |
|---|---|---|---|---|---|---|
| 1125 | 4-CF₃Ph— | —F | —F | —CH₃ | 1 | mp 160.0-161.5 |
| 1126 | 3,4-Cl₂Ph— | —F | —F | —CH₃ | 1 | mp 207-209 |
| 1127 | 4-CF₃Ph— | —F | —F | —C₂H₅ | 1 | ¹H NMR (DMSO-d₆)δ 1.07(3H, t, J=7.0 Hz), 2.20-2.41(4H, m), 3.20-3.30(2H, m), 3.39(2H, s), 3.39-3.52(4H, m), 4.11(2H, s), 5.97(2H, s), 6.71-6.76(1H, m), 6.78-6.88(3H, m), 7.09-7.19(2H, m), 7.92(2H, d, J=8.4 Hz), 8.15(2H, d, J=8.4 Hz), 8.20(1H, dd, J=2.7 Hz, 9.0 Hz), 8.42(1H, d, J=2.7 Hz). |
| 1128 | 3,4-Cl₂Ph— | —CH₃ | —CH₃ | —C₂H₅ | 1 | ¹H NMR (DMSO-d₆)δ 0.95(3H, t, J=7.0 Hz), 2.01(3H, s), 2.19(3H, s), 2.20-2.40(4H, m), 3.00(2H, q, J=7.0 Hz), 3.30-3.55(6H, m), 3.79(2H, s), 5.98(2H, s), 6.74(1H, dd, J=7.9 Hz, 1.4 Hz), 6.82-6.86(3H, m), 6.97(1H, d, J=8.9 Hz), 7.05(1H, s), 7.84(1H, d, J=8.4 Hz), 7.94(1H, dd, J=8.4 Hz, 2.0 Hz), 8.15(1H, dd, J=8.9 Hz, 2.7 Hz), 8.21(1H, d, J=2.0 Hz), 8.42(1H, d, J=2.6 Hz), 10.51(1H, brs). |

TABLE 247-continued

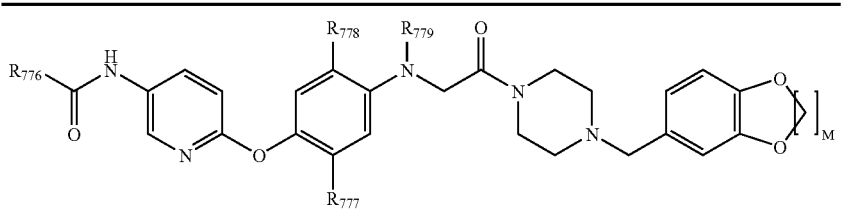

| Example No. | $R_{776}$ | $R_{777}$ | $R_{778}$ | $R_{779}$ | M | mp (° C.) or $^1$H NMR |
|---|---|---|---|---|---|---|
| 1129 | 4-CF$_3$Ph— | —CH$_3$ | —CH$_3$ | —C$_2$H$_5$ | 1 | $^1$H NMR (DMSO-d$_6$)δ 0.95(3H, t, J=7.0 Hz), 2.02(3H, s), 2.19(3H, s), 2.20-2.40(4H, m), 3.00(2H, q, J=7.0 Hz), 3.30-3.60(6H, m), 3.79(2H, s), 5.98(2H, s), 6.74(1H, d, J=7.9 Hz), 6.82-6.85(3H, m), 6.98(1H, d, J=8.6 Hz), 7.05(1H, s), 7.91-7.95(2H, m), 8.14-8.20(3H, m), 8.44(1H, d, J=1.8 Hz), 10.59(1H, brs). |
| 1130 | 4-CF$_3$Ph— | —OCH$_3$ | —H | —H | 2 | $^1$H NMR (CDCl$_3$)δ 2.44(4H, brs), 3.43(4H, brs), 3.49(2H, s), 3.66(3H, s), 3.83(2H, brs), 4.25(4H, s), 4.67(1H, brs), 6.10(1H, dd, J=8.6 Hz, 2.5 Hz), 6.23(1H, d, J=2.5 Hz), 6.75-6.96(5H, m), 7.67(2H, d, J=8.3 Hz), 7.96(2H, d, J=8.1 Hz), 8.10(1H, dd, J=8.9 Hz, 2.6 Hz), 8.20-8.24(1H, m), 8.56(1H, s). |

TABLE 248

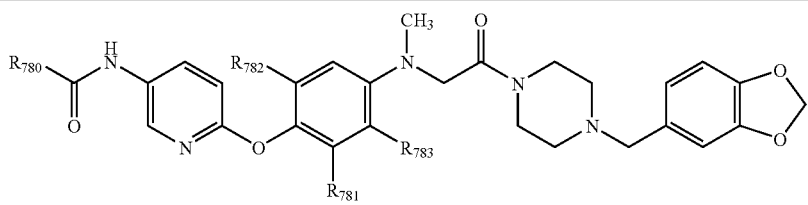

| Example No. | $R_{780}$ | $R_{781}$ | $R_{782}$ | $R_{783}$ | mp (° C.) or $^1$H NMR (solvent) δppm |
|---|---|---|---|---|---|
| 1131 | 5-chloro-2-methylbenzofuran | | —CH$_3$ | —H | —H | $^1$H NMR (CDCl$_3$)2.13(3H, s), 2.43(4H, t, J=4.8 Hz), 3.02(3H, s), 3.44(2H, s), 3.50(2H, brs), 3.64(2H, brs), 4.08(2H, s), 5.94(2H, s), 6.53-6.58(2H, m), 6.74(2H, brs), 6.83(1H, d, J=8.9 Hz), 6.85(1H, s), 6.93(1H, d, J=8.4 Hz), 7.42(1H, dd, J=8.9 Hz, 2.0 Hz), 7.50(1H, d, J=8.9 Hz), 7.53(1H, s), 7.69(1H, d, J=1.8 Hz), 8.19(1H, dd, J=8.9 Hz, 2.8 Hz), 8.26(1H, brs), 8.31(1H, d, J=2.6 Hz). |
| 1132 | 3,4-Cl$_2$Ph— | —F | —F | —H | mp 203.5-204.5 |
| 1133 | 4-CF$_3$Ph— | —F | —F | —H | mp 230.0-231.5 |
| 1134 | 4-ClPh— | —CH$_3$ | —H | —H | $^1$H NMR (CDCl$_3$)2.08(3H, s), 2.42(4H, brs), 2.97(3H, s), 3.43(2H, s), 3.49(2H, brs), 3.60(2H, brs), 4.05(2H, s), 5.94(2H, s), 6.48-6.52(2H, m), 6.74-6.89(5H, m), 7.41(2H, d, J=8.6 Hz), 7.80(2H, d, J=8.4 Hz), 8.08(1H, dd, J=8.9 Hz, 2.8 Hz), 8.21(1H, d, J=2.6 Hz), 8.29(1H, s). |
| 1135 | 2,6-dichlorostyryl | —CH$_3$ | —H | —H | $^1$H NMR (CDCl$_3$)2.11(3H, s), 2.43-2.44(4H, m), 3.00(3H, s), 3.43(2H, s), 3.47-3.49(2H, m), 3.63(2H, brs), 4.07(2H, s), 5.95(2H, s), 6.51-6.57(2H, m), 6.69-6.93(6H, m), 7.19(1H, dd, J=8.7 Hz, 7.5 Hz), 7.35-7.38(2H, m), 7.55(1H, brs), 7.86(1H, d, J=15.8 Hz), 8.17-8.20(2H, m). |

TABLE 248-continued

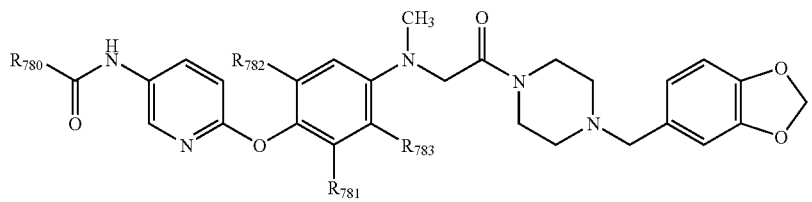

| Example No. | $R_{780}$ | $R_{781}$ | $R_{782}$ | $R_{783}$ | mp (° C.) or $^1$H NMR (solvent) δppm |
|---|---|---|---|---|---|
| 1136 | 2-F-C6H4-CH=CH-CH3 (2-fluorophenyl propenyl) | —CH3 | —H | —H | $^1$H NMR (CDCl$_3$)2.10(3H, s), 2.43(4H, brs), 3.00(3H, s), 3.43(2H, s), 3.50(2H, brs), 3.64(2H, brs), 4.07(2H, s), 5.95(2H, s), 6.50-6.56(2H, m), 6.67-6.92(6H, m), 7.07-7.19(2H, m), 7.31-7.36(1H, m), 7.47-7.52(1H, m), 7.73(1H, brs), 7.80(1H, d, J=15.7 Hz), 8.14-8.20(2H, m). |
| 1137 | Ph-CH=CH-CH=CH-CH3 | —CH3 | —H | —H | $^1$H NMR (CDCl$_3$)2.11(3H, s), 2.41-2.44(4H, m), 3.00(3H, s), 3.43(2H, s), 3.47-3.49(2H, m), 3.63(2H, brs), 4.06(2H, s), 5.94(2H, s), 6.09(1H, d, J=14.7 Hz), 6.51-6.56(2H, m), 6.70-6.96(7H, m), 7.30-7.55(7H, m), 8.14(1H, d, J=2.5 Hz), 8.14(1H, brs). |
| 1138 | 4-CF$_3$Ph— | —F | —H | —F | mp 169.0-170.0 |
| 1139 | 3,4-Cl$_2$Ph— | —F | —H | —F | mp 138.0-139.0 |

TABLE 249

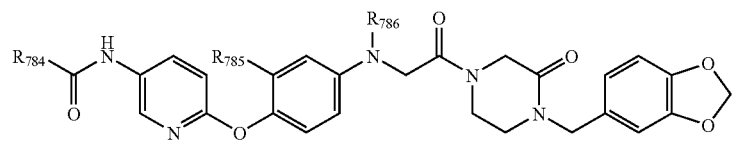

| Example No. | $R_{784}$ | $R_{785}$ | $R_{786}$ | $^1$H NMR (solvent) δppm |
|---|---|---|---|---|
| 1140 | 3,4-Cl$_2$Ph— | —CH$_3$ | —CH$_3$ | (DMSO-d$_6$)2.00(3H, s), 2.93(3H, s), 3.23(1H, brs), 3.36(1H, brs), 3.63(1H, brs), 3.72(1H, brs), 4.07(1H, s), 4.27(1H, s), 4.29(2H, s), 4.47(2H, s), 5.99(2H, s), 6.43-6.63(2H, m), 6.77(1H, dd, J=8.0 Hz, 1.5 Hz), 6.77-6.88(2H, m), 6.82(1H, d, J=8.8 Hz), 6.90(1H, d, J=8.6 Hz), 7.83(1H, d, J=8.4 Hz), 7.94(1H, dd, J=8.4 Hz, 2.0 Hz), 8.12(1H, dd, J=8.8 Hz, 2.6 Hz), 8.21(1H, d, J=2.0 Hz), 8.40(1H, d, J=2.6 Hz), 10.48(1H, s). |
| 1141 | 4-CF$_3$Ph— | —CH$_3$ | —CH$_3$ | (CDCl$_3$)2.10(3H, s), 2.90-3.06(3H, m), 3.20-3.34(2H, m), 3.62-3.84(2H, m), 4.08(2H, s), 4.20-4.33(2H, m), 4.52(2H, s), 5.95(2H, s), 6.53(1H, dd, J=8.6 Hz, 3.0 Hz), 6.58(1H, d, J=3.0 Hz), 6.67-6.79(3H, m), 6.82(1H, d, J=8.9 Hz), 6.91(1H, d, J=8.1 Hz), 7.74(2H, d, J=8.2 Hz), 7.99(2H, d, J=8.2 Hz), 8.10(1H, s), 8.15(1H, dd, J=9.2 Hz, 2.3 Hz), 8.22(1H, d, J=2.3 Hz). |
| 1142 | 3,4-Cl$_2$Ph— | —OCH$_3$ | —C$_2$H$_5$ | (CDCl$_3$)1.17(3H, t, J=6.4 Hz), 3.17-3.30(2H, m), 3.32-3.52(2H, m), 3.70(3H, s), 3.62-3.86(2H, m), 4.03(2H, s), 4.29(2H, s), 4.50 (2H, s), 5.95(2H, s), 6.22(1H, d, J=8.9 Hz), 6.37(1H, s), 6.70(1H, d, J=8.2 Hz), 6.75(1H, s), 6.76(1H, d, J=8.9 Hz), 6.86(1H, d, J=8.9 Hz), 6.94(1H, d, J=8.7 Hz), 7.54(1H, d, J=8.4 Hz), 7.70 (1H, dd, J=8.4 Hz, 2.0 Hz), 7.98(1H, d, J=2.0 Hz), 8.08(1H, s), 8.08(1H, dd, J=8.9 Hz, 2.3 Hz), 8.20(1H, d, J=2.3 Hz). |
| 1143 | 4-CF$_3$Ph— | —OCH$_3$ | —C$_2$H$_5$ | (CDCl$_3$)1.18(3H, t, J=6.7 Hz), 3.16-3.33(2H, m), 3.33-3.50(2H, m), 3.72(2H, s), 3.62-3.85(3H, m), 4.04(2H, s), 4.29(2H, s), 4.50(2H, s), 5.95(2H, s), 6.23(1H, dd, J=8.7 Hz, 2.8 Hz), 6.38(1H, s), 6.71(1H, d, J=8.1 Hz), 6.76(1H, s), 6.76(1H, d, J=8.7 Hz), 6.88(1H, d, J=8.7 Hz), 6.95(1H, d, J=8.7 Hz), 7.74(2H, d, J=8.0 Hz), 7.99(2H, d, J= |

TABLE 249-continued

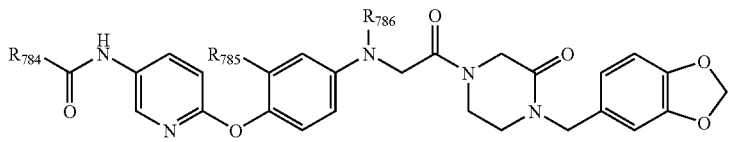

| Example No. | R<sub>784</sub> | R<sub>785</sub> | R<sub>786</sub> | ¹H NMR (solvent) δppm |
|---|---|---|---|---|

8.0 Hz), 8.03(1H, s), 8.13(1H, dd, J=8.7 Hz, 2.4 Hz), 8.21(1H, d, J=2.4 Hz).

TABLE 250

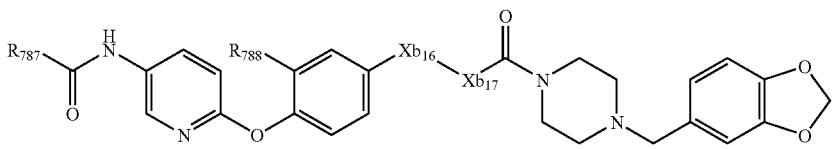

| Example No. | R$_{787}$ | R$_{788}$ | Xb$_{16}$ | Xb$_{17}$ | Form | ¹H NMR (solvent) δppm |
|---|---|---|---|---|---|---|
| 1144 | 4-CF$_3$Ph— | —H | —N(CH$_3$)— | —CH(CH$_3$)— | free | (CDCl$_3$)1.30(3H, d, J=6.3 Hz), 2.16-2.48(4H, m), 2.77(3H, s), 3.26-3.56(3H, m), 3.39(2H, s), 3.78(1H, brs), 4.56(1H, q, J=6.6 Hz), 5.92(2H, s), 6.68-6.77(4H, m), 6.82(1H, s), 6.91(1H, d, J=8.9 Hz), 7.04(2H, d, J=9.1 Hz), 7.76(2H, d, J=8.2 Hz), 7.90(1H, brs), 7.99(2H, d, J=8.1 Hz), 8.17(1H, dd, J=8.9 Hz, 2.6 Hz), 8.25(1H, d, J=2.6 Hz). |
| 1145 | 4-CF$_3$Ph— | —CH$_3$ | —N(CH$_3$)— | —CH(CH$_3$)— | free | (CDCl$_3$)1.29(3H, d, J=6.6 Hz), 2.14(3H, s), 2.14-2.22(1H, m), 2.29-2.35(2H, m), 2.48(1H, brs), 2.76(3H, s), 3.26-3.56(3H, m), 3.39(2H, s), 3.78(1H, brs), 4.57(1H, q, J=6.6 Hz), 5.93(2H, s), 6.58-6.62(2H, m), 6.68-6.75(2H, m), 6.83(1H, brs), 6.86(1H, d, J=8.9 Hz), 6.95(1H, d, J=9.2 Hz), 7.76(2H, d, J=8.3 Hz), 7.90(1H, brs), 7.99(2H, d, J=8.3 Hz), 8.16(1H, dd, J=8.9 Hz, 2.8 Hz), 8.23(1H, d, J=2.5 Hz). |
| 1146 | 3,4-Cl$_2$Ph— | —H | —CH$_2$— | —NH— | hydrochloride | (DMSO-d$_6$)2.78-3.10(2H, m), 3.10-3.35(4H, m), 4.00-4.19(2H, m), 4.18-4.32(4H, m), 6.07(2H, s), 6.95-7.10(3H, m), 7.06(2H, d, J=8.6 Hz), 7.23(1H, s), 7.30(2H, d J=8.6 Hz), 7.39(1H, t, J=5.5 Hz), 7.84(1H, d, J=8.4 Hz), 7.97(1H, dd, J=8.4 Hz, 2.0 Hz), 8.19(1H, dd, J=8.7 Hz, 2.6 Hz), 8.25(1H, d, J=2.0 Hz), 8.48(1H, d, J=2.6 Hz), 10.62(1H, s). |
| 1147 | 4-CF$_3$Ph— | —H | —CH$_2$— | —NH— | hydrochloride | (DMSO-d$_6$)2.80-3.05(2H, m), 3.11-3.38(4H, m), 4.00-4.35(4H, m), 4.24(2H, s), 6.07(2H, s), 6.98(1H, d, J=8.7 Hz), 6.92-7.10(2H, m), 7.06(2H, d, J=8.6 Hz), 7.24(1H, d, J=1.3 Hz), 7.30(2H, d, J=8.6 Hz), 7.35-7.45(1H, m), 7.93(2H, d, J=8.3 Hz), 8.19(2H, d, J=8.3 Hz), 8.22(1H, dd, J=8.7 Hz, 2.5 Hz), 8.51(1H, d, J=2.5 Hz), 10.70(1H, s). |

TABLE 251

| Example No. | R₇₈₉ | R₇₉₀ | R₇₉₁ | ¹H NMR (solvent) δppm |
|---|---|---|---|---|
| 1148 | 4-CF₃Ph— | —CH₃ | —H | (CDCl₃)2.17(3H, s), 2.50-2.55(4H, m), 3.46(2H, s), 3.71-3.74(2H, m), 4.26(2H, brs), 5.95(2H, s), 6.74-6.75(2H, m), 6.86(1H, brs), 6.91-6.95(1H, m), 7.04(1H, d, J=8.7 Hz), 7.43(1H, dd, J=8.7 Hz, 2.5 Hz), 7.56(1H, d, J=2.3 Hz), 7.76(2H, d, J=8.4 Hz), 7.94(1H, brs), 7.99(2H, d, J=8.1 Hz), 8.20-8.23(2H, m), 9.17(1H, brs). |
| 1149 | 3,4-Cl₂Ph— | —CH₃ | —H | (CDCl₃)2.18(3H, s), 2.50-2.56(4H, m), 3.47(2H, s), 3.72-3.75(2H, m), 4.25-4.29(2H, m), 5.96(2H, s), 6.75(2H, brs), 6.86(1H, brs), 6.93(1H, d, J=8.7 Hz), 7.04(1H, d, J=8.7 Hz), 7.44(1H, dd, J=8.7 Hz, 2.6 Hz), 7.56-7.57(1H, m), 7.58(1H, d, J=8.3 Hz), 7.70(1H, brs), 7.71(1H, dd, J=8.3 Hz, 2.1 Hz), 7.98(1H, d, J=2.1 Hz), 8.15-8.21(2H, m), 9.16(1H, brs). |
| 1150 | 3,4-Cl₂Ph— | —CH₃ | —CH₃ | (DMSO-d₆)2.10-2.49(7H, m), 3.26-3.57(9H, m), 5.96-5.99(2H, m), 6.69-6.89(3H, m), 7.05-7.11(2H, m), 7.16-7.28(1H, m), 7.30-7.37(1H, m), 7.84(1H, d, J=8.4 Hz), 7.94(1H, dd, J=8.4 Hz, 2.0 Hz), 8.18-8.22(2H, m), 8.42-8.47(1H, m), 10.54(1H, brs). |
| 1151 | 4-CF₃Ph— | —CH₃ | —CH₃ | (DMSO-d₆)2.10-2.46(7H, m), 3.26-3.57(9H, m), 5.96-6.00(2H, m), 6.69-6.89(3H, m), 7.06-7.12(2H, m), 7.17-7.29(1H, m), 7.31-7.37(1H, m), 7.94(1H, d, J=8.6 Hz), 8.16(2H, d, J=8.6 Hz), 8.21-8.25(2H, m), 8.45-8.49(1H, m), 10.61(1H, brs). |
| 1152 | 4-CF₃Ph— | —H | —SO₂CH₃ | (CDCl₃)2.45(4H, brs), 3.19(3H, s), 3.39(2H, brs), 3.46(2H, s), 3.62(2H, brs), 4.52(2H, s), 5.94(2H, s), 6.74(2H, brs), 6.84(1H, brs), 7.00(1H, d, J=8.7 Hz), 7.10(2H, d, J=8.7 Hz), 7.57(2H, d, J=8.7 Hz), 7.75(2H, d, J=8.1 Hz), 8.00(2H, d, J=8.1 Hz), 8.15-8.24(2H, m), 8.31(1H, brs). |
| 1153 | 3,4-Cl₂Ph— | —CH₃ | —SO₂CH₃ | (CDCl₃)2.16(3H, s), 2.46(4H, brs), 3.20(3H, s), 3.40(2H, brs), 3.47(2H, s), 3.63(2H, brs), 4.52(2H, s), 5.94(2H, s), 6.70-6.77(2H, m), 6.83(1H, brs), 6.95(1H, d, J=9.1 Hz), 6.99(1H, d, J=8.7 Hz), 7.38-7.57(3H, m), 7.71(1H, dd, J=8.4 Hz, 2.0 Hz), 7.97(1H, d, J=2.0 Hz), 8.11(1H, brs), 8.17(1H, dd, J=8.9 Hz, 2.6 Hz), 8.25(1H, d, J=2.6 Hz). |
| 1154 | 4-CF₃Ph— | —CH₃ | —SO₂CH₃ | (CDCl₃)2.18(3H, s), 2.42-2.46(4H, m), 3.21(3H, s), 3.39-3.40(2H, m), 3.44(2H, s), 3.62(2H, brs), 4.53(2H, s), 5.94(2H, s), 6.70-6.77(2H, m), 6.84(1H, brs), 6.96-7.03(2H, m), 7.41-7.46(2H, m), 7.76(2H, d, J=8.2 Hz), 7.98-8.01(3H, m), 8.21(1H, dd, J=8.7 Hz, 2.8 Hz), 8.26(1H, d, J=2.3 Hz). |
| 1155 | 3,4-Cl₂Ph— | —H | —SO₂CH₃ | (CDCl₃)2.41-2.45(4H, m), 3.19(3H, s), 3.38(2H, brs), 3.44(2H, s), 3.61(2H, brs), 4.52(2H, s), 5.94(2H, s), 6.72-6.74(2H, m), 6.83(1H, brs), 6.98(1H, d, J=8.7 Hz), 7.09(2H, d, J=8.7 Hz), 7.55(1H, d, J=8.4 Hz), 7.56(2H, d, J=8.7 Hz), 7.72(1H, dd, J=8.4 Hz, 2.1 Hz), 7.98(1H, d, J=2.1 Hz), 8.18(1H, dd, J=8.7 Hz, 2.8 Hz), 8.27(1H, brs), 8.30(1H, d, J=2.1 Hz). |

TABLE 252

| Example No. | R₇₉₂ | R₇₉₃ | R₇₉₄ | ¹H NMR (CDCl₃) δppm |
|---|---|---|---|---|
| 1156 | 4-CF₃Ph— | —H | —CH₃ | 1.21(3H, t, J=6.8 Hz), 2.05-2.14(1H, m), 2.44-2.51(1H, m), 2.70-2.74(1H, m), 2.83-3.32(6H, m), 3.55-3.59(1H, m), 3.84-4.08(4H, m), 5.94(2H, s), 6.66(2H, d, J=8.9 Hz), 6.74(2H, brs), 6.81-6.85 |

TABLE 252-continued

| Example No. | R₇₉₂ | R₇₉₃ | R₇₉₄ | ¹H NMR (CDCl₃) δppm |
|---|---|---|---|---|
| | | | | (2H, m), 6.97(2H, d, J=8.4 Hz), 7.72(2H, d, J=8.3 Hz), 7.98(2H, d, J=8.3 Hz), 8.11(1H, d, J=9.1 Hz), 8.25(1H, d, J=2.5 Hz), 8.31(1H, brs). |
| 1157 | 4-CF₃Ph— | —CH₃ | —H | 1.26-1.39(3H, m), 1.99-2.04(1H, m), 2.13-2.17(1H, m), 2.64-2.67(1H, m), 2.79-2.83(1H, m), 2.98(4H, brs), 3.31-3.53(3H, m), 3.97-4.66(3H, m), 5.95(2H, s), 6.64(2H, d, J=9.1 Hz), 6.74(2H, brs), 6.82(1H, d, J=8.9 Hz), 6.87(1H, brs), 6.96(2H, d, J=9.1 Hz), 7.71(2H, d, J=7.9 Hz), 7.98(2H, d, J=8.3 Hz), 8.10(1H, dd, J=8.9 Hz, 2.5 Hz), 8.25(1H, d, J=2.5 Hz), 8.40(1H, brs). |
| 1158 | 3,4-Cl₂Ph— | —H | —CH₃ | 1.21(3H, t, J=6.8 Hz), 2.07-2.14(1H, m), 2.43-2.52(1H, m), 2.70(1H, brs), 2.83-3.32(6H, m), 3.55-3.60(1H, m), 3.83-4.08(4H, m), 5.94(2H, s), 6.64(2H, d, J=9.1 Hz), 6.74(2H, brs), 6.81(1H, d, J=8.9 Hz), 6.85(1H, brs), 6.96(2H, d, J=8.7 Hz), 7.53(1H, d, J=8.4 Hz), 7.71(1H, dd, J=8.3 Hz, 2.1 Hz), 7.98(1H, d, J=2.0 Hz), 8.05(1H, dd, J=8.9 Hz, 2.6 Hz), 8.24(1H, d, J=2.5 Hz), 8.31(1H, brs). |
| 1159 | 3,4-Cl₂Ph— | —CH₃ | —H | 1.26-1.39(3H, m), 1.99-2.17(2H, m), 2.64-2.68(1H, m), 2.79-2.84(1H, m), 2.99(4H, brs), 3.31-3.54(3H, m), 4.01-4.68(3H, m), 5.95(2H, s), 6.64(2H, d, J=9.1 Hz), 6.74(2H, brs), 6.81(1H, d, J=8.9 Hz), 6.87(1H, brs), 6.96(2H, d, J=8.9 Hz), 7.53(1H, d, J=8.4 Hz), 7.71(1H, dd, J=8.4 Hz, 2.0 Hz), 7.98(1H, d, J=2.0 Hz), 8.06(1H, dd, J=8.9 Hz, 2.5 Hz), 8.24(1H, d, J=2.3 Hz), 8.26(1H, brs). |

TABLE 253

| Example No. | R₇₉₅ | R₇₉₆ | R₇₉₇ | ¹H NMR (CDCl₃) δppm |
|---|---|---|---|---|
| 1160 | 3,4-Cl₂Ph— | —H | —CH₃ | 1.16-1.19(6H, m), 2.04-2.14(1H, m), 2.43-2.52(1H, m), 2.66-2.74(1H, m), 2.83-3.36(5H, m), 3.59-3.63(1H, m), 3.84-4.08(4H, m), 5.94(2H, s), 6.59(2H, d, J=8.9 Hz), 6.74(2H, brs), 6.79(1H, d, J=8.9 Hz), 6.85(1H, brs), 6.92(2H, d, J=8.9 Hz), 7.50(1H, d, J=8.4 Hz), 7.71(1H, dd, J=8.4 Hz, 2.1 Hz), 7.98(1H, d, J=2.0 Hz), 8.03(1H, dd, J=8.9 Hz, 2.6 Hz), 8.25(1H, d, J=2.3 Hz), 8.64(1H, brs). |
| 1161 | 4-CF₃Ph— | —H | —CH₃ | 1.09-1.15(6H, m), 2.04-2.13(1H, m), 2.43-2.51(1H, m), 2.66-2.74(1H, m), 2.83-3.38(5H, m), 3.58-3.63(1H, m), 3.84-4.08(4H, m), 5.94(2H, s), 6.61(2H, d, J=8.9 Hz), 6.74(2H, brs), 6.81(1H, d, J=8.9 Hz), 6.85(1H, brs), 6.94(2H, d, J=8.3 Hz), 7.71(2H, d, J=7.8 Hz), 7.99(2H, d, J=8.1 Hz), 8.10(1H, d, J=9.1 Hz), 8.26(1H, d, J=2.5 Hz), 8.50(1H, brs). |
| 1162 | 3,4-Cl₂Ph— | —CH₃ | —H | 1.15(3H, t, J=7.1 Hz), 1.26-1.43(3H, m), 2.00(1H, brs), 2.13(1H, brs), 2.64-2.68(1H, m), 2.79-2.83(1H, m), 3.02-4.68(9H, m), 5.95(2H, s), 6.61(2H, d, J=9.1 Hz), 6.74(2H, brs), 6.81(1H, d, J=8.7 Hz), 6.87(1H, brs), 6.94(2H, d, J=8.9 Hz), 7.53(1H, d, J=8.4 Hz), 7.71(1H, dd, J=8.4 Hz, 2.1 Hz), 7.99(1H, d, J=2.0 Hz), 8.06(1H, d, J=8.9 Hz), 8.25(1H, d, J=2.6 Hz), 8.32(1H, brs). |

TABLE 253-continued

![Structure for Table 253: R795-C(=O)-NH-pyridine-O-phenyl-N(CH2CH3)-C(=O)-piperazine(R796,R797)-CH2-benzodioxole]

| Example No. | R795 | R796 | R797 | 1H NMR (CDCl3) δppm |
|---|---|---|---|---|
| 1163 | 4-CF3Ph— | —CH3 | —H | 1.15(3H, t, J=6.9 Hz), 1.26-1.39(3H, m), 1.99(1H, brs), 2.13(1H, brs), 2.63-2.67(1H, m), 2.79-2.83(1H, m), 3.00-4.67(9H, m), 5.95(2H, s), 6.61(2H, d, J=8.4 Hz), 6.74(2H, brs), 6.82(1H, d, J=8.7 Hz), 6.87(1H, brs), 6.95(2H, d, J=8.9 Hz), 7.71(2H, d, J=7.9 Hz), 7.99(2H, d, J=8.1 Hz), 8.10(1H, d, J=8.3 Hz), 8.27(1H, d, J=2.5 Hz), 8.38(1H, brs). |

TABLE 254

![Structure for Table 254: R798-C(=O)-NH-pyridine-O-phenyl-N(R799)-C(=O)-CH2-piperazine-CH2-benzodioxole]

| Example No. | R798 | R799 | 1H NMR (CDCl3) δ ppm |
|---|---|---|---|
| 1164 | 4-CF3Ph— | —H | 2.52(4H, brs), 2.64(4H, brs), 3.12(2H, s), 3.45(2H, brs), 5.94(2H, s), 6.75 (2H, brs), 6.86(1H, brs), 6.95(1H, d, J=8.7 Hz), 7.11(2H, d, J=8.9 Hz), 7.60(2H, d, J=8.9 Hz), 7.76(2H, d, J=8.3 Hz), 7.98(1H, brs), 8.00(2H, d, J=8.3 Hz), 8.21(1H, dd, J=8.9 Hz, 2.8 Hz), 8.26(1H, d, J=2.5 Hz), 9.16(1H, brs). |
| 1165 | 3,4-Cl2Ph— | —H | 2.52(4H, brs), 2.62-2.64(4H, m), 3.12(2H, s), 3.45(2H, brs), 5.95(2H, s), 6.75(2H, bre), 6.86(1H, brs), 6.94(1H, d, J=8.7 Hz), 7.10(2H, d, J=8.9 Hz), 7.57(1H, d, J=8.4 Hz), 7.59(2H, d, J=8.9 Hz), 7.72(1H, dd, J=8.4 Hz, 2.1 Hz), 7.99(2H, brs), 8.17(1H, dd, J=8.9 Hz, 2.8 Hz), 8.25(1H, d, J=2.8 Hz), 9.17(1H, brs). |
| 1166 | 3,4-Cl2Ph— | —CH3 | 2.44(8H, brs), 2.95(2H, s), 3.26(3H, s), 3.39(2H, s), 5.92(2H, s), 6.71(2H, brs), 6.81(1H, brs), 7.02(1H, d, J=8.7 Hz), 7.14-7.22(4H, m), 7.58(1H, d, J=8.4 Hz), 7.77(1H, dd, J=8.4 Hz, 2.1 Hz), 8.05(1H, d, J=2.1 Hz), 8.27(1H, dd, J=8.7 Hz, 2.6 Hz), 8.32(1H, d, J=2.6 Hz), 8.33(1H, brs). |
| 1167 | 4-CF3Ph— | —CH3 | 2.50(8H, brs), 2.95(2H, s), 3.24(3H, s), 3.47(2H, s), 5.92(2H, s), 6.72(2H, brs), 6.81(1H, brs), 7.02(1H, d, J=8.7 Hz), 7.13-7.21(4H, m), 7.74(2H, d, J=8.4 Hz), 8.05(2H, d, J=8.1 Hz), 8.30(1H, dd, J=8.9 Hz, 2.5 Hz), 8.35(1H, d, J=2.3 Hz), 8.61(1H, brs). |

TABLE 255

![Structure for Table 255: R800-C(=O)-NH-pyridine-O-phenyl-N(CH3)-(CH2)M-C(=O)-piperazine-R801]

| Example No. | R800 | R801 | M | Form | 1H NMR (solvent) δ ppm |
|---|---|---|---|---|---|
| 1168 | 3,4-Cl2Ph— | piperonyl | 2 | hydrochloride | (DMSO-d6) 2.60-2.61(2H, m), 2.75-3.08(6H, m), 3.22-3.60 (5H, m), 4.03(1H, d, J=13.9 Hz), 4.20(2H, d, J=4.3 Hz), 4.46(1H, d, J=13.9 |

TABLE 255-continued

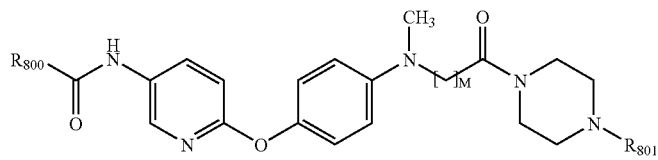

| Example No. | $R_{800}$ | $R_{801}$ | M | Form | $^1$H NMR (solvent) δ ppm |
|---|---|---|---|---|---|
| | | | | | Hz), 6.06(2H, s), 6.73(2H, d, J=8.9 Hz), 6.93-6.99(5H, m), 7.20(1H, brs), 7.83(1H, d, J=8.4 Hz), 7.96(1H, dd, J=8.4 Hz, 2.1 Hz), 8.14(1H, dd, J=8.9 Hz, 2.6 Hz), 8.23(1H, d, J=2.0 Hz), 8.45(1H, d, J=2.6 Hz), 10.57(1H, brs), 11.00(1H, brs). |
| 1169 | 4-CF$_3$Ph— | piperonyl | 2 | hydrochloride | (DMSO-d$_6$) 2.60-2.62(2H, m), 2.88-3.08(6H, m), 3.23-3.60 (5H, m), 4.01-4.06(1H, m), 4.20-4.21(2H, m), 4.43-4.49(1H, m), 6.07(2H, s), 6.73(2H, d, J=8.6 Hz), 6.94-6.99(5H, m), 7.20(1H, brs), 7.93(2H, d, J=8.2 Hz), 8.14-8.19(3H, m), 8.47(1H, d, J=2.5 Hz), 10.64(1H, brs), 11.00(1H, brs). |
| 1170 | 4-CF$_3$Ph— | benzyl | 0 | free | (CDCl$_3$) 2.25(4H, t, J=4.9 Hz), 3.19(3H, s), 3.23(4H, t, J=4.9 Hz), 3.43(2H, s), 6.95(1H, d, J=8.7 Hz), 7.08(4H, s), 7.20-7.32(5H, m), 7.75(2H, d, J=8.0 Hz), 8.02(2H, d, J=8.0 Hz), 8.24(1H, dd, J=8.7 Hz, 2.5 Hz), 8.31(1H, d, J=2.5 Hz), 8.34(1H, s). |
| 1171 | 3,4-Cl$_2$Ph— | benzyl | 0 | hydrochloride | (DMSO-d$_6$) 2.70-3.00(2H, m), 3.14(3H, s), 2.95-3.30(4H, m), 3.72(2H, d, J=13.7 Hz), 4.29(2H, s), 7.08(1H, d, J=8.7 Hz), 7.11(2H, d, J=8.9 Hz), 7.23(2H, d, J=8.9 Hz), 7.39-7.48(3H, m), 7.51-7.60(2H, m), 7.84(1H, d, J=8.5 Hz), 7.97(1H, dd, J=8.5 Hz, 2.0 Hz), 8.22(1H, dd, J=8.7 Hz, 2.6 Hz), 8.25(1H, d, J=2.0 Hz), 8.53(1H, d, J=2.6 Hz), 10.67(1H, s). |

TABLE 256

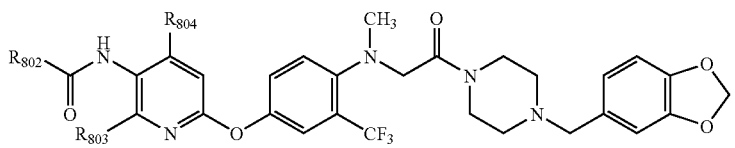

| Example No. | $R_{802}$ | $R_{803}$ | $R_{804}$ | $^1$H NMR (CDCl$_3$) δ ppm |
|---|---|---|---|---|
| 1172 | 3,4-Cl$_2$Ph— | —H | —CH$_3$ | 2.34(3H, s), 2.34-2.50(4H, m), 2.78(3H, s), 3.42(2H, s), 3.50-3.70(4H, m), 3.80(2H, s), 5.95(2H, s), 6.70-6.80(2H, m), 6.85-6.89(2H, m), 7.26-7.35(1H, m), 7.40(1H, d, J=2.8 Hz), 7.51 (1H, d, J=8.9 Hz), 7.57-7.61(2H, m), 7.74(1H, dd, J=8.3 Hz, 2.0 Hz), 8.01(1H, d, J=2.0 Hz), 8.29(1H, s). |
| 1173 | 4-CF$_3$Ph— | —H | —CH$_3$ | 2.36(3H, s), 2.36-2.50(4H, m), 2.79(3H, s), 3.42(2H, s), 3.50-3.65(4H, m), 3.80(2H, s), 5.94(2H, s), 6.70-6.75(2H, m), 6.856.90(2H, m), 7.30(1H, dd, J=8.8 Hz, 2.7 Hz), 7.40(1H, d, J=2.8 Hz), 7.51(1H, d, J=8.8 Hz), 7.68(1H, brs), 7.76-7.80(2H, m), 8.01-8.04(2H, m), 8.34(1H, s). |

TABLE 256-continued

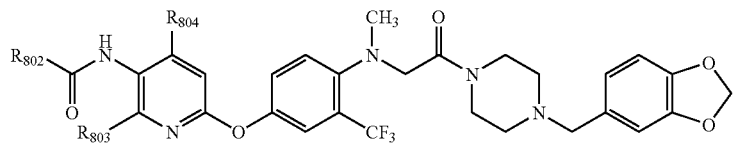

| Example No. | $R_{802}$ | $R_{803}$ | $R_{804}$ | $^1$H NMR (CDCl$_3$) δ ppm |
|---|---|---|---|---|
| 1174 | 3,4-Cl$_2$Ph— | —CH$_3$ | —H | 2.30-2.44(4H, m), 2.44(3H, s), 2.79(3H, s), 3.42(2H, s), 3.50-3.65(4H, m), 3.80(2H, s), 5.95(2H, s), 6.65-6.81(3H, m), 6.85(1H, s), 7.29(1H, dd, J=8.8 Hz, 2.8 Hz), 7.41(1H, d, J=2.7 Hz), 7.49(1H, d, J=8.8 Hz), 7.59(1H, d, J=8.3 Hz), 7.67(1H, brs), 7.72(1H, dd, J=8.3 Hz, 2.1 Hz), 8.00(1H, d, J=2.0 Hz), 8.09(1H, d, J=8.7 Hz). |
| 1175 | 4-CF$_3$Ph— | —CH$_3$ | —H | 2.35-2.45(4H, m), 2.45(3H, s), 2.79(3H, s), 3.42(2H, s), 3.50-3.65(4H, m), 3.80(2H, s), 5.95(2H, s), 6.65-6.82(2H, m), 6.85(1H, s), 7.30(1H, dd, J=8.8 Hz, 2.8 Hz), 7.41(1H, d, J=2.8 Hz), 7.50(1H, d, J=8.8 Hz), 7.72(1H, brs), 7.77-7.80(2H, m), 8.00-8.03(2H, m), 8.15(1H, d, J=8.6 Hz). |

TABLE 257

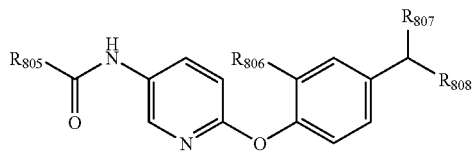

| Example No. | $R_{805}$ | $R_{806}$ | $R_{807}$ | $R_{808}$ | Form | $^1$H NMR (DMSO-d$_6$) δ ppm |
|---|---|---|---|---|---|---|
| 1176 | 3,4-Cl$_2$Ph— | —H | —H | (5-methyl-2,4-dioxothiazolidin-5-yl) | free | 3.14(1H, dd, J=14.0 Hz, 9.4 Hz), 3.40(1H, dd, J=14.0 Hz, 4.5 Hz), 4.93(1H, dd, J=9.4 Hz, 4.5 Hz), 7.07(1H, d, J=8.9 Hz), 7.07(2H, d, J=8.4 Hz), 7.29(2H, d, J=8.4 Hz), 7.84(1H, d, J=8.4 Hz), 7.95(1H, dd, J=8.4 Hz, 2.0 Hz), 8.20(1H, dd, J=8.9 Hz, 2.5 Hz), 8.22(1H, d, J=2.0 Hz), 8.48(1H, d, J=2.5 Hz), 10.56(1H, s), 12.06(1H, s). |
| 1177 | 4-CF$_3$OPh— | —CH$_3$ | —H | (5-methyl-2,4-dioxothiazolidin-5-yl) | hydrochloride | 2.09(3H, s), 3.09(1H, dd, J=14.3 Hz, 9.6 Hz), 3.40(1H, dd, J=14.3 Hz, 4.3 Hz), 4.93(1H, dd, J=9.6 Hz, 4.3 Hz), 6.99(1H, d, J=8.1 Hz), 7.02 (1H, d, J=8.9 Hz), 7.12(1H, d, J=8.1 Hz), 7.20 (1H, s), 7.55(2H, d, J=8.8 Hz) 8.10(2H, d, J=8.8 Hz), 8.20(1H, dd, J=8.9 Hz, 2.6 Hz), 8.44 (1H, d, J=2.6 Hz), 10.54(1H, s), 12.10(1H, s). |
| 1178 | 3,4-Cl$_2$Ph— | —H | —CH$_3$ | morpholino | hydrochloride | 1.70(3H, d, J=6.9 Hz), 2.94-3.01 (2H, m), 3.63-4.02(6H, m), 4.50 (1H, t, J=6.6 Hz), 7.13 (1H, d, J=9.1 Hz), 7.23(2H, d, J=8.7 Hz), 7.64 (2H, d, J=8.7 Hz), 7.85(1H, d, J=8.4 Hz), 7.96 (1H, dd, J=8.4 Hz, 2.2 Hz), 8.23(1H, dd, J=8.9 Hz, 2.6 Hz), 8.24(1H, d, J=2.1 Hz), 8.54(1H, d, J=2.1 Hz), 10.63(1H, brs), 10.89(1H, brs). |

TABLE 257-continued
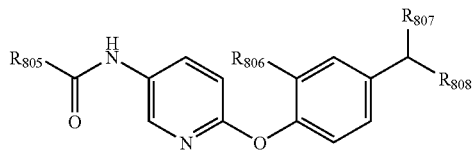
| Example No. | $R_{805}$ | $R_{806}$ | $R_{807}$ | $R_{808}$ | Form | $^1$H NMR (DMSO-$d_6$) δ ppm |
|---|---|---|---|---|---|---|
| 1179 | 4-CF$_3$Ph— | —H | —CH$_3$ | morpholino | hydrochloride | 1.72(3H, d, J=6.6 Hz), 2.92(2H, brs), 3.35(2H, brs), 3.69-3.99(4H, m), 4.49(1H, brs), 7.14(1H, d, J=8.7 Hz), 7.22(2H, d, J=8.3 Hz), 7.69(2H, d, J=8.3 Hz), 7.94(2H, d, j =8.3 Hz), 8.20(2H, d, J=8.1 Hz), 8.28(1H, d, J=8.9 Hz), 8.58(1H, brs), 10.77(1H, brs), 11.47(1H, brs). |
| 1180 | Ph— | —H | —CH$_3$ | morpholino | hydrochloride | 1.70(3H, d, J=6.8 Hz), 2.94(2H, brs), 3.38-3.43 (2H, m), 3.62-4.02(4H, m), 4.50(1H, t, J=6.6 Hz), 7.12(1H, d, J=8.7 Hz), 7.29(2H, d, J=8.6 Hz), 7.52-7.65(5H, m), 7.96-8.O0(2H, m), 8.26(1H, dd, J=8.7 Hz, 2.8 Hz), 8.56(1H, d, J=2.8 Hz), 10.47(1H, brs), 10.91(1H, brs). |
TABLE 258
| Example No. | Chemical structure | mp (° C.) |
|---|---|---|
| 1181 | 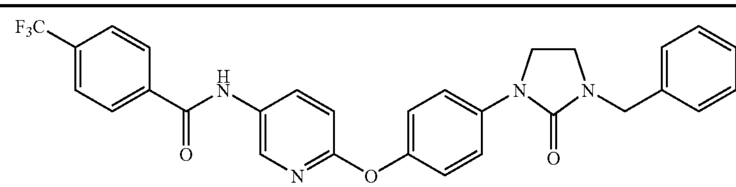 | 203.0-204.0 |
| 1182 | 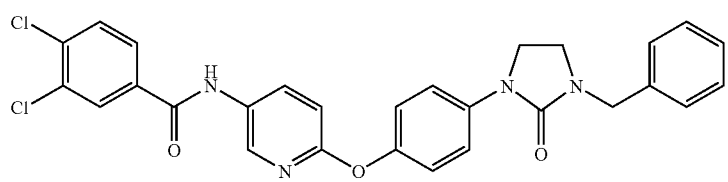 | 186.0-187.0 |
| 1183 | 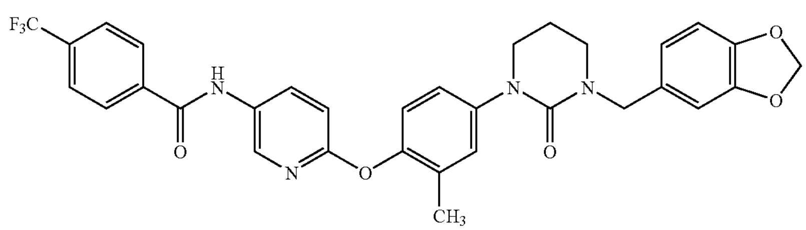 | 165.0-166.0 |
| 1184 | 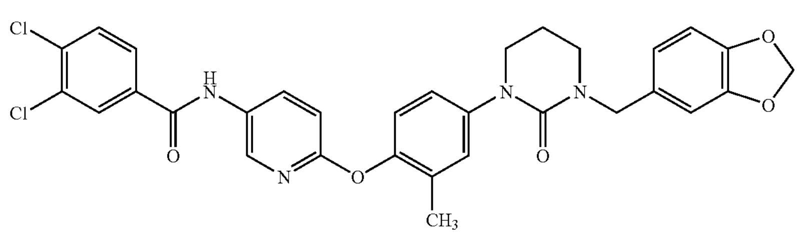 | 122.0-124.0 |

TABLE 258-continued
| Example No. | Chemical structure | mp (° C.) |
|---|---|---|
| 1185 | 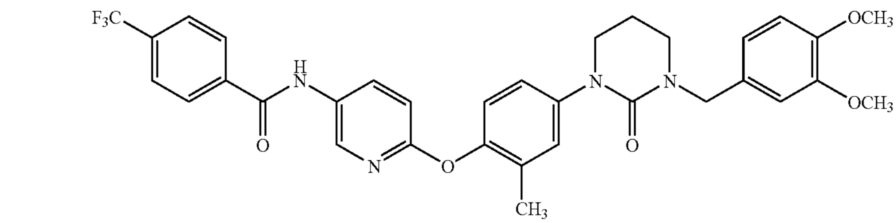 | 155.0-157.0 |
| 1186 | 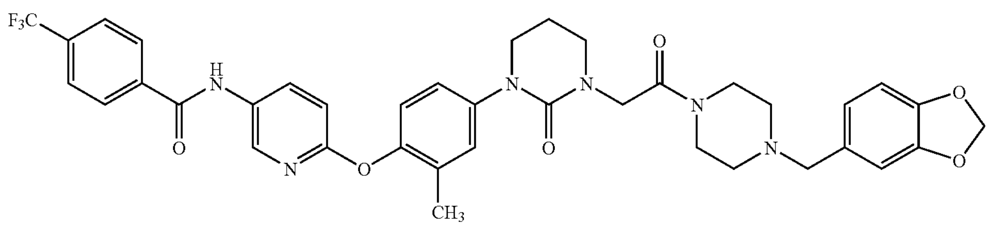 | 182.0-183.5 |
| 1187 | 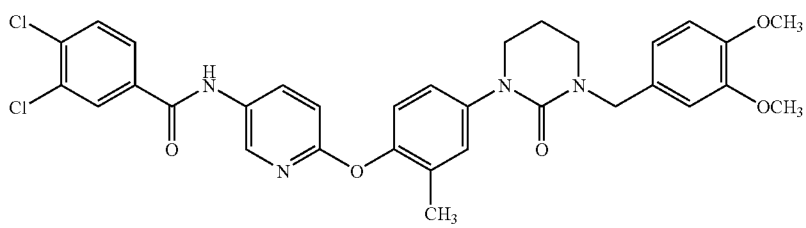 | 117.0-118.0 |
| 1188 | 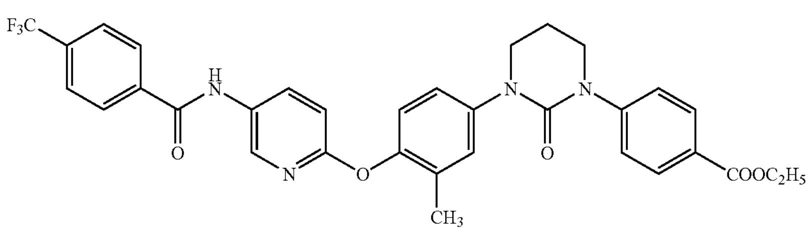 | 160.0-161.0 |
TABLE 259
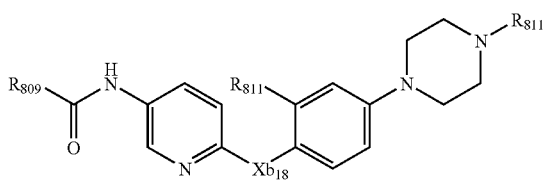
| Example No. | $R_{809}$ | $R_{810}$ | $R_{811}$ | $Xb_{18}$ | $^1$H NMR (CDCl$_3$) δ ppm |
|---|---|---|---|---|---|
| 1189 | 4-CF$_3$Ph— | —COOCH$_3$ | benzyl | —O— | 2.62(4H, brs), 3.23(4H, brs), 3.58(2H, s), 3.67(3H, s), 6.95(1H, d, J=9.7 Hz), 7.06-7.14(2H, m), 7.26-7.36(5H, m), 7.49 (1H, d, J=2.3 Hz), 7.74(2H, d, J=8.3 Hz), 7.87(1H, s), 7.98(2H, d, J=8.1 Hz), 8.16-8.18(2H, m). |
| 1190 | 3,4-Cl$_2$Ph— | H | —COOC(CH$_3$)$_3$ | —O— | 1.49(9H, s), 3.11(4H, t, J=4.8 Hz), 3.58 (4H, t, J=4.8 Hz), 6.92(1H, d, J=9.0 Hz), 6.96(2H, d, J=8.5 Hz), 7.06(2H, d, J=8.5 Hz), 7.58(1H, d, J=8.5 Hz), 7.70 (1H, dd, J=8.5 Hz, 2.0 Hz), |

TABLE 259-continued

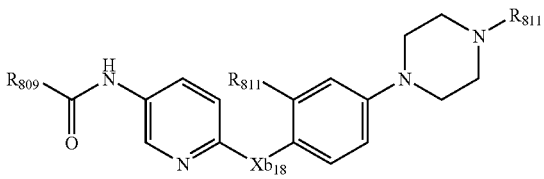

| Example No. | $R_{809}$ | $R_{810}$ | $R_{811}$ | $Xb_{18}$ | $^1$H NMR (CDCl$_3$) δ ppm |
|---|---|---|---|---|---|
| 1191 | 4-CF$_3$Ph— | —H | —COOC(CH$_3$)$_3$ | —O— | 7.74(1H, brs), 7.98(1H, d, J=2.0 Hz), 8.15(1H, brd, J=9.0 Hz), 8.24 (1H, d, J=2.5 Hz). 1.49(9H, s), 3.11(4H, t, J=5.0 Hz), 3.58 (4H, t, J=5.0 Hz), 6.93(1H, d, J=9.0 Hz), 6.96(2H, d, J=9.0 Hz), 7.06(2H, d, J=9.0 Hz), 7.77(2H, d, J=8.0 Hz), 7.82 (2H, brs), 7.99(2H, d, J=8.0 Hz), 8.19 (1H, dd, J=9.0 Hz, 2.5 Hz), 8.25(1H, d, J=2.5 Hz). |
| 1192 | 4-CF$_3$Ph— | —H | —CH$_2$COOC$_2$H$_5$ | —N(CH$_3$)— | 1.30(3H, t, J=7.1 Hz), 2.77(4H, t, J=5.0 Hz), 3.28(4H, t, J=5.0 Hz), 3.29(2H, s), 3.42(3H, s), 4.22(2H, q, J=7.1 Hz), 6.47(1H, d, J=9.2 Hz), 6.96(2H, d, J=9.0 Hz), 7.15(2H, d, J=9.0 Hz), 7.69(1H, brs), 7.70 (1H, d, J=2.5 Hz), 7.74(2H, d, J=8.1 Hz), 7.98(2H, d, J=8.1 Hz), 8.26 (1H, d, J=2.5 Hz). |

TABLE 260

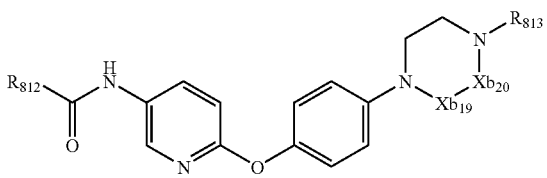

| Example No. | $R_{812}$ | $R_{813}$ | $Xb_{19}$ | $Xb_{20}$ | $^1$H NMR (solvent) δ ppm |
|---|---|---|---|---|---|
| 1193 | 3,4-Cl$_2$Ph— | —COOC(CH$_3$)$_3$ | —CO— | —CH$_2$— | (CDCl$_3$) 1.51(9H, s), 3.75(2H, m), 3.79(2H, m), 4.26(2H, s), 6.98(1H, d, J=8.8 Hz), 7.14(2H, dd, J=6.9 Hz, 2.1 Hz), 7.28(2H, dd, J=6.9 Hz, 2.1 Hz), 7.58(1H, d, J=8.3 Hz), 7.72(1H, dd, J=8.3 Hz, 2.1 Hz), 7.99 (1H, d, J=2.1 Hz), 8.13(1H, dd, J=8.8 Hz, 2.7 Hz), 8.29(1H, d, J=2.7 Hz). |
| 1194 | 3,4-Cl$_2$Ph— | piperonyl | —CH$_2$— | —CO— | (DMSO-d$_6$) 3.22-3.50(4H, m), 3.84(2H, s), 4.50(2H, s), 6.00(2H, s), 6.77(1H, dd, J=8.0 Hz, 1.4 Hz), 6.84(1H, d, J=1.4 Hz), 6.87(1H, d, J=8.0 Hz), 6.98(2H, d, J=8.6 Hz), 6.97-7.06(3H, m), 7.84(1H, d, J=8.4 Hz), 7.94(1H, dd, J=8.4 Hz, 2.0 Hz), 8.15 (1H, dd, J=8.9 Hz, 2.8 Hz), 8.22(1H, d, J=2.0 Hz), 8.44(1H, d, J=2.3 Hz), 10.51 (1H, s). |
| 1195 | 4-CF$_3$Ph— | piperonyl | —CH$_2$— | —CO— | (DMSO-d$_6$) 3.27-3.40(2H, m), 3.40-3.50 (2H, m), 3.85(2H, s), 4.50(2H, s), 6.00(2H, s), 6.77(1H, dd, J=7.9 Hz, 1.5 Hz), 6.84 (1H, d, J=1.5 Hz), 6.88(1H, d, J=7.9 Hz), 6.957.07(5H, m), 7.93(2H, d, J=8.1 Hz), 8.16(2H, d, J=8.1 Hz), 8.17(1H, dd, J=8.8 Hz, 2.5 Hz), 8.46(1H, d, J=2.5 Hz), 10.60(1H, s). |

TABLE 261

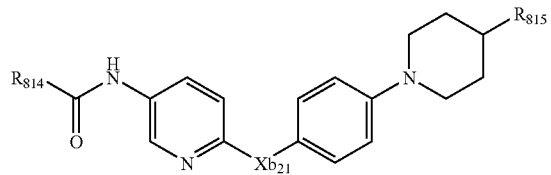

| Example No. | $R_{814}$ | $R_{815}$ | $Xb_{21}$ | $^1$H NMR (CDCl$_3$) δ ppm |
|---|---|---|---|---|
| 1196 | 3,4-Cl$_2$Ph— | —COOC$_2$H$_5$ | —O— | 1.28(3H, t, J=7.0 Hz), 1.88-1.93(2H, m), 2.03(2H, brd, J=10.0 Hz), 2.42(1H, m), 2.78(1H, t, J=10.5 Hz), 3.59(2H, dt, J=12.5 Hz, 3.5 Hz), 4.16(2H, q, J=7.0 Hz), 6.90(1H, d, J=9.0 Hz), 6.95(2H, d, J=9.0 Hz), 7.03(2H, d, J=9.0 Hz), 7.58(1H, d, J=8.5 Hz), 7.70(1H, brs), 7.71(1H, dd, J=8.5 Hz, 2.0 Hz), 7.98 (1H, d, J=2.0 Hz), 8.14(1H, dd, J=9.0 Hz, 2.5 Hz), 8.24(1H, d, J=2.5 Hz). |
| 1197 | 3,4-Cl$_2$Ph— | —CH$_2$COOC$_2$H$_5$ | —O— | 1.27(3H, t, J=7.0 Hz), 1.40-1.46(2H, m), 1.82(2H, brd, J=13.0 Hz), 1.90(1H, m), 2.27(2H, d, J=7.0 Hz), 2.69(2H, brt, J=13.0 Hz), 3.57(2H, brd, J=12.0 Hz), 4.15 (2H, q, J=7.0 Hz), 6.83(1H, d, J=9.0 Hz), 6.90(2H, d, J=9.0 Hz), 6.97(2H, d, J=9.0 Hz), 7.49(1H, d, J=8.5 Hz), 7.68(1H, dd, J=8.5 Hz, 2.0 Hz), 7.95(1H, d, J=2.0 Hz), 8.10(1H, dd, J=9.0 Hz, 2.5 Hz), 8.2 1(1H, d, J=2.5 Hz), 8.48(1H, brs). |
| 1198 | 4-CF$_3$Ph— | —CH$_2$COOC$_2$H$_5$ | —N(CH$_3$)— | 1.28(3H, t, J=7.1 Hz), 1.46(2H, qd, J=12.2 Hz, 3.4 Hz), 1.86(2H, d, J=13.5 Hz), 1.85-2.10(1H, m), 2.30 (2H, d, J=7.1 Hz) 2.76(2H, td, J=12.2 Hz, 2.2 Hz), 3.42(3H, s), 3.68(2H, d, J=12.2 Hz), 4.16(2H, q, J=7.1 Hz), 6.46(1H, d, J=9.0 Hz), 6.96(2H, d, J=8.9 Hz), 7.13(2H, d, J=8.9 Hz), 7.72(1H, dd, J=9.0 Hz, 2.5 Hz), 7.73(1H, d, J=2.5 Hz), 7.74(2H, d, J=8.2 Hz), 7.98(2H, d, J=8.2 Hz), 8.26(1H, d, J=2.5 Hz). |
| 1199 | 4-CF$_3$Ph— | —CH$_2$COOC$_2$H$_5$ | —O— | 1.28(3H, t, J=7.0 Hz), 1.44(2H, dq, J=3.5 Hz, 12.0 Hz), 1.84(2H, brd, J=13.0 Hz), 1.93(1H, m), 2.29 (2H, d, J=7.0 Hz), 2.73(2H, dt, J=2.5 Hz, 12.0 Hz), 3.61(2H, brd, J=12.0 Hz), 4.15(2H, q, J=7.0 Hz), 6.91(1H, d, J=9.0 Hz), 6.96(2H, d, J=9.0 Hz), 7.04 (2H, d, J=9.0 Hz), 7.74(1H, brs), 7.77(2H, d, J=8.5 Hz), 7.99(2H, d, J=8.5 Hz), 8.18(1H, dd, J=9.0 Hz, 2.5 Hz), 8.25(1H, d, J=2.5 Hz). |
| 1200 | 4-CF$_3$Ph— | —COOC$_2$H$_5$ | —O— | 1.26(3H, t, J=7.1 Hz), 1.77-1.98(4H, m), 2.35-2.43(1H, m), 2.68-2.76(2H, m), 3.51-3.55(2H, m), 4.14(2H, q, J=7.1 Hz), 6.78(1H, d, J=8.9 Hz), 6.85-6.95(4H, m), 7.61(2H, d, J=8.2 Hz), 7.93(2H, d, J=8.1 Hz), 8.09(1H, dd, J=8.9 Hz, 2.6 Hz), 8.25(1H, d, J=2.6 Hz), 9.00(1H, s). |

TABLE 262

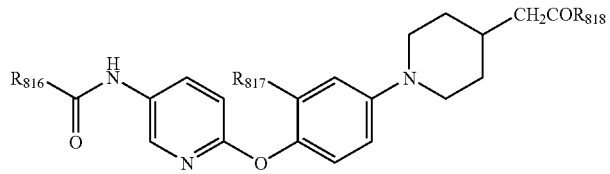

| Example No. | R816 | R817 | R818 | $^1$H NMR (CDCl$_3$) δ ppm |
|---|---|---|---|---|
| 1201 | 4-CF$_3$Ph— | —CH$_3$ | 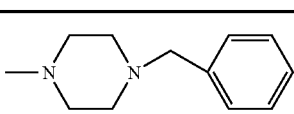 | 1.31-1.43(2H, m), 1.80-1.98(3H, m), 2.10(3H, s), 2.26(2H, d, J=6.8 Hz), 2.38-2.44(4H, m), 2.66(2H, t, J=12.2 Hz), 3.46-3.63(8H, m), 6.72-6.81(3H, m), 6.90(1H, d, J=8.6 Hz), 7.26 7.33(5H, m), 7.70(2H, d, J=8.2 Hz), 8.00(2H, d, J=8.1 Hz), 8.15(1H, dd, J=8.9 Hz, 2.8 Hz), 8.25(1H, d, J=2.5 Hz), 8.60(1H, s). |
| 1202 | 4-CF$_3$Ph— | —CH$_3$ | 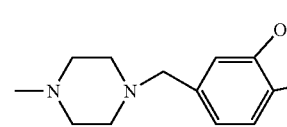 | 1.31-1.43(2H, m), 1.79-1.98(3H, m), 2.11(3H, s), 2.26(2H, d, J=6.8 Hz), 2.36-2.39(4H, m), 2.66(2H, t, J=12.0 Hz), 3.42(2H, s), 3.45-3.61(6H, m), 6.70-6.92(7H, m), 7.70(2H, d, J=8.2 Hz), 7.99(2H, d, J=8.1 Hz), 8.15(1H, dd, J=8.9 Hz, 2.8 Hz), 8.25(1H, d, J=2.5 Hz), 8.55(1H, s). |
| 1203 | 4-Cl$_2$Ph— | —CH$_3$ | 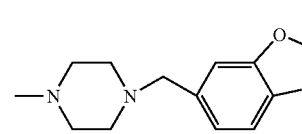 | 1.29-1.41(2H, m), 1.77-1.98(3H, m), 2.09(3H, s), 2.26(2H, d, J=6.8 Hz), 2.34-2.40(4H, m), 2.62(2H, t, J=12.0 Hz), 3.41(2H, s), 3.46-3.60(6H, m), 6.70-6.90(7H, m), 7.49(1H, d, J=8.4 Hz), 7.73(1H, dd, J=8.2 Hz, 2.0 Hz), 7.99(1H, d, J=2.0 Hz), 8.12(1H, dd, J=8.9 Hz, 2.6 Hz), 8.25(1H, d, J=2.6 Hz), 8.99(1H, s). |
| 1204 | 4-Cl$_2$Ph— | —CH$_3$ | 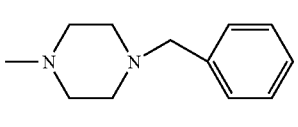 | 1.29-1.41(2H, m), 1.77-1.98(3H, m), 2.09(3H, s), 2.26(2H, d, J=6.8 Hz), 2.37-2.44(4H, m), 2.63(2H, t, J=11.9 Hz), 3.48-3.63(8H, m), 6.70 6.78(2H, m), 6.88(1H, d, J=8.6 Hz), 7.26-7.33(6H, m), 7.48(1H, d, J=8.4 Hz), 7.72(1H, dd, J=8.4 Hz, 2.1 Hz), 7.99(1H, d, J=2.1 Hz), 8.12(1H, dd, J=8.9 Hz, 2.6 Hz), 8.26(1H, d, J=2.6 Hz), 9.03(1H, s). |
| 1205 | 4-CF$_3$Ph— | —OCH$_3$ | —OC$_2$H$_5$ | 1.27(3H, t, J=7.1 Hz), 1.39-1.42(2H, m), 1.80-1.85(3H, m), 2.28(2H, d, J=6.9 Hz), 2.70(3H, t, J=10.1 Hz), 3.56(2H, d, J=12.2 Hz), 3.66(3H, s), 4.14(2H, q, J=7.3 Hz), 6.43(1H, dd, J=8.7 Hz, 2.5 Hz), 6.51(1H, d, J=2.5 Hz), 6.78(1H, d, J=8.9 Hz), 6.90(1H, d, J=8.7 Hz), 7.63(2H, d, J=8.6 Hz), 7.96(2H, d, J=8.2 Hz), 8.08(1H, dd, J=8.9 Hz, 2.6 Hz), 8.18(1H, d, J=2.6 Hz), 8.95(1H, s). |

TABLE 263

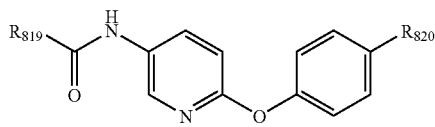

| Example No. | R<sub>819</sub> | R<sub>820</sub> | mp (° C.) or $^1$H NMR (solvent) δ ppm |
|---|---|---|---|
| 1206 | 3,4-Cl$_2$Ph— | morpholino | $^1$H NMR (DMSO-d$_6$) 3.07-3.10(4H, m), 3.73-3.77(4H, m), 6.96-7.04(5H, m), 7.83(1H, d, J=8.2 Hz), 7.94(1H, dd, J=8.2 Hz, 2.0 Hz), 8.15(1H, dd, J=8.9 Hz, 2.6 Hz), 8.22 (1H, d, J=2.0 Hz), 8.45(1H, d, J=2.6 Hz), 10.51(1H, brs). |
| 1207 | 3,4-Cl$_2$Ph— | *N-ethyl-2-piperidinone group* | $^1$H NMR (CDCl$_3$) 1.72-1.90(4H, m), 2.40-2.53(2H, m), 3.20-3.32(2H, m), 4.58(2H, s), 6.95(1H, d, J=8.9 Hz), 7.08(2H, d, J=8.6 Hz), 7.27(2H, d, J=8.6 Hz), 7.58(1H, d, J=8.6 Hz), 7.73(1H, dd, J=8.6 Hz, 2.0 Hz), 8.01(1H, d, J=2.0 Hz), 8.11(1H, s), 8.19(1H, dd, J=8.9 Hz, 2.3 Hz), 8.28(1H, d, J=2.3 Hz). |
| 1208 | 4-CF$_3$Ph— | —NHCONHPh | mp 240.0-240.5 |
| 1209 | 3,4-Cl$_2$Ph— | *N-methylpiperidine-3-COOC$_2$H$_5$* | $^1$H NMR (CDCl$_3$) 1.28(3H, t, J=7.0 Hz), 1.60-1.70(2H, m), 1.83(1H, m), 2.03(1H, m), 2.69(1H, m), 2.82(1H, brt, J=12.0 Hz), 3.03(1H, dd, J=12.0 Hz, 10.0 Hz), 3.42(1H, brd, J=12.0 Hz), 3.65(1H, brd, J=12.0 Hz), 4.17(2H, q, J=7.0 Hz), 6.90(1H, d, J=9.0 Hz), 6.97(2H, d, J=9.0 Hz), 7.03(2H, d, J=9.0 Hz), 7.58(1H, d, J=8.5 Hz), 7.70 (1H, dd, J=8.5 Hz, 2.0 Hz), 7.75(1H, s), 7.97(1H, d, J=2.0 Hz), 8.14(1H, brd, J=9.0 Hz), 8.23(1H, d, J=2.5 Hz). |
| 1210 | 3,4-Cl$_2$Ph— | *N-methylpyrrolidin-2-one-4-CO-piperazine-CH$_2$-benzodioxole* | $^1$H NMR (DMSO-d$_6$) 2.33-2.38(4H, m), 2.65-2.83(2H, m), 3.41(2H, s), 3.45-3.57(4H, m), 3.65-3.75(1H, m), 3.91-4.08(2H, m), 6.00(2H, s), 6.76(1H, dd, J=1.5 Hz, 8.1 Hz), 6.84-6.88(2H, m), 7.07(1H, d, J=8.9 Hz), 7.14(2H, d, J=8.9 Hz), 7.67(2H, d, J=9.1 Hz), 7.85(1H, d, J=8.4 Hz), 7.95(1H, dd, J=2.0 Hz, 8.4 Hz), 8.19(1H, dd, J=2.6 Hz, 8.9 Hz), 8.23(1H, d, J=2.1 Hz), 8.47(1H, d, J=2.6 Hz), 10.56(1H, s). |
| 1211 | 4-CF$_3$Ph— | *N-methylpyrrolidin-2-one-4-CO-piperazine-CH$_2$-benzodioxole* | $^1$H NMR (DMSO-d$_6$) 2.33-2.38(4H, m), 2.65-2.83(2H, m), 3.41(2H, s), 3.51(4H, brs), 3.65-3.75(1H, m), 3.91-4.08 (2H, m), 5.99(2H, s), 6.76(1H, dd, J=1.3 Hz, 7.9 Hz), 6.84-6.88(2H, m), 7.08(1H, d, J=8.9 Hz), 7.15(2H, d, J=6.9 Hz), 7.68(2H, d, J=6.9 Hz), 7.94(2H, d, J=8.6 Hz), 8.17(2H, d, J=8.1 Hz), 8.23(1H, dd, 10.64(1H, 8.9 Hz), 8.50(1H, d, J=2.6 Hz), s). |

TABLE 264

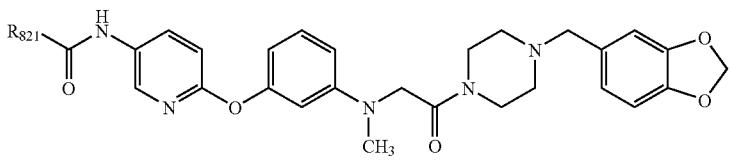

| Example No. | $R_{821}$ | $^1$H NMR (DMSO-$d_6$) δ ppm |
|---|---|---|
| 1212 | 3,4-Cl$_2$Ph— | 2.25-2.33(4H, m), 2.92(3H, s), 3.36(2H, s), 3.42(4H, brs), 4.23(2H, s), 5.98(2H, s), 6.29-6.32(2H, m), 6.42-6.45(1H, m), 6.70-6.74(1H, m), 6.80-6.84(2H, m), 6.97(1H, d, J=8.9 Hz), 7.11-7.17(1H, m), 7.84(1H, d, J=8.4 Hz), 7.95(1H, dd, J=8.4 Hz, 2.0 Hz), 8.16-8.22(2H, m), 8.52(1H, d, J=2.5 Hz), 10.55(1H, s). |
| 1213 | 4-CF$_3$Ph— | 2.26-2.33(4H, m), 2.92(3H, s), 3.37-3.41(6H, m), 4.23(2H, s), 5.98(2H, s), 6.29-6.34 (2H, m), 6.42-6.45(1H, m), 6.70-6.74(1H, m), 6.80-6.84(2H, m), 6.98(1H, d, J=8.9 Hz), 7.11-7.17(1H, m), 7.93(2H, d, J=8.3 Hz), 8.16(2H, d, J=8.1 Hz), 8.2 1(1H, dd, J=8.9 Hz, 2.6 Hz), 8.54(1H, d, J=2.3 Hz), 10.63(1H, s). |

TABLE 265

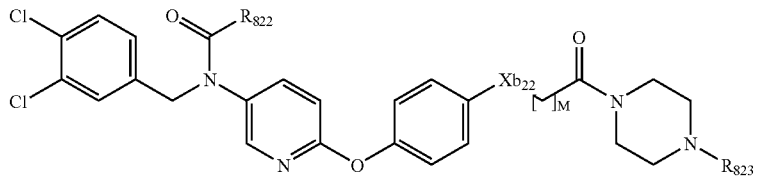

| Example No. | $R_{822}$ | $R_{823}$ | $Xb_{22}$ | M | Form | $^1$H NMR (solvent) δ ppm |
|---|---|---|---|---|---|---|
| 1214 | —CH$_3$ | piperonyl | —N(CH$_3$)— | 1 | free | (CDCl$_3$) 1.90(3H, s), 2.41-2.45(4H, m), 3.03(3H, s), 3.43(2H, s), 3.49(2H, brs), 3.63(2H, brs), 4.09 (2H, s), 4.77(2H, s), 5.95(2H, s), 6.70(2H, d, J=9.1 Hz), 6.74-6.75(2H, m), 6.81-6.85(2H, m), 7.00 (2H, d, J=9.1 Hz), 7.04(1H, dd, J=8.4 Hz, 2.1 Hz), 7.24(1H, dd, J=8.7 Hz, 2.8 Hz), 7.31(1H, d, J=2.1 Hz), 7.35(1H, d, J=8.1 Hz), 7.83(1H, d, J=2.6 Hz). |
| 1215 | —C$_2$H$_5$ | piperonyl | —N(CH$_3$)— | 1 | free | (CDCl$_3$) 1.08(3H, t, J=7.4 Hz) 2.07(2H, q, J=7.4 Hz), 2.4 F2.45(4H, m), 3.03(3H, s), 3.43(2H, s), 3.48(2H, brs), 3.63(2H, brs), 4.09(2H, s), 4.77(2H, s), 5.95(2H, s), 6.70(2H, d, J=9.2 Hz), 6.73-6.74 (2H, m), 6.82(1H, d, J=8.7 Hz), 6.85(1H, brs), 7.00(2H, d, J=9.1 Hz), 7.04(1H, dd, J=8.3 Hz, 2.0 Hz), 7.22 (1H, dd, J=8.7 Hz, 2.8 Hz), 7.30(1H, d, J=2.0 Hz), 7.34(1H, d, J=8.3 Hz), 7.82(1H, d, J=2.5 Hz). |
| 1216 | —CH$_3$ | benzyl | none | 0 | hydrochloride | (DMSO-$d_6$) 1.87(3H, s), 3.14(2H, brs), 3.37(6H, brs), 4.35(2H, s), 4.85(2H, s), 7.13(1H, d, J=8.9 Hz), 7.22(2H, d, J=8.4 Hz), 7.41-7.58(10H, m), 7.80(1H, dd, J=8.9 Hz, 2.6 Hz), 8.03(1H, d, J=2.6 Hz), 10.88(1H, brs). |

Example 1217

Production of 1H-indole-2-carboxylic acid {6-[4-(2,4-dioxothiazolidine-5-ylmethyl)-2-methylphenoxy]pyridin-3-yl}amide To a solution of 5-[4-(5-aminopyridin-2-yloxy)-3-methylbenzyl]thiazolidine-2,4-dione (150 mg, 0.46 mmol) in DMF (5 mL) were added indole-2-carboxylic acid (74 mg, 0.46 mmol), 1-hydroxybenzotriazole monohydrate (70 mg, 0.46 mmol) and 1-ethyl-3-(3-dimethylaminopropyl)carbodiimide hydrochloride (110 mg, 0.57 mmol), and the resulting solution was stirred for 5 days at room temperature. This reaction solution was concentrated under reduced pressure. Water was added to the residue, and extracted with ethyl acetate. The ethyl acetate layer was washed with a saturated sodium bicarbonate solution and brine, dried over anhydrous magnesium sulfate, evaporated, and the residue was then purified by silica gel column chromatography (chloroform:methanol=30:1). To the obtained powdery substance was added ethanol, the resulting solution was filtered and the filtrate was washed with ethanol, to thereby yield 100 mg of the title compound.
Appearance: White powder
$^1$H NMR (DMSO-$d_6$) δ 2.10 (3H, s), 3.09 (1H, dd, J=14.2 Hz, 9.7 Hz), 3.40 (1H, dd, J=14.2 Hz, 4.2 Hz), 4.94 (1H, dd, J=9.7 Hz, 4.2 Hz), 6.99 (1H, d, J=8.2 Hz), 7.04 (1H, d, J=8.9 Hz), 7.05-7.16 (2H, m), 7.20 (1H, s), 7.24 (1H, dd, J=7.0 Hz, 1.0 Hz), 7.39 (1H, d, J=1.6 Hz), 7.46 (1H, d, J=8.2 Hz), 7.68 (1H, d, J=7.7 Hz), 8.21 (1H, dd, J=8.9 Hz, 2.8 Hz), 8.49 (1H, d, J=2.8 Hz), 10.37 (1H, s), 11.80 (1H, s), 12.09 (1H, s).

The following compounds were produced in the same manner as in Example 1217.

TABLE 266

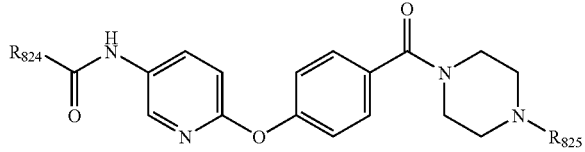

| Example No. | $R_{824}$ | $R_{825}$ | Form | $^1$H NMR (solvent) δ ppm |
|---|---|---|---|---|
| 1218 | 3,4-(CH$_3$)$_2$Ph— | 4-CH$_3$OPhCH$_2$— | free | (CDCl$_3$) 2.34(6H, s), 2.45(4H, brs), 3.45(2H, s), 3.47-3.79(4H, m), 3.81(3H, s), 6.83-6.89(2H, m), 6.97(1H, d, J=8.9 Hz), 7.11-7.16(2H, m), 7.21-7.26(3H, m), 7.41-7.46(2H, m), 7.59-7.62 (1H, m), 7.67(1H, d, J=1.9 Hz), 7.92(1H, brs), 8.23-8.30(1H, m), 8.31(1H, d, J=2.4 Hz). |
| 1219 | 2-(CH$_3$)$_2$NPh— | benzyl | trihydrochloride | (DMSO-$d_6$) 3.07(6H, s), 3.17-3.48(8H, m), 4.35(2H, s), 7.16-7.21(3H, m), 7.41-7.54(6H, m), 7.59-770(4H, m), 7.92(1H, d, J=7.1 Hz), 8.27(1H, dd, J=2.8 Hz, 8.7 Hz), 8.55(1H, d, J=2.1 Hz), 11.30(1H, s). |
| 1220 | 3,5-(CH$_3$)$_2$Ph— | benzyl | hydrochloride | (DMSO-$d_6$) 2.36(6H, s), 3.00-3.20(2H, m), 3.20-3.40(2H, m), 3.47(2H, brs), 4.40(2H, brs), 4.33(2H, s), 7.13(1H, d, J=8.9 Hz), 7.19(2H, d, J=8.6 Hz), 7.24(1H, s), 7.40-7.70(7H, m), 7.51(2H, d, J=8.6 Hz), 8.26(1H, dd, J=8.9 Hz, 2.6 Hz), 8.56(1H, d, J=2.6 Hz), 10.41(1H, s). |
| 1221 | 2,3-(CH$_3$O)$_2$Ph— | benzyl | hydrochloride | (DMSO-$d_6$) 3.00-3.65(6H, m), 3.80(3H, s), 3.86(3H, s), 4.20(2H, brs), 4.33(2H, brs), 7.09-7.25(6H, m), 7.40-7.80(7H, m), 8.23(1H, dd, J=8.9 Hz, 2.3 Hz), 8.52(1H, d, J=2.3 Hz), 10.43(1H, s). |
| 1222 | 2,4-(CH$_3$)$_2$NPh— | benzyl | free | (CDCl$_3$) 2.48(4H, brs), 3.06(6H, s), 3.55(2H, s), 3.70(4H, brs), 6.71(2H, d, J=9.0 Hz), 6.96(1H, d, J=9.6 Hz), 7.13(2H, d, J=8.7 Hz), 7.2&7.38(5H, m), 7.43(2H, d, J=8.7 Hz), 7.71 (1H, brs), 7.78(2H, d, J=9.0 Hz), 8.20-8.30(2H, m). |
| 1223 | 1-naphthyl | benzyl | free | (DMSO-$d_6$) 2.41(4H, brs), 3.51(4H, brs), 3.52 (2H, s), 7.17(3H, d, J=8.7 Hz), 7.21-7.38(5H, m), 7.44(2H, d, J=8.7 Hz), 7.55-7.69(3H, m), 7.80(1H, d, J=6.4 Hz), 7.98-8.06(1H, m), 8.10 (1H, d, J=8.1 Hz), 8.18-8.27(1H, m), 8.32(1H, dd, J=8.7 Hz, 2.6 Hz), 8.58(1H, d, J=2.6 Hz), 10.76(1H, s). |

TABLE 267

![Structure with R826-C(O)-NH-pyridine-O-phenyl-C(O)-piperazine-CH2-phenyl]

| Example No. | R826 | Form | mp (° C.) |
|---|---|---|---|
| 1224 | 3-CF3, 5-F-phenyl | maleate | 172-175 |
| 1225 | 2-F, 3-CF3-phenyl (with methyl) | maleate | 143-146 |
| 1226 | 4-(H3COOC)-phenyl-CH3 | free | 187-189 |

TABLE 267-continued

| Example No. | R826 | Form | mp (° C.) |
|---|---|---|---|
| 1227 | 2-F, 3-CH3-phenyl (with methyl) | free | 191-192 |
| 1228 | 2,6-(H3CO)2, 3-CH3-pyridine | maleate | 180-182 |
| 1229 | 2,5-(CF3)2Ph— | dihydrochloride | 152-156 |
| 1230 | 2,5-F2Ph— | maleate | 182-184 |
| 1231 | 2,3-Cl2Ph— | free | 195-196 |
| 1232 | 3-PhOPh— | free | 171-172 |
| 1233 | 3-CF3Ph— | dihydrochloride | 146-149 |

TABLE 268

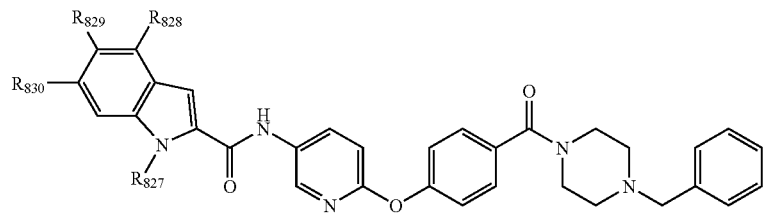

| Example No. | R827 | R828 | R829 | R830 | MS (M+ + H) |
|---|---|---|---|---|---|
| 1234 | —H | —H | —H | —H | 532 |
| 1235 | —H | —H | —OCH3 | —H | 562 |
| 1236 | —H | —H | —Cl | —H | 566 |
| 1237 | —H | —H | —F | —H | 550 |
| 1238 | —CH3 | —H | —H | —H | 546 |
| 1239 | —H | —H | —Br | —H | 612 |
| 1240 | —H | —H | —CH3 | —H | 546 |
| 1241 | —H | —H | —OCF3 | —H | 616 |
| 1242 | —H | —OCH3 | —H | —H | 562 |
| 1243 | —H | —Cl | —H | —H | 566 |
| 1244 | —H | —H | —H | —OCH3 | 562 |
| 1245 | —H | —Cl | —H | —Cl | 600 |
| 1246 | —H | —H | —H | —Cl | 566 |
| 1247 | —H | —H | —OCH3 | —OCH3 | 592 |

TABLE 269

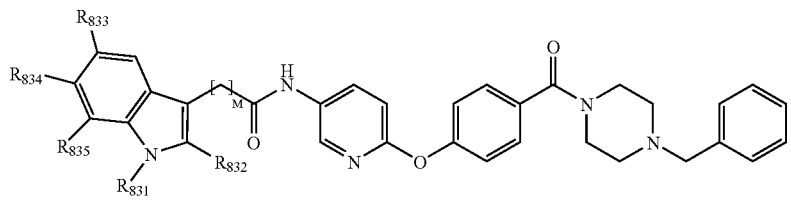

| Example No. | $R_{831}$ | $R_{832}$ | $R_{833}$ | $R_{834}$ | $R_{835}$ | M | MS (M$^+$ + H) |
|---|---|---|---|---|---|---|---|
| 1248 | —H | —H | —H | —H | —H | 0 | 532 |
| 1249 | —H | —H | —H | —H | —H | 2 | 560 |
| 1250 | —H | —H | —H | —H | —H | 1 | 546 |
| 1251 | —H | —H | —Cl | —H | —H | 1 | 580 |
| 1252 | —H | —CH$_3$ | —H | —H | —H | 1 | 560 |
| 1253 | —H | —CH$_3$ | —CH$_3$ | —H | —H | 1 | 574 |
| 1254 | —H | —CH$_3$ | —OCH$_3$ | —H | —H | 1 | 590 |
| 1255 | —H | —CH$_3$ | —F | —H | —H | 1 | 578 |
| 1256 | —H | —CH$_3$ | —C(CH$_3$)$_3$ | —H | —H | 1 | 616 |
| 1257 | —H | —CH$_3$ | —CH$_3$ | —H | —CH$_3$ | 1 | 588 |
| 1258 | —H | —CH$_3$ | —Br | —H | —F | 1 | 658 |
| 1259 | —H | —CH$_3$ | —H | —H | —F | 1 | 578 |
| 1260 | —H | —CH$_3$ | —C$_2$H$_5$ | —H | —H | 1 | 588 |
| 1261 | —H | —H | —F | —H | —H | 1 | 564 |
| 1262 | —H | —H | —H | —F | —H | 1 | 564 |
| 1263 | —CH$_3$ | —H | —H | —H | —H | 1 | 560 |
| 1264 | —H | —H | —OCH$_3$ | —H | —H | 1 | 576 |
| 1265 | —H | —H | —H | —H | —CH$_3$ | 1 | 560 |
| 1266 | —H | —H | —CH$_3$ | —H | —H | 1 | 560 |
| 1267 | —H | —H | —Br | —H | —H | 1 | 626 |

TABLE 270

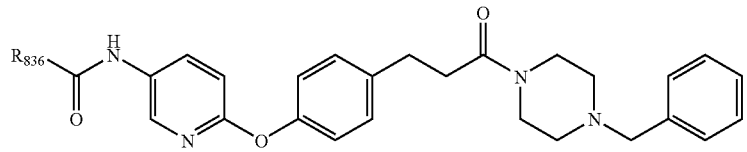

| Example No. | $R_{836}$ | $^1$H NMR (solvent) δ ppm |
|---|---|---|
| 1268 | 3-CNPh— | (CDCl$_3$) 2.37-2.44(4H, m), 2.57-2.63(2H, m), 2.88-2.95(2H, m), 3.42-3.45(2H, m), 3.55(2H, s), 3.60-3.64(2H, m), 6.90(1H, d, J= 8.9 Hz), 7.00(2H, d, J=8.6 Hz), 7.16(2H, d, J=8.6 Hz), 7.25 7.31(5H, m), 7.54-7.76(1H, m), 7.76-7.80(1H, m), 8.19-8.26(3H, m), 8.37(1H, d, J=2.6 Hz), 9.4 1(1H, brs). |
| 1269 | 2-CNPh— | (CDCl$_3$) 2.35-2.45(4H, m), 2.60-2.66(2H, m), 2.95-3.01(2H, m), 3.40-3.44(2H, m), 3.52(2H, s), 3.63-3.67(2H, m), 7.05-7.13(3H, m), 7.23-7.32(8H, m), 7.69-7.80(3H, m), 7.93-7.96(2H, m), 8.23(1H, d, J=2.5Hz). |
| 1270 | 3-N(CH$_3$)$_2$Ph— | (CDCl$_3$) 2.35-2.44(4H, m), 2.57-2.62(2H, m), 2.91-2.98(8H, m), 3.39-3.43(2H, m), 3.53(2H, s), 3.62-3.65(2H, m), 6.84-6.92(2H, m), 7.02(2H, d, J=8.6 Hz), 7.11(1H, d, J=7.9 Hz), 7.19(2H, d, J=8.6 Hz), 7.25-7.35(7H, m), 8.22-8.37 (3H, m). |
| 1271 | 3-CH$_3$Ph— | (CDCl$_3$) 2.36-2.46(7H, m), 2.57-2.63(2H, m), 2.91-2.97(2H, m), 3.40-3.44(2H, m), 3.56(2H, s), 3.62-3.66(2H, m), 6.91(1H, d, J= 8.9 Hz), 7.00-7.05(2H, m), 7.19(2H, d, J=8.6 Hz), 7.25-7.35(7H, m), 7.66-7.71(2H, m), 8.23-8.31(2H, m), 8.43(1H, brs). |
| 1272 | 3,4-(CH$_3$)$_2$Ph— | (CDCl$_3$) 2.31(3H, s), 2.32(3H, s), 2.36-2.46(4H, m), 2.58-2.64(2H, m), 2.92-2.98 (2H, m), 3.41-3.44(2H, m), 3.56(2H, s), 3.63-3.67(2H, m), 6.90-6.94(1H, m), 7.03(2H, d, J=8.4 Hz), 7.19-7.37(8H, m), 7.58-7.73(2H, m), 8.21-8.28(3H, m). |
| 1273 | 2-FPh— | (DMSO-d$_6$) 2.28-2.31(4H, m), 2.59-2.64(2H, m), 2.78-2.84(2H, m), 3.44-3.47 (6H, m), 7.01(2H, d, J=8.4 Hz), 7.02-7.05(1H, m), 7.26(2H, d, J=8.4 Hz), 7.3 1-7.40(7H, m), 7.5 1-7.61(1H, m), 7.64-7.72(1H, m), 8.18(1H, dd, J=8.9 Hz, 2.6 Hz), 8.45(1H, d, J=2.5 Hz), 10.54(1H, brs). |
| 1274 | 3-FPh— | (DMSO-d$_6$) 2.30(4H, brs), 2.62(2H, brs), 2.81(2H, brs), 3.47(6H, brs), 7.03(3H, brs), 7.25-7.30(7H, m), 7.47(1H, brs), 7.60(1H, d, J= |

TABLE 270-continued

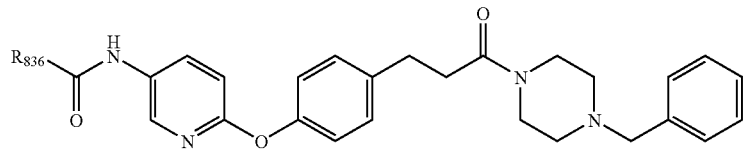

| Example No. | R836 | ¹H NMR (solvent) δ ppm |
|---|---|---|
| | | 6.1 Hz), 7.77-7.81(2H, m), 8.20(1H, d, J=7.6 Hz), 8.49(1H, brs), 10.46(1H, brs). |
| 1275 | 4-FPh— | (DMSO-$d_6$) 2.28-2.30(4H, m), 2.58-2.64(2H, m), 2.77-2.83(2H, ni), 3.43-3.46 (6H, m), 7.00(2H, d, J=8.6 Hz), 7.02(1H, d, J=8.7 Hz), 7.25(2H, d, J=8.6 Hz), 7.29-7.40(7H, m), 8.01-8.06(2H, m), 8.18(1H, dd, J=8.7 Hz, 2.6 Hz), 8.46(1H, d, J=2.5 Hz), 10.39(1H, brs). |
| 1276 | 4-AcPh— | (DMSO-$d_6$) 2.28-2.32(4H, m), 2.59-2.65(5H, m), 2.79-2.84(2H, m), 3.443.47 (6H, m), 6.99-7.06(3H, m), 7.27-7.36(7H, m), 8.09(4H, brs), 8.21(1H, dd, J=8.9 Hz, 2.8 Hz), 8.50(1H, d, J=2.6 Hz), 10.56(1H, brs). |
| 1277 | 3,4-$F_2$Ph— | (DMSO-$d_6$) 2.28-2.32(4H, m), 2.59-2.65(2H, m), 2.79-2.84(2H, m), 3.443.47 (6H, m), 7.0 1(2H, d, J=8.4 Hz), 7.04(1H, d, J=8.7 Hz), 7.27(2H, d, J=8.4 Hz), 7.3 1-7.36(5H, m), 7.597.69(1H, m), 7.85 7.89(1H, m), 8.00-8.07(1H, m), 8.18(1H, dd, J=8.9 Hz, 2.6 Hz), 8.46(1H, d, J=2.5 Hz), 10.46(1H, brs). |

TABLE 271

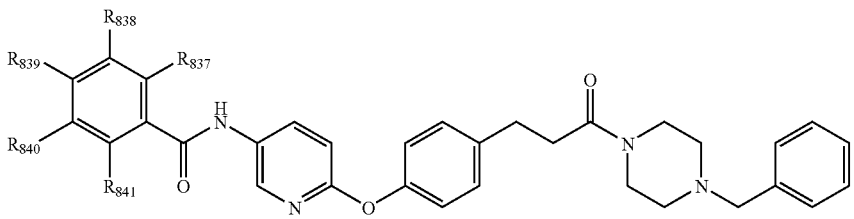

| Example No. | R837 | R838 | R839 | R840 | R841 | ¹H NMR (solvent) δ ppm or MS |
|---|---|---|---|---|---|---|
| 1278 | —H | —F | —H | —F | —H | ¹H NMR (DMSO-$d_6$) 2.29-2.32(4H, m), 2.59-2.65(2H, m), 2.79-2.85(2H, m), 3.44-3.48(6H, m), 7.00-7.06(3H, m), 7.25-7.36(7H, m), 7.51-7.59(1H, m), 7.677.71(2H, m), 8.19(1H, dd, J=8.7 Hz, 2.6 Hz), 8.48(1H, d, J=2.5 Hz), 10.5 1(1H, brs). |
| 1279 | —H | —H | —$SO_2NH_2$ | —H | —H | ¹H NMR (DMSO-$d_6$) 2.25-2.35(4H, m), 2.60-2.66(2H, m), 2.74-2.85(2H, m), 3.31 (2H, s), 3.40-3.50(4H, m), 7.00-7.06(3H, m), 7.25-7.34(7H, m), 7.53(2H, s), 7.97 (2H, d, J=8.6 Hz), 8.12(2H, d, J=8.6 Hz), 8.2 1(1H, dd, J=8.9 Hz, 2.7 Hz), 8.49 (1H, d, J=2.7 Hz), 10.56(1H, s). |
| 1280 | —H | —H | —NHAc | —H | —H | MS 576($M^+$ − 1) |
| 1281 | —F | —H | —$CF_3$ | —H | —H | MS 607($M^+$ + H) |
| 1282 | —$COOC_2H_5$ | —H | —H | —H | —H | MS 593($M^+$ + 1) |
| 1283 | —Cl | —Cl | —H | —H | —H | MS 590($M^+$ + 2) |
| 1284 | —H | —H | —$COOCH_3$ | —H | —H | MS 579($M^+$ + H) |
| 1285 | —$OCH_3$ | —H | —$OCH_3$ | —H | —H | MS 580($M^+$) |
| 1286 | —Cl | —H | —Cl | —H | —H | MS 589($M^+$) |
| 1287 | —$CH_3$ | —H | —$CH_3$ | —H | —H | MS 548($M^+$) |
| 1288 | —F | —H | —F | —H | —H | MS 557($M^+$ + H) |
| 1289 | —H | —$OCH_3$ | —$OCH_3$ | —H | —H | MS 580($M^+$) |
| 1290 | —$CF_3$ | —H | —H | —H | —H | MS 589($M^+$ + 1) |
| 1291 | —H | $CF_3$ | —H | —H | —H | MS 588($M^+$) |
| 1292 | —H | —$COOCH_3$ | —H | —H | —H | MS 579($M^+$ + 1) |
| 1293 | —F | —H | —H | —H | —F | MS 557($M^+$ + 1) |

TABLE 271-continued

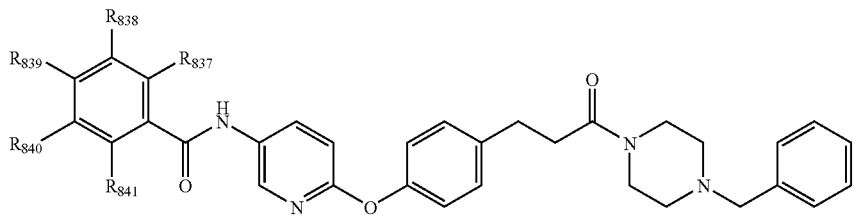

| Example No. | $R_{837}$ | $R_{838}$ | $R_{839}$ | $R_{840}$ | $R_{841}$ | $^1$H NMR (solvent) δ ppm or MS |
|---|---|---|---|---|---|---|
| 1294 | —F | —F | —H | —H | —H | MS 557(M$^+$ + H) |
| 1295 | —CF$_3$ | —H | —H | —CF$_3$ | —H | MS 656(M$^+$) |
| 1296 | —H | —F | —H | —CF$_3$ | —H | MS 606(M$^+$) |
| 1297 | —F | —CF$_3$ | —H | —H | —H | MS 607(M$^+$ + H) |
| 1298 | —F | —H | —H | —CF$_3$ | —H | MS 607(M$^+$ + 1) |
| 1299 | —CH$_3$ | —H | —H | —CH$_3$ | —H | MS 549(M$^+$ + 1) |
| 1300 | —F | —H | —H | —F | —H | MS 557(M$^+$ + H) |
| 1301 | —Cl | —H | —F | —H | —H | MS 572(M$^+$) |
| 1302 | —H | —OAc | —H | —H | —H | MS 579(M$^+$ + 1) |
| 1303 | —OCF$_3$ | —H | —H | —H | —H | MS 604(M$^+$) |

TABLE 272

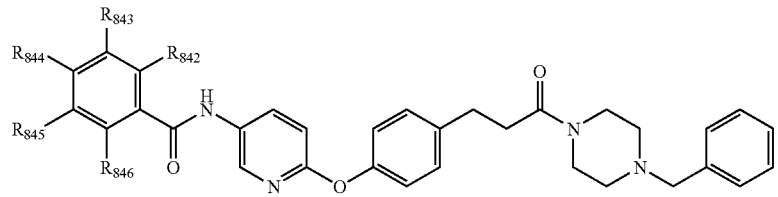

| Example No. | $R_{842}$ | $R_{843}$ | $R_{844}$ | $R_{845}$ | $R_{846}$ | $^1$H NMR or MS |
|---|---|---|---|---|---|---|
| 1304 | —H | —CF$_3$ | —F | —H | —H | MS 607(M$^+$ + 1) |
| 1305 | —OCH$_3$ | —H | —H | —OCH$_3$ | —H | MS 580(M$^+$) |
| 1306 | —Cl | —H | —H | —Cl | —H | MS 590(M$^+$ + 1) |
| 1307 | —CH$_3$ | —H | —H | —F | —H | MS 552(M$^+$) |
| 1308 | —N(CH$_3$)$_2$ | —H | —H | —H | —H | MS 564(M$^+$ + H) |
| 1309 | —OCH$_3$ | —H | —H | —H | —OCH$_3$ | MS 581(M$^+$ + H) |
| 1310 | —H | —OPh | —H | —H | —H | MS 613(M$^+$ + H) |
| 1311 | —H | —OCH$_3$ | —H | —OCH$_3$ | —H | MS 581(M$^+$ + H) |
| 1312 | —H | —Cl | —H | —Cl | —H | MS 589(M$^+$ + H) |
| 1313 | —H | —CH$_3$ | —H | —CH$_3$ | —H | MS 549(M$^+$ + H) |
| 1314 | —OCH$_3$ | —OCH$_3$ | —H | —H | —H | MS 581(M$^+$ + H) |
| 1315 | —CH$_3$ | —CH$_3$ | —H | —H | —H | MS 549(M$^+$ + H) |
| 1316 | —CH$_3$ | —F | —H | —H | —H | MS 553(M$^+$ + H) |
| 1317 | —H | —H | —N(CH$_3$)$_2$ | —H | —H | MS 564(M$^+$ + H) |
| 1318 | —H | —CF$_3$ | —H | —CF$_3$ | —H | MS 656(M$^+$) |
| 1319 | —Cl | —H | —H | —CF$_3$ | —H | MS 622(M$^+$) |
| 1320 | —H | —CH$_3$ | —NHAc | —H | —H | MS 591(M$^+$) |
| 1321 | —H | —Cl | —NHAc | —H | —H | MS 611(M$^+$) |
| 1322 | —H | —OCH$_3$ | —NHAc | —H | —H | MS 607(M$^+$) |
| 1323 | —H | —NHAc | —CH$_3$ | —H | —H | MS 591(M$^+$) |
| 1324 | —H | —NHAc | —Cl | —H | —H | MS 611(M$^+$) |
| 1325 | —H | —NHAc | —OCH$_3$ | —H | —H | MS 607(M$^+$) |
| 1326 | —H | —NHAc | —F | —H | —H | MS 595(M$^+$) |
| 1327 | —H | —CH$_3$ | —NHCOPh | —H | —H | MS 653(M$^+$) |
| 1328 | —H | —Cl | —NHCOPh | —H | —H | MS 673(M$^+$) |
| 1329 | —H | —OCH$_3$ | —NHCOPh | —H | —H | MS 669(M$^+$) |
| 1330 | —H | —NHCOPh | —CH$_3$ | —H | —H | MS 653(M$^+$) |
| 1331 | —H | —NHCOPh | —Cl | —H | —H | MS 673(M$^+$) |
| 1332 | —H | —NHCOPh | —OCH$_3$ | —H | —H | MS 669(M$^+$) |
| 1333 | —H | —NHCOPh | —F | —H | —H | MS 657(M$^+$) |
| 1334 | —COOH | —H | —Cl | —Cl | —H | $^1$HNMR (DMSO-d$_6$) δ 2.42(4H, brs), 2.62(2H, t, J= 7.1 Hz), 2.81(2H, t, J= 7.$^1$Hz), 3.33(1H, brs), 3.47(4H, brs), 3.60(2H, s), |

TABLE 272-continued

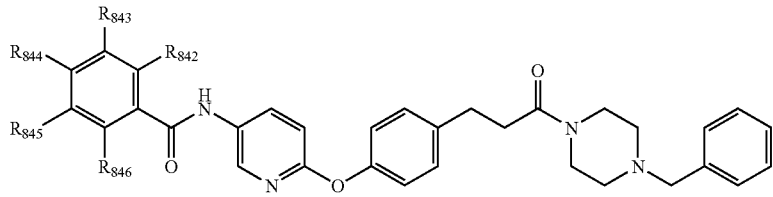

| Example No. | $R_{842}$ | $R_{843}$ | $R_{844}$ | $R_{845}$ | $R_{846}$ | $^1$H NMR or MS |
|---|---|---|---|---|---|---|
| | | | | | | 7.00(2H, d, J=8.6 Hz), 7.02(1H, d, J=4.7 Hz), 7.26(2H, d, J=8.6 Hz), 7.28-7.38(5H, m), 7.94(1H, s),8.05(1H, s), 8.10(1H, dd, J=8.7 Hz, 2.8 Hz), 8.36(1H, d, J=2.8 Hz), 10.68(1H, s). |

TABLE 273

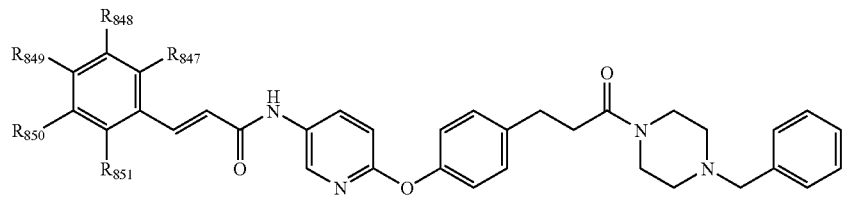

| Example No. | $R_{847}$ | $R_{848}$ | $R_{849}$ | $R_{850}$ | $R_{851}$ | MS |
|---|---|---|---|---|---|---|
| 1335 | —H | —H | —H | —H | —H | 546(M$^+$) |
| 1336 | —H | —OCH$_3$ | —H | —H | —H | 577(M$^+$ + H) |
| 1337 | —Cl | —H | —H | —H | —H | 581(M$^+$ + H) |
| 1338 | —H | —Cl | —H | —H | —H | 581(M$^+$ + H) |
| 1339 | —H | —H | —Cl | —H | —H | 581(M$^+$ + H) |
| 1340 | —F | —H | —H | —H | —H | 565(M$^+$ + H) |
| 1341 | —H | —F | —H | —H | —H | 565(M$^+$ + H) |
| 1342 | —H | —H | —F | —H | —H | 565(M$^+$ + H) |
| 1343 | —H | —H | —N(CH$_3$)$_2$ | —H | —H | 590(M$^+$ + 1) |
| 1344 | —H | —OCH$_3$ | —OCH$_3$ | —H | —H | 606(M$^+$) |
| 1345 | —Cl | —H | —H | —H | —Cl | 615(M$^+$ + 1) |
| 1346 | —H | —Cl | —Cl | —H | —H | 615(M$^+$ + H) |
| 1347 | —F | —H | —H | —H | —F | 583(M$^+$ + H) |
| 1348 | —H | —F | —H | —F | —H | 583(M$^+$ + H) |
| 1349 | —H | —OCH$_2$O— | | —H | —H | 591(M$^+$ + H) |
| 1350 | —H | —OCH$_3$ | —H | —OCH$_3$ | —H | 607(M$^+$ + H) |
| 1351 | —H | —H | —CH$_3$ | —H | —H | 561(M$^+$ + H) |
| 1352 | —H | —CF$_3$ | —H | —H | —H | 615(M$^+$ + H) |
| 1353 | —H | —H | OCH$_3$ | —H | —H | 577(M$^+$ + 1) |
| 1354 | —OCH$_3$ | —OCH$_3$ | —H | —H | —H | 606(M$^+$) |
| 1355 | —OCH$_3$ | —H | —H | —OCH$_3$ | —H | 607(M$^+$ + 1) |
| 1356 | —H | —OCH$_3$ | —OCH$_3$ | —OCH$_3$ | —H | 637(M$^+$ + 1) |

TABLE 274

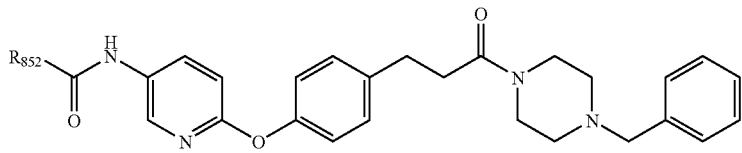

| Example No. | $R_{852}$ | $^1$H NMR (solvent) δ ppm |
|---|---|---|
| 1357 | Ac-N(piperidin-4-yl) | (CDCl$_3$) 1.68-1.86(2H, m), 1.91-2.03 2H, m , 2.12 3H, s , 2.34-2.40(2H, m), 2.40-2.46(2H, m), 2.48-2.56(1H, m), 2.62(2H, t, J=7.9 Hz), 2.66-2.75(1H, m), 2.96(2H, t, J=7.9 Hz), 3.08-3.18(1H, m), 3.38-3.45(2H, m), 3.51(2H, s), 3.59-3.69(2H, m), 3.88-3.97(1H, m), 4.59-4.69(1H, m), 6.89(1H, d, J=9.7 Hz), 7.02(2H, d, J=8.4 Hz), 7.22(2H, d, J=8.4 Hz), 7.25-7.31(1H, m), 7.31-7.38(4H, m), 7.54(1H, brs), 8.08-8.16(2H, m). |
| 1358 | chroman-2-yl | (CDCl$_3$) 2.05-2.18(1H, m), 2.32-2.40(2H, m), 2.40-2.47(2H, m), 2.49-2.56 (1H, m), 2.63(2H, t, J=7.9 Hz), 2.80-2.90(1H, m), 2.90-3.02(3H, m), 3.36-3.46(2H, m), 3.51(2H, s), 3.60-3.70(2H, m), 4.64-4.70(1H, m), 6.88-7.02(3H, m), 7.04(2H, d, J=8.4 Hz), 7.09-7.15(1H, m), 7.15-7.22(1H, m), 7.22-7.25(1H, m), 7.25-7.30(2H, m), 7.30-7.38(4H, m), 8.14(1H, dd, J=8.8, 2.8 Hz), 8.25(1H, d, J=2.8 Hz), 8.54(1H, brs). |
| 1359 | —CH$_2$OCH$_3$ | (CDCl$_3$) 2.30-2.38(2H, m), 2.38-2.45(2H, m), 2.62(2H, t, J=7.9 Hz), 2.96 (2H, t, J=7.9 Hz), 3.35-3.43(2H, m), 3.50(2H, s), 3.52(3H, s), 3.58-3.68(2H, m), 4.04(2H, s), 6.90(1H, d, J=8.8 Hz), 7.03(2H, d, J=8.4 Hz), 7.22(2H, d, J=8.4 Hz), 7.25-7.29(1H, m), 7.29-7.37(4H, m), 8.14(1H, dd, J=8.8, 2.8 Hz), 8.18-8.25(2H, m). |
| 1360 | —CH$_3$ | (CDCl$_3$) 2.18(3H, s), 2.32-2.39(2H, m), 2.39-2.45(2H, m), 2.61(2H, t, J=7.9 Hz), 2.95(2H, t, J=7.9 Hz), 3.36-3.44(2H, m), 3.50(2H, s), 3.60-3.68(2H, m), 6.85-6.92(1H, m), 7.02(2H, d, J=8.4 Hz), 7.21(2H, d, J=8.4 Hz), 7.25-7.30(1H, m), 7.30 7.35(4H, m), 7.38(1H, brs), 8.06-8.15(2H, m). |
| 1361 | —C(CH$_3$)$_3$ | (CDCl$_3$) 1.32(9H, s), 2.32-2.38(2H, m), 2.38-2.44(2H, m) 2.62(2H, t, J=7.9 Hz), 2.96(2H, t, J=7.9 Hz), 3.37-3.43(2H, m), 3.50(2H, s), 3.60-3.69(2H, m), 6.87(1H, d, J=9.8 Hz), 7.02(2H, d, J=8.4 Hz), 7.22(2H, d, J=8.4 Hz), 7.25-7.30(1H, m), 7.30-7.37(5H, m), 8.07-8.15(2H, m). |
| 1362 | —(CH$_2$)$_2$OPh | (DMSO-d$_6$) 2.23-2.33(4H, m), 2.56-2.67(2H, m), 2.73-2.86(4H, m), 3.37-3.50(6H, m), 4.26(2H, t, J=6.0 Hz), 6.90-6.96(3H, m), 6.96-7.02(3H, m), 7.20-7.35(9H, m), 8.07(1H, dd, J=8.8, 2.7 Hz), 8.33(1H, d, J=2.7 Hz), 10.23(1H, s). |
| 1363 | 3-CH$_3$OPhOCH$_2$— | (DMSO-d$_6$) 2.23-2.34(4H, m), 2.58-2.68(2H, m), 2.76-2.85(2H, m), 3.38-3.50(6H, m), 3.74(3H, s), 4.68(2H, s), 6.51-6.62(3H, m), 6.95-7.04(3H, m), 7.18-7.28(4H, m), 7.28-7.37(4H, m), 8.09(1H, dd, J=8.9, 2.7 Hz), 8.36 (1H, d, J=2.7 Hz), 10.22(1H, s). |
| 1364 | 3-CH$_3$PhOCH$_2$— | (DMSO-d$_6$) 2.23-2.34(7H, m), 2.56-2.66(2H, m), 2.74-2.84(2H, m), 6.88(1H, m), 6.96-7.03(3H, m), 7.14-7.21(1H, m), 7.21-7.28 (3H, m), 7.28-7.36(4H, m), 8.09(1H, dd, J=8.9, 2.7 Hz), 8.36(1H, d, J=2.7 Hz), 10.21(1H, s). |
| 1365 | 4-CH$_3$PhOCH$_2$— | (DMSO-d$_6$) 2.23(3H, s), 2.26-2.32(4H, m), 2.57-2.65(2H, m), 2.73-2.83(2H, m), 3.36-3.50(6H, m), 4.65(2H, s), 6.90(2H, d, J=8.5 Hz), 6.95-7.02(3H, m), 7.11(2H, d, J=8.5 Hz), 7.20-7.29(3H, m), 7.29-7.35(4H, m), 8.08(1H, dd, J=8.9, 2.7 Hz), 8.36(1H, d, J=2.7 Hz), 10.21(1H, s). |

TABLE 275

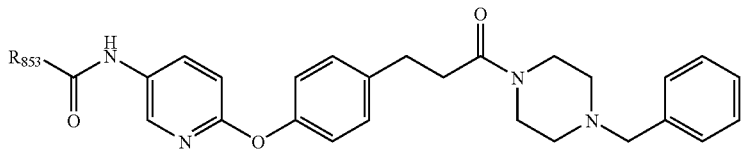

| Example No. | R_853 | $^1$H NMR (DMSO-d$_6$) δ ppm or MS |
|---|---|---|
| 1366 | PhOCH$_2$— | $^1$H NMR 2.23-2.34(4H, m), 2.57-2.65(2H, m), 2.76-2.85(2H, m), 3.38-3.50(6H, m), 4.70(2H, s), 6.92 7.05(6H, m), 7.20-7.27(3H, m), 7.27-7.38(6H, m), 8.09(1H, dd, J=8.9, 2.7 Hz), 8.36(1H, d, J=2.7 Hz), 10.24(1H, s). |
| 1367 | 4-CH$_3$PhCH$_2$— | $^1$H NMR 2.21-2.32(7H, m), 2.56-2.65(2H, m), 2.73-2.82(2H, m), 3.37-3.49(6H, m), 3.58(2H, s), 6.92-7.00(3H, m), 7.09-7.16(2H, m), 7.19-7.21(2H, m), 7.21-7.27(3H, m), 7.27-7.35(4H, m), 8.04(1H, dd, J=8.9, 2.7 Hz), 8.30(1H, d, J=2.7 Hz), 10.27(1H, s). |
| 1368 | 4-ClPhCH$_2$— | $^1$H NMR 2.21-2.32(4H, m), 2.55-2.65(2H, m), 2.73-2.82(2H, m), 3.38-3.49(6H, m), 3.66(2H, s), 6.93 7.00(3H, m), 7.20-7.26(3H, m), 7.26-7.35(6H, m), 7.35 7.42(2H, m), 8.04(1H, dd, J=8.9, 2.7 Hz), 8.30 (1H, d, J=2.7 Hz), 10.33(1H, s). |
| 1369 | 4-CH$_3$OPhCH$_2$— | $^1$H NMR 2.22-2.33(4H, m), 2.56-2.65(2H, m), 2.75-2.83(2H, m), 3.38-3.50(6H, m), 3.56(2H, a), 3.73(3H, s), 6.84-6.90(2H, m), 6.92-7.00(3H, m), 7.19-7.28(5H, m), 7.28-7.36(4H, m), 8.04(1H, dd, J=8.9, 2.7 Hz), 8.30(1H, d, J=2.7 Hz), 10.25(1H, s). |
| 1370 | 4-FPhCH$_2$— | $^1$H NMR 2.23-2.32(4H, m), 2.56-2.65(2H, m), 2.75-2.84(2H, m), 3.39-3.50(6H, m), 3.64(2H, a), 6.93-7.00(3H, m), 7.11-7.19(2H, m), 7.21-7.29(3H, m), 7.29-7.40(6H, m), 8.04(1H, dd, J=8.9, 2.7 Hz), 8.30 (1H, d, J=2.7 Hz), 10.31(1H, s). |
| 1371 | benzyl | $^1$H NMR 2.22-2.33(4H, m), 2.56-2.67(2H, m), 2.72-2.84(2H, m), 3.37-3.50(6H, m), 3.64(2H, s), 6.90-7.00(3H, m), 7.20-7.29(4H, m), 7.29-7.38(8H, m), 8.05(1H, dd, J=8.8, 2.7 Hz), 8.31(1H, d, J=2.7 Hz), 10.32(1H, s). |
| 1372 | —(CH$_2$)$_3$Ph | MS 563(M$^+$ + 1) |
| 1373 | —(CH$_2$)$_2$CH$_3$ | MS 487(M$^+$ + 1) |
| 1374 | —CH(CH$_3$)$_2$ | MS 486(M$^+$) |
| 1375 | cyclopentyl | MS 512(M$^+$) |
| 1376 | ![structure] | MS 630(M$^+$) |
| 1377 | —(CH$_2$)$_2$Ph | MS 549(M$^+$ + H) |
| 1378 | 2-furyl | MS 511(M$^+$ + H) |
| 1379 | 2-thienyl | MS 527(M$^+$ + H) |
| 1380 | 2-thenyl | MS 541(M$^+$ + H) |
| 1381 | cyclohexyl | MS 527(M$^+$ + H) |
| 1382 | cycloheptyl | MS 541(M$^+$ + H) |
| 1383 | cyclopentylmethyl | MS 527(M$^+$ + H) |
| 1384 | cyclohexylmethyl | MS 541(M$^+$ + H) |
| 1385 | 2-CH$_3$OPhOCH$_2$— | MS 581(M$^+$ + 1) |

TABLE 276

| Example No. | R854 | MS |
|---|---|---|
| 1386 | (CH3)2N-CH2-(4-methylcyclohexyl) | 584(M+ + 1) |
| 1387 | 2,6-dimethoxy-3-methylpyridin-4-yl | 582(M+ + 1) |
| 1388 | 2-(pyrrol-1-yl)-5-methylpyridin-yl | 587(M+ + H) |
| 1389 | 3-(propenyl)pyridinyl | 547(M+) |
| 1390 | 4-(propenyl)pyridinyl | 547(M+) |
| 1391 | 1-methyl-1-phenylcyclopropyl | 561(M+ + 1) |
| 1392 | 2-CH3PhOCH2— | 565(M+ + H) |
| 1393 | 2-ClPhOCH2— | 585(M+) |
| 1394 | 3-ClPhOCH2— | 585(M+ + H) |
| 1395 | 4-CNPhOCH2— | 575(M+) |
| 1396 | 6-ethoxy-1,3-benzodioxol-5-yl | 595(M+ + H) |
| 1397 | 3,4,5-(CH3O)3PhOCH2— | 641(M+ + 1) |
| 1398 | 2-chloro-3-methylpyridinyl | 556(M+ + 1) |
| 1399 | 6-chloro-3-methylpyridinyl | 556(M+ + H) |

TABLE 276-continued

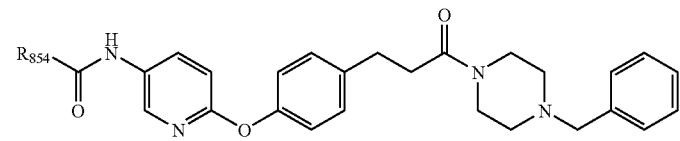

| Example No. | R854 | MS |
|---|---|---|
| 1400 | 2,3-dichloro-5-methylpyridin-... | 590(M⁺ + H) |
| 1401 | 2-methylthio-3-methylpyridin-... | 567(M⁺) |
| 1402 | 2-chloro-4-methylpyridin-... | 556(M⁺) |

TABLE 277

| Example No. | R855 | MS |
|---|---|---|
| 1403 | 4-(ethylthio)pyridinyl | 566 (M⁺−1) |
| 1404 | 2-methylindol-... | 559 (M⁺) |
| 1405 | 2-methylindolin-... | 562 (M⁺ + H) |
| 1406 | 5-methyl-2-oxopyrrolidin-... | 528 (M⁺ + 1) |
| 1407 | 2-quinolyl | 571 (M⁺) |
| 1408 | 3-quinolyl | 572 (M⁺ + H) |
| 1409 | 4-quinolyl | 571 (M⁺) |
| 1410 | 6-quinolyl | 571 (M⁺) |
| 1411 | 1-isoquinolyl | 571 (M⁺) |
| 1412 | 3-isoquinolyl | 572 (M⁺ + H) |

TABLE 277-continued

| Example No. | R855 | MS |
|---|---|---|
| 1413 | 2-methylbenzofuran-... | 560 (M⁺) |
| 1414 | 7-methoxy-2-methylbenzofuran-... | 590 (M⁺) |
| 1415 | 3,4-Cl₂PhCH₂— | 603 (M⁺ + H) |
| 1416 | 2-CH₃OPhCH₂— | 564 (M⁺) |
| 1417 | —CH(CH₂Ph)NHAc | 605 (M⁺) |
| 1418 | CH(CH₃)₂-CH(NHAc)- | 557 (M⁺) |
| 1419 | —CH₂NHAc | 515 (M⁺) |
| 1420 | —CH(CH₃)NHAc | 529 (M⁺) |
| 1421 | —CH(CH₂Ph)NHCOPh | 667 (M⁺) |
| 1422 | PhCONH-CH(CH(CH₃)₂)- | 619 (M⁺) |
| 1423 | —CH₂NHCOPh | 577 (M⁺) |

TABLE 278

R$_{856}$ group structure (pyridyl amide linked to phenoxy-phenyl-propanoyl-piperazine-benzyl)

| Example No. | R$_{856}$ | MS |
|---|---|---|
| 1424 | —CH(CH$_3$)NHCOPh | 591 (M$^+$) |
| 1425 | 2-pyridyl | 522 (M$^+$ + H) |
| 1426 | 3-pyridyl | 522 (M$^+$ + H) |
| 1427 | 4-pyridyl | 522 (M$^+$ + H) |
| 1428 | 1-naphthyl | 571 (M$^+$ + H) |
| 1429 | 3-methyl-2-methoxypyridyl | 551 (M$^+$) |
| 1430 | 2-pyrrolyl | 509 (M$^+$) |
| 1431 | 3-pyridylmethyl | 536 (M$^+$ + H) |
| 1432 | 3-furyl | 510 (M$^+$) |
| 1433 | 3-thienyl | 526 (M$^+$) |
| 1434 | 3-thenyl | 541 (M$^+$ + H) |
| 1435 | ethyladamantyl | 592 (M$^+$) |
| 1436 | 3-CH$_3$PhCH$_2$— | 549 (M$^+$ + H) |
| 1437 | 3-ClPhCH$_2$— | 569 (M$^+$ + H) |
| 1438 | 2-FPhCH$_2$— | 553 (M$^+$ + H) |
| 1439 | 3-FPhCH$_2$— | 553 (M$^+$ + H) |
| 1440 | 2,5-(CH$_3$O)$_2$PhCH$_2$— | 594 (M$^+$) |
| 1441 | 2,4-Cl$_2$PhCH$_2$— | 603 (M$^+$ + H) |
| 1442 | 2,6-Cl$_2$PhCH$_2$— | 602 (M$^+$) |
| 1443 | 3,4,5-(CH$_3$O)$_3$PhCH$_2$— | 624 (M$^+$) |
| 1444 | —CH(OCH$_3$)Ph | 564 (M$^+$) |
| 1445 | 1,2-diphenylpropenyl | 622 (M$^+$) |
| 1446 | 4-methyl-3,4-dihydroquinolin-2(1H)-one | 588 (M$^+$ + H) |
| 1447 | N-acetyl-N-cyclohexyl-4-methylaniline | 659 (M$^+$) |
| 1448 | 2,6-dichloro-3-methylpyridyl | 589 (M$^+$) |

TABLE 279

R$_{857}$ group structure (pyridyl amide linked to phenoxy-phenyl-propanoyl-piperazine-benzyl)

| Example No. | R$_{857}$ | MS |
|---|---|---|
| 1449 | 4-CF$_3$-3-methylpyridyl | 589 (M$^+$) |
| 1450 | 2-CF$_3$-5-methylpyridyl | 590 (M$^+$ + H) |
| 1451 | phenylpentadienyl | 573 (M$^+$ + H) |
| 1452 | 4-CH$_3$OPhO(CH$_2$)$_2$— | 595 (M$^+$ + H) |
| 1453 | 4-CH$_3$OPh(CH$_2$)$_2$— | 579 (M$^+$ + H) |
| 1454 | 3,4,5-(CH$_3$O)$_3$Ph(CH$_2$)$_2$— | 638 (M$^+$) |
| 1455 | 2,4-Cl$_2$PhOCH$_2$— | 618 (M$^+$) |
| 1456 | PhSCH$_2$— | 567 (M$^+$ + H) |
| 1457 | —(CH$_2$)$_2$COPh | 577 (M$^+$ + H) |
| 1458 | 3-ethylindolyl | 573 (M$^+$) |
| 1459 | 3-propylindolyl | 588 (M$^+$ + H) |
| 1460 | 5-methoxy-2-methylindolyl | 590 (M$^+$ + H) |
| 1461 | 5-chloro-2-methylindolyl | 594 (M$^+$ + H) |
| 1462 | 5-fluoro-2-methylindolyl | 578 (M$^+$ + H) |

TABLE 279-continued

R857-C(=O)-NH-(pyridin-5-yl)-O-(phenyl)-CH2CH2-C(=O)-N(piperazine)-CH2-phenyl

| Example No. | R857 | MS |
|---|---|---|
| 1463 | 1,2-dimethyl-1H-indol-yl | 573 (M+) |
| 1464 | 4-CH3OPh(CH2)3— | 593 (M+ + H) |
| 1465 | 2-methylbenzo[b]thiophen-yl | 576 (M+) |

TABLE 280

R858-C(=O)-NH-(pyridin-5-yl)-O-(phenyl)-CH2CH2-C(=O)-N(piperazine)-CH2-(benzo[d][1,3]dioxol-5-yl) · oxalic acid

| Example No. | R858 | mp (° C.) or $^1$H NMR (DMSO-$d_6$) δ ppm |
|---|---|---|
| 1466 | 2,5-F$_2$Ph— | mp 173-176 |
| 1467 | 2,6-dimethoxy-3-methylpyridin-yl | mp 181-182 |
| 1468 | 4-methyl-(methoxycarbonyl)phenyl (COOCH$_3$) | mp 199-201 |
| 1469 | 2,3-Cl$_2$Ph— | mp 149-151 |
| 1470 | 2,4-Cl$_2$Ph— | $^1$HNMR 2.54 (4H, brs), 2.64 (2H, t, J=7.5Hz), 2.81 (2H, t, J= 7.5Hz), 3.51 (4H, brs), 3.65 (2H, brs), 6.01 (2H, s), 6.81 (1H, d, J=8.0Hz), 6.89 (1H, d, J=8.0Hz), 6.92(1H, s), 7.01 (2H, d, J=8.5Hz), 7.04 (1H, d, J=9.0Hz), 7.26 (2H, d, J=8.5Hz), 7.57 (1H, dd, J=8.5Hz, 2.0Hz), 7.65 (1H, d, J=8.5Hz), 7.78 (1H, d, J=2.0Hz), 8.15 (1H, dd, J=9.0Hz, 2.5Hz), 8.41 (1H, d, J=2.5Hz), 10.69 (1H, s). |
| 1471 | 2,5-(CF$_3$)$_2$Ph— | $^1$HNMR 2.54 (4H, brs), 2.64 (2H, t, J=7.5Hz), 2.81 (2H, t, J= 7.5Hz), 3.49 (4H, brs), 3.59 (2H, brs), 6.00 (2H, s), 6.79 (1H, d, J=8.0Hz), 6.88 (1H, d, J=8.0Hz), 6.90 (1H, s), 7.02 (2H, d, J=8.5Hz), 7.05 (1H, d, J=9.0Hz), 7.27 (2H, d, J=8.5Hz), 8.12-8.14 (3H, m), 8.21 (1H, s), 8.37 (1H, d, J=2.5Hz), 10.84 (1H, s). |
| 1472 | 3-CF$_3$Ph— | $^1$HNMR 2.54 (4H, brs), 2.64 (2H, t, J=7.5Hz), 2.82 (2H, t, J= 7.5Hz), 3.51 (4H, brs), 3.63 (2H, brs), 6.01 (2H, s), 6.81 (1H, d, J=8.0Hz), 6.89 (1H, d, J=8.0Hz), 6.92 (1H, s), 7.02 (2H, d, J=8.5Hz), 7.05 (1H, d, J=9.0Hz), 7.27 (2H, d, J=8.5Hz), 7.80 (1H, t, J=8.0Hz), 7.99 (1H, d, J=8.0Hz), 8.19 (1H, dd, J=9.0Hz, 2.5Hz), 8.27 (1H, d, J=8.0Hz), 8.30 (1H, s), 8.48 (1H, d, J=2.5Hz), 10.61 (1H, s). |
| 1473 | 2,3-F$_2$Ph— | $^1$HNMR 2.54 (4H, brs), 2.64 (2H, t, J=7.5Hz), 2.81 (2H, t, J= 7.5Hz), 3.51 (4H, brs), 3.62 (2H, brs), 6.01 (2H, s), 6.80 (1H, d, J=8.0Hz), 6.89 (1H, d, J=8.0Hz), 6.92 (1H, s), 7.02 (2H, d, J=8.5Hz), 7.04 (1H, d, J=9.0Hz), 7.26 (2H, d, J=8.5Hz), 7.36 (1H, m), 7.50 (1H, m), 7.60 (1H, m), 8.16 (1H, dd, J= 9.0Hz, 2.5Hz), 8.43 (1H, d, J=2.5Hz), 10.67 (1H, s). |

TABLE 281

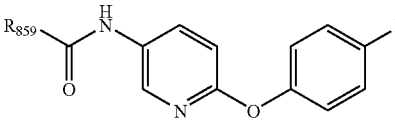

| Example No. | R₈₅₉ | Xb₂₃ | Form | mp (° C.) or ¹H NMR (solvent) δ ppm |
|---|---|---|---|---|
| 1474 | 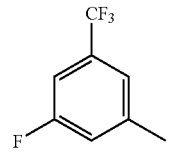 | —N(Ac)— | free | mp 142-144 |
| 1475 | 3,4-F₂Ph— | —CH₂— | free | ¹HNMR (CDCl₃) 2.31-2.40(4H, m), 2.59-2.65 (2H, m), 2.92-2.98 (2H, m), 3.38-3.41 (4H, m), 3.60-3.64 (2H, m), 5.94 (2H, s), 6.70-6.77 (2H, m), 6.84 (1H, s), 6.94 (1H, d, J=8.9Hz), 7.01-7.07 (2H, m), 7.19-7.24 (2H, m), 7.29-7.33 (1H, m), 7.62-7.68 (1H, m), 7.74-7.81 (1H, m), 8.01 (1H, brs), 8.16-8.20 (1H, m), 8.24 (1H, d, J=2.2Hz). |
| 1476 | 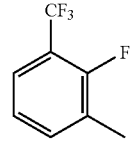 | —CH₂— | hydro-chloride | ¹HNMR (DMSO-d₆) 2.60-2.98 (6H, m), 3.01-3.15 (1H, m), 3.26 (2H, t, J=15.0Hz), 3.46-3.59 (1H, m), 4.00-4.11 (1H, m), 4.15-4.27 (2H, m), 4.30-4.51 (1H, m), 6.05 (2H, s), 6.97 (1H, d, J=7.9Hz), 6.98-7.09 (4H, m), 7.20-7.31 (3H, m), 7.97 (1H, d, J=8.4Hz), 8.11-8.23 (3H, m), 8.50 (1H, d,J=2.7Hz), 10.78 (1H, s), 11.38 (1H, brs). |
| 1477 |  | —CH₂— | hydro-chloride | ¹HNMR (DMSO-d₆) 2.60-2.99 (6H, m), 3.01-3.17 (1H, m), 3.25 (2H, t, J=15.0Hz), 3.48-3.60 (1H, m), 4.00-4.12 (1H, m), 4.15-4.28 (2H, m), 4.39-4.51 (1H, m), 6.05 (2H, s), 6.96 (1H, d, J=8.8Hz), 6.99-7.08 (4H, m), 7.19-7.31 (3H, m), 7.55 (1H, t, J=7.8Hz), 7.90-8.04 (2H, m),8.16 (1H, dd, J=8.8Hz, 2.7Hz), 8.43 (1H, d, J=2.7Hz), 10.82 (1H, s), 11.44 (1H, brs). |
| 1478 | 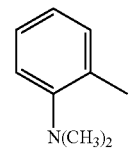 | —CH₂— | hydro-chloride | mp 213-215 |
| 1479 |  | —CH₂— | trihydro-chloride | ¹HNMR (DMSO-d₆) 2.69-3.40 (15H, m), 3.99-4.49 (5H, m), 6.07 (2H, s), 6.97-7.09 (5H, m), 7.21-7.30 (3H, m), 7.43-7.47 (1H, m), 7.65-7.70 (2H, m), 7.91 (1H, d, J=9.4Hz), 8.21 (1H, dd, J=8.9Hz, 2.6Hz), 8.48 (1H, d, J=2.1Hz), 11.23 (1H, s). |
| 1480 | 3-PhOPh— | —CH₂— | hydro-chloride | ¹HNMR (DMSO-d₆) 2.60-3.09 (7H, m), 3.18-3.31 (2H, m), 3.38-3.50 (1H, m), 4.08 (1H, d, J=14.0Hz), 4.22 (2H, brs), 4.45 (1H, d, J=14.0Hz), 6.07 (2H, s), 6.90-7.08 (7H, m), 7.15-7.26 (5H, m), 7.44 (2H, t, J=7.9Hz), 7.56 (1H, t, J=7.9Hz), 7.61 (1H, s), 7.79 (1H, d, J=7.6Hz), 8.19 (1H, dd, J=8.9Hz, 2.6Hz), 8.45 (1H, d, J=2.6Hz), 10.45 (1H, s), 10.90-11.20 (1H, m). |

TABLE 282

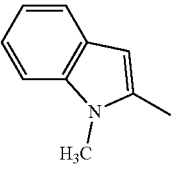

| Example No. | R860 | R861 | Xb24 | Form | mp (° C.) or ¹H NMR (solvent) δ ppm |
|---|---|---|---|---|---|
| 1481 | 1-naphthyl | —H | —CH₂— | hydrochloride | ¹HNMR (DMSO-d₆) 2.50-3.60 (10H, m), 4.00-4.20 (1H, m), 4.22 (2H, s), 4.35-4.51 (1H, m), 6.07 (2H, s), 6.91-7.08 (2H, m), 7.04 (2H, d, J=8.6Hz), 7.08 (1H, d, J=8.9Hz), 7.21 (1H, s), 7.39 (2H, d, J=8.6Hz), 7.55-7.67 (3H, m), 7.79 (1H, d, J=7.1Hz), 7.98-8.05 (1H, m), 8.10 (1H, d, J=8.2Hz), 8.16-8.22 (1H, m), 8.26 (1H, dd, J=8.9Hz, 2.5Hz), 8.54 (1H, d, 2.5Hz), 10.72 (1H, s) |
| 1482 | 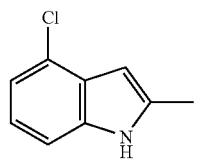 | —CH₃ | —N(CH₃)— | free | ¹HNMR (CDCl₃) 2.13 (3H, s), 2.43 (4H, t, J=4.8Hz), 3.01 (3H, s), 3.44 (2H, s), 3.45-3.56 (2H, m), 3.56-3.70 (2H, m), 4.08 (2H, s), 4.09 (3H, s), 5.95 (2H, s), 6.51-6.60 (2H, m), 6.72-6.76 (2H, m), 6.82 (1H, d, J=8.9Hz), 6.85 (1H, s), 6.92 (1H, d, J=8.4Hz), 7.04 (1H, s), 7.14-7.23 (1H, m), 7.28-7.40 (1H, m), 7.42 (1H, d, J=7.9Hz), 7.67 (1H, d, J=7.9Hz), 7.94 (1H, s), 8.14 (1H, dd, J=8.9Hz, 2.8Hz), 8.22 (1H, d, J=2.8Hz). |
| 1483 | 3,5-(CH₃)₂Ph— | —H | —CH₂— | hydrochloride | HNMR (DMSO-d₆) 2.36 (6H, s), 2.60-3.60 (10H, m), 4.00-4.60 (2H, m), 4.29 (2H, s), 6.07 (2H, s), 6.85-7.10 (5H, m), 7.22 (2H, s), 7.27 (2H, d, J=8.5Hz), 7.57 (2H, s), 8.19 (1H, dd, J=8.9Hz, 2.7Hz), 8.48 (1H, d, J=2.7Hz), 10.34 (1H, s). |
| 1484 | 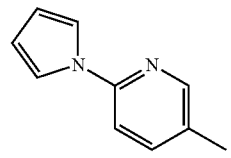 | —CH₃ | —N(CH₃)— | free | mp 143-144 |
| 1485 | 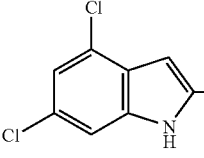 | —CH₃ | —N(CH₃)— | free | mp 163-165 |
| 1486 |  | —CH₃ | —N(CH₃)— | free | mp 224-227 dec |

TABLE 282-continued

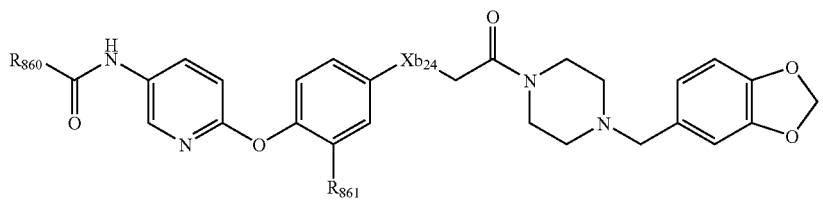

| Example No. | R<sub>860</sub> | R<sub>861</sub> | Xb<sub>24</sub> | Form | mp (° C.) or $^1$H NMR (solvent) δ ppm |
|---|---|---|---|---|---|
| 1487 | (thiomorpholine-N-tolyl group) | —CH$_3$ | —N(CH$_3$)— | free | mp 131-134 |

TABLE 283

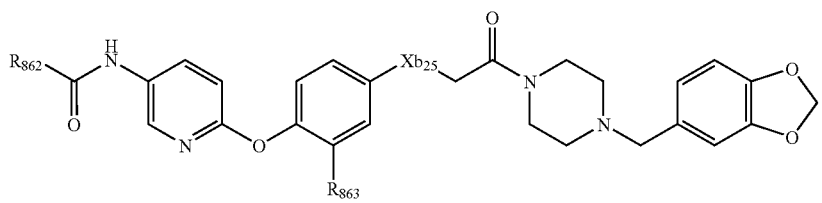

| Example No. | R$_{862}$ | R$_{863}$ | Xb$_{25}$ | Form | $^1$H NMR (solvent) δ ppm |
|---|---|---|---|---|---|
| 1488 | 2,3-(CH$_3$O)$_2$Ph— | —H | —CH$_2$— | hydro-chloride | (DMSO-d$_6$) 3.80 (3H, s), 3.86 (3H, s), 2.60-3.60 (10H, m), 4.00-4.20 (1H, m), 4.22 (2H, s), 4.40-4.55 (1H, m), 6.07 (2H, s), 6.90-7.30 (11H, m) 8.18 (1H dd, J = 8.8Hz, 2.6Hz), 8.45 (1H, d, J=2.6Hz), 10.37 (1H, s). |
| 1489 | (N-tolylpyrrole) | —CH$_3$ | —N(CH$_3$)— | free | (CDCl$_3$) 2.12 (3H, s), 2.35-2.50 (4H, m), 3.01 (3H, s), 3.43 (2H, s), 3.45-3.55 (2H, m), 3.57-3.70 (2H m), 4.07 (2H, s) 5.95 (2H, s), 6.40 (2H, t, J=2.2Hz, 6.50-6.59 (2H, m), 6.74 (2H, s), 6.81 (1H, d, J=8.9Hz), 6.85 (1H, s), 6.92 (1H, d, J= 8.6Hz), 7.17 (2H, t, J=2.2Hz), 7.49 (2H, d, J=8.8Hz), 7.90 (1H, brs), 7.95 (2H, d, J=8.8Hz), 8.15 (1H, dd, J= 8.9Hz, 2.3Hz), 8.22 (1H, d, J=2.3Hz). |
| 1490 | (5-chloro-2-methylthiophene) | —CH$_3$ | —N(CH$_3$)— | free | (CDCl$_3$) 2.04 (3H, s), 2.39-2.46 (4H, m), 2.94 (3H, s) 3.43-3.51 (4H, m), 3.59-3.63 (2H, m), 4.05 (2H, s), 5.94 (2H, s) 6.41-6.48 (2H, m), 6.67-6.84 (6H, m), 7.44 (1H, d, J=4.1Hz), 8.01 (1H, dd, J= 8.9Hz, 2.6Hz), 8.17 (1H, d, J=2.6Hz), 8.82 (1H, brs). |
| 1491 | (2-chloro-propenylbenzene) | —CH$_3$ | —N(CH$_3$)— | maleate | (DMSO-d$_6$) 2.01 (3H, s), 2.50 (4H, brs), 2.93 (3H, s), 3.33 (4H, brs), 4.03 (2H, s) 4.29 (2H, s), 6.06 (2H, s), 6.10 (2H, s), 6.48 (1H, dd, J=8.9Hz, 2.8Hz), 6.56 (1H, s) 6.81-7.01 (6H, m), 7.43-7.53 (2H, m), 7.57 (1H, dd, J=5.9Hz, 3.6Hz), 7.77 (1H, dd, J=5.8Hz, 3.6Hz), 7.88 (1H, d, J=15.7Hz), 8.11 (1H, dd, J=8.7Hz, 2.5Hz), 8.36 (1H, d, J= 2.6Hz), 10.42 (1H, s). |
| 1492 | 4-(CH$_3$)$_2$NPh— | —H | —CH$_2$— | free | (CDCl$_3$) 2.33 (2H, t, J=5.0Hz), 2.39 (2H, t, J=5.0Hz), 2.61 (2H, t, J=7.5Hz), 2.97 (2H, t, J=7.5Hz), 3.05 (6H, s), 3.32-3.45 (2H, m), 3.41 (2H, s), 3.63 (2H, |

TABLE 283-continued

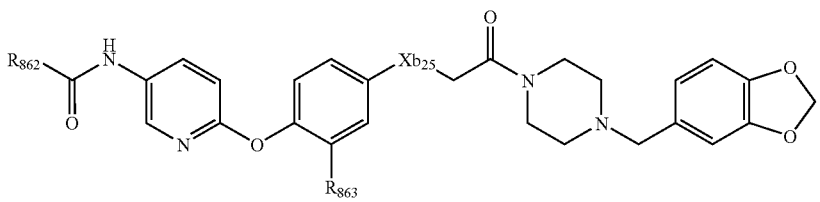

| Example No. | R₈₆₂ | R₈₆₃ | Xb₂₅ | Form | ¹H NMR (solvent) δ ppm |
|---|---|---|---|---|---|
| | | | | | t, J=5.0Hz), 5.94 (2H, s), 6.70 (2H, d, J=9.0Hz), 6.74 (2H, s) 6.85 (1H, s), 6.92 (1H, d, J=9.0Hz), 7.04 (2H, d, J=8.6Hz), 7.22 (2H, d, J=8.6Hz), 7.72 (1H, s), 7.78 (2H, d, J=9.0Hz), 8.21 (1H, d, J=2.8Hz), 8.23 (1H, dd, J=8.6Hz, 2.8Hz). |
| 1493 | 2,4-Cl₂PhOCH₂— | —CH₃ | —N(CH₃)— | free | (CDCl₃) 2.11 (3H, s), 2.42 (4H, brs), 3.00 (3H, s), 3.43 (2H, s), 3.49 (2H, brs), 3.63 (2H, brs), 4.07 (2H, s), 4.62 (2H, s), 5.94 (2H, s), 6.54 (1H, dd, J=11.1Hz, 2.3Hz), 6.74-6.92 (6H, m), 7.24 (1H, dd, J=8.7Hz, 2.5Hz), 7.43 (1H, d, J=2.5Hz), 8.06 (1H, dd, J=8.9Hz, 2.8Hz), 8.23(1H, d, J=2.6Hz), 8.55 (1H, s). |

TABLE 284

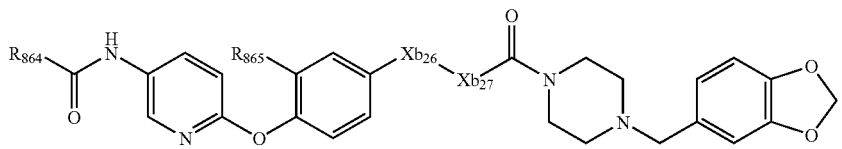

| Example No. | R₈₆₄ | R₈₆₅ | XB₂₆ | Xb₂₇ | Form | mp (° C.) or ¹H NMR (solvent) δ ppm |
|---|---|---|---|---|---|---|
| 1494 | 3,4-Cl₂-Ph-CH=CH- | —CH₃ | —N(CH₃)— | —CH₂— | free | ¹HNMR (CDCl₃) 2.10 (3H, s), 2.45 (4H, brs), 3.01 (3H, s), 3.45 (2H, s), 3.51 (2H, brs), 3.64 (2H, brs), 4.08 (2H, s), 5.95 (2H, s), 6.51-6.59 (3H, m), 6.75-6.92 (5H, m), 7.33 (1H, d, J=8.3Hz), 7.45 (1H, d J=8 4Hz), 7.61-7.76 (3H,m), 8.16 (1H, d, J=8.9Hz), 8.18 (1H, s). |
| 1495 | H₃CO-5-methoxy-2-methylindol-3-yl | —CH₃ | —N(CH₃)— | —CH₂— | free | ¹HNMR (CDCl₃) 2.09 (3H, s) 2.34-2.48 (4H, m), 2.98 (3H, s, 3.42 (2H, s), 3.40-3.55 (2H, m), 3.55-3.70 (2H, m) 3.84 (3H, s), 4.06 (2H, s) 5.94 (2H s) 6.46-6.55 (2H, m), 6.67-6.76 (2H, m), 6.77 (1H, d, J=8.9Hz), 6.85 (1H, s), 6.89 (1H d J=8.5Hz), 6.93-6.98 (1H, m), 6.97 (1H, dd, J=8.9Hz, 2.3Hz), 7.04 (1H, d, J=2.3Hz), 7.30 (1H, d, J=8.9Hz), 8.11 (1H, dd, J=8.9Hz, 2.5Hz), 8.22 (1H, s), 8.25 (1H, d, J=2.5Hz), 9.45 (1H, s). |
| 1496 | 3,4-(CH₃)₂Ph— | —H | —CH₂— | —CH₂— | free | ¹HNMR (CDCl₃) 2.31-2.38 (10H, m), 2.57-2.63 (2H, m), 2.91-2.97 (2H, m), 3.37-3.40 (4H, m), 3.59-3.63 (2H, m), 5.93 (2H, s), 6.70-6.77 (2H, m), 6.84 (1H, s), 6.91 (1H, d, J=8.9Hz), 7.00-7.05 (2H, m), 7.17-7.22 (3H, m), 7.60 (1H, dd, J=7.8Hz, 1.9Hz), 7.66 (1H, d, J=1.9Hz), 8.16-8.26 (3H, m). |

TABLE 284-continued

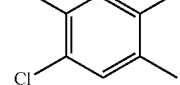

| Example No. | R864 | R865 | XB26 | Xb27 | Form | mp (° C.) or ¹H NMR (solvent) δ ppm |
|---|---|---|---|---|---|---|
| 1497 | 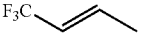 | —H | —CH₂— | —CH₂— | free | ¹HNMR (DMSO-d₆) 2.41 (4H, brs), 2.62 (2H, t, J=7.5Hz) 2.81 (2H, t, J=7.5Hz), 3.32 (1H, brs), 3.47 (4H, brs), 3.52 (2H, s), 6.00 (2H, s), 6.78 (1H, d, J=8.0Hz), 6.87 (1H, d, J=8.0Hz), 6.88 (1H, d, J=2.0Hz), 7.00 (2H, d, J=8.5Hz), 7.03 (1H, d, J=8.9Hz), 7.26 (2H, d, J=8.5Hz), 7.94 (1H, s), 8.05 (1H, s), 8.10 (1H, dd, J=8.9Hz, 2.6Hz), 8.36 (1H, d, J=2.6Hz), 10.72 (1H, s). |
| 1498 | F₃C— (propenyl) | —CH₃ | —N(CH₃)— | —CH₂— | hydro-chloride | mp 145.0-148.0 |
| 1499 | 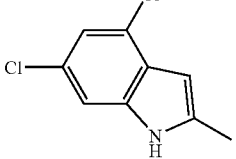 | —CH₃ | —N(CH₃)— | —CO— | free | mp 269.0-272.0 |

TABLE 285

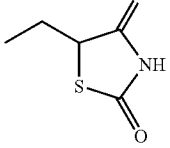

| Example No. | R866 | R867 | R868 | Form | ¹H NMR (solvent) δ ppm |
|---|---|---|---|---|---|
| 1500 | 3,4-Cl₂Ph— | —CH₃ | 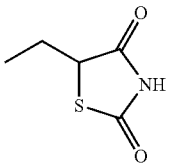 | hydro-chloride | (DMSO-d₆) 2.08 (3H, s), 3.09 (1H, dd, J=14.2Hz, 9.7Hz), 3.40 (1H, dd, J=14.2Hz, 4.2Hz), 4.93 (1H, dd, J=9.7Hz, 4.2Hz), 7.00 (1H, d, J=8.3Hz), 7.02 (1H, d, J=8.9Hz), 7.11 (1H, dd, J=8.3Hz, 2.0Hz), 7.20 (1H, d, J=2.0Hz), 7.83 (1H, d, J=8.4Hz), 7.95 (1H, dd, J=8.4Hz, 2.0Hz), 8.18 (1H, dd, J=8.9Hz, 2.5Hz), 8.23 (1H, d, J=2.0Hz), 8.44 (1H, d, J=2.5Hz), 10.57 (1H,s), 12.08 (1H, s). |
| 1501 | 4-CF₃Ph— | —CH₃ | (same structure) | free | (DMSO-d₆) 2.09 (3H, s), 3.09 (1H, dd, J=14.1Hz, 9.6Hz), 3.40 (1H, dd, J=14.1Hz, 4.3Hz), 4.93 (1H, dd, J=9.6Hz, 4.3Hz), 6.99 (1H, d, J=8.2Hz), 7.03 (1H, d, J=8.9Hz), 7.12 (1H, dd, J=8.2Hz, 2.0Hz), 7.20 (1H, d, J=2.0Hz), 7.93 (2H, d, J=8.2Hz), 8.16 (2H,d, J=8.2Hz), 8.20 (1H, dd, J=8.9Hz, 2.5Hz), 8.45 (1H, d, J=2.5Hz), 10.60 (1H, s), 12.07 (1H, s). |

TABLE 285-continued

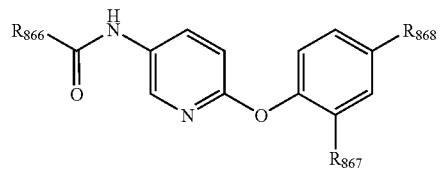

| Example No. | $R_{866}$ | $R_{867}$ | $R_{868}$ | Form | $^1$H NMR (solvent) δ ppm |
|---|---|---|---|---|---|
| 1502 | 3-CF$_3$Ph— | —H | ![structure]CH$_2$COOC$_2$H$_5$ | free | (CDCl$_3$) 1.28 (3H, t, J=7.0Hz), 1.46 (2H, dq, J=4.0Hz, 12.5Hz), 1.85 (2H, brd, J=12.5Hz), 1.93 (1H, m), 2.73 (2H, dt, J=2.5Hz, 12.0Hz), 3.61 (2H, brd, J=12.0Hz), 4.15 (2H, q, J=7.0Hz), 6.90 (1H, d, J=9.0Hz), 6.96 (2H, d, J=9.0Hz), 7.03 (2H, d, J=9.0Hz), 7.65 (1H, t, J=8.0Hz), 7.83 (1H, d, J=8.0Hz), 7.86 (1H, brs), 8.07 (1H, d, J=8.0Hz), 8.14 (1H, brs), 8.18 (1H, dd, J = 9.0Hz, 2.5Hz), 8.27 (1H, d, J 2.5Hz). |

Example 1503

Production of N-[6-(4-{[2-(4-piperonylpiperazin-1-yl)-2-oxoethyl]methylamino}-2-methylphenoxy)pyridin-3-yl]-4-trifluoromethylbenzamide To a suspension of 1-(4-piperonylpiperazin-1-yl)-2-{methyl-[3-methyl-4-(5-nitropyridin-2-yloxy)phenyl]amino}ethanone (2.65 g, 5.10 mmol) in ethyl acetate (50 mL) was added 5% platinum-carbon (0.20 g) under a nitrogen atmosphere, and the resulting mixture was stirred for 11 hours under a hydrogen atmosphere. The platinum-carbon was separated off by filtration using Celite. To a solution of the resulting filtrate in ethyl acetate was added triethylamine (0.78 mL, 5.61 mmol) under ice cooling, and then to the resulting solution was added 4-(trifluoromethyl)benzoyl chloride (0.80 mL, 5.36 mmol). This reaction solution was stirred for 16 hours, and then added a saturated sodium bicarbonate solution. The resulting solution was stirred at room temperature, and after 20 minutes, extracted with ethyl acetate. The ethyl acetate layer was washed with water, and then dried over anhydrous magnesium sulfate. The solvent was evaporated, and the residue was recrystallized from acetone-diethyl ether, to thereby yield 3.03 g of the title compound.

Appearance: Pale yellow powder
Melting point: 153.0-154.5° C.; $^1$H NMR (CDCl$_3$) δ 2.12 (3H, s), 2.31-2.52 (4H, m), 3.01 (3H, s), 3.38-3.72 (6H, m), 4.07 (2H, s), 5.95 (2H, s), 6.49-6.61 (2H, m), 6.69-6.78 (2H, m), 6.79-6.88 (2H, m), 6.92 (1H, d, J=8.6 Hz), 7.76 (2H, d, J=8.3 Hz), 7.81-7.90 (1H, m), 7.99 (2H, d, J=8.3 Hz), 8.13 (1H, dd, J=8.8 Hz, 2.6 Hz), 8.23 (1H, d, J=2.6 Hz).

A crude titled product (5.00 g, 7.6 mmol) obtained using the same procedures was recrystallized from ethanol (15 mL), to thereby yield 3.90 g of the title compound.

Appearance: Pale yellow powder
Melting point: 156-158° C.
The following compounds were produced in the same manner as in Example 1503.

Example 1504

N-{6-[2-methyl-4-(2-oxo-3-piperonylimidazolidin-1-yl)phenoxy]pyridin-3-yl}-4-trifluoromethylbenzamide mp 188.0-189.0° C.

TABLE 286

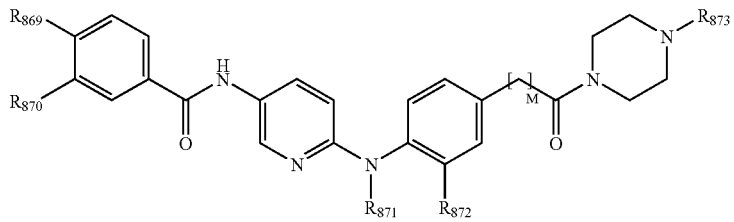

| Example No. | $R_{869}$ | $R_{870}$ | $R_{871}$ | $R_{872}$ | $R_{873}$ | M | Form | mp (° C.) or $^1$H NMR (solvent) δ ppm |
|---|---|---|---|---|---|---|---|---|
| 1505 | —Cl | —Cl | cyclopentyl | —H | piperonyl | 2 | oxalate | mp 135-139 |
| 1506 | —Cl | —Cl | —(CH$_2$)$_2$CH$_3$ | —H | piperonyl | 2 | free | $^1$HNMR (DMSO-d$_6$) 0.86 (3H, t, J=7.5Hz), 1.56 (2H, q, J=7.5Hz), |

TABLE 286-continued

| Example No. | $R_{869}$ | $R_{870}$ | $R_{871}$ | $R_{872}$ | $R_{873}$ | M | Form | mp (° C.) or $^1$H NMR (solvent) δ ppm |
|---|---|---|---|---|---|---|---|---|
| | | | | | | | | 2.27 (2H, brs), 2.64 (2H, t, J=7.4Hz), 2.83 (2H, t, J=7.4Hz), 3.37-3.48 (6H, m), 3.84 (2H, t, J=7.5Hz), 5.98 (2H, s), 6.36 (1H, d, J=9.1Hz), 6.74 (1H, d, J=7.9Hz), 6.83 (1H, d, J=7.9Hz), 6.86 (1H, s), 7.16 (2H, d, J=8.2Hz), 7.30 (2H, d, J=8.2Hz), 7.70 (1H, dd, J=9.1Hz, 2.6Hz), 7.81 (1H, d, J=8.4Hz), 7.93 (1H, dd, J=8.4Hz, 1.9Hz), 8.19 (1H, d, J=1.9Hz), 8.43 (1H, d, J=2.6Hz), 10.27 (1H, s). |
| 1507 | —Cl | —Cl | —CH₃ | —OCH₃ | piperonyl | 2 | free | $^1$HNMR (CDCl₃) 2.34-2.41 (4H, m), 2.62-2.68 (2H, m), 2.95-3.01 (2H, m), 3.34 (3H, s), 3.38-3.45 (4H, m), 3.62-3.65 (2H, m), 3.75 (3H, s), 5.94 (2H, s), 6.25 (1H, d, J=9.2Hz), 6.70-6.84 (5H, m), 7.12 (1H, d, J=7.6Hz), 7.53 (1H, d, J=8.2Hz), 7.67-7.72 (2H, m), 7.97 (2H, d, J=2.0Hz), 8.24 (1H, d, J=2.5Hz). |
| 1508 | —CF₃ | —H | —CH₃ | —OCH₃ | piperonyl | 2 | free | $^1$HNMR (CDCl₃) 2.36-2.37 (4H, m), 2.62-2.67 (2H, m), 2.94-2.99 (2H, m), 3.28-3.45 (7H, m), 3.60-3.64 (2H, m), 3.74 (3H, s), 5.93 (2H, s), 6.25 (1H, d, J=9.1Hz), 6.70-6.84 (5H, m), 7.11 (1H, d, J=7.6Hz), 7.67-7.75 (3H, m), 7.97 (2H, d, J=7.9Hz), 8.16-8.32 (2H, m). |
| 1509 | —Cl | —Cl | —CH₃ | —H | benzyl | 0 | oxalate | mp 228-230 |

TABLE 287

| Example No. | R₈₇₄ | R₈₇₅ | R₈₇₆ | R₈₇₇ | R₈₇₈ | Form | mp (° C.) or ¹H NMR (solvent) δ ppm |
|---|---|---|---|---|---|---|---|
| 1510 | —Cl | —Cl | —H | H₃C-N(CH₃)-CH₂-C(=O)- | piperonyl | dioxalate | ¹HNMR (DMSO-d₆) 2.36-2.50 (4H, m), 2.73 (6H, s), 3.42-3.56 (6H, m), 3.94 (2H, s), 4.56 (2H, s), 5.98 (2H, s), 6.76 (1H, d, J=8.0Hz), 6.85 (1H, d, J=8.0Hz), 6.88 (1H, s), 7.13 (1H, d, J=8.9Hz), 7.23 (2H, d, J=8.8Hz), 7.45 (2H, d, J=8.8Hz), 7.83 (1H, d, J=8.4Hz), 7.93 (1H, dd, J=8.4Hz, 2.0Hz), 8.20-8.25 (2H, m), 8.52 (1H, d, J=2.7Hz), 10.63 (1H, s). |
| 1511 | —CF₃ | —H | —CH₃ | —H | piperonyl | free | ¹HNMR (CDCl₃) 2.11 (3H, s), 2.42-2.48 (4H, m), 3.45-3.48 (4H, m), 3.66-3.70 (2H, m), 3.86 (2H, s), 4.83 (1H, brs), 5.96 (2H, s), 6.46-6.52 (2H, m), 6.71-6.78 (2H, m), 6.83-6.91 (3H, m), 7.75-7.82 (3H, m), 7.99 (2H, d, J=8.1Hz), 8.16 (1H, dd, J=8.9Hz, 2.8Hz), 8.22 (1H, d, J=2.8Hz). |
| 1512 | —Cl | —Cl | —CH₃ | —CH₃ | piperonyl | hydrochloride | mp 183-185 dec |
| 1513 | —CF₃ | —H | —CH₃ | —C₂H₅ | benzyl | maleate | mp 165-167 |
| 1514 | —Cl | —Cl | —CH₃ | —C₂H₅ | benzyl | free | mp 102-105 |
| 1515 | —CF₃ | —H | —CH₃ | —CH₃ | benzyl | free | mp 110-111 |
| 1516 | —Cl | —Cl | —CH₃ | —CH₃ | benzyl | free | mp 111-113 |

TABLE 288

| Example No. | R₈₇₉ | Form | mp (° C.) or MS |
|---|---|---|---|
| 1517 | 3,4-Cl₂Ph— | maleate | mp 203-205 |
| 1518 | 3-PhOPh— | free | MS 686 (M⁺ + H) |
| 1519 | 3,5-Cl₂Ph— | free | MS 662 (M⁺ + H) |
| 1520 | 3,5-(CH₃)₂Ph— | free | MS 622 (M⁺ + H) |
| 1521 | 2,3-(CH₃)₂Ph— | free | MS 622 (M⁺ + H) |
| 1522 | 2,3-Cl₂Ph— | free | MS 662 (M⁺ + H) |
| 1523 | 1-naphthyl | free | MS 644 (M⁺ + H) |
| 1524 | 2,4-(CH₃)₂Ph— | free | MS 622 (M⁺ + H) |
| 1525 | 3,4-(CH₃)₂Ph— | free | MS 622 (M⁺ + H) |
| 1526 | 3,4-F₂Ph— | free | MS 630 (M⁺ + H) |
| 1527 | 3-CF₃Ph— | free | MS 663 (M⁺ + H) |
| 1528 | 3-CF₃OPh— | free | MS 678 (M⁺ + H) |
| 1529 | 4-CF₃OPh— | free | MS 678 (M⁺ + H) |
| 1530 | 3-ClPhOCH₂— | free | MS 658 (M⁺ + H) |
| 1531 | 2-quinolyl | free | MS 645 (M⁺ + H) |
| 1532 | 4-quinolyl | free | MS 645 (M⁺ + H) |
| 1533 | 1-isoquinolyl | free | MS 645 (M⁺ + H) |

TABLE 288-continued

[Structure: R₈₇₉-C(=O)-NH-pyridyl-O-phenyl-N(CH₂CH₃)-CH₂-C(=O)-N(piperazine)-CH₂-benzodioxole]

| Example No. | R₈₇₉ | Form | mp (° C.) or MS |
|---|---|---|---|
| 1534 | 3-isoquinolyl | free | MS 645 (M⁺ + H) |
| 1535 | 3,4-Cl₂PhCH₂— | free | MS 676 (M⁺ + H) |
| 1536 | 2,4-Cl₂PhCH₂— | free | MS 676 (M⁺ + H) |
| 1537 | 3,5-(CF₃)₂Ph— | free | MS 731 (M⁺ + H) |
| 1538 | 2,4-Cl₂PhOCH₂— | free | MS 691 (M⁺ + H) |
| 1539 | 4-CH₃OPh— | free | MS 624 (M⁺ + H) |
| 1540 | 4-CH₃PhCH₂— | free | MS 622 (M⁺ + H) |
| 1541 | PhOCH₂— | free | MS 624 (M⁺ + H) |
| 1542 | 3-pyridyl | free | MS 595 (M⁺ + H) |
| 1543 | —CH(CH₃)₂ | free | MS 560 (M⁺ + H) |
| 1544 | cyclopentyl | free | MS 586 (M⁺ + H) |
| 1545 | cyclohexyl | free | MS 600 (M⁺ + H) |
| 1546 | cycloheptyl | free | MS 614 (M⁺ + H) |
| 1547 | cycloheptylmethyl | free | MS 628 (M⁺ + H) |
| 1548 | 3-CH₃Ph— | free | MS 608 (M⁺ + H) |
| 1549 | 3-(CH₃)₂NPh— | free | MS 637 (M⁺ + H) |
| 1550 | 4-(CH₃)₂NPh— | free | MS 637 (M⁺ + H) |
| 1551 | 2,5-(CH₃)₂Ph— | free | MS 622 (M⁺ + H) |
| 1552 | —CH(CH₃)Ph | free | MS 622 (M⁺ + H) |
| 1553 | —C(CH₃)₃ | free | MS 574 (M⁺ + H) |

TABLE 289

[Structure: R₈₈₀-C(=O)-NH-pyridyl-O-phenyl-N(CH₂CH₃)-CH₂-C(=O)-N(piperazine)-CH₂-benzodioxole]

| Example No. | R₈₈₀ | MS (M⁺ + H) |
|---|---|---|
| 1554 | 2-fluoro-6-methylphenyl (F, CH₃ substituted phenyl) | 626 |
| 1555 | 4-fluoro-3-(trifluoromethyl)phenyl | 681 |
| 1556 | 3-fluoro-5-(trifluoromethyl)phenyl | 681 |
| 1557 | 6-(trifluoromethyl)pyridin-3-yl | 663 |

TABLE 289-continued
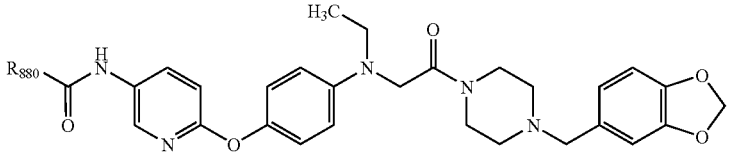
| Example No. | R880 | MS (M+ + H) |
|---|---|---|
| 1558 | 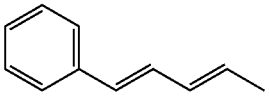 | 646 |
| 1559 | 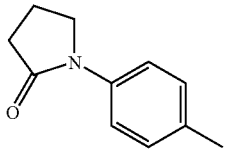 | 677 |
| 1560 | 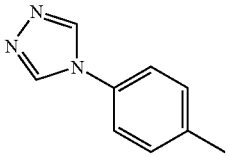 | 661 |
| 1561 | 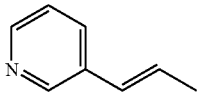 | 621 |
| 1562 | 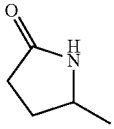 | 601 |
| 1563 | 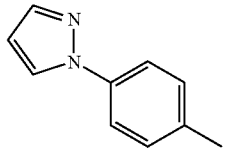 | 660 |
| 1564 | 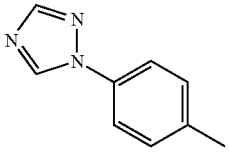 | 661 |
| 1565 | 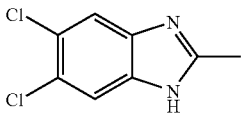 | 702 |

TABLE 290
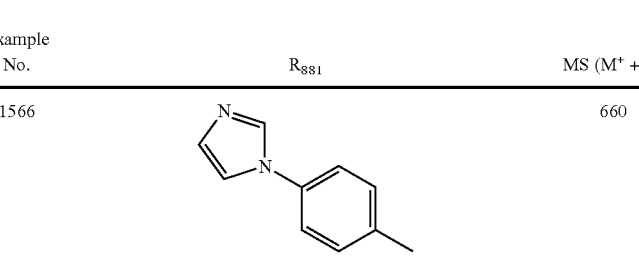
| Example No. | R_881 | MS (M⁺ + H) |
|---|---|---|
| 1566 | 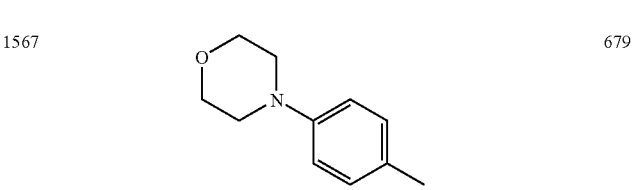 | 660 |
| 1567 | 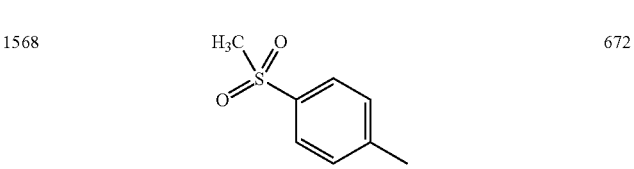 | 679 |
| 1568 | 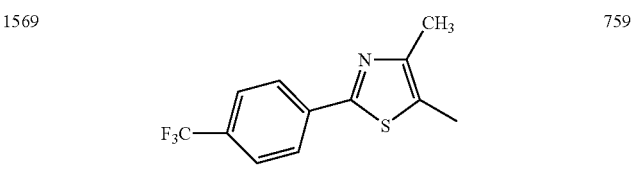 | 672 |
| 1569 | 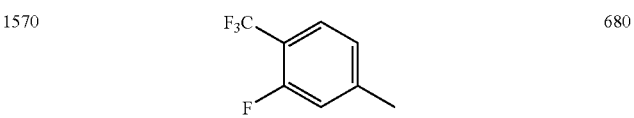 | 759 |
| 1570 | 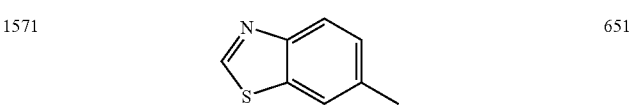 | 680 |
| 1571 | 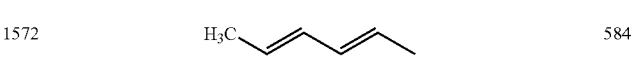 | 651 |
| 1572 | 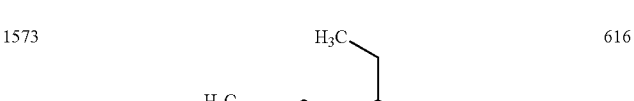 | 584 |
| 1573 | 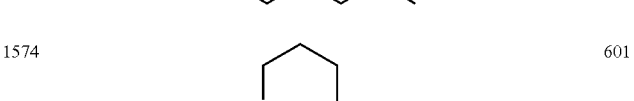 | 616 |
| 1574 | 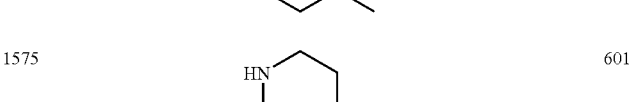 | 601 |
| 1575 |  | 601 |

TABLE 290-continued
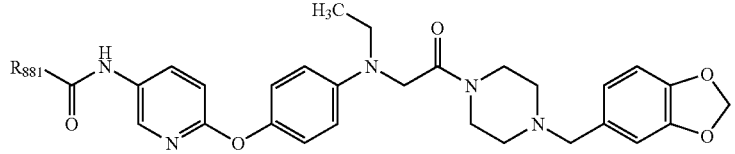
| Example No. | R₈₈₁ | MS (M⁺ + H) |
|---|---|---|
| 1576 | 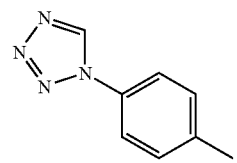 | 662 |
| 1577 | 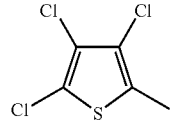 | 704 |
| 1578 | 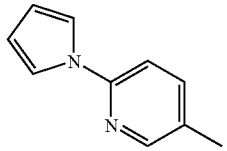 | 660 |
TABLE 291
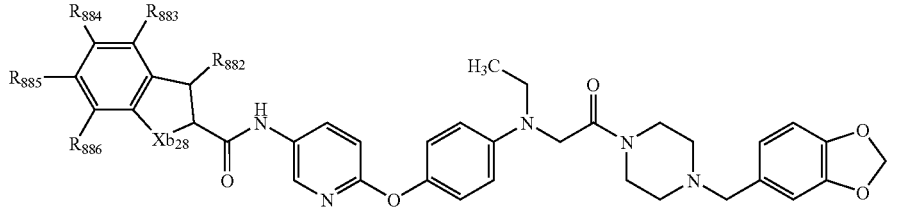
| Example No. | Xb₂₈ | R₈₈₂ | R₈₈₃ | R₈₈₄ | R₈₈₅ | R₈₈₆ | MS (M⁺ + H) |
|---|---|---|---|---|---|---|---|
| 1579 | —NH— | —H | —H | —H | —H | —H | 634 |
| 1580 | —O— | —H | —H | —H | —H | —H | 634 |
| 1581 | —O— | —H | —H | —H | —H | —OCH₃ | 664 |
| 1582 | —NH— | —H | —H | —OCH₃ | —H | —H | 663 |
| 1583 | —NH— | —H | —H | —Cl | —H | —H | 667 |
| 1584 | —NH— | —H | —H | —F | —H | —H | 651 |
| 1585 | —N(CH₃)— | —H | —H | —H | —H | —H | 647 |
| 1586 | —S— | —H | —H | —H | —H | —H | 650 |
| 1587 | —NH— | —H | —H | —Br | —H | —H | 711 |
| 1588 | —NH— | —H | —H | —CH₃ | —H | —H | 648 |
| 1589 | —NH— | —H | —H | —OCF₃ | —H | —H | 717 |
| 1590 | —NH— | —H | —OCH₃ | —H | —H | —H | 664 |
| 1591 | —NH— | —H | —Cl | —H | —H | —H | 667 |
| 1592 | —NH— | —H | —H | —H | —OCH₃ | —H | 663 |
| 1593 | —NH— | —H | —Cl | —H | —Cl | —H | 701 |
| 1594 | —NH— | —H | —Cl | —H | —H | —H | 667 |
| 1595 | —NH— | —H | —H | —OCH₃ | —OCH₃ | —H | 693 |
| 1596 | —O— | —CH₃ | —H | —H | —H | —H | 648 |
| 1597 | —O— | —H | —H | —OCH₃ | —H | —H | 664 |
| 1598 | —O— | —H | —H | —Cl | —H | —H | 668 |

TABLE 292

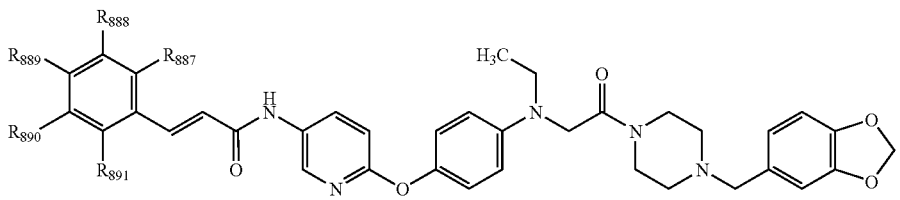

| Example No. | $R_{887}$ | $R_{888}$ | $R_{889}$ | $R_{890}$ | $R_{891}$ | MS (M$^+$ + H) |
|---|---|---|---|---|---|---|
| 1599 | —H | —OCH$_3$ | —H | —H | —H | 650 |
| 1600 | —H | —H | —OCH$_3$ | —H | —H | 650 |
| 1601 | —H | —Cl | —H | —H | —H | 654 |
| 1602 | —F | —H | —H | —H | —H | 638 |
| 1603 | —H | —F | —H | —H | —H | 638 |
| 1604 | —OCH$_3$ | —OCH$_3$ | —H | —H | —H | 680 |
| 1605 | —OCH$_3$ | —H | —H | —OCH$_3$ | —H | 680 |
| 1606 | —H | —OCH$_3$ | —OCH$_3$ | —H | —H | 680 |
| 1607 | —Cl | —H | —H | —H | —Cl | 688 |
| 1608 | —H | —Cl | —Cl | —H | —H | 688 |
| 1609 | —F | —H | —H | —H | —F | 656 |
| 1610 | —H | —F | —H | —F | —H | 656 |
| 1611 | —H | —OCH$_2$O— | | —H | —H | 664 |
| 1612 | —H | —OCH$_3$ | —OCH$_3$ | —OCH$_3$ | —H | 711 |
| 1613 | —H | —OCH$_3$ | —H | —OCH$_3$ | —H | 681 |
| 1614 | —H | —CF$_3$ | —H | —H | —H | 689 |

Example 1615

Production of 3,4-dichloro-N-[6-(2-fluoro-4-{methyl[2-oxo-2-(4-piperonylpiperazin-1-yl)ethyl]amino}phenoxy)pyridin-3-yl]benzenesulfonamide To a solution of 2-{[4-(5-aminopyridin-2-yloxy)-3-fluorophenyl]methylamino}-1-(4-piperonylpiperazin-1-yl)ethanone (15.85 g, 1.9 mmol) in dichloromethane (150 mL) were added 3,4-dichlorobenzenesulfonyl chloride (12.92 g, 1.9 mmol) and pyridine (11 mL, 12.4 mmol), and the resulting solution was stirred for 1 hour at room temperature. Water was added to the reaction solution, and extracted with ethyl acetate. The organic layer was washed with water and brine, and then dried over anhydrous magnesium sulfate. The solvent was evaporated under reduced pressure, and the residue was purified by silica gel column chromatography (ethyl acetate), and recrystallized from ethanol, to thereby yield 5.6 g of the title compound.

Appearance: White powder; Melting point: 185.6-187.0° C.; $^1$H NMR (CDCl$_3$) δ 2.45 (4H, t, J=4.6 Hz), 3.01 (3H, s), 3.44 (2H, s), 3.47 (2H, brs), 3.64 (2H, brs), 4.07 (2H, s), 5.95 (2H, s), 6.33-6.44 (2H, m), 6.71-6.78 (2H, m), 6.84-6.87 (2H, m), 6.98 (1H, t, J=9.1 Hz), 7.47 (1H, dd, J=8.4 Hz, 2.0 Hz), 7.51 (2H, dd, J=8.4 Hz, 2.8 Hz), 7.68 (1H, d, J=2.1 Hz), 7.83 (1H, d, J=1.8 Hz); MS 701 (M$^+$).

The following compounds were produced in the same manner as in Example 1615.

TABLE 293

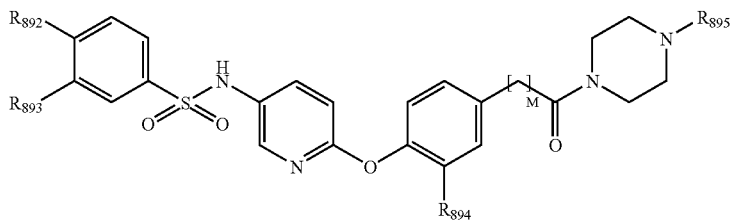

| Example No. | $R_{892}$ | $R_{893}$ | $R_{894}$ | $R_{895}$ | M | $^1$H NMR (solvent) δ ppm |
|---|---|---|---|---|---|---|
| 1616 | —CH$_3$ | —H | —H | benzyl | 2 | (CDCl$_3$) 2.29-2.37 (2H, m), 2.37-2.45 (5H, m), 2.61 (2H, t, J=7.9Hz), 2.95 (2H, t, J=7.9Hz), 3.35-3.42 (2H, m), 3.50 (2H, s), 3.59-3.68 (2H, m), 6.58 (1H, brs), 6.83 (1H, d, J=8.8Hz), 7.00 (2H, d, J=8.4Hz), 7.18-7.38 (9H, m), 7.55-7.63 (3H, m), 7.68 (1H, d, J=2.8Hz). |
| 1617 | —CF$_3$ | —H | —H | benzyl | 0 | (CDCl$_3$) 2.46 (4H, brs), 3.54 (2H, s), 3.54 (2H, brs), 3.79 (2H, brs), 6.88 (1H, d, J=8.7Hz), (2H, d, J=8.6Hz), 7.28-7.33 (5H, m), 7.42 (2H, d, J=8.6Hz), 7.59 (1H, dd, J=8.7Hz), 2.8Hz), 7.73 (2H, d, J=8.4Hz), 7.74 (1H, s), 7.86 (2H, d, J=8.4Hz). |

TABLE 293-continued

| Example No. | $R_{892}$ | $R_{893}$ | $R_{894}$ | $R_{895}$ | M | $^1$H NMR (solvent) δ ppm |
|---|---|---|---|---|---|---|
| 1618 | —CF$_3$ | —H | —CH$_3$ | piperonyl | 2 | (DMSO-d$_6$) 1.96 (3H, s), 2.20-2.40 (4H, m), 2.56-2.62 (2H, m), 2.73-2.78 (2H, m), 3.32 (2H, s), 3.37-3.43 (4H, m), 5.99 (2H, s), 6.74 (1H, dd, J=7.9Hz, 1.3Hz), 6.82-6.93 (4H, m), 7.05 (1H, dd, J=8.2Hz, 1.9Hz), 7.12 (1H, s), 7.52 (1H, dd, J=8.8Hz, 2.7Hz), 7.73 (1H, d, J=2.7Hz), 7.89-7.98 (4H, m), 10.45 (1H, brs). |
| 1619 | —Cl | —Cl | —OCH$_3$ | piperonyl | 2 | (DMSO-d$_6$) 2.20-2.40 (4H, m), 2.58-2.64 (2H, m), 2.75-2.81 (2H, m), 3.37-3.43 (6H, m), 3.60 (3H, s), 5.97 (2H, s), 6.70-7.00 (7H, m), 7.47 (1H, dd, J=8.8Hz, 2.8Hz), 7.61 (1H, dd, J=8.5Hz, 2.1Hz), 7.68 (1H, d, J=2.6Hz), 7.82-7.86 (2H, m), 10.32 (1H, brs). |
| 1620 | —CF$_3$ | —H | —OCH$_3$ | piperonyl | 2 | (DMSO-d$_6$) 2.20-2.40 (4H, m), 2.55-2.70 (2H, m), 2.75-2.85 (2H, m), 3.30-3.50 (6H, m), 3.58 (3H, s), 5.97 (2H, s), 6.71-7.00 (7H, m), 7.47 (1H, dd, J=8.8Hz, 2.7Hz), 7.67 (1H, d, J=2.7Hz), 7.87-7.98 (4H, m), 10.40 (1H, brs). |
| 1621 | —Cl | —Cl | —CH$_3$ | piperonyl | 2 | (DMSO-d$_6$) 1.97 (3H, s), 2.20-2.35 (4H, m), 2.56-2.62 (2H, m), 2.73-2.79 (2H, m), 3.37-3.50 (6H, m), 5.98 (2H, s), 6.72-6.76 (1H, m), 6.82-6.94 (4H, m), 7.00-7.13 (2H, m), 7.52 (1H, dd, J=8.8Hz, 2.8Hz), 7.62 (1H, dd, J=8.4Hz, 2.1Hz), 7.72 (1H, d, J=2.6Hz), 7.83 (1H, d, J=2.1Hz), 7.85 (1H, d, J=8.5Hz), 10.36 (1H, brs). |
| 1622 | —CF$_3$ | —H | —F | piperonyl | 2 | (DMSO-d$_6$) 2.20-2.35 (4H, m), 2.60-2.66 (2H, m), 2.78-2.84 (2H, m), 3.39 (2H, s), 3.42-3.50 (4H, m), 5.99 (2H, s), 6.72-6.76 (1H, m), 6.83-6.86 (2H, m), 7.03-7.24 (4H, m), 7.55 (1H, dd, J=8.8Hz, 2.7Hz), 7.75 (1H, d, J=2.7Hz), 7.90-7.99 (4H, m), 10.52 (1H, brs). |

TABLE 294

| Example No. | $R_{896}$ | $R_{897}$ | $R_{898}$ | mp (° C.) or $^1$H NMR (solvent) δ ppm |
|---|---|---|---|---|
| 1623 | —CF$_3$ | —H | (4-methylphenyl-NH-C(O)-NH-phenyl) | mp 208.0-209.0 |

TABLE 294-continued

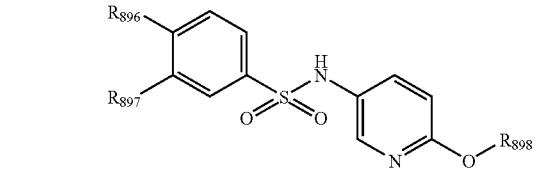

| Example No. | $R_{896}$ | $R_{897}$ | $R_{898}$ | mp (° C.) or $^1$H NMR (solvent) δ ppm |
|---|---|---|---|---|
| 1624 | —Cl | —Cl | 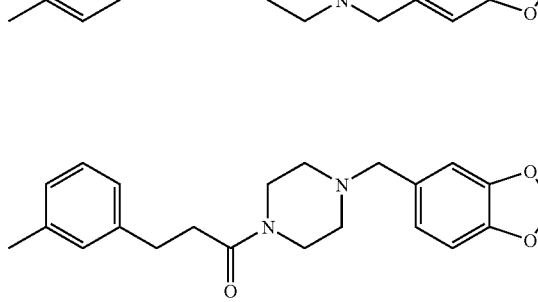 | $^1$HNMR (CDCl$_3$) 1.70 (1H, brs), 2.42 (4H, t, J=5.1 Hz) 3.39 (4H, t, J=5.1Hz) 3.43 (2H, s), 4.38 (2H, d, J=5.4Hz), 4.80 (1H, t, J=5.4Hz), 5.94 (2H, s), 6.73 (2H, s), 6.84 (1H, s), 6.86 (1H, d, J=8.5Hz), 7.00 (2H, d, J=8.6Hz), 7.27 (2H, d, J=8.6Hz), 7.51 (2H, d, J=2.5Hz), 7.58 (1H, dd, J=8.7Hz, 2.7Hz), 7.73 (1H, dd, J=2.7Hz, 0.7Hz), 7.83 (1H, t, J=2.5Hz). |
| 1625 | —Cl | —Cl | 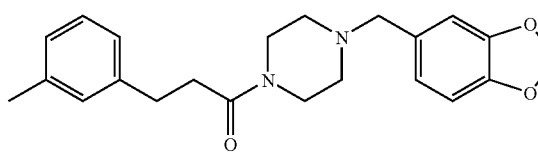 | $^1$HNMR (DMSO-d$_6$) 2.20-2.35 (4H, m), 2.56-2.62 (2H, m), 2.77-2.82 (2H, m), 3.30-3.50 (6H, m), 5.98 (2H, s), 6.70-6.80 (1H, m), 6.82-6.90 (3H, m), 6.93-6.97 (2H, m), 7.05-7.10 (1H, m), 7.24-7.35 (1H, m), 7.54 (1H, dd, J=8.8Hz, 2.8Hz), 7.64 (1H, dd, J=8.5Hz, 2.0Hz), 7.80 (1H, d, J=2.8Hz), 7.86 (1H, d, J=8.4Hz), 7.89 (1H, d, J=2.0Hz), 10.43 (1H, brs). |
| 1626 | —CF$_3$ | —H | 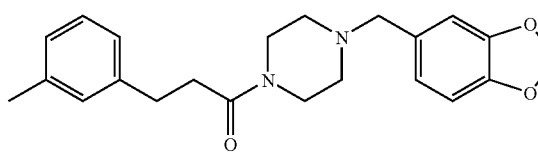 | $^1$H NMR (DMSO-d$_6$) 2.20-2.30 (4H, m), 2.55-2.61 (2H, m), 2.76-2.82 (2H, m), 3.30-3.40 (6H, m), 5.98 (2H, s), 6.70-6.80 (1H, m), 6.82-6.95 (5H, m), 7.05 (1H, d, J=7.7Hz), 7.23-7.30 (1H, m), 7.54 (1H, dd, J=8.8Hz, 2.8Hz), 7.80 (1H, d, J=2.8Hz), 7.90-7.99 (4H, m), 10.52 (1H, brs). |
| 1627 | —Cl | —Cl | 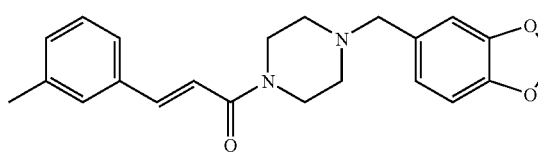 | $^1$HNMR (DMSO-d$_6$) 2.25-2.45 (4H, m), 3.42 (2H, s), 3.50-3.75 (4H, m), 5.99 (2H, s), 6.75-6.80 (1H, m), 6.83-6.88 (2H, m), 7.00 (1H, d J 8.8Hz), 7.05-7.10 (1H, m), 7.25-7.29 (1H, m), 7.35-7.65 (6H, m), 7.880 (1H, d, J=2.7Hz), 7.86 (1H, d, J=8.4Hz), 7.90 (1H, d, J=2.1Hz) 10.44 (1H, brs). |

TABLE 295

| Example No. | $R_{899}$ | $R_{900}$ | M | mp (° C.) or $^1$H NMR (DMSO-d$_6$) δ ppm |
|---|---|---|---|---|
| 1628 | 4-CF$_3$Ph— | piperonyl | 2 | $^1$HNMR 1.89-2.06 (5H, m), 3.17-3.31 (2H, m), 3.52-3.71 (2H, m), 4.39 (2H, s), 5.98 (2H, m), 6.75 (1H, dd, J=1.2Hz, 7.9Hz), 6.83 (1H, d, J=1.2Hz), 6.86 (1H, d, J=7.9Hz), |

TABLE 295-continued

| Example No. | $R_{899}$ | $R_{900}$ | M | mp (° C.) or $^1$H NMR (DMSO-$d_6$) δ ppm |
|---|---|---|---|---|
| | | | | 6.92 (1H, d, J=8.6Hz), 6.95 (1H, d, J=8.8Hz), 7.09 (1H, dd, J=2.5Hz, 8.6Hz), 7.18 (1H, d, J=2.5Hz), 7.53 (1H, dd, J=2.8Hz, 8.8Hz), 7.75 (1H, d, J=2.8Hz), 7.90 (2H, d, J=8.4Hz), 7.96 (2H, d, J=8.4Hz), 10.47 (1H, s). |
| 1629 | 3,4-Cl$_2$Ph— | piperonyl | 2 | $^1$HNMR 1.89-2.09 (5H, m), 3.19-3.33 (2H, m), 3.50-3.71 (2H, m), 4.39 (2H, s), 5.98 (2H, s), 6.73-6.78 (1H, m), 6.83 (1H, d, J=1.3Hz), 6.86 (1H, d, J=7.9Hz), 6.93 (1H, d, J=8.6Hz), 6.97 (1H, d, J=8.8Hz), 7.10 (1H, d, J=2.4Hz, 8.6Hz), 7.19 (1H, d, J=2.4Hz), 7.53 (1H, dd, J=2.7Hz, 8.8Hz), 7.62 (1H, dd, J=2.1Hz, 8.4Hz), 7.75 (1H, d, J=2.7Hz), 7.83 (1H, d, J=2.1Hz) 7.85 (1H, d, J=8.4Hz), 10.37 (1H, s). |
| 1630 | 4-CF$_3$Ph— | piperonyl | 1 | mp 163.0-164.0 |
| 1631 | 3,4-Cl$_2$Ph— | piperonyl | 1 | mp 190.5-191.0 |
| 1632 | 4-CF$_3$Ph— | 3,4-(CH$_3$O)$_2$PhCH$_2$— | 2 | mp 141.0-143.0 |
| 1633 | 3,4-Cl$_2$Ph— | 3,4-(CH$_3$O)$_2$PhCH$_2$— | 2 | mp 135.0-136.0 |
| 1634 | 3,4-Cl$_2$Ph— | —C$_6$H$_4$—COOC$_2$H$_5$ | 2 | mp 181.0-183.0 |

TABLE 296

| Example No. | $R_{901}$ | $R_{902}$ | M | $^1$H NMR (CDCl$_3$) δ ppm |
|---|---|---|---|---|
| 1635 | 3,4-Cl$_2$Ph— | —CH$_3$ | 0 | 1.27 (3H, t, J=7.1Hz) 1.84-2.05 (4H, m), 2.06 (3H, s), 2.40-2.48 (1H, m), 2.71-2.81 (2H, m), 3.56-3.61 (2H, m), 4.16 (2H, q, J=7.1Hz) 6.74-6.79 (3H, m), 6.89 (1H, d, J=8.6Hz), 7.47-7.57 (4H, m), 7.76-7.79 (2H, m). |
| 1636 | 4-CF$_3$Ph— | —CH$_3$ | 0 | 1.27 (3H, t, J=7.1Hz), 1.84-2.00 (4H, m), 2.03 (3H, s), 2.42-2.51 (1H, m), 2.70-2.79 (2H, m), 3.55-3.60 (2H, m), 4.16 (2H, q, J=7.1Hz) 6.68-6.78 (3H, m), 6.87 (1H, d, J=8.6Hz), 7.55 (1H, dd, J=8.7Hz, 2.6Hz), 7.67 (2H, d, J=8.2Hz), 7.79-7.84 (3H, m), 8.10 (1H, s). |
| 1637 | 3,4-Cl$_2$Ph— | —H | 1 | 1.27 (3H, t, J=7.1Hz) 1.39-1.48 (2H, m), 1.81-1.92 (3H, m), 2.29 (2H, d, J=6.9Hz), 2.71 (2H, dd, J=12.2Hz, 9.9Hz), 3.59 (2H, d, J=12.4Hz), 4.15 (2H, q, J=7.3Hz), 6.78 (1H, d, J=8.7Hz), 6.90-6.98 (4H, m), 7.50 (2H, d, J=1.2Hz), 7.55 (1H, dd, J=8.7Hz, 2.6Hz), 7.78-7.81 (3H, m). |
| 1638 | 4-CF$_3$Ph— | —H | 1 | 1.27 (3H, t, J=7.1Hz) 1.36-1.48 (2H, m), 1.81-1.92 (3H, m), 2.29 (2H, d, J=6.9Hz), 2.70 (2H, dd, J=12.2Hz, 9.9Hz), 3.59 (2H, d, J=12.2Hz), 4.15 (2H, q, J=7.3Hz), 6.75 (1H, d, J=8.9Hz), 6.89-6.97 (4H, m), 7.55 (1H, dd, J=8.7Hz, 2.6Hz), 7.68 (2H, d, J=8.7Hz), 7.79-7.85 (4H, m). |
| 1639 | 4-CF$_3$Ph— | —OCH$_3$ | 1 | 1.27 (3H, t, J=7.1Hz) 1.30-1.48 (2H, m), 1.82-2.05 (3H, m), 2.29 (2H, d, J=6.9Hz), 2.69-2.77 (2H, m), 3.60 (2H, d, J=12.2Hz), 3.68 (3H, s), 4.15 (2H, q, J=7.1Hz) 6.48 (1H, dd, J=8.6Hz, 2.5Hz), 6.56 (1H, d, J=2.6Hz), 6.76 (1H, d, J=8.7Hz), 6.94 (1H, d, J=8.7Hz), 7.54 (1H, |

TABLE 296-continued

[Structure: R₉₀₁-S(O)₂-NH-(pyridine)-O-(phenyl with R₉₀₂)-N(piperidine-CH-[CH₂]ₘ-COOC₂H₅)]

| Example No. | R₉₀₁ | R₉₀₂ | M | ¹H NMR (CDCl₃) δ ppm |
|---|---|---|---|---|
| 1640 | 3,4-Cl₂Ph— | —OCH₃ | 1 | dd, J=8.7Hz, 2.8z), 7.66-7.73 (4H, m), 7.83 (2H, d, J=8.2Hz). 1.28 (3H, t, J=7.1Hz) 1.30-1.48 (2H, m), 1.82-2.05 (3H, m), 2.29 (2H, d, J=6.9Hz), 2.73 (2H, t, J=12.0Hz), 3.60 (2H, d, J=12.2Hz), 3.69 (3H, s), 4.16 (2H, q, J=7.1Hz), 5.29 (2H, s), 6.48 (1H, dd, J=8.7Hz, 2.6Hz), 6.56 (1H, d, J=2.6Hz), 6.77 (1H, d, J=8.7Hz), 6.94 (1H, d, J=8.6Hz), 7.46-7.75 (3H, m), 7.79-7.80 (3H, m). |
| 1641 | 4-CF₃Ph— | —H | 0 | 1.27 (3H, t, J=7.1Hz) 1.81-1.94 (2H, m), 2.00-2.05 (2H, m), 2.40-2.54 (1H, m), 2.71-2.82 (2H, m), 3.56-3.60 (2H, m), 4.16 (2H, q, J=7.1Hz) 6.78 (1H, d, J=8.9Hz), 6.90-6.99 (5H, m), 7.56 (1H, dd, J=8.9Hz, 2.8z), 7.70 (2H, d, J=8.4Hz), 7.77 (1H, d, J=2.8Hz), 7.84 (2H, d, J=8.2Hz). |
| 1642 | 3,4-Cl₂Ph— | —H | 0 | 1.27 (3H, t, J=7.3Hz), 1.89-1.94 (2H, m), 2.01-2.05 (2H, m), 2.38-2.54 (1H, m), 2.72-2.82 (2H, m), 3.56-3.61 (2H, m), 4.16 (2H, q, J=7.1Hz) 6.80 (1H, d, J=8.7Hz), 6.91-7.00 (4H, m), 7.26 (1H, brs), 7.51-7.58 (3H, m), 7.77 (1H, d, J=2.8Hz), 7.82 (1H, s). |

TABLE 297

[Structure: R₉₀₃-S(O)₂-NH-(pyridine)-O-(phenyl with R₉₀₄)-N(piperidine-CH-[CH₂]ₘ-COOC₂H₅)]

| Example No. | R₉₀₃ | R₉₀₄ | M | ¹H NMR (CDCl₃) δ ppm |
|---|---|---|---|---|
| 1643 | 4-CF₃Ph— | —CH₃ | 1 | 1.27 (3H, t, J=7.1Hz) 1.38-1.43 (2H, m), 1.80-2.01 (3H, m), 2.02 (3H, s), 2.29 (2H, d, J=6.9Hz), 2.69 (2H, t, J=12.0Hz), 3.58 (2H, d, J=12.0Hz), 4.15 (2H, q, J=7.3Hz), 6.67-6.87 (4H, m), 7.53-7.68 (3H, m), 7.79-7.84 (4H, m). |
| 1644 | 3,4-Cl₂Ph— | —CH₃ | 1 | 1.27 (3H, t, J=7.1Hz) 1.30-1.48 (2H, m), 1.80-2.04 (3H, m), 2.05 (3H, s), 2.29 (2H, d, J=6.9Hz), 2.69 (2H, t, J=12.0Hz), 3.58 (2H, d, J=12.0Hz), 4.15 (2H, q, J=7.1Hz) 6.71-6.79 (3H, m), 6.88 (1H, d, J=8.6Hz), 7.49-7.57 (4H, m), 7.77 (2H, d, J=2.8Hz). |

TABLE 298

[Structure: R₉₀₅-S(O)₂-NH-(pyridine with R₉₀₇ and R₉₀₆)-O-phenyl-CH₂CH₂-C(O)-N(piperazine)-CH₂-(benzo[1,3]dioxole)]

| Example No. | R₉₀₅ | R₉₀₆ | R₉₀₇ | Form | mp (° C.) |
|---|---|---|---|---|---|
| 1645 | 4-CF₃Ph— | —H | —CH₃ | hydrochloride | 189.0-191.0 |
| 1646 | 3,4-Cl₂Ph— | —H | —CH₃ | free | 180.0-182.0 |
| 1647 | 4-CF₃Ph— | —CH₃ | —H | free | 129.5-131.0 |
| 1648 | 3,4-Cl₂Ph— | —CH₃ | —H | free | 129.0-130.0 |

TABLE 299

| Example No. | R_908 | R_909 | $^1$H NMR (DMSO-d$_6$) δ ppm |
|---|---|---|---|
| 1649 | 5-F,2-Cl-Ph— | —F | 2.20-2.35 (4H, m), 2.60-2.66 (2H, m), 2.77-2.83 (2H, m), 3.39 (2H, s), 3.39-3.50 (4H, m), 5.99 (2H, s), 6.65-6.76 (1H, m), 6.83-6.86 (2H, m), 7.01-7.25 (4H, m), 7.30-7.40 (1H, m), 7.55 (1H, dd, J=8.8Hz, 2.8Hz), 7.72 (1H, dd, J=8.7Hz, 2.6Hz), 7.78 (1H, d, J=2.3Hz), 8.00-8.05 (1H, m), 10.65 (1H, brs). |
| 1650 | 5-F,2-Cl-Ph— | —CH$_3$ | 1.94 (3H, s), 2.20-2.35 (4H, m), 2.56-2.61 (2H, m), 2.72-2.78 (2H, m), 3.38 (2H, s), 3.38-3.50 (4H, m), 5.98 (2H, s), 6.72-6.75 (1H, m), 6.82-6.91 (4H, m), 7.03-7.12 (2H, m), 7.30-7.45 (1H, m), 7.52 (1H, dd, J=8.8Hz, 2.2Hz), 7.71 (1H, dd, J=8.7Hz, 2.1Hz) 7.78 (1H, d, J=2.7Hz), 7.98-8.04 (1H, m), 10.58 (1H, brs). |
| 1651 | 3,4-Cl$_2$Ph— | —H | 2.20-2.35 (4H, m), 2.57-2.63 (2H, m), 2.76-2.82 (2H, m), 3.39 (2H, s), 3.39-3.43 (4H, m), 5.99 (2H, s), 6.70-6.76 (1H, m), 6.82-6.86 (2H, m), 6.93-6.98 (3H, m), 7.22-7.26 (2H, m), 7.51-7.55 (1H, m), 7.63 (1H, dd, J=8.5Hz, 2.0Hz), 7.79 (1H, d, J=2.7Hz), 7.86 (1H, d, J=8.5Hz), 7.88 (1H, d, J=2.1Hz) 10.41 (1H, brs). |
| 1652 | 4-CF$_3$Ph— | —H | 2.20-2.35 (4H, m), 2.57-2.63 (2H, m), 2.76-2.82 (2H, m), 3.32 (2H, s), 3.32-3.50 (4H, m), 5.98 (2H, s), 6.70-6.76 (1H, m), 6.82-6.86 (2H, m), 6.92-6.98 (3H, m), 7.22-7.25 (2H, m), 7.52 (1H, dd, J=8.8Hz, 2.8Hz), 7.78 (1H, d, J=2.7Hz), 7.90-7.99 (4H, m), 10.50 (1H, brs). |
| 1653 | 3,4-Cl$_2$Ph— | —F | 2.20-2.35 (4H, m), 2.60-2.66 (2H, m), 2.78-2.84 (2H, m), 3.39 (2H, s), 3.42-3.50 (4H, m), 5.99 (2H, s), 6.70-6.76 (1H, m), 6.82-6.86 (2H, m), 7.04-7.30 (4H, m), 7.55 (1H, dd, J=8.8Hz, 2.8Hz), 7.63 (1H, dd, J=8.5Hz, 2.2Hz), 7.75 (1H, d, J=2.6Hz), 7.85 (1H, d, J=8.5Hz), 7.88 (1H, d, J=2.1Hz), 10.43 (1H, brs). |

TABLE 300

| Example No. | R_910 | R_911 | R_912 | R_913 | mp (° C.) or $^1$H NMR (solvent) δ ppm |
|---|---|---|---|---|---|
| 1654 | 4-CF$_3$Ph— | —F | —H | —CH$_3$ | mp 186.0-188.0 |
| 1655 | 3,4-Cl$_2$Ph— | —F | —H | —C$_2$H$_5$ | mp 157.3-160.1 |
| 1656 | 4-CF$_3$Ph— | —F | —H | —C$_2$H$_5$ | mp 173.0-176.8 |
| 1657 | 4-CF$_3$Ph— | —OCH$_3$ | —H | —C$_2$H$_5$ | mp 179.0-181.0 |
| 1658 | 3,4-Cl$_2$Ph— | —OCH$_3$ | —H | —C$_2$H$_5$ | mp 175.0-176.0 |
| 1659 | 4-CF$_3$Ph— | —CH$_3$ | —H | —CH$_3$ | mp 170.0-172.0 |
| 1660 | 3,4-Cl$_2$Ph— | —CH$_3$ | —H | —CH$_3$ | mp 170.0-173.0 |
| 1661 | 3,4-Cl$_2$Ph— | —H | —H | —CH$_3$ | mp 135.0-137.0 |
| 1662 | 4-CF$_3$Ph— | —H | —H | —CH$_3$ | mp 189.0-190.0 |
| 1663 | 4-CF$_3$Ph— | —F | —F | —CH$_3$ | mp 159.5-160.0 |
| 1664 | 3,4-Cl$_2$Ph— | —F | —F | —CH$_3$ | mp 136.0-137.0 |
| 1665 | Ph— | —H | —H | —CH$_3$ | $^1$HNMR (CDCl$_3$) 2.41-2.45 (4H, m), 3.01 (3H, s), 3.43 (2H, s), 3.47-3.49 (2H, m), 3.63 (2H, brs), 4.07 (2H, s), 5.95 (2H, s), 6.63 (1H, brs), 6.66 (2H, d, J=9.1Hz), 6.71-6.77 (3H, m), 6.85 (1H, brs), 6.93 (2H, d, J=9.1Hz), 7.42-7.59 (4H, m), 7.68-7.73 (3H, m). |
| 1666 | —(CH$_2$)$_3$CH$_3$ | —H | —H | —CH$_3$ | $^1$HNMR (CDCl$_3$) 0.93 (3H, t, J=7.3Hz), 1.36-1.50 (2H, m), 1.75-1.87 (2H, m), 2.41-2.45 (4H, m), 3.01-3.06 (5H, m), 3.44 (2H, s), |

TABLE 300-continued

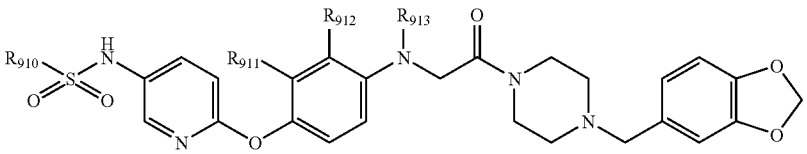

| Example No. | R910 | R911 | R912 | R913 | mp (° C.) or $^1$H NMR (solvent) δ ppm |
|---|---|---|---|---|---|
| | | | | | 3.47-3.49 (2H, m), 3.63 (2H, brs), 4.09 (2H, s), 5.95 (2H, s), 6.37 (1H, brs), 6.69 (2H, d, J=9.1Hz), 6.72-6.77 (2H, m), 6.82-6.96 (2H, m), 6.99 (2H, d, J=9.1Hz), 7.65 (1H, dd, J=8.7Hz, 2.8Hz), 8.00 (1H, d, J=2.8Hz). |
| 1667 | 4-CH₃Ph— | —H | —H | —CH₃ | $^1$HNMR (CDCl₃) 2.39 (3H, s), 2.41-2.44 (4H, m), 3.01 (3H, s), 3.43 (2H, s), 3.47-3.49 (2H, m), 3.62 (2H, brs), 4.07 (2H, s), 5.95 (2H, s), 6.46-6.51 (1H, m), 6.66 (2H, d, J=8.9Hz), 6.70-6.77 (3H, m), 6.85 (1H, brs), 6.94 (2H, d, J=8.9Hz), 7.23 (2H, d, J=8.1Hz), 7.50 (1H, dd, J=8.2Hz, 2.8Hz), 7.58 (2H, d, J=8.4Hz), 7.66 (1H, d, J=2.6Hz). |
| 1668 | 4-F, 2-Cl, methylphenyl | —F | —H | —CH₃ | $^1$HNMR (DMSO-d₆) 2.25-2.45 (4H, m), 2.91 (3H, s), 3.42 (6H, brs), 4.26 (2H, s), 5.99 (2H, s), 6.30-6.40 (1H, m), 6.45-6.55 (1H, m) 6.74-6.77 (1H, m), 6.83-7.05 (4H, m), 7.30-7.45 (1H, m), 7.51 (1H, dd, J=8.9Hz, 2.8Hz), 7.71 (1H, dd, J=8.7Hz, 2.5Hz), 7.79 (1H, d, J=2.7Hz), 8.02 (1H, dd, J=8.9Hz, 5.9Hz), 10.60 (1H, brs). |
| 1669 | 3,4-Cl₂Ph— | —COOCH₃ | —H | —C₂H₅ | $^1$HNMR (DMSO-d₆) 1.11 (3H, t, J=7.0Hz), 2.20-2.5 (4H, m), 3.30-3.50 (11H, m), 4.22 (2H, s), 5.99 (2H, s), 6.75-7.00 (7H, m), 7.45-7.55 (1H, m), 7.60-7.70 (2H, m), 7.83-7.87 (2H, m), 10.31 (1H, brs). |

TABLE 301

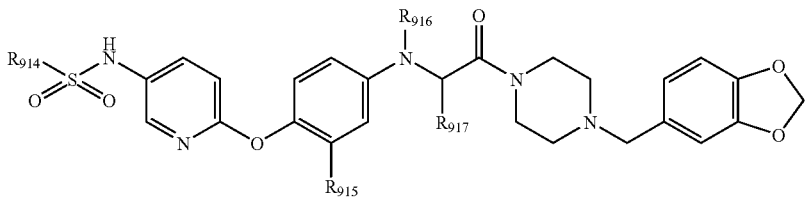

| Example No. | R914 | R915 | R916 | R917 | $^1$H NMR (solvent) δ ppm |
|---|---|---|---|---|---|
| 1670 | 4-OCH₃, 2-methyl, H₃C-phenyl | —F | —CH₃ | —H | (DMSO-d₆) 2.23 (3H, s), 2.25-2.45 (4H, m), 2.91 (3H, s), 3.41 (6H, brs), 3.83 (3H, s), 4.25 (2H, s), 5.99 (2H, s), 6.30-6.40 (1H, m), 6.45-6.55 (1H, m), 6.75-6.77 (1H, m), 6.83-6.99 (4H, m), 7.07 (1H, d, J=8.5Hz), 7.30-7.40 (1H, m), 7.48 (1H, d, J=1.9Hz), 7.51 (1H, dd, J=8.8Hz, 2.7Hz), 7.74 (1H, d, J=2.6Hz), 9.85 (1H, brs). |
| 1671 | 3,4-Cl₂Ph— | —CH₃ | —CH₃ | —CH₃ | (CDCl₃) 1.28 (3H, d, J=6.6Hz), 2.05 (3H, s), 2.08-2.21 (1H, m), 2.33 (2H, brs), 2.50 (1H, brs), 2.75 (3H, s), 3.29-3.57 (3H, m), 3.38 (2H, s), 3.77 (1H, brs), 4.55 (1H, q, J=6.6Hz), 5.94 (2H, s), 6.56-6.59 (2H, m), 6.68-6.75 (2H, m), 6.79-6.82 (2H, m), 6.89-6.93 (1H, m), 7.51-7.52 (2H, m), 7.57 (1H, dd, J=8.9Hz, 2.8Hz), 7.71 (1H, dd, J=2.8Hz, 0.5Hz), 7.79 (1H, dd, J=1.7Hz, 0.8Hz). |
| 1672 | 4-CF₃Ph— | —CH₃ | —CH₃ | —CH₃ | (CDCl₃) 1.28 (3H, d, J=6.4Hz), 2.07 (3H, s), 2.17-2.20 (1H, m), 2.33-2.36 (2H, m), 2.47-2.49 (1H, m), 2.75 (3H, s), 3.28-3.30 (1H, m), 3.38 (2H, s), 3.38-3.50 (1H, m), |

TABLE 301-continued

| Example No. | $R_{914}$ | $R_{915}$ | $R_{916}$ | $R_{917}$ | $^1$H NMR (solvent) δ ppm |
|---|---|---|---|---|---|
| | | | | | 3.52-3.56 (1H, m), 3.77-3.82 (1H, m), 4.55 (1H, q, J=6.6Hz), 5.94 (2H, s), 6.55-6.59 (2H, m), 6.68-6.75 (2H, m), 6.78-6.82 (2H, m), 6.89-6.92 (1H, m), 7.57 (1H, dd, J=8.7Hz, 2.8Hz), 7.70 (1H, dd, J=2.8Hz, 0.5Hz), 7.73 (2H, d, J=8.3Hz), 7.85 (2H, d, J=8.3Hz). |
| 1673 | NC-(3-Cl-4-Me-Ph) | —F | —CH$_3$ | —H | (DMSO-d$_6$) 2.20-2.50 (4H, m), 2.91 (3H, s), 3.35-3.50 (6H, m), 4.26 (2H, s), 5.99 (2H, s), 6.20-6.30 (1H, m), 6.45-6.55 (1H, m), 6.75-6.80 (1H, m), 6.84-7.01 (4H, m), 7.52 (1H, dd, J=8.8Hz, 2.7Hz), 7.79 (1H, d, J=2.8Hz), 7.97 (1H, dd, J=8.2Hz, 1.5Hz), 8.09 (1H, d, J=8.2Hz), 8.29(1H, d, J=1.5Hz), 10.80 (1H, brs). |
| 1674 | 4-PhOPh— | —F | —CH$_3$ | —H | (DMSO-d$_6$) 2.20-2.45 (4H, m), 2.92 (3H, s), 3.35-3.50 (6H, m), 4.26 (2H, s), 5.99 (2H, s), 6.35-6.45 (1H, m), 6.45-6.60 (1H, m), 6.76 (1H, d, J=7.9Hz), 6.83-6.87 (2H, m), 6.93-7.14 (6H, m), 7.20-7.30 (1H, m), 7.43-7.55 (3H, m), 7.68-7.74 (3H, m), 10.17 (1H, brs). |
| 1675 | 3,4-Cl$_2$Ph— | —CF$_3$ | —C$_2$H$_5$ | —H | (DMSO-d$_6$) 1.11 (3H, t, J=6.9Hz), 2.25-2.45 (4H, m), 3.35-3.55 (8H, m), 4.27 (2H, s), 5.99 (2H, s), 6.67-6.88 (5H, m), 6.94-7.05 (2H, m), 7.52 (1H, dd, J=8.8Hz, 2.8Hz), 7.63 (1H, dd, J=8.4Hz, 2.2Hz), 7.75 (1H, d, J=2.7Hz), 7.83-7.87 (2H, m), 10.38 (1H, brs). |

TABLE 302

| Example No. | $R_{918}$ | $R_{919}$ | $R_{920}$ | $R_{921}$ | $R_{922}$ | Form | Property |
|---|---|---|---|---|---|---|---|
| 1676 | 4-CF$_3$Ph— | —F | —F | —H | —CH$_3$ | free | mp 199.0-200.0° C. |
| 1677 | 3,4-Cl$_2$Ph— | —F | —F | —H | —CH$_3$ | free | mp 198.0-199.0° C. |
| 1678 | 4-CF$_3$Ph— | —F | —H | —F | —CH$_3$ | free | mp 176.0-177.0° C. |
| 1679 | 3,4-Cl$_2$Ph— | —F | —H | —F | —CH$_3$ | free | mp 115.0-116.0° C. |
| 1680 | 4-CF$_3$Ph— | —F | —H | —F | —C$_2$H$_5$ | free | mp 173.0-174.0° C. |
| 1681 | 3,4-Cl$_2$Ph— | —F | —H | —F | —C$_2$H$_5$ | free | mp 156.0-157.0° C. |
| 1682 | 3,4-Cl$_2$Ph— | —CH$_3$ | —H | —CH$_3$ | —C$_2$H$_5$ | hydrochloride | $^1$HNMR (DMSO-d$_6$) δ0.95 (3H, t, J=7.0Hz), 1.97(3H, s), 2.28 (3H, s), 2.70-4.40 (14H, m), 6.07 (2H, s), 6.86 (1H, brs), 6.93-7.10 (3H, m), 7.20-7.40 (2H, m), 7.56 (1H, dd, J=8.8Hz, 2.7Hz), 7.66 (1H, dd, J=8.5Hz, 2.1Hz), 7.78 (1H, d, J=2.6Hz), 7.85-7.88 (2H, m), 10.55 (1H, brs), 11.47 (1H, brs). |
| 1683 | 4-CF$_3$Ph— | —CH$_3$ | —H | —CH$_3$ | —C$_2$H$_5$ | free | $^1$HNMR (DMSO-d$_6$) δ0.92 (3H, t, J=7.0Hz), 1.91 (3H, s), 2.16 (3H, |

TABLE 302-continued

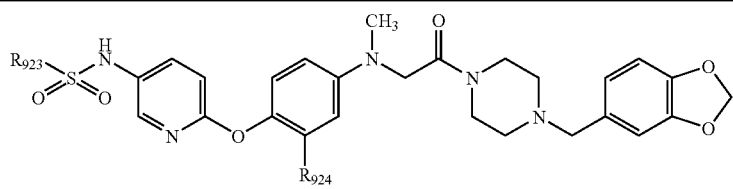

| Example No. | R918 | R919 | R920 | R921 | R922 | Form | Property |
|---|---|---|---|---|---|---|---|
| | | | | | | | s), 2.20-2.40 (4H, m), 2.98 (2H, q, J=7.0Hz), 3.30-3.50 (6H, m), 3.77 (2H, s), 5.98 (2H, s), 6.72-6.76 (2H, m), 6.82-6.90 (3H, m), 7.01 (1H, s), 7.51 (1H, dd, J=8.8Hz, 2.8Hz), 7.75 (1H, d, J=2.7Hz), 7.89-7.99 (4H, m), 10.45 (1H, brs). |
| 1684 | 3,4-Cl₂Ph— | —F | —H | —H | —H | hydro-chloride | ¹HNMR (DMSO-d₆) δ2.75-3.65 (7H, m), 3.85-4.55 (6H, m), 6.08 (2H, s), 6.47-6.50 (1H, m), 6.59 (1H, dd, J=13.5Hz, 2.6Hz), 6.92-7.01 (4H, m), 7.20 (1H, s), 7.52 (1H, dd, J=8.7Hz, 2.6Hz), 7.64 (1H, dd, J=8.4Hz, 2.1Hz), 7.76 (1H, d, J=2.5Hz), 7.86 (1H, d, J=8.6Hz), 7.89 (1H, d, J=2.2Hz), 10.45 (1H, s), 10.90 (1H, brs). |
| 1685 | 4-CH₃OPh— | —H | —H | —H | —CH₃ | free | MS 646 (M⁺ + H) |
| 1686 | 1-naphthyl | —H | —H | —H | —CH₃ | free | MS 666 (M⁺ + H) |
| 1687 | 2-naphthyl | —H | —H | —H | —CH₃ | free | MS 666 (M⁺ + H) |
| 1688 | 2-CH₃Ph— | —H | —H | —H | —CH₃ | free | MS 630 (M⁺ + H) |
| 1689 | 4-FPh— | —H | —H | —H | —CH₃ | free | MS 634 (M⁺ + H) |
| 1690 | 2-CF₃Ph— | —H | —H | —H | —CH₃ | free | MS 684 (M⁺ + H) |
| 1691 | 2-ClPh— | —H | —H | —H | —CH₃ | free | MS 650 (M⁺ + H) |

TABLE 303

| Example No. | R923 | R924 | MS (M⁺ + H) |
|---|---|---|---|
| 1692 | 2-thienyl | —H | 622 |
| 1693 | 2-CF₃OPh— | —H | 700 |
| 1694 | 3-CF₃OPh— | —H | 700 |
| 1695 | 3-CH₃OPh— | —H | 646 |
| 1696 | 3-FPh— | —H | 634 |
| 1697 | 2,3-Cl₂Ph— | —H | 684 |
| 1698 | 3-CF₃Ph— | —H | 684 |
| 1699 | 4-CF₃OPh— | —H | 700 |
| 1700 | 4-biphenylyl | —H | 692 |
| 1701 | 3,4-(CH₃O)₂Ph— | —H | 676 |
| 1702 | 2,5-(CH₃O)₂Ph— | —H | 676 |
| 1703 | 3-CH₃Ph— | —H | 630 |
| 1704 | 2,5-Cl₂Ph— | —H | 684 |
| 1705 | 3-ClPh— | —H | 650 |
| 1706 | 2,4-Cl₂Ph— | —H | 684 |
| 1707 | 2,3,4-Cl₃Ph— | —H | 720 |
| 1708 | —C₂H₅ | —H | 568 |
| 1709 | 2,6-Cl₂Ph— | —H | 684 |
| 1710 | 4-CH₃OPh— | —F | 664 |
| 1711 | 4-ClPh— | —F | 668 |
| 1712 | 1-naphthyl | —F | 684 |
| 1713 | 2-naphthyl | —F | 684 |
| 1714 | 2-CH₃Ph— | —F | 648 |
| 1715 | 4-FPh— | —F | 652 |

TABLE 303-continued

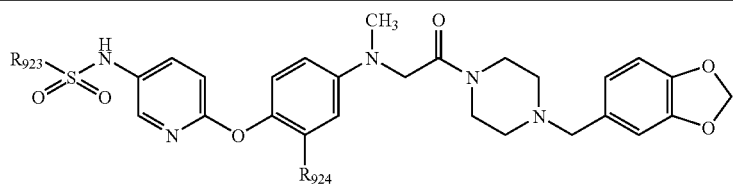

| Example No. | $R_{923}$ | $R_{924}$ | MS (M$^+$ + H) |
|---|---|---|---|
| 1716 | 2-CF$_3$Ph— | —F | 702 |
| 1717 | 2-thienyl | —F | 640 |
| 1718 | 2-ClPh— | —F | 668 |
| 1719 | 2-CF$_3$OPh— | —F | 718 |
| 1720 | 3-CF$_3$OPh— | —F | 718 |
| 1721 | 2-CNPh— | —F | 660 |
| 1722 | 3-CH$_3$OPh— | —F | 664 |
| 1723 | 3-FPh— | —F | 652 |
| 1724 | 2,3-Cl$_2$Ph— | —F | 702 |
| 1725 | 3-CF$_3$Ph— | —F | 702 |
| 1726 | 4-CF$_3$OPh— | —F | 718 |
| 1727 | 4-biphenylyl | —F | 710 |
| 1728 | 3,4-(CH$_3$O)$_2$Ph— | —F | 694 |
| 1729 | 2,5-(CH$_3$O)$_2$Ph— | —F | 694 |

TABLE 304

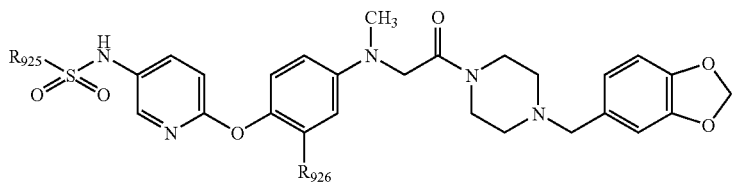

| Example No. | $R_{925}$ | $R_{926}$ | MS (M$^+$ + H) |
|---|---|---|---|
| 1730 | 3-CH$_3$Ph— | —F | 648 |
| 1731 | 2,5-Cl$_2$Ph— | —F | 702 |
| 1732 | 3-ClPh— | —F | 668 |
| 1733 | 2,4-Cl$_2$Ph— | —F | 702 |
| 1734 | —CH$_3$ | —F | 572 |
| 1735 | 2,3,4-Cl$_3$Ph— | —F | 738 |
| 1736 | —(CH$_2$)$_3$CH$_3$ | —F | 614 |
| 1737 | —C$_2$H$_5$ | —F | 586 |
| 1738 | 2,6-Cl$_2$Ph— | —F | 702 |
| 1739 | 4-CH$_3$OPh— | —CH$_3$ | 660 |
| 1740 | 4-ClPh— | —CH$_3$ | 664 |
| 1741 | 1-naphthyl | —CH$_3$ | 680 |
| 1742 | 2-naphthyl | —CH$_3$ | 680 |
| 1743 | 2-CH$_3$Ph— | —CH$_3$ | 644 |
| 1744 | 4-FPh— | —CH$_3$ | 648 |
| 1745 | 2-CF$_3$Ph— | —CH$_3$ | 698 |
| 1746 | 2-thienyl | —CH$_3$ | 636 |
| 1747 | 2-ClPh— | —CH$_3$ | 664 |
| 1748 | 2-CF$_3$OPh— | —CH$_3$ | 714 |
| 1749 | 2-CNPh— | —CH$_3$ | 656 |
| 1750 | 3-CH$_3$OPh | —CH$_3$ | 660 |
| 1751 | 3-FPh— | —CH$_3$ | 648 |
| 1752 | 2,3-Cl$_2$Ph— | —CH$_3$ | 698 |
| 1753 | 3-CF$_3$Ph— | —CH$_3$ | 698 |
| 1754 | 4-CF$_3$OPh— | —CH$_3$ | 714 |
| 1755 | 4-biphenylyl | —CH$_3$ | 706 |
| 1756 | 3,4-(CH$_3$O)$_2$Ph— | —CH$_3$ | 690 |
| 1757 | 2,5-(CH$_3$O)$_2$Ph— | —CH$_3$ | 690 |
| 1758 | 3-CH$_3$Ph— | —CH$_3$ | 644 |
| 1759 | 2,5-Cl$_2$Ph— | —CH$_3$ | 698 |
| 1760 | 3-ClPh— | —CH$_3$ | 664 |
| 1761 | 2,4-Cl$_2$Ph— | —CH$_3$ | 698 |
| 1762 | —CH$_3$ | —CH$_3$ | 568 |
| 1763 | 2,3,4-Cl$_3$Ph— | —CH$_3$ | 734 |
| 1764 | —(CH$_2$)$_3$CH$_3$ | —CH$_3$ | 610 |

TABLE 304-continued

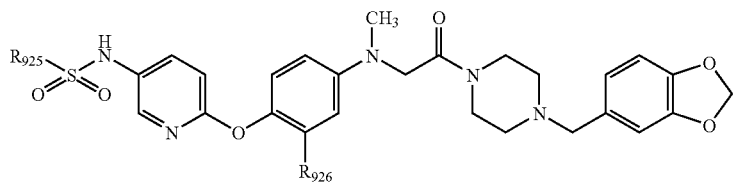

| Example No. | $R_{925}$ | $R_{926}$ | MS ($M^+ + H$) |
|---|---|---|---|
| 1765 | —$C_2H_5$ | —$CH_3$ | 582 |
| 1766 | 2,6-$Cl_2$Ph— | —$CH_3$ | 698 |
| 1767 | 2,4,5-$Cl_3$Ph— | —H | 719 |

TABLE 305

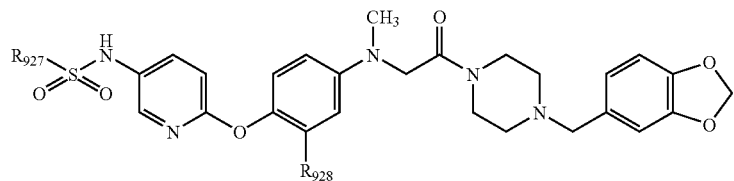

| Example No. | $R_{927}$ | $R_{928}$ | MS ($M^+ + H$) |
|---|---|---|---|
| 1768 | 2,4,6-$(CH_3)_3$Ph— | —H | 658 |
| 1769 | 4-$C_2H_5$Ph— | —H | 644 |
| 1770 | 2,5-$(CH_3)_2$Ph— | —H | 644 |
| 1771 | 2-FPh— | —H | 634 |
| 1772 | 2,4,6-$(CH_3)_3$Ph— | —F | 676 |
| 1773 | 4-$CH_3$Ph— | —F | 648 |
| 1774 | 4-$C_2H_5$Ph— | —F | 662 |
| 1775 | 2,5-$(CH_3)_2$Ph— | —F | 662 |
| 1776 | 2-FPh— | —F | 652 |
| 1777 | 2,4,5-$Cl_3$Ph— | —$CH_3$ | 732 |
| 1778 | 2,4,6-$(CH_3)_3$Ph— | —$CH_3$ | 672 |
| 1779 | 4-$CH_3$Ph— | —$CH_3$ | 644 |
| 1780 | 4-$C_2H_5$Ph— | —$CH_3$ | 658 |
| 1781 | 2,5-$(CH_3)_2$Ph— | —$CH_3$ | 658 |
| 1782 | 2-FPh— | —$CH_3$ | 648 |
| 1783 | 4-BrPh— | —H | 696 |
| 1784 | —$CH(CH_3)_2$ | —H | 582 |
| 1785 | 8-quinolyl | —H | 667 |
| 1786 | 3-CNPh— | —H | 641 |
| 1787 | 4-PhOPh— | —H | 708 |
| 1788 | 3-BrPh— | —H | 696 |
| 1789 | 4-CNPh— | —H | 641 |
| 1790 | 2,4-$F_2$Ph— | —H | 652 |
| 1791 | 4-BrPh— | —F | 714 |
| 1792 | —$CH(CH_3)_2$ | —F | 600 |
| 1793 | 8-quinolyl | —F | 685 |
| 1794 | 3-CNPh— | —F | 659 |
| 1795 | 4-CNPh— | —F | 659 |
| 1796 | 2,4-$F_2$Ph— | —F | 670 |
| 1797 | 4-BrPh— | —$CH_3$ | 710 |
| 1798 | —$CH(CH_3)_2$ | —$CH_3$ | 596 |
| 1799 | 8-quinolyl | —$CH_3$ | 681 |
| 1800 | 3-CNPh— | —$CH_3$ | 655 |
| 1801 | 3-BrPh— | —$CH_3$ | 710 |
| 1802 | 4-CNPh— | —$CH_3$ | 655 |
| 1803 | 2,4-$F_2$Ph— | —$CH_3$ | 666 |
| 1804 | 2,4,6-$Cl_3$Ph— | —H | 720 |
| 1805 | 2,4,6-$Cl_3$Ph— | —F | 738 |

TABLE 306
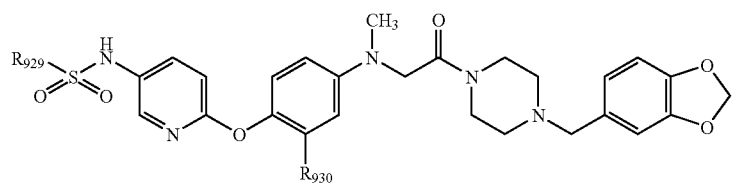
| Example No. | R929 | R930 | MS (M+ + H) |
|---|---|---|---|
| 1806 | 2,4,5-Cl3Ph— | —F | 738 |
| 1807 | 2,4,6-Cl3Ph— | —CH3 | 734 |
| 1808 | Ph— | —F | 634 |
| 1809 | Ph— | —CH3 | 630 |
| 1810 | 2,5-F2Ph— | —F | 670 |
| 1811 | 2,5-F2Ph— | —CH3 | 666 |
| 1812 | 2,6-F2Ph— | —CH3 | 666 |
| 1813 | 3,4-F2Ph— | —CH3 | 666 |
| 1814 | 2,6-F2Ph— | —H | 652 |
| 1815 | 3,4-F2Ph— | —H | 652 |
| 1816 | 2,6-F2Ph— | —F | 670 |
| 1817 | 3,4-F2Ph— | —F | 670 |
| 1818 | —CH3 | —H | 554 |
| 1819 | 4-Cl-2-Me-C6H3(OCH3)— | —H | 680 |
| 1820 | 2,4-Me2-C6H3(OCH3)— | —H | 660 |
| 1821 | 4-Cl-2-Me-C6H3(OCH3)— | —F | 698 |
| 1822 | 4-Cl-2-Me-C6H3(OCH3)— | —CH3 | 694 |
| 1823 | 2,4-Me2-C6H3(OCH3)— | —CH3 | 674 |
| 1824 | 2-Cl-4-CF3-C6H3(CH3)— | —H | 718 |
| 1825 | 2-Cl-4-F-C6H3(CH3)— | —H | 668 |
| 1826 | 2,5-Cl2-4-Me-C6H2(CH3)— | —H | 698 |

TABLE 306-continued
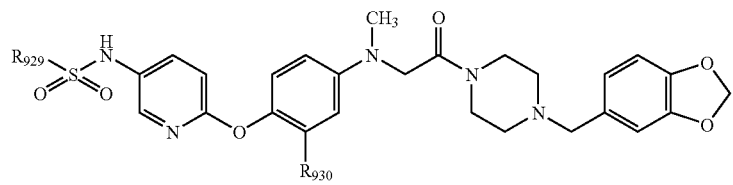
| Example No. | R929 | R930 | MS (M+ + H) |
|---|---|---|---|
| 1827 | 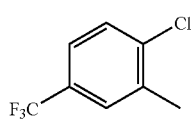 | —H | 718 |
TABLE 307
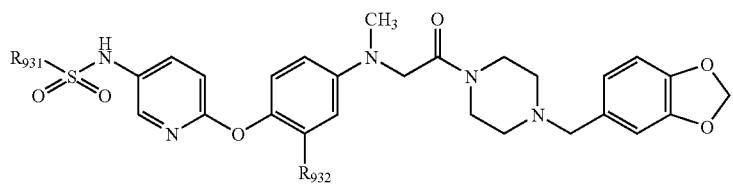
| Example No. | R931 | R932 | MS (M+ + H) |
|---|---|---|---|
| 1828 | 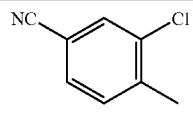 | —H | 675 |
| 1829 | 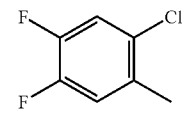 | —H | 686 |
| 1830 | 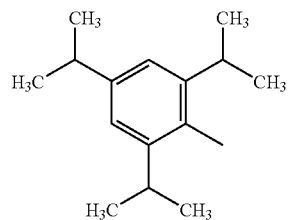 | —H | 742 |
| 1831 | 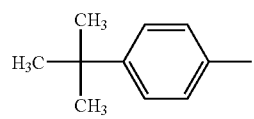 | —H | 672 |
| 1832 | 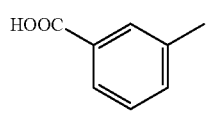 | —H | 660 |
| 1833 | 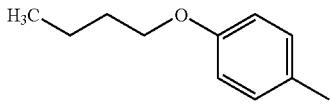 | —H | 688 |

TABLE 307-continued

Structure: R931-SO2-NH-(pyridine)-O-(phenyl with R932)-N(CH3)-CH2-C(O)-N(piperazine)-CH2-(benzodioxole)

| Example No. | R931 | R932 | MS (M+ + H) |
|---|---|---|---|
| 1834 | 2,5-dichloro-4-methylphenyl (with H3C) | —F | 716 |
| 1835 | 2-chloro-4-(trifluoromethyl)-5-methylphenyl | —F | 736 |
| 1836 | 3,5-dichloro-4-hydroxy-2-methylphenyl | —F | 718 |
| 1837 | 3-(HOOC)phenyl | —F | 678 |
| 1838 | 2-bromo-4-chloro-5-methylphenyl | —F | 747 |
| 1839 | 4-(butoxy)-methylphenyl | —F | 706 |
| 1840 | 2,5-dichloro-4-methylphenyl (with H3C) | —CH3 | 712 |

TABLE 308

Structure: R933-SO2-NH-(pyridine)-O-(phenyl with R934)-N(CH3)-CH2-C(O)-N(piperazine)-CH2-(benzodioxole)

| Example No. | R933 | R934 | MS (M+ + H) |
|---|---|---|---|
| 1841 | 2-chloro-4-(trifluoromethyl)-5-methylphenyl | —CH3 | 732 |

TABLE 308-continued
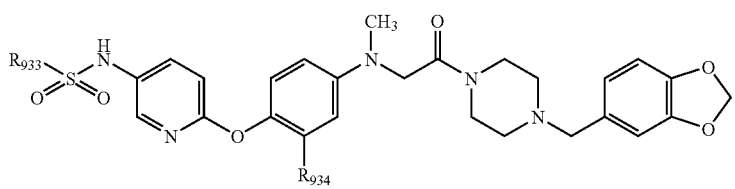
| Example No. | R₉₃₃ | R₉₃₄ | MS (M⁺ + H) |
|---|---|---|---|
| 1842 | NC–⟨C₆H₃⟩–Cl, CH₃ | —CH₃ | 689 |
| 1843 | F,F–⟨C₆H₂⟩–Cl, CH₃ | —CH₃ | 700 |
| 1844 | Cl,Cl–⟨C₆H₂⟩–OH, CH₃ | —CH₃ | 714 |
| 1845 | HOOC–⟨C₆H₄⟩–CH₃ | —CH₃ | 674 |
| 1846 | Br,Cl–⟨C₆H₂⟩–CH₃ | —CH₃ | 743 |
| 1847 | H₃C–CH₂CH₂CH₂–O–⟨C₆H₃⟩–CH₃ | —CH₃ | 702 |
| 1848 | Cl,Cl–⟨C₆H₂⟩–OH, CH₃ | —H | 700 |
| 1849 | (H₃C)₂N–naphthyl–CH₃ | —H | 709 |
| 1850 | H₃C–naphthyl–CH₃ | —H | 680 |

TABLE 308-continued
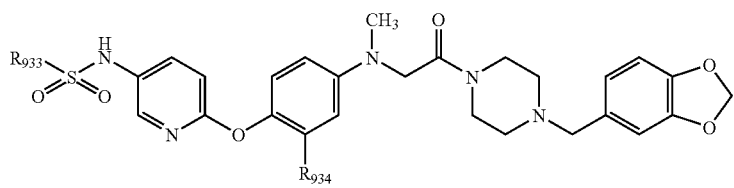
| Example No. | R_933 | R_934 | MS (M⁺ + H) |
|---|---|---|---|
| 1851 | 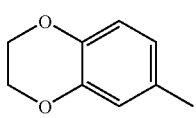 | —H | 674 |
| 1852 | 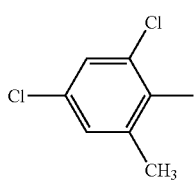 | —H | 698 |
TABLE 309
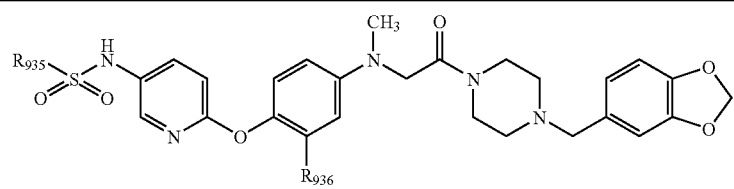
| Example No. | R_935 | R_936 | MS (M⁺ + H) |
|---|---|---|---|
| 1853 | 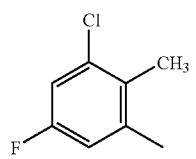 | —H | 682 |
| 1854 | 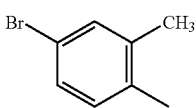 | —H | 710 |
| 1855 | 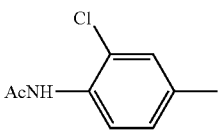 | —H | 707 |
| 1856 | 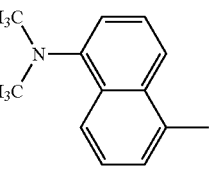 | —F | 727 |

TABLE 309-continued
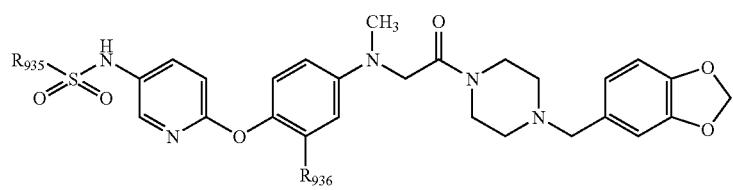
| Example No. | R935 | R936 | MS (M+ + H) |
|---|---|---|---|
| 1857 | 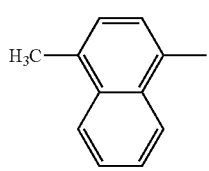 | —F | 698 |
| 1858 | 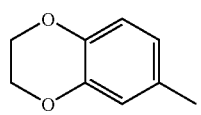 | —F | 692 |
| 1859 | 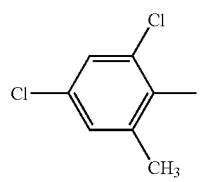 | —F | 716 |
| 1860 | 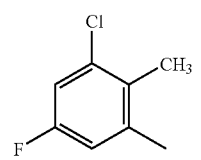 | —F | 700 |
| 1861 | 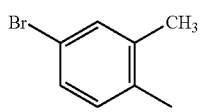 | —F | 728 |
| 1862 | 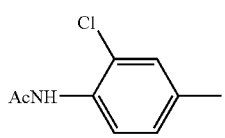 | —F | 725 |
| 1863 | 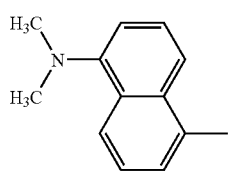 | —CH3 | 723 |

TABLE 310

| Example No. | R937 | R938 | MS (M+ + H) |
|---|---|---|---|
| 1864 | 1,4-dimethylnaphthalen-yl | —CH3 | 694 |
| 1865 | 6-methyl-2,3-dihydro-1,4-benzodioxin-yl | —CH3 | 688 |
| 1866 | 2,4-dichloro-5,6-dimethylphenyl | —CH3 | 712 |
| 1867 | 2-chloro-5-fluoro-3,4-dimethylphenyl (Cl, CH3, F, CH3) | —CH3 | 696 |
| 1868 | 4-bromo-2,3-dimethylphenyl | —CH3 | 724 |
| 1869 | 2-chloro-4-acetamido-3-methylphenyl | —CH3 | 721 |
| 1870 | 4-bromo-2-chloro-5-methylphenyl (Br, Cl, CH3) | —H | 730 |
| 1871 | 3-chloro-5-trifluoromethyl-4-methylphenyl | —F | 736 |
| 1872 | 2-chloro-4,5-difluoro-3-methylphenyl | —F | 704 |

TABLE 310-continued
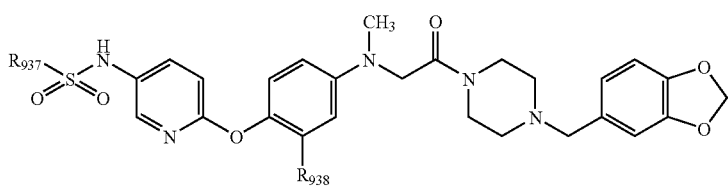
| Example No. | $R_{937}$ | $R_{938}$ | MS (M$^+$ + H) |
|---|---|---|---|
| 1873 | 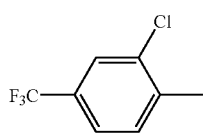 | —CH$_3$ | 732 |
| 1874 | 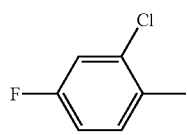 | —CH$_3$ | 682 |
| 1875 | 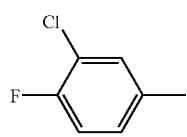 | —H | 668 |
TABLE 311
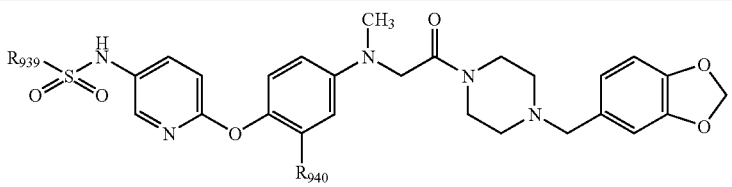
| Example No. | $R_{939}$ | $R_{940}$ | MS (M$^+$ + H) |
|---|---|---|---|
| 1876 | 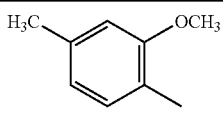 | —H | 660 |
| 1877 | 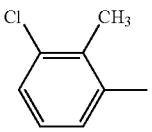 | —H | 664 |
| 1878 | 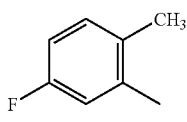 | —H | 648 |
| 1879 | 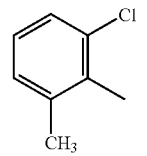 | —H | 664 |

TABLE 311-continued
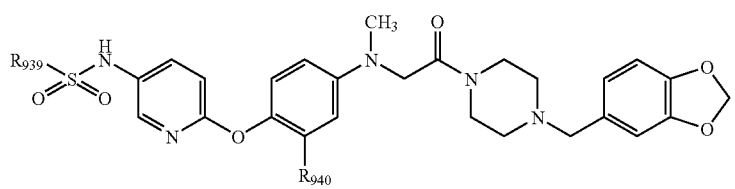
| Example No. | R939 | R940 | MS (M+ + H) |
|---|---|---|---|
| 1880 | 4-Br, 2-F phenyl | —H | 714 |
| 1881 | 2-Cl, 4-CH3 phenyl | —H | 664 |
| 1882 | 5-CH3, 2-OCH3 phenyl (with methyl) | —F | 678 |
| 1883 | 2-Cl, 3-CH3 phenyl (with methyl) | —F | 682 |
| 1884 | 4-F, 2-CH3 phenyl (with methyl) | —F | 666 |
| 1885 | 2-Cl, 6-CH3 phenyl (with methyl) | —F | 682 |
| 1886 | 2-Cl, 4-F phenyl | —F | 686 |
| 1887 | 2-Cl, 4-F phenyl | —CH3 | 682 |
| 1888 | 2-Cl, 4-CH3 phenyl | —F | 682 |

TABLE 312
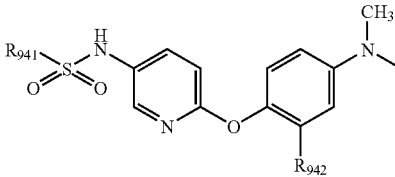
| Example No. | R941 | R942 | MS (M+ + H) |
|---|---|---|---|
| 1889 | 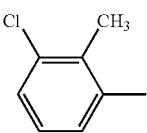 | —CH3 | 674 |
| 1890 | 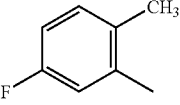 | —CH3 | 678 |
| 1891 | 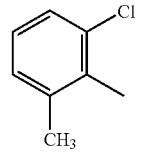 | —CH3 | 662 |
| 1892 | 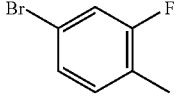 | —CH3 | 678 |
| 1893 | 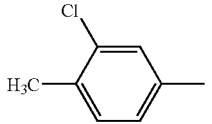 | —CH3 | 728 |
| 1894 | 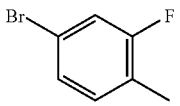 | —CH3 | 678 |
| 1895 | 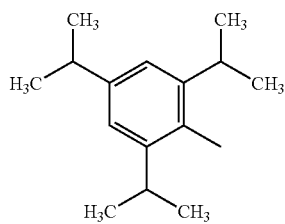 | —F | 732 |
| 1896 | 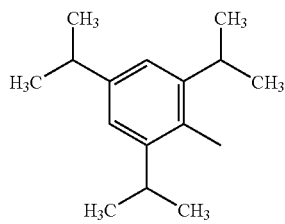 | —F | 760 |
| 1897 | 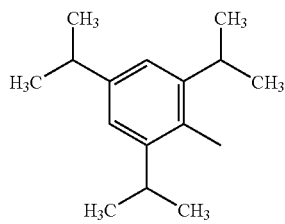 | —CH3 | 756 |

TABLE 312-continued
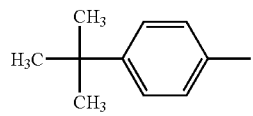
| Example No. | R941 | R942 | MS (M+ + H) |
|---|---|---|---|
| 1898 | 3-BrPh— | —F | 714 |
| 1899 | 4-PhOPh— | —CH3 | 722 |
| 1900 | 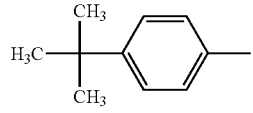 | F | 690 |
| 1901 | 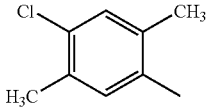 | —CH3 | 686 |
TABLE 313
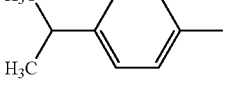
| Example No. | R943 | R944 | MS (M+ + H) |
|---|---|---|---|
| 1902 | 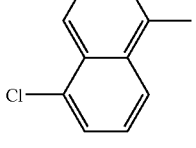 | —H | 678 |
| 1903 | 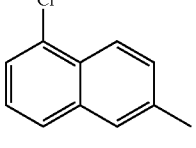 | —H | 658 |
| 1904 | 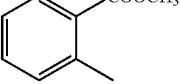 | —H | 700 |
| 1905 | | —H | 700 |
| 1906 | | —H | 674 |

TABLE 313-continued
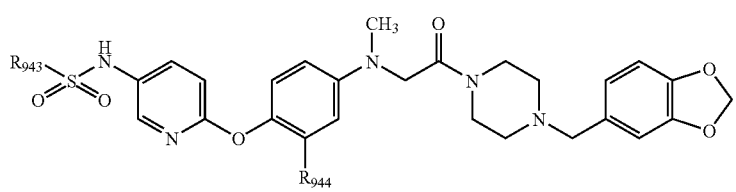
| Example No. | R$_{943}$ | R$_{944}$ | MS (M$^+$ + H) |
|---|---|---|---|
| 1907 | 1,4-dimethylimidazol-5-yl | —H | 620 |
| 1908 | 2-chloro-4,5-dimethylphenyl | —F | 696 |
| 1909 | 4-isopropylphenyl | —F | 676 |
| 1910 | 5-chloro-8-methylnaphthalen-1-yl | —F | 718 |
| 1911 | 8-chloro-3-methylnaphthalen-2-yl | —F | 718 |
| 1912 | 2-(methoxycarbonyl)-6-methylphenyl | —F | 692 |
| 1913 | 1,4-dimethylimidazol-5-yl | —F | 638 |

TABLE 314

[Structure: R945-S(O)(O)-NH-(pyridine)-O-(phenyl with R946)-N(CH3)-C(O)-CH2-N(piperazine)-CH2-(benzodioxole)]

| Example No. | R945 | R946 | MS (M+ + H) |
|---|---|---|---|
| 1914 | 2-Cl-4,5-dimethylphenyl (with CH3 groups) | —CH3 | 692 |
| 1915 | 4-isopropylphenyl | —CH3 | 672 |
| 1916 | 5-chloronaphthalen-1-yl | —CH3 | 714 |
| 1917 | 8-chloronaphthalen-2-yl | —CH3 | 714 |
| 1918 | 2-(methoxycarbonyl)phenyl | —CH3 | 688 |
| 1919 | 1-methyl-4-methylimidazol-? | —CH3 | 634 |
| 1920 | AcNH-phenyl- | —H | 673 |
| 1921 | vinyl | —H | 566 |
| 1922 | —(CH2)3Cl | —H | 616 |
| 1923 | cyclohexylmethyl | —H | 636 |
| 1924 | AcNH-phenyl- | —F | 691 |
| 1925 | vinyl | —F | 584 |
| 1926 | —(CH2)3Cl | —F | 634 |
| 1927 | cyclohexylmethyl | —F | 654 |
| 1928 | AcNH-phenyl- | —CH3 | 687 |
| 1929 | vinyl | —CH3 | 580 |
| 1930 | —(CH2)3Cl | —CH3 | 630 |

TABLE 314-continued
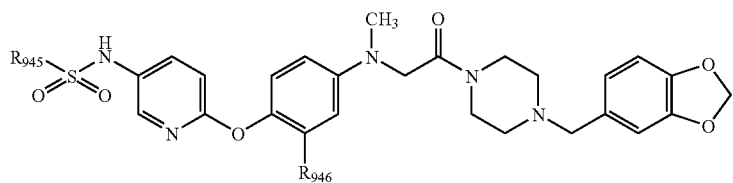
| Example No. | $R_{945}$ | $R_{946}$ | MS ($M^+ + H$) |
|---|---|---|---|
| 1931 | cyclohexylmethyl | —CH$_3$ | 650 |
| 1932 | 2-BrPh— | —H | 696 |
| 1933 | ![Cl-thiophene-CH3] | —H | 656 |
TABLE 315
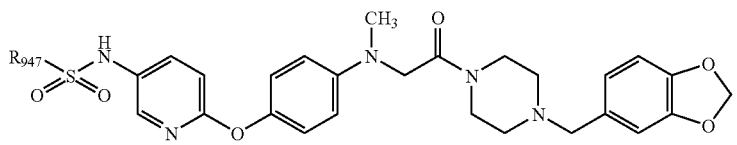
| Example No. | $R_{947}$ | MS ($M^+ + H$) |
|---|---|---|
| 1934 | 3,5-Cl$_2$Ph | 684 |
| 1935 | 5-(4-methylphenyl)oxazole | 683 |
| 1936 | 1-(4-methylphenyl)pyrazole | 682 |
| 1937 | 4-CH$_3$-Ph-(CH$_2$)$_2$COOCH$_3$ | 702 |
| 1938 | 4-methyl-7-methyl-3,4-dihydro-2H-benzo[1,4]oxazine | 687 |
| 1939 | 3-methyl-8-methylquinoline | 681 |
| 1940 | 5-methyl-8-AcNH-naphthyl | 723 |
| 1941 | 5-isoquinolyl | 667 |

TABLE 315-continued
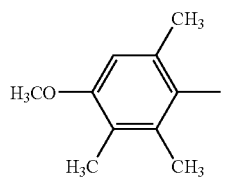
| Example No. | R_947 | MS (M+ + H) |
|---|---|---|
| 1942 | —CH$_2$CF$_3$ | 622 |
| 1943 | 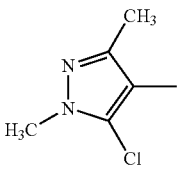 | 688 |
| 1944 | 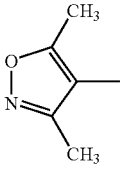 | 668 |
| 1945 | 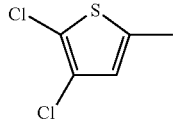 | 635 |
| 1946 | 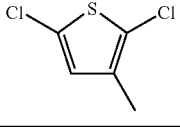 | 690 |
| 1947 |  | 690 |
TABLE 316
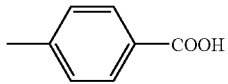
| Example No. | R_948 | R_949 | MS (M+ + H) |
|---|---|---|---|
| 1948 | —CH$_2$Cl | —H | 588 |
| 1949 | (5-bromo-2-methylthiophene) | —H | 702 |
| 1950 | (4-carboxyphenylmethyl) | —H | 660 |

TABLE 316-continued
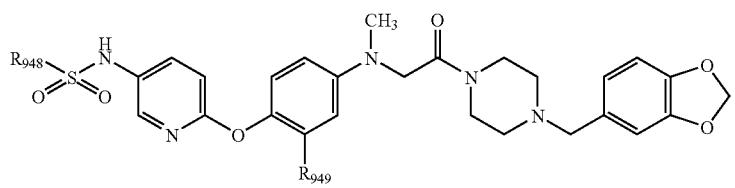
| Example No. | R948 | R949 | MS (M+ + H) |
|---|---|---|---|
| 1951 | AcNH-(4,5-dimethylthiazol-2-yl) | —H | 694 |
| 1952 | 3-methyl-2-(methoxycarbonyl)thiophene | —H | 680 |
| 1953 | 4-bromo-2-methyl-methoxyphenyl | —H | 726 |
| 1954 | benzyl | —H | 630 |
| 1955 | PhCH=CH— | —H | 642 |
| 1956 | —(CH2)2CH3 | —H | 582 |
| 1957 | 2-BrPh— | —F | 714 |
| 1958 | 5-chloro-2-methylthiophene | —F | 674 |
| 1959 | 3,5-Cl2Ph | —F | 702 |
| 1960 | 5-(4-methylphenyl)oxazole | —F | 701 |
| 1961 | 1-(4-methylphenyl)pyrazole | —F | 700 |
| 1962 | 4-methylphenyl-(CH2)2COOCH3 | —F | 720 |
| 1963 | 4-methyl-6-methyl-3,4-dihydro-2H-benzo[b][1,4]oxazine | —F | 705 |
| 1964 | 3,8-dimethylquinoline | —F | 699 |

TABLE 316-continued
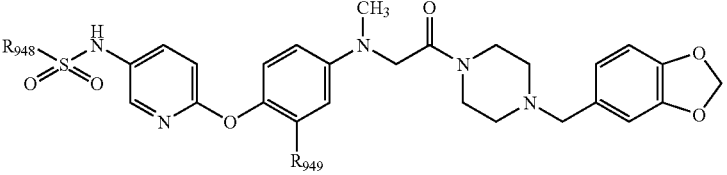
| Example No. | R_948 | R_949 | MS (M$^+$ + H) |
|---|---|---|---|
| 1965 | (8-AcNH-5-methyl-naphthyl) | —F | 741 |
TABLE 317
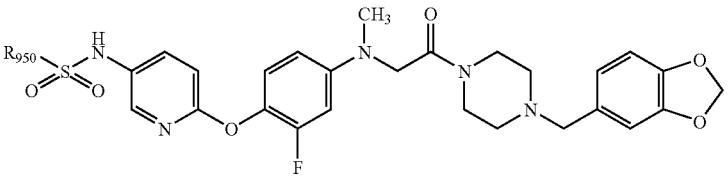
| Example No. | R_950 | MS (M$^+$ + H) |
|---|---|---|
| 1966 | 5-isoquinolyl | 685 |
| 1967 | —CH$_2$CF$_3$ | 640 |
| 1968 | 4-methoxy-2,3,5,6-tetramethylphenyl | 706 |
| 1969 | 5-chloro-1,3,4-trimethyl-1H-pyrazol-yl | 686 |
| 1970 | 3,4,5-trimethylisoxazolyl | 653 |
| 1971 | 2-hydroxy-5-methyl-benzoic acid | 694 |
| 1972 | 2,4-dichloro-5-methylthiophen-yl | 708 |

TABLE 317-continued

Structure: R_950−SO2−NH−(pyridine)−O−(fluorophenyl)−N(CH3)−CH2−C(O)−N(piperazine)−CH2−(benzodioxole)

| Example No. | R_950 | MS (M⁺ + H) |
|---|---|---|
| 1973 | 2,5-dichloro-3-methylthiophene | 708 |
| 1974 | —CH₂Cl | 606 |
| 1975 | 5-bromo-2-methylthiophene | 720 |
| 1976 | 4-methylphenyl-COOH | 678 |
| 1977 | 2-AcNH-4,5-dimethylthiazole | 712 |
| 1978 | 3-methyl-2-COOCH₃-thiophene | 698 |
| 1979 | 4-bromo-2-methyl-1-methoxybenzene | 744 |
| 1980 | benzyl | 648 |
| 1981 | PhCH=CH— | 660 |

TABLE 318

Structure: R_951−SO2−NH−(pyridine)−O−(phenyl with R_952)−N(CH3)−CH2−C(O)−N(piperazine)−CH2−(benzodioxole)

| Example No. | R_951 | R_952 | MS (M⁺ + H) |
|---|---|---|---|
| 1982 | —(CH₂)₂CH₃ | —F | 600 |
| 1983 | 2-BrPh— | —CH₃ | 710 |
| 1984 | 5-chloro-2-methylthiophene | —CH₃ | 670 |
| 1985 | 3,5-Cl₂Ph | —CH₃ | 698 |

TABLE 318-continued

| Example No. | R₉₅₁ | R₉₅₂ | MS (M⁺ + H) |
|---|---|---|---|
| 1986 | 5-(4-methylphenyl)oxazole | —CH₃ | 697 |
| 1987 | 1-(4-methylphenyl)pyrazole | —CH₃ | 696 |
| 1988 | 4-methylphenyl-(CH₂)₂COOCH₃ | —CH₃ | 716 |
| 1989 | 4-methyl-6-methyl-3,4-dihydro-2H-benzo[1,4]oxazine | —CH₃ | 701 |
| 1990 | 3,8-dimethylquinolin-5-yl | —CH₃ | 695 |
| 1991 | 8-acetamido-5-methylnaphthalenyl | —CH₃ | 737 |
| 1992 | 5-isoquinolyl | —CH₃ | 681 |
| 1993 | —CH₂CF₃ | —CH₃ | 636 |
| 1994 | 4-methoxy-2,3,5,6-tetramethylphenyl | —CH₃ | 702 |
| 1995 | 5-chloro-1,3,4-trimethylpyrazol-yl | —CH₃ | 682 |

TABLE 318-continued
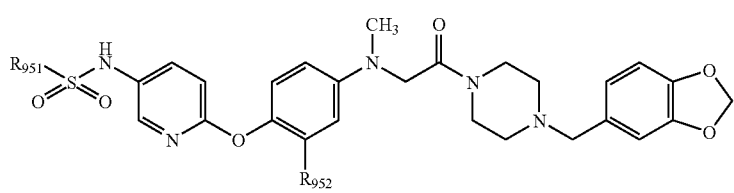
| Example No. | R$_{951}$ | R$_{952}$ | MS (M$^+$ + H) |
|---|---|---|---|
| 1996 | 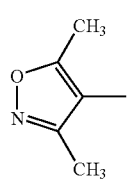 | —CH$_3$ | 649 |
TABLE 319
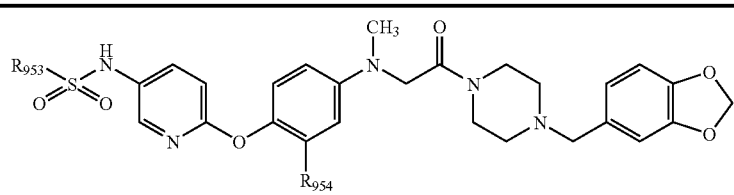
| Example No. | R$_{953}$ | R$_{954}$ | MS (M$^+$ + H) |
|---|---|---|---|
| 1997 | 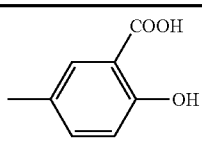 | —CH$_3$ | 690 |
| 1998 | 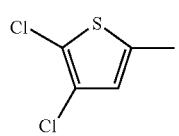 | —CH$_3$ | 704 |
| 1999 | 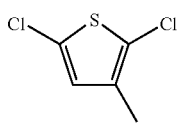 | —CH$_3$ | 704 |
| 2000 | —CH$_2$Cl | —CH$_3$ | 602 |
| 2001 | 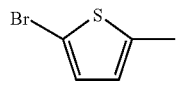 | —CH$_3$ | 716 |
| 2002 | 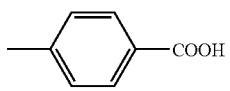 | —CH$_3$ | 674 |
| 2003 | 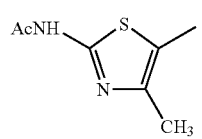 | —CH$_3$ | 708 |

TABLE 319-continued

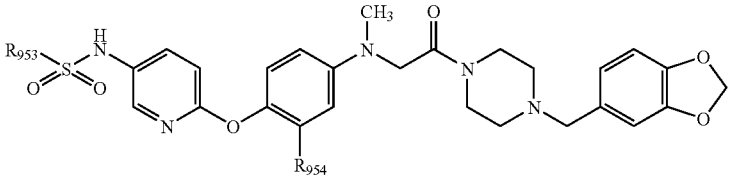

| Example No. | R₉₅₃ | R₉₅₄ | MS (M⁺ + H) |
|---|---|---|---|
| 2004 | (thiophene-2-COOCH₃, 3-methyl) | —CH₃ | 694 |
| 2005 | (4-Br, 2-methyl, OCH₃ phenyl) | —CH₃ | 740 |
| 2006 | benzyl | —CH₃ | 644 |
| 2007 | —CHCl₂ | —CH₃ | 636 |
| 2008 | PhCH=CH— | —CH₃ | 656 |
| 2009 | —(CH₂)₂CH₃ | —CH₃ | 596 |
| 2010 | 2,3,4-F₃Ph— | —H | 670 |
| 2011 | 2,3,4-F₃Ph— | —F | 688 |
| 2012 | 2,3,4-F₃Ph— | —CH₃ | 684 |

TABLE 320

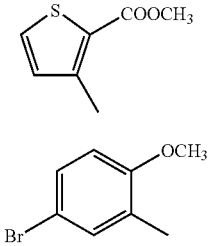

| Example No. | R₉₅₅ | R₉₅₆ | R₉₅₇ | Xb₂₉ | ¹H NMR (solvent) δ ppm |
|---|---|---|---|---|---|
| 2013 | 3,4-Cl₂Ph— | —CH₃ | —H | —CO— | (CDCl₃) 2.12 (3H, s), 2.50-2.52 (4H, m), 3.45 (2H, s), 3.72 (2H, brs), 4.24 (2H, brs), 5.95 (2H, s), 6.71-6.78 (2H, m), 6.85-6.89 (2H, m), 7.00 (1H, d, J=8.6Hz), 7.42 (1H, dd, J=8.6Hz, 2.5Hz), 7.52-7.55 (3H, m), 7.60 (1H, dd, J=8.7Hz, 2.8Hz), 7.70 (1H, d, J=2.6Hz), 7.79 (1H, brs), 9.17 (1H, brs). |
| 2014 | 4-CF₃Ph— | —CH₃ | —H | —CO— | (CDCl₃) 2.10 (3H, s), 2.50-2.54 (4H, m), 3.45 (2H, s), 3.70-3.73 (2H, m), 4.23 (2H, brs), 5.95 (2H, s), 6.71-6.78 (2H, m), 6.83-6.87 (2H, m), 6.99 (1H, d, J=8.6Hz), 7.42 (1H, dd, J=8.6Hz, 2.6Hz), 7.54 (1H, d, J=2.5Hz), 7.60 (1H, dd, J=8.7Hz, 3.3Hz), 7.70 (1H, d, J=3.3Hz), 7.72 (2H, d, J=8.9Hz), 7.85 (2H, d, J=8.3Hz), 9.18 (1H, brs). |
| 2015 | 3,4-Cl₂Ph— | —CH₃ | —CH₃ | —CO— | (CDCl₃) 2.12 (3H, brs), 2.20-2.50 (4H, m), 3.27-3.46 (9H, m), 5.95-5.96 (2H, m), 6.66-6.77 (3H, m), 6.85-7.04 (2H, m), 7.08-7.22 (2H, m), 7.51-7.53 (2H, m), 7.55-7.72 (2H, m), 7.78-7.80 (1H, m). |
| 2016 | 4-CF₃Ph— | —CH₃ | —CH₃ | —CO— | (DMSO-d₆) 2.11 (3H, s), 2.19-2.51 (4H, m), 3.28-3.71 (9H, m), 5.96 (2H, s), 6.65-6.78 (3H, m), 6.85-7.04 (2H, m), 7.08-7.22 (2H, m), 7.57-7.65 (1H, m), 7.70-7.73 (3H, m), 7.84-7.87 (2H, m). |
| 2017 | 3,4-Cl₂Ph— | —H | —SO₂CH₃ | —CH₂— | (CDCl₃) 2.42 (4H, brs), 3.20 (3H, s), 3.37-3.39 (2H, m), 3.42 (2H, s), 3.61 (2H, brs), 4.54 (2H, s), 5.95 (2H, s), 6.70-6.77 (2H, m), 6.83 (1H, brs), 6.93 (1H, d, J=8.6Hz), 7.08 (2H, d, J=8.9Hz), 7.53-7.54 (2H, m), |

TABLE 320-continued

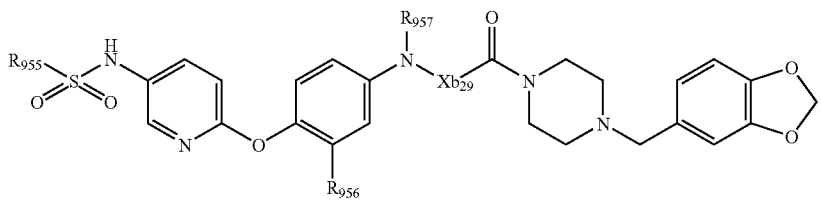

| Example No. | R$_{955}$ | R$_{956}$ | R$_{957}$ | Xb$_{29}$ | $^1$H NMR (solvent) δ ppm |
|---|---|---|---|---|---|
| 2018 | 4-CF$_3$Ph— | —H | —SO$_2$CH$_3$— | —CH$_2$— | 7.58-7.63 (3H, m), 7.77 (1H, d, J=2.6Hz), 7.88 (1H, d, J=1.0Hz). (CDCl$_3$) 2.42 (4H, brs), 3.19 (3H, s), 3.37 (2H, brs), 3.42 (2H, s), 3.61 (2H, brs), 4.53 (2H, s), 5.95 (2H, s), 6.73-6.77 (2H, m), 6.83 (1H, brs), 6.92 (1H, d, J=8.7Hz), 7.08 (2H, d, J=8.7Hz), 7.59 (2H, d, J=8.7Hz), 7.61 (1H, dd, J=8.7Hz, 2.8Hz), 7.73-7.76 (3H, m), 7.87 (2H, d, J=8.6Hz). |
| 2019 | 3,4-Cl$_2$Ph— | —CH$_3$ | —SO$_2$CH$_3$ | —CH$_2$— | (CDCl$_3$) 2.12 (3H, s), 2.42 (4H, brs), 3.21 (3H, s), 3.38 (2H, brs), 3.42 (2H, s), 3.61 (2H, brs), 4.53 (2H, s), 5.95 (2H, s), 6.70-6.77 (2H, m), 6.83 (1H, brs), 6.91 (1H, d, J=8.7Hz), 6.98 (1H, d, J=8.4Hz), 7.40-7.50 (2H, m), 7.53-7.56 (2H, m), 7.60 (1H, dd, J=8.7Hz, 2.8Hz), 7.71 (1H, d, J=2.3Hz), 7.80 (1H, dd, J=1.7Hz, 0.8Hz). |

TABLE 321

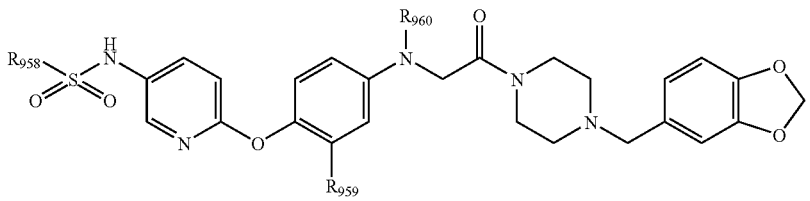

| Example No. | R$_{958}$ | R$_{959}$ | R$_{960}$ | $^1$H NMR (solvent) δ ppm |
|---|---|---|---|---|
| 2020 | 4-CF$_3$Ph— | —CH$_3$ | —SO$_2$CH$_3$ | (CDCl$_3$) 2.10 (3H, s), 2.40-2.42 (4H, m), 3.20 (3H, s), 3.37 (2H, brs), 3.42 (2H, s), 3.60 (2H, brs), 4.53 (2H, s), 5.94 (2H, s), 6.69-6.76 (2H, m), 6.83 (1H, brs), 6.87 (1H, d, J=8.7Hz), 6.96 (1H, d, J=8.4Hz), 7.40 (1H, d, J=8.6Hz), 7.44 (1H, brs), 7.59 (1H, dd, J=8.7Hz, 2.8Hz), 7.72 (2H, d, J=8.2Hz), 7.73 (1H, d, J=2.8Hz), 7.86 (2H, d, J=8.2Hz). |
| 2021 | 4-CF$_3$Ph— | —CF$_3$ | —C$_2$H$_5$ | (DMSO-d$_6$) 1.11 (3H, t, J=6.9Hz), 2.25-2.45 (4H, m), 3.35-3.55 (8H, m), 4.26 (2H, s), 5.99 (2H, s), 6.67-7.04 (7H, m), 7.52 (1H, dd, J=8.8Hz, 2.8Hz), 7.74 (1H, d, J=2.6Hz), 7.88-7.98 (4H, m), 10.48 (1H, brs). |
| 2022 | 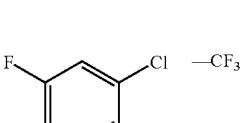 | —CF$_3$ | —C$_2$H$_5$ | (DMSO-d$_6$) 1.11 (3H, t, J=6.9Hz), 2.25-2.45 (4H, m), 3.35-3.55 (8H, m), 4.26 (2H, s), 5.99 (2H, s), 6.67-7.03 (7H, m), 7.30-7.45 (1H, m), 7.52 (1H, dd, J=8.8Hz, 2.6Hz, 7.71 (1H, dd, J=8.7Hz, 2.5Hz), 7.79 (1H, d, J=2.7Hz), 7.99-8.05 (1H, m), 10.61 (1H, brs). |
| 2023 | 3,4-Cl$_2$Ph— | —CF$_3$ | —CH$_3$ | (DMSO-d$_6$) 2.20-2.45 (4H, m), 2.97 (3H, s), 3.40-3.55 (6H, m), 4.34 (2H, s), 5.99 (2H, s), 6.70-6.80 (2H, m), 6.83-6.88 (3H, m), 6.97 (1H, d, J=8.8Hz), 7.03-7.07 (1H, m), 7.52 (1H, dd, J=8.8Hz, 2.8Hz), 7.63 (1H, dd, J=8.6Hz, 2.2Hz), 7.75 (1H, d, J=2.7Hz), 7.83-7.87 (2H, m), 10.39 (1H, brs). |

TABLE 321-continued

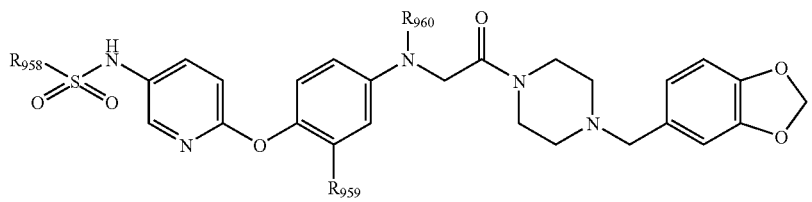

| Example No. | $R_{958}$ | $R_{959}$ | $R_{960}$ | $^1$H NMR (solvent) δ ppm |
|---|---|---|---|---|
| 2024 | 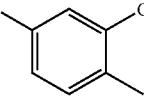 4-F, 2-Cl (with methyl) | —CF$_3$ | —CH$_3$ | (DMSO-d$_6$) 2.25-2.50 (4H, m), 2.97 (3H, s), 3.35-3.55 (6H, m), 4.34 (2H, s), 5.99 (2H, s), 6.74-7.05 (7H, m), 7.30-7.45 (1H, m), 7.52 (1H, dd, J=8.8Hz, 2.7Hz), 7.71 (1H, dd, J=8.7Hz, 2.5Hz), 7.80 (1H, d, J=2.7Hz), 8.00-8.06 (1H, m), 10.61 (1H, brs). |
| 2025 | 3,4-Cl$_2$Ph— | —CN | —CH$_3$ | (DMSO-d$_6$) 2.25-2.50 (4H, m), 2.94 (3H, s), 3.35-3.50 (6H, m), 4.33 (2H, s), 5.99 (2H, s), 6.74-7.11 (7H, m), 7.50-7.65 (2H, m), 7.78 (1H, d, J=2.6Hz), 7.83 (1H, d, J=8.5Hz), 7.89 (1H, d, J=1.5Hz), 10.45 (1H, brs). |
| 2026 | 4-CF$_3$Ph— | —OCH$_3$ | —SO$_2$CH$_3$ | (CDCl$_3$) 2.43 (4H, brs), 3.20 (3H, s), 3.38 (2H, brs), 3.43 (2H, s), 3.61 (2H, brs), 3.68 (3H, s), 4.54 (2H, s), 5.94 (2H, s), 6.73-6.76 (2H, m), 6.80-6.90 (2H, m), 7.04 (1H, d, J=8.4Hz), 7.15-7.19 (1H, m), 7.24-7.26 (1H, m), 7.57 (1H, dd, J=8.7Hz, 2.8Hz), 7.70-7.72 (4H, m); 7.85 (2H, d, J=8.2Hz). |
| 2027 | 3,4-Cl$_2$Ph— | —OCH$_3$ | —SO$_2$CH$_3$ | (CDCl$_3$) 2.43 (4H, brs), 3.21 (3H, s), 3.37 (2H, brs), 3.43 (2H, s), 3.61 (2H, brs), 3.71 (3H, s), 4.54 (2H, s), 5.95 (2H, s), 6.73-6.77 (2H, m), 6.83 (1H, s), 6.92 (1H, d, J=8.7Hz), 7.06 (1H, d, J=8.6Hz), 7.18 (1H, dd, J=8.4Hz, 2.3Hz), 7.25 (2H, s), 7.52 (2H, s), 7.57 (1H, dd, J=8.7Hz, 2.8Hz), 7.70 (1H, d, J=2.6Hz), 7.81 (1H, s). |

TABLE 322

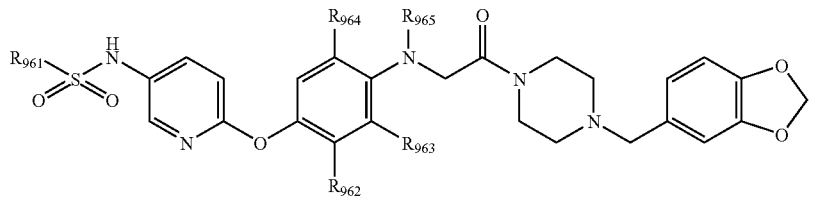

| Example No. | $R_{961}$ | $R_{962}$ | $R_{963}$ | $R_{964}$ | $R_{965}$ | $^1$H NMR (DMSO-d$_6$) δ ppm |
|---|---|---|---|---|---|---|
| 2028 | 3,4-Cl$_2$Ph— | —CH$_3$ | —H | —CH$_3$ | —CH$_3$ | 1.93 (3H, s), 2.16 (3H, s), 2.20-2.40 (4H, m), 2.63 (3H, s), 3.39 (2H, s), 3.39-3.50 (4H, m), 3.74 (2H, s), 5.99 (2H, s), 6.72-6.92 (5H, m), 6.98 (1H, s), 7.51 (1H, dd, J=8.8Hz, 2.4Hz), 7.63 (1H, dd, J=8.5Hz, 1.4Hz), 7.73 (1H, d, J=2.6Hz), 7.82-7.87 (2H, m), 10.35 (1H, brs). |
| 2029 |  4-F, 2-Cl (with methyl) | —CH$_3$ | —H | —CH$_3$ | —CH$_3$ | 1.90 (3H, s), 2.15 (3H, s), 2.25-2.40 (4H, m), 2.62 (3H, s), 3.38 (2H, s), 3.38-3.50 (4H, m), 3.73 (3H, s), 5.98 (2H, s), 6.72-6.76 (2H, m), 6.82-6.88 (3H, m), 6.97 (1H, s), 7.30-7.45 (1H, m), 7.51 (1H, dd, J=8.8Hz, 2.7Hz), 7.72 (1H, dd, J=8.7Hz, 2.6Hz), 7.78 (1H, d, J=2.8Hz), 7.98-8.04 (1H, m), 10.56 (1H, brs). |
| 2030 | 3,4-Cl$_2$Ph— | —H | —CF$_3$ | —H | —C$_2$H$_5$ | 0.92 (3H, t, J=7.1Hz), 2.20-2.40 (4H, m), 3.11 (2H, q, J=7.1Hz), 3.35-3.50 (6H, m), 3.83 (2H, s), 5.98 (2H, s), 6.70-6.90 (3H, m), 7.05 (1H, d, J=8.8Hz), 7.32-7.36 (2H, m), 7.56-7.75 (3H, m), 7.81-7.91 (3H, m), 10.48 (1H, brs). |

Example 2031

N-{4-[4-(4-benzenesulfonylpiperazin-1-yl)phenoxy]phenyl}-3,4-dichlorobenzamide

Melting point: 191-192° C.

The following compounds were produced in the same manner as in Reference Example 292.

TABLE 323

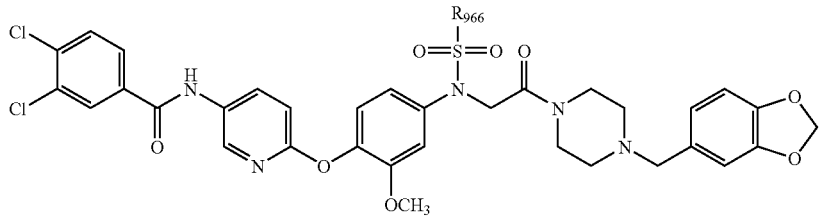

| Example No. | R_966 | $^1$H NMR (CDCl$_3$) δ ppm |
|---|---|---|
| 2032 | —CH$_3$ | 2.41 (4H, brs), 3.20 (3H, s), 3.36 (2H, brs), 3.42 (2H, s), 3.59 (2H, brs), 3.66 (3H, s), 4.50 (2H, s), 5.94 (2H, s), 6.70-6.76 (2H, m), 6.83 (1H, s), 6.93 (1H, d, J =8.7Hz), 6.99-7.04 (2H, m), 7.13 (1H, dd, J =8.4Hz, 2.1Hz), 7.51 (1H, d, J =2.3Hz), 7.69 (1H, dd, J =8.4Hz, 2.1Hz), 7.95 (1H, d, J =2.1Hz), 8.12 (1H, dd, J =8.7Hz, 2.6Hz), 8.23 (1H, d, J=2.6Hz), 8.53 (1H, s). |
| 2033 | —C$_2$H$_5$ | 1.37 (3H, t, J=7.4Hz), 2.42 (4H, brs), 3.38-3.46 (6H, m), 3.60 (2H, brs), 3.71 (3H, s), 4.53 (2H, s), 5.94 (2H, s), 6.70-6.77 (2H, m), 6.84 (1H, s), 6.97 (1H, d, J =8.7Hz), 7.06 (1H, d, J =8.6Hz), 7.14-7.18 (1H, m), 7.26 (1H, s), 7.55 (1H, d, J=8.4Hz), 7.71 (1H, dd, J=8.4Hz, 2.1Hz), 7.98 (1H, d, J=2.1Hz), 8.16-8.23 (3H, m). |

Example 2034

Production of t-butyl 4-{4-[5-(3,4-dichlorobenzoyl-amino)pyridin-2-yloxy]phenylcarbamoyl}piperidine-1-carboxylate To a solution of N-[6-(4-aminophenoxy)pyridin-3-yl]-3,4-dichlorobenzamide dihydrochloride (1.0 g, 2.24 mmol) in DMF (15 mL) were added, piperidine-1,4-dicarboxylic acid mono-t-butyl ester (510 mg, 2.22 mmol), triethylamine (0.94 mL, 6.74 mmol), 1-hydroxybenzotriazole monohydrate (350 mg, 2.29 mmol) and 1-ethyl-3-(3-dimethylaminopropyl)carbodiimide hydrochloride (514 mg, 2.68 mmol) under ice cooling. The resulting solution was then stirred under ice cooling for 1 hour, and at room temperature for 17 hours. This reaction solution was concentrated under reduced pressure. The residue was diluted with water and ethyl acetate, whereupon a white powder was precipitated. The white powder was filtered, then washed with water, and subsequently washed with ethyl acetate, to thereby yield 1.04 g of the title compound.

Appearance: White powder $^1$H NMR (DMSO-d$_6$) δ 1.41 (9H, s), 1.35-1.50 (2H, m), 1.70-1.85 (2H, m), 2.40-2.60 (1H, m), 2.65-2.90 (2H, m), 3.90-4.11 (2H, m), 7.03 (1H, d, J=8.9 Hz), 7.06 (2H, d, J=8.9 Hz), 7.62 (2H, d, J=8.9 Hz), 7.84 (1H, d, J=8.5 Hz), 7.94 (1H, dd, J=8.5 Hz, 2.0 Hz), 8.17 (1H, dd, J=8.9 Hz, 2.6 Hz), 8.22 (1H, d, J=2.0 Hz), 8.46 (1H, d, J=2.6 Hz), 9.96 (1H, s), 10.54 (1H, s).

The following compound was produced in the same manner as in Example 2034.

Example 2035

3,4-Dichloro-N-(6-{4-[2-(2,4-dioxothiazolidine-5-yl)-acetylamino]phenoxy}pyridin-3-yl)benzamide $^1$H NMR (DMSO-d$_6$) δ 3.07 (1H, dd, J=16.5 Hz, 8.9 Hz), 3.24 (1H, dd, J=16.5 Hz, 4.0 Hz), 4.73 (1H, dd, J=9.0 Hz, 4.0 Hz), 7.04 (1H, d, J=8.9 Hz), 7.08 (2H, d, J=8.9 Hz), 7.58 (2H, d, J=8.9 Hz), 7.84 (1H, d, J=8.2 Hz), 7.94 (1H, dd, J=8.2 Hz, 2.0 Hz), 8.18 (1H, dd, J=8.9 Hz, 2.6 Hz), 8.22 (1H, d, J=2.0 Hz), 8.46 (1H, d, J=2.6 Hz), 10.21 (1H, s), 10.53 (1H, s), 12.00 (1H, s).

Example 2036

Production of 3,4-dichloro-N-(6-{4-[4-piperonyl-piperazin-1-ylmethyl]phenoxy}pyridin-3-yl)benzamide To a solution of 3,4-dichloro-N-[6-(4-piperazin-1-ylmethylphenoxy)pyridin-3-yl]benzamide (300 mg, 0.66 mmol) in DMF (10 mL) were added piperonylic acid (120 mg, 0.72 mmol), 1-ethyl-3-(3-dimethylaminopropyl)carbodiimide hydrochloride (140 mg, 0.73 mmol) and 1-hydroxybenzotriazole monohydrate (100 mg, 0.74 mmol) under ice cooling. The resulting reaction solution was stirred overnight at room temperature. To the residue was added a saturated sodium bicarbonate solution, and extracted with ethyl acetate. The ethyl acetate layer was washed with a saturated sodium bicarbonate solution and brine. The ethyl acetate layer was dried over anhydrous magnesium sulfate, and evaporated, to thereby yield 110 mg of the title compound.

Appearance: White powder $^1$H NMR (CDCl$_3$) δ 2.46 (4H, brs), 3.53 (2H, s), 3.60 (4H, brs), 5.99 (2H, s), 6.79 (1H, d, J=7.9 Hz), 6.85-6.96 (3H, m), 7.08 (2H, d, J=8.6 Hz), 7.33 (2H, d, J=8.3 Hz), 7.54 (1H, d, J=8.3 Hz), 7.69-7.73 (1H, m), 7.99 (1H, d, J=2.3 Hz), 8.16-8.21 (1H, m), 8.27-8.30 (2H, m).

The following compounds were produced in the same manner as in Example 2036.

TABLE 324

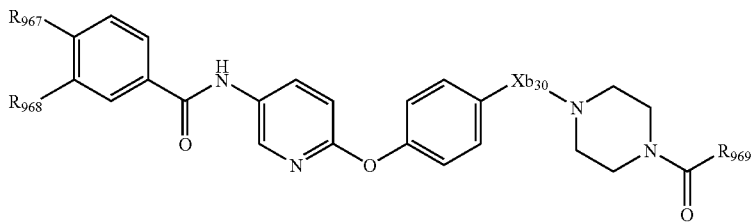

| Example No. | $R_{967}$ | $R_{968}$ | $Xb_{30}$ | $R_{969}$ | mp (° C.) or $^1$H NMR (solvent) δ ppm |
|---|---|---|---|---|---|
| 2037 | —CF$_3$ | —H | —CO— | 6-methyluracil-3-yl | $^1$HNMR (DMSO-d$_6$) 3.52 (4H, brs), 3.60 (4H, brs), 5.57 (1H, s), 7.17 (1H, d, J=8.9Hz), 7.20 (2H, d, J=8.9Hz), 7.51 (2H, d, J=8.4Hz), 7.95 (2H, d, J=8.1Hz), 8.17 (2H, d, J=8.1Hz), 8.27 (1H, dd, J=8.9Hz, 2.6Hz), 8.55 (1H, d, J=2.6Hz), 10.69 (1H, brs), 11.18 (1H, brs), 11.32 (1H, brs). |
| 2038 | —Cl | —Cl | —CH$_2$— | 6-methyl-3,4-dihydroquinolin-2(1H)-one | mp 250-251 |
| 2039 | —CF$_3$ | —H | —CH$_2$— | 2-CNPh- | mp 189-192 |
| 2040 | —CF$_3$ | —H | —CH$_2$— | 4-pyridyl | mp 122-124 |
| 2041 | —CF$_3$ | —H | —CH$_2$— | 3-pyridyl | mp 167-168 |
| 2042 | —CF$_3$ | —H | —CH$_2$— | 2-pyridyl | mp 189-191 |
| 2043 | —CF$_3$ | —H | —CH$_2$— | 4-methylimidazol-5-yl | $^1$HNMR (DMSO-d$_6$) 2.45 (4H, brs), 3.36 (2H, s), 3.54-4.18 (4H, m), 7.09 (3H, d, J=8.9Hz), 7.36 (2H, d, J=8.4Hz), 7.59 (1H, brs), 7.72 (1H, s), 7.94 (2H, d, J=8.4Hz), 8.18 (2H, d, J=8.4Hz), 8.24 (1H, dd, J=8.9Hz, 2.6Hz), 8.53 (1H, d, J=2.6Hz), 10.67 (1H,s), 12.48 (1H, brs). |
| 2044 | —CF$_3$ | —H | —CH$_2$— | 5-ethyl-thiazolidine-2,4-dione | $^1$HNMR (CDCl$_3$+CD$_3$OD) 2.98-3.15 (5H, m), 3.34-3.47 (1H, m), 3.61-3.76 (4H, m), 4.18 (2H, s), 4.57 (1H, dd, J=10.2Hz, 3.1Hz), 7.04 (1H, d, J=8.7Hz), 7.19 (2H, d, J=8.6Hz), 7.49 (2H, d, J=8.6Hz), 7.79 (2H, d, J=8.3Hz), 8.11 (2H, d, J=8.1Hz), 8.25(1H, dd, J=8.9Hz, 2.8Hz), 8.52 (1H, d, J=2.3Hz). |
| 2045 | —CF$_3$ | —H | —(CH$_2$)$_3$— | 6-methyl-1,3-benzodioxol-5-yl | $^1$HNMR (CDCl$_3$) 1.81-1.89 (2H, m), 2.40-2.45 (6H, m), 2.62-2.68 (2H, m), 3.61 (4H, brs), 5.98 (2H, s), 6.76-693 (4H, m), 7.03 (2H, d, J=8.4Hz), 7.19 (2H, d, J=8.4Hz), 7.68 (2H, d, J=8.4Hz), 7.99 (2H, d, J=8.3Hz), 8.18-8.23 (1H, m), 8.30 (1H, d, J=2.6Hz), 8.73 (1H, s). |
| 2046 | —CF$_3$ | —H | —(CH$_2$)$_3$— | 3,4-(CH$_3$O)$_2$Ph— | $^1$HNMR (CDCl$_3$) 1.78-1.89 (2H, m), 2.39-2.45 (6H, m), 2.63-2.68 (2H, m), 3.62 (4H, brs), 3.85 (3H, s), 3.89 (3H, s), 6.82-6.85 (1H, m), 6.91-6.95 (3H, m), 7.01-7.06 (2H, m), 7.18-7.23 (2H, m), 7.70 (2H, d, J=8.2Hz), 7.99 (2H, d, J=8.2Hz), 8.20-8.24 (1H, m), 8.29 (1H, d, J=2.6Hz), 8.51 (1H, brs). |

TABLE 325

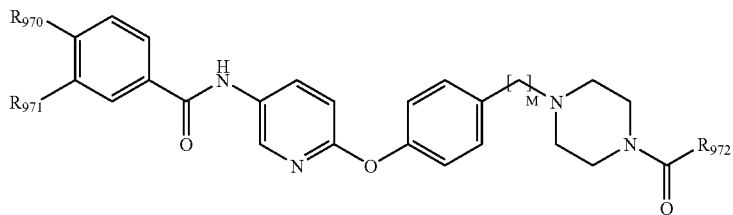

| Example No. | $R_{970}$ | $R_{971}$ | $R_{972}$ | M | Form | $^1$H NMR (solvent) δ ppm |
|---|---|---|---|---|---|---|
| 2047 | —CF$_3$ | —H | ethyl-thiazolidinone with N-N=C(CH$_3$)$_2$ hydrazone | 1 | free | (DMSO-d$_6$) 1.94(6H, s), 2.49-2.51 (4H, m), 2.76-2.93 (1H, m), 3.17-3.51 (7H, m), 4.20 (1H, dd, J=10.4Hz, 3.0Hz), 7.09-7.13 (3H, m), 7.42 (2H, brs), 7.94 (2H, d, J=8.4Hz), 8.16-8.26 (3H, m), 8.54 (1H, d, J=2.5Hz), 10.67 (1H, s), 11.68 (1H, brs). |
| 2048 | —CF$_3$ | —H | 5-(4-methylbenzyl)-thiazolidine-2,4-dione | 1 | free | (CDCl$_3$+CD$_3$OD) 2.46-2.59 (4H, m), 3.16 (1H, dd, J=14.2Hz, 9.4Hz), 3.32 (4H, brs), 3.51 (1H, dd, J=14.0Hz, 3.8Hz), 3.79 (2H, brs), 4.50 (1H, dd, J=9.4Hz, 4.0Hz), 6.93 (1H, d, J=8.9Hz), 7.06 (2H, d, J=8.4Hz), 7.26-7.46 (6H, m), 7.72 (2H, d, J=8.3Hz), 8.05 (2H, d, J=8.1Hz), 8.27 (1H, d, J=2.1Hz), 8.33 (1H, dd, J=8.9Hz, 2.8Hz). |
| 2049 | —CF$_3$ | —H | 5-(4-methylbenzylidene)-thiazolidine-2,4-dione | 1 | free | (DMSO-d$_6$) 2.49-2.52 (4H, m), 3.34-3.40 (4H, m), 3.57 (2H, s), 7.06-7.10 (3H, m), 7.36 (2H, d, J=8.6Hz), 7.54 (2H, d, J=8.1Hz), 7.67 (2H, d, J=8.4Hz), 7.79 (1H, s), 7.94 (2H, d, J=8.6Hz), 8.15-8.25 (3H, m), 8.51 (1H, d, J=2.8Hz), 10.64 (1H, s). |
| 2050 | —CF$_3$ | —H | 4-pyridyl | 3 | hydro-chloride | (DMSO-d$_6$) 2.04 (2H, brs), 2.63-2.69 (2H, m), 3.10-3.59 (9H, m), 4.54 (1H, brs), 7.05-7.08 (3H, m), 7.28 (2H, d, J=8.2Hz), 7.45 (2H, d, J=4.9Hz), 7.94 (2H, d, J=8.2Hz), 8.18-8.26 (3H, m), 8.53 (1H, d, J=2.3Hz), 8.70 (2H, d, J=5.4Hz), 10.72 (1H, s), 11.27 (1H, brs). |
| 2051 | —Cl | —Cl | 3,4-F$_2$Ph— | 1 | free | (CDCl$_3$) 2.46 (4H, brs), 3.47-3.72 (6H, m), 6.91 (1H, d, J=8.9Hz), 7.05-7.33 (7H, m), 7.50 (1H, d, J=8.4Hz), 7.71 (1H, dd, J=8.4Hz, 2.1Hz), 7.97 (1H, d, J=2.1Hz), 8.14-8.18 (1H, m), 8.28 (1H, d, J=2.6Hz), 8.68 (1H, s). |

TABLE 326

| Example No. | Chemical structure | mp (° C.) or ¹H NMR |
|---|---|---|
| 2052 | 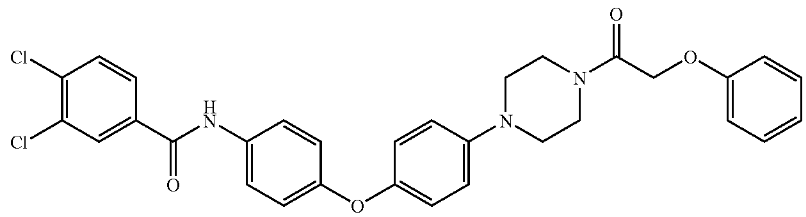 | mp 171-173 |
| 2053 | 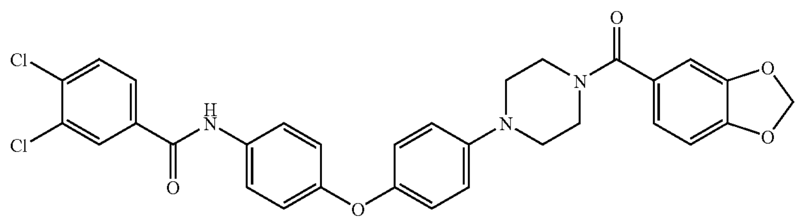 | mp 116-118 |
| 2054 | 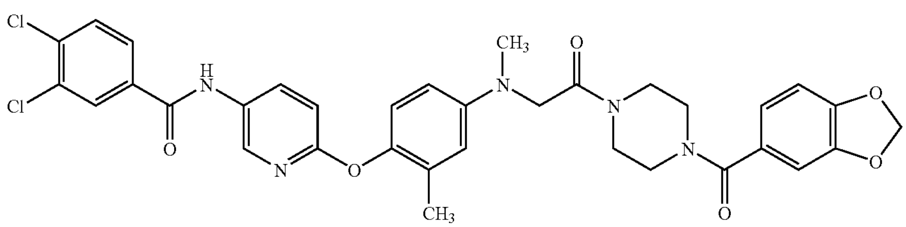 | mp 133-135 |
| 2055 | 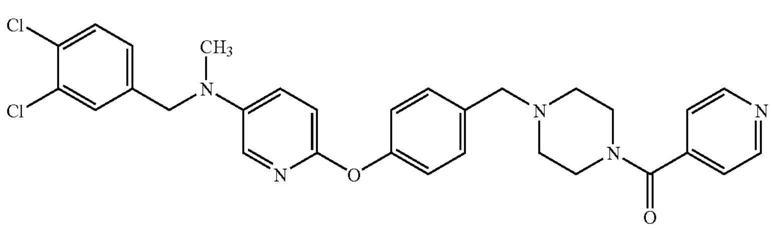 | ¹HNMR (CDCl₃) δ2.39 (2H, brs), 2.55 (2H, brs), 3.00 (3H, s), 3.35 (2H, brs), 3.51 (2H, s), 3.79 (2H, brs), 4.40 (2H, s), 6.82 (1H, d, J=8.9Hz), 6.99-7.13 (4H, m), 7.25-7.29 (5H, m), 7.32 (1H, d, J=1.8Hz), 7.39 (1H, d, J=3.3Hz), 8.68-8.70 (2H, m). |

Example 2056

Production of N-{6-[4-(4-chloroacetylpiperazino)phenoxy]-3-pyridyl}-4-(trifluoromethyl)benzamide To a solution of N-[6-(4-piperazinophenoxy)-3-pyridyl]-4-(trifluoromethyl)benzamide (885 mg, 2.00 mmol) in DMF (20 mL) were added triethylamine (0.418 mL, 3.00 mmol) and chloroacetyl chloride (0.191 g, 2.40 mmol), and the resulting reaction solution was stirred for 10 minutes at room temperature. To this reaction solution was added ethyl acetate. The resulting solution was washed with water, and then dried over anhydrous magnesium sulfate. The solvent was evaporated, to thereby yield 1.00 g of the title compound.

Appearance: White powder

¹H NMR (CDCl₃) δ 3.17 (2H, t, J=5.0 Hz), 3.22 (2H, t, J=5.0 Hz), 3.70 (2H, t, J=5.0 Hz), 3.80 (2H, t, J=5.0 Hz), 6.95 (1H, d, J=9.0 Hz), 6.97 (2H, d, J=9.0 Hz), 7.08 (2H, d, J=9.0 Hz), 7.77 (1H, brs), 7.78 (2H, d, J=8.0 Hz), 7.99 (2H, d, J=8.0 Hz), 8.20 (1H, dd, J=9.0 Hz, 2.5 Hz), 8.26 (1H, d, J=2.5 Hz).

The following compounds were produced in the same manner as in Example 2056.

TABLE 327

[Structure: R973, R974-substituted benzamide linked to pyridine-O-phenyl-Xb31-piperazine-C(O)-R975]

| Example No. | R973 | R974 | Xb31 | R975 | mp (° C.) or ¹H NMR (solvent) δ ppm |
|---|---|---|---|---|---|
| 2057 | —CF₃ | —H | —CO— | 4-CNPh— | ¹HNMR (DMSO-d₆) 3.29-3.69 (8H, m), 7.14-7.20 (3H, m), 7.49 (2H, d, J=8.6Hz), 7.63 (2H, d, J=8.1Hz), 7.93-7.95 (4H, m), 8.17 (2H, d, J=8.1Hz), 8.27 (1H, dd, J=8.9Hz, 2.4Hz), 8.55 (1H, d, J=2.4Hz), 10.66 (1H, s). |
| 2058 | —CF₃ | —H | —CO— | —CH₃ | ¹HNMR (CDCl₃) 2.13 (3H, s), 3.35-3.90 (8H, m), 7.02 (1H, d, J=8.8Hz), 7.17 (2H, d, J=8.6Hz), 7.44 (2H, d, J=8.6Hz), 7.75 (2H, d, J=8.1Hz), 8.02 (2H, d, J=8.1Hz), 8.25 (1H, dd, J=8.8Hz, 2.5Hz), 8.33 (1H, d, J=2.5Hz), 8.38 (1H, brs). |
| 2059 | —Cl | —Cl | —CH₂— | —Ph | ¹HNMR (CDCl₃) 2.08-2.55 (4H, m), 3.43-3.45 (2H, m), 3.55 (2H, s), 3.79-3.81 (2H, m), 6.96 (1H, d, J=8.9Hz), 7.07-7.12 (2H, m), 7.33-7.46 (7H, m), 7.57 (1H, d, J=8.6Hz), 7.69-7.73 (1H, m), 7.94-7.99 (2H, m), 8.17-8.21 (1H, m), 8.27 (1H, d, J=2.6Hz). |
| 2060 | —Cl | —Cl | —CH₂— | 4-CNPh— | ¹HNMR (CDCl₃) 2.44 (2H, brs), 2.58 (2H, brs), 3.39 (2H, brs), 3.56 (2H, s), 3.81 (2H, brs), 6.96 (1H, d, J=8.9Hz), 7.08-7.12 (2H, m), 7.34 (2H, d, J=8.4Hz), 7.48-7.51 (2H, m), 7.57 (1H, d, J=8.4Hz), 7.69-7.77 (3H, m), 7.95 (1H, brs), 7.98 (1H, d, J=2.0Hz), 8.14-8.21 (1H, m), 8.27 (1H, d, J=2.3Hz). |
| 2061 | —CF₃ | —H | —CH₂— | 4-CNPh— | mp 167-168 |
| 2062 | —CF₃ | —H | —CH₂— | —Ph | ¹HNMR (CDCl₃) 2.41-2.53 (4H, m), 3.43 (2H, brs), 3.53 (2H, s), 3.78 (2H, brs), 6.95 (1H, d, J=8.9Hz), 7.06-7.11 (2H, m), 7.33-7.41 (7H, m), 7.71 (2H, d, J=8.4Hz), 7.99 (2H, d, J=8.4Hz), 8.23 (1H, dd, J=8.9Hz, 2.7Hz), 8.31 (1H, d, J=2.7Hz), 8.39 (1H, s). |
| 2063 | —CF₃ | —H | —CH₂— | 3,4-F₂Ph— | mp 130-133 |
| 2064 | —CF₃ | —H | —CH₂— | 3-CNPh— | ¹HNMR (CDCl₃) 2.43 (2H, brs), 2.56 (2H, brs), 3.39 (2H, brs), 3.55 (2H, s), 3.79 (2H, brs), 6.97 (1H, d, J=8.9Hz), 7.07-7.12 (2H, m), 7.32-7.37 (2H, m), 7.50-7.77 (6H, m), 8.00 (2H, d, J=8.1Hz), 8.07 (1H, brs), 8.23 (1H, dd, J=8.9Hz, 2.7Hz), 8.28 (1H, d, J=2.7 Hz). |
| 2065 | —CF₃ | —H | —CH₂— | 4-CH₃Ph— | mp 193-194 |
| 2066 | —CF₃ | —H | —CH₂— | 4-ClPh— | mp 176-178 |
| 2067 | —CF₃ | —H | —CH₂— | 4-CH₃OPh— | mp 190-191 |

TABLE 328

[Structure: R976-pyridine-O-phenyl-(CH₂)ₘ-piperazine-C(O)-R977]

| Example No. | R976 | R977 | M | ¹H NMR (CDCl₃) δ ppm |
|---|---|---|---|---|
| 2068 | 3,4-Cl₂PhCH₂N(CH₃)— | —Ph | 1 | 2.38 (2H, brs), 2.53 (2H, brs), 2.99 (3H, s), 3.42 (2H, brs), 3.50 (2H, s), 3.79 (2H, brs), 4.39 (2H, s), 6.81 (1H, d, J=8.9Hz), 6.99-7.12 (4H, m), 7.26-7.39 (9H, m), 7.69 (1H, d, J=3.1 Hz). |

TABLE 328-continued

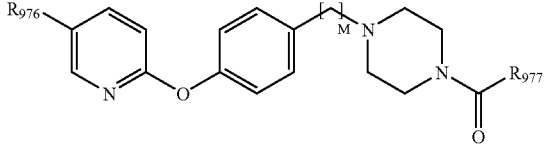

| Example No. | R976 | R977 | M | 1H NMR (CDCl3) δ ppm |
|---|---|---|---|---|
| 2069 | 3,4-Cl2PhCH2N(CH3)— | 4-CNPh— | 1 | 2.39 (2H, brs), 2.55 (2H, brs), 3.01 (3H, s), 3.35 (2H, brs), 3.51 (2H, s), 3.79 (2H, brs), 4.40 (2H, s), 6.82 (1H, d, J=8.9Hz), 6.99-7.13 (4H, m), 7.25-7.33 (3H, m), 7.39 (1H, d, J=8.1Hz), 7.48-7.52 (2H, m), 7.69-7.73 (3H, m). |
| 2070 | 3,4-Cl2PhCH2N(CH3)— | 4-ClPh— | 1 | 2.34-2.59 (4H, m), 3.00 (3H, s), 3.36 (2H, brs), 3.52 (2H, s), 3.83 (2H, brs), 4.40 (2H, s), 6.82 (1H, d, J=8.9Hz), 6.98-7.13 (4H, m), 7.25-7.41 (8H, m), 7.70 (1H, d, J=3.3Hz). |
| 2071 | 3,4-Cl2PhCH2N(CH3)— | 3,4-F2Ph— | 1 | 2.33-2.57 (4H, m), 3.00 (3H, s), 3.37-3.51 (4H, m), 3.75 (2H, brs), 4.40 (2H, s), 6.82 (1H, d, J=8.9Hz), 7.00-7.32 (10H, m), 7.39 (1H, d, J=8.1Hz), 7.69 (1H, d, J=3.1Hz). |
| 2072 | 4-CF3PhCONH— | —Ph | 3 | 1.78-1.89 (2H, m), 2.39-2.49 (6H, m), 2.66 (2H, t, J=7.6Hz), 3.44 (2H, brs), 3.79 (2H, brs), 6.94 (1H, d, J=8.7Hz), 7.02-7.07 (2H, m), 7.18-7.23 (2H, m), 7.35-7.42 (5H, m), 7.72 (2H, d, J=8.2Hz), 7.99 (2H, d, J=8.1Hz), 8.19-8.29 (3H, m). |
| 2073 | 4-CF3PhCONH— | 4-CNPh— | 3 | 1.79-1.90 (2H, m), 2.41-2.69 (8H, m), 3.39 (2H, brs), 3.81 (2H, brs), 6.95 (1H, d, J=8.9Hz), 7.02-7.07 (2H, m), 7.18-7.23 (2H, m), 7.49 (2H, d, J=7.9Hz), 7.69-7.77 (4H, m), 8.00 (2H, d, J=8.1Hz), 8.06 (1H, brs), 8.21 (1H, dd, J=8.9Hz, 2.6Hz), 8.28 (1H, d, J=2.6Hz). |
| 2074 | 4-CF3PhCONH— | 3,4-F2Ph— | 3 | 1.82-1.87 (2H, m), 2.41-2.69 (8H, m), 3.47-3.76 (4H, m), 6.95 (1H, d, J=8.7Hz), 7.02-7.07 (2H, m), 7.11-7.28 (5H, m), 7.75 (2H, d, J=8.4Hz), 7.99-8.06 (3H, m), 8.19-8.23 (1H, m), 8.28 (1H, d, J=2.6Hz). |

TABLE 329

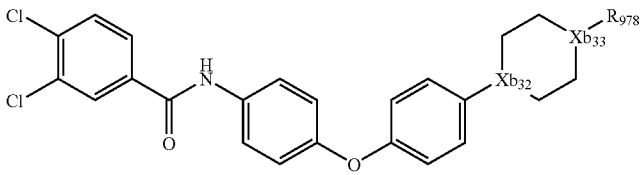

| Example No. | Xb32 | Xb33 | R978 | mp (° C.) or 1H NMR (solvent) δ ppm |
|---|---|---|---|---|
| 2075 | 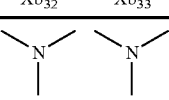 | 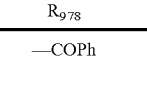 | —COPh | mp 136-138 |
| 2076 | 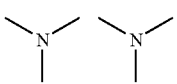 | 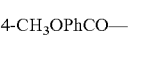 | 4-CH3OPhCO— | mp 161-162 |
| 2077 | 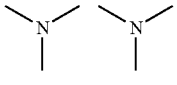 | 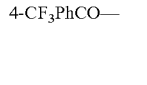 | 4-CF3PhCO— | mp 143-144 |
| 2078 | 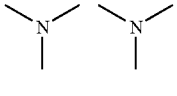 | 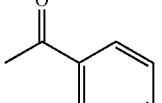 | 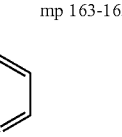 | mp 163-165 |

TABLE 329-continued

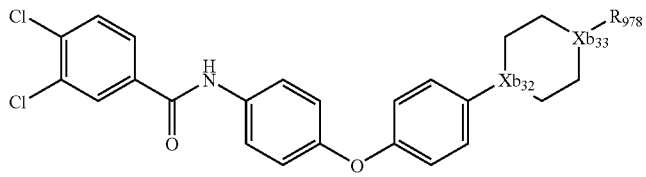

| Example No. | Xb$_{32}$ | Xb$_{33}$ | R$_{978}$ | mp (° C.) or $^1$H NMR (solvent) δ ppm |
|---|---|---|---|---|
| 2079 | \N/ N— | \N/ N— | 4-ClPhCO— | mp 147-151 |
| 2080 | \N/ N— | \HC/ N— | —N(CH$_3$)COPh | mp 231-232 |
| 2081 | \N/ N— | \HC/ N— | —N(CH$_3$)COCH$_2$Cl | $^1$HNMR (CDCl$_3$) 1.70-1.76 (2H, m), 1.80-1.90 (2H, m), 2.80-2.88 (2H, m), 2.98 (3H, s), 3.56-3.68 (2H, m), 4.10 (2H, s), 4.57 (1H, m), 6.94-6.99 (6H, m), 7.53-7.58 (3H, m), 7.69-7.71 (2H, m), 7.97 (1H, d, J=2.0Hz). |
| 2082 | \N/ N— | \N/ N— | —COCH$_2$Cl | $^1$HNMR (DMSO-d$_6$) 3.08 (2H, m), 3.14 (2H, m), 3.61 (4H, m), 4.44 (2H, s), 6.93-7.02 (6H, m), 7.71 (2H, d, J=9.0Hz), 7.82 (1H, d, J=8.5Hz), 7.93 (1H, dd, J=8.5Hz, 2.0Hz), 8.21 (1H, d, J=2.0Hz), 10.39 (1H, s). |
| 2083 | \HC/ N— | \N/ N— | —COCH$_2$Cl | $^1$HNMR (CDCl$_3$) 1.66 (1H, m), 1.74 (1H, m), 1.91-1.98 (2H, m), 2.72-2.77 (2H, m), 3.24 (1H, m), 3.99 (1H, brd, J=13.0Hz), 4.11 (2H, s), 4.73 (1H, brd, J=13.0Hz), 6.96 (2H, d, J=8.5Hz), 7.02 (2H, d, J=9.0Hz), 7.15 (2H, d, J=8.5Hz), 7.56-7.79 (3H, m), 7.71 (1H, dd, J=8.5Hz,2.0Hz), 7.90 (1H, brs), 7.98 (1H, d, J=2.0Hz). |

TABLE 330

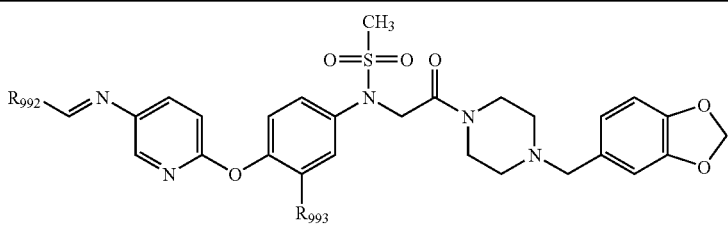

| Example No. | R$_{979}$ | R$_{980}$ | Xb$_{34}$ | Xb$_{35}$ | Xb$_{36}$ | R$_{981}$ | mp (° C.) or MS |
|---|---|---|---|---|---|---|---|
| 2084 | 3,4-Cl$_2$Ph— | —H | none | none | \HC/ N— | —N(CH$_3$)COCH$_2$Ph | MS 616 (M$^+$) |
| 2085 | 4-CF$_3$Ph— | —CH$_3$ | —N(CH$_3$)— | —CH$_2$— | \N/ N— | 4-CNPhCO— | mp 131-132 |
| 2086 | 4-CF$_3$Ph— | —CH$_3$ | —N(CH$_3$)— | —CH$_2$— | \N/ N— | (benzo[1,3]dioxol-5-yl)C(O)— | mp 143-145 |

TABLE 331

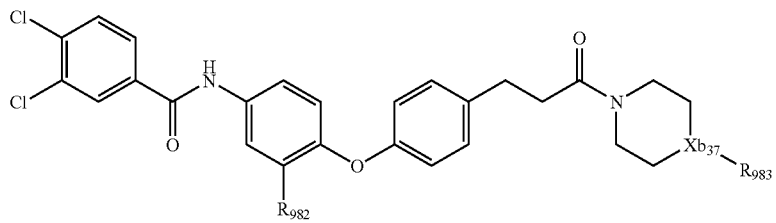

| Example No. | $R_{982}$ | $Xb_{37}$ | $R_{983}$ | Property |
|---|---|---|---|---|
| 2087 | —H | \N/ (N-CH) | —Ac | mp 138-140° C. |
| 2088 | —F | \HC/ | —N(CH₃)COCH₂Ph | MS 661 (M⁺) |
| 2089 | —H | \N/ (N-CH) | —COCH₂Cl | ¹HNMR (CDCl₃) δ2.62 (2H, t, J=7.6Hz), 2.95 (2H, t, J=7.6Hz), 3.31-3.73 (8H, m), 4.05 (2H, s), 6.91 (2H, d, J=8.5Hz), 6.97 (2H, d, J=8.9Hz), 7.15 (2H, d, J=8.5Hz), 7.49-7.60 (3H, m), 7.68 (1H, dd, J=8.3Hz, 2.1Hz), 7.91 (1H, brs), 7.95 (1H, d, J=2.1Hz). |

TABLE 332

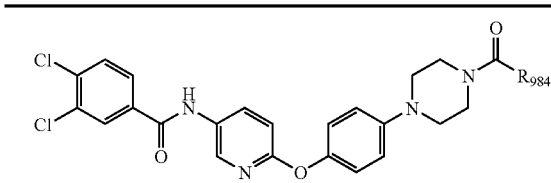

| Example No. | $R_{984}$ | mp (° C.) |
|---|---|---|
| 2090 | 2-pyridyl | 217-218 |
| 2091 | 3-pyridyl | 191-192 |
| 2092 | 4-pyridyl | 204-205 |

TABLE 333

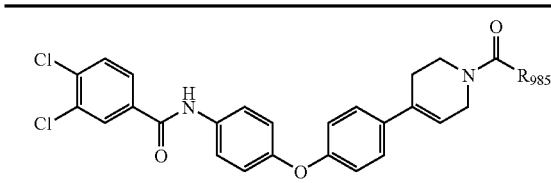

| Example No. | $R_{985}$ | mp (° C.) or ¹H NMR (CDCl₃) δ ppm |
|---|---|---|
| 2093 | —Ph | mp 185-186 |
| 2094 | —CH₂Cl | a mixture of the rotational isomers ¹HNMR 2.57 (0.4H, brs), 2.65 (0.6H, brs), 3.74 (0.6H, t, J=6.0Hz), 3.85 (0.4H, t, J=6.0Hz), 4.13 (0.8H, s), 4.15 (1.2H, s), 4.22 (1.2H, m), 4.25 (0.8H, m), 5.89 (0.4H, brs), 6.04 (0.6H, brs), 6.98 (2H, d, J=8.5Hz), 7.04 (2H, d, J=9.0Hz), 7.34 (2H, dd, J=8.5Hz, 4.0Hz), 7.56-7.60 (3H, m), 7.71 (1H, dd, J=8.5Hz, 2.0Hz), 7.89 (1H, brs), 7.89 (1H, d, J=2.0Hz). |

Example 2095

Production of 1-{4-[4-(3,4-dichlorobenzoylamino)-phenoxy]phenyl}-4-benzoyloxypiperidine To a solution of 1-{4-[4-(3,4-dichlorobenzoylamino)phenoxy]phenyl}-4-hydroxypiperidine (200 mg, 0.44 mmol) in dichloromethane (8 mL) were added with triethylamine (0.091 mL, 0.65 mmol), benzoyl chloride (74 mg, 0.53 mmol) and 4-(dimethylamino)pyridine (3 mg, 0.025 mmol), and the resulting solution was stirred for 2.5 days at room temperature. This reaction solution was purified by silica gel column chromatography (methanol:dichloromethane=7:93), to thereby yield 80 mg of the title compound.
Appearance: White powder
Melting point: 188-190° C.

Example 2096

Production of 3,4-dichloro-N-(6-{4-[[2-oxo-2-(4-piperonylpiperazin-1-yl)ethyl](2,2,2-trifluoroacetyl)amino]phenoxy}pyridin-3-yl)benzamide To a solution of 3,4-dichloro-N-(6-{4-[2-oxo-2-(4-piperonylpiperazin-1-yl)ethylamino]phenoxy}pyridin-3-yl)benzamide (0.152 g, 0.239 mmol) in THF (5 mL) were added triethylamine (0.0500 mL, 0.359 mmol) and trifluoroacetic anhydride (0.0410 mL, 0.287 mmol), and the resulting solution was stirred for 6 hours. Water was added to the resulting reaction solution, and extracted with ethyl acetate. The ethyl acetate layer was washed with brine, dried over anhydrous magnesium sulfate, and evaporated. The residue was purified by silica gel column chromatography (dichloromethane:methanol=20:1) to yield a solid. This solid was recrystallized from methanol, to thereby yield 28.8 mg of the title compound.
Appearance: White powder
Melting point: 211-213° C.

The following compound was produced in the same manner as in Example 2096.

Example 2097

N-[6-(4-Acetyl[2-oxo-2-(4-piperonylpiperazin-1-yl)ethyl]amino}-2-methoxyphenoxy)pyridin-3-yl]-3,4-dichlorobenzamide $^1$H NMR (CDCl$_3$) δ 1.90 (3H, s), 2.28 (2H, brs), 2.38 (2H, brs), 3.37 (4H, brs), 3.49 (2H, brs), 3.67 (3H, s), 4.43 (2H, s), 5.93 (2H, s), 6.68-6.75 (2H, m), 6.82 (1H, s), 6.91-6.97 (2H, m), 7.07-7.10 (2H, m), 7.53 (1H, d, J=8.4 Hz), 7.76 (1H, dd, J=8.4 Hz, 2.0 Hz), 8.05 (1H, d, J=2.0 Hz), 8.20 (1H, dd, J=8.9 Hz, 2.8 Hz), 8.37 (1H, d, J=2.6 Hz), 9.26 (1H, s).

Example 2098

Production of N-[6-(benzoyl{4-[3-oxo-3-(4-piperonylpiperazin-1-yl)propyl]phenyl}amino)pyridin-3-yl]-3,4-dichlorobenzamide monooxalate To a solution of 3,4-dichloro-N-(6-{4-[3-oxo-3-(4-piperonylpiperazin-1-yl)propyl]phenylamino}-pyridin-3-yl)benzamide (250 mg, 0.395 mmol) in THF (5 mL) were added triethylamine (0.132 mL, 0.949 mmol) and benzoyl chloride (0.0550 mL, 0.474 mmol), and the resulting solution was stirred for 7 hours at room temperature. Water was added to the resulting reaction solution, and extracted with ethyl acetate. The ethyl acetate layer was washed with brine, dried over anhydrous magnesium sulfate, and evaporated. The residue was purified by silica gel column chromatography (dichloromethane:methanol=10:1) to yield 0.300 g of a free form. To this free form were added isopropanol (5 mL) and oxalic acid dihydrate (100 mg, 0.793 mmol), and the resulting solution was dissolved under heat. The solvent was evaporated, and the resulting solid was recrystallized from isopropanol, to thereby yield 80.0 mg of the title compound.

Appearance: Yellow powder
Melting point: 140-143° C.

The following compound was produced in the same manner as in Example 2098.

Example 2099

N-[6-(Acetyl{4-[3-oxo-3-(4-piperonylpiperazin-1-yl)propyl]phenyl}amino)pyridin-3-yl]-3,4-dichlorobenzamide Melting point: 150-165° C.
$^1$H NMR (DMSO-d$_6$) δ 1.98 (3H, s), 2.62-2.98 (7H, m), 3.04 (1H, t, J=12.1 Hz), 3.26 (2H, t, J=14.7 Hz), 3.35-3.50 (2H, m), 4.06 (1H, d, J=13.8 Hz), 4.13-4.26 (2H, m), 4.44 (1H, d, J=13.8 Hz), 6.07 (2H, s), 6.95-7.02 (2H, m), 7.20-7.24 (3H, m), 7.28 (2H, d, J=8.3 Hz), 7.52 (1H, d, J=8.9 Hz), 7.85 (1H, d, J=8.4 Hz), 7.96 (1H, dd, J=2.0 Hz, 8.4 Hz), 8.23-8.26 (2H, m), 8.77 (1H, s), 10.77 (1H, s), 11.10 (1H, brs).

Example 2100

Production of 6-{4-[3-(4-piperonylpiperazin-1-yl)-3-oxopropyl]phenoxy}-N-(3,4-dichlorophenyl)nicotinamide To a solution of 6-{4-[3-(4-piperonylpiperazin-1-yl)-3-oxopropyl]phenoxy}nicotinic acid (1.23 g, 2.5 mmol) in THF (35 mL) was added N,N'-carbonyldiimidazole (540 mg, 3.3 mmol), and the resulting solution was stirred for 30 minutes at room temperature. The resulting reaction solution was concentrated under reduced pressure, and to the residue was added 3,4-dichloroaniline (4.07 g, 25 mmol). The resulting solution was stirred for 3 days at room temperature. The solvent was evaporated under reduced pressure. The residue was purified by silica gel column chromatography (ethyl acetate), and the resulting product was recrystallized from diethyl ether, to thereby yield 510 mg of the title compound.

Appearance: White powder
$^1$H NMR (CDCl$_3$) δ 2.33 (4H, brs), 2.59-2.65 (2H, m), 2.91-2.97 (2H, m), 3.40 (4H, brs), 3.59 (2H, s), 5.94 (2H, s), 6.70-6.76 (2H, m), 6.83 (1H, s), 6.96-7.06 (3H, m), 7.20-7.26 (2H, m), 7.40 (1H, d, J=8.6 Hz), 7.50-7.54 (1H, m), 7.86 (1H, d, J=1.8 Hz), 8.18-8.22 (1H, m), 8.44 (1H, brs), 8.66 (1H, brs).

The following compounds were produced in the same manner as in Example 2100.

TABLE 334

| Example No. | R$_{986}$ | Xb$_{38}$ | Xb$_{39}$ | R$_{987}$ | mp (° C.) or $^1$H NMR (CDCl$_3$) δ ppm |
|---|---|---|---|---|---|
| 2101 | 3,4-Cl$_2$Ph— | none | none | benzyl | mp 206-207 |
| 2102 | 4-CF$_3$Ph— | none | none | benzyl | $^1$HNMR 2.44 (4H, brs), 3.53-3.70 (6H, m), 6.93 (1H, d, J=8.4Hz), 7.11-7.14 (2H, m), 7.27-7.40 (7H, m), 7.56 (2H, d, J=8.9Hz), 7.83 (2H, d, J=8.4Hz), 8.23-8.27 (1H, m), 8.71 (1H, d, J=2.4Hz), 9.39 (1H, brs). |
| 2103 | 4-CF$_3$Ph— | —N(CH$_3$)— | —CH$_2$— | piperonyl | $^1$HNMR 2.42 (4H, brs), 3.03 (3H, s), 3.43-3.52 (4H, m), 3.60 (2H, brs), 4.10 (2H, s), 5.95 (2H, s), 6.66-6.77 (4H, m), 6.85 (1H, brs), 6.89 (1H, d, J=8.6Hz), 6.98 (2H, d, J=6.6Hz), 7.60 (2H, d, J=8.4Hz), 7.76 (2H, d, J=8.4Hz), 8.14 (1H, dd, J=8.6Hz, 2.6Hz), 8.33 (1H, brs), 8.63 (1H, brs). |

TABLE 334-continued

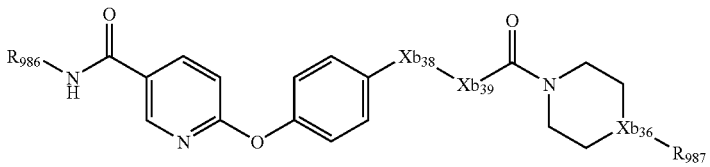

| Example No. | $R_{986}$ | $Xb_{38}$ | $Xb_{39}$ | $R_{987}$ | mp (° C.) or $^1$H NMR (CDCl$_3$) δ ppm |
|---|---|---|---|---|---|
| 2104 | 3,4-Cl$_2$Ph— | —N(CH$_3$)— | —CH$_2$— | piperonyl | $^1$HNMR 2.42-2.44 (4H, m), 3.05 (3H, s), 3.44 (2H, brs), 3.47-3.57 (2H, m), 3.63 (2H, brs), 4.11 (2H, s), 5.95 (2H, s), 6.68-6.74 (4H, m), 6.85 (1H, brs), 6.92 (1H, d, J=8.9Hz), 7.00 (2H, d, J=8.7Hz), 7.42-7.44 (2H, m), 7.80-7.86 (1H, m), 7.87 (1H, d, J=2.1Hz), 8.13 (1H, dd, J=8.7Hz, 2.6Hz), 8.63 (1H, d, J=2.1 Hz). |
| 2105 | 4-CF$_3$Ph— | none | none | piperonyl | $^1$HNMR 2.71 (4H, brs), 3.46-3.92 (6H, m), 5.91 (2H, s), 6.65-6.73 (2H, m), 6.81 (1H, d, J=1.5Hz), 7.01 (1H, d, J=9.1Hz), 7.14 (2H, d, J=8.7Hz), 7.43 (2H, d, J=8.7Hz), 7.60 (2H, d, J=8.6Hz), 7.82 (2H, d, J=8.6Hz), 8.29 (1H, dd, J=2.6Hz, 8.6Hz), 8.71 (1H, d, J=2.1Hz), 8.87 (1H, brs). |

Example 2106

Production of (4-benzylpiperazin-1-yl){4-[5-(3,4-dichlorophenylsulfanyl)pyridin-2-yloxy]phenyl}methanone To a solution of [4-(5-aminopyridin-2-yloxy)phenyl](4-benzylpiperazin-1-yl)methanone (0.73 g, 1.88 mmol) in concentrated sulfuric acid (0.38 mL)-water (1.1 mL) were added dropwise a solution of sodium nitrate (0.13 g, 1.88 mmol) in water (0.6 mL) under ice cooling. The reaction mixture was stirred for 10 minutes. This reaction mixture was added to a solution of 3,4-dichlorobenzenethiol (0.24 mL, 1.88 mmol) in 2 N aqueous sodium hydroxide (2 mL) under cooling with ice. Water was added to the resulting reaction solution, and extracted with dichloromethane. The dichloromethane layer was dried over anhydrous magnesium sulfate, and evaporated. The residue was purified by silica gel chromatography (dichloromethane:methanol=80:1), to thereby yield 0.1 g of the title compound.

Appearance: Yellow oil $^1$H NMR (CDCl$_3$) δ 2.49 (4H, brs), 3.56 (2H, s), 3.56 (2H, brs), 3.78 (2H, brs), 6.99 (1H, d, J=8.9 Hz), 7.20 (2H, d, J=8.7 Hz), 7.25-7.39 (5H, m), 7.46 (1H, dd, J=8.2 Hz, 2.0 Hz), 7.47 (2H, d, J=8.7 Hz), 7.56 (1H, d, J=8.2 Hz), 7.76 (1H, d, J=2.0 Hz), 7.86 (1H, dd, J=8.9 Hz, 2.5 Hz), 8.50 (1H, d, J=2.5 Hz).

The following compound was produced in the same manner as in Example 2106.

Example 2107

2-({4-[5-(3,4-Dichlorophenylsulfanyl)pyridin-2-yloxy]-3-methoxyphenyl}ethylamino)-1-(4-piperonylpiperazin-1-yl)ethanone $^1$H NMR (CDCl$_3$) δ 1.20 (3H, t, J=7.0 Hz), 2.43 (4H, t, J=4.9 Hz), 3.43 (2H, s), 3.35-3.50 (2H, m), 3.49-3.60 (2H, m), 3.60-3.70 (2H, m), 3.73 (3H, s), 4.05 (2H, s), 5.95 (2H, s), 6.22 (1H, dd, J=8.9 Hz, 2.7 Hz), 6.35 (1H, d, J=2.7 Hz), 6.70-6.76 (2H, m), 6.85 (1H, s), 6.90 (1H, d, J=9.0 Hz), 6.98 (1H, d, J=8.8 Hz), 7.46 (1H, dd, J=8.2 Hz, 2.0 Hz), 7.55 (1H, d, J=8.2 Hz), 7.75 (1H, d, J=2.0 Hz), 7.78 (1H, dd, J=9.0 Hz, 2.5 Hz), 8.49 (1H, d, J=2.5 Hz).

Example 2108

Production of 1-(6-{4-[3-(4-piperonylpiperazin-1-yl)-3-oxopropyl]phenoxy}pyridin-3-yl)-3-(3,4-dichlorophenyl)urea To a solution of 3-[4-(5-aminopyridin-2-yloxy)phenyl]-1-(4-piperonylpiperazin-1-yl)propane-1-one (600 mg, 1.3 mmol) in toluene (20 mL) were added ethyldiisopropylamine (0.454 mL, 2.6 mmol) and 3,4-dichlorophenylisocyanate (270 mg, 1.4 mmol), and the resulting solution was stirred for 1 day under reflux. The reaction solution was evaporated under reduced pressure. The residue was purified by silica gel column chromatography (methanol:chloroform=1:19), and then recrystallized from ethyl acetate to thereby yield 280 mg of the title compound.

Appearance: Pale yellow powder $^1$H NMR (CDCl$_3$) δ 2.37-2.39 (4H, m), 2.61-2.67 (2H, m), 2.89-2.94 (2H, m), 3.41-3.47 (4H, m), 3.61-3.65 (2H, m), 5.94 (2H, s), 6.69-6.83 (4H, m), 6.95 (2H, d, J=8.4 Hz), 7.10-7.26 (4H, m), 7.49 (1H, d, J=2.3 Hz), 7.93-7.96 (2H, m), 8.15 (1H, s), 8.21 (1H, s).

The following compounds were produced in the same manner as in Example 2108.

TABLE 335

[Core structure: 3,4-dichlorophenyl-NH-C(=O)-NH-pyridin-5-yl with 2-O-R988]

| Example No. | R988 | $^1$H NMR (solvent) δ ppm |
|---|---|---|
| 2109 | [structure: N(C2H5)(4-methyl-3-methoxyphenyl)-CH2-C(=O)-piperazine-N-CH2-benzo[1,3]dioxole · HCl] | (DMSO-d$_6$) 1.13 (3H, t, J=6.9Hz), 2.20-2.60 (1H, m), 2.75-3.20 (2H, m), 3.20-3.65 (7H, m), 3.64 (3H, s), 4.05-4.52 (4H, m), 6.07 (2H, brs), 6.10 (1H, dd, J=8.8Hz, 2.7Hz), 6.27 (1H, brs), 6.80 (1H, d, J=8.6Hz), 6.84 (1H, d, J=8.6Hz), 7.01 (2H, brs), 7.19 (1H, brs), 7.33 (1H, dd, J=8.9Hz,2.6Hz), 7.51 (1H, d, J=8.9Hz), 7.85 (1H, dd, J=8.9Hz, 2.6Hz), 7.86 (1H, d, J=2.6Hz), 8.07 (1H, d, J=2.6Hz), 8.94 (1H, s), 9.28 (1H, s). |
| 2110 | [structure: N(C2H5)(4-methyl-3-COOCH3-phenyl)-CH2-C(=O)-piperazine-N-CH2-benzo[1,3]dioxole] | (CDCl$_3$) 1.14 (3H, t, J=7.0Hz), 2.35-2.55 (4H, m), 3.38 (2H, q, J=7.0Hz), 3.44 (2H, s), 3.45-3.55 (2H, m), 3.60 (3H, s), 3.60-3.75 (2H, m), 4.02 (2H, s), 5.95 (2H, s), 6.60-6.80 (4H, m), 6.85 (1H, s), 6.92 (1H, d, J=8.9Hz), 7.00-7.15 (2H, m), 7.22 (1H, d, J=8.7Hz), 7.45 (1H, d, J=2.3Hz),7.75-7.85 (2H, m), 7.95 (1H, s), 7.97 (1H, s). |
| 2111 | [structure: N(C2H5)(4-methyl-2-CF3-phenyl)-CH2-C(=O)-piperazine-N-CH2-benzo[1,3]dioxole] | (CDCl$_3$) 1.09 (3H, t, J=7.1Hz), 2.35-2.45 (4H, m), 3.10 (2H, q, J=7.1Hz), 3.43 (2H, s), 3.55-3.65 (4H, m), 3.85 (2H, s), 5.95 (2H, s), 6.70-6.80 (2H, m), 6.85 (1H, s), 6.90 (1H, d, J=8.8Hz), 7.05-7.35 (4H, m), 7.46 (1H, d, J=8.8Hz), 7.53 (1H, d, J=2.4Hz), 7.79 (1H, brs), 7.85 (1H, brs), 7.93 (1H,d, J=2.6Hz), 7.99 (1H, dd, J=8.8Hz, 2.8 Hz). |
| 2112 | [structure: tetrahydropyrimidin-2-one with N-(3-methyl-4-methylphenyl) and N'-CH2COOC(CH3)3] | (CDCl$_3$) 1.44 (9H, s), 1.96 (3H, s), 2.10-2.30 (2H, m), 3.42-3.61 (2H, m), 3.62-3.78 (2H, m), 4.04 (2H, s), 6.58 (1H, d, J=8.8Hz), 6.60 (1H, d, J=8.5Hz), 6.91 (1H, dd, J=2.6Hz, 8.5Hz), 7.00 (1H, d, J=2.6Hz), 7.31 (1H, d, J=8.8Hz), 7.36 (1H, dd, J=2.3Hz, 8.8Hz), 7.69 (1H, d, J=2.3Hz), 7.79(1H, dd, J=2.8Hz, 8.8Hz), 7.91 (1H, d, J=2.8Hz), 7.93 (1H, s), 8.05 (1H, s). |

Example 2113

Production of 4-piperonylpiperazine-1-carboxylic acid 14-[5-(3,4-dichlorobenzoylamino)pyridin-2-yloxy]phenyl}amide hydrochloride To a solution of {4-[5-(3,4-dichlorobenzoyl-amino)pyridin-2-yloxy]phenyl}-carbamic acid phenyl ester (320 mg, 0.65 mmol) in DMF (4 mL) was added 1-piperonylpiperazine (285 mg, 1.29 mmol), and the resulting solution was stirred for 17 hours at room temperature. This reaction solution was concentrated under reduced pressure. Water was added to the residue, and extracted with ethyl acetate. The ethyl acetate layer was washed with brine, dried over anhydrous magnesium sulfate, and evaporated. The residue was then purified by silica gel column chromatography (dichloromethane:methanol=25:1). The obtained residue was dissolved in a mixed solvent of ethanol-ethyl acetate. To the resulting solution was added a solution of 4 N hydrogen chloride in ethyl acetate to bring the pH to 3. The precipitated white powder was then filtered off and washed with ethanol, to thereby yield 330 mg of the title compound.

Appearance: White powder $^1$H NMR (DMSO-d$_6$) δ 2.85-3.09 (2H, m), 3.20-3.50 (4H, m), 4.12-4.38 (4H, m), 6.08 (2H, s), 7.02 (2H, d, J=9.0 Hz), 6.93-7.12 (3H, m), 7.28 (1H, d, J=1.5 Hz), 7.49 (2H, d, J=9.0 Hz), 7.83 (1H, d, J=8.5 Hz), 7.97 (1H, dd, J=8.5 Hz, 2.0 Hz), 8.19 (1H, dd, J=8.8 Hz, 2.6 Hz), 8.25 (1H, d, J=2.0 Hz), 8.50 (1H, d, J=2.6 Hz), 8.92 (1H, s), 10.63 (1H, s).

The following compound was produced in the same manner as in Example 2113.

Example 2114

4-Benzylpiperazine-1-carboxylic acid {4-[5-(3,4-dichlorobenzoylamino)pyridin-2-yloxy]phenyl}amide hydrochloride $^1$H NMR (DMSO-d$_6$) δ 2.90-3.20 (2H, m), 3.22-3.45 (4H, m), 4.27 (2H, d, J=13.6 Hz), 4.35 (2H, d, J=5.0 Hz), 7.02 (1H, d, J=8.9 Hz), 7.03 (2H, d, J=8.9 Hz), 7.41-7.52 (3H, m), 7.48

(2H, d, J=8.9 Hz), 7.55-7.69 (2H, m), 7.84 (1H, d, J=8.4 Hz), 7.97 (1H, dd, J=8.4 Hz, 2.0 Hz), 8.19 (1H, dd, J=8.9 Hz, 2.6 Hz), 8.25 (1H, d, J=2.0 Hz), 8.49 (1H, d, J=2.6 Hz), 8.90 (1H, s), 10.62 (1H, s).

Example 2115

Production of 2-[(4-{5-[(3,4-dichlorobenzylidene)-amino]pyridin-2-yloxy}phenyl)methylamino]-1-(4-piperonylpiperazin-1-yl)ethanone 2-{[(4-(5-aminopyridin-2-yloxy)phenyl]methylamino}-1-(4-piperonylpiperazin-1-yl)ethanone (7.80 g, 16.4 mmol) was dissolved in methanol (400 mL), and to the resulting solution was added 3,4-dichlorobenzaldehyde (2.87 g, 16.4 mmol). This solution was refluxed for 16 hours. The resulting reaction solution was concentrated under reduced pressure, to thereby yield 10.4 g of the title compound.

Appearance: Brown oil $^1$H NMR (CDCl$_3$) δ 2.44 (4H, brs), 3.03 (3H, s), 3.44-3.45 (2H, m), 3.50 (2H, brs), 3.63 (2H, brs), 4.09 (2H, s), 5.94 (2H, s), 6.65-6.77 (4H, m), 6.84-6.88 (2H, m), 7.03 (2H, d, J=9.1 Hz), 7.54 (1H, d, J=8.3 Hz), 7.58 (1H, dd, J=8.9 Hz, 2.8 Hz), 7.70 (1H, dd, J=8.4 Hz, 2.0 Hz), 8.00 (1H, d, J=2.0 Hz), 8.10 (1H, d, J 2.8 Hz), 8.39 (1H, s).

The following compounds were produced in the same-manner as in Example 2115.

TABLE 336

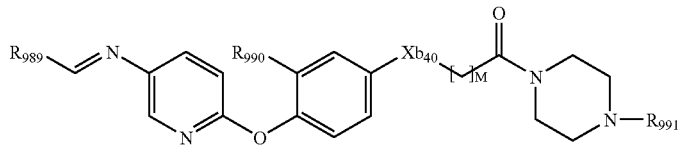

| Example No. | R$_{989}$ | R$_{990}$ | R$_{991}$ | Xb$_{40}$ | M | $^1$H NMR (solvent) δ ppm |
|---|---|---|---|---|---|---|
| 2116 | 3,4-Cl$_2$Ph— | —H | benzyl | none | 0 | (DMSO-d$_6$) 2.41 (4H, brs), 3.34-3.51 (6H, m), 7.19 (1H, d, J=8.7Hz), 7.20 (2H, d, J=7.9Hz), 7.29-7.33 (5H, m), 7.45 (2H, d, J=7.9Hz), 7.81 (1H, d, J=8.3Hz), 7.91-7.96 (2H, m), 8.15 (1H, brs), 8.18 (1H, d, J=2.6Hz), 8.75 (1H, s). |
| 2117 | 3,4-Cl$_2$Ph— | —H | benzyl | none | 2 | (DMSO-d$_6$) 2.30 (4H, brs), 2.60-2.62 (2H, m), 2.79-2.85 (2H, m), 3.44-3.48 (6H, m), 7.05 (2H, d, J=8.4Hz), 7.09 (1H, d, J=8.7Hz), 7.25-7.36 (7H, m), 7.81 (1H, d, J=8.2Hz), 7.88-7.93 (2H, m), 8.13-8.14 (2H, m), 8.74 (1H, s). |
| 2118 | 4-CF$_3$Ph— | —H | benzyl | none | 0 | (CDCl$_3$) 2.47 (4H, brs), 3.55 (2H, brs), 3.55 (2H, s), 3.79 (2H, brs), 7.00 (1H, d, J=8.7Hz), 7.18 (2H, d, J=8.6Hz), 7.22-7.40 (5H, m), 7.47 (2H, d, J=8.6Hz), 7.67 (1H, dd, J=8.7Hz, 2.6Hz), 7.74 (2H, d, J=8.1Hz), 8.03 (2H, d, J=8.1Hz), 8.14 (1H, d, J=2.6Hz), 8.54 (1H, s). |
| 2119 | 4-CF$_3$Ph— | —H | piperonyl | —N(CH$_3$)— | 1 | (CDCl$_3$) 2.45 (4H, brs), 3.04 (3H, s), 3.45-3.51 (4H, m), 3.65 (2H, s), 4.09 (2H, s), 5.95 (2H, s) 6.71-6.74 (4H, m), 6.86-6.89 (2H, m), 7.04 (2H, d, J=9.1Hz), 7.61 (1H, dd, J=8.7Hz, 2.6Hz), 7.73 (2H, d, J=8.3Hz), 8.01 (2H, d, J=8.4Hz), 8.14 (1H, d, J=2.6Hz), 8.53 (1H, s). |
| 2120 | 4-CF$_3$Ph— | —F | benzyl | none | 0 | (CDCl$_3$) 2.49 (4H, brs), 3.43-3.75 (6H, m), 7.07 (1H, d, J=8.6Hz), 7.29-7.34 (8H, m), 7.69 (1H, dd, J=8.7Hz, 2.8Hz), 7.74 (2H, d, J=8.3Hz), 8.02 (2H, d, J=8.3Hz), 8.05 (1H, d, J=2.6Hz), 8.53 (1H, s). |
| 2121 | 3,4-Cl$_2$Ph— | —H | piperonyl | —N(CH$_3$)— | 2 | (CDCl$_3$) 2.34-2.41 (4H m), 2.55-2.61 (2H, m), 2.95 (3H, s), 3.41 (4H, brs) 3.61-3.65 (2H, m), 3.68-3.76 (2H, m), 5.94 (2H, s), 6.70-6.77 (4H, m), 6.84 (1H, d, J=1.0Hz), 6.89 (1H, dd, J=8.7Hz, 0.5Hz), 7.04 (2H, d, J=9.2Hz), 7.55 (1H, d, J=8.3Hz), 7.60 (1H, dd, J=8.7Hz, 2.8Hz), 7.71 (1H, dd J=8.3Hz, 2.0Hz), 8.01 (1H, d, J=1.8Hz), 8.11 (1H, dd, J=2.8Hz, 0.5Hz), 8.40 (1H, brs). |
| 2122 | 4-CF$_3$Ph— | —H | piperonyl | —N(CH$_3$)— | 2 | (CDCl$_3$) 2.34-2.41 (4H, m), 2.55-2.61 (2H, m), 2.95 (3H, s), 3.39-3.42 (4H, m), 3.61-3.64 (2H, m), 3.68-3.76 (2H, m), 5.94 (2H, s), 6.70-6.77 (4H, m), 6.84 (1H, d, J=0.8Hz), 6.90 (1H, dd, J=8.7Hz, 0.7Hz), 7.05 (2H, d, J=9.2Hz), 7.63 (1H, dd, J=8.7Hz, 2.8Hz), 7.73 (2H, d, J=8.3Hz), 8.01 (2H, d, J=8.6Hz), 8.13 (1H, dd, J=2.8Hz, 0.7Hz), 8.53 (1H, brs). |

TABLE 337

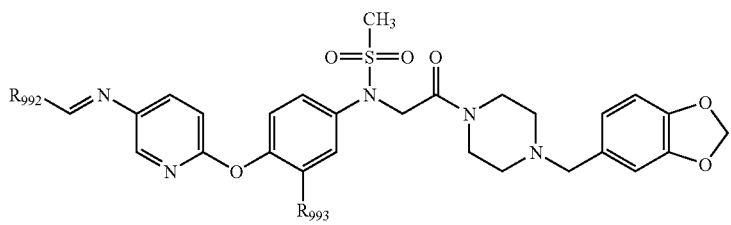

| Example No. | R_992 | R_993 | $^1$H NMR (CDCl$_3$) δ ppm |
|---|---|---|---|
| 2123 | 3,4-Cl$_2$Ph— | —H | 2.43 (4H, brs), 3.22 (3H, s), 3.38 (2H, brs), 3.43 (2H, s), 3.62 (2H, brs), 4.55 (2H, s), 5.95 (2H, s), 6.74 (2H, brs), 6.84 (1H, brs), 7.01 (1H, d, J=8.6Hz), 7.15 (2H, d, J=8.7Hz), 7.57 (1H, d, J=8.3Hz), 7.61-7.68 (3H, m), 7.72 (1H, dd, J=8.3Hz, 1.8Hz), 8.03 (1H, d, J=1.8Hz), 8.11 (1H, d, J=2.8Hz), 8.42 (1H, brs). |
| 2124 | 3,4-Cl$_2$Ph— | —CH$_3$ | 2.20 (3H, s), 2.42-2.43 (4H, m), 3.23 (3H, s), 3.38 (2H, brs), 3.43 (2H, s), 3.62 (2H, brs), 4.54 (2H, s), 5.94 (2H, s), 6.70-6.77 (2H, m), 6.84 (1H, brs), 6.97 (1H, dd, J=8.7Hz, 0.5Hz), 7.05 (1H, d, J=8.6Hz), 7.43-7.49 (2H, m), 7.55 (1H, d, J=8.2Hz), 7.62-7.66 (1H, m), 7.69-7.74 (1H, m), 8.01 (1H, d, J=2.0Hz), 8.07 (1H, d, J=2.1Hz), 8.40 (1H, brs). |
| 2125 | 4-CF$_3$Ph— | —CH$_3$ | 2.20 (3H, s), 2.41-2.43 (4H, m), 3.23 (3H, s), 3.38 (2H, brs), 3.43 (2H, s), 3.60 (2H, brs), 4.55 (2H, s), 5.95 (2H, s), 6.73-6.74 (2H, m), 6.84 (1H, brs), 6.98 (1H, d, J=8.7Hz), 7.05 (1H, d, J=8.4Hz), 7.43-7.49 (2H, m), 7.65-7.75 (3H, m), 8.00-8.10 (3H, m), 8.53 (1H, brs). |
| 2126 | 4-CF$_3$Ph— | —OCH$_3$ | 2.43 (4H, brs), 3.24 (3H, s), 3.39 (2H, brs), 3.43 (2H, s), 3.63 (2H, brs), 3.77 (3H, s), 4.57 (2H, s), 5.94 (2H, s), 6.73-6.77 (2H, m), 6.84 (1H, s), 7.02 (1H, d, J=8.6Hz), 7.13 (1H, d, J=8.4Hz), 7.22 (1H, dd, J=8.4Hz, 2.3Hz), 7.30 (1H, d, J=2.3Hz), 7.66 (1H, dd, J=8.7Hz, 2.8Hz), 7.73 (2H, d, J=8.1Hz), 8.01 (2H, d, J=8.1Hz), 8.08 (1H, d, J=2.5Hz), 8.53 (1H, s). |

TABLE 338

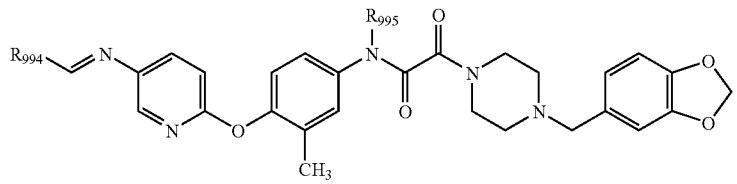

| Example No. | R_994 | R_995 | $^1$H NMR (solvent) δ ppm |
|---|---|---|---|
| 2127 | 3,4-Cl$_2$Ph— | —H | (CDCl$_3$) 2.20 (3H, s), 2.49-2.55 (4H, m), 3.45 (2H, s), 3.71-3.75 (2H, m), 4.25-4.29 (2H, m), 5.95 (2H, s), 6.75 (2H, brs), 6.86 (1H, brs), 6.92 (1H, d, J=8.6Hz), 7.06 (1H, d, J=8.6Hz), 7.44 (1H, dd, J=8.6Hz, 2.6Hz), 7.53-7.65 (3H, m), 7.70 (1H, dd, J=8.2Hz, 2.0Hz), 8.01 (1H, d, J=1.8Hz), 8.07 (1H, d, J=2.8Hz), 8.40 (1H, brs), 9.17 (1H, brs). |
| 2128 | 4-CF$_3$Ph— | —H | (CDCl$_3$) 2.20 (3H, s), 2.49-2.55 (4H, m), 3.45 (2H, s), 3.71-3.75 (2H, m), 4.25-4.28 (2H, m), 5.95 (2H, s), 6.75 (2H, brs), 6.86 (1H, brs), 6.93 (1H, d, J=8.7Hz), 7.07 (1H, d, J=8.7Hz), 7.45 (1H, dd, J=8.7Hz, 2.6Hz), 7.58 (1H, d, J=2.5Hz), 7.65 (1H, dd, J=8.6Hz, 2.6Hz), 7.73 (2H, d, J=8.2Hz), 8.01 (2H, d, J=8.1Hz), 8.10 (1H, d, J=2.8Hz), 8.53 (1H, s), 9.19 (1H, brs). |
| 2129 | 3,4-Cl$_2$Ph— | —CH$_3$ | a mixture of the rotational isomers (DMSO-d$_6$) 2.10-2.44 (7H, m), 3.16-3.57 (9H, m), 5.96-5.99 (2H, m), 6.67-6.89 (3H, m), 7.09-7.26 (3H, m), 7.29-7.38 (1H, m), 7.81 (1H, d, J=8.41Hz), 7.89-7.96 (2H, m), 8.10-8.15 (2H, m), 8.74 (1H, s). |
| 2130 | 4-CF$_3$Ph— | —CH$_3$ | a mixture of the rotational isomers (DMSO-d$_6$) 2.11-2.44 (7H, m), 3.18-3.57 (9H, m), 5.96-6.00 (2H, m), 6.67-6.90 (3H, m), 7.09-7.27 (3H, m), 7.29-7.38 (1H, m), 7.90 (2H, d, J=8.24Hz), 7.95-8.00 (1H, m), 8.11-8.16 (3H, m), 8.85 (1H, s). |

TABLE 339

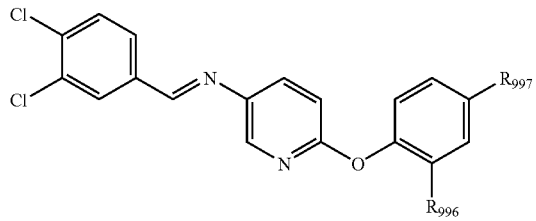

| Example No. | R996 | R997 | ¹H NMR (CDCl₃) δ ppm |
|---|---|---|---|
| 2131 | —H | ![piperazine-N-ethyl with COOC(CH₃)₃] | 1.46 (9H, s), 2.41-2.45 (4H, m), 3.43-3.47 (4H, m), 3.53 (2H, s), 6.96 (1H, d, J=8.7Hz), 7.08-7.14 (2H, m), 7.36 (2H, d, J=8.4Hz), 7.55 (1H, d, J=8.2Hz), 7.63 (1H, dd, J=8.7Hz, 2.6Hz), 7.71 (1H, dd, J=8.2Hz, 2.0Hz), 8.01 (1H, d, J=1.8Hz), 8.11-8.12 (1H, m), 8.41 (1H, s). |
| 2132 | —CH₃ | ![ethyl thiazolidinedione] | 2.19 (3H, s), 3.12 (1H, dd, J=14.0Hz, 9.9Hz), 3.55 (1H, dd, J=14.0Hz, 3.8Hz), 4.54 (1H, dd, J=9.9Hz, 3.8Hz), 6.95 (1H, d, J=8.7Hz), 7.04 (1H, d, J=8.1Hz), 7.12 (1H, dd, J=8.1Hz, 2.1Hz), 7.16 (1H, d, J=2.1Hz), 7.56 (1H, d, J=8.4Hz), 7.64 (1H, dd, J=8.7Hz, 2.3Hz), 7.71 (1H, dd, J=8.4Hz, 1.8Hz), 8.02 (1H, d, J=1.8Hz), 8.08 (1H, d, J=2.3Hz), 8.18 (1H, brs), 8.41 (1H, s). |

Example 2133

Production of 3-({4-[5-(3,4-dichlorobenzylamino)-pyridin-2-yloxy]phenyl}methylamino)-1-(4-piperonylpiperazin-1-yl)propane-1-one 3-[(4-{5-(3,4-dichlorobenzylidene)pyridin-2-yloxy}phenyl)methylamino]-1-(4-piperonylpiperazin-1-yl)propane-1-one (3.88 g, 6.0 mmol) was dissolved in a mixed solvent of methanol (150 mL) and THF (50 mL). To the resulting solution was slowly added sodium borohydride (1.13 g, 30.0 mmol) and that resulting solution was stirred for 13 hours at room temperature. This reaction solution was concentrated under reduced pressure. The resulting residue was diluted with ethyl acetate, and washed with a saturated sodium bicarbonate solution and brine. The organic layer was dried over anhydrous magnesium sulfate, and evaporated. The residue was then purified by silica gel column chromatography (dichloromethane:methanol=40:1), to thereby yield 3.60 g of the title compound.

Appearance: White powder
¹H NMR (CDCl₃) δ 2.32-2.39 (4H, m), 2.52-2.57 (2H, m), 2.91 (3H, s), 3.36-3.40 (4H, m), 3.59-3.63 (2H, m), 3.66-3.71 (2H, m), 3.97 (1H, brs), 4.27 (2H, d, J=5.0 Hz), 5.94 (2H, s), 6.65-6.76 (5H, m), 6.83 (1H, d, J=1.0 Hz), 6.94 (1H, dd, J=8.9 Hz, 3.0 Hz), 6.97 (2H, d, J=9.2 Hz), 7.18 (1H, dd, J=8.3 Hz, 2.0 Hz), 7.40 (1H, d, J=8.4 Hz), 7.45 (1H, d, J=2.0 Hz), 7.56 (1H, d, J=2.5 Hz); MS 647 (M⁺).

The following compounds were produced in the same manner as in Example 2133.

TABLE 340

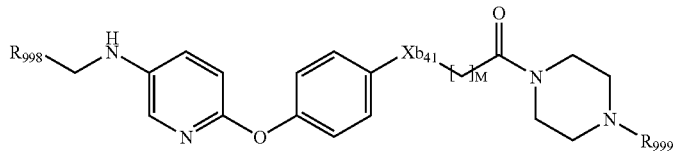

| Example No. | R998 | R999 | Xb41 | M | ¹H NMR (solvent) δ ppm |
|---|---|---|---|---|---|
| 2134 | 4-CF₃Ph— | piperonyl | —N(CH₃)— | 1 | (CDCl₃) 2.42 (4H, brs), 2.99 (3H, s), 3.43-3.49 (4H, m), 3.62 (2H, brs), 4.04 (2H, s), 4.37 (2H, s), 5.95 (2H, s), 6.67-6.75 (5H, m), 6.86 (1H, brs), 6.92-6.97 (3H, m), 7.47 (2H, d, J=7.9Hz), 7.58-7.61 (3H, m). |
| 2135 | 4-CF₃Ph— | piperonyl | —N(CH₃)— | 2 | (CDCl₃) 2.32-2.39 (4H, m), 2.52-2.57 (2H, m), 2.91 (3H, s), 3.36-3.39 (4H, m), 3.59-3.63 (2H, m), 3.66-3.71 (2H, m), 4.00 (1H, brs), 4.37 (2H, d, J=4.3Hz), 5.94 (2H, s), 6.66-6.76 (5H, m), 6.83 (1H, d, J=1.0Hz), 6.95 (1H, dd, J=8.9Hz, 3.0Hz), 6.97 (2H, d, J=9.1Hz), 7.46 (2H, d, J=8.1Hz), 7.57-7.61 (3H, m). |

TABLE 340-continued

| Example No. | R$_{998}$ | R$_{999}$ | Xb$_{41}$ | M | $^1$H NMR (solvent) δ ppm |
|---|---|---|---|---|---|
| 2136 | 3,4-Cl$_2$Ph— | piperonyl | —N(CH$_3$)— | 1 | (CDCl$_3$) 2.39-2.43 (4H, m), 2.99 (3H, s), 3.42 (2H, brs), 3.46-3.50 (2H, m), 3.60-3.62 (2H, m), 3.97 (1H, t, J=5.8Hz), 4.05 (2H, s), 4.26 (2H, d, J=5.8Hz), 5.95 (2H, s), 6.65-6.77 (5H, m), 6.85 (1H, brs), 6.93 (1H, dd, J=8.6Hz, 3.1Hz), 6.96 (2H, d, J=9.1Hz), 7.18 (1H, dd, J=8.3Hz, 2.1Hz), 7.40 (1H, d, J=8.3Hz), 7.45 (1H, d, J=2.1Hz), 7.57 (1H, d, J=2.8Hz) |
| 2137 | 3,4-Cl$_2$Ph— | benzyl | none | 2 | (DMSO-d$_6$) 2.26-2.28 (4H, m), 2.57 (2H, t, J=7.9Hz), 2.76 (2H, t, J=7.9Hz), 3.40-3.46 (6H, m), 4.28 (2H, d, J=5.9Hz), 6.36 (1H, t, J=6.1Hz), 6.77 (1H, d, J=8.7Hz), 6.85 (2H, d, J=8.3Hz), 7.09 (1H, dd, J=8.7Hz, 3.0Hz), 7.17 (2H, d, J=8.4Hz), 7.24-7.37 (6H, m), 7.50 (1H, d, J=3.0Hz), 7.58 (1H, d, J=8.3Hz), 7.62 (1H, d, J=1.8Hz). |
| 2138 | 3,4-Cl$_2$Ph— | benzyl | none | 0 | (DMSO-d$_6$) 2.38 (4H, brs), 3.33-3.50 (6H, m), 4.30 (2H, d, J=6.3Hz), 6.47 (1H, t, J=6.3Hz), 6.87 (1H, d, J=8.7Hz), 6.97 (2H, d, J=8.6Hz), 7.12 (1H, dd, J=8.7Hz, 3.0Hz), 7.25-7.39 (8H, m), 7.56 (1H, d, J=3.0Hz), 7.58-7.64 (2H, m). |
| 2139 | 4-CF$_3$Ph— | benzyl | none | 0 | (CDCl$_3$) 2.45 (4H, brs), 3.52 (2H, brs), 3.53 (2H, s), 3.73 (2H, brs), 4.16 (1H, brs), 4.41 (2H, s), 6.80 (1H, d, J=8.7Hz), 6.99 (1H, dd, J=8.7Hz, 3.0Hz), 7.03 (2H, d, J=8.5Hz), 7.20-7.37 (5H, m), 7.38 (2H, d, J=8.5Hz), 7.48 (2H, d, J=8.1Hz), 7.61 (2H, d, J=8.1Hz), 7.64 (1H, d, J=3.0 Hz). |

TABLE 341

| Example No. | R$_{1000}$ | R$_{1001}$ | $^1$H NMR (CDCl$_3$) δ ppm |
|---|---|---|---|
| 2140 | 3,4-Cl$_2$Ph— | —H | 2.41 (4H, brs), 3.19 (3H, s), 3.33-3.35 (2H, m), 3.42 (2H, s), 3.60 (2H, brs), 4.08 (1H, brs), 4.30 (2H, d, J=5.3Hz), 4.50 (2H, s), 5.95 (2H, s), 6.73-6.74 (2H, m), 6.80-6.84 (2H, m), 6.99 (1H, dd, J=8.6Hz, 3.1Hz), 7.02 (2H, d, J=8.7Hz), 7.20 (1H, dd, J=8.3Hz, 2.0Hz), 7.42 (1H, d, J=8.3Hz), 7.66 (1H, d, J=2.1Hz), 7.54 (2H, d, J=8.9Hz), 7.60 (1H, d, J=2.8Hz). |
| 2141 | 3,4-Cl$_2$Ph— | —CH$_3$ | 2.19 (3H, s), 2.41 (4H, brs), 3.19 (3H, s), 3.35 (2H, brs), 3.41 (2H, s), 3.60 (2H, brs), 4.07-4.15 (1H, m), 4.27 (2H, s), 4.50 (2H, s), 5.93 (2H, s), 6.69-6.78 (3H, m), 6.83 (1H, brs), 6.88 (1H, d, J=8.6Hz), 6.98 (1H, dd, J=8.7Hz, 3.0Hz), 7.17-7.20 (1H, m), 7.34-7.44 (4H, m), 7.53 (1H, d, J=3.0Hz). |
| 2142 | 4-CF$_3$Ph— | —CH$_3$ | 2.20 (3H, s), 2.41 (4H, brs), 3.19 (3H, s), 3.35-3.37 (2H, m), 3.41 (2H, s), 3.60-3.62 (2H, m), 4.15 (1H, brs), 4.38 (2H, s), 4.50 (2H, s), 5.94 (2H, s), 6.73 (2H, brs), 6.76 (1H, d, J=8.7Hz), 6.83 (1H, brs), 6.88 (1H, d, J=8.6Hz), 7.00 (1H, dd, J= |

TABLE 341-continued

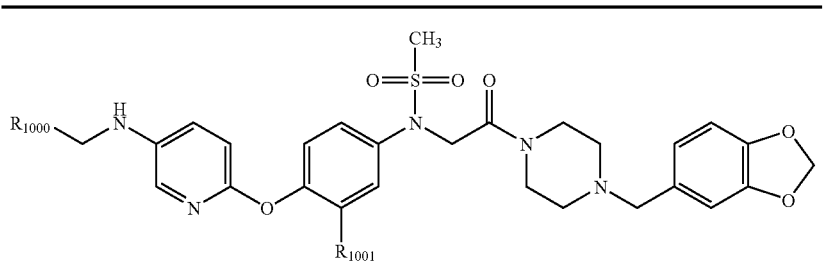

| Example No. | $R_{1000}$ | $R_{1001}$ | $^1$H NMR (CDCl$_3$) δ ppm |
|---|---|---|---|
|  |  |  | 8.7Hz, 3.0Hz), 7.36 (1H, dd, J=8.6Hz, 2.6Hz), 7.42 (1H, d, J=2.5Hz), 7.47 (2H, d, J=8.1Hz), 7.56 (1H, d, J=2.8Hz), 7.59 (2H, d, J=8.1Hz). |
| 2143 | 4-CF$_3$Ph— | —OCH$_3$ | 2.41 (4H, brs), 3.21 (3H, s), 3.36 (2H, brs), 3.42 (2H, s), 3.60 (2H, brs), 3.76 (3H, s), 4.09 (1H, brs), 4.37 (2H, s), 4.52 (2H, s), 5.94 (2H, s), 6.70-6.83 (4H, m), 6.97-7.02 (2H, m), 7.12-7.16 (1H, m), 7.23-7.26 (1H, m), 7.44-7.60 (5H, m). |

TABLE 342

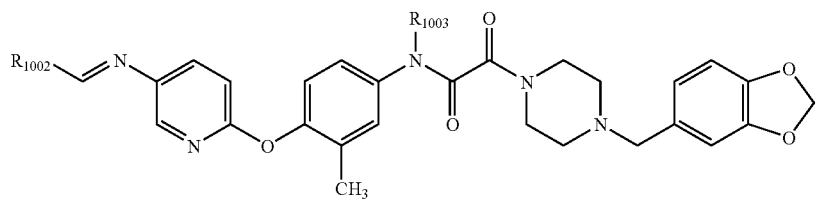

| Example No. | $R_{1002}$ | $R_{1003}$ | $^1$H NMR (solvent) δ ppm |
|---|---|---|---|
| 2144 | 3,4-Cl$_2$Ph— | —H | (CDCl$_3$) 2.17 (3H, s), 2.48-2.53 (4H, m), 3.44 (2H, s), 3.69-3.73 (2H, m), 3.97 (1H, brs), 4.23-4.27 (4H, m), 5.95 (2H, s), 6.70-6.74 (3H, m), 6.85 (1H, brs), 6.94 (1H, d, J=8.7Hz), 6.96 (1H, dd, J=8.7Hz, 3.1Hz), 7.18 (1H, dd, J=8.2Hz, 2.0Hz), 7.36 (1H, dd, J=8.7Hz, 2.5Hz), 7.40 (1H, d, J=8.2Hz), 7.45 (1H, d, J=2.1Hz), 7.51 (1H, d, J=2.3Hz), 7.55 (1H, d, J=3.0Hz), 9.11 (1H, brs). |
| 2145 | 4-CF$_3$Ph— | —H | (CDCl$_3$) 2.19 (3H, s), 2.48-2.53 (4H, m), 3.44 (2H, s), 3.70-3.73 (2H, m), 4.00 (1H, brs), 4.23-4.27 (2H, m), 4.37 (2H, s), 5.95 (2H, s), 6.72 (1H, d, J=8.7Hz), 6.74-6.77 (2H, m), 6.85 (1H, brs), 6.94 (1H, d, J=8.7Hz), 6.97 (1H, dd, J=8.7Hz, 3.1Hz), 7.37 (1H, dd, J=8.7Hz, 2.6Hz), 7.47 (2H, d, J=8.4Hz), 7.51 (1H, d, J=2.5Hz), 7.57 (1H, d, J=3.1Hz), 7.60 (2H, d, J=8.1Hz), 9.11 (1H, brs). |
| 2146 | 3,4-Cl$_2$Ph— | —CH$_3$ | a mixture of the rotational isomers (DMSO-d$_6$) 2.25-2.42 (7H, m), 3.22-3.55 (9H, m), 4.27 (2H, d, J=6.27Hz), 5.77-5.99 (2H, m), 6.38 (1H, t, J=6.27Hz), 6.65-6.90 (5H, m), 7.06-7.14 (2H, m), 7.22-7.28 (1H, m), 7.32-7.36 (1H, m), 7.46 (1H, d, J=2.80Hz), 7.56-7.61 (2H, m). |
| 2147 | 4-CF$_3$Ph— | —CH$_3$ | a mixture of the rotational isomers (DMSO-d$_6$) 2.24-2.41 (7H, m), 3.20-3.54 (9H, m), 4.34-4.36 (2H, m), 5.95-5.98 (2H, m), 6.38-6.41 (1H, m), 6.65-6.88 (5H, m), 7.03-7.13 (2H, m), 7.21-7.27 (1H, m), 7.45 (1H, d, J=2.64Hz), 7.55 (2H, d, J=7.75Hz), 7.67 (2H, d, J=7.75Hz). |

TABLE 343

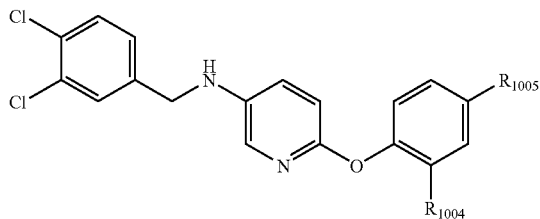

| Example No. | $R_{1004}$ | $R_{1005}$ | $^1$H NMR (CDCl$_3$) δ ppm |
|---|---|---|---|
| 2148 | —H | ![piperazine-CH2CH3, N-COOC(CH3)3] | 1.45 (9H, s), 2.37-2.40 (4H, m), 3.40-3.44 (4H, m), 3.47 (2H, s), 4.28 (2H, s), 6.77 (1H, d, J=8.7Hz), 6.95-7.01 (3H, m), 7.17-7.21 (1H, m), 7.26-7.29 (2H, m), 7.41 (1H, d, J=8.1Hz), 7.45 (1H, d, J=1.8Hz), 7.60 (1H, d, J=3.0 Hz). |
| 2149 | —CH$_3$ | ![ethyl-thiazolidinedione] | 2.19 (3H, s), 3.05 (1H, dd, J=14.0Hz, 10.0Hz), 3.50 (1H, dd, J=14.0Hz, 3.8Hz), 4.02 (1H, brs), 4.27 (2H, s), 4.49 (1H, dd, J=10.0Hz, 3.8Hz), 6.73 (1H, d, J=8.7Hz), 6.99 (1H, d, J=8.2Hz), 6.97 (1H, dd, J=8.7Hz, 2.9Hz), 7.02 (1H, dd, J=8.2Hz, 2.0Hz), 7.09 (1H, d, J=2.0Hz), 7.18 (1H, dd, J=8.2Hz, 2.0Hz), 7.41 (1H, d, J=8.2Hz), 7.45 (1H, d, J=2.0Hz), 7.55 (1H, d, J=2.9Hz), 8.61 (1H, brs). |

Example 2150

Production of 1-(4-benzylpiperazin-1-yl)-3-(4-{5-(piperonylamino)pyridin-2-yloxy}phenyl)propane-1-one 3-[4-(5-aminopyridin-2-yloxy)phenyl]-1-(4-piperonylpiperazin-1-yl)propane-1-one (1.04 g, 2.5 mmol) was dissolved in methanol (25 mL). To the resulting solution was added piperonal (0.39 g, 2.63 mmol), and this solution was refluxed overnight. The resulting reaction solution was cooled with ice, and then sodium borohydride (0.28 g, 7.50 mmol) was added. The resulting solution was stirred for 2 hours at room temperature. This reaction solution was concentrated under reduced pressure. The residue was diluted with ethyl acetate, and washed with water, saturated sodium bicarbonate solution and brine. The organic layer was dried over anhydrous magnesium sulfate, and evaporated. The residue was then purified by silica gel column chromatography (ethyl acetate), to thereby yield 0.80 g of the title compound.

Appearance: Yellow oil $^1$H NMR (DMSO-d$_6$) δ 2.28 (4H, brs), 2.57 (2H, t, J=7.9 Hz), 2.76 (2H, t, J=7.9 Hz), 3.40-3.46 (6H, m), 4.15 (2H, d, J=6.1 Hz), 5.97 (2H, s), 6.21 (1H, t, J=6.1 Hz), 6.76 (1H, d, J=8.6 Hz), 6.82-6.86 (4H, m), 6.92 (1H, brs), 7.08 (1H, dd, J=8.7 Hz, 3.0Hz), 7.17 (2H, d, J=8.4 Hz), 7.24-7.32 (5H, m), 7.51 (1H, d, J=3.0 Hz).

The following compounds were produced in the same manner as in Example 2150.

TABLE 344

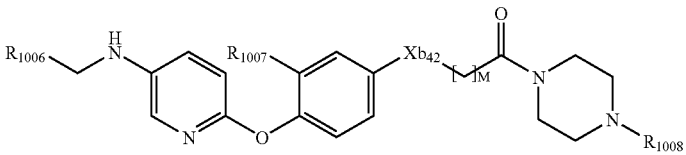

| Example No. | $R_{1006}$ | $R_{1007}$ | $R_{1008}$ | $Xb_{42}$ | M | $^1$H NMR (solvent) δ ppm |
|---|---|---|---|---|---|---|
| 2151 | 4-CF$_3$Ph— | —CH$_3$ | piperonyl | —N(C$_2$H$_5$)— | 1 | (CDCl$_3$) 1.15 (3H, t, J=7.1Hz), 2.11 (3H, s), 2.30-2.50 (4H, m), 3.39 (2H, q, J=7.1Hz), 3.42 (2H, s), 3.42-3.55 (2H, m), 3.56-3.70 (2H, m), 3.80-4.05 (1H, m), 3.99 (2H, s), 4.36 (2H, s), 5.94 (2H, s), 6.44-6.55 (2H, m), 6.58-6.64 (1H, m), 6.69-6.78 (2H, m), 6.80-6.89 (2H, m), 6.94 (1H, dd, J=8.8Hz, 3.1Hz), 7.46 (2H, d, J=8.0Hz), 7.55-7.63 (3H, m). |
| 2152 | 3,4-Cl$_2$Ph— | —CH$_3$ | piperonyl | —N(C$_2$H$_5$)— | 1 | (CDCl$_3$) 1.15 (3H, t, J=7.1Hz), 2.11 (3H, s), 2.32-2.49 (4H, m), 3.39 (2H, q, J=7.1Hz), 3.42 (2H, s), 3.44-3.55 (2H, m), 3.56-3.69 (2H, m), |

TABLE 344-continued

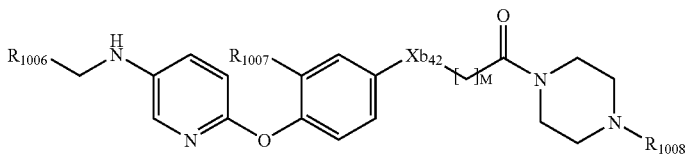

| Example No. | $R_{1006}$ | $R_{1007}$ | $R_{1008}$ | $Xb_{42}$ | M | $^1$H NMR (solvent) δ ppm |
|---|---|---|---|---|---|---|
| | | | | | | 3.79-3.94 (1H, m), 3.99 (2H, s), 4.15-4.30 (2H, m), 5.94 (2H, s), 6.50 (1H, dd, J=8.5Hz, 3.0Hz), 6.54 (1H, d, J=3.0Hz), 6.58-6.65 (1H, m), 6.69-6.78 (2H, m), 6.82-6.88 (2H, m), 6.92 (1H, dd, J=8.8Hz, 3.0Hz), 7.18 (1H, dd, J=8.2Hz, 2.0Hz), 7.40 (1H, d, J=8.2Hz), 7.45 (1H, d, J=2.0Hz), 7.57 (1H, d, J=3.0 Hz). |
| 2153 | 4-CF$_3$Ph— | —H | benzyl | none | 2 | (DMSO-d$_6$) 2.28 (4H, brs), 2.54-2.60 (2H, m), 2.73-2.79 (2H, m), 3.42-3.46 (6H, m), 4.37 (2H, d, J=5.9Hz), 6.41 (1H, t, J=6.1Hz), 6.77 (1H, d, J=8.7Hz), 6.84 (2H, d, J=8.6Hz), 7.08 (1H, dd, J=8.7Hz, 3.0Hz), 7.17 (2H, d, J=8.6Hz), 7.22-7.35 (5H, m), 7.50 (1H, d, J=3.0Hz), 7.58 (2H, d, J=7.9Hz), 7.69 (2H, d, J=7.9Hz). |
| 2154 | 4-ClPh— | —H | benzyl | none | 2 | (DMSO-d$_6$) 2.28 (4H, t, J=4.8Hz), 2.57 (2H, t, J=7.3Hz), 2.76 (2H, t, J=7.3Hz), 3.38-3.46 (6H, m), 4.25 (2H, d, J=6.1Hz), 6.32 (1H, t, J=6.1Hz), 6.76(1H, d, J=8.6Hz), 6.84 (2H, d, J=8.6Hz), 7.07 (1H, dd, J=8.7Hz, 3.1Hz), 7.17 (2H, d, J=8.6Hz), 7.24-7.32 (5H, m), 7.38 (4H, brs), 7.50 (1H, d, J=3.1Hz). |
| 2155 | 3,4-F$_2$Ph— | —H | benzyl | none | 2 | (DMSO-d$_6$) 2.26-2.28 (4H, m), 2.57-2.60 (2H, m), 2.73-2.79 (2H, m), 3.37-3.46 (6H, m), 4.25 (2H, d, J=5.8Hz), 6.32 (1H, t, J=5.8Hz), 6.77 (1H, d, J=8.6Hz), 6.84 (2H, d, J=8.3Hz), 7.08 (1H, dd, J=8.6Hz, 3.0Hz), 7.17 (2H, d, J=8.4Hz), 7.22-7.43 (8H, m), 7.50 (1H, d, J=3.1Hz). |

TABLE 345

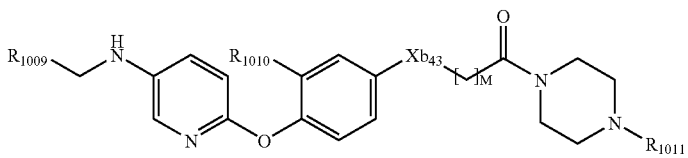

| Example No. | $R_{1009}$ | $R_{1010}$ | $R_{1011}$ | $Xb_{43}$ | M | mp (° C.) or $^1$H NMR (solvent) δ ppm |
|---|---|---|---|---|---|---|
| 2156 | 4-CF$_3$Ph— | —CH$_3$ | piperonyl | —N(CH$_3$)— | 1 | $^1$H NMR (CDCl$_3$) 2.12 (3H, s), 2.42 (4H, t, J=5.0Hz), 2.98 (3H, s), 3.41-3.55 (4H, m), 3.56-3.67 (2H, m), 3.77-3.99 (1H, m), 4.04 (2H, s), 4.36 (2H, s), 5.94 (2H, s), 6.52 (1H, dd, J=8.7Hz, 3.0Hz), 6.56 (1H, d, J=3.0Hz), 6.59-6.64 (1H, m), 6.69-6.78 (2H, m), 6.85 (1H, s) 6.87 (1H, d, J=8.7Hz, 6.93 (1H, dd, J=8.8Hz, 3.0Hz), 7.46 (2H, d, J=8.0Hz), 7.54-7.63 (3H, m). |
| 2157 | 3,4-Cl$_2$Ph— | —CH$_3$ | piperonyl | —N(CH$_3$)— | 1 | mp 132-134 |
| 2158 | 4-CF$_3$Ph— | —CH$_3$ | piperonyl | —N(Ac)— | 1 | $^1$HNMR (CDCl$_3$) 1.94 (3H, s), 2.09 (3H, s), 2.30-2.50 (4H, m), 3.29-3.51 (4H, m), 3.52-3.69 (2H, |

TABLE 345-continued

![Structure: R1009-CH2-NH-pyridine(R1010)-O-phenyl-Xb43-(CH2)M-C(O)-N-piperazine-N-R1011]

| Example No. | R1009 | R1010 | R1011 | Xb43 | M | mp (° C.) or ¹H NMR (solvent) δ ppm |
|---|---|---|---|---|---|---|
| | | | | | | m), 3.92-4.17 (1H, m), 4.29-4.51 (4H, m), 5.94 (2H, s), 6.69-6.77 (2H, m), 6.78 (1H, d, J=8.7Hz), 6.81-6.86 (1H, m), 6.91 (1H, d, J=8.5Hz), 7.01 (1H, dd, J=8.7Hz, 3.1Hz), 7.18 (1H, dd, J=8.5Hz, 2.5Hz), 7.28 (1H, d, J=2.5Hz), 7.48 (2H, d, J=8.1Hz), 7.56-7.64 (3H, m). |
| 2159 | 3,4-Cl₂Ph— | —CH₃ | piperonyl | —N(Ac)— | 1 | ¹HNMR (CDCl₃) 1.95 (3H, s), 2.07 (3H, s), 2.30-2.51 (4H, m), 3.29-3.50 (4H, m), 3.51-3.71 (2H, m), 3.92-4.18 (1H, m), 4.29 (2H, s), 4.42 (2H, s), 5.94 (2H, s), 6.69-6.78 (3H, m), 6.82-6.87 (1H, m), 6.91 (1H, d, J=8.5Hz), 7.00 (1H, dd, J=8.7Hz, 3.0Hz), 7.14-7.23 (2H, m), 7.26-7.31 (1H, m), 7.41 (1H, d, J=8.2Hz), 7.46 (1H, d, J=2.0Hz), 7.57 (1H, d, J=3.0 Hz). |
| 2160 | Ph— | —H | benzyl | none | 2 | ¹HNMR (DMSO-d₆) 2.27 (4H, brs), 2.54-2.60 (2H, m), 2.73-2.79 (2H, m), 3.40-3.46 (6H, m), 4.25 (2H, d, J=5.9Hz), 6.28 (1H, J=5.9Hz), 6.76 (1H, d, J=8.7Hz), 6.84 (2H, d, J=8.4Hz), 7.09 (1H, dd, J=8.7Hz, 3.0Hz), 7.17 (2H, d, J=8.7Hz), 7.23-7.38 (10H, m), 7.52 (1H, d, J=3.0Hz). |
| 2161 | 4-CF₃Ph— | —OCH₃ | piperonyl | —N(CH₃)— | 1 | mp 102-103 |
| 2162 | 3,4-Cl₂Ph— | —OCH₃ | piperonyl | —N(CH₃)— | 1 | mp 145-146 |
| 2163 | 4-CF₃Ph— | —OCH₃ | piperonyl | —N(C₂H₅)— | 1 | mp 160.0-160.5 |
| 2164 | 3,4-Cl₂Ph— | —OCH₃ | piperonyl | —N(C₂H₅)— | 1 | mp 133-134 |
| 2165 | 3,4-Cl₂Ph— | —F | piperonyl | —N(CH₃)— | 1 | mp 134-137 |

TABLE 346

![Structure: R1012-CH2-NH-pyridine(R1013)-O-phenyl-Xb44-(CH2)M-C(O)-N-piperazine-N-CH2-benzodioxole]

| Example No. | R1012 | R1013 | Xb44 | M | mp (° C.) or ¹H NMR (CDCl₃) δ ppm |
|---|---|---|---|---|---|
| 2166 | 4-CF₃Ph— | —OCH₃ | none | 2 | ¹H NMR 2.38-2.44(4H, m), 2.56-2.67(2H, m), 2.88-2.99(2H, m), 3.31-3.45(2H, m), 3.40(2H, s), 3.57-3.69(2H, m), 3.76(3H, s), 3.80-4.06(1H, m), 4.37(2H, s), 5.94(2H, s), 6.68-6.81(4H, m), 6.83-6.87(2H, m), 6.96(1H, d, J=8.0Hz), 6.98(1H, dd, J=8.7Hz, 3.0Hz), 7.46(2H, d, J=8.0Hz), 7.54(1H, d, J=2.6Hz), 7.59(2H, d, J=8.0Hz). |
| 2167 | 4-CF₃Ph— | —F | —N(C₂H₅)— | 1 | mp 106-107 |
| 2168 | 4-CF₃Ph— | —F | —N(CH₃)— | 1 | mp 163-164 |
| 2169 | 3,4-Cl₂Ph— | —F | —N(C₂H₅)— | 1 | mp 107.5-109.0 |
| 2170 | 4-CF₃Ph— | —H | —N(SO₂CH₃)— | 1 | ¹H NMR 2.41(4H, brs), 3.18(3H, s), 3.35(2H, brs), 3.42(2H, s), 3.62(2H, brs), 4.14(1H, brs), 4.41(2H, s), 4.50(2H, s), 5.94(2H, s), 6.70-6.76(2H, m), 6.80-6.83(2H, m), 6.98-7.04(3H, m), 7.47-7.56(4H, m), 7.60-7.63(3H, m). |

Example 2171

Production of 1-(4-benzylpiperazin-1-yl)-3-[4-(5-dibenzylaminopyridin-2-yloxy)phenyl]propane-1-one 3-[4-(5-aminopyridin-2-yloxy)phenyl]-1-(4-benzylpiperazin-1-yl)propane-1-one (1.0 g, 2.4 mmol) was dissolved in DMF (30 mL). To this solution were added potassium carbonate (0.73 g, 5.28 mmol), sodium iodide (0.76 g, 5.04 mmol) and benzyl bromide (0.60 mL, 5.04 mmol), and the resulting solution was stirred at room temperature overnight. This reaction solution was concentrated under reduced pressure. The residue was diluted with chloroform, and washed with water, saturated sodium bicarbonate solution and brine. The organic layer was dried over anhydrous magnesium sulfate, and evaporated. The residue was then purified by silica gel column chromatography (chloroform methanol=80:1), to thereby yield 0.67 g of the title compound.

Appearance: Yellow oil $^1$H NMR (DMSO-d$_6$) δ 2.27 (4H, brs), 2.50-2.59 (2H, m), 2.73-2.78 (2H, m), 3.37-3.45 (6H, m), 4.68 (4H, s), 6.78 (1H, d, J=8.9 Hz), 6.85 (2H, d, J=8.4 Hz), 7.17 (2H, d, J=8.6 Hz), 7.20-7.36 (16H, m), 7.54 (1H, d, J=3.1 Hz).

Example 2172

Production of 2-[(4-{5-[(3,4-dichlorobenzyl)-ethylamino]pyridin-2-yloxy}phenyl)methylamino]-1-(4-piperonylpiperazin-1-yl)ethanone 2-({4-[5-(3,4-dichlorobenzylamino)pyridin-2-yloxy]phenyl}methylamino)-1-(4-piperonylpiperazin-1-yl)ethanone (1.59 g, 2.5 mmol) was dissolved in dichloroethane (80 mL). To this solution were added acetoaldehyde (1.40 mL, 25.0 mmol) and sodium triacetyloxy borohydride (1.59 mL, 7.5 mmol) under ice cooling. To the resulting solution was added dropwise acetic acid (0.43 mL, 7.5 mmol), and this solution was stirred at room temperature for 16 hours. The resulting reaction solution was washed with a saturated sodium bicarbonate solution and brine. The organic layer was dried over anhydrous magnesium sulfate, and evaporated. The residue was then purified by silica gel column chromatography (chloroform:methanol=50:1). The obtained solid was recrystallized from ethanol, to thereby yield 0.65 g of the title compound.

Appearance: White powder $^1$H NMR (CDCl$_3$) δ 1.17 (3H, t, J=7.1 Hz), 2.41 (4H, brs), 2.99 (3H, s), 3.36-3.44 (4H, m), 3.48 (2H, brs), 3.62 (2H, brs), 4.04 (2H, s), 4.35 (2H, s), 5.95 (2H, s), 6.67-6.77 (5H, m), 6.85 (1H, brs), 6.97 (2H, d, J=9.1 Hz), 7.01 (1H, dd, J=8.9 Hz, 3.1 Hz), 7.07 (1H, dd, J=8.2 Hz, 2.0 Hz), 7.32 (1H, d, J=2.0 Hz), 7.37 (1H, d, J=8.3 Hz), 7.63 (1H, d, J=3.0 Hz); MS 661 (M$^+$).

The following compounds were produced in the same manner as in Example 2172.

TABLE 347

| Example No. | R$_{1014}$ | R$_{1015}$ | R$_{1016}$ | Xb$_{45}$ | M | $^1$H NMR (CDCl$_3$) δppm |
|---|---|---|---|---|---|---|
| 2173 | 4-CF$_3$Ph— | —H | piperonyl | —N(CH$_3$)— | 1 | 2.44(4H, brs), 2.99(6H, s), 3.39-3.62(6H, m), 4.04(2H, s), 4.48(2H, s), 5.95(2H, s), 6.62-6.78(5H, m), 6.86(1H, brs), 6.97(2H, d, J=9.1Hz), 7.08(1H, dd, J=8.9Hz, 3.1Hz), 7.34(2H, d, J=7.9Hz), 7.57(2H, d, J=8.1Hz), 7.69(1H, d, J=3.1Hz). |
| 2174 | 3,4-Cl$_2$Ph— | —H | piperonyl | —N(CH$_3$)— | 2 | 2.32-2.40(4H, m,) 2.53-2.58(2H, m), 2.92(3H, s), 2.97(3H, s), 3.37-3.40(4H, m), 3.59-3.63(2H, m), 3.66-3.72(2H, m), 4.37(2H, s), 5.94(2H, s), 6.66-6.76(5H, m), 6.83(1H, d, J=1.0Hz), 6.98(2H, d, J=9.1Hz), 7.04-7.11(2H, m), 7.32(1H, d, J=2.0Hz), 7.38(1H, d, J=8.3Hz), 7.67(1H, d, J=3.1Hz). |
| 2175 | 4-CF$_3$Ph— | —H | piperonyl | —N(CH$_3$)— | 2 | 2.32-2.39(4H, m), 2.52-2.57(2H, m), 2.92(3H, s), 2.99(3H, s), 3.36-3.40(4H, m), 3.59-3.63(2H, m) 3.66-3.72(2H, m), 4.48(2H, s), 5.94(2H, s), 6.67-6.76(5H, m), 6.83(1H, d, J=1.0Hz), 6.98(2H, d, J=9.2Hz), 7.09(1H, dd, J=9.1Hz, 3.1Hz), 7.34(2H, d, J=7.9Hz), 7.57(2H, d, J=8.1Hz), 7.68(1H, d, J=2.8Hz). |

TABLE 347-continued

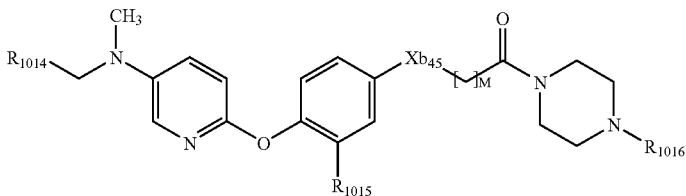

| Example No. | $R_{1014}$ | $R_{1015}$ | $R_{1016}$ | $Xb_{45}$ | M | $^1$H NMR (CDCl$_3$) δppm |
|---|---|---|---|---|---|---|
| 2176 | 3,4-Cl$_2$Ph— | —H | piperonyl | —N(CH$_3$)— | 1 | 2.40-2.44(4H, m), 2.96(3H, s), 3.00(3H, s), 3.43(2H, brs), 3.49(2H, brs), 3.62(2H, brs), 4.05(2H, s), 4.36(2H, s), 5.95(2H, s), 6.67-6.77(5H, m), 6.85(1H, brs), 6.97(2H, d, J=9.1Hz), 7.06(1H, dd, J=8.3Hz, 1.7Hz), 7.07(1H, dd, J=8.9Hz, 3.1Hz), 7.32(1H, d, J=2.0Hz), 7.38(1H, d, J=8.3Hz), 7.69(1H, d, J=3.1Hz). |
| 2177 | 4-CF$_3$Ph— | —F | benzyl | none | 0 | 2.46(4H, brs), 3.02(3H, s), 3.54(6H, brs), 4.52(2H, s), 6.89(1H, d, J=8.9Hz), 7.14(1H, dd, J=8.9Hz, 3.1Hz), 7.17-7.21(2H, m), 7.28-7.35(8H, m), 7.58(2H, d, J=8.1Hz), 7.62(1H, d, J=2.8Hz). |
| 2178 | 3,4-Cl$_2$Ph— | —F | benzyl | none | 0 | 2.47(4H, brs), 3.00(3H, s), 3.55-3.73(6H, m), 4.40(2H, s), 6.89(1H, d, J=8.9Hz), 7.06(1H, dd, J=8.2Hz, 1.7 Hz), 7.14(1H, dd, J=8.9Hz, 3.1Hz), 7.17-7.22(3H, m), 7.28-7.33(6H, m), 7.39(1H, d, J=8.3Hz), 7.61(1H, d, J=3.3Hz). |

TABLE 348

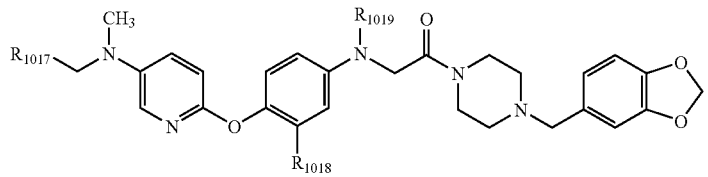

| Example No. | $R_{1017}$ | $R_{1018}$ | $R_{1019}$ | Form | mp (° C.) or $^1$H NMR (DMSO-d$_6$) δppm |
|---|---|---|---|---|---|
| 2179 | 4-CF$_3$Ph— | —CH$_3$ | —C$_2$H$_5$ | fumarate | mp 157-159 dec |
| 2180 | 3,4-Cl$_2$Ph— | —CH$_3$ | —C$_2$H$_5$ | fumarate | mp 148-151 dec |
| 2181 | 4-CF$_3$Ph— | —CH$_3$ | —CH$_3$ | fumarate | mp 151-154 |
| 2182 | 3,4-Cl$_2$Ph— | —CH$_3$ | —CH$_3$ | hydrochloride | mp 139-142 |
| 2183 | 4-CF$_3$Ph— | —CH$_3$ | —Ac | hydrochloride | mp 199.5-201.5 |
| 2184 | 3,4-Cl$_2$Ph— | —CH$_3$ | —Ac | hydrochloride | mp 188.5-190.0 |
| 2185 | 4-CF$_3$Ph— | —OCH$_3$ | —CH$_3$ | oxalate | $^1$H NMR 2.48-2.81(4H, m), 2.93(3H, s), 2.94(3H, s), 3.36-3.85(9H, m), 4.25(2H, s), 4.56(2H, s), 6.01(2H, s), 6.12(1H, dd, J=8.8Hz, 2.8Hz), 6.29(1H, d, J=2.8Hz), 6.66(1H, d, J=9.0Hz), 6.77(1H, d, J=8.8Hz), 6.79-6.98(3H, m), 7.22(1H, dd, J=9.0Hz, 3.2 Hz), 7.42(2H, d, J=8.1Hz), 7.52(1H, d, J=3.2Hz), 7.67(2H, d, J=8.1Hz). |
| 2186 | 3,4-Cl$_2$Ph— | —OCH$_3$ | —CH$_3$ | hydrochloride | $^1$H NMR 2.75-3.18(8H, m), 3.21-3.42(2H, m), 3.63(3H, s), 3.83-4.52(10H, m), 6.06(2H, s), 6.16(1H, dd, J=8.8Hz, 2.7Hz), 6.34(1H, d, J=2.7Hz), 6.68(1H, d, J=9.0Hz), 6.79(1H, d, J=8.8Hz), 6.94-7.06(2H, m), 7.16-7.24(2H, m), 7.27(1H, dd, J=9.0Hz, 3.2Hz), 7.47(1H, d, |

TABLE 348-continued

| Example No. | $R_{1017}$ | $R_{1018}$ | $R_{1019}$ | Form | mp (° C.) or $^1$H NMR (DMSO-$d_6$) δppm |
|---|---|---|---|---|---|
| | | | | | J=2.0Hz), 7.53(1H, d, J=3.2Hz), 7.56(1H, d, J=8.2Hz), 10.91-11.26(1H, m). |
| 2187 | 4-CF$_3$Ph— | —OCH$_3$ | —C$_2$H$_5$ | fumarate | mp 159-162 |
| 2188 | 3,4-Cl$_2$Ph— | —OCH$_3$ | —C$_2$H$_5$ | fumarate | mp 154-157 |
| 2189 | 4-CF$_3$Ph— | —F | —CH$_3$ | hydrobromide | mp 211-212 |
| 2190 | 3,4-Cl$_2$Ph— | —F | —CH$_3$ | hydrobromide | mp 206.5-207.0 |
| 2191 | 4-CF$_3$Ph— | —F | —C$_2$H$_5$ | hydrobromide | mp 151.0-152.5 |
| 2192 | 3,4-Cl$_2$Ph— | —F | —C$_2$H$_5$ | hydrobromide | mp 172.5-174.5 |

TABLE 349

| Example No. | $R_{1020}$ | $R_{1021}$ | $R_{1022}$ | M | Form | $^1$H NMR (DMSO-$d_6$) δppm |
|---|---|---|---|---|---|---|
| 2193 | Ph— | —CH$_3$ | —H | 2 | dihydro-chloride | 2.50-3.07(10H, m), 3.22-3.31(2H, m), 3.45-3.50(1H, m), 4.03-4.08(1H, m), 4.30(2H, d, J=3.8Hz), 4.42-4.55(3H, m), 6.85-6.92(3H, m), 7.19-7.26(5H, m), 7.30-7.35(3H m), 7.45-7.47(3H, m), 7.58-7.60(2H, m), 7.66(1H, d, J=2.8Hz), 11.33(2H, brs). |
| 2194 | 3,4-Cl$_2$Ph— | —CH$_3$ | —H | 0 | dihydro-chloride | 2.50-2.51(2H, m), 3.03(3H, s), 3.13-3.48(6H, m), 4.34-4.37(2H, m), 4.58(2H, s), 6.97(1H, d, J=8.9Hz), 7.04(2H, d, J=8.4Hz), 7.23(1H, dd, J=8.4Hz, 1.5Hz), 7.34(1H, dd, J=8.9Hz, 3.1Hz), 7.44-7.47(5H, m), 7.51(1H, d, J=1.5Hz), 7.58-7.61(3H, m), 7.70(1H, d, J=3.3Hz), 11.52(2H, brs). |
| 2195 | 4-CF$_3$Ph— | —CH$_3$ | —H | 0 | dihydro-chloride | 3.06(3H, s), 3.00-3.20(2H, m), 3.20-3.40(2H, m), 3.45(2H, brs), 4.20-4.50(2H, m), 4.34(2H, s), 4.69(2H, s), 6.97(1H, d, J=8.9Hz), 7.04(2H, d, J=8.8Hz), 7.33(1H, dd, J=8.9Hz, 3.1Hz), 7.41-7.49(7H, m), 7.55-7.68(2H, m), 7.70(1H, d, J=3.1Hz), 7.71(2H, d, J=8.0Hz). |
| 2196 | 3,4-Cl$_2$Ph— | —CH$_3$ | —H | 2 | dihydro-chloride | 2.49-3.07(10H, m), 3.23-3.27(2H, m), 3.45-3.55(1H, m), 4.03-4.08(1H, m), 4.30(2H, d, J=4.3Hz), 4.42-4.47(1H, m), 4.54(2H, s), 6.87(1H, d, J=9.1Hz), 6.90(2H, d, J=8.6Hz), 7.19-7.23(3H, m), 7.32(1H, dd, J=8.9Hz, 3.3Hz), 7.45-7.50(4H, m), 7.57-7.64(4H, m), 11.33(2H, brs). |
| 2197 | 4-CF$_3$Ph— | —C$_2$H$_5$ | —F | 0 | hydro-chloride | 1.21(3H, t, J=6.9Hz), 2.50-2.51(2H, m), 3.14-3.38(6H, m), 3.49(2H, q, J=6.9Hz), 4.34(2H, brs), 4.61(2H, brs), 6.98(1H, d, J=8.9Hz), 7.25-7.29(3H, m), 7.42-7.50(7H, m), 7.58(2H, brs), 7.69(2H, d, J=8.1Hz), 11.12(1H, brs). |

TABLE 349-continued

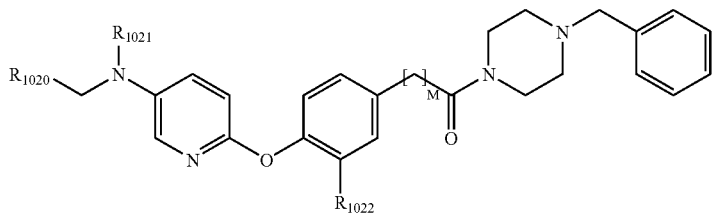

| Example No. | $R_{1020}$ | $R_{1021}$ | $R_{1022}$ | M | Form | $^1$H NMR (DMSO-$d_6$) δppm |
|---|---|---|---|---|---|---|
| 2198 | 3,4-Cl$_2$Ph— | —C$_2$H$_5$ | —F | 0 | hydro-chloride | 1.10(3H, t, J=7.0Hz), 2.49-2.52(2H, m), 3.13(2H, brs), 3.32-3.58(6H, m), 4.33(2H, brs), 4.50(2H, brs), 6.99(1H, d, J=9.1Hz), 7.20-7.31(4H, m), 7.42-7.57 (6H, m), 7.58-7.60(3H, m), 11.14(1H, brs). |

TABLE 350

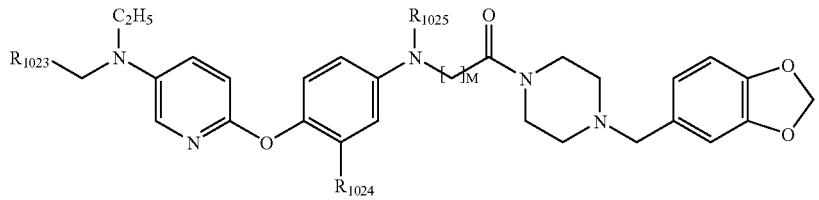

| Example No. | $R_{1023}$ | $R_{1024}$ | $R_{1025}$ | M | Form | mp (° C.) or $^1$H NMR (solvent) δppm |
|---|---|---|---|---|---|---|
| 2199 | 3,4-Cl$_2$Ph— | —H | —CH$_3$ | 2 | free | $^1$H NMR (CDCl$_3$) 1.17(3H, t, J=7.1Hz), 2.32-2.39(4H, m), 252-2.57(2H, m), 2.91(3H, s), 3.36-3.44(6H, m), 3.59-3.63(2H, m), 3.66-3.71(2H, m), 4.35(2H, s), 5.95 (2H, s), 6.67-6.76(5H, m), 6.83(1H, d, J=1.0Hz), 6.98(2H, d, J=9.1Hz), 7.03(1H, dd, J=9.1Hz, 3.3Hz), 7.07(1H, dd, J=8.9Hz, 2.1Hz), 7.32(1H, d, J=2.0Hz), 7.47(1H, d, J=8.3Hz), 7.62(1H, d, J=3.1Hz). |
| 2200 | 4-CF$_3$Ph— | —H | —CH$_3$ | 2 | free | $^1$H NMR (CDCl$_3$) 1.19(3H, t, J=7.1Hz), 2.32-2.38(4H, m), 2.52-2.57(2H, m), 2.91(3H, s), 3.36-3.47(6H, m), 3.59-3.63(2H, m), 3.66-3.71(2H, m), 4.47(2H, s), 5.94(2H, s), 6.67-6.76(5H, m), 6.83(1H, d, J=1.0Hz), 6.97(2H, d, J=9.2Hz), 7.03(1H, dd, J=9.1Hz, 3.1Hz), 7.35(2H, d, J=7.9Hz), 7.56(2H, d, J=7.9Hz), 7.63(1H, d, J=2.8Hz). |
| 2201 | 3,4-Cl$_2$Ph— | —CH$_3$ | —CH$_3$ | 1 | hydrochloride | mp 167-170 dec |
| 2202 | 4-CF$_3$Ph— | —CH$_3$ | —Ac | 1 | hydrochloride | mp 186-189 |
| 2203 | 3,4-Cl$_2$Ph— | —CH$_3$ | —Ac | 1 | hydrochloride | mp 188.5-191.0 |
| 2204 | 4-CF$_3$Ph— | —OCH$_3$ | —CH$_3$ | 1 | oxalate | $^1$H NMR (DMSO-$d_6$) 1.08(3H, t, J=7.0Hz), 2.50-2.81(4H, m), 2.93(3H, s), 3.41(2H, q, J=7.0Hz), 3.33-3.72(7H, m), 3.77(2H, s), 4.25(2H, s), 4.52(2H, s), 6.01(2H, s), 6.12(1H, dd, J=8.8Hz, 2.7Hz), 6.28(1H, d, J=2.7Hz), 6.64(1H, d, J=9.0Hz), 6.76(1H, d, J=8.7Hz), 6.80-6.94(2H, m), 6.97(1H, brs), 7.15(1H, dd, J=9.0Hz, 3.2Hz), 7.34-7.50(3H, m), 7.66(2H, d, J=8.1Hz). |
| 2205 | 3,4-Cl$_2$Ph— | —OCH$_3$ | —CH$_3$ | 1 | hydrochloride | $^1$H NMR (DMSO-$d_6$) 1.06(3H, t, J=6.9Hz), 2.75-3.16(5H, m), 3.21-3.48(4H, m), 3.62(3H, s), 3.71- |

TABLE 350-continued

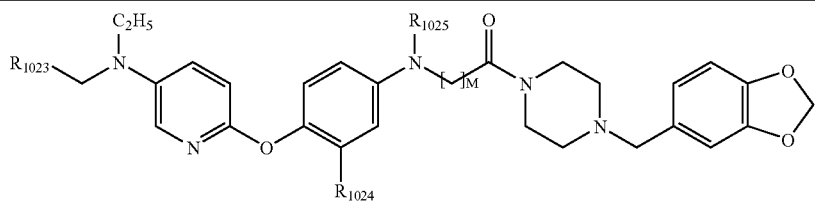

| Example No. | $R_{1023}$ | $R_{1024}$ | $R_{1025}$ | M | Form | mp (° C.) or $^1$H NMR (solvent) δppm |
|---|---|---|---|---|---|---|
| | | | | | | 4.52(10H, m), 6.06(2H, s), 6.16(1H, dd, J=8.8Hz, 2.7Hz), 6.34(1H, d, J=2.7Hz), 6.67(1H, d, J=8.9Hz), 6.78(1H, d, J=8.8Hz), 6.94-7.06 (2H, m), 7.13-7.28(3H, m), 7.41-7.52(2H, m), 7.56(1H, d, J=8.3Hz), 10.83-11.19(1H, m). |

TABLE 351

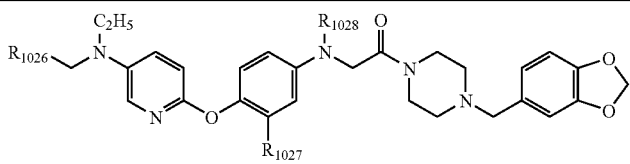

| Example No. | $R_{1026}$ | $R_{1027}$ | $R_{1028}$ | Form | mp (° C.) |
|---|---|---|---|---|---|
| 2206 | 4-CF$_3$Ph— | —CH$_3$ | —C$_2$H$_5$ | oxalate | 126-128 |
| 2207 | 3,4-Cl$_2$Ph— | —CH$_3$ | —C$_2$H$_5$ | oxalate | 111-113 |
| 2208 | 4-CF$_3$Ph— | —CH$_3$ | —C$_2$H$_5$ | oxalate | 120-123 |
| 2209 | 4-CF$_3$Ph— | —OCH$_3$ | —CH$_3$ | hydrobromide | 205-208 |
| 2210 | 3,4-Cl$_2$Ph— | —OCH$_3$ | —C$_2$H$_5$ | hydrobromide | 133-135 |
| 2211 | 4-CF$_3$Ph— | —F | —CH$_3$ | hydrobromide | 203-205 |
| 2212 | 3,4-Cl$_2$Ph— | —F | —CH$_3$ | hydrobromide | 185-188 |
| 2213 | 4-CF$_3$Ph— | —F | —C$_2$H$_5$ | oxalate | 121.0-122.5 |
| 2214 | 3,4-Cl$_2$Ph— | —F | —C$_2$H$_5$ | hydrobromide | 165.0-166.5 |

TABLE 352

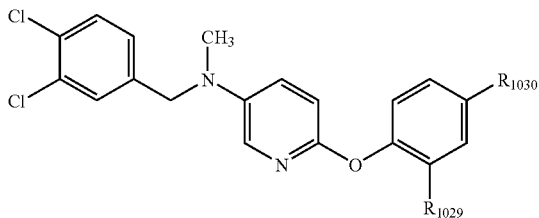

| Example No. | $R_{1029}$ | $R_{1030}$ | $^1$H NMR (CDCl$_3$) δppm |
|---|---|---|---|
| 2215 | —H | ![structure with ethyl-piperazine-COOC(CH$_3$)$_3$] | 1.45(9H, s), 2.39-2.43(4H, m), 3.01(3H, s), 3.41-3.44(4H, m), 3.50(2H, s), 4.41(2H, s), 6.82(1H, d, J=8.9Hz), 7.01(2H, d, J=8.4Hz), 7.08-7.13(2H, m), 7.27-7.41(4H, m), 7.70(1H, d, J=8.6Hz). |
| 2216 | —CH$_3$ | ![ethyl-thiazolidine-2,4-dione] | 2.20(3H, s), 2.98(3H, s), 3.06(1H, dd, J=14.0Hz, 10.1Hz), 3.52(1H, dd, J=14.0Hz, 3.8Hz), 4.38(2H, s), 4.50(1H, dd, J=10.1Hz, 3.8Hz), 6.77(1H, d, J=8.9Hz), 6.91(1H, d, J=8.3Hz), 7.03(1H, dd, J=8.3Hz, 2.1Hz), 7.05-7.16(3H, m), 7.32(1H, d, J=2.1Hz), 7.39(1H, d, J=8.3Hz), 7.67(1H, d, J=3.1Hz). |

TABLE 353

[Structure: R1031-CH2-N(R1032)-pyridine-O-phenyl(R1033)-N(SO2CH3)-CH2-C(O)-piperazine-CH2-benzodioxole]

| Example No. | R1031 | R1032 | R1033 | 1H NMR (CDCl3) δppm |
|---|---|---|---|---|
| 2217 | 3,4-Cl2Ph— | —CH3 | —H | 2.41(4H, brs), 3.02(3H, s), 3.19(3H, s), 3.36(2H, brs), 3.42(2H, s), 3.60(2H, brs), 4.41(2H, s), 4.51(2H, s), 5.95(2H, s), 6.73-6.77(2H, m), 6.84-6.87(2H, m), 7.03(2H, d, J=8.9Hz), 7.07(1H, dd, J=8.3Hz, 2.0Hz), 7.12(1H, dd, J=8.9Hz, 3.1Hz), 7.33(1H, d, J=2.0Hz), 7.40(1H, d, J=8.3Hz), 7.59(2H, d, J=8.9Hz), 7.69(1H, d, J=3.1Hz). |
| 2218 | 3,4-Cl2Ph— | —C2H5 | —H | 1.21(3H, t, J=7.1Hz), 2.41(4H, brs), 3.18(3H, s), 3.36(2H, brs), 3.42(2H, s), 3.46(2H, q, J=7.1Hz), 3.60(2H, brs), 4.40(2H, s), 4.50(2H, s), 5.94(2H, s), 6.73-6.77(2H, m), 6.81-6.84(2H, m), 7.01-7.10(4H, m), 7.33(1H, d, J=2.0Hz), 7.39(1H, d, J=8.3Hz), 7.54(2H, d, J=9.1Hz), 7.64(1H, d, J=3.0Hz). |
| 2219 | 4-CF3Ph— | —CH3 | —H | 2.41(4H, brs), 3.05(3H, s), 3.19(3H, s), 3.34-3.36(2H, m), 3.42(2H, s), 3.60(2H, brs), 4.50(2H, s), 4.54(2H, s), 5.95(2H, s), 6.73-6.74(2H, m), 6.83(1H, brs), 6.85(1H, d, J=8.9Hz), 7.03(2H, d, J=8.9Hz), 7.13(1H, dd, J=8.9Hz, 3.3Hz), 7.34(2H, d, J=7.9Hz), 7.54(2H, d, J=8.9Hz), 7.59(2H, d, J=8.1Hz), 7.70(1H, d, J=3.1Hz). |
| 2220 | 4-CF3Ph— | —C2H5 | —H | 1.22(3H, t, J=7.1Hz), 2.41(4H, brs), 3.19(3H, s), 3.35(2H, brs), 3.42(2H, s), 3.48(2H, q, J=7.1Hz), 3.60(2H, brs), 4.50(2H, s), 4.52(2H, s), 5.95(2H, s), 6.70-6.77(2H, m), 6.82(1H, d, J=8.7Hz), 6.84(1H, brs), 7.02(2H, d, J=8.9Hz), 7.07(1H, dd, J=8.9Hz, 3.1Hz), 7.36(2H, d, J=7.9Hz), 7.54(2H, d, J=8.9Hz), 7.58(2H, d, J=8.1Hz), 7.65(1H, d, J=3.0Hz). |
| 2221 | 3,4-Cl2Ph— | —CH3 | —CH3 | 2.21(3H, s), 2.42(4H, brs), 3.00(3H, s), 3.21(3H, s), 3.34-3.38(2H, m), 3.42(2H, s), 3.59-3.62(2H, m), 4.39(2H, s), 4.51(2H, s), 5.95(2H, s), 6.73-6.77(2H, m), 6.80-6.83(2H, m), 6.91(1H, d, J=8.6Hz), 7.06(1H, dd, J=8.2Hz, 2.1Hz), 7.12(1H, dd, J=8.9Hz, 3.1Hz), 7.32-7.44(4H, m), 7.65(1H, d, J=3.1Hz). |
| 2222 | 4-CF3Ph— | —CH3 | —CH3 | 2.21(3H, s), 2.42(4H, brs), 3.02(3H, s), 3.20(3H, s), 3.34-3.38(2H, m), 3.42(2H, s), 3.58-3.62(2H, m), 4.51(4H, brs), 5.94(2H, s), 6.70-6.76(2H, m), 6.79-6.83(2H, m), 6.90(1H, d, J=8.6Hz) 7.12(1H, dd, J=8.9Hz, 3.3Hz), 7.32-7.39(3H, m), 7.43(1H, d, J=2.5Hz), 7.58(2H, d, J=8.1Hz), 7.66(1H, d, J=3.0Hz). |

TABLE 354

[Structure: R1034-CH2-N(R1035)-pyridine-O-phenyl(R1036)-N(SO2CH3)-CH2-C(O)-piperazine-CH2-benzodioxole]

| Example No. | R1034 | R1035 | R1036 | 1H NMR (CDCl3) δppm |
|---|---|---|---|---|
| 2223 | 3,4-Cl2Ph— | —C2H5 | —CH3 | 1.19(3H, t, J=7.1Hz), 2.21(3H, s), 2.41(4H, brs), 3.20(3H, s), 3.34-3.37(2H, m), 3.42(2H, s), 3.43(2H, q, J=7.1Hz), 3.58-3.62(2H, m), |

TABLE 354-continued

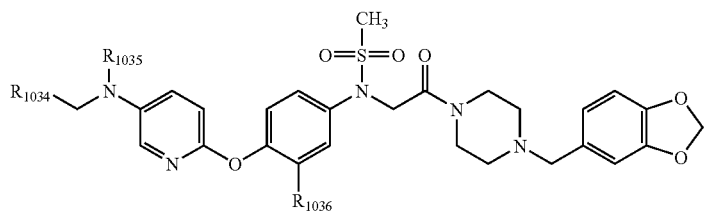

| Example No. | $R_{1034}$ | $R_{1035}$ | $R_{1036}$ | $^1$H NMR (CDCl$_3$) δppm |
|---|---|---|---|---|
| | | | | 4.38(2H, s), 4.50(2H, s), 5.95(2H, s), 6.70-6.77(2H, m), 6.79(1H, d, J=8.9Hz), 6.83(1H, d, J=0.8Hz), 6.91(1H, d, J=8.6Hz), 7.04-7.09(2H, m), 7.32-7.43(4H, m), 7.60(1H, d, J=3.0Hz). |
| 2224 | 4-CF$_3$Ph— | —C$_2$H$_5$ | —CH$_3$ | 1.21(3H, t, J=7.1Hz), 2.21(3H, s), 2.41(4H, brs), 3.20(3H, s), 3.34-3.37(2H, m), 3.42(2H, s), 3.46(2H, q, J=7.1Hz), 3.58-3.62(2H, m), 4.50(4H, brs), 5.94(2H, s), 6.70-6.74(2H, m), 6.78(1H, d, J=9.2Hz), 6.83(1H, brs), 6.90(1H, d, J=8.6Hz), 7.04-7.08(1H, m), 7.34-7.43(4H, m), 7.57(2H, d, J=8.1Hz), 7.60(1H, d, J=3.0Hz). |
| 2225 | 4-CF$_3$Ph— | —CH$_3$ | —OCH$_3$ | 2.42(4H, brs), 3.01(3H, s), 3.21(3H, s), 3.37(2H, brs), 3.42(2H, s), 3.61(2H, brs), 3.78(3H, s), 4.27(2H, s), 4.53(2H, s), 5.94(2H, s), 6.72-6.76(2H, m), 6.84(2H, d, J=8.4Hz), 7.00(1H, d, J=8.4Hz), 7.10-7.16(2H, m), 7.24-7.26(1H, m), 7.33(2H, d, J=8.1Hz), 7.57(2H, d, J=7.9Hz), 7.62(1H, d, J=3.0Hz). |
| 2226 | 4-CF$_3$Ph— | —C$_2$H$_5$ | —OCH$_3$ | 1.20(3H, t, J=6.9Hz), 2.42(4H, brs), 3.21(3H, s), 3.36(2H, brs), 3.40-3.48(4H, m), 3.61(2H, brs), 3.77(3H, s), 4.48(2H, s), 4.52(2H, s), 5.94(2H, s), 6.73-6.76(2H, m), 6.81-6.85(2H, m), 6.99(1H, d, J=8.6Hz), 7.07(1H, dd, J=9.1Hz, 3.3Hz), 7.14(1H, dd, J=8.4Hz, 2.3Hz), 7.24(1H, d, J=2.5Hz), 7.34(2H, d, J=8.1Hz), 7.54-7.57(3H, m). |

TABLE 355

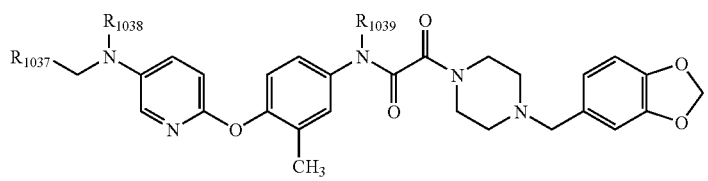

| Example No | $R_{1037}$ | $R_{1038}$ | $R_{1039}$ | $^1$H NMR (solvent) δppm |
|---|---|---|---|---|
| 2227 | 3,4-Cl$_2$Ph— | —CH$_3$ | —H | (CDCl$_3$) 2.20(3H, s), 2.48-2.54(4H, m), 2.97(3H, s), 3.44(2H, s), 3.70-3.73(2H, m), 4.23-4.27(2H, m), 4.37(2H, s), 5.95(2H, s), 6.73-6.77(3H, m), 6.85(1H, brs), 6.95(1H, d, J=8.6Hz), 7.06(1H, dd, J=8.2Hz, 2.0Hz), 7.10(1H, dd, J=8.9Hz, 3.1Hz), 7.32(1H, d, J=2.0Hz), 7.37(1H, dd, J=8.6Hz, 2.6Hz), 7.38(1H, d, J=8.2Hz), 7.52(1H, d, J=2.5Hz), 7.66(1H, d, J=2.8Hz), 9.12(1H, brs). |
| 2228 | 4-CF$_3$Ph— | —CH$_3$ | —H | (CDCl$_3$) 2.20(3H, s), 2.48-2.54(4H, m), 3.00(3H, s), 3.44(2H, s), 3.72(2H, t, J=5.0Hz), 4.23-4.27(2H, m), 4.49(2H, s), 5.95(2H, s), 6.73-6.77(3H, m), 6.85(1H, brs), 6.95(1H, d, J=8.7Hz), 7.10(1H, dd, J=8.9Hz, 3.3Hz), 7.32-7.39(3H, m), 7.52(1H, d, J=2.5Hz), 7.57(2H, d, J=8.1Hz), 7.67(1H, d, J=3.3Hz), 9.12(1H, brs). |
| 2229 | 3,4-Cl$_2$Ph— | —C$_2$H$_5$ | —H | (CDCl$_3$) 1.18(3H, t, J=7.1Hz), 2.20(3H, s), 2.48-2.53(4H, m), 3.41(2H, q, J=7.1Hz), 3.44(2H, s), 3.70-3.73(2H, m), 4.23-4.27(2H, m), 4.36(2H, s), 5.95(2H, s), 6.72-6.77(3H, m), 6.85(1H, brs), 6.95(1H, d, J=8.6Hz), 7.02-7.09(2H, m), 7.32-7.39(3H, m), 7.51(1H, d, J=2.6Hz), 7.60(1H, d, J=3.1Hz), 9.12(1H, brs). |

TABLE 355-continued

Structure: R1037—CH2—N(R1038)—[pyridine]—O—[phenyl(CH3)]—N(R1039)—C(O)—C(O)—[piperazine]—CH2—[benzo[1,3]dioxole]

| Example No | R1037 | R1038 | R1039 | $^1$H NMR (solvent) δppm |
|---|---|---|---|---|
| 2230 | 4-CF$_3$Ph— | —C$_2$H$_5$ | —H | (CDCl$_3$) 1.19(3H, t, J=7.1Hz), 2.20(3H, s), 2.48-2.53(4H, m), 3.43(2H, q, J=7.1Hz), 3.44(2H, s), 3.70-3.73(2H, m), 4.23-4.27(2H, m), 4.48(2H, s), 5.95(2H, s), 6.71-6.77(3H, m), 6.85(1H, brs), 6.95(1H, d, J=8.7Hz), 7.04(1H, dd, J=8.9Hz, 3.1Hz), 7.32-7.38(3H, m), 7.51(1H, d, J=2.5Hz), 7.56(2H, d, J=8.1Hz), 7.61(1H, d, J=3.1Hz), 9.11(1H, brs). |
| 2231 | 3,4-Cl$_2$Ph— | —C$_2$H$_5$ | —CH$_3$ | a mixture of the rotational isomers (DMSO-d$_6$) 1.09(3H, t, J=6.93Hz), 2.29-2.42(7H, m), 3.22-3.54(11H, m), 4.48(2H, s), 5.97-5.99(2H, m), 6.64-6.94(5H, m), 7.07-7.27(4H, m), 7.46 7.59(3H, m). |
| 2232 | 4-CF$_3$Ph— | —C$_2$H$_5$ | —CH$_3$ | a mixture of the rotational isomers (DMSO-d$_6$) 1.12(3H, t, J=6.93Hz), 2.07-2.42(7H, m), 3.22-3.55(11H, m), 4.59(2H, s), 5.97-5.99(2H, m), 6.65-6.94(5H, m), 7.07-7.18(1H, m), 7.23-7.29(2H, m), 7.44(2H, d, J=8.08Hz), 7.53(1H, d, J=3.13Hz), 7.67(2H, d, J=8.41Hz). |

TABLE 356

Structure: R1040—CH2—N(CH3)—[pyridine]—O—[phenyl(CH3)]—N(CH3)—C(O)—C(O)—[piperazine]—CH2—[benzo[1,3]dioxole] · HCl

| Example No. | R1040 | $^1$NMR (DMSO-d$_6$) δppm |
|---|---|---|
| 2233 | 3,4-Cl$_2$Ph— | a mixture of the rotational isomers 2.09-2.12(3H, m), 2.66-4.53(18H, m), 6.05-6.08(2H, m), 6.88-6.93(2H, m), 6.96-7.11(3H, m), 7.19-7.25(3H, m), 7.32-7.36(1H, m), 7.48(1H, d, J=2.1Hz), 7.55-7.60(2H, m), 11.35(1H, brs). |
| 2234 | 4-CF$_3$Ph— | a mixture of the rotational isomers 2.10-2.12(3H, m), 2.66-4.64(18H, m), 6.05-6.08(2H, m), 6.87-6.92(2H, m), 6.96-7.11(3H, m), 7.18-7.25(2H, m), 7.30-7.35(1H, m), 7.43(2H, d, J=8.1Hz), 7.60-7.61(1H, m), 7.68(2H, d, J=8.2Hz), 11.27(1H, brs). |

Example 2235

Production of (4-{5-[benzyl-(3,4-dichlorobenzyl)-amino]pyridin-2-yloxy}(4-benzylpiperazin-1-yl) methanone (4-benzylpiperazin-1-yl){4-[5-(3,4-dichlorobenzylamino)pyridin-2-yloxy]phenyl}methanone (1.09 g, 2.0 mmol) was dissolved in DMF (30 mL). To this solution were added potassium carbonate (0.28 g, 2.0 mmol) and benzyl bromide (0.24 mL, 2.0 mmol), and the resulting solution was stirred at room temperature for 2 hours, then subsequently stirred for 1 hour at 70° C. To the resulting solution were further added potassium carbonate (0.03 g, 0.2 mmol) and benzyl bromide (0.02 mL, 0.2 mmol), and this solution was stirred for 3 hours at 70° C. To the resulting solution were again added potassium carbonate (0.03 g, 0.2 mmol), benzyl bromide (0.02 mL, 0.2 mmol) and sodium iodide (0.15 g, 1.0 mmol), and this solution was stirred for overnight at 70° C. The resulting reaction solution was concentrated under reduced pressure. The residue was diluted with chloroform, and this solution was washed with water, saturated sodium bicarbonate solution and brine. The organic layer was dried over anhydrous magnesium sulfate, and evaporated. The residue was then purified by silica gel column chromatography (ethyl acetate), to thereby yield 0.64 g of the title compound.

Appearance: Pale yellow oil $^1$H NMR (CDCl$_3$) δ 2.37 (4H, brs), 3.28-3.50 (6H, m), 4.71 (2H, s), 4.73 (2H, s), 6.90 (1H, d, J=8.9 Hz), 6.99 (2H, d, J=8.6 Hz), 7.22-7.37 (14H, m), 7.52 (1H, d, J=2.0 Hz), 7.58-7.61 (2H, m).

The following compounds were produced in the same manner as in Example 2235.

TABLE 357

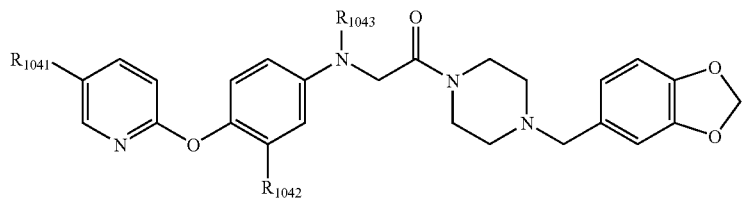

| Example No. | R<sub>1041</sub> | R<sub>1042</sub> | R<sub>1043</sub> | $^1$H NMR (CDCl$_3$) δppm |
|---|---|---|---|---|
| 2236 | 3,4-Cl$_2$PhCON(CH$_3$)— | —OCH$_3$ | —C$_2$H$_5$ | 1.19(3H, t, J=7.1Hz), 2.42(4H, t, J=4.8Hz), 3.30-3.55(4H, m), 3.43(2H, s), 3.44(3H, s), 3.58-3.70(2H, m), 3.67(3H, s), 4.03(2H, s), 5.95(2H, s), 6.19(1H, dd, J=8.8Hz, 2.8Hz), 6.30(1H, d, J=2.8Hz), 6.70-6.75(2H, m), 6.79(1H, d, J=8.9Hz), 6.85(1H, s), 6.92(1H, d, J=8.8Hz), 7.05(1H, dd, J=8.1Hz, 2.0Hz), 7.27(1H, d, J=8.1Hz), 7.35(1H, dd, J=8.9Hz, 2.6Hz), 7.41(1H, d, J=2.0Hz), 7.80(1H, d, J=2.6Hz). |
| 2237 | 4-CF$_3$PhCON(CH$_3$)— | —CH$_3$ | —CH$_3$ | 1.97(3H, s), 2.43(4H, t, J=5.0Hz), 3.00(3H, s), 3.44(2H, s), 3.47(3H, s), 3.42-3.57(2H, m), 3.63(2H, brs), 4.06(2H, s), 5.95(2H, s), 6.44-6.55(2H, m), 6.67-6.79(3H, m), 6.82-6.90(2H, m), 7.40-7.47(1H, m), 7.37(2H, d, J=8.1Hz), 7.48(2H, d, J=8.1Hz), 7.81(1H, brs). |
| 2238 | 4-CF$_3$PhCON(CH$_3$)— | —OCH$_3$ | —C$_2$H$_5$ | 1.18(3H, t, J=7.1Hz), 2.41(4H, t, J=4.9Hz), 3.40(2H, q, J=7.1Hz), 3.42(2H, t, J=3.5Hz), 3.47(3H, s), 3.42-3.59(2H, m), 3.63(5H, s), 4.02(2H, s), 5.95(2H, s), 6.18(1H, dd, J=8.7Hz, 2.8Hz), 6.28(1H, d, J=2.8Hz), 6.69-6.78(2H, m), 6.77(1H, d, J=8.8Hz), 6.85(1H, s), 6.90(1H, d, J=8.7Hz), 7.35(1H, d, J=8.8Hz), 7.38(2H, d, J=8.4Hz), 7.48(2H, d, J=8.4Hz), 7.79(1H, brs). |
| 2239 | 3,4-Cl$_2$PhN(CH$_3$)CO— | —CH$_3$ | —C$_2$H$_5$ | 1.18(3H, t, J=7.1Hz), 2.42(4H, t, J=5.0Hz), 3.42(2H, s), 3.43(2H, q, J=7.1Hz), 3.45(3H, s), 3.55(2H, brs), 3.65(5H, brs), 4.02(2H, s), 5.95(2H, s), 6.19(1H, dd, J=8.7Hz, 2.8Hz), 6.29(1H, d, J=2.8Hz), 6.71-6.74(3H, m), 6.85(1H, brs), 6.87(1H, dd, J=8.6Hz, 2.5Hz), 6.92(1H, d, J=8.7Hz), 7.20(1H, d, J=2.5Hz), 7.32(1H, d, J=8.4Hz), 7.64(1H, dd, J=8.6Hz, 2.3Hz), 8.05(1H, d, J=1.8Hz). |
| 2240 | 3,4-Cl$_2$PhSO$_2$N(CH$_3$)— | —F | —CH$_3$ | 2.44(2H, brs), 3.03(3H, s), 3.19(3H, s), 3.44(2H, brs), 3.47(2H, brs), 3.62(2H, brs), 4.08(2H, brs), 4.08(2H, brs), 5.95(2H, s), 6.41(1H, dd, J=8.2Hz, 3.1Hz), 6.42-6.50(1H, m), 6.70-6.79(2H, m), 6.85(1H, brs), 6.90(1H, d, J=8.7Hz), 7.04(1H, t, J=7.8Hz), 7.34(1H, dd, J=8.4Hz, 2.2Hz), 7.50(1H, dd, J=8.7Hz, 2.8Hz), 7.56(1H, d, J=8.4Hz), 7.72(1H, d, J=2.2Hz), 7.77(1H, d, J=2.8Hz). |

TABLE 358

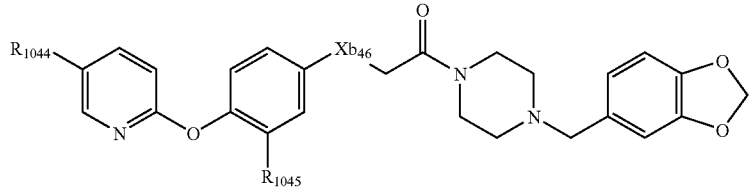

| Example No. | $R_{1044}$ | $R_{1045}$ | $Xb_{46}$ | Form | mp (° C.) or $^1$H NMR |
|---|---|---|---|---|---|
| 2241 | 4-CF$_3$PhCON(CH$_3$)— | —CH$_3$ | —N(SO$_2$CH$_3$)— | free | $^1$H NMR (CDCl$_3$) δ 2.05(3H, s), 2.42(4H, brs), 3.20(3H, s), 3.34-3.37(2H, m), 3.42(2H, s), 3.48(3H, s), 3.59-3.61(2H, m), 4.52(2H, s), 5.95(2H, s), 6.70-6.77(2H, m), 6.84(1H, brs), 6.86(1H, d, J=8.7Hz), 6.97(1H, d, J=8.1Hz), 7.37-7.51(7H, m), 7.79(1H, brs). |
| 2242 | 3,4-Cl$_2$PhCON(CH$_3$)— | —CH$_3$ | —N(SO$_2$CH$_3$)— | free | $^1$H NMR (CDCl$_3$) δ 2.09(3H, s), 2.42(4H, brs), 3.21(3H, s), 3.37(2H, brs), 3.43(2H, s), 3.46(3H, s), 3.61(2H, brs), 4.52(2H, s), 5.95(2H, s), 6.70-6.80(2H, m), 6.84(1H, brs), 6.89(1H, d, J=8.7Hz), 6.99(1H, d, J=8.4Hz), 7.09(1H, dd, J=8.2Hz, 1.8Hz), 7.29(1H, d, J=8.2Hz), 7.38(1H, d, J=2.0Hz), 7.42-7.46(3H, m), 7.80(1H, d, J=2.5Hz). |
| 2243 | 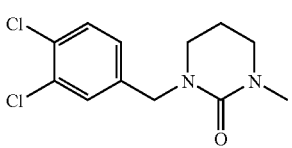 | —H | —CH$_2$— | free | mp 133.0-134.0 |
| 2244 | 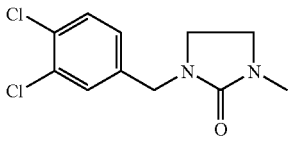 | —H | —CH$_2$— | free | mp 117.0-118.0 |
| 2245 | 4-CF$_3$PhN(CH$_3$)SO$_2$— | —H | —CH$_2$— | free | $^1$H NMR (CDCl$_3$) δ 2.33-2.41(4H, m), 2.63(2H, t, J=7.3Hz), 2.99(2H, t, J=7.3Hz), 3.22(3H, s), 3.40(4H, brs), 3.61-3.64(2H, m), 5.93(2H, s), 6.69-6.76(2H, m), 6.84(1H, s), 6.94(1H, d, J=8.7Hz), 7.06(2H, d, J=8.6Hz), 7.27-7.31(4H, m), 7.59(2H, d, J=8.4Hz), 7.71(1H, dd, J=8.7Hz, 2.6Hz), 8.37(1H, d, J=2.6Hz). |
| 2246 | F$_3$CCH=CHCON(CH$_3$)— | —CH$_3$ | —N(CH$_3$)— | hydro-chloride | mp 161.0-164.0 |

TABLE 359

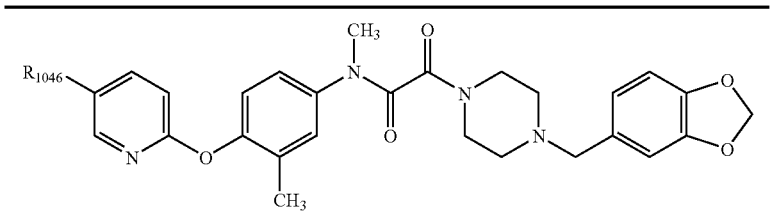

| Example No. | $R_{1046}$ | $^1$H NMR (solvent) δppm |
|---|---|---|
| 2247 | 3,4-Cl$_2$PhCON(CH$_3$)— | a mixture of the rotational isomers (DMSO-d$_6$) 1.93(3H, brs), 2.08-2.42(4H, m), 3.21-3.56(12H, m), 5.97-5.99(2H, m), 6.66-6.89(3H, m), 6.90-7.07(2H, m), 7.13-7.32(3H, m), 7.48-7.54(2H, m), 7.85-7.89(2H, m). |
| 2248 | 4-CF$_3$PhCON(CH$_3$)— | a mixture of the rotational isomers (DMSO-d$_6$) 1.87(3H, brs), 2.07-2.41(4H, m), 3.20-3.55(12H, m), 5.97-5.99(2H, m), 6.66-6.89(3H, m), 6.98-7.04(2H, m), 7.12-7.21(1H, m), 7.24-7.30(1H, m), 7.47(2H, brs), 7.61-7.64(2H, m), 7.86-7.89(2H, m). |
| 2249 | 3,4-Cl$_2$PhSO$_2$N(CH$_3$)— | (CDCl$_3$) 2.17(3H, s), 2.23-2.53(4H, m), 3.21(3H, brs), 3.32-3.82(9H, m), 5.93-5.95(2H, m), 6.65-6.78(3H, m), 6.85-6.95(1H, m), 7.02-7.06(1H, m), 7.07-7.18(2H, m), 7.38-7.42(1H, m), 7.53-7.58(1H, m), 7.67-7.68(1H, m), 7.78-7.80(1H, m). |
| 2250 | 4-CF$_3$PhSO$_2$N(CH$_3$)— | a mixture of the rotational isomers (DMSO-d$_6$) 2.07-2.43(7H, m), 3.16-3.56(12H, m), 6.67-6.70(2H, m), 6.76-6.89(3H, m), 7.05-7.36(4H, m), 7.61-7.66(1H, m), 7.77-7.80(2H, m), 7.91-7.80(3H, m). |
| 2251 | 4-CF$_3$PhSO$_2$N(C$_2$H$_5$)— | (CDCl$_3$) 1.13(3H, t, J=7.1Hz), 2.18(3H, s), 2.23-2.52(4H, m), 3.32-3.66(11H, m), 5.93-5.95(2H, m), 6.66-6.95(4H, m), 7.04-7.19(3H, m), 7.46(1H, dd, J=8.7Hz, 2.6Hz), 7.73-7.80(5H, m). |

TABLE 360

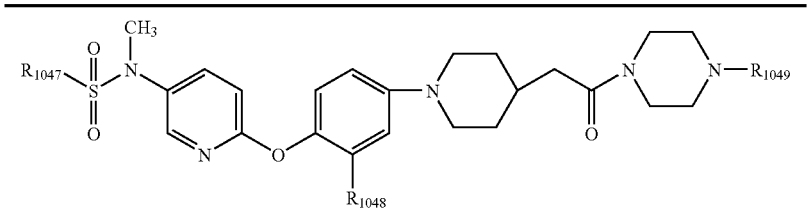

| Example No. | $R_{1047}$ | $R_{1048}$ | $R_{1049}$ | $^1$H NMR (CDCl$_3$) δppm |
|---|---|---|---|---|
| 2252 | 4-CF$_3$Ph— | —H | benzyl | 1.34-1.46(2H, m), 1.85-2.03(3H, m), 2.29(2H, d, J=6.8Hz), 2.43(4H, brs), 2.73(2H, t, J=12.0Hz), 3.19(3H, s), 3.47-3.65(8H, m), 6.83(1H, d, J=8.7Hz), 6.92-7.03(4H, m), 7.26-7.33 (5H, m), 7.48(1H, dd, J=8.9Hz, 2.8Hz), 7.70-7.78(5H, m). |
| 2253 | 3,4-Cl$_2$Ph— | —H | piperonyl | 1.33-1.46(2H, m), 1.85-2.04(3H, m), 2.29(2H, d, J=6.8Hz), 2.39-2.42(4H, m), 2.74(2H, t, J=12.2Hz), 3.19(3H, s), 3.43(2H, s), 3.46-3.64(6H, m), 5.94(2H, s), 6.70-6.77(2H, m), 6.83(2H, d, J=8.9Hz), 6.92-7.03(4H, m), 7.38(1H, dd, J=8.4Hz, 2.1Hz), 7.49(1H, dd, J=8.9Hz, 2.8Hz), 7.56(1H, d, J=8.4Hz), 7.70(1H, d, J=2.1Hz), 7.81(1H, d, J=2.3Hz). |
| 2254 | 4-CF$_3$Ph— | —H | piperonyl | 1.34-1.46(2H, m), 1.85-2.02(3H, m), 2.28(2H, d, J=6.8Hz), 2.39-2.42(4H, m), 2.74(2H, t, J=12.0Hz), 3.20(3H, s), 3.43(2H, s), 3.46-3.64(6H, m), 5.94(2H, s), 6.70-6.77(2H, m), 6.81-7.03(6H, m), 7.49(1H, dd, J=8.7Hz, 2.8Hz), 7.71-7.78(5H, m). |
| 2255 | 4-CF$_3$Ph— | —OCH$_3$ | benzyl | 1.31-1.42(2H, m), 1.86-2.00(3H, m), 2.29(2H, d, J=6.8Hz), 2.42-2.45(4H, m), 2.76(2H, t, J=12.0Hz), 3.19(3H, s), 3.49-3.69(8H, m), 3.75(3H, s), 6.51(1H, dd, J=8.7Hz, 2.5Hz), 6.59(1H, d, J=2.5Hz), 6.83(1H, d, J=8.7Hz), 6.98(1H, d, |

TABLE 360-continued

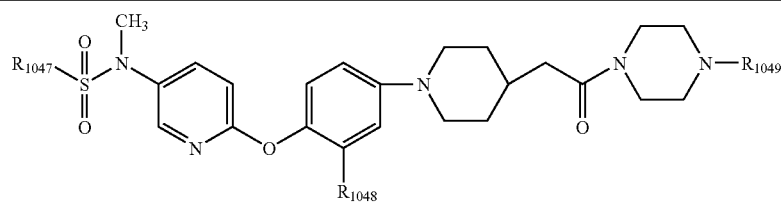

| Example No. | $R_{1047}$ | $R_{1048}$ | $R_{1049}$ | $^1$H NMR (CDCl$_3$) δppm |
|---|---|---|---|---|
| | | | | J=8.7Hz), 7.26-7.33(5H, m), 7.47(1H, dd, J=8.9Hz, 2.8Hz), 7.69-7.75(5H, m). |
| 2256 | 3,4-Cl$_2$Ph— | —H | benzyl | 1.39-1.42(2H, m), 1.84-2.02(3H, m), 2.28(2H, d, J=6.8Hz), 2.41-2.45(4H, m), 2.73(2H, t, J=12.2Hz), 3.19(3H, s), 3.48-3.95(8H, m), 6.83(1H, d, J=8.7Hz), 6.92-7.03(4H, m), 7.27-7.39(6H, m), 7.48(1H, dd, J=8.7Hz, 2.8Hz), 7.55(1H, d, J=8.4Hz), 7.70(1H, d, J=2.1Hz), 7.81(1H, d, J=2.3Hz). |
| 2257 | 3,4-Cl$_2$Ph— | —OCH$_3$ | benzyl | 1.34-1.42(2H, m), 1.82-2.00(3H, m), 2.29(2H, d, J=6.8Hz), 2.41-2.45(4H, m), 2.76(2H, t, J=12.2Hz), 3.19(3H, s), 3.49-3.65(8H, m), 3.75(3H, s), 6.51(1H, dd, J=8.7Hz, 2.6Hz), 6.58(1H, d, J=2.6Hz), 6.84(1H, d, J=8.7Hz), 6.98(1H, d, J=8.6Hz), 7.26-7.39(6H, m), 7.46(1H, dd, J=8.7Hz, 2.6Hz), 7.54(1H, d, J=8.4Hz), 7.69(1H, d, J=2.0Hz), 7.78(1H, d, J=2.5Hz). |

TABLE 361

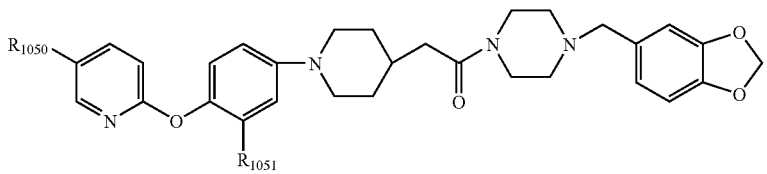

| Example No. | $R_{1050}$ | $R_{1051}$ | $^1$H NMR (CDCl$_3$) δppm |
|---|---|---|---|
| 2258 | 4-CF$_3$PhN(CH$_3$)SO$_2$— | —H | 1.34-1.46(2H, m), 1.85-2.00(3H, m), 2.28(2H, d, J=6.8 Hz), 2.39-2.43(4H, m), 2.75(2H, t, J=12.2 Hz), 3.21(3H, s), 3.43(2H, s), 3.46-3.64(6H, m), 5.94(2H, s), 6.70-6.77(2H, m), 6.85-7.02(6H, m), 7.26-7.31(2H, m), 7.59(2H, d, J=8.6 Hz), 7.67(1H, dd, J=8.7 Hz, 2.6 Hz), 8.39(1H, d, J=2.1 Hz). |
| 2259 | 4-CF$_3$PhSO$_2$N(C$_2$H$_5$)— | —OCH$_3$ | 1.11(3H, t, J=7.1 Hz), 1.30-1.42(2H, m), 1.85-2.00(3H, m), 2.29(2H, d, J=6.8 Hz), 2.39-2.44(4H, m), 2.76(2H, t, J=12.2 Hz), 3.40-3.70(10H, m), 3.75(3H, s), 5.94(2H, s), 6.51(1H, dd, J=8.7 Hz, 2.6 Hz), 6.59(1H, d, J=2.6 Hz), 6.74-6.87(4H, m), 6.99(1H, d, J=8.7 Hz), 7.37-7.48(2H, m), 7.54(1H, d, J=8.4 Hz), 7.73-7.75(2H, m). |
| 2260 | 4-CF$_3$PhSO$_2$N(C$_2$H$_5$)— | —H | 1.11(3H, t, J=7.1 Hz), 1.35-1.47(2H, m), 1.85-2.00(3H, m), 2.29(2H, d, J=6.8 Hz), 2.40-2.42(4H, m), 2.74(2H, t, J=12.0 Hz), 3.42-3.48(4H, m), 3.57-3.64(6H, m), 5.94(2H, s), 6.74-6.77(2H, m), 6.82-7.04(6H, m), 7.41(1H, dd, J=8.7 Hz, 2.8 Hz), 7.72-7.94(5H, m). |
| 2261 | 4-CF$_3$PhSO$_2$N(CH$_3$)— | —OCH$_3$ | 1.39-1.47(2H, m), 1.86-2.00(3H, m), 2.29(2H, d, J=6.8 Hz), 2.41(4H, brs), 2.76(2H, t, J=12.0 Hz), 3.19(3H, s), 3.43(2H, s), 3.48(2H, brs), 3.60(4H, brs), 3.64(3H, s), 5.93(2H, s), 6.51(1H, dd, J=8.7 Hz, 2.5 Hz), 6.59(1H, d, J=2.5 Hz), 6.74-6.84(4H, m), 6.98(1H, d, J=8.6 Hz), 7.46(1H, dd, J=8.7 Hz, 2.6 Hz), 7.69-7.76(5H, m). |
| 2262 | 4-CF$_3$PhN(CH$_3$)SO$_2$— | —CH$_3$ | 1.34-1.45(2H, m), 1.85-2.01(3H, m), 2.07(3H, s), 2.29(2H, d, J=6.8 Hz), 2.41-2.43(4H, m), 2.73(2H, t, J=12.0 Hz), 3.22(3H, s), 3.43(2H, s), 3.46-3.77(6H, m), 5.94(2H, s), 6.74-6.94(7H, m), 7.29(2H, d, J=8.2 Hz), 7.58(2H, d, J=8.4 Hz), 7.68(1H, dd, J=8.7 Hz, 2.6 Hz), 8.38(1H, d, J=2.5 Hz). |

TABLE 361-continued

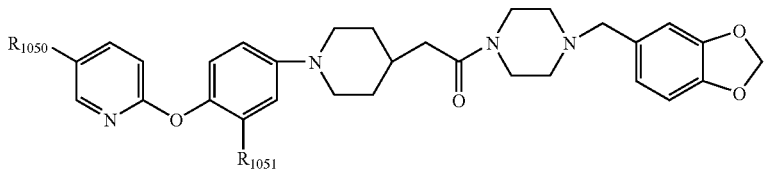

| Example No. | $R_{1050}$ | $R_{1051}$ | $^1$H NMR (CDCl$_3$) δppm |
|---|---|---|---|
| 2263 | 3,4-Cl$_2$PhSO$_2$N(CH$_3$)— | —CH$_3$ | 1.38-1.41(2H, m), 1.84-1.98(3H, m), 2.11(3H, s), 2.29(2H, d, J=6.8 Hz), 2.41(4H, brs), 2.72(2H, t, J=12.0 Hz), 3.19(3H, s), 3.43-3.64(8H, m), 5.94(2H, s), 6.74-6.85(6H, m), 6.93(1H, d, J=8.6 Hz), 7.39(1H, dd, J=8.4 Hz, 2.1 Hz), 7.49(1H, dd J=8.7 Hz, 2.8 Hz), 7.56(1H, d, J=8.4 Hz), 7.67(1H, d, J=2.0 Hz), 7.78(1H, d, J=2.3 Hz). |
| 2264 | 3,4-Cl$_2$PhSO$_2$N(CH$_3$)— | —OCH$_3$ | 1.39-1.47(2H, m), 1.85-2.02(3H, m), 2.29(2H, d, J=6.8 Hz), 2.39-2.44(4H, m), 2.76(2H, t, J=12.2 Hz), 3.19(3H, s), 3.43(2H, s), 3.49(2H, brs) 3.59-3.73(4H, m), 3.75(3H, s), 5.94(2H, s), 6.51(1H, dd, J=8.7 Hz, 2.6 Hz), 6.59(1H, d, J=2.6 Hz), 6.74-6.85(4H, m), 6.98(1H, d, J=8.6 Hz), 7.38(1H, dd, J=8.2 Hz, 2.0 Hz), 7.46(1H, dd, J=8.7 Hz, 2.8 Hz), 7.55(1H, d, J=8.4 Hz), 7.69(1H, d, J=2.1 Hz), 7.78(1H, d, J=2.8 Hz). |

TABLE 362

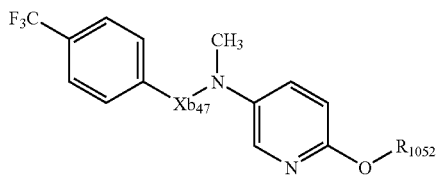

| Example No. | Xb$_{47}$ | R$_{1052}$ | $^1$H NMR (CDCl$_3$) δppm |
|---|---|---|---|
| 2265 | —CO— | ![structure] | 2.33(2H, d, J=5.1Hz), 2.38(2H, d, J=5.1Hz), 2.60(2H, t, J=5.1Hz), 2.96(2H, t, J=8.0Hz), 3.33-3.46(2H, m), 3.40 (2H, s), 3.47(3H, s), 3.62(2H, t, J=2.0Hz), 5.94(2H, s), 6.67-6.79(2H, m), 6.83(1H, d, J=8.7Hz), 6.84(1H, s), 6.99(2H, d, J=8.4Hz), 7.22(2H, d, J=8.4Hz), 7.34-7.45(1H, m), 7.40(2H, d, J=8.2Hz), 7.50(2H, d, J=8.2Hz), 7.85(1H, brs). |
| 2266 | —CO— | ![structure] | 3.17(3H, s), 3.21(3H, s), 3.48(3H, s), 6.70(1H, d, J=8.7Hz), 6.72-6.84(6H, m), 6.95(1H, t, J=7.4Hz), 7.07(2H, t, J=7.8Hz), 7.31-7.45(3H, m), 7.46-7.58(2H, m), 7.79-7.92(1H, m). |
| 2267 | —SO$_2$— | ![structure] | 1.78-2.04(4H, m), 2.11(3H, s), 2.44 (4H, brs), 2.53-2.76(3H, m), 3.19(3H, s), 3.53(4H, brs), 3.67(4H, brs), 6.76-6.81(3H, m), 6.93(1H, d, J=8.6Hz), 7.26-7.33(5H, m), 7.49(1H, dd, J=8.9Hz, 2.8 Hz), 7.70-7.79(5H, m). |

TABLE 363

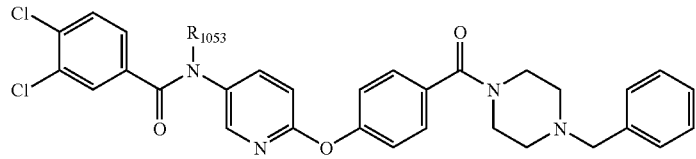

| Example No. | $R_{1053}$ | Form | $^1$H NMR (DMSO-$d_6$) δppm |
|---|---|---|---|
| 2268 | —CH$_3$ | free | 2.39(4H, brs), 3.32-3.51(9H, m), 7.08(1H, d, J=8.7Hz), 7.09(2H, d, J=8.4Hz), 7.25-7.31(6H, m), 7.41(2H, d, J=8.6Hz), 7.55-7.58(2H, m), 7.87(1H, dd, J=8.7Hz, 2.8Hz), 8.03(1H, brs). |
| 2269 | benzyl | hydro-chloride | 3.12-3.43(8H, m), 4.33(2H, s), 5.09(2H, s), 7.02(1H, d, J=8.7Hz), 7.07(2H, d, J=7.8Hz), 7.26-7.33(6H, m), 7.45-7.48(5H, m), 7.55-7.58(3H, m), 7.67(1H, brs), 7.77(1H, d, J=8.7Hz), 7.85(1H, brs), 11.09(1H, brs). |

Example 2270

Production of 1-(t-butoxycarbonyl)-4-{4-[4-(3,4-dichlorobenzoylamino)phenoxy]phenyl}-4-hydroxypiperidine To a solution of N-[4-(4-bromophenoxy)phenyl]-3,4-dichlorobenzamide (4.94 g, 11.3 mmol) in THF (100 mL) was stirred at −85° C., and added a solution of 2.46 M n-butyl lithium hexane (9.65 mL, 23.7 mmol) dropwise over 10 minutes. Upon stirring for 20 minutes at the same temperature, crystals were precipitated. To this reaction solution was added a solution of 1-(t-butoxycarbonyl)-4-piperidone (2.48 g, 12.4 mmol) in THF (20 mL). The temperature of the solution was raised over 3 hours to −40° C., and then aqueous saturated ammonium chloride was added to the solution. The resulting reaction solution was extracted with ethyl acetate, and dried over anhydrous magnesium sulfate. The solvent was then evaporated, and the residue was purified by silica gel column chromatography (ethyl acetate:n-hexane=2:3 to 1:1), to yield 2.30 g of a white powder. These crystals were washed with ether, to thereby yield 1.80 g of the title compound.

Appearance: White powder
Melting point: 208-209° C.

Example 2271

Production of 1-(t-butoxycarbonyl)-4-(4-{4-[4-(3,4-dichlorobenzoylamino)phenoxy]phenyl}-1,2,5,6-tetrahydropyridine To a solution of 1-(t-butoxycarbonyl)-4-{4-[4-(3,4-dichlorobenzoylamino)phenoxy]phenyl}-4-hydroxypiperidine (1.56 g, 2.80 mmol) in toluene (32 mL) was added p-toluenesulfonic acid hydrate (53 mg, 0.28 mmol), and the resulting solution was refluxed for 18 hours. The resulting reaction solution was purified by silica gel column chromatography (dichloromethane:methanol=20:1), to thereby yield 1.35 g of the title compound.

Appearance: White powder
Melting point: 173-174° C.

Example 2272

Production of 1-{4-[4-(3,4-dichlorobenzoylamino)-phenoxy]phenyl}-4-hydroxypiperidine To a solution of 1-{4-[4-(3,4-dichlorobenzoylamino)phenoxy]phenyl}-4-(methoxymethoxy)piperidine (5.50 g, 11.0 mmol) in ethanol (110 mL) was added 2 M hydrochloric acid (55 mL, 110 mmol), and the resulting solution was stirred for 8 hours at 60° C. To the resulting reaction solution was added potassium carbonate (16 g) at room temperature, and the solvent was evaporated under reduced pressure. Water (200 mL) was added to the residue. Precipitated crystals were collected by filtration, to thereby yield 5.0 g of the title compound.

Appearance: Pale brown powder
Melting point: 178-180° C.

Example 2273

Production of 1-(3-{4-[4-(3,4-dichlorobenzoylamino)-phenoxy]phenyl}propionyl)piperazine monohydrochloride To a solution of 1-(t-butoxycarbonyl)-4-(3-{4-[4-(3,4-dichlorobenzoylamino)phenoxy]phenyl}-propionyl)piperazine (2.40 g, 4.01 mmol) in dichloromethane (24 mL) was added trifluoroacetic acid (12 mL) under ice cooling, and the resulting solution was stirred for 3 hours at the same temperature. The solvent was evaporated. To the residue was added acetone (5 mL), and then added a saturated sodium bicarbonate solution to make the solution basic. The formed solids were collected by filtration and dried, whereby 2.00 g of a white powder free form was obtained. This free form (0.500 g) was dissolved in ethanol (10 mL) and 5 M hydrochloric acid (0.4 mL) by heating. The solvent was then evaporated, and the obtained solid was recrystallized from isopropanol, to thereby yield 0.388 g of the title compound.

Appearance: White powder
Melting point: 127-130° C.

The following compounds were produced in the same manner as in Example 2273.

TABLE 364

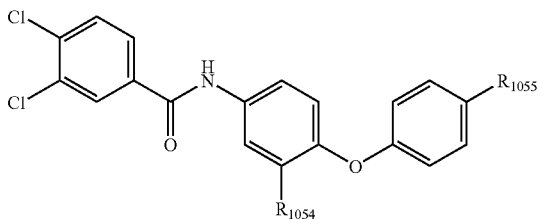

| Example No. | $R_{1054}$ | $R_{1055}$ | Form | mp (° C.) or $^1$H NMR (solvent) δppm |
|---|---|---|---|---|
| 2274 | —F | butyryl-piperazine | hydro-chloride | mp 149-151 |
| 2275 | —H | acetyl-piperazine | free | mp 198-199 |
| 2276 | —H | methyl-piperazine | free | mp 170-174 |
| 2277 | —H | methyl-tetrahydropyridine | free | $^1$H NMR (CDCl$_3$) 2.43-2.46(2H, m), 3.11(2H, t, J=5.5Hz), 3.53(2H, q, J=3Hz), 6.10(1H, m), 6.97(2H, d, J=8.5Hz), J=9.0Hz), 7.36(2H, d, J=8.5Hz), 7.56-7.59(3H, m), 7.68-7.69(2H, m), 7.97(1H, d, J=2.0Hz). |
| 2278 | —H | N-methyl-piperidinyl-NHCH$_3$ | free | $^1$H NMR (DMSO-d$_6$) 1.32-1.36(2H, m), 1.85-1.91(2H, m), 2.32(3H, s), 2.45(1H, m), 2.66-2.71(2H, m), 3.54-3.56(2H, m), 4.13(1H, m), 6.89-6.97(6H, m), 7.65-7.71(3H, m), 7.82(1H, d, J=8.5Hz), 7.93(1H, dd, J=8.5Hz, 2.0Hz), 8.21(1H, d, J=2.0Hz), 10.36(1H, s). |
| 2279 | —H | 4-methyl-piperidine | free | $^1$H NMR (CDCl$_3$) 1.63(2H, m), 1.83(2H, brd, J=14.0Hz), 2.61(1H, m), 2.75(2H, dt, J=2.5Hz, 12.0Hz), 3.20(2H, brd, J=12.0Hz), 6.95(2H, d, J=8.5Hz), 7.03(2H, d, J=9.0 Hz), 7.19(2H, d, J=8.5Hz), 7.55(1H, d, J=8.0Hz), 7.58(2H, d, J=8.5Hz), 7.69(1H, dd, J=8.0Hz, 2.0Hz), 7.69(1H, brs), 7.97(1H, d, J=2.0Hz). |

TABLE 365

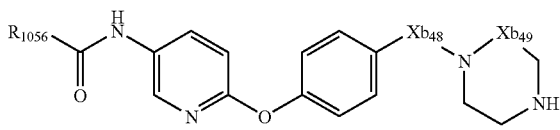

| Example No. | $R_{1056}$ | $Xb_{48}$ | $Xb_{49}$ | Form | $^1$H NMR (solvent) δppm |
|---|---|---|---|---|---|
| 2280 | 3,4-Cl$_2$Ph— | none | —CO— | trifluoro-acetate | (DMSO-d$_6$) 3.56(2H, brs), 3.87(2H, m), 3.92(2H, brs), 7.14(1H, d, J=8.8Hz), 7.20(2H, dd, J=6.7Hz, 2.2Hz), 7.35(2H, dd, J=6.7Hz, 2.2Hz), 7.85(1H, d, J=8.4Hz), 7.95(1H, dd, J=8.4Hz, 2.1Hz), 8.22(1H, dd, J=8.8Hz, 2.7Hz), 8.23(1H, d, J=2.1Hz), |

TABLE 365-continued

![Structure: R1056-C(=O)-NH-pyridine-O-phenyl-Xb48-N(Xb49)-piperazine-NH]

| Example No. | R1056 | Xb48 | Xb49 | Form | $^1$H NMR (solvent) δppm |
|---|---|---|---|---|---|
| 2281 | 4-CF$_3$Ph— | none | —CH$_2$— | free | 8.51(1H, d, J=2.7Hz), 9.30(2H, brs), 10.59(1H, s). (CDCl$_3$) 3.07(4H, t, J=5.0Hz), 3.15(4H, t, J=5.0Hz), 6.92(1H, d, J=9.0Hz), 6.96(2H, d, J=9.0Hz), 7.06(2H, d, J=9.0Hz), 7.77(1H, brs), 7.78(2H, d, J=8.0Hz), 7.99(2H, d, J=8.0Hz), 8.19(1H, brd, J=9.0Hz), 8.25(1H, d, J=2.5Hz). |
| 2282 | 3,4-Cl$_2$Ph— | none | —CH$_2$— | free | (CDCl$_3$) 3.18(4H, dd, J=5.5Hz, 2.5Hz), 3.16(4H, dd, J=5.5Hz, 2.5Hz), 6.90(1H, d, J=9.0Hz), 6.95(2H, d, J=9.0Hz), 7.05(2H, d, J=9.0Hz), 7.58(1H, d, J=8.5Hz), 7.71(1H, dd, J=8.5Hz, 2.0Hz), 7.88(1H, brs), 7.98(1H, d, J=2.0Hz), 8.16(1H, dd, J=9.0Hz, 2.5Hz), 8.24(1H, d, J=2.5Hz). |
| 2283 | 3,4-Cl$_2$Ph— | —CH$_2$— | —CH$_2$— | free | (DMSO-d$_6$) 2.45-2.47(4H, m), 2.88-2.92(4H, m), 3.49(2H, s), 7.05-7.09(3H, m), 7.33(2H, d, J=8.6Hz), 7.84(1H, d, J=8.6Hz), 7.95-7.99(1H, m), 8.18-8.25(2H, m), 8.51(1H, d, J=2.6Hz), 10.62(1H, s). |
| 2284 | 3,4-Cl$_2$Ph— | —CO— | —CH$_2$— | free | (DMSO-d$_6$) 2.69(4H, brs), 3.40(4H, brs), 7.12-7.17(3H, m), 7.41-7.44(2H, m), 7.84(1H, d, J=8.4Hz), 7.96(1H, dd, J=8.4Hz, 2.2Hz), 8.21-8.26(2H, m), 8.52(1H, d, J=2.7Hz), 10.62(1H, brs). |
| 2285 | 4-CF$_3$Ph— | —CH$_2$— | —CH$_2$— | free | (DMSO-d$_6$) 2.44-2.46(4H, m), 2.89-2.92(4H, m), 3.49(2H, s), 4.79(1H, brs), 7.06-7.09(3H, m), 7.33(2H, d, J=8.6Hz), 7.94(2H, d, J=8.1Hz), 8.16-8.25(3H, m), 8.52(1H, d, J=2.7Hz), 10.65 (1H, s). |
| 2286 | 3,4-(CH$_3$)$_2$Ph— | —CO— | —CH$_2$— | free | (DMSO-d$_6$) 2.29(3H, s), 2.30(3H, s), 2.73(4H, brs), 3.44(4H, brs), 7.09-7.16(3H, m), 7.29(1H, d, J=7.9Hz), 7.40-7.44(2H, m), 7.69-7.72(1H, m), 7.75(1H, brs), 8.22-8.26(1H, m), 8.53(1H, d, J=2.8Hz), 10.31(1H, s). |

TABLE 366

![Structure: R1057-pyridine-O-phenyl-(CH2)M-Xb50-N-piperazine-NH]

| Example No. | R1057 | Xb50 | M | $^1$H NMR (solvent) δppm |
|---|---|---|---|---|
| 2287 | 3,4-Cl$_2$PhCH$_2$N(CH$_3$)— | none | 1 | (DMSO-d$_6$) 2.51-2.54(4H, m), 3.00(3H, s), 3.06-3.08(4H, m), 3.50(2H, s), 4.55(2H, s), 6.88(1H, d, J=8.9Hz), 6.94(2H, d, J=8.4 Hz), 7.19-7.32(4H, m), 7.49(1H, d, J=1.5Hz), 7.58(1H, d, J=8.2Hz), 7.64(1H, d, J=3.1Hz), 8.73(1H, brs). |
| 2288 | 4-CF$_3$PhCONH— | none | 3 | (CDCl$_3$) 1.77-1.96(6H, m), 2.35-2.44(6H, m), 2.61-2.66(2H, m), 6.92(1H, d, J=8.6Hz), 7.01-7.05(2H, m), 7.17-7.23(2H, m), 7.74(2H, d, J=8.4Hz), 8.00(2H, d, J=8.4Hz), |

TABLE 366-continued

R₁₀₅₇—[pyridine]—O—[phenyl]—[CH₂]ₘ—Xb₅₀—[piperazine]NH

| Example No. | R₁₀₅₇ | Xb₅₀ | M | ¹H NMR (solvent) δppm |
|---|---|---|---|---|
| 2289 | 3,4-Cl₂PhCONH— | —CO— | 2 | (DMSO-d₆) 2.59-2.69(6H, m), 2.79-2.85(2H, m), 3.37-3.43(4H, m), 4.31(1H, brs), 7.00-7.06(3H, m), 7.27(2H, d, J=8.6Hz), 7.84(1H, d, J=8.4Hz), 7.95(1H, dd, J=8.4Hz, 2.1Hz), 8.16-8.22(2H, m), 8.21(1H, dd, J=8.6Hz, 2.6Hz), 8.27-8.28(2H, m). 8.46(1H, d, J=2.3Hz), 10.54(1H, s). |
| 2290 | 4-CF₃PhCONH— | —COCO— | 1 | (CDCl₃) 1.69(1H, brs), 2.51(2H, t, J=5.1Hz), 2.77(2H, t, J=5.1Hz), 3.15(2H, t, J=5.1Hz), 3.53(2H, t, 5.1Hz), 4.05(2H, s), 6.98(1H, d, J=8.7Hz), 7.11(2H, d, J=8.5Hz), 7.29(2H, d, J=8.5Hz), 7.76(2H, d, J=8.2Hz), 7.99(2H, d, J=8.2Hz), 8.01(1H, brs), 8.21(1H, dd, J=8.7Hz, 2.7Hz), 8.25(1H, d, J=2.7Hz). |

Example 2291

[3-(4-{5-[3-(3,4-Dichlorophenyl)ureido]pyridin-2-yloxy}-3-methylphenyl)-2-oxotetrahydropyrimidin-1-yl]acetic acid ¹H NMR (DMSO-d₆) δ 1.87-2.15 (5H, m), 3.25-3.47 (2H, m), 3.58-3.75 (2H, m), 3.95 (2H, s), 6.82-7.00 (2H, m), 7.01-7.12 (1H, m), 7.17 (1H, d, J=2.4 Hz), 7.29-7.32 (1H, m), 7.50 (1H, d, J=8.8 Hz), 7.85 (1H, d, J=2.4 Hz), 7.89-8.02 (1H, m), 8.11 (1H, d, J=2.7 Hz), 8.95 (1H, s), 9.17 (1H, s), 12.50 (1H, s).

The following compounds were produced in the same manner as in Reference Example 922.

TABLE 367

R₁₀₅₈—C(=O)—NH—[pyridine]—O—[phenyl]—R₁₀₅₉ · 2HCl

| Example No. | R₁₀₅₈ | R₁₀₅₉ | ¹H NMR (DMSO-D₆) δppm |
|---|---|---|---|
| 2292 | 3,4-Cl₂Ph— | 1-acetyl-4-(N-methylamino)piperidin-4-yl | 1.40-1.65(2H, m), 1.95-2.18(2H, m), 2.40-2.65(3H, m), 3.00(2H, brs), 3.25(1H, brs), 3.85(1H, brs), 4.40(1H, brs), 7.15(1H, d, J=9.0Hz), 7.19(2H, d, J=8.7Hz), 7.43(2H, d, J=8.7Hz), 7.84(1H, d, J=8.4Hz), 7.99(1H, dd, J=8.4Hz, 2.0Hz), 8.22-8.30(2H, m), 8.56(1H, d, J=2.0Hz), 10.71(1H, s). |
| 2293 | 3,4-Cl₂Ph— | N-methyl-piperidine-4-carboxamide | 1.70-2.05(4H, m), 2.60-2.80(1H, m), 2.80-3.05(2H, m), 3.44(2H, d, J=7.1Hz), 7.03(1H, d, J=8.7Hz), 7.07(2H, d, J=8.9Hz), 7.65(2H, d, J=8.9Hz), 7.84(1H, d, J=8.4Hz), 7.98(1H, dd, J=8.4Hz, 2.0Hz), 8.20(1H, dd, J=8.7Hz, 2.7Hz), 8.26(1H, d, J=2.0Hz), 8.50(1H, d, J=2.7Hz), 10.22(1H, s), 10.65(1H, s). |
| 2294 | 4-CF₃Ph— | 4-(N-methyl-acetamido)piperidine | 1.75-1.90(2H, m), 1.95-2.30(2H, m), 2.84(3H, s), 2.70-3.15(2H, m), 3.20-3.42(2H, m), 4.55(1H, brs), 6.51(1H, brs), 7.16(1H, d, J=8.8Hz), 7.17(2H, d, J=8.4Hz), 7.47(2H, d, J=8.4Hz), 7.94(2H, d, J=8.1Hz), 8.22(2H, d, J=8.1Hz), 8.31(1H, dd, J=8.8Hz, 2.6Hz), 8.60(1H, d, J=2.6Hz), 10.84(1H, s). |

TABLE 368

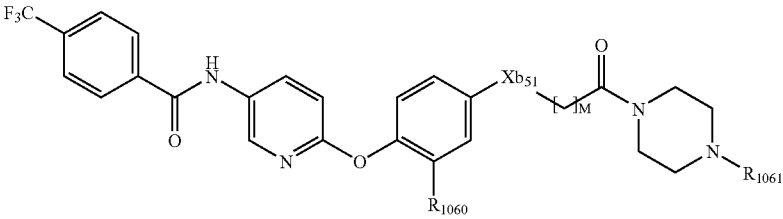

| Example No. | $R_{1060}$ | $R_{1061}$ | $Xb_{51}$ | M | Form | $^1$H NMR (solvent) δppm |
|---|---|---|---|---|---|---|
| 2295 | —H | —H | none | 0 | dihydrochloride | (DMSO-$d_6$) 3.16(4H, brs), 3.75(4H, brs), 7.16(1H, d, J=8.9Hz), 7.19(2H, d, J=8.7Hz), 7.53(2H, d, J=8.7Hz), 7.93(2H, d, J=8.1Hz), 8.21 (2H, d, J=8.1Hz), 8.30(1H, dd, J=8.9Hz, 2.5Hz), 8.60(1H, d, J=2.5Hz), 10.81(1H, s). |
| 2296 | —H | —H | none | 2 | dihydrochloride | (DMSO$d_6$) 2.68(1H, d, J=6.5Hz), 2.71(1H, d, J=8.4Hz), 2.82(1H, d, J=8.4Hz), 2.84(1H, d, J=6.5Hz), 3.04(4H, brs), 3.70(4H, t, J=5.0Hz), 7.03(2H, d, J=8.6Hz), 7.05(1H, d, J=8.9Hz), 7.29(2H, d, J=8.6Hz), 7.41(1H, brs), 7.92 (2H, d, J=8.5Hz), 8.21(2H, d, J=8.5Hz), 8.25(1H, dd, J=8.9Hz, 2.8Hz), 8.54(1H, d, J=2.8Hz), 10.80(1H, s). |
| 2297 | —CH$_3$ | —H | —N(CH$_3$)— | 1 | free | (CDCl$_3$) 2.11(3H, s), 2.74-2.96(4H, m), 3.01(3H, s), 3.39-3.70(4H, m), 4.08(2H, s), 6.54(1H, dd, J=8.6Hz, 3.0Hz), 6.57(1H, d, J=3.0Hz), 6.81 (1H, d, J=8.9Hz), 6.91(1H, d, J=8.6Hz), 7.75(2H, d, J=8.2Hz), 7.93-8.02(3H, m), 8.13(1H, dd, J=8.9Hz, 2.7Hz), 8.24(1H, d, J=2.7Hz). |
| 2298 | —H | —CH$_2$CONHNH$_2$ | none | 0 | trihydrochloride | (DMSO-$d_6$) 3.42(4H, brs), 3.75(4H, brs), 4.21(2H, s), 7.17(1H, d, J=8.8Hz), 7.21(2H, d, J=8.6Hz), 7.53 (2H, d, J=8.6Hz), 7.94(2H, d, J=8.1Hz), 8.22(2H, d, J=8.1Hz), 8.31(1H, dd, J=8.8Hz, 2.6Hz), 8.62(1H, d, J=2.6Hz), 10.87(1H, s). |

Example 2299

Production of 1-(3-{4-[4-(3,4-dichlorobenzoylamino)-phenoxy]phenyl}propionyl)-4-piperonylpiperazine monohydrochloride To a suspension consisting of 1-(3-{4-[4-(3,4-dichlorobenzoylamino)phenoxy]phenyl}propionyl)-piperazine (0.500 g, 1.00 mmol) and diisopropyl-ethylamine (0.262 mL, 1.50 mmol) in acetonitrile (12 mL) was added piperonyl chloride (0.188 g, 1.10 mmol), and the resulting solution was heated to reflux for 1.5 hours. Water was added to this reaction solution, and extracted with ethyl acetate. The ethyl acetate layer was washed with brine, dried over anhydrous magnesium sulfate, and evaporated. The residue was purified by silica gel column chromatography (dichloromethane:methanol=30:1), to thereby yield 0.486 g of a free form. This free form was dissolved in ethanol (10 mL) and 5 M hydrochloric acid (0.3 mL) by heating. The solvent was then evaporated, and the obtained solid was recrystallized from 90% ethanol (17.5 mL), to thereby yield 0.322 g of the title compound.

Appearance: White powder
Melting point: 221-224° C.

A crude titled product (9.95 g, 14.9 mmol) obtained using the same procedures was recrystallized from 80% ethanol (350 mL), to thereby yield 9.37 g of the title compound.

Appearance: White powder
Melting point: 232-234° C.

The following compounds were produced in the same manner as in Example 2299.

TABLE 369

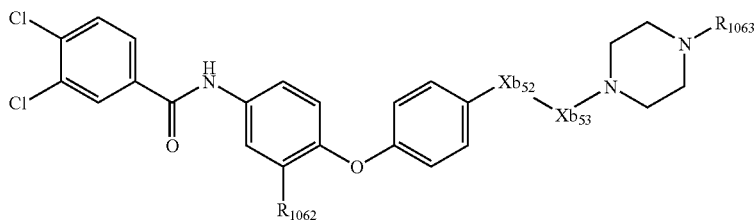

| Example No. | $R_{1062}$ | $Xb_{52}$ | $Xb_{53}$ | $R_{1063}$ | Form | mp (° C.) or $^1$H NMR (CDCl$_3$) δppm |
|---|---|---|---|---|---|---|
| 2300 | —H | —(CH$_2$)$_2$— | —CO— | —(CH$_2$)$_2$Ph— | hydrochloride | mp 205-207 |
| 2301 | —H | —(CH$_2$)$_2$— | —CO— | —(CH$_2$)$_2$OH— | hydrochloride | mp 101-105 |
| 2302 | —H | —(CH$_2$)$_2$— | —CO— | —(CH$_2$)$_2$Ph— | ½ fumarate | mp 156-159 |
| 2303 | —F | —(CH$_2$)$_2$— | —CO— | 4-CH$_3$PhCH$_2$— | free | mp 105-107 |
| 2304 | —F | —(CH$_2$)$_2$— | —CO— | 4-CH$_3$OPhCH$_2$— | free | mp 137-139 |
| 2305 | —F | —(CH$_2$)$_2$— | —CO— | 2-CF$_3$PhCH$_2$— | free | mp 130-132 |
| 2306 | —F | —(CH$_2$)$_2$— | —CO— | 2-naphthylmethyl | hydrochloride | mp 172-175 |
| 2307 | —H | —(CH$_2$)— | —CO— | —CH$_2$COOC$_2$H$_5$ | free | $^1$H NMR 1.25(3H, t, J=7.1Hz), 2.39-2.53(4H, m), 2.58(2H, t, J=7.8Hz), 2.90(2H, t, J=7.8Hz), 3.19(2H, s), 3.36-3.48(2H, m), 3.58-3.69(2H, m), 4.16(2H, q, J=7.1Hz), 6.89(2H, d, J=8.6Hz), 6.96(2H, d, J=8.9Hz), 7.12 (2H, d, J=8.6Hz), 7.47-7.59(3H, m), 7.69(1H, dd, J=8.3Hz, 2.1Hz), 7.96 (1H, d, J=2.1Hz), 8.14(1H, brs). |
| 2308 | —H | none | —CO— | —(CH$_2$)$_2$Ph | hydrochloride | mp 210-218 |
| 2309 | —H | none | none | —(CH$_2$)$_2$Ph | free | mp 214-215 |
| 2310 | —H | none | none | benzyl | free | mp 189-190 |
| 2311 | —H | none | none | —(CH$_2$)$_3$Cl | free | $^1$H NMR 2.00(2H, m), 2.56(2H, t, J=7.0Hz), 2.62-2.64(4H, m), 3.16-3.18(4H, m), 3.64(2H, t, J=7.0Hz), 6.92(2H, d, J=7.0Hz), 6.95-6.98(4H, m), 7.52(2H, d, J=9.0Hz), 7.57(1H, d, J=8.0Hz), 7.69(1H, dd, J=8.0Hz, 2.0Hz), 7.70(1H, s), 7.96(1H, d, J=2.0Hz). |
| 2312 | —H | none | none | —CH$_2$COOC$_2$H$_5$ | free | $^1$H NMR 1.30(3H, t, J=7.0Hz), 2.76(4H, t, J=5.0Hz), 3.21(4H, t, J=5.0Hz), 3.28(2H, s), 4.21(2H, q, J=7.0Hz), 6.91-6.98(6H, m), 7.52(2H, d, J=9.0Hz), 7.57(1H, d, J=8.5Hz), 7.69 (1H, dd, J=8.5Hz, 2.0Hz), 7.72(1H, brs), 7.96(1H, d, J=2.0Hz). |

TABLE 370

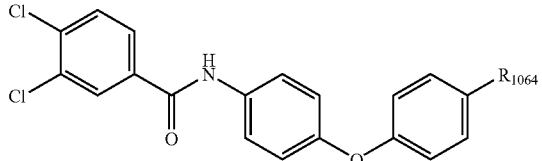

| Example No. | R<sub>1064</sub> | mp (° C.) or $^1$H NMR (CDCl$_3$) δppm |
|---|---|---|
| 2313 | 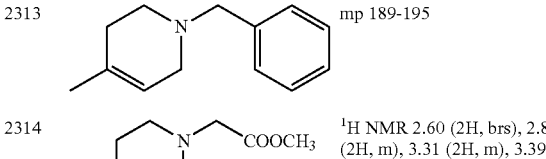 | mp 189-195 |
| 2314 | 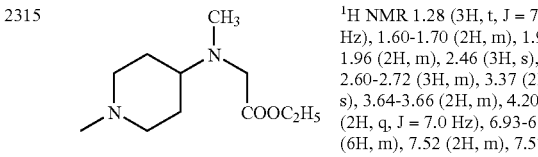 | $^1$H NMR 2.60 (2H, brs), 2.85 (2H, m), 3.31 (2H, m), 3.39 (2H, s), 3.76 (3H, s), 6.00 (1H, brs), 6.95 (2H, d, J = 8.5 Hz), 7.03 (2H, d, J = 8.5 Hz), 7.34 (2H, d, J = 8.5 Hz), 7.57 (2H, d, J = 8.5 Hz), 7.57 (1H, brs), 7.70 (1H, d, J = 7.0 Hz), 7.75 (1H, brs), 7.97 (1H, s). |
| 2315 | 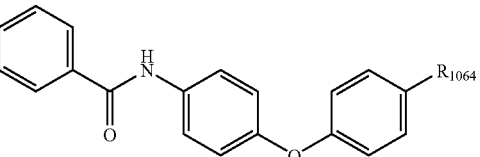 | $^1$H NMR 1.28 (3H, t, J = 7.0 Hz), 1.60-1.70 (2H, m), 1.93-1.96 (2H, m), 2.46 (3H, s), 2.60-2.72 (3H, m), 3.37 (2H, s), 3.64-3.66 (2H, m), 4.20 (2H, q, J = 7.0 Hz), 6.93-6.98 (6H, m), 7.52 (2H, m), 7.57 (1H, d, J = 8.5 Hz), 7.68-7.70 (2H, m), 7.96 (1H, d, J = 2.0 Hz). |

TABLE 370-continued

| Example No. | R<sub>1064</sub> | mp (° C.) or $^1$H NMR (CDCl$_3$) δppm |
|---|---|---|
| 2316 | (N-piperidinyl-CH$_2$-COOC$_2$H$_5$, 4-methyl) | $^1$H NMR 1.29 (3H, t, J = 7.0 Hz), 1.81-1.88 (4H, m), 2.30 (2H, brt, J = 11.0 Hz), 2.49 (1H, m), 3.06 (2H, brd, J = 11.0 Hz), 4.21 (2H, q, J = 7.0 Hz), 6.94 (2H, d, J = 8.5 Hz), 7.01 (2H, d, J = 9.0 Hz), 7.18 (2H, d, J = 8.5 Hz), 7.55-7.68 (3H, m), 7.69 (1H, d, J = 2.0 Hz), 7.75 (1H, brs), 7.97 (1H, d, J = 2.0 Hz). |
| 2317 | (tetrahydropyridinyl-CH$_2$CH$_2$CH$_2$Cl) | $^1$H NMR 2.04 (2H, m), 2.56 (2H, brs), 2.62 (2H, t, J = 7.0 Hz), 2.72 (2H, t, J = 5.5 Hz), 3.17 (2H, brs), 3.64 (2H, t, J = 6.5 Hz), 6.02 (1H, brs), 6.96 (2H, d, J = 9.0 Hz), 7.04 (2H, d, J = 9.0 Hz), 7.36 (2H, d, J = 9.0 Hz), 7.58 (3H, m), 7.70 (1H, dd, J = 8.5 Hz, 2.0 Hz), 7.77 (1H, brs), 7.98 (1H, d, J = 2.0 Hz). |

TABLE 371

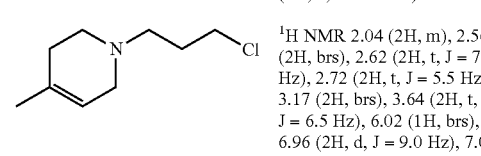

| Example No. | R<sub>1065</sub> | R<sub>1066</sub> | $^1$H NMR (solvent) δppm |
|---|---|---|---|
| 2318 | 4-CF$_3$Ph— | —(CH$_2$)$_2$Ph | (DMSO-d$_6$) 2.31-2.60 (6H, m), 2.67-2.81 (2H, m), 3.51 (4H, brs), 7.16 (1H, d, J = 8.8 Hz), 7.17 (2H, d, J = 8.5 Hz), 7.10-7.33 (5H, m), 7.44 (2H, d, J = 8.5 Hz), 7.94 (2H, d, J = 8.2 Hz), 8.17 (2H, d, J = 8.2 Hz), 8.26 (1H, dd, J = 8.8 Hz, 2.6 Hz), 8.55 (1H, d, J = 2.6 Hz), 10.67 (1H, s). |
| 2319 | 3,4-Cl$_2$Ph— | 4-CNPhCH$_2$— | (CDCl$_3$) 2.46 (4H, brs), 3.59 (2H, s), 3.75 (4H, brs), 6.97 (1H, d, J = 8.9 Hz), 7.11-7.14 (2H, m), 7.40-7.43 (2H, m), 7.46 (2H, d, J = 7.8 Hz), 7.56-7.65 (3H, m), 7.72-7.76 (1H, m), 8.02 (1H, d, J = 2.2 Hz), 8.16 (1H, dd, J = 8.9 Hz, 2.7 Hz), 8.27 (1H, brs), 8.30 (1H, d, J = 2.7 Hz). |
| 2320 | 3,4-Cl$_2$Ph— | —CH$_2$COPh | (CDCl$_3$) 2.65 (4H, brs), 3.60-3.82 (4H, m), 3.89 (2H, s), 6.99 (1H, d, J = 8.7 Hz), 7.15 (2H, d, J = 8.6 Hz) 7.43-7.50 (4H, m) 7.56-7.60 (2H, m), 7.72-7.76 (1H, m), 7.97-8.02 (3H, m), 8.13-8.21 (2H, m), 8.30 (1H, d, J = 2.5 Hz). |
| 2321 | 3,4-Cl$_2$Ph— | 3,4-(CH$_3$)$_2$PhCH$_2$— | (CDCl$_3$) 2.25 (3H, s), 2.26 (3H, s), 2.44 (4H, brs), 3.47 (2H, s), 3.73 (4H, brs), 6.89 (1H, d, J = 8.9 Hz), 7.01-7.10 (5H, m), 7.32-7.36 (2H, m), 7.51 (1H, d, J = 8.4 Hz), 7.74-7.78 (1H, m), 8.05 (1H, d, J = 8.1 Hz), 8.09 (1H, dd, J = 8.8 Hz, 2.7 Hz), 8.30 (1H, d, J = 2.7 Hz), 9.06 (1H, brs). |

TABLE 371-continued $R_{1065}$—C(=O)—NH—[pyridine(N, O-linked)]—O—[phenyl]—C(=O)—N[piperazine]N—$R_{1066}$

| Example No. | $R_{1065}$ | $R_{1066}$ | $^1$H NMR (solvent) δppm |
|---|---|---|---|
| 2322 | 3,4-Cl$_2$Ph— | 4-C(CH$_3$)$_3$COPhCH$_2$— | (CDCl$_3$) 1.36 (9H, s), 2.48 (4H, brs), 3.58 (2H, s), 3.70 (4H, brs), 6.96 (1H, d, J = 8.7 Hz), 7.11-7.14 (2H, m), 7.39-7.43 (4H, m), 7.57 (1H, d, J = 8.4 Hz), 7.69 (2H, d, J = 8.3 Hz), 7.73-7.77 (1H, m), 8.03 (1H, d, J = 2.0 Hz), 8.15 (1H, dd, J = 8.9 Hz, 2.7 Hz), 8.30 (1H, d, J = 2.7 Hz), 8.37 (1H, brs). |
| 2323 | 3,4-Cl$_2$Ph— | 4-PhCH$_2$OPhCH$_2$— | (CDCl$_3$) 2.45 (4H, brs), 3.49 (2H, s), 3.73 (4H, brs), 5.06 (2H, s), 6.92-6.98 (3H, m), 7.11-7.15 (2H, m), 7.23 (2H, d, J = 8.6 Hz), 7.32-7.46 (7H, m), 7.57 (1H, d, J = 8.1 Hz), 7.75 (1H, dd, J = 8.4 Hz, 2.2 Hz), 8.03 (1H, d, J = 2.2 Hz), 8.16 (1H, dd, J = 8.9 Hz, 2.7 Hz), 8.26 (1H, brs), 8.29 (1H, d, J = 2.7 Hz). |
| 2324 | 3,4-Cl$_2$Ph— | 4-C(CH$_3$)$_3$PhCH$_2$— | (CDCl$_3$) 1.32 (9H, s), 2.48 (4H, brs), 3.53 (2H, s) 3.70 (4H, brs), 6.98 (1H, d, J = 8.4 Hz), 7.13 (2H, d, J = 8.6 Hz), 7.21-7.27 (2H, m), 7.36 (2H, d, J = 8.4 Hz), 7.43 (2H, d, J = 8.6 Hz) 7.59 (1H, d, J = 8.1 Hz), 7.72-7.76 (1H, m), 8.02 (1H, d, J = 2.2 Hz), 8.13 (1H, brs), 8.16-8.20 (1H, m), 8.30 (1H, d, J = 2.2 Hz). |
| 2325 | 3,4-Cl$_2$Ph— | 3-CH$_3$PhCH$_2$— | (CDCl$_3$) 2.36 (3H, s), 2.47 (4H, brs), 3.52 (2H, s), 3.74 (4H, brs), 6.97 (1H, d, J = 8.7 Hz), 7.08-7.26 (6H, m), 7.41-7.44 (2H, m), 7.58 (1H, d, J = 8.4 Hz), 7.76 (1H, dd, J = 8.4 Hz, 2.1 Hz), 8.04 (1H, d, J = 2.1 Hz), 8.14-8.19 (1H, m), 8.26 (1H, brs), 8.30 (1H, d, J = 2.2 Hz). |

TABLE 372

$R_{1067}$—C(=O)—NH—[pyridine(N, O-linked)]—O—[phenyl]—C(=O)—N[piperazine]N—$R_{1068}$

| Example No. | $R_{1067}$ | $R_{1068}$ | $^1$H NMR (CDCl$_3$) δppm |
|---|---|---|---|
| 2326 | 3,4-Cl$_2$Ph— | 4-CH(CH$_3$)$_2$PhCH$_2$— | 1.25 (6H, d, J = 7.3 Hz), 2.46 (4H, brs), 2.85-2.96 (1H, m), 3.52 (2H, s), 3.75 (4H, brs), 6.95 (1H, d, J = 8.9 Hz) 7.10-7.13 (2H, m), 7.17-7.26 (4H, m), 7.38-7.42 (2H, m), 7.57 (1H, d, J = 8.1 Hz), 7.75 (1H, dd, J = 8.4 Hz, 2.2 Hz), 8.04 (1H, d, J = 2.2 Hz), 8.14 (1H, dd, J = 8.9 Hz, 2.7 Hz), 8.30 (1H, d, J = 2.7 Hz), 8.41 (1H, brs). |
| 2327 | 3,4-Cl$_2$Ph— | 4-CH$_3$PhCH$_2$— | 2.34 (3H, s), 2.45 (4H, brs), 3.51 (2H, s), 3.73 (4H, brs), 6.93 (1H, d, J = 8.7 Hz), 7.07-7.22 (6H, m), 7.35-7.38 (2H, m), 7.54 (1H, d, J = 8.4 Hz), 7.77 (1H, dd, J = 8.4 Hz, 2.2 Hz), 8.05 (1H, d, J = 2.2 Hz), 8.12 (1H, dd, J = 8.9 Hz, 2.7 Hz), 8.30 (1H, d, J = 2.7 Hz), 8.82 (1H, s). |
| 2328 | 3,4-Cl$_2$Ph— | 3,4-F$_2$PhCH$_2$— | 2.45 (4H, brs), 3.49-3.73 (6H, m), 6.96 (1H, d, J = 8.7 Hz), 7.01-7.23 (5H, m), 7.39-7.42 (2H, m), 7.56 (1H, d, J = 8.4 Hz), 7.76 (1H, dd, J = 8.4 Hz, 2.1 Hz), 8.03 (1H, d, J = 2.1 Hz), 8.17 (1H, dd, J = 8.7 Hz, 2.7 Hz), 8.30 (1H, d, J = 2.7 Hz), 8.50 (1H, s). |
| 2329 | 3,4-Cl$_2$Ph— | 4-CH$_3$OPhCH$_2$— | 2.43 (4H, brs), 3.48 (2H, s), 3.73 (4H, brs), 3.81 (3H, s), 6.85-6.93 (3H, m), 7.06-7.10 (2H, m), 7.21-7.24 (2H, m) 7.34-7.37 (2H, m), 7.53 (1H, d, J = 8.4 Hz), 7.77 (1H, dd, J = 8.4 Hz, 2.1 Hz), 8.05 (1H, d, J = 2.1 Hz), 8.10 (1H, dd, J = 8.9 Hz, 2.7 Hz), 8.30 (1H, d J = 2.7 Hz) 8.90 (1H, s). |

TABLE 372-continued

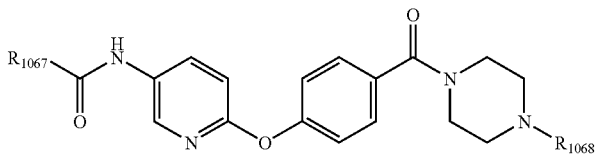

| Example No. | $R_{1067}$ | $R_{1068}$ | $^1$H NMR (CDCl$_3$) δppm |
|---|---|---|---|
| 2330 | 4-CF$_3$Ph— | 4-CF$_3$PhCH$_2$— | 2.48 (4H, brs), 3.60 (2H, s), 3.70 (4H, brs), 7.00 (1H, d, J = 8.9 Hz), 7.12-7.17 (2H, m), 7.41-7.48 (4H, m), 7.60 (2H, d, J = 7.9 Hz), 7.77 (2H, d, J = 8.1 Hz), 8.02 (2H, d, J = 8.1 Hz), 8.14 (1H, brs), 8.19-8.24 (1H, m), 8.32 (1H, d, J = 2.3 Hz). |
| 2331 | 4-CF$_3$Ph— | 3,4-(CH$_3$)$_2$PhCH$_2$— | 2.25 (3H, s), 2.26 (3H, s), 2.45 (4H, brs), 3.47 (2H, s), 3.40-3.90 (4H, m), 6.98 (1H, d, J = 8.7 Hz), 6.97-7.10 (3H, m), 7.13 (2H, d, J = 8.7 Hz), 7.42 (2H, d, J = 8.7 Hz), 7.76 (2H, d, J = 8.1 Hz), 8.02 (2H, d, J = 8.1 Hz), 8.18 (1H, brs), 8.20 (1H, dd, J = 8.7 Hz, 2.5 Hz), 8.31 (1H, d, J = 2.5 Hz). |
| 2332 | 4-CF$_3$Ph— | 3-CH$_3$PhCH$_2$— | 2.35 (3H, s), 2.46 (4H, brs), 3.35-3.90 (4H, m), 3.50 (2H, s), 6.98 (1H, d, J = 8.9 Hz), 7.12 (2H, d, J = 8.6 Hz), 7.05-7.30 (4H, m), 7.41 (2H, d, J = 8.6 Hz), 7.76 (2H, d, J = 8.1 Hz), 8.02 (2H, d, J = 8.1 Hz), 8.19 (1H, dd, J = 8.9 Hz, 2.6 Hz), 8.28 (1H, brs), 8.31 (1H, d, J = 2.6 Hz). |
| 2333 | 4-CF$_3$Ph— | 4-CH$_3$PhCH$_2$— | 2.34 (3H, s) 2.44 (4H, brs), 3.50 (2H, s), 3.35-3.85 (4H, m), 6.97 (1H, d, J = 8.9 Hz), 7.12 (2H, d, J = 8.8 Hz), 7.12 (2H, d, J = 8.1 Hz), 7.20 (2H, d, J = 8.1 Hz), 7.40 (2H, d, J = 8.8 Hz), 7.75 (2H, d, J = 8.1 Hz), 8.02 (2H, d, J = 8.1 Hz), 8.18 (1H, dd, J = 8.9 Hz, 2.5 Hz), 8.32 (1H, d, J = 2.5 Hz), 8.38 (1H, s). |

TABLE 373

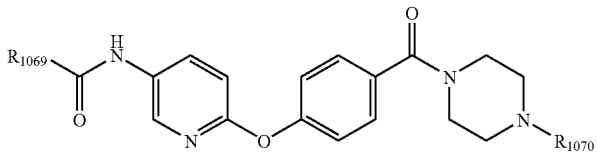

| Example No. | $R_{1069}$ | $R_{1070}$ | $^1$H NMR (CDCl$_3$) δppm |
|---|---|---|---|
| 2334 | 3,4-Cl$_2$Ph— | 3-CH$_3$OPhCH$_2$— | 2.47 (4H, brs), 3.46-3.82 (6H, m), 3.86 (3H, s), 6.80-6.84 (1H, m), 6.88-6.92 (2H, m), 6.95 (1H, d, J = 8.8 Hz), 7.10-7.13 (2H, m), 7.23 (1H, d, J = 8.1 Hz), 7.38-7.41 (2H, m), 7.56 (1H, d, J = 8.3 Hz), 7.73-7.77 (1H, m), 8.04 (1H, d, J = 2.1 Hz), 8.12-8.16 (1H, m), 8.29 (1H, d, J = 2.7 Hz), 8.44 (1H, brs). |
| 2335 | 3,4-Cl$_2$Ph— | 2-quinolylmethyl | 2.58 (4H, brs), 3.58-3.76 (4H, m), 3.88 (2H, s), 6.94 (1H, d, J = 8.8 Hz), 7.11 (2H, d, J = 8.4 Hz), 7.40 (2H, d, J = 8.6 Hz), 7.51-7.57 (2H, m), 7.62 (1H, d, J = 8.4 Hz), 7.68-7.84 (3H, m), 8.04 (1H, d, J = 2.1 Hz), 8.07 (1H, d, J = 8.6 Hz), 8.12-8.17 (2H, m), 8.29 (1H, d, J = 2.5 Hz), 8.65 (1H, brs). |
| 2336 | 3,4-Cl$_2$Ph— | 4-CF$_3$PhCH$_2$— | 2.47 (4H, brs), 3.44-3.85 (6H, m), 6.98 (1H, d, J = 8.9 Hz), 7.11-7.16 (2H, m), 7.39-7.48 (4H, m), 7.56-7.61 (3H, m), 7.75 (1H, dd, J = 8.4 Hz, 2.1 Hz), 8.02 (1H, d, J = 2.1 Hz), 8.14-8.18 (1H, m), 8.24 (1H, brs), 8.30 (1H, d, J = 2.6 Hz). |
| 2337 | 3,4-Cl$_2$Ph— | 4-CF$_3$OPhCH$_2$— | 2.46 (4H, brs), 3.46-3.84 (6H, m), 6.96 (1H, d, J = 8.9 Hz), 7.10-7.20 (4H, m), 7.34-7.41 (4H, m), 7.56 (1H, d, J = 8.4 Hz), 7.76 (1H, dd, J = 8.4 Hz, 2.1 Hz), 8.03 (1H, d, J = 2.1 Hz), 8.11-8.16 (1H, m), 8.30 (1H, d, J = 2.5 Hz), 8.49 (1H, brs). |
| 2338 | 3,4-Cl$_2$Ph— | PhO(CH$_2$)$_2$— | 2.60 (4H, brs), 2.85 (2H, t, J = 5.4 Hz), 3.53-3.75 (4H, m), 4.12 (2H, t, J = 5.4 Hz), 6.88-6.99 (4H, m), 7.06-7.13 (2H, m), 7.25-7.37 (4H, m), 7.51 (1H, d, J = 8.4 Hz), 7.77 (1H, dd, J = 8.4 Hz, |

TABLE 373-continued

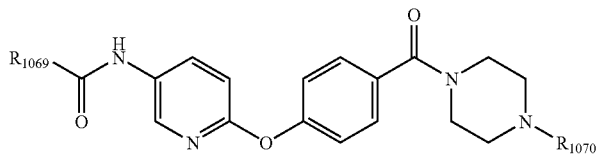

| Example No. | R_{1069} | R_{1070} | ¹H NMR (CDCl₃) δppm |
|---|---|---|---|
| | | | 2.1 Hz), 8.05 (1H, d, J = 2.1 Hz), 8.07-8.12 (1H, m), 8.32 (1H, d, J = 2.6 Hz), 9.10 (1H, brs). |
| 2339 | 4-CF₃Ph— | 4-CNPhCH₂— | 2.45 (4H, brs), 3.58 (2H, s), 3.63 (4H, brs), 6.98 (1H, d, J = 8.8 Hz), 7.13 (2H, d, J = 8.7 Hz), 7.41 (2H, d, J = 8.7 Hz), 7.46 (2H, d, J = 8.1 Hz), 7.62 (2H, d, J = 8.1 Hz), 7.75 (2H, d, J = 8.1 Hz), 8.01 (2H, d, J = 8.1 Hz), 8.20 (1H, dd, J = 8.8 Hz, 2.6 Hz), 8.28 (1H, brs), 8.33 (1H, d, J = 2.6 Hz). |
| 2340 | 4-CF₃Ph— | 3,4-F₂PhCH₂— | 2.44 (4H, brs), 3.48 (2H, s), 3.64 (4H, brs), 6.98 (1H, d, J = 8.9 Hz), 6.97-7.25 (3H, m), 7.12 (2H, d, J = 8.7 Hz), 7.41 (2H, d, J = 8.7 Hz), 7.75 (2H, d, J = 8.0 Hz), 8.01 (2H, d, J = 8.0 Hz), 8.19 (1H, dd, J = 8.9 Hz, 2.3 Hz), 8.30 (1H, brs), 8.32 (1H, d, J = 2.3 Hz). |
| 2341 | 4-CF₃Ph— | 4-CH₃OPhCH₂— | 2.43 (4H, brs), 3.48 (2H, s), 3.60 (4H, brs), 3.80 (3H, s), 6.86 (2H, d, J = 8.7 Hz), 6.96 (1H, d, J = 8.7 Hz), 7.11 (2H, d, J = 8.7 Hz), 7.22 (2H, d, J = 8.7 Hz), 7.38 (2H, d, J = 8.7 Hz), 7.74 (2H, d, J = 8.1 Hz), 8.02 (2H, d, J = 8.1 Hz), 8.17 (1H, dd, J = 8.7 Hz, 2.4 Hz) 8.32 (1H, d, J = 2.4 Hz), 8.52 (1H, s). |

TABLE 374

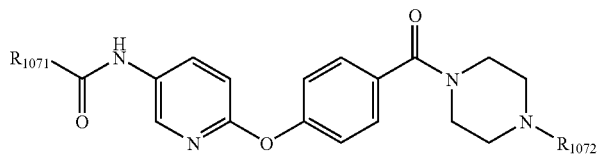

| Example No. | R_{1071} | R_{1072} | mp (° C.) or ¹H NMR (CDCl₃) δppm |
|---|---|---|---|
| 2342 | 3,4-(CH₃)₂Ph— | 4-CNPhCH₂— | ¹H NMR 2.33 (6H, s), 2.45 (4H, brs), 3.58 (2H, s), 3.64 (4H, brs), 6.97 (1H, d, J = 8.7 Hz), 7.11-7.16 (2H, m), 7.24 (1H, d, J = 7.6 Hz), 7.41-7.47 (4H, m), 7.58-7.67 (4H, m), 7.94 (1H, brs), 8.24 (1H, dd, J = 8.7 Hz, 2.7 Hz), 8.31 (1H, d, J = 2.7 Hz). |
| 2343 | 3,4-(CH₃)₂Ph— | 3,4-F₂PhCH₂— | ¹H NMR 2.34 (6H, s), 2.45 (4H, brs), 3.48 (2H, s), 3.65 (4H, brs), 6.98 (1H, d, J = 8.9 Hz), 7.03-7.23 (6H, m), 7.41-7.46 (2H, m), 7.59-7.62 (1H, m), 7.67 (1H, d, J = 1.8 Hz), 7.95 (1H, brs), 8.26 (1H, dd, J = 8.9 Hz, 2.7 Hz), 8.31 (1H, d, J = 2.7 Hz). |
| 2344 | 4-CF₃Ph— | 3-CH₃OPhCH₂— | mp 118-120 |
| 2345 | 4-CF₃Ph— | 2-quinolylmethyl | ¹H NMR 2.56 (4H, brs), 3.43-3.81 (4H, m), 3.87 (2H, s), 6.94 (1H, d, J = 8.9 Hz), 7.08-7.13 (2H, m), 7.35-7.40 (2H, m), 7.51-7.57 (1H, m), 7.61 (1H, d, J = 8.4 Hz), 7.68-7.74 (3H, m), 7.81-7.84 (1H, m), 8.01-8.20 (5H, m), 8.33 (1H, d, J = 2.7 Hz), 8.94 (1H, s). |
| 2346 | 4-CF₃Ph— | PhO(CH₂)₂— | mp 161-162 |
| 2347 | 4-CF₃Ph— | ![benzoxazole structure] | ¹H NMR 2.48 (4H, brs), 3.55 (2H, brs), 3.66 (2H, s), 3.75 (2H, brs), 6.97 (1H, d, J = 8.7 Hz), 7.12 (2H, d, J = 8.4 Hz), 7.32-7.43 (1H, m), 7.41 (2H, d, J = 8.4 Hz), 7.55 (1H, d, J = 8.4 Hz), 7.70-7.80 (1H, m), 7.75 (2H, d, J = 8.1 Hz), 8.02 (2H, d, J = 8.1 Hz), 8.10 (1H, s), 8.20 (1H, dd, J = 8.7 Hz, 2.6 Hz), 8.32 (1H, d, J = 2.6 Hz), 8.41 (1H, s). |

TABLE 375

| Example No. | R1073 | R1074 | 1H NMR (CDCl3) δppm |
|---|---|---|---|
| 2348 | 3,4-Cl2Ph— | 2,6-F2PhCH2— | 2.42 (4H, brs), 2.54-2.60 (2H, m), 2.83-2.88 (2H, m), 3.38-3.42 (2H, m), 3.55-3.58 (2H, m), 3.69 (2H, s), 6.85-6.98 (5H, m), 7.12 (2H, d, J = 8.6 Hz), 7.19-7.31 (1H, m), 7.48 (1H, d, J = 8.4 Hz), 7.74 (1H, dd, J = 8.4 Hz, 2.1 Hz), 7.99 (1H, d, J = 2.1 Hz), 8.14-8.18 (1H, m), 8.30 (1H, d, J = 2.8 Hz), 9.19 (1H, brs). |
| 2349 | 3,4-Cl2Ph— | 4-CF3PhCH2— | 2.33-2.41 (4H, m), 2.59-2.65 (2H, m), 2.92-2.97 (2H, m), 3.40-3.44 (2H, m), 3.55 (2H, s), 3.61-3.64 (2H, m), 6.93 (1H, d, J = 8.8 Hz), 7.02-7.06 (2H, m), 7.20 (2H, d, J = 8.6 Hz), 7.44 (2H, d, J = 8.4 Hz), 7.54-7.60 (3H, m), 7.74 (1H, dd, J = 8.4 Hz, 2.2 Hz), 8.01 (1H, d, J = 2.2 Hz), 8.17-8.21 (1H, m), 8.28 (1H, d, J = 2.6 Hz), 8.44 (1H, brs). |
| 2350 | 4-CF3Ph— | 5-ethyl-benzoxazol-2-yl | 2.28 (2H, t, J = 4.9 Hz), 2.43 (2H, t, J = 4.9 Hz), 2.61 (2H, t, J = 7.5 Hz), 2.96 (2H, t, J = 7.5 Hz), 3.30 (2H, t, J = 4.9 Hz), 3.59 (2H, s), 3.63 (2H, t, J = 4.9 Hz), 6.96 (1H, d, J = 8.3 Hz), 7.04 (2H, d, J = 8.5 Hz), 7.21 (2H, d, J = 8.5 Hz), 7.36 (1H, dd, J = 8.5 Hz, 1.5 Hz), 7.53 (1H, d, J = 8.4 Hz), 7.73 (1H, brs), 7.75 (2H, d, J = 8.3 Hz), 8.01 (1H, s), 8.02 (2H, d, J = 8.3 Hz), 8.25 (1H, s), 8.27 (1H, dd, J = 8.3 Hz, 2.6 Hz), 8.58 (1H, s). |
| 2351 | 3,4-Cl2Ph— | 3,4-F2PhCH2— | 2.31-2.40 (4H, m), 2.60-2.65 (2H, m), 2.93-2.99 (2H, m), 3.39-3.45 (4H, m), 3.61-3.65 (2H, m), 6.95 (1H, d, J = 8.8 Hz), 7.03-7.24 (7H, m), 7.57 (1H, d, J = 8.3 Hz), 7.73 (1H, dd, J = 8.4 Hz, 2.1 Hz), 8.00 (1H, d, J = 2.1 Hz), 8.10 (1H, brs), 8.16-8.20 (1H, m), 8.26 (1H, d, J = 2.3 Hz). |
| 2352 | 3,4-Cl2Ph— | 3,5-F2PhCH2— | 2.32-2.38 (4H, m), 2.58-2.64 (2H, m), 2.89-2.94 (2H, m), 3.40-3.46 (4H, m), 3.59-3.62 (2H, m), 6.66-6.74 (1H, m), 6.85-7.03 (5H, m), 7.17 (2H, d, J = 8.6 Hz), 7.52 (1H, d, J = 8.2 Hz), 7.71-7.75 (1H, m), 7.99 (1H, d, J = 2.0 Hz), 8.16-8.20 (1H, m), 8.28 (1H, d, J = 2.6 Hz), 8.77 (1H, brs). |

TABLE 376

| Example No. | R1075 | Xb54 | R1076 | 1H NMR (CDCl3) δppm |
|---|---|---|---|---|
| 2353 | 3,4-Cl2Ph— | —CO— | —CH3 | 3.03 (2H, t, J = 5.2 Hz), 3.39 (2H, s), 3.51 (2H, s), 3.76 (2H, t, J = 5.2 Hz), 3.77 (3H, s), 6.98 (1H, d, J = 8.9 Hz), 7.15 (2H, dd, J = 8.8 Hz, 2.1 Hz), 7.30 (2H, dd, J = 8.8 Hz, 2.1 Hz), 7.59 (1H, d, J = 8.4 Hz), 7.72 (1H, dd, J = 8.4 Hz, 2.1 Hz), 7.99 (1H, d, J = 2.1 Hz), 8.15 (1H, dd, J = 8.9 Hz, 2.7 Hz), 8.29 (1H, d, J = 2.7 Hz). |
| 2354 | 3,4-Cl2Ph— | —CH2— | —CH3 | 2.75 (4H, t, J = 5.0 Hz), 3.23 (4H, t, J = 5.0 Hz), 3.30 (2H, s), 3.75 (3H, s), 6.90 (1H, d, J = 9.0 Hz), 6.95 (2H, d, J = 9.0 Hz), 7.04 (2H, d, J = 9.0 Hz), 7.58 (1H, d, J = 8.5 Hz), 7.70 (1H, dd, J = 8.5 Hz, 2.0 Hz), 7.76 (1H, brs), 7.98 (1H, d, J = 2.0 Hz), |

TABLE 376-continued

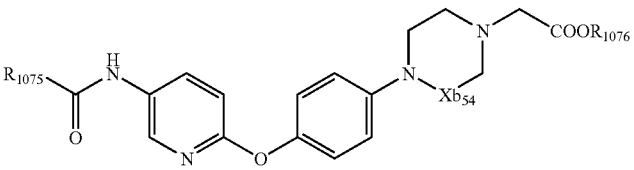

| Example No. | $R_{1075}$ | $Xb_{54}$ | $R_{1076}$ | $^1$H NMR (CDCl$_3$) δppm |
|---|---|---|---|---|
| 2355 | 3,4-Cl$_2$Ph— | —CH$_2$— | —C$_2$H$_5$ | 8.15 (1H, dd, J = 9.0 Hz, 3.0 Hz), 8.23 (1H, d, J = 3.0 Hz). 1.31 (3H, t, J = 7.0 Hz), 2.75 (4H, t, J = 5.0 Hz), 3.23 (4H, t, J = 5.0 Hz), 3.28 (2H, s), 4.21 (2H, q, J = 7.0 Hz), 6.90 (1H, d, J = 9.0 Hz), 6.95 (2H, d, J = 9.0 Hz), 7.04 (2H, d, J = 9.0 Hz), 7.57 (1H, d, J = 8.5 Hz), 7.71 (1H, dd, J = 8.5 Hz, 2.0 Hz), 7.88 (1H, brs), 7.98 (1H, d, J = 2.0 Hz), 8.15 (1H, dd, J = 9.0 Hz, 2.5 Hz), 8.24 (1H, d, J = 2.5 Hz). |
| 2356 | 4-CF$_3$Ph— | —CH$_2$— | —CH$_3$ | 2.75 (4H, t, J = 5.0 Hz), 3.24 (4H, t, J = 5.0 Hz), 3.30 (2H, s), 3.75 (3H, s), 6.92 (1H, d, J = 9.0 Hz), 6.96 (2H, d, J = 9.0 Hz), 7.06 (2H, d, J = 9.0 Hz), 7.74 (1H, brs), 7.78 (2H, d, J = 8.0 Hz), 7.99 (2H, d, J = 8.0 Hz), 8.19 (1H, dd, J = 9.0 Hz, 2.5 Hz), 8.25 (1H, d, J = 2.5 Hz). |

Example 2357

Production of 3,4-dichloro-N-[6-(4-{4-[(3,4-difluorobenzyl)methylamino]piperidine-1-carbonyl}phenoxy)pyridin-3-yl]benzamide 3,4-dichloro-N-{6-[4-(4-methylamino-piperidine-1-carbonyl)phenoxy]pyridin-3-yl}benzamide dihydrochloride (114 mg, 0.2 mmol) was dissolved in DMF (3 mL). To the resulting solution were added 4-bromomethyl-1,2-difluorobenzene (31 µl, 0.24 mmol) and potassium carbonate (111 mg, 0.8 mmol), and this solution was stirred for 4 hours at room temperature. The resulting reaction solution was concentrated under reduced pressure. The residue was diluted with ethyl acetate and washed with water and brine. The organic layer was dried over anhydrous magnesium sulfate, and evaporated. This residue was purified by silica gel column chromatography (chloroform:methanol=50:1), to thereby yield 60 mg of the title compound.

Appearance: White powder $^1$H NMR (CDCl$_3$) δ 1.64 (4H, brs), 1.84 (2H, brs), 2.20 (3H, s), 2.65-2.90 (3H, m), 3.54 (2H, s), 6.95-7.08 (4H, m), 7.13 (2H, d, J=9.3 Hz), 7.41 (2H, d, J=9.2 Hz), 7.57 (1H, d, J=8.4 Hz), 7.75 (1H, dd, J=8.4 Hz, 2.0 Hz), 8.03 (1H, d, J=2.0 Hz), 8.15 (1H, dd, J=8.9 Hz, 2.8 Hz), 8.30 (1H, brs), 8.31 (1H, d, J=2.2 Hz).

The following compounds were produced in the same manner as in Example 2357.

TABLE 377

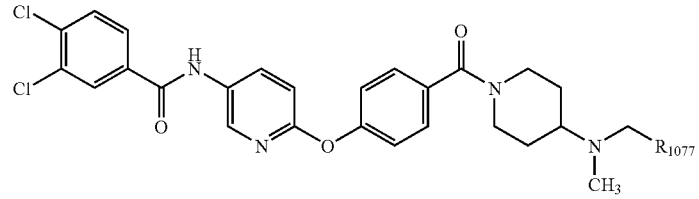

| Example No. | $R_{1077}$ | $^1$H NMR (CDCl$_3$) δppm |
|---|---|---|
| 2358 | 2,4-F$_2$Ph— | 1.66 (4H, brs), 1.91 (2H, brs), 2.25 (3H, s), 2.73-3.08 (3H, m), 3.63 (2H, s), 6.75-6.89 (3H, m), 6.97 (1H, d, J = 8.7 Hz), 7.13 (2H, d, J = 9.2 Hz), 7.42 (2H, d, J = 9.2 Hz), 7.57 (1H, d, J = 8.3 Hz), 7.76 (1H, dd, J = 8.3 Hz, 2.1 Hz), 8.04 (1H, d, J = 2.1 Hz), 8.16 (1H, dd, J = 8.9 Hz, 2.8 Hz), 8.31 (1H, d, J = 2.3 Hz), 8.37 (1H, brs). |
| 2359 | 2,5-F$_2$Ph— | 1.72 (4H, brs), 1.88 (2H, brs), 2.25 (3H, s), 2.67-2.96 (3H, m), 3.62 (2H, s), 6.85-7.02 (3H, m), 7.09-7.23 (3H, m), 7.39 (2H, d, J = 8.9 Hz), 7.55 (1H, d, J = 8.3 Hz), 7.77 (1H, dd, J = 8.4 Hz, 2.1 Hz), 8.05 (1H, d, J = 2.1 Hz), 8.12 (1H, dd, J = 8.9 Hz, 2.8 Hz), 8.31 (1H, d, J = 2.6 Hz), 8.66 (1H, brs). |
| 2360 | 4-CH(CH$_3$)$_2$Ph— | 1.25 (6H, d, J = 6.9 Hz), 1.57-2.21 (7H, m), 2.66-3.07 (4H, m), 3.56 (2H, s), 3.90 (1H, brs), 4.66 (1H, brs), 6.90 (1H, d, J = 8.9 Hz), 7.04-7.10 (2H, m), 7.16-7.25 (4H, m), 7.31-7.36 (2H, m), 7.50 (1H, d, J = 8.4 Hz), 7.77 (1H, dd, J = 8.4 Hz, 2.1 Hz), 8.06-8.10 (2H, m), 8.33 (1H, d, J = 2.5 Hz), 9.37 (1H, s). |

TABLE 377-continued

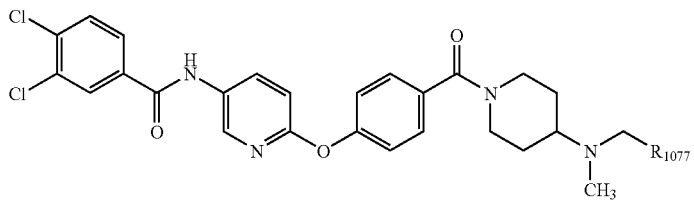

| Example No. | $R_{1077}$ | $^{1}$H NMR (CDCl$_3$) δppm |
|---|---|---|
| 2361 | 4-C(CH$_3$)$_3$Ph— | 1.32 (9H, s), 1.58 (2H, brs), 1.89 (2H, brs), 2.22 (3H, s), 2.62-3.10 (3H, m), 3.57 (2H, s), 3.92 (1H, brs), 4.69 (1H, brs), 6.92 (1H, d, J = 8.6 Hz), 7.06-7.11 (2H, m), 7.22-7.25 (2H, m), 7.32-7.37 (4H, m), 7.53 (1H, d, J = 8.6 Hz), 7.78 (1H, dd, J = 8.4 Hz, 2.2 Hz), 8.07 (1H, d, J = 2.2 Hz), 8.11 (1H, d, J = 2.7 Hz), 8.32 (1H, d, J = 2.7 Hz), 9.07 (1H, brs). |

TABLE 378

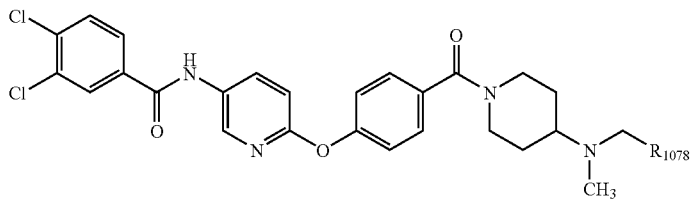

| Example No. | $R_{1078}$ | $^{1}$H NMR (CDCl$_3$) δppm |
|---|---|---|
| 2362 | 4-CNPh— | 1.54 (1H, brs), 1.86 (3H, brs), 2.20 (3H, s), 2.64-3.04 (3H, m), 3.64 (2H, s) 3.91 (1H, brs), 4.69 (1H, brs), 6.91 (1H, d, J = 8.9 Hz), 7.05-7.10 (2H, 7.32-7.37 (2H, m), 7.45 (2H, d, J = 8.4 Hz), 7.50 (1H, d, J = 8.4 Hz), 7.59-7.62 (2H, m), 7.75-7.79 (1H, m), 8.05 (1H, d, J = 2.0 Hz), 8.10 (1H, dd, J = 8.9 Hz, 2.7 Hz), 8.35 (1H, d, J = 2.7 Hz), 9.31 (1H, brs). |
| 2363 | Ph— | 1.55 (2H, brs), 1.87 (2H, brs), 2.22 (3H, s), 2.61-2.80 (2H, m), 2.90 (1H, brs), 3.60 (2H, s), 3.93 (1H, brs) 4.72 (1H, brs), 6.98 (1H, d, J = 8.9 Hz), 7.14 (2H, d, J = 8.7 Hz), 7.18-7.37 (5H, m), 7.43 (2H, d, J = 8.7 Hz), 7.58 (1H, d, J = 8.4 Hz), 7.75 (1H, dd, J = 8.4 Hz, 2.0 Hz), 8.02 (1H, d, J = 2.0 Hz), 8.16 (1H, dd, J = 8.9 Hz, 2.4 Hz), 8.19 (1H, brs, 8.30 (1H, d, J = 2.4 Hz). |
| 2364 | 2-ClPh— | 1.50 (2H, brs), 1.90 (2H, brs), 2.26 (3H, s), 2.68-2.85 (2H, m), 2.98 (1H, brs), 3.70 (2H, s), 3.95 (1H, brs), 4.75 (1H, brs), 6.98 (1H, d, J = 8.7 Hz), 7.14 (2H, d, J = 8.5 Hz), 7.15-7.30 (2H, m), 7.34 (1H, dd, J = 7.2 Hz, 2.0 Hz), 7.43 (2H, d, J = 8.5 Hz), 7.47 (1H, dd, J = 7.2 Hz, 2.0 Hz), 7.58 (1H, d, J = 8.4 Hz), 7.75 (1H, dd, J = 8.4 Hz, 2.0 Hz), 8.04 (1H, d, J = 2.0 Hz), 8.16 (1H, dd, J = 8.7 Hz, 2.8 Hz), 8.31 (1H, d, J = 2.8 Hz), 8.32 (1H, brs). |
| 2365 | 3-ClPh— | 1.50 (2H, brs), 1.87 (2H, brs), 2.21 (3H, s), 2.55-3.20 (3H, m), 3.57 (2H, s), 3.95 (1H, brs), 4.70 (1H, brs), 6.99 (1H, d, J = 8.8 Hz), 7.14 (2H, d, J = 8.7 Hz), 7.15-7.28 (3H, m), 7.33 (1H, brs), 7.44 (2H, d, J = 8.7 Hz), 7.59 (1H, d, J = 8.4 Hz) 7.74 (1H, dd, J = 8.4 Hz, 2.0 Hz) 8.02 (1H, d, J = 2.0 Hz), 8.09 (1H, brs), 8.17 (1H, dd, J = 8.8 Hz, 2.8 Hz), 8.30 (1H, d, J = 2.8 Hz). |
| 2366 | 3,4-Cl$_2$Ph— | 1.50 (2H, brs), 1.85 (2H, brs), 2.20 (3H, s), 2.60-3.15 (3H, m), 3.54 (2H, s), 3.95 (1H, brs), 4.70 (1H, brs), 6.97 (1H, d, J = 8.9 Hz), 7.13 (2H, d, J = 8.6 Hz), 7.10-7.19 (1H, m), 7.36 (1H, s), 7.41 (2H, d, J = 8.6 Hz), 7.35-7.47 (1H, m), 7.57 (1H, d, J = 8.4 Hz), 7.75 (1H, dd, J = 8.4 Hz, 2.1 Hz), 8.03 (1H, d, J = 2.1 Hz), 8.14 (1H, dd, J = 8.9 Hz, 2.5 Hz), 8.30 (1H, d, J = 2.5 Hz), 8.40 (1H, s). |
| 2367 | 2,3-Cl$_2$Ph— | 1.60 (2H, brs), 1.90 (2H, brs), 2.26 (3H, s), 2.65-3.20 (3H, m), 3.72 (2H, s), 3.90 (1H, brs), 4.72 (1H, brs), 6.97 (1H, d, J = 8.8 Hz), 7.13 (2H, d, J = 8.6 Hz), 7.20 (1H, d, J = 8.0 Hz), 7.36 (1H, dd, J = 8.0 Hz, 1.5 Hz), 7.42 (2H, d, J = 8.6 Hz), 7.37-7.46 (1H, m), 7.57 (1H, d, J = 8.2 Hz), 7.75 (1H, dd, J = 8.4 Hz, 2.0 Hz), 8.04 (1H, d, J = 2.0 Hz), 8.14 (1H, dd, J = 8.8 Hz, 2.7 Hz), 8.30 (1H, d, J = 2.7 Hz), 8.38 (1H, brs). |
| 2368 | 2-FPh— | 1.55 (2H, brs), 1.85 (2H, brs), 2.25 (3H, s), 2.50-3.20 (3H, m), 3.65 (2H, s) 3.95 (1H, brs), 4.70 (1H, brs), 6.97 (1H, d, J = 8.8 Hz), 6.95-7.17 (2H, 7.13 (2H, d, J = 8.7 Hz), 7.18-7.29 (1H, m), 7.32-7.45 (1H, m), 7.42 (2H, d, J = 8 7 Hz), 7.57 (1H, d, J = 8.2 Hz), 7.75 (1H, dd, J = 8.2 Hz, 2.1 Hz), 8.04 (1H, d, J = 2.1 Hz), 8.14 (1H, dd, J = 8.8 Hz, 2.5 Hz), 8.30 (1H, d, J = 2.5 Hz), 8.34 (1H, brs). |

TABLE 378-continued

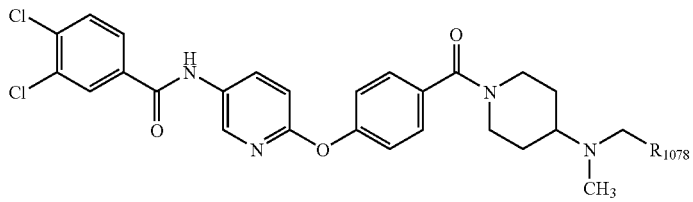

| Example No. | R₁₀₇₈ | ¹H NMR (CDCl₃) δppm |
|---|---|---|
| 2369 | 2-CH₃Ph— | 1.67 (4H, brs), 1.89 (2H, brs), 2.19 (3H, s), 2.36 (3H, s), 2.67-2.96 (3H, m), 3.57 (2H, s), 6.96 (1H, d, J = 8.7 Hz), 7.07-7.26 (6H, m), 7.41 (2H, d, J = 8.1 Hz), 7.57 (1H, d, J = 8.4 Hz), 7.77 (1H, dd, J = 8.4 Hz, 2.0 Hz), 8.05 (1H, d, J = 2.0 Hz) 8.14 (1H, dd, J = 8.9 Hz, 2.6 Hz), 8.31 (1H, d, J = 2.6 Hz), 8.51 (1H, brs). |

TABLE 379

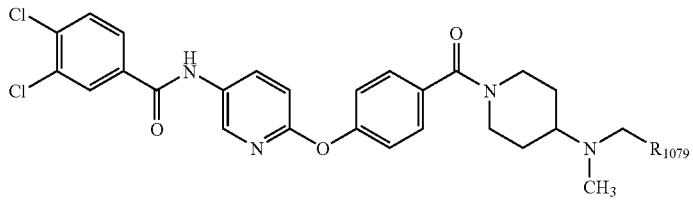

| Example No. | R₁₀₇₉ | Form | ¹H NMR (solvent) δppm |
|---|---|---|---|
| 2370 | 3,5-(CH₃O)₂Ph— | hydrochloride | (DMSO-d₆) 1.67-1.93 (2H, m), 2.08-2.30 (2H, m), 2.61 (3H, d, J = 4.8 Hz), 2.95 (1H, brs), 3.31-3.75 (4H, m), 3.77 (6H, s), 4.02-4.18 (1H, m), 4.31-4.45 (1H, m), 6.57 (1H, t, J = 2.0 Hz), 6.83 (2H, d, J = 2.0 Hz), 7.16 (1H, d, J = 8.7 Hz), 7.20 (2H, d, J = 8.6 Hz), 7.49 (2H, d, J = 8.6 Hz), 7.85 (1H, d, J = 8.4 Hz), 7.97 (1H, dd, J = 8.4 Hz, 2.1 Hz), 8.24 (1H, d, J = 2.1 Hz), 8.24 (1H, dd, J = 8.7 Hz, 2.6 Hz), 8.55 (1H, d, J = 2.6 Hz), 10.64 (1H, brs). |
| 2371 | 3-CH₃OPh— | free | (CDCl₃) 1.60 (2H, brs), 1.87 (2H, brs), 2.23 (3H, s), 2.52-3.20 (3H, m), 3.58 (2H, s), 3.81 (3H, s), 3.95 (1H, brs), 4.70 (1H, brs), 6.75-6.90 (3H, m), 6.97 (1H, d, J = 8.9 Hz), 7.13 (2H, d, J = 8.6 Hz), 7.21 (1H, d, J = 8.0 Hz), 7.41 (2H, d, J = 8.6 Hz), 7.57 (1H, d, J = 8.4 Hz), 7.75 (1H, dd, J = 8.4 Hz, 2.0 Hz), 8.04 (1H, d, J = 2.0 Hz), 8.14 (1H, dd, J = 8.9 Hz, 2.6 Hz), 8.30 (1H, d, J = 2.6 Hz), 8.36 (1H, brs). |
| 2372 | 3-CH₃Ph— | free | (CDCl₃) 1.61 (4H, brs), 1.88 (2H, brs), 2.22 (3H, s), 2.35 (3H, s), 2.68-3.01 (3H, m), 3.56 (2H, s), 6.98 (1H, d, J = 8.9 Hz), 7.06-7.29 (6H, m), 7.42 (2H, d, J = 8.6 Hz), 7.58 (1H, d, J = 8.2 Hz), 7.76 (1H, dd, J = 8.3 Hz, 2.0 Hz), 8.04 (1H, d, J = 2.0 Hz), 8.16 (1H, dd, J = 8.9 Hz, 2.6 Hz), 8.31 (1H, d, J = 2.3 Hz), 8.38 (1H, brs). |
| 2373 | 3,5-F₂Ph— | free | (CDCl₃) 1.42-1.96 (4H, m), 2.21 (3H, s), 2.65-3.10 (3H, m), 3.56 (2H, s), 3.90 (1H, brs), 4.68 (1H, brs), 6.64-6.70 (1H, m), 6.85-6.92 (3H, m), 7.04-7.09 (2H, m), 7.31-7.36 (2H, m), 7.50 (1H, d, J = 8.4 Hz), 7.74-7.79 (1H, m), 8.05-8.10 (2H, m), 8.33 (1H, d, J = 2.5 Hz), 9.30 (1H, brs). |
| 2374 | 3,4-(CH₃)₂Ph— | free | (CDCl₃) 1.59 (4H, brs), 1.90-1.98 (2H, m), 2.22 (3H, s), 2.25 (3H, s), 2.26 (3H, s), 2.67-2.97 (3H, m), 3.59 (2H, s), 6.99 (1H, d, J = 8.7 Hz), 7.05-7.10 (3H, m), 7.15 (2H, d, J = 9.4 Hz), 7.44 (2H, d, J = 9.4 Hz), 7.59 (1H, d, J = 8.3 Hz), 7.74 (1H, dd, J = 8.3 Hz, 2.2 Hz), 8.02 (1H, d, J = 2.0 Hz), 8.03 (1H, brs), 8.18 (1H, dd, J = 8.7 Hz, 2.8 Hz), 8.31 (1H, d, J = 2.8 Hz). |
| 2375 | 3-FPh— | free | (CDCl₃) 1.59-1.85 (6H, m), 2.22 (3H, s), 2.67-2.99 (3H, m), 3.59 (2H, s), 6.94-6.97 (2H, m), 7.05-7.13 (5H, m), 7.39 (2H, d, J = 8.4 Hz), 7.56 (1H, d, J = 8.4 Hz), 7.77 (1H, dd, J = 8.4 Hz, 2.0 Hz), 8.05 (1H, d, J = 2.0 Hz), 8.13 (1H, dd, J = 8.7 Hz, 2.6 Hz), 8.31 (1H, d, J = 2.5 Hz), 8.63 (1H, brs). |

TABLE 379-continued

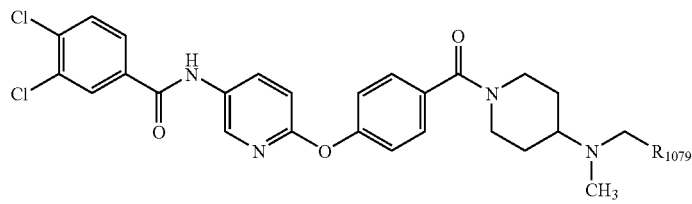

| Example No. | R₁₀₇₉ | Form | ¹H NMR (solvent) δppm |
|---|---|---|---|
| 2376 | 2,6-F₂Ph— | free | (CDCl₃) 1.65 (4H, brs), 1.81-1.91 (2H, m), 2.28 (3H, s), 2.69-3.03 (3H, m), 3.69 (2H, s), 6.83-6.92 (3H, m), 6.99 (1H, d, J = 8.9 Hz), 7.15 (2H, d, J = 9.2 Hz), 7.44 (2H, d, J = 9.2 Hz), 7.59 (1H, d, J = 8.4 Hz), 7.75 (1H, dd, J = 8.4 Hz, 2.2 Hz), 8.03 (1H, d, J = 2.2 Hz), 8.17 (1H, brs), 8.18 (1H, dd, J = 8.7 Hz, 2.8 Hz), 8.31 (1H, d, J = 2.6 Hz). |

TABLE 380

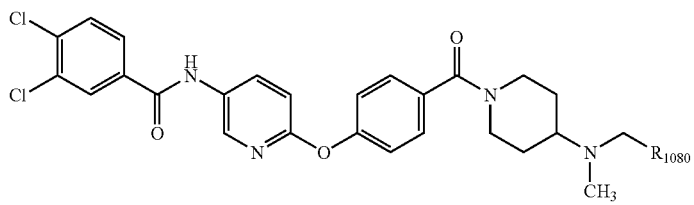

| Example No. | R₁₀₈₀ | mp (° C.) or MS |
|---|---|---|
| 2377 | 4-CF₃Ph— | mp 180-181 |
| 2378 | 2-NO₂Ph— | MS 634 (M⁺ + H) |
| 2379 | 3-NO₂Ph— | MS 634 (M⁺ + H) |
| 2380 | 4-NO₂Ph— | MS 634 (M⁺ + H) |
| 2381 | 2-CF₃Ph— | MS 657 (M⁺ + H) |
| 2382 | 3-CF₃Ph— | MS 657 (M⁺ + H) |
| 2383 | 4-CF₃Ph— | MS 657 (M⁺ + H) |
| 2384 | 2-CF₃OPh— | MS 673 (M⁺ + H) |
| 2385 | 4-methyl-COOCH₃-phenyl | MS 647 (M⁺ + H) |
| 2386 | 4-biphenylyl | MS 665 (M⁺ + H) |
| 2387 | 3-methyl-COOCH₃-phenyl | MS 647 (M⁺ + H) |
| 2388 | 1,1,4,4-tetramethyl-7-methyl-tetrahydronaphthyl | MS 699 (M⁺ + H) |
| 2389 | 2-pyridyl | MS 590 (M⁺ + H) |
| 2390 | 2-quinolyl | MS 640 (M⁺ + H) |

TABLE 380-continued

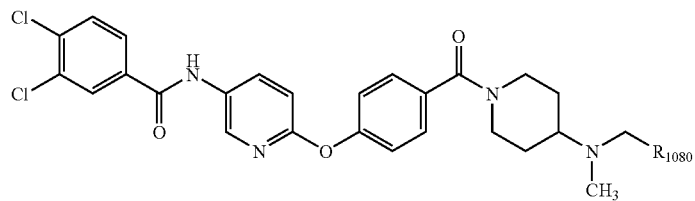

| Example No. | $R_{1080}$ | mp (° C.) or MS |
|---|---|---|
| 2391 | | MS 671 (M+ + H) |
| 2392 | | MS 609 (M+ + H) |
| 2393 | 2,4-Cl$_2$Ph— | MS 657 (M+ + H) |
| 2394 | 2,5-Cl$_2$Ph— | MS 657 (M+ + H) |
| 2395 | 2,6-Cl$_2$Ph— | MS 657 (M+ + H) |

TABLE 381

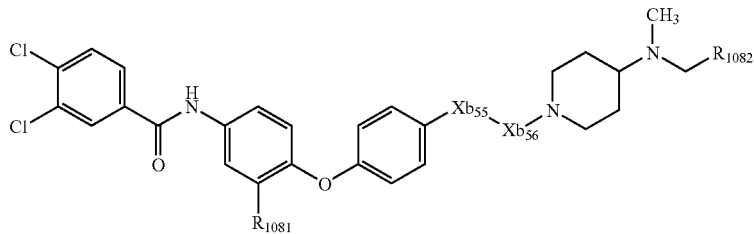

| Example No. | $R_{1081}$ | $Xb_{55}$ | $Xb_{56}$ | $R_{1082}$ | mp (° C.) or MS |
|---|---|---|---|---|---|
| 2396 | —H | none | none | Ph— | mp 155-158 |
| 2397 | —F | —(CH$_2$)$_2$— | —CO— | Ph— | MS 634 (M+ + H) |
| 2398 | —F | —(CH$_2$)$_2$— | —CO— | 2-ClPh— | MS 668 (M+ + H) |
| 2399 | —F | —(CH$_2$)$_2$— | —CO— | 3-ClPh— | MS 668 (M+ + H) |
| 2400 | —F | —(CH$_2$)$_2$— | —CO— | 4-ClPh— | MS 668 (M+ + H) |
| 2401 | —F | —(CH$_2$)$_2$— | —CO— | 2,3-Cl$_2$Ph— | MS 702 (M+ + 1) |
| 2402 | —F | —(CH$_2$)$_2$— | —CO— | 2,4-Cl$_2$Ph— | MS 701 (M+) |
| 2403 | —F | —(CH$_2$)$_2$— | —CO— | 2,5-Cl$_2$Ph— | MS 702 (M+ + 1) |
| 2404 | —F | —(CH$_2$)$_2$— | —CO— | 2,6-Cl$_2$Ph— | MS 702 (M+ + H) |
| 2405 | —F | —(CH$_2$)$_2$— | —CO— | 3,4-Cl$_2$Ph— | MS 703 (M+) |
| 2406 | —F | —(CH$_2$)$_2$— | —CO— | 3-pyridyl | MS 634 (M+) |
| 2407 | —F | —(CH$_2$)$_2$— | —CO— | 2-guinolyl | MS 685 (M+ + H) |
| 2408 | —F | —(CH$_2$)$_2$— | —CO— | 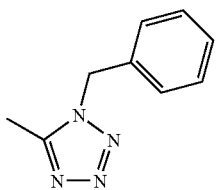 | MS 716 (M+ + H) |

TABLE 381-continued

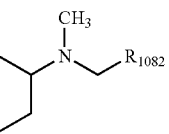

| Example No. | R₁₀₈₁ | Xb₅₅ | Xb₅₆ | R₁₀₈₂ | mp (° C.) or MS |
|---|---|---|---|---|---|
| 2409 | —F | —(CH₂)₂— | —CO— | (1-ethyl-5-methyl-tetrazol-yl) | MS 654 (M⁺ + H) |
| 2410 | —F | —(CH₂)₂— | —CO— | (1-phenethyl-5-methyl-tetrazol-yl) | MS 730 (M⁺ + H) |
| 2411 | —F | —(CH₂)₂— | —CO— | 3-CH₃OPh— | MS 662 (M⁺ + 1) |
| 2412 | —F | —(CH₂)₂— | —CO— | 3,5-(CH₃O)₂Ph— | MS 693 (M⁺) |
| 2413 | —F | —(CH₂)₂— | —CO— | 2-CH₃Ph— | MS 648 (M⁺ + H) |
| 2414 | —F | —(CH₂)₂— | —CO— | 3-CH₃Ph— | MS 648 (M⁺ + H) |
| 2415 | —F | —(CH₂)₂— | —CO— | 4-CH₃Ph— | MS 648 (M⁺ + H) |
| 2416 | —F | —(CH₂)₂— | —CO— | 3,4-(CH₃)₂Ph— | MS 662 (M⁺ + 1) |
| 2417 | —F | —(CH₂)₂— | —CO— | 2-FPh— | MS 652 (M⁺ + H) |
| 2418 | —F | —(CH₂)₂— | —CO— | 3-FPh— | MS 652 (M⁺ + H) |
| 2419 | —F | —(CH₂)₂— | —CO— | 4-FPh— | MS 652 (M⁺ + 1) |
| 2420 | —F | —(CH₂)₂— | —CO— | 2,4-F₂Ph— | MS 670 (M⁺ + H) |
| 2421 | —F | —(CH₂)₂— | —CO— | 2,5-F₂Ph— | MS 670 (M⁺ + H) |
| 2422 | —F | —(CH₂)₂— | —CO— | 2,6-F₂Ph— | MS 671 (M⁺ + 2) |
| 2423 | —F | —(CH₂)₂— | —CO— | 3,4-F₂Ph— | MS 670 (M⁺ + H) |
| 2424 | —F | —(CH₂)₂— | —CO— | 3,5-F₂Ph— | MS 670 (M⁺ + H) |

TABLE 382

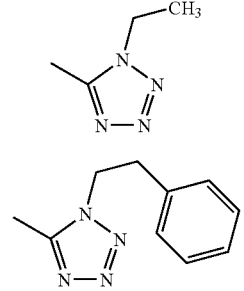

| Example No. | R₁₀₈₃ | MS |
|---|---|---|
| 2425 | 2-NO₂Ph— | 679 (M⁺ + H) |
| 2426 | 3-NO₂Ph— | 678 (M⁺) |
| 2427 | 4-NO₂Ph— | 679 (M⁺ + H) |
| 2428 | 2-CF₃Ph— | 701 (M⁺) |
| 2429 | 3-CF₃Ph— | 702 (M⁺ + H) |
| 2430 | 4-CF₃Ph— | 701 (M⁺) |
| 2431 | 4-CNPh— | 659 (M⁺ + H) |
| 2432 | 2-CF₃OPh— | 718 (M⁺ + H) |
| 2433 | 3-CF₃OPh— | 718 (M⁺ + H) |
| 2434 | 4-CF₃OPh | 718 (M⁺ + H) |
| 2435 | 4-(COOCH₃)Ph— | 692 (M⁺ + H) |
| 2436 | 4-biphenylyl | 710 (M⁺ + H) |

TABLE 382-continued

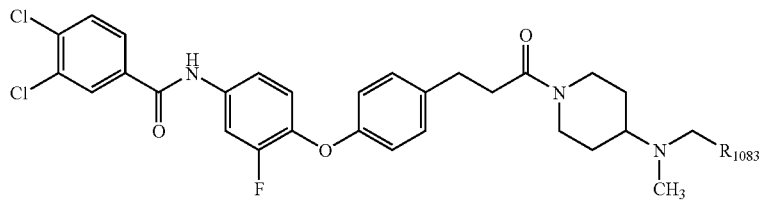

| Example No. | R_{1083} | MS |
|---|---|---|
| 2437 | 3-COOCH_3-phenyl (m-methylbenzoate) | 692 (M+ + H) |
| 2438 | 4-C_2H_5Ph— | 662 (M+ + H) |
| 2439 | 4-CH(CH_3)_2Ph— | 676 (M+ + H) |
| 2440 | 4-C(CH_3)_3Ph— | 690 (M+ + H) |
| 2441 | 5,5,8,8-tetramethyl-2-methyl-tetrahydronaphthyl | 744 (M+ + H) |
| 2442 | 2-naphthyl | 684 (M+ + H) |
| 2443 | 2-pyridyl | 635 (M+ + H) |

Example 2444

Production of 1-(4-piperonylpiperazin-1-yl)-2-{4-[5-(4-trifluromethylphenoxymethyl)pyridin-2-yloxy]-phenylamino}ethanone 4-[5-(4-trifluoromethylphenoxymethyl)pyridin-2-yloxy] phenylamine (4.50 g, 12.5 mmol) was dissolved in DMF (150 mL). To the resulting solution were added potassium carbonate (2.60 g, 18.8 mmol) and sodium iodide (1.87 g, 12.5 mmol), and then to this solution was added 2-chloro-1-(4-piperonylpiperazin-1-yl)ethanone (4.21 g, 12.5 mmol). The resulting solution was stirred for 11 hours under a nitrogen atmosphere at 80° C. The resulting reaction solution was concentrated under reduced pressure. To the residue was added ethyl acetate and washed with a saturated sodium bicarbonate solution and brine. The organic layer was dried over anhydrous magnesium sulfate, and evaporated. The residue was purified by silica gel column chromatography (dichloromethane:methanol=80:1), to thereby yield 5.2 g of the title compound.

Appearance: White powder $^1$H NMR (CDCl_3) δ 2.44-2.46 (4H, m), 3.43-3.47 (4H, m), 3.69 (2H, t, J=5.0 Hz), 3.86 (2H, s), 4.91 (1H, brs), 5.02 (2H, s), 5.94 (2H, s), 6.64 (2H, d, J=8.9 Hz), 6.74-6.75 (2H, m), 6.85-6.89 (2H, m), 6.96-7.03 (4H, m), 7.55 (2H, d, J=8.4 Hz), 7.72 (1H, dd, J=8.4 Hz, 2.5 Hz), 8.22 (1H, d, J=2.0 Hz).

Example 2445

Production of N-{6-[4-(4-thiazole-2-ylmethylpiperazine-1-carbonyl)phenoxy]pyridin-3-yl}-4-trifluoromethyl-benzamide To a suspension of N-{6-[4-(piperazine-1-carbonyl)phenoxy]pyridin-3-yl}-4-trifluoromethyl-benzamide dihydrochloride (400 mg, 0.74 mmol) in 1,2-dichloroethane (20 mL) were added 2-formylthiazole (125 mg, 1.10 mmol) and triethylamine (0.21 mL, 1.50 mmol). After the resulting solution was stirred at room temperature for 30 minutes, sodium triacetyloxy borohydride (312 mg, 1.47 mmol) was added under ice cooling. The reaction mixture was stirred at the same temperature for 30 minutes and at room temperature for 1 hour. Acetic acid (0.085 mL, 1.48 mmol) was added to the reaction mixture, and stirred at room temperature for 17 hours. The reaction mixture was poured into ice water, and extracted with chloroform. The chloroform layer was washed with a saturated sodium bicarbonate solution and brine, and dried over anhydrous magnesium sulfate. A significant part of the solvent was evaporated. The white precipitate was then filtered off and washed with ethyl acetate, to thereby yield 293 mg of the title compound.

Appearance: White powder $^1$H NMR (DMSO-d_6) δ 2.55 (4H, brs), 3.55 (4H, brs), 3.90 (2H, s), 7.15 (1H, d, J=8.7 Hz), 7.16 (2H, d, J=8.6 Hz), 7.45 (2H, d, J=8.6 Hz), 7.68 (1H, d, J=3.2 Hz), 7.73 (1H, d, J=3.2 Hz), 7.94 (2H, d, J=8.1 Hz), 8.17 (2H, d, J=8.1 Hz), 8.26 (1H, dd, J=8.7 Hz, 2.3 Hz), 8.55 (1H, d, J=2.3 Hz), 10.68 (1H, s).

The following compounds were produced in the same manner as in Example 2445.

TABLE 383

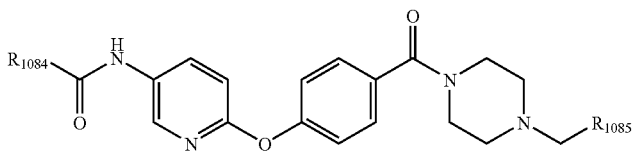

| Example No. | R1084 | R1085 | ¹H NMR (solvent) δppm |
|---|---|---|---|
| 2446 | 3,4-Cl₂Ph— | 3,4-(CH₃)₂Ph— | (CDCl₃) 2.27 (3H, s), 2.29 (3H, s), 2.42 (4H, brs), 3.49 (2H, s), 3.70 (4H, brs), 6.90 (1H, d, J = 8.9 Hz), 7.05-7.10 (5H, m), 7.34-7.36 (2H, m), 7.50 (1H, d, J = 8.4 Hz), 7.75-7.79 (1H, m), 8.00-8.14 (2H, m), 8.33 (1H, d, J = 2.7 Hz), 9.30 (1H, brs). |
| 2447 | 4-CF₃Ph— | 2-FPh— | (CDCl₃) 2.50 (4H, brs), 3.55 (2H, brs), 3.70 (2H, brs), 3.62 (2H, s), 6.98 (1H, d, J = 8.8 Hz), 6.95-7.17 (2H, m), 7.12 (2H, d, J = 8.7 Hz), 7.20-7.41 (2H, m), 7.40 (2H, d, J = 8.7 Hz), 7.76 (2H, d, J = 8.2 Hz), 8.02 (2H, d, J = 8.2 Hz), 8.19 (1H, dd, J = 8.8 Hz, 2.8 Hz), 8.31 (1H, s), 8.32 (1H, d, J = 2.8 Hz). |
| 2448 | 4-CF₃Ph— | 3-pyridyl | (CDCl₃) 2.46 (4H, brs), 3.55 (2H, s), 3.58-3.73 (4H, m), 6.97 (1H, d, J = 8.7 Hz), 7.10-7.15 (2H, m), 7.25-7.30 (1H m), 7.38-7.43 (2H, m), 7.65-7.69 (1H, m), 7.74 (1H, d, J = 8.1 Hz), 8.03 (2H, d, J = 8.1 Hz), 8.19-8.23 (1H, m), 8.32 (1H, d, J = 2.3 Hz), 8.51-8.53 (1H, m), 8.54 (1H, d, J = 1.5 Hz), 8.62 (1H, brs). |
| 2449 | 4-CF₃Ph— | cyclohexyl | (DMSO-d₆) 0.60-1.90 (11H, m), 2.10 (2H, d, J = 7.2 Hz), 2.34 (4H, brs), 3.50 (4H, brs), 7.15 (1H, d, J = 8.8 Hz), 7.16 (2H, d, J = 8.7 Hz), 7.43 (2H, d, J = 8.7 Hz), 7.94 (2H, d, J = 8.1 Hz), 8.17 (2H, d, J = 8.1 Hz), 8.26 (1H, dd, J = 8.8 Hz, 2.7 Hz), 8.55 (1H, d, J = 2.7 Hz), 10.66 (1H, s). |
| 2450 | 4-CF₃Ph— | 3-furyl | (CDCl₃) 2.46 (4H, brs), 3.42 (2H, s), 3.40-3.90 (4H, m), 6.39 (1H, brs), 6.98 (1H, d, J = 8.9 Hz), 7.13 (2H, d, J = 8.7 Hz), 7.34 (1H, brs), 7.33-7.42 (1H, m), 7.41 (2H, d, J = 8.7 Hz), 7.76 (2H, d, J = 8.1 Hz), 8.02 (2H, d, J = 8.1 Hz), 8.20 (1H, dd, J = 8.9 Hz, 2.5 Hz), 8.29 (1H, s), 8.32 (1H, d, J = 2.5 Hz). |
| 2451 | 4-CF₃Ph— | 4-pyridyl | (CDCl₃) 2.45 (4H, brs), 3.41-3.81 (6H, m), 6.95 (1H, d, J = 8.9 Hz), 7.08-7.13 (2H, m), 7.28 (2H, d, J = 5.9 Hz), 7.35-7.40 (2H, m), 7.70 (2H, d, J = 8.4 Hz), 8.02 (2H, d, J = 8.4 Hz), 8.21 (1H, dd, J = 8.9 Hz, 2.7 Hz), 8.33 (1H, d, J = 2.7 Hz), 8.53-8.55 (2H, m), 9.02 (1H, s). |
| 2452 | 4-CF₃Ph | 2-furyl | (CDCl₃) 2.50 (4H, brs), 3.59 (2H, s), 3.73 (4H, brs), 6.23 (1H, d, J = 3.0 Hz), 6.33 (1H, dd, J = 3.0 Hz, 2.0 Hz), 6.99 (1H, d, J = 8.9 Hz), 7.13 (2H, d, J = 8.8 Hz), 7.41 (2H, d, J = 8.8 Hz), 7.35-7.48 (1H, m), 7.76 (2H, d, J = 8.1 Hz), 8.02 (2H, d, J = 8.1 Hz), 8.20 (1H, dd, J = 8.9 Hz, 2.5 Hz), 8.24 (1H, brs), 8.32 (1H, d, J = 2.5 Hz) |
| 2453 | 4-CF₃Ph | 4-NO₂Ph— | (CDCl₃) 2.48 (4H, brs), 3.63 (2H, s), 3.73 (4H, brs), 7.00 (1H, d, J = 8.8 Hz), 7.14 (2H, d, J = 8.7 Hz), 7.43 (2H, d, J = 8.7 Hz), 7.53 (2H, d, J = 8.4 Hz), 7.76 (2H, d, J = 8.0 Hz), 8.01 (2H, d, J = 8.0 Hz), 8.15 (1H, brs), 8.20 (2H, d, J = 8.4 Hz), 8.21 (1H, dd, J = 8.8 Hz, 2.5 Hz), 8.32 (1H, d, J = 2.5 Hz). |

TABLE 384

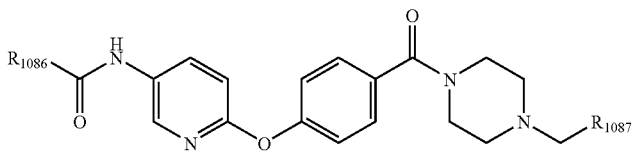

| Example No. | R1086 | R1087 | mp (° C.) or ¹H NMR (solvent) δppm |
|---|---|---|---|
| 2454 | 4-CF₃Ph— |  | ¹H NMR (CDCl₃) 2.43 (4H, brs), 3.46 (2H, s), 3.55 (4H, brs), 3.65 (3H, s), 5.95-6.08 (2H, m), 6.61 (1H, t, J = 2.2 Hz), 6.98 (1H, d, J = 8.9 Hz), 7.13 (2H, d, J = 8.8 Hz), 7.41 (2H, d, J = 8.8 Hz), 7.76 (2H, d, J = 8.1 Hz), 8.02 (2H, d, J = 8.1 Hz), 8.20 (1H, dd, J = 8.9 Hz, 2.5 Hz), 8.25 (1H, brs), 8.31 (1H, d, J = 2.5 Hz). |

TABLE 384-continued

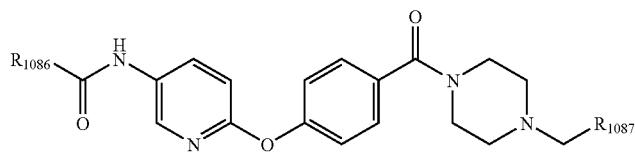

| Example No. | $R_{1086}$ | $R_{1087}$ | mp (° C.) or $^1$H NMR (solvent) δppm |
|---|---|---|---|
| 2455 | 4-CF$_3$Ph— | 2-pyridyl | mp 175-176 |
| 2456 | 4-CF$_3$Ph— | 4-OHPh— | $^1$H NMR (DMSO-d$_6$) 2.36 (4H, brs), 3.32 (2H, s), 3.49 (4H, brs), 6.70 (2H, d, J = 8.4 Hz), 7.09 (2H, d, J = 8.4 Hz), 7.15 (1H, d, J = 8.9 Hz), 7.16 (2H, d, J = 8.6 Hz), 7.43 (2H, d, J = 8.6 Hz), 7.94 (2H, d, J = 8.0 Hz), 8.17 (2H, d, J = 8.0 Hz), 8.26 (1H, dd, J = 8.9 Hz, 2.5 Hz), 8.54 (1H, d, J = 2.5 Hz), 9.27 (1H, s), 10.66 (1H, s). |
| 2457 | 4-CF$_3$Ph— | 2-OHPh— | $^1$H NMR (CDCl$_3$) 2.59 (4H, brs), 3.68 (4H, brs), 3.75 (2H, s), 6.72-6.88 (2H, m), 6.92-7.10 (1H, m), 7.01 (1H, d, J = 8.8 Hz), 7.15 (2H, d, J = 8.8 Hz), 7.10-7.25 (1H, m), 7.44 (2H, d, J = 8.8 Hz), 7.76 (2H, d, J = 8.1 Hz), 8.01 (2H, d, J = 8.1 Hz), 8.12 (1H, brs), 8.22 (1H, dd, J = 8.8 Hz, 2.3 Hz), 8.31 (1H, d, J = 2.3 Hz). |
| 2458 | 4-CF$_3$Ph— | 4-AcNHPh— | $^1$H NMR (DMSO-d$_6$) 2.02 (3H, s), 2.38 (4H, brs), 3.45 (2H, s), 3.45 (4H, brs), 7.15 (1H, d, J = 8.9 Hz), 7.16 (2H, d, J = 8.6 Hz), 7.22 (2H, d, J = 8.4 Hz), 7.44 (2H, d, J = 8.6 Hz), 7.52 (2H, d, J = 8.4 Hz), 7.94 (2H, d, J = 8.1 Hz), 8.17 (2H, d, J = 8.1 Hz), 8.26 (1H, dd, J = 8.9 Hz, 2.6 Hz), 8.54 (1H, d, J = 2.6 Hz), 9.90 (1H, s), 10.66 (1H, s). |
| 2459 | 4-CF$_3$Ph— | 2,3-(CH$_3$)$_2$Ph— | $^1$H NMR (CDCl$_3$) 2.25 (3H, s), 2.28 (3H, s), 2.42 (4H, brs), 3.47 (2H, s), 3.67 (4H, brs), 6.95 (1H, d, J = 8.7 Hz), 6.95-7.12 (3H, m), 7.10 (2H, d, J = 8.6 Hz), 7.38 (2H, d, J = 8.6 Hz), 7.73 (2H, d, J = 8.1 Hz), 8.00 (2H, d, J = 8.1 Hz), 8.17 (1H, dd, J = 8.7 Hz, 2.7 Hz), 8.30 (1H, d, J = 2.7 Hz), 8.43 (1H, s). |
| 2460 | 4-CF$_3$Ph— | 3-thienyl | $^1$H NMR (CDCl$_3$) 2.45 (4H, brs), 3.55 (2H, brs), 3.56 (2H, s), 3.72 (2H, brs), 6.97 (1H, d, J = 8.9 Hz), 7.05 (1H, dd, J = 5.0 Hz, 1.1 Hz), 7.08-7.17 (1H, m), 7.12 (2H, d, J = 8.7 Hz), 7.29 (1H, dd, J = 5.0 Hz, 3.0 Hz), 7.39 (2H, d, J = 8.7 Hz), 7.75 (2H, d, J = 8.1 Hz), 8.02 (2H, d, J = 8.1 Hz), 8.19 (1H, dd, J = 8.9 Hz, 2.8 Hz), 8.32 (1H, d, J = 2.8 Hz), 8.41 (1H, brs). |
| 2461 | 3,4-Cl$_2$Ph— | 3-pyridyl | $^1$H NMR (CDCl$_3$) 2.46 (4H, brs), 3.46 (2H, s), 3.55-3.80 (4H, m), 6.96 (1H, d, J = 8.9 Hz), 7.12 (2H, d, J = 8.4 Hz), 7.26-7.30 (1H, m), 7.40 (2H, d, J = 8.4 Hz), 7.56 (1H, d, J = 8.4 Hz), 7.65-7.78 (2H, m), 8.04 (1H, d, J = 2.2 Hz), 8.16 (1H, dd, J = 8.9 Hz, 2.7 Hz), 8.29 (1H, d, J = 2.2 Hz), 8.51-8.56 (2H, m), 8.61 (1H, brs). |

TABLE 385

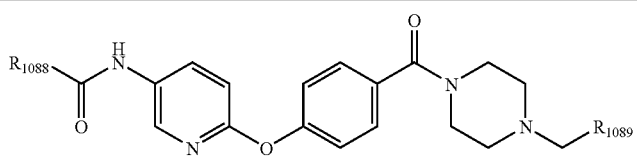

| Example No. | $R_{1088}$ | $R_{1089}$ | Form | $^1$H NMR (solvent) δppm |
|---|---|---|---|---|
| 2462 | 4-CF$_3$Ph— | cyclopropyl | free | (CDCl$_3$) 0.11 (2H, dd, J = 10.5 Hz, 4.5 Hz), 0.54 (2H, dd, J = 12.5 Hz, 6.5 Hz), 0.77-0.93 (1H, m), 2.29 (2H, d, J = 6.5 Hz), 2.52 (4H, brs), 3.55 (2H, brs), 3.75 (2H, brs), 6.98 (1H, d, J = 8.9 Hz), 7.14 (2H, d, J = 8.7 Hz), 7.42 (2H, d, J = 8.7 Hz), 7.76 (2H, d, J = 8.1 Hz), 8.03 (2H, d, J = 8.1 Hz), 8.20 (1H, dd, J = 8.9 Hz, 2.5 Hz), 8.33 (1H, d, J = 2.5 Hz), 8.36 (1H, brs). |

TABLE 385-continued

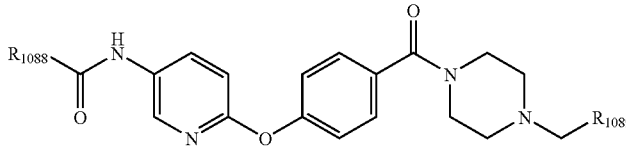

| Example No. | R<sub>1088</sub> | R<sub>1089</sub> | Form | $^1$H NMR (solvent) δppm |
|---|---|---|---|---|
| 2463 | 4-CF$_3$Ph— | 3-OHPh— | hydrochloride | (DMSO-d$_6$) 2.90-3.70 (6H, m), 3.90-4.20 (2H, m), 4.24 (2H, d, J = 3.9 Hz), 6.86 (1H, dd, J = 8.1 Hz, 1.7 Hz), 6.97 (1H, brs), 7.01 (1H, d, J = 7.7 Hz), 7.16 (1H, d, J = 8.9 Hz), 7.20 (2H, d, J = 8.6 Hz), 7.25 (1H, t, J = 7.7 Hz), 7.52 (2H, d, J = 8.6 Hz), 7.94 (2H, d, J = 8.1 Hz), 8.20 (2H, d, J = 8.1 Hz), 8.29 (1H, dd, J = 8.9 Hz, 2.5 Hz), 8.58 (1H, d, J = 2.5 Hz), 10.77 (1H, s). |
| 2464 | 4-CF$_3$Ph— | —C(CH$_3$)$_3$ | free | (CDCl$_3$) 0.88 (9H, s), 2.09 (2H, s), 2.52 (4H, brs), 3.49 (2H, brs), 3.68 (2H, brs), 6.97 (1H, d, J = 8.8 Hz), 7.12 (2H, d, J = 8.5 Hz), 7.39 (2H, d, J = 8.5 Hz), 7.75 (2H, d, J = 8.1 Hz), 8.03 (2H, d, J = 8.1 Hz), 8.19 (1H, dd, J = 8.8 Hz, 2.5 Hz), 8.33 (1H, d, J = 2.5 Hz), 8.47 (1H, s). |
| 2465 | 4-CF$_3$Ph— | 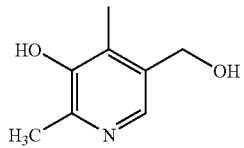 | free | (CDCl$_3$) 2.42 (3H, s), 2.59 (4H, brs), 3.48-3.76 (4H, m), 3.91 (2H, s), 4.56 (2H, s), 7.00 (1H, d, J = 8.9 Hz), 7.13 (2H, d, J = 8.7 Hz), 7.39 (2H, d, J = 8.6 Hz), 7.71 (2H, d, J = 8.3 Hz), 7.79 (1H, s), 8.00 (2H, d, J = 8.1 Hz), 8.22-8.29 (2H, m), 8.81 (1H, brs). |
| 2466 | 4-CF$_3$Ph— | 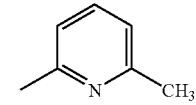 | free | (CDCl$_3$) 2.55 (3H, s), 2.35-2.70 (4H, m), 3.66 (2H, s), 3.40-3.95 (4H, m), 6.98 (1H, d, J = 8.7 Hz), 7.05 (1H, d, J = 7.6 Hz), 7.12 (2H, d, J = 8.5 Hz), 7.22 (1H, d, J = 7.6 Hz), 7.42 (2H, d, J = 8.5 Hz), 7.56 (1H, t, J = 7.6 Hz), 7.75 (2H, d, J = 8.2 Hz), 8.02 (2H, d, J = 8.2 Hz), 8.21 (1H, dd, J = 8.7 Hz, 2.8 Hz), 8.31 (1H, d, J = 2.8 Hz), 8.38 (1H, s). |
| 2467 | 3,4-Cl$_2$Ph— | 4-AcNHPh— | free | (DMSO-d$_6$) 2.02 (3H, s), 2.38 (4H, brs), 3.44 (2H, s), 3.55 (4H, brs), 7.14 (1H, d, J = 8.8 Hz), 7.16 (2H, d, J = 8.7 Hz), 7.21 (2H, d, J = 8.4 Hz), 7.43 (2H, d, J = 8.7 Hz), 7.52 (2H, d, J = 8.4 Hz), 7.84 (1H, d, J = 8.4 Hz), 7.95 (1H, dd, J = 8.4 Hz, 2.0 Hz), 8.22 (1H, d, J = 2.0 Hz), 8.23 (1H, dd, J = 8.8 Hz, 2.6 Hz), 8.51 (1H, d, J = 2.6 Hz), 9.90 (1H, s), 10.59 (1H, s). |

TABLE 386

[Structure: F3C-C6H4-C(=O)-Xb57-pyridine(R1090)(O-)-phenyl-Xb58-C(=O)-N-piperazine-N-R1091]

| Example No. | Xb57 | R1090 | R1091 | Xb58 | Form | ¹H NMR (solvent) δppm |
|---|---|---|---|---|---|---|
| 2468 | —NH— | —H | 1-methyl-2-ethyl-pyrrole (H3C on N, ethyl on ring) | —CH2— | trihydrochloride | (DMSO-d$_6$) 2.60-3.20 (7H, m), 3.22-3.60 (3H, m), 3.71 (3H, s), 4.10 (1H, d, J = 13.2 Hz), 4.30 (2H, d, J = 4.8 Hz), 4.48 (1H, d, J = 13.2 Hz), 6.05 (1H, t, J = 2.5 Hz), 6.32 (1H, dd, J = 3.6 Hz, 1.9 Hz), 6.87 (1H, t, J = 2.5 Hz), 7.04 (2H, d, J = 8.4 Hz), 7.06 (1H, d, J = 8.8 Hz), 7.29 (2H, d, J = 8.4 Hz), 7.93 (2H, d, J = 8.5 Hz), 8.19 (2H, d, J = 8.5 Hz), 8.22 (1H, dd, J = 8.8 Hz, 2.6 Hz), 8.51 (1H, d, J = 2.6 Hz), 10.70 (1H, s). |
| 2469 | —NH— | —H | 3-furylmethyl | —CH2— | free | (CDCl$_3$) 2.25-2.45 (4H m), 2.60 (2H, t, J = 7.7 Hz), 2.93 (2H, t, J = 7.7 Hz), 3.37 (2H, s), 3.40 (2H, t, J = 5.0 Hz), 3.60 (2H, t, J = 5.0 Hz), 6.37 (1H, d, J = 1.5 Hz), 6.93 (1H, d, J = 8.8 Hz), 7.02 (2H, d, J = 8.6 Hz), 7.19 (2H, d, J = 8.6 Hz), 7.33 (1H, s), 7.39 (1H, t, J = 1.5 Hz), 7.73 (2H, d, J = 8.1 Hz), 8.01 (2H, d, J = 8.1 Hz), 8.21 (1H, dd, J = 8.8 Hz, 2.6 Hz), 8.28 (1H, d, J = 2.6 Hz), 8.46 (1H, s). |
| 2470 | —NH— | —H | furfuryl | —CH2— | free | (CDCl$_3$) 2.31-2.52 (4H m), 2.60 (2H, t, J = 7.2 Hz), 2.93 (2H, t, J = 7.2 Hz), 3.43 (2H, t, J = 5.0 Hz), 3.55 (2H, s), 3.63 (2H, t, J = 5.0 Hz), 6.21 (1H, d, J = 2.6 Hz), 6.32 (1H, d, J = 3.0 Hz), 6.94 (1H, d, J = 8.9 Hz), 7.02 (2H, d, J = 8.5 Hz), 7.19 (2H, d, J = 8.5 Hz), 7.38 (1H, d, J = 2.8 Hz), 7.74 (2H, d, J = 8.0 Hz), 8.00 (2H, d, J = 8.0 Hz), 8.21 (1H, dd, J = 8.9 Hz 2.5 Hz), 8.28 (1H, d, J = 2.5 Hz, 8.35 (1H, s). |
| 2471 | none | —CH3 | piperonyl | —N(CH3)— | free | (CDCl$_3$) 2.12 (3H, s), 2.42-2.45 (4H, m), 3.03 (3H, s), 3.44 (2H, s), 3.47-3.52 (2H, m), 3.62-3.65 (2H, m), 4.09 (2H, s), 5.95 (2H, s), 6.54-6.59 (2H, m), 6.71-6.77 (2H, m), 6.85 (1H, s), 6.92-6.96 (2H, m), 7.75 (2H, d, J = 8.4 Hz), 7.87 (2H, d, J = 8.1 Hz), 8.17 (1H, dd, J = 8.6 Hz, 2.5 Hz), 8.58 (1H, d, J = 2.1 Hz). |

TABLE 387

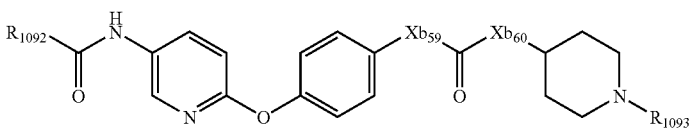

| Example No. | $R_{1092}$ | $Xb_{59}$ | $Xb_{60}$ | $R_{1093}$ | $^1$H NMR (DMSO-$d_6$) δppm |
|---|---|---|---|---|---|
| 2472 | 3,4-Cl$_2$Ph— | —NH— | none | benzyl | 1.55-1.82 (4H, m), 1.96 (2H, t, J = 10.5 Hz), 2.21-2.40 (1H, m), 2.87 (2H, d, J = 10.5 Hz), 3.47 (2H, s), 7.02 (1H, d, J = 8.9 Hz), 7.05 (2H, d, J = 9.1 Hz), 7.18-7.42 (5H, m), 7.62 (2H, d, J = 9.1 Hz), 7.84 (1H, d, J = 8.4 Hz), 7.94 (1H, dd, J = 8.4 Hz, 2.0 Hz), 8.17 (1H, dd, J = 8.9 Hz, 2.6 Hz), 8.22 (1H, d, J = 2.0 Hz), 8.46 (1H, d, J = 2.6 Hz), 9.89 (1H, s), 10.53 (1H, s). |
| 2473 | 3,4-Cl$_2$Ph— | —NH— | none | 3-furylmethyl | 1.55-1.85 (4H, m), 1.85-2.07 (2H, m), 2.18-2.40 (1H, m), 2.80-3.00 (2H, m), 3.32 (2H, s), 6.44 (1H, s), 7.02 (1H, d, J = 8.9 Hz), 7.05 (2H, d, J = 8.9 Hz), 7.57 (1H, s) 7.57-7.66 (1H, m), 7.62 (2H, d, J = 8.9 Hz), 7.84 (1H, d, J = 8.4 Hz), 7.94 (1H, dd, J = 8.4 Hz, 2.0 Hz), 8.17 (1H, dd, J = 8.9 Hz, 2.6 Hz), 8.22 (1H, d, J = 2.0 Hz), 8.45 (1H, d, J = 2.6 Hz), 9.89 (1H, s), 10.54 (1H, s). |
| 2474 | 4-CF$_3$Ph | none | —N(CH$_3$)— | benzyl | 1.50-2.30 (6H, m), 2.84 (5H, brs), 3.44 (2H, brs), 4.27 (1H, brs), 7.16 (3H, d, J = 8.6 Hz), 7.18-7.39 (5H, m), 7.41 (2H, d, J = 8.5 Hz), 7.95 (2H, d, J = 8.1 Hz), 8.17 (2H, d, J = 8.1 Hz), 8.27 (1H, dd, J = 8.9 Hz, 2.5 Hz), 8.56 (1H, d, J = 2.5 Hz), 10.68 (1H, s). |
| 2475 | 4-CF$_3$Ph— | none | —N(CH$_3$)— | 3-furylmethyl | 1.50-2.20 (6H, m), 2.83 (3H, s), 2.72-3.02 (2H, m), 3.30 (2H, d, J = 3.5 Hz), 4.28 (1H, brs), 6.41 (1H, s), 7.15 (1H, d, J = 8.8 Hz), 7.16 (2H, d, J = 8.4 Hz), 7.41 (2H, d, J = 8.4 Hz), 7.53 (1H, s), 7.60 (1H, s), 7.95 (2H, d, J = 8.1 Hz), 8.17 (2H, d, J = 8.1 Hz), 8.27 (1H, dd, J = 8.8 Hz, 2.5 Hz), 8.55 (1H, d, J = 2.5 Hz), 10.68 (1H, s). |

TABLE 388

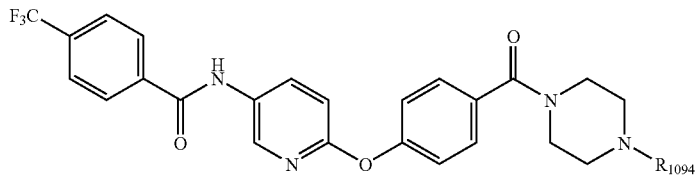

| Example No. | $R_{1094}$ | $^1$H NMR (CDCl$_3$) δppm |
|---|---|---|
| 2476 | cyclohexyl | 1.00-1.40 (5H, m), 1.52-1.70 (1H, m), 1.70-1.92 (4H, m), 2.21-2.40 (1H, m), 2.57 (4H, brs), 3.52 (2H, brs), 3.73 (2H, brs), 6.98 (1H, d, J = 8.9 Hz), 7.13 (2H, d, J = 8.8 Hz), 7.41 (2H, d, J = 8.8 Hz), 7.76 (2H, d, J = 8.2 Hz), 8.03 (2H, d, J = 8.2 Hz), 8.19 (1H, dd, J = 8.9 Hz, 2.5 Hz), 8.33 (1H, d, J = 2.5 Hz), 8.36 (1H, brs). |

TABLE 388-continued

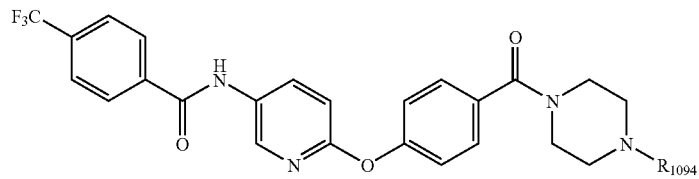

| Example No. | $R_{1094}$ | $^1$H NMR (CDCl$_3$) δppm |
|---|---|---|
| 2477 | 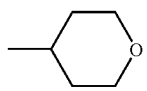 | 1.40-1.85 (4H, m), 2.38-2.60 (1H, m), 2.57 (4H, brs), 3.38 (2H, t, J = 11.0 Hz), 3.72 (4H, brs), 4.03 (2H, dd, J = 11.0 Hz, 3.5 Hz), 7.00 (1H, d, J = 8.7 Hz), 7.15 (2H, d, J = 8.7 Hz), 7.43 (2H, d, J = 8.7 Hz), 7.77 (2H, d, J = 8.5 Hz), 8.02 (2H, d, J = 8.5 Hz), 8.16 (1H, brs), 8.21 (1H, dd, J = 8.7 Hz, 2.5 Hz), 8.32 (1H, d, J = 2.5 Hz). |
| 2478 | cyclopropyl | 0.33-0.58 (4H, m), 1.45-1.72 (1H, m), 2.62 (4H, brs), 3.49 (2H, brs), 3.68 (2H, brs), 7.00 (1H, d, J = 8.9 Hz), 7.15 (2H, d, J = 8.4 Hz), 7.43 (2H, d, J = 8.4 Hz), 7.77 (2H, d, J = 8.4 Hz), 8.02 (2H, d, J = 8.4 Hz), 8.21 (1H, s), 8.21 (1H, dd, J = 8.9 Hz, 2.6 Hz), 8.33 (1H, d, J = 2.6 Hz). |

TABLE 389

| Example No. | Chemical structure | $^1$H NMR (solvent) δppm |
|---|---|---|
| 2479 | 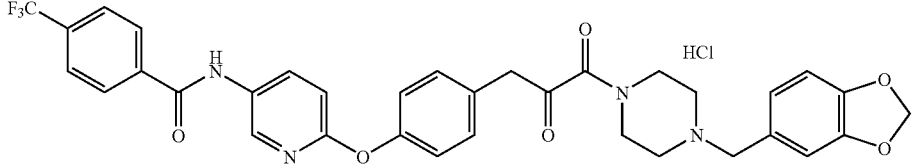 | (DMSO-d$_6$) 2.77-3.10 (2H, m), 3.17-3.63 (4H, m), 3.71-3.89 (1H, m), 4.18 (2H, s), 4.24 (2H, s), 4.27-4.44 (1H, m), 6.07 (2H, s), 6.92-7.06 (2H, m), 7.09 (3H, d, J = 8.6 Hz), 7.22 (1H, s), 7.28 (2H, d, J = 8.6 Hz), 7.92 (2H, d, J = 8.0 Hz), 8.18 (2H, d, J = 8.0 Hz), 8.24 (1H, dd, J = 8.8 Hz, 2.5 Hz), 8.53 (1H, d, J = 2.5 Hz), 10.69 (1H, s). |

TABLE 389-continued

| Example No. | Chemical structure | ¹H NMR (solvent) δppm |
|---|---|---|
| 2480 | [Structure: 4-(trifluoromethyl)benzamide linked to pyridine-O-phenyl-CH2-CH(OH)-C(O)-piperazine-CH2-benzodioxole] | (CDCl₃) 2.25-2.52 (4H, m), 2.77-2.95 (2H, m), 3.12-3.29 (1H, m), 3.29-3.46 (1H, m), 3.41 (2H, s), 3.43-3.59 (1H, m), 3.65-3.84 (2H, m), 5.30 (1H, brs), 5.92 (2H, s), 6.73 (2H, s), 6.84 (1H, s), 6.95 (1H, d, J = 9.0 Hz), 7.05 (2H, d, J = 8.4 Hz), 7.23 (2H, d, J = 8.4 Hz), 7.75 (2H, d, J = 8.1 Hz), 7.98 (2H, d, J = 8.1 Hz), 8.03 (1H, brs), 8.20 (1H, dd, J = 9.0 Hz, 2.5 Hz), 8.22 (1H, s). |
| 2481 | [Structure: 4-(trifluoromethyl)phenyl-SO2-NH-pyridine-O-phenyl-piperidine-CH2-C(O)-piperazine-CH2-phenyl] | (CDCl₃) 1.32-1.44 (2H, m), 1.83-2.02 (3H, m), 2.30 (2H, d, J = 6.8 Hz), 2.42-2.47 (4H, m), 2.69 (2H, t, J = 12.0 Hz), 3.48-3.66 (8H, m), 6.86-6.99 (6H, m), 7.25-7.32 (7H, m), 7.50 (2H, d, J = 8.6 Hz), 7.98 (1H, dd, J = 8.7 Hz, 2.6 Hz), 8.59 (1H, d, J = 2.0 Hz). |

Example 2482

Production of N-(6-{4-[4-((1S,2S)-2-hydroxycyclohexyl)piperazine-1-carbonyl]phenoxy}pyridin-3-yl)-4-trifluoromethylbenzamide To a solution of N-{6-[4-(piperazine-1-carbonyl)phenoxy]-pyridin-3-yl}-4-trifluoromethyl-benzamide (430 mg, 0.91 mmol) in methanol was added 1,2-epoxycyclohexane (180 mg, 1.83 mmol), and the resulting solution was stirred for 1 day under reflux. The resulting reaction solution was concentrated under reduced pressure. The residue was purified by silica gel column chromatography (chloroform:methanol=35:1), and then ethyl acetate was added. The precipitated white powder was filtered off and washed with ethyl acetate, to thereby yield 284 mg of the title compound.

Appearance: White powder

¹H NMR (CDCl₃) δ 1.03-1.38 (4H, m), 1.42-1.88 (3H, m), 2.06-2.35 (2H, m), 2.31 (2H, brs), 2.74 (2H, brs), 3.30-4.00 (6H, m), 7.00 (1H, d, J=8.9 Hz), 7.15 (2H, d, J=8.7 Hz), 7.43 (2H, d, J=8.7 Hz), 7.77 (2H, d, J=8.1 Hz), 8.02 (2H, d, J=8.1 Hz), 8.21 (1H, brs), 8.22 (1H, dd, J=8.9 Hz, 2.7 Hz), 8.33 (1H, d, J=2.7 Hz).

Example 2483

Production of 3,4-dichloro-N-[6-({4-[3-oxo-3-(4-piperonylpiperazin-1-yl)propyl]phenyl}methylamino)-pyridin-3-yl]benzamide dioxalate To a solution of 3,4-dichloro-N-(6-{4-[3-oxo-3-(4-piperonylpiperazin-1-yl)propyl]phenylamino}-pyridin-3-yl)benzamide (250 mg, 0.395 mmol) in methanol (3 mL) were added acetic acid (0.500 mL) and 37% aqueous formaldehyde (0.640 mL, 7.89 mmol), and the resulting solution was stirred for 30 minutes at 50° C. To the reaction solution was added sodium cyanoborohydride (0.160 g, 2.55 mmol) at room temperature, and stirred for 8 hours at 50° C. Water was added to the reaction solution and extracted with ethyl acetate. The ethyl acetate layer was washed with a saturated sodium bicarbonate solution and brine, dried over anhydrous magnesium sulfate, and evaporated. The residue was purified by silica gel column chromatography (dichloromethane:methanol=10:1), to yield a free form. This free form was dissolved in isopropanol (5 mL) and oxalic acid dihydrate (70 mg, 0.555 mmol) by heating. The solvent was evaporated, and the resulting solid was recrystallized from isopropanol, to thereby yield 0.193 g of the title compound.

Appearance: Pale yellow powder
Melting point: 127-129° C.

The following compound was produced in the same manner as in Example 2483.

Example 2484

2-(Ethyl{4-[5-(4-trifluoromethylphenoxymethyl) pyridin-2-yloxy]phenyl}amino)-1-(4-piperonylpiperazin-1-yl)ethanone $^1$H NMR (CDCl$_3$) δ 1.18 (3H, t, J=7.1 Hz), 2.41-2.44 (4H, m), 3.39-3.47 (4H, m), 3.51 (2H, brs), 3.64 (2H, brs), 4.03 (2H, s), 5.03 (2H, s), 5.94 (2H, s), 6.68 (2H, d, J=9.1 Hz), 6.73-6.74 (2H, m), 6.85-6.88 (2H, m), 6.99 (2H, d, J=9.1 Hz), 7.01 (2H, d, J=8.4 Hz), 7.55 (2H, d, J=8.7 Hz), 7.71 (1H, dd, J=8.6 Hz, 2.5 Hz), 8.22 (1H, d, J=2.3 Hz).

Example 2485

Production of 3,4-dichloro-N-[6-(4-thiomorpholine-4-ylmethylphenoxy)pyridin-3-yl]benzamide monohydrochloride 3,4-dichloro-N-[6-(4-chloromethylphenoxy)-pyridin-3-yl]benzamide (0.61 g, 1.5 mmol) was dissolved in DMF (5 mL). To the resulting solution were added triethylamine (0.84 mL, 6.0 mmol) and thiomorpholine (0.15 mL, 1.5 mmol), and this solution was stirred overnight at 40° C. The resulting reaction solution was concentrated under reduced pressure. To the residue was added ethyl acetate and washed with a saturated sodium bicarbonate solution and brine. The organic layer was dried over anhydrous magnesium sulfate and evaporated. This residue was purified by silica gel column chromatography (chloroform:methanol=80:1). The obtained solid (0.56 g, 1.18 mmol) was dissolved in ethyl acetate (50 mL), and a solution of 4 N hydrogen chloride in ethyl acetate (0.295 mL, 1.18 mmol) was added, and this solution was stirred for 1 hour at room temperature. The precipitated crystals were collected by suction filtration, and recrystallized from methanol, to thereby yield 0.38 g of the title compound.

Appearance: White powder $^1$H NMR (DMSO-d$_6$) δ 2.80-2.83 (2H, m), 3.09-3.17 (4H, m), 3.61 (2H, m), 4.35 (2H, s), 7.14 (1H, d, J=8.9 Hz), 7.21 (2H, d, J=8.3 Hz), 7.60 (2H, d, J=8.3 Hz), 7.85 (1H, d, J=8.6 Hz), 7.96 (1H, dd, J=8.3 Hz, 2.0 Hz), 8.23 (1H, dd, J=8.9 Hz, 2.6 Hz), 8.24 (1H, d, J-2.0 Hz), 8.53 (1H, d, J=2.6 Hz), 10.45 (1H, brs), 10.62 (1H, brs).

The following compounds were produced in the same manner as in Example 2485.

Example 2486

3,4-Dichloro-N-(4-{4-[1-(3-imidazole-1-ylpropyl)-1,2,3,6-tetrahydropyridine-4-yl]phenoxy}phenyl)-benzamide Melting point: 169-171° C.

TABLE 390

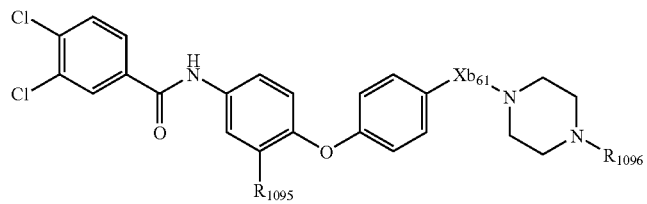

| Example No. | R$_{1095}$ | Xb$_{61}$ | R$_{1096}$ | Form | mp (° C.) |
|---|---|---|---|---|---|
| 2487 | —F | —CH$_2$— | benzyl | dihydrochloride | 178-179 |
| 2488 | —F | —CH$_2$— | piperonyl | dihydrochloride | 192-195 |
| 2489 | —F | —(CH$_2$)$_2$— | benzyl | dihydrochloride | 208-210 |
| 2490 | —F | —(CH$_2$)$_2$— | piperonyl | dihydrochloride | 202-205 |
| 2491 | —F | —(CH$_2$)$_3$— | benzyl | dihydrochloride | 260-262 |
| 2492 | —F | —(CH$_2$)$_3$— | piperonyl | dihydrochloride | 258-260 |
| 2493 | —F | —(CH$_2$)$_4$— | benzyl | dihydrochloride | 245-248 |
| 2494 | —F | —(CH$_2$)$_4$— | piperonyl | dihydrochloride | 256-258 |
| 2495 | —H | none |  | free | 172-173 |

TABLE 390-continued

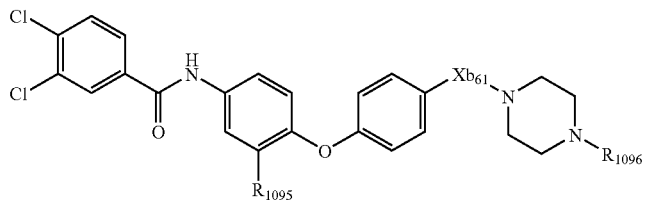

| Example No. | R_{1095} | Xb_{61} | R_{1096} | Form | mp (° C.) |
|---|---|---|---|---|---|
| 2496 | —H | none | (butyl-morpholine) | free | 131-134 |

TABLE 391

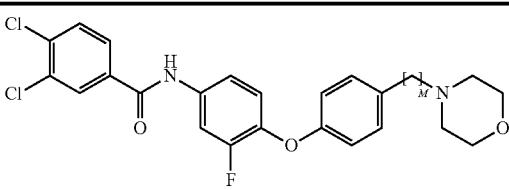

| Example No. | M | Form | mp (° C.) |
|---|---|---|---|
| 2497 | 1 | hydrochloride | 165-168 |
| 2498 | 2 | free | 143-144 |
| 2499 | 3 | oxalate | 173-175 |
| 2500 | 4 | hydrochloride | 226-228 |

TABLE 392

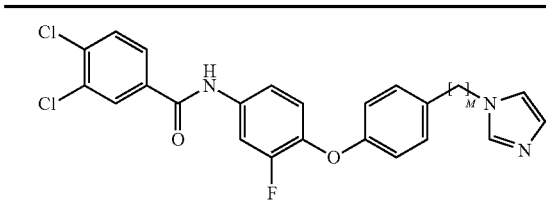

| Example No. | M | mp (° C.) |
|---|---|---|
| 2501 | 1 | 183-185 |
| 2502 | 4 | 141-143 |

TABLE 393

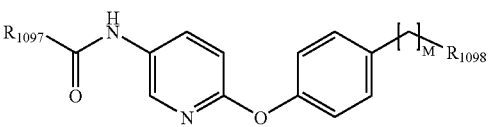

| Example No. | R_{1097} | R_{1098} | M | Form | $^1$H NMR (solvent) δppm |
|---|---|---|---|---|---|
| 2503 | 3,4-Cl$_2$Ph— | piperidino | 1 | free | (CDCl$_3$)1.42-1.58(6H, m), 2.36-2.38(4H, m), 3.44(2H, s), 6.86(1H, d, J=8.9 Hz), 6.99(2H, dd, J=6.6 Hz, 2.0 Hz), 7.26-7.31(2H, m), 7.47(1H, d, J=8.3 Hz), 7.67(1H, dd, J=8.3 Hz, 2.0 Hz), 7.94(1H, d, J=2.3 Hz), 8.10(1H, dd, J=8.9 Hz, 2.6 Hz), 8.21(1H, d, J=2.6 Hz), 8.69(1H, brs). |
| 2504 | 3,4-Cl$_2$Ph— | piperidino | 3 | dihydro-chloride | (DMSO-d$_6$)1.67-1.77(6H, m), 1.99-2.10 (2H, m), 2.61-3.05(6H, m),3.40-3.43(2H, m), 6.01(1H, brs), 7.04-7.08(3H, m), 7.28(2H, d, J=8.6 Hz), 7.84(1H, d, J=8.4 Hz), 7.96-8.00(1H, m), 8.19-8.23(1H, m), 8.26(1H, d, J=1.9 Hz), 8.51(1H, d, J=2.7 Hz), 10.24(1H, brs), 10.67(1H, s). |
| 2505 | 3,4-Cl$_2$Ph— | piperidino | 4 | free | (CDCl$_3$)1.40-1.50(2H, m), 1.50-1.75(8H, m) 2.25-2.50(6H, m), 2.63(2H, t, J=7.0 Hz), 6.93(1H, d, J=9.0 Hz), 7.03(2H, d, J=8.5 Hz), 7.19(2H, d, J=8.5 Hz), 7.58(1H, d, J=8.5 Hz), 7.71(1H, dd, J=8.5 Hz, 2.0 Hz) 7.82(1H, s), 7.98(1H, d, J=2.0 Hz), 8.16(1H, dd, J=9.0 Hz, 3.0 Hz), 8.25(1H, d, J=3.0 Hz). |
| 2506 | 3,4-Cl$_2$Ph— | piperidino | 5 | free | (CDCl$_3$)1.20-1.80(12H, m), 2.31(2H, t, J=7.8 Hz), 2.40(4H, brs), 2.61(2H, t, J= |

TABLE 393-continued

R1097—NH—[pyridine]—O—[phenyl]—(CH2)M—R1098

| Example No. | R1097 | R1098 | M | Form | ¹H NMR (solvent) δppm |
|---|---|---|---|---|---|
| | | | | | 7.8 Hz), 6.94(1H, d, J=8.8 Hz), 7.04(2H, d, J=8.4 Hz), 7.20(2H, d, J=8.4 Hz), 7.58(1H, d, J=8.2 Hz), 7.72(1H, s), 7.71(1H, dd, J=8.2 Hz, 2.0 Hz), 7.98(1H, d, J=2.3 Hz), 8.16(1H, dd, J=8.8 Hz, 2.8 Hz), 8.24(1H, d, J=2.8 Hz). |
| 2507 | 4-CF₃Ph— | morpholino | 1 | free | (DMSO-d₆)2.37(4H, t, J=4.6 Hz), 3.46(2H, s), 3.59(4H, t, J=4.6 Hz), 7.07(3H, d, J=8.6 Hz), 7.33(2H, d, J=8.6 Hz), 7.93(2H, d, J=8.6 Hz), 8.15-8.24(3H, m), 8.51(1H, d, J=2.6 Hz), 10.63(1H, s). |
| 2508 | 3,4-Cl₂Ph— | morpholino | 1 | free | (CDCl₃)2.56(4H, t, J=4.6 Hz), 3.60(2H, s), 3.82(4H, t, J=4.6 Hz), 7.05(1H, d, J=8.6 Hz), 7.18(2H, dd, J=6.6 Hz, 2.0 Hz), 7.45(2H, d, J=8.6 Hz), 7.67(1H, d, J=8.6 Hz), 7.80(1H, dd, J=8.3 Hz, 2.0 Hz), 7.99(1H, brs), 8.07(1H, d, J=2.0 Hz), 8.25-8.29(1H, m), 8.35(1H, d, J=2.6 Hz). |
| 2509 | 3,4-Cl₂Ph— | morpholino | 2 | free | (CDCl₃)2.54-2.85(8H, m), 3.74-3.78(4H, m), 6.95(1H, d, J=8.9 Hz), 7.04-7.07(2H, m), 7.22-7.26(2H, m), 7.58(1H, d, J=8.6 Hz), 7.68-7.72(1H, m), 7.79(1H, brs), 7.98(1H, d, J=2.0 Hz), 8.17(1H, dd, J=8.9 Hz, 2.6 Hz), 8.24(1H, d, J=2.6 Hz). |
| 2510 | 3,4-Cl₂Ph— | morpholino | 3 | free | (CDCl₃)1.78-1.83(2H, m), 2.34-2.45(6H, m), 2.60-2.66(2H, m), 3.70-3.73(4H, m), 6.88(1H, d, J=8.6 Hz), 7.00(2H, d, J=8.6 Hz), 7.18(2H, d, J=8.6 Hz), 7.51(1H, d, J=8.6 Hz), 7.66-7.70(1H, m), 7.94(1H, d, J=2.2 Hz), 8.10-8.14(1H, m), 8.22(1H, d, J=2.7 Hz), 8.40(1H, brs). |

TABLE 394

3,4-Cl₂-C₆H₃—C(=O)—NH—[pyridine]—O—[phenyl]—(CH2)M—R1099

| Example No. | R1099 | M | Form | ¹H NMR (solvent) δppm |
|---|---|---|---|---|
| 2511 | morpholino | 4 | dihydro-chloride | (DMSO-d₆)1.55-1.90(4H, m), 2.63(2H, t, J=7.2 Hz), 2.90-3.20(4H, m), 3.30-3.50(2H, m), 3.79(2H, t, J=11.2 Hz), 3.93(2H, s), 7.04(2H, d, J=8.2 Hz), 7.05(1H, d, J=9.0 Hz), 7.26(2H, d, J=8.2 Hz), 7.84(1H, d, J=8.2 Hz), 7.98(1H, dd, J=8.2 Hz, 2.0 Hz), 8.20(1H, dd, J=9.0 Hz, 2.7 Hz), 8.25(1H, d, J=2.0 Hz), 8.50(1H, d, J=2.7 Hz), 10.65(1H, s). |
| 2512 | morpholino | 5 | free | (CDCl₃)1.30-1.45(2H, m), 1.45-1.75(4H, m), 2.33(2H, t, J=7.2 Hz), 2.44(4H, t, J=4.6 Hz), 2.62(2H, t, J=7.7 Hz), 3.72(4H, t, J=4.6 Hz), 6.94(1H, d, J=9.0 Hz), 7.04(2H, d, J=8.5 Hz), 7.20(2H, d, J=8.5 Hz) 7.58(1H, d, J=8.2 Hz), 7.65-7.75(2H, m), 7.98(1H, d, J=2.0 Hz), 8.16(1H, dd, J=9.0 Hz, 2.6 Hz), 8.24(1H, d, J=2.6 Hz). |
| 2513 | 3-(2,4-dioxothiazolidin-3-yl) | 3 | free | (CDCl₃)1.97-2.03(2H, m), 2.67(2H, t, J=7.6 Hz), 3.68-3.73(2H, m), 3.88(2H, s), 6.95(1H, d, J=8.9 Hz), 7.05(2H, d, J=8.6 Hz), 7.21(2H, d, J=8.6 Hz), 7.56(1H, d, J=8.3 Hz), 7.69-7.74(2H, m), 7.98(1H, d, j=2.3 Hz), 8.14-8.18(1H, m), 8.23(1H, d, J=3.0 Hz). |

TABLE 394-continued

Structure: 3,4-dichlorobenzamide-NH-pyridine-O-phenyl-(CH)$_M$-R$_{1099}$

| Example No. | R$_{1099}$ | M | Form | $^1$H NMR (solvent) δppm |
|---|---|---|---|---|
| 2514 | N-methylimidazole | 1 | free | (DMSO-d$_6$)5.20(2H, s), 6.91(1H, s), 7.07(1H, d, J=8.6 Hz), 7.10(2H, d, J=8.6 Hz), 7.22(1H, s), 7.31(2H, d, J=8.6 Hz), 7.77(1H, s), 7.84(1H, d, J=8.6 Hz), 7.94(1H, dd, J=8.6 Hz, 2.0 Hz), 8.19(1H, dd, J=8.6 Hz, 2.3 Hz), 8.22(1H, d, J=2.0 Hz), 8.46(1H, d, J=2.3 Hz), 10.57 (1H, s). |
| 2515 | 1,2,4-triazole | 1 | hydro-chloride | (DMSO-d$_6$)5.48(2H, s), 7.09(1H, d, J=8.5 Hz), 7.12(2H, d, J=8.6 Hz), 7.38(2H, d, J=8.6 Hz), 7.83(1H, d, J=8.5 Hz, 2.0 Hz), 7.98(1H, dd, J=8.5 Hz, 2.0 Hz), 8.23(1H, dd, J=8.5 Hz, 2.3 Hz), 8.26(1H s), 8.26(1H, d, J=2.0 Hz), 8.51(1H, d, J=2.3 Hz), 9.05(1H, s), 10.70(1H, s). |
| 2516 | 1,2,3-triazole | 1 | free | (DMSO-d$_6$)5.63(2H, d, J=8.6 Hz), 7.09(1H, d, J=8.6 Hz), 7.11(2H, d, J=8.6 Hz), 7.36(2H, d, J=8.6 Hz), 7.76(1H, d, J=1.0 Hz), 7.84(1H, d, J=8.3 Hz), 7.94(1H, dd, J=8.3 Hz, 2.0 Hz), 8.20(1H, dd, J=8.6 Hz, 2.6 Hz), 8 23(2H, d, J=2.6 Hz), 10.55(1H, s). |
| 2517 | pyrazole | 1 | hydro-chloride | (DMSO-d$_6$)5.66(2H, s), 7.09(1H, d, J=8.6 Hz), 7.10(2H, d, J=8.6 Hz), 7.32(2H, d, J=8.6 Hz), 7.83(2H, s), 7.83(1H, d, J=8.5 Hz), 7.96(1H, dd, J=8.5 Hz, 2.0 Hz), 8.21(1H, dd, J=8.5 Hz, 2.3 Hz), 8.23(1H, d, J=2.0 Hz), 8.47(1H, d, J=2.3 Hz), 10.61(1H, s). |
| 2518 | pyrazole | 1 | hydro-chloride | (DMSO-d$_6$)5.34(2H, s), 6.28(1H, t, J=2.0 Hz), 7.06(1H, d, J=9.0 Hz), 7.07(2H, d, J=8.6 Hz), 7.26(2H, d, J=8.6 Hz), 7.47(1H, d, J=2.0 Hz), 7.83(1H, d, J=8.6 Hz), 7.85(1H, d, J=2.0 Hz), 7.96(1H, dd, J=8.6 Hz, 2.0 Hz), 8.20(1H, dd, J=9.0 Hz, 2.6 Hz), 8.23(1H, d, J=2.0 Hz), 8.47(1H, d, J=2.6 Hz), 10.61(1H, s). |
| 2519 | N-methylimidazole | 2 | free | (CDCl$_3$)3.04(2H, t, J=7.0 Hz), 4.17(2H, t, J=7.0 Hz), 6.87(1H, t, J=1.3 Hz), 6.94(1H, d, J=8.7 Hz), 7.02(1H, brs), 7.05(4H, s), 7.30(1H, brs), 7.56(1H, d, J=8.3 Hz), 7.75(1H, dd, J=8.3 Hz, 2.1 Hz), 8.03(1H, d, J=2.1 Hz), 8.17(1H, dd, J=8.7 Hz, 2.3 Hz), 8.23(1H, d, J=2.3 Hz), 8.61(1H, brs). |

TABLE 395

Structure: R$_{1100}$-C(O)NH-pyridine-O-phenyl-CH$_2$-piperazine-R$_{1101}$

| Example No. | R$_{1100}$ | R$_{1101}$ | $^1$H NMR (solvent) δppm |
|---|---|---|---|
| 2520 | 4-ClPh— | piperonyl | (CDCl$_3$)2.48(8H, brs), 3.42(2H, s), 3.50(2H, s), 5.93(2H, s), 6.74(2H, s), 6.85(1H, s), 6.94(1H, d, J=8.6 Hz), 7.07(2H, d, J=8.6 Hz), 7.33(2H, d, J=8.6 Hz), 7.49(2H, d, J=8.6 Hz), 7.73(1H, brs), 7.82(2H, d, J=8.6 Hz), 8.18-8.24(2H, m). |
| 2521 | 4-CNPh— | piperonyl | (CDCl$_3$)2.48(8H, brs), 3.42(2H, s), 3.51(2H, s), 5.93(2H, s), 6.73-6.74(2H, m), 6.85(1H, s), 6.96(1H, d, J=8.9 Hz), 7.07(2H, d, J=8.6 Hz), 7.34(2H, d, J=8.6 Hz), 7.79 7.82(3H, m), 7.99(2H, d, J=8.2 Hz), 8.19(1H, dd, J=8.9 Hz, 2.6 Hz), 8.26(1H, d, J=2.6 Hz). |
| 2522 | 3,4-Cl$_2$Ph— | benzyl | (CDCl$_3$)2.51(8H, brs), 3.52(2H, s), 3.53(2H, s), 6.95(1H, d, J=8.9 Hz), 7.07(2H, d, J=8.2 Hz), 7.26-7.36(7H, m), |

TABLE 395-continued

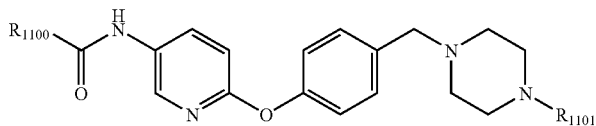

| Example No. | $R_{1100}$ | $R_{1101}$ | $^1$H NMR (solvent) δppm |
|---|---|---|---|
| | | | 7.59(1H, d, J=8.6 Hz), 7.69-7.73(2H, m), 7.99(1H, d, J=2.0 Hz), 8.18(1H, dd, J=8.9 Hz, 2.6 Hz), 8.25(1H, d, J=2.6 Hz). |
| 2523 | 3,4-Cl$_2$Ph— | —COOC(CH$_3$)$_3$ | (CDCl$_3$)1.46(9H, s), 2.40(4H, t, J=5.0 Hz), 3.43(4H, t, J=5.0 Hz), 3.50(2H, s), 6.95(1H, d, J=8.9 Hz), 7.08(2H, d, J=8.6 Hz), 7.34(2H, d, J=8.6 Hz), 7.57(1H, d, J=8.3 Hz), 7.70-7.74(1H, m), 8.00(1H, d, J=2.0 Hz), 8.07(1H, brs), 8.17-8.21(1H, m), 8.27(1H, d, J=2.6 Hz). |
| 2524 | 3,4-Cl$_2$Ph— | —C$_2$H$_5$ | (CDCl$_3$)1.08(3H, t, J=7.3 Hz), 2.38-2.49(10H, m), 3.48(2H, s), 6.88(1H, d, J=8.9 Hz), 7.01(2H, d, J=8.3 Hz), 7.30(2H, d, J=8.6 Hz), 7.49(1H, d, J=8.3 Hz), 7.66-7.70(1H, m), 7.95(1H, d, J=2.0 Hz), 8.13(1H, dd, J=8.9 Hz, 2.6 Hz), 8.23(1H, d, J=2.6 Hz), 8.58(1H, brs). |
| 2525 | 3,4-Cl$_2$Ph— | —PH | (CDCl$_3$)2.64(4H, t, J=5.0 Hz), 3.22(4H, t, J=5.0 Hz), 3.57(2H, s), 6.83-6.88(1H, m), 6.92-6.99(3H, m), 7.10(2H, d, J=8.6 Hz), 7.23-7.29(2H, m), 7.39(2H, d, J=8.6 Hz), 7.59(1H, d, J=8.6 Hz), 7.71(1H, dd, J=8.3 Hz, 2.0 Hz), 7.76(1H, s), 7.99(1H, d, J=2.0 Hz), 8.19(1H, dd, J=8.6 Hz, 2.6 Hz), 8.26(1H, d, J=2.6 Hz). |
| 2526 | 4-CF$_3$Ph— | —COOC(CH$_3$)$_3$ | (DMSO-d$_6$)1.40(9H, s), 2.32-2.36(4H, m), 3.30-3.35(4H, m), 3.49(2H, s), 7.06-7.09(3H, m), 7.32-7.36(2H, m), 7.94(2H, d, J=8.4 Hz), 8.18(2H, d, J=8.1 Hz), 8.24(1H, dd, J=8.9 Hz, 2.7 Hz), 8.52 (1H, d, J=2.7 Hz), 10.64(1H, s). |
| 2527 | 3,4-Cl$_2$Ph— | —CH$_3$ | (CDCl$_3$)2.27(3H, s), 2.45(8H, brs), 3.47(2H, s), 6.87(1H, d, J=8.9 Hz), 6.99-7.03(2H, m), 7.27-7.31(2H, m), 7.48(1H, dd, J=8.3 Hz, 2.6 Hz), 7.68(1H, dd, J=8.6 Hz, 2.0 Hz), 7.94(1H, d, J=2.0 Hz), 8.12(1H, dd, J=8.9 Hz, 2.6 Hz), 8.23(1H, d, J=2.6 Hz), 8.76(1H, brs). |
| 2528 | 3,4-Cl$_2$Ph— | piperonyl | (CDCl$_3$)2.47(8H, brs), 3.42(2H, s), 3.49(2H, s), 5.93(2H, s), 6.73(2H, d, J=0.7 Hz), 6.84(1H, s), 6.91(1H, d, J=8.9 Hz), 7.04(2H, d, J=8.6 Hz), 7.31(2H, d, J=8.6 Hz), 7.53(1H, d, J=8.2 Hz), 7.70(1H, dd, J=8.3 Hz, 2.0 Hz), 7.97(1H, d, J=2.3 Hz), 8.13-8.18(1H, m), 8.24(2H, d, J=2.6 Hz). |

TABLE 396

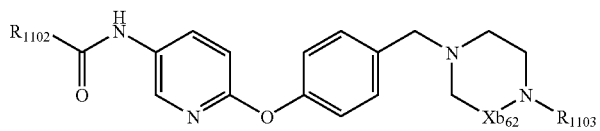

| Example No. | $R_{1102}$ | $Xb_{62}$ | $R_{1103}$ | Form | $^1$H NMR (solvent) δppm |
|---|---|---|---|---|---|
| 2529 | 3,4-Cl$_2$Ph— | —(CH$_2$)$_2$- | piperonyl | free | (CDCl$_3$)1.97-2.01(2H, m), 2.85-2.90(8H, m), 3.68(2H, s), 3.75(2H, s), 5.95(2H, s), 6.74-6.84(2H, m), 6.94-6.97(2H, m), 7.08(2H, d, J=8.6 Hz), 7.41(2H, d, J=8.6 Hz), 7.57(1H, d, J=8.6 Hz), 7.75(1H, dd, J=8.6 Hz, 2.3 Hz), 8.01-8.02(2H, m), 8.20(1H, dd, J=8.9 Hz, 2.6 Hz), 8.31(1H, d, J=2.6 Hz). |
| 2530 | 3,4-Cl$_2$Ph— | —(CH$_2$)$_2$- | benzyl | trihydro-chloride | (DMSO-d$_6$)2.25(2H, brs), 3.38(4H, brs), 3.78(4H, brs), 4.38(4H, s), 7.12-7.22(3H, m), 7.46-7.48(3H, m), 7.62-7.67(4H, m), 7.84(1H, d, J=8.6 Hz), 7.98(1H, dd, J=8.6 Hz, 2.0 Hz), 8.22-8.27(2H, m), 8.55 (1H, d, J=2.6 Hz), 10.68(1H, s). |

TABLE 396-continued

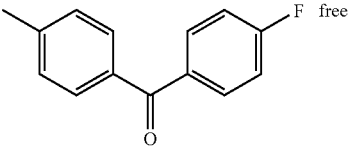

| Example No. | R₁₁₀₂ | Xb₆₂ | R₁₁₀₃ | Form | ¹H NMR (solvent) δppm |
|---|---|---|---|---|---|
| 2531 | 3,4-Cl₂Ph— | —CO— | benzyl | free | (CDCl₃)2.66(2H, t, J=5.9 Hz), 3.22-3.25(4H, m), 3.55(2H, s), 4.60(2H, s), 6.95(1H, d, J=8.9 Hz), 7.08(2H, d, J=8.6 Hz), 7.23-7.35(7H, m), 7.56(1H, d, J=8.3 Hz), 7.72(1H, dd, J=2.0 Hz, 8.6 Hz), 8.00(1H, d, J=2.0 Hz), 8.10(1H, s), 8.18(1H, dd, J=2.6 Hz, 8.6 Hz), 8.28 (1H, d, J=2.6 Hz). |
| 2532 | 4-CF₃Ph— | —CH₂- | (4-methylphenyl)(4-fluorophenyl)methanone | free | (CDCl₃)2.61(4H, brs), 3.38(4H, brs), 3.55(2H, s), 6.85-6.94(3H, m), 7.06-7.14 (4H, m), 7.36(2H, d, J=8.3 Hz), 7.64(2H, d, J=8.3 Hz), 7.70-7.75(4H, m), 7.99 (2H, t, J=8.3 Hz), 8.24(1H, dd, J=8.7 Hz, 2.5 Hz), 8.40(1H, d, J=2.6 Hz), 9.19(1H, s). |
| 2533 | 4-CF₃Ph— | —CH₂- | 4-methylbenzyl-4-fluorophenyl | free | (CDCl₃)2.58-2.62(4H, m), 3.14-3.17(4H, m), 3.54(2H, s), 3.86(2H, s), 6.83-7.14(11H, m), 7.36(2H, d, J=8.4 Hz), 7.71 (2H, d, J=8.3 Hz), 7.96(2H, d, J=8.1 Hz), 8.15-8.26(3H, m). |

TABLE 397

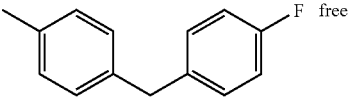

| Example No. | R₁₁₀₄ | R₁₁₀₅ | M | ¹H NMR (CDCl₃) δppm |
|---|---|---|---|---|
| 2534 | 3,4-Cl₂Ph— | —CH₃ | 2 | 2.30(3H, s), 2.50-2.81(12H, m), 6.86(1H, d, J=8.6 Hz), 6.98(2H, d, J=8.6 Hz), 7.18(2H, d, J=8.3 Hz), 7.47(1H, d, J=8.3 Hz), 7.67(1H, dd, J=8.3 Hz, 2.0 Hz), 7.94(1H, d, J=2.0 Hz), 8.11(1H, dd, J=8.9 Hz, 2.6 Hz), 8.21(1H, d, J=2.6 Hz), 8.66(1H, brs). |
| 2535 | 3,4-Cl₂Ph— | piperonyl | 2 | 2.51-2.83(12H, in), 3.43(2H, a), 5.93(2H, s), 6.74 (2H, d, J =1.0 Hz), 6.86-7.03(4H, in), 7.20(2H, d, J =8.3 Hz), 7.53(1H, d, J =8.6 Hz), 7.68 7.72(1H, in), 7.97(1H, d, J 2.0 Hz), 8.15(1H, dd, J =8.9 Hz, 2.6 Hz), 8.23(2H, d, J =2.6 Hz). |
| 2536 | 3,4-Cl₂Ph— | —CH₃ | 3 | 1.78-1.84(2H, m), 2.29(3H, s), 2.36-2.48(10H, m), 2.59-2.65(2H, m), 6.89(1H, d, J=8.4 Hz), 7.00(2H, d, J=8.4 Hz), 7.18(2H, d, J=8.4 Hz), 7.52(1H, d, J=8.6 Hz), 7.67-7.71(1H, m), 7.96(1H, d, J=2.2 Hz), 8.11-8.15(1H, m), 8.23(1H, d, J=2.7 Hz), 8.31(1H, brs). |
| 2537 | 3,4-Cl₂Ph— | piperonyl | 3 | 1.78-1.84(2H, m), 2.36-2.47(10H, m), 2.60-2.65 (2H, m), 3.41(2H, s), 5.93(2H, s), 6.73(2H, d, J=0.8 Hz), 6.85(1H, s), 6.91(1H, d, J=8.9 Hz), 7.02(2H, d, J=8.4 Hz), 7.19(2H, d, J=8.6 Hz), 7.55(1H, d, J=8.1 Hz), 7.68-7.71(1H, m), 7.96-7.97(2H, m), 8.14-8.17(1H, m), 8.23(1H, d, J=2.7 Hz). |
| 2538 | 4-CF₃Ph— | —COOC(CH₃)₃ | 3 | 1.46(9H, s), 1.78-1.89(2H, m), 2.36-2.42(6H, m), 2.62-2.68(2H, m), 3.42-3.45(4H, m), 6.94(1H, d, J=8.9 Hz), 7.01-7.06(2H, m), 7.18-7.23(2H, m), 7.76(2H, d, J=8.2 Hz), 7.99-8.03(3H, m), 8.22(1H, dd, J=8.9 Hz, 2.6 Hz), 8.28(1H, d, J=2.6 Hz). |

TABLE 397-continued

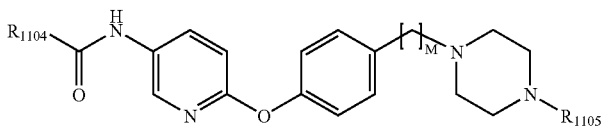

| Example No. | R<sub>1104</sub> | R<sub>1105</sub> | M | $^1$H NMR (CDCl$_3$) δppm |
|---|---|---|---|---|
| 2539 | 3,4-Cl$_2$Ph— | —CH$_3$ | 4 | 1.50-1.80(4H, m), 2.32(3H, s), 2.38(2H, t, J=7.3 Hz), 2.30-2.70(8H, m), 2.64(2H, t, J=7.3 Hz), 6.94(1H, d, J=8.8 Hz), 7.03(2H, d, J=8.2 Hz), 7.19(2H, d, J=8.2 Hz), 7.58(1H, d, J=8.2 Hz), 7.72(1H, dd, J=8.2 Hz, 2.0 Hz), 7.84(1H, s), 8.00(1H, d, J=2.0 Hz), 8.18(1H, dd, J=8.8 Hz, 2.6 Hz), 8.26(1H, d, J=2.6 Hz). |
| 2540 | 3,4-Cl$_2$Ph— | benzyl | 4 | 1.45-1.75(4H, m), 2.36(2H, t, J=7.5 Hz), 2.30-2.65(8H, m), 2.62(2H, t, J=7.7 Hz), 3.51(2H, s), 6.92(1H, d, J=8.6 Hz), 7.03(2H, d, J=8.6 Hz), 7.19(2H, d, J=8.6 Hz), 7.15-7.40(5H, m), 7.57(1H, d, J=8.2 Hz), 7.71(1H, dd, J=8.2 Hz, 2.0 Hz), 7.85(1H, s), 7.98(1H, d, J=2.0 Hz), 8.16(1H, dd, J=8.6 Hz, 2.5 Hz), 8.24(1H, d, J=2.5 Hz). |
| 2541 | 3,4-Cl$_2$Ph— | benzyl | 5 | 1.25-1.45(2H, m), 1.45-1.75(4H, m), 2.34(2H, t, J=7.7 Hz), 2.30-2.70(8H, m), 2.61(2H, t, J=7.7 Hz), 3.51(2H, s), 6.93(1H, d, J=8.7 Hz), 7.03(2H, d, J=8.6 Hz), 7.19(2H, d, J=8.6 Hz), 7.20-7.40(5H, m), 7.58(1H, d, J=8.3 Hz), 7.70(1H, dd, J=8.3 Hz, 2.0 Hz), 7.71(1H, d, J=2.0 Hz), 7.98(1H, d, J=2.0 Hz), 8.16(1H, dd, J=8.7 Hz, 2.6 Hz), 8.24(1H, d, J=2.6 Hz). |

TABLE 398

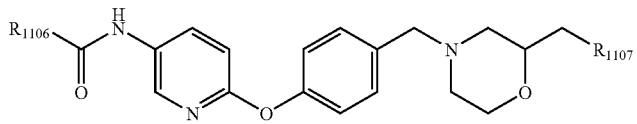

| Example No. | R<sub>1106</sub> | R<sub>1107</sub> | Form | $^1$H NMR (DMSO-d$_6$) δppm |
|---|---|---|---|---|
| 2542 | 3,4-Cl$_2$Ph— | —H | hydrochloride | 1.12(3H, d, J=6.3 Hz), 2.75-3.03(2H, m), 3.24-3.39(2H, m), 3.78-3.98(3H, m), 4.31(2H, brs), 7.13(1H d, J=8.6 Hz), 7.20(2H, d, J=8.3 Hz), 7.63(2H, d, J=8.3 Hz), 7.84(1H, d, J=8.2 Hz), 7.98(1H, dd, J=8.2 Hz, 2.6 Hz), 8.24(1H, dd, J=8.9 Hz, 2.6 Hz), 8.25(1H, d, J=2.0 Hz), 8.55(1H, d, J=2.6 Hz), 10.67(1H, brs), 11.10(1H, brs). |
| 2543 | 3,4-Cl$_2$Ph— | —O(CH$_2$)$_3$CH$_3$ | hydrochloride | 0.87(3H, t, J=7.3 Hz), 1.22-1.36(2H, m), 1.41-1.51(2H, m), 2.90-3.07(2H, m), 3.23-3.50(6H, m), 3.80-3.88(1H, m), 3.99-4.02(2H, m), 4.35(2H, brs), 7.13(1H, d, J=8.9 Hz), 7.21(2H, d, J=8.6 Hz), 7.63(2H, d, J=8.3 Hz), 7.84(1H, d, J=8.6 Hz), 7.97(1H, dd, J=8.3 Hz, 2.0 Hz), 8.24(1H, dd, J=8.9 Hz, 2.6 Hz), 8.25(1H, d, J=2.0 Hz), 8.54(1H, d, J=2.6 Hz), 10.66(1H, brs), 11.17(1H, brs). |
| 2544 | 3,4-Cl$_2$Ph— | piperidino | dihydrochloride | 1.38-1.77(6H, m), 2.92-3.10(5H, m), 3.22-3.33(4H, m), 3.47-3.51(1H, m), 3.97-4.06(2H, m), 4.27-4.55(3H, m), 7.13 (1H, d, J=8.9 Hz), 7.21(2H, d, J=8.6 Hz), 7.67(2H, d, J=8.6 Hz), 7.84(1H, d, J=8.6 Hz), 7.99(1H, dd, J=8.2 Hz, 2.0 Hz), 8.26(1H, dd, J=8.6 Hz, 3.0 Hz) 8.28(1H, d, J=2.3 Hz), 8.57(1H, d, J=2.6 Hz), 10.27(1H, brs), 10.74(1H, brs), 11.91(1H, brs). |
| 2545 | 4-CF$_3$Ph— | —H | hydrochloride | 1.12(3H, d, J=6.1 Hz), 2.68-2.80(1H, m), 2.98-3.06(1H, m), 3.24-3.28(2H, m), |

TABLE 398-continued

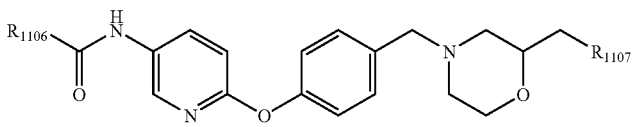

| Example No. | $R_{1106}$ | $R_{1107}$ | Form | $^1$H NMR (DMSO-$d_6$) δppm |
|---|---|---|---|---|
| | | | | 3.80-3.90(3H, m), 4.31(2H, brs), 7.14(1H, d, J=8.7 Hz), 7.21(2H, d, J=8.4 Hz), 7.64(2H, d, J=8.1 Hz), 7.93(2H, d, J=8.4 Hz), 8.19(2H, d, J=8.2 Hz), 8.27(1H, dd, J=8.9 Hz, 2.6 Hz), 8.57(1H, d, J=2.6 Hz), 10.75(1H, brs), 11.19(1H, brs). |
| 2546 | 4-CF$_3$Ph— | —OCH$_3$ | hydro-chloride | 2.92-3.12(2H, m), 3.26(3H, s), 3.34-3.47(4H, m), 3.80-4.02(3H, m), 4.34(2H, brs), 7.14(1H, d, J=8.9 Hz), 7.21(2H, d, J=8.6 Hz), 7.63(2H, d, J=8.2 Hz), 7.94(2H, d, J=8.4 Hz), 8.18 (2H, d, J=8.1 Hz), 8.27(1H, dd, J=8.7 Hz, 2.6 Hz), 8.57(1H, d, J=2.6 Hz), 10.73(1H, brs), 11.13(1H, brs). |
| 2547 | 3,4-Cl$_2$Ph— | —OCH$_3$ | hydro-chloride | 2.92-3.11(2H, m), 3.26(3H, s), 3.31-3.52(4H, m), 3.79-3.87(1H, m), 3.95-4.04(2H, m), 4.34(2H, brs), 7.14(1H, d, J=8.9 Hz), 7.21(2H, d, J=8.6 Hz), 7.62(2H, d, J=8.6 Hz), 7.84(1H, d, J=8.4 Hz), 7.97(1H, dd, J=8.4 Hz, 2.2 Hz), 8.24-8.26(2H, m), 8.54(1H, d, J=2.6 Hz), 10.66(1H, brs), 11.02(1H, brs). |

TABLE 399

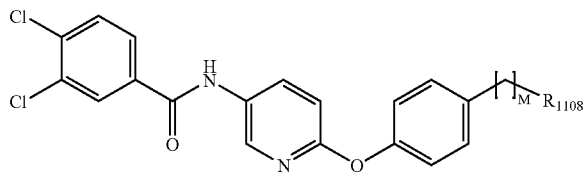

| Example No. | $R_{1108}$ | M | Form | $^1$H NMR (solvent) δppm |
|---|---|---|---|---|
| 2548 | —N(piperazine)N—CH$_3$ (4-methylpiperazinyl) | 5 | free | (CDCl$_3$)1.30-1.45(2H, m), 1.45-1.75(4H, m), 2.30(3H, s), 2.25-2.40(2H, m), 2.49(8H, brs), 2.62(2H, t, J=7.5 Hz), 6.94(1H, d, J=8.9 Hz), 7.04(2H, d, J=8.6 Hz), 7.20(2H, d, J=8.6 Hz), 7.59(1H, d, J=8.2 Hz), 7.65-7.75(2H, m), 7.98(1H, d, J=2.0 Hz), 8.17(1H, dd, J=8.9 Hz, 3.0 Hz), 8.24(1H, d, J=3.0 Hz). |
| 2549 | (2,6-dimethylmorpholinyl, cis) | 1 | hydro-chloride | (DMSO-$d_6$)1.13(6H, d, J=6.6 Hz), 2.66-2.76(2H, m), 3.25-3.34 (2H, m), 3.91-3.99(2H, m), 4.30(2H, s), 7.14(1H, d, J=8.6 Hz), 7.21 (2H, d, J=8.6 Hz), 7.62(2H, d, J=8.3 Hz), 7.85(1H, d, J=8.6 Hz), 7.97(1H, dd, J=8.6 Hz, 2.0 Hz), 8.24(1H, dd, J=8.6 Hz, 3.0 Hz), 8.25(1H, d, J=2.3 Hz), 8.55(1H, d, J=2.6 Hz), 10.65(1H, brs), 10.96(1H, brs). |
| 2550 | (2,6-dimethylmorpholinyl) | 1 | hydro-chloride | (DMSO-$d_6$) 1.11(3H, d, J=6.3 Hz), 1.40(3H, d, J=6.9 Hz), 2.67-2.75(1H, m), 3.10(2H, m), 3.25-3.33(1H, m), 4.02-4.32(4H, m), 7.14(1H, d, J=8.9 Hz), 7.21(2H, d, J=8.3 Hz), 7.65(2H, d, J=8.6 Hz), 7.85(1H, d, J=8.2 Hz), 7.97(1H, dd, J=8.6 Hz, 2.0 Hz), 8.21-8.26(2H, m), 8.54(1H, d, J=2.3 Hz), 10.46(1H, brs), 10.64(1H, brs). |

Example 2551

Production of 1-(3-{4-[4-(3,4-dichlorobenzoylamino)-phenoxy]phenyl}propionyl)-4-[2-(morpholino)acetyl]-piperazine To a solution of 1-chloroacetyl-4-(3-{4-[4-(3,4-dichlorobenzoylamino)phenoxy]phenyl}propionyl)-piperazine (0.515 g, 0.896 mmol) and diisopropylethylamine (0.234 mL, 1.34 mmol) in acetonitrile (11 mL) was added morpholine (0.117 mL, 1.34 mmol), and the resulting solution was refluxed for 1 hour. This reaction solution was concentrated under reduced pressure. To the residue was added a saturated sodium bicarbonate solution, and extracted with chloroform. The chloroform layer was dried over anhydrous magnesium sulfate, and evaporated. The obtained solid was recrystallized from water-containing acetone, to thereby yield 0.441 g of the title compound.

Appearance: White powder

Melting point: 187-190° C.

The following compounds were produced in the same manner as in Example 2551.

TABLE 400

| Example No. | $R_{1109}$ | Form | mp (° C.) or $^1$H NMR |
|---|---|---|---|
| 2552 | —COCH$_2$N(C$_2$H$_5$)$_2$ | 3/2 oxalate | mp 107-118 |
| 2553 | —COCH$_2$NHCH$_2$Ph | hydrochloride | mp 199-202 |
| 2554 | —COCH$_2$N(C$_2$H$_5$)CH$_2$Ph | fumarate | $^1$H NMR (DMSO-d$_6$) δ 0.99(3H, t, J= 7.1 Hz), 2.56-2.70(2H, m), 2.73-2.86(2H, m), 3.09-3.50 (12H, m), 3.59(2H, s), 6.61(2H, s), 6.91(2H, d, J= 8.0 Hz), 6.98(2H, d, J=9.0 Hz), 7.14-7.37(7H, m), 7.74(2H, d, J=9.0 Hz), 7.81(1H, d, J=8.4 Hz), 7.92(1H, dd, J=8.4 Hz, 2.1 Hz), 8.20(1H, d, J= 2.1 Hz), 10.39(1H, s), 13.09(2H, brs). |
| 2555 | 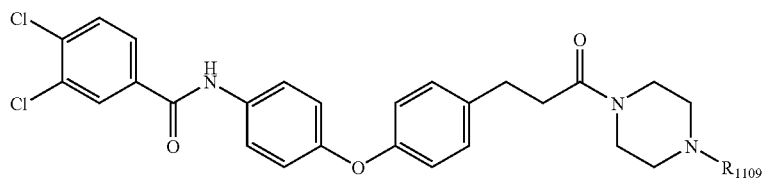 | dihydrochloride | mp 173-176 |
| 2556 | —COCH$_2$N(C$_2$H$_5$)Ph | free | mp 140-143 |

TABLE 401

| Example No. | $R_{1110}$ | mp (° C.) |
|---|---|---|
| 2557 | (N-piperazinyl-CH$_2$-phenyl) | 206-210 |
| 2558 | (N-piperazinyl-CH$_2$-benzodioxole) | 154-156 |
| 2559 | morpholino | 177-178 |
| 2560 | (N-imidazolyl) | 204-206 |
| 2561 | —N(CH$_3$)CH$_2$Ph | 182-184 |

TABLE 402
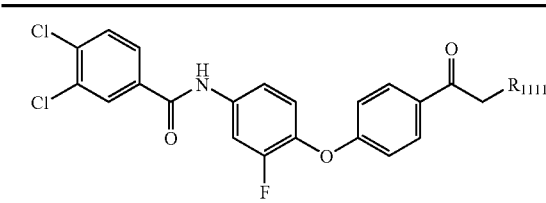
| Example No. | R<sub>1111</sub> | mp (° C.) |
|---|---|---|
| 2562 | 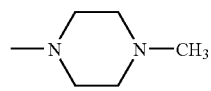 | 151-152 |
| 2563 | morpholino | 177-178 |
| 2564 | 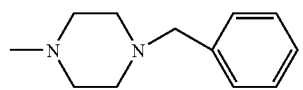 | 146-147 |
TABLE 403
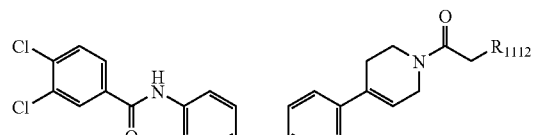
| Example No. | R<sub>1112</sub> | mp (° C.) |
|---|---|---|
| 2565 | morpholino | 195-197 |
| 2566 | 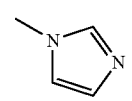 | 146-148 |
| 2567 | 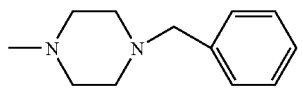 | 173-176 |
| 2568 | 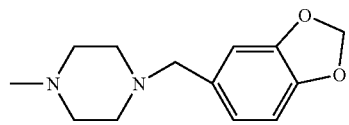 | 150-153 |
TABLE 404
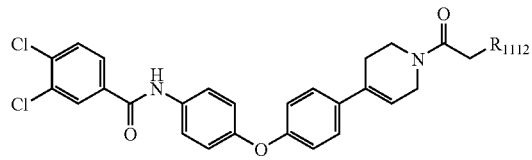
| Example No. | R<sub>1113</sub> | Form | mp (° C.) |
|---|---|---|---|
| 2569 | 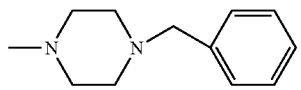 | dihydrochloride | 152-155 |
| 2570 | 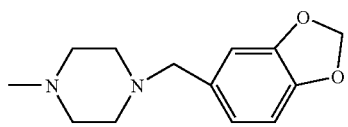 | dihydrochloride | 181-185 |
| 2571 | morpholino | hydrochloride | 146-150 |

TABLE 405

Structure: 3,4-dichlorobenzamide-NH-phenyl-O-phenyl-N-piperidine-N(CH₃)-C(O)-R₁₁₁₄

| Example No. | R₁₁₁₄ | mp (° C.) |
|---|---|---|
| 2572 | morpholino | 157-160 |
| 2573 | 1-methylimidazolyl | 241-243 |
| 2574 | 4-benzylpiperazin-1-yl | 193-196 |

TABLE 405-continued

| Example No. | R₁₁₁₄ | mp (° C.) |
|---|---|---|
| 2575 | 4-(benzo[d][1,3]dioxol-5-ylmethyl)piperazin-1-yl | 180-182 |

TABLE 406

Structure: R₁₁₁₅-C(O)-NH-pyridine-O-phenyl-Xb₆₃-C(O)-R₁₁₁₆

| Example No. | R₁₁₁₅ | Xb₆₃ | R₁₁₁₆ | mp (° C.) or ¹H NMR |
|---|---|---|---|---|
| 2576 | 3,4-Cl₂Ph— | none | morpholino | ¹H NMR (DMSO-d₆) δ 2.50-2.53(4H, m), 3.55-3.61(4H, m), 3.82(2H, s), 7.20(1H, d, J=8.7 Hz), 7.21(2H, d, J=8.1 Hz), 7.85(1H, d, J=8.4 Hz), 7.96(1H, dd, J=8.4 Hz, 1.2 Hz), 8.06(2H, d, J=8.4 Hz), 8.23(1H, d, J=1.5 H.z), 8.27(1H, dd, J=8.9 Hz, 2.8 Hz), 8.55(1H, d, J=2.8 Hz), 10.61(1H, brs). |
| 2577 | 4-CF₃Ph— | piperazin-1,4-diyl | 4-benzylpiperazin-1-yl | mp 179-181 |
| 2578 | 4-CF₃Ph— | piperazin-1,4-diyl | 4-(benzo[d][1,3]dioxol-5-ylmethyl)piperazin-1-yl | mp 172-174 |
| 2579 | 4-CF₃Ph— | piperazin-1,4-diyl | morpholino | mp 144-146 |
| 2580 | 4-CF₃Ph— | piperazin-1,4-diyl | —N(CH₃)CH₂Ph | mp 188-190 |
| 2581 | 4-CF₃Ph— | piperazin-1,4-diyl | 1-methylimidazolyl | mp 192-193 |

The following compound was produced in the same manner as in Reference Example 860.

Example 2582

1-{4-[5-(3,4-Dichlorobenzoylamino)pyridin-2-yloxy]benzyl}piperazine-4-carboxylic acid ethyl ester Appearance: Pale yellow oil $^1$H NMR (CDCl$_3$) δ 1.25 (3H, t, J=7.0 Hz), 1.76 (2H, m), 1.77 (2H, m), 2.03 (2H, t, J=11.5 Hz), 2.28 (1H, m), 2.87 (2H, brd, J=11.5 Hz), 3.48 (2H, s), 4.13 (2H, q, J=7.0 Hz), 6.94 (1H, d, J=9.0 Hz), 7.06 (2H, d, J=8.5 Hz), 7.33 (2H, d, J=9.0 Hz), 7.57 (1H, d, J=8.5 Hz), 7.70 (1H, dd, J=8.5 Hz, 2.0 Hz), 7.88 (1H, brs), 7.97 (1H, d, J=2.0 Hz), 8.17 (1H, dd, J=9.0 Hz, 3.0 Hz), 8.24 (1H, d, J=3.0 Hz).

Example 2583

Production of 3,4-dichloro-N-{6-[4-(2,4-dioxo-3,4-dihydro-2H-pyrimidin-1-ylmethyl)phenoxy]pyridin-3-yl}benzamide To uracil (200 mg, 1.8 mmol) was added hexamethyldisilazane (5 mL), and the resulting solution was stirred for 5.5 hours at 150° C. Insoluble matter was removed by filtration, and the filtrate was concentrated under reduced pressure. The residue was dissolved in a solution of acetonitrile (10 mL)-THF (5 mL), and to this solution were added 3,4-dichloro-N-[6-(4-chloromethylphenoxy)pyridin-3-yl]benzamide (500 mg, 1.2 mmol) and tin tetrachloride (3 drops). The resulting solution was refluxed for 2.5 hours. To this reaction solution was added methanol (1 mL), and the resulting solution was stirred for 30 minutes at room temperature. The resulting reaction solution was concentrated under reduced pressure, and the residue was purified by silica gel column chromatography (methanol:chloroform=1:99→3:97), to thereby yield 20 mg of the title compound.

Appearance: White powder $^1$H NMR (DMSO-d$_6$) δ 4.88 (2H, s), 5.61 (1H, dd, J=7.9 Hz, 2.3 Hz), 7.07-7.13 (3H, m), 7.35 (2H, d, J=8.6 Hz), 7.79-7.85 (2H, m), 7.95 (1H, dd, J=8.6 Hz, 2.0 Hz), 8.18 (1H, d, J=2.6 Hz), 8.22 (1H, d, J=2.0 Hz), 8.47 (1H, d, J=2.6 Hz), 10.55 (1H, s), 11.33 (1H, s);

MS: m/z 482 (M$^+$).

Example 2584

Production of N-{6-[4-(4-benzyl-2-oxopiperazin-1-ylmethyl)phenoxy]pyridin-3-yl}-3,4-dichlorobenzamide dihydrochloride To a solution of 4-benzylpiperazin-2-one (0.56 g, 2.95 mmol) in DMF (10 mL) was added 60% sodium hydride (0.12 g, 2.95 mmol), and this solution was stirred at room temperature for 30 minutes. 2-(4-chloromethylphenoxy)-5-nitropyridine (0.78 g, 2.95 mmol) was added to the reaction mixture, and the mixture was stirred for 1 hour at room temperature. To this mixture was added brine (50 mL), and extracted with ethyl acetate (50 mL). The ethyl acetate layer was washed with brine, dried over anhydrous magnesium sulfate, and evaporated under reduced pressure. The remaining oil was dissolved in ethyl acetate (5 mL), and to the resulting solution was added iron powder (0.33 g, 5.89 mmol). This solution was stirred for 2 hours at room temperature. The resulting reaction solution was concentrated under reduced pressure, and a saturated sodium bicarbonate solution (50 mL) was added to the residue. The obtained mixture was extracted with ethyl acetate (50 mL). The ethyl acetate layer was washed with brine, dried over anhydrous sodium sulfate, and evaporated. The remaining oil was dissolved in THF (10 mL). To the resulting solution were added triethylamine (0.21 mL, 1.47 mmol) and 3,4-dichlorobenzoyl chloride (0.31 mL, 1.47 mmol), and this solution was stirred at room temperature for 2 hours. A saturated sodium bicarbonate solution (50 mL) was added to the solution, and extracted with ethyl acetate (50 mL). The ethyl acetate layer was washed with brine, dried over anhydrous magnesium sulfate, and evaporated under reduced pressure. The residue was purified by silica gel column chromatography (chloroform:methanol=40:1). The obtained oil was dissolved in ethyl acetate (5 mL), and to the resulting solution was added a solution of 4 N hydrogen chloride in ethyl acetate (1.5 mL, 6 mmol). The formed white powder was collected by suction filtration, to thereby yield 0.045 g of the title compound.

Appearance: White powder $^1$H NMR (DMSO-d$_6$) δ 3.54 (4H, m), 3.86 (2H, brs), 4.42 (2H, s), 4.59 (2H, brs), 7.06-7.12 (3H, m), 7.34 (2H, d, J=8.6 Hz), 7.48-7.51 (3H, m), 7.57-7.60 (2H, m), 7.84 (1H, d, J=8.6 Hz), 7.97 (1H, dd, J=2.0 Hz, 8.3 Hz), 8.18-8.24 (2H, m), 8.49 (1H, d, J=2.6 Hz), 10.61 (1H, s).

The following compound was produced in the same manner as in Reference Example 656.

Example 2585

2-({4-[5-(3,4-Dichlorophenylamino)pyridin-2-yloxy]-2-trifluoromethylphenyl}ethylamino)-1-(4-piperonylpiperazin-1-yl)ethanone $^1$H NMR (CDCl$_3$) δ 1.02 (3H, t, J=7.1 Hz), 2.30-2.45 (4H, m), 3.22 (2H, q, J=7.1 Hz), 3.40 (2H, s), 3.45-3.65 (4H, m), 3.85 (2H, s), 5.57 (1H, brs), 5.94 (2H, s), 6.65-6.80 (3H, m), 6.85 (1H, s), 6.95 (1H, d, J=8.7 Hz), 7.00 (1H, d, J=2.7 Hz), 7.29-7.31 (2H, m), 7.39 (1H, d, J=2.7 Hz), 7.53 (1H, dd, J=8.7 Hz, 2.9 Hz), 7.64 (1H, d, J=8.8 Hz), 7.99 (1H, d, J=2.7 Hz).

The following compounds were produced in the same manner as in Reference Example 658.

TABLE 407

| Example No. | R$_{1117}$ | R$_{1118}$ | M | mp (° C.) or $^1$H NMR (DMSO-d$_6$) δppm |
|---|---|---|---|---|
| 2586 | 4-CF$_3$Ph— | —H | 2 | $^1$H NMR 2.14-2.30(2H, m), 2.62-3.12(7H, m), 3.20-3.58(3H, m), 3.77(2H, t, J=5.9 Hz), 3.81-4.15(3H, m), 4.16-4.32(2H, m), 4.49-4.57(1H, m), 6.08(2H, s), |

TABLE 407-continued

| Example No. | $R_{1117}$ | $R_{1118}$ | M | mp (° C.) or $^1$H NMR (DMSO-$d_6$) δppm |
|---|---|---|---|---|
| | | | | 6.96-7.09(5H, m), 7.21(1H, s), 7.29(2H, d, J=8.5 Hz), 7.58(2H, d, J=8.5 Hz), 7.70(2H, d, J=8.8 Hz), 7.86(1H, dd, J=2.8 Hz, 8.8 Hz), 8.13(1H, d, J=2.8 Hz), 10.78-11.01(1H, m). |
| 2587 | 3,4-Cl$_2$Ph— | —H | 2 | mp 182.0-183.0 |
| 2588 | 3-CF$_3$Ph— | —H | 1 | mp 200.0-203.0 |
| 2589 | 4-CF$_3$Ph— | —OCH$_3$ | 1 | mp 153.0-154.0 |
| 2590 | 3,4-Cl$_2$Ph— | —OCH$_3$ | 1 | mp 169.0-171.0 |
| 2591 | 4-CF$_3$Ph— | —OCH$_3$ | 2 | mp 134.0-136.0 |
| 2592 | 3,4-Cl$_2$Ph— | —OCH$_3$ | 2 | mp 130.0-132.0 |

TABLE 408

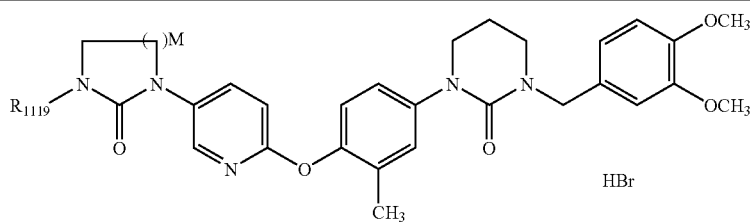

| Example No. | $R_{1119}$ | M | mp (° C.) or $^1$H NMR (DMSO-$d_6$) δppm |
|---|---|---|---|
| 2593 | 4-CF$_3$Ph— | 1 | $^1$H NMR 1.90-2.06(2H, m), 2.07(3H, s), 3.18-3.32(2H, m), 3.55-3.70(2H, m), 3.73(3H, s), 3.74(3H, s), 3.91-4.12(4H, m), 4.43(2H, s), 4.49-4.93(1H, m), 6.81(1H, dd, J=1.8 Hz, 8.1 Hz), 6.88(1H, d, J=1.8 Hz), 6.92(1H, d, J=8.1 Hz), 6.97(1H, d, J=8.5 Hz), 7.06(1H, d, J=9.0 Hz), 7.12(1H, dd, J=2.4 Hz, 8.5 Hz), 7.21(1H, d, J=2.4 Hz), 7.71(2H, d, J=8.9 Hz), 7.83(2H, d, J=8.9 Hz), 8.19(1H, dd, J=2.9 Hz, 9.0 Hz), 8.27(1H, d, J=2.9 Hz). |
| 2594 | 3,4-Cl$_2$Ph— | 1 | mp 146.0-148.0 |
| 2595 | 3,4-Cl$_2$Ph— | 2 | $^1$H NMR 1.91-2.11(5H, m), 2.12-2.24(2H, m), 3.19-3.32(2H, m), 3.58-3.83(10H, m), 3.85-4.22(3H, m), 4.42(2H, s), 6.81(1H, dd, J=1.8 Hz, 8.1 Hz), 6.87(1H, d, J=1.8 Hz), 6.91(1H, d, J=8.1 Hz), 6.94-7.02(2H, m), 7.12(1H, dd, J=2.5 Hz, 8.6 Hz), 7.21(1H, d, J=2.5 Hz), 7.35(1H, dd, J=2.5 Hz, 8.8 Hz), 7.57(1H, d, J=8.8 Hz), 7.66(1H, d, J=2.5 Hz), 7.82(1H, dd, J=2.5 Hz, 8.8 Hz), 8.07(1H, d, J=2.5 Hz). |

Example 2596

Production of 3-(4-{5-[4-(3,4-dichlorophenyl)piperazin-1-yl]pyridin-2-yloxy}phenyl)-1-(4-piperonylpiperazin-1-yl)propane-1-one To a solution of 3-[4-(5-bromopyridin-2-yloxy)phenyl]-1-(4-piperonylpiperazin-1-yl)propane-1-one (359 mg, 0.69 mmol) and 1-(3,4-dichlorophenyl)-piperazine (206 mg, 0.89 mmol) in toluene (16 mL) were added with Pd$_2$(dba)$_3$ (25 mg, 0.027 mmol), Xantphos (32 mg, 0.055 mmol) and sodium t-butoxide (99 mg, 1.03 mmol), and the resulting solution was refluxed under an argon atmosphere for 3 hours. The solution was left to cool, water was added to this reaction mixture. The resulting solution was extracted with dichloromethane, dried over anhydrous magnesium sulfate, and evaporated under reduced pressure. The residue was purified by silica gel column chromatography (dichloromethane:methanol=30:1), to thereby yield 236 mg of the title compound.

Appearance: Pale yellow powder $^1$H NMR (CDCl$_3$) δ 2.31-2.40 (4H, m), 2.58-2.64 (2H, m), 2.92-2.98 (2H, m), 3.23-3.38 (8H, m), 3.41 (4H, brs), 3.63 (2H, t, J=4.9 Hz), 5.94 (2H, s), 6.72-6.73 (2H, m), 6.78 (1H, dd, J=8.9 Hz, 2.8 Hz), 6.84-6.90 (2H, m), 6.99-7.06 (3H, m), 7.19-7.24 (3H, m), 7.32 (1H, dd, J=9.4 Hz, 3.1 Hz), 7.88 (1H, d, J=3.0 Hz). Tris(dibenzylideneacetone)dipalladium is abbreviated to Pd$_2$(dba)$_3$. Hereinafter, the same. 4,5-bis(diphenylphosphino)-9,9-dimethylxanthene is abbreviated to Xantphos. Hereinafter the same.

The following compounds were produced in the same manner as in Example 2596.

TABLE 409

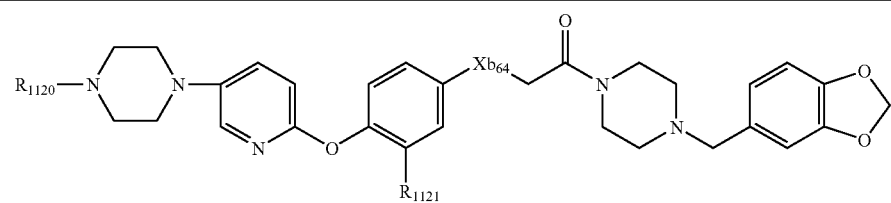

| Example No. | $R_{1120}$ | $R_{1121}$ | $Xb_{64}$ | $^1$H NMR (CDCl$_3$) δppm |
|---|---|---|---|---|
| 2597 | 4-CF$_3$PhCH$_2$— | —H | —CH$_2$— | 2.31-2.38(4H, m), 2.60-2.64(6H, m), 2.95(2H, t, J=7.3 Hz), 3.11-3.15(4H, m), 3.40(4H, brs), 3.61(4H, brs), 5.93(2H, s), 6.73(2H, s), 6.83(2H, d, J=9.1 Hz), 6.99(2H, d, J=8.4 Hz), 7.19(2H, d, J=8.4 Hz), 7.29(1H, dd, J=8.9 Hz, 3.1 Hz), 7.47(2H, d, J=8.2 Hz), 7.58(2H, d, J=8.1 Hz), 7.83(1H, d, J=3.0 Hz). |
| 2598 | 3,4-Cl$_2$Ph— | —CH$_3$ | —N(CH$_3$)— | 2.13(3H, s), 2.40-2.44(4H, m), 3.00(3H, s), 3.18-3.38(8H, m), 3.43(2H, s), 3.49(2H, brs), 3.63(2H, brs), 4.06(2H, s), 5.94(2H, s), 6.52-6.57(2H, m), 6.69-6.91(6H, m), 7.00(1H, d, J=3.0 Hz), 7.26-7.32(2H, m), 7.86(1H, d, J=2.8 Hz). |
| 2599 | 4-CF$_3$Ph— | —CH$_3$ | —N(CH$_3$)— | 2.13(3H, s), 2.41-2.44(4H, m), 3.00(3H, s), 320-3.24(4H, m), 3.34-3.43(6H, m), 3.49(2H, brs), 3.63(2H, brs), 4.06(2H, s), 5.94(2H, s), 6.52-6.58(2H, m), 6.70-6.77(3H, m), 6.85-6.98(4H, m), 7.31(1H, dd, J=9.1 Hz, 3.1 Hz), 7.50(2H, d, J=8.6 Hz), 7.87(1H, d, J=2.6 Hz). |
| 2600 | 4-CF$_3$Ph— | —H | —CH$_2$— | 2.31-2.40(4H, m), 2.61(2H, t, J=7.3 Hz), 2.96(2H, t, J=7.3 Hz), 3.23-3.27(4H, m), 3.38-3.45(8H, m), 3.63(2H, t, J=4.8 Hz), 5.94(2H, s), 6.70-6.76(2H, m), 6.84-7.06(6H, m), 7.19-7.26(2H, m), 7.36(1H, dd, J=8.9 Hz, 3.1 Hz), 7.5 1(2H, d, J=8.9 Hz), 7.89(1H, d, J=3.0 Hz). |

The following compounds were produced in the same manner as in Reference Example 659.

TABLE 410

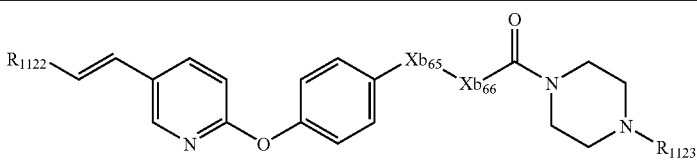

| Example No. | $R_{1122}$ | $Xb_{65}$ | $Xb_{66}$ | $R_{1123}$ | $^1$H NMR (CDCl$_3$) δppm |
|---|---|---|---|---|---|
| 2601 | 4-CF$_3$Ph— | —N(CH$_3$)— | —CH$_2$— | piperonyl | 2.41-2.44(4H, m), 3.03(3H, s), 3.43(2H, s), 3.47-3.50(2H, m), 3.61-3.65(2H, m), 4.09(2H, s), 5.93(2H, s), 6.68-6.77(4H, m), 6.83-6.86(2H, m), 6.99(1H, d, J=16.5 Hz), 7.00-7.06(2H, m), 7.10 (1H, d, J=16.5 Hz), 7.54-7.61(4H, m), 7.84(1H, dd, J=8.6 Hz, 2.5 Hz), 8.26(1H, d, J=2.5 Hz). |
| 2602 | 3,4-Cl$_2$Ph— | —N(CH$_3$)— | —CH$_2$— | piperonyl | 2.42-2.45(4H, m), 3.04(3H, s), 3.44(2H, s), 3.48-3.52(2H, m), 3.62-3.66(2H, m), 4.09(2H, s), 5.95(2H, s), 6.68-6.86(6H, m), 6.94(1H, d, J=17.3 Hz), 6.99-7.04(3H, m), 7.31(1H, dd, J=8.4 Hz, 2.0 Hz), 7.42(1H, d, J=8.4 Hz), 7.57(1H, d, J=2.0 Hz), 7.82(1H, d, J=8.4 Hz), 8.24(1H, brs). |
| 2603 | 4-CF$_3$Ph— | —CH$_2$— | —CH$_2$— | piperonyl | 2.32-2.41(4H, m), 2.60-2.66(2H, m), 2.96-3.01(2H, m), 3.39-3.43(4H, m), 3.62-3.66(2H, m), 5.95 (2H, s), 6.70-6.77(2H, m), 6.84-6.85(1H, m), 6.93 (1H, d, J=8.6 Hz), 7.00-7.09(3H, m), 7.12(1H, d, J=16.5 Hz), 7.23-7.27(2H, m), 7.56-7.64(4H, m), 7.90(1H, dd, J=8.7 Hz, 2.6 Hz), 8.27(1H, d, J=2.6 Hz). |

TABLE 410-continued

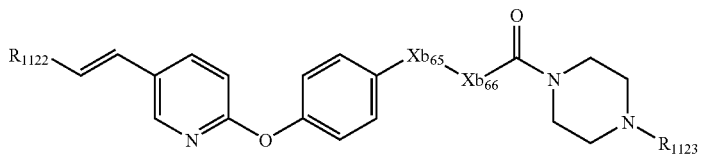

| Example No. | $R_{1122}$ | $Xb_{65}$ | $Xb_{66}$ | $R_{1123}$ | $^1$H NMR (CDCl$_3$) δppm |
|---|---|---|---|---|---|
| 2604 | 4-CF$_3$Ph— | none | none | benzyl | 2.47(4H, brs), 3.55-3.77(6H, m), 6.97(1H, d, J=8.6 Hz), 7.05(1H, d, J=16.3 Hz), 7.10-7.27(3H, m), 7.28 7.34(5H, m), 7.45-7.50(2H, m), 7.57-7.64(4H, m), 7.93(1H, dd, J=8.6 Hz, 2.4 Hz), 8.29(1H, d, J=2.4 Hz). |
| 2605 | 3,4-Cl$_2$Ph— | none | none | benzyl | 2.52(4H, brs), 3.49-3.90(6H, m), 6.89-6.98(2H, m), 7.03(1H, d, J=16.5 Hz), 7.15-7.20(2H, m), 7.30-7.50(9H, m), 7.58(1H, d, J=2.1 Hz), 7.90 (1H, dd, J=8.7 Hz, 2.5 Hz), 8.26(1H, d, J=2.5 Hz). |

TABLE 411

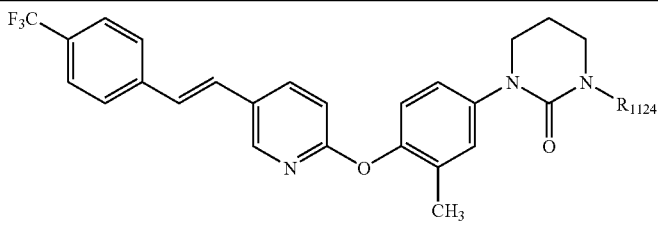

| Example No. | $R_{1124}$ | Form | $^1$H NMR (solvent) δppm |
|---|---|---|---|
| 2606 | piperonyl | hydrobromide | (DMSO-d$_6$)1.89-2.06(2H, m), 2.06(3H, s), 3.18-3.35(2H, m), 3.57-3.71(2H, m), 4.40(2H, s), 4.42-4.80(1H, m, 5.99(2H, s), 6.77(1H, dd, J=1.6 Hz, 7.9 Hz), 6.84(1H, d, J=1.6 Hz), 6.87(1H, d, J=7.9 Hz), 7.01(1H, d, J=8.6 Hz), 7.07(1H, d, J=8.6 Hz), 7.13(1H, dd, J=2.5 Hz, 8.6 Hz), 7.23(1H, d, J=2.5 Hz), 7.32(1H, d, J=16.5 Hz), 7.42(1H, d, J=16.5 Hz), 7.72(2H, d, J=8.5 Hz), 7.79(2H, d, J=8.5 Hz), 8.19(1H, dd, J=2.4 Hz, 8.6 Hz), 8.30(1H, d, J=2.4 Hz). |
| 2607 | 3,4-(CH$_3$O)$_2$PhCH$_2$— | free | (CDCl$_3$)1.99-2.14(2H, m), 2.18(3H, s), 3.22-3.38(2H, m), 3.63-3.79(2H, m), 3.89(3H, s), 3.90(3H, s), 4.57(2H, s), 6.76-6.95(4H, m), 6.97-7.20(4H, m), 7.51-7.67(4H, m), 7.88(1H, dd, J=2.5 Hz, 8.6 Hz), 8.27(1H, d, J=2.5 Hz). |

Example 2608

Production of 1-(3,4-dimethoxybenzyl)-3-{3-methyl-4-[5-(4-trifluoromethylphenylethynyl)pyridin-2-yloxy]phenyl}tetrahydropyrimidin-2-one To a solution of 1-[4-(5-bromopyridin-2-yloxy)-3-methylphenyl]-3-(3,4-dimethoxybenzyl)tetrahydropyrimidin-2-one (0.3 g, 0.59 mmol) in N-methylpyrrolidone (10 mL) were added bis(triphenylphosphine)palladium dichloride (20 mg, 0.03 mmol), copper iodide (11 mg, 0.059 mmol), 4-ethynyl-α,α,α-trifluorotoluene (0.14 mL, 0.88 mmol) and triethylamine (0.14 mL, 10 mmol) under a nitrogen atmosphere. The resulting solution was stirred for 3 hours at 110 to 120° C. After being left to cool, water was added to the reaction solution. The resulting solution was extracted with ethyl acetate. The ethyl acetate layer was washed with water and dried over anhydrous magnesium sulfate. The solvent was then evaporated, and the residue was purified by silica gel chromatography (n-hexane:ethyl acetate=4:1→1:1), to thereby yield 0.28 g of the title compound.

Appearance: Pale brown amorphous powder $^1$H NMR (CDCl$_3$) δ 1.97-2.15 (2H, m), 2.16 (3H, s), 3.31 (2H, t, J=6.0 Hz), 3.72 (2H, t, J=6.0 Hz), 3.88 (3H, s), 3.89 (3H, s), 4.57 (2H, s), 6.72-6.95 (5H, m), 7.04 (1H, d, J=8.6 Hz), 7.17 (1H, dd, J=2.6 Hz, 8.6 Hz), 7.55-7.68 (4H, m), 7.78 (1H, dd, J=2.3 Hz, 8.6 Hz), 8.36 (1H, d, J=2.3 Hz).

Example 2609

Production of 3-(3-methyl-4-{5-[2-oxo-2-(4-trifluoromethylphenyl)ethyl]pyridin-2-yloxy}phenyl)-1-piperonyltetrahydropyrimidin-2-one hydrobromide To a solution of 3-[4-(5-bromopyridin-2-yloxy)-3-methylphenyl]-1-piperonyltetrahydropyrimidin-2-one (0.11 g, 0.22 mmol) in toluene (10 mL) were added $Pd_2(dba)_3$ (10 mg, 0.01 mmol) and Xantphos (15 mg, 0.03 mmol) under a nitrogen atmosphere. The resulting solution was stirred for 5 minutes, and then 4'-(trifluoromethyl)acetophenone (63 mg, 0.33 mmol) and potassium bis(trimethylsilyl)amide (66 mg, 0.33 mmol) were added to the reaction solution. The resulting solution was stirred at 70 to 80° C. for 30 minutes, and left to cool. Water was added to the reaction solution, and extracted with ethyl acetate. The ethyl acetate layer was dried over anhydrous magnesium sulfate, and evaporated. The residue was purified by silica gel column chromatography (n-hexane: ethyl acetate=2:1→1:1), to yield 50 mg of a free form. To this free form was added an equivalent amount of hydrobromic acid, to thereby yield 50 mg of the title compound.

Appearance: Colorless amorphous powder $^1$H NMR (DMSO-$d_6$) δ 1.85-2.10 (2H, m), 2.06 (3H, s), 3.14-3.47 (2H, m), 3.50-3.76 (2H, m), 4.40 (2H, s), 4.49 (2H, s), 4.70-5.40 (1H, m), 5.98 (2H, s), 6.70-6.80 (1H, m), 6.81-6.90 (2H, m), 6.90-7.04 (2H, m), 7.12 (1H, d, J=2.2 Hz, 8.6 Hz), 7.18-7.26 (1H, m), 7.72 (1H, dd, J=2.2 Hz, 8.5 Hz), 7.93 (2H, d, J=8.2 Hz), 7.95-8.02 (1H, m), 8.24 (2H, d, J=8.2 Hz).

The following compounds were produced in the same manner as in Example 2609.

TABLE 412

| Example No. | $R_{1125}$ | $R_{1126}$ | $^1$H NMR (CDCl$_3$) δppm |
|---|---|---|---|
| 2610 | 3,4-Cl$_2$Ph— | piperonyl | 1.82-2.10(2H, m), 2.07(3H, s), 3.12-3.32(2H, m), 3.53-3.72(2H, m), 4.40(2H, s), 4.45(2H, s), 4.80-5.40(1H, m), 5.99(2H, s), 6.71-6.80(1H, m), 6.81-6.90(2H, m), 6.98(2H, dd, J=2.4 Hz, 8.5 Hz), 7.12(1H, dd, J=2.4 Hz, 8.5 Hz), 7.21(1H, d, J=2.4 Hz), 7.70(1H, dd, J=2.2 Hz, 8.4 Hz), 7.84(1H, d, J=8.4 Hz), 7.96(1H, d, J=2.2 Hz), 8.00(1H, dd, J=2.0 Hz, 8.4 Hz), 8.25(1H, d, J=2.0 Hz). |
| 2611 | 4-CF$_3$Ph— | 3,4-(CH$_3$O)$_2$Ph— | 1.87-2.11(5H, m), 3.15-3.32(2H, m), 3.43-3.71(3H, m), 3.74(3H, s), 3.75(3H, s), 4.44(2H, s), 4.51(2H, s), 6.78-6.86(1H, m), 6.87-6.91(1H, m), 6.93(1H, d, J=8.5 Hz), 6.99(1H, d, J=8.5 Hz), 7.00(1H, d, J=8.5 Hz), 7.14(1H, dd, J=2.4 Hz, 8.5 Hz), 7.19-7.25(1H, m), 7.73(1H, dd J=2.4 Hz, 8.5 Hz), 7.94(1H, d, J=8.3 Hz), 7.97-8.01(1H, m), 8.25(1H, d, J=8.3 Hz). |

TABLE 413

| Example No. | $R_{1127}$ | mp (° C.) or $^1$H NMR (solvent) δppm |
|---|---|---|
| 2612 | (4-methylbenzoyl-piperazinyl-methyl-benzodioxole) | $^1$H NMR (CDCl$_3$) 2.44(4H, brs), 3.44(2H, s), 3.54(2H, brs), 3.73(2H, brs), 4.29(2H, s), 5.94(2H, s), 6.74(2H, s), 6.85(1H, s), 6.94(1H, d, J=8.4 Hz), |

TABLE 413-continued

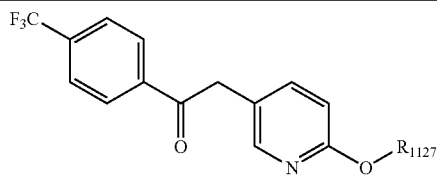

| Example No. | R<sub>1127</sub> | | mp (° C.) or $^1$H NMR (solvent) δppm |
|---|---|---|---|
| 2613 | (structure with F, CH₃, N, F, piperazine, benzodioxole) | CH₃SO₂H | 7.16(2H, d, J=8.6 Hz), 7.45(2H, d, J= 8.6 Hz), 7.63(1H, dd, J=8.4 Hz, 2.5 Hz), 7.76(2H, d, J=8.1 Hz), 8.07(1H, d, J=2.5 Hz), 8.11(2H, d, J=8.1 Hz). $^1$H NMR (DMSO-d₆)2.31(3H, s), 2.76- 3.45(9H, m), 3.69-4.57(8H, m), 6.07(2H, s), 6.81-7.22(6H, m), 7.74(1H, dd, J= 2.2 Hz, 8.4 Hz), 7.89-8.00(2H, m), 8.24 (1H, d, J=8.4 Hz), 9.49-9.79(1H, m). |
| 2614 | (structure with tolyl, CH₂CH₂, C=O, piperazine, benzodioxole) | HCl | mp 164.0-166.0 |

The following compounds were produced in the same manner as in Reference Example 111.

TABLE 414

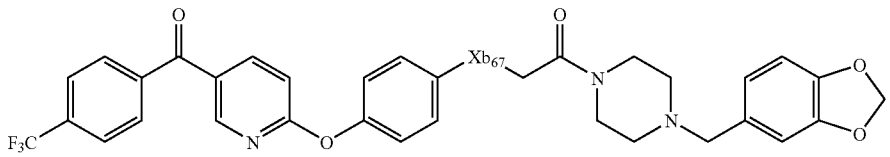

| Example No. | Xb₆₇ | $^1$H NMR (solvent) δppm |
|---|---|---|
| 2615 | —N(CH₃)— | 2.42-2.45(4H, m), 3.05(3H, s), 3.44(2H, s), 3.47-3.51(2H, m), 3.62-3.65(2H, m), 4.11(2H, s), 5.95(2H, s), 6.69-6.77(4H, m), 6.85(1H, s), 6.97(1H, d, J=8.7 Hz), 7.01-7.07 (2H, m), 7.75(2H, d, J=8.4 Hz), 7.87(2H, d, J=8.1 Hz), 8.17(1H, dd, J=8.7 Hz, 2.3 Hz), 8.58(1H, d, J=2.3 Hz). |
| 2616 | —CH₂— | 2.32-2.41(4H, m), 2.61-2.67(2H, m), 2.97-3.03(2H, m), 3.41-3.43(4H, m), 3.62-3.66(2H, m), 5.95(2H, s), 6.70-6.77(2H, m), 6.84(1H, s), 7.03-7.13(3H, m), 7.28-7.32(2H, m), 7.76(2H, d, J=8.1 Hz), 7.88(2H, d, J=8.1 Hz), 8.22(1H, dd, J=8.6 Hz, 2.4 Hz), 8.58(1H, d, J=2.4 Hz). |

TABLE 415

[Structure: 4-CF3-phenyl-NH-SO2- attached to pyridine with Br, linked via O to phenyl(R1128) with piperidine-R1129]

| Example No. | R$_{1128}$ | R$_{1129}$ | $^1$H NMR (CDCl$_3$) δppm |
|---|---|---|---|
| 2617 | —H | —CH$_2$COOC$_2$H$_5$ | 1.27(3H, t, J=7.1 Hz), 1.34-1.48(2H, m), 1.81-1.99(3H, m), 2.29(2H, d, J=6.9 Hz), 2.73(2H, t, J=12.2 Hz), 3.63(2H, d, J=12.2 Hz), 4.15(2H, q, J=7.3 Hz), 6.91-7.01(4H, m), 7.18-7.26(3H, m), 7.54(2H, d, J=8.9 Hz), 8.26(1H, d, J=2.3 Hz), 8.43(1H, d, J=2.3 Hz). |
| 2618 | —CH$_3$ | —CH$_2$COOC$_2$H$_5$ | 1.28(3H, t, J=7.1 Hz), 1.30-1.39(2H, m), 1.80-1.96(3H, m), 2.07(3H, s), 2.29(2H, d, J=6.9 Hz), 2.70(2H, t, J=12.0 Hz), 3.61(2H, d, J=12.4 Hz), 4.17(2H, q, J=7.3 Hz), 6.74-6.78(2H, m), 6.92(1H, d, J=8.6 Hz), 7.20-7.26(3H, m), 7.52(2H, d, J=8.4 Hz), 8.28(1H, d, J=2.3 Hz), 8.41(1H, d, J=2.3 Hz). |
| 2619 | —H | —COOC$_2$H$_5$ | 1.27(3H, t, J=7.1 Hz), 1.92-2.00(2H, m), 2.01-2.05(2H, m), 2.38-2.47(1H, m), 2.74-2.84(2H, m), 3.59-3.63(2H, m), 4.15(2H, q, J=7.1 Hz), 6.93-7.02(4H, m), 7.17-7.26(3H, m), 7.54(2H, d, J=8.4 Hz), 8.26(1H, d, J=2.3 Hz), 8.43(1H, d, J=2.3 Hz). |

TABLE 416

[Structure: R1130-NH-C(O)-pyridine-O-phenyl(CH3)-cyclic urea-R1131·HBr]

| Example No. | R$_{1130}$ | R$_{1131}$ | mp (° C.) or $^1$H NMR (DMSO-d$_6$) δppm |
|---|---|---|---|
| 2620 | 4-CF$_3$Ph— | piperonyl | mp 129.0-130.5 |
| 2621 | 4-CF$_3$Ph— | 3,4-(CH$_3$O)$_2$PhCH$_2$— | mp 130.0-132.0 |
| 2622 | 3,4-Cl$_2$Ph— | 3,4-(CH$_3$O)$_2$PhCH$_2$— | $^1$H NMR 1.85-2.14(5H, m), 3.13-3.33(2H, m), 3.58-3.71 (2H, m), 3.73(3H, s), 3.74(3H, s), 4.12-4.78(3H, m), 6.73-6.94(3H, m), 7.04(1H, d, J=8.6 Hz), 7.11-7.20(2H, m), 7.25(1H, d, J=2.4 Hz), 7.61(1H, d, J=8.8 Hz), 7.71(1H, dd, J=2.4 Hz, 8.8 Hz), 8.11(1H, d, J=2.4 Hz), 8.34(1H, dd J=2.4 Hz, 8.8 Hz), 8.66(1H, d, J=2.4 Hz), 10.53(1H, s). |

Example 2623

Production of 2-[4-(3-{4-[4-(3,4-dichlorobenzoylamino)-phenoxy]phenyl}propionyl)piperazin-1-yl]acetic acid hydrochloride To a solution of ethyl 2-[4-(3-{4-[4-(3,4-dichlorobenzoylamino)phenoxy]phenyl}propionyl)piperazin-1-yl]acetate (0.493 g, 0.843 mmol) in THF (5 mL) and ethanol (5 mL) were added 5 M aqueous sodium hydroxide (0.253 mL, 1.27 mmol) and water (1 mL), and the resulting solution was refluxed for 1 hour. This reaction solution was concentrated under reduced pressure, and the residue was dissolved in 50% aqueous ethanol. To the resulting solution was added 5 M hydrochloric acid (0.253 mL, 1.27 mmol), and the obtained solid was collected by filtration. To this solid was dissolved in ethanol (10 mL) and 5 M hydrochloric acid (0.3 mL) by heating. The solvent was then evaporated, and the obtained solid was recrystallized from ethanol-diethyl ether, to thereby yield 0.381 g of the title compound.

Appearance: White powder

Melting point: 215-218° C.

The following compounds were produced in the same manner as in Example 2623.

TABLE 417

[Structure: 3,4-dichlorobenzamide linked via NH to phenyl-O-phenyl-R1132]

| Example No. | R1132 | ¹H NMR (solvent) δppm |
|---|---|---|
| 2624 | 4-methylpiperazin-1-yl-CH2-COOH | (DMSO-d6) 2.71-2.73(4H, m), 3.12-3.14(4H, m), 3.21(2H, s), 6.91-6.98 (6H, m), 7.71(2H, dd, J=7.0 Hz, 2.0 Hz), 7.82(1H, d, J =8.0 Hz), 7.93(1H, dd, J=8.0 Hz, 2.0 Hz), 8.21(1H, d, J= 2.0 Hz), 10.38(1H, s). |
| 2625 | 4-methyl-3,6-dihydro-2H-pyridin-1-yl-CH2-COOH | (CDCl3) 2.68(2H, m), 3.05(2H, m), 3.35(2H, s), 3.49(2H, m), 6.00(1H, m), 6.98(2H, d, J=8.5 Hz), 7.05(2H, d, J=8.5 Hz), 7.35(2H, d, J=8.5 Hz), 7.58(2H, d, J=8.5 Hz), 7.58(1H, brs), 7.77(2H, m), 7.97(1H, s). |
| 2626 | 1-methylpiperidin-4-yl-COOH | (DMSO-d6) 1.60-1.70(2H, m), 1.85-1.90(2H, m), 2.50(1H, m), 2.65-2.73 (2H, m), 3.55(2H, brd, J=12.5 Hz), 6.90-6.98(6H, m), 7.71(2H, d, J=9.0 Hz), 7.81(1H, d, J=8.5 Hz), 7.93(1H, dd, J=8.5 Hz, 2.0 Hz), 8.21(1H, d, J=2.0 Hz), 10.37(1H, s), 12.20(1H, brs). |
| 2627 | 1-methylpiperidin-4-yloxy-CH2-COOH | (DMSO-d6) 1.51-1.58(2H, m), 1.90-1.95(2H, m), 2.78-2.82(2H, m), 3.43 (2H, m), 3.52(1H, m), 3.92(2H, s), 6.89-6.98(6H, m), 7.70(2H, d, J=9.0 Hz), 7.82(1H, d, J=8.5 Hz), 7.93(1H, dd, J=8.5 Hz, 2.0 Hz), 8.21(1H, d, J=2.0 Hz), 10.40(1H, s). |
| 2628 | (1-methylpiperidin-4-yl)(methyl)amino-CH2-COOH | (DMSO-d6) 1.59-1.66(2H, m), 1.94-1.97(2H, m), 2.54(3H, s), 3.62(2H, t, J=11.0 Hz), 2.98(1H, m), 3.29(2H, s), 3.67 3.70(2H, m), 6.90-6.99(6H, m), 7.71(2H, d, J=9.0 Hz), 7.82(1H, d, J=8.5 Hz), 7.93(1H, dd, J=8.5 Hz, 2.0 Hz), 8.21(1H, d, J=2.0 Hz), 10.39(1H, s). |
| 2629 | 4-methylpiperidin-1-yl-CH2-COOH | (CDCl3) 1.80-1.83(4H, m), 2.61-2.65(3H, m), 3.24(2H, s), 3.25(2H, brd, J=11.0 Hz), 6.94(2H, d, J=8.5 Hz), 7.03(2H, d, J=9.0 Hz), 7.25(2H, d, J=8.5 Hz), 7.76(2H, d, J=9.0 Hz), 7.83(1H, d, J=8.5 Hz), 7.94(1H, dd, J=8.5 Hz, 2.0 Hz), 8.21(1H, d, J=2.0 Hz), 10.41(1H, s). |

TABLE 418

[Structure: R1133-C(O)-NH-pyridyl-Xb68-phenyl-Xb69-N(piperidine)-(CH2)M-COOH]

| Example No. | R1133 | Xb68 | Xb69 | M | ¹H NMR (DMSO-d6) δppm |
|---|---|---|---|---|---|
| 2630 | 4-CF3Ph— | —N(CH3)— | none | 1 | 1.20-1.45(2H, m), 1.70-1.95(3H, m), 2.20(2H, d, J=6.6 Hz), 2.67(2H, t, J=12.4 Hz), 3.32(3H, s), 3.67(2H, d, J=12.4 Hz), 6.42(1H, d, J=9.1 Hz), 6.99(2H, d, J=8.9 Hz), 7.11(2H, d, J=8.9 Hz), 7.73(1H, dd, J= 9.1 Hz, 2.3 Hz), 7.90(2H, d, J=8.2 Hz), 8.15(2H, d, J=8.2 Hz), 8.46(1H, d, J=2.3 Hz), 10.33(1H, s). |
| 2631 | 3,4-Cl2Ph— | —O— | —CH2— | 0 | 1.57(2H, brs), 1.81(2H, brs), 2.00(2H, brs), 2.23(1H, brs), 2.77(2H, brs), 3.44(2H, brs), 7.05(1H, d, J=9.0 Hz), 7.07(2H, d, J=8.5 Hz), 7.35(2H, d, J=8.5 Hz), 7.84(1H, d, J=8.5 Hz), 7.95(1H, d, J=8.5 Hz), 8.20 (1H, dd, J=9.0 Hz, 3.0 Hz), 8.22(1H, d, J=2.0 Hz), 8.49(1H, d, J=3.0 Hz), 10.56(1H, s), 12.15(1H, brs). |

TABLE 418-continued

R$_{1133}$—C(O)—NH—[pyridine]—Xb$_{68}$—[phenyl]—Xb$_{69}$—N[piperidine]—(CH$_2$)$_M$—COOH

| Example No. | R$_{1133}$ | Xb$_{68}$ | Xb$_{69}$ | M | $^1$H NMR (DMSO-d$_6$) δppm |
|---|---|---|---|---|---|
| 2632 | 3,4-Cl$_2$Ph— | —O— | —CO— | 0 | 1.52(2H, m), 1.86(2H, brs), 2.52(1H, m), 3.10(2H, brs), 3.65(1H, brs), 4.31(1H, brs), 7.15(1H, d, J=9.0 Hz), 7.16(2H, d, J=8.5 Hz), 7.43(2H, d, J=8.5 Hz), 7.84 (2H, d, J=8.5 Hz), 7.95(1H, dd, J=8.5 Hz, 2.0 Hz), 8.23(1H, d, J=2.0 Hz), 8.24(1H, dd, J=9.0 Hz, 3.0 Hz), 8.52(1H, d, J=3.0 Hz), 10.60(1H, s). |
| 2633 | 4-CF$_3$Ph— | —O— | —CO— | 0 | 1.52(2H, m), 1.86(2H, brs), 2.54(1H, m), 3.05(2H, brs), 3.63(1H, brs), 4.31(1H, brs), 7.15(1H, d, J=9.0 Hz), 7.16(2H, d, J=8.5 Hz), 7.44(2H, d, J=8.5 Hz), 7.94 (2H, d, J=8.5 Hz), 8.17(2H, d, J=8.5 Hz), 8.27(1H, dd, J=9.0 Hz, 2.5 Hz), 8.55(1H, d, J=2.5 Hz), 10.67(1H, s). |
| 2634 | 3,4-Cl$_2$Ph— | —O— | none | 0 | 1.63-1.71(2H, m), 1.92(2H, brd, J=10.0 Hz), 2.74(2H, t, J=11.5 Hz), 3.58(2H, brd, J=12.5 Hz), 6.96(1H, d, J=9.0 Hz), 6.98(4H, s), 7.83(1H, d, J=8.5 Hz), 7.94(1H, dd, J=8.5 Hz, 2.0 Hz), 8.14(1H, dd, J=9.0 Hz, 2.5 Hz), 8.21(1H, d, J=2.0 Hz), 8.44(1H, d, J=2.5 Hz), 10.50 (1H, s), 12.20(1H, brs). |
| 2635 | 3,4-Cl$_2$Ph— | —O— | none | 1 | 1.31-1.34(2H, m), 1.77(2H, brd, J=11.5 Hz), 2.20(2H, t, J=6.5 Hz), 2.64(2H, brt, J=10.5 Hz), 3.61(2H, brd, J=12.5 Hz), 6.96(1H, d, J=9.0 Hz), 6.96(4H, s), 7.83 (1H, d, J=8.5 Hz), 7.94(1H, dd, J=8.5 Hz, 2.0 Hz), 8.14(1H, dd, J=9.0 Hz, 2.5 Hz), 8.21(1H, d, J=2.0 Hz), 8.44(1H, d, J=2.5 Hz), 10.50(1H, s), 12.06(1H, brs). |

TABLE 419

R$_{1134}$—C(O)—NH—[pyridine]—Xb$_{70}$—[phenyl]—Xb$_{71}$—N—Xb$_{72}$—[piperazine]—CH$_2$COOH

| Example No. | R$_{1134}$ | Xb$_{70}$ | Xb$_{71}$ | Xb$_{72}$ | $^1$H NMR (DMSO-d$_6$) δppm |
|---|---|---|---|---|---|
| 2636 | 4-CF$_3$Ph— | —O— | —CO— | —CH$_2$— | 3.30(4H, brs), 3.77(4H, brs), 3.99(2H, s), 7.17(1H, d, J=8.8 Hz), 7.21(2H, d, J=8.6 Hz), 7.51(2H, d, J=8.6 Hz), 7.94(2H, d, J=8.0 Hz), 8.20(2H, d, J=8.0 Hz), 8.29(1H, dd, J=8.8 Hz, 2.6 Hz), 8.59(1H, d, J=2.6 Hz), 10.79(1H, s). |
| 2637 | 3,4-Cl$_2$Ph— | —O— | none | —CH$_2$— | 2.71(4H, t, J=5.0 Hz), 3.13(2H, s), 3.14(4H, t, J 32 5.0 Hz), 6.96-7.00(5H, m), 7.82(1H, d, J=8.5 Hz), 7.96(1H, dd, J=8.5 Hz, 2.0 Hz), 8.16(1H, dd, J=9.0 Hz, 2.5 Hz), 8.24(1H, d, J=2.0 Hz), 8.37(1H, s), 8.46(1H, d, J=2.5 Hz), 10.62(1H, brs). |
| 2638 | 4-CF$_3$Ph— | —N(CH$_3$)— | none | —CH$_2$— | 2.64(4H, brs), 2.95(2H, s), 3.15(4H, brs), 3.33(3H, s), 6.42(1H, d, J=9.1 Hz), 6.99(2H, d, J=8.9 Hz), 7.13 (2H, d, J=8.9 Hz), 7.75(1H, dd, J=9.1 Hz, 2.5 Hz), 7.89(2H, d, J=8.2 Hz), 8.17(2H, d, J=8.2 Hz), 8.49 (1H, d, J=2.5 Hz), 10.46(1H, s). |

TABLE 419-continued

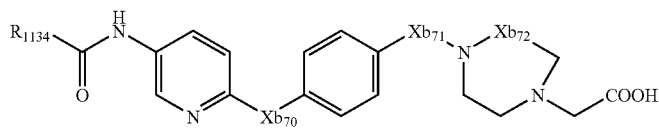

| Example No. | R1134 | Xb70 | Xb71 | Xb72 | 1H NMR (DMSO-d6) δppm |
|---|---|---|---|---|---|
| 2639 | 4-CF3Ph— | —O— | none | —CH2— | 2.72(4H, t, J=5.0 Hz), 3.15(4H, t, J=5.0 Hz), 3.20 (2H, s), 6.96-7.01(5H, m), 7.93(2H, d, J=8.5 Hz), 8.16(2H, d, J=8.5 Hz), 8.18(1H, dd, J=9.0 Hz, 2.5 Hz), 8.46(1H, d, J=2.5 Hz), 10.60(1H, s). |
| 2640 | 3,4-Cl2Ph— | —O— | none | —CO— | 3.13(2H, brs), 3.17(2H, s), 3.48(2H, brs), 3.71(2H, brs), 7.12(1H, d, J=8.9 Hz), 7.15(2H, dd, J=6.8 Hz, 2.1 Hz), 7.36(2H, dd, J=6.8 Hz, 2.1 Hz), 7.84(1H, d, J=8.4 Hz), 7.95(1H, dd, J=8.4 Hz, 2.1 Hz), 8.22(1H, dd, J=8.9 Hz, 2.7 Hz), 8.23(1H, d, J=2.1 Hz), 8.49 (1H, d, J=2.7 Hz), 10.58(1H, s). |

TABLE 420

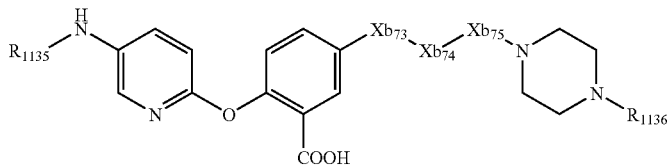

| Example No. | R1135 | Xb73 | Xb74 | Xb75 | R1136 | 1H NMR (solvent) δppm |
|---|---|---|---|---|---|---|
| 2641 | 4-CF3PhCO— | none | none | none | benzyl | (CD3OD) 3.47(8H, brs), 4.43(2H, s), 6.96 (1H, d, J=8.9 Hz), 7.14 (1H, d, J=8.9 Hz), 7.30(1H, dd, J=8.9 Hz, 3.0 Hz), 7.51-7.59 (6H, m), 7.82(2H, d, J=8.3 Hz), 8.12-8.18(3H, m), 8.36(1H, d, J=2.5 Hz). |
| 2642 | 3,4-Cl2PhSO2— | —N(C2H5)— | —CH2— | —CO— | piperonyl | (DMSO-d6) 1.11(3H, t, J=7.0 Hz), 2.20-2.45 (4H, m), 3.30-3.55(8H, m), 4.22(2H, s), 5.99 (2H, s), 6.70-7.00(7H, m) 7.40-7.50(1H, m), 7.55-7.60(1H, m), 7.66(1H, d, J=2.7 Hz), 7.84(1H, d, J=8.4 Hz), 7.88(1H, d, J=2.1 Hz), 10.27(1H, brs), 12.51(1H, brs). |
| 2643 | 3,4-Cl2PhNHCO— | —N(C2H5)— | —CH2— | —CO— | piperonyl | (DMSO-d6) 1.13(3H, t, J=7.0 Hz), 2.20-2.50 (4H, m), 3.30-3.60(8H, m), 4.21(2H, s), 5.99 (2H, s), 6.60-7.05(7H, m), 7.30-7.40(1H, m), 7.47(1H, d, J=8.8 Hz), 7.65-7.85(1H, m), 7.90(1H, d, J=2.3 Hz), 8.06(1H, d, J=2.6 Hz), 9.80(2H, brs), 12.40(1H, brs). |

TABLE 421

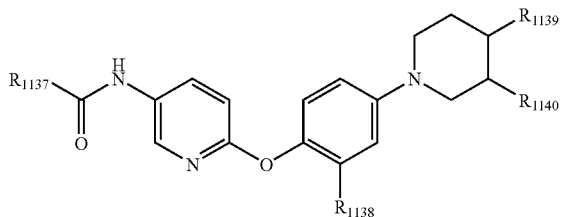

| Example No. | R<sub>1137</sub> | R<sub>1138</sub> | R<sub>1139</sub> | R<sub>1140</sub> | $^1$H NMR (solvent) δppm |
|---|---|---|---|---|---|
| 2644 | 3,4-Cl<sub>2</sub>Ph— | —H | —H | —COOH | (CDCl<sub>3</sub>) 1.80(1H, m), 1.86-1.94(3H, m), 2.82(1H, m), 3.14(2H, m), 3.32 (2H, m), 6.94(1H, d, J=9.0 Hz), 7.06(4H, s), 7.57 (1H, d, J=8.5 Hz), 7.72(1H, d, J=8.5 Hz), 7.93 (1H, brs), 7.99(1H, s), 8.18(1H, brd, J= 9.0 Hz), 8.26(1H, d, J=2.5 Hz). |
| 2645 | 4-CF<sub>3</sub>Ph— | —H | —CH<sub>2</sub>COOH | —H | (CDCl<sub>3</sub>) 1.44-1.50(2H, m), 1.90(2H, brd, J=13.5 Hz), 1.94(1H, m), 2.36 (2H, d, J=7.0 Hz), 2.75(2H, dt, J= 2.5 Hz, 12.0 Hz), 3.63(2H, brd, J= 12.0 Hz), 6.92(1H, d, J=9.0 Hz), 6.97(2H, d, J=9.0 Hz), 7.04(2H, d, J=9.0 Hz), 7.72(1H, s), 7.78(2H, d, J=8.0 Hz), 7.99(2H, d, J=8.0 Hz), 8.19 (1H, dd, J=9.0 Hz, 2.5 Hz), 8.25(1H, d, J=2.5 Hz). |
| 2646 | 3-CF<sub>3</sub>Ph— | —H | —CH<sub>2</sub>COOH | —H | (CDCl<sub>3</sub>) 1.46-1.49(2H, m), 1.89(2H, brd, J=15.0 Hz), 1.95(1H, m), 2.36(2H, d, J=7.0 Hz), 2.74(2H, dt, J=2.0 Hz, 12.0 Hz), 3.63(2H, brd, J=12.0 Hz), 6.92(1H, d, J=9.0 Hz), 6.97(2H, d, J=9.0 Hz), 7.05 (2H, d, J=9.0 Hz), 7.66(1H, t, J= 7.5 Hz), 7.73(2H, brs), 7.84(1H, d, J= 7.5 Hz), 8.07 (1H, d, J=7.5 Hz), 8.14(1H, brs), 8.17(1H, dd, J=9.0 Hz, 2.5 Hz), 8.27(1H, d, J=2.5 Hz). |
| 2647 | 4-CF<sub>3</sub>Ph— | —OCH<sub>3</sub> | —CH<sub>2</sub>COOH | —H | (DMSO-d<sub>6</sub>) 1.31-1.36(2H, m), 1.77-1.81(3H, m), 2.2 1(2H, d, J=7.4 Hz), 2.68-2.75(2H, m), 3.64(2H, brs), 3.68(3H, s), 6.52(1H, brs), 6.68(1H, brs), 6.89-6.96(2H, m), 7.92(2H, d, J=8.4 Hz), 8.09-8.17(3H, m), 8.38(1H, d, J=2.5 Hz), 10.54(1H, s), 12.10(1H, brs). |
| 2648 | 4-CF<sub>3</sub>Ph— | —H | —COOH | —H | (CDCl<sub>3</sub> + CD<sub>3</sub>OD) 1.82-1.96(2H, m), 2.04-2.09 (2H, m), 2.38-2.48(1H, m), 2.74-2.84(2H, m), 3.52-3.61(2H, m), 6.86(1H, dd, J=8.9 Hz, 0.5 Hz), 6.96-7.05(4H, m), 7.69-7.76(2H, m), 8.06 (2H, d, J=8.1 Hz), 8.16(1H, d, J=8.1 Hz), 8.23-8.33(2H, m). |

TABLE 422

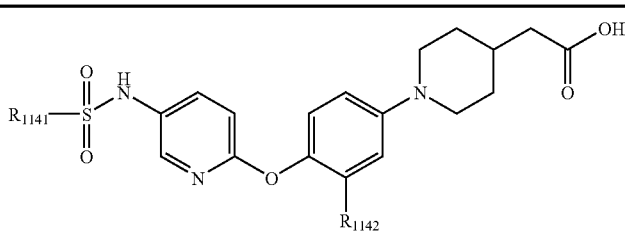

| Example No. | R<sub>1141</sub> | R<sub>1142</sub> | $^1$H NMR (DMSO-d<sub>6</sub>) δppm |
|---|---|---|---|
| 2649 | 4-CF<sub>3</sub>Ph— | —CH<sub>3</sub> | 1.41(2H, brs), 1.84-1.96(3H, m), 1.97(3H, s), 2.22(2H, d, J= 6.6 Hz), 2.55-2.75(2H, m), 3.58(2H, d, J=11.9 Hz), 6.72- |

TABLE 422-continued

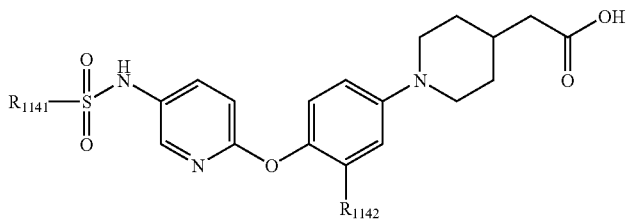

| Example No. | $R_{1141}$ | $R_{1142}$ | $^1$H NMR (DMSO-$d_6$) δppm |
|---|---|---|---|
| 2650 | 3,4-Cl$_2$Ph— | —CH$_3$ | 7.11(4H, m), 7.52(1H, dd, J=8.9 Hz, 2.8 Hz), 7.74(1H, d, J= 2.6 Hz), 7.89-7.99(4H, m), 10.49(1H, s), 12.14(1H, brs). 1.38(2H, brs), 1.82-1.96(3H, m), 1.97(3H, s), 2.22(2H, d, J= 6.4 Hz), 2.55-2.75(2H, m), 3.59(2H, d, J=11.9 Hz), 6.88 6.91(4H, m), 7.51(1H, dd, J=8.7 Hz, 2.5 Hz), 7.63(1H, dd, J= 8.4 Hz, 2.1 Hz), 7.74(1H, d, J=2.8 Hz), 7.83-7.87(2H, m), 10.38(1H, s), 12.12(1H, brs). |
| 2651 | 3,4-Cl$_2$Ph— | —H | 1.30-1.37(2H, m), 1.75-1.91(3H, m), 2.20(2H, d, J=6.9 Hz), 2.51-2.62(2H, m), 3.60(2H, d, J=12.0 Hz), 6.87-6.94(5H, m), 7.50(1H, dd, J=8.7 Hz, 2.8 Hz), 7.62(1H, dd, J=8.6 Hz, 2.3 Hz), 7.77(1H, d, J=2.8 Hz), 7.84-7.89(2H, m), 10.39(1H, s), 12.09(1H, brs). |
| 2652 | 4-CF$_3$Ph— | —H | 1.29-1.33(2H, m), 1.74-1.91(3H, m), 2.19(2H, d, J=6.8 Hz), 2.63-2.75(2H, m), 3.59(2H, d, J=12.2 Hz), 6.86-6.93(5H, m), 7.50(1H, dd, J=8.9 Hz, 2.8 Hz), 7.77(1H, d, J=2.6 Hz), 7.89-7.99(4H, m), 10.47(1H, s), 12.09(1H, brs). |
| 2653 | 4-CF$_3$Ph— | —OCH$_3$ | 1.41(2H, brs), 1.81-1.85(3H, m), 2.25(2H, d, J=6.4 Hz), 2.55-2.79(2H, m), 3.64(3H, s), 3.68(2H, brs), 6.73-6.95(4H, m), 7.51(1H, dd, J=8.7 Hz, 2.5 Hz), 7.73(1H, d, J=2.6 Hz), 7.92-8.02(4H, m), 10.45(1H, s), 12.14(1H, brs). |
| 2654 | 3,4-Cl$_2$Ph— | —OCH$_3$ | 1.42(2H, brs), 1.79-1.91(3H, m), 2.23(2H, d, J=6.6 Hz), 2.76-2.83(2H, m), 3.63(5H, brs), 6.63-6.98(4H, m), 7.48(1H, dd, J=8.7 Hz, 2.6 Hz), 7.63(1H, dd, J=8.4 Hz, 2.0 Hz), 7.71(1H, d, J=2.8 Hz), 7.85-7.88(2H, m), 10.36(1H, s), 12.33(1H, brs). |

TABLE 423

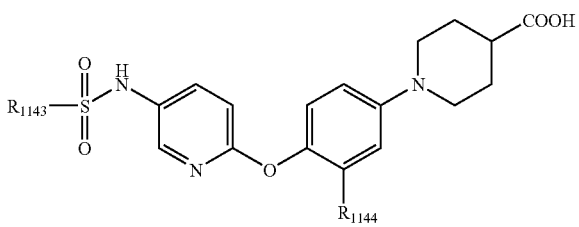

| Example No. | $R_{1143}$ | $R_{1144}$ | $^1$H NMR (DMSO-$d_6$) δppm |
|---|---|---|---|
| 2655 | 4-CF$_3$Ph— | —CH$_3$ | 1.81-1.99(4H, m), 2.00(3H, s), 2.41-2.44(1H, m), 2.75(2H, brs), 3.58(2H, d, J=12.2 Hz), 6.91-7.20(4H, m), 7.53(1H, dd, J=8.9 Hz, 2.6 Hz), 7.75(1H, d, J=2.6 Hz), 7.90 7.99(4H, m), 10.52(1H, s), 12.41(1H, brs). |
| 2656 | 3,4-Cl$_2$Ph— | —CH$_3$ | 1.63-1.71(2H, m), 1.91-1.94(2H, m), 1.95(3H, s), 2.41 2.48(1H, m), 2.75-2.80(2H, m), 3.58(2H, d, J=12.9 Hz), 6.85-6.89(3H, m), 7.50(1H, dd, J=8.7 Hz, 2.6 Hz), 7.68 7.79(2H, m), 7.81-7.98(4H, m), 10.43(1H, s), 12.35(1H, brs). |
| 2657 | 3,4-Cl$_2$Ph— | —H | 1.74(2H, brs), 1.93-1.98(2H, m), 2.49-2.51(2H, m), 2.88(1H, brs), 3.55-3.60(2H, m), 6.90-7.01(5H, m), 7.50-7.89(5H, m), 1O.41(1H, s), 12.13(1H, brs). |
| 2658 | 4-CF$_3$Ph— | —H | 1.66-1.71(2H, m), 1.88-1.92(2H, m), 2.34-2.42(1H, m), 2.68-2.76(2H, m), 3.56(2H, d, J=12.4 Hz), 6.85-6.92(5H, m), 7.48(1H, d, J=2.8 Hz), 7.51(LH, d, J=2.8 Hz), 7.77 7.99(4H, m), 10.47(1H, s), 12.21(1H, s). |

TABLE 424

| Example No. | R$_{1145}$ | R$_{1146}$ | $^1$H NMR (DMSO-d$_6$) δppm |
|---|---|---|---|
| 2659 | —H | —CH$_2$COOH | 1.26-1.32(2H, m), 1.74-1.91(3H, m), 2.20(2H, d, J=6.6 Hz), 2.66(2H, t, J=11.0 Hz), 3.63(2H, d, J=12.5 Hz), 6.93-7.03(4H, m), 7.13-7.35(2H, m), 7.65(2H, d, J=8.6 Hz), 8.42(1H, d, J=2.3 Hz), 8.47(1H, d, J=2.3 Hz), 11.00(1H, s), 12.07(1H, brs). |
| 2660 | —CH$_3$ | —CH$_2$COOH | 1.30-1.41(2H, m), 1.80-2.00(3H, m), 1.99(3H, s), 2.20(2H, d, J=6.6 Hz), 2.68-2.76(2H, m), 3.62(2H, d, J=12.2 Hz), 6.88-6.96(3H, m), 7.33(2H, d, J=8.2 Hz), 7.65(2H, d, J=8.6 Hz), 8.44(2H, s), 11.00(1H, s), 12.10(1H, brs). |
| 2661 | —H | —COOH | 1.63-1.70(2H, m), 1.88-1.92(2H, m), 2.41-2.45(1H, m), 2.71-2.79(2H, m), 3.61(2H, d, J=12.5 Hz), 6.93-7.00(4H, m), 7.31(2H, d, J=8.6 Hz), 7.63(2H, d, J=8.7 Hz), 8.40 8.47(2H, m), 10.63(1H, s), 12.21(1H, s). |

TABLE 425

| Example No. | R$_{1147}$ | $^1$H NMR (DMSO-d$_6$) δppm |
|---|---|---|
| 2662 | 4-CF$_3$PhCO— | 2.08(3H, s), 2.09-2.32(2H, m), 3.65-3.93(4H, m), 7.01(1H, d, J=8.6 Hz), 7.06(1H, d, J=8.9 Hz), 7.19(1H, dd, J=2.6 Hz, 8.6 Hz), 7.29(1H, d, J=2.6 Hz), 7.42-7.51(2H, m), 7.81-7.98(4H, m), 8.10-8.18(2H, m), 8.21(1H, dd, J=2.6 Hz, 8.9 Hz), 8.43(1H, d, J=2.6 Hz), 10.60(1H, s), 12.60-12.91(1H, m). |
| 2663 | 3,4-Cl$_2$PhSO$_2$— | 1.99(3H, s), 2.07-2.31(2H, m), 3.60-3.91(4H, m), 6.97(1H, d, J=8.5 Hz), 6.98(1H, d, J=8.8 Hz), 7.16(1H, dd, J=2.4 Hz, 8.5 Hz), 7.25(1H, d, J=2.2 Hz), 7.40-7.51(2H, m), 7.54 (1H, dd, J=2.8 Hz, 8.8 Hz), 7.62(1H, dd, J=2.2 Hz, 8.5 Hz), 7.75(1H, d, J=2.8 Hz), 7.79-7.93(4H, m). |

Example 2664

Production of (4-{5-[(4-trifluoromethylphenylamino)-methyl]-pyridin-2-yloxy}phenyl)(4-piperonylpiperazin-1-yl)methanone Methanesulfonic acid 6-[4-(4-piperonylpiperazine-1-carbonyl)phenoxy]pyridin-3-yl ester (0.433 g, 0.824 mmol) and 4-trifluoromethyl phenylamine (0.310 mL, 2.47 mmol) were mixed together, and the resulting mixture was stirred for 2 hours at 100° C. The formed yellow mass was stirred together with a saturated sodium bicarbonate solution, ethyl acetate and THF (20 ml of each). The organic layer was collected, washed with brine, dried over anhydrous magnesium sulfate, and evaporated under reduced pressure. The residue was purified by silica gel column chromatography (dichloromethane:methanol=50:1), to thereby yield 0.236 g of the title compound.

Appearance: Pale yellow amorphous powder $^1$H NMR (CDCl$_3$) δ 2.44 (4H, brs), 3.45 (2H, s), 3.57 (2H, brs), 3.75 (2H, brs), 4.30-4.35 (1H, m), 4.36 (2H, s), 5.95 (2H, s), 6.63 (2H, d, J=8.7 Hz), 6.74-6.77 (2H, m), 6.85 (1H, s), 6.93 (1H, d, J=8.4 Hz), 7.15 (2H, d, J=8.4 Hz), 7.39-7.47 (4H, m), 7.71 (1H, dd, J=2.5 Hz, 8.4 Hz), 8.18 (1H, d, J=2.3 Hz).

The following compounds were produced in the same manner as in Example 2664.

TABLE 426

![Structure with R1148-O-CH2-pyridine-O-phenyl-Xb76-Xb77-C(O)-piperazine-CH2-benzodioxole]

| Example No. | R1148 | Xb76 | Xb77 | Form | $^1$H NMR (solvent) δppm |
|---|---|---|---|---|---|
| 2665 | 3,4-Cl$_2$Ph— | —N(CH$_3$)— | —CH$_2$— | free | (CDCl$_3$) 2.42-2.44(4H, m), 3.03(3H, s), 3.43(2H, brs), 3.49-3.50(2H, m), 3.63(2H, brs), 4.08(2H, s), 4.94(2H, s), 5.94(2H, s), 6.70(2H, d, J=9.2 Hz), 6.74(2H, brs), 6.80(1H, dd, J=8.9 Hz, 2.8 Hz), 6.83-6.86(2H, m), 7.01(2H, d, J=9.1 Hz), 7.05(1H, d, J=2.8 Hz), 7.32(1H, d, J=8.9 Hz), 7.86(1H, dd, J=8.6 Hz, 2.5 Hz), 8.19(1H, d, J=1.8 Hz). |
| 2666 | 4-CF$_3$Ph— | —N(CH$_3$)— | —CH$_2$— | free | (CDCl$_3$) 2.41-2.44(4H, m), 3.03(3H, s), 3.43(2H, brs), 3.49(2H, brs), 3.63(2H, brs), 4.08(2H, s), 5.02(2H, s), 5.95(2H, s), 6.69-6.74(4H, m), 6.85-6.88(2H, m), 7.00-7.03(4H, m), 7.56(2H, d, J=8.6 Hz), 7.72(1H, dd, J=8.6 Hz, 2.5 Hz), 8.22(1H, d, J=2.3 Hz). |
| 2667 | 4-CF$_3$Ph— | none | none | hydrochloride | (DMSO-d$_6$) 3.10-3.42(8H, m), 4.24(2H, brs), 5.20(2H, s), 6.07(2H, s), 6.97-7.04(2H, m), 7.15 (1H, d, J=8.6 Hz), 7.21-7.24(5H, m), 7.52(2H, d, J=8.6 Hz), 7.68(2H, d, J=8.7 Hz), 8.01(1H, dd, J=2.5 Hz, 8.4 Hz), 8.29(1H, d, J=2.3 Hz), 11.00(1H, brs). |

Example 2668

Production of 2-(methyl-{4-[5-(5-trifluoromethyl-pyridin-2-yloxymethyl)pyridin-2-yloxy]phenyl}amino)-1-(4-piperonylpiperazin-1-yl)ethanone 2-{[4-(5-hydroxymethylpyridin-2-yloxy)phenyl]methylamino}-1-(4-piperonylpiperazin-1-yl)ethanone (0.98 g, 2.0 mmol) was dissolved in DMF (30 mL). To the resulting solution was added 60% sodium hydride (60%, 88 mg, 2.2 mmol) under ice cooling, and this solution was stirred for 30 minutes at 0° C. To the reaction solution was added 2-chloro-5-(trifluoromethyl)pyridine (0.36 g, 2.0 mol), and this solution was stirred under a nitrogen atmosphere for 3 hours at 60° C. The resulting reaction solution was concentrated under reduced pressure. To the residue was added ethyl acetate, and this solution was washed with water and brine. The organic layer was dried over anhydrous magnesium sulfate, and evaporated. The residue was purified by silica gel column chromatography (n-hexane:ethyl acetate=1:5), to thereby yield 0.68 g of the title compound.

Appearance: White powder $^1$H NMR (CDCl$_3$) δ 2.41-2.44 (4H, m), 3.02 (3H, s), 3.43 (2H, s), 3.48 (2H, brs), 3.63 (2H, brs), 4.08 (2H, s), 5.37 (2H, s), 5.94 (2H, s), 6.68-6.77 (4H, m), 6.81-6.84 (3H, m), 7.00 (2H, d, J=9.1 Hz), 7.72-7.79 (2H, m), 8.27 (1H, d, J=2.3 Hz), 8.44 (1H, brs).

The following compounds were produced in the same manner as in Example 2668.

TABLE 427

![Structure with R1149-O-CH2-pyridine-O-phenyl-CH2CH2-C(O)-piperazine-CH2-benzodioxole·HCl]

| Example No. | R1149 | mp (° C.) |
|---|---|---|
| 2669 | 4-CF$_3$Ph— | 165.0-166.0 |
| 2670 | 3-CF$_3$Ph— | 163.0-165.0 |
| 2671 | 3,4-Cl$_2$Ph— | 160.0-161.5 |

Example 2672

3,4-dichloro-N-{6-[4-(3,5-dioxoisoxazolidine-4-ylidenemethyl)phenoxy]pyridin-3-yl}benzamide To a solution of hydroxylamine hydrochloride (500 mg, 1.0 mmol) in water (0.2 mL) were added sodium carbonate (1.05 g, 9.91 mmol) and a solution of 2-{4-[5-(3,4-dichlorobenzoylamino)pyridin-2-yloxy]benzylidene}malonic acid dimethyl ester (500 mg, 1.0 mmol) in THF (5 mL). To the resulting solution was subsequently added methanol (5 mL) and stirred for 8 hours at 60° C. The reaction solution was concentrated under reduced pressure. Water was added to the residue, and extracted with ethyl acetate. The ethyl acetate layer was washed with a saturated sodium bicarbonate solution and brine, dried over anhydrous magnesium sulfate, and evaporated. The residue was purified by silica gel column chromatography (dichloromethane:methanol=30:1). To the resulting white precipitate was added ethyl acetate, filtered, and the filtrate was washed with diethyl ether, to thereby yield 105 mg of the title compound.

Appearance: White powder $^1$H NMR (DMSO-d$_6$) δ 7.12 (1H, d, J=8.9 Hz), 7.14 (2H, d, J=8.8 Hz), 7.63 (2H, d, J=8.8 Hz), 7.84 (1H, d, J=8.4 Hz), 7.95 (1H, dd, J=8.4 Hz, 2.0 Hz), 8.15 (1H, s), 8.22 (1H, dd, J=8.9 Hz, 2.6 Hz), 8.22 (1H, d, J=2.0 Hz), 8.51 (1H, d, J=2.6 Hz), 10.57 (1H, s), 11.16 (1H, s).

Example 2673

Production of 3,4-dichloro-N-{6-[4-(5-methyl-[1,2,4]oxadiazol-3-ylmethyl)phenoxy]pyridin-3-yl}benzamide monohydrochloride To 3,4-dichloro-N-{6-[4-(N-acetoxycarbamimidoylmethyl)phenoxy]pyridin-3-yl}benzamide (340 mg, 0.788 mmol) was added acetic acid (4 mL), and the resulting solution was stirred under reflux for 10 minutes. This reaction solution was concentrated under reduced pressure. To the residue was added a saturated sodium bicarbonate solution, and the resulting solution was extracted with ethyl acetate. The ethyl acetate layer was washed with brine, dried over anhydrous magnesium sulfate, and evaporated. The residue was purified by silica gel column chromatography (chloroform:methanol=40:1), and the obtained reside was dissolved in ethyl acetate (5 mL). To this solution was added a solution of 4 N hydrogen chloride in ethyl acetate until the compound no longer precipitated out. The obtained white powder was filtered, and washed with diethyl ether, to thereby yield 154 mg of the title compound.

Appearance: White powder $^1$H NMR (DMSO-d$_6$) δ 2.55 (3H, s), 4.05 (2H, s), 7.07 (1H, d, J=8.7 Hz), 7.07 (2H, d, J=8.6 Hz), 7.33 (2H, d, J=8.6 Hz), 7.83 (1H, d, J=8.4 Hz), 7.96 (1H, dd, J=8.4 Hz, 2.0 Hz), 8.21 (1H, dd, J=8.7 Hz, 2.6 Hz), 8.24 (1H, d, J=2.0 Hz), 8.48 (1H, d, J=2.6 Hz), 10.62 (1H, s).

Example 2674

Production of 1-(3-{4-[5-(3,4-dichlorobenzoylamino)-2-pyridylmethyl]phenyl}propionyl)-4-piperonylpiperazine monohydrochloride To a solution of ethyl 3-(4-{5-[bis(3,4-dichlorobenzoyl)amino]-2-pyridylmethyl}phenyl) propionate (177 mg, 0.281 mmol) in THF (5 mL) and ethanol (5 mL) were added 5 M aqueous sodium hydroxide (0.0929 mL, 0.463 mmol) and water (1 mL), and the resulting solution was refluxed for 1 hour. To this reaction solution was added 5 M hydrochloric acid (0.12 mL), and extracted with ethyl acetate. The ethyl acetate layer was washed with brine, dried over anhydrous magnesium sulfate, and evaporated. The residue was dissolved in DMF (3 mL), and to the resulting solution were then added 1-piperonylpiperazine (102 mg, 0.463 mmol), triethylamine (0.137 mL, 0.983 mmol) and diethyl cyanophosphonate (0.0703 mL, 463 mmol), and stirred for 1.5 hours at room temperature. Water was added to the resulting reaction solution, and extracted with ethyl acetate. The ethyl acetate layer was washed with a saturated sodium bicarbonate solution and brine, dried over anhydrous magnesium sulfate, and evaporated. The residue was purified by silica gel column chromatography (dichloromethane:methanol=70:1→40:1→20:1), to thereby yield 44.1 mg of a free form. This free form was dissolved in ethanol (5 mL) and 5 M hydrochloric acid (0.03 mL) by heating. The solvent was then evaporated, and the obtained solid was recrystallized from water-containing isopropanol, to thereby yield 19.6 mg of the title compound.

Appearance: Pale yellow powder

Melting point: 181-183° C.

Example 2675

Production of N-(6-{4-[4-(5-oxo-4,5-dihydro-[1,3,4]oxadiazole-2-ylmethyl)piperazine-1-carbonyl]-phenoxy}pyridin-3-yl)-4-trifluoromethylbenzamide monooxalate To a suspension of N-{6-[4-(4-hydrazinocarbonylmethylpiperazine-1-carbonyl)phenoxy]pyridin-3-yl}-4-trifluoromethylbenzamide trihydrochloride (300 mg, 0.46 mmol) in THF (7 mL) was added triethylamine (0.29 mL, 2.08 mmol), and the resulting solution was stirred for 10 minutes at room temperature. To the solution was added N,N'-carbonyldiimidazole (97 mg, 0.60 mmol) under ice cooling, and the resulting solution was stirred for 1 hour at room temperature. The reaction solution was concentrated under reduced pressure. To the residue was added a saturated sodium bicarbonate solution, and extracted with ethyl acetate. The ethyl acetate layer was dried over anhydrous magnesium sulfate, and evaporated. The residue was then purified by silica gel column chromatography (chloroform:methanol=15:1). The obtained residue was dissolved in ethanol, and to the resulting solution was added oxalic acid. Ethanol was evaporated under reduced pressure, after which the solidified white substance was filtered, and washed with diethyl ether, to thereby yield 140 mg of the title compound.

Appearance: White powder $^1$H NMR (DMSO-d$_6$) δ 2.31-2.69 (4H, m), 3.53 (2H, s), 3.53 (4H, brs), 7.16 (1H, d, J=8.9 Hz), 7.17 (2H, d, J=8.5 Hz), 7.45 (2H, d, J=8.5 Hz), 7.94 (2H, d, J=8.1 Hz), 8.17 (2H, d, J=8.1 Hz), 8.26 (1H, dd, J=8.9 Hz, 2.7 Hz), 8.55 (1H, d, J=2.7 Hz), 10.67 (1H, s), 12.27 (1H, s).

Example 2676

Production of 4-(4-{4-[4-(3,4-dichlorobenzoylamino)-2-fluorophenoxy]phenyl}-4-hydroxybutyryl)morpholine To a suspension of 4-(4-{4-[4-(3,4-dichlorobenzoylamino)-2-fluorophenoxy]phenyl}-4-oxobutyryl)morpholine (1.00 g, 1.83 mmol) in THF (20 mL) and methanol (5 mL) was added sodium borohydride (0.0694 g, 1.83 mmol), and the resulting solution was stirred for 1 hour at room temperature. To this reaction solution were added water and saturated aqueous ammonium chloride, and extracted with ethyl acetate. The ethyl acetate layer was washed with brine, dried over anhydrous magnesium sulfate, evaporated, and the residue was purified by silica gel column chromatography (dichloromethane:methanol=30:1). The obtained solid was recrystallized from water-containing isopropanol, to thereby yield 0.850 g of the title compound.

Appearance: White powder

Melting point: 108-111° C.

The following compounds were produced in the same manner as in Example 2676.

TABLE 428
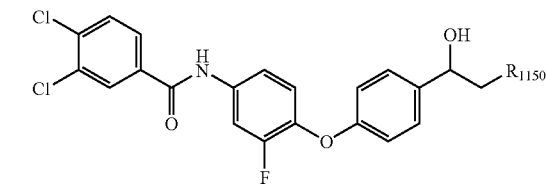
| Example No. | R<sub>1150</sub> | Form | mp (° C.) |
|---|---|---|---|
| 2677 | morpholino | free | 142-145 |
| 2678 | 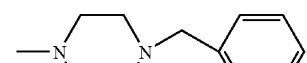 | free | 150-152 |
| 2679 | 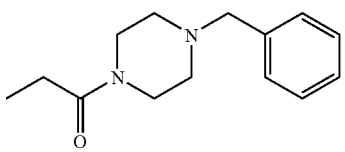 | hydrochloride | 197-199 |
TABLE 428-continued
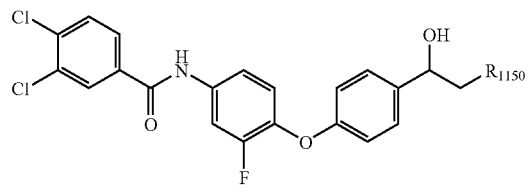
| Example No. | R<sub>1150</sub> | Form | mp (° C.) |
|---|---|---|---|
| 2680 | 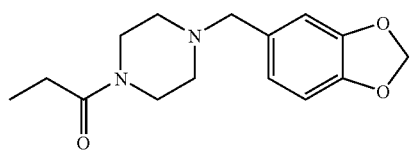 | hydrochloride | 222-225 |
TABLE 429
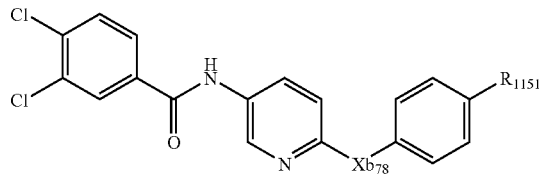
| Example No. | Xb$_{78}$ | R$_{1151}$ | Form | mp (° C.) or $^1$H NMR |
|---|---|---|---|---|
| 2681 | —O— | 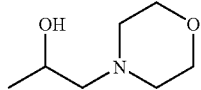 | free | $^1$H NMR (DMSO-d$_6$) δ 2.38-2.54(6H, m), 3.58(4H, t, J=4.5 Hz), 4.73-4.77(1H, m), 5.06 (1H, d, J=3.8 Hz), 7.04-7.07(3H, m), 7.38(2H, d, J=8.4 Hz), 7.84 (1H, d, J=8.4 Hz), 7.95(1H, dd, J=8.4 Hz, 1.2 Hz), 8.22(1H, d, J=2.0 Hz), 8.19(1H, dd, J=8.9 Hz, 2.8 Hz), 8.48(1H, d, J=2.6 Hz), 10.55(1H, brs). |
| 2682 | —CH(OH)— | 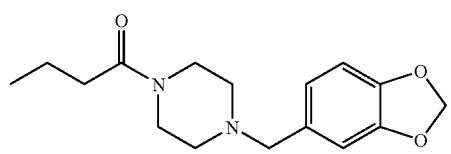 | oxalate | mp 102-108 |

TABLE 430

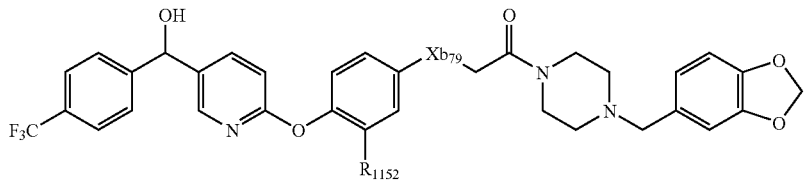

| Example No. | $R_{1152}$ | $Xb_{79}$ | $^1$H NMR (CDCl$_3$) δppm |
|---|---|---|---|
| 2683 | —OCH$_3$ | —CH$_2$— | 2.30-2.39(4H, m), 2.57-2.62(2H, m), 2.90-2.95(2H, m), 3.36-3.43(4H, m), 3.58-3.61(2H, m), 3.70(3H, s), 5.83(1H, s), 5.93(2H, s), 6.69-6.88(6H, m), 6.99(1H, d, J=8.1 Hz), 7.47 7.62(5H, m), 8.07(1H, d, J=2.3 Hz). |
| 2684 | —H | —N(CH$_3$)— | 2.38-2.43(4H, m), 2.99(3H, s), 3.42-3.60(6H, m), 4.05(2H, s), 5.77(1H, s), 5.94(2H, s), 6.64-6.84(6H, m), 6.93-6.99(2H, m), 7.47(2H, d, J=8.1 Hz), 7.53-7.59(3H, m), 8.10(1H, d, J=2.1 Hz). |

Example 2685

Production of {6-[4-(4-piperonylpiperazin-1-ylmethyl)phenoxy]pyridin-3-ylmethyl}-(4-trifluoromethylphenyl)amine To a suspension of lithium aluminum hydride (0.106 g, 2.80 mmol) in THF (10 mL) was added dropwise a solution of 6-[4-(4-piperonylpiperazine-1-carbonyl)-phenoxy]-N-(4-trifluoromethylphenyl)nicotinamide (0.423 g, 0.700 mmol) in THF (10 mL) under ice cooled stirring. Once the entire amount was added dropwise, the solution temperature was slowly raised, and stirred under reflux for 2 hours. After cooling, ice water (50 mL) was added to the solution, and the mixture was extracted with ethyl acetate. The ethyl acetate layer was washed with brine, dried over anhydrous magnesium sulfate, and evaporated. The residue was purified by silica gel column chromatography (dichloromethane:methanol=40:1), to thereby yield 0.125 g of the title compound.

Appearance: Pale yellow oil
MS 576 (M$^+$)

The following compounds were produced in the same manner as in Example 2685.

Example 2686

N-[6-(2-fluoro-4-{methyl[2-(4-piperonylpiperazin-1-yl)ethyl]amino}phenoxy)pyridin-3-yl]-3,4-dichlorobenzenesulfonamide $^1$H NMR (CDCl$_3$) δ 2.50-2.55 (10H, m), 2.92 (3H, s), 3.41-3.45 (4H, m), 5.93 (2H, s), 6.39-6.49 (2H, m), 6.73-6.74 (2H, m), 6.84-6.89 (2H, m), 6.99 (1H, t, J=9.1 Hz), 7.42-7.70 (4H, m), 7.81 (1H, brs).

Example 2687

Production of 3-(3-methyl-4-{5-[2-(4-trifluoromethyl-phenyl)ethyl]pyridin-2-yloxy}phenyl)-1-piperonyl-tetrahydropyrimidin-2-one hydrobromide To a solution of 3-(3-methyl-4-{5-[(E)-2-(4-trifluoromethylphenyl)vinyl]pyridin-2-yloxy}phenyl)-1-piperonyltetrahydropyrimidin-2-one (0.16 g, 0.27 mmol) in ethyl acetate (15 mL) was added 5% platinum-carbon (0.05 g) under a nitrogen atmosphere, and the resulting solution was then stirred under a hydrogen atmosphere for 4.5 hours at room temperature. The resulting reaction solution was filtered through Celite, and the filtrate was concentrated under reduced pressure. The residue was purified by silica gel chromatography (ethyl acetate:=n-hexane 1:4-1:2), and to the resulting product was added hydrobromide, to thereby yield 50 mg of the title compound.

Appearance: Colorless amorphous powder
$^1$H NMR (DMSO-d$_6$) δ 1.85-2.09 (5H, m), 2.77-3.02 (4H, m), 3.15-3.33 (2H, m), 3.55-3.70 (2H, m), 3.75-4.15 (1H, m), 4.40 (2H, s), 5.99 (2H, s), 6.76 (1H, dd, J=1.5 Hz, 7.8 Hz), 6.80-6.98 (4H, m), 7.10 (1H, dd, J=2.6 Hz, 8.5 Hz), 7.19 (1H, d, J=2.6 Hz), 7.44 (2H, d, J=8.1 Hz), 7.62 (2H, d, J=8.1 Hz), 7.71 (1H, dd, J=2.4 Hz, 8.4 Hz), 7.91 (1H, d, J=2.4 Hz).

The following compounds were produced in the same manner as in Reference Example 673.

TABLE 431

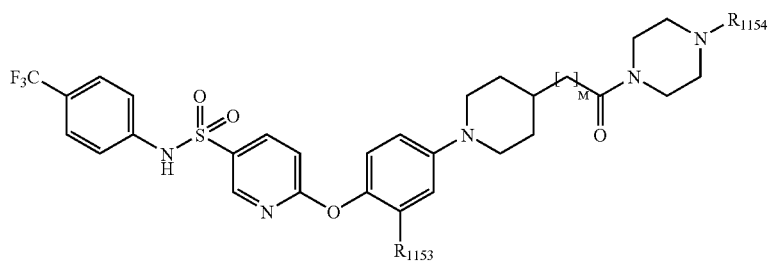

| Example No. | $R_{1153}$ | $R_{1154}$ | M | $^1$H NMR (CDCl$_3$) δppm |
|---|---|---|---|---|
| 2688 | —H | piperonyl | 1 | 1.31-1.45(2H, m), 1.84-2.02(3H, m), 2.30(2H, d, J=6.8 Hz), 2.41-2.43(4H, m), 2.72(2H, t, J=12.2 Hz), 3.43(2H, s), 3.44-3.65(6H, m), 5.95(2H, s), 6.71-6.77(2H, m), 6.85-7.00(6H, m), 7.21-7.26(3H, m), 7.51(2H, d, J=8.6 Hz), 7.98(1H, dd, J=8.7 Hz, 2.6 Hz), 8.60(1H, d, J=2.6 Hz). |
| 2689 | —H | —H | 1 | 1.38-1.46(2H, m), 1.84-2.00(3H, m), 2.31(2H, d, J=6.8 Hz), 2.71(2H, t, J=12.2 Hz), 2.86-2.89(4H, m), 3.48-3.63(7H, m), 6.86-6.99(5H, m), 7.23-7.29(3H, m), 7.49(2H, d, J=8.4 Hz), 7.97(1H, dd, J=8.9 Hz, 2.6 Hz), 8.60(1H, d, J=2.1 Hz). |
| 2690 | —CH$_3$ | piperonyl | 1 | 1.36-1.40(2H, m), 1.82-2.02(3H, m), 2.03(3H, s), 2.30(2H, d, J=6.8 Hz), 2.41-2.43(4H, m), 2.68(2H, J=12.0 Hz), 3.43(2H, s), 3.493.65(6H, m), 5.94(2H, s), 6.74-6.89(8H, m), 7.24(2H, d, J=8.2 Hz), 7.49(2H, d, J=8.6 Hz), 7.99(1H, dd, J=8.7 Hz, 2.5 Hz), 8.58(1H, d, J=2.1 Hz). |
| 2691 | —H | piperonyl | 0 | 1.78-2.03(4H, m), 2.46(4H, brs), 2.55-2.77(3H, m), 3.46(2H, s), 3.55(2H, brs), 3.67(4H, brs), 5.95(2H, s), 6.75-6.78(2H, m), 6.85-7.01(6H, m), 7.21-7.26(3H, m), 7.52(2H, d, J=8.6 Hz), 7.98(1H, dd, J=8.7 Hz, 2.6 Hz), 8.60(1H, d, J=2.5 Hz). |

Example 2692

Production of 1-[3-(4-{1-[5-(3,4-dichlorobenzoylamino)-2-pyridyl]-1-hydroxyimino}methylphenyl)propionyl]-4-piperonylpiperazine To a solution of 1-(3-{4-[5-(3,4-dichloro-benzoylamino)pyridine-2-carbonyl]phenyl}propionyl)-4-piperonylpiperazine (0.330 g, 0.511 mmol) in pyridine (7 mL) was added hydroxylamine hydrochloride (53.3 mg, 0.767 mmol), and the resulting solution was refluxed for 0.5 hours. The reaction solution was concentrated under reduced pressure, and to the residue was added brine. This solution was extracted with dichloromethane. The dichloromethane layer was dried over anhydrous magnesium sulfate, and evaporated. The residue was purified by silica gel column chromatography (dichloromethane:methanol=15:1), whereby 0.225 g of the title compound was obtained as a mixture of the syn form and the anti form (1:1) of the oxime.

Appearance: Colorless amorphous powder $^1$H NMR (CDCl$_3$) δ 2.21-2.39 (4H, m), 2.49-2.60 (2H, m), 2.78-2.90 (2H, m), 3.29-3.44 (4H, m), 3.55 (2H, s), 5.90 (2H, s), 6.62-6.73 (2H, m), 6.80 (1H, s), 7.07 (1H, d, J=7.7 Hz), 7.12 (1H, d, J=7.7 Hz), 7.15-7.30 (2.5H, m), 7.39 (0.5H, d, J=8.4 Hz), 7.42 (0.5H, d, J=8.4 Hz), 7.45-7.51 (0.5H, m), 7.62-7.74 (1H, m), 7.94 (0.5H, d, J=2.0 Hz), 7.99 (0.5H, d, J=2.0 Hz), 8.09-8.28 (1H, m), 8.62 (0.5H, s), 8.85 (0.5H, s), 9.40 (0.5H, brs), 9.62 (0.5H, brs), 10.21 (0.5H, brs), 13.85 (0.5H, brs).

Example 2693

Production of 4-(2-oxo-3-{4-[5-(4-trifluoromethylbenzoylamino)pyridin-2-yloxy]phenyl}propionyl)-piperazine-1-carboxylic acid t-butyl ester To a solution of 4-(2-hydroxy-3-{4-[5-(4-trifluoromethylbenzoylamino)pyridin-2-yloxy]phenyl}propionyl)piperazine-1-carboxylic acid t-butyl ester (0.58 g, 0.94 mmol) in dichloromethane (4 mL) was added a Dess-Martin reagent (0.8 g, 1.89 mmol), and the resulting solution was then stirred under a nitrogen gas flow for 4 hours at room temperature. The reaction solution was concentrated under reduced pressure. To the residue was added 1 N aqueous sodium hydroxide (50 mL), and extracted with ethyl acetate. The ethyl acetate layer was washed with brine, dried over anhydrous magnesium sulfate, and evaporated. The residue was purified by silica gel chromatography (dichloromethane:methanol=50:1), to thereby yield 0.31 g of the title compound.

Appearance: Yellow powder $^1$H NMR (CDCl$_3$) δ 1.41 (9H, s), 2.99-3.22 (4H, m), 3.25-3.41 (2H, m), 3.42-3.60 (2H, m), 4.04 (2H, s), 6.97 (1H, d, J=8.9 Hz), 7.10 (2H, d, J=8.4 Hz), 7.27 (2H, d, J=8.4 Hz), 7.73 (2H, d, J=8.0 Hz), 7.99 (2H, d, J=8.0 Hz), 8.13 (1H, d, J=2.8 Hz), 8.30 (1H, dd, J=8.9 Hz, 2.8 Hz), 8.45 (1H, brs).

Example 2694

Production of 3,4-dichloro-N-{3-fluoro-4-[4-(l-hydroxy-2-morpholine-4-ylethyl)phenoxy]phenyl}benzamide 3,4-Dichloro-N-{3-fluoro-4-[4-(1-hydroxy-2-morpholine-4-ylethyl)phenoxy]phenyl}benzamide (37.4 g) was recrystallized from ethanol (700 mL) to yield 34.34 g of the title compound.
Appearance: White powder
Melting point: 175-176° C.

Example 2695

Production of N-[6-(4-{[2-(4-piperonylpiperazin-1-yl)-2-oxoethyl]ethylamino}-2-fluorophenoxy)pyridin-3-yl]-3,4-dichlorobenzenesulfonamide N-[6-(4-{[2-(4-Piperonylpiperazin-1-yl)-2-oxoethyl]ethylamino}-2-fluorophenoxy)pyridin-3-yl]-3,4-dichlorobenzenesulfonamide (8.15 g) was recrystallized from ethanol (60 mL) to yield 7.78 g of the title compound.
Appearance: White powder
Melting point: 163-166° C.

Example 2696

Production of N-[6-(4-{[2-(4-piperonylpiperazin-1-yl)-2-oxoethyl]methylamino}-2-methylphenoxy)pyridin-3-yl]-4-trifluoromethylbenzamide N-[6-(4-{[2-(4-Piperonylpiperazin-1-yl)-2-oxoethyl]methylamino}-2-methylphenoxy)pyridin-3-yl]-4-trifluoromethylbenzamide (5.1 g, 7.7 mmol) was recrystallized from acetone (15 mL) to yield 3.7 g of the title compound.
Appearance: White powder
Melting point: 128-131° C.

Example 2697

Production of N-{6-[4-(4-benzylpiperazine-1-carbonyl)phenoxy]pyridin-3-yl}-4-trifluoromethyl-benzamide N-{6-[4-(4-Benzylpiperazine-1-carbonyl)-phenoxy]pyridin-3-yl}-4-trifluoromethylbenzamide (78.86 g) was recrystallized from ethanol (530 mL) to yield 96.66 g of the title compound.
Appearance: White needles
Melting point: 177.6-179.2° C.

Example 2698

Production of N-(6-{4-[4-(2-oxo-1,2,3,4-tetrahydroquinoline-6-ylmethyl)piperazine-1-carbonyl]phenoxy}-pyridin-3-yl)-4-trifluoromethylbenzamide To a solution of 4-[5-(4-trifluoromethylbenzoylamino)pyridin-2-yloxy]benzoic acid (4.30 g, 10.7 mmol) in DMF (150 mL) were added 1-(2-oxo-1,2,3,4-tetrahydroquinoline-6-ylmethyl)-piperazine (2.6 g, 10.7 mmol), 1-hydroxybenzotriazole monohydrate (1.64 g, 10.7 mmol) and 1-ethyl-3-(3-dimethylaminopropyl)carbodiimide hydrochloride (2.46 g, 12.8 mmol) under ice cooling, and the resulting solution was stirred for 1 hour under ice cooling and for 17 hours at room temperature. This reaction solution was concentrated under reduced pressure. To the residue was added a saturated sodium bicarbonate solution, and extracted with ethyl acetate. The ethyl acetate layer was washed with a saturated sodium bicarbonate solution and brine, dried over anhydrous magnesium sulfate, and evaporated. The residue was recrystallized from ethyl acetate, to thereby yield 5.24 g of the title compound.
Appearance: White powder
Melting point: 250.5-252.5° C.

Example 2699

Production of N-(6-{4-(4-(4-benzylpiperidine-1-carbonyl)piperazine-1-carbonyl]phenoxy}pyridin-3-yl)-3,4-dichlorobenzamide To a solution of 1-{4-[5-(3,4-dichlorobenzoylamino)pyridin-2-yloxy]benzoyl}piperidine-4-carboxylic acid (4.5 g, 8.8 mmol) in DMF (88 mL) were added 1-benzylpiperazine (1.83 mL, 10.5 mmol), 1-hydroxybenzotriazole monohydrate (1.61 g, 10.5 mmol) and 1-ethyl-3-(3-dimethylaminopropyl)carbodiimide hydrochloride (2.02 g, 10.5 mmol) under ice cooling, and the resulting solution was stirred overnight at room temperature. To this reaction solution was added a saturated sodium bicarbonate solution, and the resulting solution was extracted with ethyl acetate. The ethyl acetate layer was washed with a saturated sodium bicarbonate solution and brine, dried over anhydrous magnesium sulfate, and evaporated. The residue was recrystallized from isopropyl alcohol (700 mL), to thereby yield 3.2 g of the title compound.
Appearance: White powder
Melting point: 223-225° C.

Example 2700

Production of N-[6-(4-{[2-(4-benzylpiperazin-1-yl)-2-oxoethyl]methylamino}-2-methylphenoxy)pyridin-3-yl]-4-trifluoromethylbenzamide To a suspension of 1-(4-benzylpiperazin-1-yl)-2-{methyl[3-methyl-4-(5-nitropyridin-2-yloxy)phenyl]amino}ethanone (2.85 g, 6.0 mmol) in ethyl acetate (30 mL) was added 5% platinum-carbon (0.30 g) under a nitrogen atmosphere, and the resulting solution was stirred for 3 hours at 40° C. under a hydrogen atmosphere. The platinum-carbon was separated off with Celite, and the filtrate was concentrated. The residue was dissolved in THF (30 mL), and to this solution was added triethylamine (1.26 mL, 9.1 mmol) under ice cooling. To the resulting solution was then added dropwise 4-(trifluoromethyl)benzoyl chloride (1.16 mL, 7.8 mmol). This reaction solution was stirred overnight, then a saturated sodium bicarbonate solution was added, and the mixture was extracted with ethyl acetate. The ethyl acetate layer was washed with water, and then dried over anhydrous sodium sulfate. The solvent was evaporated, and the residue was purified by silica gel column chromatography (dichloromethane:methanol=20:1). The resulting product was then recrystallized from a mixed solvent consisting of diisopropyl ether-acetone, to thereby yield 1.37 g of the title compound.
Appearance: White powder
Melting point: 112-113° C.

Example 2701

Production of (4-benzylpiperazin-1-yl)(4-{5-[methyl(4-trifluoromethylbenzyl)amino]pyridin-2-yloxy}phenyl)-methanone To a solution of (4-benzylpiperazin-1-yl){4-[5-(4-trifluoromethylbenzylamino)pyridin-2-yloxy]phenyl}methanone (5.40 g, 9.88 mmol) in methanol (150 mL) were added 37% aqueous formaldehyde (2.8 mL), sodium cyanoborohydride (1.86 g, 29.6 mmol) and acetic acid (1.7 mL) under ice cooling, and the resulting solution was stirred at room temperature for 2 hours. The solvent was evaporated under reduced pressure. Water was added to the residue, and this solution was neutralized with a saturated sodium bicarbonate solution, and extracted with chloroform. The organic layer was washed with water, and then dried over anhydrous magnesium sulfate. The solvent was evaporated, and the residue was purified by silica gel column chromatography (chloroform:methanol=60:1). To the resulting product was then added a solution of 4 M hydrogen chloride in ethyl acetate until the resulting solution had a pH of 1. The precipitates were collected by filtration and recrystallized from ethanol (80 mL), to thereby yield 2.5 g of the title compound.
Appearance: White powder
Melting point: 180-183.5° C.

Example 2702

Production of 4-piperonylpiperazine-1-carboxyl 4-[5-(3,4-dichlorobenzoylamino)pyridin-2-yloxy] benzylamide hydrochloride To a solution of 4-piperonylpiperazine-1-carboxyl 4-(5-aminopyridin-2-yloxy)benzylamide (2.48 g, 5.4 mmol) in THF (50 mL) were added triethylamine (0.9 mL, 6.5 mmol) and 3,4-dichlorobenzoyl chloride (1.13 g, 5.4 mmol) under ice cooling, and the resulting solution was stirred under ice cooling for 10 minutes. Water was added to the residue, and extracted with ethyl acetate. The ethyl acetate layer was washed with water and brine, dried over anhydrous magnesium sulfate, and evaporated. The residue was purified by silica gel column chromatography (dichloromethane:methanol=25:1) to yield 2.97 g of a white powder. This white powder was dissolved in ethanol (45 mL), and to the resulting solution was added a solution of 4 M hydrogen chloride in ethyl acetate until the solution had a pH of 1. The precipitates were collected by filtration and recrystallized from 83% ethanol (36 mL), to thereby yield 2.72 g of the title compound.
Appearance: White powder
Melting point: 243.5-246.5° C.

Example 2703

Production of N-[6-(4-{4-[2-(4-piperonylpiperazin-1-yl)-2-oxoethyl]piperidin-1-yl}-2-methylphenoxy) pyridin-3-yl]-4-trifluoromethylbenzenesulfonamide N-[6-(4-{4-[2-(4-Piperonylpiperazin-1-yl)-2-oxoethyl] piperidin-1-yl}-2-methylphenoxy)pyridin-3-yl]-4-trifluoromethylbenzenesulfonamide (1.35 g) was recrystallized from ethanol (20 mL) to yield 1.23 g of the title compound.
Appearance: White powder
Melting point: 156-158° C.

Example 2704

Production of N-(6-{4-[4-(4-piperonylpiperazine-1-carbonyl)piperidin-1-yl]phenoxy}pyridin-3-yl)-3,4-dichlorobenzenesulfonamide N-(6-{4-[4-(4-Piperonylpiperidine-1-carbonyl)piperidin-1-yl]phenoxy}pyridin-3-yl)-3,4-dichlorobenzenesulfonamide (1.95 g) was recrystallized from ethanol (35 mL) to yield 1.70 g of the title compound.
Appearance: White powder
Melting point: 130-133° C.

Example 2705

Production of N-[6-(4-{[2-(4-piperonylpiperazin-1-yl)-2-oxoethyl]methylamino}-2-methylphenoxy) pyridin-3-yl]-4-trifluoromethylbenzamide N-[6-(4-{[2-(4-Piperonylpiperazin-1-yl)-2-oxoethyl]methylamino}-2-methylphenoxy)pyridin-3-yl]-4-trifluoromethylbenzamide (0.86 g, 1.30 mmol) was recrystallized from a mixed solvent of acetone (3 mL) diethyl ether (4 mL) and n-hexane (1 mL) to yield 0.72 g of the title compound.
Appearance: Pale yellow powder
Melting point: 154-155° C.

Example 2706

Production of N-(6-{4-[4-(4-benzylpiperazine-1-carbonyl)piperidin-1-yl]phenoxy}pyridin-3-yl)-4-trifluoromethylbenzensulfonamide N-(6-{4-[4-(4-Benzylpiperidin-1-carbonyl)piperidin-1-yl]phenoxy}pyridin-3-yl)-4-trifluoromethylbenzensulfonamide (1.55 g) was recrystallized from ethanol (60 mL) to yield 1.41 g of the title compound.
Appearance: White powder
Melting point: 199-201° C.

Example 2707

Production of N-[6-(4-{4-[2-(4-benzylpiperazin-1-yl)-2-oxoethyl]piperidin-1-yl}-2-methylphenoxy) pyridin-3-yl]-3,4-dichlorobenzenesulfonamide To a solution of (1-{4-[5-(3,4-dichlorobenzenesulfonylamino)pyridin-2-yloxy]-3-methylphenyl}piperidine-4-yl) acetic acid (1.70 g, 3.1 mmol) and 1-benzylpiperazine (0.71 g, 4.0 mmol) in DMF (40 mL) were added triethylamine (1.08 mL, 7.8 mmol) and diethyl cyanophosphonate (0.76 g, 4.3 mmol) under ice cooling, and the resulting solution was stirred for 1 hour under ice cooling. To this reaction solution was added a saturated sodium bicarbonate solution, and extracted with ethyl acetate. The ethyl acetate layer was washed with a saturated sodium bicarbonate solution and brine, dried over anhydrous sodium sulfate, and evaporated. The residue was purified by silica gel column chromatography (dichloromethane:methanol=40:1), after which the resulting product was recrystallized from ethanol, to thereby yield 1.61 g of the title compound.
Appearance: White needles
Melting point: 151-155° C.

Example 2708

Production of N-[6-(4-{[2-(4-benzothiazole-6-ylmethylpiperazin-1-yl)-2-oxoethyl]methylamino}-phenoxy)pyridin-3-yl]-3,4-dichlorobenzamide dihydrochloride To a solution of ({4-[5-(3,4-dichlorobenzoyl-amino)pyridin-2-yloxy]phenyl}methylamino)acetic acid (1.02 g, 2.3 mmol) and 1-(benzothiazole-6-ylmethyl)-piperazine (0.58 g, 2.5 mmol) in DMF (15 mL) were added triethylamine (0.95 mL, 6.9 mmol) and diethyl cyanophosphonate (0.447 mL, 2.7 mmol) under ice cooling, and the resulting solution was stirred for 30 minutes under ice cooling and for 45 minutes at room temperature. Water was added to the solution, and extracted with ethyl acetate. The ethyl acetate layer was washed with a saturated sodium bicarbonate solution and brine, dried over anhydrous sodium sulfate, and evaporated. The residue was purified by silica gel column chromatography (dichloromethane:methanol=30:1) to obtain 1.28 g of a white powder. This white powder was dissolved in ethanol (15 mL), and to the resulting solution was added a solution of 4 M hydrogen chloride in ethyl acetate until the resulting solution had a pH of 1. The precipitates were collected by filtration and recrystallized from 85% ethanol (30 mL), to thereby yield 1.06 g of the title compound.
Appearance: White powder
Melting point: 202-223° C.

Example 2709

Production of 3,4-dichloro-N-{6-[4-({2-[4-(2,3-dihydrobenzo[1,4]dioxin-6-ylmethyl)piperazin-1-yl]-2-oxoethyl}methylamino)phenoxy]pyridin-3-yl}benzamide maleate To a solution of ({4-[5-(3,4-dichlorobenzoyl-amino)pyridin-2-yloxy]phenyl}methylamino)acetic acid (2.50 g, 5.6 mmol) in DMF (55 mL) were added 1-(2,3-dihydrobenzo[1,4]dioxin-6-ylmethyl)piperazine (1.7 g, 7.3 mmol), 1-hydroxybenzotriazole monohydrate (0.86 g, 5.6 mmol) and 1-ethyl-3-(3-dimethylaminopropyl)carbodiimide hydrochloride (1.29 g, 6.7 mmol) under ice cooling, and the resulting solution was stirred for 30 minutes under ice cooling and for 17 hours at room temperature. This reaction solution was concentrated under reduced pressure. Water was added to the residue, and extracted with ethyl acetate. The ethyl acetate layer was washed with a saturated sodium bicarbonate solution and brine, dried over anhydrous magnesium sulfate, and evaporated. The residue was dissolved in ethanol (30 mL). To the resulting solution was added maleic acid (0.32 g, 2.7 mmol), and this solution was left to stand. The precipitates were collected by filtration, to thereby yield 1.45 g of the title compound.
Appearance: Pale yellow powder
Melting point: 188-190° C.

Example 2710

Production of N-(6-{4-[4-(4-benzylpiperazine-1-carbonyl)piperidin-1-yl]phenoxy}pyridin-3-yl)-3,4-dichlorobenzenesulfonamide N-(6-{4-[4-(4-Benzylpiperazine-1-carbonyl)piperidin-1-yl]phenoxy}pyridin-3-yl)-3,4-dichlorobenzenesulfonamide (0.79 g) was recrystallized from ethanol (15 mL) to yield 0.67 g of the title compound.
Appearance: White powder
Melting point: 185-189° C.

Example 2711

Production of N-[6-(4-{[2-(4-piperonylpiperazin-1-yl)-2-oxoethyl]methylamino}-2-methylphenoxy)pyridin-3-yl]-4-pyrrole-1-ylbenzamide N-[6-(4-{[2-(4-Piperonylpiperazin-1-yl)-2-oxoethyl]methylamino}-2-methylphenoxy)pyridin-3-yl]-4-pyrrole-1-ylbenzamide (2.49 g) was recrystallized from a mixed solvent consisting of acetone (20 mL) and diethyl ether (30 mL) to yield 2.26 g of the title compound.
Appearance: Pale yellow powder
Melting point: 163.1-166.5° C.

Example 2712

Production of N-[6-(4-{[2-(4-piperonylpiperazin-1-yl)-2-oxoethyl]ethylamino}-2-fluorophenoxy)pyridin-3-yl]-4-trifluoromethylbenzenesulfonamide N-[6-(4-{[2-(4-Piperonylpiperazin-1-yl)-2-oxoethyl]ethylamino}-2-fluorophenoxy)pyridin-3-yl]-4-trifluoromethylbenzenesulfonamide (8.18 g) was recrystallized from a mixed solvent consisting of ethyl acetate (70 mL) and n-hexane (20 mL) to yield 6.93 g of the title compound.
Appearance: White powder
Melting point: 177.8-180.1° C.

Example 2713

Production of 6-(4-{4-[2-(4-piperonylpiperazin-1-yl)-2-oxoethyl]piperidin-1-yl]-2-methylphenoxy}pyridine-3-sulfonyl-(4-trifluoromethylphenyl)amide 6-(4-{4-[2-(4-Piperonylpiperazin-1-yl)-2-oxoethyl]piperidin-1-yl]-2-methylphenoxy}pyridine-3-sulfonyl-(4-trifluoromethylphenyl)amide (1.50 g) was recrystallized from ethanol (20 mL) to yield 1.40 g of the title compound.
Appearance: White powder
Melting point: 156-160° C.

Example 2714

Production of N-[6-(4-{[2-(4-piperonylpiperazin-1-yl)-2-oxoethyl]methylamino}-2-methylphenoxy)pyridin-3-yl]-4-trifluoromethylbenzamide N-[6-(4-{[2-(4-Piperonylpiperazin-1-yl)-2-oxoethyl]methylamino}-2-methylphenoxy)pyridin-3-yl]-4-trifluoromethylbenzamide (2.1 g, 3.2 mmol) was heated to dissolve in acetone (5 mL), and to the resulting solution was then added diethyl ether (10 mL), whereby recrystallization yielded 2.0 g of the title compound.
Appearance: White powder
Melting point: 113-116° C.

Example 2715

Production of 3,4-dichloro-N-{3-fluoro-4-[4-(1-hydroxy-2-morpholine-4-ylethyl)phenoxy]phenyl}benzamide 3,4-Dichloro-N-{3-fluoro-4-[4-(1-hydroxy-2-morpholine-4-ylethyl)phenoxy]phenyl}benzamide (5 g) was recrystallized from ethyl acetate-n-hexane to yield 4.73 g of the title compound.
Appearance: White powder
Melting point: 169-170° C.

Example 2716

Production of N-(6-{4-[4-(4-piperonylpiperazine-1-carbonyl)piperidine-1-carbonyl]phenoxy}pyridin-3-yl)-3,4-dichlorobenzamide To a solution of 1-{4-[5-(3,4-dichlorobenzoylamino)pyridin-2-yloxy]benzoyl}piperidine-4-carboxylic acid (7.96 g, 15.5 mmol) in DMF (160 mL) were added 1-piperonylpiperazine (3.75 g, 17.6 mmol), 1-hydroxybenzotriazole monohydrate (2.85 g, 18.6 mmol) and 1-ethyl-3-(3-dimethylaminopropyl)carbodiimide hydrochloride (3.56 g, 18.6 mmol) under ice cooling, and the resulting solution was stirred for overnight at room temperature. This reaction solution was concentrated under reduced pressure. To the residue were added water and ethyl acetate, and the resulting solution was vigorously stirred. The resulting precipitates were collected by filtration and recrystallized from a dichloromethane-methanol mixed solvent, to thereby yield 7.36 g of the title compound.

Appearance: White powder
Melting point: 236-238° C.

Example 2717

Production of N-{6-[(4-{4-[2-(4-piperonylpiperazin-1-yl)-2-oxoethyl]piperidin-1-yl}phenyl)methylamino]-pyridin-3-yl]-4-trifluoromethylbenzamide To a solution of [1-(4-{methyl[5-(4-trifluoromethylbenzoylamino)pyridin-2-yl]amino}phenyl)piperidine-4-yl]acetic acid (0.80 g, 1.6 mmol) in DMF (10 mL) were added 1-piperonylpiperazine (0.41 g, 1.9 mmol), 1-hydroxybenzotriazole monohydrate (0.24 g, 1.6 mmol) and 1-ethyl-3-(3-dimethylaminopropyl)carbodiimide hydrochloride (0.39 g, 2.0 mmol) under ice cooling, and the resulting solution was stirred for 3 hours at room temperature. This reaction solution was concentrated under reduced pressure. To the residue was added a saturated sodium bicarbonate solution, and extracted with dichloromethane. The dichloromethane layer was washed with a saturated sodium bicarbonate solution and brine, dried over anhydrous magnesium sulfate, and evaporated. The residue was purified by silica gel column chromatography (dichloromethane:methanol=20:1). The resulting product was then recrystallized from a mixed solvent consisting of 95% ethanol-dichloromethane, to thereby yield 1.05 g of the title compound.

Appearance: White powder
Melting point: 210-212° C.

Formulation Example 1

100 g of the N-[6-(4-{4-[2-(piperonyl-piperazin-1-yl)-2-oxoethyl]piperidin-1-yl}phenoxy)-pyridin-3-yl]-4-trifluoromethylbenzamide obtained in Example 319, 40 g of Avicel (Tradename, manufactured by Asahi Kasei Corporation), 30 g of cornstarch and 2 g of magnesium stearate were mixed and ground together. The resulting mixture was then formed into a sugar-coated R 10-mm-tablets using a pestle. The obtained tablets were coated with a film coating agent containing 10 g of TC-5 (Tradename, manufactured by Shin-Etsu Chemical Co., Ltd., hydroxypropylmethyl cellulose), 3 g of polyethylene glycol 6000, 40 g of castor oil and a suitable amount of ethanol, to thereby prepare a film-coated tablet.

Pharmacological Test

LI90 cells, a human stellate cell line, were seeded on 12-well plastic plates in DMEM (DULBECCO'S modified eagle medium) supplemented with 10% fetal bovine serum, and were cultured for 24 hours in a carbon dioxide ($CO_2$) incubator (set temperature: 37° C., set $CO_2$ concentration: 5%). The cultured cells were then washed with D-PBS(-) (DULBECCO's phosphate buffered saline), and subsequently further cultured for 3 days in MEM (Eagle's minimum essential medium) supplemented with 0.1% fetal bovine serum. The cultured cells were again washed with D-PBS(-), and cultured for 16 hours in MEM (0.1% fetal bovine serum with respect to a total MEM volume) which contained a test compound and 10 pM h-TGF-β1 (human transforming growth factor β1). Next, the cultured LI90 cells were washed with D-PBS(-), and cultured for 24 hours in MEM containing $^3$H-proline (radioactive labelled compound) and 0.25 mM ascorbic acid. The produced collagen was labelled with RI (radioactive isotope). From this culture supernatant, an acid-soluble fraction was extracted. Radioactivity was measured for this fraction. The measured value was taken to be the collagen synthesis activity.

Radioactivity of the culture supernatant cultured with the test compound was compared with that of the culture supernatant cultured without the test compound to calculate a collagen synthesis inhibitory activity (T/C) and determine a concentration (μM) at which collagen synthesis was inhibited by 50% (IC50=a concentration of the test compound at which T/C corresponded to 0.5).

T/C=(Radioactivity of culture supernatant cultured with the test compound)/(radioactivity of culture supernatant cultured without the test compound)

These results are shown in Table 432.

TABLE 432

| Text compound | Collagen synthesis inhibitory activity IC50 (μM) |
|---|---|
| Example No. 148 | 0.0230 |
| Example No. 305 | 0.0069 |
| Example No. 319 | 0.0019 |
| Example No. 433 | 0.0130 |
| Example No. 582 | 0.0370 |
| Example No. 590 | 0.0380 |
| Example No. 592 | 0.0950 |
| Example No. 768 | 0.0860 |
| Example No. 790 | 0.0055 |
| Example No. 800 | 0.0290 |
| Example No. 1039 | 0.0220 |
| Example No. 1049 | 0.0490 |
| Example No. 1110 | 0.0390 |
| Example No. 1503 | 0.0078 |
| Example No. 2063 | 0.0300 |
| Example No. 2100 | 0.0790 |
| Example No. 2322 | 0.0640 |
| Example No. 2362 | 0.0440 |
| Example No. 2600 | 0.0220 |
| Example No. 2601 | 0.0260 |

The invention claimed is:
1. An aromatic compound represented by the general formula (1) or a salt thereof:

[Formula 1]

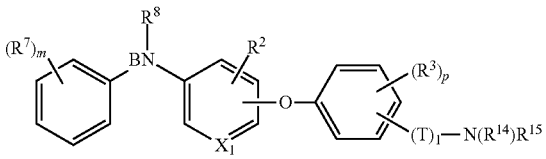

(1)

[wherein $X_1$ represents a nitrogen atom,
$R^8$ represents a hydrogen atom, a lower alkyl group that may have a lower alkoxy group as a substituent, a lower alkanoyl group, a lower alkylsulfonyl group, or a phenyl lower alkyl group,
B represents a group —CO— or a lower alkylene group, $R^7$ represents a hydrogen atom, a phenyl group, a carboxy group, a hydroxyl group, a halogen atom, a lower alkyl group that may have a halogen atom as a substituent, a phenoxy group, a lower alkoxy group that may have a halogen atom as a substituent, a lower alkylenedioxy group, an amino group that may have a group, as a substituent, selected from the group consisting of a lower alkyl group, a lower alkanoyl group, a benzoyl group and a cycloalkyl group, a cyano group, a lower alkanoyl group that may have a halogen atom as a substituent, a lower alkylsulfonyl group, an aminosulfonyl group, a lower alkoxycarbonyl group, a lower alkanoyloxy group, a lower alkoxycarbonyl lower alkyl group, or a 5- or 6-membered saturated or unsaturated heterocyclic group having 1 to 4 nitrogen atoms, oxygen atoms, or sulfur atoms (wherein said heterocyclic ring may be substituted by an oxo group), m represents an integer between 1 and 5, wherein when m represents 2 to 5, two to five $R^7$s may be identical or different, $R^2$ represents a hydrogen atom, a halogen atom, or a lower alkyl group, p represents 1 or 2, $R^3$ represents a hydrogen atom, a lower alkoxy group, a halogen atom, a lower alkyl group that may have a halogen atom as a substituent, a lower alkoxycarbonyl group, a carboxy group, a group —$CONR^{11}R^{12}$, or a cyano group, each of $R^{11}$ and $R^{12}$, which are identical or different, represents a hydrogen atom, a lower alkyl group, a cycloalkyl group, or a phenyl group; or $R^{11}$ and $R^{12}$, together with the nitrogen atom to which they bind, may bind to each other, directly or via a nitrogen atom, a sulfur atom, or an oxygen atom to form a 5- to 7-membered saturated heterocyclic ring, T represents a lower alkylene group, a group —$N(R^{17})$—$B_3$—CO—, a group —$B_{19}$—$N(R^{18})$—CO—, a group —$B_4$—CO—, a group -Q-$B_5$—CO—, a group —$B_6$—$N(R^{19})$—$B_7$—CO—, a group —CO—$B_8$—, a group —CH(OH)—$B_9$—, a group —CO—$B_{10}$—CO—, a group —CH(OH)—$B_{11}$—CO—, a group —CO—, a group —$SO_2$—, or a group —$B_{23a}$—CO—CO—, $R^{17}$ represents a hydrogen atom, a lower alkyl group, a cycloalkyl group, a cycloalkylcarbonyl group, a lower alkanoyl group that may have a halogen atom as a substituent, a lower alkenyl group, an amino-substituted lower alkanoyl group that may have a lower alkyl group as a substituent, or a lower alkylsulfonyl group, $B_3$ represents a lower alkylene group, $B_{19}$ represents a lower alkylene group, $R^{18}$ represents a hydrogen atom or a lower alkyl group, $B_4$ represents a lower alkenylene group, or a lower alkylene group that may have a hydroxyl group as a substituent, Q represents an oxygen atom or a group —S(O)n- (wherein n has the same meaning as described above), $B_5$ represents a lower alkylene group, $B_6$ represents a lower alkylene group, $R^{19}$ represents a hydrogen atom or a lower alkanoyl group, $B_7$ represents a lower alkylene group, $B_8$ represents a lower alkylene group, $B_9$ represents a lower alkylene group, $B_{10}$ represents a lower alkylene group, $B_{11}$ represents a lower alkylene group, $B_{23a}$ represents a lower alkylene group, l represents 0 or 1, $R^{14}$ and $R^{15}$, together with the nitrogen atom to which they bind, form a piperidinyl group or a piperazinyl group, wherein a substituent on the piperidinyl group or the piperazinyl group represents a phenyl-substituted lower alkyl group, which may have a pyridyl group on the lower alkyl group, having 1 to 2 phenyl groups that may be substituted by 1 to 3 groups, as substituent on the phenyl ring, selected from the group consisting of a lower alkanoyl group, an amino group that may have a lower alkanoyl group as a substituent, a lower alkoxycarbonyl group, a cyano group, a nitro group, a phenyl group, a halogen atom, a lower alkyl group that may have a halogen atom as a substituent, a lower alkoxy group that may have a halogen atom as a substituent, a phenyl lower alkoxy group, a hydroxyl group, and a lower alkylenedioxy group].

2. The aromatic compound or a salt thereof according to claim 1, wherein $R^{14}$ and $R^{15}$ in the general formula (1), together with the nitrogen atom to which they bind, form a piperidinyl group.

3. The aromatic compound or a salt thereof according to claim 2, wherein l in the general formula (1) represents 1, and T represents a group —$N(R^{17})$—$B_3$—CO—.

4. The aromatic compound or a salt thereof according to claim 2, wherein l in the general formula (1) represents 1, and T represents a group —$B_4$—CO—.

5. The aromatic compound or a salt thereof according to claim 2, wherein l in the general formula (1) represents 1, and T represents a group —CO—.

6. The aromatic compound or a salt thereof according to claim 2, wherein l in the general formula (1) represents 0.

7. The aromatic compound or a salt thereof according to claim 1, wherein $R^{14}$ and $R^{15}$ in the general formula (1), together with the nitrogen atom to which they bind, form a piperazinyl group.

8. The aromatic compound or a salt thereof according to claim 7, wherein l in the general formula (1) represents 1, and T represents a group —$N(R^{17})$—$B_3$—CO—.

9. The aromatic compound or a salt thereof according to claim 7, wherein l in the general formula (1) represents 1, and T represents a group —$B_4$—CO—.

10. The aromatic compound or a salt thereof according to claim 7, wherein l in the general formula (1) represents 1, and T represents a group —CO—.

11. The aromatic compound or a salt thereof according to claim 7, wherein l in the general formula (1) represents 0.

12. The aromatic compound or a salt thereof according to any one of claims 8 to 11, wherein $R^{14}$ and $R^{15}$ in the general formula (1), together with the nitrogen atom to which they bind, form a piperonyl group-substituted or benzyl group-substituted piperazinyl group.

13. The aromatic compound or a salt thereof according to claim 1, wherein $R^7$ in the general formula (1) represents a halogen atom, or a lower alkyl group that may have a halogen atom as a substituent, m represents 1 or 2, $R^8$ represents a hydrogen atom, B represents a group —CO—, $R^2$ represents a hydrogen atom, $X_1$ represents a nitrogen atom, $R^3$ represents a hydrogen atom, a lower alkoxy group, a halogen atom, or a lower alkyl group that may have a halogen atom as a substituent, T represents a group —$N(R^{17})$—$B_3$—CO—, a group —$B_4$—CO—, or a group —CO—, $R^{17}$ represents a hydrogen atom or a lower alkyl group, and $B_4$ represents a lower alkylene group.

14. The aromatic compound or a salt thereof according to claim 1, wherein the aromatic compound represented by the general formula (1) is an aromatic compound selected from the group consisting of:
(1) N-[6-(4-{[2-(4-piperonylpiperazin-1-yl)-2-oxoethyl]ethylamino}-2-methoxyphenoxy)pyridin-3-yl]-3,4-dichlorobenzamide,
(2) N-{2-[4-(1,3-benzodioxol-5-ylmethyl)piperazin-1-yl]-2-oxoethyl}-N-{4-[(5-{methyl[4-(trifluoromethyl)benzyl]amino}pyridin-2-yl)oxy]phenyl}acetamide,
(3) N-(6-{4-[3-(4-piperonylpiperazin-1-yl)-3-oxopropyl]phenoxy}pyridin-3-yl)-4-trifluoromethylbenzamide,
(4) N-[6-(4-{[2-(4-piperonylpiperazin-1-yl)-2-oxoethyl]ethylamino}-2-methoxyphenoxy)pyridin-3-yl]-4-trifluoromethylbenzamide,
(5) N-[6-(4-{[2-(4-piperonylpiperazin-1-yl)-2-oxoethyl]methylamino}-2-methylphenoxy)pyridin-3-yl]-4-trifluoromethylbenzamide, and
(6) N-[6-(4-{[4-(4-pivaloylbenzyl)piperazin-1-yl]oxomethyl}phenoxy)pyridin-3-yl]-3,4-dichlorobenzamide.

\* \* \* \* \*